US012486326B2

(12) United States Patent
Tan et al.

(10) Patent No.: US 12,486,326 B2
(45) **Date of Patent: *Dec. 2, 2025**

(54) ANTI-TCR ANTIBODY MOLECULES AND USES THEREOF

(71) Applicant: Marengo Therapeutics, Inc., Cambridge, MA (US)

(72) Inventors: Seng-Lai Tan, Sudbury, MA (US); Brian Edward Vash, Cambridge, MA (US); Jonathan Hsu, Waltham, MA (US); Dilini Charmain Gunasekera, Cambridge, MA (US); Sangeetha Sagar Palakurthi, East Walpole, MA (US); Andreas Loew, Boston, MA (US); Madan Katragadda, Acton, MA (US); Peter Marek, Hudson, MA (US); Gurkan Guntas, Newton, MA (US)

(73) Assignee: Marengo Therapeutics, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/341,688

(22) Filed: Jun. 26, 2023

(65) Prior Publication Data

US 2023/0374133 A1 Nov. 23, 2023

Related U.S. Application Data

(63) Continuation of application No. 17/855,332, filed on Jun. 30, 2022, which is a continuation of application No. PCT/US2020/067543, filed on Dec. 30, 2020.

(60) Provisional application No. 63/070,596, filed on Aug. 26, 2020, provisional application No. 62/957,024, filed on Jan. 3, 2020.

(51) Int. Cl.

| | |
|---|---|
| ***C07K 16/28*** | (2006.01) |
| ***A61P 35/00*** | (2006.01) |
| ***A61P 37/04*** | (2006.01) |
| ***C07K 16/46*** | (2006.01) |

(52) U.S. Cl.

CPC .......... *C07K 16/2809* (2013.01); *A61P 35/00* (2018.01); *A61P 37/04* (2018.01); *C07K 2317/52* (2013.01); *C07K 2317/565* (2013.01)

(58) Field of Classification Search

CPC .......................... C07K 16/00; A61K 39/39541
See application file for complete search history.

(56) References Cited

U.S. PATENT DOCUMENTS

| | | | |
|---|---|---|---|
| 861,745 | A | 7/1907 | Maxwell |
| 4,433,059 | A | 2/1984 | Chang et al. |
| 4,439,196 | A | 3/1984 | Higuchi |
| 4,444,878 | A | 4/1984 | Paulus |
| 4,447,224 | A | 5/1984 | DeCant, Jr. et al. |
| 4,447,233 | A | 5/1984 | Mayfield |
| 4,475,196 | A | 10/1984 | La Zor |
| 4,486,194 | A | 12/1984 | Ferrara |
| 4,487,603 | A | 12/1984 | Harris |
| 4,522,811 | A | 6/1985 | Eppstein et al. |
| 4,596,556 | A | 6/1986 | Morrow et al. |
| 4,676,980 | A | 6/1987 | Segal et al. |
| 4,737,456 | A | 4/1988 | Weng et al. |
| 4,790,824 | A | 12/1988 | Morrow et al. |
| 4,816,567 | A | 3/1989 | Cabilly et al. |
| 4,941,880 | A | 7/1990 | Burns |
| 5,057,423 | A | 10/1991 | Hiserodt et al. |
| 5,064,413 | A | 11/1991 | McKinnon et al. |
| 5,116,615 | A | 5/1992 | Gokcen et al. |
| 5,208,020 | A | 5/1993 | Chari et al. |
| 5,223,409 | A | 6/1993 | Ladner et al. |
| 5,225,539 | A | 7/1993 | Winter |
| 5,273,743 | A | 12/1993 | Ahlem et al. |
| 5,312,335 | A | 5/1994 | Mckinnon et al. |
| 5,374,548 | A | 12/1994 | Caras |
| 5,383,851 | A | 1/1995 | McKinnon, Jr. et al. |
| 5,391,377 | A | 2/1995 | Barnwell |
| 5,399,163 | A | 3/1995 | Peterson et al. |
| 5,399,331 | A | 3/1995 | Loughrey et al. |
| 5,416,016 | A | 5/1995 | Low et al. |
| 5,416,064 | A | 5/1995 | Chari et al. |
| 5,500,362 | A | 3/1996 | Robinson et al. |
| 5,534,254 | A | 7/1996 | Huston et al. |
| 5,571,894 | A | 11/1996 | Wels et al. |
| 5,582,996 | A | 12/1996 | Curtis |
| 5,585,089 | A | 12/1996 | Queen et al. |

(Continued)

FOREIGN PATENT DOCUMENTS

| | | | |
|---|---|---|---|
| AU | 5245399 | A | 2/2000 |
| AU | 2001278662 | B2 | 9/2006 |

(Continued)

OTHER PUBLICATIONS

Paul, Fundamental Immunology, 3rd Edition, 1993, pp. 292-295 (Year: 1993).*

(Continued)

*Primary Examiner* — Michael Allen

(74) *Attorney, Agent, or Firm* — Wilson Sonsini Goodrich & Rosati

(57) ABSTRACT

The disclosure provides antibody molecules that bind to TCR Vβ regions and multispecific molecules comprising said antibody molecules. Additionally, disclosed are nucleic acids encoding the same, methods of producing the aforesaid molecules, pharmaceutical compositions comprising aforesaid molecules, and methods of treating a cancer using the aforesaid molecules.

10 Claims, 258 Drawing Sheets

Specification includes a Sequence Listing.

(56) References Cited

U.S. PATENT DOCUMENTS 5,587,458 A 12/1996 King et al.
5,591,828 A 1/1997 Bosslet et al.
5,624,821 A 4/1997 Winter et al.
5,626,561 A 5/1997 Butler et al.
5,635,483 A 6/1997 Pettit et al.
5,635,602 A 6/1997 Cantor et al.
5,637,481 A 6/1997 Ledbetter et al.
5,641,870 A 6/1997 Rinderknecht et al.
5,648,237 A 7/1997 Carter
5,648,260 A 7/1997 Winter et al.
5,693,761 A 12/1997 Queen et al.
5,693,762 A 12/1997 Queen et al.
5,712,374 A 1/1998 Kuntsmann et al.
5,714,586 A 2/1998 Kunstmann et al.
5,731,116 A 3/1998 Matsuo et al.
5,731,168 A 3/1998 Carter et al.
5,739,116 A 4/1998 Hamann et al.
5,747,036 A 5/1998 Brenner et al.
5,750,373 A 5/1998 Garrard et al.
5,766,947 A 6/1998 Rittershaus et al.
5,767,285 A 6/1998 Hamann et al.
5,770,429 A 6/1998 Lonberg et al.
5,770,701 A 6/1998 McGahren et al.
5,770,710 A 6/1998 McGahren et al.
5,773,001 A 6/1998 Hamann et al.
5,776,459 A 7/1998 Vandenbark
5,780,588 A 7/1998 Pettit et al.
5,787,900 A 8/1998 Butler et al.
5,789,199 A 8/1998 Joly et al.
5,811,097 A 9/1998 Allison et al.
5,821,337 A 10/1998 Carter et al.
5,831,012 A 11/1998 Nilsson et al.
5,837,242 A 11/1998 Holliger et al.
5,837,821 A 11/1998 Wu
5,840,523 A 11/1998 Simmons et al.
5,843,069 A 12/1998 Butler et al.
5,844,094 A 12/1998 Hudson et al.
5,849,500 A 12/1998 Breitling et al.
5,849,589 A 12/1998 Tedder et al.
5,861,155 A 1/1999 Lin
5,864,019 A 1/1999 King et al.
5,869,046 A 2/1999 Presta et al.
5,869,620 A 2/1999 Whitlow et al.
5,877,296 A 3/1999 Hamann et al.
5,902,745 A 5/1999 Butler et al.
5,910,573 A 6/1999 Plueckthun et al.
5,913,998 A 6/1999 Butler et al.
5,932,448 A 8/1999 Tso et al.
5,959,083 A 9/1999 Bosslet et al.
5,959,177 A 9/1999 Hein et al.
5,968,753 A 10/1999 Tseng-Law et al.
5,980,889 A 11/1999 Butler et al.
5,989,830 A 11/1999 Davis et al.
6,005,079 A 12/1999 Casterman et al.
6,040,498 A 3/2000 Stomp et al.
6,075,181 A 6/2000 Kucherlapati et al.
6,120,766 A 9/2000 Hale et al.
6,150,584 A 11/2000 Kucherlapati et al.
6,171,586 B1 1/2001 Lam et al.
6,171,799 B1 1/2001 Skibbens et al.
6,172,197 B1 1/2001 McCafferty et al.
6,194,551 B1 2/2001 Idusogie et al.
6,239,259 B1 5/2001 Davis et al.
6,248,516 B1 6/2001 Winter et al.
6,267,958 B1 7/2001 Andya et al.
6,291,158 B1 9/2001 Winter et al.
6,294,353 B1 9/2001 Pack et al.
6,333,396 B1 12/2001 Filpula et al.
6,352,694 B1 3/2002 June et al.
6,417,429 B1 7/2002 Hein et al.
6,420,548 B1 7/2002 Vezina et al.
6,476,198 B1 11/2002 Kang
6,511,663 B1 1/2003 King et al.
6,534,055 B1 3/2003 June et al.
6,582,915 B1 6/2003 Griffiths et al.
6,593,081 B1 7/2003 Griffiths et al.
6,602,684 B1 8/2003 Umana et al.
6,630,579 B2 10/2003 Chari et al.
6,632,427 B1 10/2003 Finiels et al.
6,670,453 B2 12/2003 Frenken et al.
6,696,245 B2 2/2004 Winter et al.
6,703,199 B1 3/2004 Koide
6,737,056 B1 5/2004 Presta
6,743,896 B2 6/2004 Filpula et al.
6,756,523 B1 6/2004 Kahn et al.
6,765,087 B1 7/2004 Casterman et al.
6,809,185 B1 10/2004 Schoonjans et al.
6,818,418 B1 11/2004 Lipovsek et al.
6,833,441 B2 12/2004 Wang et al.
6,838,254 B1 1/2005 Hamers et al.
6,905,680 B2 6/2005 June et al.
6,979,546 B2 12/2005 Moretta et al.
6,982,321 B2 1/2006 Winter
7,041,870 B2 5/2006 Tomizuka et al.
7,083,785 B2 8/2006 Browning et al.
7,087,409 B2 8/2006 Barbas, III et al.
7,105,149 B1 9/2006 Dalla-Favera
7,125,978 B1 10/2006 Vezina et al.
7,129,330 B1 10/2006 Little et al.
7,183,076 B2 2/2007 Arathoon et al.
7,186,804 B2 3/2007 Gillies et al.
7,189,826 B2 3/2007 Rodman
7,250,297 B1 7/2007 Beste et al.
7,276,241 B2 10/2007 Schneider et al.
7,332,581 B2 2/2008 Presta
7,361,360 B2 4/2008 Kitabwalla et al.
7,371,826 B2 5/2008 Presta
7,402,314 B2 7/2008 Sherman
7,431,380 B1 10/2008 Buresh
7,476,724 B2 1/2009 Dennis et al.
7,498,298 B2 3/2009 Doronina et al.
7,501,121 B2 3/2009 Tchistiakova et al.
7,517,966 B2 4/2009 Moretta et al.
7,521,056 B2 4/2009 Chang et al.
7,521,541 B2 4/2009 Eigenbrot et al.
7,527,787 B2 5/2009 Chang et al.
7,527,791 B2 5/2009 Adams et al.
7,534,866 B2 5/2009 Chang et al.
7,563,441 B2 7/2009 Graus et al.
7,601,803 B1 10/2009 Fiedler et al.
7,612,181 B2 11/2009 Wu et al.
7,642,228 B2 1/2010 Carter et al.
7,700,739 B2 4/2010 Lacy et al.
7,741,446 B2 6/2010 Pardridge et al.
7,750,128 B2 7/2010 Gegg et al.
7,767,429 B2 8/2010 Bookbinder et al.
7,799,902 B2 9/2010 Browning et al.
7,803,376 B2 9/2010 Velardi et al.
7,807,160 B2 10/2010 Presta et al.
7,829,289 B2 11/2010 Lantz et al.
7,855,275 B2 12/2010 Eigenbrot et al.
7,858,759 B2 12/2010 Brandt et al.
7,906,118 B2 3/2011 Chang et al.
7,919,257 B2 4/2011 Hoogenboom et al.
7,943,743 B2 5/2011 Korman et al.
7,999,077 B2 8/2011 Pastan et al.
8,003,774 B2 8/2011 Stavenhagen et al.
8,008,449 B2 8/2011 Korman et al.
8,012,465 B2 9/2011 Elias et al.
8,034,326 B2 10/2011 Hjorth et al.
8,202,517 B2 6/2012 Bookbinder et al.
8,216,805 B2 7/2012 Carter et al.
8,227,577 B2 7/2012 Klein et al.
8,299,220 B2 10/2012 Dalla-Favera
8,354,509 B2 1/2013 Carven et al.
8,362,213 B2 1/2013 Elkins et al.
8,450,470 B2 5/2013 Bookbinder et al.
8,466,260 B2 6/2013 Elkins et al.
8,552,156 B2 10/2013 Takayanagi et al.
8,580,252 B2 11/2013 Bookbinder et al.
8,586,713 B2 11/2013 Davis et al.
8,592,562 B2 11/2013 Kannan et al.
8,609,089 B2 12/2013 Langermann et al.
8,617,545 B2 12/2013 Hsu et al.

(56) References Cited

U.S. PATENT DOCUMENTS 8,617,559 B2 12/2013 Elkins et al.
8,658,135 B2 2/2014 O'Connor-Mccourt et al.
8,703,132 B2 4/2014 Imhof-Jung et al.
8,772,246 B2 7/2014 Bookbinder et al.
8,790,895 B2 7/2014 Fiedler et al.
8,821,883 B2 9/2014 Ambrose et al.
8,846,042 B2 9/2014 Zhou
8,871,912 B2 10/2014 Davis et al.
8,920,776 B2 12/2014 Gaiger et al.
8,945,571 B2 2/2015 Mössner et al.
8,993,524 B2 3/2015 Bedi et al.
9,000,130 B2 4/2015 Bhakta et al.
9,034,324 B2 5/2015 Kalled et al.
9,056,905 B2 6/2015 Olson et al.
9,145,588 B2 9/2015 Throsby et al.
9,200,060 B2 12/2015 Kannan et al.
9,243,058 B2 1/2016 Armitage et al.
9,309,311 B2 4/2016 Gurney et al.
9,340,621 B2 5/2016 Kufer et al.
9,358,286 B2 6/2016 De et al.
9,359,437 B2 6/2016 Davis et al.
9,382,323 B2 7/2016 Brinkmann et al.
9,387,237 B2 7/2016 Kalled et al.
9,416,187 B2 8/2016 Tedder et al.
9,447,159 B2 9/2016 Ast et al.
9,447,185 B2 9/2016 Romagne et al.
9,545,086 B2 1/2017 Mackay et al.
9,593,376 B2 3/2017 Zitvogel et al.
9,663,577 B2 5/2017 Pierres et al.
9,676,863 B2 6/2017 Lo
9,833,476 B2 12/2017 Zhang et al.
10,150,816 B2 12/2018 Abbot et al.
10,294,300 B2 5/2019 Raum et al.
10,308,721 B2 6/2019 Williams et al.
10,478,509 B2 11/2019 Torgov et al.
10,610,571 B2 4/2020 Ptacin et al.
10,676,516 B2 6/2020 Viney et al.
10,730,942 B2 8/2020 Pule et al.
10,815,311 B2 10/2020 Wesche et al.
11,033,634 B2 6/2021 Stull et al.
11,291,721 B2 4/2022 Loew et al.
11,292,838 B2 4/2022 Schendel et al.
11,673,953 B2 6/2023 Zhang et al.
11,692,031 B2 7/2023 Dahlhoff et al.
11,845,797 B2 12/2023 Tan et al.
11,965,025 B2 4/2024 Tan et al.
12,152,073 B2 11/2024 Loew et al.
12,247,060 B2 3/2025 Loew et al.
12,286,477 B2 4/2025 Tan et al.
2002/0004587 A1 1/2002 Miller et al.
2002/0041865 A1 4/2002 Austin et al.
2002/0062010 A1 5/2002 Arathoon et al.
2002/0076406 A1 6/2002 Leung
2002/0103345 A1 8/2002 Zhu
2002/0115214 A1 8/2002 June et al.
2002/0164328 A1 11/2002 Shinkawa et al.
2003/0099647 A1 5/2003 Deshpande et al.
2003/0115614 A1 6/2003 Kanda et al.
2003/0130496 A1 7/2003 Winter et al.
2003/0157108 A1 8/2003 Presta
2003/0175884 A1 9/2003 Umana et al.
2003/0207346 A1 11/2003 Arathoon et al.
2003/0211078 A1 11/2003 Heavner
2004/0009530 A1 1/2004 Wilson et al.
2004/0093621 A1 5/2004 Shitara et al.
2004/0109865 A1 6/2004 Niwa et al.
2004/0110282 A1 6/2004 Kanda et al.
2004/0110704 A1 6/2004 Yamane et al.
2004/0132140 A1 7/2004 Satoh et al.
2004/0175756 A1 9/2004 Kolkman et al.
2004/0219643 A1 11/2004 Winter et al.
2004/0220388 A1 11/2004 Mertens et al.
2004/0241817 A1 12/2004 Umana et al.
2004/0242847 A1 12/2004 Fukushima et al.
2005/0003403 A1 1/2005 Rossi et al.
2005/0004352 A1 1/2005 Kontermann et al.
2005/0014934 A1 1/2005 Hinton et al.
2005/0048512 A1 3/2005 Kolkman et al.
2005/0053973 A1 3/2005 Kolkman et al.
2005/0069552 A1 3/2005 Bleck et al.
2005/0079170 A1 4/2005 Le Gall et al.
2005/0079574 A1 4/2005 Bond
2005/0090648 A1 4/2005 Tsurushita et al.
2005/0100543 A1 5/2005 Hansen et al.
2005/0119455 A1 6/2005 Fuh et al.
2005/0123546 A1 6/2005 Umana et al.
2005/0136049 A1 6/2005 Ledbetter et al.
2005/0136051 A1 6/2005 Scallon
2005/0163782 A1 7/2005 Glaser et al.
2005/0260186 A1 11/2005 Bookbinder et al.
2005/0266000 A1 12/2005 Bond et al.
2005/0266425 A1 12/2005 Zauderer et al.
2006/0008844 A1 1/2006 Stemmer et al.
2006/0025576 A1 2/2006 Miller et al.
2006/0083747 A1 4/2006 Winter et al.
2006/0104968 A1 5/2006 Bookbinder et al.
2006/0120960 A1 6/2006 Deyev et al.
2006/0141581 A1 6/2006 Gillies et al.
2006/0204493 A1 9/2006 Huang et al.
2006/0263367 A1 11/2006 Fey et al.
2007/0004909 A1 1/2007 Johnson et al.
2007/0036783 A1 2/2007 Humeau et al.
2007/0061900 A1 3/2007 Murphy et al.
2007/0087381 A1 4/2007 Kojima
2007/0105105 A1 5/2007 Clelland et al.
2007/0117126 A1 5/2007 Sidhu et al.
2007/0128150 A1 6/2007 Norman
2007/0141049 A1 6/2007 Bredehorst et al.
2007/0154901 A1 7/2007 Thogersen et al.
2007/0160598 A1 7/2007 Dennis et al.
2007/0178106 A1 8/2007 Romagne
2007/0184052 A1 8/2007 Lin et al.
2007/0231322 A1 10/2007 Romagne et al.
2007/0237764 A1 10/2007 Birtalan et al.
2007/0274985 A1 11/2007 Dubel et al.
2007/0292936 A1 12/2007 Barthelemy et al.
2008/0050370 A1 2/2008 Glaser et al.
2008/0063717 A1 3/2008 Romagne et al.
2008/0069820 A1 3/2008 Fuh et al.
2008/0152645 A1 6/2008 Pardridge et al.
2008/0171855 A1 7/2008 Rossi et al.
2008/0241884 A1 10/2008 Shitara et al.
2008/0247944 A1 10/2008 Graziano et al.
2008/0254512 A1 10/2008 Capon
2008/0260738 A1 10/2008 Moore et al.
2008/0299137 A1 12/2008 Svendsen et al.
2009/0002360 A1 1/2009 Chen et al.
2009/0010843 A1 1/2009 Spee et al.
2009/0130106 A1 5/2009 Christopherson et al.
2009/0148905 A1 6/2009 Ashman et al.
2009/0155275 A1 6/2009 Wu et al.
2009/0162359 A1 6/2009 Klein et al.
2009/0162360 A1 6/2009 Klein et al.
2009/0175851 A1 7/2009 Klein et al.
2009/0175867 A1 7/2009 Thompson et al.
2009/0214533 A1 8/2009 Clynes
2009/0232811 A1 9/2009 Klein et al.
2009/0234105 A1 9/2009 Gervay-Hague et al.
2009/0263392 A1 10/2009 Igawa et al.
2009/0274649 A1 11/2009 Qu et al.
2009/0280116 A1 11/2009 Smith et al.
2009/0324538 A1 12/2009 Wong et al.
2010/0015133 A1 1/2010 Igawa et al.
2010/0015153 A1 1/2010 Moretta et al.
2010/0028330 A1 2/2010 Collins et al.
2010/0047169 A1 2/2010 Mandelboim et al.
2010/0168393 A1 7/2010 Clube et al.
2010/0260704 A1 10/2010 Berenguer et al.
2010/0316645 A1 12/2010 Imhof-Jung et al.
2011/0014659 A1 1/2011 Balazs et al.
2011/0054151 A1 3/2011 Lazar et al.
2011/0091372 A1 4/2011 Ghayur et al.
2011/0150892 A1 6/2011 Thudium et al.
2011/0177073 A1 7/2011 Van Berkel et al.

(56) References Cited

U.S. PATENT DOCUMENTS

| | | | |
|---|---|---|---|
| 2011/0177093 | A1 | 7/2011 | Kalled et al. |
| 2011/0250170 | A1 | 10/2011 | Pedretti et al. |
| 2011/0287056 | A1 | 11/2011 | Gu et al. |
| 2011/0293613 | A1 | 12/2011 | Brinkmann et al. |
| 2012/0034221 | A1 | 2/2012 | Bonvini et al. |
| 2012/0039906 | A1 | 2/2012 | Olive |
| 2012/0114649 | A1 | 5/2012 | Langermann et al. |
| 2012/0149876 | A1 | 6/2012 | Von Kreudenstein et al. |
| 2012/0184716 | A1 | 7/2012 | Fischer et al. |
| 2012/0201746 | A1 | 8/2012 | Liu et al. |
| 2012/0213768 | A1 | 8/2012 | Oh et al. |
| 2012/0294857 | A1 | 11/2012 | Sentman et al. |
| 2013/0017200 | A1 | 1/2013 | Scheer et al. |
| 2013/0022601 | A1 | 1/2013 | Brinkmann et al. |
| 2013/0078249 | A1 | 3/2013 | Ast et al. |
| 2013/0129723 | A1 | 5/2013 | Blankenship et al. |
| 2013/0164293 | A1 | 6/2013 | Florio et al. |
| 2013/0165638 | A1 | 6/2013 | Hsu et al. |
| 2013/0178605 | A1 | 7/2013 | Blein et al. |
| 2013/0195849 | A1 | 8/2013 | Spreter Von Kreudenstein et al. |
| 2013/0243775 | A1 | 9/2013 | Papadopoulos et al. |
| 2013/0266568 | A1 | 10/2013 | Brinkmann et al. |
| 2013/0267686 | A1 | 10/2013 | Brinkmann et al. |
| 2013/0273055 | A1 | 10/2013 | Borges et al. |
| 2013/0273089 | A1 | 10/2013 | Getts et al. |
| 2013/0280208 | A1 | 10/2013 | Stepkowski et al. |
| 2013/0303396 | A1 | 11/2013 | Igawa et al. |
| 2013/0317200 | A1 | 11/2013 | Elson et al. |
| 2014/0037621 | A1 | 2/2014 | Tsurushita et al. |
| 2014/0044728 | A1 | 2/2014 | Takayanagi et al. |
| 2014/0051833 | A1 | 2/2014 | Fischer et al. |
| 2014/0051835 | A1 | 2/2014 | Dixit et al. |
| 2014/0072528 | A1 | 3/2014 | Gerdes et al. |
| 2014/0072581 | A1 | 3/2014 | Dixit et al. |
| 2014/0079689 | A1 | 3/2014 | Elliott et al. |
| 2014/0079691 | A1 | 3/2014 | Mcconnell et al. |
| 2014/0099254 | A1 | 4/2014 | Chang et al. |
| 2014/0154254 | A1 | 6/2014 | Kannan et al. |
| 2014/0199294 | A1 | 7/2014 | Mimoto et al. |
| 2014/0200331 | A1 | 7/2014 | Corper et al. |
| 2014/0227265 | A1 | 8/2014 | Wu et al. |
| 2014/0242075 | A1 | 8/2014 | Parren et al. |
| 2014/0242077 | A1 | 8/2014 | Choi et al. |
| 2014/0256916 | A1 | 9/2014 | Kruip et al. |
| 2014/0308285 | A1 | 10/2014 | Yan et al. |
| 2014/0322212 | A1 | 10/2014 | Brogdon et al. |
| 2014/0322221 | A1 | 10/2014 | Miller et al. |
| 2014/0348839 | A1 | 11/2014 | Chowdhury et al. |
| 2014/0363426 | A1 | 12/2014 | Moore et al. |
| 2014/0377269 | A1 | 12/2014 | Mabry et al. |
| 2015/0017187 | A1 | 1/2015 | Thanos et al. |
| 2015/0018529 | A1 | 1/2015 | Humphreys et al. |
| 2015/0056199 | A1 | 2/2015 | Kumar et al. |
| 2015/0098900 | A1 | 4/2015 | Ebens et al. |
| 2015/0133638 | A1 | 5/2015 | Wranik et al. |
| 2015/0166661 | A1 | 6/2015 | Chen et al. |
| 2015/0166670 | A1 | 6/2015 | Castoldi et al. |
| 2015/0175707 | A1 | 6/2015 | De Jong et al. |
| 2015/0203591 | A1 | 7/2015 | Yancopoulos et al. |
| 2015/0211001 | A1 | 7/2015 | Ohrn et al. |
| 2015/0218260 | A1 | 8/2015 | Klein et al. |
| 2015/0232560 | A1 | 8/2015 | Heindl et al. |
| 2015/0315296 | A1 | 11/2015 | Schaefer et al. |
| 2015/0337049 | A1 | 11/2015 | Labrijn et al. |
| 2015/0344570 | A1 | 12/2015 | Igawa et al. |
| 2015/0353636 | A1 | 12/2015 | Parren et al. |
| 2015/0368351 | A1 | 12/2015 | Vu et al. |
| 2015/0368352 | A1 | 12/2015 | Liu |
| 2015/0376287 | A1 | 12/2015 | Vu et al. |
| 2016/0015749 | A1 | 1/2016 | Gottschalk et al. |
| 2016/0039947 | A1 | 2/2016 | Demarest et al. |
| 2016/0075785 | A1 | 3/2016 | Ast et al. |
| 2016/0102135 | A1 | 4/2016 | Escobar-Cabrera |
| 2016/0114057 | A1 | 4/2016 | Dixit et al. |
| 2016/0130347 | A1 | 5/2016 | Bruenker et al. |
| 2016/0131654 | A1 | 5/2016 | Berenson et al. |
| 2016/0145340 | A1 | 5/2016 | Borges et al. |
| 2016/0145354 | A1 | 5/2016 | Bacac et al. |
| 2016/0176973 | A1 | 6/2016 | Kufer et al. |
| 2016/0194389 | A1 | 7/2016 | Regula et al. |
| 2016/0229915 | A1 | 8/2016 | Igawa et al. |
| 2016/0244523 | A1 | 8/2016 | Blank et al. |
| 2016/0257763 | A1 | 9/2016 | Von Kreudenstein et al. |
| 2016/0264685 | A1 | 9/2016 | Fouque et al. |
| 2016/0297885 | A1 | 10/2016 | Kuo et al. |
| 2016/0311915 | A1 | 10/2016 | Puléet al. |
| 2016/0368985 | A1 | 12/2016 | Hotzel et al. |
| 2016/0368988 | A1 | 12/2016 | Bakker et al. |
| 2017/0022284 | A1 | 1/2017 | Timmer et al. |
| 2017/0035905 | A1 | 2/2017 | Abrams et al. |
| 2017/0037128 | A1 | 2/2017 | Little et al. |
| 2017/0051068 | A1 | 2/2017 | Pillarisetti et al. |
| 2017/0066827 | A1 | 3/2017 | Puléet al. |
| 2017/0151281 | A1 | 6/2017 | Wagner et al. |
| 2017/0204176 | A1 | 7/2017 | Bonvini et al. |
| 2017/0269092 | A1 | 9/2017 | Kralovics |
| 2017/0275362 | A1 | 9/2017 | Brentjens et al. |
| 2017/0298445 | A1 | 10/2017 | Ogg |
| 2017/0334998 | A1 | 11/2017 | Puléet al. |
| 2017/0368169 | A1 | 12/2017 | Loew et al. |
| 2018/0153938 | A1 | 6/2018 | Keating et al. |
| 2018/0235887 | A1 | 8/2018 | Garidel et al. |
| 2018/0256716 | A1 | 9/2018 | Schendel et al. |
| 2019/0062448 | A1 | 2/2019 | Soros et al. |
| 2019/0209612 | A1 | 7/2019 | Puléet al. |
| 2019/0315883 | A1 | 10/2019 | Ast et al. |
| 2019/0322763 | A1 | 10/2019 | Ast et al. |
| 2020/0071417 | A1 | 3/2020 | Loew et al. |
| 2020/0109195 | A1 | 4/2020 | Watkins et al. |
| 2020/0129638 | A1 | 4/2020 | Van Berkel et al. |
| 2020/0140549 | A1 | 5/2020 | Cordoba et al. |
| 2020/0172591 | A1 | 6/2020 | Hosse et al. |
| 2020/0172868 | A1 | 6/2020 | Wickham et al. |
| 2020/0200756 | A1 | 6/2020 | Puléet al. |
| 2020/0230208 | A1 | 7/2020 | Wang et al. |
| 2020/0277384 | A1 | 9/2020 | Chang et al. |
| 2020/0291089 | A1 | 9/2020 | Loew et al. |
| 2020/0299349 | A1 | 9/2020 | Garcia et al. |
| 2020/0306301 | A1 | 10/2020 | Andresen et al. |
| 2020/0308242 | A1 | 10/2020 | Lowe et al. |
| 2020/0317787 | A1 | 10/2020 | Li et al. |
| 2020/0332003 | A1 | 10/2020 | Britanova et al. |
| 2020/0377571 | A1 | 12/2020 | Loew et al. |
| 2020/0385472 | A1 | 12/2020 | Loew et al. |
| 2021/0009711 | A1 | 1/2021 | Loew et al. |
| 2021/0024631 | A1 | 1/2021 | Kley et al. |
| 2021/0079114 | A1 | 3/2021 | Hudson |
| 2021/0137982 | A1 | 5/2021 | Loew et al. |
| 2021/0198369 | A1 | 7/2021 | Chang et al. |
| 2021/0221863 | A1 | 7/2021 | Kang et al. |
| 2021/0230311 | A1 | 7/2021 | Nezu et al. |
| 2021/0238280 | A1 | 8/2021 | Loew et al. |
| 2021/0246227 | A1 | 8/2021 | Loew et al. |
| 2021/0277119 | A1 | 9/2021 | Tan et al. |
| 2021/0363250 | A1 | 11/2021 | Kamikawaji et al. |
| 2021/0371523 | A1 | 12/2021 | Loew et al. |
| 2021/0380670 | A1 | 12/2021 | Loew et al. |
| 2021/0380682 | A1 | 12/2021 | Loew et al. |
| 2021/0380691 | A1 | 12/2021 | Loew et al. |
| 2021/0380692 | A1 | 12/2021 | Loew et al. |
| 2021/0380715 | A1 | 12/2021 | Yoshida et al. |
| 2022/0064255 | A1 | 3/2022 | Loew et al. |
| 2022/0064297 | A1 | 3/2022 | Tan et al. |
| 2022/0112286 | A1 | 4/2022 | Britanova et al. |
| 2022/0288200 | A1 | 9/2022 | Loew et al. |
| 2023/0025484 | A1 | 1/2023 | Tan et al. |
| 2023/0031734 | A1 | 2/2023 | Tan et al. |
| 2023/0034161 | A1 | 2/2023 | Tan et al. |
| 2023/0048244 | A1 | 2/2023 | Loew |
| 2023/0102344 | A1 | 3/2023 | Katragadda et al. |
| 2023/0127740 | A1 | 4/2023 | Tan et al. |
| 2023/0142522 | A1 | 5/2023 | Tan et al. |
| 2023/0174650 | A1 | 6/2023 | Tan et al. |
| 2023/0192848 | A1 | 6/2023 | Loew |

(56) References Cited

U.S. PATENT DOCUMENTS

| | | | |
|---|---|---|---|
| 2023/0227552 | A1 | 7/2023 | Tan et al. |
| 2023/0333112 | A1 | 10/2023 | Loew et al. |
| 2023/0348593 | A1 | 11/2023 | Loew et al. |
| 2023/0357395 | A1 | 11/2023 | Loew et al. |
| 2024/0002543 | A1 | 1/2024 | Loew et al. |
| 2024/0076377 | A1 | 3/2024 | Tan et al. |
| 2024/0301060 | A1 | 9/2024 | Tan et al. |

FOREIGN PATENT DOCUMENTS

| | | | |
|---|---|---|---|
| CA | 3016563 | A1 | 9/2017 |
| CA | 3214757 | A1 | 10/2022 |
| CN | 101802010 | A | 8/2010 |
| CN | 101985476 | A | 3/2011 |
| CN | 104203981 | A | 12/2014 |
| CN | 104769103 | A | 7/2015 |
| CN | 105916876 | A | 8/2016 |
| CN | 106103475 | A | 11/2016 |
| CN | 106163547 | A | 11/2016 |
| CN | 107206024 | A | 9/2017 |
| CN | 107903325 | A | 4/2018 |
| CN | 108026171 | A | 5/2018 |
| CN | 108949698 | A | 12/2018 |
| CN | 109153728 | A | 1/2019 |
| CN | 113543807 | A | 10/2021 |
| CN | 114026122 | A | 2/2022 |
| DE | 10261223 | A1 | 7/2004 |
| EP | 0125023 | A1 | 11/1984 |
| EP | 0171496 | A2 | 2/1986 |
| EP | 0173494 | A2 | 3/1986 |
| EP | 0184187 | A2 | 6/1986 |
| EP | 0346087 | A2 | 12/1989 |
| EP | 0368684 | A1 | 5/1990 |
| EP | 0388151 | A1 | 9/1990 |
| EP | 0404097 | A2 | 12/1990 |
| EP | 0519596 | A1 | 12/1992 |
| EP | 0171496 | B1 | 5/1993 |
| EP | 0616640 | A1 | 9/1994 |
| EP | 0425235 | B1 | 9/1996 |
| EP | 0403156 | B1 | 9/1997 |
| EP | 1176195 | A1 | 1/2002 |
| EP | 0125023 | B2 | 3/2002 |
| EP | 0368684 | B2 | 9/2004 |
| EP | 0616640 | B1 | 9/2004 |
| EP | 1301605 | B1 | 11/2005 |
| EP | 1692172 | A2 | 8/2006 |
| EP | 1870459 | A1 | 12/2007 |
| EP | 2581113 | A1 | 4/2013 |
| EP | 1846020 | B1 | 8/2013 |
| EP | 2699259 | A1 | 2/2014 |
| EP | 2467165 | B1 | 1/2015 |
| EP | 2847231 | A1 | 3/2015 |
| EP | 2982694 | A1 | 2/2016 |
| EP | 3023437 | A1 | 5/2016 |
| EP | 1870459 | B1 | 6/2016 |
| EP | 2982694 | B1 | 6/2016 |
| EP | 3029068 | A1 | 6/2016 |
| EP | 2699259 | B1 | 7/2016 |
| EP | 3055329 | A1 | 8/2016 |
| EP | 3137500 | A1 | 3/2017 |
| EP | 3059246 | B1 | 7/2018 |
| EP | 2723380 | B1 | 8/2019 |
| EP | 3294768 | B1 | 8/2019 |
| EP | 3149031 | B1 | 12/2019 |
| EP | 3590967 | A1 | 1/2020 |
| EP | 3626739 | A1 | 3/2020 |
| EP | 3642228 | A1 | 4/2020 |
| EP | 3189132 | B1 | 6/2020 |
| EP | 3303392 | B1 | 8/2020 |
| EP | 4087871 | A1 | 11/2022 |
| GB | 2188638 | A | 10/1987 |
| GB | 2599228 | A | 3/2022 |
| GB | 2616354 | A | 9/2023 |
| JP | H0787994 | A | 4/1995 |
| JP | H08502246 | A | 3/1996 |
| JP | H09509307 | A | 9/1997 |
| JP | 2011524743 | A | 9/2011 |
| JP | 2013515509 | A | 5/2013 |
| JP | 2014527802 | A | 10/2014 |
| JP | 2016512557 | A | 4/2016 |
| JP | 6153947 | B2 | 6/2017 |
| JP | 2017143838 | A | 8/2017 |
| JP | 2018517712 | A | 7/2018 |
| JP | 2018531939 | A | 11/2018 |
| WO | WO-8500817 | A1 | 2/1985 |
| WO | WO-8601533 | A1 | 3/1986 |
| WO | WO-8702671 | A1 | 5/1987 |
| WO | WO-9002809 | A1 | 3/1990 |
| WO | WO-9100906 | A1 | 1/1991 |
| WO | WO-9103493 | A1 | 3/1991 |
| WO | WO-9110741 | A1 | 7/1991 |
| WO | WO-9117271 | A1 | 11/1991 |
| WO | WO-9201047 | A1 | 1/1992 |
| WO | WO-9203917 | A1 | 3/1992 |
| WO | WO-9203918 | A1 | 3/1992 |
| WO | WO-9209690 | A2 | 6/1992 |
| WO | WO-9215679 | A1 | 9/1992 |
| WO | WO-9218619 | A1 | 10/1992 |
| WO | WO-9220791 | A1 | 11/1992 |
| WO | WO-9209690 | A3 | 12/1992 |
| WO | WO-9301161 | A1 | 1/1993 |
| WO | WO-9301288 | A1 | 1/1993 |
| WO | WO-9308829 | A1 | 5/1993 |
| WO | WO-9311161 | A1 | 6/1993 |
| WO | WO-9311236 | A1 | 6/1993 |
| WO | WO-9323537 | A1 | 11/1993 |
| WO | WO-9404678 | A1 | 3/1994 |
| WO | WO-9405801 | A1 | 3/1994 |
| WO | WO-9409131 | A1 | 4/1994 |
| WO | WO-9411026 | A2 | 5/1994 |
| WO | WO-9412625 | A2 | 6/1994 |
| WO | WO-9425591 | A1 | 11/1994 |
| WO | WO-9429351 | A2 | 12/1994 |
| WO | WO-9509917 | A1 | 4/1995 |
| WO | WO-9516038 | A2 | 6/1995 |
| WO | WO-9637621 | A2 | 11/1996 |
| WO | WO-9730087 | A1 | 8/1997 |
| WO | WO-9814206 | A1 | 4/1998 |
| WO | WO-9856915 | A2 | 12/1998 |
| WO | WO-9858964 | A1 | 12/1998 |
| WO | WO-9904820 | A2 | 2/1999 |
| WO | WO-9916873 | A1 | 4/1999 |
| WO | WO-9922764 | A1 | 5/1999 |
| WO | WO-9945110 | A1 | 9/1999 |
| WO | WO-9951642 | A1 | 10/1999 |
| WO | WO-9964460 | A1 | 12/1999 |
| WO | WO-0006605 | A2 | 2/2000 |
| WO | WO-0034784 | A1 | 6/2000 |
| WO | WO-0060070 | A1 | 10/2000 |
| WO | WO-0061739 | A1 | 10/2000 |
| WO | WO-0104144 | A2 | 1/2001 |
| WO | WO-0129246 | A1 | 4/2001 |
| WO | WO-0136630 | A2 | 5/2001 |
| WO | WO-0164942 | A1 | 9/2001 |
| WO | WO-0198357 | A2 | 12/2001 |
| WO | WO-0231140 | A1 | 4/2002 |
| WO | WO-02070647 | A2 | 9/2002 |
| WO | WO-02072635 | A2 | 9/2002 |
| WO | WO-03002609 | A2 | 1/2003 |
| WO | WO-03011878 | A2 | 2/2003 |
| WO | WO-03014161 | A2 | 2/2003 |
| WO | WO-03056914 | A1 | 7/2003 |
| WO | WO-03084570 | A1 | 10/2003 |
| WO | WO-03085107 | A1 | 10/2003 |
| WO | WO-03085119 | A1 | 10/2003 |
| WO | WO-03093318 | A1 | 11/2003 |
| WO | WO-2004003019 | A2 | 1/2004 |
| WO | WO-2004024927 | A1 | 3/2004 |
| WO | WO-2004033685 | A1 | 4/2004 |
| WO | WO-2004056312 | A2 | 7/2004 |
| WO | WO-2004056392 | A1 | 7/2004 |
| WO | WO-2004056873 | A1 | 7/2004 |
| WO | WO-2004057002 | A2 | 7/2004 |
| WO | WO-2004058821 | A2 | 7/2004 |

(56) References Cited

FOREIGN PATENT DOCUMENTS

| | | | |
|---|---|---|---|
| WO | WO-2004065540 | A2 | 8/2004 |
| WO | WO-2004081026 | A2 | 9/2004 |
| WO | WO-2004081051 | A1 | 9/2004 |
| WO | WO-2004101790 | A1 | 11/2004 |
| WO | WO-2004106368 | A1 | 12/2004 |
| WO | WO-2005035572 | A2 | 4/2005 |
| WO | WO-2005035586 | A1 | 4/2005 |
| WO | WO-2005035778 | A1 | 4/2005 |
| WO | WO-2005053742 | A1 | 6/2005 |
| WO | WO-2005100402 | A1 | 10/2005 |
| WO | WO-2006000830 | A2 | 1/2006 |
| WO | WO-2006020258 | A2 | 2/2006 |
| WO | WO-2006029879 | A2 | 3/2006 |
| WO | WO-2006044908 | A2 | 4/2006 |
| WO | WO-2006079372 | A1 | 8/2006 |
| WO | WO-2006106905 | A1 | 10/2006 |
| WO | WO-2006121168 | A1 | 11/2006 |
| WO | WO-2006135886 | A2 | 12/2006 |
| WO | WO-2007005874 | A2 | 1/2007 |
| WO | WO-2007044887 | A2 | 4/2007 |
| WO | WO-2007059782 | A1 | 5/2007 |
| WO | WO-2007005874 | A3 | 7/2007 |
| WO | WO-2007095338 | A2 | 8/2007 |
| WO | WO-2007110205 | A2 | 10/2007 |
| WO | WO-2007137760 | A2 | 12/2007 |
| WO | WO-2008017859 | A2 | 2/2008 |
| WO | WO-2008077546 | A1 | 7/2008 |
| WO | WO-2008087219 | A1 | 7/2008 |
| WO | WO-2008119353 | A1 | 10/2008 |
| WO | WO-2009021754 | A2 | 2/2009 |
| WO | WO-2009068630 | A1 | 6/2009 |
| WO | WO-2009077993 | A2 | 6/2009 |
| WO | WO-2009089004 | A1 | 7/2009 |
| WO | WO-2009101611 | A1 | 8/2009 |
| WO | WO-2009103538 | A1 | 8/2009 |
| WO | WO-2009114335 | A2 | 9/2009 |
| WO | WO-2009147137 | A1 | 12/2009 |
| WO | WO-2010019570 | A2 | 2/2010 |
| WO | WO-2010027797 | A1 | 3/2010 |
| WO | WO-2010027827 | A2 | 3/2010 |
| WO | WO-2010029513 | A2 | 3/2010 |
| WO | WO-2010077634 | A1 | 7/2010 |
| WO | WO-2010129304 | A2 | 11/2010 |
| WO | WO-2011066342 | A2 | 6/2011 |
| WO | WO-2011090762 | A1 | 7/2011 |
| WO | WO-2011131746 | A2 | 10/2011 |
| WO | WO-2011155607 | A1 | 12/2011 |
| WO | WO-2012079000 | A1 | 6/2012 |
| WO | WO-2012088309 | A1 | 6/2012 |
| WO | WO-2012107417 | A1 | 8/2012 |
| WO | WO-2012131555 | A2 | 10/2012 |
| WO | WO-2012138475 | A1 | 10/2012 |
| WO | WO-2012143498 | A1 | 10/2012 |
| WO | WO-2012170438 | A2 | 12/2012 |
| WO | WO-2013019615 | A2 | 2/2013 |
| WO | WO-2013033626 | A2 | 3/2013 |
| WO | WO-2013037484 | A2 | 3/2013 |
| WO | WO-2013060867 | A2 | 5/2013 |
| WO | WO-2013079174 | A1 | 6/2013 |
| WO | WO-2013103912 | A1 | 7/2013 |
| WO | WO-2013170168 | A1 | 11/2013 |
| WO | WO-2014008218 | A1 | 1/2014 |
| WO | WO-2014100823 | A1 | 6/2014 |
| WO | WO-2014159940 | A1 | 10/2014 |
| WO | WO-2015052230 | A1 | 4/2015 |
| WO | WO-2015066379 | A2 | 5/2015 |
| WO | WO-2015095811 | A2 | 6/2015 |
| WO | WO-2015107015 | A1 | 7/2015 |
| WO | WO-2015107025 | A1 | 7/2015 |
| WO | WO-2015107026 | A1 | 7/2015 |
| WO | WO-2015121383 | A1 | 8/2015 |
| WO | WO-2015127158 | A1 | 8/2015 |
| WO | WO-2015132598 | A1 | 9/2015 |
| WO | WO-2015164815 | A1 | 10/2015 |
| WO | WO-2015166073 | A1 | 11/2015 |
| WO | WO-2015181805 | A1 | 12/2015 |
| WO | WO-2015197582 | A1 | 12/2015 |
| WO | WO-2015197593 | A1 | 12/2015 |
| WO | WO-2015197598 | A2 | 12/2015 |
| WO | WO-2016016299 | A1 | 2/2016 |
| WO | WO-2016019969 | A1 | 2/2016 |
| WO | WO-2016026943 | A1 | 2/2016 |
| WO | WO-2016033555 | A1 | 3/2016 |
| WO | WO-2016071376 | A2 | 5/2016 |
| WO | WO-2016071377 | A1 | 5/2016 |
| WO | WO-2016079081 | A1 | 5/2016 |
| WO | WO-2016087416 | A1 | 6/2016 |
| WO | WO-2016087514 | A1 | 6/2016 |
| WO | WO-2016087650 | A1 | 6/2016 |
| WO | WO-2016090327 | A2 | 6/2016 |
| WO | WO-2016110468 | A1 | 7/2016 |
| WO | WO-2016110584 | A1 | 7/2016 |
| WO | WO-2016115274 | A1 | 7/2016 |
| WO | WO-2016118641 | A1 | 7/2016 |
| WO | WO-2016168149 | A1 | 10/2016 |
| WO | WO-2016180969 | A1 | 11/2016 |
| WO | WO-2016193301 | A1 | 12/2016 |
| WO | WO-2017021349 | A1 | 2/2017 |
| WO | WO-2017021450 | A1 | 2/2017 |
| WO | WO-2017037634 | A1 | 3/2017 |
| WO | WO-2017040930 | A2 | 3/2017 |
| WO | WO-2017055391 | A1 | 4/2017 |
| WO | WO-2017059551 | A1 | 4/2017 |
| WO | WO-2017062604 | A1 | 4/2017 |
| WO | WO-2017077382 | A1 | 5/2017 |
| WO | WO-2017134140 | A1 | 8/2017 |
| WO | WO-2017165464 | A1 | 9/2017 |
| WO | WO-2017167919 | A1 | 10/2017 |
| WO | WO-2017180913 | A2 | 10/2017 |
| WO | WO-2018057955 | A1 | 3/2018 |
| WO | WO-2018067992 | A1 | 4/2018 |
| WO | WO-2018098365 | A2 | 5/2018 |
| WO | WO-2018144777 | A2 | 8/2018 |
| WO | WO-2018201047 | A1 | 11/2018 |
| WO | WO-2018224844 | A1 | 12/2018 |
| WO | WO-2018237192 | A1 | 12/2018 |
| WO | WO-2019005641 | A1 | 1/2019 |
| WO | WO-2019035938 | A1 | 2/2019 |
| WO | WO-2019040700 | A1 | 2/2019 |
| WO | WO-2019040780 | A1 | 2/2019 |
| WO | WO-2019055677 | A1 | 3/2019 |
| WO | WO-2019067805 | A1 | 4/2019 |
| WO | WO-2019086865 | A1 | 5/2019 |
| WO | WO-2019101695 | A1 | 5/2019 |
| WO | WO-2019132738 | A1 | 7/2019 |
| WO | WO-2019139987 | A1 | 7/2019 |
| WO | WO-2019158764 | A1 | 8/2019 |
| WO | WO-2019178362 | A1 | 9/2019 |
| WO | WO-2019178364 | A2 | 9/2019 |
| WO | WO-2019178364 | A3 | 10/2019 |
| WO | WO-2019191519 | A1 | 10/2019 |
| WO | WO-2019226617 | A1 | 11/2019 |
| WO | WO-2019231920 | A1 | 12/2019 |
| WO | WO-2020005819 | A1 | 1/2020 |
| WO | WO-2020010250 | A2 | 1/2020 |
| WO | WO-2020018708 | A1 | 1/2020 |
| WO | WO-2020010250 | A3 | 2/2020 |
| WO | WO-2020025928 | A1 | 2/2020 |
| WO | WO-2020057646 | A1 | 3/2020 |
| WO | WO-2020082048 | A1 | 4/2020 |
| WO | WO-2020084290 | A1 | 4/2020 |
| WO | WO-2020086758 | A1 | 4/2020 |
| WO | WO-2020088459 | A1 | 5/2020 |
| WO | WO-2020089644 | A1 | 5/2020 |
| WO | WO-2020091635 | A2 | 5/2020 |
| WO | WO-2020106708 | A1 | 5/2020 |
| WO | WO-2020139171 | A1 | 7/2020 |
| WO | WO-2020139175 | A2 | 7/2020 |
| WO | WO-2020142672 | A2 | 7/2020 |
| WO | WO-2020142672 | A3 | 8/2020 |
| WO | WO-2020172571 | A1 | 8/2020 |
| WO | WO-2020172596 | A1 | 8/2020 |
| WO | WO-2020172598 | A1 | 8/2020 |
| WO | WO-2020172601 | A1 | 8/2020 |

(56) References Cited

FOREIGN PATENT DOCUMENTS

| | | | |
|---|---|---|---|
| WO | WO-2020172605 | A1 | 8/2020 |
| WO | WO-2020183245 | A2 | 9/2020 |
| WO | WO-2020249757 | A1 | 12/2020 |
| WO | WO-2021089704 | A1 | 5/2021 |
| WO | WO-2021097325 | | 5/2021 |
| WO | WO-2021138407 | A2 | 7/2021 |
| WO | WO-2021138474 | A2 | 7/2021 |
| WO | WO-2021140190 | A1 | 7/2021 |
| WO | WO-2021138474 | A3 | 9/2021 |
| WO | WO-2021188454 | A1 | 9/2021 |
| WO | WO-2021217085 | A1 | 10/2021 |
| WO | WO-2022046920 | A2 | 3/2022 |
| WO | WO-2022046922 | A2 | 3/2022 |
| WO | WO-2022047046 | A1 | 3/2022 |
| WO | WO-2022046920 | A3 | 4/2022 |
| WO | WO-2022046922 | A3 | 4/2022 |
| WO | WO-2022175413 | A1 | 8/2022 |
| WO | WO-2022179580 | A1 | 9/2022 |
| WO | WO-2022216993 | A2 | 10/2022 |
| WO | WO-2022216993 | A3 | 11/2022 |
| WO | WO-2022240688 | A1 | 11/2022 |
| WO | WO-2023081412 | A2 | 5/2023 |
| WO | WO-2023122206 | A2 | 6/2023 |
| WO | WO-2023141297 | A2 | 7/2023 |
| WO | WO-2023081412 | A3 | 8/2023 |
| WO | WO-2023122206 | A3 | 8/2023 |
| WO | WO-2023141297 | A3 | 8/2023 |
| WO | WO-2024081329 | A1 | 4/2024 |
| WO | WO-2024081381 | A1 | 4/2024 |
| WO | WO-2024197082 | A2 | 9/2024 |
| WO | WO-2024226532 | A2 | 10/2024 |
| WO | WO-2024227109 | A1 | 10/2024 |
| WO | WO-2024197082 | A3 | 11/2024 |
| WO | WO-2024254611 | A2 | 12/2024 |
| WO | WO-2024226532 | A3 | 1/2025 |
| WO | WO-2024254611 | A3 | 3/2025 |
| WO | WO-2025049771 | A1 | 3/2025 |
| WO | WO-2025080685 | A2 | 4/2025 |

OTHER PUBLICATIONS

Bendig M. M. (Methods: A Companion to Methods in Enzymology, 1995; 8:83-93) (Year: 1995).*

Rudikoff et al. (Proceedings of the National Academy of Sciences USA, vol. 79, p. 1979-1983, 1982) (Year: 1982).*

Panka (Proceedings of the National Academy of Sciences, USA, vol. 85, p. 3080-3084, 1988) (Year: 1988).*

Bonsignori (Cell, vol. 165, p. 449-463, 2016) (Year: 2016).*

Burgess et al., J of Cell Bio. 111:2129-2138, 1990 (Year: 1990).*

Lazar et al. Molecular and Cellular Biology 8:1247-1252, 1988 (Year: 1988).*

Ju (Proceedings of the National Academy of Sciences, U.S.A., vol. 88, p. 2658-2662, 1991) (Year: 1991).*

Baker (Immunity, vol. 13, p. 475-484, 2000) (Year: 2000).*

Huang (The Journal of Biological Chemistry, vol. 272, No. 43, p. 27155-27159, 1997) (Year: 1997).*

Montrose-Rafizadeh (The Journal of Biological Chemistry, vol. 272, p. 21201-21206, 1997) (Year: 1997).*

Adachi, Osamu, et al., Targeted Disruption of the MyD88 Gene Results in Loss of IL-1-and IL-8-Mediated Function. Immunity 9(1):143-150 (1998).

Agostinis, Patrizia, et al., Photodynamic Therapy of Cancer: An Update. CA: A Cancer Journal for Clinicians 61(4):250-281 (2011).

Aigner et al., An effective tumor vaccine optimized for costimulation via bispecific and trispecific fusion proteins. Int J Oncol. 32(4):777-789 (2008).

Akiyama et al.: TNFalpha induces rapid activation and nuclear translocation of telomerase in human lymphocytes. Biochem Biophys Res Commun. 316(2):528-532 (2004).

Ala-Aho, Risto, et al., Collagenases in Cancer. Biochimie 87(3-4):273-286 (2005).

Al-Aghbar, M.A. et al., "High-affinity ligands can trigger T cell receptor signaling without CD45 segregation," Frontiers in Immunology, 2018;9(713):1-18.

Ali et al.: Modulation of human natural killer cytotoxicity by influenza virus and its subunit protein. Immunology 52(4):687-695 (1984).

Al-Lazikani, B. et al., "Standard Conformations for Canonical Structures of Immunoglobulins", J. Mol. Biol., 1997, vol. 273 , pp. 927-948.

Altschul, S F, et al., Basic Local Alignment Search Tool. Journal of Molecular Biology 215(3):403-410 (1990).

Altschul, Stephen, et al., Gapped Blast and PSI-Blast: A New Generation Of Protein Database Search Programs. Nucleic Acids Research 25(17):3389-3402 (1997).

Amarante-Mendes GP, Griffith TS. Therapeutic applications of Trail receptor agonists in cancer and beyond. Pharmacol Ther. Nov. 2015; 155:117-31. Epub Sep. 5, 2015.

Arai, R. et al., "Design of the linkers which effectively separate domains of a bifunctional fusion protein", Protein Engineering, 2001, vol. 14, No. 8, pp. 529-532.

Arenas-Ramirez et al.: Interleukin-2: Biology, Design and Application. Trends in Immunology 36(12):763-777 (2015).

Arnon, T.I. et al, "Recognition of viral hemagglutinins by NKp44 but not by NKp30", Eur J. Immunol., 2001, vol. 31, No. 9, pp. 2680-2689.

Aslan, J.E. et al., "S6K1 and mTOR regulate Rac1-driven platelet activation and aggregation", Blood, 2011, vol. 118, No. 11, pp. 3129-3136.

Aversa, Ilenia, et al., Molecular T-Cell Repertoire Analysis as Source of Prognostic and Predictive Biomarkers for Checkpoint blockade Immunotherapy. International Journal of Molecular Sciences 21(7):2378, 1-19 (2020).

Banerjee, Hridesh, et al., 33rd Annual Meeting & Pre-Conference Programs of the Society for Immunotherapy of Cancer (SITC). Journal for Immunotherapy of Cancer 6(1):1-192 (2018).

Barbas, Carlos, et al., Assembly of Combinatorial Antibody Libraries on Phage Surfaces: The Gene III Site. Proceedings of the National Academy of Sciences of the United States of America 88(18):7978-7982 (1991).

Beidler, C B, et al., Cloning and High Level Expression of a Chimeric Antibody With Specificity for Human Carcinoembryonic Antigen. Journal of Immunology 141(11):4053-4060 (1988).

Berge, Ten, et al., Selective Expansion of a Peripheral Blood Cd8+ Memory T Cell Subset Expressing Both Granzyme B and L-selectin During Primary Viral Infection in Renal Allograft Recipients. Transplantation Proceedings 30(8):3975-3977 (1998).

Better, M. et al., "*Escherichia coli* Secretion of an Active Chimeric Antibody Fragment", Science, 1988, vol. 240, No. 4855, pp. 1041-1043.

Beun, G. et al., "T cell Retargeting Using Bispecific Monoclonal Antibodies in a Rat Colon Carcinoma Model", The Journal of Immunology, 1993, vol. 150, No. 6, pp. 2305-2315.

Bierer, B E, et al., Cyclosporin a and Fk506: Molecular Mechanisms of Immunosuppression and Probes for Transplantation Biology. Current Opinion in Immunology 5(5):763-773 (1993).

Biomunex Pharmaceuticals, "Disruptive biological approaches in immunotherapy, based on next generation BiXAb® bi-and multi-specific antibody platform for cancer treatment," Mar. 2023 [PowerPoint Slides].

Bird, R.E. et al., Single-Chain Antigen-binding Proteins, Science, vol. 242, 4877 (1988):423-426.

Bluemel, C. et al., "Epitope distance to the target cell membrane and antigen size determine the potency of T cell-mediated lysis by BiTE antibodies specific for a large melanoma surface antigen", Cancer Immunology, Immunotherapy, 2010, vol. 59, No. 8, pp. 1197-1209.

Bolt, S. et al., "The generation of a humanized, non-mitogenic CD3 monoclonal antibody which retains in vitro immunosuppressive properties," Eur. J. Immunol., 1993;23:403-411.

Breman, E. et al., "Overcoming target driven fratricide for T Cell Therapy," Frontiers in Immunology, 2018;9(2940):1-11.

Bruggemann, M. et al., Designer Mice: The Production of Human Antibody Repertories in Transgenic Animals, Terhorst C. Malavasi

(56) References Cited

OTHER PUBLICATIONS

F, Albertini A (eds): Generation of Antibodies by Cell and Gene Immortalization, Year Immunol, 1993, vol. 7, pp. 33-40.
Bruggemann, M. et al., "Human antibody production in transgenic mice: expression from 100kb of the human IgH locus", Eur J. Immunol, 1991, vol. 21, pp. 1323-1326.
Buchwald et al. Long-term, continuous intravenous heparin administration by an implantable infusion pump in ambulatory patients with recurrent venous thrombosis. Surgery 88:507-516 (1980).
Cadwell, R. C. et al., "Randomization of Genes by PCR Mutagenesis", PCR Methods Appl., 1992, vol. 2, No. 1, pp. 28-33.
Cain, Chris, et al., Crossing over to Bispecificity. SciBX 4(28):1-3 (2011).
Chancellor, A. et al., "CD1b-restricted GEM T cell responses are modulated by *Mycobacterium tuberculosis* mycolic acid meromycolate chains," PNAS, 2017;114(51):E10956-E10964.
Chang et al.: A therapeutic T cell receptor mimic antibody targets tumor-associated PRAME peptide/HLA-I antigens. J Clin Invest. 127(7):2705-2718 (2017).
Chao, G. et al., "Isolating and engineering human antibodies using yeast surface display", Nature Protocols, 2006, vol. 1, No. 2, pp. 755-768.
Chaudry, et al. EpCAM an immunotherapeutic target for gastrointestinal malignancy: current experience and future challenges. Br J Cancer. Apr. 10, 2007;96(7):1013-9. Epub Feb. 27, 2007.
Chen et al.: Chromosome X-encoded cancer/testis antigens show distinctive expression patterns in developing gonads and in testicular seminoma. Hum Reprod. 26(12):3232-3243 doi:10.1093/humrep/der330 (2011).
Chen et al.: The nuclear localization sequences of the BRCA1 protein interact with the importin-alpha subunit of the nuclear transport signal receptor. J Biol Chem. 271(51):32863-32868 (1996).
Chiang, E. et al., "Abstract 3527: Potent anti-tumor activity of AbGn-100, an anti-CD326 x anti-TCR bispecific antibody to CD326-expressing solid tumors," Cancer Res., 2012;72(8_supplement):3527.
Chichili, V.P.R. et al., "Linkers in the structural biology of protein-protein interactions," Protein Science, 2013;22:153-167.
Chinese Patent Application No. 201780028089.4 2nd Office Action dated Apr. 18, 2022.
Cho, Bryan, et al., Single-Chain Fv/Folate Conjugates Mediate Efficient Lysis of Folate-Receptor-Positive Tumor Cells. Bioconjugate Chemistry 8(3):338-346 (1997).
Chothia, C. et al., "Canonical Structures for the Hypervariable Regions of Immunoglobulins", J. Mol. Biol, 1987, vol. 196, pp. 901-917.
Chothia et al., Structural repertoire of the human VH segments. J Mol Biol 227:799-817 (1992).
Ciccone, E. et al., "A monoclonal antibody specific for a common determinant of the human T cell receptor gamma/delta directly activates CD3+WT31-lymphocytes to express their functional program(s)," J Exp Med., 1988; 168(1):1-11.
Clackson, T. et al., Making antibody fragments using phage display libraries, Nature, 1991, vol. 352, pp. 624-628.
Colcher, David, et al., Single-Chain Antibodies in Pancreatic Cancer. Annals of the New York Academy of Sciences 880:263-280 (1999).
Coloma, J. et al., "Design and production of novel tetravalent bispecific antibodies", Nature Biotech, 1997, vol. 15, pp. 159-163.
Consonni, M. et al., "Human T cells engineered with a leukemia lipid-specific TCR enables donor-unrestricted recognition of CD1c-expressing leukemia," Nat Commun., 2021;12(1):4844.
Costa-Mattioli, Mauro, et al., RAPping Production of type I Interferon in pDCs through mTOR. Nature Immunology 9(10):1097-1099 (2008).
Cui, et al., "T cell receptor B-chain repertoire analysis of tumor-infiltrating lymphocytes in pancreatic cancer" Cancer Science (2018) 60-71.
Dao, Tao, et al., Targeting the Intracellular Wt1 Oncogene Product With a Therapeutic Human Antibody. Science Translational Medicine 5(176):176ra33, 1-22 (2013).
Davis, J. et al., "SEEDbodies: fusion proteins based on strand-exchange engineered domain (SEED) CH3 heterodimers in an Fc analogue platform for asymmetric binders or immunofusions and bispecific antibodies", Protein Engineering, Design & Selection, 2010, vol. 23, No. 4, pp. 195-202.
Dela Cruz et al.: Anti-HER2/neu IgG3-(IL-2) and anti-HER2/neu IgG3-(GM-CSF) promote HER2/neu processing and presentation by dendritic cells: Implications in immunotherapy and vaccination strategies. Molecular Immunology 43(6):667-676 (2006).
Dickopf, S. et a., "Formal and geometries matter: Structure-based design defines the functionality of bispecific antibodies", Computational and Structural Biotechnology Journal, 2020, vol. 18, pp. 1221-1227.
Dimasi et al. Development of a trispecific antibody designed to simultaneously and efficiently target three different antigens on tumor cells. Mol Pharm 12(9):3490-3501 (2015).
Doyle, Sean, et al., IRF3 Mediates a TLR3/TLR4-Specific Antiviral Gene Program. Immunity 17(3):251-263 (2002).
Duhen et al., Co-expression of $CD_{39}$ and $CD_{103}$ identifies tumor-reactive CD8 T cells in human solid tumors. Nat Commun. 9(1):2724, pp. 1-13 (2018).
During, M J, et al., Controlled Release of Dopamine From a Polymeric Brain Implant: in Vivo Characterization. American Neurological Association 25(4):351-356 (1989).
El Achi, H. et al., "CD123 as a Biomarker in Hematolymphoid Malignancies: Principles of Detection and Targeted Therapies," Cancers, 2020;12(11):3087.
European Patent Application No. 17 718 441.3 Office Action dated Jan. 24, 2022.
European Search Report issued in EP20736073, dated Aug. 2, 2022.
Falini et al.: Cytoplasmic nucleophosmin in acute myelogenous leukemia with a normal karyotype. N Engl J Med. 352(3):254-266 doi: 10.1056/NEJMoa041974 (2005).
Farrar et al.: The Molecular Cell Biology Of Interferon-gamma And Its Receptor. Annu Rev Immunol 11:571-611 (1993).
Fernandez-Malave, Edgar, et al., An Natural Anti-T-Cell Receptor Monoclonal Antibody Protects Against Experimental Autoimmune Encephalomyelitis. Journal of Neuroimmunology 234(1-2):63-70 (2011).
Foley, K.. et al., Combination immunotherapies implementing adoptive T-cell transfer for advanced-stage melanoma, Melanoma Research, vol. 28, 3 (2018): 171-184.
Frost, Gregory, et al., A Microtiter-Based Assay for Hyaluronidase Activity Not Requiring Specialized Reagents. Analytical Biochemistry 251(2):263-269 (1997).
Fuchs, P. et al., "Targeting Recombinant Antibodies to the surface of *Escherichia coli*: Fusion to the Peptidoglycan associated Lipoprotein", Nature Publishing Group, 1991, vol. 9, No. 12, pp. 1369-1372.
Funayama et al.: Embryonic axis induction by the armadillo repeat domain of beta-catenin: evidence for intracellular signaling. J Cell Biol. 128(5):959-968 (1995).
Gao et al.: Alg14 recruits Alg13 to the cytoplasmic face of the endoplasmic reticulum to form a novel bipartite UDP-N-acetylglucosamine transferase required for the second step of N-linked glycosylation. J Biol Chem. 280(43):36254-36262 doi: 10.1074/jbc.M507569200 (2005).
Garland, R.J., et al., "The use of Teflon cell culture bags to expand functionally active CD8+ cytotoxic T lymphocytes", Journal of Immunological Methods, 1999, vol. 227, pp. 53-63.
Garrard, L. et al., "FAB Assembly and Enrichment in a Monovalent Phage Display System", Nature Publishing Group, 1991, vol. 9, pp. 1373-1377.
Garrity, David, et al., The Activating NKG2D Receptor Assembles in the Membrane With Two Signaling Dimers Into a Hexameric Structure. Proceedings of the National Academy of Sciences of the United States of America 102(21):7641-7646 (2005).
GB Exam Report for GB2109794.4 dated Jun. 21, 2020.
Geissinger, E. et al., "Identification of the Tumor Cells in Peripheral T-Cell Lymphomas by Combined Polymerase Chain Reaction-

(56) References Cited

OTHER PUBLICATIONS

Based T-Cell Receptor [3 Spectrotyping and Immunohistological Detection with T-Cell Receptor [3 Chain Variable Region Segment-Specific Antibodies," J. of Mol Diag., 2005;7(4):455-464.
Gillies, S.D. et al., "Bi-functional cytokine fusion proteins for gene therapy and antibody-targeted treatment of cancer," Cancer Immunol Immunotherapy, 2002;51:449-460.
Gjerstorff et al.: GAGE cancer-germline antigens are recruited to the nuclear envelope by germ cell-less (GCL). PLoS One 7(9):e45819:1-12 doi:10.1371/journal.pone.0045819 (2012).
Goel, M. et a., "Plasticity within the Antigen-Combining site may manifest as molecular mimicry in the humoral immune response," J Immunology, 2004; 173(12):7358-7367.
Gohal, G. et al., "T-cell receptor phenotype pattern in atopic children using commercial fluorescently labeled antibodies against 21 human class-specific v segments for the tcrβ chain (vβ) of peripheral blood: a cross sectional study," Allergy Asthma Clin Immunol., 2016;12:10.
Gokden et al.: Diagnostic utility of renal cell carcinoma marker in cytopathology. Appl Immunohistochem Mol Morphol. Abstract Only. 11(2):116-119 doi:10.1097/00129039-200306000-00004 (2003).
Gordon, E.D. et al., "Alternative splicing of interleukin-33 and type 2 inflammation in asthma," PNAS, 2016;113(31):8765-8770.
Gram, H. et al, In vitro selection and affinity maturation of anti-bodies from a naïve combinatorial immunoglobulin library, PNAS, 1992, vol. 89, pp. 3576-3580.
Green, Edward, et al., TCR Validation Toward Gene Therapy for Cancer. Methods in Enzymology 629(21):419-441 (2019).
Green, L.L. et al, "Antigen-specific human monoclonal antibodies from mice engineered with human Ig heavy and light chain YACS", Nature Genet, 1994, vol. 7, pp. 13-21.
Griffiths, A.D. et al, "Human anti-self antibodies with high speci-ficity from phage display libraries", The EMBO Journal, 1993, vol. 12, No. 2, pp. 725-734.
Gulley, J.L. et al., "New drugs on the horizon," Eur J Cancer, 2022;174(S1):S5.
Gupta, S. et al., "T cell activation via the T cell receptor: a comparison between WT31 (defining alpha/beta TcR)-induced and anti-CD3-induced activation of human T lymphocytes," Cell Immunol., 1991;132(1):26-44.
Haanen, J. et al., "Selective Expansion of Cross-reactive CD8+ Memory T Cells by Viral Variants", J. Exp. Med., 1999, vol. 190, No. 9, pp. 1319-1328.
Hacken, Elisa, et al., Calreticulin as a Novel B-Cell Receptor Antigen in Chronic Lymphocytic Leukemia. Haematologica 102(10):e394-e396 (2017).
Halin, C. et al., "Synergistic Therapeutic Effects of a Tumor Targeting Antibody Fragment, Fused to Interleukin 12 and to Tumor Necrosis Factor al," Cancer Research, 2003;63:3202-3210.
Hall, MacLean, et al., Expansion of Tumor-Infiltrating Lympho-cytes (TIL) from Human Pancreatic Tumors. Journal for Immuno Therapy of Cancer 4:61, 1-12 (2016).
Hamid, O. et al., "Safety and Tumor Responses with Lambrolizumab (Anti-PD-1) in Melanoma", The New England Journal of Medicine, 2013, vol. 369, No. 2, pp. 134-144.
Hamming et al. Crystal Structure of Interleukin-21 Receptor (IL-21R) Bound to IL-21 Reveals That Sugar Chain Interacting with WSXWS Motif Is Integral Part of IL-21R. The Journal of Biological Chemistry 287(12):9454-9460 (2012).
Hawkins, R. et al., "Selection of phage antibodies by binding affinity. Mimicking affinity maturation", J. Mol. Biol., 1992, vol. 226, No. 3, pp. 889-896.
Hay, B. et al., "Bacteriophage cloning and *Escherichia coli* expres-sion of a human IgM Fab" Hum Antibodies Hybridomas, 1992, vol. 3, No. 2, pp. 81-85.
Henderson, D J, et al., Comparison of the Effects of FK-506, Cyclosporin A and Rapamycin on IL-2 Production. Immunology 73(3):316-321 (1991).
Herskovitz, O. et al., "NKp44 receptor mediates interaction of the envelope glycoproteins from the West-Nile and dengue viruses with Natural Killer cells," The Journal of Immunology, 2009;183(4):2610-2621.
Hirai et al.: Nucleolar scaffold protein, WDR46, determines the granular compartmental localization of nucleolin and DDX21. Genes Cells 18(9):780-797 (2013).
Hiyama, K, et al., Action of Chondroitinases. I. The Mode of Action of Two Chondroitinase-AC Preparations of Different Origin. Jour-nal of Biochemistry 80(6):1201-1207 (1976).
Hiyama, K, et al., Crystallization and Some Properties of Chondroitinase from Arthrobacter Aurescens. The Journal of Biological Chemistry 250(5):1824-1828 (1975).
Hollinger, Philipp, et al., Engineered Antibody Fragments and the Rise of Single Domains. Nature Biotechnology 23(9):1126-1136 (2005).
Hombach, A.A. et al., "Antibody-IL2 Fusion Proteins for Tumor Targeting," Antibody Engineering, 2012:611-626.
Hoogenboom, H.R. et al, "Multi-subunit proteins on the surface of filamentous phage: methodologies for displaying antibody (Fab) heavy and light chains", Nuc Acid Res, 1991, vol. 19, No. 15, pp. 4133-4137.
Howard, M A, et al., Intracerebral Drug Delivery in Rats with Lesion-induced Memory Deficits. Journal of Neurosurgery 71(1):105-112 (1989).
Hudson, K.R. et al., "Two Adjacent Residues in Staphylococcal EnterotoxIns A and E Determine T Cell Receptor Vbeta Specificity," J.Exp. Med., 1993;177:175-184.
Hudspeth et al.: Natural cytotoxicity receptors: broader expression patterns and functions in innate and adaptive immune cells. Fron-tiers in Immunology 4(69):1-15 (2013).
Hunig, T. et al., "A monoclonal antibody to a constant determinant of the rat t cell antigen receptor that induces t cell activation", J. Exp. Med., 1989, vol. 169, pp. 73-86.
Huse, W. et al., "Generation of a large combinatorial library of the immunoglobulin repertoire in phage lambda" Science, 1989, vol. 246, No. 4935, pp. 1275-1281.
Huston, James, et al., Protein Engineering Of Antibody Binding Sites: Recovery Of Specific Activity In An Anti-digoxin Single-chain Fv Analogue Produced In *Escherichia coli*. Proceedings of the National Academy of Sciences of the United States of America 85(16):5879-5883 (1988).
International Preliminary Report on Patentability issued in PCT/US2017/023483, dated Sep. 25, 2018.
International Preliminary Report on Patentability issued in PCT/US2019/040592, dated Jan. 5, 2021.
International Preliminary Report on Patentability issued in PCT/US2020/012162, dated Jun. 16, 2021.
International Preliminary Report on Patentability issued in PCT/US2020/019291, dated Aug. 10, 2021.
International Preliminary Report on Patentability issued in PCT/US2020/019319, dated Aug. 10, 2021.
International Preliminary Report on Patentability issued in PCT/US2020/019321, dated Aug. 10, 2021.
International Preliminary Report on Patentability issued in PCT/US2020/060557 dated May 17, 2022.
International Preliminary Report on Patentability issued in PCT/US/2020/067543, dated Jul. 5, 2022.
International Preliminary Report on Patentability issued in PCT/US2021/022408, dated Sep. 20, 2022.
International Preliminary Report on Patentability issued in PCT/US2021/028970, dated Oct. 25, 2022.
International Search Report and Written Opinion for corresponding PCT Application No. PCT/US2019/022282 issued Jul. 1, 2019.
International Search Report and Written Opinion issued in PCT/US2017/023483, mailed Aug. 29, 2017.
International Search Report and Written Opinion issued in PCT/US2019/040592, mailed Jan. 9, 2020.
International Search Report and Written Opinion issued in PCT/US2020/012162 mailed Jun. 26, 2020.
International Search Report and Written Opinion issued in PCT/US2020/019291, mailed Jun. 15, 2020.

(56) References Cited

OTHER PUBLICATIONS

International Search Report and Written Opinion issued in PCT/US2020/019319, mailed Jun. 26, 2020.
International Search Report and Written Opinion issued in PCT/US2020/019321, mailed Aug. 10, 2020.
International Search Report and Written Opinion issued in PCT/US2020/060557, mailed Mar. 30, 2021.
International Search Report and Written Opinion issued in PCT/US2020/067543, mailed Jul. 7, 2021.
International Search Report and Written Opinion issued in PCT/US2021/022408, mailed Aug. 31, 2021.
International Search Report and Written Opinion issued in PCT/US2021/028970 mailed Oct. 4, 2021.
International Search Report and Written Opinion issued in PCT/US2021/047571, dated Feb. 14, 2022.
International Search Report and Written Opinion issued in PCT/US2022/023922, mailed Oct. 17, 2022.
Islam, D, et al., Changes in the Peripheral Blood T-Cell Receptor V Beta Repertoire in Vivo and in Vitro During Shigellosis. Infection and Immunity 64(4):1391-1399 (1996).
Jameson, Stephen C., "T cell receptor antagonism in vivo, at last", Proc. Natl. Acad. Sci., 1998, vol. 95, pp. 14001-14002.
Jiang, B. et al., "A novel peptide isolated from a phage display peptide library with trastuzumab can mimic antigen epitope of HER-2*," The Journal of Biological Chemistry, 2005;280(6):4656-4662.
Jiang et al.: Nuclear expression of CDK4 correlates with disease progression and poor prognosis in human nasopharyngeal carcinoma. Histopathology 64(5):722-730 doi:10.1111/his.12319 (2013).
Jones et al., Replacing The Complementarity-determining Regions In A Human Antibody With Those From A Mouse. Nature 321(6069):522-525 (1986).
Ju et al.: Structure-function analysis of human interleukin-2. Identification of amino acid residues required for biological activity. The Journal of Biological Chemistry 262(12):5723-5731 (1987).
Kanagawa, et al., "In Vivo T Cell Tumor Therapy With Monoclonal Antibody Directed to the VB chain of T Cell Antigen Receptor" J. Exp. Med., vol. 170, (1989) p. 1513-1519.
Kanagawa, O, et al., The T Cell Receptor VB6 Domain Imparts Reactivity to the Mls-1a Antigen. Cellular Immunology 119(2):412-426 (1989).
Kasmar, A.G. et al., "CD1b tetramers bind αβ T cell receptors to identify a mycobacterial glycolipid-reactive T cell repertoire in humans," J Exp Med., 2011;208(9):1741-1747.
Kato et al.: The structure and binding mode of interleukin-18. Nature Structural Biology 10(11):366-971 (2003).
Kato, Y. et al., "Molecular analysis of the pathophysiological binding of the platelet aggregation-inducing factor podoplanin to the C-type lectin-like receptor CLEC-2", Cancer Sci, Jan. 2008, vol. 99, No. 1, pp. 54-61.
Kawaguchi, M, et al., Differential Activation Through the TCR-CD3 Complex Affects the Requirement for Costimulation of Human T Cells. Human immunology 43(2):136-148 (1995).
Kellner et al.: Enhancing natural killer cell-mediated lysis of lymphoma cells by combining therapeutic antibodies with CD20-specific immunoligands engaging NKG2D or NKp30. Oncoimmunology 5(1 )e1058459 [1-12] (2016).
Kerkela, E, et al., Expression of Human Macrophage Metalloelastase (MMP-12) by Tumor Cells in Skin Cancer. Journal of Investigative Dermatology 114(6):1113-1119 (2000).
Kiefer, J.D. et al., "Immunocytokines and bispecific antibodies: two complementary strategies for the selective activation of immune cells at the tumor site," Immunol Rev., 2016;270(1):178-192.
Kim, E.J. et al., "Interleukin-2 fusion protein with anti-CD3 single-chain Fv (sFv) selectively protects T cells from dexamethasone-induced apoptosis," Vaccine, 2002;20:608-615.
Kirkin, et al. Melanoma-associated antigens recognized by cytotoxic T lymphocytes. APMIS. Jul. 1998;106(7):665-79.
Kitaura, K. et al., "A new high-throughput sequencing method for determining diversity and similarity of T cell receptor (TCR) α and β repertoires and identifying potential new invariant TCR α chains," BMC Immunology, 2016, vol. 17, No. 38, pp. 1-16.
Klampfl, T. et al., "Somatic Mutations of Calreticulin in Myeloproliferative Neoplasms", N Engl J Med., 2013, vol. 369, No. 25, pp. 2379-2390.
Klein, Christian, et al., Progress in Overcoming the Chain Association Issue in Bispecific Heterodimeric IgG Antibodies. mAbs 4(6):653-663 (2012).
Koch et al.: Activating natural cytotoxicity receptors of natural killer cells in cancer and infection. Trends Immunol. 34(4):182-191 doi:10.1016/j.it.2013.01.003 (2013).
Kronenberg, M. et al., "A 'GEM' of a cell," Nat Immunol., 2013;14(7):694-695.
Kunkel, Thomas A., "Rapid and efficient site-specific mutagenesis without phenotypic selection", Proc Natl Acad Sci, 1985, vol. 82, No. 2, pp. 488-492.
Kushner et al.: Aberrant expression of cyclin A and cyclin B1 proteins in oral carcinoma. J Oral Pathol Med. 28(2):77-81 (1999).
Labrijn, Aran, et al., Controlled Fab-arm Exchange for the Generation of Stable Bispecific IgG1. Nature Protocols 9(10):2450-2463 (2014).
Labrijn, Aran, et al., Efficient Generation of Stable Bispecific IgG1 by Controlled Fab-arm Exchange. Proceedings of the National Academy of Sciences of the United States of America 110(13):5145-5150 (2013).
Lain et al.: Accumulating active p53 in the nucleus by inhibition of nuclear export: a novel strategy to promote the p53 tumor suppressor function. Exp Cell Res. 253(2):315-324 (1999).
Langer, Robert, et al., Chemical and Physical Structure of Polymers as Carriers for Controlled Release of Bioactive Agents: A Review. Journal of Macromolecular Science-Reviews in Macromolecular Chemistry and Physics 23(1):61-126 (1983).
Langer, Robert, et al., Medical Applications of Controlled Release. 2:115-138 (1984).
Langer, Robert, New Methods of Drug Delivery. Science 249(4976): 1527-1533 (1990).
Lanier, L.L. et al., "Distinct epitopes on the t cell antigen receptor of HPB-ALL tumor cells identified by monoclonal antibodies," 1986;137(7):2286-2292.
Leclercq, G. et al., "Dissecting the mechanism of cytokine release induced by T-cell engagers highlights the contribution of neutrophils," Oncoimmunology, 2022;11(1):e2039432.
Lee, C. M. et al., "Selection of human antibody fragments by phage display", Nat Protoc., 2007, vol. 2, No. 11, pp. 3001-3008.
Lee, K.D. et al., "Construction and characterization of a novel fusion protein consisting of anti-CD3 antibody fused to recombinant interleukin-2," Oncology Reports, 2006;15:1211-1216.
Leonard, E.K. et al., "Engineered cytokine/antibody fusion proteins improve delivery of IL-2 to pro-inflammatory cells and promote antitumor activity," bioRxiv, 2023:1-36.
Leong et al.: Optimized expression and specific activity of IL-12 by directed molecular evolution. Proc. Natl. Acad. Sci. USA; 100(3): 1163-1168 (2003).
Leutkens et al.: Functional autoantibodies against SSX-2 and NY-ESO-1 in multiple myeloma patients after allogeneic stem cell transplantation. Cancer Immunol Immunother. 63(11):1151-1162 (2014).
Levy, R J, et al., Inhibition of Calcification of Bioprosthetic Heart Valves by Local Controlled-Release Diphosphonate. Science 228(4696):190-192 (1985).
Li, B. et al., "Landscape of tumor-infiltrating T cell repertoire of human cancers," Nature Genetics, 2016, vol. 48, No. 7, pp. 725-735.
Li, F. et al., "T cell receptor B-chain-targeting chimeric antigen receptor T cells against T cell malignancies," Nature Communications, 2022;13:4334.
Li, Hanchen, et al., Tumor Microenvironment: The Role of the Tumor Stroma in Cancer. Journal of Cellular Biochemistry 101(4):805-815 (2007).
Li, Peng, et al., Design and Synthesis of Paclitaxel Conjugated with an ErbB2-recognizing Peptide, EC-1. Biopolymers 87(4):225-230 (2007).
Liddy et al.: Monoclonal TCR-redirected tumor cell killing. Nat Med. 18(6):980-987 doi:10.1038/nm.2764 (2012).

(56) References Cited

OTHER PUBLICATIONS

Liu, Alvin, et al., Chimeric Mouse-human IgG1 Antibody that can Mediate Lysis of Cancer Cells. Proceedings of the National Academy of Sciences of the United States of America 84(10):3439- 3443 (1987).
Liu, Alvin, et al., Production of a Mouse-human Chimeric Monoclonal Antibody to CD20 With Potent Fc-dependent Biologic Activity. Journal of Immunology 139(10):3521-3526 (1987).
Liu, Der-Zen, et al., Synthesis of 2'-paclitaxel Methyl 2-glucopyranosyl Succinate for Specific Targeted Delivery to Cancer Cells. Bioorganic & Medicinal Chemistry Letters 17(3):617-620 (2007).
Liu, D.V. et al., "Engineered Interleukin-2 Antagonists for the Inhibition of Regulatory T Cells," J. Immunother., 2009;32(9):887-894.
Liu, Hongyan, et al., Fc Engineering for Developing Therapeutic Bispecific Antibodies and Novel Scaffolds. Frontiers in Immunology 8(38) 1-15 (2017).
Liu, J, et al., Calcineurin is a Common Target of Cyclophilin-Cyclosporin A and FKBP-FK506 Complexes. Cell 66(4):807-815 (1991).
Liu, K. et al., "CD123 and its potential clinical application in leukemias," Life Sciences, 2015;122:59-64.
Lloyd et al., Modelling the Human Immune Response: Performance of a 10" Human Antibody Repertoire Against a Broad Panel of Therapeutically Relevant Antigens. Protein Engineering Design & Selection. 22(3):159-168 (2009).
Lobuglio, Albert, et al., Phase I Clinical Trial of CO17-1A Monoclonal Antibody. Hybridomia 5(1):S117-S123 (1986).
Lonberg, Nils, et al., Antigen-Specific Human Antibodies From Mice Comprising Four Distinct Genetic Modifications. Nature 368(6474):856-859 (1994).
Lopez, K. et al., "CD1b Tetramers Broadly Detect T Cells That Correlate With Mycobacterial Exposure but Not Tuberculosis Disease State," Front Immunol., 2020;11:199.
Luo, S. et al., "Worldwide genetic variation of the IGHV and TRBV immune receptor gene families in humans" (2019) Life Sciences Alliance, vol. 2, No. 2, p. 1-9.
Lustgarten, J. et al., "Redirecting Effector T Cells through their IL-2 receptors," J Immunology, 1999;162:359-365.
Maciocia, P. M. et al., "Targeting the T cell receptor β-chain constant region for immunotherapy of T cell malignancies", Nature Medicine, 2017, vol. 23, No. 12, pp. 1416-1423.
Mackay, C.R. et al., "Gamma/delta T cells express a unique surface molecule appearing late during thymic development," Eur J Immunol., 1989;19(8):1477-1483.
Macor, P. et al., "Bispecific antibodies targeting tumor-associated antigens and neutralizing complement regulators increase the efficacy of antibody-based immunotherapy in mice", Leukemia, 2015, vol. 29, pp. 406-414.
Mandelboim, O. et al., "Recognition of hemagglutinins on virus-infected cells by NKp46 activates lysis by human NK cells", Nature, 2001, vol. 409, No. 6823, pp. 1055-1060.
Mao et al.: Inhibition of human natural killer cell activity by influenza virions and hemagglutinin. Journal of Virology 84(9 ):4148-4157 (2010).
Martens, Tobias, et al., A Novel One-Armed Anti-c-Met Antibody Inhibits Glioblastoma Growth In Vivo. Clinical Cancer Research 12(20 Pt 1):6144-6152 (2006).
Martin, A. et al., "Chapter 3: Protein Sequence and Structure Analysis of Antibody Variable Domains", In: Antibody Engineering Lab Manual (Ed: Duebel, S. and Kontermann, R., Springer-Verlag, Heidelberg), 2010, vol. 2, pp. 33-51.
Martin, F. et al., "The affinity-selection of a minibody polypeptide inhibitor of human interleukin-6", EMBO J., 1994, vol. 13, No. 22, pp. 5303-5309.
McConnell, Stephen, et al., Tendamistat as a Scaffold for Conformationally Constrained Phage Peptide Libraries. Journal of Molecular Biology 250(4):460-470 (1995).
McElroy et al.: Structural and Biophysical Studies of the Human IL-7/IL-7R alpha Complex. Structure 17(1):54-65 (2009).
Merchant, A.M. et al., "An efficient route to human bispecific IgG," Nature Biotechnology, 1998;16(7):677-681.
Meschendoerfer, W. et al., "SPR-based assays enable the full functional analysis of bispecific molecules," Journal of Pharmaceutical and Biomedical Analysis, 2017, vol. 5, No. 132, pp. 141-147.
Meyers, E. et al., "Optimal alignments in linear space", CABIOS, 1988, vol. 4, No. 1, pp. 11-17.
Michelacci, Y M, et al., A Comparative Study Between a Chondroitinase B and a Chondroitinase AC From Flavobacterium Heparinum: Isolation of a Chondroitinase AC-Susceptible Dodecasaccharide From Chondroitin Sulphate B. The Biochemical Journal 151(1):121-129 (1975).
Michelacci, Yara, et al., Isolation and Partial Characterization of an Induced Chondroitinase B from Flavobacterium Heparinum. Biochemical and Biophysical Research Communications 56(4):973-980 (1974).
Miller et al.: Trispecific Killer Engagers (TriKEs) that contain IL-15 to make NK cells antigen specific and to sustain their persistence and expansion. Blood 126(23):232-232 (2015).
Milone, Michael, et al., Chimeric Receptors Containing CD137 Signal Transduction Domains Mediate Enhanced Survival of T Cells and Increased Antileukemic Efficacy in Vivo. Molecular Therapy 17(8):1453-1464 (2009).
Mitra, S. et al., "Interleukin-2 Activity can be Fine-Tuned with Engineering Receptor Signaling Clamps," Immunity, 2015;42(5):826-838.
Miyahara, Y et al., Anti-TCRβ mAb induces long-term allograft survival by reducing antigen-reactive T cells and sparing regulatory T cells, American journal of transplantation: official Journal of the American Society of Transplantation and the American Society of Transplant Surgeons, vol. 12, 6 (2012): 1409-18.
Modak et al.: Disialoganglioside GD2 and a novel tumor antigen: potential targets for immunotherapy of desmoplastic small round cell tumor. Med Pediatr Oncol. 39(6):547-551 (2002).
Moore, Gregory, et al., A Novel Bispecific Antibody Format Enables Simultaneous Bivalent and Monovalent Co-engagement of Distinct Target Antigens. mAbs 3(6):546-557 (2011).
Morel et al.: Processing of some antigens by the standard proteasome but not by the immunoproteasome results in poor presentation by dendritic cells. Immunity. 12(1):107-117 doi:10.1016/s1074-7613(00)80163-6 (2000).
Morrison, Sherie, et al., Chimeric Human Antibody Molecules: Mouse Antigen-binding Domains With Human Constant Region Domains. Proceedings of the National Academy of Sciences of the United States of America 81(21):6851-6855 (1984).
Morrison, Sherie, Transfectomas Provide Novel Chimeric Antibodies. Science 229(4719):1202-1207 (1985).
Muller, K P, et al., T Cell Receptor Targeting to Thymic Cortical Epithelial Cells in Vivo Induces Survival, Activation and Differentiation of Immature Thymocytes. European Journal of Immunology 23(7):1661-1670 (1993).
Murer, P. et al., "Antibody-cytokine fusion proteins: A novel class of biopharmaceuticals for the therapy of cancer and of chronic inflammation", New Biotechnology, 2019, vol. 52, pp. 42-53.
Murzin, A G, et al., SCOP: A Structural Classification of Proteins Database for the Investigation of Sequences and Structures. Journal of Molecular Biology 247(4):536-540 (1995).
Nagarajan et al.: Ligand binding and phagocytosis by CD16 (Fc gamma receptor III) isoforms. Phagocytic signaling by associated zeta and gamma subunits in Chinese hamster ovary cells. Journal of Biological Chemistry J Biol Chem. 270(43):25762-25770 (1995).
Naing, et al., "Strategies for improving the management of immune-related adverse events" Journal for ImmunoTherapy of Cancer, (2020) p. 1-9.
Nandi et al.: CD28-mediated costimulation is necessary for optimal proliferation of murine NK cells. J Immunol. 152(7):3361-3369 (1994).
Nangalia, J. et al., "Somatic CALR Mutations in Myeloproliferative Neoplasms with Nonmutated JAK2", N Engl J Med., 2013, vol. 369, No. 25, pp. 2391-2405.
Needleman, Saul, et al., A General Method Applicable to the Search for Similarities in the Amino Acid Sequence of Two Proteins. Journal of Molecular Biology 48(3):444-453 (1970).

(56) References Cited

OTHER PUBLICATIONS

Newman et al.: Combining Early Heat Shock Protein Vaccination with Directed IL-2 Leads to Effective Anti-Tumor Immunity in Autologous Hematopoietic Cell Transplantation Recipients. 118(21):998-998 (2011).
Niederberger, N. et al., "Thymocyte stimulation by anti-TCR-b, but not by anti-TCR-a, leads to induction of developmental transcription program," Journal of Leukoeyte Biology, 2005;77(5):830-841.
Nishimura, Yushi, et al., Recombinant Human-Mouse Chimeric Monoclonal Antibody Specific for Common Acute Lymphocytic Leukemia Antigen. Cancer Research 47(4):999-1005 (1987).
No Author "PE anti-human TCR VB23 Antibody" (2012).
No Author "PE anti-mouse TCR VB6 Antibody" (2012).
Nolo, R. et al., "Targeting P-selection blocks neuroblastoma growth", Oncotarget, 2017, vol. 8, No. 49, pp. 86657-86670.
Novellino et al.: A listing of human tumor antigens recognized by T cells: Mar. 2004 update. Cancer Immunol Immunother. 54(3):187-207 doi:10.1007/s00262-004-0560-6 (2005).
Oh, Julyun, et al., Single Variable Domains From the T Cell Receptor B Chain Function as Mono- and Bifunctional CARs and TCRs. Scientific Reports 9(1):17291, 1-12 (2019).
Ol, Vernon, et al., Chimeric Antibodies. BioTechniques 4(3):214-221 (1986).
Ortiz-Sanchez, Elizabeth, et al., Antibody-Cytokine Fusion Proteins: Applications in Cancer Therapy. Expert Opinion on Biological Therapy 8(5):609-632 (2008).
Page, David, et al., Deep Sequencing of T-cell Receptor DNA as a Biomarker of Clonally Expanded TILs in Breast Cancer after Immunotherapy. Cancer Immunology Research 4(10):835-844 (2016).
Pardoll, D.M., "The blockade of immune checkpoints in cancer immunotherapy", Nat Rev Cancer, 2012, Vo. 12, pp. 252-264.
Park, Y.P. et al., "Complex Regulation of human NKG2D-DAP10 cell surface expression: opposing roles of the γc cytokines and TGF-β1", Blood, 2011, vol. 118, No. 11, pp. 3019-3027.
Pasche, N. et al., "Immunocytokines: a novel class of potent armed antibodies," Drug Discovery Today, 2012;17(11):583-590.
Paul, S. et al., "TCR beta chain-directed bispecific antibodies for the treatment of T-cell cancers," Science Translational Medicine, 2021, pp. 1-21.
PCT/US2017/023483 International Search Report and Written Opinion dated Aug. 29, 2017.
PCT/US2018/029951 International Preliminary Report on Patentability dated Oct. 29, 2019.
PCT/US2018/029951 International Search Report and Written Opinion dated Mar. 7, 2018.
PCT/US2019/012900 International Search Report and Written Opinion dated May 7, 2019.
PCT/US2019/022284 International Preliminary Report on Patentability dated Sep. 15, 2020.
PCT/US2019/022284 International Search Report and Written Opinion dated Sep. 10, 2019.
PCT/US2020/019324 International Preliminary Report on Patentability dated Aug. 10, 2021.
PCT/US2020/019324 International Search Report and Written Opinion dated Jun. 10, 2020.
Pettit et al.: Structure-function studies of interleukin 15 using site-specific mutagenesis, polyethylene glycol conjugation, and homology modeling. J Biol Chem. 272(4):2312-2318 (1997).
Pilch, H, et al., Improved Assessment of T-Cell Receptor (TCR) VB Repertoire in Clinical Specimens: Combination of TCR-CDR3 Spectratyping with Flow Cytometry-Based TCR VB Frequency Analysis. Clinical and Diagnostic Laboratory Immunology 9(2):257-266 (2002).
Posnett, D.N. et al., "Inherited polymorphism of the human T-cell antigen receptor detected by a monoclonal antibody," PNAS, 1986;83:7888-7892.
Presta, Leonard, Antibody Engineering. Current Opinion in Structural Biology 2(4):593-596 (1992).
Provenzano et al.: Enzymatic targeting of the stroma ablates physical barriers to treatment of pancreatic ductal adenocarcinoma. Cancer Cell. 21(3):418-429 doi:10.1016/j.ccr.2012.01.007 (2012).
Qi, et al., "Potent and selective antitumor activity of a T cell-engaging bispecific antibody targeting a membrane-proximal epitope of ROR1," PNAS, 2018;115(24):E5467-E5476.
Rabia, L. et al., "Understanding and overcoming trade-offs between antibody affinity, specificity, stability and solubility," Biochemical Engineering Journal, 2018;137:365-374.
Rakoff-Nahoum, Seth, et al., Toll-like Receptors and Cancer. Nature Reviews Cancer 9(1):57-63 (2009).
Rath, et al., "Engineering Strategies to Enhance TCR-Based Adoptive T Cell Therapy" (2020) Cells, 9, 1485, p. 1-34.
Reinink, P. et al., "A TCR β-Chain Motif Biases toward Recognition of Human CD1 Proteins," J Immunol., 2019;203(12):3395-3406.
Reiter, Yoram, et al., Antibody Engineering of Recombinant Fv Immunotoxins for Improved Targeting of Cancer: Disulfide-stabilized Fv Immunotoxins. Clin Cancer Res 2(2):245-252 (1996).
Ridgway, John, et al., Knobs-Into-Holes Engineering of Antibody CH3 Domains for Heavy Chain Heterodimerization. Protein Engineering 9(7):617-621 (1996).
Riechmann, L, et al., Reshaping Human Antibodies for Therapy. Nature 332(6162):323-327 (1988).
Riemer, A.B. et al., "Matching of trastuzumab (Herceptin) epitope mimics onto the surface of Her-2/neu—a new method of epitope definition," Molecular Immunology, 2005;42:1121-1124.
Ring et al.: Mechanistic and structural insight into the functional dichotomy between interleukin-2 and interleukin-15. Nat Immunol. 13(12):1187-1195 (2012).
Roda-Navarro, P. et al., "Understanding the Spatial Topology of Artificial Immunology Synapses Assembled in T Cell-Redirecting Strategies: A Major Issue in Cancer Immunotherapy", Frontiers in Cell and Developmental Biology, 2020, vol. 7, No. 370.
Rohena-Rivera et al.: IL-15 regulates migration, invasion, angiogenesis and genes associated with lipid metabolism and inflammation in prostate cancer. PloS one 12(4):e0172786:1-27 (2017).
Rosenberg, Steven, et al., Use of Tumor-Infiltrating Lymphocytes and Interleukin-2 in the Immunotherapy of Patients with Metastatic Melanoma. The New England Journal of Medicine 319(25):1676-1680 (1988).
Rudikoff et al.: Single Amino Acid Substitution Altering Antigen-binding Specificity. PNAS USA 79(6):1979-1983 (1982).
Ruggiero, Eliana, et al., High-resolution Analysis of the Human T-Cell Receptor Repertoire. Nature Communication 6:8081, 1-7 (2014).
Salameire, et al., "Accurate detection of the tumor clone in peripheral T-cell lymphoma biopsies by flow cytometric analysis of TCR-V B repertoire" Modern Pathology (2012) 25, p. 1246-1257.
Saleh, Mansoor, et al., A Phase II Trial of Murine Monoclonal Antibody 17-1A and Interferon-gamma: Clinical and Immunological Data. Cancer Immunology, Immunotherapy 32(3):185-190 (1990).
Sano, Y. et al., "Properties of Blocking and Non-blocking Monoclonal Antibodies Specific for Human Macrophage Galactose-type C-type Lectin (MGL/ClecSF10A/CD301)," J. Biochem., 2007;127-136.
Sastry, Konduru, et al., Targeting Hepatitis B virus-infected cells with a T-Cell Receptor-like Antibody. Journal of Virology 85(5):1935-1942 (2011).
Saudek et al. A preliminary trial of the programmable implantable medication system for insulin delivery. N. Engl. J. Med. 321(9):574-579 (1989).
Saunders, Kevin, Conceptual Approaches to Modulating Antibody Effector Functions and Circulation Half-Life. Frontiers in Immunology 10:1296, 1-20 (2019).
Schleinitz, N. et al., "Natural killer cells in human autoimmune diseases," Immunology, 2010;131(4):451-458.
Schliemann et al.: Targeting interleukin-2 to the bone marrow stroma for therapy of acute myeloid leukemia relapsing after allogeneic hematopoietic stem cell transplantation. Cancer immunology research 3(5 ):547-556 (2015).

(56) References Cited

OTHER PUBLICATIONS

Schmittnaegel, Martina, et al., Activation of Cytomegalovirus-Specific CD8+ T-cell response by Antibody-Mediated peptide-major Histocompatibility class I Complexes. OncoImmunology 5(1):e1052930, 1-3 (2015).
Scodeller, Pablo, Hyaluronidase and Other Extracellular Matrix Degrading Enzymes for Cancer Therapy: New Uses and Nano-Formulations, Journal of Carcinogenesis & Mutagenesis 5(4):1-5 (2014).
Sefton, Michael, Implantable Pumps. Critical Reviews in Biomedical Engineering 14(3):201-240 (1987).
Seidel, U. et al., "Natural killer cell mediated antibody-dependent cellular cytotoxicity in tumor immunotherapy with therapeutic antibodies", frontiers in Immunology, 2013, vol. 4, No. 76, pp. 1-8.
Sekine, T. et al., "A feasible method for expansion of peripheral blood lymphocytes by culture with immobilized anti-CD3 monoclonal antibody and interleukin-2 for use in adoptive immunotherapy of cancer patients," Biomed & Pharmacother, 1993;47:73-78.
Sen, S. et al., "Expression of epithelial cell adhesion molecule (EpCAM) in oral squamous cell carcinoma," Histopathology, 2015:6:897-904. Abstract only.
Sergeeva, Anna, et al., An Anti-PR1/HLA-A2 T-cell Receptor-like Antibody Mediates Complement-Dependent Cytotoxicity Against Acute Myeloid Leukemia Progenitor Cells. Blood 117(16):4262-4272 (2011).
Shaw, Denise, et al., Mouse/Human Chimeric Antibodies to a Tumor-Associated Antigen: Biologic Activity of the Four Human IgG Subclasses. Journal of the National Cancer Institute 80(19):1553-1559 (1988).
Shi, M. et al., "A recombinant anti-erbB2, scFv-Fc-IL-2 fusion protein retains antigen specificity and cytokine function," Biotechnology letters, 2003;25:815-819.
Shimabukuro-Vornhagen, Alexander, et al., Cytokine Release Syndrome. Journal for ImmunoTherapy of Cancer 6(56):1-14 (2018).
Shitaoka, Kiyomi, et al., Identification of Tumoricidal TCRs from Tumor-Infiltrating Lymphocytes by Single-Cell Analysis. Cancer Immunology Research 6(4):378-388 (2018).
Shpilberg, O, et al., Subcutaneous Administration of Rituximab (MabThera) and Trastuzumab (Herceptin) using Hyaluronidase. British Journal of Cancer 109(6):1556-1561 (2013).
Skegro, D. et al., "Immunoglobulin domain interface exchange as a platform technology for the generation of Fc heterodimers and bispecific antibodies," J Biol Chem, 2017, vol. 292, No. 23, pp. 9745-9759.
Spiess, C. et al., "Alternative molecular formats and therapeutic applications for bispecific antibodies", Molecular Immunology, 2015, vol. 67, pp. 95-106.
Stauber, D.J. et al., "Crystal structure of the IL-2 signaling complex: Paradigm for a heterotrimeric cytokine receptor," PNAS, 2006;103(8):2788-2793.
Stauber et al.: Nuclear and cytoplasmic survivin: molecular mechanism, prognostic, and therapeutic potential. Cancer Res. 67(13):5999-6002 (2007).
Stein, H, et al., A New Monoclonal Antibody (CAL2) Detects Calreticulin Mutations in Formalin-fixed and Paraffin-embedded Bone Marrow Biopsies. Leukemia 30(1):131-135 (2016).
Stivala, Alex, et al., Automatic Generation of Protein Structure Cartoons With Pro-origami. Bioinformatics 27(23):3315-3316 (2011).
Sun, Lee, et al., Chimeric Antibody With Human Constant Regions and Mouse Variable Regions Directed Against Carcinoma-Associated Antigen 17-1A. Proceedings of the National Academy of Sciences of the United States of America 84(1):214-218 (1987).
Suzuki, Sakaru, et al., Formation of Three Types of Disulfated Disaccharides from Chondroitin Sulfates by Chondroitinase Digestion. The Journal of Biological Chemistry 243(7):1543-1550 (1968).
Swencki-Underwood, B. et al., "Engineering human IL-18 with increased bioactivity and bioavailability," Cytokine, 2006, vol. 34, pp. 114-124.
Tang, et al., "Anti-TCR Antibody Treatment Activates a Novel Population of Nonintestinal CD8aa+TCRaB+ Regulatory T Cells and Prevents Experimental Autoimmune Encephalomyelitis" The Journal of Immunology (2007) p. 1-9.
Tassev, D V, et al., Retargeting NK92 Cells using an HLA-A2-Restricted, EBNA3C-Specific Chimeric Antigen Receptor. Cancer Gene Ther 19(2):84-100 (2012).
Thorpe, Philip, Vascular Targeting Agents as Cancer Therapeutics. Clinical Cancer Research 10(2):415-427 (2004).
Tomlinson, Ian, et al., The Repertoire of Human Germline VH Sequences Reveals About Fifty Groups of VH Segments With Different Hypervariable Loops. Journal of Molecular Biology 227(3):776-798 (1992).
Tomonari, K. et al., "Epitope-specific binding of CD8 regulates activation of T cells and induction of cytotoxicity," International Immunology, 1990;2(12):1189-1194.
Tramontano et al.: The making of the minibody: an engineered beta-protein for the display of conformationally constrained peptides. J. Mol. Recognition. 7:9-24 (1994).
Trenevska et al.: Therapeutic Antibodies against Intracellular Tumor Antigens. Front Immunol. 8:1001 doi:10.3389/fimmu.2017.01001 [1-12] (2017).
Tsytsikov, V.N. et al., "Identification and Characterization of Two Alternative Splice Variants of Human Interleukin-2*" The Journal of Biological Chemistry, 1996;71(38):23055-23060.
Tuaillon, Nadine, et al., Human Immunoglobulin Heavy-Chain Minilocus Recombination in Transgenic Mice: Gene-Segment Use in Mu and Gamma Transcripts. Proceedings of the National Academy of Sciences of the United States of America 90(8):3720-3724 (1993).
U.S. Appl. No. 17/529,017 Non-Final Office Action dated Apr. 27, 2022.
U.S. Appl. No. 17/820,794 Notice of Allowance dated Feb. 1, 2024.
Vallera et al.: Heterodimeric bispecific single-chain variable-fragment antibodies against EpCAM and CD16 induce effective antibody-dependent cellular cytotoxicity against human carcinoma cells. Cancer Biother Radiopharm. 28(4):274-282 doi:10.1089/cbr.2012.1329 (2013).
Van Rhijn, I. et al., "A conserved human T cell population targets mycobacterial antigens presented by CD1b," Nat Immunol., 2013; 14(7):706-713.
Van Rhijn, I. et al., "TCR bias and affinity define two compartments of the CD1b-glycolipid-specific T Cell repertoire," J Immunol., 2014;192(9):4054-4060.
Vannucchi, et al., "Calreticulin mutation-specific immunostaining in myeloproliferative neoplasms: pathogenetic insight and diagnostic value" Leukemia (2014) 28, p. 1811-1818.
Verhoeyen, M. et al., "Reshaping Human Antibodies: Grafting an Antilysozyme Activity", Science, 1988, vol. 239, pp. 1534-1536.
Verma, Bhavna, et al., TCR Mimic Monoclonal Antibody Targets a Specific Peptide/HLA Class I Complex and Significantly Impedes Tumor Growth In Vivo Using Breast Cancer Models. J Immunol 184(4):2156-2165 (2010).
Verwilghen, J. et al., "Differences in the stimulating capacity of immobilized anti-CD3 monoclonal antibodies: variable dependence on interleukin-1 as a helper signal for T-cell activation," 1991;72:269-276.
Vonderheid, Eric, et al., Evidence for Restricted VB Usage in the Leukemic Phase of Cutaneous T Cell Lymphoma. The Journal of Investigative Dermatology 124(3):650-661 (2005).
Vyas, M. et al., "Natural ligands and antibody-based fusion proteins: harnessing the immune system against cancer", Trends in Molecular Medicine, 2014, vol. 20, No. 2, pp. 72-82.
Wadia, P. et al., "Impaired lymphocyte responses and their restoration in oral cancer patients expressing distinct TCR variable region," Cancer Investigation, 2008;26:471-480.
Wagner, E.K. et al., "Engineering therapeutics antibodies to combat infectious disease," Current Opinion in Chemical Engineering, 2018:19;131-141.
Wan, Y.Y. et al., "'Yin-Yang' functions of TGF-b and tregs in immune regulation," Immunol Rev., 2007;220:199-213.
Wang, Chun-Yan, et al., αβ T-Cell Receptor Bias in Disease and Therapy (Review). International Journal of Oncology 48(6):2247-2256 (2016).

(56) References Cited

OTHER PUBLICATIONS

Wang et al.: Cloning genes encoding MHC class II-restricted antigens: mutated CDC27 as a tumor antigen. Science 284(5418):1351-1354 doi:10.1126/science.284.5418.1351 (1999).
Wang et al.: RNA interference targeting CML66, a novel tumor antigen, inhibits proliferation, invasion and metastasis of HeLa cells. Cancer Lett. 269(1):127-138 (2008).
Wang, H. et al., "Preparation and functional identification of a monoclonal antibody against the recombinant soluble human NKp30 receptor," Internal Immunopharmacology, 2011;11(11):1732-1739.
Warren, H.S. et al., "Evidence that the cellular ligand for the Human NK Cell Activation Receptor NKp30 is not a Heparan Sulfate Glycosaminoglycan," The Journal of Immunology, 2005;175(1):207-212.
Wei, Shan, et al., Identification of a Novel Human T-cell Receptor Vβ Subfamily by Genomic Cloning. Human Immunology 41(3):201-206 (1994).
Weidle, U. et al., "The Intriguing Options of Multispecific Antibody Formats for Treatment of Cancer", Cancer Genomics & Proteomics, 2013, vol. 1, pp. 1-18.
Weidle, U.H. et al., "Tumor-Antigen-Binding Bispecific Antibodies for Cancer Treatment", Seminars in Oncology, 2014, vol. 41, No. 5, pp. 653-660.
Williemsen, R A, et al., A Phage Display Selected Fab Fragment with MHC Class I-Restricted Specificity for MAGE-A1 allows for Retargeting of Primary Human T Lymphocytes. Gene Therapy 8(21):1601-1608 (2001).
Wood, Clive, et al., The Synthesis and in Vivo Assembly of Functional Antibodies in Yeast. Nature 314(6010):446-449 (1985).
Wu, M.R. et al., "B7H6-Specific Bispecific T Cell Engagers Lead to Tumor Elimination and Host Antitumor Immunity", The Journal of Immunology, 2015, vol. 194, No. 11, pp. 5305-5311.
Wurzer et al.: Nuclear Ras: unexpected subcellular distribution of oncogenic forms.J Cell Biochem Suppl. Suppl 36:1-11 doi:10.1002/jcb.1070 (2001).
Xiao, Y.F. et al., "Peptide-based treatment: A promising cancer therapy", Journal of Immunology Research, 2015, pp. 1-14.
Xiaoying, C. et al., "Fusion protein linkers: Property, design and functionality", Advanced Drug Delivery Reviews, 2012, vol. 65, No. 10, pp. 1357-1369.
Xu, Xiao-Jun, et al., Cytokine Release Syndrome in Cancer Immunotherapy with Chimeric Antigen Receptor Engineered T Cells. Cancer Letters 343(2):172-178 (2014).
Yamagata, Tatsuya, et al., Purification and Properties of Bacterial Chondroitinases and Chondrosulfatases. The Journal of Biological Chemistry 243(7):1523-1535 (1968).
Yassai, Maryam, et al., A Clonotype Nomenclature for T Cell Receptors. Immunogenetics 61(7):493-502 (2009).
Yoon et al.: Charged residues dominate a unique interlocking topography in the heterodimeric cytokine interleukin-12. The EMBO J. 19(14):3530-3541 (2000).
Yoon, S.T. et al., "Both high and low avidity antibodies to the T cell receptor can have agonist or antagonist activity," Immunity, 1994;1(7):563-569.
Zhang, T. et al., "Cancer Immunotherapy Using a Bispecific NK Receptor Fusion Protein that Engages both T Cells and Tumor Cells", Cancer Research, 2011, vol. 71, No. 6, pp. 2066-2076.
Hashimoto, M. et al., PD-1 combination therapy with IL-2 modifies CD8+ T cell exhaustion program, Nature, vol. 610, 7930 (2022):173-181.
Deak, L.C. et al., PD-1-cis IL-2R agonism yields better effectors from stem-like CD8+ T cells, Nature, vol. 610, 7930 (2022):161-172.
Agata, Yasutoshi. et al. Expression of the PD-1 Antigen on the Surface of Stimulated Mouse T and B Lymphocytes. International Immunology 8(5):765-772 (1996).
Aggen, DH. et al. Single-chain VαVβ T-cell Receptors Function Without Mispairing With Endogenous TCR Chains. Gene Therapy 19(4):365-374 (2012).
Akers, Michael J. et al. Formulation Development of Protein Dosage Forms. Pharmaceutical Biotechnology 14:47-127 (2002).
Akers, Michael J., et al. Peptides and proteins as parenteral solutions. Pharmaceutical formulation development of peptides and proteins. London: Taylor & Francis. pp. 145-77.(2000).
Allison, A C. The Mode of Action of Immunological Adjuvants. Developments in Biological Standardization 92:3-11 (1998).
Almagro, Juan C, and Johan Fransson. Humanization of Antibodies. Frontiers in Bioscience 13:1619-1633 (2008).
Amarante-Mendes, Gustavo P, and Thomas S. Griffith. Therapeutic applications of Trail receptor agonists in cancer and beyond. Pharmacology & therapeutics 155:117-131 (2015).
Anderson, et al. Anti-CD3 + IL-2-stimulated murine killer cells. In vitro generation and in vivo antitumor activity. J Immunol 142 (4): 1383-1394 (1989).
Baca, Manuel. et al. Antibody Humanization Using Monovalent Phage Display. The Journal of Biological Chemistry 272(16):10678-10684 (1997).
Batzer, Mark A. et al. Enhanced Evolutionary PCR Using Oligonucleotides With Inosine At The 3'-Terminus. Nucleic Acids Research 19(18):5081 (1991).
Baxter, et al. Acquired mutation of the tyrosine kinase JAK2 in human myeloproliferative disorders. The Lancet. 2005. 365(9464):1054-1061.
Benati, Daniela. et al. Public T Cell Receptors Confer High-avidity CD4 Responses to HIV Controllers. Journal of Clinical Investigation 126(6):2093-2108 (2016).
Berge, Stephen M. et al. Pharmaceutical Salts. Journal of Pharmaceutical Sciences 66(1):1-19 (1977).
Blank, Christian. et al. Interaction of PD-L1 on Tumor Cells with PD-1 on Tumor-Specific T cells as a Mechanism of Immune Evasion: Implications for Tumor Immunotherapy. Cancer Immunology, Immunotherapy 54(4):307-314 (2005). Published Online on Dec. 15, 2004.
Bloeman, PGM. et al. Adhesion Molecules: A New Target for Immunoliposome-mediated Drug Delivery. FEBS Letters 357:140-144 (1995).
Boerner, Paula. et al. Production Of Antigen-Specific Human Monoclonal Antibodies From In Vitro-primed Human Splenocytes. Journal of Immunology 147(1):86-95 (1991).
Borrebaeck, Carl A K. Antibody Engineering, Second Edition. Oxford University Press: 1-11 (1995).
Bovay, Amandine. et al. T Cell Receptor Alpha Variable 12-2 Bias in the Immunodominant Response to Yellow Fever Virus. European Journal of Immunology 48(2):258-272 (2018).
Brennan, Maureen. et al. Preparation of Bispecific Antibodies by Chemical Recombination of Monoclonal Immunoglobulin G1 Fragments. Science 229(4708):81-83 (1985).
Brennan, Rebekah M. et al. Predictable Alphabeta T-cell Receptor Selection Toward an HLA-B*3501-restricted Human Cytomegalovirus Epitope. Journal of Virology 81(13):7269-7273 (2007).
Brey, et al. A gB/CD3 bispecific BiTE antibody construct for targeting Human Cytomegalovirus-infected cells. Sci Rep 28;8(1):17453 (2018). 12 pages.
Briscoe, Page. et al. Delivery of Superoxide Dismutase to Pulmonary Epithelium via pH-sensitive Liposomes. American Journal of Physiology 268(3 Pt 1):L374-L380 (1995).
Brodeur, Bernard R. et al. Monoclonal Antibody Production Techniques and Applications. New York: Marcel Dekker:51-63 (1987).
Buckland, et al. Fusion glycoprotein of measles virus: nucleotide sequence of the gene and comparison with other paramyxoviruses. Journal of General Virology 68(6):1695-1703 (1987).
Bulek, Anna M. et al. Structural Basis of Human β-cell Killing by CD8+ T cells in Type 1 Diabetes. Nature Immunology 13(3):283-289 (2012).
Cain, C. Crossing over to bispecificity. Science-Business exchange 4, 783. (2011).
Caldas, Cristina. et al. Humanization of the anti-CD18 antibody 6.7: an unexpected effect of a framework residue in binding to antigen. Molecular immunology 39(15):941-952 (2003).
Campbell, Peter J. The long-term outlook for essential thrombocythemia. Mayo Clin Proc 81(2):157-8 (2006).

(56) References Cited

OTHER PUBLICATIONS

Campbell, Peter J. The myeloproliferative disorders. N Engl J Med 355(23):2452-66 (2006).
Campisi, Laura. et al. Clonally Expanded CD8 T Cells Characterize Amyotrophic Lateral Sclerosis-4. Nature 606(7916):945-952 (2022).
Carnero Contentti, Edgar, et al. Mucosal-Associated Invariant T Cell Features and TCR Repertoire Characteristics During the Course of Multiple Sclerosis. Frontiers in Immunology 10:1-17 (2019).
Carter, Laura L. et al. PD-1: PD-L Inhibitory Pathway Affects both CD4(+) and CD8(+) T Cells and is Overcome by IL-2. European Journal of Immunology 32(3):634-643 (2002).
Carter, Paul. et al. Humanization of an Anti-p185HER2 Antibody for Human Cancer Therapy. PNAS USA 89(10):4285-4289 (1992).
Cazzola, Mario, and Robert Kralovics. From Janus Kinase 2 to Calreticulin: The Clinically Relevant Genomic Landscape of Myeloproliferative Neoplasms. Blood 123(24):3714-3719 (2014).
Chang, et al. Opportunities and challenges for TCR mimic antibodies in cancer therapy. Expert Opinion on Biological Therapy 16(8):979-987 (2016).
Chari, Ravi V.J. et al. Immunoconjugates Containing Novel Maytansinoids: Promising Anticancer Drugs. Cancer Research 52(1):127-131 (1992).
Charlton, Keith A. Expression and Isolation of Recombinant Antibody Fragments in *E. coli*. Chapter 14. Methods in Molecular Biology 248:245-254 (2003).
Chen, Lan. et al. The T Cell Repertoires from Nickel Sensitized Joint Implant Failure Patients. International Journal of Molecular Sciences 22(5):2428, 1-13 (2021).
Chen, Yvonne. et al. Selection and Analysis of an Optimized Anti-VEGF Antibody: Crystal Structure of an Affinity-matured Fab in Complex With Antigen. Journal of Molecular Biology 293(4):865-881 (1999).
Choi, Yangwon. et al. A method for production of antibodies to human T-cell receptor beta-chain variable regions. Proc Natl Acad Sci USA 88(19):8357-8361 (1991).
Chowdhury, Partha S. Engineering Hot Spots for Affinity Enhancement of Antibodies. Methods in Molecular Biology 207:179-196 (2003).
ClinicalTrials.gov Identifier: NCT00001846. Collection and Distribution of Blood Components From Healthy Donors for In Vitro Research Use, Record created Nov. 3, 1999. pp. 1-10. [retrieved on Aug. 22, 2024] Available at URL: https://clinicaltrials.gov/study/NCT00001846.
ClinicalTrials.gov Identifier: NCT01004822. A Safety, Tolerability, And Pharmacokinetic Trial With CVX-241 In Patients With Advanced Solid Tumors, Record created Oct. 28, 2009. pp. 1-17. [retrieved on Jul 12, 2024] Available at URL: https://clinicaltrials.gov/study/NCT01004822?cond=NCT01004822&rank=1.
ClinicalTrials.gov Identifier: NCT03427411. M7824 in Subjects With HPV Associated Malignancies, Record created Feb. 8, 2018. pp. 1-19. [retrieved on Aug. 22, 2024] Available at URL: https://clinicaltrials.gov/study/NCT03427411?term=NCT03427411&rank=1.
Clynes, Raphael. et al. Fc Receptors Are Required in Passive and Active Immunity to Melanoma. Proceedings of the National Academy of Sciences of the United States of America 95(2):652-656 (1998).
Cole, David K. et al. Germ Line-governed Recognition of a Cancer Epitope by an Immunodominant Human T-cell Receptor. Journal of Biological Chemistry 284(40):27281-27289 (2009).
Connolly, James L et al. Tumor Structure and Tumor Stroma Generation. 6th Edition. Holland-Frei Cancer Medicine :1-5 (2003).
Co-pending U.S. Appl. No. 18/286,062, inventors Andreas; Loew et al., filed Oct. 6, 2023.
Co-pending U.S. Appl. No. 18/654,860, inventors Hayday; Adrian et al., filed May 3, 2024.
Co-pending U.S. Appl. No. 18/659,544, inventors Andreas; Loew et al., filed May 9, 2024.
Co-pending U.S. Appl. No. 18/749,969, inventors Hsu; Jonathan et al., filed Jun. 21, 2024.
Co-pending U.S. Appl. No. 18/779,692, inventor Andreas; Loew, filed Jul. 22, 2024.
Cragg, Mark S, and Martin J Glennie. et al. Antibody Specificity Controls in Vivo Effector Mechanisms of anti-CD20 Reagents. Blood 103(7):2738-2743 (2004).
Cragg, Mark S. et al. Complement-mediated Lysis by Anti-CD20 mAb Correlates with Segregation into Lipid Rafts. Blood 101(3):1045-1052 (2003).
Crowther, Michael D. et al. Genome-wide CRISPR-Cas9 Screening Reveals Ubiquitous T Cell Cancer Targeting via the Monomorphic MHC Class I-related Protein MR1. Nature Immunology 21(2):178-185 (2020).
Cunningham, Brian C, and James A. Wells. High-resolution Epitope Mapping of hGH-receptor Interactions by Alanine-scanning Mutagenesis. Science 244(4908):1081-1085 (1989).
Dahal-Koirala, S. et al. TCR Sequencing of Single Cells Reactive to DQ2.5-glia-α2 and DQ2.5-glia-ω2 Reveals Clonal Expansion and Epitope-specific V-gene Usage. 9(3):587-596 (2016).
Dall'Acqua, William F. et al. Antibody Humanization by Framework Shuffling. Methods 36(1):43-60 (2005).
Delhommeau, François et al. Mutation in TET2 in Myeloid Cancers. N Engl J Med 360(22):2289-2301 (2009).
Dimasi, Nazzareno. et al. The Design and Characterization of Oligospecific Antibodies for Simultaneous Targeting of Multiple Disease Mediators. Journal of Molecular Biology 393(3):672-692 (2009).
Diskin, Ron. et al. Increasing the Potency and Breadth of an HIV Antibody by Using Structure-based Rational Design. Science 334(6060):1289-1293 (2011).
Dong, Haidong, and Lieping Chen. B7-H1 Pathway and its Role in the Evasion of Tumor Immunity. Journal of Molecular Medicine 81(5):281-287 (2003).
Draghi, et al. P530 Novel bispecific antibody targeting NKp30 receptor enhances NK-mediated killing activity against multiple myeloma cells and overcomes CD16A deficiency. Abstract. In Meeting Abstracts: 33rd Annual Meeting & Pre-Conference Programs of the Society for Immunotherapy of Cancer (STIC 2018). 8 pages.
Du, Jiamu. et al. Molecular basis of recognition of human osteopontin by 23C3, a potential therapeutic antibody for treatment of rheumatoid arthritis. Journal of molecular biology 382(4):835-842 (2008).
Dubowchik, Gene M. et al. Doxorubicin Immunoconjugates Containing Bivalent, Lysosomally-cleavable Dipeptide Linkages. Bioorganic & Medicinal Chemistry Letters 12(11):1529-1532 (2002).
Duncan, Alexander R, and Greg Winter. The Binding Site for C1q on IgG. Nature 332(6166):738-740 (1988).
Dupuis, Marc. et al. Dendritic Cells Internalize Vaccine Adjuvant After Intramuscular Injection. Cell Immunology 186(1):18-27 (1998).
Edwards, et al. The Remarkable Flexibility of the Human Antibody Repertoire; Isolation of Over One Thousand Different Antibodies to a Single Protein, BLyS. Journal of Molecular Biology 334(1):103-118 (2003).
Ernst, et al. Inactivating mutations of the histone methyltransferase gene EZH2 in myeloid disorders. Nat Genet 42(8):722-6 (2010).
Fellouse, Frederic A. et al. Synthetic Antibodies From a Four-amino-acid Code: a Dominant Role for Tyrosine in Antigen Recognition. Proceedings of the National Academy of Sciences 24:101(34):12467-12472 (2004).
Fernandez-Sesma, Ana. et al. A bispecific antibody recognizing influenza A virus M2 protein redirects effector cells to inhibit virus replication in vitro. Journal of virology 70(7):4800-4804 (1996).
Ferrari De Andrade, et al. Natural killer cells are essential for the ability of BRAF inhibitors to control BRAFV600E-mutant metastatic melanoma. Cancer research 74(24):7298-7308 (2014).
Fix, J A. et al. Oral Controlled Release Technology for Peptides: Status and Future Prospects. Pharmaceutical research 13(12):1760-1764 (1996).
Flatman, Stephen. et al. Process Analytics for Purification of Monoclonal Antibodies. Journal of Chromatography 848:79-87 (2007). Published Online on Dec. 11, 2006.
Fontana, Angelo. et al. Probing the Partly Folded States of Proteins by Limited Proteolysis. Folding & Design 2(2):R17-R26 (1997).

(56) References Cited

OTHER PUBLICATIONS

Freeman, Gordon. et al. Engagement of the PD-1 Immunoinhibitory Receptor by a Novel B7 Family Member Leads To Negative Regulation Of Lymphocyte Activation. Journal Of Experimental Medicine 192(7):1027-1034 (2000).
Frick, Rahel. et al. A TRAV26-1-encoded Recognition Motif Focuses the Biased T Cell Response in Celiac Disease. European Journal of Immunology 50(1):142-145 (2020).
Gabrilovich, D I. et al. IL-12 And Mutant P53 Peptide-Pulsed Dendritic Cells For The Specific Immunotherapy Of Cancer. Journal of Immunotherapy with Emphasis on Tumor Immunology 19(6):414-418 (1996).
Gacerez, Albert T. et al. How Chimeric Antigen Receptor Design Affects Adoptive T Cell Therapy. Journal of cellular physiology 231(12):2590-2598 (2016).
Galvin, Teresa A. Effect of different promoters on immune responses elicited by HIV-1gag/env multigenic DNA vaccine in Macaca mulatta and Macaca nemestrina. Vaccine 18(23):2566-2583 (2000).
Gamvrellis, Anita. et al. Vaccines That Facilitate Antigen Entry Into Dendritic Cells. Immunology & Cell Biology 82(5):506-516 (2004).
Garland et al. The use of Teflon cell culture bags to expand functionally active CD8+ cytotoxic T lymphocytes. J Immunol Meth 227(1-2):53-63 (1999).
Gazzano-Santoro, Helene. et al. A Non-radioactive Complement-dependent Cytotoxicity Assay For Anti-cd20 Monoclonal Antibody. Journal Of Immunological Methods 202(2):163-171 (1996).
Gedda, Mallikarjuna R. et al. Longitudinal transcriptional analysis of peripheral blood leukocytes in COVID-19 convalescent donors. J Transl Med 20(1):587, 1-16 (2022).
GenBank Accession No. 2ERJ_D. Version 2ERJ_D. Chain D, Interleukin-2. Record created Mar. 21, 2006. 2 pages. Retrieved Jul. 15, 2024 at URL: https://www.ncbi.nlm.nih.gov/protein/90109213.
GenBank Accession No. AAA62478.2. Version No. AAA62478.2. induced by lymphocyte activation; similar to Human receptor protein encoded by GenBank Accession No. U03397 [*Homo sapiens*]. Record created Jun. 12, 1993. 2 Pages. Retrieved Aug. 1, 2024 at URL: https://www.ncbi.nlm.nih.gov/protein/AAA62478.
GenBank Accession No. AAH66254. Version No. AAH66254.1. Interleukin 2 [*Homo sapiens*]. Record created Feb. 12, 2004. 2 Pages. Retrieved Jul. 12, 2024 at URL: https://www.ncbi.nlm.nih.gov/protein/AAH66254.
GenBank Accession No. BAG36664. Version No. BAG36664.1. unnamed protein product [*Homo sapiens*]. Record created May 23, 2008. 2 Pages. Retrieved Aug. 1, 2024 at URL: https://www.ncbi.nlm.nih.gov/protein/BAG36664.
GenBank Accession No. NM_005191. Version No. NM_005191.4. *Homo sapiens* CD80 Molecule (CD80), mRNA. Record created May 24, 1999. Retrieved Aug. 2, 2024. Retrieved from: https://www.ncbi.nlm.nih.gov/nuccore/NM_005191.
GenBank Accession No. NP002174. Version No. NP_002174.1. interleukin-3 receptor subunit alpha isoform 1 precursor [*Homo sapiens*]. Record created Mar. 14, 2021. 3 Pages. Retrieved Aug. 1, 2024 at URL: https://www.ncbi.nlm.nih.gov/protein/NP_002174.
Gerngross, Tillman U. Advances In The Production Of Human Therapeutic Proteins In Yeasts and Filamentous Fungi. Nature Biotechnology 22(11):1409-1414 (2004).
Giaccone, Giuseppe. et al. A phase I study of the natural killer T-cell ligand alpha-galactosylceramide (KRN7000) in patients with solid tumors. Clinical cancer research 8(12):3702-3709 (2002).
Godfrey, Dale I. et al. The Burgeoning Family of Unconventional T Cells. Nature Immunology 16(11):1114-1123 (2015).
Graham, F L. et al. Characteristics of a Human Cell line Transformed by DNA from Human Adenovirus type 5. Journal of General Virology 36(1):59-72 (1977).
Gruber, Meegan. et al. Efficient Tumor Cell Lysis Mediated By A Bispecific Single Chain Antibody Expressed In *Escherichia coli*. Journal Of Immunology 152(11):5368-5374 (1994).
Gussow et al., Chapter 5: Humanization of Monoclonal Antibodies. Methods in Enzymology. 203:99-121 (1991).
Hamers-Casterman, C. et al. Naturally Occurring Antibodies Devoid of Light Chains. Nature 363(6428):446-448 (1993).
Harutyunyan, et al. p53 lesions in leukemic transformation. N Engl J Med 364(5):488-90 (2011).
Harutyunyan, et al. Rare germline variants in regions of loss of heterozygosity may influence clinical course of hematological malignancies. Leukemia 25(11):1782-4 (2011).
He, X.Y. et al. TRAV gene expression in PBMCs and TILs in patients with breast cancer analyzed by a DNA melting curve (FQ-PCR) technique for TCR α chain CDR3 spectratyping. Neoplasma 59(6):693-699 (2012).
Helliwell, P S, and W J Taylor. Classification and Diagnostic Criteria for Psoriatic Arthritis. Annals of the Rheumatic Diseases 64(Suppl 2):ii3-ii8 (2005).
Hinks, Timothy S. C. and Xia-Wei Zhang. MAIT Cell Activation and Functions. Frontiers in Immunology 11:1014, 1-10 (2020).
Hinman, Lois M. et al. Preparation And Characterization Of Monoclonal Antibody Conjugates Of The Calicheamicins: A Novel And Potent Family Of Antitumor Antibiotics. Cancer Research 53(14):3336-3342 (1993).
Hollinger, Philipp. et al. "Diabodies": Small Bivalent And Bispecific Antibody Fragments. Proceedings Of The National Academy Of Sciences Of The United States Of America 90(4):6444-6448 (1993).
Holmström, M O. et al. The calreticulin (CALR) exon 9 mutations are promising targets for cancer immune therapy. Leukemia 32(2):429-437 (2018).
Holmström, Morten Orebo, and Hans Carl Hasselbalch. Cancer immune therapy for myeloid malignancies: present and future. Seminars in Immunopathology 41(1):97-109 (2019).
Holmstrom, M O. et al. The CALR Exon 9 Mutations Are Shared Neoantigens in Patients With Calr Mutant Chronic Myeloproliferative Neoplasms. Leukemia 30(12):2413-2416 (2016).
Hong, Sung Noh. et al. Reduced diversity of intestinal T-cell receptor repertoire in patients with Crohn's disease. Frontiers in Cellular and Infection Microbiology 12:1-12 (2022).
Hoogenboom, Hennie R, and Greg Winter. By-Passing Immunisation: Human Antibodies From Synthetic Repertoires Of Germline VH Gene Segments Rearranged In Vitro. Journal of Molecular Biology 227(2):381-388 (1992).
Hoogenboom, Hennie R. Overview Of Antibody Phage-display Technology And Its Applications. Methods In Molecular Biology 178:1-37 (2002).
Horna, Pedro. et al. Utility of TRBC1 expression in the diagnosis of peripheral blood involvement by cutaneous T-cell lymphoma. Journal of Investigative Dermatology 141(4):821-829.e2 (2021).
Howson, Lauren J. et al. MAIT cell clonal expansion and TCR repertoire shaping in human volunteers challenged with *Salmonella paratyphi* A. Nat Commun 9(1):253, 1-11 (2018).
Hsu, Jonathan. et al. AT cell receptor β chain-directed antibody fusion molecule activates and expands subsets of T cells to promote antitumor activity. Science translational medicine 15(724):eadi0258, 1-18 (2023).
Hsu, Jonathan. et al. Supplementary Materials for: A T Cell Receptor β Chain-directed Antibody Fusion Molecule Activates and Expands Subsets of T Cells to Promote Antitumor Activity. Science Translational Medicine 15(724):eadi0258, 1-39 (2023).
Huang, Huang. et al. Select sequencing of clonally expanded CD8+ T cells reveals limits to clonal expansion. Proc Natl Acad Sci U S A 116(18):8995-9001 (2019).
Huda, Taha I. et al. Specific HLA Alleles, Paired With TCR V- and J-gene Segment Usage, Link to Distinct Multiple Myeloma Survival Rates. Leukemia & Lymphoma 62(7):1711-1720 (2021).
Hudson, Peter J, and Christelle Souriau. Engineered Antibodies. Nature Medicine 9(1):129-134 (2003).
Human NKp30/NCR3 Antibody. Catalog No. MAB1849. Clone 210845 was used by HLDA to establish CD designation. [Website] R&D Systems. Retrieved Jul. 27, 2024 at URL: https://www.rndsystems.com/products/human-nkp30-ncr3-antibody-210845_mab1849. 7 pages.
Human NKp30/NCR3 Antibody. Catalog No. MAB18491. Source: Monoclonal Mouse IgG2A Clone No. 210847. [Website] R&D Systems. Retrieved Nov. 23, 2023 at URL: https://www.rndsystems.

(56) References Cited

OTHER PUBLICATIONS com/products/human-nkp30-ncr3-antibody-210847_mab18491#productdetails. 6 pages.
Hussain, Khiyam. et al. 1392 An Atypical Central Memory like Phenotype Can be Induced in Human T Cells by Innate TCRa Engagement. J. Immuno Ther. Cancer 10(suppl 2):A1447 (2022).
Idusogie, Eshoe E. et al. Mapping of the C1q Binding Site on Rituxan, A Chimeric Antibody with a Human IgG1 Fc. The Journal of Immunology 164(8):4178-4184 (2000).
Imai-Nishiya, Harue. et al. Double Knockdown of Alpha1,6-fucosyltransferase (FUT8) And GDP-mannose 4,6-dehydratase (GMD) In Antibody-producing Cells: A New Strategy For Generating Fully Non-fucosylated Therapeutic Antibodies With Enhanced ADCC. BMC Biotechnology 7:84, 1-13 (2007).
Ipilimumab. CAS 477202-00-9. chemicalbook.com [Website] Retrieved Oct. 8, 2024 at: https://www.chemicalbook.com/CASEN_477202-00-9.htm. 3 pages.
James, et al. A JAK2 mutation in myeloproliferative disorders: pathogenesis and therapeutic and scientific prospects. Trends Mol Med 11(12):546-54 (2005).
James, et al. A unique clonal JAK2 mutation leading to constitutive signalling causes polycythaemia vera. Nature. 2005;434:1144-1148.
Jeffrey, Scott C. et al. Dipeptide-based Highly Potent Doxorubicin Antibody Conjugates. Bioorganic Medicinal Chemistry Letters 16(2):358-362 (2006).
Johnsson, Bo. et al. Comparison Of Methods for Immobilization To Carboxymethyl Dextran Sensor Surfaces By Analysis Of The Specific Activity Of Monoclonal Antibodies. Journal of Molecular Recognition 8(1-2):125-131 (1995).
Johnsson, Bo. et al. Immobilization of Proteins To A Carboxymethyldextran-modified Gold Surface For Biospecific Interaction Analysis In Surface Plasmon Resonance Sensors. Analytical Biochemistry 198(2):268-277 (1991).
Jonsson, U. et al. Introducing a Biosensor Based Technology for Real-time Biospecific Interaction Analysis. Annals of Clinical Biology 51(1):19-26 (1993).
Jonsson, U. et al. Real-time Biospecific Interaction Analysis Using Surface Plasmon Resonance and a Sensor Chip Technology. BioTechniques 11(5):620-627 (1991).
Jung, S. et al. Prevention and therapy of experimental autoimmune neuritis by an antibody against T cell receptors-alpha/beta. Journal of immunology 148(12):3768-3775 (1992).
Kabat, Elvin A. et al. Sequences of Proteins of Immunological Interest. Fifth Edition, NIH Pub. No. 91-3242. Public Health Service, U.S. Department of Health and Human Services, National Institutes of Health: 647-669 (1991).
Kam, Nadine Wong Shi. et al. Carbon Nanotubes as Multifunctional Biological Transporters and Near-infrared Agents for Selective Cancer Cell Destruction. Proceedings of the National Academy of Sciences of the United States of America 102(33):11600-11605 (2005).
Kanda, Yutaka. et al. Comparison of Cell Lines for Stable Production of Fucose-negative Antibodies With Enhanced ADCC. Biotechnology and Bioengineering 94(4):680-688 (2006).
Karlin, Samuel. et al. Applications and Statistics for Multiple High-scoring Segments in Molecular Sequences. PNASUSA 90(12):5873-5877 (1993).
Kashmiri, Syed V S. et al. SDR Grafting—a New Approach to Antibody Humanization. Methods 36(1):25-34 (2005).
Keinanen, A, and M L Laukkanen. Biosynthetic Lipid-tagging of Antibodies. FEBS letters 346(1):123-126 (1994).
Killion, J J, and I J Fidler. Systemic Targeting of Liposome-encapsulated Immunomodulators to Macrophages for Treatment of Cancer Metastasis. ImmunoMethods 4(3):273-279 (1994).
King, H Dalton. et al. Monoclonal Antibody Conjugates of Doxorubicin Prepared With Branched Peptide Linkers: Inhibition of Aggregation by Methoxytriethyleneglycol Chains. Journal of Medicinal Chemistry 45(19):4336-4343 (2002).
Klampfl, Thorsten. et al. Genome Integrity of Myeloproliferative Neoplasms in Chronic Phase and During Disease Progression. Blood 118(1):167-176 (2011).
Klimka, A. et al. Human Anti-CD30 Recombinant Antibodies by Guided Phage Antibody Selection Using Cell Panning. British Journal of Cancer 83(2):252-260 (2000).
Knappik, et al. Fully synthetic human combinatorial antibody libraries (HuCAL) based on modular consensus frameworks and CDRs randomized with trinucleotides. J Mol Biol. Feb. 11, 2000;296(1):57-86.
Konishi, Jun. et al. B7-H1 Expression on Non-small Cell Lung Cancer Cells and Its Relationship With Tumor-infiltrating Lymphocytes and Their PD-1 Expression. Clinical Cancer Research 10(15):5094-5100 (2004).
Kostelny, S A. et al. Formation of a Bispecific Antibody by the Use of Leucine Zippers. Journal of Immunology 148(5):1547-1553 (1992).
Kozbor, D. et al. A Human Hybrid Myeloma for Production of Human Monoclonal Antibodies. Journal of Immunology 133(6):3001-3005 (1984).
Kralovics, et al. Altered gene expression in myeloproliferative disorders correlates with activation of signaling by the V617F mutation of Jak2. Blood 106(10):3374-6 (2005).
Kralovics, et al. Molecular pathogenesis of Philadelphia chromosome negative myeloproliferative disorders. Blood Rev 19(1):1-13 (2005).
Kralovics, Robert. et al. A Gain-of-function Mutation of JAK2 in Myeloproliferative Disorders. The New England Journal of Medicine 352(17):1779-1790 (2005).
Kralovics, Robert. Genetic Complexity of Myeloproliferative Neoplasms. Leukemia 22(10):1841-1848 (2008).
Kratz, F. et al. Prodrugs of Anthracyclines in Cancer Chemotherapy. Current Medicinal Chemistry 13(5):477-523 (2006).
Kunik, Vered. et al. Structural consensus among antibodies defines the antigen binding site. PLoS computational biology 8(2):e1002388, 1-12 (2012).
Latchman, Yvette. et al. PD-L2 is a Second Ligand for PD-1 and Inhibits T Cell Activation. Nature Immunology 2(3):261-268 (2001).
Lee, Chingwei V. et al. Bivalent Antibody Phage Display Mimics Natural Immunoglobulin. Journal of Immunological Methods 284(1-2):119-132 (2004).
Lee, Chingwei V. et al. High-affinity Human Antibodies From Phage-displayed Synthetic Fab Libraries With a Single Framework Scaffold. Journal of Molecular Biology 340(5):1073-1093 (2004).
Lepore, Marco. et al. Functionally Diverse Human T cells Recognize non-microbial Antigens Presented by MR1.Elife 6:e24476, 1-22 (2017).
Levine, et al. The JAK2V617F activating mutation occurs in chronic myelomonocytic leukemia and acute myeloid leukemia, but not in acute lymphoblastic leukemia or chronic lymphocytic leukemia. Blood 106(10):3377-9 (2005).
Levine, Ross L. et al. Activating Mutation in the Tyrosine Kinase JAK2 in Polycythemia Vera, Essential Thrombocythemia, and Myeloid Metaplasia With Myelofibrosis. Cancer Cell 7(4):387-397 (2005).
Li, Huijuan. et al. Optimization of Humanized IgGs in Glycoengineered Pichia Pastoris. Nature Biotechnology 24(2):210-215 (2006).
Li, Jian. et al. Human Antibodies for Immunotherapy Development Generated via a Human B Cell Hybridoma Technology. Proceedings of the National Academy of Sciences of the United States of America 103(10):3557-3562 (2006).
Li, Yangqiu. et al. Restricted TRBV repertoire in CD4+ and CD8+ T-cell subsets from CML patients. Hematology 16(1):43-49 (2011).
Lifely, M R. et al. Glycosylation and biological activity of CAMPATH-1H Expressed in different Cell lines and Grown under different Culture Conditions. Glycobiology 5(8):813-822 (1995).
Lode, Holger N. et al. Targeted Therapy With a Novel Enediyene Antibiotic Calicheamicin Theta(I)1 Effectively Suppresses Growth and Dissemination of Liver Metastases in a Syngeneic Model of Murine Neuroblastoma. Cancer Research 58(14):2925-2928 (1998).
Lonberg, Nils. Fully Human Antibodies From Transgenic Mouse and Phage Display Platforms. Current Opinion in Immunology 20(4):450-459 (2008).

(56) References Cited

OTHER PUBLICATIONS

Lonberg, Nils. Human Antibodies From Transgenic Animals. Nature Biotechnology 23(9):1117-1125 (2005).
Lossius, Andreas. et al. High-throughput Sequencing of TCR Repertoires in Multiple Sclerosis Reveals Intrathecal Enrichment of EBV-reactive CD8+ T Cells. European Of Journal Immunnology 44(11):3439-3452 (2014).
Lu, Chenyang. et al. Clinical Significance of T Cell Receptor Repertoire in Primary Sjogren's Syndrome. EBioMedicine 84:104252, 1-12 (2022).
Maciocia, Paul M. et al. Supplemental Figures: Targeting the T cell receptor β-chain constant region for immunotherapy of T cell malignancies. Nature Medicine 23(12):1416-1423 (2017). Retrieved Oct. 8, 2024 at URL: https://static-content.springer.com/esm/art%3A10.1038%2Fnm.4444/MediaObjects/41591_2017_BFnm4444_MOESM1_ESM.pdf. 6 pages.
Maeda, T. et al. Amelioration of acute graft-versus-host disease and re-establishment of tolerance by short-term treatment with an anti-TCR antibody. Journal of immunology 153(9):4311-4320 (1994).
Marks, James D, and Andrew Bradbury. Selection of Human Antibodies From Phage Display Libraries. Methods in Molecular Biology 48:161-176 (2004).
Marks, James D. et al. By-passing Immunization Human Antibodies from V-gene Libraries Displayed on Phage. Journal of Molecular Biology 222(3):581-597 (1991).
Martin, Andrew CR. Protein Sequence and Structure Analysis of Antibody Variable Domains. Antibody Engineering:422-439 (2001).
Matsumoto, Y. et al. Successful prevention and treatment of autoimmune encephalomyelitis by short-term administration of anti-T-cell receptor alpha beta antibody. Immunology 81(1):1-7 (1994).
Mayer, Gene. et al. Chapter 10: Major Histocompatibility Complex (MHC) And T-Cell Receptors—Role In Immune Responses. In: Microbiology and Immunology on-line, University of South Carolina School of Medicine: 1-6 (2010).
McCafferty, J. et al. Phage Antibodies: Filamentous Phage Displaying Antibody Variable Domains. Nature 348(6301):552-554 (1990).
McGoff, Paul, and David S. Scher. Solution Formulation of Proteins/Peptides:In McNally EJ., ed, Protein Formulation and Delivery:139-158 (2000).
McLellan, Jason S. et al. Structure of HIV-1 gp120 V1/V2 Domain with Broadly Neutralizing Antibody PG9. Nature 480(7377):336-343 (2011).
Meermeier, Erin W. et al. Human TRAV1-2-negative MR1-restricted T cells detect *S. pyogenes* and alternatives to MAIT riboflavin-based antigens. Nat Commun 7:12506, 1-12 (2016).
Meeting Abstracts. 33rd Annual Meeting & Pre-Conference Programs of the Society for Immunotherapy of Cancer (SITC 2018). Journal for Immunotherapy of Cancer 6(Suppl 1):207-398 (2018).
Meilleur, Courtney. et al. Bacterial Superantigens Expand and Activate, Rather than Delete or Incapacitate, Preexisting Antigen-Specific Memory CD8+ T Cells. J Infect Dis 219(8):1307-1317 (2019). Published online Nov. 12, 2018.
Milosevic, Jelena D, and Robert Kralovics. Genetic and Epigenetic Alterations of Myeloproliferative Disorders. International Journal of Hematology 97(2):183-197 (2013). Published Online Dec. 12, 2012.
Milstein, C, and A C Cuello. Hybrid Hybridomas and Their Use in Immunohistochemistry. Nature 305(5934):537-540 (1983).
Moore, et al. Abstract C180: A novel bispecific platform for potent redirected killing of B-cell lymphoma. Mol Cancer Ther 8 (12_Supplement): C180 (2009).
Mosca, Paul J. et al. Dendritic cell vaccines. Frontiers in Bioscience 12:4050-4060 (2007).
Motozono, Chihiro. et al. Molecular Basis of a Dominant T Cell Response to an HIV Reverse Transcriptase 8-mer Epitope Presented by the Protective Allele HLA-B*51:01. Journal of Immunology 192(7):3428-3434 (2014).
Myers, et al. Optimal alignments in linear space. CABIOS 4(1):11-17 (1988).
Nagy, Attila. et al. Stability of Cytotoxic Luteinizing Hormone-releasing Hormone Conjugate (AN-152) Containing Doxorubicin 14-O-Hemiglutarate in Mouse and Human Serum in vitro: Implications for the Design of Preclinical Studies. Proc Natl Acad Sci U S A 97(2):829-834 (2000).
Nair et al., Epitope Recognition by Diverse Antibodies Suggests Conformational Convergence in an Antibody Response. The Journal of Immunology, 168:2371-2382 (2002).
Natsume, Akito et al. Engineered Antibodies of IgG1/IgG3 Mixed Isotype with Enhanced Cytotoxic Activities. Cancer Research 68(10):3863-3872 (2008).
Ni, Jian. Research Progress and Prospects of Antibodymoics and Antibody-Based Drugs, Modern Immunology 26(4):265-268 (2006). Abstract Only. One page.
No Author, "33rd Annual Meeting & Pre-Conference Programs of the Society for Immunotherapy of Cancer (SITC 2018)", Journal for Immuno Therapy of Cancer, 2018, vol. 6(1), No. 115, pp. 1-192.
Nomoto, K. et al. Tolerance induction in a fully allogeneic combination using anti-T cell receptor-alpha beta monoclonal antibody, low dose irradiation, and donor bone marrow transfusion. Transplantation 59(3):395-401 (1995).
Ohtsuka, Eiko. et al. An Alternative Approach to Deoxyoligonucleotides as Hybridization Probes by Insertion of Deoxyinosine at Ambiguous Codon Positions. Journal of Biological Chemistry 260(5):2605-2608 (1985).
Okazaki, Akira. et al. Fucose Depletion From Human IgG1 Oligosaccharide Enhances Binding Enthalpy and Association Rate Between IgG1 and FcgammaRIIIa. Journal of Molecular Biology 336(5):1239-1249 (2004).
Osbourn, Jane. et al. From Rodent Reagents to Human Therapeutics Using Antibody Guided Selection. Methods 36(1):61-68 (2005).
Owais, Mohammad. et al. Chloroquine Encapsulated in Malaria-infected Erythrocyte-specific Antibody-bearing Liposomes Effectively Controls Chloroquine-resistant Plasmodium Berghei Infections in Mice. Antimicrobial Agents and Chemotherapy 39(1):180-184 (1995).
Padlan, Eduardo A. A Possible Procedure for Reducing the Immunogenicity of Antibody Variable Domains While Preserving Their Ligand-binding Properties. Molecular Immunology 28(4-5):489-498 (1991).
Pardanani, Animesh D. et al. MPL515 Mutations in Myeloproliferative and Other Myeloid Disorders: a Study of 1182 Patients. Blood 108(10):3472-3476 (2006).
Pardanani, et al. Discordant distribution of JAK2V617F mutation in siblings with familial myeloproliferative disorders. Blood 107(11):4572-3 (2006).
Payne, J. et al., "Two Monoclonal Rat Antibodies with Specificity for the β-Chain Variable Region Vβ6 of the Murine T-Cell Receptor", Proc. Natl. Acad. Sci., 1988, vol. 85, pp. 7695-7698.
PCT/US2020/019329 International Search Report and Written Opinion dated Jun. 26, 2020.
PCT/US2020/060557 International Search Report and Written Opinion dated Mar. 30, 2021.
PCT/US2021/047574 International Search Report and Written Opinion dated Feb. 17, 2022.
PCT/US2021/047773 International Search Report and Written Opinion dated Dec. 23, 2021.
PCT/US2022/023922 International Search Report and Written Opinion dated Oct. 6, 2022.
PCT/US2022/049039 International Search Report and Written Opinion dated May 10, 2023.
PCT/US2022/053705 International Search Report and Written Opinion dated Jul. 7, 2023.
PCT/US2023/011280 International Search Report and Written Opinion dated Jun. 28, 2023.
PCT/US2023/034966 International Search Report and Written Opinion dated Mar. 29, 2024.
PCT/US2023/035056 International Search Report and Written Opinion dated Mar. 5, 2024.
PCT/US2024/026686 International Search Report and Written Opinion dated Sep. 23, 2024.

(56) References Cited

OTHER PUBLICATIONS

Pearson, William R, and David J Lipman. Improved Tools For Biological Sequence Comparison. PNAS USA 85(8):2444-2448 (1988).
Pejchal, Robert. et al. A Potent and Broad Neutralizing Antibody Recognizes and Penetrates the HIV Glycan Shield. Science 334(6059):1097-1103 (2011).
Petersen, Jan. et al. Diverse T Cell Receptor Gene Usage in HLA-DQ8-associated Celiac Disease Converges Into a Consensus Binding Solution. Structure 24(10):1643-1657 (2016).
Petkova, Stefka B. et al. Enhanced Half-life of Genetically Engineered Human IgG1 Antibodies in a Humanized FcRn Mouse Model: Potential Application in Humorally Mediated Autoimmune Disease. International Immunology 18(12):1759-1769 (2006).
Pikman, et al. MPLW515L Is a Novel Somatic Activating Mutation in Myelofibrosis with Myeloid Metaplasia. PLoS Med. 2006;3(7):e270.
Pluckthun, A. Chapter 11: Antibodies From *Escherichia coli*. The Pharmacology of Monoclonal Antibodies 113:269-315 (1994).
Porritt, Rebecca A. et al. HLA Class I-associated Expansion of TRBV11-2 T Cells in Multisystem Inflammatory Syndrome in Children. The Journal of Clinical Investigation 131(10):e146614, 1-13 (2021).
Presta: Antibody Engineering. Curr Op Struct Biol 2:593-596 (1992).
Presta, Leonard G. et al. Humanization of an Antibody Directed Against IgE. Journal of Immunology 151(5): 2623-2632 (1993).
Presta, Leonard G. et al. Humanization of an Anti-vascular Endothelial Growth Factor Monoclonal Antibody for the Therapy of Solid Tumors and Other Disorders. Cancer Research 57(20):4593-4599 (1997).
Queen, Cary. et al. A Humanized Antibody That Binds to the Interleukin 2 Receptor. Proceedings of the National Academy of Sciences 86(24):10029-10033 (1989).
Ranade, Vasant V. Drug Delivery Systems. 1. Site-specific Drug Delivery Using Liposomes as Carriers. Journal of Clinical Pharmacology 29(8):685-694 (1989).
Riechmann, Lutz. et al. Reshaping Human Antibodies for Therapy. Nature 332(6162):323-327 (1988).
Ripka, James et al. Two Chinese Hamster Ovary Glycosylation Mutants Affected in the Conversion of GDP-mannose to GDP-fucose. Archives of Biochemistry and Biophysics 249(2):533-545 (1986).
Rosok, Mae Joanne. et al. A Combinatorial Library Strategy for the Rapid Humanization of Anticarcinoma BR96 Fab. The Journal of Biological Chemistry 271(37):22611-22618 (1996).
Rossolini, Gian Maria. et al. Use Of Deoxyinosine-containing Primers Vs Degenerate Primers For Polymerase Chain Reaction Based On Ambiguous Sequence Information. Molecular and Cellular Probes 8(2):91-98 (1994).
Rowntree, Louise C. et al. A Shared TCR Bias Toward an Immunogenic EBV Epitope Dominates in HLA-B*07:02-Expressing Individuals. Journal of Immunology 205(6):1524-1534 (2020).
Samanen, James. et al. Chemical Approaches to Improve the Oral Bioavailability of Peptidergic Molecules. Journal of Pharmacy and Pharmacology 48(2):119-135 (1996).
Sanchez-Ruiz, Jose M. et al. Differential Scanning Calorimetry of the Irreversible Thermal Denaturation of Thermolysin. Biochemistry 27(5):1648-1652 (1988).
Schachter, Harry. et al. Biosynthetic Controls that Determine the Branching and Microheterogeneity of Protein-bound Oligosaccharides. Biochemistry and Cell Biology 64(3):163-181 (1986).
Scheid, Johannes F. et al. Sequence and Structural Convergence of Broad and Potent HIV Antibodies that Mimic CD4 Binding. Science 333(6049):1633-1637 (2011).
Scheuermann, R.H. and Racila, E. CD19 Antigen in Leukemia and Lymphoma Diagnosis and Immunotherapy. Leukemia & Lymphoma 18(5-6):385-397 (1995).
Schreier, Hans. et al. Targeting of Liposomes to Cells Expressing CD4 Using Glycosylphosphatidylinositol-anchored gp120. Influence of Liposome Composition on Intracellular Trafficking. The Journal of Biological Chemistry 269(12):9090-9098 (1994).
Scott, et al. JAK2 exon 12 mutations in polycythemia vera and idiopathic erythrocytosis. N Engl J Med 356(5):459-68 (2007).
Shields, Robert L. et al. High Resolution Mapping of the Binding Site on Human IgG1 for Fc Gamma RI, Fc Gamma RII, Fc Gamma RIII, and FcRn and design of IgG1 Variants with Improved Binding to the Fc Gamma R. Journal of Biological Chemistry 276(9):6591-6604 (2001).
Sidhu, Sachdev S. et al. Phage-displayed Antibody Libraries of Synthetic Heavy Chain Complementarity Determining Regions. Journal of Molecular Biology 338(2):299-310 (2004).
Sim, Gek Kee. et al. Primary Structure Of Human T-Cell Receptor Alpha-chain. Nature 312(5996):771-775 (1984).
Sims, Martin J. et al. A Humanized CD18 Antibody Can Block Function Without Cell Destruction. Journal of Immunology 151(4):2296-2308 (1993).
Smith, et al. T cell inactivation and cytokine deviation promoted by anti-CD3 mAbs. Curr Opin Immunol 9(5):648-54 (1997).
Smith, Temple F, and Waterman Michael S. Comparison of Biosequences. Advances in applied mathematics 2(4):482-489 (1981).
Song, De-Gang. et al. CD27 Costimulation Augments the Survival and Antitumor Activity of Redirected Human T cells in vivo. Blood 119(3):696-706 (2012).
Srivastava, Shivani, and Stanley R Riddell. Engineering CAR-T cells: Design concepts. Trends in immunology 36(8):494-502 (2015).
Staerz, Uwe D, and Michael J. Bevan. Activation of resting T lymphocytes by a monoclonal antibody directed against an allotypic determinant on the T cell receptor. Eur. J. Immunol 16:263-270 (1986).
Stegelmann, F. et al. DNMT3a Mutations in Myeloproliferative Neoplasms. Leukemia 25(7):1217-1219 (2011).
Stein, et al. Disruption of the ASXL1 gene is frequent in primary, post-essential thrombocytosis and post-polycythemia vera myelofibrosis, but not essential thrombocytosis or polycythemia vera: analysis of molecular genetics and clinical phenotypes. Haematologica 96(10):1462-9 (2011).
Stein, et al. Natural Killer (NK)- and T-Cell Engaging Antibody-Derived Therapeutics. Antibodies 1(1):88-123 (2012).
Stein, Sokrates. et al. Protective Roles of SIRT1 in Atherosclerosis. Cell Cycle 10(4):640-647 (2011).
Streltsov, Victor A. et al. Structure of a Shark IgNAR Antibody Variable Domain and Modeling of an Early-developmental Isotype. Protein Science 14(11):2901-2909 (2005).
Surman, Sherri L. et al. Clonally Related CD8+ T Cells Responsible for Rapid Population of Both Diffuse Nasal-associated Lymphoid Tissue and Lung After Respiratory Virus Infection. Journal of Immunology 187(2):835-841 (2011).
Suzuki-Inoue, et al. Involvement of the Snake Toxin Receptor CLEC-2, in Podoplanin-mediated Platelet Activation, by Cancer Cells. The Journal of Biological Chemistry, 282(36):25993-26001 (2007).
Szeto, Christopher. et al. Molecular Basis of a Dominant SARS-CoV-2 Spike-Derived Epitope Presented by HLA-A*02:01 Recognised by a Public TCR. Cells 10(10):2646, 1-15 (2021).
Tan, Huo. et al. Clonal expanded TRA and TRB subfamily T cells in peripheral blood from patients with diffuse large B-cell lymphoma. Hematology 15(2):81-87 (2010).
Tang, Yong. et al. Regulation of Antibody-dependent Cellular Cytotoxicity by IgG Intrinsic and Apparent Affinity for Target Antigen. Journal of Immunology 179(5):2815-2823 (2007).
Tastan, Cihan. et al. Tuning of human MAIT cell activation by commensal bacteria species and MR1-dependent T-cell presentation. Mucosal Immunol 11(6):1591-1605 (2018).
Ten Berg et al. Selective expansion of a peripheral blood CD8+ memory T cell subset expressing both granzyme B and L-selectin during primary viral infection in renal allograft recipients. Transplant Proc 30(8):3975-3977 (1998).
Torgov, Michael Y. et al. Generation of an Intensely Potent Anthracycline by a Monoclonal Antibody-beta-galactosidase Conjugate. Bioconjugate Chemistry 16(3):717-721 (2005).

(56) References Cited

OTHER PUBLICATIONS

Traunecker, André et al. Bispecific Single Chain Molecules (Janusins) Target Cytotoxic Lymphocytes on HIV Infected Cells. The EMBO Journal 10(12):3655-3659 (1991).
Tutt, Alison. et al. Trispecific F(ab')3 Derivatives that Use Cooperative Signaling via the TCR/CD3 Complex and CD2 to Activate and Redirect Resting Cytotoxic T cells. Journal of Immunology 147(1):60-69 (1991).
Umezawa, F, and Y Eto. Liposome Targeting to Mouse Brain: Mannose as a Recognition Marker. Biochemical and Biophysical Research Communications 153(3):1038-1044 (1988).
UniProt reference No. P04626. Receptor Tyrosine-Protein Kinase erbB-2. Record created Nov. 1, 1988. pp. 1-19. Retrieved Sep. 27, 2024 at URL: https://www.uniprot.org/uniprotkb/P04626/entry.
UniProt reference No. Q9HBE4. Interleukin-21. Record created Mar. 1, 2001. pp. 1-9. Retrieved Sep. 27, 2024 at URL: https://www.uniprot.org/uniprotkb/Q9HBE4/entry.
UniProtKB Accession No. A0A075B6N4. T cell receptor beta variable 25-1. Record created Oct. 1, 2014. pp. 1-9. Retrieved Sep. 9, 2024 at URL: https://www.uniprot.org/uniprotkb/A0A075B6N4/entry.
UniProtKB Accession No. A0AOB4J240. T cell receptor alpha variable 10. Record created Mar. 11, 2015. pp. 1-9. Retrieved Sep. 9, 2024 at URL: https://www.uniprot.org/uniprotkb/A0A0B4J240/entry.
UniProtKB Accession No. A0A1G7UTW6_9SPHI. Uncharacterized protein Pedobacter terrae (Nov. 22, 2017). Retrieved Jul. 16, 2024 at URL: https://rest.uniprot.org/unisave/A0A1G7UTW6?format=txt&versions=1. One page.
UniProtKB Accession No. A0A2V7GPM2_9BACT. Uncharacterized protein Gemmatimonadetes bacterium (Sep. 12, 2018). Retrieved Jul. 16, 2024 at URL: https://rest.uniprot.org/unisave/A0A2V7GPM2?format=txt&versions=1. One page.
UniProtKB Accession No. O00220. Tumor necrosis factor receptor superfamily member 10A. Record created Jul. 1, 1997. Retrieved Aug. 16, 2024 at URL: https://www.uniprot.org/uniprotkb/O00220/entry pp. 1-9.
UniProtKB Accession No. O14763. Tumor necrosis factor receptor superfamily member 10B. Record created Jan. 1, 1998. Retrieved Aug. 16, 2024 at URL: https://www.uniprot.org/uniprotkb/O14763/entry pp. 1-10.
UniProtKB Accession No. O95760. Interleukin-33. Record created May 1, 1999. pp. 1-10. Retrieved Sep. 9, 2024 at URL: https://www.uniprot.org/uniprotkb/O95760/entry.
UniProtKB Accession No. O95866. Megakaryocyte and platelet inhibitory receptor G6b. Record created May 1, 1999. Retrieved Aug. 16, 2024 at URL: https://www.uniprot.org/uniprotkb/O95866/entry pp. 1-11.
UniProtKB Accession No. P01137. Transforming growth factor beta-1 proprotein. Record created Nov. 1, 1988. Retrieved Aug. 16, 2024 at URL: https://www.uniprot.org/uniprotkb/P01137/entry pp. 1-17.
UniProtKB Accession No. P01562. Interferon alpha-1/13. Record created Nov. 1, 1988. pp. 1-10. Retrieved Sep. 9, 2024 at URL: https://www.uniprot.org/uniprotkb/P01562/entry.
UniProtKB Accession No. P01563. Interferon alpha-2. Record created Nov. 1, 1988. pp. 1-12. Retrieved Oct. 9, 2024 at URL: https://www.uniprot.org/uniprotkb/P01563/entry.
UniProtKB Accession No. P01566. Interferon alpha-10. Record created Nov. 1, 1988. pp. 1-10. Retrieved Sep. 9, 2024 at URL: https://www.uniprot.org/uniprotkb/P01566/entry.
UniProtKB Accession No. P01567. Interferon alpha-7. Record created Nov. 1, 1988. pp. 1-7. Retrieved Sep. 9, 2024 at URL: https://www.uniprot.org/uniprotkb/P01567/entry.
UniProtKB Accession No. P01568. IFN21_HUMAN. Record created Nov. 1, 1988. pp. 1-7. Retrieved Sep. 9, 2024 at URL: https://www.uniprot.org/uniprotkb/P01568/entry.
UniProtKB Accession No. P01569. Interferon alpha-5. Record created Nov. 1, 1988. pp. 1-10. Retrieved Sep. 9, 2024 at URL: https://www.uniprot.org/uniprotkb/P01569/entry.
UniProtKB Accession No. P01570. IFN14_HUMAN. Record created Nov. 1, 1988. pp. 1-7. Retrieved Sep. 9, 2024 at URL: https://www.uniprot.org/uniprotkb/P01570/entry.
UniProtKB Accession No. P01574. Interferon beta. Record created Nov. 1, 1988. pp. 1-9. Retrieved Sep. 9, 2024 at URL: https://www.uniprot.org/uniprotkb/P01574/entry.
UniProtKB Accession No. P05013. Interferon alpha-6. Record created Nov. 1, 1988. pp. 1-11. Retrieved Sep. 9, 2024 at URL: https://www.uniprot.org/uniprotkb/P05013/entry.
UniProtKB Accession No. P05014. Interferon alpha-4. Record created Nov. 1, 1988. pp. 1-11. Retrieved Sep. 9, 2024 at URL: https://www.uniprot.org/uniprotkb/P05014/entry.
UniProtKB Accession No. P05106. Integrin beta-3. Record created Nov. 1, 1988. Retrieved Aug. 16, 2024 at URL: https://www.uniprot.org/uniprotkb/P05106/entry pp. 1-20.
UniProtKB Accession No. P05107. Integrin beta-2. Record created Nov. 1, 1988. Retrieved Aug. 16, 2024 at URL: https://www.uniprot.org/uniprotkb/P05107/entry pp. 1-15.
UniProtKB Accession No. P07359. Platelet glycoprotein Ib alpha chain. Record created Nov. 1, 1988. Retrieved Aug. 16, 2024 at URL: https://www.uniprot.org/uniprotkb/P07359/entry pp. 1-15.
UniProtKB Accession No. P08514. Integrin alpha-IIb. Record created Nov. 1, 1988. Retrieved Aug. 16, 2024 at URL: https://www.uniprot.org/uniprotkb/P08514/entry pp. 1-15.
UniProtKB Accession No. P10600. Transforming growth factor beta-3 proprotein. Record created Jul. 1, 1989. Retrieved Aug. 16, 2024 at URL: https://www.uniprot.org/uniprotkb/P10600/entry pp. 1-11.
UniProtKB Accession No. P10721. Mast/stem cell growth factor receptor Kit. Record created Jul. 1, 1989. Retrieved Aug. 16, 2024 at URL: https://www.uniprot.org/uniprotkb/P10721/entry pp. 1-20.
UniProtKB Accession No. P12318. Low affinity immunoglobulin gamma Fc region receptor II-a. Record created Oct. 1, 1989. Retrieved Aug. 16, 2024 at URL: https://www.uniprot.org/uniprotkb/P12318/entry pp. 1-9.
UniProtKB Accession No. P16109. P-selectin. Record created Apr. 1, 1990. Retrieved Aug. 16, 2024 at URL: https://www.uniprot.org/uniprotkb/P16109/entry pp. 1-12.
UniProtKB Accession No. P28906. Hematopoietic progenitor cell antigen CD34. Record created Dec. 1, 1992. Retrieved Aug. 16, 2024 at URL: https://www.uniprot.org/uniprotkb/P28906/entry pp. 1-10.
UniProtKB Accession No. P29459. Interleukin-12 subunit alpha. Record created Apr. 1, 1993. pp. 1-13. Retrieved Sep. 9, 2024 at URL: https://www.uniprot.org/uniprotkb/P29459/entry.
UniProtKB Accession No. P29460. Interleukin-12 subunit beta. Record created Apr. 1, 1993. pp. 1-10. Retrieved Sep. 9, 2024 at URL: https://www.uniprot.org/uniprotkb/P29460/entry.
UniProtKB Accession No. P30408. Transmembrane 4 L6 family member 1. Record created Apr. 1, 1993. Retrieved Aug. 16, 2024 at URL: https://www.uniprot.org/uniprotkb/P30408/entry pp. 1-7.
UniProtKB Accession No. P32881. Interferon alpha-8. Record created Oct. 1, 1993. pp. 1-7. Retrieved Sep. 9, 2024 at URL: https://www.uniprot.org/uniprotkb/P32881/entry.
UniProtKB Accession No. P36888. Receptor-type tyrosine-protein kinase FLT3. Record created Jun. 1, 1994. Retrieved Aug. 16, 2024 at URL: https://www.uniprot.org/uniprotkb/P36888/entry pp. 1-13.
UniProtKB Accession No. P36897. TGF-beta receptor type-1. Record created Jun. 1, 1994. Retrieved Aug. 16, 2024 at URL: https://www.uniprot.org/uniprotkb/P36897/entry pp. 1-16.
UniProtKB Accession No. P37173. TGF-beta receptor type-2. Record created Oct. 1, 1994. Retrieved Aug. 16, 2024 at URL: https://www.uniprot.org/uniprotkb/P37173/entry pp. 1-18.
UniProtKB Accession No. P40238. Thrombopoietin receptor. Record created Feb. 1, 1995. Retrieved Aug. 16, 2024 at URL: https://www.uniprot.org/uniprotkb/P40238/entry pp. 1-11.
UniProtKB Accession No. P40933. Interleukin-15. Record created Feb. 1, 1995. pp. 1-9. Retrieved Sep. 9, 2024 at URL: https://www.uniprot.org/uniprotkb/P40933/entry.
UniProtKB Accession No. P56856. CLD_Human. 14 pages. Retrieved Oct. 7, 2024 at URL: https://www.uniprot.org/uniprotkb/P56856/entry.

(56) References Cited

OTHER PUBLICATIONS

UniProtKB Accession No. P60568. Interleukin-2. Record created Mar. 15, 2004. pp. 1-12. Retrieved Jul. 12, 2024 at URL: https://www.uniprot.org/uniprotkb/P60568/entry.
UniProtKB Accession No. P61812. Transforming growth factor beta-2 proprotein. Record created Jun. 7, 2004. Retrieved Aug. 16, 2024 at URL: https://www.uniprot.org/uniprotkb/P61812/entry pp. 1-12.
UniProtKB Accession No. Q02487. Desmocollin-2. Record created Feb. 1, 1994. Retrieved Aug. 16, 2024 at URL: https://www.uniprot.org/uniprotkb/Q02487/entry pp. 1-15.
UniProtKB Accession No. Q03167. Transforming growth factor beta receptor type 3. Record created Feb. 1, 1994. Retrieved Aug. 16, 2024 at URL: https://www.uniprot.org/uniprotkb/Q03167/entry pp. 1-10.
UniProtKB Accession No. Q14116. Interleukin-18. Record created Nov. 1, 1996. pp. 1-10. Retrieved Sep. 9, 2024 at URL: https://www.uniprot.org/uniprotkb/Q14116/entry.
UniProtKB Accession No. Q9H293. Interleukin-25. Record created Mar. 1, 2001. pp. 1-11. Retrieved Sep. 9, 2024 at URL: https://www.uniprot.org/uniprotkb/Q9H293/entry.
UniProtKB Accession No. Q9NPF7. Interleukin-23 subunit alpha. Record created Oct. 1, 2000. pp. 1-13. Retrieved Sep. 9, 2024 at URL: https://www.uniprot.org/uniprotkb/Q9NPF7/entry.
UniProtKB Accession No. Q9NYJ7. DLL3_Human. Record created Oct. 1, 2000. pp. 1-13. Retrieved Jul. 12, 2024 at URL: https://www.uniprot.org/uniprotkb/Q9NYJ7.
Urakami, Akane et al. An Envelope-Modified Tetravalent Dengue Virus-Like-Particle Vaccine Has Implications for Flavivirus Vaccine Design. Journal of virology 91(23):e00090-17, 1-16 (2017).
U.S. Appl. No. 15/465,564 Notice of Allowance dated Nov. 10, 2021.
U.S. Appl. No. 15/465,564 Notice of Allowance dated Oct. 29, 2021.
U.S. Appl. No. 15/465,564 Office Action dated Apr. 29, 2020.
U.S. Appl. No. 15/465,564 Office Action dated May 26, 2021.
U.S. Appl. No. 15/465,564 Office Action dated Oct. 13, 2020.
U.S. Appl. No. 15/465,564 Office Action dated Sep. 9, 2019.
U.S. Appl. No. 16/960,704 Office Action dated Dec. 22, 2023.
U.S. Appl. No. 16/960,704 Office Action dated Jul. 5, 2024.
U.S. Appl. No. 16/980,730 Notice of Allowance dated Jun. 13, 2024.
U.S. Appl. No. 16/980,730 Office Action dated Feb. 12, 2024.
U.S. Appl. No. 16/980,771 Office Action dated Jan. 10, 2024.
U.S. Appl. No. 17/256,917 Notice of Allowance dated Sep. 7, 2023.
U.S. Appl. No. 17/366,638 Office Action dated Apr. 25, 2024.
U.S. Appl. No. 17/366,638 Office Action dated Aug. 27, 2024.
U.S. Appl. No. 17/402,325 Office Action dated Sep. 24, 2024.
U.S. Appl. No. 17/529,017 Office Action dated Nov. 18, 2022.
U.S. Appl. No. 17/820,634 Office Action dated Apr. 19, 2023.
U.S. Appl. No. 17/820,634 Office Action dated Aug. 11, 2023.
U.S. Appl. No. 17/820,634 Office Action dated Aug. 15, 2023.
U.S. Appl. No. 17/820,794 Office Action dated Dec. 29, 2023.
U.S. Appl. No. 17/820,794 Office Action dated Mar. 31, 2023.
U.S. Appl. No. 17/820,794 Office Action dated Sep. 15, 2023.
U.S. Appl. No. 17/820,800 Office Action dated Feb. 21, 2023.
U.S. Appl. No. 17/820,800 Office Action dated Jun. 1, 2023.
U.S. Appl. No. 17/820,805 Office Action dated Apr. 26, 2024.
U.S. Appl. No. 17/820,805 Office Action dated Aug. 14, 2023.
U.S. Appl. No. 17/820,806 Office Action dated Apr. 12, 2023.
U.S. Appl. No. 17/820,806 Office Action dated Aug. 15, 2023.
U.S. Appl. No. 17/820,811 Office Action dated Feb. 14, 2024.
U.S. Appl. No. 17/820,811 Office Action dated May 25, 2023.
U.S. Appl. No. 17/820,818 Office Action dated Jun. 1, 2023.
U.S. Appl. No. 17/820,818 Office Action dated Mar. 12, 2024.
Valkenburg, Sophie A. et al. Molecular Basis for Universal HLA-A*0201-restricted CD8+ T-cell Immunity Against Influenza Viruses. Proceedings of the National Academy of Sciences of the United States of America 113(16):4440-4445 (2016).
Van Dijk, Marc A. et al. Human Antibodies as Next Generation Therapeutics. Current Opinion in Chemical Biology 5(4):368-374 (2001).
Van Mierlo, Carlo PM, and Elles Steensma. Protein Folding and Stability Investigated by Fluorescence, Circular Dichroism (CD), and Nuclear Magnetic Resonance (NMR) Spectroscopy: the Flavodoxin Story. Journal of Biotechnology 79(3):281-298 (2000).
Vantourout, Pierre et al. Innate TCRβ-chain engagement drives human T cells toward distinct memory-like effector phenotypes with immunotherapeutic potentials. Science Advances 9(49):eadj6174, 1-19 (2023).
Viney, Joanne L. et al. Generation of Monoclonal Antibodies Against a Human T Cell Receptor Beta Chain Expressed in Transgenic Mice. Hybridoma 11(6):701-713 (1992).
Vitetta, Ellen S. et al. Redesigning Nature's Poisons to Create Anti-tumor Reagents. Science 238(4830):1098-1104 (1987).
Vollmers, H P. et al. Death by Stress: Natural IgM-induced Apoptosis. Methods and Findings in Experimental and Clinical Pharmacology 27(3):185-191 (2005).
Vollmers, H P. et al. The "Early Birds": Natural IgM Antibodies and Immune Surveillance. Histology and Histopathology 20(3):927-937 (2005).
Vyas, et al., "Natural ligands and antibody-based fusion proteins: harnessing the immune system against cancer" Cell (2013) p. 1-11.
Vyas, M. et al., "Natural ligands and antibody-based fusion proteins: harnessing the immune system against cancer", Trends Mol Med, 2014, vol. 20, No. 2, pp. 72-82.
Walker, Laura M. et al. Broad and Potent Neutralizing Antibodies from an African Donor Reveal a New HIV-1 Vaccine Target. Science 326(5950):285-289 (2009).
Walker, Laura M. et al. Broad Neutralization Coverage of Hiv by Multiple Highly Potent Antibodies. Nature 477(7365):466-470 (2011).
Wang, Zhenguang et al. Current status and perspectives of chimeric antigen receptor modified T cells for cancer treatment. Protein and Cell 8(12):896-925 (2017).
Watanabe, M. et al. Interleukin-21 Can Efficiently Restore Impaired Antibody-dependent Cell-mediated Cytotoxicity in Patients With Oesophageal Squamous Cell Carcinoma. British Journal of Cancer 102(3):520-529 (2010).
Willemsen, R A. et al. Grafting Primary Human T Lymphocytes With Cancer-specific Chimeric Single Chain and Two Chain TCR. Gene Therapy 7(16):1369-1377 (2000).
Winkler et al., Changing the Antigen Binding Specificity by Single Point Mutations of an Anti-p24 (HIV-1) Antibody. Journal of Immunology 165(8):4505-4514 (2000).
Winter, Greg. et al. Making Antibodies by Phage Display Technology. Annual Review of Immunology 12(1):433-455 (1994).
Wright, Ann, and Sherie L. Morrison. et al. Effect of Glycosylation on Antibody Function: Implications for Genetic Engineering. Trends in Biotechnology 15(1):26-32 (1997).
Xiang, Jianhua H. et al. Modification in Framework Region I Results in a Decreased Affinity of Chimeric Anti-TAG72 antibody. Molecular Immunology 28(1-2): 141-148 (1991).
Xu, Jian. et al. MIR548P and TRAV39 Are Potential Indicators of Tumor Microenvironment and Novel Prognostic Biomarkers of Esophageal Squamous Cell Carcinoma. Journal of Clinical Oncology 2022:3152114, 1-20 (2022).
Yamane-Ohnuki, Naoko. et al. Establishment of FUT8 Knockout Chinese Hamster Ovary Cells: an Ideal Host Cell Line for Producing Completely Defucosylated Antibodies With Enhanced Antibody-dependent Cellular Cytotoxicity. Biotechnology and Bioengineering 87(5):614-622 (2004).
Yang, Xinbo. et al. Structural basis for clonal diversity of the human T-cell response to a dominant influenza virus epitope. J Biol Chem 292(45):18618-18627 (2017).
Yazaki, Paul J, and Anna M Wu. Expression of Recombinant Antibodies in Mammalian Cell Lines. Methods in Molecular Biology 248:255-268 (2004).
Yohannes, Dawit A. et al. Deep Sequencing of Blood and Gut T-cell Receptor B-chains Reveals Gluten-induced Immune Signatures in Celiac Disease. Scientific Reports 7(1):17977, 1-12 (2017).

(56) References Cited

OTHER PUBLICATIONS

Zhang, Tong. et al. An NKp30-Based Chimeric Antigen Receptor Promotes T cell Effector Functions and Antitumor Efficacy In Vivo. Journal of Immunology 189(5):2290-2299 (2012).
Zhang, Tong. et al. Transgenic TCR Expression: Comparison of Single Chain With Full-length Receptor Constructs for T-cell Function. Cancer Gene Therapy 11(7):487-496 (2004).
Zhou, Hongyu. et al. A Novel Risk Score System of Immune Genes Associated With Prognosis in Endometrial Cancer. Cancer Cell International 20:240, 1-12 (2020).
Zitti, et al. Natural killer cells in inflammation and autoimmunity. Cytokine & Growth Factor Reviews 42:37-46 (2018).
Almagro et al.: Progress and Challenges in the Design and Clinical Development of Antibodies for Cancer Therapy. Frontiers in immunology; 8, 1751 (2018) doi:10.3389/fimmu.2017.01751 https://www.frontiersin.org/articles/10.3389/fimmu.2017.01751/full.
Barthelemy, Pierre A. et al. Comprehensive analysis of the factors contributing to the stability and solubility of autonomous human VH domains. The Journal of biological chemistry 283(6):3639-3654 (2008).
Beiboer, Sigrid HW. et al. Guided selection of a pan carcinoma specific antibody reveals similar binding characteristics yet structural divergence between the original murine antibody and its human equivalent. Journal of Molecular Biology 296(3):833-849 (2000).
Benmebarek, et al., Killing Mechanisms of Chimeric Antigen Receptor (CAR) T Cells. International Journal of Molecular Sciences 20(6):1283 (2019).
Blythe, Martin J, and Darren R Flower. Benchmarking B cell epitope prediction: underperformance of existing methods. Protein science 14(1):246-248 (2005). Published online Dec. 2, 2004.
British Medical Association. Definition of Polypeptide. p. 457. The British Medical Association Illustrated Medical Dictionary, First UK Edition, 2002, Dorling Kindersley, London, England.
Chiu, et al. Antibody Structure and Function: The Basis for Engineering Therapeutics. Antibodies 8(4):55 (2019). 80 pages.
Choi, Yoonjoo, and Charlotte M Deane. Predicting antibody complementarity determining region structures without classification. Molecular bioSystems 7(12):3327-3334 (2011).
Co-pending U.S. Appl. No. 19/080,243, inventors Tan; Seng-Lai et al., filed Mar. 14, 2025.
Co-pending U.S. Appl. No. 19/175,269, inventors Bayliffe; Andrew et al., filed Apr. 10, 2025.
Co-pending U.S. Appl. No. 19/175,671, inventor Bayliffe; Andrew, filed Apr. 10, 2025.
Co-pending U.S. Appl. No. 19/208,873, inventors Loew; Andreas et al., filed May 15, 2025.
Co-pending U.S. Appl. No. 19/214,564, inventors Tan; Seng-Lai et al., filed May 21, 2025.
Couzi, Lionel. et al. Antibody-dependent anti-cytomegalovirus activity of human Gamma delta T cells expressing CD16 (FcgammaRIIIa). Blood 119(6):1418-1427 (2012).
De Genst, Erwin. et al. Antibody Repertoire Development in Camelids. Developmental and Comparative Immunology 30(1-2):187-198 (2006).
Desmyter, Aline. et al. Camelid Nanobodies: Killing Two Birds with One Stone. Current Opinion in Structural Biology 32:1-8 (2015).
Dondelinger, Mathieu. et al. Understanding the significance and implications of antibody numbering and antigen-binding surface/residue definition. Frontiers in Immunology 9(2278):1-15 (2018).
George, Richard A, and Jaap Heringa. An analysis of protein domain linkers: their classification and role in protein folding. Protein engineering 15(11):871-879 (2002).
Gershoni, Jonathan M. et al. Epitope mapping: the first step in developing epitope-based vaccines. BioDrugs 21(3):145-156 (2007).
Gherardin, Nicholas A. et al. Human blood MAIT cell subsets defined using MR1 tetramers. Immunology and cell biology 96(5):507-525 (2018).
Grabstein, et al. Cloning of a T cell growth factor that interacts with the β chain of the interleukin-2 receptor. Science 264(5161): 965-968 (1994).
International Search Report and Written Opinion issued in PCT/US2019/040592, mailed Jan. 3, 2020.
Janeway Jr, Charles A. et al. The rearrangement of antigen-receptor gene segments controls lymphocyte development. Immunobiology: The Immune System in Health and Disease. 5th Edition. New York: Garland Science. 1-17 (2001).
Kriegsmann, Katharina. et al. NKT cells—New players in CAR cell immunotherapy? European Journal of Haematology 101(6):750-757 (2018).
Ladner, Robert C. Mapping the epitopes of antibodies. Biotechnology and genetic engineering reviews 24(1):1-30 (2007).
Lin, Yuan. et al. Improved Affinity of a Chicken Single-chain Antibody to Avian Infectious Bronchitis Virus by Site-directed Mutagenesis of Complementarity-determining Region H3. African Journal of Biotechnology 10(79):18294-18302 (2011).
Lydard, Peter. et al. In Antibodies: Generation of diversity. Immunology :76-85 (2011).
Makins, Marian, ed. Definition of Polypeptide. p. 1207. Collins English Dictionary, Third Edition, Updated 1995, HarperCollins Publishers, Glasgow, Scotland.
McLaughlin-Taylor, Elizabeth. et al. Identification of the major late human cytomegalovirus matrix protein pp65 as a target antigen for CD8+ virus-specific cytotoxic T lymphocytes. Journal of medical virology 43(1):103-110 (1994).
PCT/US2018/029951 International Search Report and Written Opinion dated Jul. 3, 2018.
PCT/US2024/020796 International Search Report and Written Opinion dated Aug. 8, 2024.
PCT/US2024/025875 International Search Report and Written Opinion dated Dec. 17, 2024.
PCT/US2024/033300 International Search Report and Written Opinion dated Jan. 29, 2025.
PCT/US2024/044469 International Search Report and Written Opinion dated Feb. 14, 2025.
Schreiber, Andreas. et al. 3D-Epitope-Explorer (3DEX): localization of conformational epitopes within three-dimensional structures of proteins. Journal of computational chemistry 26(9):879-887 (2005).
Sela-Culang, Inbal. et al. The structural basis of antibody-antigen recognition. Frontiers in immunology 4:302, 1-13 (2013).
Shore, David A. et al. Chapter 12: Glycosylation and the function of the T cell co-receptor CD8. Advances in experimental medicine and biology 564:71-84 (2005).
Sze, Daniel M. et al. Clonal cytotoxic T cells are expanded in myeloma and reside in the CD8(+)CD57(+)CD28(−) compartment. Blood 98(9):2817-2827 (2001).
Tutt, Alison L. et al. Activation and preferential expansion of rat cytotoxic (CD8) T cells in vitro and in vivo with a bispecific (anti-TCR alpha/beta x anti-CD2) F(ab')2 antibody. Journal of immunology 155(6):2960-2971 (1995).
UniProtKB Accession No. O14931. Natural cytotoxicity triggering receptor 3. Record created Jan. 1, 1998. Retrieved Nov. 14, 2024 at URL: https://www.uniprot.org/uniprotkb/O14931/entry pp. 1-10.
UniProtKB Accession No. P01854. Immunoglobulin heavy constant epsilon. Record created Nov. 1, 1988. Retrieved Nov. 15, 2024 at URL: https://www.uniprot.org/uniprotkb/P01854/entry pp. 1-10.
UniProtKB Accession No. P01859. Immunoglobulin heavy constant gamma 2. Record created Nov. 1, 1988. pp. 1-9. Retrieved Oct. 11, 2024 at URL: https://www.uniprot.org/uniprotkb/P01859/entry.
UniProtKB Accession No. P01860. Immunoglobulin heavy constant gamma 3. Record created Nov. 1, 1988. pp. 1-14. Retrieved Oct. 11, 2024 at URL: https://www.uniprot.org/uniprotkb/P01860/entry.
UniProtKB Accession No. P01861. Immunoglobulin heavy constant gamma 4. Record created Nov. 1, 1988. pp. 1-13. Retrieved Oct. 11, 2024 at URL: https://www.uniprot.org/uniprotkb/P01861/entry.
UniProtKB Accession No. P01871. Immunoglobulin heavy constant mu. Record created Nov. 1, 1988. Retrieved Nov. 15, 2024 at URL: https://www.uniprot.org/uniprotkb/P01871/entry pp. 1-12.

(56) References Cited

OTHER PUBLICATIONS

UniProtKB Accession No. P01876. Immunoglobulin heavy constant alpha 1. Record created Nov. 1, 1988. Retrieved Nov. 15, 2024 at URL: https://www.uniprot.org/uniprotkb/P01876/entry pp. 1-9.
UniProtKB Accession No. P01877. Immunoglobulin heavy constant alpha 2. Record created Nov. 1, 1988. Retrieved Nov. 15, 2024 at URL: https://www.uniprot.org/uniprotkb/P01877/entry pp. 1-9.
UniProtKB Accession No. PODOX5. Immunoglobulin gamma-1 heavy chain. Record created Mar. 15, 2017. Retrieved Nov. 6, 2024 at URL: https://www.uniprot.org/uniprotkb/P0DOX5/entry pp. 1-4.
UniProtKB Accession No. Q685J3. MUC17_Human. Record created Oct. 11, 2004. Retrieved Apr. 24, 2025. Available at URL: https://www.uniprot.org/uniprotkb/Q685J3/entry pp. 1-8.
UniProtKB Accession No. Q96NY8. Nectin-4. Record created Dec. 1, 2001. pp. 1-10. Retrieved Apr. 23, 2025. Available at URL: https://www.uniprot.org/uniprotkb/Q96NY8/entry.
UniProtKB Accession No. Q9H293. Interleukin-25. Record created Mar. 1, 2001. pp. 1-7. Retrieved Sep. 9, 2024 at URL: https://www.uniprot.org/uniprotkb/Q9H293/entry.
U.S. Appl. No. 16/960,704 Corrected Notice of Allowability dated Dec. 20, 2024.
U.S. Appl. No. 16/960,704 Notice of Allowance dated Dec. 19, 2024.
U.S. Appl. No. 17/366,638 Office Action dated Apr. 17, 2025.
U.S. Appl. No. 17/402,318 Office Action dated Mar. 19, 2025.
U.S. Appl. No. 17/402,320 Notice of Allowance dated Apr. 15, 2025.
U.S. Appl. No. 17/402,320 Office Action dated Dec. 12, 2024.
U.S. Appl. No. 17/402,322 Office Action dated Nov. 19, 2024.
U.S. Appl. No. 17/402,325 Notice of Allowance dated Apr. 14, 2025.
U.S. Appl. No. 17/402,329 Office Action dated May 8, 2025.
U.S. Appl. No. 17/402,329 Office Action dated Nov. 5, 2024.
U.S. Appl. No. 17/584,892 Office Action dated Feb. 3, 2025.
U.S. Appl. No. 17/820,805 Notice of Allowance dated Jan. 24, 2025.
U.S. Appl. No. 17/820,805 Office Action dated Oct. 31, 2024.
U.S. Appl. No. 17/932,416 Office Action dated May 29, 2025.
U.S. Appl. No. 18/472,920 Notice of Allowance dated Apr. 9, 2025.
U.S. Appl. No. 18/472,920 Office Action dated Nov. 4, 2024.
Ward, E Sally. et al. Binding Activities of a Repertoire of Single Immunoglobulin Variable Domains Secreted from *Escherichia coli*. Nature 341(6242):544-546 (1989).
Watson, C.T. et al. Revisiting the T-cell receptor alpha/delta locus and possible associations with multiple sclerosis. Genes and immunity 12(2):59-66 (2011).
Weisser, Nina E, and J Christopher Hall. Applications of single-chain variable fragment antibodies in therapeutics and diagnostics. Biotechnology advances 27(4):502-520 (2009).
Wu, Zhihua. et al. T cell receptor beta-chain CDR3 spectratyping and cytomegalovirus activation in allogeneic hematopoietic stem cell transplant recipients. Journal of Zhejiang University Medical Sciences 45(5):515-521 (2016). With English abstract.
Wucherpfennig, Kai W. et al. T cell receptor V alpha-V beta repertoire and cytokine gene expression in active multiple sclerosis lesions. The Journal of experimental medicine 175(4):993-1002 (1992).

* cited by examiner

VH

Framework 1 / CDR 1

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 |
|---|---|---|---|---|---|---|---|---|---|---|---|---|---|---|---|---|---|---|---|---|---|---|---|---|---|---|---|---|---|---|---|---|---|---|---|
| SEQ ID NO: 1 | Q | V | Q | L | Q | Q | S | G | P | E | L | V | K | P | G | T | S | V | K | I | S | C | K | A | S | G | Y | S | F | T | T | Y | Y | I | H |
| SEQ ID NO: 9 | Q | V | Q | L | V | Q | S | G | A | E | V | K | K | P | G | S | S | V | K | V | S | C | K | A | S | G | Y | S | F | T | T | Y | Y | I | H |

Framework 2 / CDR 2

| | 36 | 37 | 38 | 39 | 40 | 41 | 42 | 43 | 44 | 45 | 46 | 47 | 48 | 49 | 50 | 51 | 52 | 52a | 53 | 54 | 55 | 56 | 57 | 58 | 59 | 60 | 61 | 62 | 63 | 64 | 65 |
|---|---|---|---|---|---|---|---|---|---|---|---|---|---|---|---|---|---|---|---|---|---|---|---|---|---|---|---|---|---|---|---|
| SEQ ID NO: 1 | W | V | K | Q | R | P | G | Q | G | L | E | W | I | G | **W** | **F** | ***F*** | ***P*** | ***G*** | ***S*** | ***G*** | ***N*** | **I** | **K** | **Y** | **N** | **E** | **K** | **F** | **K** | **G** |
| SEQ ID NO: 9 | W | V | R | Q | A | P | G | Q | G | L | E | W | M | G | **W** | **F** | ***F*** | ***P*** | ***G*** | ***S*** | ***G*** | ***N*** | **I** | **K** | **Y** | **N** | **E** | **K** | **F** | **K** | **G** |

| | 66 | 67 | 68 | 69 | 70 | 71 | 72 | 73 | 74 | 75 | 76 | 77 | 78 | 79 | 80 | 81 | 82 | 82a | 82b | 82c | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|---|---|---|---|---|---|---|---|---|---|---|---|---|
| SEQ ID NO: 1 | K | A | T | L | T | A | D | T | S | S | S | T | A | Y | M | Q | L | S | S | L | T | S | E | E | S | A | V | Y | F | C | A | G |
| SEQ ID NO: 9 | R | V | T | I | T | A | D | T | S | T | S | T | A | Y | M | E | L | S | S | L | R | S | E | D | T | A | V | Y | Y | C | A | G |

CDR 3 / Framework 4

| | 95 | 96 | 97 | 98 | 99 | 100 | 100a | 100b | 101 | 102 | 103 | 104 | 105 | 106 | 107 | 108 | 109 | 110 | 111 | 112 | 113 |
|---|---|---|---|---|---|---|---|---|---|---|---|---|---|---|---|---|---|---|---|---|---|
| SEQ ID NO: 1 | ***S*** | ***Y*** | ***Y*** | ***S*** | ***Y*** | ***D*** | ***V*** | ***L*** | ***D*** | ***Y*** | W | G | H | G | T | T | L | T | V | S | S |
| SEQ ID NO: 9 | ***S*** | ***Y*** | ***Y*** | ***S*** | ***Y*** | ***D*** | ***V*** | ***L*** | ***D*** | ***Y*** | W | G | Q | G | T | T | V | T | V | S | S |

FIG. 1A

VL

| | Framework 1 | | | | | | | | | | | | | | | | | | | | | | CDR 1 | | | | | | | | | | |
|---|---|---|---|---|---|---|---|---|---|---|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 |
| SEQ ID NO: 2 | D | I | L | M | T | Q | S | Q | K | F | M | S | T | S | L | G | D | R | V | S | V | S | C | *K* | *A* | *S* | *Q* | *N* | *V* | *G* | *I* | *N* | *V* | *V* |
| SEQ ID NO: 10 | D | I | Q | M | T | Q | S | P | S | F | L | S | A | S | V | G | D | R | V | T | I | T | C | *K* | *A* | *S* | *Q* | *N* | *V* | *G* | *I* | *N* | *V* | *V* |
| SEQ ID NO: 11 | D | I | Q | M | T | Q | S | P | S | S | L | S | A | S | V | G | D | R | V | T | I | T | C | *K* | *A* | *S* | *Q* | *N* | *V* | *G* | *I* | *N* | *V* | *V* |

| | Framework 2 | | | | | | | | | | | | | | CDR 2 | | | | | | |
|---|---|---|---|---|---|---|---|---|---|---|---|---|---|---|---|---|---|---|---|---|---|
| | 35 | 36 | 37 | 38 | 39 | 40 | 41 | 42 | 43 | 44 | 45 | 46 | 47 | 48 | 49 | 50 | 51 | 52 | 53 | 54 | 55 | 56 |
| SEQ ID NO: 2 | W | H | Q | Q | K | P | G | Q | S | P | K | A | L | I | Y | *S* | *S* | *S* | *H* | *R* | *Y* | *S* |
| SEQ ID NO: 10 | W | H | Q | Q | K | P | G | K | A | P | K | A | L | I | Y | *S* | *S* | *S* | *H* | *R* | *Y* | *S* |
| SEQ ID NO: 11 | W | H | Q | Q | K | P | G | K | V | P | K | A | L | I | Y | *S* | *S* | *S* | *H* | *R* | *Y* | *S* |

| | Framework 3 | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|
| | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 | 85 | 86 | 87 | 88 |
| SEQ ID NO: 2 | G | V | P | D | R | F | T | G | S | G | S | G | T | D | F | T | L | T | I | N | N | V | Q | S | E | D | L | A | E | Y | F | C |
| SEQ ID NO: 10 | G | V | P | S | R | F | S | G | S | G | S | G | T | E | F | T | L | T | I | S | S | L | Q | P | E | D | F | A | T | Y | F | C |
| SEQ ID NO: 11 | G | V | P | S | R | F | S | G | S | G | S | G | T | D | F | T | L | T | I | S | S | L | Q | P | E | D | V | A | T | Y | F | C |

| | CDR 3 | | | | | | | | | Framework 4 | | | | | | | | | |
|---|---|---|---|---|---|---|---|---|---|---|---|---|---|---|---|---|---|---|---|
| | 89 | 90 | 91 | 92 | 93 | 94 | 95 | 96 | 97 | 98 | 99 | 100 | 101 | 102 | 103 | 104 | 105 | 106 | 107 |
| SEQ ID NO: 2 | *Q* | *Q* | *F* | *K* | *S* | *Y* | *P* | *L* | *T* | F | G | A | G | T | K | L | E | L | K |
| SEQ ID NO: 10 | *Q* | *Q* | *F* | *K* | *S* | *Y* | *P* | *L* | *T* | F | G | Q | G | T | K | L | E | I | K |
| SEQ ID NO: 11 | *Q* | *Q* | *F* | *K* | *S* | *Y* | *P* | *L* | *T* | F | G | Q | G | T | K | L | E | I | K |

FIG. 1B

VH

Framework 1 / CDR 1

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 |
|---|---|---|---|---|---|---|---|---|---|---|---|---|---|---|---|---|---|---|---|---|---|---|---|---|---|---|---|---|---|---|---|---|---|---|---|
| SEQ ID NO: 15 | D | V | Q | L | V | E | S | G | G | G | L | V | Q | P | G | G | S | R | K | L | S | C | A | A | S | G | F | T | F | S | N | F | G | M | H |
| SEQ ID NO: 23 | Q | V | Q | L | V | E | S | G | G | G | V | V | Q | P | G | R | S | L | R | L | S | C | A | A | S | G | F | T | F | S | N | F | G | M | H |
| SEQ ID NO: 24 | E | V | Q | L | V | E | S | G | G | G | L | V | Q | P | G | G | S | L | R | L | S | C | A | A | S | G | F | T | F | S | N | F | G | M | H |
| SEQ ID NO: 25 | E | V | Q | L | V | E | S | G | G | G | L | V | Q | P | G | G | S | L | R | L | S | C | A | A | S | G | F | T | F | S | N | F | G | M | H |

Framework 2 / CDR 2

| | 36 | 37 | 38 | 39 | 40 | 41 | 42 | 43 | 44 | 45 | 46 | 47 | 48 | 49 | 50 | 51 | 52 | 52a | 53 | 54 | 55 | 56 | 57 | 58 | 59 | 60 | 61 | 62 | 63 | 64 | 65 |
|---|---|---|---|---|---|---|---|---|---|---|---|---|---|---|---|---|---|---|---|---|---|---|---|---|---|---|---|---|---|---|---|
| SEQ ID NO: 15 | W | V | R | Q | A | P | D | K | G | L | E | W | V | A | Y | I | S | S | G | S | S | T | I | Y | Y | A | D | T | L | K | G |
| SEQ ID NO: 23 | W | V | R | Q | A | P | G | K | G | L | E | W | V | A | Y | I | S | S | G | S | S | T | I | Y | Y | A | D | T | L | K | G |
| SEQ ID NO: 24 | W | V | R | Q | A | P | G | K | G | L | E | W | V | S | Y | I | S | S | G | S | S | T | I | Y | Y | A | D | T | L | K | G |
| SEQ ID NO: 25 | W | V | R | Q | A | P | G | K | G | L | E | W | V | S | Y | I | S | S | G | S | S | T | I | Y | Y | A | D | T | L | K | G |

Framework 3

| | 66 | 67 | 68 | 69 | 70 | 71 | 72 | 73 | 74 | 75 | 76 | 77 | 78 | 79 | 80 | 81 | 82 | 82a | 82b | 82c | 83 | 84 | 85 | 86 | 87 | 88 | 89 | 90 | 91 | 92 | 93 | 94 |
|---|---|---|---|---|---|---|---|---|---|---|---|---|---|---|---|---|---|---|---|---|---|---|---|---|---|---|---|---|---|---|---|---|
| SEQ ID NO: 15 | R | F | T | I | S | R | D | N | P | K | N | T | L | F | L | Q | M | T | S | L | R | S | E | D | T | A | M | Y | Y | C | A | R |
| SEQ ID NO: 23 | R | F | T | I | S | R | D | N | S | K | N | T | L | Y | L | Q | M | N | S | L | R | A | E | D | T | A | V | Y | Y | C | A | R |
| SEQ ID NO: 24 | R | F | T | I | S | R | D | N | A | K | N | S | L | Y | L | Q | M | N | S | L | R | A | E | D | T | A | V | Y | Y | C | A | R |
| SEQ ID NO: 25 | R | F | T | I | S | R | D | N | S | K | N | T | L | Y | L | Q | M | N | S | L | R | A | E | D | T | A | V | Y | Y | C | A | R |

CDR 3 / Framework 4

| | 95 | 96 | 97 | 98 | 99 | 100 | 101 | 102 | 103 | 104 | 105 | 106 | 107 | 108 | 109 | 110 | 111 | 112 | 113 |
|---|---|---|---|---|---|---|---|---|---|---|---|---|---|---|---|---|---|---|---|
| SEQ ID NO: 15 | R | G | E | G | A | M | D | Y | W | G | Q | G | T | S | V | T | V | S | S |
| SEQ ID NO: 23 | R | G | E | G | A | M | D | Y | W | G | Q | G | T | T | V | T | V | S | S |
| SEQ ID NO: 24 | R | G | E | G | A | M | D | Y | W | G | Q | G | T | T | V | T | V | S | S |
| SEQ ID NO: 25 | R | G | E | G | A | M | D | Y | W | G | Q | G | T | T | V | T | V | S | S |

FIG. 2A

VL — Framework 1 / CDR 1

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 |
|---|---|---|---|---|---|---|---|---|---|---|---|---|---|---|---|---|---|---|---|---|---|---|---|---|---|---|---|---|---|---|---|---|---|---|
| SEQ ID NO: 16 | E | N | V | L | T | Q | S | P | A | I | M | S | A | S | L | G | E | K | V | T | M | S | C | *R* | *A* | *S* | *S* | *S* | *V* | - | *N* | *Y* | *I* | *Y* |
| SEQ ID NO: 26 | D | N | Q | L | T | Q | S | P | S | F | L | S | A | S | V | G | D | R | V | T | I | T | C | *R* | *A* | *S* | *S* | *S* | *V* | - | *N* | *Y* | *I* | *Y* |
| SEQ ID NO: 27 | D | N | Q | L | T | Q | S | P | S | S | L | S | A | S | V | G | D | R | V | T | I | T | C | *R* | *A* | *S* | *S* | *S* | *V* | - | *N* | *Y* | *I* | *Y* |
| SEQ ID NO: 28 | E | N | V | L | T | Q | S | P | A | T | L | S | V | S | P | G | E | R | A | T | L | S | C | *R* | *A* | *S* | *S* | *S* | *V* | - | *N* | *Y* | *I* | *Y* |
| SEQ ID NO: 29 | Q | N | V | L | T | Q | P | P | S | - | A | S | G | T | P | G | Q | R | V | T | I | S | C | *R* | *A* | *S* | *S* | *S* | *V* | - | *N* | *Y* | *I* | *Y* |
| SEQ ID NO: 30 | S | N | E | L | T | Q | P | P | S | - | V | S | V | S | P | G | Q | T | A | R | I | T | C | *R* | *A* | *S* | *S* | *S* | *V* | - | *N* | *Y* | *I* | *Y* |

Framework 2 / CDR 2

| | 35 | 36 | 37 | 38 | 39 | 40 | 41 | 42 | 43 | 44 | 45 | 46 | 47 | 48 | 49 | 50 | 51 | 52 | 53 | 54 | 55 | 56 |
|---|---|---|---|---|---|---|---|---|---|---|---|---|---|---|---|---|---|---|---|---|---|---|
| SEQ ID NO: 16 | W | Y | Q | Q | K | S | D | A | S | P | K | L | W | I | Y | *Y* | *T* | *S* | *N* | *L* | *A* | *P* |
| SEQ ID NO: 26 | W | Y | Q | Q | K | P | G | K | A | P | K | L | L | I | Y | *Y* | *T* | *S* | *N* | *L* | *A* | *P* |
| SEQ ID NO: 27 | W | Y | Q | Q | K | P | G | K | A | P | K | L | L | I | Y | *Y* | *T* | *S* | *N* | *L* | *A* | *P* |
| SEQ ID NO: 28 | W | Y | Q | Q | K | P | G | Q | A | P | R | L | L | I | Y | *Y* | *T* | *S* | *N* | *L* | *A* | *P* |
| SEQ ID NO: 29 | W | Y | Q | Q | L | P | G | T | A | P | K | L | L | I | Y | *Y* | *T* | *S* | *N* | *L* | *A* | *P* |
| SEQ ID NO: 30 | W | Y | Q | Q | K | S | G | Q | A | P | V | L | V | I | Y | *Y* | *T* | *S* | *N* | *L* | *A* | *P* |

FIG. 2B

Framework 3

| | 57 | 58 | 59 | 60 | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 | 85 | 86 | 87 | 88 |
|---|---|---|---|---|---|---|---|---|---|---|---|---|---|---|---|---|---|---|---|---|---|---|---|---|---|---|---|---|---|---|---|---|
| SEQ ID NO: 16 | G | V | P | T | R | F | S | G | S | G | S | G | N | S | Y | S | L | T | I | S | S | M | E | G | E | D | A | A | T | Y | Y | C |
| SEQ ID NO: 26 | G | V | P | S | R | F | S | G | S | G | S | G | N | E | Y | T | L | T | I | S | S | L | Q | P | E | D | F | A | T | Y | Y | C |
| SEQ ID NO: 27 | G | V | P | S | R | F | S | G | S | G | S | G | N | D | Y | T | L | T | I | S | S | L | Q | P | E | D | F | A | T | Y | Y | C |
| SEQ ID NO: 28 | G | I | P | A | R | F | S | G | S | G | S | G | N | E | Y | T | L | T | I | S | S | L | Q | S | E | D | F | A | V | Y | Y | C |
| SEQ ID NO: 29 | G | V | P | D | R | F | S | G | S | G | S | G | N | S | Y | S | L | A | I | S | G | L | R | S | E | D | E | A | D | Y | Y | C |
| SEQ ID NO: 30 | G | I | P | E | R | F | S | G | S | G | S | G | N | M | Y | T | L | T | I | S | G | A | Q | V | E | D | E | A | D | Y | Y | C |

CDR 3 Framework 4

| | 89 | 90 | 91 | 92 | 93 | 94 | 95 | 96 | 97 | 98 | 99 | 100 | 101 | 102 | 103 | 104 | 105 | 106 | 107 |
|---|---|---|---|---|---|---|---|---|---|---|---|---|---|---|---|---|---|---|---|
| SEQ ID NO: 16 | *Q* | *Q* | *F* | *T* | *S* | *S* | *P* | *F* | *T* | F | G | S | G | T | K | L | E | I | K |
| SEQ ID NO: 26 | *Q* | *Q* | *F* | *T* | *S* | *S* | *P* | *F* | *T* | F | G | Q | G | T | K | L | E | I | K |
| SEQ ID NO: 27 | *Q* | *Q* | *F* | *T* | *S* | *S* | *P* | *F* | *T* | F | G | Q | G | T | K | L | E | I | K |
| SEQ ID NO: 28 | *Q* | *Q* | *F* | *T* | *S* | *S* | *P* | *F* | *T* | F | G | Q | G | T | K | L | E | I | K |
| SEQ ID NO: 29 | *Q* | *Q* | *F* | *T* | *S* | *S* | *P* | *F* | *T* | F | G | T | G | T | K | V | T | V | L |
| SEQ ID NO: 30 | *Q* | *Q* | *F* | *T* | *S* | *S* | *P* | *F* | *T* | F | G | T | G | T | K | V | T | V | L |

FIG. 2C

```
6DKP_Vb6_4  -IAGITQAPTSQILAAGRRMTLRCTQ-DMRHNAMYWYRQDLGLGLRLIHYSNTAGTTG--KGEVPDGYSVSRANTDDFPLTLASAVPSQTSVYFCASS-WSFGT--EA
2BNU_Vb6_5  ---GVTQTPKFQVLKTGQSMTLQCAQ-DMNHEYMSWYRQDPGMGLRLIHYSVGAGITD--QGEVPNGYNVSRSTTEDFPLRLLSAAPSQTSVYFCASS-YVGNTG-EL
4ZDH_Vb28   ---KVTQSSRYLVKRTGEKVFLECVQ-DMDHENMFWYRQDPGLGLRLIYFSYDVKMKE--KGDIPEGYSVSREKKERFSLILASASTDQTSMYLCASS-FLGTGV-EQ
5HHM_Vb19   --GGITQSPKYLFRKEGQNVTLSCEQ-NLNHDAMYWYRQDPGQGLRLIYYSQIVNDFQ--KGDIAEGYSVSREKKESFPLTVTSAQKNPTAFYLCASS--SRSSY-EQ
5KSA_Vb9    ---GVTQTPKHLITATGQRVTLRCSP-RSGDLSVYWYQQSLDQGLQFLIQYYNGEERA--KGNILERFSAQQFPDLHSELNLSSLELGDSALYFCASS-VAGTPSYEQ
5BS0_Vb5_1  --AGVTQTPRYLIKTRGQQVTLSCSP-ISGHRSVSWYQQTPGQGLQFLFEYFSETQRN--KGNFPGRFSGRQFSNSRSEMNVSTLELGDSALYLCASS-FNMATG--Q
3MFG_Vb20_1--AVVSQHPSRVIVKSGTSVKIECRSLDFQATTMFWYRQFP--SLMLMATSNEGSKATYEQGVEKDKFLINHASLTLSTLTVTSAHPEDSGFYICSA-----LAQDTQ
5C0C_Vb12_4MDAGVIQSPRHEVTEMGQQVTLRCKPIS-GHDYLFWYRQTMMRGLELLIYFNNNVPID-DSGMPEDRFSAKMPNASFSTLKIQPSEPRDSAVYFCASSLWEKLAKNIQ
```

FIG. 24B

| | Molecule F | aCD3/CD19 |
|---|---|---|
| IC50 | 0.01543 | 0.04246 |

| | Molecule G | aCD3/BCMA |
|---|---|---|
| IC50 | 0.044 | 0.0782 |

PBMC's

Purified T Cells

| | OKT3 | TCRvβ 6-5 v1 |
|---|---|---|
| EC50 | 0.01729 | 7.458 |

| | OKT3 | TCRvβ 6-5 v1 |
|---|---|---|
| EC50 | 0.03211 | 1.128 |

| | OKT3 | TCRvβ 6-5 v1 |
|---|---|---|
| EC50 | 0.03211 | 1.128 |

FIG. 102A
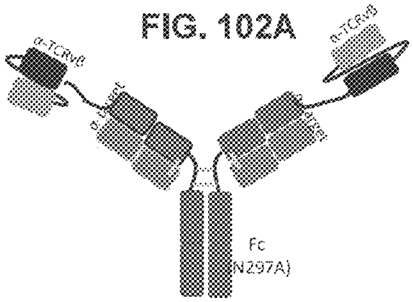
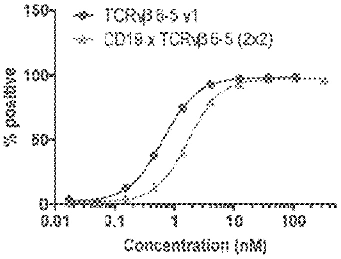
| | TCRvβ 6-5 v1 | CD19 x TCRvβ 6-5 (2x2) |
|---|---|---|
| EC50 | 0,6466 | 1,720 |
FIG. 102B
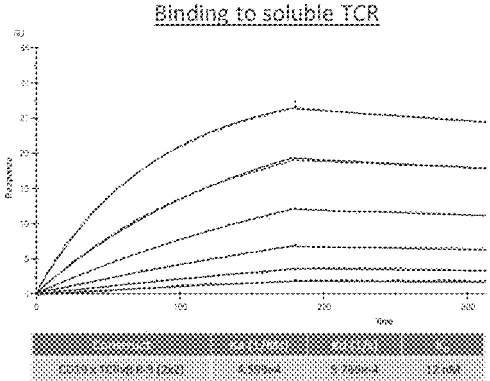
| [illegible] | [illegible] | [illegible] | [illegible] |
|---|---|---|---|
| CD19 x TCRvβ 6-5 (2x2) | [illegible] | [illegible] | 12 nM |
FIG. 102C CD19xTCRvβ 6-5 (2x2) bsAb induce B cell depletion post 6 Days*

EC50: Day 6 → 0.08 nM

CD19xCD3 (Blinatumomab) induce B cell depletion as soon as post 2 Days

EC50: Day 6 → 0.012 nM
Day 4 → 0.017 nM
Day 2 → 0.015 nM

EC50: Day 6 → 0.002 nM

EC50: Day 6 → 0.003 nM
Day 3 → 0.97 nM
Day 2 → 0.8 nM

Table 9: Alignment of TCRBV amino acid sequences (SEQ ID NOS: 3457-3516, respectively, in order of appearance)

| | | | | | | | | | | | |
|---|---|---|---|---|---|---|---|---|---|---|---|
| | FR1-IMGT | | CDR1-IMGT | FR2-IMGT | | CDR2-IMGT | | FR3-IMGT | | | CDR3-IMGT |
| | (1-26) | | (27-38) | (39-55) | | (56-65) | | (66-104) | | | (105-117) |
| Gene | A | B | BC | C | C' | C'C" | C" | D | E | F | FG |
| | (1-15) | (16-26) | (27-38) | (39-46) | (47-55) | (56-65) | (66-74) | (75-84) | (85-96) | (97-104) | |
| | ------------> | ------------> | | ------------> | ------------> | | ------------> | ------------> | ------------> | ------------> | |
| | 1 10 15 | 16 23 26 | 27 38 | 39 41 46 | 47 55 | 56 65 | 66 74 | 75 84 | 85 89 96 | 97 104 | 105 |
| | \|.........\|....\| | \|......\|..\| | \|..........\| | \|.\|....\| | \|.......\| | \|........\| | \|.......\| | \|........\| | \|...\|......\| | \|.......\| | \|..... |
| TRBV1 | DTGITQTPKYLVTAM | GSKRTMKREHL | GH........DS | MYWYRQKA | KKSLEFMFY | YNC....KEF | IENKTVP.N | RFTPECP.DS | SRLYLHVVALQQ | EDSAAYLC | TSSQ |
| TRBV2 | EPEVTQTPSHQVTQM | GQEVILRCVPI | SNH.......LY | FYWYRQIL | GQKVEFLVS | FYN....NEI | SEKSEIFDD | QFSVERP.DG | SNFTLKIRSTKL | EDSAMYFC | ASSE |
| TRBV3-1 | DTAVSQTPKYLVTQM | GNDKSIKCEQN | LGH.......DT | MYWYKQDS | KKFLKIMFS | YNN....KEL | IINETVP.N | RFSPKSP.DK | AHLNLHINSLEL | GDSAVYFC | ASSQ |
| TRBV3-2 | DTAVSQTPKYLVTQM | GKKESLK*EQN | LGH.......NA | MYWYKQDS | KKFLKTMFI | YSN....KEP | ILNETVP.N | RFSPDSP.DK | AHLNLHINSLEL | GDSAVYFC | ASSQ |
| TRBV4-1 | DTEVTQTPKHLVMGM | TNKKSLKCEQH | MGH.......RA | MYWYKQKA | KKPPELMFV | YSY....EKL | SINESVP.S | RFSPECP.NS | SLLNLHLHALQP | EDSALYLC | ASSQ |
| TRBV4-2 | ETGVTQTPRHLVMGM | TNKKSLKCEQH | LGH.......NA | MYWYKQSA | KKPLELMFV | YNF....KEQ | TENNSVP.S | RFSPECP.NS | SHLFLHLHTLQP | EDSALYLC | ASSQ |
| TRBV4-3 | ETGVTQTPRHLVMGM | TNKKSLKCEQH | LGH.......NA | MYWYKQSA | KKPLELMFV | YSL....EER | VENNSVP.S | RFSPECP.NS | SHLFLHLHTLQP | EDSALYLC | ASSQ |
| TRBV5-1 | KAGVTQTPRYLIKTR | GQQVTLSCSPI | SGH.......RS | VSWYQQTP | GQGLQFLFE | YFS....ETQ | RNKGNFP.G | RFSGRQF.SN | SRSEMNVSTLEL | GDSALYLC | ASSL |
| TRBV5-3 | EAGVTQSPTHLIKTR | GQQVTLRCSPI | SGH.......SS | VSWYQQAP | GQGPQFIFE | YAN....ELR | RSEGNFP.N | RFSGRQF.HD | CCSEMNVSALEL | GDSALYLC | ARSL |
| TRBV5-4 | ETGVTQSPTHLIKTR | GQQVTLRCSSQ | SGH.......NT | VSWYQQAL | GQGPQFIFQ | YYR....EEE | NGRGNFP.P | RFSGLQF.PN | YSSELNVNALEL | DDSALYLC | ASSL |
| TRBV5-5 | DAGVTQSPTHLIKTR | GQQVTLRCSPI | SGH.......KS | VSWYQQVL | GQGPQFIFQ | YYE....KEE | NGRGNFP.D | RFSARQF.PN | YSSELNVNALLL | GDSALYLC | ASSL |
| TRBV5-6 | DAGVTQSPTHLIKTR | GQQVTLRCSPK | SGH.......DT | VSWYQQAL | GQGPQFIFQ | YYE....EEE | RQRGNFP.D | RFSGHQF.PN | YSSELNVNALLL | GDSALYLC | ASSL |

FIG. 109A

| | |
|---|---|
| TRBV5-7 | DAGVTQSPTHLIKTR GQHVTLRCSPI SGH.......TS VSSYQQAL GQGPQFIFQ YYE....KEE RGRGNFP.D QFSGHQF.PN YSSELNVNALLL GDSALYLC ASSL |
| TRBV5-8 | EAGVTQSPTHLIKTR GQQATLRCSPI SGH.......TS VYWYQQAL GLGLQFLLW YDE....GEE RNRGNFP.P RFSGRQF.PN YSSELNVNALEL EDSALYLC ASSL |
| TRBV6-1 | NAGVTQTPKFQVLKT GQSMTLQCAQD MNH.......NS MYWYRQDP GMGLRLIYY SAS....EGT TDKGEVP.N GYNVSRL.NK REFSLRLESAAP SQTSVYFC ASSE |
| TRBV6-2 | NAGVTQTPKFRVLKT GQSMTLLCAQD MNH.......EY MYWYRQDP GMGLRLIHY SVG....EGT TAKGEVP.D GYNVSRL.KK QNFLLGLESAAP SQTSVYFC ASSY |
| TRBV6-3 | NAGVTQTPKFRVLKT GQSMTLLCAQD MNH.......EY MYWYRQDP GMGLRLIHY SVG....EGT TAKGEVP.D GYNVSRL.KK QNFLLGLESAAP SQTSVYFC ASSY |
| TRBV6-4 | IAGITQAPTSQILAA GRRMTLRCTQD MRH.......NA MYWYRQDL GLGLRLIHY SNT....AGT TGKGEVP.D GYSVSRA.NT DDFPLTLASAVP SQTSVYFC ASSD |
| TRBV6-5 | NAGVTQTPKFQVLKT GQSMTLQCAQD MNH.......EY MSWYRQDP GMGLRLIHY SVG....AGI TDQGEVP.N GYNVSRS.TT EDFPLRLLSAAP SQTSVYFC ASSY |
| TRBV6-6 | NAGVTQTPKFRILKI GQSMTLQCTQD MNH.......NY MYWYRQDP GMGLKLIYY SVG....AGI TDKGEVP.N GYNVSRS.TT EDFPLRLELAAP SQTSVYFC ASSY |
| TRBV6-7 | NAGVTQTPKFHVLKT GQSMTLLCAQD MNH.......EY MYWYRQDP GKGLRLIYY SVA....AAL TDKGEVP.N GYNVSRS.NT EDFPLKLESAAP SQTSVYFC ASSY |
| TRBV6-8 | NAGVTQTPKFHILKT GQSMTLQCAQD MNH.......GY MSWYRQDP GMGLRLIYY SAA....AGT TDK.EVP.N GYNVSRL.NT EDFPLRLVSAAP SQTSVYLC ASSY |
| TRBV6-9 | NAGVTQTPKFHILKT GQSMTLQCAQD MNH.......GY LSWYRQDP GMGLRRIHY SVA....AGI TDKGEVP.D GYNVSRS.NT EDFPLRLESAAP SQTSVYFC ASSY |
| TRBV7-1 | GAGVSQSLRHKVAKK GKDVALRYDPI SGH.......NA LYWYRQSL GQGLEFPIY FQG....KDA ADKSGLPRD RFSAQRS.EG SISTLKFQRTQQ GDLAVYLC ASSS |
| TRBV7-2 | GAGVSQSPSNKVTEK GKDVELRCDPI SGH.......TA LYWYRQSL GQGLEFLIY FQG....NSA PDKSGLPSD RFSAERT.GG SVSTLTIQRTQQ EDSAVYLC ASSL |
| TRBV7-3 | GAGVSQTPSNKVTEK GKYVELRCDPI SGH.......TA LYWYRQSL GQGPEFLIY FQG....TGA ADDSGLPND RFFAVRP.EG SVSTLKIQRTER GDSAVYLC ASSL |
| TRBV7-4 | GAGVSQSPRYKVAKR GRDVALRCDSI SGH.......VT LYWYRQTL GQGSEVLTY SQS....DAQ RDKSGRPSG RFSAERP.ER SVSTLKIQRTEQ GDSAVYLC ASSL |
| TRBV7-6 | GAGVSQSPRYKVTKR GQDVALRCDPI SGH.......VS LYWYRQAL GQGPEFLTY FNY....EAQ QDKSGLPND RFSAERP.EG SISTLTIQRTEQ RDSAMYRC ASSL |
| TRBV7-7 | GAGVSQSPRYKVTKR GQDVTLRCDPI SSH.......AT LYWYQQAL GQGPEFLTY FNY....EAQ PDKSGLPSD RFSAERP.EG SISTLTIQRTEQ RDSAMYRC ASSL |
| TRBV7-8 | GAGVSQSPRYKVAKR GQDVALRCDPI SGH.......VS LFWYQQAL GQGPEFLTY FQN....EAQ LDKSGLPSD RFFAERP.EG SVSTLKIQRTQQ EDSAVYLC ASSL |
| TRBV7-9 | DTGVSQNPRHKITKR GQNVTFRCDPI SEH.......NR LYWYRQTL GQGPEFLTY FQN....EAQ LEKSRLLSD RFSAERP.KG SFSTLEIQRTEQ GDSAMYLC ASSL |

FIG. 109B

| | |
|---|---|
| TRBV9 | DSGVTQTPKHLITAT GQRVTLRCSPR SGD.......LS VYWYQQSL DQGLQFLIQ YYN....GEE RAKGNIL.E RFSAQQF.PD LHSELNLSSLEL GDSALYFC ASSV |
| TRBV10-1 | DAEITQSPRHKITET GRQVTLACHQT WNH.......NN MFWYRQDL GHGLRLIHY SYG....VQD TNKGEVS.D GYSVSRS.NT EDLPLTLESAAS SQTSVYFC ASSE |
| TRBV10-2 | DAGITQSPRYKITET GRQVTLMCHQT WSH.......SY MFWYRQDL GHGLRLIYY SAA....ADI TDKGEVP.D GYVVSRS.KT ENFPLTLESATR SQTSVYFC ASSE |
| TRBV10-3 | DAGITQSPRHKVTET GTPVTLRCHQT ENH.......RY MYWYRQDP GHGLRLIHY SYG....VKD TDKGEVS.D GYSVSRS.KT EDFLLTLESATS SQTSVYFC AISE |
| TRBV11-1 | EAEVAQSPRYKITEK SQAVAFWCDPI SGH.......AT LYWYRQIL GQGPELLVQ FQD....ESV VDDSQLPKD RFSAERL.KG VDSTLKIQPAEL GDSAMYLC ASSL |
| TRBV11-2 | EAGVAQSPRYKIIEK RQSVAFWCNPI SGH.......AT LYWYQQIL GQGPKLLIQ FQN....NGV VDDSQLPKD RFSAERL.KG VDSTLKIQPAKL EDSAVYLC ASSL |
| TRBV11-3 | EAGVVQSPRYKIIEK KQPVAFWCNPI SGH.......NT LYWYLQNL GQGPELLIR YEN....EEA VDDSQLPKD RFSAERL.KG VDSTLKIQPAEL GDSAVYLC ASSL |
| TRBV12-1 | DAGVIQSPRHKVTEM GQSVTLRCEPI SGH.......ND LLWYRQTF VQGLELLNY FCS....WTL VDDSGVSKD *FSAQMP.DV SFSTLKIQPMEP RDLGLYFC ASSF |
| TRBV12-2 | DAGIIQSPKHEVTEM GQTVTLRCEPI FGH.......NF LFWYRDTF VQGLELLSY FRS....*SI IDNAGMPTE RFSAERP.DG SFSTLKIQPAEQ GDSAVYVC ASRL |
| TRBV12-3 | DAGVIQSPRHEVTEM GQEVTLRCKPI SGH.......NS LFWYRQTM MRGLELLIY FNN....NVP IDDSGMPED RFSAKMP.NA SFSTLKIQPSEP RDSAVYFC ASSL |
| TRBV12-4 | DAGVIQSPRHEVTEM GQEVTLRCKPI SGH.......DY LFWYRQTM MRGLELLIY FNN....NVP IDDSGMPED RFSAKMP.NA SFSTLKIQPSEP RDSAVYFC ASSL |
| TRBV12-5 | DARVTQTPRHKVTEM GQEVTMRCQPI LGH.......NT VFWYRQTM MQGLELLAY FRN....RAP LDDSGMPKD RFSAEMP.DA TLATLKIQPSEP RDSAVYFC ASGL |
| TRBV13 | AAGVIQSPRHLIKEK RETATLKCYPI PRH.......DT VYWYQQGP GQDPQFLIS FYE....KMQ SDKGSIP.D RFSAQQF.SD YHSELNMSSLEL GDSALYFC ASSL |
| TRBV14 | EAGVTQFPSHSVIEK GQTVTLRCDPI SGH.......DN LYWYRRVM GKEIKFLLH FVK....ESK QDESGMPNN RFLAERT.GG TYSTLKVQPAEL EDSGVYFC ASSQ |
| TRBV15 | DAMVIQNPRYQVTQF GKPVTLSCSQT LNH.......NV MYWYQQKS SQAPKLLFH YYD....KDF NNEADTP.D NFQSRRP.NT SFCFLDIRSPGL GDTAMYLC ATSR |
| TRBV16 | GEEVAQTPKHLVRGE GQKAKLYCAPI KGH.......SY VFWYQQVL KNEFKFLIS FQN....ENV FDETGMPKE RFSAKCL.PN SPCSLEIQATKL EDSAVYFC ASSQ |
| TRBV17 | EPGVSQTPRHKVTNM GQEVILRCDPS SGH.......MF VHWYRQNL RQEMKLLIS FQY....QNI AVDSGMPKE RFTAERP.NG TSSTLKIHPAEP RDSAVYLY SSG |
| TRBV18 | NAGVMQNPRHLVRRR GQEARLRCSPM KGH.......SH VYWYRQLP EEGLKFMVY LQK....ENI IDESGMPKE RFSAEFP.KE GPSILRIQQVVR GDSAAYFC ASSP |
| TRBV19 | DGGITQSPKYLFRKE GQNVTLSCEQN LNH.......DA MYWYRQDP GQGLRLIYY SQI....VND FQKGDIA.E GYSVSRE.KK ESFPLTVTSAQK NPTAFYLC ASSI |

FIG. 109C

| | |
|---|---|
| TRBV20-1 | GAVVSQHPSWVICKS GTSVKIECRSL DFQ.....ATT MFWYRQFP KQSLMLMAT SNEG...SKA TYEQGVEKD KFLINHA.SL TLSTLTVTSAHP EDSSFYIC SAR |
| TRBV21-1 | DTKVTQRPRLLVKAS EQKAKMDCVPI KAH.......SY VYWYRKKL EEELKFLVY FQN...EEL IQKAEIINE RFLAQCS.KN SSCTLEIQSTES GDTALYFC ASSK |
| TRBV23-1 | HAKVTQTPGHLVKGK GQKTKMDCTPE KGH.......TF VYWYQQNQ NKEFMLLIS FQN...EQV LQETEMHKK RFSSQCP.KN APCSLAILSSEP GDTALYLC ASSQ |
| TRBV24-1 | DADVTQTPRNRITKT GKRIMLECSQT KGH.......DR MYWYRQDP GLGLRLIYY SFD...VKD INKGEIS.D GYSVSRQ.AQ AKFSLSLESAIP NQTALYFC ATSDL |
| TRBV25-1 | EADIYQTPRYLVIGT GKKITLECSQT MGH.......DK MYWYQQDP GMELHLIHY SYG...VNS TEKGDLS.S ESTVSRI.RT EHFPLTLESARP SHTSQYLC ASSE |
| TRBV26 | DAVVTQFPRHRIIGT GKEFILQCSQN MNH.......VT MYWYRQDP GLGLKLVYY SPG...TGS TEKGDIS.E GYHVS*N.TI ASFPLTLKSAST NQTSVYLY ASSS |
| TRBV27 | EAQVTQNPRYLITVT GKKLTVTCSQN MNH.......EY MSWYRQDP GLGLRQIYY SMN...VEV TDKGDVP.E GYKVSRK.EK RNFPLILESPSP NQTSLYFC ASSL |
| TRBV28 | DVKVTQSSRYLVKRT GEKVFLECVQD MDH.......EN MFWYRQDP GLGLRLIYF SYD...VKM KEKGDIP.E GYSVSRE.KK ERFSLILESAST NQTSMYLC ASSL |
| TRBV29-1 | SAVISQKPSRDICQR GTSLTIQCQVD SQV.......TM MFWYRQQP GQSLTLIAT ANQG...SEA TYESGFVID KFPISRP.NL TFSTLTVSNMSP EDSSIYLC SVE |
| TRBV30 | SQTIHQWPATLVQPV GSPLSLECTVE GTS.....NPN LYWYRQAA GRGLQLLFY SVG....IG QISSEVP.Q NLSASRP.QD RQFILSSKKLLL SDSGFYLC AWS |

FIG. 109D

| TCRBV | SEQ ID NO | TCRBV | SEQ ID NO | TCRBV | SEQ ID NO | TCRBV | SEQ ID NO |
|---|---|---|---|---|---|---|---|
| TRBV1 | 3457 | TRBV6-2 | 3472 | TRBV7-9 | 3487 | TRBV15 | 3502 |
| TRBV2 | 3458 | TRBV6-3 | 3473 | TRBV9 | 3488 | TRBV16 | 3503 |
| TRBV3-1 | 3459 | TRBV6-4 | 3474 | TRBV10-1 | 3489 | TRBV17 | 3504 |
| TRBV3-2 | 3460 | TRBV6-5 | 3475 | TRBV10-2 | 3490 | TRBV18 | 3505 |
| TRBV4-1 | 3461 | TRBV6-6 | 3476 | TRBV10-3 | 3491 | TRBV19 | 3506 |
| TRBV4-2 | 3462 | TRBV6-7 | 3477 | TRBV11-1 | 3492 | TRBV20-1 | 3507 |
| TRBV4-3 | 3463 | TRBV6-8 | 3478 | TRBV11-2 | 3493 | TRBV21-1 | 3508 |
| TRBV5-1 | 3464 | TRBV6-9 | 3479 | TRBV11-3 | 3494 | TRBV23-1 | 3509 |
| TRBV5-3 | 3465 | TRBV7-1 | 3480 | TRBV12-1 | 3495 | TRBV24-1 | 3510 |
| TRBV5-4 | 3466 | TRBV7-2 | 3481 | TRBV12-2 | 3496 | TRBV25-1 | 3511 |
| TRBV5-5 | 3467 | TRBV7-3 | 3482 | TRBV12-3 | 3497 | TRBV26 | 3512 |
| TRBV5-6 | 3468 | TRBV7-4 | 3483 | TRBV12-4 | 3498 | TRBV27 | 3513 |
| TRBV5-7 | 3469 | TRBV7-6 | 3484 | TRBV12-5 | 3499 | TRBV28 | 3514 |
| TRBV5-8 | 3470 | TRBV7-7 | 3485 | TRBV13 | 3500 | TRBV29-1 | 3515 |
| TRBV6-1 | 3471 | TRBV7-8 | 3486 | TRBV14 | 3501 | TRBV30 | 3516 |

FIG. 109E

Alignment of affinity matured humanized Antibody A-H VL sequences (SEQ ID NOS: 3377-3389, respectively, in order of appearance)

```
a5-VL                             DIQMTQSPSFLSASVGDRVTITCKASQNVENKVAWHQQKPGKAPKALIYSSSHRYKGVPS    60
c1d2d4-VL                         DIQMTQSPSFLSASVGDRVTITCKASQNVDNKVAWHQQKPGKAPKALIYSSSHRYKGVPS    60
h3-VL                             DIQMTQSPSFLSASVGDRVTITCKASQNVDNRVAWHQQKPGKAPKALIYSSSHRYKGVPS    60
f5-VL                             DIQMTQSPSFLSASVGDRVTITCKASQNVEDRVAWHQQKPGKAPKALIYSSSHRYKGVPS    60
e4b6g3c6h2c2d1a6c3a3e6d6g2-VL     DIQMTQSPSFLSASVGDRVTITCKASQNVDDRVAWYQQKPGKAPKALIYSSSHRYKGVPS    60
e3-VL                             DIQMTQSPSFLSASVGDRVTITCKASQNVGDRVAWHQQKPGKAPKALIYSSSHRYKGVPS    60
d5-VL                             DIQMTQSPSFLSASVGDRVTITCKASQNVEDKVAWYQQKPGKAPKALIYSSSHRYKGVPS    60
d3f1g1-VL                         DIQMTQSPSFLSASVGDRVTITCKASQNVADRVAWYQQKPGKAPKALIYSSSHRYKGVPS    60
c4f4f2a2a1-VL                     DIQMTQSPSFLSASVGDRVTITCKASQNVEDRVAWYQQKPGKAPKALIYSSSHRYKGVPS    60
b5h4a4-VL                         DIQMTQSPSFLSASVGDRVTITCKASQNVDNRVAWYQQKPGKAPKALIYSSSHRYKGVPS    60
b2c5b3e2g4h6-VL                   DIQMTQSPSFLSASVGDRVTITCKASQNVGDRVAWYQQKPGKAPKALIYSSSHRYKGVPS    60
b1-VL                             DIQMTQSPSFLSASVGDRVTITCKASQNVGNRVAWYQQKPGKAPKALIYSSSHRYSGVPS    60
b4e1f3-VL                         DIQMTQSPSFLSASVGDRVTITCKASQNVGNRVAWYQQKPGKAPKALIYSSSHRYKGVPS    60
                                  ***************************** ::***:*******************.****
```

FIG. 110A

```
a5-VL                              RFSGSGSGTEFTLTISSLQPEDFATYFCQQFKSYPLTFGQGTKLEIK    107
c1d2d4-VL                          RFSGSGSGTEFTLTISSLQPEDFATYFCQQFKSYPLTFGQGTKLEIK    107
h3-VL                              RFSGSGSGTEFTLTISSLQPEDFATYFCQQFKSYPLTFGQGTKLEIK    107
f5-VL                              RFSGSGSGTEFTLTISSLQPEDFATYFCQQFKSYPLTFGQGTKLEIK    107
e4b6g3c6h2c2d1a6c3a3e6d6g2-VL      RFSGSGSGTEFTLTISSLQPEDFATYFCQQFKSYPLTFGQGTKLEIK    107
e3-VL                              RFSGSGSGTEFTLTISSLQPEDFATYFCQQFKSYPLTFGQGTKLEIK    107
d5-VL                              RFSGSGSGTEFTLTISSLQPEDFATYFCQQFKSYPLTFGQGTKLEIK    107
d3f1g1-VL                          RFSGSGSGTEFTLTISSLQPEDFATYFCQQFKSYPLTFGQGTKLEIK    107
c4f4f2a2a1-VL                      RFSGSGSGTEFTLTISSLQPEDFATYFCQQFKSYPLTFGQGTKLEIK    107
b5h4a4-VL                          RFSGSGSGTEFTLTISSLQPEDFATYFCQQFKSYPLTFGQGTKLEIK    107
b2c5b3e2g4h6-VL                    RFSGSGSGTEFTLTISSLQPEDFATYFCQQFKSYPLTFGQGTKLEIK    107
b1-VL                              RFSGSGSGTEFTLTISSLQPEDFATYFCQQFKSYPLTFGQGTKLEIK    107
b4e1f3-VL                          RFSGSGSGTEFTLTISSLQPEDFATYFCQQFKSYPLTFGQGTKLEIK    107
                                   ***********************************************
```

Consensus VL: SEQ ID NO: 230
DIQMTQSPSFLSASVGDRVTITCKASQNV G/E/A/D N/D R/K VAW Y/H
QQKPGKAPKALIYSSSHRY K/S
GVPSRFSGSGSGTEFTLTISSLQPEDFATYFCQQFKSYPLTFGQGTKLEIK
Consensus VL: SEQ ID NO: 3289
DIQMTQSPSFLSASVGDRVTITCKASQNV$X_1X_2X_3$VAW$X_4$QQKPGKAPKALIYSSSHRY$X_5$
GVPSRFSGSGSGTEFTLTISSLQPEDFATYFCQQFKSYPLTFGQGTKLEIK, wherein X1 is G, E, A or D; X2 is N or D; X3 is R or K; X4 is Y or H; and X5 is K or S

FIG. 110B

| VL sequence | SEQ ID NO: |
|---|---|
| a5-VL | 3377 |
| c1d2d4-VL | 3378 |
| h3-VL | 3379 |
| f5-VL | 3380 |
| e4b6g3c6h2c2d1a6c3a3e6d6g2-VL | 3381 |
| e3-VL | 3382 |
| d5-VL | 3383 |
| d3f1g1-VL | 3384 |
| c4f4f2a2a1-VL | 3385 |
| b5h4a4-VL | 3386 |
| b2c5b3e2g4h6-VL | 3387 |
| b1-VL | 3388 |
| b4e1f3-VL | 3389 |

FIG. 110C

Alignment of affinity matured humanized Antibody A-H VH sequences (SEQ ID NOS: 3390-3436, respectively, in order of appearance)

```
A-H.52-VH    QVQLVQSGAEVKKPGSSVKVSCKASGYSFTLGYIHWVRQAPGQGLEWMGWFFPGSGNIKY 60
A-H.53-VH    QVQLVQSGAEVKKPGSSVKVSCKASGYSFRLTYIHWVRQAPGQGLEWMGWFFPGSGNIKY 60
A-H.54-VH    QVQLVQSGAEVKKPGSSVKVSCKASGYSFHNWYIHWVRQAPGQGLEWMGWFFPGSGNIKY 60
A-H.51-VH    QVQLVQSGAEVKKPGSSVKVSCKASGYSFTTYYIHWVRQAPGQGLEWMGWFFPGSGNIKY 60
A-H.50-VH    QVQLVQSGAEVKKPGSSVKVSCKASGYSFTTYYIHWVRQAPGQGLEWMGRIFPGSGNIKY 60
A-H.47-VH    QVQLVQSGAEVKKPGSSVKVSCKASGYSFTTYYIHWVRQAPGQGLEWMGWFFPGSGNTKY 60
A-H.49-VH    QVQLVQSGAEVKKPGSSVKVSCKASGYSFTTYYIHWVRQAPGQGLEWMGWFSPGSGNTKY 60
A-H.48-VH    QVQLVQSGAEVKKPGSSVKVSCKASGYSFTTYYIHWVRQAPGQGLEWMGWFSPGSGNTKY 60
A-H.45-VH    QVQLVQSGAEVKKPGSSVKVSCKASGYSFTTYYIHWVRQAPGQGLEWMGWFSAGSGNTKY 60
A-H.46-VH    QVQLVQSGAEVKKPGSSVKVSCKASGYSFTTYYIHWVRQAPGQGLEWMGWFSAGSGNTKY 60
c2-VH        QVQLVQSGAEVKKPGSSVKVSCKASGGTFRLTYIHWVRQAPGQGLEWMGRVYPGSGNTKY 60
f5-VH        QVQLVQSGAEVKKPGSSVKVSCKASGHDFKLTYIHWVRQAPGQGLEWMGRVSPGSGNTKY 60
f3-VH        QVQLVQSGAEVKKPGSSVKVSCKASGTDFRLTYIHWVRQAPGQGLEWMGRISPGSGNTKY 60
e2-VH        QVQLVQSGAEVKKPGSSVKVSCKASGTDFKLTYIHWVRQAPGQGLEWMGRISPGSGNTKY 60
e1-VH        QVQLVQSGAEVKKPGSSVKVSCKASGTDFKLTYIHWVRQAPGQGLEWMGRVSAGSGNVKY 60
c1-VH        QVQLVQSGAEVKKPGSSVKVSCKASGTDFRLTYIHWVRQAPGQGLEWMGRVSPGSGNTKY 60
```

FIG. 110D

```
a1-VH        QVQLVQSGAEVKKPGSSVKVSCKASGTDFKLTYIHWVRQAPGQGLEWMGRVSPGSGNTKY 60
b3-VH        QVQLVQSGAEVKKPGSSVKVSCKASGTDFKLTYIHWVRQAPGQGLEWMGRVSPGSGNVKY 60
h3-VH        QVQLVQSGAEVKKPGSSVKVSCKASGTDFKLTYIHWVRQAPGQGLEWMGRISPGSGNVKY 60
c3-VH        QVQLVQSGAEVKKPGSSVKVSCKASGTDFRLTYIHWVRQAPGQGLEWMGRIFPGSGNTKY 60
a5b5c4-VH    QVQLVQSGAEVKKPGSSVKVSCKASGTDFKLTYIHWVRQAPGQGLEWMGRIFPGSGNVKY 60
d6-VH        QVQLVQSGAEVKKPGSSVKVSCKASGTDFKLTYIHWVRQAPGQGLEWMGRIFPGSGNTKY 60
h2-VH        QVQLVQSGAEVKKPGSSVKVSCKASGGTFKLTYIHWVRQAPGQGLEWMGRVSAGSGNVKY 60
c5-VH        QVQLVQSGAEVKKPGSSVKVSCKASGGTFRLTYIHWVRQAPGQGLEWMGRISAGSGNVKY 60
f2-VH        QVQLVQSGAEVKKPGSSVKVSCKASGTDFKLTYIHWVRQAPGQGLEWMGRISAGSGNTKY 60
d3-VH        QVQLVQSGAEVKKPGSSVKVSCKASGHDFRLTYIHWVRQAPGQGLEWMGRISAGSGNVKY 60
a4e4-VH      QVQLVQSGAEVKKPGSSVKVSCKASGHDFKLTYIHWVRQAPGQGLEWMGRISAGSGNVKY 60
d2-VH        QVQLVQSGAEVKKPGSSVKVSCKASGTDFKLTYIHWVRQAPGQGLEWMGRISAGSGNVKY 60
g1-VH        QVQLVQSGAEVKKPGSSVKVSCKASGHDFDKTYIHWVRQAPGQGLEWMGRIYPGSGNVKY 60
c6-VH        QVQLVQSGAEVKKPGSSVKVSCKASGGTFDKTYIHWVRQAPGQGLEWMGRISAGSGNTKY 60
g2-VH        QVQLVQSGAEVKKPGSSVKVSCKASGTDFDKTYIHWVRQAPGQGLEWMGRISAGSGNVKY 60
b4-VH        QVQLVQSGAEVKKPGSSVKVSCKASGTDFDKIYIHWVRQAPGQGLEWMGRVSAGSGNTKY 60
a6-VH        QVQLVQSGAEVKKPGSSVKVSCKASGTDFDKIYIHWVRQAPGQGLEWMGRIFAGSGNTKY 60
a2g4-VH      QVQLVQSGAEVKKPGSSVKVSCKASGTDFDKIYIHWVRQAPGQGLEWMGRISAGSGNVKY 60
b6f1-VH      QVQLVQSGAEVKKPGSSVKVSCKASGTDFDKIYIHWVRQAPGQGLEWMGRISAGSGNTKY 60
g3-VH        QVQLVQSGAEVKKPGSSVKVSCKASGTDFDKIYIHWVRQAPGQGLEWMGRISAGSGNIKY 60
d1-VH        QVQLVQSGAEVKKPGSSVKVSCKASGHDFDKFYIHWVRQAPGQGLEWMGRISAGSGNTKY 60
h4-VH        QVQLVQSGAEVKKPGSSVKVSCKASGHDFDKFYIHWVRQAPGQGLEWMGRVSAGSGNTKY 60
b2-VH        QVQLVQSGAEVKKPGSSVKVSCKASGHDFDKFYIHWVRQAPGQGLEWMGRIFAGSGNVKY 60
h6-VH        QVQLVQSGAEVKKPGSSVKVSCKASGTDFDKFYIHWVRQAPGQGLEWMGRVSAGSGNVKY 60
```

FIG. 110E

```
b1-VH    QVQLVQSGAEVKKPGSSVKVSCKASGHDFDKFYIHWVRQAPGQGLEWMGRVSAGSGNVKY 60
f4-VH    QVQLVQSGAEVKKPGSSVKVSCKASGHDFDKTYIHWVRQAPGQGLEWMGRVSAGSGNVKY 60
a3-VH    QVQLVQSGAEVKKPGSSVKVSCKASGHDFRDFYIHWVRQAPGQGLEWMGRVYPGSGSYRY 60
e6-VH    QVQLVQSGAEVKKPGSSVKVSCKASGTDFHLWYIHWVRQAPGQGLEWMGRVFAGSGSYRY 60
e3-VH    QVQLVQSGAEVKKPGSSVKVSCKASGHDFHLWYIHWVRQAPGQGLEWMGRISPGSGNVKY 60
d4-VH    QVQLVQSGAEVKKPGSSVKVSCKASGHDFHLWYIHWVRQAPGQGLEWMGRVSAGSGNVKY 60
d5-VH    QVQLVQSGAEVKKPGSSVKVSCKASGHDFHLWYIHWVRQAPGQGLEWMGRVFAGSGNTKY 60
         **************************  *  *****************  .  ***. :*
```

FIG. 110F

| | | |
|---|---|---|
| A-H.52-VH | NEKFKGRVTITADTSTSTAYMELSSLRSEDTAVYYCAGSYYSYDVLDYWGQGTTVTVSS | 119 |
| A-H.53-VH | NEKFKGRVTITADTSTSTAYMELSSLRSEDTAVYYCAGSYYSYDVLDYWGQGTTVTVSS | 119 |
| A-H.54-VH | NEKFKGRVTITADTSTSTAYMELSSLRSEDTAVYYCAGSYYSYDVLDYWGQGTTVTVSS | 119 |
| A-H.51-VH | NEKFKGRVTITADTSTSTAYMELSSLRSEDTAVYYCAGSIYSAGVLDYWGQGTTVTVSS | 119 |
| A-H.50-VH | NEKFKGRVTITADTSTSTAYMELSSLRSEDTAVYYCAGSYYSYDVLDYWGQGTTVTVSS | 119 |
| A-H.47-VH | NEKFKGRVTITADTSTSTAYMELSSLRSEDTAVYYCAGSYYSYDVLDYWGQGTTVTVSS | 119 |
| A-H.49-VH | NEKFKGRVTITADTSTSTAYMELSSLRSEDTAVYYCAGSYYSYDVLDYWGQGTTVTVSS | 119 |
| A-H.48-VH | NEKFKGRVTITADTSTSTAYMELSSLRSEDTAVYYCAVSYYSYDVLDYWGQGTTVTVSS | 119 |
| A-H.45-VH | NEKFKGRVTITADTSTSTAYMELSSLRSEDTAVYYCAVSYYSYDVLDYWGQGTTVTVSS | 119 |
| A-H.46-VH | NEKFKGRVTITADTSTSTAYMELSSLRSEDTAVYYCAGSYYSYDVLDYWGQGTTVTVSS | 119 |
| c2-VH | NEKFKGRVTITADTSTSTAYMELSSLRSEDTAVYYCAGSYYSYDVLDYWGQGTTVTVSS | 119 |
| f5-VH | NEKFKGRVTITADTSTSTAYMELSSLRSEDTAVYYCAGSYYSYDVLDYWGQGTTVTVSS | 119 |
| f3-VH | NEKFKGRVTITADTSTSTAYMELSSLRSEDTAVYYCAGSYYSYDVLDYWGQGTTVTVSS | 119 |
| e2-VH | NEKFKGRVTITADTSTSTAYMELSSLRSEDTAVYYCAGSYYSYDVLDYWGQGTTVTVSS | 119 |
| e1-VH | NEKFKGRVTITADTSTSTAYMELSSLRSEDTAVYYCAGSYYSYDVLDYWGQGTTVTVSS | 119 |
| c1-VH | NEKFKGRVTITADTSTSTAYMELSSLRSEDTAVYYCAGSYYSYDVLDYWGQGTTVTVSS | 119 |
| a1-VH | NEKFKGRVTITADTSTSTAYMELSSLRSEDTAVYYCAGSYYSYDVLDYWGQGTTVTVSS | 119 |
| b3-VH | NEKFKGRVTITADTSTSTAYMELSSLRSEDTAVYYCAGSYYSYDVLDYWGQGTTVTVSS | 119 |
| h3-VH | NEKFKGRVTITADTSTSTAYMELSSLRSEDTAVYYCAGSYYSYDVLDYWGQGTTVTVSS | 119 |
| c3-VH | NEKFKGRVTITADTSTSTAYMELSSLRSEDTAVYYCAGSYYSYDVLDYWGQGTTVTVSS | 119 |
| a5b5c4-VH | NEKFKGRVTITADTSTSTAYMELSSLRSEDTAVYYCAGSYYSYDVLDYWGQGTTVTVSS | 119 |
| d6-VH | NEKFKGRVTITADTSTSTAYMELSSLRSEDTAVYYCAGSYYSYDVLDYWGQGTTVTVSS | 119 |
| h2-VH | NEKFKGRVTITADTSTSTAYMELSSLRSEDTAVYYCAGSYYSYDVLDYWGQGTTVTVSS | 119 |
| c5-VH | NEKFKGRVTITADTSTSTAYMELSSLRSEDTAVYYCAGSYYSYDVLDYWGQGTTVTVSS | 119 |
| f2-VH | NEKFKGRVTITADTSTSTAYMELSSLRSEDTAVYYCAGSYYSYDVLDYWGQGTTVTVSS | 119 |
| d3-VH | NEKFKGRVTITADTSTSTAYMELSSLRSEDTAVYYCAGSYYSYDVLDYWGQGTTVTVSS | 119 |

FIG. 110G

```
a4e4-VH     NEKFKGRVTITADTSTSTAYMELSSLRSEDTAVYYCAGSYYSYDVLDYWGQGTTVTVSS 119
d2-VH       NEKFKGRVTITADTSTSTAYMELSSLRSEDTAVYYCAGSYYSYDVLDYWGQGTTVTVSS 119
g1-VH       NEKFKGRVTITADTSTSTAYMELSSLRSEDTAVYYCAGSYYSYDVLDYWGQGTTVTVSS 119
c6-VH       NEKFKGRVTITADTSTSTAYMELSSLRSEDTAVYYCAGSYYSYDVLDYWGQGTTVTVSS 119
g2-VH       NEKFKGRVTITADTSTSTAYMELSSLRSEDTAVYYCAGSYYSYDVLDYWGQGTTVTVSS 119
b4-VH       NEKFKGRVTITADTSTSTAYMELSSLRSEDTAVYYCAGSYYSYDVLDYWGQGTTVTVSS 119
a6-VH       NEKFKGRVTITADTSTSTAYMELSSLRSEDTAVYYCAGSYYSYDVLDYWGQGTTVTVSS 119
a2g4-VH     NEKFKGRVTITADTSTSTAYMELSSLRSEDTAVYYCAGSYYSYDVLDYWGQGTTVTVSS 119
b6f1-VH     NEKFKGRVTITADTSTSTAYMELSSLRSEDTAVYYCAGSYYSYDVLDYWGQGTTVTVSS 119

g3-VH       NEKFKGRVTITADTSTSTAYMELSSLRSEDTAVYYCAGSYYSYDVLDYWGQGTTVTVSS 119
d1-VH       NEKFKGRVTITADTSTSTAYMELSSLRSEDTAVYYCAGSYYSYDVLDYWGQGTTVTVSS 119
h4-VH       NEKFKGRVTITADTSTSTAYMELSSLRSEDTAVYYCAGSYYSYDVLDYWGQGTTVTVSS 119
b2-VH       NEKFKGRVTITADTSTSTAYMELSSLRSEDTAVYYCAGSYYSYDVLDYWGQGTTVTVSS 119
h6-VH       NEKFKGRVTITADTSTSTAYMELSSLRSEDTAVYYCAGSYYSYDVLDYWGQGTTVTVSS 119
b1-VH       NEKFKGRVTITADTSTSTAYMELSSLRSEDTAVYYCAGSYYSYDVLDYWGQGTTVTVSS 119
f4-VH       NEKFKGRVTITADTSTSTAYMELSSLRSEDTAVYYCAGSYYSYDVLDYWGQGTTVTVSS 119
a3-VH       NEKFKGRVTITADTSTSTAYMELSSLRSEDTAVYYCAGSYYSYDVLDYWGQGTTVTVSS 119
e6-VH       NEKFKGRVTITADTSTSTAYMELSSLRSEDTAVYYCAGSYYSYDVLDYWGQGTTVTVSS 119
e3-VH       NEKFKGRVTITADTSTSTAYMELSSLRSEDTAVYYCAGSYYSYDVLDYWGQGTTVTVSS 119
d4-VH       NEKFKGRVTITADTSTSTAYMELSSLRSEDTAVYYCAGSYYSYDVLDYWGQGTTVTVSS 119
d5-VH       NEKFKGRVTITADTSTSTAYMELSSLRSEDTAVYYCAGSYYSYDVLDYWGQGTTVTVSS 119
            ************************************** * **.***************
```

FIG. 110H

Consensus VH: SEQ ID NO: 231

QVQLVQSGAEVKKPGSSVKVSCKASG H/T/G/Y D/T/S F H/R/D/K/T L/D/K/T/N W/F/T/I/Y/G YIHWVRQAPGQGLEWMG R/W V/I/F F/S/Y A/P GSG N/S T/V/Y/I K/R YNEKFKGRVTITADTSTSTAYMELSSLRSEDTAVYYCA G/V S Y/I YS Y/A D/G VLDYWGQGTTVTVSS

Consensus VH: SEQ ID NO: 3290

QVQLVQSGAEVKKPGSSVKVSCKASG$X_1X_2$F$X_3X_4X_5$YIHWVRQAPGQGLEWMG$X_6X_7X_8X_9$GSG$X_{10}X_{11}X_{12}$YNEKFKGRVTITADTSTSTAYMELSSLRSEDTAVYYCA$X_{13}$S$X_{14}$YS$X_{15}X_{16}$VLDYWGQGTTVTVSS, wherein: X1 is H or T or G or Y; X2 is D or T or S; X3 is H or R or D or K or T; X4 is L or D or K or T or N; X5 is W or F or T or I or Y or G; X6 is R or W; X7 is V or I or F; X8 is F or S or Y; X9 is A or P; X10 is N or S; X11 is T or V or Y or I; X12 is K or R; X13 is G or V; X14 is Y or I; X15 is Y or A; and X16 is D or G

FIG. 110I

| VH sequences | SEQ ID NO: | VH sequences | SEQ ID NO: |
|---|---|---|---|
| A-H.52-VH | 3390 | f2-VH | 3414 |
| A-H.53-VH | 3391 | d3-VH | 3415 |
| A-H.54-VH | 3392 | a4e4-VH | 3416 |
| A-H.51-VH | 3393 | d2-VH | 3417 |
| A-H.50-VH | 3394 | g1-VH | 3418 |
| A-H.47-VH | 3395 | c6-VH | 3419 |
| A-H.49-VH | 3396 | g2-VH | 3420 |
| A-H.48-VH | 3397 | b4-VH | 3421 |
| A-H.45-VH | 3398 | a6-VH | 3422 |
| A-H.46-VH | 3399 | a2g4-VH | 3423 |
| c2-VH | 3400 | b6f1-VH | 3424 |
| f5-VH | 3401 | g3-VH | 3425 |
| f3-VH | 3402 | d1-VH | 3426 |
| e2-VH | 3403 | h4-VH | 3427 |
| e1-VH | 3404 | b2-VH | 3428 |
| c1-VH | 3405 | h6-VH | 3429 |
| a1-VH | 3406 | b1-VH | 3430 |
| b3-VH | 3407 | f4-VH | 3431 |
| h3-VH | 3408 | a3-VH | 3432 |
| c3-VH | 3409 | e6-VH | 3433 |
| a5b5c4-VH | 3410 | e3-VH | 3434 |
| d6-VH | 3411 | d4-VH | 3435 |
| h2-VH | 3412 | d5-VH | 3436 |
| c5-VH | 3413 | | |

FIG. 110J

ANTI-TCR ANTIBODY MOLECULES AND USES THEREOF

CROSS-REFERENCE TO RELATED APPLICATIONS

This application is a continuation of U.S. application Ser. No. 17/855,332 filed Jun. 30, 2022, which is a continuation of International Application No. PCT/US2020/067543, filed on Dec. 30, 2020, which claims the benefit of U.S. Provisional Application 62/957,024 filed on Jan. 3, 2020, and U.S. Provisional Application 63/070,596 filed on Aug. 26, 2020, the entire contents of each of which are hereby incorporated by reference.

SEQUENCE LISTING

This application contains a Sequence Listing which has been submitted electronically in XML format. The Sequence Listing XML is incorporated herein by reference. Said XML file, created on Apr. 13, 2023, is named 53676-736_302_SL.xml and is 1,498,604 bytes in size.

BACKGROUND

Current molecules designed to redirect T cells to promote tumor cell lysis for cancer immunotherapy typically target the CD3 epsilon (CD3e) subunit of the T cell receptor (TCR). However, there are limitations to this approach. Previous studies have shown that, e.g., low doses of anti-CD3e monoclonal antibody (mAb) can cause T cell dysfunction and exert immunosuppressive effects. In addition, anti-CD3e mAbs bind to all T cells and thus activate a large number of T cells. Such non-physiological massive activation of T cells by these anti-CD3e mAbs can result in the production of proinflammatory cytokines such as IFN-gamma, IL-1-beta, IL-6, IL-10 and TNF-alpha, causing a "cytokine storm" known as the cytokine release syndrome (CRS), which is also associated with neurotoxicity (NT). Thus, it might be advantageous to develop antibodies that avoid or reduce CRS and/or NT.

SUMMARY OF THE INVENTION

In an aspect, provided herein is, inter alia, a composition comprising a molecule that comprises an antigen binding domain that binds to a T cell receptor beta variable (TCRβV) region, wherein the antigen binding domain comprises:

(A) a heavy chain variable region (VH) comprising:

(a) a heavy chain complementarity determining region 3 (HC CDR3) comprising the sequence SYYSYDVLDY (SEQ ID NO: 47); and (i) a heavy chain complementarity determining region 1 (HC CDR1) comprising the sequence TYYIH (SEQ ID NO: 45), and a heavy chain complementarity determining region 2 (HC CDR2) comprising the sequence WFFPGSGNIKYNEKFKG (SEQ ID NO: 46);

(ii) a HC CDR1 comprising the sequence GHDFRLTYIH (amino acids 26-35 of SEQ ID NO: 1346), and a HC CDR2 comprising the sequence RVSAGSGNVKYNEKFKG (amino acids 50-66 of SEQ ID NO: 1346);

(iii) a HC CDR1 comprising the sequence GHDFRLTYIH (amino acids 26-35 of SEQ ID NO: 1356), and a HC CDR2 comprising the sequence RVYAGSGNTKYNEKFKG (amino acids 50-66 of SEQ ID NO: 1356); or (iv) a HC CDR1 comprising the sequence GHDFKLTYIH (amino acids 26-35 of SEQ ID NO: 1370), and a HC CDR2 comprising the sequence RVSAGSGNVNYAQKFQG (amino acids 50-66 of SEQ ID NO: 1370); or (b) a HC CDR3 comprising the sequence of SLNWDYGLDY (SEQ ID NO: 1104); and (i) a HC CDR1 comprising the sequence SAYMH (SEQ ID NO: 1102), and a HC CDR2 comprising the sequence RIDPATGKTKYAPKFQA (SEQ ID NO: 1103); or (ii) a HC CDR1 comprising the sequence DTYMY (SEQ ID NO: 1120); and a HC CDR2 comprising the sequence RIDPANGNTKYDPKFQD (SEQ ID NO: 1121); and (B) a light chain variable region (VL) comprising:

(a) a light chain complementarity determining region 3 (LC CDR3) comprising the sequence QQFKSYPLT (SEQ ID NO: 53); and (i) a light chain complementarity determining region 1 (LC CDR1) comprising the sequence KASQNVGINVV (SEQ ID NO: 51), and a light chain complementarity determining region 2 (LC CDR2) comprising the sequence SSSHRYS (SEQ ID NO: 52);

(ii) a LC CDR1 comprising the sequence KASQNVADRVV (amino acids 24-34 of SEQ ID NO: 1349), and a LC CDR2 comprising the sequence SSSHRYK (amino acids 50-56 of SEQ ID NO: 1349);

(iii) a LC CDR1 comprising the sequence KASQNVEDRVV (amino acids 24-34 of SEQ ID NO: 1357), and a LC CDR2 comprising the sequence SSSHRYK (amino acids 50-56 of SEQ ID NO: 1349); or (iv) a LC CDR1 comprising the sequence RASQNVDNRLG (amino acids 24-34 of SEQ ID NO: 1365), and a LC CDR2 comprising the sequence SSSHRYK (amino acids 50-56 of SEQ ID NO: 1349);

(b) a LC CDR3 comprising the sequence QQFTSSPFT (SEQ ID NO: 65), a LC CDR1 comprising the sequence RASSSVNYIY (SEQ ID NO: 63), and the LC CDR2 comprising the sequence YTSNLAP (SEQ ID NO: 64);

(c) a LC CDR3 comprising the sequence QQSIEDPWT (SEQ ID NO: 1109), a LC CDR1 comprising the sequence RASKSVSILGTHLIH (SEQ ID NO: 1107), and the LC CDR2 comprising the sequence AASNLES (SEQ ID NO: 1108);

(d) a LC CDR3 comprising the sequence QQSNEDPYT (SEQ ID NO:1128), a LC CDR1 comprising the sequence RASESVDSYGNSFMH (SEQ ID NO: 1126), and the LC CDR2 comprising the sequence RASNLES (SEQ ID NO:1127);

In some embodiments, the VH comprises:

(i) the HC CDR3 comprising the sequence SYYSYDVLDY (SEQ ID NO: 47);

(ii) the HC CDR1 comprising the sequence TYYIH (SEQ ID NO: 45); and (iii) the HC CDR2 comprising the sequence WFFPGSGNIKYNEKFKG (SEQ ID NO: 46).

In some embodiments, the VH comprises:

(i) the HC CDR3 comprising the sequence SYYSYDVLDY (SEQ ID NO: 47);

(ii) the HC CDR1 comprising the sequence GHDFRLTYIH (amino acids 26-35 of SEQ ID NO: 1346); and (iii) the HC CDR2 comprising the sequence RVSAGSGNVKYNEKFKG (amino acids 50-66 of SEQ ID NO: 1346).

In some embodiments, the VH comprises:

(i) the HC CDR3 comprising the sequence SYYSYDVLDY (SEQ ID NO: 47);

(ii) the HC CDR1 comprising the sequence GHDFRLTYIH (amino acids 26-35 of SEQ ID NO: 1356); and (iii) the HC CDR2 comprising the sequence RVYAGSGNTKYNEKFKG (amino acids 50-66 of SEQ ID NO: 1356).

In some embodiments, the VH comprises:

(i) the HC CDR3 comprising the sequence SYYSYDVLDY (SEQ ID NO: 47);

(ii) the HC CDR1 comprising the sequence GHDFKLTYIH (amino acids 26-35 of SEQ ID NO: 1370); and (iii) the HC CDR2 comprising the sequence RVSAGSGNVNYAQKFQG (amino acids 50-66 of SEQ ID NO: 1370).

In some embodiments, the VH comprises:

(i) the HC CDR3 comprising the sequence SLNWDYGLDY (SEQ ID NO: 1104);

(ii) the HC CDR1 comprising the sequence SAYMH (SEQ ID NO: 1102); and (iii) the HC CDR2 comprising the sequence RIDPATGKTKYAPKFQA (SEQ ID NO: 1103).

In some embodiments, the VH comprises:

(i) the HC CDR3 comprising the sequence SLNWDYGLDY (SEQ ID NO: 1104);

(ii) the HC CDR1 comprising the sequence DTYMY (SEQ ID NO: 1120); and (iii) the HC CDR2 comprising the sequence RIDPANGNTKYDPKFQD (SEQ ID NO: 1121).

In some embodiments, the VL comprises:

(A) (i) the LC CDR3 comprising the sequence QQSIEDPWT (SEQ ID NO:1109);

(ii) the LC CDR1 comprising the sequence RASKSVSILGTHLIH (SEQ ID NO:1107); and (iii) the LC CDR2 comprising the sequence AASNLES (SEQ ID NO: 1108);

(B) (i) the LC CDR3 comprising the sequence QQSNEDPYT (SEQ ID NO: 1128);

(ii) the LC CDR1 comprising the sequence RASESVDSYGNSFMH (SEQ ID NO:1126); and (iii) the LC CDR2 comprising the sequence RASNLES (SEQ ID NO:1127);

(C) (i) the LC CDR3 comprising the sequence QQFKSYPLT (SEQ ID NO: 53);

(ii) the LC CDR1 comprising the sequence KASQNVGINVV (SEQ ID NO: 51); and (iii) the LC CDR2 comprising the sequence SSSHRYS (SEQ ID NO: 52);

(D) (i) the LC CDR3 comprising the sequence QQFTSSPFT (SEQ ID NO: 65);

(ii) the LC CDR1 comprising the sequence RASSSVNYIY (SEQ ID NO: 63); and (iii) the LC CDR2 comprising the sequence YTSNLAP (SEQ ID NO: 64);

(E) (i) the LC CDR3 comprising the sequence QQFKSYPLT (SEQ ID NO: 53);

(ii) the LC CDR1 comprising the sequence KASQNVADRVV (amino acids 24-34 of SEQ ID NO: 1349); and (iii) the LC CDR2 comprising the sequence SSSHRYK (amino acids 50-56 of SEQ ID NO: 1349);

(F) (i) the LC CDR3 comprising the sequence QQFKSYPLT (SEQ ID NO: 53);

(ii) the LC CDR1 comprising the sequence KASQNVEDRVV (amino acids 24-34 of SEQ ID NO: 1357); and (iii) the LC CDR2 comprising the sequence SSSHRYK (amino acids 50-56 of SEQ ID NO: 1349); or (G) (i) the LC CDR3 comprising the sequence QQFKSYPLT (SEQ ID NO: 53);

(ii) the LC CDR1 comprising the sequence RASQNVDNRLG (amino acids 24-34 of SEQ ID NO: 1365); and (iii) the LC CDR2 comprising the sequence SSSHRYK (amino acids 50-56 of SEQ ID NO: 1349).

In some embodiments, the VL comprises:

(i) the LC CDR3 comprising the sequence QQFKSYPLT (SEQ ID NO: 53);

(ii) the LC CDR1 comprising the sequence KASQNVGINVV (SEQ ID NO: 51); and (iii) the LC CDR2 comprising the sequence SSSHRYS (SEQ ID NO: 52).

In some embodiments, the VL comprises:

(i) the LC CDR3 comprising the sequence QQFKSYPLT (SEQ ID NO: 53);

(ii) the LC CDR1 comprising the sequence KASQNVADRVV (amino acids 24-34 of SEQ ID NO: 1349); and (iii) the LC CDR2 comprising the sequence SSSHRYK (amino acids 50-56 of SEQ ID NO: 1349).

In some embodiments, the VL comprises:

(i) the LC CDR3 comprising the sequence QQFKSYPLT (SEQ ID NO: 53);

(ii) the LC CDR1 comprising the sequence KASQNVEDRVV (amino acids 24-34 of SEQ ID NO: 1357); and (iii) the LC CDR2 comprising the sequence SSSHRYK (amino acids 50-56 of SEQ ID NO: 1349).

In some embodiments, the VL comprises:

(i) the LC CDR3 comprising the sequence QQFKSYPLT (SEQ ID NO: 53);

(ii) the LC CDR1 comprising the sequence RASQNVDNRLG (amino acids 24-34 of SEQ ID NO: 1365); and (iii) the LC CDR2 comprising the sequence SSSHRYK (amino acids 50-56 of SEQ ID NO: 1349).

In some embodiments, the VL comprises:

(i) the LC CDR3 comprising the sequence QQSIEDPWT (SEQ ID NO:1109);

(ii) a LC CDR1 comprising the sequence RASKSVSILGTHLIH (SEQ ID NO:1107); and (iii) a LC CDR2 comprising the sequence AASNLES (SEQ ID NO: 1108).

In some embodiments, the antigen binding domain comprises:

(i) a VH comprising a sequence having at least 80% sequence identity to SEQ ID NO: 1100, and a VL comprising a sequence having at least 80% sequence identity to SEQ ID NO: 1101;

(ii) a VH comprising a sequence having at least 80% sequence identity to SEQ ID NO: 1346, and a VL comprising a sequence having at least 80% sequence identity to SEQ ID NO: 1349;

(iii) a VH comprising a sequence having at least 80% sequence identity to SEQ ID NO: 1356, and a VL comprising a sequence having at least 80% sequence identity to SEQ ID NO: 1357;

(iv) a VH comprising a sequence having at least 80% sequence identity to SEQ ID NO: 1370, and a VL comprising a sequence having at least 80% sequence identity to SEQ ID NO: 1365; or (v) a VH comprising a sequence having at least 80% sequence identity to SEQ ID NO: 1112, SEQ ID NO: 1113, SEQ ID NO: 1114, SEQ ID NO: 1115, or SEQ ID NO: 1116, and a VL comprising a sequence having at least 80% sequence identity to SEQ ID NO: 1111, SEQ ID NO: 1117, SEQ ID NO: 1118, or SEQ ID NO: 1119.

In some embodiments, the antigen binding domain comprises:

(i) a VH comprising the sequence of SEQ ID NO: 1100, and a VL comprising the sequence of SEQ ID NO: 1101;

(ii) a VH comprising the sequence of SEQ ID NO: 1346, and a VL comprising the sequence of SEQ ID NO: 1349;

(iii) a VH comprising the sequence of SEQ ID NO: 1356, and a VL comprising the sequence of SEQ ID NO: 1357;

(iv) a VH comprising the sequence of SEQ ID NO: 1370, and a VL comprising the sequence of SEQ ID NO: 1365; or (v) a VH comprising the sequence of SEQ ID NO: 1112, SEQ ID NO: 1113, SEQ ID NO: 1114, SEQ ID NO: 1115, or SEQ ID NO: 1116, and a VL comprising a sequence having at least 80% sequence identity to SEQ ID NO: 1111, SEQ ID NO: 1117, SEQ ID NO: 1118, or SEQ ID NO: 1119.

In some embodiments, the antigen binding domain is a Fab or a single chain Fv (scFv).

In some embodiments, the molecule comprises at least two non-contiguous polypeptide chains, wherein a first polypeptide chain of the at least two non-contiguous polypeptide chains comprises a first Fc region, and a second polypeptide chain of the at least two non-contiguous polypeptide chains comprises a second Fc region; and wherein the first Fc region and the second Fc region comprise an Fc interface with a knob-in-a hole.

In some embodiments, the molecule comprises the first polypeptide chain, the second polypeptide chain, and a third polypeptide chain, wherein the first polypeptide chain, the second polypeptide chain, and the third polypeptide chain are non-contiguous, and wherein:

(i) the first polypeptide chain comprises a VH comprising the sequence of SEQ ID NO: 1346, wherein the VH is linked to the first Fc region, (ii) the second polypeptide chain comprises a cytokine molecule, wherein the cytokine molecule is linked to the second Fc region, and wherein the cytokine molecule comprises: (a) IL-2 or functional variant thereof comprising the sequence of SEQ ID NO: 2270, or (b) IL-15 or functional variant thereof comprising the sequence of SEQ ID NO: 2170, wherein the IL-15 or functional variant thereof is covalently linked to an IL15Ralpha dimerizing domain, and (iii) the third polypeptide chain comprises a VL comprising the sequence of SEQ ID NO: 1349, wherein the VL is linked to a light chain constant region comprising the sequence of SEQ ID NO: 39.

In some embodiments, the molecule comprises the first polypeptide chain, the second polypeptide chain, and a third polypeptide chain, wherein the first polypeptide chain, the second polypeptide chain, and the third polypeptide chain are non-contiguous, and wherein:

(i) the first polypeptide chain comprises a VH comprising the sequence of SEQ ID NO: 1113, wherein the VH is linked to the first Fc region, (ii) the second polypeptide chain comprises a cytokine molecule, wherein the cytokine molecule is linked to the second Fc region, and wherein the cytokine molecule comprises: (a) IL-2 or functional variant thereof comprising the sequence of SEQ ID NO: 2270, or (b) IL-15 or functional variant thereof comprising the sequence of SEQ ID NO: 2170, wherein the IL-15 or functional variant thereof is covalently linked to an IL15Ralpha dimerizing domain, and (iii) the third polypeptide chain comprises a VL comprising a sequence having at least 80% sequence identity to SEQ ID NO: 1111, wherein the VL is linked to a light chain constant region comprising the sequence of SEQ ID NO: 39.

In some embodiments, the molecule comprises the first polypeptide chain, the second polypeptide chain, and a third polypeptide chain, wherein the first polypeptide chain, the second polypeptide chain, and the third polypeptide chain are non-contiguous, and wherein:

(i) the first polypeptide chain comprises a VH comprising the sequence of SEQ ID NO: 1100, wherein the VH is linked to the first Fc region, (ii) the second polypeptide chain comprises a cytokine molecule, wherein the cytokine molecule is linked to the second Fc region, and wherein the cytokine molecule comprises: (a) IL-2 or functional variant thereof comprising the sequence of SEQ ID NO: 2270, or (b) IL-15 or functional variant thereof comprising the sequence of SEQ ID NO: 2170, wherein the IL-15 or functional variant thereof is covalently linked to an IL15Ralpha dimerizing domain, and (iii) the third polypeptide chain comprises a VL comprising a sequence having at least 80% sequence identity to SEQ ID NO: 1101, wherein the VL is linked to a light chain constant region comprising the sequence of SEQ ID NO: 39.

In some embodiments, the molecule comprises the first polypeptide chain, the second polypeptide chain, and a third polypeptide chain, wherein the first polypeptide chain, the second polypeptide chain, and the third polypeptide chain are non-contiguous, and wherein:

(i) the first polypeptide chain comprises a VH comprising the sequence of SEQ ID NO: 1356, wherein the VH is linked to the first Fc region, (ii) the second polypeptide chain comprises a cytokine molecule, wherein the cytokine molecule is linked to the second Fc region, and wherein the cytokine molecule comprises: (a) IL-2 or functional variant thereof comprising the sequence of SEQ ID NO: 2270, or (b) IL-15 or functional variant thereof comprising the sequence of SEQ ID NO: 2170, wherein the IL-15 or functional variant thereof is covalently linked to an IL15Ralpha dimerizing domain, and (iii) the third polypeptide chain comprises a VL comprising a sequence having at least 80% sequence identity to SEQ ID NO: 1357, wherein the VL is linked to a light chain constant region comprising the sequence of SEQ ID NO: 39.

In some embodiments, the molecule comprises the first polypeptide chain, the second polypeptide chain, and a third polypeptide chain, wherein the first polypeptide chain, the second polypeptide chain, and the third polypeptide chain are non-contiguous, and wherein:

(i) the first polypeptide chain comprises a VH comprising the sequence of SEQ ID NO: 1370, wherein the VH is linked to the first Fc region, (ii) the second polypeptide chain comprises a cytokine molecule, wherein the cytokine molecule is linked to the second Fc region, wherein the cytokine molecule comprises: (a) IL-2 or functional variant thereof comprising the sequence of SEQ ID NO: 2270, or (b) IL-15 or functional variant thereof comprising the sequence of SEQ ID NO: 2170, wherein the IL-15 or functional variant thereof is covalently linked to an IL15Ralpha dimerizing domain, and (iii) the third polypeptide chain comprises a VL comprising a sequence having at least 80% sequence identity to SEQ ID NO: 1365, wherein the VL is linked to a light chain constant region comprising the sequence of SEQ ID NO: 39.

In some embodiments, (1) the first Fc region and the second Fc region each comprises an Asn297Ala mutation;

(2) (i) the first Fc region and the second Fc region each comprises a sequence having at least 98% sequence identity to SEQ ID NO: 41 or SEQ ID NO: 42, or (ii) (a) the first Fc region comprising the sequence of amino acids 1-328 of SEQ ID NO: 42, with the proviso that Tyr at the position 349, Thr at the position 366, Leu at the position 368, and Tyr at the position 407 according to EU Numbering are replaced with Cys, Ser, Ala, and Val, respectively; and (b) the second polypeptide chain comprises the cytokine molecule linked to the second Fc region via the sequence of SEQ ID NO: 3308, wherein the second Fc region comprises the sequence of amino acids 104-328 of SEQ ID NO: 42, with the proviso that Ser at the position 354 and Thr at the position 366 according to EU Numbering are replaced with Cys and Trp, respectively; or (3) any combination thereof.

In some embodiments, (1) the first Fc region and the second Fc region each comprises an Asn297Ala mutation;

(2) (i) the first Fc region and the second Fc region each comprises a sequence having at least 98% sequence identity to SEQ ID NO: 41 or SEQ ID NO: 42, or (ii) (a) the first Fc region comprising the sequence of amino acids 1-328 of SEQ ID NO: 42, with the proviso that Tyr at the position 349, Thr at the position 366, Leu at the position 368, and Tyr at the position 407 according to EU Numbering are replaced with Cys, Ser, Ala, and Val, respectively; and (b) the second polypeptide chain comprises the cytokine molecule linked to the second Fc region via the sequence of SEQ ID NO: 3308, wherein the second Fc region comprises the sequence of amino acids 104-328 of SEQ ID NO: 42, with the proviso that Ser at the position 354 and Thr at the position 366 according to EU Numbering are replaced with Cys and Trp, respectively; or (3) any combination thereof.

In some embodiments, (1) the first Fc region and the second Fc region each comprises an Asn297Ala mutation;

(2) (i) the first Fc region and the second Fc region each comprises a sequence having at least 98% sequence identity to SEQ ID NO: 41 or SEQ ID NO: 42, or (ii) (a) the first Fc region comprising the sequence of amino acids 1-328 of SEQ ID NO: 42, with the proviso that Tyr at the position 349, Thr at the position 366, Leu at the position 368, and Tyr at the position 407 according to EU Numbering are replaced with Cys, Ser, Ala, and Val, respectively; and (b) the second polypeptide chain comprises the cytokine molecule linked to the second Fc region via the sequence of SEQ ID NO: 3308, wherein the second Fc region comprises the sequence of amino acids 104-328 of SEQ ID NO: 42, with the proviso that Ser at the position 354 and Thr at the position 366 according to EU Numbering are replaced with Cys and Trp, respectively; or (3) any combination thereof.

In some embodiments, (1) the first Fc region and the second Fc region each comprises an Asn297Ala mutation;

(2) (i) the first Fc region and the second Fc region each comprises a sequence having at least 98% sequence identity to SEQ ID NO: 41 or SEQ ID NO: 42, or (ii) (a) the first Fc region comprising the sequence of amino acids 1-328 of SEQ ID NO: 42, with the proviso that Tyr at the position 349, Thr at the position 366, Leu at the position 368, and Tyr at the position 407 according to EU Numbering are replaced with Cys, Ser, Ala, and Val, respectively; and (b) the second polypeptide chain comprises the cytokine molecule linked to the second Fc region via the sequence of SEQ ID NO: 3308, wherein the second Fc region comprises the sequence of amino acids 104-328 of SEQ ID NO: 42, with the proviso that Ser at the position 354 and Thr at the position 366 according to EU Numbering are replaced with Cys and Trp, respectively; or (3) any combination thereof.

In some embodiments, the second polypeptide chain comprises the antigen binding domain comprising the sequence of SEQ ID NO: 1331, and a cytokine molecule, wherein the cytokine molecule comprises IL-2 or functional variant thereof comprising the sequence of SEQ ID NO: 2270, and wherein the antigen binding domain, the cytokine molecule, and the second Fc region are linked.

In another aspect, provided herein is a method of treating cancer in a human subject in need thereof comprising administering to the human subject a therapeutically effective amount of a molecule comprising an antigen binding domain that binds to a T cell receptor beta variable (TCRβV) region, wherein the antigen binding domain comprises:

(A) a heavy chain variable region (VH) comprising:

(a) a heavy chain complementarity determining region 3 (HC CDR3) comprising the sequence SYYSYDVLDY (SEQ ID NO: 47); and (i) a heavy chain complementarity determining region 1 (HC CDR1) comprising the sequence TYYIH (SEQ ID NO: 45), and a heavy chain complementarity determining region 2 (HC CDR2) comprising the sequence WFFPGSGNIKYNEKFKG (SEQ ID NO: 46);

(ii) a HC CDR1 comprising the sequence GHDFRLTYIH (amino acids 26-35 of SEQ ID NO: 1346), and a HC CDR2 comprising the sequence RVSAGSGNVKYNEKFKG (amino acids 50-66 of SEQ ID NO: 1346);

(iii) a HC CDR1 comprising the sequence GHDFRLTYIH (amino acids 26-35 of SEQ ID NO: 1356), and a HC CDR2 comprising the sequence RVYAGSGNTKYNEKFKG (amino acids 50-66 of SEQ ID NO: 1356); or (iv) a HC CDR1 comprising the sequence GHDFKLTYIH (amino acids 26-35 of SEQ ID NO: 1370), and a HC CDR2 comprising the sequence RVSAGSGNVNYAQKFQG (amino acids 50-66 of SEQ ID NO: 1370); or (b) a HC CDR3 comprising the sequence of SLNWDYGLDY (SEQ ID NO: 1104); and (i) a HC CDR1 comprising the sequence SAYMH (SEQ ID NO: 1102), and a HC CDR2 comprising the sequence RIDPATGKTKYAPKFQA (SEQ ID NO: 1103); or (ii) a HC CDR1 comprising the sequence DTYMY (SEQ ID NO: 1120); and a HC CDR2 comprising the sequence RIDPANGNTKYDPKFQD (SEQ ID NO: 1121); and (B) a light chain variable region (VL) comprising:

(a) a light chain complementarity determining region 3 (LC CDR3) comprising the sequence QQFKSYPLT (SEQ ID NO: 53); and (i) a light chain complementarity determining region 1 (LC CDR1) comprising the sequence KASQNVGINVV (SEQ ID NO: 51), and a light chain complementarity determining region 2 (LC CDR2) comprising the sequence SSSHRYS (SEQ ID NO: 52);

(ii) a LC CDR1 comprising the sequence KASQNVADRVV (amino acids 24-34 of SEQ ID NO: 1349), and a LC CDR2 comprising the sequence SSSHRYK (amino acids 50-56 of SEQ ID NO: 1349);

(iii) a LC CDR1 comprising the sequence KASQNVEDRVV (amino acids 24-34 of SEQ ID NO: 1357), and a LC CDR2 comprising the sequence SSSHRYK (amino acids 50-56 of SEQ ID NO: 1349); or (iv) a LC CDR1 comprising the sequence RASQNVDNRLG (amino acids 24-34 of SEQ ID NO: 1365), and a LC CDR2 comprising the sequence SSSHRYK (amino acids 50-56 of SEQ ID NO: 1349);

(b) a LC CDR3 comprising the sequence QQFTSSPFT (SEQ ID NO: 65), a LC CDR1 comprising the sequence RASSSVNYIY (SEQ ID NO: 63), and the LC CDR2 comprising the sequence YTSNLAP (SEQ ID NO: 64);

(c) a LC CDR3 comprising the sequence QQSIEDPWT (SEQ ID NO: 1109), a LC CDR1 comprising the sequence RASKSVSILGTHLIH (SEQ ID NO: 1107), and the LC CDR2 comprising the sequence AASNLES (SEQ ID NO: 1108);

(d) a LC CDR3 comprising the sequence QQSNEDPYT (SEQ ID NO:1128), a LC CDR1 comprising the sequence RASESVDSYGNSFMH (SEQ ID NO: 1126), and the LC CDR2 comprising the sequence RASNLES (SEQ ID NO: 1127), thereby treating the cancer in the human subject.

In another aspect, provided herein is a method of expanding an immune cell population comprising contacting the immune cell population with a composition comprising a molecule comprising an antigen binding domain that binds to a T cell receptor beta variable (TCRβV) region, wherein the antigen binding domain comprises:

(A) a heavy chain variable region (VH) comprising:

(a) a heavy chain complementarity determining region 3 (HC CDR3) comprising the sequence SYYSYDVLDY (SEQ ID NO: 47); and (i) a heavy chain complementarity determining region 1 (HC CDR1) comprising the sequence TYYIH (SEQ ID NO: 45), and a heavy chain complementarity determining region 2 (HC CDR2) comprising the sequence WFFPGSGNIKYNEKFKG (SEQ ID NO: 46);

(ii) a HC CDR1 comprising the sequence GHDFRLTYIH (amino acids 26-35 of SEQ ID NO: 1346), and a HC CDR2 comprising the sequence RVSAGSGNVKYNEKFKG (amino acids 50-66 of SEQ ID NO: 1346);

(iii) a HC CDR1 comprising the sequence GHDFRLTYIH (amino acids 26-35 of SEQ ID NO: 1356), and a HC CDR2 comprising the sequence RVYAGSGNTKYNEKFKG (amino acids 50-66 of SEQ ID NO: 1356); or (iv) a HC CDR1 comprising the sequence GHDFKLTYIH (amino acids 26-35 of SEQ ID NO: 1370), and a HC CDR2 comprising the sequence RVSAGSGNVNYAQKFQG (amino acids 50-66 of SEQ ID NO: 1370); or (b) a HC CDR3 comprising the sequence of SLNWDYGLDY (SEQ ID NO: 1104); and (i) a HC CDR1 comprising the sequence SAYMH (SEQ ID NO: 1102), and a HC CDR2 comprising the sequence RIDPATGKTKYAPKFQA (SEQ ID NO: 1103); or (ii) a HC CDR1 comprising the sequence DTYMY (SEQ ID NO: 1120); and a HC CDR2 comprising the sequence RIDPANGNTKYDPKFQD (SEQ ID NO: 1121); and (B) a light chain variable region (VL) comprising:

(a) a light chain complementarity determining region 3 (LC CDR3) comprising the sequence QQFKSYPLT (SEQ ID NO: 53); and (i) a light chain complementarity determining region 1 (LC CDR1) comprising the sequence KASQNVGINVV (SEQ ID NO: 51), and a light chain complementarity determining region 2 (LC CDR2) comprising the sequence SSSHRYS (SEQ ID NO: 52);

(ii) a LC CDR1 comprising the sequence KASQNVADRVV (amino acids 24-34 of SEQ ID NO: 1349), and a LC CDR2 comprising the sequence SSSHRYK (amino acids 50-56 of SEQ ID NO: 1349);

(iii) a LC CDR1 comprising the sequence KASQNVEDRVV (amino acids 24-34 of SEQ ID NO: 1357), and a LC CDR2 comprising the sequence SSSHRYK (amino acids 50-56 of SEQ ID NO: 1349); or (iv) a LC CDR1 comprising the sequence RASQNVDNRLG (amino acids 24-34 of SEQ ID NO: 1365), and a LC CDR2 comprising the sequence SSSHRYK (amino acids 50-56 of SEQ ID NO: 1349);

(b) a LC CDR3 comprising the sequence QQFTSSPFT (SEQ ID NO: 65), a LC CDR1 comprising the sequence RASSSVNYIY (SEQ ID NO: 63), and the LC CDR2 comprising the sequence YTSNLAP (SEQ ID NO: 64);
(c) a LC CDR3 comprising the sequence QQSIEDPWT (SEQ ID NO: 1109), a LC CDR1 comprising the sequence RASKSVSILGTHLIH (SEQ ID NO: 1107), and the LC CDR2 comprising the sequence AASNLES (SEQ ID NO: 1108);
(d) a LC CDR3 comprising the sequence QQSNEDPYT (SEQ ID NO:1128), a LC CDR1 comprising the sequence RASESVDSYGNSFMH (SEQ ID NO: 1126), and the LC CDR2 comprising the sequence RASNLES (SEQ ID NO: 1127), thereby expanding the immune cell population, and wherein the expansion occurs in vivo or ex vivo.

BRIEF DESCRIPTION OF THE DRAWINGS

FIGS. 1A-1B shows the alignment of the Antibody A source mouse VH and VL framework 1, CDR 1, framework 2, CDR 2, framework 3, CDR3, and framework 4 regions with their respective humanized sequences. Kabat CDRs are shown in bold, Chothia CDRs are shown in italics, and combined CDRs are shown in boxes. The framework positions that were back mutated are double underlined. FIG. 1A shows VH sequences for murine Antibody A (SEQ ID NO: 1) and humanized Antibody A-H (SEQ ID NO: 9). FIG. 1B shows VL sequences for murine Antibody A (SEQ ID NO: 2) and humanized Antibody A-H (SEQ ID NO: 10 and SEQ ID NO: 11).

FIGS. 2A-2C shows the alignment of the Antibody B source mouse VH and VL framework 1, CDR 1, framework 2, CDR 2, framework 3, CDR3, and framework 4 regions with their respective humanized sequences. Kabat CDRs are shown in bold, Chothia CDRs are shown in italics, and combined CDRs are shown in boxes. The framework positions that were back mutated are double underlined. FIG. 2A shows the VH sequence for murine Antibody B (SEQ ID NO: 15) and humanized VH sequences B-H.1A to B-H.1C (SEQ ID NOs: 23-25). FIG. 2B shows the VL sequence for murine Antibody B (SEQ ID NO: 16) and humanized VL sequences B-H.1D to B-H.1H (SEQ ID NOs: 26-30). FIG. 2C shows the VL sequence for murine Antibody B (SEQ ID NO: 16) and humanized VL sequences B-H.1D to B-H.1H (SEQ ID NOs: 26-30) continued from FIG. 2B.

FIG. 4A shows two scatter plots (left: activated with OKT3; and right: activated with A-H.1) of expanded T cells assessed for TCR Vβ13.1 surface expression using anti-TCR Vβ13.1 (A-H.1) followed by a secondary fluorochrome-conjugated antibody for flow cytometry analysis. FIG. 4B shows two scatter plots (left: activated with OKT3; and right: activated with A-H.1) of expanded T cells assessed for TCR Vβ13.1 surface expression using anti-TCR Vβ13.1 (A-H.1) followed by a secondary fluorochrome-conjugated antibody for flow cytometry analysis, continued from FIG. 4A. FIG. 4C shows percentage (%) of TCR Vβ13.1 positive T cells activated by anti-TCR Vβ13.1 (A-H.1) or anti-CD3e (OKT3) plotted against total T cells (CD3+). FIG. 4D shows relative cell count acquired by counting the number of events in each T cell subset gate (CD3 or TCR Vβ13.1) for 20 seconds at a constant rate of 60 μl/min. Data shown as mean value from 3 donors.

FIG. 5A depicts target cell lysis of human CD3+ T cells activated with A-H.1 or OKT3. Human CD3+ T cells were isolated using magnetic-bead separation (negative selection) and activated with immobilized (plate-coated) A-H.1 or OKT3 at the indicated concentrations for 4 days prior to co-culture with RPMI 8226 cells at a (E:T) ratio of 5:1 for 2 days. Samples were next analyzed for cell lysis of RPMI 8226 cells by FACS staining for CFSE/CD138-labeled, and membrane-impermeable DNA dyes (DRAQ7) using flow cytometry analysis. FIG. 5B shows target cell lysis of human CD3+ T cells activated with A-H.1 or OKT3 incubated with RPMI-8226 at a (E:T) ratio of 5:1 for 6 days followed by cell lysis analysis of RPMI 8226 cells as described above. Percentage (%) target cell lysis was determined by normalizing to basal target cell lysis (i.e. without antibody treatment) using the following formula, [(x−basal)/(100%−basal), where x is cell lysis of sample]. Data shown is a representative of n=1 donor.

FIG. 6A is a graph comparing the production of IFNg in human PBMCs activated with the antibodies indicated activated with anti-TCR Vβ13.1 antibodies (A-H.1 or A-H.2) or anti-CD3e antibodies (OKT3 or SP34-2) on Day 1, 2, 3, 5, or 6 post-activation. FIG. 6B shows IFNg production in human PBMCs activated with the antibodies indicated activated with the indicated anti-TCR Vβ13.1 antibodies or anti-CD3e antibody (OKT3) on Day 1, 2, 3, 5, or 6 post-activation.

FIG. 11A shows IFNg secretion data from 4 donors. FIG. 11B shows IFNg secretion data from 4 additional donors. Data shown is representative of n=8 donors.

FIG. 13A is a graph depicting proliferation of T cells activated with anti-CD3 (OKT3) antibody or anti-TCRVb antibody. FIG. 13B shows selective expansion of CD45RA+ effector memory CD8+ and CD4+ T cells (TEMRA) cells with anti-TCRVb antibodies. Tn=naïve T cell; Tscm=stem cell memory T cell; Tcm=central memory T cell; Tem=effector memory T cell; Temra=effector memory CD45RA+ T cell. FIG. 13C is a graph showing IFN-g secretion by PBMCs stimulated with an anti-TCRVb antibody, or anti-CD3 antibodies. FIG. 13D shows target cell lysis by T cells stimulated with an anti-TCRVb antibody, or anti-CD3 antibodies. Cells were stimulated for 4 days followed by 2 days incubation with multiple myeloma target cells for assessment of cell killing. FIG. 13E is a graph showing perforin secretion by T cells stimulated with an anti-TCRVb antibody, or an anti-CD3 antibody. Perforin was analyzed by FACS staining in TCRVB-positive and TCRVB-negative T cells in PBMCs after 5 days of stimulation with 100 ng/ml plate-bound antibody. FIG. 13F is a graph showing Granzyme B by T cells stimulated with an anti-TCRVb antibody, or an anti-CD3 antibody. Granzyme B was analyzed by FACS staining in TCRVB-positive and TCRVB-negative T cells in PBMCs after 5 days of stimulation with 100 ng/ml plate-bound antibody.

FIG. 14A shows secretion of IL-2 or IL-15 in T cells stimulated with an anti-TCRVb antibody, or anti-CD3 antibodies. FIG. 14B depicts flow cytometry dot plots showing NKp46 staining vs CD56 antibody staining in cells stimulated with an anti-TCRVb antibody or an anti-CD3 antibody or a control sample. FIG. 14C depicts flow cytometry dot plots showing NKp46 staining vs CD56 antibody staining in cells stimulated with an anti-TCRVb antibody or an anti-CD3 antibody or a control sample, continued from FIG. 14B.

FIG. 15A, IL-6; FIG. 15B, IL-1p; FIG. 15C, TNFα

FIG. 16A shows in vitro killing by one of the following dual-targeting antibody molecules: BCMA-TCRVb (Molecule I), BCMA-CD3, or Control-TCRVb; or an isotype control. FIG. 16B shows in vivo killing of MM cells by a dual-targeting BCM-TCRVb antibody (Molecule I).

FIG. 18A shows that human PBMCs activated by anti-TCR Vβ8a antibodies (B-H.1) produce similar or reduced levels of IFNγ. FIG. 18B shows human PBMCs activated by anti-TCR Vβ8a antibodies (B-H.1) produce higher levels of IL-2 when compared to those activated by anti-CD3ϵ antibodies (OKT3 or SP34-2). Data shown is representative of n=6 donors.

FIG. 20A shows that human PBMCs activated by anti-TCRβV Antibody D antibody produce similar or reduced levels of IFNγ. FIG. 20B shows human PBMCs activated by anti-TCRβV Antibody D antibody produce higher levels of IL-2 when compared to those activated by anti-CD3ϵ antibodies (OKT3). Human PBMCs activated by anti-TCRβV Antibody D antibody do not significantly produce IL-1beta (FIG. 20C), IL-6, (FIG. 20D), or TNFalpha (FIG. 20E). Data shown is representative of n=4 donors.

FIG. 21A shows that human PBMCs activated by anti-TCR Vβ5 antibody produce similar or reduced levels of IFNγ compared to PBMCS activated by anti-CD3ϵ antibodies (OKT3 or SP34-2). FIG. 21B shows human PBMCs activated by the anti-TCR Vβ5 1 antibody produce higher levels of IL-2 when compared to those activated by anti-CD3ϵ antibodies (OKT3 or SP34-2). Data shown is representative of n=4 donors.

FIG. 23A shows that human PBMCs activated by the bispecific molecule produce similar or reduced levels of IFNγ as PBMCS activated by anti-CD3ϵ antibodies (OKT3). FIG. 23B shows human PBMCs activated by the bispecific molecule produce higher levels of IL-2 when compared to PBMCs activated by anti-CD3ϵ antibodies (OKT3). Human PBMCs activated by the bispecific molecule do not significantly produce IL-1beta (FIG. 23C), IL-6, (FIG. 23D), TNFalpha (FIG. 23E), or IL-10 (FIG. 23F). Data shown is representative of n=3 donors.

FIGS. 24A-24B show the structure and sequence of eight TCRβV proteins from seven different subfamilies: TCRβV6 subfamily (TCRβV6-5 and TCRβV6-4 are shown), TCRβV28 subfamily, TCRβV19 subfamily, TCRβV9 subfamily, TCRβV5 subfamily, TCRβV20 subfamily and TCRβV12 subfamily. FIG. 24A shows the structural alignment of the different TCRβV proteins. The circled area represents the outward facing region comprising the proposed binding site for the anti-TCRβV antibodies disclosed herein. FIG. 24B shows the amino acid sequence alignment of the proteins shown in FIG. 24A (SEQ ID NOS: 3449-3456, respectively, in order of appearance). The various TCRβV proteins (from 7 different TCRβV subfamilies) have diverse sequences but share a conserved (similar) structure and function.

FIG. 25A, IFNγ; FIG. 25B, IL-2; FIG. 25C, IL-1β; FIG. 25D, IL-6; FIG. 25E, IL-10; FIG. 25F, IL-4; FIG. 25G, TNFα; FIG. 25H, IL-12p70; FIG. 25I, IL-13; FIG. 25J, IL-8.

FIG. 26A, Eotaxin; FIG. 26B, Eotaxin-3; FIG. 26C, IL-8 (HA); FIG. 26D, IP-10; FIG. 26E, MCP-1; FIG. 26F, MCP-4; FIG. 26G, MDC; FIG. 26H, MIP-1a.

FIG. 27A, MIP-1B; FIG. 27B, TARC; FIG. 27C, GM-CSF; FIG. 27D, IL-12-23p40; FIG. 27E, IL-15; FIG. 27F, IL-16; FIG. 27G, IL-17a; FIG. 27H, IL-1a; FIG. 27I, IL-5; FIG. 27J, IL-7; FIG. 27K, TNF-B; FIG. 27L, VEGF.

FIG. 29A shows mean tumor burden at days 16 to 37 in NOD/SCID/IL-2Rγnull (NSG) mice engrafted with Raji-luc cells. FIG. 29B shows mean tumor burden (Total Flux) at days 16 to 30 in animals engrafted with K562-luc cells.

FIG. 31A shows data generated using anti-TCR Vβ13.1/anti-CD19 (Molecule F), anti-CD3/anti-CD19, and anti-TCR Vβ13.1 (A-H.1). FIG. 31B shows data generated using anti-TCR Vβ13.1/anti-BCMA (Molecule G), anti-CD3/anti-BCMA, and anti-TCR Vβ13.1 (A-H.1).

FIG. 34A, Day 0, Day 1, Day 2; FIG. 34B, Day 4, Day 6, Day 8.

FIG. 90AA is a bar graph showing the level of secreted IL-5 by T cells activated/expanded with the indicated antibody (isotype control; anti-TCRβV 6-5 v1 with anti-BCMA antibody; anti-TCRβV 6-5 v1; anti-TCRβV 123/4 v1, or SP34-2) and cultured with said antibody for the indicated number of days (1, 2, 3, 4, 5, 6, or 8). FIG. 90BB is a bar graph showing the level of secreted IL-7 by T cells activated/expanded with the indicated antibody (isotype control; anti-TCRβV 6-5 v1 with anti-BCMA antibody; anti-TCRβV 6-5 v1; anti-TCRβV 123/4 v1, or SP34-2) and cultured with said antibody for the indicated number of days (1, 2, 3, 4, 5, 6, or 8). FIG. 90CC is a bar graph showing the level of secreted TNF-β by T cells activated/expanded with the indicated antibody (isotype control; anti-TCRβV 6-5 v1 with anti-BCMA antibody; anti-TCRβV 6-5 v1; anti-TCRβV 123/4 v1, or SP34-2) and cultured with said antibody for the indicated number of days (1, 2, 3, 4, 5, 6, or 8). FIG. 90DD is a bar graph showing the level of secreted VEGF by T cells activated/expanded with the indicated antibody (isotype control; anti-TCRβV 6-5 v1 with anti-BCMA antibody; anti-TCRβV 6-5 v1; anti-TCRβV 123/4 v1, or SP34-2) and cultured with said antibody for the indicated number of days (1, 2, 3, 4, 5, 6, or 8).

FIGS. 102A-102C show binding of a CD19×TCRvβ bispecific molecule to a TCR molecule. FIG. 102A is a schematic of the bispecific molecule used in this study. FIG. 102B is a graph showing the binding of a CD19×TCRvβ bispecific molecule to soluble TCR. FIG. 102C is a graph showing binding of a CD19×TCRvβ bispecific molecule to TCR expressed on Jurkat cells.

FIG. 103A is a schematic of the bispecific molecule used in this study. FIG. 103B is a graph showing the binding kinetics of murine CD19×TCRvβ 13-2/3. FIG. 103C are dot plots showing the expansion of TCRVB+ T cells following a 6 day incubation with murine CD19×TCRvβ 13-2/3. FIG. 103D is a graph showing the relative count of splenic B cells after a 6 day in vitro incubation with murine CD19×TCRvβ 13-2/3 bispecific antibody.

FIG. 106A is a schematic of the bispecific molecule used in this study. FIG. 106B is a graph showing target cell lysis by pre-expanded TCRVB+ T cells or CD3+ expanded pan T cells. FIG. 106C shows depletion of purified B cells by purified T cells treated with a CD19×TCRvβ bispecific molecule. FIG. 106D shows depletion of purified B cells by purified T cells treated with a CD19×CD3 bispecific molecule. FIG. 106E shows depletion of B cells in a PBMC preparation treated with a CD19×TCRvβ bispecific molecule. FIG. 106F shows depletion of B cells in a PBMC preparation treated with a CD19×CD3 bispecific molecule.

FIG. 108A is a schematic of the experimental design. FIG. 108B is a graph showing the concentration of CD19×TCRvβ 6-5 at the indicated timepoints after treatment. FIG. 108C shows the detection reagents used to detect CD19×TCRvβ 6-5.

FIGS. 109A-109E depicts Table 9 showing the alignment of TCRBV amino acid sequences (SEQ ID NOs: 3457-3516, respectively, in order of appearance). FIG. 109A shows-the alignment of TCRBV amino acid sequences (SEQ ID NOs: 3457-3516, respectively, in order of appearance). FIG. 109B shows the alignment of TCRBV amino acid sequences (SEQ ID NOs: 3457-3516, respectively, in order of appearance), continued from FIG. 109A. FIG. 109C shows the alignment of TCRBV amino acid sequences (SEQ ID NOs: 3457-3516, respectively, in order of appearance), continued from FIG. 109B. FIG. 109D shows the alignment of TCRBV amino acid sequences (SEQ ID NOs: 3457-3516, respectively, in order of appearance), continued from FIG. 109C. FIG. 109E depicts a table showing TCRBV families and/or subfamilies, and corresponding SEQ ID NOs assigned to the sequence of each of TCRBV families and/or subfamilies (SEQ ID NOs: 3457-3516).

FIGS. 110A-110J show the alignment of affinity matured humanized Antibody A-H VL and VH sequences. FIG. 110A shows the alignment of affinity matured humanized Antibody A-H VL sequences (SEQ ID NOS 3377-3389, respectively, in order of appearance), and FIG. 110B shows the alignment of affinity matured humanized Antibody A-H VL sequences (SEQ ID NOS 3377-3389, respectively, in order of appearance), continued from FIG. 110A, and the consensus VL sequence SEQ ID NO: 230, and the consensus VL sequence SEQ ID NO: 3289. FIG. 110C depicts a table showing the affinity matured humanized Antibody A-H VL sequences, and corresponding SEQ ID NOs assigned to each of the affinity matured humanized Antibody A-H VL full sequences (SEQ ID NOs: 3377-3389). FIG. 110D shows the alignment of affinity matured humanized Antibody A-H VH sequences (SEQ ID NOS 3390-3436, respectively, in order of appearance); FIG. 110E shows the alignment of affinity matured humanized Antibody A-H VH sequences (SEQ ID NOS 3390-3436, respectively, in order of appearance), continued from FIG. 110D; FIG. 110F shows the alignment of affinity matured humanized Antibody A-H VH sequences (SEQ ID NOS 3390-3436, respectively, in order of appearance), continued from FIG. 110E; FIG. 110G shows the alignment of affinity matured humanized Antibody A-H VH sequences (SEQ ID NOS 3390-3436, respectively, in order of appearance), continued from FIG. 110F; and FIG. 110H shows the alignment of affinity matured humanized Antibody A-H VH sequences (SEQ ID NOS 3390-3436, respectively, in order of appearance), continued from FIG. 110G. FIG. 110I shows the consensus VH sequence SEQ ID NO: 231 and the consensus VH sequence SEQ ID NO: 3290. FIG. 110J depicts a table showing the affinity matured humanized Antibody A-H VH sequences, and corresponding SEQ ID NOs assigned to each of the affinity matured humanized Antibody A-H VH full sequences (SEQ ID NOs: 3390-3436).

DETAILED DESCRIPTION OF THE INVENTION

Figure 3:
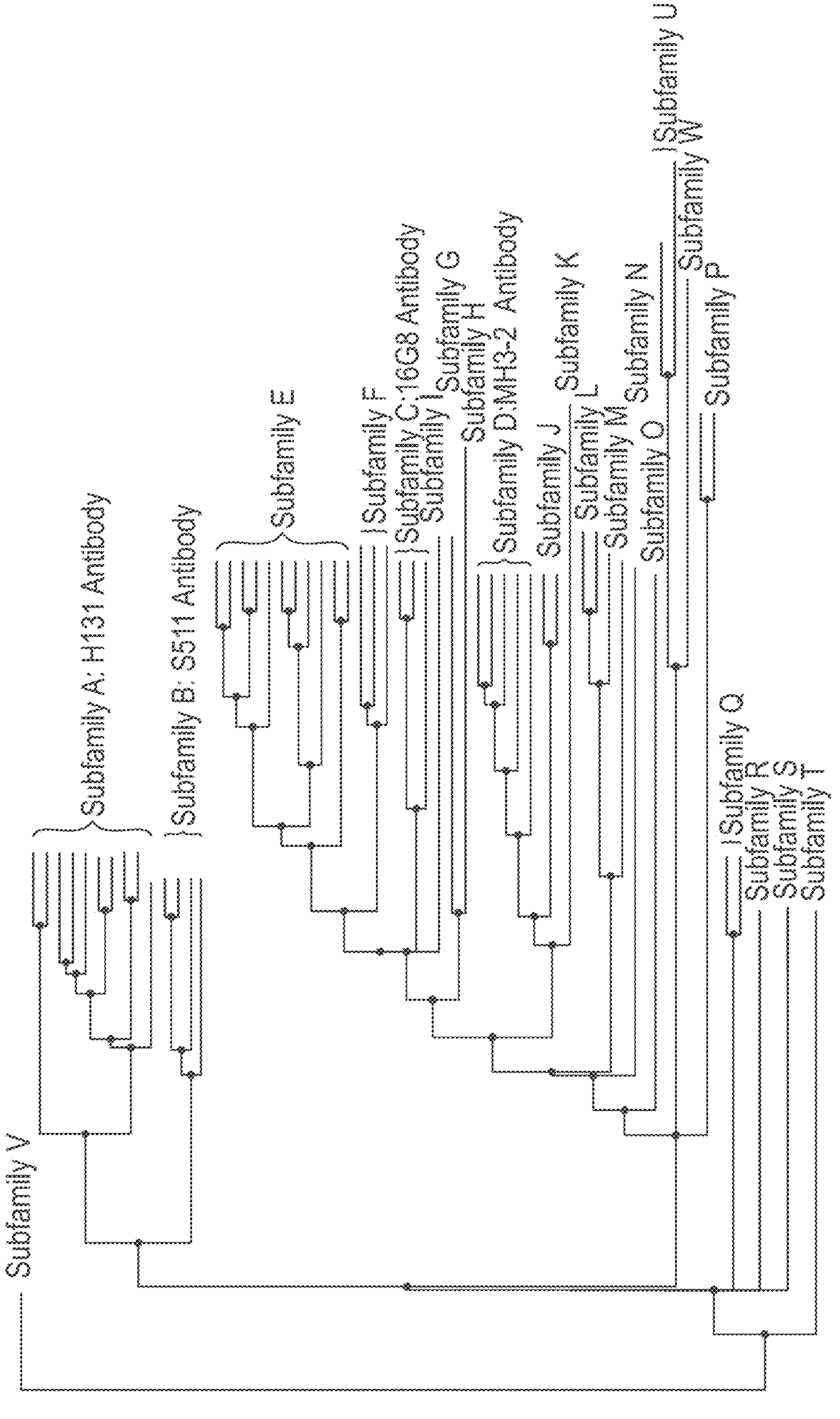
FIG. 3 depicts the phylogenetic tree of TCRBV gene family and subfamilies with corresponding antibodies mapped. Subfamily identities are as follows: Subfamily A: TCRβ V6; Subfamily B: TCRβ V10; Subfamily C: TCRβ V12; Subfamily D: TCRβ V5; Subfamily E: TCRβ V7; Subfamily F: TCRβ V11; Subfamily G: TCRβ V14; Subfamily H: TCRβ V16; Subfamily I: TCRβ V18; Subfamily J: TCRβ V9; Subfamily K: TCRβ V13; Subfamily L: TCRβ V4; Subfamily M: TCRβ V3; Subfamily N: TCRβ V2; Subfamily O: TCRβ V15; Subfamily P: TCRβ V30; Subfamily Q: TCRβ V19; Subfamily R: TCRβ V27; Subfamily S: TCRβ V28; Subfamily T: TCRβ V24; Subfamily U: TCRβ V20; Subfamily V: TCRβ V25; and Subfamily W: TCRβ V29 subfamily. Subfamily members are described in detail herein in the Section titled "TCR beta V (TCRβV)".

Current bispecific constructs designed to redirect T cells to promote tumor cell lysis for cancer immunotherapy typically utilize antibody fragments (Fab, scFv, VH, etc.) that are derived from monoclonal antibodies (mAb) directed against the CD3ε subunit of the T cell receptor (TCR). However, there are limitations to this approach which may prevent the full realization of the therapeutic potential for such bispecific constructs. Previous studies have shown that even low "activating" doses of anti-CD3ε mAb can cause long-term T cell dysfunction and exert immunosuppressive effects. In addition, anti-CD3ε mAbs have been associated with side effects that result from massive T cell activation. The large number of activated T cells secrete substantial amounts of cytokines, the most important of which is Interferon gamma (IFNg). This excess amount of IFNg in turn activates macrophages which then overproduce proinflammatory cytokines such as IL-1beta, IL-6, IL-10 and TNF-alpha, causing a "cytokine storm" known as the cytokine release syndrome (CRS) (Shimabukuro-Vornhagen et al., J Immunother Cancer. 2018 Jun. 15; 6(1):56, herein incorporated by reference in its entirety). Thus, the need exists for developing antibodies that are capable of binding and activating only a subset of effector T cells, e.g., to reduce the CRS and/or neurotoxicity (NT).

This invention features molecules targeting the TCRβV chain of TCR and methods thereof. Without wishing to be bound by theory, such molecules are capable of binding, activating, and/or expanding only a subset of T cells, avoiding or reducing CRS and/or NT and minimizing potential immunosuppressive effects of anti-CD3 mAbs.

TCR is a disulfide-linked membrane-anchored heterodimeric protein normally consisting of the highly variable alpha (α) and beta (β) chains expressed as part of a complex with the invariant CD3 chain molecules. TCR on αβ T cells is formed by a heterodimer of one alpha chain and one beta chain. Each alpha or beta chain consists of a constant domain and a highly variable domain classified as the Immunoglobulin superfamily (IgSF) fold. The TCRβV chains can be further classified into 30 subfamilies (TRBV1-30). Despite their high structural and functional homology, the amino acid sequence homology in the TRBV genes is very low. Only 4 amino acids out of ~95 are identical while 10 additional amino acids are conserved among all subfamilies (see an alignment of TCRBV amino acid sequences in Table 9). Nevertheless, TCRs formed between alpha and beta chains of highly diverse sequences show a remarkable structural homology (FIGS. 24A and 24B) and elicit a similar function, e.g., activation of T cells.

Disclosed herein is the discovery of a novel class of antibodies, i.e., anti-TCRβV antibody molecules disclosed herein, which despite having low sequence similarity (e.g., low sequence identity among the different antibody molecules that recognize different TCRβV subfamilies), recognize a structurally conserved, yet sequence-wise variable, region, e.g., domain, on the TCRβV protein (as denoted by the circled area in FIG. 24A) and have a similar function (e.g., activation of T cells and a similar cytokine profile as described herein). Thus, the anti-TCRβV antibody molecules disclosed herein share a structure-function relationship.

Figure 24A:
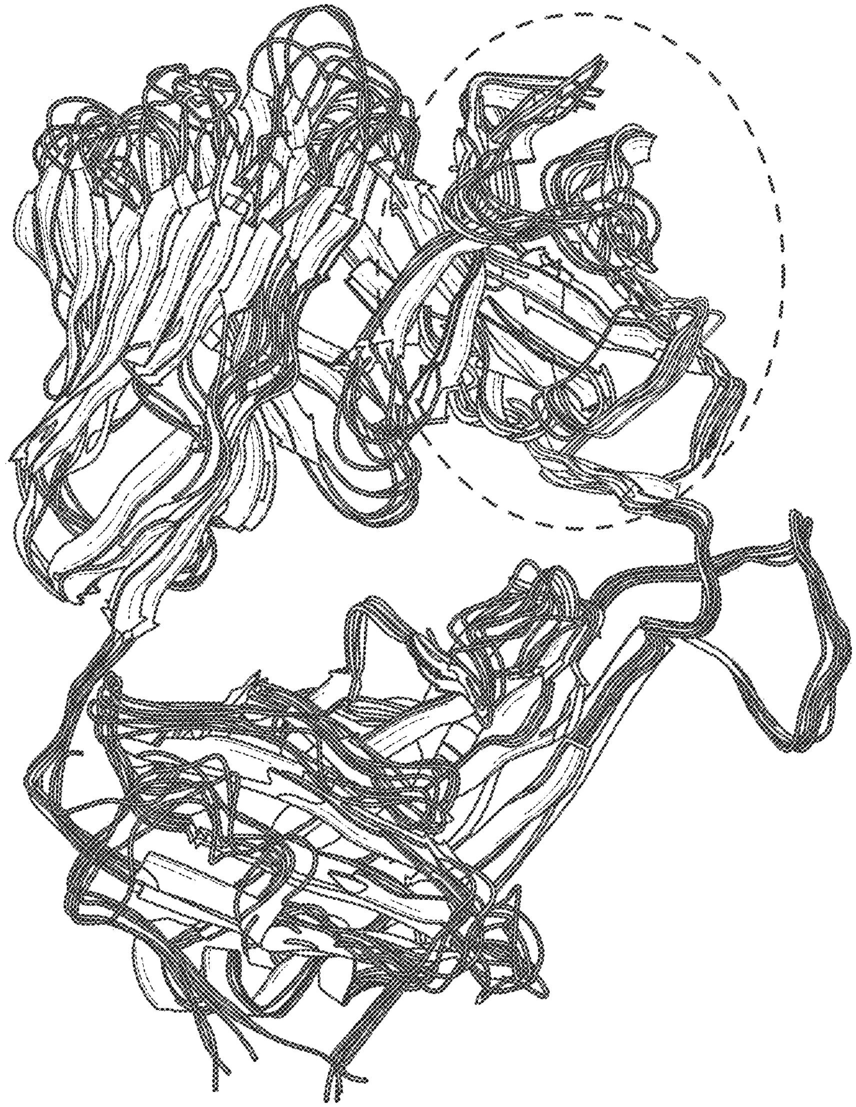

Without wishing to be bound by theory, it is believed that in some embodiments, the anti-TCRβV antibody molecules disclosed herein bind to an outward facing epitope of a TCRβV protein when it is in a complex with a TCRalpha protein, e.g., as denoted by the circled area in FIG. 24A. In some embodiments, the anti-TCRβV antibody molecules disclosed herein recognize (e.g., bind to), a domain (e.g., an epitope) on the TCRβV protein that is: (1) structurally conserved among different TCRβV subfamilies; and (2) has minimal sequence identity among the different TCRβV subfamilies. As shown in Table 9, TCRβV proteins from the different TCRBV subfamilies share minimal sequence similarity. However, as shown in FIG. 24A-B, TCRβV proteins which have minimal sequence similarity, share a similar 3D conformation and structure.

In some embodiments, the anti-TCRβV antibody molecules disclosed herein do not recognize, e.g., bind to, an interface of a TCRβV:TCRalpha complex.

In some embodiments, the anti-TCRβV antibody molecules disclosed herein do not recognize, e.g., bind to, a constant region of a TCRBV protein.

In some embodiments, the anti-TCRβV antibody molecules disclosed herein do not recognize, e.g., bind to, one or more (e.g., all) of a complementarity determining region (e.g., CDR1, CDR2 and/or CDR3) of a TCRβV protein.

This disclosure provides, inter alia, antibody molecules directed to the variable chain of the beta subunit of TCR (TCRβV) which bind and, e.g., activate a subset of T cells. The anti-TCRβV antibody molecules disclosed herein result in lesser or no production of cytokines associated with CRS, e.g., IL-6, IL-1beta, IL-10 and TNF alpha; and enhanced and/or delayed production of IL-2 and IFNg. In some embodiments, the anti-TCRβV antibodies disclosed herein have a cytokine profile, e.g., as described herein, which differs from a cytokine profile of a T cell engager that binds to a receptor or molecule other than a TCRβV region ("a non-TCRβV-binding T cell engager"). In some embodiments, the anti-TCRβV antibodies disclosed herein result in expansion of TCRβV+ T cells, e.g., a subset of memory effector T cells known as TEMRA. Without wishing to be bound by theory, it is believed that in some embodiments, TEMRA cells can promote tumor cell lysis but not CRS. Accordingly, provided herein are methods of making said anti-TCRβV antibody molecules and uses thereof. Also disclosed herein are multispecific molecules, e.g., bispecific molecules comprising said anti-TCRβV antibody molecules. In some embodiments, compositions comprising anti-TCRβV antibody molecules of the present disclosure, can be used, e.g., to: (1) activate and redirect T cells to promote tumor cell lysis for cancer immunotherapy; and/or (2) expand TCRβV+ T cells. In some embodiments, compositions comprising anti-TCRβV antibody molecules as disclosed herein limit the harmful side-effects of CRS and/or NT, e.g., CRS and/or NT associated with anti-CD3e targeting.

In some embodiments, the anti-TCRβV antibody molecule does not bind to TCRβ V12, or binds to TCRβ V12 with an affinity and/or binding specificity that is less than (e.g., less than about 10%, 20%, 30%, 40%, 50%, 60%, 70%, 80%, 90% or about 2-, 5-, or 10-fold) the affinity and/or binding specificity of the 16G8 murine antibody or a humanized version thereof as described in U.S. Pat. No. 5,861,155.

In some embodiments, the anti-TCRβV antibody molecule binds to TCRβ V12 with an affinity and/or binding specificity that is greater than (e.g., greater than about 10%, 20%, 30%, 40%, 50%, 60%, 70%, 80%, 90% or about 2-, 5-, or 10-fold) the affinity and/or binding specificity of the 16G8 murine antibody or a humanized version thereof as described in U.S. Pat. No. 5,861,155.

In some embodiments, the anti-TCRβV antibody molecule binds to a TCRβV region other than TCRβ V12 (e.g., TCRβV region as described herein, e.g., TCRβ V6 subfamily (e.g., TCRβ V6-5*01) with an affinity and/or binding specificity that is greater than (e.g., greater than about 10%, 20%, 30%, 40%, 50%, 60%, 70%, 80%, 90% or about 2-, 5-, or 10-fold) the affinity and/or binding specificity of the 16G8 murine antibody or a humanized version thereof as described in U.S. Pat. No. 5,861,155.

In some embodiments, the anti-TCRβV antibody molecule does not comprise the CDRs of the Antibody B murine antibody.

In some embodiments, the anti-TCRβV antibody molecule does not bind to TCRβ V5-5*01 or TCRβ V5-1*01, or binds to TCRβ V5-5*01 or TCRβ V5-1*01 with an affinity and/or binding specificity that is less than (e.g., less than about 10%, 20%, 30%, 40%, 50%, 60%, 70%, 80%, 90% or about 2-, 5-, or 10-fold) the affinity and/or binding specificity of the TM23 murine antibody or a humanized version thereof as described in U.S. Pat. No. 5,861,155.

In some embodiments, the anti-TCRβV antibody molecule binds to TCRβ V5-5*01 or TCRβ V5-1*01 with an affinity and/or binding specificity that is greater than (e.g., greater than about 10%, 20%, 30%, 40%, 50%, 60%, 70%, 80%, 90% or about 2-, 5-, or 10-fold) the affinity and/or binding specificity of the TM23 murine antibody or a humanized version thereof as described in U.S. Pat. No. 5,861,155.

In some embodiments, the anti-TCRβV antibody molecule binds to a TCRβV region other than TCRβ V5-5*01 or TCRβ V5-1*01 (e.g., TCRβV region as described herein, e.g., TCRβ V6 subfamily (e.g., TCRβ V6-5*01) with an affinity and/or binding specificity that is greater than (e.g., greater than about 10%, 20%, 30%, 40%, 50%, 60%, 70%, 80%, 90% or about 2-, 5-, or 10-fold) the affinity and/or binding specificity of the TM23 murine antibody or a humanized version thereof as described in U.S. Pat. No. 5,861,155.

In some embodiments, the anti-TCRβV antibody molecule does not comprise the CDRs of the TM23 murine antibody.

Accordingly, provided herein are, inter alia, anti-TCRβV antibody molecules, multispecific or multifunctional molecules (e.g., multispecific or multifunctional antibody molecules) that comprise anti-TCRβV antibody molecules, nucleic acids encoding the same, methods of producing the aforesaid molecules, pharmaceutical compositions comprising aforesaid molecules, and methods of treating a disease or disorder, e.g., cancer, using the aforesaid molecules. The antibody molecules and pharmaceutical compositions disclosed herein can be used (alone or in combination with other agents or therapeutic modalities) to treat, prevent and/or diagnose disorders and conditions, e.g., cancer, e.g., as described herein.

Definitions

Unless defined otherwise, all technical and scientific terms used herein have the same meaning as commonly understood by one of ordinary skill in the art to which the invention pertains.

The term "a" and "an" refers to one or to more than one (i.e., to at least one) of the grammatical object of the article. By way of example, "an element" means one element or more than one element.

The term "about" when referring to a measurable value such as an amount, a temporal duration, and the like, is meant to encompass variations of ±20% or in some instances ±10%, or in some instances ±5%, or in some instances ±1%, or in some instances ±0.1% from the specified value, as such variations are appropriate to perform the disclosed methods.

The term "acquire" or "acquiring" as the terms are used herein, refer to obtaining possession of a physical entity (e.g., a sample, a polypeptide, a nucleic acid, or a sequence), or a value, e.g., a numerical value, by "directly acquiring" or "indirectly acquiring" the physical entity or value. "Directly acquiring" means performing a process (e.g., performing a synthetic or analytical method) to obtain the physical entity or value. "Indirectly acquiring" refers to receiving the physical entity or value from another party or source (e.g., a third party laboratory that directly acquired the physical entity or value). Directly acquiring a physical entity includes performing a process that includes a physical change in a physical substance, e.g., a starting material. Directly acquiring a value includes performing a process that includes a physical change in a sample or another substance, e.g., performing an analytical process which includes a physical change in a substance, e.g., a sample.

As used herein, the term "T cell receptor beta variable chain" or "TCRβV," refers to an extracellular region of the T cell receptor beta chain which comprises the antigen recognition domain of the T cell receptor. The term TCRβV includes isoforms, mammalian, e.g., human TCRβV, species homologs of human and analogs comprising at least one common epitope with TCRβV. Human TCRβV comprises a gene family comprising subfamilies including, but not limited to: a TCRβ V6 subfamily, a TCRβ V10 subfamily, a TCRβ V12 subfamily, a TCRβ V5 subfamily, a TCRβ V7 subfamily, a TCRβ V11 subfamily, a TCRβ V14 subfamily, a TCRβ V16 subfamily, a TCRβ V18 subfamily, a TCRβ V9 subfamily, a TCRβ V13 subfamily, a TCRβ V4 subfamily, a TCRβ V3 subfamily, a TCRβ V2 subfamily, a TCRβ V15 subfamily, a TCRβ V30 subfamily, a TCRβ V19 subfamily, a TCRβ V27 subfamily, a TCRβ V28 subfamily, a TCRβ V24 subfamily, a TCRβ V20 subfamily, TCRβ V25 subfamily, a TCRβ V29 subfamily, a TCRβ V1 subfamily, a TCRβ V17 subfamily, a TCRβ V21 subfamily, a TCRβ V23 subfamily, or a TCRβ V26 subfamily, as well as family members of said subfamilies, and variants thereof (e.g., a structural or functional variant thereof). In some embodiments, the TCRβ V6 subfamily comprises: TCRβ V6-4*01, TCRβ V6-4*02, TCRβ V6-9*01, TCRβ V6-8*01, TCRβ V6-5*01, TCRβ V6-6*02, TCRβ V6-6*01, TCRβ V6-2*01, TCRβ V6-3*01 or TCRβ V6-1*01. In some embodiments, TCRβV comprises TCRβ V6-5*01, or a variant thereof, e.g., a variant having 85%, 90%, 95%, 99% or more identity the naturally-occurring sequence. TCRβ V6-5*01 is also known as TRBV65; TCRBV6S5; TCRBV13S1, or TCRβ V13.1. The amino acid sequence of TCRβ V6-5*01, e.g., human TCRβ V6-5*01, is known in that art, e.g., as provided by IMGT ID L36092. In some embodiments, TCRβ V6-5*01 is encoded by the nucleic acid sequence of SEQ ID NO: 43, or a sequence having 85%, 90%, 95%, 99% or more identity thereof. In some embodiments, TCRβ V6-5*01 comprises the amino acid sequence of SEQ ID NO: 44, or a sequence having 85%, 90%, 95%, 99% or more identity thereof.

The term "human-like antibody molecule" as used herein refers to a humanized antibody molecule, human antibody molecule or an antibody molecule having at least 95% identity with a non-murine germline framework region, e.g., FR1, FR2, FR3 and/or FR4. In some embodiments, the human-like antibody molecule comprises a framework region having at least 95% identity to a human germline framework region, e.g., a FR1, FR2, FR3 and/or FR4 of a human germline framework region. In some embodiments, the human-like antibody molecule is a recombinant antibody. In some embodiments, the human-like antibody molecule is a humanized antibody molecule. In some embodiments, the human-like antibody molecule is human antibody molecule. In some embodiments, the human-like antibody molecule is a phage display or a yeast display antibody molecule. In some embodiments, the human-like antibody molecule is a chimeric antibody molecule. In some embodiments, the human-like antibody molecule is a CDR grafted antibody molecule.

The term "cytokine profile" as used herein, refers to the level and/or activity of on one or more cytokines or chemokines, e.g., as described herein. In some embodiments, a cytokine profile comprises the level and/or activity of a naturally occurring cytokine, a fragment or a variant thereof. In an embodiment, a cytokine profile comprises the level and/or activity of one or more cytokines and/or one or more chemokines (e.g., as described herein). In some embodiments, a cytokine profile comprises the level and/or activity of a naturally occurring cytokine, a fragment or a variant thereof. In some embodiments, a cytokine profile comprises the level and/or activity of a naturally occurring chemokine, a fragment or a variant thereof. In an embodiment, a cytokine profile comprises the level and/or activity of one or more of: IL-2 (e.g., full length, a variant, or a fragment thereof); IL-1beta (e.g., full length, a variant, or a fragment thereof); IL-6 (e.g., full length, a variant, or a fragment thereof); TNFα (e.g., full length, a variant, or a fragment thereof); IFNg (e.g., full length, a variant, or a fragment thereof) IL-10 (e.g., full length, a variant, or a fragment thereof); IL-4 (e.g., full length, a variant, or a fragment thereof); TNF alpha (e.g., full length, a variant, or a fragment thereof); IL-12p70 (e.g., full length, a variant, or a fragment thereof); IL-13 (e.g., full length, a variant, or a fragment thereof); IL-8 (e.g., full length, a variant, or a fragment thereof); Eotaxin (e.g., full length, a variant, or a fragment thereof); Eotaxin-3 (e.g., full length, a variant, or a fragment thereof); IL-8 (HA) (e.g., full length, a variant, or a fragment thereof); IP-10 (e.g., full length, a variant, or a fragment thereof); MCP-1 (e.g., full length, a variant, or a fragment thereof); MCP-4 (e.g., full length, a variant, or a fragment thereof); MDC (e.g., full length, a variant, or a fragment thereof); MIP-1a (e.g., full length, a variant, or a fragment thereof); MIP-1b (e.g., full length, a variant, or a fragment thereof); TARC (e.g., full length, a variant, or a fragment thereof); GM-CSF (e.g., full length, a variant, or a fragment thereof); IL-12 23p40 (e.g., full length, a variant, or a fragment thereof); IL-15 (e.g., full length, a variant, or a fragment thereof); IL-16 (e.g., full length, a variant, or a fragment thereof); IL-17a (e.g., full length, a variant, or a fragment thereof); IL-1a (e.g., full length, a variant, or a fragment thereof); IL-5 (e.g., full length, a variant, or a fragment thereof); IL-7 (e.g., full length, a variant, or a fragment thereof); TNF-beta (e.g., full length, a variant, or a fragment thereof); or VEGF (e.g., full length, a variant, or a fragment thereof). In some embodiments, a cytokine profile includes secretion of one or more cytokines or chemokines.

In an embodiment, a cytokine in a cytokine profile can be modulated, e.g., increased or decreased, by an anti-TCRBV antibody molecule described herein. In one embodiment, the cytokine profile includes cytokines associated with a cytokine storm or cytokine release syndrome (CRS), e.g., IL-6, IL-1beta, TNFalpha and IL-10.

The term "variant" refers to a polypeptide that has a substantially identical amino acid sequence to the naturally-occurring sequence, or are encoded by a substantially identical nucleotide sequence. In some embodiments, the variant is a functional variant. In some embodiments, a TCRβV variant can bind to TCRα and form a TCR α:β complex.

The term "functional variant" refers to a polypeptide that has a substantially identical amino acid sequence to the naturally-occurring sequence, or are encoded by a substantially identical nucleotide sequence, and are capable of having one or more activities of the naturally-occurring sequence.

As used herein, a "multifunctional" or a "multispecific" molecule refers to molecule, e.g., a polypeptide, that has two or more functionalities, e.g., two or more binding specificities. In some embodiments, the functionalities can include one or more immune cell engagers, one or more tumor binding molecules, one or more cytokine molecules, one or more stromal modifiers, and other moieties described herein. In some embodiments, the multispecific molecule is a multispecific antibody molecule, e.g., a bispecific antibody molecule. In some embodiments, the multispecific molecule includes an anti-TCRVb antibody molecule as described herein.

In some embodiments, the multifunctional molecule includes an immune cell engager. "An immune cell engager" refers to one or more binding specificities that bind and/or activate an immune cell, e.g., a cell involved in an immune response. In embodiments, the immune cell is chosen from a T cell, an NK cell, a B cell, a dendritic cell, and/or the macrophage cell. The immune cell engager can be an antibody molecule, a receptor molecule (e.g., a full length receptor, receptor fragment, or fusion thereof (e.g., a receptor-Fc fusion)), or a ligand molecule (e.g., a full length ligand, ligand fragment, or fusion thereof (e.g., a ligand-Fc fusion)) that binds to the immune cell antigen (e.g., the T cell, the NK cell antigen, the B cell antigen, the dendritic cell antigen, and/or the macrophage cell antigen). In embodiments, the immune cell engager specifically binds to the target immune cell, e.g., binds preferentially to the target immune cell. For example, when the immune cell engager is an antibody molecule, it binds to an immune cell antigen (e.g., a T cell antigen, an NK cell antigen, a B cell antigen, a dendritic cell antigen, and/or a macrophage cell antigen) with a dissociation constant of less than about 10 nM.

In some embodiments, the multifunctional molecule includes a cytokine molecule. As used herein, a "cytokine molecule" refers to full length, a fragment or a variant of a cytokine; a cytokine further comprising a receptor domain, e.g., a cytokine receptor dimerizing domain; or an agonist of a cytokine receptor, e.g., an antibody molecule (e.g., an agonistic antibody) to a cytokine receptor, that elicits at least one activity of a naturally-occurring cytokine. In some embodiments the cytokine molecule is chosen from interleukin-2 (IL-2), interleukin-7 (IL-7), interleukin-12 (IL-12), interleukin-10 (IL-10), interleukin-15 (IL-15), interleukin-18 (IL-18), interleukin-21 (IL-21), or interferon gamma, or a fragment or variant thereof, or a combination of any of the aforesaid cytokines. The cytokine molecule can be a monomer or a dimer. In embodiments, the cytokine molecule can further include a cytokine receptor dimerizing domain. In other embodiments, the cytokine molecule is an agonist of a cytokine receptor, e.g., an antibody molecule (e.g., an agonistic antibody) to a cytokine receptor chosen from an IL-15Ra or IL-21R.

As used herein, the term "molecule" as used in, e.g., antibody molecule, cytokine molecule, receptor molecule, includes full-length, naturally-occurring molecules, as well as variants, e.g., functional variants (e.g., truncations, fragments, mutated (e.g., substantially similar sequences) or derivatized form thereof), so long as at least one function and/or activity of the unmodified (e.g., naturally-occurring) molecule remains.

In some embodiments, the multifunctional molecule includes a stromal modifying moiety. A "stromal modifying moiety," as used herein refers to an agent, e.g., a protein (e.g., an enzyme), that is capable of altering, e.g., degrading a component of, the stroma. In embodiments, the component of the stroma is chosen from, e.g., an ECM component, e.g., a glycosaminoglycan, e.g., hyaluronan (also known as hyaluronic acid or HA), chondroitin sulfate, chondroitin, dermatan sulfate, heparin sulfate, heparin, entactin, tenascin, aggrecan and keratin sulfate; or an extracellular protein, e.g., collagen, laminin, elastin, fibrinogen, fibronectin, and vitronectin.

Certain terms are defined below.

As used herein, the articles "a" and "an" refer to one or more than one, e.g., to at least one, of the grammatical object of the article. The use of the words "a" or "an" when used in conjunction with the term "comprising" herein may mean "one," but it is also consistent with the meaning of "one or more," "at least one," and "one or more than one."

As used herein, "about" and "approximately" generally mean an acceptable degree of error for the quantity measured given the nature or precision of the measurements. Exemplary degrees of error are within 20 percent (%), typically, within 10%, and more typically, within 5% of a given range of values.

"Antibody molecule" as used herein refers to a protein, e.g., an immunoglobulin chain or fragment thereof, comprising at least one immunoglobulin variable domain structure and/or sequence. An antibody molecule encompasses antibodies (e.g., full-length antibodies) and antibody fragments. In an embodiment, an antibody molecule comprises an antigen binding or functional fragment of a full length antibody, or a full length immunoglobulin chain. For example, a full-length antibody is an immunoglobulin (Ig) molecule (e.g., an IgG antibody) that is naturally occurring or formed by normal immunoglobulin gene fragment recombinatorial processes). In embodiments, an antibody molecule refers to an immunologically active, antigen-binding portion of an immunoglobulin molecule, such as an antibody fragment. An antibody fragment, e.g., functional fragment, is a portion of an antibody, e.g., Fab, Fab', $F(ab')_2$, $F(ab)_2$, variable fragment (Fv), domain antibody (dAb), or single chain variable fragment (scFv). A functional antibody fragment binds to the same antigen as that recognized by the intact (e.g., full-length) antibody. The terms "antibody fragment" or "functional fragment" also include isolated fragments consisting of the variable regions, such as the "Fv" fragments consisting of the variable regions of the heavy and light chains or recombinant single chain polypeptide molecules in which light and heavy variable regions are connected by a peptide linker ("scFv proteins"). In some embodiments, an antibody fragment does not include portions of antibodies without antigen binding activity, such as Fc fragments or single amino acid residues. Exemplary antibody molecules include full length antibodies and antibody fragments, e.g., dAb (domain antibody), single chain, Fab, Fab', and $F(ab')_2$ fragments, and single chain variable fragments (scFvs). In some embodiments, the antibody molecule is an antibody mimetic. In some embodiments, the antibody molecule is, or comprises, an antibody-like framework or scaffold, such as, fibronectins, ankyrin repeats (e.g., designed ankyrin repeat proteins (DARPins)), avimers, affibody affinity ligands, anticalins, or affilin molecules.

As used herein, an "immunoglobulin variable domain sequence" refers to an amino acid sequence which can form the structure of an immunoglobulin variable domain. For example, the sequence may include all or part of the amino acid sequence of a naturally-occurring variable domain. For example, the sequence may or may not include one, two, or more N- or C-terminal amino acids, or may include other alterations that are compatible with formation of the protein structure.

In embodiments, an antibody molecule is monospecific, e.g., it comprises binding specificity for a single epitope. In some embodiments, an antibody molecule is multispecific, e.g., it comprises a plurality of immunoglobulin variable domain sequences, where a first immunoglobulin variable domain sequence has binding specificity for a first epitope and a second immunoglobulin variable domain sequence has binding specificity for a second epitope. In some embodiments, an antibody molecule is a bispecific antibody molecule. "Bispecific antibody molecule" as used herein refers to an antibody molecule that has specificity for more than one (e.g., two, three, four, or more) epitope and/or antigen.

"Antigen" (Ag) as used herein refers to a molecule that can provoke an immune response, e.g., involving activation of certain immune cells and/or antibody generation. Any macromolecule, including almost all proteins or peptides, can be an antigen. Antigens can also be derived from genomic recombinant or DNA. For example, any DNA comprising a nucleotide sequence or a partial nucleotide sequence that encodes a protein capable of eliciting an immune response encodes an "antigen." In embodiments, an antigen does not need to be encoded solely by a full length nucleotide sequence of a gene, nor does an antigen need to be encoded by a gene at all. In embodiments, an antigen can be synthesized or can be derived from a biological sample, e.g., a tissue sample, a tumor sample, a cell, or a fluid with other biological components. As used, herein a "tumor antigen" or interchangeably, a "cancer antigen" includes any molecule present on, or associated with, a cancer, e.g., a cancer cell or a tumor microenvironment that can provoke an immune response. As used, herein an "immune cell antigen" includes any molecule present on, or associated with, an immune cell that can provoke an immune response.

The "antigen-binding site," or "binding portion" of an antibody molecule refers to the part of an antibody molecule, e.g., an immunoglobulin (Ig) molecule, that participates in antigen binding. In embodiments, the antigen binding site is formed by amino acid residues of the variable (V) regions of the heavy (H) and light (L) chains. Three highly divergent stretches within the variable regions of the heavy and light chains, referred to as hypervariable regions, are disposed between more conserved flanking stretches called "framework regions," (FRs). FRs are amino acid sequences that are naturally found between, and adjacent to, hypervariable regions in immunoglobulins. In embodiments, in an antibody molecule, the three hypervariable regions of a light chain and the three hypervariable regions of a heavy chain are disposed relative to each other in three dimensional space to form an antigen-binding surface, which is complementary to the three-dimensional surface of a bound antigen. The three hypervariable regions of each of the heavy and light chains are referred to as "complementarity-determining regions," or "CDRs." The framework region and CDRs have been defined and described, e.g., in Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917. Each variable chain (e.g., variable heavy chain and variable light chain) is typically made up of three CDRs and four FRs, arranged from amino-terminus to carboxy-terminus in the amino acid order: FR1, CDR1, FR2, CDR2, FR3, CDR3, and FR4.

"Cancer" as used herein can encompass all types of oncogenic processes and/or cancerous growths. In embodiments, cancer includes primary tumors as well as metastatic tissues or malignantly transformed cells, tissues, or organs. In embodiments, cancer encompasses all histopathologies and stages, e.g., stages of invasiveness/severity, of a cancer. In embodiments, cancer includes relapsed and/or resistant cancer. The terms "cancer" and "tumor" can be used interchangeably. For example, both terms encompass solid and liquid tumors. As used herein, the term "cancer" or "tumor" includes premalignant, as well as malignant cancers and tumors.

As used herein, an "immune cell" refers to any of various cells that function in the immune system, e.g., to protect against agents of infection and foreign matter. In embodiments, this term includes leukocytes, e.g., neutrophils, eosinophils, basophils, lymphocytes, and monocytes. Innate leukocytes include phagocytes (e.g., macrophages, neutrophils, and dendritic cells), mast cells, eosinophils, basophils, and natural killer cells. Innate leukocytes identify and eliminate pathogens, either by attacking larger pathogens through contact or by engulfing and then killing microorganisms, and are mediators in the activation of an adaptive immune response. The cells of the adaptive immune system are special types of leukocytes, called lymphocytes. B cells and T cells are important types of lymphocytes and are derived from hematopoietic stem cells in the bone marrow. B cells are involved in the humoral immune response, whereas T cells are involved in cell-mediated immune response. The term "immune cell" includes immune effector cells.

"Immune effector cell," as that term is used herein, refers to a cell that is involved in an immune response, e.g., in the promotion of an immune effector response. Examples of immune effector cells include, but are not limited to, T cells, e.g., alpha/beta T cells and gamma/delta T cells, B cells, natural killer (NK) cells, natural killer T (NK T) cells, and mast cells.

The term "effector function" or "effector response" refers to a specialized function of a cell. Effector function of a T cell, for example, may be cytolytic activity or helper activity including the secretion of cytokines.

The compositions and methods of the present invention encompass polypeptides and nucleic acids having the sequences specified, or sequences substantially identical or similar thereto, e.g., sequences at least 80%, 85%, 90%, 95% identical or higher to the sequence specified. In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences that contain a common structural domain having at least about 80%, 85%, 90%, 91%, 92%, 93%, 94%, 95%, 96%, 97%, 98% or 99% identity to a reference sequence, e.g., a sequence provided herein.

In the context of nucleotide sequence, the term "substantially identical" is used herein to refer to a first nucleic acid sequence that contains a sufficient or minimum number of nucleotides that are identical to aligned nucleotides in a second nucleic acid sequence such that the first and second nucleotide sequences encode a polypeptide having common functional activity, or encode a common structural polypeptide domain or a common functional polypeptide activity. For example, nucleotide sequences having at least about 80%, 85%, 90%, 91%, 92%, 93%, 94%, 95%, 96%, 97%, 98% or 99% identity to a reference sequence, e.g., a sequence provided herein.

The term "variant" refers to a polypeptide that has a substantially identical amino acid sequence to a reference amino acid sequence, or is encoded by a substantially identical nucleotide sequence. In some embodiments, the variant is a functional variant.

The term "functional variant" refers to a polypeptide that has a substantially identical amino acid sequence to a reference amino acid sequence, or is encoded by a substantially identical nucleotide sequence, and is capable of having one or more activities of the reference amino acid sequence.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology").

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch ((1970) *J. Mol. Biol.* 48:444-453) algorithm which has been incorporated into the GAP program in the GCG software package (available at the website of gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at the website of gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller ((1989) *CABIOS,* 4:11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215: 403-10. BLAST nucleotide searches can be performed with the NBLAST program, score=100, wordlength=12 to obtain nucleotide sequences homologous to a nucleic acid molecule of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997) *Nucleic Acids Res.* 25:3389-3402. When utilizing BLAST and Gapped BLAST programs, the default parameters of the respective programs (e.g., XBLAST and NBLAST) can be used.

It is understood that the molecules of the present invention may have additional conservative or non-essential amino acid substitutions, which do not have a substantial effect on their functions.

The term "amino acid" is intended to embrace all molecules, whether natural or synthetic, which include both an amino functionality and an acid functionality and capable of being included in a polymer of naturally-occurring amino acids. Exemplary amino acids include naturally-occurring amino acids; analogs, derivatives and congeners thereof, amino acid analogs having variant side chains; and all stereoisomers of any of any of the foregoing. As used herein the term "amino acid" includes both the D- or L-optical isomers and peptidomimetics.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The terms "polypeptide", "peptide" and "protein" (if single chain) are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. The polypeptide can be isolated from natural sources, can be a produced by recombinant techniques from a eukaryotic or prokaryotic host, or can be a product of synthetic procedures.

The terms "nucleic acid," "nucleic acid sequence," "nucleotide sequence," or "polynucleotide sequence," and "polynucleotide" are used interchangeably. They refer to a polymeric form of nucleotides of any length, either deoxyribonucleotides or ribonucleotides, or analogs thereof. The polynucleotide may be either single-stranded or double-stranded, and if single-stranded may be the coding strand or non-coding (antisense) strand. A polynucleotide may comprise modified nucleotides, such as methylated nucleotides and nucleotide analogs. The sequence of nucleotides may be interrupted by non-nucleotide components. A polynucleotide may be further modified after polymerization, such as by conjugation with a labeling component. The nucleic acid may be a recombinant polynucleotide, or a polynucleotide of genomic, cDNA, semisynthetic, or synthetic origin which either does not occur in nature or is linked to another polynucleotide in a non-natural arrangement.

The term "isolated," as used herein, refers to material that is removed from its original or native environment (e.g., the natural environment if it is naturally occurring). For example, a naturally-occurring polynucleotide or polypeptide present in a living animal is not isolated, but the same polynucleotide or polypeptide, separated by human intervention from some or all of the co-existing materials in the natural system, is isolated. Such polynucleotides could be part of a vector and/or such polynucleotides or polypeptides could be part of a composition, and still be isolated in that such vector or composition is not part of the environment in which it is found in nature.

Various aspects of the invention are described in further detail below. Additional definitions are set out throughout the specification.

Human T Cell Receptor (TCR) Complex

T cell receptors (TCR) can be found on the surface of T cells. TCRs recognize antigens, e.g., peptides, presented on, e.g., bound to, major histocompatibility complex (MHC) molecules on the surface of cells, e.g., antigen-presenting cells. TCRs are heterodimeric molecules and can comprise an alpha chain, a beta chain, a gamma chain or a delta chain. TCRs comprising an alpha chain and a beta chain are also referred to as TCRαβ. The TCR beta chain consists of the following regions (also known as segments): variable (V), diversity (D), joining (J) and constant (C) (see Mayer G. and Nyland J. (2010) Chapter 10: Major Histocompatibility Complex and T-cell Receptors-Role in Immune Responses. In: Microbiology and Immunology on-line, University of South Carolina School of Medicine). The TCR alpha chain consists of V, J and C regions. The rearrangement of the T-cell receptor (TCR) through somatic recombination of V (variable), D (diversity), J (joining), and C (constant) regions is a defining event in the development and maturation of a T cell. TCR gene rearrangement takes place in the thymus.

TCRβ can comprise a receptor complex, known as the TCR complex, which comprises a TCR heterodimer comprising of an alpha chain and a beta chain, and dimeric signaling molecules, e.g., CD3 co-receptors, e.g., CD3δ/ε, and/or CD3γ/ε.

TCR Beta V (TCRβV)

Diversity in the immune system enables protection against a huge array of pathogens. Since the germline genome is limited in size, diversity is achieved not only by the process of V(D)J recombination but also by junctional (junctions between V-D and D-J segments) deletion of nucleotides and addition of pseudo-random, non-templated nucleotides. The TCR beta gene undergoes gene arrangement to generate diversity.

The TCR V beta repertoire varies between individuals and populations because of, e.g., 7 frequently occurring inactivating polymorphisms in functional gene segments and a large insertion/deletion-related polymorphism encompassing 2 V beta gene segments.

This disclosure provides, inter alia, antibody molecules and fragments thereof, that bind, e.g., specifically bind, to a human TCR beta V chain (TCRβV), e.g., a TCRβV gene family (also referred to as a group), e.g., a TCRβV subfamily (also referred to as a subgroup), e.g., as described herein. TCR beta V families and subfamilies are known in the art, e.g., as described in Yassai et al., (2009) *Immunogenetics* 61(7) pp: 493-502; Wei S. and Concannon P. (1994) *Human Immunology* 41(3) pp: 201-206. The antibodies described herein can be recombinant antibodies, e.g., recombinant non-murine antibodies, e.g., recombinant human or humanized antibodies.

The terms TCRBV, TCRVB, TRBV, TCRβV, TCRVβ or TRβV are used interchangeably herein and refer to a TCR beta V chain, e.g., as described herein.

In an aspect, the disclosure provides an anti-TCRβV antibody molecule that binds to human TCRβV, e.g., a TCRβV family, e.g., gene family or a variant thereof. In some embodiments a TCRBV gene family comprises one or more subfamilies, e.g., as described herein, e.g., in FIG. 3, Table 8A or Table 8B. In some embodiments, the TCRβV gene family comprises: a TCRβ V6 subfamily, a TCRβ V10 subfamily, a TCRβ V12 subfamily, a TCRβ V5 subfamily, a TCRβ V7 subfamily, a TCRβ V11 subfamily, a TCRβ V14 subfamily, a TCRβ V16 subfamily, a TCRβ V18 subfamily, a TCRβ V9 subfamily, a TCRβ V13 subfamily, a TCRβ V4 subfamily, a TCRβ V3 subfamily, a TCRβ V2 subfamily, a TCRβ V15 subfamily, a TCRβ V30 subfamily, a TCRβ V19 subfamily, a TCRβ V27 subfamily, a TCRβ V28 subfamily, a TCRβ V24 subfamily, a TCRβ V20 subfamily, TCRβ V25 subfamily, a TCRβ V29 subfamily, a TCRβ V1 subfamily, a TCRβ V17 subfamily, a TCRβ V21 subfamily, a TCRβ V23 subfamily, or a TCRβ V26 subfamily.

In some embodiments, TCRβ V6 subfamily is also known as TCRβ V13.1. In some embodiments, the TCRβ V6 subfamily comprises: TCRβ V6-4*01, TCRβ V6-4*02, TCRβ V6-9*01, TCRβ V6-8*01, TCRβ V6-5*01, TCRβ V6-6*02, TCRβ V6-6*01, TCRβ V6-2*01, TCRβ V6-3*01 or TCRβ V6-1*01, or a variant thereof. In some embodiments, TCRβ V6 comprises TCRβ V6-4*01, or a variant thereof. In some embodiments, TCRβ V6 comprises TCRβ V6-4*02, or a variant thereof. In some embodiments, TCRβ V6 comprises TCRβ V6-9*01, or a variant thereof. In some embodiments, TCRβ V6 comprises TCRβ V6-8*01, or a variant thereof. In some embodiments, TCRβ V6 comprises TCRβ V6-5*01, or a variant thereof. In some embodiments, TCRβ V6 comprises TCRβ V6-6*02, or a variant thereof. In some embodiments, TCRβ V6 comprises TCRβ V6-6*01, or a variant thereof. In some embodiments, TCRβ V6 comprises TCRβ V6-2*01, or a variant thereof. In some embodiments, TCRβ V6 comprises TCRβ V6-3*01, or a variant thereof. In some embodiments, TCRβ V6 comprises TCRβ V6-1*01, or a variant thereof.

In some embodiments, TCRβ V6 comprises TCRβ V6-5*01, or a variant thereof. In some embodiments, TCRβ V6, e.g., TCRβ V6-5*01, is recognized, e.g., bound, by SEQ ID NO: 1 and/or SEQ ID NO: 2. In some embodiments, TCRβ V6, e.g., TCRβ V6-5*01, is recognized, e.g., bound, by SEQ ID NO: 9 and/or SEQ ID NO: 10. In some embodiments, TCRβ V6 is recognized, e.g., bound, by SEQ ID NO: 9 and/or SEQ ID NO: 11.

In some embodiments, TCRβ V10 subfamily is also known as TCRβ V12. In some embodiments, the TCRβ V10 subfamily comprises: TCRβ V10-1*01, TCRβ V10-1*02, TCRβ V10-3*01 or TCRβ V10-2*01, or a variant thereof.

In some embodiments, TCRβ V12 subfamily is also known as TCRβ V8.1. In some embodiments, the TCRβ V12 subfamily comprises: TCRβ V12-4*01, TCRβ V12-3*01, or TCRβ V12-5*01, or a variant thereof. In some embodiments, TCRβ V12 is recognized, e.g., bound, by SEQ ID NO: 15 and/or SEQ ID NO: 16. In some embodiments, TCRβ V12 is recognized, e.g., bound, by any one of SEQ ID NOs 23-25, and/or any one of SEQ ID NO: 26-30:

In some embodiments, the TCRβ V5 subfamily is chosen from: TCRβ V5-5*01, TCRβ V5-6*01, TCRβ V5-4*01, TCRβ V5-8*01, TCRβ V5-1*01, or a variant thereof.

In some embodiments, the TCRβ V7 subfamily comprises TCRβ V7-7*01, TCRβ V7-6*01, TCRβ V7-8*02, TCRβ V7-4*01, TCRβ V7-2*02, TCRβ V7-2*03, TCRβ V7-2*01, TCRβ V7-3*01, TCRβ V7-9*03, or TCRβ V7-9*01, or a variant thereof.

In some embodiments, the TCRβ V11 subfamily comprises: TCRβ V11-1*01, TCRβ V11-2*01 or TCRβ V11-3*01, or a variant thereof.

In some embodiments, the TCRβ V14 subfamily comprises TCRβ V14*01, or a variant thereof.

In some embodiments, the TCRβ V16 subfamily comprises TCRβ V16*01, or a variant thereof.

In some embodiments, the TCRβ V18 subfamily comprises TCRβ V18*01, or a variant thereof.

In some embodiments, the TCRβ V9 subfamily comprises TCRβ V9*01 or TCRβ V9*02, or a variant thereof.

In some embodiments, the TCRβ V13 subfamily comprises TCRβ V13*01, or a variant thereof.

In some embodiments, the TCRβ V4 subfamily comprises TCRβ V4-2*01, TCRβ V4-3*01, or TCRβ V4-1*01, or a variant thereof.

In some embodiments, the TCRβ V3 subfamily comprises TCRβ V3-1*01, or a variant thereof.

In some embodiments, the TCRβ V2 subfamily comprises TCRβ V2*01, or a variant thereof.

In some embodiments, the TCRβ V15 subfamily comprises TCRβ V15*01, or a variant thereof.

In some embodiments, the TCRβ V30 subfamily comprises TCRβ V30*01, or TCRβ V30*02, or a variant thereof.

In some embodiments, the TCRβ V19 subfamily comprises TCRβ V19*01, or TCRβ V19*02, or a variant thereof.

In some embodiments, the TCRβ V27 subfamily comprises TCRβ V27*01, or a variant thereof.

In some embodiments, the TCRβ V28 subfamily comprises TCRβ V28*01, or a variant thereof.

In some embodiments, the TCRβ V24 subfamily comprises TCRβ V24-1*01, or a variant thereof.

In some embodiments, the TCRβ V20 subfamily comprises TCRβ V20-1*01, or TCRβ V20-1*02, or a variant thereof.

In some embodiments, the TCRβ V25 subfamily comprises TCRβ V25-1*01, or a variant thereof.

In some embodiments, the TCRβ V29 subfamily comprises TCRβ V29-1*01, or a variant thereof.

TABLE 8A

List of TCRβV subfamilies and subfamily members

| Reference in FIG. 3 | Subfamily | Subfamily members |
|---|---|---|
| A | TCRβ V6<br>Also referred to as:<br>TCR VB 13.1 | TCRβ V6-4*01, TCRβ V6-4*02, TCRβ V6-9*01, TCRβ V6-8*01, TCRβ V6-5*01, TCRβ V6-6*02, TCRβ V6-6*01, TCRβ V6-2*01, TCRβ V6-3*01 or TCRβ V6-1*01. |
| B | TCRβ V10<br>Also referred to as:<br>TCRβ V12 | TCRβ V10-1*01, TCRβ V10-1*02, TCRβ V10-3*01 or TCRβ V10-2*01 |
| C | TCRβ V12<br>Also referred to as:<br>TCRβ V8.1 | TCRβ V12-4*01, TCRβ V12-3*01, or TCRβ V12-5*01 |
| D | TCRβ V5 | TCRβ V5-5*01, TCRβ V5-6*01, TCRβ V5-4*01, TCRβ V5-8*01, TCRβ V5-1*01 |
| E | TCRβ V7 | TCRβ V7-7*01, TCRβ V7-6*01, TCRβ V7 -8*02, TCRβ V7 -4*01, TCRβ V7-2*02, TCRβ V7-2*03, TCRβ V7-2*01, TCRβ V7-3*01, TCRβ V7-9*03, or TCRβ V7-9*01 |
| F | TCRβ V11 | TCRβ V11-1*01, TCRβ V11-2*01 or TCRβ V11-3*01 |
| G | TCRβ V14 | TCRβ V14*01 |
| H | TCRβ V16 | TCRβ V16*01 |
| I | TCRβ V18 | TCRβ V18*01 |
| J | TCRβ V9 | TCRβ V9*01 or TCRβ V9*02 |
| K | TCRβ V13 | TCRβ V13*01 |
| L | TCRβ V4 | TCRβ V4-2*01, TCRβ V4-3*01, or TCRβ V4-1*01 |
| M | TCRβ V3 | TCRβ V3-1*01 |
| N | TCRβ V2 | TCRβ V2*01 |
| O | TCRβ V15 | TCRβ V15*01 |
| P | TCRβ V30 | TCRβ V30*01, or TCRβ V30*02 |
| Q | TCRβ V19 | TCRβ V19*01, or TCRβ V19*02 |
| R | TCRβ V27 | TCRβ V27*01. |
| S | TCRβ V28 | TCRβ V28*01. |
| T | TCRβ V24 | TCRβ V24-1*01 |
| U | TCRβ V20 | TCRβ V20-1*01, or TCRβ V20-1*02 |
| V | TCRβ V25 | TCRβ V25-1*01 |
| W | TCRβ V29 | TCRβ V29-1*01 |

TABLE 8B

| Additional TCRβV subfamilies<br>Subfamily |
|---|
| TCRβ V1 |
| TCRβ V17 |
| TCRβ V21 |
| TCRβ V23 |
| TCRβ V26 |

The various TCRβV subfamilies and/or subfamily members can be expressed at different levels in individuals, e.g., healthy individuals, as disclosed in Kitaura K. et al (2016), BMC Immunology vol 17: 38, the entire contents of which are hereby incorporated by reference. For example, TCRβ V6-5 is represented in approximately 3-6% healthy donors.

The representation of various TCRBV subfamilies and/or subfamily members can also be different in cancer cells. For example, TCRβV is present in about 3-6% of tumor infiltrating T cells irrespective of tumor type (see Li B. et al., *Nature Genetics,* 2016, vol: 48(7):725-32 the entire contents of which are hereby incorporated by references). Li et al., also disclose that TCRβ V6-5 is present at a high frequency in tumor cells.

Exemplary amino acid sequences for TCRβV subfamily members can be found on the ImMunoGeneTics Information System website of imgt.org, or in a similar resource.

The alignment of TCRBV amino acid sequences in Table 9 underscores the diversity of TCR sequences. In particular, the TRBV sequences from different subfamilies are considerably different from each other.

Anti-TCRβV Antibodies

Disclosed herein, is the discovery of a novel class of antibodies, i.e. anti-TCRβV antibody molecules disclosed herein, which despite having low sequence similarity (e.g., low sequence identity among the different antibody molecules that recognize different TCRβV subfamilies), recognize a structurally conserved region, e.g., domain, on the TCRβV protein (e.g., as denoted by the circled area in FIG. 24A) and have a similar function (e.g., a similar cytokine profile). Thus, the anti-TCRβV antibody molecules disclosed herein share a structure-function relationship.

Without wishing to be bound by theory, it is believed that in some embodiments, the anti-TCRβV antibody molecules disclosed herein bind to an outward facing epitope of a TCRβV protein when it is in a complex with a TCRalpha protein, e.g., as described by the circled area in FIG. 24A. In some embodiments, the anti-TCRβV antibody molecules disclosed herein recognize (e.g., bind to), a structurally conserved domain on the TCRβV protein (e.g., as denoted by the circled area in FIG. 24A).

In some embodiments, the anti-TCRβV antibody molecules disclosed herein do not recognize, e.g., bind to, an interface of a TCRβV:TCRalpha complex.

In some embodiments, the anti-TCRβV antibody molecules disclosed herein do not recognize, e.g., bind to, a constant region of a TCRβV protein. An exemplary antibody that binds to a constant region of a TCRBV region is JOVI.1 as described in Viney et al., (*Hybridoma.* 1992 December; 11(6):701-13).

In some embodiments, the anti-TCRβV antibody molecules disclosed herein do not recognize, e.g., bind to, one or more (e.g., all) of a complementarity determining region (e.g., CDR1, CDR2 and/or CDR3) of a TCRβV protein.

In some embodiments, the anti-TCRβV antibody molecules disclosed herein binds (e.g., specifically binds) to a TCRBV region. In some embodiments, binding of anti-TCRβV antibody molecules disclosed herein results in a cytokine profile that differs from a cytokine profile of a T cell engager that binds to a receptor or molecule other than a TCRβV region ("a non-TCRβV-binding T cell engager"). In some embodiments, the non-TCRβV-binding T cell engager comprises an antibody that binds to a CD3 molecule (e.g., CD3 epsilon (CD3ε) molecule); or a TCR alpha (TCRα) molecule. In some embodiments, the non-TCRβV-binding T cell engager is an OKT3 antibody or an SP34-2 antibody.

In an aspect, the disclosure provides an anti-TCRβV antibody molecule that binds to human TCRβV, e.g., a TCRβV gene family, e.g., one or more of a TCRβV subfamily, e.g., as described herein, e.g., in FIG. 3, Table 8A, or Table 8B. In some embodiments, the anti-TCRβV antibody molecule binds to one or more TCRβV subfamilies chosen from: a TCRβ V6 subfamily, a TCRβ V10 subfamily, a TCRβ V12 subfamily, a TCRβ V5 subfamily, a TCRβ V7 subfamily, a TCRβ V11 subfamily, a TCRβ V14 subfamily, a TCRβ V16 subfamily, a TCRβ V18 subfamily, a TCRβ V9 subfamily, a TCRβ V13 subfamily, a TCRβ V4 subfamily, a TCRβ V3 subfamily, a TCRβ V2 subfamily, a TCRβ V15 subfamily, a TCRβ V30 subfamily, a TCRβ V19 subfamily, a TCRβ V27 subfamily, a TCRβ V28 subfamily, a TCRβ V24 subfamily, a TCRβ V20 subfamily, TCRβ V25 subfamily, a TCRβ V29 subfamily, a TCRβ V1 subfamily, a TCRβ V17 subfamily, a TCRβ V21 subfamily, a TCRβ V23 subfamily, or a TCRβ V26 subfamily, or a variant thereof.

In some embodiments, the anti-TCRβV antibody molecule binds to a TCRβ V6 subfamily comprising: TCRβ V6-4*01, TCRβ V6-4*02, TCRβ V6-9*01, TCRβ V6-8*01, TCRβ V6-5*01, TCRβ V6-6*02, TCRβ V6-6*01, TCRβ V6-2*01, TCRβ V6-3*01 or TCRβ V6-1*01, or a variant thereof. In some embodiments the TCRβ V6 subfamily comprises TCRβ V6-5*01, or a variant thereof. In some embodiments, TCRβ V6 comprises TCRβ V6-4*01, or a variant thereof. In some embodiments, TCRβ V6 comprises TCRβ V6-4*02, or a variant thereof. In some embodiments, TCRβ V6 comprises TCRβ V6-9*01, or a variant thereof. In some embodiments, TCRβ V6 comprises TCRβ V6-8*01, or a variant thereof. In some embodiments, TCRβ V6 comprises TCRβ V6-5*01, or a variant thereof. In some embodiments, TCRβ V6 comprises TCRβ V6-6*02, or a variant thereof. In some embodiments, TCRβ V6 comprises TCRβ V6-6*01, or a variant thereof. In some embodiments, TCRβ V6 comprises TCRβ V6-2*01, or a variant thereof. In some embodiments, TCRβ V6 comprises TCRβ V6-3*01, or a variant thereof. In some embodiments, TCRβ V6 comprises TCRβ V6-1*01, or a variant thereof.

In some embodiments, the anti-TCRβV antibody molecule binds to a TCRβ V10 subfamily comprising: TCRβ V10-1*01, TCRβ V10-1*02, TCRβ V10-3*01 or TCRβ V10-2*01, or a variant thereof.

In some embodiments, the anti-TCRβV antibody molecule binds to a TCRβ V12 subfamily comprising: TCRβ V12-4*01, TCRβ V12-3*01 or TCRβ V12-5*01, or a variant thereof.

In some embodiments, the anti-TCRβV antibody molecule binds to a TCRβ V5 subfamily comprising: TCRβ V5-5*01, TCRβ V5-6*01, TCRβ V5-4*01, TCRβ V5-8*01, TCRβ V5-1*01, or a variant thereof.

Exemplary anti-TCRβV antibody molecules and the corresponding TCRβV subfamily recognized by said anti-TCRβV antibody molecules is disclosed in Table 10A.

TABLE 10A

Exemplary anti-TCRβV antibody molecules

| TRBV gene name | TRBV allele name | Reagents monoclonal antibodies: Clone name and Specificity | Company product | Isotype |
|---|---|---|---|---|
| TRBV2 | TRBV2*01<br>TRBV2*02<br>TRBV2*03 | IsMMU 546 (TRBV2) | Serotec V BETA 22<br>Coulter Vbeta22 | Mouse IgG1 |
| TRBV3-1 | TRBV3-1*01 | FIN9 (TRBV3-1)<br>AMKB1-2 (TRBV3-1) | Serotec Vbeta9<br>Coulter Vbeta9 | Mouse IgG2a |
| | TRBV3-1*02 | | BD Biosciences Vbeta9 | Mouse IgG1 |
| TRBV4-1 | TRBV4-1*01 | ZOE (TRBV4-1, TRBV4-2, TRBV4-3) | Serotec V BETA 7<br>Coulter Vbeta7 | Mouse IgG2a |
| | TRBV4-1*02 | 3G5 (TRBV4-1) | Pierce EndogenV beta 7.1 | Mouse IgG2b |

TABLE 10A-continued

Exemplary anti-TCRβV antibody molecules

| TRBV gene name | TRBV allele name | Reagents monoclonal antibodies: Clone name and Specificity | Company product | Isotype |
|---|---|---|---|---|
| TRBV4-2 | TRBV4-2*01 | ZOE (TRBV4-1, TRBV4-2, | Serotec V BETA 7 | Mouse |
| | TRBV4-2*02 | TRBV4-3) | Coulter Vbeta7 | IgG2a |
| TRBV4-3 | TRBV4-3*01 | ZOE (TRBV4-1, TRBV4-2, | Serotec V BETA 7 | Mouse |
| | TRBV4-3*02 | TRBV4-3) | Coulter Vbeta7 | IgG2a |
| | TRBV4-3*03 | | | |
| | TRBV4-3*04 | ZIZOU4 (TRBV4-3) | Coulter Vbeta7.2 | Mouse |
| | | | | IgG2a |
| TRBV5-1 | TRBV5-1*01 | IMMU157 (TRBV5-1) | Serotec Vbeta5.1 | Mouse |
| | | | Coulter Vbeta5.1 | IgG2a |
| | TRBV5-1*02 | LC4 (TRBV5-1) | Pierce Endogen V beta 5(c) | Mouse |
| | | | BD Biosciences | IgGl |
| | | | Vbeta5(c) | |
| TRBV5-4 | TRBV5-4*01 | | | |
| | TRBV5-4*02 | | | |
| | TRBV5-4*03 | | | |
| | TRBV5-4*04 | | | |
| TRBV5-5 | TRBV5-5*01 | 3D11 (TRBV5-5) | Serotec VBETA5.3 | Mouse |
| | | 1C1 (TRBV5-5, TRBV5-6) | Coulter Vbeta5.3 | IgG1 |
| | TRBV5-5*02 | W112 (TRBV5-5) | Pierce Endogen V beta 5(a) | Mouse |
| | | MH3-2 (TRBV5-5, TRBV5-6) | BD Biosciences | IgG1 |
| | | | Vbeta5(a) | |
| | TRBV5-5*03 | | Pierce Endogen V beta 5(b) | Mouse |
| | | | Serotec V beta 5.2/5.3 | IgG1 |
| | | | BD Biosciences | |
| | | | Vbeta5(b) | |
| | | | BD Biosciences Vbeta5 | Mouse |
| | | | | IgG2a |
| | | 4H11 (TM27) as disclosed in | | |
| | | U.S. Pat. No. 5,861,155 | | |
| TRBV5-6 | TRBV5-6*01 | 36213 (TRBV5-6) | Serotec Vbeta 5.2 | Mouse |
| | | 1C1 (TRBV5-5, TRBV5-6) | BD Bioscience | IgG1 |
| | | MH3-2 (TRBV5-5, TRBV5-6) | Vbeta5(a) | Mouse |
| | | | BD Biosciences Vbeta5 | IgG1 |
| | | | | Mouse |
| | | | | IgG2a |
| TRBV5-8 | TRBV5-8*01 | | | |
| | TRBV5-8*02 | | | |
| TRBV6-1 | TRBV6-1*01 | BAM13 (TRBV6-1, TRBV6-5) | Pierce Endogen V beta 13 | Mouse |
| | | | BD Biosciences | IgG1 |
| | | | Vbeta13.1, 13.3 | |
| TRBV6-2 | TRBV6-2*01 | H132 | Coulter Vbeta13.2 | Mouse |
| | | | | IgG1 |
| TRBV6-3 | TRBV6-3*01 | | | |
| TRBV6-4 | TRBV6-4*01 | | | |
| | TRBV6-4*02 | | | |
| TRBV6-5 | TRBV6-5*01 | IMMU 222 (TRBV6-5, | Serotec V BETA 13.1 | Mouse |
| | | TRBV6-6 and TRBV6-9) | Coulter Vbeta13.1 | IgG2b |
| | | BAM13 (TRBV6-1, TRBV6-5) | Pierce Endogen V beta 13 | Mouse |
| | | | BD Biosciences | IgG1 |
| | | | Vbeta 13.1, 13.3 | |
| TRBV6-6 | TRBV6-6*01 | JU-74 (TRBV6-6) | Serotec Vbeta 13.6 | Mouse |
| | TRBV6-6*02 | JU74.3 (TRBV6-6) | Coulter Vbeta 13.6 | IgG1 |
| | TRBV6-6*03 | | | |
| | TRBV6-6*04 | IMMU 222 (TRBV6-5, | Serotec V BETA 13.1 | Mouse |
| | TRBV6-6*05 | TRBV6-6 and TRBV6-9) | Coulter Vbeta13.1 | IgG2b |
| TRBV6-8 | TRBV6-8*01 | | | |
| TRBV6-9 | TRBV6-9*01 | IMMU 222 (TRBV6-5, | Serotec VBETA 13.1 | Mouse |
| | | TRBV6-6 and TRBV6-9) | Coulter Vbeta 13.1 | IgG2b |
| TRBV7-2 | TRBV7-2*01 | OT145 (TRBV7-2) | Pierce Endogen V beta 6.7 | Mouse |
| | TRBV7-2*02 | | BD Biosciences Vbeta6.7 | IgG1 |
| | TRBV7-2*03 | | | |
| | TRBV7-2*04 | | | |
| TRBV7-3 | TRBV7-3*01 | | | |
| | TRBV7-3*04 | | | |
| | TRBV7-3*05 | | | |
| TRBV7-4 | TRBV7-4*01 | | | |
| TRBV7-6 | TRBV7-6*01 | | | |
| | TRBV7-6*02 | | | |
| TRBV7-7 | TRBV7-7*01 | | | |
| | TRBV7-7*02 | | | |
| TRBV7-8 | TRBV7-8*01 | | | |
| | TRBV7-8*02 | | | |
| | TRBV7-8*03 | | | |
| TRBV7-9 | TRBV7-9*01 | | | |

TABLE 10A-continued

| Exemplary anti-TCRβV antibody molecules | | | | |
|---|---|---|---|---|
| TRBV | TRBV | Reagents monoclonal antibodies | | |
| gene name | allele name | Clone name and Specificity | Company product | Isotype |
| | TRBV7-9*02 | | | |
| | TRBV7-9*03 | | | |
| | TRVB7-9*04 | | | |
| | TRBV7-9*05 | | | |
| | TRBV7-9*06 | | | |
| | TRBV7-9*07 | | | |
| TRBV9 | TRBV9*01 | BL37.2 (TRBV9) | Serotec Vbeta1 | Rat |
| | TRBV9*02 | | Coulter Vbeta1 | IgG1 |
| | TRBV9*03 | | | |
| TRBV10-1 | TRBV10-1*01 | S511 (TRBV10-1, TRBV10-2, | Pierce Endogen V beta 12 | Mouse |
| | TRBV10-1*02 | TRBV10-3) | BD Biosciences Vbeta12 | IgG2b |
| TRBV10-2 | TRBV10-2*01 | | | |
| | TRBV10-2*02 | | | |
| TRBV10-3 | TRBV10-3*01 | VER2.32.1 (TRBV10-3) | Serotec Vbeta12 | Mouse |
| | TRBV10-3*02 | S511 (TRBV10-1, TRBV10-2, | Coulter Vbeta12 | IgG2a |
| | TRBV10-3*03 | TRBV10-3) | Pierce Endogen V beta 12 | Mouse |
| | TRBV10-3*04 | | BD Biosciences Vbeta12 | IgG2b |
| TRBV11-1 | TRBV11-1*01 | | | |
| TRBV11-2 | TRBV11-2*01 | IG125 (TRBV 11-2) | Serotec Vbeta21.3 | Mouse |
| | TRBV11-2*02 | | Coulter Vbeta21.3 | IgG2a |
| | TRBV11-2*03 | | | |
| TRBV11-3 | TRBV11-3*01 | | | |
| | TRBV11-3*02 | | | |
| | TRBV11-3*03 | | | |
| | TRBV11-3*04 | | | |
| TRBV12-3 | TRBV12-3*01 | 56C5 (TRBV12-3, TRBV12-4) | Serotec Vbeta8.1/8.2 | Mouse |
| | | 56C5.2 (TRBV 12-3, TRBV 12-4) | Coulter Vbeta8 | IgG2a |
| TRBV12-4 | TRBV12-4*01 | 16G8 (TRBV12-3, TRBV12-4) | Pierce Endogen V beta 8(a) | Mouse |
| | | MX-6 (TRBV12-3, TRBV12-4) | BD Biosciences Vbeta8 | IgG2b |
| | TRBV12-4*02 | JR2 (TRBV 12-3, TRBV 12-4, | Pierce Endogen V beta 8(b) | Mouse |
| | | TRBV12-5) | | IgG2a |
| | | | BD Biosciences Vbeta8 | Mouse |
| | | | | IgG2b |
| TRBV12-5 | TRBV12-5*01 | JR2 (TRBV 12-3, TRBV 12-4, | BD Biosciences Vbeta8 | Mouse |
| | | TRBV12-5) | | IgG2b |
| TRBV13 | TRBV13*01 | AF-23 (TRBV13) | Serotec Vbeta23 | Mouse |
| | TRBV13*02 | AF23 (TRBV13) | Coulter Vbeta23 | |
| | | AHUT7 (Vbeta23) | BD Biosciences Vbeta23 | IgG1 |
| TRBV14 | TRBV14*01 | TAMAYA1.2 (TRBV14) | Serotec Vbeta16 | Mouse |
| | TRBV14*02 | | Coulter Vbeta16 | IgG1 |
| TRBV15 | TRBV15*01 | | | |
| | TRBV15*02 | | | |
| | TRBV15*03 | | | |
| TRBV16 | TRBV16*01 | | | |
| | TRBV16*03 | | | |
| TRBV18 | TRBV18*01 | BA62 (TRBV 18) | Serotec V BETA 18 | Mouse |
| | | BA62.6 (TRBV 18) | Coulter Vbeta18 | IgG1 |
| TRBV19 | TRBV19*01 | C1 (TRBV 19) | Pierce Endogen V beta 17 | Mouse |
| | | E17.5F3 (TRBV19) | BD Biosciences Vbeta17 | IgG1 |
| | TRBV19*02 | E17.5F3.15.13 (TRBV19) | Serotec Vbeta17 | Mouse |
| | TRBV19*03 | | Coulter Vbeta17 | IgG1 |
| TRBV20-1 | TRBV20-1*01 | MPB2D5 (TRBV20-1) | Serotec VBETA2 | Mouse |
| | TRBV20-1*02 | | Coulter Vbeta2 | IgG1 |
| | TRBV20-1*03 | | | |
| | TRBV20-1*04 | | | |
| | TRBV20-1*05 | | | |
| | TRBV20-1*06 | | | |
| | TRBV20-1*07 | | | |
| TRBV24-1 | TRBV24-1*01 | | | |
| TRBV25-1 | TRBV25-1*01 | C21 (TRBV25-1) | Serotec V BETA 11 | Mouse |
| | | | Coulter Vbeta11 | IgG2a |
| TRBV27 | TRBV27*01 | CAS1.1.3 (TRBV27) | Serotec Vbeta14 | Mouse |
| | | | Coulter Vbeta14 | IgG1 |
| TRBV28 | TRBV28*01 | CH92 (TRBV28) | Serotec Vbeta3 | Mouse |
| | | 8F10 (TRBV28) | Coulter Vbeta3 | IgM |
| | | JOVI-3 (TRBV28) | Pierce Endogen V beta 3.1 | Mouse |
| | | | | IgG1 |
| | | | BD Biosciences Vbeta3 | Mouse |
| | | | | IgG2a |
| TRBV29-1 | TRBV29-1*01 | WJF24 | Coulter Vbeta4 | Rat |
| | TRBV29-1*02 | | | IgM |
| | TRBV29-1*03 | | | |

TABLE 10A-continued

| Exemplary anti-TCRβV antibody molecules | | | | |
|---|---|---|---|---|
| TRBV | TRBV | Reagents monoclonal antibodies | | |
| gene name | allele name | Clone name and Specificity | Company product | Isotype |
| TRBV30 | TRBV30*01<br>TRBV30*02<br>TRBV30*04<br>TRBV30*05 | ELL1.4 (TRBV30) | Serotec Vbeta20<br>Coulter Vbeta20 | Mouse<br>IgG1 |

In some embodiments, the anti-TCRβV antibody molecule does not bind to TCRβ V12, or binds to TCRβ V12 with an affinity and/or binding specificity that is less than (e.g., less than about 10%, 20%, 30%, 40%, 50%, 60%, 70%, 80%, 90% or about 2-, 5-, or 10-fold) the affinity and/or binding specificity of the 16G8 murine antibody or a humanized version thereof as described in U.S. Pat. No. 5,861,155.

In some embodiments, the anti-TCRβV antibody molecule binds to TCRβ V12 with an affinity and/or binding specificity that is greater than (e.g., greater than about 10%, 20%, 30%, 40%, 50%, 60%, 70%, 80%, 90% or about 2-, 5-, or 10-fold) the affinity and/or binding specificity of the 16G8 murine antibody or a humanized version thereof as described in U.S. Pat. No. 5,861,155.

In some embodiments, the anti-TCRβV antibody molecule binds to a TCRβV region other than TCRβ V12 (e.g., TCRβV region as described herein, e.g., TCRβ V6 subfamily (e.g., TCRβ V6-5*01) with an affinity and/or binding specificity that is greater than (e.g., greater than about 10%, 20%, 30%, 40%, 50%, 60%, 70%, 80%, 90% or about 2-, 5-, or 10-fold) the affinity and/or binding specificity of the 16G8 murine antibody or a humanized version thereof as described in U.S. Pat. No. 5,861,155.

In some embodiments, the anti-TCRβV antibody molecule does not bind to TCRβ V5-5*01 or TCRβ V5-1*01, or binds to TCRβ V5-5*01 or TCRβ V5-1*01 with an affinity and/or binding specificity that is less than (e.g., less than about 10%, 20%, 30%, 40%, 50%, 60%, 70%, 80%, 90% or about 2-, 5-, or 10-fold) the affinity and/or binding specificity of the TM23 murine antibody or a humanized version thereof as described in U.S. Pat. No. 5,861,155.

In some embodiments, the anti-TCRβV antibody molecule binds to TCRβ V5-5*01 or TCRβ V5-1*01 with an affinity and/or binding specificity that is greater than (e.g., greater than about 10%, 20%, 30%, 40%, 50%, 60%, 70%, 80%, 90% or about 2-, 5-, or 10-fold) the affinity and/or binding specificity of the TM23 murine antibody or a humanized version thereof as described in U.S. Pat. No. 5,861,155.

In some embodiments, the anti-TCRβV antibody molecule binds to a TCRβV region other than TCRβ V5-5*01 or TCRβ V5-1*01 (e.g., TCRβV region as described herein, e.g., TCRβ V6 subfamily (e.g., TCRβ V6-5*01) with an affinity and/or binding specificity that is greater than (e.g., greater than about 10%, 20%, 30%, 40%, 50%, 60%, 70%, 80%, 90% or about 2-, 5-, or 10-fold) the affinity and/or binding specificity of the TM23 murine antibody or a humanized version thereof as described in U.S. Pat. No. 5,861,155.

Anti-TCRβ V6 Antibodies

Accordingly, in one aspect, the disclosure provides an anti-TCRβV antibody molecule that binds to human TCRβ V6, e.g., a TCRβ V6 subfamily comprising: TCRβ V6-4*01, TCRβ V6-4*02, TCRβ V6-9*01, TCRβ V6-8*01, TCRβ V6-5*01, TCRβ V6-6*02, TCRβ V6-6*01, TCRβ V6-2*01, TCRβ V6-3*01 or TCRβ V6-1*01. In some embodiments the TCRβ V6 subfamily comprises TCRβ V6-5*01 or a variant thereof. In some embodiments, TCRβ V6 comprises TCRβ V6-4*01, or a variant thereof. In some embodiments, TCRβ V6 comprises TCRβ V6-4*02, or a variant thereof. In some embodiments, TCRβ V6 comprises TCRβ V6-9*01, or a variant thereof. In some embodiments, TCRβ V6 comprises TCRβ V6-8*01, or a variant thereof. In some embodiments, TCRβ V6 comprises TCRβ V6-5*01, or a variant thereof. In some embodiments, TCRβ V6 comprises TCRβ V6-6*02, or a variant thereof. In some embodiments, TCRβ V6 comprises TCRβ V6-6*01, or a variant thereof. In some embodiments, TCRβ V6 comprises TCRβ V6-2*01, or a variant thereof. In some embodiments, TCRβ V6 comprises TCRβ V6-3*01, or a variant thereof. In some embodiments, TCRβ V6 comprises TCRβ V6-1*01, or a variant thereof.

In some embodiments, TCRβ V6-5*01 is encoded by the nucleic acid sequence of SEQ ID NO: 43, or a sequence having 85%, 90%, 95%, 99% or more identity thereof.

```
                                          SEQ ID NO: 43
ATGAGCATCGGCCTCCTGTGCTGTGCAGCCTTGTCTCTCCTGTGGGCAG

GTCCAGTGAATGCTGGTGTCACTCAGACCCCAAAATTCCAGGTCCTGAA

GACAGGACAGAGCATGACACTGCAGTGTGCCCAGGATATGAACCATGAA

TACATGTCCTGGTATCGACAAGACCCAGGCATGGGGCTGAGGCTGATTC

ATTACTCAGTTGGTGCTGGTATCACTGACCAAGGAGAAGTCCCCAATGG

CTACAATGTCTCCAGATCAACCACAGAGGATTTCCCGCTCAGGCTGCTG

TCGGCTGCTCCCTCCCAGACATCTGTGTACTTCTGTGCCAGCAGTTACT

C
```

In some embodiments, TCRβ V6-5*01 comprises the amino acid sequence of SEQ ID NO: 44, or an amino acid sequence having 85%, 90%, 95%, 99% or more identity thereof.

```
                                          SEQ ID NO: 44
MSIGLLCCAALSLLWAGPVNAGVTQTPKFQVLKTGQSMTLQCAQDMNHE

YMSWYRQDPGMGLRLIHYSVGAGITDQGEVPNGYNVSRSTTEDFPLRLL

SAAPSQTSVYFCASSY
```

In some embodiments, the anti-TCRβV antibody molecule, e.g., anti-TCRβ V6 (e.g., anti-TCRβ V6-5*01) antibody molecule, is a non-murine antibody molecule, e.g., a human or humanized antibody molecule. In some embodiments, the anti-TCRβV antibody molecule, e.g., anti-TCRβ V6 (e.g., anti-TCRβ V6-5*01) antibody molecule is a human antibody molecule. In some embodiments, the anti- TCRβV antibody molecule, e.g., anti-TCRβ V6 (e.g., anti-TCRβ V6-5*01) antibody molecule is a humanized antibody molecule.

In some embodiments, the anti-TCRβV antibody molecule, e.g., anti-TCRβ V6 (e.g., anti-TCRβ V6-5*01) antibody molecule, is isolated or recombinant.

In some embodiments, the anti-TCRβV antibody molecule, e.g., anti-TCRβ V6 (e.g., anti-TCRβ V6-5*01) antibody molecule, comprises at least one antigen-binding region, e.g., a variable region or an antigen-binding fragment thereof, from an antibody described herein, e.g., an antibody chosen from any one of A-H.1 to A-H.85, e.g., A-H.1, A-H.2 or A-H.68, or an antibody described in Table 1, or encoded by a nucleotide sequence in Table 1, or a sequence substantially identical (e.g., at least 80%, 85%, 90%, 92%, 95%, 97%, 98%, 99% or higher identical) to any of the aforesaid sequences.

In some embodiments, the anti-TCRβV antibody molecule, e.g., anti-TCRβ V6 (e.g., anti-TCRβ V6-5*01) antibody molecule, comprises at least one, two, three or four variable regions from an antibody described herein, e.g., an antibody chosen from any one of A-H.1 to A-H.85, e.g., A-H.1, A-H.2 or A-H.68, or an antibody described in Table 1, or encoded by a nucleotide sequence in Table 1, or a sequence substantially identical (e.g., at least 80%, 85%, 90%, 92%, 95%, 97%, 98%, 99% or higher identical) to any of the aforesaid sequences.

In some embodiments, the anti-TCRβV antibody molecule, e.g., anti-TCRβ V6 (e.g., anti-TCRβ V6-5*01) antibody molecule, comprises at least one or two heavy chain variable regions from an antibody described herein, e.g., an antibody chosen from any one of A-H.1 to A-H.85, e.g., A-H.1, A-H.2 or A-H.68, or an antibody molecule described in Table 1, or encoded by a nucleotide sequence in Table 1, or a sequence substantially identical (e.g., at least 80%, 85%, 90%, 92%, 95%, 97%, 98%, 99% or higher identical) to any of the aforesaid sequences.

In some embodiments, the anti-TCRβV antibody molecule comprises a heavy chain variable region (VH) having a consensus sequence of SEQ ID NO: 231 or 3290.

In some embodiments, the anti-TCRβV antibody molecule, e.g., anti-TCRβ V6 (e.g., anti-TCRβ V6-5*01) antibody molecule, comprises at least one or two light chain variable regions from an antibody described herein, e.g., an antibody chosen from any one of A-H.1 to A-H.85, e.g., A-H.1, A-H.2 or A-H.68, or an antibody described in Table 1, or encoded by a nucleotide sequence in Table 1, or a sequence substantially identical (e.g., at least 80%, 85%, 90%, 92%, 95%, 97%, 98%, 99% or higher identical) to any of the aforesaid sequences.

In some embodiments, the anti-TCRβV antibody molecule comprises a light chain variable region (VL) having a consensus sequence of SEQ ID NO: 230 or 3289.

In some embodiments, the anti-TCRβV antibody molecule, e.g., anti-TCRβ V6 (e.g., anti-TCRβ V6-5*01) antibody molecule, comprises a heavy chain constant region for an IgG4, e.g., a human IgG4. In still another embodiment, the anti-TCRβV antibody molecule, e.g., anti-TCRβ V6 (e.g., anti-TCRβ V6-5*01) antibody molecule includes a heavy chain constant region for an IgG1, e.g., a human IgG1. In one embodiment, the heavy chain constant region comprises an amino sequence set forth in Table 3, or a sequence substantially identical (e.g., at least 80%, 85%, 90%, 92%, 95%, 97%, 98%, 99% or higher identical) thereto.

In some embodiments, the anti-TCRβV antibody molecule, e.g., anti-TCRβ V6 (e.g., anti-TCRβ V6-5*01) antibody molecule, includes a kappa light chain constant region, e.g., a human kappa light chain constant region. In one embodiment, the light chain constant region comprises an amino sequence set forth in Table 3, or a sequence substantially identical (e.g., at least 80%, 85%, 90%, 92%, 95%, 97%, 98%, 99% or higher identical) thereto.

In some embodiments, the anti-TCRβV antibody molecule, e.g., anti-TCRβ V6 (e.g., anti-TCRβ V6-5*01) antibody molecule, includes at least one, two, or three complementarity determining regions (CDRs) from a heavy chain variable region (VH) of an antibody described herein, e.g., an antibody chosen from any one of A-H.1 to A-H.85, e.g., A-H.1, A-H.2 or A-H.68, or an antibody described in Table 1, or encoded by a nucleotide sequence in Table 1, or a sequence substantially identical (e.g., at least 80%, 85%, 90%, 92%, 95%, 97%, 98%, 99% or higher identical) to any of the aforesaid sequences.

In some embodiments, the anti-TCRβV antibody molecule, e.g., anti-TCRβ V6 (e.g., anti-TCRβ V6-5*01) antibody molecule, includes at least one, two, or three CDRs (or collectively all of the CDRs) from a heavy chain variable region comprising an amino acid sequence shown in Table 1, or encoded by a nucleotide sequence shown in Table 1. In one embodiment, one or more of the CDRs (or collectively all of the CDRs) have one, two, three, four, five, six or more changes, e.g., amino acid substitutions or deletions, relative to the amino acid sequence shown in Table 1, or encoded by a nucleotide sequence shown in Table 1.

In some embodiments, the anti-TCRβV antibody molecule, e.g., anti-TCRβ V6 (e.g., anti-TCRβ V6-5*01) antibody molecule, includes at least one, two, or three complementarity determining regions (CDRs) from a light chain variable region of an antibody described herein, e.g., an antibody chosen from any one of A-H.1 to A-H.85, e.g., A-H.1, A-H.2 or A-H.68, or an antibody described in Table 1, or encoded by a nucleotide sequence in Table 1, or a sequence substantially identical (e.g., at least 80%, 85%, 90%, 92%, 95%, 97%, 98%, 99% or higher identical) to any of the aforesaid sequences.

In some embodiments, the anti-TCRβV antibody molecule, e.g., anti-TCRβ V6 (e.g., anti-TCRβ V6-5*01) antibody molecule, includes at least one, two, or three CDRs (or collectively all of the CDRs) from a light chain variable region comprising an amino acid sequence shown in Table 1, or encoded by a nucleotide sequence shown in Table 1. In one embodiment, one or more of the CDRs (or collectively all of the CDRs) have one, two, three, four, five, six or more changes, e.g., amino acid substitutions or deletions, relative to the amino acid sequence shown in Table 1, or encoded by a nucleotide sequence shown in Table 1.

In some embodiments, the anti-TCRβV antibody molecule, e.g., anti-TCRβ V6 (e.g., anti-TCRβ V6-5*01) antibody molecule, includes at least one, two, three, four, five or six CDRs (or collectively all of the CDRs) from a heavy and light chain variable region comprising an amino acid sequence shown in Table 1, or encoded by a nucleotide sequence shown in Table 1. In one embodiment, one or more of the CDRs (or collectively all of the CDRs) have one, two, three, four, five, six or more changes, e.g., amino acid substitutions or deletions, relative to the amino acid sequence shown in Table 1, or encoded by a nucleotide sequence shown in Table 1.

In some embodiments, the anti-TCRβV antibody molecule, e.g., anti-TCRβ V6 (e.g., anti-TCRβ V6-5*01) antibody molecule, molecule includes all six CDRs from an antibody described herein, e.g., an antibody chosen from any one of A-H.1 to A-H.85, e.g., A-H.1, A-H.2 or A-H.68, or an antibody described in Table 1, or encoded by a nucleotide sequence in Table 1, or closely related CDRs, e.g., CDRs which are identical or which have at least one amino acid alteration, but not more than two, three or four alterations (e.g., substitutions, deletions, or insertions, e.g., conservative substitutions). In some embodiments, the anti-TCRβV antibody molecule, e.g., anti-TCRβ V6 (e.g., anti-TCRβ V6-5*01) antibody molecule, may include any CDR described herein.

In some embodiments, the anti-TCRβV antibody molecule, e.g., anti-TCRβ V6 (e.g., anti-TCRβ V6-5*01) antibody molecule includes at least one, two, or three CDRs according to Kabat et al. (e.g., at least one, two, or three CDRs according to the Kabat definition as set out in Table 1) from a heavy chain variable region of an antibody described herein, e.g., an antibody chosen from any one of A-H.1 to A-H.85, e.g., A-H.1, A-H.2 or A-H.68, or an antibody described in Table 1, or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, or three CDRs according to Kabat et al. shown in Table 1.

In some embodiments, the anti-TCRβV antibody molecule, e.g., anti-TCRβ V6 (e.g., anti-TCRβ V6-5*01) antibody molecule includes at least one, two, or three CDRs according to Kabat et al. (e.g., at least one, two, or three CDRs according to the Kabat definition as set out in Table 1) from a light chain variable region of an antibody described herein, e.g., an antibody chosen from any one of A-H.1 to A-H.85, e.g., A-H.1, A-H.2 or A-H.68, or an antibody described in Table 1, or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, or three CDRs according to Kabat et al. shown in Table 1.

In some embodiments, the anti-TCRβV antibody molecule, e.g., anti-TCRβ V6 (e.g., anti-TCRβ V6-5*01) antibody molecule, includes at least one, two, three, four, five, or six CDRs according to Kabat et al. (e.g., at least one, two, three, four, five, or six CDRs according to the Kabat definition as set out in Table 1) from the heavy and light chain variable regions of an antibody described herein, e.g., an antibody chosen from any one of A-H.1 to A-H.85, e.g., A-H.1, A-H.2 or A-H.68, or an antibody described in Table 1, or encoded by a nucleotide sequence in Table 1; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, three, four, five, or six CDRs according to Kabat et al. shown in Table 1.

In some embodiments, the anti-TCRβV antibody molecule, e.g., anti-TCRβ V6 (e.g., anti-TCRβ V6-5*01) antibody molecule, includes all six CDRs according to Kabat et al. (e.g., all six CDRs according to the Kabat definition as set out in Table 1) from the heavy and light chain variable regions of an antibody described herein, e.g., an antibody chosen from any one of A-H.1 to A-H.85, e.g., A-H.1, A-H.2 or A-H.68, or an antibody described in Table 1, or encoded by a nucleotide sequence in Table 1; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to all six CDRs according to Kabat et al. shown in Table 1. In one embodiment, the anti-TCRβV antibody molecule, e.g., anti-TCRβ V6 (e.g., anti-TCRβ V6-5*01) antibody molecule, may include any CDR described herein.

In some embodiments, the anti-TCRβV antibody molecule, e.g., anti-TCRβ V6 (e.g., anti-TCRβ V6-5*01) antibody molecule, includes at least one, two, or three hypervariable loops that have the same canonical structures as the corresponding hypervariable loop of an antibody described herein, e.g., an antibody chosen from chosen from any one of A-H.1 to A-H.85, e.g., A-H.1, A-H.2 or A-H.68, e.g., the same canonical structures as at least loop 1 and/or loop 2 of the heavy and/or light chain variable domains of an antibody described herein. See, e.g., Chothia et al., (1992) J. Mol. Biol. 227:799-817; Tomlinson et al., (1992) J. Mol. Biol. 227:776-798 for descriptions of hypervariable loop canonical structures. These structures can be determined by inspection of the tables described in these references.

In some embodiments, the anti-TCRβV antibody molecule, e.g., anti-TCRβ V6 (e.g., anti-TCRβ V6-5*01) antibody molecule includes at least one, two, or three CDRs according to Chothia et al. (e.g., at least one, two, or three CDRs according to the Chothia definition as set out in Table 1) from a heavy chain variable region of an antibody described herein, e.g., an antibody chosen from any one of A-H.1 to A-H.85, e.g., A-H.1, A-H.2 or A-H.68, or as described in Table 1, or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, or three CDRs according to Chothia et al. shown in Table 1.

In some embodiments, the anti-TCRβV antibody molecule, e.g., anti-TCRβ V6 (e.g., anti-TCRβ V6-5*01) antibody molecule includes at least one, two, or three CDRs according to Chothia et al. (e.g., at least one, two, or three CDRs according to the Chothia definition as set out in Table 1) from a light chain variable region of an antibody described herein, e.g., an antibody chosen from any one of A-H.1 to A-H.85, e.g., A-H.1, A-H.2 or A-H.68, or an antibody described in Table 1, or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, or three CDRs according to Chothia et al. shown in Table 1.

In some embodiments, the anti-TCRβV antibody molecule, e.g., anti-TCRβ V6 (e.g., anti-TCRβ V6-5*01) antibody molecule, includes at least one, two, three, four, five, or six CDRs according to Chothia et al. (e.g., at least one, two, three, four, five, or six CDRs according to the Chothia definition as set out in Table 1) from the heavy and light chain variable regions of an antibody described herein, e.g., an antibody chosen from any one of A-H.1 to A-H.85, e.g., A-H.1, A-H.2 or A-H.68, or an antibody described in Table 1, or encoded by the nucleotide sequence in Table 1; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, three, four, five, or six CDRs according to Chothia et al. shown in Table 1.

In some embodiments, the anti-TCRβV antibody molecule, e.g., anti-TCRβ V6 (e.g., anti-TCRβ V6-5*01) antibody molecule, includes all six CDRs according to Chothia et al. (e.g., all six CDRs according to the Chothia definition as set out in Table 1) from the heavy and light chain variable regions of an antibody described herein, e.g., an antibody chosen from any one of A-H.1 to A-H.85, e.g., A-H.1, A-H.2 or A-H.68, or an antibody described in Table 1, or encoded by a nucleotide sequence in Table 1; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to all six CDRs according to Chothia et al. shown in Table 1. In one embodiment, the anti-TCRβV antibody molecule, e.g., anti-TCRβ V6 (e.g., anti-TCRβ V6-5*01) antibody molecule, may include any CDR described herein.

In some embodiments, the anti-TCRβV antibody molecule, e.g., anti-TCRβ V6 (e.g., anti-TCRβ V6-5*01) antibody molecule, molecule includes a combination of CDRs or hypervariable loops defined according to Kabat et al., Chothia et al., or as described in Table 1.

In some embodiments, the anti-TCRβV antibody molecule, e.g., anti-TCRβ V6 (e.g., anti-TCRβ V6-5*01) antibody molecule, can contain any combination of CDRs or hypervariable loops according to the Kabat and Chothia definitions.

In some embodiments, a combined CDR as set out in Table 1 is a CDR that comprises a Kabat CDR and a Chothia CDR.

In some embodiments, the anti-TCRβV antibody molecule, e.g., anti-TCRβ V6 (e.g., anti-TCRβ V6-5*01) antibody molecule, molecule includes a combination of CDRs or hypervariable loops identified as combined CDRs in Table 1. In some embodiments, the anti-TCRβV antibody molecule, e.g., anti-TCRβ V6 (e.g., anti-TCRβ V6-5*01) antibody molecule, can contain any combination of CDRs or hypervariable loops according the "combined" CDRs are described in Table 1.

In an embodiment, e.g., an embodiment comprising a variable region, a CDR (e.g., a combined CDR, Chothia CDR or Kabat CDR), or other sequence referred to herein, e.g., in Table 1, the antibody molecule is a monospecific antibody molecule, a bispecific antibody molecule, a bivalent antibody molecule, a biparatopic antibody molecule, or an antibody molecule that comprises an antigen binding fragment of an antibody, e.g., a half antibody or antigen binding fragment of a half antibody. In certain embodiments the antibody molecule comprises a multispecific molecule, e.g., a bispecific molecule, e.g., as described herein.

In an embodiment, the anti-TCRβV antibody molecule, e.g., anti-TCRβ V6 (e.g., anti-TCRβ V6-5*01) antibody molecule includes:

(i) one, two or all of a light chain complementarity determining region 1 (LC CDR1), a light chain complementarity determining region 2 (LC CDR2), and a light chain complementarity determining region 3 (LC CDR3) of SEQ ID NO: 2, SEQ ID NO: 10 or SEQ ID NO: 11, and/or (ii) one, two or all of a heavy chain complementarity determining region 1 (HC CDR1), heavy chain complementarity determining region 2 (HC CDR2), and a heavy chain complementarity determining region 3 (HC CDR3) of SEQ ID NO: 1 or SEQ ID NO: 9.

In some embodiments, the anti-TCRβV antibody molecule, e.g., anti-TCRβ V6 (e.g., anti-TCRβ V6-5*01) antibody molecule comprises a LC CDR1, LC CDR2, and LC CDR3 of SEQ ID NO: 2, and a HC CDR1, HC CDR2, and HC CDR3 of SEQ ID NO: 1.

In some embodiments the anti-TCRβV antibody molecule, e.g., anti-TCRβ V6 (e.g., anti-TCRβ V6-5*01) antibody molecule comprises a LC CDR1, LC CDR2, and LC CDR3 of SEQ ID NO: 10, and a HC CDR1, HC CDR2, and HC CDR3 of SEQ ID NO: 9.

In some embodiments, the anti-TCRβV antibody molecule, e.g., anti-TCRβ V6 (e.g., anti-TCRβ V6-5*01) antibody molecule comprises a LC CDR1, LC CDR2, and LC CDR3 of SEQ ID NO: 11, and a HC CDR1, HC CDR2, and HC CDR3 of SEQ ID NO: 9.

In an embodiment, the anti-TCRβV antibody molecule, e.g., anti-TCRβ V6 (e.g., anti-TCRβ V6-5*01) antibody molecule comprises:

(i) a LC CDR1 amino acid sequence of SEQ ID NO: 6, a LC CDR2 amino acid sequence of SEQ ID NO: 7, or a LC CDR3 amino acid sequence of SEQ ID NO: 8; and/or (ii) a HC CDR1 amino acid sequence of SEQ ID NO: 3, a HC CDR2 amino acid sequence of SEQ ID NO: 4, or a HC CDR3 amino acid sequence of SEQ ID NO: 5.

In some embodiments, the anti-TCRβV antibody molecule, e.g., anti-TCRβ V6 (e.g., anti-TCRβ V6-5*01) antibody molecule comprises:

(i) a light chain variable region (VL) comprising a LC CDR1 amino acid sequence of SEQ ID NO: 6, a LC CDR2 amino acid sequence of SEQ ID NO: 7, or a LC CDR3 amino acid sequence of SEQ ID NO: 8; and/or (ii) a heavy chain variable region (VH) comprising a HC CDR1 amino acid sequence of SEQ ID NO: 3, a HC CDR2 amino acid sequence of SEQ ID NO: 4, or a HC CDR3 amino acid sequence of SEQ ID NO: 5.

In an embodiment, the anti-TCRβV antibody molecule, e.g., anti-TCRβ V6 (e.g., anti-TCRβ V6-5*01) antibody molecule comprises:

(i) a LC CDR1 amino acid sequence of SEQ ID NO: 51, a LC CDR2 amino acid sequence of SEQ ID NO: 52, or a LC CDR3 amino acid sequence of SEQ ID NO: 53; and/or (ii) a HC CDR1 amino acid sequence of SEQ ID NO: 45, a HC CDR2 amino acid sequence of SEQ ID NO: 46, or a HC CDR3 amino acid sequence of SEQ ID NO: 47.

In some embodiments, the anti-TCRβV antibody molecule, e.g., anti-TCRβ V6 (e.g., anti-TCRβ V6-5*01) antibody molecule comprises:

(i) a light chain variable region (VL) comprising a LC CDR1 amino acid sequence of SEQ ID NO: 51, a LC CDR2 amino acid sequence of SEQ ID NO: 52, or a LC CDR3 amino acid sequence of SEQ ID NO: 53; and/or (ii) a heavy chain variable region (VH) comprising a HC CDR1 amino acid sequence of SEQ ID NO: 45, a HC CDR2 amino acid sequence of SEQ ID NO: 46, or a HC CDR3 amino acid sequence of SEQ ID NO: 47.

In an embodiment, the anti-TCRβV antibody molecule, e.g., anti-TCRβ V6 (e.g., anti-TCRβ V6-5*01) antibody molecule comprises:

(i) a LC CDR1 amino acid sequence of SEQ ID NO: 54, a LC CDR2 amino acid sequence of SEQ ID NO: 55, or a LC CDR3 amino acid sequence of SEQ ID NO: 56; and/or (ii) a HC CDR1 amino acid sequence of SEQ ID NO: 48, a HC CDR2 amino acid sequence of SEQ ID NO: 49, or a HC CDR3 amino acid sequence of SEQ ID NO: 50.

In some embodiments, the anti-TCRβV antibody molecule, e.g., anti-TCRβ V6 (e.g., anti-TCRβ V6-5*01) antibody molecule comprises:

(i) a light chain variable region (VL) comprising a LC CDR1 amino acid sequence of SEQ ID NO: 54, a LC CDR2 amino acid sequence of SEQ ID NO: 55, or a LC CDR3 amino acid sequence of SEQ ID NO: 56; and/or (ii) a heavy chain variable region (VH) comprising a HC CDR1 amino acid sequence of SEQ ID NO: 48, a HC CDR2 amino acid sequence of SEQ ID NO: 49, or a HC CDR3 amino acid sequence of SEQ ID NO: 50.

In one embodiment, the light or the heavy chain variable framework (e.g., the region encompassing at least FR1, FR2, FR3, and optionally FR4) of the anti-TCRβV antibody molecule, e.g., anti-TCRβ V6 (e.g., anti-TCRβ V6-5*01) antibody molecule can be chosen from: (a) a light or heavy chain variable framework including at least 80%, 85%, 87% 90%, 92%, 93%, 95%, 97%, 98%, or 100% of the amino acid residues from a human light or heavy chain variable framework, e.g., a light or heavy chain variable framework residue from a human mature antibody, a human germline sequence, or a human consensus sequence; (b) a light or heavy chain variable framework including from 20% to 80%, 40% to 60%, 60% to 90%, or 70% to 95% of the amino acid residues from a human light or heavy chain variable framework, e.g., a light or heavy chain variable framework residue from a human mature antibody, a human germline sequence, or a human consensus sequence; (c) a non-human framework (e.g., a rodent framework); or (d) a non-human framework that has been modified, e.g., to remove antigenic or cytotoxic determinants, e.g., deimmunized, or partially humanized. In one embodiment, the light or heavy chain variable framework region (particularly FR1, FR2 and/or FR3) includes a light or heavy chain variable framework sequence at least 70, 75, 80, 85, 87, 88, 90, 92, 94, 95, 96, 97, 98, 99% identical or identical to the frameworks of a VL or VH segment of a human germline gene.

In some embodiments, the anti-TCRβV antibody molecule, e.g., anti-TCRβ V6 (e.g., anti-TCRβ V6-5*01) antibody molecule, comprises a heavy chain variable domain having at least one, two, three, four, five, six, seven, ten, fifteen, twenty or more changes, e.g., amino acid substitutions or deletions, from an amino acid sequence of any one of A-H.1 to A-H.85, e.g., A-H.1, A-H.2 or A-H.68, e.g., the amino acid sequence of the FR region in the entire variable region, e.g., shown in FIG. 1A, or in SEQ ID NO: 9.

Alternatively, or in combination with the heavy chain substitutions described herein, the anti-TCRβV antibody molecule, e.g., anti-TCRβ V6 (e.g., anti-TCRβ V6-5*01) antibody molecule, comprises a light chain variable domain having at least one, two, three, four, five, six, seven, ten, fifteen, twenty or more amino acid changes, e.g., amino acid substitutions or deletions, from an amino acid sequence of any one of A-H.1 to A-H.85, e.g., A-H.1, A-H.2 or A-H.68, e.g., the amino acid sequence of the FR region in the entire variable region, e.g., shown in FIG. 1B, or in SEQ ID NO: 10 or SEQ ID NO: 11.

In some embodiments, the anti-TCRβV antibody molecule, e.g., anti-TCRβ V6 (e.g., anti-TCRβ V6-5*01) antibody molecule, includes one, two, three, or four heavy chain framework regions shown in FIG. 1A, or a sequence substantially identical thereto.

In some embodiments, the anti-TCRβV antibody molecule, e.g., anti-TCRβ V6 (e.g., anti-TCRβ V6-5*01) antibody molecule, includes one, two, three, or four light chain framework regions shown in FIG. 1B, or a sequence substantially identical thereto.

In some embodiments, the anti-TCRβV antibody molecule, e.g., anti-TCRβ V6 (e.g., anti-TCRβ V6-5*01) antibody molecule, comprises the light chain framework region 1 of A-H.1 or A-H.2, e.g., as shown in FIG. 1B.

In some embodiments, the anti-TCRβV antibody molecule, e.g., anti-TCRβ V6 (e.g., anti-TCRβ V6-5*01) antibody molecule, comprises the light chain framework region 2 of A-H.1 or A-H.2, e.g., as shown in FIG. 1B.

In some embodiments, the anti-TCRβV antibody molecule, e.g., anti-TCRβ V6 (e.g., anti-TCRβ V6-5*01) antibody molecule, comprises the light chain framework region 3 of A-H.1 or A-H.2, e.g., as shown in FIG. 1B.

In some embodiments, the anti-TCRβV antibody molecule, e.g., anti-TCRβ V6 (e.g., anti-TCRβ V6-5*01) antibody molecule, comprises the light chain framework region 4 of A-H.1 or A-H.2, e.g., as shown in FIG. 1B.

In some embodiments, the anti-TCRβV antibody molecule, e.g., anti-TCRβ V6 (e.g., anti-TCRβ V6-5*01) antibody molecule, comprises a light chain variable domain comprising a framework region, e.g., framework region 1 (FR1), comprising a change, e.g., a substitution (e.g., a conservative substitution) at position 10 according to Kabat numbering. In some embodiments, the FR1 comprises a Phenylalanine at position 10, e.g., a Serine to Phenyalanine substitution. In some embodiments, the substitution is relative to a human germline light chain framework region sequence.

In some embodiments, the anti-TCRβV antibody molecule, e.g., anti-TCRβ V6 (e.g., anti-TCRβ V6-5*01) antibody molecule, comprises a light chain variable domain comprising a framework region, e.g., framework region 2 (FR2), comprising a change, e.g., a substitution (e.g., a conservative substitution) at a position disclosed herein according to Kabat numbering. In some embodiments, FR2 comprises a Histidine at position 36, e.g., a substitution at position 36 according to Kabat numbering, e.g., a Tyrosine to Histidine substitution. In some embodiments, FR2 comprises an Alanine at position 46, e.g., a substitution at position 46 according to Kabat numbering, e.g., an Arginine to Alanine substitution. In some embodiments, the substitution is relative to a human germline light chain framework region sequence.

In some embodiments, the anti-TCRβV antibody molecule, e.g., anti-TCRβ V6 (e.g., anti-TCRβ V6-5*01) antibody molecule, comprises a light chain variable domain comprising a framework region, e.g., framework region 3 (FR3), comprising a change, e.g., a substitution (e.g., a conservative substitution) at a position disclosed herein according to Kabat numbering. In some embodiments, FR3 comprises a Phenyalanine at position 87, e.g., a substitution at position 87 according to Kabat numbering, e.g., a Tyrosine to Phenyalanine substitution. In some embodiments, the substitution is relative to a human germline light chain framework region sequence.

In some embodiments, the anti-TCRβV antibody molecule, e.g., anti-TCRβ V6 (e.g., anti-TCRβ V6-5*01) antibody molecule, comprises a light chain variable domain comprising: (a) a framework region 1 (FR1) comprising a Phenylalanine at position 10, e.g., a substitution at position 10 according to Kabat numbering, e.g., a Serine to Phenyalanine substitution; (b) a framework region 2 (FR2) comprising a Histidine at position 36, e.g., a substitution at position 36 according to Kabat numbering, e.g., a Tyrosine to Histidine substitution, and a Alanine at position 46, e.g., a substitution at position 46 according to Kabat numbering, e.g., a Arginine to Alanine substitution; and (c) a framework region 3 (FR3) comprising a Phenylalanine at position 87, e.g., a substitution at position 87 according to Kabat numbering, e.g., a Tyrosine to Phenyalanine substitution, e.g., as shown in the amino acid sequence of SEQ ID NO: 10. In some embodiments, the substitution is relative to a human germline light chain framework region sequence.

In some embodiments, the anti-TCRβV antibody molecule, e.g., anti-TCRβ V6 (e.g., anti-TCRβ V6-5*01) antibody molecule, comprises a light chain variable domain comprising: (a) a framework region 2 (FR2) comprising a Histidine at position 36, e.g., a substitution at position 36 according to Kabat numbering, e.g., a Tyrosine to Histidine substitution, and a Alanine at position 46, e.g., a substitution at position 46 according to Kabat numbering, e.g., a Arginine to Alanine substitution; and (b) a framework region 3 (FR3) comprising a Phenylalanine at position 87, e.g., a substitution at position 87 according to Kabat numbering, e.g., a Tyrosine to Phenyalanine substitution, e.g., as shown in the amino acid sequence of SEQ ID NO: 11. In some embodiments, the substitution is relative to a human germline light chain framework region sequence.

In some embodiments, the anti-TCRβV antibody molecule, e.g., anti-TCRβ V6 (e.g., anti-TCRβ V6-5*01) antibody molecule, comprises a light chain variable domain comprising: (a) a framework region 1 (FR1) comprising a change, e.g., a substitution (e.g., a conservative substitution) at one or more (e.g., all) positions disclosed herein according to Kabat numbering, (b) a framework region 2 (FR2) comprising a change, e.g., a substitution (e.g., a conservative substitution) at one or more (e.g., all) position disclosed herein according to Kabat numbering and (c) a framework region 3 (FR3) comprising a change, e.g., a substitution (e.g., a conservative substitution) at one or more (e.g., all) position disclosed herein according to Kabat numbering. In some embodiments, the substitution is relative to a human germline light chain framework region sequence.

In some embodiments, the anti-TCRβV antibody molecule, e.g., anti-TCRβ V6 (e.g., anti-TCRβ V6-5*01) antibody molecule, comprises the heavy chain framework region 1 of A-H.1 or A-H.2, e.g., as shown in FIG. 1A.

In some embodiments, the anti-TCRβV antibody molecule, e.g., anti-TCRβ V6 (e.g., anti-TCRβ V6-5*01) antibody molecule, comprises the heavy chain framework region 2 of A-H.1 or A-H.2, e.g., as shown in FIG. 1A In some embodiments, the anti-TCRβV antibody molecule, e.g., anti-TCRβ V6 (e.g., anti-TCRβ V6-5*01) antibody molecule, comprises the heavy chain framework region 3 of A-H.1 or A-H.2, e.g., as shown in FIG. 1A.

In some embodiments, the anti-TCRβV antibody molecule, e.g., anti-TCRβ V6 (e.g., anti-TCRβ V6-5*01) antibody molecule, comprises the heavy chain framework region 4 of A-H.1 or A-H.2, e.g., as shown in FIG. 1A.

In some embodiments, the anti-TCRβV antibody molecule, e.g., anti-TCRβ V6 (e.g., anti-TCRβ V6-5*01) antibody molecule, comprises a heavy chain variable domain comprising a framework region, e.g., framework region 3 (FR3), comprising a change, e.g., a substitution (e.g., a conservative substitution) at a position disclosed herein according to Kabat numbering. In some embodiments, FR3 comprises a Threonine at position 73, e.g., a substitution at position 73 according to Kabat numbering, e.g., a Glutamic Acid to Threonine substitution. In some embodiments, FR3 comprises a Glycine at position 94, e.g., a substitution at position 94 according to Kabat numbering, e.g., an Arginine to Glycine substitution. In some embodiments, the substitution is relative to a human germline heavy chain framework region sequence.

In some embodiments, the anti-TCRβV antibody molecule, e.g., anti-TCRβ V6 (e.g., anti-TCRβ V6-5*01) antibody molecule, comprises a heavy chain variable domain comprising a framework region 3 (FR3) comprising a Threonine at position 73, e.g., a substitution at position 73 according to Kabat numbering, e.g., a Glutamic Acid to Threonine substitution, and a Glycine at position 94, e.g., a substitution at position 94 according to Kabat numbering, e.g., a Arginine to Glycine substitution, e.g., as shown in the amino acid sequence of SEQ ID NO: 10.

In some embodiments, the anti-TCRβV antibody molecule, e.g., anti-TCRβ V6 (e.g., anti-TCRβ V6-5*01) antibody molecule, comprises the heavy chain framework regions 1-4 of A-H.1 or A-H.2, e.g., SEQ ID NO: 9, or as shown in FIGS. 1A and 1B.

In some embodiments, the anti-TCRβV antibody molecule, e.g., anti-TCRβ V6 (e.g., anti-TCRβ V6-5*01) antibody molecule, comprises the light chain framework regions 1-4 of A-H.1, e.g., SEQ ID NO: 10, or as shown in FIGS. 1A and 1B.

In some embodiments, the anti-TCRβV antibody molecule, e.g., anti-TCRβ V6 (e.g., anti-TCRβ V6-5*01) antibody molecule, comprises the light chain framework regions 1-4 of A-H.2, e.g., SEQ ID NO: 11, or as shown in FIGS. 1A and 1B.

In some embodiments, the anti-TCRβV antibody molecule, e.g., anti-TCRβ V6 (e.g., anti-TCRβ V6-5*01) antibody molecule, comprises the heavy chain framework regions 1-4 of A-H.1, e.g., SEQ ID NO: 9; and the light chain framework regions 1-4 of A-H.1, e.g., SEQ ID NO: 10, or as shown in FIGS. 1A and 1B.

In some embodiments, the anti-TCRβV antibody molecule, e.g., anti-TCRβ V6 (e.g., anti-TCRβ V6-5*01) antibody molecule, comprises the heavy chain framework regions 1-4 of A-H.2, e.g., SEQ ID NO: 9; and the light chain framework regions 1-4 of A-H.2, e.g., SEQ ID NO: 11, or as shown in FIGS. 1A and 1B.

In some embodiments, the heavy or light chain variable domain, or both, of the anti-TCRβV antibody molecule, e.g., anti-TCRβ V6 (e.g., anti-TCRβ V6-5*01) antibody molecule, includes an amino acid sequence, which is substantially identical to an amino acid disclosed herein, e.g., at least 80%, 85%, 90%, 92%, 95%, 97%, 98%, 99% or higher identical to a variable region of an antibody described herein, e.g., an antibody chosen from any one of A-H.1 to A-H.85, e.g., A-H.1, A-H.2 or A-H.68, or as described in Table 1, or encoded by the nucleotide sequence in Table 1; or which differs at least 1 or 5 residues, but less than 40, 30, 20, or 10 residues, from a variable region of an antibody described herein.

In some embodiments, the anti-TCRβV antibody molecule, e.g., anti-TCRβ V6 (e.g., anti-TCRβ V6-5*01) antibody molecule, comprises at least one, two, three, or four antigen-binding regions, e.g., variable regions, having an amino acid sequence as set forth in Table 1, or a sequence substantially identical thereto (e.g., a sequence at least about 85%, 90%, 95%, 99% or more identical thereto, or which differs by no more than 1, 2, 5, 10, or 15 amino acid residues from the sequences shown in Table 1. In another embodiment, the anti-TCRβV antibody molecule, e.g., anti-TCRβ

V6 (e.g., anti-TCRβ V6-5*01) antibody molecule includes a VH and/or VL domain encoded by a nucleic acid having a nucleotide sequence as set forth in Table 1, or a sequence substantially identical thereto (e.g., a sequence at least about 85%, 90%, 95%, 99% or more identical thereto, or which differs by no more than 3, 6, 15, 30, or 45 nucleotides from the sequences shown in Table 1.

In some embodiments, the anti-TCRβV antibody molecule, e.g., anti-TCRβ V6 (e.g., anti-TCRβ V6-5*01) antibody molecule, comprises:

- a VH domain comprising the amino acid sequence of SEQ ID NO: 9, an amino acid sequence at least about 85%, 90%, 95%, 99% or more identical to the amino acid sequence of SEQ ID NO: 9, or an amino acid sequence which differs by no more than 1, 2, 5, 10, or 15 amino acid residues from the amino acid sequence of SEQ ID NO: 9; and/or
- a VL domain comprising the amino acid sequence of SEQ ID NO: 10, an amino acid sequence at least about 85%, 90%, 95%, 99% or more identical to the amino acid sequence of SEQ ID NO: 10, or an amino acid sequence which differs by no more than 1, 2, 5, 10, or 15 amino acid residues from the amino acid sequence of SEQ ID NO: 10.

In some embodiments, the anti-TCRβV antibody molecule, e.g., anti-TCRβ V6 (e.g., anti-TCRβ V6-5*01) antibody molecule, comprises:

- a VH domain comprising the amino acid sequence of SEQ ID NO: 9, an amino acid sequence at least about 85%, 90%, 95%, 99% or more identical to the amino acid sequence of SEQ ID NO: 9, or an amino acid sequence which differs by no more than 1, 2, 5, 10, or 15 amino acid residues from the amino acid sequence of SEQ ID NO: 9; and/or
- a VL domain comprising the amino acid sequence of SEQ ID NO: 11, an amino acid sequence at least about 85%, 90%, 95%, 99% or more identical to the amino acid sequence of SEQ ID NO: 11, or an amino acid sequence which differs by no more than 1, 2, 5, 10, or 15 amino acid residues from the amino acid sequence of SEQ ID NO: 11.

In some embodiments, the anti-TCRβV antibody molecule, e.g., anti-TCRβ V6 (e.g., anti-TCRβ V6-5*01) antibody molecule is a full antibody or fragment thereof (e.g., a Fab, $F(ab')_2$, Fv, or a single chain Fv fragment (scFv)). In embodiments, the anti-TCRβV antibody molecule, e.g., anti-TCRβ V6 (e.g., anti-TCRβ V6-5*01) antibody molecule is a monoclonal antibody or an antibody with single specificity. In some embodiments, the anti-TCRβV antibody molecule, e.g., anti-TCRβ V6 (e.g., anti-TCRβ V6-5*01) antibody molecule, can also be a humanized, chimeric, camelid, shark, or an in vitro-generated antibody molecule. In some embodiments, the anti-TCRβV antibody molecule, e.g., anti-TCRβ V6 (e.g., anti-TCRβ V6-5*01) antibody molecule, is a humanized antibody molecule. The heavy and light chains of the anti-TCRβV antibody molecule, e.g., anti-TCRβ V6 (e.g., anti-TCRβ V6-5*01) antibody molecule, can be full-length (e.g., an antibody can include at least one, and preferably two, complete heavy chains, and at least one, and preferably two, complete light chains) or can include an antigen-binding fragment (e.g., a Fab, $F(ab')_2$, Fv, a single chain Fv fragment, a single domain antibody, a diabody (dAb), a bivalent antibody, or bispecific antibody or fragment thereof, a single domain variant thereof, or a camelid antibody).

In some embodiments, the anti-TCRβV antibody molecule, e.g., anti-TCRβ V6 (e.g., anti-TCRβ V6-5*01) antibody molecule, is in the form of a multispecific molecule, e.g., a bispecific molecule, e.g., as described herein.

In some embodiments, the anti-TCRβV antibody molecule, e.g., anti-TCRβ V6 (e.g., anti-TCRβ V6-5*01) antibody molecule, has a heavy chain constant region (Fc) chosen from, e.g., the heavy chain constant regions of IgG1, IgG2, IgG3, IgG4, IgM, IgA1, IgA2, IgD, and IgE. In some embodiments, the Fc region is chosen from the heavy chain constant regions of IgG1, IgG2, IgG3, and IgG4. In some embodiments, the Fc region is chosen from the heavy chain constant region of IgG1 or IgG2 (e.g., human IgG1, or IgG2). In some embodiments, the heavy chain constant region is human IgG1. In some embodiments, the Fc region comprises a Fc region variant, e.g., as described herein.

In some embodiments, the anti-TCRβV antibody molecule, e.g., anti-TCRβ V6 (e.g., anti-TCRβ V6-5*01) antibody molecule, has a light chain constant region chosen from, e.g., the light chain constant regions of kappa or lambda, preferably kappa (e.g., human kappa). In one embodiment, the constant region is altered, e.g., mutated, to modify the properties of the anti-TCRβV antibody molecule, e.g., anti-TCRβ V6 (e.g., anti-TCRβ V6-5*01) antibody molecule (e.g., to increase or decrease one or more of: Fc receptor binding, antibody glycosylation, the number of cysteine residues, effector cell function, or complement function). For example, the constant region is mutated at positions 296 (M to Y), 298 (S to T), 300 (T to E), 477 (H to K) and 478 (N to F) to alter Fc receptor binding (e.g., the mutated positions correspond to positions 132 (M to Y), 134 (S to T), 136 (T to E), 313 (H to K) and 314 (N to F) of SEQ ID NOs: 212 or 214; or positions 135 (M to Y), 137 (S to T), 139 (T to E), 316 (H to K) and 317 (N to F) of SEQ ID NOs: 215, 216, 217 or 218), e.g., relative to human IgG1.

Antibody A-H.1 comprises a heavy chain comprising the amino acid sequence of SEQ ID NO: 3278 and a light chain comprising the amino acid sequence of SEQ ID NO: 72. Antibody A-H.2 comprises a heavy chain comprising the amino acid sequence of SEQ ID NO: 3278 and a light chain comprising the amino acid sequence of SEQ ID NO: 3279. Antibody A-H.68 comprises the amino acid sequence of SEQ ID NO: 1337, or a sequence having at least 85%, 90%, 95%, 96%, 97%, 98%, or 99% identity thereto. Antibody A-H.69 comprises the amino acid sequence of SEQ ID NO: 1500, or a sequence having at least 85%, 90%, 95%, 96%, 97%, 98%, or 99% identity thereto.

Additional exemplary humanized anti-TCRB V6 antibodies are provided in Table 1. In some embodiments, the anti-TCRβ V6 is antibody A, e.g., humanized antibody A (antibody A-H), as provided in Table 1. In some embodiments, the anti-TCRβV antibody comprises one or more (e.g., all three) of a LC CDR1, LC CDR2, and LC CDR3 provided in Table 1; and/or one or more (e.g., all three) of a HC CDR1, HC CDR2, and HC CDR3 provided in Table 1, or a sequence with at least 85%, 90%, 95%, 96%, 97%, 98%, or 99% identity thereto. In some embodiments, antibody A comprises a variable heavy chain (VH) and/or a variable light chain (VL) provided in Table 1, or a sequence with at least 85%, 90%, 95%, 96%, 97%, 98%, or 99% identity thereto.

In some embodiments, the anti-TCRβV antibody molecule, e.g., anti-TCRβ V6 (e.g., anti-TCRβ V6-5*01) antibody molecule comprises a VH of A-H.1, A-H.2, A-H.3, A-H.4, A-H.5, A-H.6, A-H.7, A-H.8, A-H.9, A-H.10, A-H.11, A-H.12, A-H.13, A-H.14, A-H.15, A-H.16, A-H.17, A-H.18, A-H.19, A-H.20, A-H.21, A-H.22, A-H.23, A-H.24, A-H.25, A-H.26, A-H.27, A-H.28, A-H.29, A-H.30, A-H.31, A-H.32, A-H.33, A-H.34, A-H.35, A-H.36, A-H.37, A-H.38, A-H.39, A-H.40, A-H.1, A-H.42, A-H.43, A-H.44, A-H.45, A-H.46, A-H.47, A-H.48, A-H.49, A-H.50, A-H.51, A-H.52, A-H.53, A-H.54, A-H.55, A-H.56, A-H.57, A-H.58, A-H.59, A-H.60, A-H.61, A-H.62, A-H.63, A-H.64, A-H.65, A-H.66, A-H.67, A-H.68, A-H.69, A-H.70, A-H.71, A-H.72, A-H.73, A-H.74, A-H.75, A-H.76, A-H.77, A-H.78, A-H.79, A-H.80, A-H.81, A-H.82, A-H.83, A-H.84, or A-H.85, or a sequence with at least 80%, 85%, 90%, 95%, 96%, 97%, 98%, 99% or more identity thereto.

In some embodiments, the anti-TCRβV antibody molecule, e.g., anti-TCRβ V6 (e.g., anti-TCRβ V6-5*01) antibody molecule comprises a VL of A-H.1, A-H.2, A-H.3, A-H.4, A-H.5, A-H.6, A-H.7, A-H.8, A-H.9, A-H.10, A-H.11, A-H.12, A-H.13, A-H.14, A-H.15, A-H.16, A-H.17, A-H.18, A-H.19, A-H.20, A-H.21, A-H.22, A-H.23, A-H.24, A-H.25, A-H.26, A-H.27, A-H.28, A-H.29, A-H.30, A-H.31, A-H.32, A-H.33, A-H.34, A-H.35, A-H.36, A-H.37, A-H.38, A-H.39, A-H.40, A-H.1, A-H.42, A-H.43, A-H.44, A-H.45, A-H.46, A-H.47, A-H.48, A-H.49, A-H.50, A-H.51, A-H.52, A-H.53, A-H.54, A-H.55, A-H.56, A-H.57, A-H.58, A-H.59, A-H.60, A-H.61, A-H.62, A-H.63, A-H.64, A-H.65, A-H.66, A-H.67, A-H.68, A-H.69, A-H.70, A-H.71, A-H.72, A-H.73, A-H.74, A-H.75, A-H.76, A-H.77, A-H.78, A-H.79, A-H.80, A-H.81, A-H.82, A-H.83, A-H.84, or A-H.85, or a sequence with at least 80%, 85%, 90%, 95%, 96%, 97%, 98%, 99% or more identity thereto.

In some embodiments, the anti-TCRβV antibody molecule, e.g., anti-TCRβ V6 (e.g., anti-TCRβ V6-5*01) antibody molecule comprises a VH of A-H.1, A-H.2, A-H.3, A-H.4, A-H.5, A-H.6, A-H.7, A-H.8, A-H.9, A-H.10, A-H.11, A-H.12, A-H.13, A-H.14, A-H.15, A-H.16, A-H.17, A-H.18, A-H.19, A-H.20, A-H.21, A-H.22, A-H.23, A-H.24, A-H.25, A-H.26, A-H.27, A-H.28, A-H.29, A-H.30, A-H.31, A-H.32, A-H.33, A-H.34, A-H.35, A-H.36, A-H.37, A-H.38, A-H.39, A-H.40, A-H.1, A-H.42, A-H.43, A-H.44, A-H.45, A-H.46, A-H.47, A-H.48, A-H.49, A-H.50, A-H.51, A-H.52, A-H.53, A-H.54, A-H.55, A-H.56, A-H.57, A-H.58, A-H.59, A-H.60, A-H.61, A-H.62, A-H.63, A-H.64, A-H.65, A-H.66, A-H.67, A-H.68, A-H.69, A-H.70, A-H.71, A-H.72, A-H.73, A-H.74, A-H.75, A-H.76, A-H.77, A-H.78, A-H.79, A-H.80, A-H.81, A-H.82, A-H.83, A-H.84, or A-H.85, or a sequence with at least 80%, 85%, 90%, 95%, 96%, 97%, 98%, 99% or more identity thereto; and a VL of A-H.1, A-H.2, A-H.3, A-H.4, A-H.5, A-H.6, A-H.7, A-H.8, A-H.9, A-H.10, A-H.11, A-H.12, A-H.13, A-H.14, A-H.15, A-H.16, A-H.17, A-H.18, A-H.19, A-H.20, A-H.21, A-H.22, A-H.23, A-H.24, A-H.25, A-H.26, A-H.27, A-H.28, A-H.29, A-H.30, A-H.31, A-H.32, A-H.33, A-H.34, A-H.35, A-H.36, A-H.37, A-H.38, A-H.39, A-H.40, A-H.1, A-H.42, A-H.43, A-H.44, A-H.45, A-H.46, A-H.47, A-H.48, A-H.49, A-H.50, A-H.51, A-H.52, A-H.53, A-H.54, A-H.55, A-H.56, A-H.57, A-H.58, A-H.59, A-H.60, A-H.61, A-H.62, A-H.63, A-H.64, A-H.65, A-H.66, A-H.67, A-H.68, A-H.69, A-H.70, A-H.71, A-H.72, A-H.73, A-H.74, A-H.75, A-H.76, A-H.77, A-H.78, A-H.79, A-H.80, A-H.81, A-H.82, A-H.83, A-H.84, or A-H.85, or a sequence with at least 80%, 85%, 90%, 95%, 96%, 97%, 98%, 99% or more identity thereto.

TABLE 1

Amino acid and nucleotide sequences for murine, chimeric and humanized antibody molecules which bind to TCRVB 6, e.g., TCRVB 6-5. The antibody molecules include murine mAb Antibody A, and humanized mAb Antibody A-H Clones A-H.1 to A-H.85. The amino acid the heavy and light chain CDRs, and the amino acid and nucleotide sequences of the heavy and light chain variable regions, and the heavy and light chains are shown.

| Antibody A (murine), also referred to as H131, TCRVB 6-5 binder | | |
|---|---|---|
| SEQ ID NO: 3 | HC CDR1 (Combined) | GYSFTTYYIH |
| SEQ ID NO: 4 | HC CDR2 (Combined) | WFFPGSGNIKYNEKFKG |
| SEQ ID NO: 5 | HC CDR3 (Combined) | SYYSYDVLDY |
| SEQ ID NO: 45 | HC CDR1 (Kabat) | TYYIH |
| SEQ ID NO: 46 | HC CDR2 (Kabat) | WFFPGSGNIKYNEKFKG |
| SEQ ID NO: 47 | HC CDR3 (Kabat) | SYYSYDVLDY |
| SEQ ID NO: 48 | HC CDR1 (Chothia) | GYSFTTY |
| SEQ ID NO: 49 | HC CDR2 (Chothia) | FPGSGN |
| SEQ ID NO: 50 | HC CDR3 (Chothia) | SYYSYDVLDY |
| SEQ ID NO: 1 | VH | QVQLQQSGPELVKPGTSVKISCKASGYSFTTYYIHW<br>VKQRPGQGLEWIGWFFPGSGNIKYNEKFKGKATLT<br>ADTSSSTAYMQLSSLTSEESAVYFCAGSYYSYDVLD<br>YWGHGTTLTVSS |
| SEQ ID NO: 6 | LC CDR1 (Combined) | KASQNVGINVV |
| SEQ ID NO: 7 | LC CDR2 (Combined) | SSSHRYS |
| SEQ ID NO: 8 | LC CDR3 (Combined) | QQFKSYPLT |
| SEQ ID NO: 51 | LC CDR1 (Kabat) | KASQNVGINVV |
| SEQ ID NO: 52 | LC CDR2 (Kabat) | SSSHRYS |

TABLE 1-continued

Amino acid and nucleotide sequences for murine, chimeric and humanized antibody molecules which bind to TCRVB 6, e.g., TCRVB 6-5. The antibody molecules include murine mAb Antibody A, and humanized mAb Antibody A-H Clones A-H.1 to A-H.85. The amino acid the heavy and light chain CDRs, and the amino acid and nucleotide sequences of the heavy and light chain variable regions, and the heavy and light chains are shown.

| | | |
|---|---|---|
| SEQ ID NO: 53 | LC CDR3 (Kabat) | QQFKSYPLT |
| SEQ ID NO: 54 | LC CDR1 (Chothia) | KASQNVGINVV |
| SEQ ID NO: 55 | LC CDR2 (Chothia) | SSSHRYS |
| SEQ ID NO: 56 | LC CDR3 (Chothia) | QQFKSYPLT |
| SEQ ID NO: 2 | VL | DILMTQSQKFMSTSLGDRVSVSCKASQNVGINVVW<br>HQQKPGQSPKALIYSSSHRYSGVPDRFTGSGSGTDFT<br>LTINNVQSEDLAEYFCQQFKSYPLTFGAGTKLELK |

Antibody A humanized (A-H antibody), TCRVB 6-5 binder
A-H.1 antibody (also referred to as BHM1709)

| | | |
|---|---|---|
| SEQ ID NO: 3 | HC CDR1 (Combined) | GYSFTTYYIH |
| SEQ ID NO: 4 | HC CDR2 (Combined) | WFFPGSGNIKYNEKFKG |
| SEQ ID NO: 5 | HC CDR3 (Combined) | SYYSYDVLDY |
| SEQ ID NO: 9 | VH | QVQLVQSGAEVKKPGSSVKVSCKASGYSFTTYYIH<br>WVRQAPGQGLEWMGWFFPGSGNIKYNEKFKGRVTI<br>TADTSTSTAYMELSSLRSEDTAVYYCAGSYYSYDVL<br>DYWGQGTTVTVSS |
| SEQ ID NO: 12 | DNA VH | CAGGTGCAGCTGGTTCAGTCTGGCGCCGAAGTGA<br>AGAAACCTGGCTCCTCCGTGAAGGTGTCCTGCAA<br>GGCTTCCGGCTACTCCTTCACCACCTACTACATCC<br>ACTGGGTCCGACAGGCCCCTGGACAAGGATTGGA<br>ATGGATGGGCTGGTTCTTCCCCGGCTCCGGCAACA<br>TCAAGTACAACGAGAAGTTCAAGGGCCGCGTGAC<br>CATCACCGCCGACACCTCTACCTCTACCGCCTACA<br>TGGAACTGTCCAGCCTGAGATCTGAGGACACCGC<br>CGTGTACTACTGCGCCGGCTCCTACTACTCTTACG<br>ACGTGCTGGATTACTGGGGCCAGGGCACCACAGT<br>GACAGTGTCCTCT |
| SEQ ID NO: 69 | VH-IgM constant delta CDC | METDTLLLWVLLLWVPGSTGQVQLVQSGAEVKKP<br>GSSVKVSCKASGYSFTTYYIHWVRQAPGQGLEWMG<br>WFFPGSGNIKYNEKFKGRVTITADTSTSTAYMELSSL<br>RSEDTAVYYCAGSYYSYDVLDYWGQGTTVTVSSGS<br>ASAPTLFPLVSCENSPSDTSSVAVGCLAQDFLPDSITF<br>SWKYKNNSDISSTRGFPSVLRGGKYAATSQVLLPSK<br>DVMQGTDEHVVCKVQHPNGNKEKNVPLPVIAELPP<br>KVSVFVPPRDGFFGNPRKSKLICQATGFSPRQIQVSW<br>LREGKQVGSGVTTDQVQAEAKESGPTTYKVTSTLTI<br>KESDWLGQSMFTCRVDHRGLTFQQNASSMCVPDQ<br>DTAIRVFAIPPSFASIFLTKSTKLTCLVTDLTTYDSVTI<br>SWTRQNGEAVKTHTNISESHPNATFSAVGEASICED<br>DWNSGERFTCTVTHTDLASSLKQTISRPKGVALHRP<br>DVYLLPPAREQLNLRESATITCLVTGFSPADVFVQW<br>MQRGQPLSPEKYVTSAPMPEPQAPGRYFAHSILTVS<br>EEEWNTGETYTCVVAHEALPNRVTERTVDKSTGKP<br>TLYNVSLVMSDTAGTCY |
| SEQ ID NO: 70 | VH-IgGA1 | METDTLLLWVLLLWVPGSTGQVQLVQSGAEVKKP<br>GSSVKVSCKASGYSFTTYYIHWVRQAPGQGLEWMG<br>WFFPGSGNIKYNEKFKGRVTITADTSTSTAYMELSSL<br>RSEDTAVYYCAGSYYSYDVLDYWGQGTTVTVSSAS<br>PTSPKVFPLSLCSTQPDGNVVIACLVQGFFPQEPLSV<br>TWSESGQGVTARNFPPSQDASGDLYTTSSQLTLPAT<br>QCLAGKSVTCHVKHYTNPSQDVTVPCPVPSTPPTPS<br>PSTPPTPSPSCCHPRLSLHRPALEDLLLGSEANLTCTL<br>TGLRDASGVTFTWTPSSGKSAVQGPPERDLCGCYSV<br>SSVLPGCAEPWNHGKTFTCTAAYPESKTPLTATLSK<br>SGNTFRPEVHLLPPPSEELALNELVTLTCLARGFSPK<br>DVLVRWLQGSQELPREKYLTWASRQEPSQGTTTFA<br>VTSILRVAAEDWKKGDTFSCMVGHEALPLAFTQKTI<br>DRLAGKPTHVNVSVVMAEVDGTCY |

TABLE 1-continued

Amino acid and nucleotide sequences for murine, chimeric and humanized antibody molecules which bind to TCRVB 6, e.g., TCRVB 6-5. The antibody molecules include murine mAb Antibody A, and humanized mAb Antibody A-H Clones A-H.1 to A-H.85. The amino acid the heavy and light chain CDRs, and the amino acid and nucleotide sequences of the heavy and light chain variable regions, and the heavy and light chains are shown.

| | | |
|---|---|---|
| SEQ ID NO: 71 | VH-IgGA2 | METDTLLLWVLLLWVPGSTGQVQLVQSGAEVKKP GSSVKVSCKASGYSFTTYYIHWVRQAPGQGLEWMG WFFPGSGNIKYNEKFKGRVTITADTSTSTAYMELSSL RSEDTAVYYCAGSYYSYDVLDYWGQGTTVTVSSAS PTSPKVFPLSLDSTPQDGNVVVACLVQGFFPQEPLSV TWSESGQNVTARNFPPSQDASGDLYTTSSQLTLPAT QCPDGKSVTCHVKHYTNSSQDVTVPCRVPPPPPCCH PRLSLHRPALEDLLLGSEANLTCTLTGLRDASGATFT WTPSSGKSAVQGPPERDLCGCYSVSSVLPGCAQPW NHGETFTCTAAHPELKTPLTANITKSGNTFRPEVHLL PPPSEELALNELVTLTCLARGFSPKDVLVRWLQGSQ ELPREKYLTWASRQEPSQGTTTYAVTSILRVAAEDW KKGETFSCMVGHEALPLAFTQKTIDRMAGKPTHINV SVVMAEADGTCY |
| SEQ ID NO: 3278 | Heavy chain | METDTLLLWVLLLWVPGSTGQVQLVQSGAEVKKP GSSVKVSCKASGYSFTTYYIHWVRQAPGQGLEWMG WFFPGSGNIKYNEKFKGRVTITADTSTSTAYMELSSL RSEDTAVYYCAGSYYSYDVLDYWGQGTTVTVSSAS TKGPSVFPLAPSSKSTSGGTAALGCLVKDYFPEPVTV SWNSGALTSGVHTFPAVLQSSGLYSLSSVVTVPSSSL GTQTYICNVNHKPSNTKVDKRVEPKSCDKTHTCPPC PAPELLGGPSVFLFPPKPKDTLMISRTPEVTCVVVDV SHEDPEVKFNWYVDGVEVHNAKTKPREEQYNSTYR VVSVLTVLHQDWLNGKEYKCKVSNKALPAPIEKTIS KAKGQPREPQVYTLPPSREEMTKNQVSLTCLVKGF YPSDIAVEWESNGQPENNYKTTPPVLDSDGSFFLYS KLTVDKSRWQQGNVFSCSVMHEALHNHYTQKSLSL SPGK |
| SEQ ID NO: 6 | LC CDR1 (Combined) | KASQNVGINVV |
| SEQ ID NO: 7 | LC CDR2 (Combined) | SSSHRYS |
| SEQ ID NO: 8 | LC CDR3 (Combined) | QQFKSYPLT |
| SEQ ID NO: 10 | VL | DIQMTQSPSFLSASVGDRVTITCKASQNVGINVVWH QQKPGKAPKALIYSSSHRYSGVPSRFSGSGSGTEFTL TISSLQPEDFATYFCQQFKSYPLTFGQGTKLEIK |
| SEQ ID NO: 13 | DNA VL | GACATCCAGATGACCCAGTCTCCATCCTTCCTGTC CGCCTCTGTGGGCGACAGAGTGACCATCACATGC AAGGCCTCTCAGAACGTGGGCATCAACGTCGTGT GGCACCAGCAGAAGCCTGGCAAGGCTCCTAAGGC TCTGATCTACTCCTCCAGCCACCGGTACTCTGGCG TGCCCTCTAGATTTTCCGGCTCTGGCTCTGGCACC GAGTTTACCCTGACAATCTCCAGCCTGCAGCCTGA GGACTTCGCCACCTACTTTTGCCAGCAGTTCAAGA GCTACCCTCTGACCTTTGGCCAGGGCACCAAGCTG GAAATCAAG |
| SEQ ID NO: 72 | VL and kappa constant region/light chain | METDTLLLWVLLLWVPGSTGDIQMTQSPSFLSASVG DRVTITCKASQNVGINVVWHQQKPGKAPKALIYSSS HRYSGVPSRFSGSGSGTEFTLTISSLQPEDFATYFCQ QFKSYPLTFGQGTKLEIKRTVAAPSVFIFPPSDEQLKS GTASVVCLLNNFYPREAKVQWKVDNALQSGNSQES VTEQDSKDSTYSLSSTLTLSKADYEKHKVYACEVTH QGLSSPVTKSFNRGEC |
| A-H.2 antibody (also referred to as BHM1710) | | |
| SEQ ID NO: 3 | HC CDR1 (Combined) | GYSFTTYYIH |
| SEQ ID NO: 4 | HC CDR2 (Combined) | WFFPGSGNIKYNEKFKG |
| SEQ ID NO: 5 | HC CDR3 (Combined) | SYYSYDVLDY |
| SEQ ID NO: 9 | VH | QVQLVQSGAEVKKPGSSVKVSCKASGYSFTTYYIH WVRQAPGQGLEWMGWFFPGSGNIKYNEKFKGRVTI TADTSTSTAYMELSSLRSEDTAVYYCAGSYYSYDVL DYWGQGTTVTVSS |

TABLE 1-continued

Amino acid and nucleotide sequences for murine, chimeric and humanized antibody molecules which bind to TCRVB 6, e.g., TCRVB 6-5. The antibody molecules include murine mAb Antibody A, and humanized mAb Antibody A-H Clones A-H.1 to A-H.85. The amino acid the heavy and light chain CDRs, and the amino acid and nucleotide sequences of the heavy and light chain variable regions, and the heavy and light chains are shown.

| | | |
|---|---|---|
| SEQ ID NO: 12 | DNA VH | CAGGTGCAGCTGGTTCAGTCTGGCGCCGAAGTGAAGAAACCTGGCTCCTCCGTGAAGGTGTCCTGCAAGGCTTCCGGCTACTCCTTCACCACCTACTACATCCACTGGGTCCGACAGGCCCCTGGACAAGGATTGGAATGGATGGGCTGGTTCTTCCCCGGCTCCGGCAACATCAAGTACAACGAGAAGTTCAAGGGCCGCGTGACCATCACCGCCGACACCTCTACCTCTACCGCCTACATGGAACTGTCCAGCCTGAGATCTGAGGACACCGCCGTGTACTACTGCGCCGGCTCCTACTACTCTTACGACGTGCTGGATTACTGGGGCCAGGGCACCACAGTGACAGTGTCCTCT |
| SEQ ID NO: 3278 | Heavy chain | METDTLLLWVLLLWVPGSTGQVQLVQSGAEVKKPGSSVKVSCKASGYSFTTYYIHWVRQAPGQGLEWMGWFFPGSGNIKYNEKFKGRVTITADTSTSTAYMELSSLRSEDTAVYYCAGSYYSYDVLDYWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| SEQ ID NO: 6 | LC CDR1 (Combined) | KASQNVGINVV |
| SEQ ID NO: 7 | LC CDR2 (Combined) | SSSHRYS |
| SEQ ID NO: 8 | LC CDR3 (Combined) | QQFKSYPLT |
| SEQ ID NO: 11 | VL | DIQMTQSPSSLSASVGDRVTITCKASQNVGINVVWHQQKPGKVPKALIYSSSHRYSGVPSRFSGSGSGTDFTLTISSLQPEDVATYFCQQFKSYPLTFGQGTKLEIK |
| SEQ ID NO: 14 | DNA VL | GACATCCAGATGACCCAGTCTCCATCCTCTCTGTCCGCCTCTGTGGGCGACAGAGTGACCATCACATGCAAGGCCTCTCAGAACGTGGGCATCAACGTCGTGTGGCACCAGCAGAAACCTGGCAAGGTGCCCAAGGCTCTGATCTACTCCTCCAGCCACAGATACTCCGGCGTGCCCTCTAGATTCTCCGGCTCTGGCTCTGGCACCGACTTTACCCTGACAATCTCCAGCCTGCAGCCTGAGGACGTGGCCACCTACTTTTGCCAGCAGTTCAAGAGCTACCCTCTGACCTTTGGCCAGGGCACCAAGCTGGAAATCAAG |
| SEQ ID NO: 3279 | Light chain | METDTLLLWVLLLWVPGSTGDIQMTQSPSSLSASVGDRVTITCKASQNVGINVVWHQQKPGKVPKALIYSSSHRYSGVPSRFSGSGSGTDFTLTISSLQPEDVATYFCQQFKSYPLTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| A-H.3 antibody | | |
| SEQ ID NO: 80 | VH + VL | QVQLVQSGAEVKKPGSSVKVSCKASGTDFKLTYIHWVRQAPGQGLEWMGRVSPGSGNTKYNEKFKGRVTITADTSTSTAYMELSSLRSEDTAVYYCAGSYYSYDVLDYWGQGTTVTVSSGGGGSGGGGSGGGGSGGGGSDIQMTQSPSFLSASVGDRVTITCKASQNVEDRVAWYQQKPGKAPKALIYSSSHRYKGVPSRFSGSGSGTEFTLTISSLQPEDFATYFCQQFKSYPLTFGQGTKLEIK |
| SEQ ID NO: 81 | VL | DIQMTQSPSFLSASVGDRVTITCKASQNVEDRVAWYQQKPGKAPKALIYSSSHRYKGVPSRFSGSGSGTEFTLTISSLQPEDFATYFCQQFKSYPLTFGQGTKLEIK |

TABLE 1-continued

Amino acid and nucleotide sequences for murine, chimeric and humanized antibody molecules which bind to TCRVB 6, e.g., TCRVB 6-5. The antibody molecules include murine mAb Antibody A, and humanized mAb Antibody A-H Clones A-H.1 to A-H.85. The amino acid the heavy and light chain CDRs, and the amino acid and nucleotide sequences of the heavy and light chain variable regions, and the heavy and light chains are shown.

| | | |
|---|---|---|
| SEQ ID NO: 82 | VH | QVQLVQSGAEVKKPGSSVKVSCKASGTDFKLTYIH WVRQAPGQGLEWMGRVSPGSGNTKYNEKFKGRVT ITADTSTSTAYMELSSLRSEDTAVYYCAGSYYSYDV LDYWGQGTTVTVSS |
| | A-H.4 | |
| SEQ ID NO: 83 | VH + VL | QVQLVQSGAEVKKPGSSVKVSCKASGTDFDKIYIH WVRQAPGQGLEWMGRISAGSGNVKYNEKFKGRVT ITADTSTSTAYMELSSLRSEDTAVYYCAGSYYSYDV LDYWGQGTTVTVSSGGGGSGGGGSGGGGSGGGGS DIQMTQSPSFLSASVGDRVTITCKASQNVEDRVAWY QQKPGKAPKALIYSSSHRYKGVPSRFSGSGSGTEFTL TISSLQPEDFATYFCQQFKSYPLTFGQGTKLEIK |
| SEQ ID NO: 84 | VL | DIQMTQSPSFLSASVGDRVTITCKASQNVEDRVAWY QQKPGKAPKALIYSSSHRYKGVPSRFSGSGSGTEFTL TISSLQPEDFATYFCQQFKSYPLTFGQGTKLEIK |
| SEQ ID NO: 85 | VH | QVQLVQSGAEVKKPGSSVKVSCKASGTDFDKIYIH WVRQAPGQGLEWMGRISAGSGNVKYNEKFKGRVT ITADTSTSTAYMELSSLRSEDTAVYYCAGSYYSYDV LDYWGQGTTVTVSS |
| | A-H.5 | |
| SEQ ID NO: 86 | VH + VL | QVQLVQSGAEVKKPGSSVKVSCKASGHDFRDFYIH WVRQAPGQGLEWMGRVYPGSGSYRYNEKFKGRVT ITADTSTSTAYMELSSLRSEDTAVYYCAGSYYSYDV LDYWGQGTTVTVSSGGGGSGGGGSGGGGSGGGGS DIQMTQSPSFLSASVGDRVTITCKASQNVDDRVAW YQQKPGKAPKALIYSSSHRYKGVPSRFSGSGSGTEFT LTISSLQPEDFATYFCQQFKSYPLTFGQGTKLEIK |
| SEQ ID NO: 87 | VL | DIQMTQSPSFLSASVGDRVTITCKASQNVDDRVAW YQQKPGKAPKALIYSSSHRYKGVPSRFSGSGSGTEFT LTISSLQPEDFATYFCQQFKSYPLTFGQGTKLEIK |
| SEQ ID NO: 88 | VH | QVQLVQSGAEVKKPGSSVKVSCKASGHDFRDFYIH WVRQAPGQGLEWMGRVYPGSGSYRYNEKFKGRVT ITADTSTSTAYMELSSLRSEDTAVYYCAGSYYSYDV LDYWGQGTTVTVSS |
| | A-H.6 | |
| SEQ ID NO: 89 | VH + VL | QVQLVQSGAEVKKPGSSVKVSCKASGHDFKLTYIH WVRQAPGQGLEWMGRISAGSGNVKYNEKFKGRVT ITADTSTSTAYMELSSLRSEDTAVYYCAGSYYSYDV LDYWGQGTTVTVSSGGGGSGGGGSGGGGSGGGGS DIQMTQSPSFLSASVGDRVTITCKASQNVDNRVAW YQQKPGKAPKALIYSSSHRYKGVPSRFSGSGSGTEFT LTISSLQPEDFATYFCQQFKSYPLTFGQGTKLEIK |
| SEQ ID NO: 90 | VL | DIQMTQSPSFLSASVGDRVTITCKASQNVDNRVAW YQQKPGKAPKALIYSSSHRYKGVPSRFSGSGSGTEFT LTISSLQPEDFATYFCQQFKSYPLTFGQGTKLEIK |
| SEQ ID NO: 91 | VH | QVQLVQSGAEVKKPGSSVKVSCKASGHDFKLTYIH WVRQAPGQGLEWMGRISAGSGNVKYNEKFKGRVT ITADTSTSTAYMELSSLRSEDTAVYYCAGSYYSYDV LDYWGQGTTVTVSS |
| | A-H.7 | |
| SEQ ID NO: 92 | VH + VL | QVQLVQSGAEVKKPGSSVKVSCKASGTDFKLTYIH WVRQAPGQGLEWMGRIFPGSGNVKYNEKFKGRVTI TADTSTSTAYMELSSLRSEDTAVYYCAGSYYSYDVL DYWGQGTTVTVSSGGGGSGGGGSGGGGSGGGGSDI QMTQSPSFLSASVGDRVTITCKASQNVENKVAWHQ QKPGKAPKALIYSSSHRYKGVPSRFSGSGSGTEFTLT ISSLQPEDFATYFCQQFKSYPLTFGQGTKLEIK |

TABLE 1-continued

Amino acid and nucleotide sequences for murine, chimeric and humanized antibody molecules which bind to TCRVB 6, e.g., TCRVB 6-5. The antibody molecules include murine mAb Antibody A, and humanized mAb Antibody A-H Clones A-H.1 to A-H.85. The amino acid the heavy and light chain CDRs, and the amino acid and nucleotide sequences of the heavy and light chain variable regions, and the heavy and light chains are shown.

| | | |
|---|---|---|
| SEQ ID NO: 93 | VL | DIQMTQSPSFLSASVGDRVTITCKASQNVENKVAWH QQKPGKAPKALIYSSSHRYKGVPSRFSGSGSGTEFTL TISSLQPEDFATYFCQQFKSYPLTFGQGTKLEIK |
| SEQ ID NO: 94 | VH | QVQLVQSGAEVKKPGSSVKVSCKASGTDFKLTYIH WVRQAPGQGLEWMGRIFPGSGNVKYNEKFKGRVTI TADTSTSTAYMELSSLRSEDTAVYYCAGSYYSYDVL DYWGQGTTVTVSS |
| | A-H.8 | |
| SEQ ID NO: 95 | VH + VL | QVQLVQSGAEVKKPGSSVKVSCKASGTDFDKIYIH WVRQAPGQGLEWMGRIFAGSGNTKYNEKFKGRVTI TADTSTSTAYMELSSLRSEDTAVYYCAGSYYSYDVL DYWGQGTTVTVSSGGGGSGGGGSGGGGSGGGGSDI QMTQSPSFLSASVGDRVTITCKASQNVDDRVAWYQ QKPGKAPKALIYSSSHRYKGVPSRFSGSGSGTEFTLT ISSLQPEDFATYFCQQFKSYPLTFGQGTKLEIK |
| SEQ ID NO: 96 | VL | DIQMTQSPSFLSASVGDRVTITCKASQNVDDRVAW YQQKPGKAPKALIYSSSHRYKGVPSRFSGSGSGTEFT LTISSLQPEDFATYFCQQFKSYPLTFGQGTKLEIK |
| SEQ ID NO: 97 | VH | QVQLVQSGAEVKKPGSSVKVSCKASGTDFDKIYIH WVRQAPGQGLEWMGRIFAGSGNTKYNEKFKGRVTI TADTSTSTAYMELSSLRSEDTAVYYCAGSYYSYDVL DYWGQGTTVTVSS |
| | A-H.9 | |
| SEQ ID NO: 98 | VH + VL | QVQLVQSGAEVKKPGSSVKVSCKASGHDFDKFYIH WVRQAPGQGLEWMGRVSAGSGNVKYNEKFKGRV TITADTSTSTAYMELSSLRSEDTAVYYCAGSYYSYD VLDYWGQGTTVTVSSGGGGSGGGGSGGGGSGGGG SDIQMTQSPSFLSASVGDRVTITCKASQNVGNRVAW YQQKPGKAPKALIYSSSHRYSGVPSRFSGSGSGTEFT LTISSLQPEDFATYFCQQFKSYPLTFGQGTKLEIK |
| SEQ ID NO: 99 | VL | DIQMTQSPSFLSASVGDRVTITCKASQNVGNRVAW YQQKPGKAPKALIYSSSHRYSGVPSRFSGSGSGTEFT LTISSLQPEDFATYFCQQFKSYPLTFGQGTKLEIK |
| SEQ ID NO: 100 | VH | QVQLVQSGAEVKKPGSSVKVSCKASGHDFDKFYIH WVRQAPGQGLEWMGRVSAGSGNVKYNEKFKGRV TITADTSTSTAYMELSSLRSEDTAVYYCAGSYYSYD VLDYWGQGTTVTVSSS |
| | A-H.10 | |
| SEQ ID NO: 101 | VH + VL | QVQLVQSGAEVKKPGSSVKVSCKASGHDFDKFYIH WVRQAPGQGLEWMGRIFAGSGNVKYNEKFKGRVT ITADTSTSTAYMELSSLRSEDTAVYYCAGSYYSYDV LDYWGQGTTVTVSSGGGGSGGGGSGGGGSGGGGS DIQMTQSPSFLSASVGDRVTITCKASQNVGDRVAW YQQKPGKAPKALIYSSSHRYKGVPSRFSGSGSGTEFT LTISSLQPEDFATYFCQQFKSYPLTFGQGTKLEIKs |
| SEQ ID NO: 102 | VL | DIQMTQSPSFLSASVGDRVTITCKASQNVGDRVAW YQQKPGKAPKALIYSSSHRYKGVPSRFSGSGSGTEFT LTISSLQPEDFATYFCQQFKSYPLTFGQGTKLEIK |
| SEQ ID NO: 103 | VH | QVQLVQSGAEVKKPGSSVKVSCKASGHDFDKFYIH WVRQAPGQGLEWMGRIFAGSGNVKYNEKFKGRVT ITADTSTSTAYMELSSLRSEDTAVYYCAGSYYSYDV LDYWGQGTTVTVSS |

TABLE 1-continued

Amino acid and nucleotide sequences for murine, chimeric and humanized antibody molecules which bind to TCRVB 6, e.g., TCRVB 6-5. The antibody molecules include murine mAb Antibody A, and humanized mAb Antibody A-H Clones A-H.1 to A-H.85. The amino acid the heavy and light chain CDRs, and the amino acid and nucleotide sequences of the heavy and light chain variable regions, and the heavy and light chains are shown.

| | | |
|---|---|---|
| | A-H.11 | |
| SEQ ID NO: 104 | VH + VL | QVQLVQSGAEVKKPGSSVKVSCKASGTDFKLTYIH WVRQAPGQGLEWMGRVSPGSGNVKYNEKFKGRVT ITADTSTSTAYMELSSLRSEDTAVYYCAGSYYSYDV LDYWGQGTTVTVSSGGGGSGGGGSGGGGSGGGGS DIQMTQSPSFLSASVGDRVTITCKASQNVGDRVAW YQQKPGKAPKALIYSSSHRYKGVPSRFSGSGSGTEFT LTISSLQPEDFATYFCQQFKSYPLTFGQGTKLEIK |
| SEQ ID NO: 105 | VL | DIQMTQSPSFLSASVGDRVTITCKASQNVGDRVAW YQQKPGKAPKALIYSSSHRYKGVPSRFSGSGSGTEFT LTISSLQPEDFATYFCQQFKSYPLTFGQGTKLEIK |
| SEQ ID NO: 106 | VH | QVQLVQSGAEVKKPGSSVKVSCKASGTDFKLTYIH WVRQAPGQGLEWMGRVSPGSGNVKYNEKFKGRVT ITADTSTSTAYMELSSLRSEDTAVYYCAGSYYSYDV LDYWGQGTTVTVSS |
| | A-H.12 | |
| SEQ ID NO: 107 | VH + VL | QVQLVQSGAEVKKPGSSVKVSCKASGTDFDKIYIH WVRQAPGQGLEWMGRVSAGSGNTKYNEKFKGRVT ITADTSTSTAYMELSSLRSEDTAVYYCAGSYYSYDV LDYWGQGTTVTVSSGGGGSGGGGSGGGGSGGGGS DIQMTQSPSFLSASVGDRVTITCKASQNVGNRVAW YQQKPGKAPKALIYSSSHRYKGVPSRFSGSGSGTEFT LTISSLQPEDFATYFCQQFKSYPLTFGQGTKLEIK |
| SEQ ID NO: 108 | VL | DIQMTQSPSFLSASVGDRVTITCKASQNVGNRVAW YQQKPGKAPKALIYSSSHRYKGVPSRFSGSGSGTEFT LTISSLQPEDFATYFCQQFKSYPLTFGQGTKLEIK |
| SEQ ID NO: 109 | VH | QVQLVQSGAEVKKPGSSVKVSCKASGTDFDKIYIH WVRQAPGQGLEWMGRVSAGSGNTKYNEKFKGRVT ITADTSTSTAYMELSSLRSEDTAVYYCAGSYYSYDV LDYWGQGTTVTVSS |
| | A-H.13, also referred to as A-H.69 | |
| SEQ ID NO: 110 | VH + VL | QVQLVQSGAEVKKPGSSVKVSCKASGTDFKLTYIH WVRQAPGQGLEWMGRIFPGSGNVKYNEKFKGRVTI TADTSTSTAYMELSSLRSEDTAVYYCAGSYYSYDVL DYWGQGTTVTVSSGGGGSGGGGSGGGGSGGGGSDI QMTQSPSFLSASVGDRVTITCKASQNVDNRVAWYQ QKPGKAPKALIYSSSHRYKGVPSRFSGSGSGTEFTLT ISSLQPEDFATYFCQQFKSYPLTFGQGTKLEIK |
| SEQ ID NO: 111 | VL | DIQMTQSPSFLSASVGDRVTITCKASQNVDNRVAW YQQKPGKAPKALIYSSSHRYKGVPSRFSGSGSGTEFT LTISSLQPEDFATYFCQQFKSYPLTFGQGTKLEIK |
| SEQ ID NO: 112 | VH | QVQLVQSGAEVKKPGSSVKVSCKASGTDFKLTYIH WVRQAPGQGLEWMGRIFPGSGNVKYNEKFKGRVTI TADTSTSTAYMELSSLRSEDTAVYYCAGSYYSYDVL DYWGQGTTVTVSS |
| | A-H.14 | |
| SEQ ID NO: 113 | VH + VL | QVQLVQSGAEVKKPGSSVKVSCKASGTDFDKIYIH WVRQAPGQGLEWMGRISAGSGNTKYNEKFKGRVTI TADTSTSTAYMELSSLRSEDTAVYYCAGSYYSYDVL DYWGQGTTVTVSSGGGGSGGGGSGGGGSGGGGSDI QMTQSPSFLSASVGDRVTITCKASQNVDDRVAWYQ QKPGKAPKALIYSSSHRYKGVPSRFSGSGSGTEFTLT ISSLQPEDFATYFCQQFKSYPLTFGQGTKLEIK |
| SEQ ID NO: 114 | VL | DIQMTQSPSFLSASVGDRVTITCKASQNVDDRVAW YQQKPGKAPKALIYSSSHRYKGVPSRFSGSGSGTEFT LTISSLQPEDFATYFCQQFKSYPLTFGQGTKLEIK |

TABLE 1-continued

Amino acid and nucleotide sequences for murine, chimeric and humanized antibody molecules which bind to TCRVB 6, e.g., TCRVB 6-5. The antibody molecules include murine mAb Antibody A, and humanized mAb Antibody A-H Clones A-H.1 to A-H.85. The amino acid the heavy and light chain CDRs, and the amino acid and nucleotide sequences of the heavy and light chain variable regions, and the heavy and light chains are shown.

| | | |
|---|---|---|
| SEQ ID NO: 115 | VH | QVQLVQSGAEVKKPGSSVKVSCKASGTDFDKIYIH WVRQAPGQGLEWMGRISAGSGNTKYNEKFKGRVTI TADTSTSTAYMELSSLRSEDTAVYYCAGSYYSYDVL DYWGQGTTVTVSS |
| | A-H.15 | |
| SEQ ID NO: 116 | VH + VL | QVQLVQSGAEVKKPGSSVKVSCKASGTDFRLTYIH WVRQAPGQGLEWMGRVSPGSGNTKYNEKFKGRVT ITADTSTSTAYMELSSLRSEDTAVYYCAGSYYSYDV LDYWGQGTTVTVSSGGGGSGGGGSGGGGSGGGGS DIQMTQSPSFLSASVGDRVTITCKASQNVDNKVAW HQQKPGKAPKALIYSSSHRYKGVPSRFSGSGSGTEFT LTISSLQPEDFATYFCQQFKSYPLTFGQGTKLEIK |
| SEQ ID NO: 117 | VL | DIQMTQSPSFLSASVGDRVTITCKASQNVDNKVAW HQQKPGKAPKALIYSSSHRYKGVPSRFSGSGSGTEFT LTISSLQPEDFATYFCQQFKSYPLTFGQGTKLEIK |
| SEQ ID NO: 118 | VH | QVQLVQSGAEVKKPGSSVKVSCKASGTDFRLTYIH WVRQAPGQGLEWMGRVSPGSGNTKYNEKFKGRVT ITADTSTSTAYMELSSLRSEDTAVYYCAGSYYSYDV LDYWGQGTTVTVSS |
| | A-H.16 | |
| SEQ ID NO: 119 | VH + VL | QVQLVQSGAEVKKPGSSVKVSCKASGGTFRLTYIH WVRQAPGQGLEWMGRVYPGSGNTKYNEKFKGRVT ITADTSTSTAYMELSSLRSEDTAVYYCAGSYYSYDV LDYWGQGTTVTVSSGGGGSGGGGSGGGGSGGGGS DIQMTQSPSFLSASVGDRVTITCKASQNVDDRVAW YQQKPGKAPKALIYSSSHRYKGVPSRFSGSGSGTEFT LTISSLQPEDFATYFCQQFKSYPLTFGQGTKLEIK |
| SEQ ID NO: 120 | VL | DIQMTQSPSFLSASVGDRVTITCKASQNVDDRVAW YQQKPGKAPKALIYSSSHRYKGVPSRFSGSGSGTEFT LTISSLQPEDFATYFCQQFKSYPLTFGQGTKLEIK |
| SEQ ID NO: 121 | VH | QVQLVQSGAEVKKPGSSVKVSCKASGGTFRLTYIH WVRQAPGQGLEWMGRVYPGSGNTKYNEKFKGRVT ITADTSTSTAYMELSSLRSEDTAVYYCAGSYYSYDV LDYWGQGTTVTVSS |
| | A-H.17 | |
| SEQ ID NO: 122 | VH + VL | QVQLVQSGAEVKKPGSSVKVSCKASGTDFRLTYIH WVRQAPGQGLEWMGRIFPGSGNTKYNEKFKGRVTI TADTSTSTAYMELSSLRSEDTAVYYCAGSYYSYDVL DYWGQGTTVTVSSGGGGSGGGGSGGGGSGGGGSDI QMTQSPSFLSASVGDRVTITCKASQNVDDRVAWYQ QKPGKAPKALIYSSSHRYKGVPSRFSGSGSGTEFTLT ISSLQPEDFATYFCQQFKSYPLTFGQGTKLEIK |
| SEQ ID NO: 123 | VL | DIQMTQSPSFLSASVGDRVTITCKASQNVDDRVAW YQQKPGKAPKALIYSSSHRYKGVPSRFSGSGSGTEFT LTISSLQPEDFATYFCQQFKSYPLTFGQGTKLEIK |
| SEQ ID NO: 124 | VH | QVQLVQSGAEVKKPGSSVKVSCKASGTDFRLTYIH WVRQAPGQGLEWMGRIFPGSGNTKYNEKFKGRVTI TADTSTSTAYMELSSLRSEDTAVYYCAGSYYSYDVL DYWGQGTTVTVSS |
| | A-H.18 | |
| SEQ ID NO: 125 | VH + VL | QVQLVQSGAEVKKPGSSVKVSCKASGTDFKLTYIH WVRQAPGQGLEWMGRIFPGSGNVKYNEKFKGRVTI TADTSTSTAYMELSSLRSEDTAVYYCAGSYYSYDVL DYWGQGTTVTVSSGGGGSGGGGSGGGGSGGGGSDI QMTQSPSFLSASVGDRVTITCKASQNVEDRVAWYQ QKPGKAPKALIYSSSHRYKGVPSRFSGSGSGTEFTLT ISSLQPEDFATYFCQQFKSYPLTFGQGTKLEIK |

TABLE 1-continued

Amino acid and nucleotide sequences for murine, chimeric and humanized antibody molecules which bind to TCRVB 6, e.g., TCRVB 6-5. The antibody molecules include murine mAb Antibody A, and humanized mAb Antibody A-H Clones A-H.1 to A-H.85. The amino acid the heavy and light chain CDRs, and the amino acid and nucleotide sequences of the heavy and light chain variable regions, and the heavy and light chains are shown.

| | | |
|---|---|---|
| SEQ ID NO: 126 | VL | DIQMTQSPSFLSASVGDRVTITCKASQNVEDRVAWY QQKPGKAPKALIYSSSHRYKGVPSRFSGSGSGTEFTL TISSLQPEDFATYFCQQFKSYPLTFGQGTKLEIK |
| SEQ ID NO: 127 | VH | QVQLVQSGAEVKKPGSSVKVSCKASGTDFKLTYIH WVRQAPGQGLEWMGRIFPGSGNVKYNEKFKGRVTI TADTSTSTAYMELSSLRSEDTAVYYCAGSYYSYDVL DYWGQGTTVTVSS |
| | A-H.19 | |
| SEQ ID NO: 128 | VH + VL | QVQLVQSGAEVKKPGSSVKVSCKASGGTFRLTYIH WVRQAPGQGLEWMGRISAGSGNVKYNEKFKGRVT ITADTSTSTAYMELSSLRSEDTAVYYCAGSYYSYDV LDYWGQGTTVTVSSGGGGSGGGGSGGGGSGGGGS DIQMTQSPSFLSASVGDRVTITCKASQNVGDRVAW YQQKPGKAPKALIYSSSHRYKGVPSRFSGSGSGTEFT LTISSLQPEDFATYFCQQFKSYPLTFGQGTKLEIK |
| SEQ ID NO: 129 | VL | DIQMTQSPSFLSASVGDRVTITCKASQNVGDRVAW YQQKPGKAPKALIYSSSHRYKGVPSRFSGSGSGTEFT LTISSLQPEDFATYFCQQFKSYPLTFGQGTKLEIK |
| SEQ ID NO: 130 | VH | QVQLVQSGAEVKKPGSSVKVSCKASGGTFRLTYIH WVRQAPGQGLEWMGRISAGSGNVKYNEKFKGRVT ITADTSTSTAYMELSSLRSEDTAVYYCAGSYYSYDV LDYWGQGTTVTVSS |
| | A-H.20 | |
| SEQ ID NO: 131 | VH + VL | QVQLVQSGAEVKKPGSSVKVSCKASGGTFDKTYIH WVRQAPGQGLEWMGRISAGSGNTKYNEKFKGRVTI TADTSTSTAYMELSSLRSEDTAVYYCAGSYYSYDVL DYWGQGTTVTVSSGGGGSGGGGSGGGGSGGGGSDI QMTQSPSFLSASVGDRVTITCKASQNVDDRVAWYQ QKPGKAPKALIYSSSHRYKGVPSRFSGSGSGTEFTLT ISSLQPEDFATYFCQQFKSYPLTFGQGTKLEIK |
| SEQ ID NO: 132 | VL | DIQMTQSPSFLSASVGDRVTITCKASQNVDDRVAW YQQKPGKAPKALIYSSSHRYKGVPSRFSGSGSGTEFT LTISSLQPEDFATYFCQQFKSYPLTFGQGTKLEIK |
| SEQ ID NO: 133 | VH | QVQLVQSGAEVKKPGSSVKVSCKASGGTFDKTYIH WVRQAPGQGLEWMGRISAGSGNTKYNEKFKGRVTI TADTSTSTAYMELSSLRSEDTAVYYCAGSYYSYDVL DYWGQGTTVTVSS |
| | A-H.21 | |
| SEQ ID NO: 134 | VH + VL | QVQLVQSGAEVKKPGSSVKVSCKASGHDFDKFYIH WVRQAPGQGLEWMGRISAGSGNTKYNEKFKGRVTI TADTSTSTAYMELSSLRSEDTAVYYCAGSYYSYDVL DYWGQGTTVTVSSGGGGSGGGGSGGGGSGGGGSDI QMTQSPSFLSASVGDRVTITCKASQNVDDRVAWYQ QKPGKAPKALIYSSSHRYKGVPSRFSGSGSGTEFTLT ISSLQPEDFATYFCQQFKSYPLTFGQGTKLEIK |
| SEQ ID NO: 135 | VL | DIQMTQSPSFLSASVGDRVTITCKASQNVDDRVAW YQQKPGKAPKALIYSSSHRYKGVPSRFSGSGSGTEFT LTISSLQPEDFATYFCQQFKSYPLTFGQGTKLEIK |
| SEQ ID NO: 136 | VH | QVQLVQSGAEVKKPGSSVKVSCKASGHDFDKFYIH WVRQAPGQGLEWMGRISAGSGNTKYNEKFKGRVTI TADTSTSTAYMELSSLRSEDTAVYYCAGSYYSYDVL DYWGQGTTVTVSS |
| | A-H.22 | |
| SEQ ID NO: 137 | VH + VL | QVQLVQSGAEVKKPGSSVKVSCKASGTDFKLTYIH WVRQAPGQGLEWMGRISAGSGNVKYNEKFKGRVT ITADTSTSTAYMELSSLRSEDTAVYYCAGSYYSYDV LDYWGQGTTVTVSSGGGGSGGGGSGGGGSGGGGS |

TABLE 1-continued

Amino acid and nucleotide sequences for murine, chimeric and humanized antibody molecules which bind to TCRVB 6, e.g., TCRVB 6-5. The antibody molecules include murine mAb Antibody A, and humanized mAb Antibody A-H Clones A-H.1 to A-H.85. The amino acid the heavy and light chain CDRs, and the amino acid and nucleotide sequences of the heavy and light chain variable regions, and the heavy and light chains are shown.

| | | |
|---|---|---|
| | | DIQMTQSPSFLSASVGDRVTITCKASQNVDNKVAW<br>HQQKPGKAPKALIYSSSHRYKGVPSRFSGSGSGTEFT<br>LTISSLQPEDFATYFCQQFKSYPLTFGQGTKLEIK |
| SEQ ID NO: 138 | VL | DIQMTQSPSFLSASVGDRVTITCKASQNVDNKVAW<br>HQQKPGKAPKALIYSSSHRYKGVPSRFSGSGSGTEFT<br>LTISSLQPEDFATYFCQQFKSYPLTFGQGTKLEIK |
| SEQ ID NO: 139 | VH | QVQLVQSGAEVKKPGSSVKVSCKASGTDFKLTYIH<br>WVRQAPGQGLEWMGRISAGSGNVKYNEKFKGRVT<br>ITADTSTSTAYMELSSLRSEDTAVYYCAGSYYSYDV<br>LDYWGQGTTVTVSS |
| | A-H.23 | |
| SEQ ID NO: 140 | VH + VL | QVQLVQSGAEVKKPGSSVKVSCKASGHDFRLTYIH<br>WVRQAPGQGLEWMGRISAGSGNVKYNEKFKGRVT<br>ITADTSTSTAYMELSSLRSEDTAVYYCAGSYYSYDV<br>LDYWGQGTTVTVSSGGGGSGGGGSGGGGSGGGGS<br>DIQMTQSPSFLSASVGDRVTITCKASQNVADRVAW<br>YQQKPGKAPKALIYSSSHRYKGVPSRFSGSGSGTEFT<br>LTISSLQPEDFATYFCQQFKSYPLTFGQGTKLEIK |
| SEQ ID NO: 141 | VL | DIQMTQSPSFLSASVGDRVTITCKASQNVADRVAW<br>YQQKPGKAPKALIYSSSHRYKGVPSRFSGSGSGTEFT<br>LTISSLQPEDFATYFCQQFKSYPLTFGQGTKLEIK |
| SEQ ID NO: 142 | VH | QVQLVQSGAEVKKPGSSVKVSCKASGHDFRLTYIH<br>WVRQAPGQGLEWMGRISAGSGNVKYNEKFKGRVT<br>ITADTSTSTAYMELSSLRSEDTAVYYCAGSYYSYDV<br>LDYWGQGTTVTVSS |
| | A-H.24 | |
| SEQ ID NO: 143 | VH + VL | QVQLVQSGAEVKKPGSSVKVSCKASGHDFHLWYIH<br>WVRQAPGQGLEWMGRVSAGSGNVKYNEKFKGRV<br>TITADTSTSTAYMELSSLRSEDTAVYYCAGSYYSYD<br>VLDYWGQGTTVTVSSGGGGSGGGGSGGGGSGGGG<br>SDIQMTQSPSFLSASVGDRVTITCKASQNVDNKVAW<br>HQQKPGKAPKALIYSSSHRYKGVPSRFSGSGSGTEFT<br>LTISSLQPEDFATYFCQQFKSYPLTFGQGTKLEIK |
| SEQ ID NO: 144 | VL | DIQMTQSPSFLSASVGDRVTITCKASQNVDNKVAW<br>HQQKPGKAPKALIYSSSHRYKGVPSRFSGSGSGTEFT<br>LTISSLQPEDFATYFCQQFKSYPLTFGQGTKLEIK |
| SEQ ID NO: 145 | VH | QVQLVQSGAEVKKPGSSVKVSCKASGHDFHLWYIH<br>WVRQAPGQGLEWMGRVSAGSGNVKYNEKFKGRV<br>TITADTSTSTAYMELSSLRSEDTAVYYCAGSYYSYD<br>VLDYWGQGTTVTVSS |
| | A-H.25 | |
| SEQ ID NO: 146 | VH + VL | QVQLVQSGAEVKKPGSSVKVSCKASGHDFHLWYIH<br>WVRQAPGQGLEWMGRVFAGSGNTKYNEKFKGRVT<br>ITADTSTSTAYMELSSLRSEDTAVYYCAGSYYSYDV<br>LDYWGQGTTVTVSSGGGGSGGGGSGGGGSGGGGS<br>DIQMTQSPSFLSASVGDRVTITCKASQNVEDKVAWY<br>QQKPGKAPKALIYSSSHRYKGVPSRFSGSGSGTEFTL<br>TISSLQPEDFATYFCQQFKSYPLTFGQGTKLEIK |
| SEQ ID NO: 147 | VL | DIQMTQSPSFLSASVGDRVTITCKASQNVEDKVAWY<br>QQKPGKAPKALIYSSSHRYKGVPSRFSGSGSGTEFTL<br>TISSLQPEDFATYFCQQFKSYPLTFGQGTKLEIK |
| SEQ ID NO: 148 | VH | QVQLVQSGAEVKKPGSSVKVSCKASGHDFHLWYIH<br>WVRQAPGQGLEWMGRVFAGSGNTKYNEKFKGRVT<br>ITADTSTSTAYMELSSLRSEDTAVYYCAGSYYSYDV<br>LDYWGQGTTVTVSS |

TABLE 1-continued

Amino acid and nucleotide sequences for murine, chimeric and humanized antibody molecules which bind to TCRVB 6, e.g., TCRVB 6-5. The antibody molecules include murine mAb Antibody A, and humanized mAb Antibody A-H Clones A-H.1 to A-H.85. The amino acid the heavy and light chain CDRs, and the amino acid and nucleotide sequences of the heavy and light chain variable regions, and the heavy and light chains are shown.

| | | |
|---|---|---|
| **A-H.26** | | |
| SEQ ID NO: 149 | VH + VL | QVQLVQSGAEVKKPGSSVKVSCKASGTDFKLTYIH WVRQAPGQGLEWMGRIFPGSGNTKYNEKFKGRVTI TADTSTSTAYMELSSLRSEDTAVYYCAGSYYSYDVL DYWGQGTTVTVSSGGGGSGGGGSGGGGSGGGGSDI QMTQSPSFLSASVGDRVTITCKASQNVDDRVAWYQ QKPGKAPKALIYSSSHRYKGVPSRFSGSGSGTEFTLT ISSLQPEDFATYFCQQFKSYPLTFGQGTKLEIK |
| SEQ ID NO: 150 | VL | DIQMTQSPSFLSASVGDRVTITCKASQNVDDRVAW YQQKPGKAPKALIYSSSHRYKGVPSRFSGSGSGTEFT LTISSLQPEDFATYFCQQFKSYPLTFGQGTKLEIK |
| SEQ ID NO: 151 | VH | QVQLVQSGAEVKKPGSSVKVSCKASGTDFKLTYIH WVRQAPGQGLEWMGRIFPGSGNTKYNEKFKGRVTI TADTSTSTAYMELSSLRSEDTAVYYCAGSYYSYDVL DYWGQGTTVTVSS |
| **A-H.27** | | |
| SEQ ID NO: 153 | VH + VL | QVQLVQSGAEVKKPGSSVKVSCKASGTDFKLTYIH WVRQAPGQGLEWMGRVSAGSGNVKYNEKFKGRV TITADTSTSTAYMELSSLRSEDTAVYYCAGSYYSYD VLDYWGQGTTVTVSSGGGGSGGGGSGGGGSGGGG SDIQMTQSPSFLSASVGDRVTITCKASQNVGNRVAW YQQKPGKAPKALIYSSSHRYKGVPSRFSGSGSGTEFT LTISSLQPEDFATYFCQQFKSYPLTFGQGTKLEIK |
| SEQ ID NO: 154 | VL | DIQMTQSPSFLSASVGDRVTITCKASQNVGNRVAW YQQKPGKAPKALIYSSSHRYKGVPSRFSGSGSGTEFT LTISSLQPEDFATYFCQQFKSYPLTFGQGTKLEIK |
| SEQ ID NO: 155 | VH | QVQLVQSGAEVKKPGSSVKVSCKASGTDFKLTYIH WVRQAPGQGLEWMGRVSAGSGNVKYNEKFKGRV TITADTSTSTAYMELSSLRSEDTAVYYCAGSYYSYD VLDYWGQGTTVTVSS |
| **A-H.28** | | |
| SEQ ID NO: 156 | VH + VL | QVQLVQSGAEVKKPGSSVKVSCKASGTDFKLTYIH WVRQAPGQGLEWMGRISPGSGNTKYNEKFKGRVTI TADTSTSTAYMELSSLRSEDTAVYYCAGSYYSYDVL DYWGQGTTVTVSSGGGGSGGGGSGGGGSGGGGSDI QMTQSPSFLSASVGDRVTITCKASQNVGDRVAWYQ QKPGKAPKALIYSSSHRYKGVPSRFSGSGSGTEFTLT ISSLQPEDFATYFCQQFKSYPLTFGQGTKLEIK |
| SEQ ID NO: 157 | VL | DIQMTQSPSFLSASVGDRVTITCKASQNVGDRVAW YQQKPGKAPKALIYSSSHRYKGVPSRFSGSGSGTEFT LTISSLQPEDFATYFCQQFKSYPLTFGQGTKLEIK |
| SEQ ID NO: 158 | VH | QVQLVQSGAEVKKPGSSVKVSCKASGTDFKLTYIH WVRQAPGQGLEWMGRISPGSGNTKYNEKFKGRVTI TADTSTSTAYMELSSLRSEDTAVYYCAGSYYSYDVL DYWGQGTTVTVSS |
| **A-H.29** | | |
| SEQ ID NO: 159 | VH + VL | QVQLVQSGAEVKKPGSSVKVSCKASGHDFHLWYIH WVRQAPGQGLEWMGRISPGSGNVKYNEKFKGRVTI TADTSTSTAYMELSSLRSEDTAVYYCAGSYYSYDVL DYWGQGTTVTVSSGGGGSGGGGSGGGGSGGGGSDI QMTQSPSFLSASVGDRVTITCKASQNVGDRVAWHQ QKPGKAPKALIYSSSHRYKGVPSRFSGSGSGTEFTLT ISSLQPEDFATYFCQQFKSYPLTFGQGTKLEIK |
| SEQ ID NO: 160 | VL | DIQMTQSPSFLSASVGDRVTITCKASQNVGDRVAW HQQKPGKAPKALIYSSSHRYKGVPSRFSGSGSGTEFT LTISSLQPEDFATYFCQQFKSYPLTFGQGTKLEIK |

TABLE 1-continued

Amino acid and nucleotide sequences for murine, chimeric and humanized antibody molecules which bind to TCRVB 6, e.g., TCRVB 6-5. The antibody molecules include murine mAb Antibody A, and humanized mAb Antibody A-H Clones A-H.1 to A-H.85. The amino acid the heavy and light chain CDRs, and the amino acid and nucleotide sequences of the heavy and light chain variable regions, and the heavy and light chains are shown.

| | | |
|---|---|---|
| SEQ ID NO: 161 | VH | QVQLVQSGAEVKKPGSSVKVSCKASGHDFHLWYIH WVRQAPGQGLEWMGRISPGSGNVKYNEKFKGRVTI TADTSTSTAYMELSSLRSEDTAVYYCAGSYYSYDVL DYWGQGTTVTVSS |
| | A-H.31 | |
| SEQ ID NO: 162 | VH + VL | QVQLVQSGAEVKKPGSSVKVSCKASGHDFKLTYIH WVRQAPGQGLEWMGRISAGSGNVKYNEKFKGRVT ITADTSTSTAYMELSSLRSEDTAVYYCAGSYYSYDV LDYWGQGTTVTVSSGGGGSGGGGSGGGGSGGGGS DIQMTQSPSFLSASVGDRVTITCKASQNVDDRVAW YQQKPGKAPKALIYSSSHRYKGVPSRFSGSGSGTEFT LTISSLQPEDFATYFCQQFKSYPLTFGQGTKLEIK |
| SEQ ID NO: 163 | VL | DIQMTQSPSFLSASVGDRVTITCKASQNVDDRVAW YQQKPGKAPKALIYSSSHRYKGVPSRFSGSGSGTEFT LTISSLQPEDFATYFCQQFKSYPLTFGQGTKLEIK |
| SEQ ID NO: 164 | VH | QVQLVQSGAEVKKPGSSVKVSCKASGHDFKLTYIH WVRQAPGQGLEWMGRISAGSGNVKYNEKFKGRVT ITADTSTSTAYMELSSLRSEDTAVYYCAGSYYSYDV LDYWGQGTTVTVSS |
| | A-H.31 | |
| SEQ ID NO: 165 | VH + VL | QVQLVQSGAEVKKPGSSVKVSCKASGTDFHLWYIH WVRQAPGQGLEWMGRVFAGSGSYRYNEKFKGRVT ITADTSTSTAYMELSSLRSEDTAVYYCAGSYYSYDV LDYWGQGTTVTVSSGGGGSGGGGSGGGGSGGGGS DIQMTQSPSFLSASVGDRVTITCKASQNVDDRVAW YQQKPGKAPKALIYSSSHRYKGVPSRFSGSGSGTEFT LTISSLQPEDFATYFCQQFKSYPLTFGQGTKLEIK |
| SEQ ID NO: 166 | VL | DIQMTQSPSFLSASVGDRVTITCKASQNVDDRVAW YQQKPGKAPKALIYSSSHRYKGVPSRFSGSGSGTEFT LTISSLQPEDFATYFCQQFKSYPLTFGQGTKLEIK |
| SEQ ID NO: 167 | VH | QVQLVQSGAEVKKPGSSVKVSCKASGTDFHLWYIH WVRQAPGQGLEWMGRVFAGSGSYRYNEKFKGRVT ITADTSTSTAYMELSSLRSEDTAVYYCAGSYYSYDV LDYWGQGTTVTVSS |
| | A-H.32 | |
| SEQ ID NO: 168 | VH + VL | QVQLVQSGAEVKKPGSSVKVSCKASGTDFDKIYIH WVRQAPGQGLEWMGRISAGSGNTKYNEKFKGRVTI TADTSTSTAYMELSSLRSEDTAVYYCAGSYYSYDVL DYWGQGTTVTVSSGGGGSGGGGSGGGGSGGGGSDI QMTQSPSFLSASVGDRVTITCKASQNVADRVAWYQ QKPGKAPKALIYSSSHRYKGVPSRFSGSGSGTEFTLT ISSLQPEDFATYFCQQFKSYPLTFGQGTKLEIK |
| SEQ ID NO: 169 | VL | DIQMTQSPSFLSASVGDRVTITCKASQNVADRVAW YQQKPGKAPKALIYSSSHRYKGVPSRFSGSGSGTEFT LTISSLQPEDFATYFCQQFKSYPLTFGQGTKLEIK |
| SEQ ID NO: 170 | VH | QVQLVQSGAEVKKPGSSVKVSCKASGTDFDKIYIH WVRQAPGQGLEWMGRISAGSGNTKYNEKFKGRVTI TADTSTSTAYMELSSLRSEDTAVYYCAGSYYSYDVL DYWGQGTTVTVSS |
| | A-H.33 | |
| SEQ ID NO: 171 | VH + VL | QVQLVQSGAEVKKPGSSVKVSCKASGTDFKLTYIH WVRQAPGQGLEWMGRISAGSGNTKYNEKFKGRVTI TADTSTSTAYMELSSLRSEDTAVYYCAGSYYSYDVL DYWGQGTTVTVSSGGGGSGGGGSGGGGSGGGGSDI QMTQSPSFLSASVGDRVTITCKASQNVEDRVAWYQ QKPGKAPKALIYSSSHRYKGVPSRFSGSGSGTEFTLT ISSLQPEDFATYFCQQFKSYPLTFGQGTKLEIK |

TABLE 1-continued

Amino acid and nucleotide sequences for murine, chimeric and humanized antibody molecules which bind to TCRVB 6, e.g., TCRVB 6-5. The antibody molecules include murine mAb Antibody A, and humanized mAb Antibody A-H Clones A-H.1 to A-H.85. The amino acid the heavy and light chain CDRs, and the amino acid and nucleotide sequences of the heavy and light chain variable regions, and the heavy and light chains are shown.

| | | |
|---|---|---|
| SEQ ID NO: 172 | VL | DIQMTQSPSFLSASVGDRVTITCKASQNVEDRVAWY QQKPGKAPKALIYSSSHRYKGVPSRFSGSGSGTEFTL TISSLQPEDFATYFCQQFKSYPLTFGQGTKLEIK |
| SEQ ID NO: 173 | VH | QVQLVQSGAEVKKPGSSVKVSCKASGTDFKLTYIH WVRQAPGQGLEWMGRISAGSGNTKYNEKFKGRVTI TADTSTSTAYMELSSLRSEDTAVYYCAGSYYSYDVL DYWGQGTTVTVSS |
| | A-H.34 | |
| SEQ ID NO: 174 | VH + VL | QVQLVQSGAEVKKPGSSVKVSCKASGTDFRLTYIH WVRQAPGQGLEWMGRISPGSGNTKYNEKFKGRVTI TADTSTSTAYMELSSLRSEDTAVYYCAGSYYSYDVL DYWGQGTTVTVSSGGGGSGGGGSGGGGSGGGGSDI QMTQSPSFLSASVGDRVTITCKASQNVGNRVAWYQ QKPGKAPKALIYSSSHRYKGVPSRFSGSGSGTEFTLT ISSLQPEDFATYFCQQFKSYPLTFGQGTKLEIK |
| SEQ ID NO: 175 | VL | DIQMTQSPSFLSASVGDRVTITCKASQNVGNRVAW YQQKPGKAPKALIYSSSHRYKGVPSRFSGSGSGTEFT LTISSLQPEDFATYFCQQFKSYPLTFGQGTKLEIK |
| SEQ ID NO: 176 | VH | QVQLVQSGAEVKKPGSSVKVSCKASGTDFRLTYIH WVRQAPGQGLEWMGRISPGSGNTKYNEKFKGRVTI TADTSTSTAYMELSSLRSEDTAVYYCAGSYYSYDVL DYWGQGTTVTVSS |
| | A-H.35 | |
| SEQ ID NO: 177 | VH + VL | QVQLVQSGAEVKKPGSSVKVSCKASGHDFDKTYIH WVRQAPGQGLEWMGRVSAGSGNVKYNEKFKGRV TITADTSTSTAYMELSSLRSEDTAVYYCAGSYYSYD VLDYWGQGTTVTVSSGGGGSGGGGSGGGGSGGGG SDIQMTQSPSFLSASVGDRVTITCKASQNVEDRVAW YQQKPGKAPKALIYSSSHRYKGVPSRFSGSGSGTEFT LTISSLQPEDFATYFCQQFKSYPLTFGQGTKLEIK |
| SEQ ID NO: 178 | VL | DIQMTQSPSFLSASVGDRVTITCKASQNVEDRVAWY QQKPGKAPKALIYSSSHRYKGVPSRFSGSGSGTEFTL TISSLQPEDFATYFCQQFKSYPLTFGQGTKLEIK |
| SEQ ID NO: 179 | VH | QVQLVQSGAEVKKPGSSVKVSCKASGHDFDKTYIH WVRQAPGQGLEWMGRVSAGSGNVKYNEKFKGRV TITADTSTSTAYMELSSLRSEDTAVYYCAGSYYSYD VLDYWGQGTTVTVSS |
| | A-H.36 | |
| SEQ ID NO: 180 | VH + VL | QVQLVQSGAEVKKPGSSVKVSCKASGHDFKLTYIH WVRQAPGQGLEWMGRVSPGSGNTKYNEKFKGRVT ITADTSTSTAYMELSSLRSEDTAVYYCAGSYYSYDV LDYWGQGTTVTVSSGGGGSGGGGSGGGGSGGGGS DIQMTQSPSFLSASVGDRVTITCKASQNVEDRVAWH QQKPGKAPKALIYSSSHRYKGVPSRFSGSGSGTEFTL TISSLQPEDFATYFCQQFKSYPLTFGQGTKLEIK |
| SEQ ID NO: 181 | VL | DIQMTQSPSFLSASVGDRVTITCKASQNVEDRVAWH QQKPGKAPKALIYSSSHRYKGVPSRFSGSGSGTEFTL TISSLQPEDFATYFCQQFKSYPLTFGQGTKLEIK |
| SEQ ID NO: 182 | VH | QVQLVQSGAEVKKPGSSVKVSCKASGHDFKLTYIH WVRQAPGQGLEWMGRVSPGSGNTKYNEKFKGRVT ITADTSTSTAYMELSSLRSEDTAVYYCAGSYYSYDV LDYWGQGTTVTVSS |
| | A-H.37 | |
| SEQ ID NO: 183 | VH + VL | QVQLVQSGAEVKKPGSSVKVSCKASGHDFDKTYIH WVRQAPGQGLEWMGRIYPGSGNVKYNEKFKGRVT ITADTSTSTAYMELSSLRSEDTAVYYCAGSYYSYDV LDYWGQGTTVTVSSGGGGSGGGGSGGGGSGGGGS |

TABLE 1-continued

| Amino acid and nucleotide sequences for murine, chimeric and humanized antibody molecules which bind to TCRVB 6, e.g., TCRVB 6-5. The antibody molecules include murine mAb Antibody A, and humanized mAb Antibody A-H Clones A-H.1 to A-H.85. The amino acid the heavy and light chain CDRs, and the amino acid and nucleotide sequences of the heavy and light chain variable regions, and the heavy and light chains are shown. | | |
|---|---|---|
| | | DIQMTQSPSFLSASVGDRVTITCKASQNVADRVAW YQQKPGKAPKALIYSSSHRYKGVPSRFSGSGSGTEFT LTISSLQPEDFATYFCQQFKSYPLTFGQGTKLEIK |
| SEQ ID NO: 184 | VL | DIQMTQSPSFLSASVGDRVTITCKASQNVADRVAW YQQKPGKAPKALIYSSSHRYKGVPSRFSGSGSGTEFT LTISSLQPEDFATYFCQQFKSYPLTFGQGTKLEIK |
| SEQ ID NO: 185 | VH | QVQLVQSGAEVKKPGSSVKVSCKASGHDFDKTYIH WVRQAPGQGLEWMGRIYPGSGNVKYNEKFKGRVT ITADTSTSTAYMELSSLRSEDTAVYYCAGSYYSYDV LDYWGQGTTVTVSS |
| A-H.38 | | |
| SEQ ID NO: 186 | VH + VL | QVQLVQSGAEVKKPGSSVKVSCKASGTDFDKTYIH WVRQAPGQGLEWMGRISAGSGNVKYNEKFKGRVT ITADTSTSTAYMELSSLRSEDTAVYYCAGSYYSYDV LDYWGQGTTVTVSSGGGGSGGGGSGGGGSGGGGS DIQMTQSPSFLSASVGDRVTITCKASQNVDDRVAW YQQKPGKAPKALIYSSSHRYKGVPSRFSGSGSGTEFT LTISSLQPEDFATYFCQQFKSYPLTFGQGTKLEIK |
| SEQ ID NO: 187 | VL | DIQMTQSPSFLSASVGDRVTITCKASQNVDDRVAW YQQKPGKAPKALIYSSSHRYKGVPSRFSGSGSGTEFT LTISSLQPEDFATYFCQQFKSYPLTFGQGTKLEIK |
| SEQ ID NO: 188 | VH | QVQLVQSGAEVKKPGSSVKVSCKASGTDFDKTYIH WVRQAPGQGLEWMGRISAGSGNVKYNEKFKGRVT ITADTSTSTAYMELSSLRSEDTAVYYCAGSYYSYDV LDYWGQGTTVTVSS |
| A-H.39 | | |
| SEQ ID NO: 189 | VH + VL | QVQLVQSGAEVKKPGSSVKVSCKASGTDFDKIYIH WVRQAPGQGLEWMGRISAGSGNIKYNEKFKGRVTI TADTSTSTAYMELSSLRSEDTAVYYCAGSYYSYDVL DYWGQGTTVTVSSGGGGSGGGGSGGGGSGGGGSDI QMTQSPSFLSASVGDRVTITCKASQNVDDRVAWYQ QKPGKAPKALIYSSSHRYKGVPSRFSGSGSGTEFTLT ISSLQPEDFATYFCQQFKSYPLTFGQGTKLEIK |
| SEQ ID NO: 190 | VL | DIQMTQSPSFLSASVGDRVTITCKASQNVDDRVAW YQQKPGKAPKALIYSSSHRYKGVPSRFSGSGSGTEFT LTISSLQPEDFATYFCQQFKSYPLTFGQGTKLEIK |
| SEQ ID NO: 191 | VH | QVQLVQSGAEVKKPGSSVKVSCKASGTDFDKIYIH WVRQAPGQGLEWMGRISAGSGNIKYNEKFKGRVTI TADTSTSTAYMELSSLRSEDTAVYYCAGSYYSYDVL DYWGQGTTVTVSS |
| A-H.40 | | |
| SEQ ID NO: 192 | VH + VL | QVQLVQSGAEVKKPGSSVKVSCKASGTDFDKIYIH WVRQAPGQGLEWMGRISAGSGNVKYNEKFKGRVT ITADTSTSTAYMELSSLRSEDTAVYYCAGSYYSYDV LDYWGQGTTVTVSSGGGGSGGGGSGGGGSGGGGS DIQMTQSPSFLSASVGDRVTITCKASQNVGDRVAW YQQKPGKAPKALIYSSSHRYKGVPSRFSGSGSGTEFT LTISSLQPEDFATYFCQQFKSYPLTFGQGTKLEIK |
| SEQ ID NO: 193 | VL | DIQMTQSPSFLSASVGDRVTITCKASQNVGDRVAW YQQKPGKAPKALIYSSSHRYKGVPSRFSGSGSGTEFT LTISSLQPEDFATYFCQQFKSYPLTFGQGTKLEIK |
| SEQ ID NO: 194 | VH | QVQLVQSGAEVKKPGSSVKVSCKASGTDFDKIYIH WVRQAPGQGLEWMGRISAGSGNVKYNEKFKGRVT ITADTSTSTAYMELSSLRSEDTAVYYCAGSYYSYDV LDYWGQGTTVTVSS |

TABLE 1-continued

Amino acid and nucleotide sequences for murine, chimeric and humanized antibody molecules which bind to TCRVB 6, e.g., TCRVB 6-5. The antibody molecules include murine mAb Antibody A, and humanized mAb Antibody A-H Clones A-H.1 to A-H.85. The amino acid the heavy and light chain CDRs, and the amino acid and nucleotide sequences of the heavy and light chain variable regions, and the heavy and light chains are shown.

| | | |
|---|---|---|
| | A-H.41 | |
| SEQ ID NO: 195 | VH + VL | QVQLVQSGAEVKKPGSSVKVSCKASGGTFKLTYIH WVRQAPGQGLEWMGRVSAGSGNVKYNEKFKGRV TITADTSTSTAYMELSSLRSEDTAVYYCAGSYYSYD VLDYWGQGTTVTVSSGGGGSGGGGSGGGGSGGGG SDIQMTQSPSFLSASVGDRVTITCKASQNVDDRVAW YQQKPGKAPKALIYSSSHRYKGVPSRFSGSGSGTEFT LTISSLQPEDFATYFCQQFKSYPLTFGQGTKLEIK |
| SEQ ID NO: 196 | VL | DIQMTQSPSFLSASVGDRVTITCKASQNVDDRVAW YQQKPGKAPKALIYSSSHRYKGVPSRFSGSGSGTEFT LTISSLQPEDFATYFCQQFKSYPLTFGQGTKLEIK |
| SEQ ID NO: 197 | VH | QVQLVQSGAEVKKPGSSVKVSCKASGGTFKLTYIH WVRQAPGQGLEWMGRVSAGSGNVKYNEKFKGRV TITADTSTSTAYMELSSLRSEDTAVYYCAGSYYSYD VLDYWGQGTTVTVSS |
| | A-H.42 | |
| SEQ ID NO: 198 | VH + VL | QVQLVQSGAEVKKPGSSVKVSCKASGTDFKLTYIH WVRQAPGQGLEWMGRISPGSGNVKYNEKFKGRVTI TADTSTSTAYMELSSLRSEDTAVYYCAGSYYSYDVL DYWGQGTTVTVSSGGGGSGGGGSGGGGSGGGGSDI QMTQSPSFLSASVGDRVTITCKASQNVDNRVAWHQ QKPGKAPKALIYSSSHRYKGVPSRFSGSGSGTEFTLT ISSLQPEDFATYFCQQFKSYPLTFGQGTKLEIK |
| SEQ ID NO: 199 | VL | DIQMTQSPSFLSASVGDRVTITCKASQNVDNRVAW HQQKPGKAPKALIYSSSHRYKGVPSRFSGSGSGTEFT LTISSLQPEDFATYFCQQFKSYPLTFGQGTKLEIK |
| SEQ ID NO: 200 | VH | QVQLVQSGAEVKKPGSSVKVSCKASGTDFKLTYIH WVRQAPGQGLEWMGRISPGSGNVKYNEKFKGRVTI TADTSTSTAYMELSSLRSEDTAVYYCAGSYYSYDVL DYWGQGTTVTVSS |
| | A-H.43 | |
| SEQ ID NO: 201 | VH + VL | QVQLVQSGAEVKKPGSSVKVSCKASGHDFDKFYIH WVRQAPGQGLEWMGRVSAGSGNTKYNEKFKGRVT ITADTSTSTAYMELSSLRSEDTAVYYCAGSYYSYDV LDYWGQGTTVTVSSGGGGSGGGGSGGGGSGGGGS DIQMTQSPSFLSASVGDRVTITCKASQNVDNRVAW YQQKPGKAPKALIYSSSHRYKGVPSRFSGSGSGTEFT LTISSLQPEDFATYFCQQFKSYPLTFGQGTKLEIK |
| SEQ ID NO: 202 | VL | DIQMTQSPSFLSASVGDRVTITCKASQNVDNRVAW YQQKPGKAPKALIYSSSHRYKGVPSRFSGSGSGTEFT LTISSLQPEDFATYFCQQFKSYPLTFGQGTKLEIK |
| SEQ ID NO: 203 | VH | QVQLVQSGAEVKKPGSSVKVSCKASGHDFDKFYIH WVRQAPGQGLEWMGRVSAGSGNTKYNEKFKGRVT ITADTSTSTAYMELSSLRSEDTAVYYCAGSYYSYDV LDYWGQGTTVTVSS |
| | A-H.44 | |
| SEQ ID NO: 204 | VH + VL | QVQLVQSGAEVKKPGSSVKVSCKASGTDFDKFYIH WVRQAPGQGLEWMGRVSAGSGNVKYNEKFKGRV TITADTSTSTAYMELSSLRSEDTAVYYCAGSYYSYD VLDYWGQGTTVTVSSGGGGSGGGGSGGGGSGGGG SDIQMTQSPSFLSASVGDRVTITCKASQNVGDRVVW YQQKPGKAPKALIYSSSHRYKGVPSRFSGSGSGTEFT LTISSLQPEDFATYFCQQFKSYPLTFGQGTKLEIK |
| SEQ ID NO: 205 | VH | QVQLVQSGAEVKKPGSSVKVSCKASGTDFDKFYIH WVRQAPGQGLEWMGRVSAGSGNVKYNEKFKGRV TITADTSTSTAYMELSSLRSEDTAVYYCAGSYYSYD VLDYWGQGTTVTVSS |

TABLE 1-continued

Amino acid and nucleotide sequences for murine, chimeric and humanized antibody molecules which bind to TCRVB 6, e.g., TCRVB 6-5. The antibody molecules include murine mAb Antibody A, and humanized mAb Antibody A-H Clones A-H.1 to A-H.85. The amino acid the heavy and light chain CDRs, and the amino acid and nucleotide sequences of the heavy and light chain variable regions, and the heavy and light chains are shown.

| | | |
|---|---|---|
| | A-H.45 | |
| SEQ ID NO: 206 | VH + VL | QVQLVQSGAEVKKPGSSVKVSCKASGYSFTTYYIH<br>WVRQAPGQGLEWMGWFSAGSGNTKYNEKFKGRV<br>TITADTSTSTAYMELSSLRSEDTAVYYCAVSYYSYD<br>VLDYWGQGTTVTVSSGGGGSGGGGSGGGGSGGGG<br>SDIQMTQSPSFLSASVGDRVTITCKASQNVGINVVW<br>HQQKPGKAPKALIYSSSHRYSGVPSRFSGSGSGTEFT<br>LTISSLQPEDFATYFCQQFKSYPLTFGQGTKLEIK |
| SEQ ID NO: 207 | VH | QVQLVQSGAEVKKPGSSVKVSCKASGYSFTTYYIH<br>WVRQAPGQGLEWMGWFSAGSGNTKYNEKFKGRV<br>TITADTSTSTAYMELSSLRSEDTAVYYCAVSYYSYD<br>VLDYWGQGTTVTVSS |
| | A-H.46 | |
| SEQ ID NO: 208 | VH + VL | QVQLVQSGAEVKKPGSSVKVSCKASGYSFTTYYIH<br>WVRQAPGQGLEWMGWFSAGSGNTKYNEKFKGRV<br>TITADTSTSTAYMELSSLRSEDTAVYYCAGSYYSYD<br>VLDYWGQGTTVTVSSGGGGSGGGGSGGGGSGGGG<br>SDIQMTQSPSFLSASVGDRVTITCKASQNVGINVVW<br>HQQKPGKAPKALIYSSSHRYSGVPSRFSGSGSGTEFT<br>LTISSLQPEDFATYFCQQFKSYPLTFGQGTKLEIK |
| SEQ ID NO: 209 | VH | QVQLVQSGAEVKKPGSSVKVSCKASGYSFTTYYH<br>WVRQAPGQGLEWMGWFSAGSGNTKYNEKFKGRV<br>TITADTSTSTAYMELSSLRSEDTAVYYCAGSYYSYD<br>VLDYWGQGTTVTVSS |
| | A-H.47 | |
| SEQ ID NO: 210 | VH + VL | QVQLVQSGAEVKKPGSSVKVSCKASGYSFTTYYIH<br>WVRQAPGQGLEWMGWFFPGSGNTKYNEKFKGRVT<br>ITADTSTSTAYMELSSLRSEDTAVYYCAGSYYSYDV<br>LDYWGQGTTVTVSSGGGGSGGGGSGGGGSGGGGS<br>DIQMTQSPSFLSASVGDRVTITCKASQNVGINVVWH<br>QQKPGKAPKALIYSSSHRYSGVPSRFSGSGSGTEFTL<br>TISSLQPEDFATYFCQQFKSYPLTFGQGTKLEIK |
| SEQ ID NO: 211 | VH | QVQLVQSGAEVKKPGSSVKVSCKASGYSFTTYYIH<br>WVRQAPGQGLEWMGWFFPGSGNTKYNEKFKGRVT<br>ITADTSTSTAYMELSSLRSEDTAVYYCAGSYYSYDV<br>LDYWGQGTTVTVSS |
| | A-H.48 | |
| SEQ ID NO: 212 | VH + VL | QVQLVQSGAEVKKPGSSVKVSCKASGYSFTTYYIH<br>WVRQAPGQGLEWMGWFSPGSGNTKYNEKFKGRVT<br>ITADTSTSTAYMELSSLRSEDTAVYYCAVSYYSYDV<br>LDYWGQGTTVTVSSGGGGSGGGGSGGGGSGGGGS<br>DIQMTQSPSFLSASVGDRVTITCKASQNVGINVVWH<br>QQKPGKAPKALIYSSSHRYSGVPSRFSGSGSGTEFTL<br>TISSLQPEDFATYFCQQFKSYPLTFGQGTKLEIK |
| SEQ ID NO: 213 | VH | QVQLVQSGAEVKKPGSSVKVSCKASGYSFTTYYIH<br>WVRQAPGQGLEWMGWFSPGSGNTKYNEKFKGRVT<br>ITADTSTSTAYMELSSLRSEDTAVYYCAVSYYSYDV<br>LDYWGQGTTVTVSS |
| | A-H.49 | |
| SEQ ID NO: 214 | VH + VL | QVQLVQSGAEVKKPGSSVKVSCKASGYSFTTYYIH<br>WVRQAPGQGLEWMGWFSPGSGNTKYNEKFKGRVT<br>ITADTSTSTAYMELSSLRSEDTAVYYCAGSYYSYDV<br>LDYWGQGTTVTVSSGGGGSGGGGSGGGGSGGGGS<br>DIQMTQSPSFLSASVGDRVTITCKASQNVGINVVWH<br>QQKPGKAPKALIYSSSHRYSGVPSRFSGSGSGTEFTL<br>TISSLQPEDFATYFCQQFKSYPLTFGQGTKLEIK |

TABLE 1-continued

Amino acid and nucleotide sequences for murine, chimeric and humanized antibody molecules which bind to TCRVB 6, e.g., TCRVB 6-5. The antibody molecules include murine mAb Antibody A, and humanized mAb Antibody A-H Clones A-H.1 to A-H.85. The amino acid the heavy and light chain CDRs, and the amino acid and nucleotide sequences of the heavy and light chain variable regions, and the heavy and light chains are shown.

| | | |
|---|---|---|
| SEQ ID NO: 215 | VH | QVQLVQSGAEVKKPGSSVKVSCKASGYSFTTYYIH<br>WVRQAPGQGLEWMGWFSPGSGNTKYNEKFKGRVT<br>ITADTSTSTAYMELSSLRSEDTAVYYCAGSYYSYDV<br>LDYWGQGTTVTVSS |
| | A-H.50 | |
| SEQ ID NO: 216 | VH + VL | QVQLVQSGAEVKKPGSSVKVSCKASGYSFTTYYIH<br>WVRQAPGQGLEWMGRIFPGSGNIKYNEKFKGRVTI<br>TADTSTSTAYMELSSLRSEDTAVYYCAGSYYSYDVL<br>DYWGQGTTVTVSSGGGGSGGGGSGGGGSGGGGSDI<br>QMTQSPSFLSASVGDRVTITCKASQNVGINVVWHQ<br>QKPGKAPKALIYSSSHRYSGVPSRFSGSGSGTEFTLTI<br>SSLQPEDFATYFCQQFKSYPLTFGQGTKLEIK |
| SEQ ID NO: 217 | VH | QVQLVQSGAEVKKPGSSVKVSCKASGYSFTTYYIH<br>WVRQAPGQGLEWMGRIFPGSGNIKYNEKFKGRVTI<br>TADTSTSTAYMELSSLRSEDTAVYYCAGSYYSYDVL<br>DYWGQGTTVTVSS |
| | A-H.51 | |
| SEQ ID NO: 218 | VH + VL | QVQLVQSGAEVKKPGSSVKVSCKASGYSFTTYYIH<br>WVRQAPGQGLEWMGWFFPGSGNIKYNEKFKGRVTI<br>TADTSTSTAYMELSSLRSEDTAVYYCAGSIYSAGVL<br>DYWGQGTTVTVSSGGGGSGGGGSGGGGSGGGGSDI<br>QMTQSPSFLSASVGDRVTITCKASQNVGINVVWHQ<br>QKPGKAPKALIYSSSHRYSGVPSRFSGSGSGTEFTLTI<br>SSLQPEDFATYFCQQFKSYPLTFGQGTKLEIK |
| SEQ ID NO: 219 | VH | QVQLVQSGAEVKKPGSSVKVSCKASGYSFTTYYIH<br>WVRQAPGQGLEWMGWFFPGSGNIKYNEKFKGRVTI<br>TADTSTSTAYMELSSLRSEDTAVYYCAGSIYSAGVL<br>DYWGQGTTVTVSS |
| | A-H.52 | |
| SEQ ID NO: 220 | VH + VL | QVQLVQSGAEVKKPGSSVKVSCKASGYSFTTYYIH<br>WVRQAPGQGLEWMGWFFPGSGNIKYNEKFKGRVTI<br>TADTSTSTAYMELSSLRSEDTAVYYCAGSYYSYDVL<br>DYWGQGTTVTVSSGGGGSGGGGSGGGGSGGGGSDI<br>QMTQSPSFLSASVGDRVTITCKASQNVGINVVWHQ<br>QKPGKAPKALIYSSSHRYSGVPSRFSGSGSGTEFTLTI<br>SSLQPEDFATYFCQQFKSYPLTFGQGTKLEIK |
| SEQ ID NO: 221 | VH | QVQLVQSGAEVKKPGSSVKVSCKASGYSFTLGYIH<br>WVRQAPGQGLEWMGWFFPGSGNIKYNEKFKGRVTI<br>TADTSTSTAYMELSSLRSEDTAVYYCAGSYYSYDVL<br>DYWGQGTTVTVSS |
| | A-H.53 | |
| SEQ ID NO: 222 | VH + VL | QVQLVQSGAEVKKPGSSVKVSCKASGYSFTTYYIH<br>WVRQAPGQGLEWMGWFFPGSGNIKYNEKFKGRVTI<br>TADTSTSTAYMELSSLRSEDTAVYYCAGSYYSYDVL<br>DYWGQGTTVTVSSGGGGSGGGGSGGGGSGGGGSDI<br>QMTQSPSFLSASVGDRVTITCKASQNVGINVVWHQ<br>QKPGKAPKALIYSSSHRYSGVPSRFSGSGSGTEFTLTI<br>SSLQPEDFATYFCQQFKSYPLTFGQGTKLEIK |
| SEQ ID NO: 223 | VH | QVQLVQSGAEVKKPGSSVKVSCKASGYSFRLTYIH<br>WVRQAPGQGLEWMGWFFPGSGNIKYNEKFKGRVTI<br>TADTSTSTAYMELSSLRSEDTAVYYCAGSYYSYDVL<br>DYWGQGTTVTVSS |
| | A-H.54 | |
| SEQ ID NO: 224 | VH + VL | QVQLVQSGAEVKKPGSSVKVSCKASGYSFTTYYIH<br>WVRQAPGQGLEWMGWFFPGSGNIKYNEKFKGRVTI<br>TADTSTSTAYMELSSLRSEDTAVYYCAGSYYSYDVL<br>DYWGQGTTVTVSSGGGGSGGGGSGGGGSGGGGSDI |

TABLE 1-continued

Amino acid and nucleotide sequences for murine, chimeric and humanized antibody molecules which bind to TCRVB 6, e.g., TCRVB 6-5. The antibody molecules include murine mAb Antibody A, and humanized mAb Antibody A-H Clones A-H.1 to A-H.85. The amino acid the heavy and light chain CDRs, and the amino acid and nucleotide sequences of the heavy and light chain variable regions, and the heavy and light chains are shown.

| | | |
|---|---|---|
| | | QMTQSPSFLSASVGDRVTITCKASQNVGINVVWHQ<br>QKPGKAPKALIYSSSHRYSGVPSRFSGSGSGTEFTLTI<br>SSLQPEDFATYFCQQFKSYPLTFGQGTKLEIK |
| SEQ ID NO: 225 | VH | QVQLVQSGAEVKKPGSSVKVSCKASGYSFTTYYIH<br>WVRQAPGQGLEWMGWFFPGSGNIKYNEKFKGRVTI<br>TADTSTSTAYMELSSLRSEDTAVYYCAGSYYSYDVL<br>DYWGQGTTVTVSS |
| | A-H.55 antibody | |
| SEQ ID NO: 3 | HC CDR1 (Combined) | GYSFTTYYIH |
| SEQ ID NO: 4 | HC CDR2 (Combined) | WFFPGSGNIKYNEKFKG |
| SEQ ID NO: 5 | HC CDR3 (Combined) | SYYSYDVLDY |
| SEQ ID NO: 45 | HC CDR1 (Kabat) | TYYIH |
| SEQ ID NO: 46 | HC CDR2 (Kabat) | WFFPGSGNIKYNEKFKG |
| SEQ ID NO: 47 | HC CDR3 (Kabat) | SYYSYDVLDY |
| SEQ ID NO: 48 | HC CDR1 (Chothia) | GYSFTTY |
| SEQ ID NO: 49 | HC CDR2 (Chothia) | FPGSGN |
| SEQ ID NO: 50 | HC CDR3 (Chothia) | SYYSYDVLDY |
| SEQ ID NO: 1100 | VH | QVQLVQSGAEVKKPGSSVKVSCKASGYSFTTYYIH<br>WVRQAPGQGLEWMGWFFPGSGNIKYNEKFKGRVTI<br>TADTSTSTAYMELSSLRSEDTAVYYCAGSYYSYDVL<br>DYWGQGTTVTVSS |
| SEQ ID NO: 6 | LC CDR1 (Combined) | KASQNVGINVV |
| SEQ ID NO: 7 | LC CDR2 (Combined) | SSSHRYS |
| SEQ ID NO: 8 | LC CDR3 (Combined) | QQFKSYPLT |
| SEQ ID NO: 51 | LC CDR1 (Kabat) | KASQNVGINVV |
| SEQ ID NO: 52 | LC CDR2 (Kabat) | SSSHRYS |
| SEQ ID NO: 53 | LC CDR3 (Kabat) | QQFKSYPLT |
| SEQ ID NO: 54 | LC CDR1 (Chothia) | KASQNVGINVV |
| SEQ ID NO: 55 | LC CDR2 (chothia) | SSSHRYS |
| SEQ ID NO: 56 | LC CDR3 (chothia) | QQFKSYPLT |
| SEQ ID NO: 1101 | VL | QSVLTQPPSVSEAPRQRVTISCKASQNVGINVVWHQ<br>QLPGKAPKALIYSSSHRYSGVSDRFSGSGSGTSFSLAI<br>SGLQSEDEADYFCQQFKSYPLTFGTGTKVTVL |
| | A-H.56 | |
| SEQ ID NO: 1309 | VH + VL (ScFv) | QVQLVQSGAEVKKPGSSVKVSCKASGHDFDKFYIH<br>WVRQAPGQGLEWMGRVSAGSGNVKYNEKFKGRV<br>TITADTSTSTAYMELSSLRSEDTAVYYCAGSYYSYD<br>VLDYWGQGTTVTVSSGGGGSGGGGSGGGGSGGGG<br>SDIQMTQSPSFLSASVGDRVTITCKASQNVGNRVAW<br>YQQKPGKAPKALIYSSSHRYKGVPSRFSGSGSGTEFT<br>LTISSLQPEDFATYFCQQFKSYPLTFGQGTKLEIK |
| | A-H.57 | |
| SEQ ID NO: 1326 | VH + VL (ScFv) | QVQLVQSGAEVKKPGSSVKVSCKASGHDFRLTYIH<br>WVRQAPGQGLEWMGRVSAGSGNTKYNEKFKGRVT<br>ITADTSTSTAYMELSSLRSEDTAVYYCAVSYYSYDV<br>LDYWGQGTTVTVSSGGGGSGGGGSGGGGSGGGGS |

TABLE 1-continued

Amino acid and nucleotide sequences for murine, chimeric and humanized antibody molecules which bind to TCRVB 6, e.g., TCRVB 6-5. The antibody molecules include murine mAb Antibody A, and humanized mAb Antibody A-H Clones A-H.1 to A-H.85. The amino acid the heavy and light chain CDRs, and the amino acid and nucleotide sequences of the heavy and light chain variable regions, and the heavy and light chains are shown.

| | | |
|---|---|---|
| | | DIQMTQSPSFLSASVGDRVTITCKASQNVGDRVVW<br>HQQKPGKAPKALIYSSSHRYKGVPSRFSGSGSGTEFT<br>LTISSLQPEDFATYFCQQFKSYPLTFGQGTKLEIK |
| | A-H.58 | |
| SEQ ID NO: 1327 | VH + VL (ScFv) | QVQLVQSGAEVKKPGSSVKVSCKASGHDFRLTYIH<br>WVRQAPGQGLEWMGRVSAGSGNVKYNEKFKGRV<br>TITADTSTSTAYMELSSLRSEDTAVYYCAVSYYSYD<br>VLDYWGQGTTVTVSSGGGGSGGGGSGGGGSGGGG<br>SDIQMTQSPSFLSASVGDRVTITCKASQNVGNRVVW<br>HQQKPGKAPKALIYSSSHRYKGVPSRFSGSGSGTEFT<br>LTISSLQPEDFATYFCQQFKSYPLTFGQGTKLEIK |
| | A-H.59 | |
| SEQ ID NO: 1328 | VH + VL (ScFv) | QVQLVQSGAEVKKPGSSVKVSCKASGHDFRLTYIH<br>WVRQAPGQGLEWMGRIYAGSGNVKYNEKFKGRVT<br>ITADTSTSTAYMELSSLRSEDTAVYYCAVSYYSYDV<br>LDYWGQGTTVTVSSGGGGSGGGGSGGGGSGGGGS<br>DIQMTQSPSFLSASVGDRVTITCKASQNVADRVVW<br>HQQKPGKAPKALIYSSSHRYKGVPSRFSGSGSGTEFT<br>LTISSLQPEDFATYFCQQFKSYPLTFGQGTKLEIK |
| | A-H.60 | |
| SEQ ID NO: 1329 | VH + VL (ScFv) | QVQLVQSGAEVKKPGSSVKVSCKASGHDFKLTYIH<br>WVRQAPGQGLEWMGRVSAGSGNTKYNEKFKGRVT<br>ITADTSTSTAYMELSSLRSEDTAVYYCAVSYYSYDV<br>LDYWGQGTTVTVSSGGGGSGGGGSGGGGSGGGGS<br>DIQMTQSPSFLSASVGDRVTITCKASQNVGDRVAW<br>HQQKPGKAPKALIYSSSHRYKGVPSRFSGSGSGTEFT<br>LTISSLQPEDFATYFCQQFKSYPLTFGQGTKLEIK |
| | A-H.61 | |
| SEQ ID NO: 1330 | VH + VL (ScFv) | QVQLVQSGAEVKKPGSSVKVSCKASGHDFKLTYIH<br>WVRQAPGQGLEWMGRVSAGSGNTKYNEKFKGRVT<br>ITADTSTSTAYMELSSLRSEDTAVYYCAVSYYSYDV<br>LDYWGQGTTVTVSSGGGGSGGGGSGGGGSGGGGS<br>DIQMTQSPSFLSASVGDRVTITCKASQNVDNRVAW<br>HQQKPGKAPKALIYSSSHRYKGVPSRFSGSGSGTEFT<br>LTISSLQPEDFATYFCQQFKSYPLTFGQGTKLEIK |
| | A-H.62 | |
| SEQ ID NO: 1331 | VH + VL (ScFv) | QVQLVQSGAEVKKPGSSVKVSCKASGHDFRLTYIH<br>WVRQAPGQGLEWMGRVSAGSGNVKYNEKFKGRV<br>TITADTSTSTAYMELSSLRSEDTAVYYCAVSYYSYD<br>VLDYWGQGTTVTVSSGGGGSGGGGSGGGGSGGGG<br>SDIQMTQSPSFLSASVGDRVTITCKASQNVADRVVW<br>HQQKPGKAPKALIYSSSHRYKGVPSRFSGSGSGTEFT<br>LTISSLQPEDFATYFCQQFKSYPLTFGQGTKLEIK |
| | A-H.63 | |
| SEQ ID NO: 1332 | VH + VL (ScFv) | QVQLVQSGAEVKKPGSSVKVSCKASGHDFRLTYIH<br>WVRQAPGQGLEWMGRVYAGSGNTKYNEKFKGRV<br>TITADTSTSTAYMELSSLRSEDTAVYYCAVSYYSYD<br>VLDYWGQGTTVTVSSGGGGSGGGGSGGGGSGGGG<br>SDIQMTQSPSFLSASVGDRVTITCKASQNVEDRVVW<br>HQQKPGKAPKALIYSSSHRYKGVPSRFSGSGSGTEFT<br>LTISSLQPEDFATYFCQQFKSYPLTFGQGTKLEIK |
| | A-H.64 | |
| SEQ ID NO: 1333 | VH + VL (ScFv) | QVQLVQSGAEVKKPGSSVKVSCKASGHDFKLTYIH<br>WVRQAPGQGLEWMGRVSAGSGNTKYNEKFKGRVT<br>ITADTSTSTAYMELSSLRSEDTAVYYCAVSYYSYDV<br>LDYWGQGTTVTVSSGGGGSGGGGSGGGGSGGGGS |

TABLE 1-continued

Amino acid and nucleotide sequences for murine, chimeric and humanized antibody molecules which bind to TCRVB 6, e.g., TCRVB 6-5. The antibody molecules include murine mAb Antibody A, and humanized mAb Antibody A-H Clones A-H.1 to A-H.85. The amino acid the heavy and light chain CDRs, and the amino acid and nucleotide sequences of the heavy and light chain variable regions, and the heavy and light chains are shown.

| | | |
|---|---|---|
| | | DIQMTQSPSFLSASVGDRVTITCKASQNVADRVVW HQQKPGKAPKALIYSSSHRYKGVPSRFSGSGSGTEFT LTISSLQPEDFATYFCQQFKSYPLTFGQGTKLEIK |
| | A-H.65 | |
| SEQ ID NO: 1334 | VH + VL (ScFv) | QVQLVQSGAEVKKPGSSVKVSCKASGHDFKLTYIH WVRQAPGQGLEWMGRISAGSGNTKYNEKFKGRVTI TADTSTSTAYMELSSLRSEDTAVYYCAVSYYSYDVL DYWGQGTTVTVSSGGGGSGGGGSGGGGSGGGGSDI QMTQSPSFLSASVGDRVTITCKASQNVGDRVVWHQ QKPGKAPKALIYSSSHRYKGVPSRFSGSGSGTEFTLT ISSLQPEDFATYFCQQFKSYPLTFGQGTKLEIK |
| | A-H.66 | |
| SEQ ID NO: 1335 | VH + VL (ScFv) | QVQLVQSGAEVKKPGSSVKVSCKASGHDFKLTYIH WVRQAPGQGLEWMGRIYAGSGNTKYNEKFKGRVT ITADTSTSTAYMELSSLRSEDTAVYYCAVSYYSYDV LDYWGQGTTVTVSSGGGGSGGGGSGGGGSGGGGS DIQMTQSPSFLSASVGDRVTITCKASQNVGDRVVW HQQKPGKAPKALIYSSSHRYKGVPSRFSGSGSGTEFT LTISSLQPEDFATYFCQQFKSYPLTFGQGTKLEIK |
| | A-H.67 | |
| SEQ ID NO: 1336 | VH + VL (ScFv) | QVQLVQSGAEVKKPGSSVKVSCKASGTDFKLTYIH WVRQAPGQGLEWMGRIFPGSGNVKYNEKFKGRVTI TADTSTSTAYMELSSLRSEDTAVYYCAVSYYSYDVL DYWGQGTTVTVSSGGGGSGGGGSGGGGSGGGGSDI QMTQSPSFLSASVGDRVTITCKASQNVDNRVAWYQ QKPGKAPKALIYSSSHRYKGVPSRFSGSGSGTEFTLT ISSLQPEDFATYFCQQFKSYPLTFGQGTKLEIK |
| | A-H.68 | |
| SEQ ID NO: 1337 | VH + VL (ScFv) | QVQLVQSGAEVKKPGSSVKVSCKASGHDFRLTYIH WVRQAPGQGLEWMGRISAGSGNVKYNEKFKGRVT ITADTSTSTAYMELSSLRSEDTAVYYCAVSYYSYDV LDYWGQGTTVTVSSGGGGSGGGGSGGGGSGGGGS DIQMTQSPSFLSASVGDRVTITCKASQNVADRVAW YQQKPGKAPKALIYSSSHRYKGVPSRFSGSGSGTEFT LTISSLQPEDFATYFCQQFKSYPLTFGQGTKLEIK |
| | A-H.69 (also referred to as A-H.13) | |
| SEQ ID NO: 110 | VH + VL (ScFv) | QVQLVQSGAEVKKPGSSVKVSCKASGTDFKLTYIH WVRQAPGQGLEWMGRIFPGSGNVKYNEKFKGRVTI TADTSTSTAYMELSSLRSEDTAVYYCAGSYYSYDVL DYWGQGTTVTVSSGGGGSGGGGSGGGGSGGGGSDI QMTQSPSFLSASVGDRVTITCKASQNVDNRVAWYQ QKPGKAPKALIYSSSHRYKGVPSRFSGSGSGTEFTLT ISSLQPEDFATYFCQQFKSYPLTFGQGTKLEIK |
| | A-H humanized-matured VH | |
| SEQ ID NO: 1310 | VH-humanized matured 1 | QVQLVQSGAEVKKPGSSVKVSCKASGTDFKLTYIH WVRQAPGQGLEWMGRIFPGSGNVKYNEKFKGRVTI TADTSTSTAYMELSSLRSEDTAVYYCAGSYYSYDVL DYWGQGTTVTVSS |
| SEQ ID NO: 1311 | VH-humanized matured 2 | QVQLVQSGAEVKKPGSSVKVSCKASGTDFKLTYIH WVRQAPGQGLEWMGRIFPGSGNVKYNEKFKGRVTI TADTSTSTAYMELSSLRSEDTAVYYCAVSYYSYDVL DYWGQGTTVTVSS |
| SEQ ID NO: 1312 | VH-humanized matured 3 | QVQLVQSGAEVKKPGSSVKVSCKASGHDFRLTYIH WVRQAPGQGLEWMGRISAGSGNVKYNEKFKGRVT ITADTSTSTAYMELSSLRSEDTAVYYCAVSYYSYDV LDYWGQGTTVTVSS |

TABLE 1-continued

Amino acid and nucleotide sequences for murine, chimeric and humanized antibody molecules which bind to TCRVB 6, e.g., TCRVB 6-5. The antibody molecules include murine mAb Antibody A, and humanized mAb Antibody A-H Clones A-H.1 to A-H.85. The amino acid the heavy and light chain CDRs, and the amino acid and nucleotide sequences of the heavy and light chain variable regions, and the heavy and light chains are shown.

| | | |
|---|---|---|
| **A-H humanized-matured VL** | | |
| SEQ ID NO: 1313 | VL-humanized matured 1 | DIQMTQSPSFLSASVGDRVTITCKASQNVDNRVAWYQQKPGKAPKALIYSSSHRYKGVPSRFSGSGSGTEFTLTISSLQPEDFATYFCQQFKSYPLTFGQGTKLEIK |
| SEQ ID NO: 1314 | VL-humanized matured 2 | DIQMTQSPSFLSASVGDRVTITCKASQNVADRVAWYQQKPGKAPKALIYSSSHRYKGVPSRFSGSGSGTEFTLTISSLQPEDFATYFCQQFKSYPLTFGQGTKLEIK |
| **A-H.70** | | |
| SEQ ID NO: 1346 | VH (CDRs underlined) | QVQLVQSGAEVKKPGSSVKVSCKASGHDFRLTYIHWVRQAPGQGLEWMGRVSAGSGNVKYNEKFKGRVTITADTSTSTAYMELSSLRSEDTAVYYCAVSYYSYDVLDYWGQGTTVTVSS |
| SEQ ID NO: 1347 | VL (CDRs underlined) | DIQMTQSPSFLSASVGDRVTITCKASQNVGNRVVWHQQRPGKAPKALIYSSSHRYKGVPSRFSGSGSGTEFTLTISSLQPEDFATYFCQQFKSYPLTFGQGTKLEIK |
| **A-H.71** | | |
| SEQ ID NO: 1348 | VH (CDRs underlined) | QVQLVQSGAEVKKPGSSVKVSCKASGHDFRLTYIHWVRQAPGQGLEWMGRIYAGSGNVKYNEKFKGRVTITADTSTSTAYMELSSLRSEDTAVYYCAVSYYSYDVLDYWGQGTTVTVSS |
| SEQ ID NO: 1349 | VL (CDRs underlined) | DIQMTQSPSFLSASVGDRVTITCKASQNVADRVVWHQQKPGKAPKALIYSSSHRYKGVPSRFSGSGSGTEFTLTISSLQPEDFATYFCQQFRSYPLTFGQGTKLEIK |
| **A-H.72** | | |
| SEQ ID NO: 1350 | VH (CDRs underlined) | QVQLVQSGAEVKKPGSSVKVSCKASGHDFRLTYIHWVRQAPGQGLEWMGRVSAGSGNTKYNEKFKGRVTITADTSTSTAYMELSSLRSEDTAVYYCAVSYYSYDVLDYWGQGTTVTVSS |
| SEQ ID NO: 1351 | VL (CDRs underlined) | DIQMTQSPSFLSASVGDRVTITCKASQNVGDRVAWHQQKPGKAPKALIYSSSHRYKGVPSRFSGSGSGTEFTLTISSLQPEDFATYFCQQFRSYPLTFGQGTKLEIK |
| **A-H.73** | | |
| SEQ ID NO: 1350 | VH (CDRs underlined) | QVQLVQSGAEVKKPGSSVKVSCKASGHDFRLTYIHWVRQAPGQGLEWMGRVSAGSGNTKYNEKFKGRVTITADTSTSTAYMELSSLRSEDTAVYYCAVSYYSYDVLDYWGQGTTVTVSS |

TABLE 1-continued

Amino acid and nucleotide sequences for murine, chimeric and humanized antibody molecules which bind to TCRVB 6, e.g., TCRVB 6-5. The antibody molecules include murine mAb Antibody A, and humanized mAb Antibody A-H Clones A-H.1 to A-H.85. The amino acid the heavy and light chain CDRs, and the amino acid and nucleotide sequences of the heavy and light chain variable regions, and the heavy and light chains are shown.

| | | |
|---|---|---|
| SEQ ID NO: 1353 | VL (CDRs underlined) | DIQMTQSPSFLSASVGDRVTI TCKASQNVDNRVAWHQQK PGKAPKALIYSSSHRYKGVP SRFSGSGSGTEFTLTISSLQPE DFATYFCQQFKSYPLTFGQG TKLEIK |
| **A-H.74** | | |
| SEQ ID NO: 1346 | VH (CDRs underlined) | QVQLVQSGAEVKKPGSSVK VSCKASGHDFRLTYIHWVR QAPGQGLEWMGRVSAGSGN VKYNEKFKGRVTITADTSTS TAYMELSSLRSEDTAVYYCA VSYYSYDVLDYWGQGTTVT VSS |
| SEQ ID NO: 1349 | VL (CDRs underlined) | DIQMTQSPSFLSASVGDRVTI TCKASQNVADRVVWHQQK PGKAPKALIYSSSHRYKGVP SRFSGSGSGTEFTLTISSLQPE DFATYFCQQFKSYPLTFGQG TKLEIK |
| **A-H.75** | | |
| SEQ ID NO: 1356 | VH (CDRs underlined) | QVQLVQSGAEVKKPGSSVK VSCKASGHDFRLTYIHWVR QAPGQGLEWMGRVYAGSG NTKYNEKFKGRVTITADTST STAYMELSSLRSEDTAVYYC AVSYYSYDVLDYWGQGTTV TVSS |
| SEQ ID NO: 1357 | VL (CDRs underlined) | DIQMTQSPSFLSASVGDRVTI TCKASQNVEDRVVWHQQKP GKAPKALIYSSSHRYKGVPS RFSGSGSGTEFTLTISSLQPED FATYFCQQFKSYPLTFGQGT KLEIK |
| **A-H.76** | | |
| SEQ ID NO: 1350 | VH (CDRs underlined) | QVQLVQSGAEVKKPGSSVK VSCKASGHDFRLTYIHWVR QAPGQGLEWMGRVSAGSGN TKYNEKFKGRVTITADTSTS TAYMELSSLRSEDTAVYYCA VSYYSYDVLDYWGQGTTVT VSS |
| SEQ ID NO: 1349 | VL (CDRs underlined) | DIQMTQSPSFLSASVGDRVTI TCKASQNVADRVVWHQQK PGKAPKALIYSSSHRYKGVP SRFSGSGSGTEFTLTISSLQPE DFATYFCQQFKSYPLTFGQG TKLEIK |
| **A-H.77** | | |
| SEQ ID NO: 1360 | VH (CDRs underlined) | QVQLVQSGAEVKKPGSSVK VSCKASGHDFKLTYIHWVR QAPGQGLEWMGRISAGSGN TKYNEKFKGRVTITADTSTS TAYMELSSLRSEDTAVYYCA VSYYSYDVLDYWGQGTTVT VSS |
| SEQ ID NO: 1361 | VL (CDRs underlined) | DIQMTQSPSFLSASVGDRVTI TCKASQNVGDRVVWHQQK PGKAPKALIYSSSHRYKGVP SRFSGSGSGTEFTLTISSLQPE |

TABLE 1-continued

Amino acid and nucleotide sequences for murine, chimeric and humanized antibody molecules which bind to TCRVB 6, e.g., TCRVB 6-5. The antibody molecules include murine mAb Antibody A, and humanized mAb Antibody A-H Clones A-H.1 to A-H.85. The amino acid the heavy and light chain CDRs, and the amino acid and nucleotide sequences of the heavy and light chain variable regions, and the heavy and light chains are shown.

| | | |
|---|---|---|
| | | DFATYFCQQFKSYPLTFGQG<br>TKLEIK |
| A-H.78 | | |
| SEQ ID NO: 1362 | VH<br>(CDRs underlined) | QVQLVQSGAEVKKPGSSVK<br>VSCKASGHDFKLTYIHWVR<br>QAPGQGLEWMGRIYAGSGN<br>TKYNEKFKGRVTITADTSTS<br>TAYMELSSLRSEDTAVYYCA<br>VSYYSYDVLDYWGQGTTVT<br>VSS |
| SEQ ID NO: 1361 | VL<br>(CDRs underlined) | DIQMTQSPSFLSASVGDRVTI<br>TCKASQNVGDRVVWHQQK<br>PGKAPKALIYSSSHRYKGVP<br>SRFSGSGSGTEFTLTISSLQPE<br>DFATYFCQQFKSYPLTFGQG<br>TKLEIK |
| A-H.79 | | |
| SEQ ID NO: 1350 | VH<br>(CDRs underlined) | QVQLVQSGAEVKKPGSSVK<br>VSCKASGHDFKLTYIHWVR<br>QAPGQGLEWMGRVSAGSGN<br>TKYNEKFKGRVTITADTSTS<br>TAYMELSSLRSEDTAVYYCA<br>VSYYSYDVLDYWGQGTTVT<br>VSS |
| SEQ ID NO: 1365 | VL<br>(CDRs underlined) | DIQMTQSPSFLSASVGDRVTI<br>TCRASQNVDNRLGWHQQKP<br>GKAPKALIYSSSHRYKGVPS<br>RFSGSGSGTEFTLTISSLQPED<br>FATYFCQQFKSYPLTFGQGT<br>KLEIK |
| A-H.80 | | |
| SEQ ID NO: 1350 | VH<br>(CDRs underlined) | QVQLVQSGAEVKKPGSSVK<br>VSCKASGHDFKLTYIHWVR<br>QAPGQGLEWMGRVSAGSGN<br>TKYNEKFKGRVTITADTSTS<br>TAYMELSSLRSEDTAVYYCA<br>VSYYSYDVLDYWGQGTTVT<br>VSS |
| SEQ ID NO: 1367 | VL<br>(CDRs underlined) | DIQMTQSPSFLSASVGDRVTI<br>TCKASQNVDNRVAWHQQK<br>PGKAPKALIYAASSLQKGVP<br>SRFSGSGSGTEFTLTISSLQPE<br>DFATYFCQQFKSYPLTFGQG<br>TKLEIK |
| A-H.81 | | |
| SEQ ID NO: 1350 | VH<br>(CDRs underlined) | QVQLVQSGAEVKKPGSSVK<br>VSCKASGHDFKLTYIHWVR<br>QAPGQGLEWMGRVSAGSGN<br>TKYNEKFKGRVTITADTSTS<br>TAYMELSSLRSEDTAVYYCA<br>VSYYSYDVLDYWGQGTTVT<br>VSS |
| SEQ ID NO: 1369 | VL<br>(CDRs underlined) | DIQMTQSPSFLSASVGDRVTI<br>TCKASQNVDNRVAWHQQK<br>PGKAPKALIYSSSHRYKGVP<br>SRFSGSGSGTEFTLTISSLQPE<br>DFATYFCLQHNSYPLTFGQG<br>TKLEIK |

TABLE 1-continued

Amino acid and nucleotide sequences for murine, chimeric and humanized antibody molecules which bind to TCRVB 6, e.g., TCRVB 6-5. The antibody molecules include murine mAb Antibody A, and humanized mAb Antibody A-H Clones A-H.1 to A-H.85. The amino acid the heavy and light chain CDRs, and the amino acid and nucleotide sequences of the heavy and light chain variable regions, and the heavy and light chains are shown.

| | | |
|---|---|---|
| **A-H.82** | | |
| SEQ ID NO: 1370 | VH (CDRs underlined) | QVQLVQSGAEVKKPGSSVK VSCKASGHDFKLTYIHWVR QAPGQGLEWMGRVSAGSGN VNYAQKFQGRVTITADTSTS TAYMELSSLRSEDTAVYYCA VSYYSYDVLDYWGQGTTVT VSS |
| SEQ ID NO: 1365 | VL (CDRs underlined) | DIQMTQSPSFLSASVGDRVTI TCRASQNVDNRLGWHQQKP GKAPKALIYSSSHRYKGVPS RFSGSGSGTEFTLTISSLQPED FATYFCQQFKSYPLTFGQGT KLEIK |
| **A-H.83** | | |
| SEQ ID NO: 1370 | VH (CDRs underlined) | QVQLVQSGAEVKKPGSSVK VSCKASGHDFKLTYIHWVR QAPGQGLEWMGRVSAGSGN VNYAQKFQGRVTITADTSTS TAYMELSSLRSEDTAVYYCA VSYYSYDVLDYWGQGTTVT VSS |
| SEQ ID NO: 1367 | VL (CDRs underlined) | DIQMTQSPSFLSASVGDRVTI TCKASQNVDNRVAWHQQK PGKAPKALIYAASSLQKGVP SRFSGSGSGTEFTLTISSLQPE DFATYFCQQFKSYPLTFGQG TKLEIK |
| **A-H.84** | | |
| SEQ ID NO: 1370 | VH (CDRs underlined) | QVQLVQSGAEVKKPGSSVK VSCKASGHDFKLTYIHWVR QAPGQGLEWMGRVSAGSGN VNYAQKFQGRVTITADTSTS TAYMELSSLRSEDTAVYYCA VSYYSYDVLDYWGQGTTVT VSS |
| SEQ ID NO: 1369 | VL (CDRs underlined) | DIQMTQSPSFLSASVGDRVTI TCKASQNVDNRVAWHQQK PGKAPKALIYSSSHRYKGVP SRFSGSGSGTEFTLTISSLQPE DFATYFCLQHNSYPLTFGQG TKLEIK |
| **A-H.85** | | |
| SEQ ID NO: 1344 | VH (CDRs underlined) | QVQLVQSGAEVKKPGSSVK VSCKASGHDFRLTYIHWVR QAPGQGLEWMGRVSAGSGN TKYNEKFKGRVTITADTSTS TAYMELSSLRSEDTAVYYCA VSYYSYDVLDYWGQGTTVT VSS |
| SEQ ID NO: 1361 | VL (CDRs underlined) | DIQMTQSPSFLSASVGDRVTI TCKASQNVGDRVVWHQQK PGKAPKALIYSSSHRYKGVP SRFSGSGSGTEFTLTISSLQPE DFATYFCQQFKSYPLTFGQG TKLEIK |

In some embodiments, the anti-TCRβV antibody molecule, e.g., anti-TCRβ V6 (e.g., anti-TCRβ V6-5*01) antibody molecule comprises a VH and/or a VL of an antibody described in Table 1, or a sequence with at least 80%, 85%, 90%, 95%, 96%, 97%, 98%, 99% or more identity thereto.

In some embodiments, the anti-TCRβV antibody molecule, e.g., anti-TCRβ V6 (e.g., anti-TCRβ V6-5*01) antibody molecule comprises a VH and a VL of an antibody described in Table 1, or a sequence with at least 80%, 85%, 90%, 95%, 96%, 97%, 98%, 99% or more identity thereto.

In some embodiments, an anti-TCRVb antibody disclosed herein has an antigen binding domain having a VL having a consensus sequence of SEQ ID NO: 230, wherein position 30 is G, E, A or D; position 31 is N or D; position 32 is R or K; position 36 is Y or H; and/or position 56 is K or S.

In some embodiments, an anti-TCRVb antibody disclosed herein has an antigen binding domain having a VH having a consensus sequence of SEQ ID NO: 231, wherein: position 27 is H or T or G or Y; position 28 is D or T or S; position 30 is H or R or D or K or T; position 31 is L or D or K or T or N; position 32 is W or F or T or I or Y or G; position 49 is R or W; position 50 is V or I or F; position 51 is F or S or Y; position 52 is A or P; position 56 is N or S; position 57 is T or V or Y or I; position 58 is K or R; position 97 is G or V; position 99 is Y or I; position 102 is Y or A; and/or position 103 is D or G.

Anti-TCRβ V12 Antibodies

Accordingly, in one aspect, the disclosure provides an anti-TCRβV antibody molecule that binds to human TCRβ V12, e.g., a TCRβ V12 subfamily comprising: TCRβ V12-4*01, TCRβ V12-3*01 or TCRβ V12-5*01. In some embodiments the TCRβ V12 subfamily comprises TCRβ V12-4*01. In some embodiments the TCRβ V12 subfamily comprises TCRβ V12-3*01.

In some embodiments, the anti-TCRβV antibody molecule, e.g., anti-TCRβ V12 antibody molecule, is a non-murine antibody molecule, e.g., a human or humanized antibody molecule. In some embodiments, the anti-TCRβV antibody molecule, e.g., anti-TCRβ V12 antibody molecule is a human antibody molecule. In some embodiments, the anti-TCRβV antibody molecule, e.g., anti-TCRβ V12 antibody molecule is a humanized antibody molecule.

In some embodiments, the anti-TCRβV antibody molecule, e.g., anti-TCRβ V12 antibody molecule, is isolated or recombinant.

In some embodiments, the anti-TCRβV antibody molecule, e.g., anti-TCRβ V12 antibody molecule, comprises at least one antigen-binding region, e.g., a variable region or an antigen-binding fragment thereof, from an antibody described herein, e.g., an antibody described in Table 2, or encoded by a nucleotide sequence in Table 2, or a sequence substantially identical (e.g., at least 80%, 85%, 90%, 92%, 95%, 97%, 98%, 99% or higher identical) to any of the aforesaid sequences.

In some embodiments, the anti-TCRβV antibody molecule, e.g., anti-TCRβ V12 antibody molecule, comprises at least one, two, three or four variable regions from an antibody described herein, e.g., an antibody as described in Table 2, or encoded by a nucleotide sequence in Table 2, or a sequence substantially identical (e.g., at least 80%, 85%, 90%, 92%, 95%, 97%, 98%, 99% or higher identical) to any of the aforesaid sequences.

In some embodiments, the anti-TCRβV antibody molecule, e.g., anti-TCRβ V12 antibody molecule, comprises at least one or two heavy chain variable regions from an antibody described herein, e.g., an antibody as described in Table 2, or encoded by a nucleotide sequence in Table 2, or a sequence substantially identical (e.g., at least 80%, 85%, 90%, 92%, 95%, 97%, 98%, 99% or higher identical) to any of the aforesaid sequences.

In some embodiments, the anti-TCRβV antibody molecule, e.g., anti-TCRβ V12 antibody molecule, comprises at least one or two light chain variable regions from an antibody described herein, e.g., an antibody as described in Table 2, or encoded by a nucleotide sequence in Table 2, or a sequence substantially identical (e.g., at least 80%, 85%, 90%, 92%, 95%, 97%, 98%, 99% or higher identical) to any of the aforesaid sequences.

In some embodiments, the anti-TCRβV antibody molecule, e.g., anti-TCRβ V12 antibody molecule, comprises a heavy chain constant region for an IgG4, e.g., a human IgG4. In still another embodiment, the anti-TCRβV antibody molecule, e.g., anti-TCRβ V12 antibody molecule, includes a heavy chain constant region for an IgG1, e.g., a human IgG1. In one embodiment, the heavy chain constant region comprises an amino sequence set forth in Table 3, or a sequence substantially identical (e.g., at least 80%, 85%, 90%, 92%, 95%, 97%, 98%, 99% or higher identical) thereto.

In some embodiments, the anti-TCRβV antibody molecule, e.g., anti-TCRβ V12 antibody molecule, includes a kappa light chain constant region, e.g., a human kappa light chain constant region. In one embodiment, the light chain constant region comprises an amino sequence set forth in Table 3, or a sequence substantially identical (e.g., at least 80%, 85%, 90%, 92%, 95%, 97%, 98%, 99% or higher identical) thereto.

In some embodiments, the anti-TCRβV antibody molecule, e.g., anti-TCRβ V12 antibody molecule, includes at least one, two, or three complementarity determining regions (CDRs) from a heavy chain variable region of an antibody described herein, e.g., an antibody as described in Table 2, or encoded by the nucleotide sequence in Table 2, or a sequence substantially identical (e.g., at least 80%, 85%, 90%, 92%, 95%, 97%, 98%, 99% or higher identical) to any of the aforesaid sequences.

In some embodiments, the anti-TCRβV antibody molecule, e.g., anti-TCRβ V12 antibody molecule, includes at least one, two, or three CDRs (or collectively all of the CDRs) from a heavy chain variable region comprising an amino acid sequence shown in Table 2, or encoded by a nucleotide sequence shown in Table 2. In one embodiment, one or more of the CDRs (or collectively all of the CDRs) have one, two, three, four, five, six or more changes, e.g., amino acid substitutions or deletions, relative to the amino acid sequence shown in Table 2, or encoded by a nucleotide sequence shown in Table 2.

In some embodiments, the anti-TCRβV antibody molecule, e.g., anti-TCRβ V12 antibody molecule, includes at least one, two, or three complementarity determining regions (CDRs) from a light chain variable region of an antibody described herein, e.g., an antibody as described in Table 2, or encoded by the nucleotide sequence in Table 2, or a sequence substantially identical (e.g., at least 80%, 85%, 90%, 92%, 95%, 97%, 98%, 99% or higher identical) to any of the aforesaid sequences.

In some embodiments, the anti-TCRβV antibody molecule, e.g., anti-TCRβ V12 antibody molecule, includes at least one, two, or three CDRs (or collectively all of the CDRs) from a light chain variable region comprising an amino acid sequence shown in Table 2, or encoded by a nucleotide sequence shown in Table 2. In one embodiment, one or more of the CDRs (or collectively all of the CDRs) have one, two, three, four, five, six or more changes, e.g., amino acid substitutions or deletions, relative to the amino acid sequence shown in Table 2, or encoded by a nucleotide sequence shown in Table 2.

In some embodiments, the anti-TCRβV antibody molecule, e.g., anti-TCRβ V12 antibody molecule, includes at least one, two, three, four, five or six CDRs (or collectively all of the CDRs) from a heavy and light chain variable region comprising an amino acid sequence shown in Table 2, or encoded by a nucleotide sequence shown in Table 2. In one embodiment, one or more of the CDRs (or collectively all of the CDRs) have one, two, three, four, five, six or more changes, e.g., amino acid substitutions or deletions, relative to the amino acid sequence shown in Table 2, or encoded by a nucleotide sequence shown in Table 2.

In some embodiments, the anti-TCRβV antibody molecule, e.g., anti-TCRβ V12 antibody molecule, molecule includes all six CDRs from an antibody described herein, e.g., an antibody as described in Table 2, or encoded by the nucleotide sequence in Table 2, or closely related CDRs, e.g., CDRs which are identical or which have at least one amino acid alteration, but not more than two, three or four alterations (e.g., substitutions, deletions, or insertions, e.g., conservative substitutions). In some embodiments, the anti-TCRβV antibody molecule, e.g., anti-TCRβ V12 antibody molecule, may include any CDR described herein.

In some embodiments, the anti-TCRβV antibody molecule, e.g., anti-TCRβ V12 antibody molecule includes at least one, two, or three CDRs according to Kabat et al. (e.g., at least one, two, or three CDRs according to the Kabat definition as set out in Table 2) from a heavy chain variable region of an antibody described herein, e.g., an antibody chosen as described in Table 2, or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, or three CDRs according to Kabat et al. shown in Table 2.

In some embodiments, the anti-TCRβV antibody molecule, e.g., anti-TCRβ V12 antibody molecule includes at least one, two, or three CDRs according to Kabat et al. (e.g., at least one, two, or three CDRs according to the Kabat definition as set out in Table 2) from a light chain variable region of an antibody described herein, e.g., an antibody as described in Table 2, or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, or three CDRs according to Kabat et al. shown in Table 2.

In some embodiments, the anti-TCRβV antibody molecule, e.g., anti-TCRβ V12 antibody molecule includes at least one, two, three, four, five, or six CDRs according to Kabat et al. (e.g., at least one, two, three, four, five, or six CDRs according to the Kabat definition as set out in Table 2) from the heavy and light chain variable regions of an antibody described herein, e.g., an antibody as described in Table 2, or encoded by the nucleotide sequence in Table 2; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, three, four, five, or six CDRs according to Kabat et al. shown in Table 2.

In some embodiments, the anti-TCRβV antibody molecule, e.g., anti-TCRβ V12 antibody molecule includes all six CDRs according to Kabat et al. (e.g., all six CDRs according to the Kabat definition as set out in Table 2) from the heavy and light chain variable regions of an antibody described herein, e.g., an antibody as described in Table 2, or encoded by the nucleotide sequence in Table 2; or encoded by the nucleotide sequence in Table 2; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to all six CDRs according to Kabat et al. shown in Table 2. In some embodiments, the anti-TCRβV antibody molecule, e.g., anti-TCRβ V12 antibody molecule may include any CDR described herein.

In some embodiments, the anti-TCRβV antibody molecule, e.g., anti-TCRβ V12 antibody molecule includes at least one, two, or three hypervariable loops that have the same canonical structures as the corresponding hypervariable loop of an antibody described herein, e.g., an antibody described in Table 2, e.g., the same canonical structures as at least loop 1 and/or loop 2 of the heavy and/or light chain variable domains of an antibody described herein. See, e.g., Chothia et al., (1992) J. Mol. Biol. 227:799-817; Tomlinson et al., (1992) J. Mol. Biol. 227:776-798 for descriptions of hypervariable loop canonical structures. These structures can be determined by inspection of the tables described in these references.

In some embodiments, the anti-TCRβV antibody molecule, e.g., anti-TCRβ V12 antibody molecule includes at least one, two, or three CDRs according to Chothia et al. (e.g., at least one, two, or three CDRs according to the Chothia definition as set out in Table 2) from a heavy chain variable region of an antibody described herein, e.g., an antibody chosen as described in Table 2, or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, or three CDRs according to Chothia et al. shown in Table 2.

In some embodiments, the anti-TCRβV antibody molecule, e.g., anti-TCRβ V12 antibody molecule includes at least one, two, or three CDRs according to Chothia et al. (e.g., at least one, two, or three CDRs according to the Chothia definition as set out in Table 2) from a light chain variable region of an antibody described herein, e.g., an antibody as described in Table 2, or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, or three CDRs according to Chothia et al. shown in Table 2.

In some embodiments, the anti-TCRβV antibody molecule, e.g., anti-TCRβ V12 antibody molecule includes at least one, two, three, four, five, or six CDRs according to Chothia et al. (e.g., at least one, two, three, four, five, or six CDRs according to the Chothia definition as set out in Table 2) from the heavy and light chain variable regions of an antibody described herein, e.g., an antibody as described in Table 2, or encoded by the nucleotide sequence in Table 2; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, three, four, five, or six CDRs according to Chothia et al. shown in Table 2.

In some embodiments, the anti-TCRβV antibody molecule, e.g., anti-TCRβ V12 antibody molecule includes all six CDRs according to Chothia et al. (e.g., all six CDRs according to the Chothia definition as set out in Table 2) from the heavy and light chain variable regions of an antibody described herein, e.g., an antibody as described in Table 2, or encoded by the nucleotide sequence in Table 2; or encoded by the nucleotide sequence in Table 2; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to all six CDRs according to Chothia et al. shown in Table 2. In some embodiments, the anti-TCRβV antibody molecule, e.g., anti-TCRβ V12 antibody molecule may include any CDR described herein.

In some embodiments, the anti-TCRβV antibody molecule, e.g., anti-TCRβ V12 antibody molecule includes at least one, two, or three CDRs according to a combined CDR (e.g., at least one, two, or three CDRs according to the combined CDR definition as set out in Table 2) from a heavy chain variable region of an antibody described herein, e.g., an antibody chosen as described in Table 2, or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, or three CDRs according to combined CDR shown in Table 2.

In some embodiments, the anti-TCRβV antibody molecule, e.g., anti-TCRβ V12 antibody molecule includes at least one, two, or three CDRs according to a combined CDR (e.g., at least one, two, or three CDRs according to the combined CDR definition as set out in Table 2) from a light chain variable region of an antibody described herein, e.g., an antibody as described in Table 2, or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, or three CDRs according to a combined CDR shown in Table 2.

In some embodiments, the anti-TCRβV antibody molecule, e.g., anti-TCRβ V12 antibody molecule includes at least one, two, three, four, five, or six CDRs according to a combined CDR. (e.g., at least one, two, three, four, five, or six CDRs according to the combined CDR definition as set out in Table 2) from the heavy and light chain variable regions of an antibody described herein, e.g., an antibody as described in Table 2, or encoded by the nucleotide sequence in Table 2; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, three, four, five, or six CDRs according to a combined CDR shown in Table 2.

In some embodiments, the anti-TCRβV antibody molecule, e.g., anti-TCRβ V12 antibody molecule includes all six CDRs according to a combined CDR (e.g., all six CDRs according to the combined CDR definition as set out in Table 2) from the heavy and light chain variable regions of an antibody described herein, e.g., an antibody as described in Table 2, or encoded by the nucleotide sequence in Table 2; or encoded by the nucleotide sequence in Table 2; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to all six CDRs according to a combined CDR shown in Table 2. In some embodiments, the anti-TCRβV antibody molecule, e.g., anti-TCRβ V12 antibody molecule may include any CDR described herein.

In some embodiments, a combined CDR as set out in Table 1 is a CDR that comprises a Kabat CDR and a Chothia CDR.

In some embodiments, the anti-TCRβV antibody molecule, e e.g., anti-TCRβ V12 antibody molecule, molecule includes a combination of CDRs or hypervariable loops identified as combined CDRs in Table 1. In some embodiments, the anti-TCRβV antibody molecule, e.g., anti-TCRβ V12 antibody molecule, can contain any combination of CDRs or hypervariable loops according the "combined" CDRs are described in Table 1.

In some embodiments, the anti-TCRβV antibody molecule, e.g., anti-TCRβ V12 antibody molecule includes a combination of CDRs or hypervariable loops defined according to the Kabat et al. and Chothia et al., or as described in Table 1

In some embodiments, the anti-TCRβV antibody molecule, e.g., anti-TCRβ V12 antibody molecule can contain any combination of CDRs or hypervariable loops according to the Kabat and Chothia definitions.

In an embodiment, e.g., an embodiment comprising a variable region, a CDR (e.g., a combined CDR, Chothia CDR or Kabat CDR), or other sequence referred to herein, e.g., in Table 2, the antibody molecule is a monospecific antibody molecule, a bispecific antibody molecule, a bivalent antibody molecule, a biparatopic antibody molecule, or an antibody molecule that comprises an antigen binding fragment of an antibody, e.g., a half antibody or antigen binding fragment of a half antibody. In certain embodiments the antibody molecule comprises a multispecific molecule, e.g., a bispecific molecule, e.g., as described herein.

In some embodiments, the anti-TCRβV antibody molecule, e.g., anti-TCRβ V12 antibody molecule includes:

(i) one, two or all of a light chain complementarity determining region 1 (LC CDR1), a light chain complementarity determining region 2 (LC CDR2), and a light chain complementarity determining region 3 (LC CDR3) of SEQ ID NO: 16, SEQ ID NO: 26, SEQ ID NO: 27, SEQ ID NO: 28, SEQ ID NO: 29 or SEQ ID NO: 30, and/or (ii) one, two or all of a heavy chain complementarity determining region 1 (HC CDR1), heavy chain complementarity determining region 2 (HC CDR2), and a heavy chain complementarity determining region 3 (HC CDR3) of SEQ ID NO: 15, SEQ ID NO: 23, SEQ ID NO: 24 or SEQ ID NO: 25.

In some embodiments, the anti-TCRβV antibody molecule, e.g., anti-TCRβ V12 antibody molecule comprises:

(i) a LC CDR1 amino acid sequence of SEQ ID NO: 20, a LC CDR2 amino acid sequence of SEQ ID NO: 21, or a LC CDR3 amino acid sequence of SEQ ID NO: 22; and/or (ii) a HC CDR1 amino acid sequence of SEQ ID NO: 17, a HC CDR2 amino acid sequence of SEQ ID NO: 18, or a HC CDR3 amino acid sequence of SEQ ID NO: 19.

In some embodiments, the anti-TCRβV antibody molecule, e.g., anti-TCRβ V12 antibody molecule comprises:

(i) a light chain variable region (VL) comprising a LC CDR1 amino acid sequence of SEQ ID NO: 20, a LC CDR2 amino acid sequence of SEQ ID NO: 21, and a LC CDR3 amino acid sequence of SEQ ID NO: 2; and/or (ii) a heavy chain variable region (VH) comprising a HC CDR1 amino acid sequence of SEQ ID NO: 17, a HC CDR2 amino acid sequence of SEQ ID NO: 18, and a HC CDR3 amino acid sequence of SEQ ID NO: 19.

In some embodiments, the anti-TCRβV antibody molecule, e.g., anti-TCRβ V12 antibody molecule comprises:

(i) a LC CDR1 amino acid sequence of SEQ ID NO: 63, a LC CDR2 amino acid sequence of SEQ ID NO: 64, or a LC CDR3 amino acid sequence of SEQ ID NO: 65; and/or (ii) a HC CDR1 amino acid sequence of SEQ ID NO: 57, a HC CDR2 amino acid sequence of SEQ ID NO: 58, or a HC CDR3 amino acid sequence of SEQ ID NO: 59.

In some embodiments, the anti-TCRβV antibody molecule, e.g., anti-TCRβ V12 antibody molecule comprises:

(i) a light chain variable region (VL) comprising a LC CDR1 amino acid sequence of SEQ ID NO: 63, a LC CDR2 amino acid sequence of SEQ ID NO: 64, or a LC CDR3 amino acid sequence of SEQ ID NO: 65; and/or (ii) a heavy chain variable region (VH) comprising a HC CDR1 amino acid sequence of SEQ ID NO: 57, a HC CDR2 amino acid sequence of SEQ ID NO: 58, or a HC CDR3 amino acid sequence of SEQ ID NO: 59.

In some embodiments, the anti-TCRβV antibody molecule, e.g., anti-TCRβ V12 antibody molecule comprises:

(i) a LC CDR1 amino acid sequence of SEQ ID NO: 66, a LC CDR2 amino acid sequence of SEQ ID NO: 67, or a LC CDR3 amino acid sequence of SEQ ID NO: 68; and/or (ii) a HC CDR1 amino acid sequence of SEQ ID NO: 60, a HC CDR2 amino acid sequence of SEQ ID NO: 61, or a HC CDR3 amino acid sequence of SEQ ID NO: 62.

In some embodiments, the anti-TCRβV antibody molecule, e.g., anti-TCRβ V12 antibody molecule comprises:

(i) a light chain variable region (VL) comprising a LC CDR1 amino acid sequence of SEQ ID NO: 63, a LC CDR2 amino acid sequence of SEQ ID NO: 64, or a LC CDR3 amino acid sequence of SEQ ID NO: 65; and/or (ii) a heavy chain variable region (VH) comprising a HC CDR1 amino acid sequence of SEQ ID NO: 57, a HC CDR2 amino acid sequence of SEQ ID NO: 58, or a HC CDR3 amino acid sequence of SEQ ID NO: 59.

In one embodiment, the light or the heavy chain variable framework (e.g., the region encompassing at least FR1, FR2, FR3, and optionally FR4) of the anti-TCRβV antibody molecule, e.g., anti-TCRβ V12 antibody molecule can be chosen from: (a) a light or heavy chain variable framework including at least 80%, 85%, 87% 90%, 92%, 93%, 95%, 97%, 98%, or 100% of the amino acid residues from a human light or heavy chain variable framework, e.g., a light or heavy chain variable framework residue from a human mature antibody, a human germline sequence, or a human consensus sequence; (b) a light or heavy chain variable framework including from 20% to 80%, 40% to 60%, 60% to 90%, or 70% to 95% of the amino acid residues from a human light or heavy chain variable framework, e.g., a light or heavy chain variable framework residue from a human mature antibody, a human germline sequence, or a human consensus sequence; (c) a non-human framework (e.g., a rodent framework); or (d) a non-human framework that has been modified, e.g., to remove antigenic or cytotoxic determinants, e.g., deimmunized, or partially humanized. In one embodiment, the light or heavy chain variable framework region (particularly FR1, FR2 and/or FR3) includes a light or heavy chain variable framework sequence at least 70, 75, 80, 85, 87, 88, 90, 92, 94, 95, 96, 97, 98, 99% identical or identical to the frameworks of a VL or VH segment of a human germline gene.

In some embodiments, the anti-TCRβV antibody molecule, e.g., anti-TCRβ V12 antibody molecule, comprises a heavy chain variable domain having at least one, two, three, four, five, six, seven, ten, fifteen, twenty or more changes, e.g., amino acid substitutions or deletions, from an amino acid sequence described in Table 2. e.g., the amino acid sequence of the FR region in the entire variable region, e.g., shown in FIGS. 2A and 2B, or in SEQ ID NOs: 23-25.

Alternatively, or in combination with the heavy chain substitutions described herein the anti-TCRβV antibody molecule, e.g., anti-TCRβ V12 antibody molecule comprises a light chain variable domain having at least one, two, three, four, five, six, seven, ten, fifteen, twenty or more amino acid changes, e.g., amino acid substitutions or deletions, from an amino acid sequence of an antibody described herein. e.g., the amino acid sequence of the FR region in the entire variable region, e.g., shown in FIGS. 2A and 2B, or in SEQ ID NOs: 26-30.

In some embodiments, the anti-TCRβV antibody molecule, e.g., anti-TCRβ V12 antibody molecule includes one, two, three, or four heavy chain framework regions shown in FIG. 2A, or a sequence substantially identical thereto.

In some embodiments, the anti-TCRβV antibody molecule, e.g., anti-TCRβ V12 antibody molecule includes one, two, three, or four light chain framework regions shown in FIG. 2B, or a sequence substantially identical thereto.

In some embodiments, the anti-TCRβV antibody molecule, e.g., anti-TCRβ V12 antibody molecule comprises the light chain framework region 1 e.g., as shown in FIG. 2B.

In some embodiments, the anti-TCRβV antibody molecule, e.g., anti-TCRβ V12 antibody molecule comprises the light chain framework region 2 e.g., as shown in FIG. 2B.

In some embodiments, the anti-TCRβV antibody molecule, e.g., anti-TCRβ V12 antibody molecule comprises the light chain framework region 3, e.g., as shown in FIG. 2B.

In some embodiments, the anti-TCRβV antibody molecule, e.g., anti-TCRβ V12 antibody molecule comprises the light chain framework region 4, e.g., as shown in FIG. 2B.

In some embodiments, the anti-TCRβV antibody molecule, e.g., anti-TCRβ V12 antibody molecule comprises a light chain comprising a framework region, e.g., framework region 1 (FR1), comprising a change, e.g., a substitution (e.g., a conservative substitution) at one or more, e.g., all, position disclosed herein according to Kabat numbering. In some embodiments, FR1 comprises an Aspartic Acid at position 1, e.g., a substitution at position 1 according to Kabat numbering, e.g., an Alanine to Aspartic Acid substitution. In some embodiments, FR1 comprises an Asparagine at position 2, e.g., a substitution at position 2 according to Kabat numbering, e.g., an Isoleucine to Asparagine substitution, Serine to Asparagine substitution or Tyrosine to Asparagine substitution. In some embodiments, FR1 comprises a Leucine at position 4, e.g., a substitution at position 4 according to Kabat numbering, e.g., a Methionine to Leucine substitution.

In some embodiments, the anti-TCRβV antibody molecule, e.g., anti-TCRβ V12 antibody molecule comprises a light chain comprising a framework region, e.g., framework region 1 (FR1), comprising a substitution at position 1 according to Kabat numbering, e.g., an Alanine to Aspartic Acid substitution, a substitution at position 2 according to Kabat numbering, e.g., an Isoleucine to Asparagine substitution, Serine to Asparagine substitution or Tyrosine to Asparagine substitution, and a substitution at position 4 according to Kabat numbering, e.g., a Methionine to Leucine substitution. In some embodiments, the anti-TCRβV antibody molecule, e.g., anti-TCRβ V12 antibody molecule comprises a light chain comprising a framework region, e.g., framework region 1 (FR1), comprising a substitution at position 1 according to Kabat numbering, e.g., an Alanine to Aspartic Acid substitution, and a substitution at position 2 according to Kabat numbering, e.g., an Isoleucine to Asparagine substitution, Serine to Asparagine substitution or Tyrosine to Asparagine substitution. In some embodiments, the anti-TCRβV antibody molecule, e.g., anti-TCRβ V12 antibody molecule comprises a light chain comprising a framework region, e.g., framework region 1 (FR1), comprising a substitution at position 1 according to Kabat numbering, e.g., an Alanine to Aspartic Acid substitution, and a substitution at position 4 according to Kabat numbering, e.g., a Methionine to Leucine substitution. In some embodiments, the anti-TCRβV antibody molecule, e.g., anti-TCRβ V12 antibody molecule comprises a light chain comprising a framework region, e.g., framework region 1 (FR1), comprising a substitution at position 2 according to Kabat numbering, e.g., an Isoleucine to Asparagine substitution, Serine to Asparagine substitution or Tyrosine to Asparagine substitution, and a substitution at position 4 according to Kabat numbering, e.g., a Methionine to Leucine substitution. In some embodiments, the substitution is relative to a human germline light chain framework region sequence.

In some embodiments, the anti-TCRβV antibody molecule, e.g., anti-TCRβ V12 antibody molecule comprises a light chain comprising a framework region, e.g., framework region 3 (FR3), comprising a change, e.g., a substitution (e.g., a conservative substitution) at one or more, e.g., all, position disclosed herein according to Kabat numbering. In some embodiments, FR3 comprises a Glycine at position 66, e.g., a substitution at position 66 according to Kabat numbering, e.g., a Lysine to Glycine substitution, or a Serine to Glycine substitution. In some embodiments, FR3 comprises an Asparagine at position 69, e.g., a substitution at position 69 according to Kabat numbering, e.g., a Tyrosine to Asparagine substitution. In some embodiments, FR3 comprises a Tyrosine at position 71, e.g., a substitution at position 71 according to Kabat numbering, e.g., a Phenylalanine to Tyrosine substitution, or an Alanine to Tyrosine substitution.

In some embodiments, the anti-TCRβV antibody molecule, e.g., anti-TCRβ V12 antibody molecule comprises a light chain comprising a framework region, e.g., framework region 3 (FR3), comprising a substitution at position 66 according to Kabat numbering, e.g., a Lysine to Glycine substitution, or a Serine to Glycine substitution, and a substitution at position 69 according to Kabat numbering, e.g., a Tyrosine to Asparagine substitution. In some embodiments, the anti-TCRβV antibody molecule, e.g., anti-TCRβ V12 antibody molecule comprises a light chain comprising a framework region, e.g., framework region 3 (FR3), comprising a substitution at position 66 according to Kabat numbering, e.g., Lysine to Glycine substitution, or a Serine to Glycine substitution, and a substitution at position 71 according to Kabat numbering, e.g., a Phenylalanine to Tyrosine substitution, or an Alanine to Tyrosine substitution. In some embodiments, the anti-TCRβV antibody molecule, e.g., anti-TCRβ V12 antibody molecule comprises a light chain comprising a framework region, e.g., framework region 3 (FR3), comprising a substitution at position 69 according to Kabat numbering, e.g., a Tyrosine to Asparagine substitution and a substitution at position 71 according to Kabat numbering, e.g., a Phenylalanine to Tyrosine substitution, or an Alanine to Tyrosine substitution. In some embodiments, the anti-TCRβV antibody molecule, e.g., anti-TCRβ V12 antibody molecule comprises a light chain comprising a framework region, e.g., framework region 3 (FR3), comprising a substitution at position 66 according to Kabat numbering, e.g., a Lysine to Glycine substitution, or a Serine to Glycine substitution, a substitution at position 69 according to Kabat numbering, e.g., a Tyrosine to Asparagine substitution and a substitution at position 71 according to Kabat numbering, e.g., a Phenylalanine to Tyrosine substitution, or an Alanine to Tyrosine substitution. In some embodiments, the substitution is relative to a human germline light chain framework region sequence.

In some embodiments, the anti-TCRβV antibody molecule, e.g., anti-TCRβ V12 antibody molecule comprises a light chain comprising: a framework region 1 (FR1) comprising a substitution at position 2 according to Kabat numbering, e.g., a Isoleucine to Asparagine substitution; and a framework region 3 (FR3), comprising a substitution at position 69 according to Kabat numbering, e.g., a Threonine to Asparagine substitution and a substitution at position 71 according to Kabat numbering, e.g., a Phenylalanine to Tyrosine substitution, e.g., as shown in the amino acid sequence of SEQ ID NO: 26. In some embodiments, the substitution is relative to a human germline light chain framework region sequence.

In some embodiments, the anti-TCRβV antibody molecule, e.g., anti-TCRβ V12 antibody molecule comprises a light chain comprising: (a) a framework region 1 (FR1) comprising a substitution at position 1 according to Kabat numbering, e.g., a Alanine to Aspartic Acid substitution, and a substitution at position 2 according to Kabat numbering, e.g., a Isoleucine to Asparagine substitution; and (b) a framework region 3 (FR3), comprising a substitution at position 69 according to Kabat numbering, e.g., a Threonine to Asparagine substitution and a substitution at position 71 according to Kabat numbering, e.g., a Phenylalanine to Tyrosine substitution, e.g., as shown in the amino acid sequence of SEQ ID NO: 27 In some embodiments, the substitution is relative to a human germline light chain framework region sequence.

In some embodiments, the anti-TCRβV antibody molecule, e.g., anti-TCRβ V12 antibody molecule comprises a light chain comprising: (a) a framework region 1 (FR1) comprising a substitution at position 2 according to Kabat numbering, e.g., a Serine to Asparagine substitution; and a substitution at position 4 according to Kabat numbering, e.g., a Methionine to Leucine substitution; and (b) a framework region 3 (FR3), comprising a substitution at position 69 according to Kabat numbering, e.g., a Threonine to Asparagine substitution and a substitution at position 71 according to Kabat numbering, e.g., a Phenylalanine to Tyrosine substitution, e.g., as shown in the amino acid sequence of SEQ ID NO: 28 In some embodiments, the substitution is relative to a human germline light chain framework region sequence.

In some embodiments, the anti-TCRβV antibody molecule, e.g., anti-TCRβ V12 antibody molecule comprises a light chain comprising: (a) a framework region 1 (FR1) comprising a substitution at position 2 according to Kabat numbering, e.g., a Serine to Asparagine substitution; and (b) a framework region 3 (FR3) comprising a substitution at position 66 according to Kabat numbering, e.g., a Lysine to Glycine substitution; a substitution at position 69 according to Kabat numbering, e.g., a Threonine to Asparagine substitution; and a substitution at position 71 according to Kabat numbering, e.g., a Alanine to Tyrosine substitution, e.g., as shown in the amino acid sequence of SEQ ID NO: 29. In some embodiments, the substitution is relative to a human germline light chain framework region sequence.

In some embodiments, the anti-TCRβV antibody molecule, e.g., anti-TCRβ V12 antibody molecule comprises a light chain comprising: (a) a framework region 1 (FR1) comprising a substitution at position 2 according to Kabat numbering, e.g., a Tyrosine to Asparagine substitution; and (b) a framework region 3 (FR3) comprising a substitution at position 66 according to Kabat numbering, e.g., a Serine to Glycine substitution; a substitution at position 69 according to Kabat numbering, e.g., a Threonine to Asparagine substitution; and a substitution at position 71 according to Kabat numbering, e.g., a Alanine to Tyrosine substitution, e.g., as shown in the amino acid sequence of SEQ ID NO: 29. In some embodiments, the substitution is relative to a human germline light chain framework region sequence.

In some embodiments, the anti-TCRβV antibody molecule, e.g., anti-TCRβ V12 antibody molecule comprises a light chain variable domain comprising: (a) a framework region 1 (FR1) comprising a change, e.g., a substitution (e.g., a conservative substitution) at one or more (e.g., all) positions disclosed herein according to Kabat numbering, and (b) a framework region 3 (FR3) comprising a change, e.g., a substitution (e.g., a conservative substitution) at one or more (e.g., all) position disclosed herein according to Kabat numbering. In some embodiments, the substitution is relative to a human germline light chain framework region sequence.

In some embodiments, the anti-TCRβV antibody molecule, e.g., anti-TCRβ V12 antibody molecule comprises the heavy chain framework region 1, e.g., as shown in FIG. 2A.

In some embodiments, the anti-TCRβV antibody molecule, e.g., anti-TCRβ V12 antibody molecule comprises the heavy chain framework region 2, e.g., as shown in FIG. 2A.

In some embodiments, the anti-TCRβV antibody molecule, e.g., anti-TCRβ V12 antibody molecule comprises the heavy chain framework region 3, e.g., as shown in FIG. 2A.

In some embodiments, the anti-TCRβV antibody molecule, e.g., anti-TCRβ V12 antibody molecule comprises the heavy chain framework region 4, e.g., as shown in FIG. 2A.

In some embodiments, the anti-TCRβV antibody molecule, e.g., anti-TCRβ V12 antibody molecule comprises the heavy chain framework regions 1-4, e.g., SEQ ID NOS: 20-23, or as shown in FIG. 2A.

In some embodiments, the anti-TCRβV antibody molecule, e.g., anti-TCRβ V12 antibody molecule comprises the light chain framework regions 1-4, e.g., SEQ ID NOs: 26-30, or as shown in FIG. 2B.

In some embodiments, the anti-TCRβV antibody molecule, e.g., anti-TCRβ V12 antibody molecule comprises the heavy chain framework regions 1-4, e.g., SEQ ID NOs: 23-25; and the light chain framework regions 1-4, e.g., SEQ ID NOs: 26-30, or as shown in FIGS. 2A and 2B.

In some embodiments, the heavy or light chain variable domain, or both, of, the anti-TCRβV antibody molecule, e.g., anti-TCRβ V12 antibody molecule includes an amino acid sequence, which is substantially identical to an amino acid disclosed herein, e.g., at least 80%, 85%, 90%, 92%, 95%, 97%, 98%, 99% or higher identical to a variable region of an antibody described herein, e.g., an antibody as described in Table 2, or encoded by the nucleotide sequence in Table 2; or which differs at least 1 or 5 residues, but less than 40, 30, 20, or 10 residues, from a variable region of an antibody described herein.

In some embodiments, the anti-TCRβV antibody molecule, e.g., anti-TCRβ V12 antibody molecule comprises at least one, two, three, or four antigen-binding regions, e.g., variable regions, having an amino acid sequence as set forth in Table 2, or a sequence substantially identical thereto (e.g., a sequence at least about 85%, 90%, 95%, 99% or more identical thereto, or which differs by no more than 1, 2, 5, 10, or 15 amino acid residues from the sequences shown in Table 2. In another embodiment, the anti-TCRβV antibody molecule, e.g., anti-TCRβ V12 antibody molecule includes a VH and/or VL domain encoded by a nucleic acid having a nucleotide sequence as set forth in Table 2, or a sequence substantially identical thereto (e.g., a sequence at least about 85%, 90%, 95%, 99% or more identical thereto, or which differs by no more than 3, 6, 15, 30, or 45 nucleotides from the sequences shown in Table 2.

In some embodiments, the anti-TCRβV antibody molecule, e.g., anti-TCRβ V12 antibody molecule comprises:

a VH domain comprising an amino acid sequence chosen from the amino acid sequence of SEQ ID NO: 23, SEQ ID NO:24 or SEQ ID NO:25, an amino acid sequence at least about 85%, 90%, 95%, 99% or more identical to the amino acid sequence SEQ ID NO: 23, SEQ ID NO:24 or SEQ ID NO:25, or an amino acid sequence which differs by no more than 1, 2, 5, 10, or 15 amino acid residues from the amino acid sequence of SEQ ID NO: 23, SEQ ID NO:24 or SEQ ID NO:25; and/or a VL domain comprising an amino acid sequence chosen from the amino acid sequence of SEQ ID NO: 26, SEQ ID NO: 27, SEQ ID NO: 28, SEQ ID NO: 29 or SEQ ID NO: 30, an amino acid sequence at least about 85%, 90%, 95%, 99% or more identical to the amino acid sequence of SEQ ID NO: 26, SEQ ID NO: 27, SEQ ID NO: 28, SEQ ID NO: 29 or SEQ ID NO: 30, or an amino acid sequence which differs by no more than 1, 2, 5, 10, or 15 amino acid residues from the amino acid sequence of SEQ ID NO: 26, SEQ ID NO: 27, SEQ ID NO: 28, SEQ ID NO: 29 or SEQ ID NO: 30.

In some embodiments, the anti-TCRβV antibody molecule, e.g., anti-TCRβ V12 antibody molecule comprises:

a VH domain comprising the amino acid sequence of SEQ ID NO: 23, an amino acid sequence at least about 85%, 90%, 95%, 99% or more identical to the amino acid sequence SEQ ID NO: 23, or an amino acid sequence which differs by no more than 1, 2, 5, 10, or 15 amino acid residues from the amino acid sequence of SEQ ID NO: 23; and a VL domain comprising the amino acid sequence of SEQ ID NO: 26, an amino acid sequence at least about 85%, 90%, 95%, 99% or more identical to the amino acid sequence SEQ ID NO: 26, or an amino acid sequence which differs by no more than 1, 2, 5, 10, or 15 amino acid residues from the amino acid sequence of SEQ ID NO: 26.

In some embodiments, the anti-TCRβV antibody molecule, e.g., anti-TCRβ V12 antibody molecule comprises:

a VH domain comprising the amino acid sequence of SEQ ID NO: 23, an amino acid sequence at least about 85%, 90%, 95%, 99% or more identical to the amino acid sequence SEQ ID NO: 23, or an amino acid sequence which differs by no more than 1, 2, 5, 10, or 15 amino acid residues from the amino acid sequence of SEQ ID NO: 23; and a VL domain comprising the amino acid sequence of SEQ ID NO: 27, an amino acid sequence at least about 85%, 90%, 95%, 99% or more identical to the amino acid sequence SEQ ID NO: 27, or an amino acid sequence which differs by no more than 1, 2, 5, 10, or 15 amino acid residues from the amino acid sequence of SEQ ID NO: 27.

In some embodiments, the anti-TCRβV antibody molecule, e.g., anti-TCRβ V12 antibody molecule comprises:

a VH domain comprising the amino acid sequence of SEQ ID NO: 23, an amino acid sequence at least about 85%, 90%, 95%, 99% or more identical to the amino acid sequence SEQ ID NO: 23, or an amino acid sequence which differs by no more than 1, 2, 5, 10, or 15 amino acid residues from the amino acid sequence of SEQ ID NO: 23; and a VL domain comprising the amino acid sequence of SEQ ID NO: 28, an amino acid sequence at least about 85%, 90%, 95%, 99% or more identical to the amino acid sequence SEQ ID NO: 28, or an amino acid sequence which differs by no more than 1, 2, 5, 10, or 15 amino acid residues from the amino acid sequence of SEQ ID NO: 28.

In some embodiments, the anti-TCRβV antibody molecule, e.g., anti-TCRβ V12 antibody molecule comprises:

a VH domain comprising the amino acid sequence of SEQ ID NO: 23, an amino acid sequence at least about 85%, 90%, 95%, 99% or more identical to the amino acid sequence SEQ ID NO: 23, or an amino acid sequence which differs by no more than 1, 2, 5, 10, or 15 amino acid residues from the amino acid sequence of SEQ ID NO: 23; and a VL domain comprising the amino acid sequence of SEQ ID NO: 29, an amino acid sequence at least about 85%, 90%, 95%, 99% or more identical to the amino acid sequence SEQ ID NO: 29, or an amino acid sequence which differs by no more than 1, 2, 5, 10, or 15 amino acid residues from the amino acid sequence of SEQ ID NO: 29.

In some embodiments, the anti-TCRβV antibody molecule, e.g., anti-TCRβ V12 antibody molecule comprises:

a VH domain comprising the amino acid sequence of SEQ ID NO: 23, an amino acid sequence at least about 85%, 90%, 95%, 99% or more identical to the amino acid sequence SEQ ID NO: 23, or an amino acid sequence which differs by no more than 1, 2, 5, 10, or 15 amino acid residues from the amino acid sequence of SEQ ID NO: 23; and a VL domain comprising the amino acid sequence of SEQ ID NO: 30, an amino acid sequence at least about 85%, 90%, 95%, 99% or more identical to the amino acid sequence SEQ ID NO: 30, or an amino acid sequence which differs by no more than 1, 2, 5, 10, or 15 amino acid residues from the amino acid sequence of SEQ ID NO: 30.

In some embodiments, the anti-TCRβV antibody molecule, e.g., anti-TCRβ V12 antibody molecule comprises:

a VH domain comprising the amino acid sequence of SEQ ID NO: 24 or 25, an amino acid sequence at least about 85%, 90%, 95%, 99% or more identical to the amino acid sequence SEQ ID NO: 24 or 25, or an amino acid sequence which differs by no more than 1, 2, 5, 10, or 15 amino acid residues from the amino acid sequence of SEQ ID NO: 24 or 25; and a VL domain comprising the amino acid sequence of SEQ ID NO: 26, an amino acid sequence at least about 85%, 90%, 95%, 99% or more identical to the amino acid sequence SEQ ID NO: 26, or an amino acid sequence which differs by no more than 1, 2, 5, 10, or 15 amino acid residues from the amino acid sequence of SEQ ID NO: 26.

In some embodiments, the anti-TCRβV antibody molecule, e.g., anti-TCRβ V12 antibody molecule comprises:

a VH domain comprising the amino acid sequence of SEQ ID NO: 24 or 25, an amino acid sequence at least about 85%, 90%, 95%, 99% or more identical to the amino acid sequence SEQ ID NO: 24 or 25, or an amino acid sequence which differs by no more than 1, 2, 5, 10, or 15 amino acid residues from the amino acid sequence of SEQ ID NO: 24 or 25; and a VL domain comprising the amino acid sequence of SEQ ID NO: 27, an amino acid sequence at least about 85%, 90%, 95%, 99% or more identical to the amino acid sequence SEQ ID NO: 27, or an amino acid sequence which differs by no more than 1, 2, 5, 10, or 15 amino acid residues from the amino acid sequence of SEQ ID NO: 27.

In some embodiments, the anti-TCRβV antibody molecule, e.g., anti-TCRβ V12 antibody molecule comprises:

a VH domain comprising the amino acid sequence of SEQ ID NO: 24 or 25, an amino acid sequence at least about 85%, 90%, 95%, 99% or more identical to the amino acid sequence SEQ ID NO: 24 or 25, or an amino acid sequence which differs by no more than 1, 2, 5, 10, or 15 amino acid residues from the amino acid sequence of SEQ ID NO: 24 or 25; and a VL domain comprising the amino acid sequence of SEQ ID NO: 28, an amino acid sequence at least about 85%, 90%, 95%, 99% or more identical to the amino acid sequence SEQ ID NO: 28, or an amino acid sequence which differs by no more than 1, 2, 5, 10, or 15 amino acid residues from the amino acid sequence of SEQ ID NO: 28.

In some embodiments, the anti-TCRβV antibody molecule, e.g., anti-TCRβ V12 antibody molecule comprises:

a VH domain comprising the amino acid sequence of SEQ ID NO: 24 or 25, an amino acid sequence at least about 85%, 90%, 95%, 99% or more identical to the amino acid sequence SEQ ID NO: 24 or 25, or an amino acid sequence which differs by no more than 1, 2, 5, 10, or 15 amino acid residues from the amino acid sequence of SEQ ID NO: 24 or 25; and a VL domain comprising the amino acid sequence of SEQ ID NO: 29, an amino acid sequence at least about 85%, 90%, 95%, 99% or more identical to the amino acid sequence SEQ ID NO: 29, or an amino acid sequence which differs by no more than 1, 2, 5, 10, or 15 amino acid residues from the amino acid sequence of SEQ ID NO: 29.

In some embodiments, the anti-TCRβV antibody molecule, e.g., anti-TCRβ V12 antibody molecule comprises:

a VH domain comprising the amino acid sequence of SEQ ID NO: 24 or 25, an amino acid sequence at least about 85%, 90%, 95%, 99% or more identical to the amino acid sequence SEQ ID NO: 24 or 25, or an amino acid sequence which differs by no more than 1, 2, 5, 10, or 15 amino acid residues from the amino acid sequence of SEQ ID NO: 24 or 25; and a VL domain comprising the amino acid sequence of SEQ ID NO: 30, an amino acid sequence at least about 85%, 90%, 95%, 99% or more identical to the amino acid sequence SEQ ID NO: 30, or an amino acid sequence which differs by no more than 1, 2, 5, 10, or 15 amino acid residues from the amino acid sequence of SEQ ID NO: 30.

In some embodiments, the anti-TCRβV antibody molecule, e.g., anti-TCRβ V12 antibody molecule comprises:

a VH domain comprising the amino acid sequence of SEQ ID NO: 25 or 23, an amino acid sequence at least about 85%, 90%, 95%, 99% or more identical to the amino acid sequence SEQ ID NO: 25 or 23, or an amino acid sequence which differs by no more than 1, 2, 5, 10, or 15 amino acid residues from the amino acid sequence of SEQ ID NO: 25 or 23; and a VL domain comprising the amino acid sequence of SEQ ID NO: 26, an amino acid sequence at least about 85%, 90%, 95%, 99% or more identical to the amino acid sequence SEQ ID NO: 26, or an amino acid sequence which differs by no more than 1, 2, 5, 10, or 15 amino acid residues from the amino acid sequence of SEQ ID NO: 26.

In some embodiments, the anti-TCRβV antibody molecule, e.g., anti-TCRβ V12 antibody molecule comprises:

a VH domain comprising the amino acid sequence of SEQ ID NO: 25 or 23, an amino acid sequence at least about 85%, 90%, 95%, 99% or more identical to the amino acid sequence SEQ ID NO: 25 or 23, or an amino acid sequence which differs by no more than 1, 2, 5, 10, or 15 amino acid residues from the amino acid sequence of SEQ ID NO: 25 or 23; and a VL domain comprising the amino acid sequence of SEQ ID NO: 27, an amino acid sequence at least about 85%, 90%, 95%, 99% or more identical to the amino acid sequence SEQ ID NO: 27, or an amino acid sequence which differs by no more than 1, 2, 5, 10, or 15 amino acid residues from the amino acid sequence of SEQ ID NO: 27.

In some embodiments, the anti-TCRβV antibody molecule, e.g., anti-TCRβ V12 antibody molecule comprises:

a VH domain comprising the amino acid sequence of SEQ ID NO: 25 or 23, an amino acid sequence at least about 85%, 90%, 95%, 99% or more identical to the amino acid sequence SEQ ID NO: 25 or 23, or an amino acid sequence which differs by no more than 1, 2, 5, 10, or 15 amino acid residues from the amino acid sequence of SEQ ID NO: 25 or 23; and a VL domain comprising the amino acid sequence of SEQ ID NO: 28, an amino acid sequence at least about 85%, 90%, 95%, 99% or more identical to the amino acid sequence SEQ ID NO: 28, or an amino acid sequence which differs by no more than 1, 2, 5, 10, or 15 amino acid residues from the amino acid sequence of SEQ ID NO: 28.

In some embodiments, the anti-TCRβV antibody molecule, e.g., anti-TCRβ V12 antibody molecule comprises:

a VH domain comprising the amino acid sequence of SEQ ID NO: 25 or 23, an amino acid sequence at least about 85%, 90%, 95%, 99% or more identical to the amino acid sequence SEQ ID NO: 25 or 23, or an amino acid sequence which differs by no more than 1, 2, 5, 10, or 15 amino acid residues from the amino acid sequence of SEQ ID NO: 25 or 23; and a VL domain comprising the amino acid sequence of SEQ ID NO: 29, an amino acid sequence at least about 85%, 90%, 95%, 99% or more identical to the amino acid sequence SEQ ID NO: 29, or an amino acid sequence which differs by no more than 1, 2, 5, 10, or 15 amino acid residues from the amino acid sequence of SEQ ID NO: 29.

In some embodiments, the anti-TCRβV antibody molecule, e.g., anti-TCRβ V12 antibody molecule comprises:

a VH domain comprising the amino acid sequence of SEQ ID NO: 25 or 23, an amino acid sequence at least about 85%, 90%, 95%, 99% or more identical to the amino acid sequence SEQ ID NO: 25 or 23, or an amino acid sequence which differs by no more than 1, 2, 5, 10, or 15 amino acid residues from the amino acid sequence of SEQ ID NO: 25 or 23; and a VL domain comprising the amino acid sequence of SEQ ID NO: 30, an amino acid sequence at least about 85%, 90%, 95%, 99% or more identical to the amino acid sequence SEQ ID NO: 30, or an amino acid sequence which differs by no more than 1, 2, 5, 10, or 15 amino acid residues from the amino acid sequence of SEQ ID NO: 30.

In some embodiments, the anti-TCRβV antibody molecule, e.g., anti-TCRβ V12 antibody molecule is a full antibody or fragment thereof (e.g., a Fab, $F(ab')_2$, Fv, or a single chain Fv fragment (scFv)). In embodiments, the anti-TCRβV antibody molecule, e.g., anti-TCRβ V6 (e.g., anti-TCRβ V6-5*01) antibody molecule is a monoclonal antibody or an antibody with single specificity. In some embodiments, the anti-TCRβV antibody molecule, e.g., anti-TCRβ V12 antibody molecule, can also be a humanized, chimeric, camelid, shark, or an in vitro-generated antibody molecule. In some embodiments, the anti-TCRβV antibody molecule, e.g., anti-TCRβ V12 antibody molecule is a humanized antibody molecule. The heavy and light chains of the anti-TCRβV antibody molecule, e.g., anti-TCRβ V12 antibody molecule can be full-length (e.g., an antibody can include at least one, and preferably two, complete heavy chains, and at least one, and preferably two, complete light chains) or can include an antigen-binding fragment (e.g., a Fab, $F(ab')_2$, Fv, a single chain Fv fragment, a single domain antibody, a diabody (dAb), a bivalent antibody, or bispecific antibody or fragment thereof, a single domain variant thereof, or a camelid antibody).

In some embodiments, the anti-TCRβV antibody molecule, e.g., anti-TCRβ V12 antibody molecule is in the form of a multispecific molecule, e.g., a bispecific molecule, e.g., as described herein.

In some embodiments, the anti-TCRβV antibody molecule, e.g., anti-TCRβ V12 antibody molecule has a heavy chain constant region (Fc) chosen from, e.g., the heavy chain constant regions of IgG1, IgG2, IgG3, IgG4, IgM, IgA1, IgA2, IgD, and IgE. In some embodiments, the Fc region is chosen from the heavy chain constant regions of IgG1, IgG2, IgG3, and IgG4. In some embodiments, the Fc region is chosen from the heavy chain constant region of IgG1 or IgG2 (e.g., human IgG1, or IgG2). In some embodiments, the heavy chain constant region is human IgG1.

In some embodiments, the anti-TCRβV antibody molecule, e.g., anti-TCRβ V12 antibody molecule has a light chain constant region chosen from, e.g., the light chain constant regions of kappa or lambda, preferably kappa (e.g., human kappa). In one embodiment, the constant region is altered, e.g., mutated, to modify the properties of the anti- TCRβV antibody molecule, e.g., anti-TCRβ V12 antibody molecule (e.g., to increase or decrease one or more of: Fc receptor binding, antibody glycosylation, the number of cysteine residues, effector cell function, or complement function). For example, the constant region is mutated at positions 296 (M to Y), 298 (S to T), 300 (T to E), 477 (H to K) and 478 (N to F) to alter Fc receptor binding (e.g., the mutated positions correspond to positions 132 (M to Y), 134 (S to T), 136 (T to E), 313 (H to K) and 314 (N to F) of SEQ ID NOs: 212 or 214; or positions 135 (M to Y), 137 (S to T), 139 (T to E), 316 (H to K) and 317 (N to F) of SEQ ID NOs: 215, 216, 217 or 218).

Antibody B-H.1 comprises a first chain comprising the amino acid sequence of SEQ ID NO: 3280 and a second chain comprising the amino acid sequence of SEQ ID NO: 3281.

Additional exemplary anti-TCRβ V12 antibodies of the disclosure are provided in Table 2. In some embodiments, the anti-TCRβ V12 is antibody B, e.g., humanized antibody B (antibody B-H), as provided in Table 2. In some embodiments, the anti-TCRβV antibody comprises one or more (e.g., all three) of a LC CDR1, LC CDR2, and LC CDR3 provided in Table 2; and/or one or more (e.g., all three) of a HC CDR1, HC CDR2, and HC CDR3 provided in Table 2, or a sequence with at least 95% identity thereto. In some embodiments, antibody B comprises a variable heavy chain (VH) and/or a variable light chain (VL) provided in Table 2, or a sequence with at least 95% identity thereto.

In some embodiments, the anti-TCRVB 12 antibody molecule (e.g., anti-TCRVB 12-3 or anti-TCRVB 12-4 antibody molecule) comprises a VH of B-H.1A, B-H.1B, B-H.1C, B-H.1D, B-H.1E, B-H.1F, B-H.1G, B-H.1H, B-H.1, B-H.2, B-H.3, B-H.4, B-H.5, or B-H.6, or a sequence with at least 80%, 85%, 90%, 95%, 96%, 97%, 98%, 99% or more identity thereto.

In some embodiments, the anti-TCRVB 12 antibody molecule (e.g., anti-TCRVB 12-3 or anti-TCRVB 12-4 antibody molecule) comprises a VL of B-H.1A, B-H.1B, B-H.1C, B-H.1D, B-H.1E, B-H.1F, B-H.1G, B-H.1H, B-H.1, B-H.2, B-H.3, B-H.4, B-H.5, or B-H.6, or a sequence with at least 80%, 85%, 90%, 95%, 96%, 97%, 98%, 99% or more identity thereto.

In some embodiments, the anti-TCRVB 12 antibody molecule (e.g., anti-TCRVB 12-3 or anti-TCRVB 12-4 antibody molecule) comprises a VH of B-H.1A, B-H.1B, B-H.1C, B-H.1D, B-H.1E, B-H.1F, B-H.1G, B-H.1H, B-H.1, B-H.2, B-H.3, B-H.4, B-H.5, or B-H.6, or a sequence with at least 80%, 85%, 90%, 95%, 96%, 97%, 98%, 99% or more identity thereto; and a VL of B-H.1A, B-H.1B, B-H.1C, B-H.1D, B-H.1E, B-H.1F, B-H.1G, B-H.1H, B-H.1, B-H.2, B-H.3, B-H.4, B-H.5, or B-H.6, or a sequence with at least 80%, 85%, 90%, 95%, 96%, 97%, 98%, 99% or more identity thereto.

TABLE 2

Amino acid and nucleotide sequences for murine and humanized antibody molecules which bind to TCRVB 12, e.g., TCRVB 12-3 or TCRVB 12-4. The antibody molecules include murine mAb Antibody B and humanized mAb Antibody B-H.1 to B-H.6. The amino acid the heavy and light chain CDRs, and the amino acid and nucleotide sequences of the heavy and light chain variable regions, and the heavy and light chains are shown.

| Antibody B (murine), also referred to as 16G8 | | |
|---|---|---|
| SEQ ID NO: 17 | HC CDR1 (Combined) | GFTFSNFGMH |
| SEQ ID NO: 18 | HC CDR2 (Combined) | YISSGSSTIYYADTLKG |
| SEQ ID NO: 19 | HC CDR3 (Combined) | RGEGAMDY |
| SEQ ID NO: 57 | HC CDR1 (Kabat) | NFGMH |
| SEQ ID NO: 58 | HC CDR2 (Kabat) | YISSGSSTIYYADTLKG |
| SEQ ID NO: 59 | HC CDR3 (Kabat) | RGEGAMDY |
| SEQ ID NO: 60 | HC CDR1 (Chothia) | GFTFSNF |
| SEQ ID NO: 61 | HC CDR2 (Chothia) | SSGSST |
| SEQ ID NO: 62 | HC CDR3 (Chothia) | RGEGAMDY |
| SEQ ID NO: 15 | VH | DVQLVESGGGLVQPGGSRKLSCAASGFTFSNFGMH WVRQAPDKGLEWVAYISSGSSTIYYADTLKGRFTIS RDNPKNTLFLQMTSLRSEDTAMYYCARRGEGAMD YWGQGTSVTVSS |
| SEQ ID NO: 20 | LC CDR1 (Combined) | RASSSVNYIY |
| SEQ ID NO: 21 | LC CDR2 (Combined) | YTSNLAP |
| SEQ ID NO: 22 | LC CDR3 (Combined) | QQFTSSPFT |
| SEQ ID NO: 63 | LC CDR1 (Kabat) | RASSSVNYIY |
| SEQ ID NO: 64 | LC CDR2 (Kabat) | YTSNLAP |
| SEQ ID NO: 65 | LC CDR3 (Kabat) | QQFTSSPFT |
| SEQ ID NO: 66 | LC CDR1 (Chothia) | RASSSVNYIY |
| SEQ ID NO: 67 | LC CDR2 (Chothia) | YTSNLAP |

TABLE 2-continued

Amino acid and nucleotide sequences for murine and humanized antibody molecules which bind to TCRVB 12, e.g., TCRVB 12-3 or TCRVB 12-4. The antibody molecules include murine mAb Antibody B and humanized mAb Antibody B-H.1 to B-H.6. The amino acid the heavy and light chain CDRs, and the amino acid and nucleotide sequences of the heavy and light chain variable regions, and the heavy and light chains are shown.

| | | |
|---|---|---|
| SEQ ID NO: 68 | LC CDR3 (Chothia) | QQFTSSPFT |
| SEQ ID NO: 16 | VL | ENVLTQSPAIMSASLGEKVTMSCRASSSVNYIYWY QQKSDASPKLWIYYTSNLAPGVPTRFSGSGSGNSYS LTISSMEGEDAATYYCQQFTSSPFTFGSGTKLEIK |

Antibody B humanized (B-H)

Antibody B-H.1A HC-1

| | | |
|---|---|---|
| SEQ ID NO: 17 | HC CDR1 (Combined) | GFTFSNFGMH |
| SEQ ID NO: 18 | HC CDR2 (Combined) | YISSGSSTIYYADTLKG |
| SEQ ID NO: 19 | HC CDR3 (Combined) | RGEGAMDY |
| SEQ ID NO: 3438 | VH | EVQLVESGGGLVQPGGSLRLSCAASGFTFSNFGMH WVRQAPGKGLEWVSYISSGSSTIYYADTLKGRFTIS RDNAKNSLYLQMNSLRAEDTAVYYCARRGEGAM DYWGQGTTVTVSS |
| SEQ ID NO: 31 | DNA VH | GAGGTGCAGCTGGTTGAATCTGGCGGAGGATTG GTTCAGCCTGGCGGCTCTCTGAGACTGTCTTGTG CCGCTTCTGGCTTCACCTTCTCCAACTTCGGCATG CACTGGGTCCGACAGGCCCCTGGAAAAGGACTG GAATGGGTGTCCTACATCTCCTCCGGCTCCTCCA CCATCTACTACGCTGACACCCTGAAGGGCAGATT CACCATCTCTCGGGACAACGCCAAGAACTCCCTG TACCTGCAGATGAACAGCCTGAGAGCCGAGGAC ACCGCCGTGTACTACTGTGCTAGAAGAGGCGAG GGCGCCATGGATTATTGGGGCCAGGGAACCACA GTGACCGTGTCTAGC |

Antibody B-H.1B UC-2

| | | |
|---|---|---|
| SEQ ID NO: 17 | HC CDR1 (Combined) | GFTFSNFGMH |
| SEQ ID NO: 18 | HC CDR2 (Combined) | YISSGSSTIYYADTLKG |
| SEQ ID NO: 19 | HC CDR3 (Combined) | RGEGAMDY |
| SEQ ID NO: 25 | VH | EVQLVESGGGLVQPGGSLRLSCAASGFTFSNFGMH WVRQAPGKGLEWVSYISSGSSTIYYADTLKGRFTIS RDNSKNTLYLQMNSLRAEDTAVYYCARRGEGAM DYWGQGTTVTVSS |
| SEQ ID NO: 32 | DNA VH | GAGGTGCAGCTGGTTGAATCTGGCGGAGGATTG GTTCAGCCTGGCGGCTCTCTGAGACTGTCTTGTG CCGCTTCTGGCTTCACCTTCTCCAACTTCGGCATG CACTGGGTCCGACAGGCCCCTGGAAAAGGACTG GAATGGGTGTCCTACATCTCCTCCGGCTCCTCCA CCATCTACTACGCTGACACCCTGAAGGGCAGATT CACCATCAGCCGGGACAACTCCAAGAACACCCT GTACCTGCAGATGAACTCCCTGAGAGCCGAGGA CACCGCCGTGTACTACTGTGCTAGAAGAGGCGA GGGCGCCATGGATTATTGGGGCCAGGGAACCAC AGTGACCGTGTCTAGC |

Antibody B-H.1C HC-3

| | | |
|---|---|---|
| SEQ ID NO: 17 | HC CDR1 (Combined) | GFTFSNFGMH |
| SEQ ID NO: 18 | HC CDR2 (Combined) | YISSGSSTIYYADTLKG |
| SEQ ID NO: 19 | HC CDR3 (Combined) | RGEGAMDY |
| SEQ ID NO: 23 | VH | QVQLVESGGGVVQPGRSLRLSCAASGFTFSNFGMH WVRQAPGKGLEWVAYISSGSSTIYYADTLKGRFTIS RDNSKNTLYLQMNSLRAEDTAVYYCARRGEGAM DYWGQGTTVTVSS |

TABLE 2-continued

Amino acid and nucleotide sequences for murine and humanized antibody molecules which bind to TCRVB 12, e.g., TCRVB 12-3 or TCRVB 12-4. The antibody molecules include murine mAb Antibody B and humanized mAb Antibody B-H.1 to B-H.6. The amino acid the heavy and light chain CDRs, and the amino acid and nucleotide sequences of the heavy and light chain variable regions, and the heavy and light chains are shown.

| | | |
|---|---|---|
| SEQ ID NO: 33 | DNA VH | CAGGTGCAGCTGGTGGAATCTGGTGGCGGAGTT GTGCAGCCTGGCAGATCCCTGAGACTGTCTTGTG CCGCCTCTGGCTTCACCTTCTCCAACTTCGGCATG CACTGGGTCCGACAGGCCCCTGGAAAAGGATTG GAGTGGGTCGCCTACATCTCCTCCGGCTCCTCCA CCATCTACTACGCTGACACCCTGAAGGGCAGATT CACCATCAGCCGGGACAACTCCAAGAACACCCT GTACCTGCAGATGAACTCCCTGAGAGCCGAGGA CACCGCCGTGTACTACTGTGCTAGAAGAGGCGA GGGCGCCATGGATTATTGGGGCCAGGGAACCAC AGTGACCGTGTCTAGC |
| **Antibody B-H.1D LC-1** | | |
| SEQ ID NO: 20 | LC CDR1 (Combined) | RASSSVNYIY |
| SEQ ID NO: 21 | LC CDR2 (Combined) | YTSNLAP |
| SEQ ID NO: 22 | LC CDR3 (Combined) | QQFTSSPFT |
| SEQ ID NO: 26 | VL | DNQLTQSPSFLSASVGDRVTITCRASSSVNYIYWYQ QKPGKAPKLLIYYTSNLAPGVPSRFSGSGSGNEYTL TISSLQPEDFATYYCQQFTSSPFTFGQGTKLEIK |
| SEQ ID NO: 34 | DNA VL | GATAACCAGCTGACCCAGTCTCCTAGCTTCCTGT CTGCCTCTGTGGGCGACAGAGTGACAATTACCTG CCGGGCCTCCTCCTCCGTGAACTACATCTACTGG TATCAGCAGAAGCCCGGCAAGGCCCCTAAGCTG TGCCCTCTAGATTTTCCGGATCTGGCTCCGGCAA CGAGTATACCCTGACAATCTCCAGCCTGCAGCCT GAGGACTTCGCCACCTACTACTGCCAGCAGTTCA CCTCCTCTCCATTCACCTTTGGCCAGGGCACCAA GCTGGAAATCAAA |
| **Antibody B-H.1E LC-2** | | |
| SEQ ID NO: 20 | LC CDR1 (Combined) | RASSSVNYIY |
| SEQ ID NO: 21 | LC CDR2 (Combined) | YTSNLAP |
| SEQ ID NO: 22 | LC CDR3 (Combined) | QQFTSSPFT |
| SEQ ID NO: 27 | VL | DNQLTQSPSSLSASVGDRVTITCRASSSVNYIYWYQ QKPGKAPKLLIYYTSNLAPGVPSRFSGSGSGNDYTL TISSLQPEDFATYYCQQFTSSPFTFGQGTKLEIK |
| SEQ ID NO: 35 | DNA VL | ATAACCAGCTGACCCAGTCTCCTTCCAGCCTGTC TGCTTCTGTGGGCGACAGAGTGACAATTACCTGC CGGGCCTCCTCCTCCGTGAACTACATCTACTGGT ATCAGCAGAAGCCCGGCAAGGCCCCTAAGCTGC TGATCTACTACACCTCCAATCTGGCCCCTGGCGT GCCCTCTAGATTTTCCGGATCTGGCTCCGGCAAC GACTATACCCTGACAATCTCCAGCCTGCAGCCTG AGGACTTCGCCACCTACTACTGCCAGCAGTTCAC CTCCTCTCCATTCACCTTTGGCCAGGGCACCAAG CTGGAAATCAAA |
| **Antibody B-H.1F C-3** | | |
| SEQ ID NO: 20 | LC CDR1 (Combined) | RASSSVNYIY |
| SEQ ID NO: 21 | LC CDR2 (Combined) | YTSNLAP |
| SEQ ID NO: 22 | LC CDR3 (Combined) | QQFTSSPFT |
| SEQ ID NO: 28 | VL | ENVLTQSPATLSVSPGERATLSCRASSSVNYIYWYQ QKPGQAPRLLIYYTSNLAPGIPARFSGSGSGNEYTL TISSLQSEDFAVYYCQQFTSSPFTFGQGTKLEIK |
| SEQ ID NO: 36 | DNA VL | GAGAATGTGCTGACCCAGTCTCCTGCCACACTGT CTGTTAGCCCTGGCGAGAGAGCTACCCTGAGCTG CAGAGCCTCTTCCTCCGTGAACTACATCTACTGG TATCAGCAGAAGCCCGGCCAGGCTCCTAGACTGC |

TABLE 2-continued

Amino acid and nucleotide sequences for murine and humanized antibody molecules which bind to TCRVB 12, e.g., TCRVB 12-3 or TCRVB 12-4. The antibody molecules include murine mAb Antibody B and humanized mAb Antibody B-H.1 to B-H.6. The amino acid the heavy and light chain CDRs, and the amino acid and nucleotide sequences of the heavy and light chain variable regions, and the heavy and light chains are shown.

| | | |
|---|---|---|
| | | TGATCTACTACACCTCCAATCTGGCCCCTGGCAT<br>CCCTGCCAGATTTTCCGGATCTGGCTCCGGCAAC<br>GAGTATACCCTGACCATCTCCAGCCTGCAGTCCG<br>AGGACTTTGCTGTGTACTATTGCCAGCAGTTCAC<br>AAGCAGCCCTTTCACCTTTGGCCAGGGCACCAAG<br>CTGGAAATCAAA |
| **Antibody B-H.1G LC-4** | | |
| SEQ ID NO: 20 | LC CDR1 (Combined) | RASSSVNYIY |
| SEQ ID NO: 21 | LC CDR2 (Combined) | YTSNLAP |
| SEQ ID NO: 22 | LC CDR3 (Combined) | QQFTSSPFT |
| SEQ ID NO: 29 | VL | QNVLTQPPSASGTPGQRVTISCRASSSVNYIYWYQQ<br>LPGTAPKLLIYYTSNLAPGVPDRFSGSGSGNSYSLAI<br>SGLRSEDEADYYCQQFTSSPFTFGTGTKVTVL |
| SEQ ID NO: 37 | DNA VL | CAGAATGTGCTGACCCAACCTCCTTCCGCCTCTG<br>GCACACCTGGACAGAGAGTGACAATCTCCTGCC<br>GGGCCTCCTCCTCCGTGAACTACATCTACTGGTA<br>TCAGCAGCTGCCCGGCACCGCTCCTAAACTGCTG<br>ATCTACTACACCTCCAATCTGGCCCCTGGCGTGC<br>CCGATAGATTTTCCGGATCTGGCTCCGGCAACTC<br>CTACAGCCTGGCTATCTCTGGCCTGAGATCTGAG<br>GACGAGGCCGACTACTACTGCCAGCAGTTCACCT<br>CCTCTCCATTCACCTTTGGCACCGGCACCAAAGT<br>GACAGTTCTT |
| **Antibody B-H.1H LC-5** | | |
| SEQ ID NO: 20 | LC CDR1 (Combined) | RASSSVNYIY |
| SEQ ID NO: 21 | LC CDR2 (Combined) | YTSNLAP |
| SEQ ID NO: 22 | LC CDR3 (Combined) | QQFTSSPFT |
| SEQ ID NO: 30 | VL | SNELTQPPSVSVSPGQTARITCRASSSVNYIYWYQQ<br>KSGQAPVLVIYYTSNLAPGIPERFSGSGSGNMYTLT<br>ISGAQVEDEADYYCQQFTSSPFTFGTGTKVTVL |
| SEQ ID NO: 38 | DNA VL | TCTAATGAGCTGACCCAGCCTCCTTCCGTGTCCG<br>TGTCTCCTGGACAGACCGCCAGAATTACCTGCCG<br>GGCCTCCTCCTCCGTGAACTACATCTACTGGTAT<br>CAGCAGAAGTCCGGCCAGGCTCCTGTGCTCGTGA<br>TCTACTACACCTCCAATCTGGCCCCTGGCATCCC<br>TGAGAGATTCTCCGGATCTGGCTCCGGCAACATG<br>TACACCCTGACCATCTCTGGCGCCCAGGTGGAAG<br>ATGAGGCCGACTACTACTGCCAGCAGTTCACCTC<br>CTCTCCATTCACCTTTGGCACCGGCACCAAAGTG<br>ACAGTTCTT |
| **Antibody B-H.1** | | |
| SEQ ID NO: 3280 | Chain 1: Fc only | METDTLLLWVLLLWVPGSTGDKTHTCPPCPAPELL<br>GGPSVFLFPPKPKDTLMISRTPEVTCVVVDVSHEDP<br>EVKFNWYVDGVEVHNAKTKPREEQYNSTYRVVSV<br>LTVLHQDWLNGKEYKCKVSNKALPAPIEKTISKAK<br>GQPREPQVYTLPPCREEMTKNQVSLWCLVKGFYPS<br>DIAVEWESNGQPENNYKTTPPVLDSDGSFFLYSKLT<br>VDKSRWQQGNVFSCSVMHEALHNRFTQKSLSLSP<br>GK |
| SEQ ID NO: 3281 | Chain2: humanized B-H scFv | METDTLLLWVLLLWVPGSTGEVQLVESGGGLVQP<br>GGSLRLSCAASGFTFSNFGMHWVRQAPGKGLEWV<br>SYISSGSSTIYYADTLKGRFTISRDNSKNTLYLQMNS<br>LRAEDTAVYYCARRGEGAMDYWGQGTTVTVSSG<br>GGGSGGGGSGGGGSGGGGSDNQLTQSPSFLSASVG<br>DRVTITCRASSSVNYIYWYQQKPGKAPKLLIYYTSN<br>LAPGVPSRFSGSGSGNEYTLTISSLQPEDFATYYCQ<br>QFTSSPFTFGQGTKLEIKGGGGSDKTHTCPPCPAPE<br>LLGGPSVFLFPPKPKDTLMISRTPEVTCVVVDVSHE<br>DPEVKFNWYVDGVEVHNAKTKPREEQYNSTYRVV |

TABLE 2-continued

Amino acid and nucleotide sequences for murine and humanized antibody molecules which bind to TCRVB 12, e.g., TCRVB 12-3 or TCRVB 12-4. The antibody molecules include murine mAb Antibody B and humanized mAb Antibody B-H.1 to B-H.6. The amino acid the heavy and light chain CDRs, and the amino acid and nucleotide sequences of the heavy and light chain variable regions, and the heavy and light chains are shown.

| | | |
|---|---|---|
| | | SVLTVLHQDWLNGKEYKCKVSNKALPAPIEKTISK<br>AKGQPREPQVCTLPPSREEMTKNQVSLSCAVKGFY<br>PSDIAVEWESNGQPENNYKTTPPVLDSDGSFFLVSK<br>LTVDKSRWQQGNVFSCSVMHEALHNHYTQKSLSL<br>SPGKGGGGSGGGGSGLNDIFEAQKIEWHE |
| SEQ ID NO: 3642 | scFv | EVQLVESGGGLVQPGGSLRLSCAASGFTFSNFGMH<br>WVRQAPGKGLEWVSYISSGSSTIYYADTLKGRFTIS<br>RDNSKNTLYLQMNSLRAEDTAVYYCARRGEGAM<br>DYWGQGTTVTVSSGGGGSGGGGSGGGGSGGGGS<br>DNQLTQSPSFLSASVGDRVTITCRASSSVNYIYWYQ<br>QKPGKAPKLLIYYTSNLAPGVPSRFSGSGSGNEYTL<br>TISSLQPEDFATYYCQQFTSSPFTFGQGTKLEIK |
| | Antibody B-H.2 | |
| SEQ ID NO: 1338 | scFv | EVQLVESGGGLVQPGGSLRLSCAASGFTFSNFGMH<br>WVRQAPGKGLEWVSYISSGSSTIYYADTLKGRFTIS<br>RDNSKNTLYLQMNSLRAEDTAVYYCARRGEGAM<br>DYWGQGTTVTVSSGGGGSGGGGSGGGGSGGGGS<br>DNQLTQSPSSLSASVGDRVTITCRASSSVNYIYWYQ<br>QKPGKAPKLLIYYTSNLAPGVPSRFSGSGSGNDYTL<br>TISSLQPEDFATYYCQQFTSSPFTFGQGTKLEIK |
| | Antibody B-H.3 | |
| SEQ ID NO: 1339 | scFv | EVQLVESGGGLVQPGGSLRLSCAASGFTFSNFGMH<br>WVRQAPGKGLEWVSYISSGSSTIYYADTLKGRFTIS<br>RDNSKNTLYLQMNSLRAEDTAVYYCARRGEGAM<br>DYWGQGTTVTVSSGGGGSGGGGSGGGGSGGGGSS<br>NELTQPPSVSVSPGQTARITCRASSSVNYIYWYQQK<br>SGQAPVLVIYYTSNLAPGIPERFSGSGSGNMYTLTIS<br>GAQVEDEADYYCQQFTSSPFTFGTGTKVTVL |
| | Antibody B-H.4 | |
| SEQ ID NO: 1340 | scFv | QVQLVESGGGVVQPGRSLRLSCAASGFTFSNFGMH<br>WVRQAPGKGLEWVAYISSGSSTIYYADTLKGRFTIS<br>RDNSKNTLYLQMNSLRAEDTAVYYCARRGEGAM<br>DYWGQGTTVTVSSGGGGSGGGGSGGGGSGGGGS<br>DNQLTQSPSFLSASVGDRVTITCRASSSVNYIYWYQ<br>QKPGKAPKLLIYYTSNLAPGVPSRFSGSGSGNEYTL<br>TISSLQPEDFATYYCQQFTSSPFTFGQGTKLEIK |
| | Antibody B-H.5 | |
| SEQ ID NO: 1341 | scFv | QVQLVESGGGVVQPGRSLRLSCAASGFTFSNFGMH<br>WVRQAPGKGLEWVAYISSGSSTIYYADTLKGRFTIS<br>RDNSKNTLYLQMNSLRAEDTAVYYCARRGEGAM<br>DYWGQGTTVTVSSGGGGSGGGGSGGGGSGGGGS<br>DNQLTQSPSSLSASVGDRVTITCRASSSVNYIYWYQ<br>QKPGKAPKLLIYYTSNLAPGVPSRFSGSGSGNDYTL<br>TISSLQPEDFATYYCQQFTSSPFTFGQGTKLEIK |
| | Antibody B-H.6 | |
| SEQ ID NO: 1342 | scFv | QVQLVESGGGVVQPGRSLRLSCAASGFTFSNFGMH<br>WVRQAPGKGLEWVAYISSGSSTIYYADTLKGRFTIS<br>RDNSKNTLYLQMNSLRAEDTAVYYCARRGEGAM<br>DYWGQGTTVTVSSGGGGSGGGGSGGGGSGGGGSS<br>NELTQPPSVSVSPGQTARITCRASSSVNYIYWYQQK<br>SGQAPVLVIYYTSNLAPGIPERFSGSGSGNMYTLTIS<br>GAQVEDEADYYCQQFTSSPFTFGTGTKVTVL |

TABLE 3

| Constant region amino acid sequences of human IgG heavy chains and human kappa light chain | | |
|---|---|---|
| Human kappa constant region SEQ ID NO: 39 | LC | RTVAAPSVFI FPPSDEQLKS GTASVVCLLN NFYPREAKVQ<br>WKVDNALQSG NSQESVTEQD SKDSTYSLSS TLTLSKADYE<br>KHKVYACEVT HQGLSSPVTK SFNRGEC |
| IgG4 (S228P) mutant constant region (EU Numbering) SEQ ID NO: 40 | HC | ASTKGPSVFPLAPCSRSTSESTAALGCLVKDYFPEPVTVSWNSGALTSG<br>VHTFPAVLQSSGLYSLSSVVTVPSSSLGTKTYTCNVDHKPSNTKVDKR<br>VESKYGPPCPPCPAPEFLGGPSVFLFPPKPKDTLMISRTPEVTCVVVD<br>VSQEDPEVQFNWYVDGVEVHNAKTKPREEQFNSTYRVVSVLTVLHQDW<br>LNGKEYKCKVSNKGLPSSIEKTISKAKGQPREPQVYTLPPSQEEMTKNQ<br>VSLTCLVKGFYPSDIAVEWESNGQPENNYKTTPPVLDSDGSFFLYSRLT<br>VDKSRWQEGNVFSCSVMHEALHNHYTQKSLSLSLG |
| IgG1 wild type SEQ ID NO: 41 | HC | ASTKGPSVFPLAPSSKSTSGGTAALGCLVKDYFPEPVTVSWNSGALTSG<br>VHTFPAVLQSSGLYSLSSVVTVPSSSLGTQTYICNVNHKPSNTKVDKRV<br>EPKSCDKTHTCPPCPAPELLGGPSVFLFPPKPKDTLMISRTPEVTCVVVD<br>VSHEDPEVKFNWYVDGVEVHNAKTKPREEQYNSTYRVVSVLTVLHQ<br>DWLNGKEYKCKVSNKALPAPIEKTISKAKGQPREPQVYTLPPSREEMT<br>KNQVSLTCLVKGFYPSDIAVEWESNGQPENNYKTTPPVLDSDGSFFLY<br>SKLTVDKSRWQQGNVFSCSVMHEALHNHYTQKSLSLSPGK |
| IgG1 (N297A) mutant constant region (EU Numbering) SEQ ID NO: 42 | HC | ASTKGPSVFPLAPSSKSTSGGTAALGCLVKDYFPEPVTVSWNSGALTSG<br>VHTFPAVLQSSGLYSLSSVVTVPSSSLGTQTYICNVNHKPSNTKVDKRV<br>EPKSCDKTHTCPPCPAPELLGGPSVFLFPPKPKDTLMISRTPEVTCVVVD<br>VSHEDPEVKFNWYVDGVEVHNAKTKPREEQYASTYRVVSVLTVLHQ<br>DWLNGKEYKCKVSNKALPAPIEKTISKAKGQPREPQVYTLPPSREEMT<br>KNQVSLTCLVKGFYPSDIAVEWESNGQPENNYKTTPPVLDSDGSFFLY<br>SKLTVDKSRWQQGNVFSCSVMHEALHNHYTQKSLSLSPGK |
| IgM constant delta CDC (P311A, P313S) SEQ ID NO: 73 | HC | GSASAPTLFPLVSCENSPSDTSSVAVGCLAQDFLPDSITFSWKYKNNS<br>DISSTRGFPSVLRGGKYAATSQVLLPSKDVMQGTDEHVVCKVQHPNGNK<br>EKNVPLPVIAELPPKVSVFVPPRDGFFGNPRKSKLICQATGFSPRQIQ<br>VSWLREGKQVGSGVTTDQVQAEAKESGPTTYKVTSTLTIKESDWLGQSM<br>FTCRVDHRGLTFQQNASSMCVPDQDTAIRVFAIPPSFASIFLTKSTKLT<br>CLVTDLTTYDSVTISWTRQNGEAVKTHTNISESHPNATFSAVGEASICE<br>DDWNSGERFTCTVTHTDLASSLKQTISRPKGVALHRPDVYLLPPAREQL<br>NLRESATITCLVTGFSPADVFVQWMQRGQPLSPEKYVTSAPMPEPQAP<br>GRYFAHSILTVSEEEWNTGETYTCVVAHEALPNRVTERTVDKSTGKPT<br>LYNVSLVMSDTAGTCY |
| IgGA1 SEQ ID NO: 74 | HC | ASPTSPKVFPLSLCSTQPDGNVVIACLVQGFFPQEPLSVTWSESGQGVT<br>ARNFPPSQDASGDLYTTSSQLTLPATQCLAGKSVTCHVKHYTNPSQDVT<br>VPCPVPSTPPTPSPSTPPTPSPSCCHPRLSLHRPALEDLLLGSEANLTC<br>TLTGLRDASGVTFTWTPSSGKSAVQGPPERDLCGCYSVSSVLPGCAEPW<br>NHGKTFTCTAAYPESKTPLTATLSKSGNTFRPEVHLLPPPSEELALNEL<br>VTLTCLARGFSPKDVLVRWLQGSQELPREKYLTWASRQEPSQGTTTFA<br>VTSILRVAAEDWKKGDTFSCMVGHEALPLAFTQKTIDRLAGKPTHVN<br>VSVVMAEVDGTCY |
| IgGA2 SEQ ID NO: 75 | HC | ASPTSPKVFPLSLDSTPQDGNVVVACLVQGFFPQEPLSVTWSESGQNV<br>TARNFPPSQDASGDLYTTTSSQLTLPATQCPDGKSVTCHVKHYTNSSQD<br>VTVPCRVPPPPPCCHPRLSLHRPALEDLLLGSEANLTCTLTGLRDASG<br>ATFTWTPSSGKSAVQGPPERDLCGCYSVSSVLPGCAQPWNHGETFTCT<br>AAHPELKTPLTANITKSGNTFRPEVHLLPPPSEELALNELVTLTCLAR<br>GFSPKDVLVRWLQGSQELPREKYLTWASRQEPSQGTTTYAVTSILRVA<br>AEDWKKGETFSCMVGHEALPLAFTQKTIDRMAGKPTHINVSVVMAEAD<br>GTCY |
| Human Ig_J chain SEQ ID NO: 76 | HC | MKNHLLFWGVLAVFIKAVHVKAQEDERIVLVDNKCKCARITSRIIRSSE<br>DPNEDIVERNIRIIVPLNNRENISDPTSPLRTRFVYHLSDLCKKCDPTE<br>VELDNQIVTATQSNICDEDSATETCYTYDRNKCYTAVVPLVYGGETKMV<br>ETALTPDACYPD |

Anti-TCRβ V Antibodies

Accordingly, in one aspect, the disclosure provides an anti-TCRβV antibody molecule that binds to human TCRβ V5. In some embodiments, the TCRβ V5 subfamily comprises TCRβ V5-5*01, TCRβ V5-6*01, TCRβ V5-4*01, TCRβ V5-8*01, TCRβ V5-1*01, or a variant thereof.

Exemplary anti-TCRβ V5 antibodies of the disclosure are provided in Table 10. In some embodiments, the anti-TCRβ V5 is antibody C, e.g., humanized antibody C (antibody C-H), as provided in Table 10. In some embodiments, the anti-TCRβV antibody comprises one or more (e.g., all three) of a LC CDR1, LC CDR2, and LC CDR3 provided in Table 10; and/or one or more (e.g., all three) of a HC CDR1, HC CDR2, and HC CDR3 provided in Table 10, or a sequence with at least 95% identity thereto. In some embodiments, antibody C comprises a variable heavy chain (VH) and/or a variable light chain (VL) provided in Table 10, or a sequence with at least 95% identity thereto.

TABLE 10

Amino acid sequences for anti TCRβ V5 antibodies
Amino acid and nucleotide sequences for murine and humanized antibody molecules which bind to TCRVB 5 (e.g., TCRVB 5-5 or TCRVB 5-6). The amino acid the heavy and light chain CDRs, and the amino acid and nucleotide sequences of the heavy and light chain variable regions, and the heavy and light chains are shown.

| | | |
|---|---|---|
| Murine antibody C, also referred to as 4H11 | | |
| SEQ ID NO: 1315 | HC CDR1 (Kabat) | AYGVN |
| SEQ ID NO: 1316 | HC CDR2 (Kabat) | MIWGDGNTDYNSALKS |
| SEQ ID NO: 1317 | HC CDR3 (Kabat) | DRVTATLYAMDY |
| SEQ ID NO: 1318 | HC CDR1 (Chothia) | GFSLTAY |
| SEQ ID NO: 1319 | HC CDR2 (Chothia) | WGDGN |
| SEQ ID NO: 1317 | HC CDR3 (Chothia) | DRVTATLYAMDY |
| SEQ ID NO: 1320 | HC CDR1 (Combined) | GFSLTAYGVN |
| SEQ ID NO: 1316 | HC CDR2 (Combined) | MIWGDGNTDYNSALKS |
| SEQ ID NO: 1317 | HC CDR3 (Combined) | DRVTATLYAMDY |
| SEQ ID NO: 1321 | LC CDR1 (Kabat) | SASQGISNYLN |
| SEQ ID NO: 1322 | LC CDR2 (Kabat) | YTSSLHS |
| SEQ ID NO: 1323 | LC CDR3 (Kabat) | QQYSKLPRT |
| SEQ ID NO: 1321 | LC CDR1 (Chothia) | SASQGISNYLN |
| SEQ ID NO: 1322 | LC CDR2 (Chothia) | YTSSLHS |
| SEQ ID NO: 1323 | LC CDR3 (Chothia) | QQYSKLPRT |
| SEQ ID NO: 1321 | LC CDR1 (Combined) | SASQGISNYLN |
| SEQ ID NO: 1322 | LC CDR2 (Combined) | YTSSLHS |
| SEQ ID NO: 1323 | LC CDR3 (Combined) | QQYSKLPRT |
| SEQ ID NO: 232 | VH | DIQMTQTTSSLSASLGDRVTISCSASQGISNYLNW YQQKPDGTVKLLIYYTSSLHSGVPSRFSGSGSGTD YSLTISNLEPEDIATYYCQQYSKLPRTFGGGTKVE IK |
| SEQ ID NO: 233 | VL | QVQLKESGPGLVAPSQSLSITCTVSGFSLTAYGVN WVRQPPGKGLEWLGMIWGDGNTDYNSALKSRL SISKDNSKSQVFLKMNSLQTDDTARYYCARDRV TATLYAMDYWGQGTSVTVSS |
| Humanized antibody C C-H-1 antibody | | |
| SEQ ID NO: 1315 | HC CDR1 (Kabat) | AYGVN |
| SEQ ID NO: 1316 | HC CDR2 (Kabat) | MIWGDGNTDYNSALKS |
| SEQ ID NO: 1317 | HC CDR3 (Kabat) | DRVTATLYAMDY |
| SEQ ID NO: 1318 | HC CDR1 (Chothia) | GFSLTAY |
| SEQ ID NO: 1319 | HC CDR2 (Chothia) | WGDGN |
| SEQ ID NO: 1317 | HC CDR3 (Chothia) | DRVTATLYAMDY |
| SEQ ID NO: 1320 | HC CDR1 (Combined) | GFSLTAYGVN |
| SEQ ID NO: 1316 | HC CDR2 (Combined) | MIWGDGNTDYNSALKS |
| SEQ ID NO: 1317 | HC CDR3 (Combined) | DRVTATLYAMDY |
| SEQ ID NO: 1321 | LC CDR1 (Kabat) | SASQGISNYLN |
| SEQ ID NO: 1322 | LC CDR2 (Kabat) | YTSSLHS |
| SEQ ID NO: 1323 | LC CDR3 (Kabat) | QQYSKLPRT |

TABLE 10-continued

Amino acid sequences for anti TCRβ V5 antibodies
Amino acid and nucleotide sequences for murine and humanized antibody molecules which bind to TCRVB 5 (e.g., TCRVB 5-5 or TCRVB 5-6). The amino acid the heavy and light chain CDRs, and the amino acid and nucleotide sequences of the heavy and light chain variable regions, and the heavy and light chains are shown.

| | | |
|---|---|---|
| SEQ ID NO: 1321 | LC CDR1 (Chothia) | SASQGISNYLN |
| SEQ ID NO: 1322 | LC CDR2 (Chothia) | YTSSLHS |
| SEQ ID NO: 1323 | LC CDR3 (Chothia) | QQYSKLPRT |
| SEQ ID NO: 1321 | LC CDR1 (Combined) | SASQGISNYLN |
| SEQ ID NO: 1322 | LC CDR2 (Combined) | YTSSLHS |
| SEQ ID NO: 1323 | LC CDR3 (Combined) | QQYSKLPRT |
| SEQ ID NO: 1324 | VL | DIQMTQSPSSLSASVGDRVTITCSASQGISNYLNWYQQTPGKAPKLLIYYTSSLHSGVPSRFSGSGSGTDYTFTISSLQPEDIATYYCQQYSKLPRTFGQGTKLQIT |
| SEQ ID NO: 1325 | VH | QVQLQESGPGLVRPSQTLSLTCTVSGFSLTAYGVNWVRQPPGRGLEWLGMIWGDGNTDYNSALKSRVTMLKDTSKNQFSLRLSSVTAADTAVYYCARDRVTATLYAMDYWGQGSLVTVSS |

Humanized antibody C Variable light chain (VL)

| | | | |
|---|---|---|---|
| SEQ ID NO: 3000 | VL | C-H-VL.1 | DIQMTQSPSFLSASVGDRVTITCSASQGISNYLNWYQQKPGKAVKLLIYYTSSLHSGVPSRFSGSGSGTEYTLTISSLQPEDFATYYCQQYSKLPRTFGGGTKVEIK |
| SEQ ID NO: 3001 | VL | C-H-VL.2 | DIQMTQSPSSLSASVGDRVTITCSASQGISNYLNWYQQKPGKAVKLLIYYTSSLHSGVPSRFSGSGSGTDYTLTISSLQPEDFATYYCQQYSKLPRTFGGGTKVEIK |
| SEQ ID NO: 3002 | VL | C-H-VL.3 | DIQMTQSPSSLSASVGDRVTITCSASQGISNYLNWYQQKPGKVVKLLIYYTSSLHSGVPSRFSGSGSGTDYTLTISSLQPEDVATYYCQQYSKLPRTFGGGTKVEIK |
| SEQ ID NO: 3003 | VL | C-H-VL.4 | DIQMTQSPSSLSASVGDRVTITCSASQGISNYLNWYQQKPGQAVKLLIYYTSSLHSGVPSRFSGSGSGTDYTLTISSLQPEDVATYYCQQYSKLPRTFGGGTKVEIK |
| SEQ ID NO: 3004 | VL | C-H-VL.5 | DIQMTQSPSSLSASVGDRVTITCSASQGISNYLNWYQQKPGKAVKLLIYYTSSLHSGVPSRFSGSGSGTDYTFTISSLQPEDIATYYCQQYSKLPRTFGGGTKVEIK |
| SEQ ID NO: 3005 | VL | C-H-VL.6 | DIQMTQSPSSLSASVGDRVTITCSASQGISNYLNWYQQKPGKTVKLLIYYTSSLHSGIPSRFSGSGSGTDYTLTIRSLQPEDFATYYCQQYSKLPRTFGGGTKVEIK |
| SEQ ID NO: 3006 | VL | C-H-VL.7 | AIQMTQSPSSLSASVGDRVTITCSASQGISNYLNWYQQKPGKAVKLLIYYTSSLHSGVPSRFSGSGSGTDYTLTISSLQPEDFATYYCQQYSKLPRTFGGGTKVEIK |
| SEQ ID NO: 3007 | VL | C-H-VL.8 | DIQMTQSPSSVSASVGDRVTITCSASQGISNYLNWYQQKPGKAVKLLIYYTSSLHSGVPSRFSGSGSGTDYTLTISSLQPEDFATYYCQQYSKLPRTFGGGTKVEIK |
| SEQ ID NO: 3008 | VL | C-H-VL.9 | DIQMTQSPSSLSASVGDRVTITCSASQGISNYLNWYQQKPGKAVKRLIYYTSSLHSGVPSRFSGSGSGTEYTLTISNLQPEDFATYYCQQYSKLPRTFGGGTKVEIK |
| SEQ ID NO: 3009 | VL | C-H-VL.10 | AIRMTQSPFSLSASVGDRVTITCSASQGISNYLNWYQQKPAKAVKLFIYYTSSLHSGVPSRFSGSGSGTDYTLTISSLQPEDFATYYCQQYSKLPRTFGGGTKVEIK |
| SEQ ID NO: 3010 | VL | C-H-VL.11 | DIQMTQSPSSLSASVGDRVTITCSASQGISNYLNWYQQKPGKAVKRLIYYTSSLHSGVPSRFSGSGSGTEYTLTISSLQPEDFATYYCQQYSKLPRTFGGGTKVEIK |
| SEQ ID NO: 3011 | VL | C-H-VL.12 | DIQMTQSPSTLSASVGDRVTITCSASQGISNYLNWYQQKPGKAVKLLIYYTSSLHSGVPSRFSGSGSGTEYTLTISSLQPDDFATYYCQQYSKLPRTFGGGTKVEIK |

TABLE 10-continued

Amino acid sequences for anti TCRβ V5 antibodies
Amino acid and nucleotide sequences for murine and humanized antibody molecules which bind to TCRVB 5 (e.g., TCRVB 5-5 or TCRVB 5-6). The amino acid the heavy and light chain CDRs, and the amino acid and nucleotide sequences of the heavy and light chain variable regions, and the heavy and light chains are shown.

| | | | |
|---|---|---|---|
| SEQ ID NO:3012 | VL | C-H-VL.13 | DIQMTQSPSSLSASVGDRVTITCSASQGISNYLNWYQQKPGKAVKSLIYYTSSLHSGVPSRFSGSGSGTDYTLTISSLQPEDFATYYCQQYSKLPRTFGGGTKVEIK |
| SEQ ID NO: 3013 | VL | C-H-VL.14 | DIQMTQSPSSLSASVGDRVTITCSASQGISNYLNWYQQKPGKAVKSLIYYTSSLHSGVPSKFSGSGSGTDYTLTISSLQPEDFATYYCQQYSKLPRTFGGGTKVEIK |
| SEQ ID NO: 3014 | VL | C-H-VL.15 | DIQMTQSPSSLSASVGDRVTITCSASQGISNYLNWYQQKPEKAVKSLIYYTSSLHSGVPSRFSGSGSGTDYTLTISSLQPEDFATYYCQQYSKLPRTFGGGTKVEIK |
| SEQ ID NO: 3015 | VL | C-H-VL.16 | DIQMTQSPSAMSASVGDRVTITCSASQGISNYLNWYQQKPGKVVKRLIYYTSSLHSGVPSRFSGSGSGTEYTLTISSLQPEDFATYYCQQYSKLPRTFGGGTKVEIK |
| SEQ ID NO: 3016 | VL | C-H-VL.17 | DIVMTQSPDSLAVSLGERATINCSASQGISNYLNWYQQKPGQPVKLLIYYTSSLHSGVPDRFSGSGSGTDYTLTISSLQAEDVAVYYCQQYSKLPRTFGGGTKVEIK |
| SEQ ID NO: 3017 | VL | C-H-VL.18 | EIVMTQSPGTLSLSPGERATLSCSASQGISNYLNWYQQKPGQAVKLLIYYTSSLHSGIPDRFSGSGSGTDYTLTISRLEPEDFAVYYCQQYSKLPRTFGGGTKVEIK |
| SEQ ID NO: 3018 | VL | C-H-VL.19 | EIVMTQSPPTLSLSPGERVTLSCSASQGISNYLNWYQQKPGQAVKLLIYYTSSLHSGIPARFSGSGSGTDYTLTISSLQPEDFAVYYCQQYSKLPRTFGGGTKVEIK |
| SEQ ID NO: 3019 | VL | C-H-VL.20 | EIVMTQSPPTLSLSPGERVTLSCSASQGISNYLNWYQQKPGQAVKLLIYYTSSLHSSIPARFSGSGSGTDYTLTISSLQPEDFAVYYCQQYSKLPRTFGGGTKVEIK |
| SEQ ID NO: 3020 | VL | C-H-VL.21 | EIVMTQSPATLSLSPGERATLSCSASQGISNYLNWYQQKPGQAVKLLIYYTSSLHSGIPARFSGSGSGTDYTLTISSLEPEDFAVYYCQQYSKLPRTFGGGTKVEIK |
| SEQ ID NO: 3021 | VL | C-H-VL.22 | EIVMTQSPATLSLSPGERATLSCSASQGISNYLNWYQQKPGQAVKLLIYYTSSLHSGIPARFSGSGSGTDYTLTISRLEPEDFAVYYCQQYSKLPRTFGGGTKVEIK |
| SEQ ID NO: 3022 | VL | C-H-VL.23 | EIVMTQSPATLSLSPGERATLSCSASQGISNYLNWYQQKPGQAVKLLIYYTSSLHSGIPDRFSGSGSGTDYTLTISRLEPEDFAVYYCQQYSKLPRTFGGGTKVEIK |
| SEQ ID NO: 3023 | VL | C-H-VL.24 | EIVMTQSPATLSLSPGERATLSCSASQGISNYLNWYQQKPGLAVKLLIYYTSSLHSGIPDRFSGSGSGTDYTLTISRLEPEDFAVYYCQQYSKLPRTFGGGTKVEIK |
| SEQ ID NO: 3024 | VL | C-H-VL.25 | DIQMIQSPSFLSASVGDRVSIICSASQGISNYLNWYLQKPGKSVKLFIYYTSSLHSGVSSRFSGRGSGTDYTLTIISLKPEDFAAYYCQQYSKLPRTFGGGTKVEIK |
| SEQ ID NO: 3025 | VL | C-H-VL.26 | EIVMTQSPATLSLSPGERATLSCSASQGISNYLNWYQQKPGQAVKLLIYYTSSLHSGIPARFSGSGSGTDYTLTISSLQPEDFAVYYCQQYSKLPRTFGGGTKVEIK |
| SEQ ID NO: 3026 | VL | C-H-VL.27 | EIVMTQSPATLSLSPGERATLSCSASQGISNYLNWYQQKPGQAVKLLIYYTSSLHSGIPARFSGSGPGTDYTLTISSLEPEDFAVYYCQQYSKLPRTFGGGTKVEIK |
| SEQ ID NO: 3027 | VL | C-H-VL.28 | DIVMTQTPLSLSVTPGQPASISCSASQGISNYLNWYLQKPGQSVKLLIYYTSSLHSGVPDRFSGSGSGTDYTLKISRVEAEDVGVYYCQQYSKLPRTFGGGTKVEIK |
| SEQ ID NO: 3028 | VL | C-H-VL.29 | DIVMTQTPLSLSVTPGQPASISCSASQGISNYLNWYLQKPGQPVKLLIYYTSSLHSGVPDRFSGSGSGTDYTLKISRVEAEDVGVYYCQQYSKLPRTFGGGTKVEIK |
| SEQ ID NO: 3029 | VL | C-H-VL.30 | DIVMTQSPAFLSVTPGEKVTITCSASQGISNYLNWYQQKPDQAVKLLIYYTSSLHSGVPSRFSGSGSGTDYTFTISSLEAEDAATYYCQQYSKLPRTFGGGTKVEIK |

TABLE 10-continued

Amino acid sequences for anti TCRβ V5 antibodies
Amino acid and nucleotide sequences for murine and humanized antibody molecules which bind to TCRVB 5 (e.g., TCRVB 5-5 or TCRVB 5-6). The amino acid the heavy and light chain CDRs, and the amino acid and nucleotide sequences of the heavy and light chain variable regions, and the heavy and light chains are shown.

| | | | |
|---|---|---|---|
| SEQ ID NO: 3030 | VL | C-H-VL.31 | DIVMTQSPLSLPVTPGEPASISCSASQGISNYLNWYLQKPGQSVKLLIYYTSSLHSGVPDRFSGSGSGTDYTLKISRVEAEDVGVYYCQQYSKLPRTFGGGTKVEIK |
| SEQ ID NO: 3031 | VL | C-H-VL.32 | DIVMTQTPLSLPVTPGEPASISCSASQGISNYLNWYLQKPGQSVKLLIYYTSSLHSGVPDRFSGSGSGTDYTLKISRVEAEDVGVYYCQQYSKLPRTFGGGTKVEIK |
| SEQ ID NO: 3032 | VL | C-H-VL.33 | EIVMTQSPATLSVSPGERATLSCSASQGISNYLNWYQQKPGQAVKLLIYYTSSLHSGIPARFSGSGSGTEYTLTISILQSEDFAVYYCQQYSKLPRTFGGGTKVEIK |
| SEQ ID NO: 3033 | VL | C-H-VL.34 | EIVMTQSPATLSVSPGERATLSCSASQGISNYLNWYQQKPGQAVKLLIYYTSSLHSGIPARFSGSGSGTEYTLTISSLQSEDFAVYYCQQYSKLPRTFGGGTKVEIK |
| SEQ ID NO: 3034 | VL | C-H-VL.35 | DIVMTQSPLSLPVTLGQPASISCSASQGISNYLNWYQQRPGQSVKRLIYYTSSLHSGVPDRFSGSGSGTDYTLKISRVEAEDVGVYYCQQYSKLPRTFGGGTKVEIK |
| SEQ ID NO: 3035 | VL | C-H-VL.36 | EITMTQSPAFMSATPGDKVNISCSASQGISNYLNWYQQKPGEAVKFIIYYTSSLHSGIPPRFSGSGYGTDYTLTINNIESEDAAYYYCQQYSKLPRTFGGGTKVEIK |
| SEQ ID NO: 3036 | VL | C-H-VL.37 | DIVMTQTPLSSPVTLGQPASISCSASQGISNYLNWYQQRPGQPVKLLIYYTSSLHSGVPDRFSGSGAGTDYTLKISRVEAEDVGVYYCQQYSKLPRTFGGGTKVEIK |
| SEQ ID NO: 3037 | VL | C-H-VL.38 | EIVMTQSPDFQSVTPKEKVTITCSASQGISNYLNWYQQKPDQSVKLLIYYTSSLHSGVPSRFSGSGSGTDYTLTINSLEAEDAATYYCQQYSKLPRTFGGGTKVEIK |
| SEQ ID NO: 3038 | VL | C-H-VL.39 | EIVMTQTPLSLSITPGEQASISCSASQGISNYLNWYLQKARPVVKLLIYYTSSLHSGVPDRFSGSGSGTDYTLKISRVEAEDFGVYYCQQYSKLPRTFGGGTKVEIK |
| SEQ ID NO: 3039 | VL | C-H-VL.40 | EIVMTQTPLSLSITPGEQASMSCSASQGISNYLNWYLQKARPVVKLLIYYTSSLHSGVPDRFSGSGSGTDYTLKISRVEAEDFGVYYCQQYSKLPRTFGGGTKVEIK |

Humanized antibody C Variable HEAVY chain (VH)

| | | | |
|---|---|---|---|
| SEQ ID NO: 3040 | VH | C-H-VH.1 | QVTLKESGPVLVKPTETLTLTCTVSGFSLTAYGVNWVRQPPGKALEWLGMIWGDGNTDYNSALKSRLTISKDNSKSQVVLTMTNMDPVDTATYYCARDRVTATLYAMDYWGQGTLVTVSS |
| SEQ ID NO: 3041 | VH | C-H-VH.2 | QVTLKESGPALVKPTETLTLTCTVSGFSLTAYGVNWVRQPPGKALEWLGMIWGDGNTDYNSALKSRLIISKDNSKSQVVLTMTNMDPVDTATYYCARDRVTATLYAMDYWGQGTLVTVSS |
| SEQ ID NO: 3042 | VH | C-H-VH.3 | QVTLKESGPALVKPTQTLTLTCTVSGFSLTAYGVNWVRQPPGKALEWLGMIWGDGNTDYNSALKSRLTISKDNSKSQVVLTMTNMDPVDTATYYCARDRVTATLYAMDYWGQGTLVTVSS |
| SEQ ID NO: 3043 | VH | C-H-VH.4 | QVQLQESGPGLVKPSGTLSLTCAVSGFSLTAYGVNWVRQPPGKGLEWLGMIWGDGNTDYNSALKSRLTISKDNSKSQVSLKLSSVTAADTAVYYCARDRVTATLYAMDYWGQGTLVTVSS |
| SEQ ID NO: 3044 | VH | C-H-VH.5 | QVTLKESGPTLVKPTQTLTLTCTVSGFSLTAYGVNWVRQPPGKALEWLGMIWGDGNTDYNSALKSRLTITKDNSKSQVVLTMTNMDPVDTATYYCARDRVTATLYAMDYWGQGTLVTVSS |
| SEQ ID NO: 3045 | VH | C-H-VH.6 | QVTLKESGPALVKPTQTLTLTCTVSGFSLTAYGVNWVRQPPGKALEWLGMIWGDGNTDYNSALKSRLTITKDNSKSQVVLTMTNMDPVDTATYYCARDRVTATLYAMDYWGQGTLVTVSS |
| SEQ ID NO: 3046 | VH | C-H-VH.7 | QVQLQESGPGLVKPSQTLSLTCTVSGFSLTAYGVNWVRQPPGKGLEWLGMIWGDGNTDYNSALKSRLTISKDNSKSQVSLKLSSVTAADTAVYYCARDRVTATLYAMDYWGQGTLVTVSS |
| SEQ ID NO: 3047 | VH | C-H-VH.8 | QVQLQESGPGLVKPSETLSLTCTVSGFSLTAYGVNWVRQPPGKGLEWLGMIWGDGNTDYNSALKSRLTISKDNSKSQVSLKLSSVTAADTAVYYCARDRVTATLYAMDYWGQGTLVTVSS |

TABLE 10-continued

Amino acid sequences for anti TCRβ V5 antibodies
Amino acid and nucleotide sequences for murine and humanized antibody molecules which bind to TCRVB 5 (e.g., TCRVB 5-5 or TCRVB 5-6). The amino acid the heavy and light chain CDRs, and the amino acid and nucleotide sequences of the heavy and light chain variable regions, and the heavy and light chains are shown.

| | | | |
|---|---|---|---|
| SEQ ID NO: 3048 | VH | C-H-VH.9 | QVQLQESGPGLVKPSQTLSLTCAVSGFSLTAYGVNWVRQPPGKGLEWLGMIWGDGNTDYNSALKSRLTISKDNSKSQVSLKLSSVTAADTAVYYCARDRVTATLYAMDYWGQGTLVTVSS |
| SEQ ID NO: 3049 | VH | C-H-VH.10 | QVQLQESGPGLVKPSDTLSLTCTVSGFSLTAYGVNWVRQPPGKGLEWLGMIWGDGNTDYNSALKSRLTISKDNSKSQVSLKLSSVTAADTAVYYCARDRVTATLYAMDYWGQGTLVTVSS |
| SEQ ID NO: 3050 | VH | C-H-VH.11 | QVQLQESGPGLVKPSQTLSLTCTVSGFSLTAYGVNWVRQHPGKGLEWLGMIWGDGNTDYNSALKSRLTISKDNSKSQVSLKLSSVTAADTAVYYCARDRVTATLYAMDYWGQGTLVTVSS |
| SEQ ID NO: 3051 | VH | C-H-VH.12 | QVQLQESGPGLVKPSQTLSLTCTVSGFSLTAYGVNWVRQPAGKGLEWLGMIWGDGNTDYNSALKSRLTISKDNSKSQVSLKLSSVTAADTAVYYCARDRVTATLYAMDYWGQGTLVTVSS |
| SEQ ID NO: 3052 | VH | C-H-VH.13 | QVQLQESGPGLVKPSQTLSLTCAVSGFSLTAYGVNWVRQPPGKGLEWLGMIWGDGNTDYNSALKSRLTISKDNSKSQVSLKLSSVTAVDTAVYYCARDRVTATLYAMDYWGQGTLVTVSS |
| SEQ ID NO: 3053 | VH | C-H-VH.14 | QVQLQESGPGLVKPSETLSLTCTVSGFSLTAYGVNWVRQPPGKGLEWLGMIWGDGNTDYNSALKSRLTISKDNSKSHVSLKLSSVTAADTAVYYCARDRVTATLYAMDYWGQGTLVTVSS |
| SEQ ID NO: 3054 | VH | C-H-VH.15 | QVQLQESGPGLVKPSETLSLTCAVSGFSLTAYGVNWVRQPPGKGLEWLGMIWGDGNTDYNSALKSRLTISKDNSKSQVSLKLSSVTAADTAVYYCARDRVTATLYAMDYWGQGTLVTVSS |
| SEQ ID NO: 3055 | VH | C-H-VH.16 | QVQLQESGPGLVKPSQTLSLTCAVYGFSLTAYGVNWVRQPPGKGLEWLGMIWGDGNTDYNSALKSRLTISKDNSKSQVSLKLSSVTAADTAVYYCARDRVTATLYAMDYWGQGTLVTVSS |
| SEQ ID NO: 3056 | VH | C-H-VH.17 | RVQLQESGPGLVKPSETLSLTCTVSGFSLTAYGVNWVRQPPGKGLEWLGMIWGDGNTDYNSALKSRLTISKDNSKSQVPLKLSSVTAADTAVYYCARDRVTATLYAMDYWGQGTLVTVSS |
| SEQ ID NO: 3057 | VH | C-H-VH.18 | QVQLQESGPGLVKPSQTLSLTCTVSGFSLTAYGVNWVRQHPGKGLEWLGMIWGDGNTDYNSALKSLLTISKDNSKSQVSLKLSSVTAADTAVYYCARDRVTATLYAMDYWGQGTLVTVSS |
| SEQ ID NO: 3058 | VH | C-H-VH.19 | QVQLQESGPGLVKPSDTLSLTCAVSGFSLTAYGVNWVRQPPGKGLEWLGMIWGDGNTDYNSALKSRLTISKDNSKSQVSLKLSSVTALDTAVYYCARDRVTATLYAMDYWGQGTLVTVSS |
| SEQ ID NO: 3059 | VH | C-H-VH.20 | QVQLQESGPGLVKPSDTLSLTCAVSGFSLTAYGVNWVRQPPGKGLEWLGMIWGDGNTDYNSALKSRLTISKDNSKSQVSLKLSSVTAVDTAVYYCARDRVTATLYAMDYWGQGTLVTVSS |
| SEQ ID NO: 3060 | VH | C-H-VH.21 | QVQLQESGSGLVKPSQTLSLTCAVSGFSLTAYGVNWVRQPPGKGLEWLGMIWGDGNTDYNSALKSRLTISKDNSKSQVSLKLSSVTAADTAVYYCARDRVTATLYAMDYWGQGTLVTVSS |
| SEQ ID NO: 3061 | VH | C-H-VH.22 | EVQLVESGGGLVQPGRSLRLSCTVSGFSLTAYGVNWVRQAPGKGLEWLGMIWGDGNTDYNSALKSRLTISKDNSKSIVYLQMNSLKTEDTAVYYCARDRVTATLYAMDYWGQGTLVTVSS |
| SEQ ID NO: 3062 | VH | C-H-VH.23 | EVQLVESGGGLVQPGPSLRLSCTVSGFSLTAYGVNWVRQAPGKGLEWLGMIWGDGNTDYNSALKSRLTISKDNSKSIVYLQMNSLKTEDTAVYYCARDRVTATLYAMDYWGQGTLVTVSS |
| SEQ ID NO: 3063 | VH | C-H-VH.24 | QVQLQESGSGLVKPSQTLSLTCAVSGFSLTAYGVNWVRQSPGKGLEWLGMIWGDGNTDYNSALKSRLTISKDNSKSQVSLKLSSVTAADTAVYYCARDRVTATLYAMDYWGQGTLVTVSS |
| SEQ ID NO: 3064 | VH | C-H-VH.25 | QVQLQESGPGLVKPSETLSLTCTVSGFSLTAYGVNWVRQPAGKGLEWLGMIWGDGNTDYNSALKSRLTISKDNSKSQVSLKLSSVTAADTAVYYCARDRVTATLYAMDYWGQGTLVTVSS |
| SEQ ID NO: 3065 | VH | C-H-VH.26 | EVQLVESGGGLVKPGRSLRLSCTVSGFSLTAYGVNWVRQAPGKGLEWLGMIWGDGNTDYNSALKSRLTISKDNSKSIVYLQMNSLKTEDTAVYYCARDRVTATLYAMDYWGQGTLVTVSS |

TABLE 10-continued

Amino acid sequences for anti TCRβ V5 antibodies
Amino acid and nucleotide sequences for murine and humanized antibody molecules which bind to TCRVB 5 (e.g., TCRVB 5-5 or TCRVB 5-6). The amino acid the heavy and light chain CDRs, and the amino acid and nucleotide sequences of the heavy and light chain variable regions, and the heavy and light chains are shown.

| | | | |
|---|---|---|---|
| SEQ ID NO: 3066 | VH | C-H-VH.27 | QVQLQESGPGLVKPSETLSLTCAVYGFSLTAYGVNWVRQPPGKGLEWLGMIWGDGNTDYNSALKSRLTISKDNSKSQVYLKLSSVTAADTAVYYCARDRVTATLYAMDYWGQGTLVTVSS |
| SEQ ID NO: 3067 | VH | C-H-VH.28 | QVQLQESGPGLVKPSDTLSLTCAVSGFSLTAYGVNWVRQPPGKGLEWLGMIWGDGNTDYNSALKSRLTISKDNSKSQVSLKLSSVTAVDTGVYYCARDRVTATLYAMDYWGQGTLVTVSS |
| SEQ ID NO: 3068 | VH | C-H-VH.29 | EVQLVESGGGLVQPGGSLRLSCAVSGFSLTAYGVNWVRQAPGKGLEWLGMIWGDGNTDYNSALKSRLTISKDNSKSSVYLQMNSLKTEDTAVYYCARDRVTATLYAMDYWGQGTLVTVSS |
| SEQ ID NO: 3069 | VH | C-H-VH.30 | EVQLVESGGGLVKPGGSLRLSCAVSGFSLTAYGVNWVRQAPGKGLEWLGMIWGDGNTDYNSALKSRLTISKDNSKSTVYLQMNSLKTEDTAVYYCARDRVTATLYAMDYWGQGTLVTVSS |
| SEQ ID NO: 3070 | VH | C-H-VH.31 | QVQLQQSGPGLVKPSQTLSLTCAVSGFSLTAYGVNWVRQSPSRGLEWLGMIWGDGNTDYNSALKSRLTINKDNSKSQVSLQLNSVTPEDTAVYYCARDRVTATLYAMDYWGQGTLVTVSS |
| SEQ ID NO: 3071 | VH | C-H-VH.32 | QVQLVESGGGLVQPGGSLRLSCSVSGFSLTAYGVNWVRQAPGKGLEWLGMIWGDGNTDYNSALKSRLTISKDNSKSTVYLQMNSLRAEDTAVYYCARDRVTATLYAMDYWGQGTLVTVSS |
| SEQ ID NO: 3072 | VH | C-H-VH.33 | QVQLQQWGAGLLKPSETLSLTCAVYGFSLTAYGVNWVRQPPGKGLEWLGMIWGDGNTDYNSALKSRLTISKDNSKSQVSLKLSSVTAADTAVYYCARDRVTATLYAMDYWGQGTLVTVSS |
| SEQ ID NO: 3073 | VH | C-H-VH.34 | QVQLVESGGGVVQPGRSLRLSCAVSGFSLTAYGVNWVRQAPGKGLEWLGMIWGDGNTDYNSALKSRLTISKDNSTSTVFLQMNSLRAEDTAVYYCARDRVTATLYAMDYWGQGTLVTVSS |
| SEQ ID NO: 3074 | VH | C-H-VH.35 | EVQLVESGGGLVQPGGSLRLSCAVSGFSLTAYGVNWVRQAPGKGLEWLGMIWGDGNTDYNSALKSRLTISKDNSKSTVYLQMNSLRAEDTAVYYCARDRVTATLYAMDYWGQGTLVTVSS |
| SEQ ID NO: 3075 | VH | C-H-VH.36 | EVQLVESGGGLVQPGGSLRLSCAVSGFSLTAYGVNWVRQAPGKGLEWLGMIWGDGNTDYNSALKSRLTISKDNAKSSVYLQMNSLRDEDTAVYYCARDRVTATLYAMDYWGQGTLVTVSS |
| SEQ ID NO: 3076 | VH | C-H-VH.37 | EVQLLESGGGLVQPGGSLRLSCAVSGFSLTAYGVNWVRQAPGKGLEWLGMIWGDGNTDYNSALKSRLTISKDNSKSTVYLQMNSLRAEDTAVYYCARDRVTATLYAMDYWGQGTLVTVSS |
| SEQ ID NO: 3077 | VH | C-H-VH.38 | QVQLVESGGGLVKPGGSLRLSCAVSGFSLTAYGVNWVRQAPGKGLEWLGMIWGDGNTDYNSALKSRLTISKDNAKSSVYLQMNSLRAEDTAVYYCARDRVTATLYAMDYWGQGTLVTVSS |
| SEQ ID NO: 3078 | VH | C-H-VH.39 | EVQLVESGGGLVQPGGSLKLSCAVSGFSLTAYGVNWVRQASGKGLEWLGMIWGDGNTDYNSALKSRLTISKDNSKSTVYLQMNSLKTEDTAVYYCARDRVTATLYAMDYWGQGTLVTVSS |
| SEQ ID NO: 3079 | VH | C-H-VH.40 | QVQLLESGGGLVKPGGSLRLSCAVSGFSLTAYGVNWVRQAPGKGLEWLGMIWGDGNTDYNSALKSRLTISKDNAKSSVYLQMNSLRAEDTAVYYCARDRVTATLYAMDYWGQGTLVTVSS |
| SEQ ID NO: 3080 | VH | C-H-VH.41 | QVQLVESGGGVVQPGRSLRLSCAVSGFSLTAYGVNWVRQAPGKGLEWLGMIWGDGNTDYNSALKSRLTISKDNSKSTVYLQMNSLRAEDTAVYYCARDRVTATLYAMDYWGQGTLVTVSS |
| SEQ ID NO: 3081 | VH | C-H-VH.42 | QVQLVESGGGVVQPGRSLRLSCAVSGFSLTAYGVNWVRQAPGKGLEWLGMIWGDGNTDYNSALKSRLTISKDNSKSRVYLQMNSLRAEDTAVYYCARDRVTATLYAMDYWGQGTLVTVSS |
| SEQ ID NO: 3082 | VH | C-H-VH.43 | QVQLVESGGGVVQPGRSLRLSCAVSGFSLTAYGVNWVRQAPGKGLEWLGMIWGDGNTDYNSALKSRLAISKDNSKSTVYLQMNSLRAEDTAVYYCARDRVTATLYAMDYWGQGTLVTVSS |
| SEQ ID NO: 3083 | VH | C-H-VH.44 | QVQLVESGGGVVQPGGSLRLSCAVSGFSLTAYGVNWVRQAPGKGLEWLGMIWGDGNTDYNSALKSRLTISKDNSKSTVYLQMNSLRAEDTAVYYCARDRVTATLYAMDYWGQGTLVTVSS |

TABLE 10-continued

| Amino acid sequences for anti TCRβ V5 antibodies Amino acid and nucleotide sequences for murine and humanized antibody molecules which bind to TCRVB 5 (e.g., TCRVB 5-5 or TCRVB 5-6). The amino acid the heavy and light chain CDRs, and the amino acid and nucleotide sequences of the heavy and light chain variable regions, and the heavy and light chains are shown. | | | |
|---|---|---|---|
| SEQ ID NO: 3084 | VH | C-H-VH.45 | EVQLVESGGGLVQPGGSLRLSCAVSGFSLTAYGVNWVRQAPGKGLEWLGMIWGDGNTDYNSALKSRLTISKDNAKSTVYLQMNSLRAEDTAVYYCARDRVTATLYAMDYWGQGTLVTVSS |
| SEQ ID NO: 3085 | VH | C-H-VH.46 | EVQLVESGGGLVQPGGSLRLSCAVSGFSLTAYGVNWVRQAPGKGLEWLGMIWGDGNTDYNSALKSRLTISKDNAKSSVYLQMNSLRAEDTAVYYCARDRVTATLYAMDYWGQGTLVTVSS |
| SEQ ID NO: 3086 | VH | C-H-VH.47 | EVQLVESGGVVVQPGGSLRLSCAVSGFSLTAYGVNWVRQAPGKGLEWLGMIWGDGNTDYNSALKSRLTISKDNSKSSVYLQMNSLRTEDTALYYCARDRVTATLYAMDYWGQGTLVTVSS |
| SEQ ID NO: 3087 | VH | C-H-VH.48 | EVQLVESGGGLVQPGGSLRLSCAVSGFSLTAYGVNWVRQAPGKGLEWLGMIWGDGNTDYNSALKSRLTISKHNSKSTVYLQMNSLRAEDTAVYYCARDRVTATLYAMDYWGQGTLVTVSS |
| SEQ ID NO: 3088 | VH | C-H-VH.49 | EVQLVESGGGLVKPGGSLRLSCAVSGFSLTAYGVNWVRQAPGKGLEWLGMIWGDGNTDYNSALKSRLTISKDNAKSSVYLQMNSLRAEDTAVYYCARDRVTATLYAMDYWGQGTLVTVSS |
| SEQ ID NO: 3089 | VH | C-H-VH.50 | EVQLVESGGGLIQPGGSLRLSCAVSGFSLTAYGVNWVRQPPGKGLEWLGMIWGDGNTDYNSALKSRLTISKDNSKSTVYLQMNSLRAEDTAVYYCARDRVTATLYAMDYWGQGTLVTVSS |

Exemplary anti-TCRβ V5 antibodies of the disclosure are provided in Table 11. In some embodiments, the anti-TCRβ V5 is antibody E, e.g., humanized antibody E (antibody E-H), as provided in Table 11. In some embodiments, the anti-TCRβ V antibody comprises one or more (e.g., all three) of a LC CDR1, LC CDR2, and LC CDR3 provided in Table 11; and/or one or more (e.g., all three) of a HC CDR1, HC CDR2, and HC CDR3 provided in Table 11, or a sequence with at least 95% identity thereto. In some embodiments, antibody E comprises a variable heavy chain (VH) and/or a variable light chain (VL) provided in Table 11, or a sequence with at least 95% identity thereto.

In some embodiments, antibody E comprises a heavy chain comprising the amino acid sequence of SEQ ID NO: 3284 and/or a light chain comprising the amino acid sequence of SEQ ID NO: 3285, or a sequence with at least 95% identity thereto.

TABLE 11

| Amino acid sequences for anti TCRβ V5 antibodies Amino acid and nucleotide sequences for murine and humanized antibody molecules which bind to TCRVB 5 (e.g., TCRVB 5-5 or TCRVB 5-6). The amino acid the heavy and light chain CDRs, and the amino acid and nucleotide sequences of the heavy and light chain variable regions, and the heavy and light chains are shown. | | |
|---|---|---|
| Murine antibody E, also referred to as MH3-2 | | |
| SEQ ID NO: 1298 | HC CDR1 (Kabat) | SSWMN |
| SEQ ID NO: 1299 | HC CDR2 (Kabat) | RIYPGDGDTKYNGKFKG |
| SEQ ID NO: 1300 | HC CDR3 (Kabat) | RGTGGWYFDV |
| SEQ ID NO: 1302 | HC CDR1 (Chothia) | GYAFSSS |
| SEQ ID NO: 1303 | HC CDR2 (Chothia) | YPGDGD |
| SEQ ID NO: 1301 | HC CDR3 (Chothia) | RGTGGWYFDV |
| SEQ ID NO: 1304 | HC CDR1 (Combined) | GYAFSSSWMN |
| SEQ ID NO: 1299 | HC CDR2 (Combined) | RIYPGDGDTKYNGKFKG |
| SEQ ID NO: 1301 | HC CDR3 (Combined) | RGTGGWYFDV |
| SEQ ID NO: 1305 | LC CDR1 (Kabat) | RASESVDSSGNSFMH |
| SEQ ID NO: 1306 | LC CDR2 (Kabat) | RASNLES |
| SEQ ID NO: 1307 | LC CDR3 (Kabat) | QQSFDDPFT |
| SEQ ID NO: 1308 | LC CDR1 (Chothia) | SESVDSSGNSF |

TABLE 11-continued

Amino acid sequences for anti TCRβ V5 antibodies
Amino acid and nucleotide sequences for murine and humanized antibody molecules which bind to TCRVB 5 (e.g., TCRVB 5-5 or TCRVB 5-6). The amino acid the heavy and light chain CDRs, and the amino acid and nucleotide sequences of the heavy and light chain variable regions, and the heavy and light chains are shown.

| | | |
|---|---|---|
| SEQ ID NO: 1306 | LC CDR2 (Chothia) | RASNLES |
| SEQ ID NO: 1307 | LC CDR3 (Chothia) | QQSFDDPFT |
| SEQ ID NO: 1305 | LC CDR1 (Combined) | RASESVDSSGNSFMH |
| SEQ ID NO: 1306 | LC CDR2 (Combined) | RASNLES |
| SEQ ID NO: 1307 | LC CDR3 (Combined) | QQSFDDPFT |
| SEQ ID NO: 3091 | VH | QVQLQQSGPELVKPGASVKISCKASGYAFSSSWM NWVKQRPGQGLEWIGRIYPGDGDTKYNGKFKG KATLTADKSSSTAYMHLSSLTSVDSAVYFCARRG TGGWYFDVWGAGTTVTVSS |
| SEQ ID NO: 3284 | Heavy chain | METDTLLLWVLLLWVPGSTGQVQLQQSGPELVK PGASVKISCKASGYAFSSSWMNWVKQRPGQGLE WIGRIYPGDGDTKYNGKFKGKATLTADKSSSTA YMHLSSLTSVDSAVYFCARRGTGGWYFDVWGA GTTVTVSSAKTTAPSVYPLAPVCGDTTGSSVTLG CLVKGYFPEPVTLTWNSGSLSSGVHTFPAVLQSD LYTLSSSVTVTSSTWPSQSITCNVAHPASSTKVDK KIEPRGPTIKPCPPCKCPAPNLLGGPSVFIFPPKIK DVLMISLSPIVTCVVVDVSEDDPDVQISWFVNNVE VHTAQTQTHREDYNSTLRVVSALPIQHQDWMSG KEFKCKVNNKDLPAPIERTISKPKGSVRAPQVYV LPPPEEEMTKKQVTLTCMVTDFMPEDIYVEWTN NGKTELNYKNTEPVLDSDGSYFMYSKLRVEKKN WVERNSYSCSVVHEGLHNHHTTKSFSRTPGK |
| SEQ ID NO: 3092 | VL | DIVLTQSPASLAVSLGQRATISCRASESVDSSGNS FMHWYQQKPGQPPQLLIYRASNLESGIPARFSGS GSRTDFTLTINPVEADDVATFYCQQSFDDPFTFGS GTKLEIK |
| SEQ ID NO: 3285 | Light chain | METDTLLLWVLLLWVPGSTGDIVLTQSPASLAVS LGQRATISCRASESVDSSGNSFMHWYQQKPGQPP QLLIYRASNLESGIPARFSGSGSRTDFTLTINPVEA DDVATFYCQQSFDDPFTFGSGTKLEIKRADAAPT VSIFPPSSEQLTSGGASVVCFLNNFYPKDINVKWK IDGSERQNGVLNSWTDQDSKDSTYSMSSTLTLTK DEYERHNSYTCEATHKTSTSPIVKSFNRNEC |

Humanized antibody E (E-H antibody)
Variable light chain (VL)

| | | | |
|---|---|---|---|
| SEQ ID NO: 3093 | VL | E-H.1 | DIVLTQSPDSLAVSLGERATINCRASESVDSSGNSFMHWYQQKPGQ PPQLLIYRASNLESGVPDRFSGSGSRTDFTLTISSLQAEDVAVYYCQ QSFDDPFTFGQGTKLEIK |
| SEQ ID NO: 3094 | VL | E-H.2 | EIVLTQSPATLSLSPGERATLSCRASESVDSSGNSFMHWYQQKPGQ APQLLIYRASNLESGIPARFSGSGSRTDFTLTISSLEPEDFAVYYCQQ SFDDPFTFGQGTKLEIK |
| SEQ ID NO: 3095 | VL | E-H.3 | EIVLTQSPATLSLSPGERATLSCRASESVDSSGNSFMHWYQQKPGQ APQLLIYRASNLESGIPARFSGSGSRTDFTLTISRLEPEDFAVYYCQQ SFDDPFTFGQGTKLEIK |
| SEQ ID NO: 3096 | VL | E-H.4 | EIVLTQSPATLSLSPGERATLSCRASESVDSSGNSFMHWYQQKPGQ APQLLIYRASNLESGIPARFSGSGSRTDFTLTISSLQPEDFAVYYCQQ SFDDPFTFGQGTKLEIK |
| SEQ ID NO: 3097 | VL | E-H.5 | DIQLTQSPSSLSASVGDRVTITCRASESVDSSGNSFMHWYQQKPGQ APQLLIYRASNLESGVPSRFSGSGSRTDFTLTISSLQPEDVATYYCQ QSFDDPFTFGQGTKLEIK |
| SEQ ID NO: 3098 | VL | E-H.6 | EIVLTQSPATLSLSPGERATLSCRASESVDSSGNSFMHWYQQKPGQ APQLLIYRASNLESGIPARFSGSGPRTDFTLTISSLEPEDFAVYYCQQ SFDDPFTFGQGTKLEIK |
| SEQ ID NO: 3099 | VL | E-H.7 | EIVLTQSPATLSLSPGERATLSCRASESVDSSGNSFMHWYQQKPGQ APQLLIYRASNLESGIPDRFSGSGSRTDFTLTISRLEPEDFAVYYCQQ SFDDPFTFGQGTKLEIK |

TABLE 11-continued

Amino acid sequences for anti TCRβ V5 antibodies
Amino acid and nucleotide sequences for murine and humanized antibody molecules which bind to TCRVB 5 (e.g., TCRVB 5-5 or TCRVB 5-6). The amino acid the heavy and light chain CDRs, and the amino acid and nucleotide sequences of the heavy and light chain variable regions, and the heavy and light chains are shown.

| | | | |
|---|---|---|---|
| SEQ ID NO: 3100 | VL | E-H.8 | DIQLTQSPSSLSASVGDRVTITCRASESVDSSGNSFMHWYQQKPGKVPQLLIYRASNLESGVPSRFSGSGSRTDFTLTISSLQPEDVATYYCQQSFDDPPFTFGQGTKLEIK |
| SEQ ID NO: 3101 | VL | E-H.9 | DIQLTQSPSSLSASVGDRVTITCRASESVDSSGNSFMHWYQQKPGKTPQLLIYRASNLESGIPSRFSGSGSRTDFTLTIRSLQPEDFATYYCQQSFDDPFTFGQGTKLEIK |
| SEQ ID NO: 3102 | VL | E-H.10 | EIVLTQSPGTLSLSPGERATLSCRASESVDSSGNSFMHWYQQKPGQAPQLLIYRASNLESGIPDRFSGSGSRTDFTLTISRLEPEDFAVYYCQQSFDDPFTFGQGTKLEIK |
| SEQ ID NO: 3103 | VL | E-H.11 | EIVLTQSPATLSLSPGERATLSCRASESVDSSGNSFMHWYQQKPGLAPQLLIYRASNLESGIPDRFSGSGSRTDFTLTISRLEPEDFAVYYCQQSFDDPFTFGQGTKLEIK |
| SEQ ID NO: 3104 | VL | E-H.12 | DIQLTQSPSSLSASVGDRVTITCRASESVDSSGNSFMHWYQQKPGKAPQLLIYRASNLESGVPSRFSGSGSRTDFTLTISSLQPEDFATYYCQQSFDDPFTFGQGTKLEIK |
| SEQ ID NO: 3105 | VL | E-H.13 | DIQLTQSPSSVSASVGDRVTITCRASESVDSSGNSFMHWYQQKPGKAPQLLIYRASNLESGVPSRFSGSGSRTDFTLTISSLQPEDFATYYCQQSFDDPFTFGQGTKLEIK |
| SEQ ID NO: 3106 | VL | E-H.14 | AIQLTQSPSSLSASVGDRVTITCRASESVDSSGNSFMHWYQQKPGKAPQLLIYRASNLESGVPSRFSGSGSRTDFTLTISSLQPEDFATYYCQQSFDDPFTFGQGTKLEIK |
| SEQ ID NO: 3107 | VL | E-H.15 | DIQLTQSPSFLSASVGDRVTITCRASESVDSSGNSFMHWYQQKPGKAPQLLIYRASNLESGVPSRFSGSGSRTEFTLTISSLQPEDFATYYCQQSFDDPFTFGQGTKLEIK |
| SEQ ID NO: 3108 | VL | E-H.16 | DIQLTQSPSSLSASVGDRVTITCRASESVDSSGNSFMHWYQQKPGKAPQLLIYRASNLESGVPSRFSGSGSRTDFTFTISSLQPEDIATYYCQQSFDDPFTFGQGTKLEIK |
| SEQ ID NO: 3109 | VL | E-H.17 | EIVLTQSPATLSVSPGERATLSCRASESVDSSGNSFMHWYQQKPGQAPQLLIYRASNLESGIPARFSGSGSRTEFTLTISILQSEDFAVYYCQQSFDDPFTFGQGTKLEIK |
| SEQ ID NO: 3110 | VL | E-H.18 | EIVLTQSPATLSVSPGERATLSCRASESVDSSGNSFMHWYQQKPGQAPQLLIYRASNLESGIPARFSGSGSRTEFTLTISSLQSEDFAVYYCQQSFDDPFTFGQGTKLEIK |
| SEQ ID NO: 3111 | VL | E-H.19 | AIRLTQSPFSLSASVGDRVTITCRASESVDSSGNSFMHWYQQKPAKAPQLFIYRASNLESGVPSRFSGSGSRTDFTLTISSLQPEDFATYYCQQSFDDPFTFGQGTKLEIK |
| SEQ ID NO: 3112 | VL | E-H.20 | DIQLTQSPSSLSASVGDRVTITCRASESVDSSGNSFMHWYQQKPGKAPQSLIYRASNLESGVPSRFSGSGSRTDFTLTISSLQPEDFATYYCQQSFDDPFTFGQGTKLEIK |
| SEQ ID NO: 3113 | VL | E-H.21 | DIQLTQSPSSLSASVGDRVTITCRASESVDSSGNSFMHWYQQKPGKAPQRLIYRASNLESGVPSRFSGSGSRTEFTLTISNLQPEDFATYYCQQSFDDPPFTFGQGTKLEIK |
| SEQ ID NO: 3114 | VL | E-H.22 | DIQLTQSPSTLSASVGDRVTITCRASESVDSSGNSFMHWYQQKPGKAPQLLIYRASNLESGVPSRFSGSGSRTEFTLTISSLQPDDFATYYCQQSFDDPFTFGQGTKLEIK |
| SEQ ID NO: 3115 | VL | E-H.23 | EIVLTQSPDFQSVTPKEKVTITCRASESVDSSGNSFMHWYQQKPDQSPQLLIYRASNLESGVPSRFSGSGSRTDFTLTINSLEAEDAATYYCQQSFDDPPFTFGQGTKLEIK |
| SEQ ID NO: 3116 | VL | E-H.24 | DIQLTQSPSSLSASVGDRVTITCRASESVDSSGNSFMHWYQQKPGKAPQSLIYRASNLESGVPSKFSGSGSRTDFTLTISSLQPEDFATYYCQQSFDDPFTFGQGTKLEIK |
| SEQ ID NO: 3117 | VL | E-H.25 | DIQLTQSPSSLSASVGDRVTITCRASESVDSSGNSFMHWYQQKPGKAPQRLIYRASNLESGVPSRFSGSGSRTEFTLTISSLQPEDFATYYCQQSFDDPFTFGQGTKLEIK |

TABLE 11-continued

Amino acid sequences for anti TCRβ V5 antibodies
Amino acid and nucleotide sequences for murine and humanized antibody molecules which bind to TCRVB 5 (e.g., TCRVB 5-5 or TCRVB 5-6). The amino acid the heavy and light chain CDRs, and the amino acid and nucleotide sequences of the heavy and light chain variable regions, and the heavy and light chains are shown.

| | | | |
|---|---|---|---|
| SEQ ID NO: 3118 | VL | E-H.26 | DIVLTQTPLSLSVTPGQPASISCRASESVDSSGNSFMHWYLQKPGQP PQLLIYRASNLESGVPDRFSGSGSRTDFTLKISRVEAEDVGVYYCQ QSFDDPFTFGQGTKLEIK |
| SEQ ID NO: 3119 | VL | E-H.27 | DIQLTQSPSSLSASVGDRVTITCRASESVDSSGNSFMHWYQQKPEK APQSLIYRASNLESGVPSRFSGSGSRTDFTLTISSLQPEDFATYYCQQ SFDDPFTFGQGTKLEIK |
| SEQ ID NO: 3120 | VL | E-H.28 | EIVLTQSPPTLSLSPGERVTLSCRASESVDSSGNSFMHWYQQKPGQ APQLLIYRASNLESGIPARFSGSGSRTDFTLTISSLQPEDFAVYYCQQ SFDDPFTFGQGTKLEIK |
| SEQ ID NO: 3121 | VL | E-H.29 | DIQLTQSPSAMSASVGDRVTITCRASESVDSSGNSFMHWYQQKPG KVPQRLIYRASNLESGVPSRFSGSGSRTEFTLTISSLQPEDFATYYCQ QSFDDPFTFGQGTKLEIK |
| SEQ ID NO: 3122 | VL | E-H.30 | DIVLTQSPLSLPVTPGEPASISCRASESVDSSGNSFMHWYLQKPGQS PQLLIYRASNLESGVPDRFSGSGSRTDFTLKISRVEAEDVGVYYCQ QSFDDPFTFGQGTKLEIK |
| SEQ ID NO: 3123 | VL | E-H.31 | DIVLTQTPLSLPVTPGEPASISCRASESVDSSGNSFMHWYLQKPGQS PQLLIYRASNLESGVPDRFSGSGSRTDFTLKISRVEAEDVGVYYCQ QSFDDPFTFGQGTKLEIK |
| SEQ ID NO: 3124 | VL | E-H.32 | DIVLTQTPLSLSVTPGQPASISCRASESVDSSGNSFMHWYLQKPGQS PQLLIYRASNLESGVPDRFSGSGSRTDFTLKISRVEAEDVGVYYCQ QSFDDPFTFGQGTKLEIK |
| SEQ ID NO: 3125 | VL | E-H.33 | EIVLTQSPPTLSLSPGERVTLSCRASESVDSSGNSFMHWYQQKPGQ APQLLIYRASNLESSIPARFSGSGSRTDFTLTISSLQPEDFAVYYCQQ SFDDPFTFGQGTKLEIK |
| SEQ ID NO: 3126 | VL | E-H.34 | DIVLTQSPLSLPVTLGQPASISCRASESVDSSGNSFMHWYQQRPGQS PQRLIYRASNLESGVPDRFSGSGSRTDFTLKISRVEAEDVGVYYCQ QSFDDPFTFGQGTKLEIK |
| SEQ ID NO: 3127 | VL | E-H.35 | DIVLTQTPLSSPVTLGQPASISCRASESVDSSGNSFMHWYQQRPGQP PQLLIYRASNLESGVPDRFSGSGARTDFTLKISRVEAEDVGVYYCQ QSFDDPFTFGQGTKLEIK |
| SEQ ID NO: 3128 | VL | E-H.36 | DIVLTQSPAFLSVTPGEKVTITCRASESVDSSGNSFMHWYQQKPDQ APQLLIYRASNLESGVPSRFSGSGSRTDFTFTISSLEAEDAATYYCQ QSFDDPFTFGQGTKLEIK |
| SEQ ID NO: 3129 | VL | E-H.37 | DIQLIQSPSFLSASVGDRVSIICRASESVDSSGNSFMHWYLQKPGKS PQLFIYRASNLESGVSSRFSGRGSRTDFTLTIISLKPEDFAAYYCQQS FDDPFTFGQGTKLEIK |
| SEQ ID NO: 3130 | VL | E-H.38 | EIVLTQTPLSLSITPGEQASISCRASESVDSSGNSFMHWYLQKARPV PQLLIYRASNLESGVPDRFSGSGSRTDFTLKISRVEAEDFGVYYCQQ SFDDPFTFGQGTKLEIK |
| SEQ ID NO: 3131 | VL | E-H.39 | EIVLTQTPLSLSITPGEQASMSCRASESVDSSGNSFMHWYLQKARP VPQLLIYRASNLESGVPDRFSGSGSRTDFTLKISRVEAEDFGVYYCQ QSFDDPFTFGQGTKLEIK |
| SEQ ID NO: 3132 | VL | E-H.40 | EITLTQSPAFMSATPGDKVNISCRASESVDSSGNSFMHWYQQKPGE APQFIIYRASNLESGIPPRFSGSGYRTDFTLTINNIESEDAAYYYCQQ SFDDPFTFGQGTKLEIK |
| Variable HEAVY chain (VH) | | | |
| SEQ ID NO: 3133 | VH | E-H.1 | QVQLVQSGAEVKKPGASVKVSCKASGYAFSSSWMNWVRQAPGQ GLEWIGRIYPGDGDTKYNGKFKGRATLTADKSTSTAYMELSSLRS EDTAVYYCARRGTGGWYFDVWGQGTTVTVSS |
| SEQ ID NO: 3134 | VH | E-H.2 | QVQLVQSGAEVKKPGSSVKVSCKASGYAFSSSWMNWVRQAPGQ GLEWIGRIYPGDGDTKYNGKFKGRATLTADKSTSTAYMELSSLRS EDTAVYYCARRGTGGWYFDVWGQGTTVTVSS |
| SEQ ID NO: 3135 | VH | E-H.3 | QVQLVQSGAEVKKPGASVKVSCKASGYAFSSSWMNWVRQAPGK GLEWIGRIYPGDGDTKYNGKFKGRATLTADKSTSTAYMELSSLRS EDTAVYYCARRGTGGWYFDVWGQGTTVTVSS |

TABLE 11-continued

Amino acid sequences for anti TCRβ V5 antibodies
Amino acid and nucleotide sequences for murine and humanized antibody molecules which bind to TCRVB 5 (e.g., TCRVB 5-5 or TCRVB 5-6). The amino acid the heavy and light chain CDRs, and the amino acid and nucleotide sequences of the heavy and light chain variable regions, and the heavy and light chains are shown.

| | | | |
|---|---|---|---|
| SEQ ID NO: 3136 | VH | E-H.4 | QVQLVQSGAEVKKPGASVKVSCKASGYAFSSSWMNWVRQAPGQ ELEWIGRIYPGDGDTKYNGKFKGRATLTADKSISTAYMELSSLRSE DTATYYCARRGTGGWYFDVWGQGTTVTVSS |
| SEQ ID NO: 3137 | VH | E-H.5 | EVQLVQSGAEVKKPGATVKISCKASGYAFSSSWMNWVQQAPGKG LEWIGRIYPGDGDTKYNGKFKGRATLTADKSTSTAYMELSSLRSE DTAVYYCARRGTGGWYFDVWGQGTTVTVSS |
| SEQ ID NO: 3138 | VH | E-H.6 | QVQLVQSGAEVKKTGSSVKVSCKASGYAFSSSWMNWVRQAPGQ ALEWIGRIYPGDGDTKYNGKFKGRATLTADKSMSTAYMELSSLRS EDTAMYYCARRGTGGWYFDVWGQGTTVTVSS |
| SEQ ID NO: 3139 | VH | E-H.7 | QVQLVQSGAEVKKPGASVKVSCKASGYAFSSSWMNWVRQAPGQ RLEWIGRIYPGDGDTKYNGKFKGRATLTADKSASTAYMELSSLRS EDMAVYYCARRGTGGWYFDVWGQGTTVTVSS |
| SEQ ID NO: 3140 | VH | E-H.8 | QVQLVQSGAEVKKPGASVKVSCKASGYAFSSSWMNWVRQAPGQ GLEWIGRIYPGDGDTKYNGKFKGRATLTADKSTSTAYMELRSLRS DDMAVYYCARRGTGGWYFDVWGQGTTVTVSS |
| SEQ ID NO: 3141 | VH | E-H.9 | QVQLVQSGAEVKKPGASVKVSCKASGYAFSSSWMNWVRQAPGQ RLEWIGRIYPGDGDTKYNGKFKGRATLTADKSASTAYMELSSLRS EDTAVYYCARRGTGGWYFDVWGQGTTVTVSS |
| SEQ ID NO: 3142 | VH | E-H.10 | QVQLVQSGAEVKKPGASVKVSCKASGYAFSSSWMNWVRQAPGQ GLEWIGRIYPGDGDTKYNGKFKGRATLTADKSTSTAYMELRSLRS DDTAVYYCARRGTGGWYFDVWGQGTTVTVSS |
| SEQ ID NO: 3143 | VH | E-H.11 | QVQLVQSGAEVKKPGASVKVSCKASGYAFSSSWMNWVRQAPGQ GLEWIGRIYPGDGDTKYNGKFKGRATLTADKSISTAYMELSRLRSD DTAVYYCARRGTGGWYFDVWGQGTTVTVSS |
| SEQ ID NO: 3144 | VH | E-H.12 | QVQLVQSGAEVKKPGASVKVSCKASGYAFSSSWMNWVRQAPGQ GLEWIGRIYPGDGDTKYNGKFKGRATLTADKSISTAYMELSRLRSD DTVVYYCARRGTGGWYFDVWGQGTTVTVSS |
| SEQ ID NO: 3145 | VH | E-H.13 | QVQLVQSGAEVKKPGASVKVSCKASGYAFSSSWMNWVRQAPGQ GLEWIGRIYPGDGDTKYNGKFKGWATLTADKSISTAYMELSRLRS DDTAVYYCARRGTGGWYFDVWGQGTTVTVSS |
| SEQ ID NO: 3146 | VH | E-H.14 | QVQLVQSGAEVKKPGASVKVSCKASGYAFSSSWMNWVRQATGQ GLEWIGRIYPGDGDTKYNGKFKGRATLTANKSISTAYMELSSLRSE DTAVYYCARRGTGGWYFDVWGQGTTVTVSS |
| SEQ ID NO: 3147 | VH | E-H.15 | QVQLVQSGSELKKPGASVKVSCKASGYAFSSSWMNWVRQAPGQG LEWIGRIYPGDGDTKYNGKFKGRAVLSADKSVSTAYLQISSLKAED TAVYYCARRGTGGWYFDVWGQGTTVTVSS |
| SEQ ID NO: 3148 | VH | E-H.16 | QVQLVQSGPEVKKPGTSVKVSCKASGYAFSSSWMNWVRQARGQ RLEWIGRIYPGDGDTKYNGKFKGRATLTADKSTSTAYMELSSLRSE DTAVYYCARRGTGGWYFDVWGQGTTVTVSS |
| SEQ ID NO: 3149 | VH | E-H.17 | EVQLVQSGAEVKKPGESLKISCKASGYAFSSSWMNWVRQMPGKG LEWIGRIYPGDGDTKYNGKFKGQATLSADKSISTAYLQWSSLKAS DTAMYYCARRGTGGWYFDVWGQGTTVTVSS |
| SEQ ID NO: 3150 | VH | E-H.18 | QVQLVQSGSELKKPGASVKVSCKASGYAFSSSWMNWVRQAPGQG LEWIGRIYPGDGDTKYNGKFKGRAVLSADKSVSMAYLQISSLKAE DTAVYYCARRGTGGWYFDVWGQGTTVTVSS |
| SEQ ID NO: 3151 | VH | E-H.19 | QVQLVQSGHEVKQPGASVKVSCKASGYAFSSSWMNWVPQAPGQ GLEWIGRIYPGDGDTKYNGKFKGRAVLSADKSASTAYLQISSLKAE DMAMYYCARRGTGGWYFDVWGQGTTVTVSS |
| SEQ ID NO: 3152 | VH | E-H.20 | EVQLVQSGAEVKKPGESLKISCKASGYAFSSSWMNWVRQMPGKG LEWIGRIYPGDGDTKYNGKFKGQATLSADKPISTAYLQWSSLKAS DTAMYYCARRGTGGWYFDVWGQGTTVTVSS |
| SEQ ID NO: 3153 | VH | E-H.21 | EVQLVQSGAEVKKPGESLRISCKASGYAFSSSWMNWVRQMPGKG LEWIGRIYPGDGDTKYNGKFKGQATLSADKSISTAYLQWSSLKAS DTAMYYCARRGTGGWYFDVWGQGTTVTVSS |

TABLE 11-continued

Amino acid sequences for anti TCRβ V5 antibodies
Amino acid and nucleotide sequences for murine and humanized antibody molecules which bind to TCRVB 5 (e.g., TCRVB 5-5 or TCRVB 5-6). The amino acid the heavy and light chain CDRs, and the amino acid and nucleotide sequences of the heavy and light chain variable regions, and the heavy and light chains are shown.

| | | | |
|---|---|---|---|
| SEQ ID NO: 3154 | VH | E-H.22 | EVQLVQSGAEVKKPGESLRISCKASGYAFSSSWMNWVRQMPGKGLEWIGRIYPGDGDTKYNGKFKGHATLSADKSISTAYLQWSSLKASDTAMYYCARRGTGGWYFDVWGQGTTVTVSS |
| SEQ ID NO: 3155 | VH | E-H.23 | QVQLVQSGAEVKKTGSSVKVSCKASGYAFSSSWMNWVRQAPRQALEWIGRIYPGDGDTKYNGKFKGRATLTADKSMSTAYMELSSLRSEDTAMYYCARRGTGGWYFDVWGQGTTVTVSS |
| SEQ ID NO: 3156 | VH | E-H.24 | EVQLVESGGGLVQPGRSLRLSCTASGYAFSSSWMNWVRQAPGKGLEWIGRIYPGDGDTKYNGKFKGRATLSADKSKSIAYLQMNSLKTEDTAVYYCARRGTGGWYFDVWGQGTTVTVSS |
| SEQ ID NO: 3157 | VH | E-H.25 | EVQLVESGGGLVQPGPSLRLSCTASGYAFSSSWMNWVRQAPGKGLEWIGRIYPGDGDTKYNGKFKGRATLSADKSKSIAYLQMNSLKTEDTAVYYCARRGTGGWYFDVWGQGTTVTVSS |
| SEQ ID NO: 3158 | VH | E-H.26 | QVQLQESGPGLVKPSQTLSLTCTASGYAFSSSWMNWVRQPPGKGLEWIGRIYPGDGDTKYNGKFKGRATLSADKSKSQASLKLSSVTAADTAVYYCARRGTGGWYFDVWGQGTTVTVSS |
| SEQ ID NO: 3159 | VH | E-H.27 | QVQLQESGPGLVKPSGTLSLTCAASGYAFSSSWMNWVRQPPGKGLEWIGRIYPGDGDTKYNGKFKGRATLSADKSKSQASLKLSSVTAADTAVYYCARRGTGGWYFDVWGQGTTVTVSS |
| SEQ ID NO: 3160 | VH | E-H.28 | EVQLVESGGGLVKPGRSLRLSCTASGYAFSSSWMNWVRQAPGKGLEWIGRIYPGDGDTKYNGKFKGRATLSADKSKSIAYLQMNSLKTEDTAVYYCARRGTGGWYFDVWGQGTTVTVSS |
| SEQ ID NO: 3161 | VH | E-H.29 | EVQLVESGGGLVQPGGSLKLSCAASGYAFSSSWMNWVRQASGKGLEWIGRIYPGDGDTKYNGKFKGRATLSADKSKSTAYLQMNSLKTEDTAVYYCARRGTGGWYFDVWGQGTTVTVSS |
| SEQ ID NO: 3162 | VH | E-H.30 | QVQLQESGPGLVKPSQTLSLTCAASGYAFSSSWMNWVRQPPGKGLEWIGRIYPGDGDTKYNGKFKGRATLSADKSKSQASLKLSSVTAADTAVYYCARRGTGGWYFDVWGQGTTVTVSS |
| SEQ ID NO: 3163 | VH | E-H.31 | EVQLVESGGGLVKPGGSLRLSCAASGYAFSSSWMNWVRQAPGKGLEWIGRIYPGDGDTKYNGKFKGRATLSADKSKSTAYLQMNSLKTEDTAVYYCARRGTGGWYFDVWGQGTTVTVSS |
| SEQ ID NO: 3164 | VH | E-H.32 | EVQLVESGGALVKPGGSLRLSCAASGYAFSSSWMNWVRQAPGKGLEWIGRIYPGDGDTKYNGKFKGRATLSADKSKSTAYLQMNSLKTEDTAVYYCARRGTGGWYFDVWGQGTTVTVSS |
| SEQ ID NO: 3165 | VH | E-H.33 | QVQLQESGPGLVKPSQTLSLTCAAYGYAFSSSWMNWVRQPPGKGLEWIGRIYPGDGDTKYNGKFKGRATLSADKSKSQASLKLSSVTAADTAVYYCARRGTGGWYFDVWGQGTTVTVSS |
| SEQ ID NO: 3166 | VH | E-H.34 | QVQLQESGSGLVKPSQTLSLTCAASGYAFSSSWMNWVRQPPGKGLEWIGRIYPGDGDTKYNGKFKGRATLSADKSKSQASLKLSSVTAADTAVYYCARRGTGGWYFDVWGQGTTVTVSS |
| SEQ ID NO: 3167 | VH | E-H.35 | EVQLVESGGGLVQPGGSLRLSCAASGYAFSSSWMNWVRQAPGKGLEWIGRIYPGDGDTKYNGKFKGRATLSADKSKSSAYLQMNSLKTEDTAVYYCARRGTGGWYFDVWGQGTTVTVSS |
| SEQ ID NO: 3168 | VH | E-H.36 | QVQLQESGPGLVKPSDTLSLTCTASGYAFSSSWMNWVRQPPGKGLEWIGRIYPGDGDTKYNGKFKGRATLSADKSKSQASLKLSSVTAADTAVYYCARRGTGGWYFDVWGQGTTVTVSS |
| SEQ ID NO: 3169 | VH | E-H.37 | QVQLQESGPGLVKPSQTLSLTCTASGYAFSSSWMNWVRQHPGKGLEWIGRIYPGDGDTKYNGKFKGRATLSADKSKSQASLKLSSVTAADTAVYYCARRGTGGWYFDVWGQGTTVTVSS |
| SEQ ID NO: 3170 | VH | E-H.38 | QVQLQESGPGLVKPSQTLSLTCTASGYAFSSSWMNWVRQHPGKGLEWIGRIYPGDGDTKYNGKFKGLATLSADKSKSQASLKLSSVTAADTAVYYCARRGTGGWYFDVWGQGTTVTVSS |
| SEQ ID NO: 3171 | VH | E-H.39 | QVQLVESGGGVVQPGRSLRLSCAASGYAFSSSWMNWVRQAPGKGLEWIGRIYPGDGDTKYNGKFKGRATLSADKSKSTAYLQMSSLRAEDTAVYYCARRGTGGWYFDVWGQGTTVTVSS |

TABLE 11-continued

Amino acid sequences for anti TCRβ V5 antibodies
Amino acid and nucleotide sequences for murine and humanized antibody molecules which bind to TCRVB 5 (e.g., TCRVB 5-5 or TCRVB 5-6). The amino acid the heavy and light chain CDRs, and the amino acid and nucleotide sequences of the heavy and light chain variable regions, and the heavy and light chains are shown.

| | | | |
|---|---|---|---|
| SEQ ID NO: 3172 | VH | E-H.40 | QVQLVESGGGLVKPGGSLRLSCAASGYAFSSSWMNWVRQAPGKGLEWIGRIYPGDGDTKYNGKFKGRATLSADKAKSSAYLQMNSLRAEDTAVYYCARRGTGGWYFDVWGQGTTVTVSS |
| SEQ ID NO: 3173 | VH | E-H.41 | QVQLVESGGGLVQPGGSLRLSCSASGYAFSSSWMNWVRQAPGKGLEWIGRIYPGDGDTKYNGKFKGRATLSADKSKSTAYLQMNSLRAEDTAVYYCARRGTGGWYFDVWGQGTTVTVSS |
| SEQ ID NO: 3174 | VH | E-H.42 | QVQLLESGGGLVKPGGSLRLSCAASGYAFSSSWMNWVRQAPGKGLEWIGRIYPGDGDTKYNGKFKGRATLSADKAKSSAYLQMNSLRAEDTAVYYCARRGTGGWYFDVWGQGTTVTVSS |
| SEQ ID NO: 3175 | VH | E-H.43 | EVQLVESGGGLVQPGGSLRLSCSASGYAFSSSWMNWVRQAPGKGLEWIGRIYPGDGDTKYNGKFKGRATLSADKSKSTAYLQMSSLRAEDTAVYYCARRGTGGWYFDVWGQGTTVTVSS |
| SEQ ID NO: 3176 | VH | E-H.44 | QVQLQESGPGLVKPSDTLSLTCAASGYAFSSSWMNWVRQPPGKGLEWIGRIYPGDGDTKYNGKFKGRATLSADKSKSQASLKLSSVTAVDTAVYYCARRGTGGWYFDVWGQGTTVTVSS |
| SEQ ID NO: 3177 | VH | E-H.45 | QVQLQESGPGLVKPSQTLSLTCAASGYAFSSSWMNWVRQPPGKGLEWIGRIYPGDGDTKYNGKFKGRATLSADKSKSQASLKLSSVTAVDTAVYYCARRGTGGWYFDVWGQGTTVTVSS |
| SEQ ID NO: 3178 | VH | E-H.46 | EVQLVESGGGLVQPGGSLRLSCSASGYAFSSSWMNWVRQAPGKGLEWIGRIYPGDGDTKYNGKFKGRATLSADKSKSTAYVQMSSLRAEDTAVYYCARRGTGGWYFDVWGQGTTVTVSS |
| SEQ ID NO: 3179 | VH | E-H.47 | QVQLVDSGGGVVQPGRSLRLSCAASGYAFSSSWMNWVRQAPGKGLEWIGRIYPGDGDTKYNGKFKGRATLSADKSKSTAYLQMNSLRAEDTAVYYCARRGTGGWYFDVWGQGTTVTVSS |
| SEQ ID NO: 3180 | VH | E-H.48 | QVQLVESGGGVVQPGRSLRLSCAASGYAFSSSWMNWVRQAPGKGLEWIGRIYPGDGDTKYNGKFKGRATLSADKSKSTAYLQMNSLRAEGTAVYYCARRGTGGWYFDVWGQGTTVTVSS |
| SEQ ID NO: 3181 | VH | E-H.49 | QVQLVESGGGVVQPGRSLRLSCAASGYAFSSSWMNWVRQAPGKGLEWIGRIYPGDGDTKYNGKFKGRATLSADKSKSTAYLQMNSLRAEDTAVYYCARRGTGGWYFDVWGQGTTVTVSS |
| SEQ ID NO: 3182 | VH | E-H.50 | EVQLVESGGGLVQPGGSLRLSCAASGYAFSSSWMNWVRQAPGKGLEWIGRIYPGDGDTKYNGKFKGRATLSADKSKSTAYLQMNSLRAEDTAVYYCARRGTGGWYFDVWGQGTTVTVSS |

In some embodiments, the anti-TCRβ V5 antibody molecule comprises a VH and/or a VL of an antibody described in Table 10, or a sequence with at least 80%, 85%, 90%, 95%, 96%, 97%, 98%, 99% or more identity thereto.

In some embodiments, the anti-TCRβ V5 antibody molecule comprises a VH and a VL of an antibody described in Table 10, or a sequence with at least 80%, 85%, 90%, 95%, 96%, 97%, 98%, 99% or more identity thereto.

In some embodiments, the anti-TCRβ V5 antibody molecule comprises a VH and/or a VL of an antibody described in Table 11, or a sequence with at least 80%, 85%, 90%, 95%, 96%, 97%, 98%, 99% or more identity thereto.

In some embodiments, the anti-TCRβ V5 antibody molecule comprises a VH and a VL of an antibody described in Table 11, or a sequence with at least 80%, 85%, 90%, 95%, 96%, 97%, 98%, 99% or more identity thereto.

Anti-TCRβ V10 Antibodies

Accordingly, in one aspect, the disclosure provides an anti-TCRβV antibody molecule that binds to a human TCRβ V10 subfamily member. In some embodiments, TCRβ V10 subfamily is also known as TCRβ V12. In some embodiments, the TCRβ V10 subfamily comprises: TCRβ V10-1*01, TCRβ V10-1*02, TCRβ V10-3*01 or TCRβ V10-2*01, or a variant thereof.

Exemplary anti-TCRβ V10 antibodies of the disclosure are provided in Table 12. In some embodiments, the anti-TCRβ V10 is antibody D, e.g., humanized antibody D (antibody D-H), as provided in Table 12. In some embodiments, antibody D comprises one or more (e.g., three) light chain CDRs and/or one or more (e.g., three) heavy chain CDRs provided in Table 12, or a sequence with at least 95% identity thereto. In some embodiments, antibody D comprises a variable heavy chain (VH) and/or a variable light chain (VL) provided in Table 12, or a sequence with at least 95% identity thereto.

TABLE 12

Amino acid sequences for anti TCRβ V10 antibodies
Amino acid and nucleotide sequences for murine and humanized antibody molecules which bind to TCRBV 10 (e.g., TCRBV 10-1, TCRBV 10-2 or TCRBV 10-3). The amino acid the heavy and light chain CDRs, and the amino acid and nucleotide sequences of the heavy and light chain variable regions, and the heavy and light chains are shown.

| | | |
|---|---|---|
| Murine antibody D, also referred to as S511 antibody | | |
| SEQ ID NO: 1288 | HC CDR1 (Kabat) | SYGMS |
| SEQ ID NO: 1289 | HC CDR2 (Kabat) | LISSGGSYTYYTDSVKG |
| SEQ ID NO: 1290 | HC CDR3 (Kabat) | HGGNFFDY |
| SEQ ID NO: 1291 | HC CDR1 (Chothia) | GFTFRSY |
| SEQ ID NO: 1292 | HC CDR2 (Chothia) | SSGGSY |
| SEQ ID NO: 1290 | HC CDR3 (Chothia) | HGGNFFDY |
| SEQ ID NO: 1293 | HC CDR1 (Combined) | GFTFRSYGMS |
| SEQ ID NO: 1289 | HC CDR2 (Combined) | LISSGGSYTYYTDSVKG |
| SEQ ID NO: 1290 | HC CDR3 (Combined) | HGGNFFDY |
| SEQ ID NO: 1294 | LC CDR1 (Kabat) | SVSSSVSYMH |
| SEQ ID NO: 1295 | LC CDR2 (Kabat) | DTSKLAS |
| SEQ ID NO: 1296 | LC CDR3 (Kabat) | QQWSSNPQYT |
| SEQ ID NO: 1297 | LC CDR1 (Chothia) | SSSVSY |
| SEQ ID NO: 1295 | LC CDR2 (Chothia) | DTSKLAS |
| SEQ ID NO: 1296 | LC CDR3 (Chothia) | QQWSSNPQYT |
| SEQ ID NO: 1294 | LC CDR1 (Combined) | SVSSSVSYMH |
| SEQ ID NO: 1295 | LC CDR2 (Combined) | DTSKLAS |
| SEQ ID NO: 1296 | LC CDR3 (Combined) | QQWSSNPQYT |
| SEQ ID NO: 3183 | VH | EVQLVESGGDLVKPGGSLKLSCAVSGFTFRSYGM SWVRQTPDKRLEWVALISSGGSYTYYTDSVKGR FTISRDNAKNTLYLQMSSLKSEDTAIYYCSRHGG NFFDYWGQGTTLTVSS |
| SEQ ID NO: 3184 | VL | QIVLTQSPSIMSASPGEKVTMTCSVSSSVSYMHW YQQKSGTSPKRWIYDTSKLASGVPARFSGSGSGT SYSLTISSMEAEDAATYYCQQWSSNPQYTFGGGT KLEIK |
| Humanized antibody D (D-H antibody) Variable light chain (VL) | | |
| SEQ ID NO: 3185 | VL D-H.1 | DIVLTQSPAFLSVTPGEKVTITCSVSSSVSYMHWYQQKPDQAPKLLI YDTSKLASGVPSRFSGSGSGTDYTFTISSLEAEDAATYYCQQWSSN PQYTFGQGTKLEIK |
| SEQ ID NO: 3186 | VL D-H.2 | AIQLTQSPSSLSASVGDRVTITCSVSSSVSYMHWYQQKPGKAPKLLI YDTSKLASGVPSRFSGSGSGTDYTLTISSLQPEDFATYYCQQWSSN PQYTFGQGTKLEIK |
| SEQ ID NO: 3187 | VL D-H.3 | DIQLTQSPSFLSASVGDRVTITCSVSSSVSYMHWYQQKPGKAPKLLI YDTSKLASGVPSRFSGSGSGTEYTLTISSLQPEDFATYYCQQWSSNP QYTFGQGTKLEIK |
| SEQ ID NO: 3188 | VL D-H.4 | DIQLTQSPSSLSASVGDRVTITCSVSSSVSYMHWYQQKPGKAPKLLI YDTSKLASGVPSRFSGSGSGTDYTLTISSLQPEDFATYYCQQWSSN PQYTFGQGTKLEIK |
| SEQ ID NO: 3189 | VL D-H.5 | DIQLTQSPSSVSASVGDRVTITCSVSSSVSYMHWYQQKPGKAPKLL IYDTSKLASGVPSRFSGSGSGTDYTLTISSLQPEDFATYYCQQWSSN PQYTFGQGTKLEIK |
| SEQ ID NO: 3190 | VL D-H.6 | DIQLTQSPSSLSASVGDRVTITCSVSSSVSYMHWYQQKPGKVPKLLI YDTSKLASGVPSRFSGSGSGTDYTLTISSLQPEDVATYYCQQWSSN PQYTFGQGTKLEIK |

TABLE 12-continued

Amino acid sequences for anti TCRβ V10 antibodies
Amino acid and nucleotide sequences for murine and humanized antibody molecules which bind to TCRBV 10 (e.g., TCRBV 10-1, TCRBV 10-2 or TCRBV 10-3). The amino acid the heavy and light chain CDRs, and the amino acid and nucleotide sequences of the heavy and light chain variable regions, and the heavy and light chains are shown.

| | | |
|---|---|---|
| SEQ ID NO: 3191 | VL D-H.7 | DIQLTQSPSSLSASVGDRVTITCSVSSSVSYMHWYQQKPGQAPKLLIYDTSKLASGVPSRFSGSGSGTDYTLTISSLQPEDVATYYCQQWSSNPQYTFGQGTKLEIK |
| SEQ ID NO: 3192 | VL D-H.8 | EIVLTQSPDFQSVTPKEKVTITCSVSSSVSYMHWYQQKPDQSPKLLIYDTSKLASGVPSRFSGSGSGTDYTLTINSLEAEDAATYYCQQWSSNPQYTFGQGTKLEIK |
| SEQ ID NO: 3193 | VL D-H.9 | AIRLTQSPFSLSASVGDRVTITCSVSSSVSYMHWYQQKPAKAPKLFIYDTSKLASGVPSRFSGSGSGTDYTLTISSLQPEDFATYYCQQWSSNPQYTFGQGTKLEIK |
| SEQ ID NO: 3194 | VL D-H.10 | DIQLTQSPSSLSASVGDRVTITCSVSSSVSYMHWYQQKPGKAPKLLIYDTSKLASGVPSRFSGSGSGTDYTFTISSLQPEDIATYYCQQWSSNPQYTFGQGTKLEIK |
| SEQ ID NO: 3195 | VL D-H.11 | EIVLTQSPATLSLSPGERATLSCSVSSSVSYMHWYQQKPGQAPKLLIYDTSKLASGIPARFSGSGSGTDYTLTISSLEPEDFAVYYCQQWSSNPQYTFGQGTKLEIK |
| SEQ ID NO: 3196 | VL D-H.12 | DIQLTQSPSTLSASVGDRVTITCSVSSSVSYMHWYQQKPGKAPKLLIYDTSKLASGVPSRFSGSGSGTEYTLTISSLQPDDFATYYCQQWSSNPQYTFGQGTKLEIK |
| SEQ ID NO: 3197 | VL D-H.13 | DIQLTQSPSSLSASVGDRVTITCSVSSSVSYMHWYQQKPGKTPKLLIYDTSKLASGIPSRFSGSGSGTDYTLTIRSLQPEDFATYYCQQWSSNPQYTFGQGTKLEIK |
| SEQ ID NO: 3198 | VL D-H.14 | EIVLTQSPPTLSLSPGERVTLSCSVSSSVSYMHWYQQKPGQAPKLLIYDTSKLASGIPARFSGSGSGTDYTLTISSLQPEDFAVYYCQQWSSNPQYTFGQGTKLEIK |
| SEQ ID NO: 3199 | VL D-H.15 | DIQLTQSPSSLSASVGDRVTITCSVSSSVSYMHWYQQKPGKAPKRLIYDTSKLASGVPSRFSGSGSGTEYTLTISSLQPEDFATYYCQQWSSNPQYTFGQGTKLEIK |
| SEQ ID NO: 3200 | VL D-H.16 | EIVLTQSPATLSLSPGERATLSCSVSSSVSYMHWYQQKPGQAPKLLIYDTSKLASGIPARFSGSGPGTDYTLTISSLEPEDFAVYYCQQWSSNPQYTFGQGTKLEIK |
| SEQ ID NO: 3201 | VL D-H.17 | EIVLTQSPATLSLSPGERATLSCSVSSSVSYMHWYQQKPGQAPKLLIYDTSKLASGIPARFSGSGSGTDYTLTISRLEPEDFAVYYCQQWSSNPQYTFGQGTKLEIK |
| SEQ ID NO: 3202 | VL D-H.18 | EIVLTQSPATLSLSPGERATLSCSVSSSVSYMHWYQQKPGQAPKLLIYDTSKLASGIPARFSGSGSGTDYTLTISSLQPEDFAVYYCQQWSSNPQYTFGQGTKLEIK |
| SEQ ID NO: 3203 | VL D-H.19 | EIVLTQSPATLSVSPGERATLSCSVSSSVSYMHWYQQKPGQAPKLLIYDTSKLASGIPARFSGSGSGTEYTLTISSLQSEDFAVYYCQQWSSNPQYTFGQGTKLEIK |
| SEQ ID NO: 3204 | VL D-H.20 | EIVLTQSPATLSVSPGERATLSCSVSSSVSYMHWYQQKPGQAPKLLIYDTSKLASGIPARFSGSGSGTEYTLTISILQSEDFAVYYCQQWSSNPQYTFGQGTKLEIK |
| SEQ ID NO: 3205 | VL D-H.21 | EIVLTQSPPTLSLSPGERVTLSCSVSSSVSYMHWYQQKPGQAPKLLIYDTSKLASSIPARFSGSGSGTDYTLTISSLQPEDFAVYYCQQWSSNPQYTFGQGTKLEIK |
| SEQ ID NO: 3206 | VL D-H.22 | DIQLTQSPSSLSASVGDRVTITCSVSSSVSYMHWYQQKPGKAPKSLIYDTSKLASGVPSRFSGSGSGTDYTLTISSLQPEDFATYYCQQWSSNPQYTFGQGTKLEIK |
| SEQ ID NO: 3207 | VL D-H.23 | DIQLTQSPSSLSASVGDRVTITCSVSSSVSYMHWYQQKPGKAPKRLIYDTSKLASGVPSRFSGSGSGTEYTLTISNLQPEDFATYYCQQWSSNPQYTFGQGTKLEIK |
| SEQ ID NO: 3208 | VL D-H.24 | DIQLTQSPSAMSASVGDRVTITCSVSSSVSYMHWYQQKPGKVPKRLIYDTSKLASGVPSRFSGSGSGTEYTLTISSLQPEDFATYYCQQWSSNPQYTFGQGTKLEIK |

TABLE 12-continued

Amino acid sequences for anti TCRβ V10 antibodies
Amino acid and nucleotide sequences for murine and humanized antibody molecules which bind to TCRBV 10 (e.g., TCRBV 10-1, TCRBV 10-2 or TCRBV 10-3). The amino acid the heavy and light chain CDRs, and the amino acid and nucleotide sequences of the heavy and light chain variable regions, and the heavy and light chains are shown.

| | | | |
|---|---|---|---|
| SEQ ID NO: 3209 | VL | D-H.25 | EIVLTQSPATLSLSPGERATLSCSVSSSVSYMHWYQQKPGQAPKLLIYDTSKLASGIPDRFSGSGSGTDYTLTISRLEPEDFAVYYCQQWSSNPQYTFGQGTKLEIK |
| SEQ ID NO: 3210 | VL | D-H.26 | EIVLTQSPATLSLSPGERATLSCSVSSSVSYMHWYQQKPGLAPKLLIYDTSKLASGIPDRFSGSGSGTDYTLTISRLEPEDFAVYYCQQWSSNPQYTFGQGTKLEIK |
| SEQ ID NO: 3211 | VL | D-H.27 | EIVLTQSPGTLSLSPGERATLSCSVSSSVSYMHWYQQKPGQAPKLLIYDTSKLASGIPDRFSGSGSGTDYTLTISRLEPEDFAVYYCQQWSSNPQYTFGQGTKLEIK |
| SEQ ID NO: 3212 | VL | D-H.28 | DIQLTQSPSSLSASVGDRVTITCSVSSSVSYMHWYQQKPGKAPKSLIYDTSKLASGVPSKFSGSGSGTDYTLTISSLQPEDFATYYCQQWSSNPQYTFGQGTKLEIK |
| SEQ ID NO: 3213 | VL | D-H.29 | DIQLTQSPSSLSASVGDRVTITCSVSSSVSYMHWYQQKPEKAPKSLIYDTSKLASGVPSRFSGSGSGTDYTLTISSLQPEDFATYYCQQWSSNPQYTFGQGTKLEIK |
| SEQ ID NO: 3214 | VL | D-H.30 | DIVLTQSPDSLAVSLGERATINCSVSSSVSYMHWYQQKPGQPPKLLIYDTSKLASGVPDRFSGSGSGTDYTLTISSLQAEDVAVYYCQQWSSNPQYTFGQGTKLEIK |
| SEQ ID NO: 3215 | VL | D-H.31 | EIVLTQTPLSLSITPGEQASMSCSVSSSVSYMHWYLQKARPVPKLLIYDTSKLASGVPDRFSGSGSGTDYTLKISRVEAEDFGVYYCQQWSSNPQYTFGQGTKLEIK |
| SEQ ID NO: 3216 | VL | D-H.32 | EIVLTQTPLSLSITPGEQASISCSVSSSVSYMHWYLQKARPVPKLLIYDTSKLASGVPDRFSGSGSGTDYTLKISRVEAEDFGVYYCQQWSSNPQYTFGQGTKLEIK |
| SEQ ID NO: 3217 | VL | D-H.33 | DIVLTQSPLSLPVTPGEPASISCSVSSSVSYMHWYLQKPGQSPKLLIYDTSKLASGVPDRFSGSGSGTDYTLKISRVEAEDVGVYYCQQWSSNPQYTFGQGTKLEIK |
| SEQ ID NO: 3218 | VL | D-H.34 | DIVLTQSPLSLPVTLGQPASISCSVSSSVSYMHWYQQRPGQSPKRLIYDTSKLASGVPDRFSGSGSGTDYTLKISRVEAEDVGVYYCQQWSSNPQYTFGQGTKLEIK |
| SEQ ID NO: 3219 | VL | D-H.35 | DIVLTQTPLSLPVTPGEPASISCSVSSSVSYMHWYLQKPGQSPKLLIYDTSKLASGVPDRFSGSGSGTDYTLKISRVEAEDVGVYYCQQWSSNPQYTFGQGTKLEIK |
| SEQ ID NO: 3220 | VL | D-H.36 | DIVLTQTPLSLSVTPGQPASISCSVSSSVSYMHWYLQKPGQSPKLLIYDTSKLASGVPDRFSGSGSGTDYTLKISRVEAEDVGVYYCQQWSSNPQYTFGQGTKLEIK |
| SEQ ID NO: 3221 | VL | D-H.37 | DIVLTQTPLSLSVTPGQPASISCSVSSSVSYMHWYLQKPGQPPKLLIYDTSKLASGVPDRFSGSGSGTDYTLKISRVEAEDVGVYYCQQWSSNPQYTFGQGTKLEIK |
| SEQ ID NO: 3222 | VL | D-H.38 | DIQLIQSPSFLSASVGDRVSIICSVSSSVSYMHWYLQKPGKSPKLFIYDTSKLASGVSSRFSGRGSGTDYTLTIISLKPEDFAAYYCQQWSSNPQYTFGQGTKLEIK |
| SEQ ID NO: 3223 | VL | D-H.39 | DIVLTQTPLSSPVTLGQPASISCSVSSSVSYMHWYQQRPGQPPKLLIYDTSKLASGVPDRFSGSGAGTDYTLKISRVEAEDVGVYYCQQWSSNPQYTFGQGTKLEIK |
| SEQ ID NO: 3224 | VL | D-H.40 | EITLTQSPAFMSATPGDKVNISCSVSSSVSYMHWYQQKPGEAPKFIIYDTSKLASGIPPRFSGSGYGTDYTLTINNIESEDAAYYYCQQWSSNPQYTFGQGTKLEIK |
| Variable HEAVY chain (VH) | | | |
| SEQ ID NO: 3225 | VH | D-H.1 | EVQLVESGGGLVKPGGSLRLSCAVSGFTFRSYGMSWVRQAPGKGLEWVALISSGGSYTYYTDSVKGRFTISRDNSKNTLYLQMNSLKTEDTAVYYCSRHGGNFFDYWGQGTTVTVSS |
| SEQ ID NO: 3226 | VH | D-H.2 | EVQLVESGGALVKPGGSLRLSCAVSGFTFRSYGMSWVRQAPGKGLEWVALISSGGSYTYYTDSVKGRFTISRDNSKNTLYLQMNSLKTEDTAVYYCSRHGGNFFDYWGQGTTVTVSS |

TABLE 12-continued

Amino acid sequences for anti TCRβ V10 antibodies
Amino acid and nucleotide sequences for murine and humanized antibody molecules which bind to TCRBV 10 (e.g., TCRBV 10-1, TCRBV 10-2 or TCRBV 10-3). The amino acid the heavy and light chain CDRs, and the amino acid and nucleotide sequences of the heavy and light chain variable regions, and the heavy and light chains are shown.

| | | | |
|---|---|---|---|
| SEQ ID NO: 3227 | VH | D-H.3 | EVQLVESGGGLVQPGGSLRLSCAVSGFTFRSYGMSWVRQAPGKGLEWVALISSGGSYTYYTDSVKGRFTISRDNAKNTLYLQMNSLRAEDTAVYYCSRHGGNFFDYWGQGTTVTVSS |
| SEQ ID NO: 3228 | VH | D-H.4 | EVQLVESGGGLVQPGGSLRLSCAVSGFTFRSYGMSWVRQAPGKGLEWVALISSGGSYTYYTDSVKGRFTISRDNAKNSLYLQMNSLRAEDTAVYYCSRHGGNFFDYWGQGTTVTVSS |
| SEQ ID NO: 3229 | VH | D-H.5 | EVQLVESGGGLVQPGGSLRLSCAVSGFTFRSYGMSWVRQAPGKGLEWVALISSGGSYTYYTDSVKGRFTISRDNSKNSLYLQMNSLKTEDTAVYYCSRHGGNFFDYWGQGTTVTVSS |
| SEQ ID NO: 3230 | VH | D-H.6 | EVQLVESGGGLVQPGGSLRLSCAVSGFTFRSYGMSWVRQAPGKGLEWVALISSGGSYTYYTDSVKGRFTISRDNAKNSLYLQMNSLRAEDMAVYYCSRHGGNFFDYWGQGTTVTVSS |
| SEQ ID NO: 3231 | VH | D-H.7 | EVQLVESGGGLVQPGGSLRLSCAVSGFTFRSYGMSWVRQAPGKGLEWVALISSGGSYTYYTDSVKGQFTISRDNAKNTLYLQMNSLRAEDMAVYYCSRHGGNFFDYWGQGTTVTVSS |
| SEQ ID NO: 3232 | VH | D-H.8 | EVQLVESGGGLVKPGRSLRLSCTVSGFTFRSYGMSWVRQAPGKGLEWVALISSGGSYTYYTDSVKGRFTISRDNSKNILYLQMNSLKTEDTAVYYCSRHGGNFFDYWGQGTTVTVSS |
| SEQ ID NO: 3233 | VH | D-H.9 | EVQLVESGGGLVKPGGSLRLSCAVSGFTFRSYGMSWVRQAPGKGLEWVALISSGGSYTYYTDSVKGRFTISRDNAKNSLYLQMNSLRAEDTAVYYCSRHGGNFFDYWGQGTTVTVSS |
| SEQ ID NO: 3234 | VH | D-H.10 | EVQLVESGGGLVQPGGSLKLSCAVSGFTFRSYGMSWVRQASGKGLEWVALISSGGSYTYYTDSVKGRFTISRDNSKNTLYLQMNSLKTEDTAVYYCSRHGGNFFDYWGQGTTVTVSS |
| SEQ ID NO: 3235 | VH | D-H.11 | QVQLVESGGGVVQPGGSLRLSCAVSGFTFRSYGMSWVRQAPGKGLEWVALISSGGSYTYYTDSVKGRFTISRDNSKNTLYLQMNSLRAEDTAVYYCSRHGGNFFDYWGQGTTVTVSS |
| SEQ ID NO: 3236 | VH | D-H.12 | QVQLVESGGGVVQPGRSLRLSCAVSGFTFRSYGMSWVRQAPGKGLEWVALISSGGSYTYYTDSVKGRFTISRDNSKNTLYLQMSSLRAEDTAVYYCSRHGGNFFDYWGQGTTVTVSS |
| SEQ ID NO: 3237 | VH | D-H.13 | EVQLVESGGGLVQPGGSLRLSCPVSGFTFRSYGMSWVRQAPGKGLEWVALISSGGSYTYYTDSVKGRFTISRDNANNSLYLQMNSLRAEDTAVYYCSRHGGNFFDYWGQGTTVTVSS |
| SEQ ID NO: 3238 | VH | D-H.14 | EVQLVESGGGLVQPGRSLRLSCTVSGFTFRSYGMSWVRQAPGKGLEWVALISSGGSYTYYTDSVKGRFTISRDNSKNILYLQMNSLKTEDTAVYYCSRHGGNFFDYWGQGTTVTVSS |
| SEQ ID NO: 3239 | VH | D-H.15 | EVQLVESGGGLVQPGPSLRLSCTVSGFTFRSYGMSWVRQAPGKGLEWVALISSGGSYTYYTDSVKGRFTISRDNSKNILYLQMNSLKTEDTAVYYCSRHGGNFFDYWGQGTTVTVSS |
| SEQ ID NO: 3240 | VH | D-H.16 | EVQLVESGGGLVQPGGSLRLSCAVSGFTFRSYGMSWVRQAPGKGLEWVALISSGGSYTYYTDSVKGRFTISRDNSKNTLYLQMNSLRAEDTAVYYCSRHGGNFFDYWGQGTTVTVSS |
| SEQ ID NO: 3241 | VH | D-H.17 | EVQLVESGGGLVQPGGSLRLSCAVSGFTFRSYGMSWVRQAPGKGLEWVALISSGGSYTYYTDSVKGRFTISRDNAKNSLYLQMNSLRDEDTAVYYCSRHGGNFFDYWGQGTTVTVSS |
| SEQ ID NO: 3242 | VH | D-H.18 | QVQLVESGGGLVKPGGSLRLSCAVSGFTFRSYGMSWVRQAPGKGLEWVALISSGGSYTYYTDSVKGRFTISRDNAKNSLYLQMNSLRAEDTAVYYCSRHGGNFFDYWGQGTTVTVSS |
| SEQ ID NO: 3243 | VH | D-H.19 | QVQLVESGGGVVQPGRSLRLSCAVSGFTFRSYGMSWVRQAPGKGLEWVALISSGGSYTYYTDSVKGRFTISRDNSKNTLYLQMNSLRAEDTAVYYCSRHGGNFFDYWGQGTTVTVSS |
| SEQ ID NO: 3244 | VH | D-H.20 | EVQLLESGGGLVQPGGSLRLSCAVSGFTFRSYGMSWVRQAPGKGLEWVALISSGGSYTYYTDSVKGRFTISRDNSKNTLYLQMNSLRAEDTAVYYCSRHGGNFFDYWGQGTTVTVSS |

TABLE 12-continued

| Amino acid sequences for anti TCRβ V10 antibodies<br>Amino acid and nucleotide sequences for murine and humanized antibody molecules which bind to TCRBV 10 (e.g., TCRBV 10-1, TCRBV 10-2 or TCRBV 10-3). The amino acid the heavy and light chain CDRs, and the amino acid and nucleotide sequences of the heavy and light chain variable regions, and the heavy and light chains are shown. | | | |
|---|---|---|---|
| SEQ ID NO: 3245 | VH | D-H.21 | EVQLVESGGGLVQPGGSLRLSCAVSGFTFRSYGMSWVRQAPGKGLEWVALISSGGSYTYYTDSVKGRFTISRHNSKNTLYLQMNSLRAEDTAVYYCSRHGGNFFDYWGQGTTVTVSS |
| SEQ ID NO: 3246 | VH | D-H.22 | EVQLVESGGGLIQPGGSLRLSCAVSGFTFRSYGMSWVRQPPGKGLEWVALISSGGSYTYYTDSVKGRFTISRDNSKNTLYLQMNSLRAEDTAVYYCSRHGGNFFDYWGQGTTVTVSS |
| SEQ ID NO: 3247 | VH | D-H.23 | EVQLVESGGGLIQPGGSLRLSCAVSGFTFRSYGMSWVRQAPGKGLEWVALISSGGSYTYYTDSVKGRFTISRDNSKNTLYLQMNSLRAEDTAVYYCSRHGGNFFDYWGQGTTVTVSS |
| SEQ ID NO: 3248 | VH | D-H.24 | EVQLVESGGGLVQPGRSLRLSCAVSGFTFRSYGMSWVRQAPGKGLEWVALISSGGSYTYYTDSVKGRFTISRDNAKNSLYLQMNSLRAEDTALYYCSRHGGNFFDYWGQGTTVTVSS |
| SEQ ID NO: 3249 | VH | D-H.25 | QVQLVESGGGVVQPGRSLRLSCAVSGFTFRSYGMSWVRQAPGKGLEWVALISSGGSYTYYTDSVKGRFTISRDNSKNRLYLQMNSLRAEDTAVYYCSRHGGNFFDYWGQGTTVTVSS |
| SEQ ID NO: 3250 | VH | D-H.26 | QVQLVESGGGVVQPGRSLRLSCAVSGFTFRSYGMSWVRQAPGKGLEWVALISSGGSYTYYTDSVKGRFTISRDNSKNTLYLQMNSLRAEGTAVYYCSRHGGNFFDYWGQGTTVTVSS |
| SEQ ID NO: 3251 | VH | D-H.27 | QVQLVESGGGVVQPGRSLRLSCAVSGFTFRSYGMSWVRQAPGKGLEWVALISSGGSYTYYTDSVKGRFAISRDNSKNTLYLQMNSLRAEDTAVYYCSRHGGNFFDYWGQGTTVTVSS |
| SEQ ID NO: 3252 | VH | D-H.28 | QVQLVDSGGGVVQPGRSLRLSCAVSGFTFRSYGMSWVRQAPGKGLEWVALISSGGSYTYYTDSVKGRFTISRDNSKNTLYLQMNSLRAEDTAVYYCSRHGGNFFDYWGQGTTVTVSS |
| SEQ ID NO: 3253 | VH | D-H.29 | EVQLVESGGGVVRPGGSLRLSCAVSGFTFRSYGMSWVRQAPGKGLEWVALISSGGSYTYYTDSVKGRFTISRDNAKNSLYLQMNSLRAEDTALYHCSRHGGNFFDYWGQGTTVTVSS |
| SEQ ID NO: 3254 | VH | D-H.30 | EVQLVESGGVVVQPGGSLRLSCAVSGFTFRSYGMSWVRQAPGKGLEWVALISSGGSYTYYTDSVKGRFTISRDNSKNSLYLQMNSLRAEDTALYYCSRHGGNFFDYWGQGTTVTVSS |
| SEQ ID NO: 3255 | VH | D-H.31 | EVQLVESGGGVVQPGGSLRLSCAVSGFTFRSYGMSWVRQAPGKGLEWVALISSGGSYTYYTDSVKGRFTISRDNSKNSLYLQMNSLRTEDTALYYCSRHGGNFFDYWGQGTTVTVSS |
| SEQ ID NO: 3256 | VH | D-H.32 | EVQLVESGGVVVQPGGSLRLSCAVSGFTFRSYGMSWVRQAPGKGLEWVALISSGGSYTYYTDSVKGRFTISRDNSKNSLYLQMNSLRTEDTALYYCSRHGGNFFDYWGQGTTVTVSS |
| SEQ ID NO: 3257 | VH | D-H.33 | EVQLVETGGGLIQPGGSLRLSCAVSGFTFRSYGMSWVRQAPGKGLEWVALISSGGSYTYYTDSVKGRFTISRDNSKNTLYLQMNSLRAEDTAVYYCSRHGGNFFDYWGQGTTVTVSS |
| SEQ ID NO: 3258 | VH | D-H.34 | EVQLVESGGGLVQPGGSLRLSCAVSGFTFRSYGMSWVRQATGKGLEWVALISSGGSYTYYTDSVKGRFTISRENAKNSLYLQMNSLRAGDTAVYYCSRHGGNFFDYWGQGTTVTVSS |
| SEQ ID NO: 3259 | VH | D-H.35 | EVQLVESRGVLVQPGGSLRLSCAVSGFTFRSYGMSWVRQAPGKGLEWVALISSGGSYTYYTDSVKGRFTISRDNSKNTLHLQMNSLRAEDTAVYYCSRHGGNFFDYWGQGTTVTVSS |
| SEQ ID NO: 3260 | VH | D-H.36 | EVQLVESGGGLVQPGRSLRLSCAVSGFTFRSYGMSWVRQAPGKGLEWVALISSGGSYTYYTDSVKGRFTISRDNAKNSLYLQMNSLRAEDMALYYCSRHGGNFFDYWGQGTTVTVSS |
| SEQ ID NO: 3261 | VH | D-H.37 | QVQLVESGGGLVQPGGSLRLSCSVSGFTFRSYGMSWVRQAPGKGLEWVALISSGGSYTYYTDSVKGRFTISRDNSKNTLYLQMNSLRAEDTAVYYCSRHGGNFFDYWGQGTTVTVSS |
| SEQ ID NO: 3262 | VH | D-H.38 | EVQLVESGGGLVQPGGSLRLSCSVSGFTFRSYGMSWVRQAPGKGLEWVALISSGGSYTYYTDSVKGRFTISRDNSKNTLYLQMSSLRAEDTAVYYCSRHGGNFFDYWGQGTTVTVSS |
| SEQ ID | VH | D-H.39 | QVQLVESGGGVVQPGRSLRLSCAVSGFTFRSYGMSWVRQAPGKG |

TABLE 12-continued

Amino acid sequences for anti TCRβ V10 antibodies
Amino acid and nucleotide sequences for murine and humanized antibody molecules which bind to TCRBV 10 (e.g., TCRBV 10-1, TCRBV 10-2 or TCRBV 10-3). The amino acid the heavy and light chain CDRs, and the amino acid and nucleotide sequences of the heavy and light chain variable regions, and the heavy and light chains are shown.

| | | | |
|---|---|---|---|
| NO: 3263 | | | LEWVALISSGGSYTYYTDSVKGRFTISRDNSTNTLFLQMNSLRAED TAVYYCSRHGGNFFDYWGQGTTVTVSS |
| SEQ ID NO: 3264 | VH | D-H.40 | QVQLLESGGGLVKPGGSLRLSCAVSGFTFRSYGMSWVRQAPGKGL EWVALISSGGSYTYYTDSVKGRFTISRDNAKNSLYLQMNSLRAED TAVYYCSRHGGNFFDYWGQGTTVTVSS |
| SEQ ID NO: 3265 | VH | D-H.41 | EVQLVESGEGLVQPGGSLRLSCAVSGFTFRSYGMSWVRQAPGKGL EWVALISSGGSYTYYTDSVKGRFTISRDNSKNTLYLQMGSLRAED MAVYYCSRHGGNFFDYWGQGTTVTVSS |
| SEQ ID NO: 3266 | VH | D-H.42 | EVQLVESGGGLVQPGGSLRLSCAVSGFTFRSYGMSWVRQAPGKGL EWVALISSGGSYTYYTDSVKGRFTISRDNSKNTLYLQMGSLRAED MAVYYCSRHGGNFFDYWGQGTTVTVSS |
| SEQ ID NO: 3267 | VH | D-H.43 | EVQLVESGGGLVQPGGSLRLSCSVSGFTFRSYGMSWVRQAPGKGL EWVALISSGGSYTYYTDSVKGRFTISRDNSKNTLYVQMSSLRAEDT AVYYCSRHGGNFFDYWGQGTTVTVSS |
| SEQ ID NO: 3268 | VH | D-H.44 | EVQLVESGGGLVQPGGSLRLSCAVSGFTFRSYGMSWVRQAPGKGL EWVALISSGGSYTYYTDSVKGRFIISRDNSRNSLYLQKNRRRAEDM AVYYCSRHGGNFFDYWGQGTTVTVSS |
| SEQ ID NO: 3269 | VH | D-H.45 | EVQLVESGGGLVQPGGSLRLSCAVSGFTFRSYGMSWVHQAPGKG LEWVALISSGGSYTYYTDSVKGRFIISRDNSRNTLYLQTNSLRAE DTAVYYCSRHGGNFFDYWGQGTTVTVSS |
| SEQ ID NO: 3270 | VH | D-H.46 | EVHLVESGGGLVQPGGALRLSCAVSGFTFRSYGMSWVRQATGKG LEWVALISSGGSYTYYTDSVKGRFTISRENAKNSLYLQMNSLRAG DTAVYYCSRHGGNFFDYWGQGTTVTVSS |
| SEQ ID NO: 3271 | VH | D-H.47 | EVQLVESGGGLVQPRGSLRLSCAVSGFTFRSYGMSWVRQAPGKGL EWVALISSGGSYTYYTDSVKGRFTISRDNSKNTLYLQMNNLRAEG TAVYYCSRHGGNFFDYWGQGTTVTVSS |
| SEQ ID NO: 3272 | VH | D-H.48 | EVQLVESGGGLVQPRGSLRLSCAVSGFTFRSYGMSWVRQAPGKGL EWVALISSGGSYTYYTDSVKGRFTISRDNSKNTLYLQMNNLRAEG TAAYYCSRHGGNFFDYWGQGTTVTVSS |
| SEQ ID NO: 3273 | VH | D-H.49 | QVQLVQSGAEVKKPGASVKVSCKVSGFTFRSYGMSWVRQAPGKG LEWVALISSGGSYTYYTDSVKGRFTITRDNSTNTLYMELSSLRSED TAVYYCSRHGGNFFDYWGQGTTVTVSS |
| SEQ ID NO: 3274 | VH | D-H.50 | QVQLVQSGSELKKPGASVKVSCKVSGFTFRSYGMSWVRQAPGQG LEWVALISSGGSYTYYTDSVKGRFVISRDNSVNTLYLQISSLKAE DTAVYYCSRHGGNFFDYWGQGTTVTVSS |

In some embodiments, the anti-TCRβ V 10 antibody molecule comprises a VH or a VL of an antibody described in Table 12, or a sequence with at least 80%, 85%, 90%, 95%, 96%, 97%, 98%, 99% or more identity thereto.

In some embodiments, the anti-TCRβ V 10 antibody molecule comprises a VH and a VL of an antibody described in Table 12, or a sequence with at least 80%, 85%, 90%, 95%, 96%, 97%, 98%, 99% or more identity thereto.

Additional anti-TCRVβ Antibodies

Additional exemplary anti-TCRβ V antibodies of the disclosure are provided in Table 13. In some embodiments, the anti-TCRβV antibody is a humanized antibody, e.g., as provided in Table 13. In some embodiments, the anti-TCRβV antibody comprises one or more (e.g., all three) of a LC CDR1, LC CDR2, and LC CDR3 provided in Table 13; and/or one or more (e.g., all three) of a HC CDR1, HC CDR2, and HC CDR3 provided in Table 13, or a sequence with at least 95% identity thereto. In some embodiments, the anti-TCRβV antibody comprises a variable heavy chain (VH) and/or a variable light chain (VL) provided in Table 13, or a sequence with at least 95% identity thereto.

TABLE 13

| | | |
|---|---|---|
| Amino acid sequences for additional anti-TCRβ V antibodies<br>Amino acid and nucleotide sequences for murine and humanized antibody molecules which bind to various TCRVB families are disclosed. The amino acid the heavy and light chain CDRs, and the amino acid and nucleotide sequences of the heavy and light chain variable regions, and the heavy and light chains are shown. Antibodies disclosed in the table include, MPB2D5, CAS1.1.3, IMMU222, REA1062, and JOVI-3. MPB2D5 binds human TCRβV 20-1 (TCRβV2 per old nomenclature). CAS1.1.3 binds human TCRβV 27 (TCRβV14 per old nomenclature). IMMU 222 binds human TCRβV 6-5, TCRβV 6-6, or TCRβV 6-9 (TCRβV13.1 per old nomenclature). REA1062 binds human TCRβV 5-1). JOVI-3 binds human TCRβV 28 (TCRβV3.1 per old nomenclature). IMMU546 binds human TCRβV 2. | | |
| MPB2D5 (murine), also referred to here as BJ1188, BJ1190 and REA654; or Antibody G<br>Binds to human TCRVβ 20-1 | | |
| SEQ ID NO: 1102 | HC CDR1 (Kabat) | SAYMH |
| SEQ ID NO: 1103 | HC CDR2 (Kabat) | RIDPATGKTKYAPKFQA |
| SEQ ID NO: 1104 | HC CDR3 (Kabat) | SLNWDYGLDY |
| SEQ ID NO: 1105 | HC CDR1 (Chothia) | GFNIKSA |
| SEQ ID NO: 1106 | HC CDR2 (Chothia) | DPATGK |
| SEQ ID NO: 1104 | HC CDR3 (Chothia) | SLNWDYGLDY |
| SEQ ID NO: 3640 | HC CDR1 (Combined) | GFNIKSAYMH |
| SEQ ID NO: 1103 | HC CDR2 (Combined) | RIDPATGKTKYAPKFQA |
| SEQ ID NO: 1104 | HC CDR3 (Combined) | SLNWDYGLDY |
| SEQ ID NO: 1107 | LC CDR1 (Kabat) | RASKSVSILGTHLIH |
| SEQ ID NO: 1108 | LC CDR2 (Kabat) | AASNLES |
| SEQ ID NO: 1109 | LC CDR3 (Kabat) | QQSIEDPWT |
| SEQ ID NO: 1110 | LC CDR1 (Chothia) | SKSVSILGTHL |
| SEQ ID NO: 1108 | LC CDR2 (Chothia) | AASNLES |
| SEQ ID NO: 1109 | LC CDR3 (Chothia) | QQSIEDPWT |
| SEQ ID NO: 1107 | LC CDR1 (Combined) | RASKSVSILGTHLIH |
| SEQ ID NO: 1108 | LC CDR2 (Combined) | AASNLES |
| SEQ ID NO: 1109 | LC CDR3 (Combined) | QQSIEDPWT |
| SEQ ID NO: 1111 | VL | DIVLTQSPASLAVSLGQRATISCRASKSVSILGTHLIHW<br>YQQKPGQPPKLLIYAASNLESGVPARFSGSGSETVFTL<br>NIHPVEEEDAATYFCQQSIEDPWTFGGGTKLGIK |
| SEQ ID NO: 1112 | VH | EVQLQQSVADLVRPGASLKLSCTASGFNIKSAYMHW<br>VIQRPDQGPECLGRIDPATGKTKYAPKFQAKATITADT<br>SSNTAYLQLSSLTSEDTAIYYCTRSLNWDYGLDYWGQ<br>GTSVTVSS |
| VH for MPB2D5 (humanized) also referred to as Antibody G-H (humanized)<br>Binds to human TCRVβ 20-1 | | |
| SEQ ID NO: 1113 | VH-1 | QVQLVQSGAEVKKPGASVKVSCKASGFNIKSAYMHW<br>VRQAPGQGLEWMGRIDPATGKTKYAPKFQARVTMT<br>ADTSTNTAYMELSSLRSEDTAVYYCARSLNWDYGLD<br>YWGQGTLVTVSS |
| SEQ ID NO: 1114 | VH-2 | QVQLVQSGAEVKKPGASVKVSCKASGFNIKSAYMHW<br>VRQAPGQEPGCMGRIDPATGKTKYAPKFQARVTMTA<br>DTSINTAYTELSSLRSEDTATYYCARSLNWDYGLDYW<br>GQGTLVTVSS |
| SEQ ID NO: 1115 | VH-3 | QVQLVQSGAEVKKPGSSVKVSCKASGFNIKSAYMHW<br>VRQAPGQGLEWMGRIDPATGKTKYAPKFQARVTITA<br>DTSTNTAYMELSSLRSEDTAVYYCARSLNWDYGLDY<br>WGQGTLVTVSS |
| SEQ ID NO: 1116 | VH-4 | QVQLVQSGAEVKKPGASVKVSCKASGFNIKSAYMHW<br>VRQAPGQRLEWMGRIDPATGKTKYAPKFQARVTITA<br>DTSANTAYMELSSLRSEDTAVYYCARSLNWDYGLDY |

TABLE 13-continued

Amino acid sequences for additional anti-TCRβ V antibodies
Amino acid and nucleotide sequences for murine and humanized antibody molecules which bind to various TCRVB families are disclosed. The amino acid the heavy and light chain CDRs, and the amino acid and nucleotide sequences of the heavy and light chain variable regions, and the heavy and light chains are shown. Antibodies disclosed in the table include, MPB2D5, CAS1.1.3, IMMU222, REA1062, and JOVI-3. MPB2D5 binds human TCRβV 20-1 (TCRβV2 per old nomenclature). CAS1.1.3 binds human TCRβV 27 (TCRβV14 per old nomenclature). IMMU 222 binds human TCRβV 6-5, TCRβV 6-6, or TCRβV 6-9 (TCRβV13.1 per old nomenclature). REA1062 binds human TCRβV 5-1). JOVI-3 binds human TCRβV 28 (TCRβV3.1 per old nomenclature). IMMU546 binds human TCRβV 2.

| | | |
|---|---|---|
| | | WGQGTLVTVSS |
| VL for MPB2D5 (humanized) also referred to as Antibody G-H (humanized) Binds to human TCRVβ 20-1 | | |
| SEQ ID NO: 1117 | VL-1 | EIVLTQSPATLSLSPGERATLSCRASKSVSILGTHLIHW YQQKPGQAPRLLIYAASNLESGIPARFSGSGSETDFTL TISSLEPEDFAVYFCQQSIEDPFGGGTKVEIK |
| SEQ ID NO: 1118 | VL-2 | EIVLTQSPATLSLSPGERATLSCRASKSVSILGTHLIHW YQQKPGLAPRLLIYAASNLESGIPDRFSGSGSETDFTLT ISRLEPEDFAVYFCQQSIEDPFGGGTKVEIK |
| SEQ ID NO: 1119 | VL-3 | EIVLTQSPGTLSLSPGERATLSCRASKSVSILGTHLIHW YQQKPGQAPRLLIYAASNLESGIPDRFSGSGSETDFTL TISRLEPEDFAVYFCQQSIEDPFGGGTKVEIK |
| CAS1.1.3 (murine) also referred to herein as BJ1460; or Antibody H Binds to human TCRVβ 27 | | |
| SEQ ID NO: 1120 | HC CDR1 (Kabat) | DTYMY |
| SEQ ID NO: 1121 | HC CDR2 (Kabat) | RIDPANGNTKYDPKFQD |
| SEQ ID NO: 1122 | HC CDR3 (Kabat) | GSYYYAMDY |
| SEQ ID NO: 1123 | HC CDR1 (Chothia) | GFKTEDT |
| SEQ ID NO: 1124 | HC CDR2 (Chothia) | DPANGN |
| SEQ ID NO: 1122 | HC CDR3 (Chothia) | GSYYYAMDY |
| SEQ ID NO: 1125 | HC CDR1 (Combined) | GFKTEDTYMY |
| SEQ ID NO: 1121 | HC CDR2 (Combined) | RIDPANGNTKYDPKFQD |
| SEQ ID NO: 1122 | HC CDR3 (Combined) | GSYYYAMDY |
| SEQ ID NO: 1126 | LC CDR1 (Kabat) | RASESVDSYGNSFMH |
| SEQ ID NO: 1127 | LC CDR2 (Kabat) | RASNLES |
| SEQ ID NO: 1128 | LC CDR3 (Kabat) | QQSNEDPYT |
| SEQ ID NO: 3641 | LC CDR1 (Chothia) | SESVDSYGNSF |
| SEQ ID NO: 1127 | LC CDR2 (Chothia) | RASNLES |
| SEQ ID NO: 1128 | LC CDR3 (Chothia) | QQSNEDPYT |
| SEQ ID NO: 1126 | LC CDR1 (Combined) | RASESVDSYGNSFMH |
| SEQ ID NO: 1127 | LC CDR2 (Combined) | RASNLES |
| SEQ ID NO: 1128 | LC CDR3 (Combined) | QQSNEDPYT |
| SEQ ID NO: 1129 | VL | DIVLTQSPASLAVSLGQRATISCRASESVDSYGNSFMH WYQQKPGQPPKLLIYRASNLESGIPARFSGSGSRTDFT LTTNPVEADDVATYYCQQSNEDPYTFGGGTKLEIK |
| SEQ ID NO: 1130 | VH | EVQLQQSGAELVKPGASVKLSCTASGFKTEDTYMYW VKQRPEQGLEWIGRIDPANGNTKYDPKFQDKATITAD SSSNTAYLQLSSLPSEDTAVYYCARGSYYYAMDYWG QGTSVTVSS |

TABLE 13-continued

Amino acid sequences for additional anti-TCRβ V antibodies
Amino acid and nucleotide sequences for murine and humanized antibody molecules which bind to various TCRVB families are disclosed. The amino acid the heavy and light chain CDRs, and the amino acid and nucleotide sequences of the heavy and light chain variable regions, and the heavy and light chains are shown. Antibodies disclosed in the table include, MPB2D5, CAS1.1.3, IMMU222, REA1062, and JOVI-3. MPB2D5 binds human TCRβV 20-1 (TCRβV2 per old nomenclature). CAS1.1.3 binds human TCRβV 27 (TCRβV14 per old nomenclature). IMMU 222 binds human TCRβV 6-5, TCRβV 6-6, or TCRβV 6-9 (TCRβV13.1 per old nomenclature). REA1062 binds human TCRβV 5-1). JOVI-3 binds human TCRβV 28 (TCRβV3.1 per old nomenclature). IMMU546 binds human TCRβV 2.

VH for CAS1.1.3 (humanized) also referred to as Antibody H-H (humanized)
Binds to human TCRVβ 27

| | | |
|---|---|---|
| SEQ ID NO: 1131 | VH-1 | QVQLVQSGAEVKKPGSSVKVSCKASGFKTEDTYMY WVRQAPGQGLEWIGRIDPANGNTKYDPKFQDRATIT ADSSTNTAYMELSSLRSEDTAVYYCARGSYYYAMDY WGQGTLVTVSS |
| SEQ ID NO: 1132 | VH-2 | QVQLVQSGAEVKKPGASVKVSCKASGFKTEDTYMY WVRQAPGQRLEWIGRIDPANGNTKYDPKFQDRATITA DSSANTAYMELSSLRSEDTAVYYCARGSYYYAMDY WGQGTLVTVSS |
| SEQ ID NO: 1133 | VH-3 | EVQLVESGGGLVQPGGSLKLSCAASGFKTEDTYMYW VRQASGKGLEWIGRIDPANGNTKYDPKFQDRATISAD SSKNTAYLQMNSLKTEDTAVYYCARGSYYYAMDYW GQGTLVTVSS |
| SEQ ID NO: 1134 | VH-4 | EVQLVQSGAEVKKPGESLRISCKASGFKTEDTYMYW VRQMPGKGLEWIGRIDPANGNTKYDPKFQDQATISAD SSINTAYLQWSSLKASDTAMYYCARGSYYYAMDYW GQGTLVTVSS |
| SEQ ID NO: 1135 | VH-5 | QVQLVQSGSELKKPGASVKVSCKASGFKTEDTYMYW VRQAPGQGLEWIGRIDPANGNTKYDPKFQDRAVISAD SSVNTAYLQISSLKAEDTAVYYCARGSYYYAMDYWG QGTLVTVSS |

VL for CAS1.1.3 (humanized) also referred to as Antibody H-H (humanized)
Binds to human TCRVβ 27

| | | |
|---|---|---|
| SEQ ID NO: 1136 | VL-1 | DIVLTQSPDSLAVSLGERATINCRASESVDSYGNSFMH WYQQKPGQPPKLLIYRASNLESGVPDRFSGSGSRTDF TLTISSLQAEDVAVYYCQQSNEDPYTFGQGTKLEIK |
| SEQ ID NO: 1137 | VL-2 | EIVLTQSPATLSLSPGERATLSCRASESVDSYGNSFMH WYQQKPGQAPKLLIYRASNLESGIPARFSGSGSRTDFT LTISRLEPEDFAVYYCQQSNEDPYTFGQGTKLEIK |
| SEQ ID NO: 1138 | VL-3 | DIQLTQSPSSLSASVGDRVTITCRASESVDSYGNSFMH WYQQKPGQAPKLLIYRASNLESGVPSRFSGSGSRTDF TLTISSLQPEDVATYYCQQSNEDPYTFGQGTKLEIK |
| SEQ ID NO: 1139 | VL-4 | AIQLTQSPSSLSASVGDRVTITCRASESVDSYGNSFMH WYQQKPGKAPKLLIYRASNLESGVPSRFSGSGSRTDF TLTISSLQPEDFATYYCQQSNEDPYTFGQGTKLEIK |
| SEQ ID NO: 1140 | VL-5 | EIVLTQSPDFQSVTPKEKVTITCRASESVDSYGNSFMH WYQQKPDQSPKLLIYRASNLESGVPSRFSGSGSRTDFT LTINSLEAEDAATYYCQQSNEDPYTFGQGTKLEIK |

IMMU222 (murine) also referred to as BJ1461; or Antibody I
Binds to human TCRVβ 6-5, 6-6, 6-9

| | | |
|---|---|---|
| SEQ ID NO: 1141 | HC CDR1 (Kabat) | SYAMS |
| SEQ ID NO: 1142 | HC CDR2 (Kabat) | HISNGGDYIYYADTVKG |
| SEQ ID NO: 1143 | HC CDR3 (Kabat) | PSYYSDPWFFDV |
| SEQ ID NO: 1144 | HC CDR1 (Chothia) | GFTFRSY |
| SEQ ID NO: 1145 | HC CDR2 (Chothia) | SNGGDY |
| SEQ ID NO: 1143 | HC CDR3 (Chothia) | PSYYSDPWFFDV |
| SEQ ID NO: 1146 | HC CDR1 (Combined) | GFTFRSYAMS |

TABLE 13-continued

| Amino acid sequences for additional anti-TCRβ V antibodies Amino acid and nucleotide sequences for murine and humanized antibody molecules which bind to various TCRVB families are disclosed. The amino acid the heavy and light chain CDRs, and the amino acid and nucleotide sequences of the heavy and light chain variable regions, and the heavy and light chains are shown. Antibodies disclosed in the table include, MPB2D5, CAS1.1.3, IMMU222, REA1062, and JOVI-3. MPB2D5 binds human TCRβV 20-1 (TCRβV2 per old nomenclature). CAS1.1.3 binds human TCRβV 27 (TCRβV14 per old nomenclature). IMMU 222 binds human TCRβV 6-5, TCRβV 6-6, or TCRβV 6-9 (TCRβV13.1 per old nomenclature). REA1062 binds human TCRβV 5-1). JOVI-3 binds human TCRβV 28 (TCRβV3.1 per old nomenclature). IMMU546 binds human TCRβV 2. | | |
|---|---|---|
| SEQ ID NO: 1142 | HC CDR2 (Combined) | HISNGGDYIYYADTVKG |
| SEQ ID NO: 1143 | HC CDR3 (Combined) | PSYYSDPWFFDV |
| SEQ ID NO: 1147 | LC CDR1 (Kabat) | SAGSSVSFMH |
| SEQ ID NO: 1148 | LC CDR2 (Kabat) | DTSKLAS |
| SEQ ID NO: 1149 | LC CDR3 (Kabat) | LQGSGFPLT |
| SEQ ID NO: 1150 | LC CDR1 (Chothia) | GSSVSF |
| SEQ ID NO: 1148 | LC CDR2 (Chothia) | DTSKLAS |
| SEQ ID NO: 1149 | LC CDR3 (Chothia) | LQGSGFPLT |
| SEQ ID NO: 1147 | LC CDR1 (Combined) | SAGSSVSFMH |
| SEQ ID NO: 1148 | LC CDR2 (Combined) | DTSKLAS |
| SEQ ID NO: 1149 | LC CDR3 (Combined) | LQGSGFPLT |
| SEQ ID NO: 1151 | VL | ENVLTQSPAIMSASPGEKVTMTCSAGSSVSFMHWYQ QKSSTSPKLWIYDTSKLASGVPGRFSGSGSGNSFSLTIS SMEAEDVAIYYCLQGSGFPLTFGSGTKLEIK |
| SEQ ID NO: 1152 | VH | DVKLVESGEGLVKPGGSLKLSCAASGFTFRSYAMSW VRQTPEKRLEWVAHISNGGDYIYYADTVKGRFTISRD NARNTLYLQMSSLKSEDTAMYYCTRPSYYSDPWFFD VWGTGTTVTVSS |
| VH for IMMU222 (humanized) also referred to as Antibody I-H Binds to human TCRVβ 6-5, 6-6, 6-9 | | |
| SEQ ID NO: 1153 | VH-1 | EVQLVESGGGLVQPGGSLRLSCAASGFTFRSYAMSW VRQAPGKGLEWVAHISNGGDYIYYADTVKGRFTISRD NAKNSLYLQMNSLRAEDTAVYYCTRPSYYSDPWFFD VWGQGTTVTVSS |
| SEQ ID NO: 1154 | VH-2 | QVQLVESGGGVVQPGRSLRLSCAASGFTFRSYAMSW VRQAPGKGLEWVAHISNGGDYIYYADTVKGRFTISRD NSKNTLYLQMSSLRAEDTAVYYCTRPSYYSDPWFFD VWGQGTTVTVSS |
| SEQ ID NO: 1155 | VH-3 | EVQLVESGGGLVQPGGSLRLSCAASGFTFRSYAMSW VRQAPGKGLEWVAHISNGGDYIYYADTVKGRFTISRD NSKNTLYLQMNSLRAEDTAVYYCTRPSYYSDPWFFD VWGQGTTVTVSS |
| SEQ ID NO: 1156 | VH-4 | QVQLVQSGSELKKPGASVKVSCKASGFTFRSYAMSW VRQAPGQGLEWVAHISNGGDYIYYADTVKGRFVISR DNSVNTLYLQISSLKAEDTAVYYCTRPSYYSDPWFFD VWGQGTTVTVSS |
| SEQ ID NO: 1157 | VH-5 | QVQLVQSGAEVKKPGASVKVSCKASGFTFRSYAMSW VRQAPGQRLEWVAHISNGGDYIYYADTVKGRFTITRD NSANTLYMELSSLRSEDTAVYYCTRPSYYSDPWFFDV WGQGTTVTVSS |
| VL for IMMU222 (humanized)) also referred to as Antibody I-H Binds to human TCRVβ 6-5, 6-6, 6-9 | | |
| SEQ ID NO: 1158 | VL-1 | ENVLTQSPATLSLSPGERATLSCSAGSSVSFMHWYQQ KPGQAPKLLIYDTSKLASGIPARFSGSGSGNDFTLTISS LEPEDFAVYYCLQGSGFPLTFGQGTKLEIK |
| SEQ ID NO: 1159 | VL-2 | ENVLTQSPDFQSVTPKEKVTITCSAGSSVSFMHWYQQ KPDQSPKLLIYDTSKLASGVPSRFSGSGSGNDFTLTINS LEAEDAATYYCLQGSGFPLTFGQGTKLEIK |

TABLE 13-continued

Amino acid sequences for additional anti-TCRβ V antibodies
Amino acid and nucleotide sequences for murine and humanized antibody molecules which bind to various TCRVB families are disclosed. The amino acid the heavy and light chain CDRs, and the amino acid and nucleotide sequences of the heavy and light chain variable regions, and the heavy and light chains are shown. Antibodies disclosed in the table include, MPB2D5, CAS1.1.3, IMMU222, REA1062, and JOVI-3. MPB2D5 binds human TCRβV 20-1 (TCRβV2 per old nomenclature). CAS1.1.3 binds human TCRβV 27 (TCRβV14 per old nomenclature). IMMU 222 binds human TCRβV 6-5, TCRβV 6-6, or TCRβV 6-9 (TCRβV13.1 per old nomenclature). REA1062 binds human TCRβV 5-1). JOVI-3 binds human TCRβV 28 (TCRβV3.1 per old nomenclature). IMMU546 binds human TCRβV 2.

| | | |
|---|---|---|
| SEQ ID NO: 1160 | VL-3 | DNQLTQSPSSLSASVGDRVTITCSAGSSVSFMHWYQQ KPGKVPKLLIYDTSKLASGVPSRFSGSGSGNDFTLTISS LQPEDVATYYCLQGSGFPLTFGQGTKLEIK |
| SEQ ID NO: 1161 | VL-4 | ANQLTQSPSSLSASVGDRVTITCSAGSSVSFMHWYQQ KPGKAPKLLIYDTSKLASGVPSRFSGSGSGNDFTLTISS LQPEDFATYYCLQGSGFPLTFGQGTKLEIK |
| SEQ ID NO: 1162 | VL-5 | DNVLTQSPDSLAVSLGERATINCSAGSSVSFMHWYQQ KPGQPPKLLIYDTSKLASGVPDRFSGSGSGNDFTLTISS LQAEDVAVYYCLQGSGFPLTFGQGTKLEIK |

REA1062 (murine), also referred to as BJ1189 or as Antibody J
Binds to human TCRVβ 5-1

| | | |
|---|---|---|
| SEQ ID NO: 1163 | HC CDR1 (Kabat) | DYNIH |
| SEQ ID NO: 1164 | HC CDR2 (Kabat) | YINPYNGRTGYNQKFKA |
| SEQ ID NO: 1165 | HC CDR3 (Kabat) | WDGSSYFDY |
| SEQ ID NO: 1166 | HC CDR1 (Chothia) | GYTFTDYNIH |
| SEQ ID NO: 1167 | HC CDR2 (Chothia) | NPYNGR |
| SEQ ID NO: 1165 | HC CDR3 (Chothia) | WDGSSYFDY |
| SEQ ID NO: 1166 | HC CDR1 (Combined) | GYTFTDYNIH |
| SEQ ID NO: 1164 | HC CDR2 (Combined) | YINPYNGRTGYNQKFKA |
| SEQ ID NO: 1165 | HC CDR3 (Combined) | WDGSSYFDY |
| SEQ ID NO: 1168 | LC CDR1 (Kabat) | SASSSVSYMH |
| SEQ ID NO: 1169 | LC CDR2 (Kabat) | EISKLAS |
| SEQ ID NO: 1170 | LC CDR3 (Kabat) | QQWNYPLLT |
| SEQ ID NO: 1297 | LC CDR1 (Chothia) | SSSVSY |
| SEQ ID NO: 1169 | LC CDR2 (Chothia) | EISKLAS |
| SEQ ID NO: 1170 | LC CDR3 (Chothia) | QQWNYPLLT |
| SEQ ID NO: 1168 | LC CDR1 (Combined) | SASSSVSYMH |
| SEQ ID NO: 1169 | LC CDR2 (Combined) | EISKLAS |
| SEQ ID NO: 1170 | LC CDR3 (Combined) | QQWNYPLLT |
| SEQ ID NO: 1171 | VL | EIVLTQSPAITAASLGQKVTITCSASSSVSYMHWYQQK SGTSPKPWIYEISKLASGVPARFSGSGSGTSYSLTISS MEAEDAAIYYCQQWNYPLLTFGAGTKLELK |
| SEQ ID NO: 1172 | VH | EVQLQQSGPVLVKPGASVRMSCKASGYTFTDYNIHW VKQSHGRSLEWVGYINPYNGRTGYNQKFKAKATLTV DKSSSTAYMDLRSLTSEDSAVYYCARWDGSSYFDYW GQGTTLTVSS |

VH for REA1062 (humanized) also referred to as Antibody J-H
Binds to human TCRVβ 5-1

| | | |
|---|---|---|
| SEQ ID NO: 1173 | VH-1 | QVQLVQSGAEVKKPGSSVKVSCKASGYTFTDYNIHW VRQAPGQGLEWVGYINPYNGRTGYNQKFKARATLTV DKSTSTAYMELSSLRSEDTAVYYCARWDGSSYFDYW GQGTTVTVSS |

TABLE 13-continued

Amino acid sequences for additional anti-TCRβ V antibodies
Amino acid and nucleotide sequences for murine and humanized antibody molecules which bind to various TCRVB families are disclosed. The amino acid the heavy and light chain CDRs, and the amino acid and nucleotide sequences of the heavy and light chain variable regions, and the heavy and light chains are shown. Antibodies disclosed in the table include, MPB2D5, CAS1.1.3, IMMU222, REA1062, and JOVI-3. MPB2D5 binds human TCRβV 20-1 (TCRβV2 per old nomenclature). CAS1.1.3 binds human TCRβV 27 (TCRβV14 per old nomenclature). IMMU 222 binds human TCRβV 6-5, TCRβV 6-6, or TCRβV 6-9 (TCRβV13.1 per old nomenclature). REA1062 binds human TCRβV 5-1). JOVI-3 binds human TCRβV 28 (TCRβV3.1 per old nomenclature). IMMU546 binds human TCRβV 2.

| | | |
|---|---|---|
| SEQ ID NO: 1174 | VH-2 | QVQLVQSGAEVKKPGASVKVSCKASGYTFTDYNIHW VRQAPGQGLEWVGYINPYNGRTGYNQKFKARATLTV DKSTSTAYMELRSLRSDDMAVYYCARWDGSSYFDY WGQGTTVTVSS |
| SEQ ID NO: 1175 | VH-3 | QVQLVQSGAEVKKPGASVKVSCKASGYTFTDYNIHW VRQATGQGLEWVGYINPYNGRTGYNQKFKARATLTV NKSISTAYMELSSLRSEDTAVYYCARWDGSSYFDYW GQGTTVTVSS |
| SEQ ID NO: 1176 | VH-4 | EVQLVESGGGLVQPGRSLRLSCTASGYTFTDYNIHWV RQAPGKGLEWVGYINPYNGRTGYNQKFKARATLSVD KSKSIAYLQMNSLKTEDTAVYYCARWDGSSYFDYWG QGTTVTVSS |
| SEQ ID NO: 1177 | VH-5 | QVQLVQSGSELKKPGASVKVSCKASGYTFTDYNIHW VRQAPGQGLEWVGYINPYNGRTGYNQKFKARAVLSV DKSVSTAYLQISSLKAEDTAVYYCARWDGSSYFDYW GQGTTVTVSS |
| | VL for REA1062 (humanized) also referred to as Antibody J-H Binds to human TCRVβ 5-1 | |
| SEQ ID NO: 1178 | VL-1 | EIVLTQSPATLSLSPGERATLSCSASSSVSYMHWYQQK PGQAPKLLIYEISKLASGIPARFSGSGSGTDYTLTISSLE PEDFAVYYCQQWNYPLLTFGQGTKLEIK |
| SEQ ID NO: 1179 | VL-2 | EIVLTQSPATLSLSPGERATLSCSASSSVSYMHWYQQK PGQAPKLLIYEISKLASGIPARFSGSGSGTDYTLTISRLE PEDFAVYYCQQWNYPLLTFGQGTKLEIK |
| SEQ ID NO: 1180 | VL-3 | EIVLTQSPDFQSVTPKEKVTITCSASSSVSYMHWYQQK PDQSPKLLIYEISKLASGVPSRFSGSGSGTDYTLTINSLE AEDAATYYCQQWNYPLLTFGQGTKLEIK |
| SEQ ID NO: 1181 | VL-4 | DIQLTQSPSFLSASVGDRVTITCSASSSVSYMHWYQQK PGKAPKLLIYEISKLASGVPSRFSGSGSGTEYTLTISSLQ PEDFATYYCQQWNYPLLTFGQGTKLEIK |
| SEQ ID NO: 1182 | VL-5 | AIQLTQSPSSLSASVGDRVTITCSASSSVSYMHWYQQK PGKAPKLLIYEISKLASGVPSRFSGSGSGTDYTLTISSL QPEDFATYYCQQWNYPLLTFGQGTKLEIK |
| SEQ ID NO: 1183 | VL-6 | AIRLTQSPFSLSASVGDRVTITCSASSSVSYMHWYQQK PAKAPKLFIYEISKLASGVPSRFSGSGSGTDYTLTISSL QPEDFATYYCQQWNYPLLTFGQGTKLEIK |
| SEQ ID NO: 1184 | VL-7 | DIVLTQSPDSLAVSLGERATINCSASSSVSYMHWYQQ KPGQPPKLLIYEISKLASGVPDRFSGSGSGTDYTLTI SSLQAEDVAVYYCQQWNYPLLTFGQGTKLEIK |
| | JOVI-3 (murine), also referred to as BJ1187 or Antibody K Binds to human TCRVβ 28 | |
| SEQ ID NO: 1185 | HC CDR1 (Kabat) | GSWMN |
| SEQ ID NO: 1186 | HC CDR2 (Kabat) | RIYPGDGDTDYSGKFKG |
| SEQ ID NO: 1187 | HC CDR3 (Kabat) | SGYFNYVPVFDY |
| SEQ ID NO: 1188 | HC CDR1 (Chothia) | GYTFSGS |
| SEQ ID NO: 1189 | HC CDR2 (Chothia) | YPGDGD |
| SEQ ID NO: 1187 | HC CDR3 (Chothia) | SGYFNYVPVFDY |
| SEQ ID NO: 1190 | HC CDR1 (Combined) | GYTFSGSWMN |
| SEQ ID NO: 1186 | HC CDR2 (Combined) | RIYPGDGDTDYSGKFKG |

TABLE 13-continued

Amino acid sequences for additional anti-TCRβ V antibodies
Amino acid and nucleotide sequences for murine and humanized antibody molecules which bind to various TCRVB families are disclosed. The amino acid the heavy and light chain CDRs, and the amino acid and nucleotide sequences of the heavy and light chain variable regions, and the heavy and light chains are shown. Antibodies disclosed in the table include, MPB2D5, CAS1.1.3, IMMU222, REA1062, and JOVI-3. MPB2D5 binds human TCRβV 20-1 (TCRβV2 per old nomenclature). CAS1.1.3 binds human TCRβV 27 (TCRβV14 per old nomenclature). IMMU 222 binds human TCRβV 6-5, TCRβV 6-6, or TCRβV 6-9 (TCRβV13.1 per old nomenclature). REA1062 binds human TCRβV 5-1). JOVI-3 binds human TCRβV 28 (TCRβV3.1 per old nomenclature). IMMU546 binds human TCRβV 2.

| | | |
|---|---|---|
| SEQ ID NO: 1187 | HC CDR3 (Combined) | SGYFNYVPVFDY |
| SEQ ID NO: 1191 | LC CDR1 (Kabat) | SANSTVGYIH |
| SEQ ID NO: 1192 | LC CDR2 (Kabat) | TTSNLAS |
| SEQ ID NO: 1193 | LC CDR3 (Kabat) | HQWSFYPT |
| SEQ ID NO: 1194 | LC CDR1 (Chothia) | NSTVGY |
| SEQ ID NO: 1192 | LC CDR2 (Chothia) | TTSNLAS |
| SEQ ID NO: 1193 | LC CDR3 (Chothia) | HQWSFYPT |
| SEQ ID NO: 1191 | LC CDR1 (Combined) | SANSTVGYIH |
| SEQ ID NO: 1192 | LC CDR2 (Combined) | TTSNLAS |
| SEQ ID NO: 1193 | LC CDR3 (Combined) | HQWSFYPT |
| SEQ ID NO: 1195 | VL | QIVLTQSPAIMSASLGEEIALTCSANSTVGYIHWYQQK SGTSPKLLIYTTSNLASGVPSRFSGSGSGTFYSLTISS VEAEDAADYFCHQWSFYPTFGGGTKLEIK |
| SEQ ID NO: 1196 | VH | QIQLQQSGPEVVKPGASVQISCKASGYTFSGSWMNW VKQRPGKGLEWIGRIYPGDGDTDYSGKFKGRATLTA DKSSSTAYMRLSSLTSEDSAVYFCARSGYFNYVPVFD YWGQGTTLSVSS |

VH for JOVI-3 (humanized) also referred to as Antibody K-H
Binds to human TCRVβ 28

| | | |
|---|---|---|
| SEQ ID NO: 1197 | VH-1 | QIQLVQSGAEVKKPGASVKVSCKASGYTFSGSWMNW VRQAPGQGLEWIGRIYPGDGDTDYSGKFKGRATLTA DKSTSTAYMELSSLRSEDTAVYYCARSGYFNYVPVFD YWGQGTTVTVSS |
| SEQ ID NO: 1198 | VH-2 | QIQLVQSGAEVKKPGSSVKVSCKASGYTFSGSWMNW VRQAPGQGLEWIGRIYPGDGDTDYSGKFKGRATLTA DKSTSTAYMELSSLRSEDTAVYYCARSGYFNYVPVFD YWGQGTTVTVSS |
| SEQ ID NO: 1199 | VH-3 | EIQLVQSGAEVKKPGESLKISCKASGYTFSGSWMNWV RQMPGKGLEWIGRIYPGDGDTDYSGKFKGQATLSAD KSISTAYLQWSSLKASDTAMYYCARSGYFNYVPVFD YWGQGTTVTVSS |
| SEQ ID NO: 1200 | VH-4 | QIQLVQSGSELKKPGASVKVSCKASGYTFSGSWMNW VRQAPGQGLEWIGRIYPGDGDTDYSGKFKGRAVLSA DKSVSTAYLQISSLKAEDTAVYYCARSGYFNYVPVFD YWGQGTTVTVSS |
| SEQ ID NO: 1201 | VH-5 | QIQLVQSGSELKKPGASVKVSCKASGYTFSGSWMNW VRQAPGQGLEWIGRIYPGDGDTDYSGKFKGRAVLSA DKSVSMAYLQISSLKAEDTAVYYCARSGYFNYVPVF DYWGQGTTVTVSS |
| SEQ ID NO: 1202 | VH-6 | EIQLVESGGGLVQPGRSLRLSCTASGYTFSGSWMNWV RQAPGKGLEWIGRIYPGDGDTDYSGKFKGRATLSAD KSKSIAYLQMNSLKTEDTAVYYCARSGYFNYVPVFD YWGQGTTVTVSS |

VL for JOVI-3 (humanized) also referred to as Antibody K-H
Binds to human TCRVβ 28

| | | |
|---|---|---|
| SEQ ID NO: 1203 | VL-1 | EIVLTQSPATLSLSPGERATLSCSANSTVGYIHWYQQK PGQAPKLLIYTTSNLASGIPARFSGSGSGTDYTLTISSL EPEDFAVYFCHQWSFYPTFGQGTKLEIK |

TABLE 13-continued

Amino acid sequences for additional anti-TCRβ V antibodies
Amino acid and nucleotide sequences for murine and humanized antibody molecules which bind to various TCRVB families are disclosed. The amino acid the heavy and light chain CDRs, and the amino acid and nucleotide sequences of the heavy and light chain variable regions, and the heavy and light chains are shown. Antibodies disclosed in the table include, MPB2D5, CAS1.1.3, IMMU222, REA1062, and JOVI-3. MPB2D5 binds human TCRβV 20-1 (TCRβV2 per old nomenclature). CAS1.1.3 binds human TCRβV 27 (TCRβV14 per old nomenclature). IMMU 222 binds human TCRβV 6-5, TCRβV 6-6, or TCRβV 6-9 (TCRβV13.1 per old nomenclature). REA1062 binds human TCRβV 5-1). JOVI-3 binds human TCRβV 28 (TCRβV3.1 per old nomenclature). IMMU546 binds human TCRβV 2.

| | | |
|---|---|---|
| SEQ ID NO: 1204 | VL-2 | DIQLTQSPSFLSASVGDRVTITCSANSTVGYIHWYQQK PGKAPKLLIYTTSNLASGVPSRFSGSGSGTEYTLTISSL QPEDFATYFCHQWSFYPTFGQGTKLEIK |
| SEQ ID NO: 1205 | VL-3 | EIVLTQSPATLSLSPGERATLSCSANSTVGYIHWYQQK PGQAPKLLIYTTSNLASGIPARFSGSGPGTDYTLTISSL EPEDFAVYFCHQWSFYPTFGQGTKLEIK |
| SEQ ID NO: 1206 | VL-4 | DIVLTQSPDSLAVSLGERATINCSANSTVGYIHWYQQ KPGQPPKLLIYTTSNLASGVPDRFSGSGSGTDYTLTISS LQAEDVAVYFCHQWSFYPTFGQGTKLEIK |
| SEQ ID NO: 1207 | VL-5 | EIVLTQSPDFQSVTPKEKVTITCSANSTVGYIHWYQQK PDQSPKLLIYTTSNLASGVPSRFSGSGSGTDYTLTINSL EAEDAATYFCHQWSFYPTFGQGTKLEIK |

ZOE (murine), also referred to as BJ1538 or as Antibody L
Binds to human TCRVβ 4-1, 4-2, 4-3

| | | |
|---|---|---|
| SEQ ID NO: 1208 | HC CDR1 (Kabat) | DYYMY |
| SEQ ID NO: 1209 | HC CDR2 (Kabat) | TISGGGSYTYSPDSVKG |
| SEQ ID NO: 1210 | HC CDR3 (Kabat) | ERDIYYGNFNAMVY |
| SEQ ID NO: 1211 | HC CDR1 (Chothia) | GFTFSDY |
| SEQ ID NO: 1212 | HC CDR2 (Chothia) | SGGGSY |
| SEQ ID NO: 1210 | HC CDR3 (Chothia) | ERDIYYGNFNAMVY |
| SEQ ID NO: 1213 | HC CDR1 (Combined) | GFTFSDYYMY |
| SEQ ID NO: 1209 | HC CDR2 (Combined) | TISGGGSYTYSPDSVKG |
| SEQ ID NO: 1210 | HC CDR3 (Combined) | ERDIYYGNFNAMVY |
| SEQ ID NO: 1214 | LC CDR1 (Kabat) | RASKSVSTSGYSYMH |
| SEQ ID NO: 1215 | LC CDR2 (Kabat) | LASNLES |
| SEQ ID NO: 1216 | LC CDR3 (Kabat) | QHSRDLPWT |
| SEQ ID NO: 1217 | LC CDR1 (Chothia) | SKSVSTSGYSY |
| SEQ ID NO: 1215 | LC CDR2 (Chothia) | LASNLES |
| SEQ ID NO: 1216 | LC CDR3 (Chothia) | QHSRDLPWT |
| SEQ ID NO: 1214 | LC CDR1 (Combined) | RASKSVSTSGYSYMH |
| SEQ ID NO: 1215 | LC CDR2 (Combined) | LASNLES |
| SEQ ID NO: 1216 | LC CDR3 (Combined) | QHSRDLPWT |
| SEQ ID NO: 1218 | VL | DIVLTQSPVSLTVSLGQRATISCRASKSVSTSGYSYMH WYQQKPGQPPKLLIYLASNLESGVPARFSGSGSGTDF TLNIHPVEEEDAATYYCQHSRDLPWTFGGGTKLEIK |
| SEQ ID NO: 1219 | VH | EVQLVESGGGLVKPGGSLKLSCAASGFTFSDYYMYWV RQTPEKRLEWVATISGGGSYTYSPDSVKGRFTISRDN AKNNLYLQMSSLRSEDTAMYFCARERDIYYGNFNAM VYWGRGTSVTVSS |

TABLE 13-continued

Amino acid sequences for additional anti-TCRβ V antibodies
Amino acid and nucleotide sequences for murine and humanized antibody molecules which bind to various TCRVB families are disclosed. The amino acid the heavy and light chain CDRs, and the amino acid and nucleotide sequences of the heavy and light chain variable regions, and the heavy and light chains are shown. Antibodies disclosed in the table include, MPB2D5, CAS1.1.3, IMMU222, REA1062, and JOVI-3. MPB2D5 binds human TCRβV 20-1 (TCRβV2 per old nomenclature). CAS1.1.3 binds human TCRβV 27 (TCRβV14 per old nomenclature). IMMU 222 binds human TCRβV 6-5, TCRβV 6-6, or TCRβV 6-9 (TCRβV13.1 per old nomenclature). REA1062 binds human TCRβV 5-1). JOVI-3 binds human TCRβV 28 (TCRβV3.1 per old nomenclature). IMMU546 binds human TCRβV 2.

VH for ZOE (humanized) also referred to as Antibody L-H
Binds to human TCRVβ 4-1, 4-2, 4-3

| | | |
|---|---|---|
| SEQ ID NO: 1220 | VH-1 | EVQLLESGGGLVQPGGSLRLSCAASGFTFSDYYMYW VRQAPGKGLEWVATISGGGSYTYSPDSVKGRFTISRD NSKNTLYLQMNSLRAEDTAVYYCARERDIYYGNFNA MVYWGRGTLVTVSS |
| SEQ ID NO: 1221 | VH-2 | EVQLVESGGGLVQPGGSLRLSCAASGFTFSDYYMYW VRQAPGKGLEWVATISGGGSYTYSPDSVKGRFTISRD NAKNSLYLQMNSLRAEDTAVYYCARERDIYYGNFNA MVYWGRGTLVTVSS |
| SEQ ID NO: 1222 | VH-3 | QVQLVESGGGVVQPGRSLRLSCAASGFTFSDYYMY WVRQAPGKGLEWVATISGGGSYTYSPDSVKGRFTIS RDNSKNTLYLQMNSLRAEDTAVYYCARERDIYYGN FNAMVYWGRGTLVTVSS |
| SEQ ID NO: 1223 | VH-4 | QVQLVESGGGLVKPGGSLRLSCAASGFTFSDYYMYWI RQAPGKGLEWVATISGGGSYTYSPDSVKGRFTISRDN AKNSLYLQMNSLRAEDTAVYYCARERDIYYGNFNAM VYWGRGTLVTVSS |

VL for ZOE (humanized) also referred to as Antibody L-H
Binds to human TCRVβ 4-1, 4-2, 4-3

| | | |
|---|---|---|
| SEQ ID NO: 1224 | VL-1 | EIVLTQSPGTLSLSPGERATLSCRASKSVSTSGYSYMH WYQQKPGQAPRLLIYLASNLESGIPDRFSGSGSGTDFT LTISRLEPEDFAVYYCQHSRDLPWTFGGGTKVEIK |
| SEQ ID NO: 1225 | VL-2 | EIVLTQSPATLSLSPGERATLSCRASKSVSTSGYSYMH WYQQKPGQAPRLLIYLASNLESGIPARFSGSGSGTDFT LTISSLEPEDFAVYYCQHSRDLPWTFGGGTKVEIK |
| SEQ ID NO: 1226 | VL-3 | DIQLTQSPSTLSASVGDRVTITCRASKSVSTSGYSYMH WYQQKPGKAPKLLIYLASNLESGVPSRFSGSGSGTEFT LTISSLQPDDFATYYCQHSRDLPWTFGGGTKVEIK |
| SEQ ID NO: 1227 | VL-4 | AIQLTQSPSSLSASVGDRVTITCRASKSVSTSGYSYMH WYQQKPGKAPKLLIYLASNLESGVPSRFSGSGSGTDF TLTISSLQPEDFATYYCQHSRDLPWTFGGGTKVEIK |

Anti-TCRvb19 (murine), also referred to as BJ1465; or Antibody M
Binds to human TCRVβ 19

| | | |
|---|---|---|
| SEQ ID NO: 1229 | HC CDR1 (Kabat) | GYFWN |
| SEQ ID NO: 1230 | HC CDR2 (Kabat) | YISYDGSNNYNPSLKN |
| SEQ ID NO: 1231 | HC CDR3 (Kabat) | PSPGTGYAVDY |
| SEQ ID NO: 1232 | HC CDR1 (Chothia) | GYSITSGY |
| SEQ ID NO: 1233 | HC CDR2 (Chothia) | SYDGSN |
| SEQ ID NO: 1231 | HC CDR3 (Chothia) | PSPGTGYAVDY |
| SEQ ID NO: 1234 | HC CDR1 (Combined) | GYSITSGYFWN |
| SEQ ID NO: 1230 | HC CDR2 (Combined) | YISYDGSNNYNPSLKN |
| SEQ ID NO: 1231 | HC CDR3 (Combined) | PSPGTGYAVDY |
| SEQ ID NO: 1235 | LC CDR1 (Kabat) | RSSQSLVHSNGNTYLH |
| SEQ ID NO: 1236 | LC CDR2 (Kabat) | KVSNRFS |
| SEQ ID NO: 1237 | LC CDR3 (Kabat) | SQSTHVPFT |

TABLE 13-continued

Amino acid sequences for additional anti-TCRβ V antibodies
Amino acid and nucleotide sequences for murine and humanized antibody molecules which bind to various TCRVB families are disclosed. The amino acid the heavy and light chain CDRs, and the amino acid and nucleotide sequences of the heavy and light chain variable regions, and the heavy and light chains are shown. Antibodies disclosed in the table include, MPB2D5, CAS1.1.3, IMMU222, REA1062, and JOVI-3. MPB2D5 binds human TCRβV 20-1 (TCRβV2 per old nomenclature). CAS1.1.3 binds human TCRβV 27 (TCRβV14 per old nomenclature). IMMU 222 binds human TCRβV 6-5, TCRβV 6-6, or TCRβV 6-9 (TCRβV13.1 per old nomenclature). REA1062 binds human TCRβV 5-1). JOVI-3 binds human TCRβV 28 (TCRβV3.1 per old nomenclature). IMMU546 binds human TCRβV 2.

| | | |
|---|---|---|
| SEQ ID NO: 1238 | LC CDR1 (Chothia) | SQSLVHSNGNTY |
| SEQ ID NO: 1236 | LC CDR2 (Chothia) | KVSNRFS |
| SEQ ID NO: 1237 | LC CDR3 (Chothia) | SQSTHVPFT |
| SEQ ID NO: 1235 | LC CDR1 (Combined) | RSSQSLVHSNGNTYLH |
| SEQ ID NO: 1236 | LC CDR2 (Combined) | KVSNRFS |
| SEQ ID NO: 1237 | LC CDR3 (Combined) | SQSTHVPFT |
| SEQ ID NO: 1239 | VL | NVVMTQTPLSLPVSLGDQASISCRSSQSLVHSNGNTYL<br>HWYLQKPGQSPKFLIYKVSNRFSGVPDRFSGGGSGTE<br>FTLKISRVEAEDLGVYFCSQSTHVPFTFGSGTKLEIK |
| SEQ ID NO: 1240 | VH | NVQLQESGPGLVKPSQSLSLTCSVAGYSITSGYFWNW<br>IRQFPGNKLEWMGYISYDGSNNYNPSLKNRISITRDTS<br>KNQFFLKLNSVTTEDTATYYCASPSPGTGYAVDYWG<br>QGTSVTVSS |

VH for Anti-TCRvb19 (humanized) also referred to as Antibody M-H
Binds to human TCRVβ 19

| | | |
|---|---|---|
| SEQ ID NO: 1241 | VH-1 | QVQLQESGPGLVKPSETLSLTCTVSGYSITSGYFWNWI<br>RQPPGKGLEWIGYISYDGSNNYNPSLKNRVTISRDTSK<br>NQFSLKLSSVTAADTAVYYCASPSPGTGYAVDYWGQ<br>GTLVTVSS |
| SEQ ID NO: 1242 | VH-2 | QVQLQESGPGLVKPSETLSLTCTVSGYSITSGYFWNWI<br>RQPPGKGLEWIGYISYDGSNNYNPSLKNRVTISRDTSK<br>NQFSLKLSSVTAADTAVYYCASPSPGTGYAVDYWGQ<br>GTLVTVSS |
| SEQ ID NO: 1243 | VH-3 | QVQLVESGGGLVQPGGSLRLSCSVSGYSITSGYFWNW<br>VRQAPGKGLEWVGYISYDGSNNYNPSLKNRFTISRDT<br>SKNTFYLQMNSLRAEDTAVYYCASPSPGTGYAVDYW<br>GQGTLVTVSS |

VL for Anti-TCRvb19 (humanized) also referred to as Antibody M-H
Binds to human TCRVβ 19

| | | |
|---|---|---|
| SEQ ID NO: 1244 | VL-1 | VVMTQSPGTLSLSPGERATLSCRSSQSLVHSNGNTYL<br>HWYQQKPGQAPRFLIYKVSNRFSGIPDRFSGSGSGTDF<br>TLTISRLEPEDFAVYFCSQSTHVPFTFGQGTKLEIK |
| SEQ ID NO: 1245 | VL-2 | EVVMTQSPATLSLSPGERATLSCRSSQSLVHSNGNTYL<br>HWYQQKPGQAPRFLIYKVSNRFSGIPARFSGSGSGTDF<br>TLTISSLEPEDFAVYFCSQSTHVPFTFGQGTKLEIK |
| SEQ ID NO: 1246 | VL-3 | EVVMTQSPATLSVSPGERATLSCRSSQSLVHSNGNTY<br>LHWYQQKPGQAPRFLIYKVSNRFSGIPARFSGSGSGTE<br>FTLTISSLQSEDFAVYFCSQSTHVPFTFGQGTKLEIK |
| SEQ ID NO: 1247 | VL-4 | DVQMTQSPSSLSASVGDRVTITCRSSQSLVHSNGNTY<br>LHWYQQKPGKAPKFLIYKVSNRFSGVPSRFSGSGSGT<br>DFTFTISSLQPEDIATYFCSQSTHVPFTFGQGTKLEIK |

BL37.2 (murine), also referred to as BJ1539 or Antibody N
Binds to human TCRVβ 9

| | | |
|---|---|---|
| SEQ ID NO: 1248 | HC CDR1 (Kabat) | DYIVH |
| SEQ ID NO: 1249 | HC CDR2 (Kabat) | WINTYTGTPTYADDFEG |
| SEQ ID NO: 1250 | HC CDR3 (Kabat) | SWRRGIRGIGFDY |
| SEQ ID NO: 1251 | HC CDR1 (Chothia) | GYTFTDY |

TABLE 13-continued

| Amino acid sequences for additional anti-TCRβ V antibodies Amino acid and nucleotide sequences for murine and humanized antibody molecules which bind to various TCRVB families are disclosed. The amino acid the heavy and light chain CDRs, and the amino acid and nucleotide sequences of the heavy and light chain variable regions, and the heavy and light chains are shown. Antibodies disclosed in the table include, MPB2D5, CAS1.1.3, IMMU222, REA1062, and JOVI-3. MPB2D5 binds human TCRβV 20-1 (TCRβV2 per old nomenclature). CAS1.1.3 binds human TCRβV 27 (TCRβV14 per old nomenclature). IMMU 222 binds human TCRβV 6-5, TCRβV 6-6, or TCRβV 6-9 (TCRβV13.1 per old nomenclature). REA1062 binds human TCRβV 5-1). JOVI-3 binds human TCRβV 28 (TCRβV3.1 per old nomenclature). IMMU546 binds human TCRβV 2. | | |
|---|---|---|
| SEQ ID NO: 1252 | HC CDR2 (Chothia) | NTYTGT |
| SEQ ID NO: 1250 | HC CDR3 (Chothia) | SWRRGIRGIGFDY |
| SEQ ID NO: 1253 | HC CDR1 (Combined) | GYTFTDYIVH |
| SEQ ID NO: 1249 | HC CDR2 (Combined) | WINTYTGTPTYADDFEG |
| SEQ ID NO: 1250 | HC CDR3 (Combined) | SWRRGIRGIGFDY |
| SEQ ID NO: 1254 | LC CDR1 (Kabat) | KASKSINKYLA |
| SEQ ID NO: 1255 | LC CDR2 (Kabat) | DGSTLQS |
| SEQ ID NO: 1256 | LC CDR3 (Kabat) | QQHNEYPPT |
| SEQ ID NO: 1257 | LC CDR1 (Chothia) | SKSINKY |
| SEQ ID NO: 1255 | LC CDR2 (Chothia) | DGSTLQS |
| SEQ ID NO: 1256 | LC CDR3 (Chothia) | QQHNEYPPT |
| SEQ ID NO: 1254 | LC CDR1 (Combined) | KASKSINKYLA |
| SEQ ID NO: 1255 | LC CDR2 (Combined) | DGSTLQS |
| SEQ ID NO: 1256 | LC CDR3 (Combined) | QQHNEYPPT |
| SEQ ID NO: 1258 | VL | DVQMTQSPYNLAASPGESVSINCKASKSINKYLAWYQ QKPGKPNKLLIYDGSTLQSGIPSRFSGSGSGTDFTLT IRGLEPEDFGLYYCQQHNEYPPTFGAGTKLELK |
| SEQ ID NO: 1259 | VH | QLQLVQSGPELREPGESVKISCKASGYTFTDYIVHWV KQAPGKGLKWMGWINTYTGTPTYADDFEGRFVFSLE ASASTANLQISNLKNEDTATYFCARSWRRGIRGIGFD YWGQGVMVTVSS |
| VH for BL37.2 (humanized) also referred to as Antibody N-H Binds to human TCRVβ 9 | | |
| SEQ ID NO: 1260 | VH-1 | QLQLVQSGAEVKKPGASVKVSCKASGYTFTDYIVHW VRQAPGQGLEWMGWINTYTGTPTYADDFEGWVTMTL DASISTAYMELSRLRSDDTAVYYCARSWRRGIRGIG FDYWGQGTMVTVSS |
| SEQ ID NO: 1261 | VH-2 | QLQLVQSGAEVKKPGASVKVSCKASGYTFTDYIVHW VRQAPGQGLEWMGWINTYTGTPTYADDFEGRVTMTL DASTSTAYMELSSLRSEDTAVYYCARSWRRGIRGIG FDYWGQGTMVTVSS |
| SEQ ID NO: 1262 | VH-3 | QLQLVQSGAEVKKPGASVKVSCKASGYTFTDYIVHW VRQAPGQRLEWMGWINTYTGTPTYADDFEGRVTITL DASASTAYMELSSLRSEDMAVYYCARSWRRGIRGIG FDYWGQGTMVTVSS |
| SEQ ID NO: 1263 | VH-4 | QLQLVQSGAEVKKPGASVKVSCKASGYTFTDYIVHW VRQATGQGLEWMGWINTYTGTPTYADDFEGRVTMTL NASISTAYMELSSLRSEDTAVYYCARSWRRGIRGIG FDYWGQGTMVTVSS |
| VL for BL37.2 (humanized) also referred to as Antibody N-H Binds to human TCRVβ 9 | | |
| SEQ ID NO: 1264 | VL-1 | EVVMTQSPGTLSLSPGERATLSCKASKSINKYLAWYQ QKPGQAPRLLIYDGSTLQSGIPDRFSGSGSGTDFTLTIS RLEPEDFAVYYCQQHNEYPPTFGQGTKLEIK |

TABLE 13-continued

| Amino acid sequences for additional anti-TCRβ V antibodies Amino acid and nucleotide sequences for murine and humanized antibody molecules which bind to various TCRVB families are disclosed. The amino acid the heavy and light chain CDRs, and the amino acid and nucleotide sequences of the heavy and light chain variable regions, and the heavy and light chains are shown. Antibodies disclosed in the table include, MPB2D5, CAS1.1.3, IMMU222, REA1062, and JOVI-3. MPB2D5 binds human TCRβV 20-1 (TCRβV2 per old nomenclature). CAS1.1.3 binds human TCRβV 27 (TCRβV14 per old nomenclature). IMMU 222 binds human TCRβV 6-5, TCRβV 6-6, or TCRβV 6-9 (TCRβV13.1 per old nomenclature). REA1062 binds human TCRβV 5-1). JOVI-3 binds human TCRβV 28 (TCRβV3.1 per old nomenclature). IMMU546 binds human TCRβV 2. | | |
|---|---|---|
| SEQ ID NO: 1265 | VL-2 | EVVMTQSPATLSLSPGERATLSCKASKSINKYLAWYQ QKPGQAPRLLIYDGSTLQSGIPARFSGSGSGTDFTLTIS SLEPEDFAVYYCQQHNEYPPTFGQGTKLEIK |
| SEQ ID NO: 1266 | VL-3 | DVQMTQSPSSLSASVGDRVTITCKASKSINKYLAWYQ QKPGKAPKLLIYDGSTLQSGVPSRFSGSGSGTDFTLTIS SLQPEDFATYYCQQHNEYPPTFGQGTKLEIK |
| SEQ ID NO: 1267 | VL-4 | AVRMTQSPSSFSASTGDRVTITCKASKSINKYLAWYQ QKPGKAPKLLIYDGSTLQSGVPSRFSGSGSGTDFTLTIS CLQSEDFATYYCQQHNEYPPTFGQGTKLEIK |
| IG125 (murine) binds to TRVβ 11-2; also referred to as Antibody O | | |
| SEQ ID NO: 1268 | HC CDR1 (Kabat) | NYGVH |
| SEQ ID NO: 1269 | HC CDR2 (Kabat) | VIWSDGSTDYDTAFIS |
| SEQ ID NO: 1270 | HC CDR3 (Kabat) | RAVVADFDY |
| SEQ ID NO: 1271 | HC CDR1 (Chothia) | GFSLTN |
| SEQ ID NO: 1272 | HC CDR2 (Chothia) | VIWSDGSTD |
| SEQ ID NO: 1270 | HC CDR3 (Chothia) | RAVVADFDY |
| SEQ ID NO: 1273 | HC CDR1 (combined) | GFSLTNYGVH |
| SEQ ID NO: 1269 | HC CDR2 (combined) | VIWSDGSTDYDTAFIS |
| SEQ ID NO: 1270 | HC CDR3 (combined) | RAVVADFDY |
| SEQ ID NO: 1274 | VH | QVQLKQSGPGLLQPSQSLSITCTVSGFSLTNYGVHWV RQSPGKGLEWLGVIWSDGSTDYDTAFISRLSISKDNSK SQVFFKLNSLQADDTAIYYCARRAVVADFDYWGQGT TLTVSS |
| SEQ ID NO: 1275 | LC CDR1 (Kabat) | KASKEVTIFGSISALH |
| SEQ ID NO: 1276 | LC CDR2 (Kabat) | NGAKLES |
| SEQ ID NO: 1277 | LC CDR3 (Kabat) | LQNKEVPFT |
| SEQ ID NO: 1275 | LC CDR1 (Chothia) | KASKEVTIFGSISALH |
| SEQ ID NO: 1276 | LC CDR2 (Chothia) | NGAKLES |
| SEQ ID NO: 1277 | LC CDR3 (Chothia) | LQNKEVPFT |
| SEQ ID NO: 1275 | LC CDR1 (combined) | KASKEVTIFGSISALH |
| SEQ ID NO: 1276 | LC CDR2 (combined) | NGAKLES |
| SEQ ID NO: 1277 | LC CDR3 (combined) | LQNKEVPFT |
| SEQ ID NO: 1278 | VL | DIVLTQSPASLAVSLGQKATISCKASKEVTIFGSISA LHWYQQKPGQPPKLIYNGAKLESGVSARFSDSGSQNR SPFGNQLSFTLTIAPVEADDAATYYCLQNKEVPFTFG SGTKLEIK |
| VL for IG125 (humanized) also referred to as Antibody O-H binds to TRVβ 11-2 | | |
| SEQ ID NO: 1279 | VL-1 | DIVLTQSPDSLAVSLGERATINCKASKEVTIFGSISALH WYQQKPGQPPKLLYNGAKLESGVSARFGVPDRFSRS GSGLDFTLTISSLQAEDVAVYYCLQNKEVPFTFGQGT KLEIK |

TABLE 13-continued

Amino acid sequences for additional anti-TCRβ V antibodies
Amino acid and nucleotide sequences for murine and humanized antibody molecules which bind to various TCRVB families are disclosed. The amino acid the heavy and light chain CDRs, and the amino acid and nucleotide sequences of the heavy and light chain variable regions, and the heavy and light chains are shown. Antibodies disclosed in the table include, MPB2D5, CAS1.1.3, IMMU222, REA1062, and JOVI-3. MPB2D5 binds human TCRβV 20-1 (TCRβV2 per old nomenclature). CAS1.1.3 binds human TCRβV 27 (TCRβV14 per old nomenclature). IMMU 222 binds human TCRβV 6-5, TCRβV 6-6, or TCRβV 6-9 (TCRβV13.1 per old nomenclature). REA1062 binds human TCRβV 5-1). JOVI-3 binds human TCRβV 28 (TCRβV3.1 per old nomenclature). IMMU546 binds human TCRβV 2.

| | | |
|---|---|---|
| SEQ ID NO: 1280 | VL-2 | EIVLTQSPDFQSVTPKEKVTITCKASKEVTIFGSISALH<br>WYQQKPDQSPKLLYNGAKLESGVSARFGVPSRFSRS<br>GSGLDFTLTINSLEAEDAATYYCLQNKEVPFTFGQGT<br>KLEIK |
| SEQ ID NO: 1281 | VL-3 | AIQLTQSPSSLSASVGDRVTITCKASKEVTIFGSISALH<br>WYQQKPGKAPKLLYNGAKLESGVSARFGVPSRFSRS<br>GSGLDFTLTISSLQPEDFATYYCLQNKEVPFTFGQGT<br>KLEIK |
| SEQ ID NO: 1282 | VL-4 | DIVLTQTPLSLSVTPGQPASISCKASKEVTIFGSISALH<br>WYLQKPGQPPKLLYNGAKLESGVSARFGVPDRFSRS<br>GSGLDFTLKISRVEAEDVGVYYCLQNKEVPFTFGQG<br>TKLEIK |
| VH for IG125 (humanized) also referred to as Antibody O-H binds to TRVβ 11-2 | | |
| SEQ ID NO: 1283 | VH-1 | QVTLKESGPVLVKPTETLTLTCTVSGFSLTNYGVHW<br>VRQPPGKALEWLGVIWSDGSTDYDTAFISRLTISKDN<br>SKSQVVLTMTNMDPVDTATYYCARRAVVADFDYW<br>GQGTTVTVSS |
| SEQ ID NO: 1284 | VH-2 | QVQLQESGPGLVKPSGTLSLTCAVSGFSLTNYGVHW<br>VRQPPGKGLEWLGVIWSDGSTDYDTAFISRLTISKDN<br>SKSQVSLKLSSVTAADTAVYYCARRAVVADFDYWG<br>QGTTVTVSS |
| SEQ ID NO: 1285 | VH-3 | QVQLQQSGPGLVKPSQTLSLTCAVSGFSLTNYGVHW<br>VRQSPSRGLEWLGVIWSDGSTDYDTAFISRLTINKDN<br>SKSQVSLQLNSVTPEDTAVYYCARRAVVADFDYWG<br>QGTTVTVSS |
| SEQ ID NO: 1286 | VH-4 | EVQLVESGGGLVQPGPSLRLSCTVSGFSLTNYGVHW<br>VRQAPGKGLEWLGVIWSDGSTDYDTAFISRLTISKDN<br>SKSIVYLQMNSLKTEDTAVYYCARRAVVADFDYWG<br>QGTTVTVSS |
| SEQ ID NO: 1287 | VH-5 | EVQLVQSGAEVKKPGESLRISCKVSGFSLTNYGVHW<br>VRQMPGKGLEWLGVIWSDGSTDYDTAFISQLTISKD<br>NSISTVYLQWSSLKASDTAMYYCARRAVVADFDYW<br>GQGTTVTVSS |
| MR5-2 (murine), binds to human TCRVβ 13-2 | | |
| SEQ ID NO: 1376 | SCFV (VH + VL) | QVQLQQSGTELMKPGASVKISCKASGYTFSNYWIEW<br>IKQRPGHGLEWVGEILPGAGPTNYNEKFKGKATFTA<br>DSSSNTAYMQLSSLTSEDSAVYYCARTDYDYDWFA<br>YWGQGTLVTVSAGGGGSGGGGSGGGGSGGGGSDIV<br>MSQSPSSLAVSVGEKVTMSCKSSQSLLYSGNQKNYL<br>AWYQQKPGQSPKLLIYWASTRESGVPDRFTGSGSGT<br>DFTLTINSVKAEDLTVYYCQQYYGYPRTFGGGTKVEI<br>K |

Anti-TCRVβ Antibody Effector Function and Fc Variants

In some embodiments, an anti-TCRVβ antibody disclosed herein comprises an Fc region, e.g., as described herein. In some embodiments, the Fc region is a wildtype Fc region, e.g., a wildtype human Fc region. In some embodiments, the Fc region comprises a variant, e.g., an Fc region comprising an addition, substitution, or deletion of at least one amino acid residue in the Fc region which results in, e.g., reduced or ablated affinity for at least one Fc receptor.

The Fc region of an antibody interacts with a number of receptors or ligands including Fc Receptors (e.g., FcγRI, FcγRIIA, FcγRIIIA), the complement protein CIq, and other molecules such as proteins A and G. These interactions are essential for a variety of effector functions and downstream signaling events including: antibody dependent cell-mediated cytotoxicity (ADCC), Antibody-dependent cellular phagocytosis (ADCP) and complement dependent cytotoxicity (CDC).

In some embodiments, an anti-TCRVβ antibody comprising a variant Fc region has reduced, e.g., ablated, affinity for an Fc receptor, e.g., an Fc receptor described herein. In some embodiments, the reduced affinity is compared to an otherwise similar antibody with a wildtype Fc region.

In some embodiments, an anti-TCRVβ antibody comprising a variant Fc region has one or more of the following properties: (1) reduced effector function (e.g., reduced ADCC, ADCP and/or CDC); (2) reduced binding to one or more Fc receptors; and/or (3) reduced binding to C1q complement. In some embodiments, the reduction in any one, or all of properties (1)-(3) is compared to an otherwise similar antibody with a wildtype Fc region.

In some embodiments, an anti-TCRVβ antibody comprising a variant Fc region has reduced affinity to a human Fc receptor, e.g., FcγR I, FcγR II and/or FcγR III. In some embodiments, the anti-TCRVβ antibody comprising a variant Fc region comprises a human IgG1 region or a human IgG4 region.

In some embodiments, an anti-TCRVβ antibody comprising a variant Fc region activates and/or expands T cells, e.g., as described herein. In some embodiments, an anti-TCRVβ antibody comprising a variant Fc region has a cytokine profile described herein, e.g., a cytokine profile that differs from a cytokine profile of a T cell engager that binds to a receptor or molecule other than a TCRβV region ("a non-TCRβV-binding T cell engager"). In some embodiments, the non-TCRβV-binding T cell engager comprises an antibody that binds to a CD3 molecule (e.g., CD3 epsilon (CD3e) molecule); or a TCR alpha (TCRα) molecule.

Exemplary Fc region variants are provided in Table 21 and also disclosed in Saunders O, (2019) *Frontiers in Immunology*; vol 10, article 1296, the entire contents of which is hereby incorporated by reference.

In some embodiments, an anti-TCRVβ antibody disclosed herein comprises any one or all, or any combination of Fc region variants disclosed in Table 21.

In some embodiments, an anti-TCRVβ antibody disclosed herein comprises any one or all, or any combination of Fc region variants, e.g., mutations, disclosed in Table 21. In some embodiments, an anti-TCRVβ antibody disclosed herein comprise an Asn297Ala (N297A) mutation. In some embodiments, an anti-TCRVβ antibody disclosed herein comprise a Leu234Ala/Leu235Ala (LALA) mutation.

TABLE 21

Exemplary Fc modifications

| Modification or mutation | Altered effector function |
|---|---|
| Leu235Glu | ADCC; |
| Leu234Ala/Leu235Ala (LALA) | ADCC; ADCP; CDC |
| Ser228Pro/Leu235Glu | |
| Leu234Ala/Leu235Ala/Pro329Gly | ADCP |
| Pro331Ser/Leu234Glu/Leu235Phe | CDC |
| Asp265Ala | ADCC, ADCP |
| Gly237Ala | ADCP |
| Glu318Ala | ADCP |
| Glu233Pro | |
| Gly236Arg/Leu328Arg | ADCC |
| His268Gln/Val309Leu/Ala330Ser/Pro331Ser | ADCC; ADCP; CDC |
| Val234Ala/Gly237Ala/Pro238Ser/ His268Ala/Val309Leu/Ala330Ser/Pro331Ser | ADCC; ADCP; CDC |
| Leu234Ala/L235Ala/Gly237Ala/P238Ser/ His268Ala/Ala330Ser/Pro331Ser | ADCC; CDC |
| Ala330Leu | CDC |
| Asp270Ala | CDC |
| Lys322Ala | CDC |
| Pro329Ala | CDC |
| Pro331Ala | CDC |
| Val264Ala | CDC |
| High mannose glycosylation | CDC |
| Phe241Ala | CDC |
| Asn297Ala or Gly or Gln | ADCC; ADCP; CDC |
| S228P/Phe234Ala/Leu235Ala | ADCC; CDC |

Antibody Molecules

In one embodiment, the antibody molecule binds to a cancer antigen, e.g., a tumor antigen or a stromal antigen. In some embodiments, the cancer antigen is, e.g., a mammalian, e.g., a human, cancer antigen. In other embodiments, the antibody molecule binds to an immune cell antigen, e.g., a mammalian, e.g., a human, immune cell antigen. For example, the antibody molecule binds specifically to an epitope, e.g., linear or conformational epitope, on the cancer antigen or the immune cell antigen.

In an embodiment, an antibody molecule is a monospecific antibody molecule and binds a single epitope. E.g., a monospecific antibody molecule having a plurality of immunoglobulin variable domain sequences, each of which binds the same epitope.

In an embodiment an antibody molecule is a multispecific or multifunctional antibody molecule, e.g., it comprises a plurality of immunoglobulin variable domains sequences, wherein a first immunoglobulin variable domain sequence of the plurality has binding specificity for a first epitope and a second immunoglobulin variable domain sequence of the plurality has binding specificity for a second epitope. In an embodiment the first and second epitopes are on the same antigen, e.g., the same protein (or subunit of a multimeric protein). In an embodiment the first and second epitopes overlap. In an embodiment the first and second epitopes do not overlap. In an embodiment the first and second epitopes are on different antigens, e.g., the different proteins (or different subunits of a multimeric protein). In an embodiment a multispecific antibody molecule comprises a third, fourth or fifth immunoglobulin variable domain. In an embodiment, a multispecific antibody molecule is a bispecific antibody molecule, a trispecific antibody molecule, or a tetraspecific antibody molecule.

In an embodiment a multispecific antibody molecule is a bispecific antibody molecule. A bispecific antibody has specificity for no more than two antigens. A bispecific antibody molecule is characterized by a first immunoglobulin variable domain sequence which has binding specificity for a first epitope and a second immunoglobulin variable domain sequence that has binding specificity for a second epitope. In an embodiment the first and second epitopes are on the same antigen, e.g., the same protein (or subunit of a multimeric protein). In an embodiment the first and second epitopes overlap. In an embodiment the first and second epitopes do not overlap. In an embodiment the first and second epitopes are on different antigens, e.g., the different proteins (or different subunits of a multimeric protein). In an embodiment a bispecific antibody molecule comprises a heavy chain variable domain sequence and a light chain variable domain sequence which have binding specificity for a first epitope and a heavy chain variable domain sequence and a light chain variable domain sequence which have binding specificity for a second epitope. In an embodiment a bispecific antibody molecule comprises a half antibody having binding specificity for a first epitope and a half antibody having binding specificity for a second epitope. In an embodiment a bispecific antibody molecule comprises a half antibody, or fragment thereof, having binding specificity for a first epitope and a half antibody, or fragment thereof, having binding specificity for a second epitope. In an embodiment a bispecific antibody molecule comprises a scFv or a Fab, or fragment thereof, have binding specificity for a first epitope and a scFv or a Fab, or fragment thereof, have binding specificity for a second epitope.

In an embodiment, an antibody molecule comprises a diabody, and a single-chain molecule, as well as an antigen-binding fragment of an antibody (e.g., Fab, $F(ab')_2$, and Fv). For example, an antibody molecule can include a heavy (H) chain variable domain sequence (abbreviated herein as VH), and a light (L) chain variable domain sequence (abbreviated herein as VL). In an embodiment an antibody molecule comprises or consists of a heavy chain and a light chain (referred to herein as a half antibody. In another example, an antibody molecule includes two heavy (H) chain variable domain sequences and two light (L) chain variable domain sequence, thereby forming two antigen binding sites, such as Fab, Fab', $F(ab')_2$, Fc, Fd, Fd', Fv, single chain antibodies (scFv for example), single variable domain antibodies, diabodies (Dab) (bivalent and bispecific), and chimeric (e.g., humanized) antibodies, which may be produced by the modification of whole antibodies or those synthesized de novo using recombinant DNA technologies. These functional antibody fragments retain the ability to selectively bind with their respective antigen or receptor. Antibodies and antibody fragments can be from any class of antibodies including, but not limited to, IgG, IgA, IgM, IgD, and IgE, and from any subclass (e.g., IgG1, IgG2, IgG3, and IgG4) of antibodies. The preparation of antibody molecules can be monoclonal or polyclonal. An antibody molecule can also be a human, humanized, CDR-grafted, or in vitro generated antibody. The antibody can have a heavy chain constant region chosen from, e.g., IgG1, IgG2, IgG3, or IgG4. The antibody can also have a light chain chosen from, e.g., kappa or lambda. The term "immunoglobulin" (Ig) is used interchangeably with the term "antibody" herein.

Examples of antigen-binding fragments of an antibody molecule include: (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a diabody (dAb) fragment, which consists of a VH domain; (vi) a camelid or camelized variable domain; (vii) a single chain Fv (scFv), see e.g., Bird et al. (1988) *Science* 242:423-426; and Huston et al. (1988) *Proc. Natl. Acad. Sci. USA* 85:5879-5883); (viii) a single domain antibody. These antibody fragments are obtained using conventional techniques known to those with skill in the art, and the fragments are screened for utility in the same manner as are intact antibodies.

Antibody molecules include intact molecules as well as functional fragments thereof. Constant regions of the antibody molecules can be altered, e.g., mutated, to modify the properties of the antibody (e.g., to increase or decrease one or more of: Fc receptor binding, antibody glycosylation, the number of cysteine residues, effector cell function, or complement function).

Antibody molecules can also be single domain antibodies. Single domain antibodies can include antibodies whose complementary determining regions are part of a single domain polypeptide. Examples include, but are not limited to, heavy chain antibodies, antibodies naturally devoid of light chains, single domain antibodies derived from conventional 4-chain antibodies, engineered antibodies and single domain scaffolds other than those derived from antibodies. Single domain antibodies may be any of the art, or any future single domain antibodies. Single domain antibodies may be derived from any species including, but not limited to mouse, human, camel, llama, fish, shark, goat, rabbit, and bovine. According to another aspect of the invention, a single domain antibody is a naturally occurring single domain antibody known as heavy chain antibody devoid of light chains. Such single domain antibodies are disclosed in WO 9404678, for example. For clarity reasons, this variable domain derived from a heavy chain antibody naturally devoid of light chain is known herein as a VHH or Nanobody® (an antibody derived from heavy-chain-only antibody) to distinguish it from the conventional VH of four chain immunoglobulins. Such a VHH molecule can be derived from antibodies raised in Camelidae species, for example in camel, llama, dromedary, alpaca and guanaco. Other species besides Camelidae may produce heavy chain antibodies naturally devoid of light chain; such VHHs are within the scope of the invention.

The VH and VL regions can be subdivided into regions of hypervariability, termed "complementarity determining regions" (CDR), interspersed with regions that are more conserved, termed "framework regions" (FR or FW).

The extent of the framework region and CDRs has been precisely defined by a number of methods (see, Kabat, E. A., et al. (1991) Sequences of Proteins of Immunological Interest, Fifth Edition, U.S. Department of Health and Human Services, NIH Publication No. 91-3242; Chothia, C. et al. (1987) *J. Mol. Biol.* 196:901-917; and the AbM definition used by Oxford Molecular's AbM antibody modeling software. See, generally, e.g., *Protein Sequence and Structure Analysis of Antibody Variable Domains*. In: Antibody Engineering Lab Manual (Ed.: Duebel, S. and Kontermann, R., Springer-Verlag, Heidelberg).

The terms "complementarity determining region," and "CDR," as used herein refer to the sequences of amino acids within antibody variable regions which confer antigen specificity and binding affinity. In general, there are three CDRs in each heavy chain variable region (HCDR1, HCDR2, HCDR3) and three CDRs in each light chain variable region (LCDR1, LCDR2, LCDR3).

The precise amino acid sequence boundaries of a given CDR can be determined using any of a number of known schemes, including those described by Kabat et al. (1991), "Sequences of Proteins of Immunological Interest," 5th Ed. Public Health Service, National Institutes of Health, Bethesda, MD ("Kabat" numbering scheme), Al-Lazikani et al., (1997) *JMB* 273, 927-948 ("Chothia" numbering scheme). As used herein, the CDRs defined according the "Chothia" number scheme are also sometimes referred to as "hypervariable loops."

For example, under Kabat, the CDR amino acid residues in the heavy chain variable domain (VH) are numbered 31-35 (HCDR1), 50-65 (HCDR2), and 95-102 (HCDR3); and the CDR amino acid residues in the light chain variable domain (VL) are numbered 24-34 (LCDR1), 50-56 (LCDR2), and 89-97 (LCDR3). Under Chothia, the CDR amino acids in the VH are numbered 26-32 (HCDR1), 52-56 (HCDR2), and 95-102 (HCDR3); and the amino acid residues in VL are numbered 26-32 (LCDR1), 50-52 (LCDR2), and 91-96 (LCDR3).

Each VH and VL typically includes three CDRs and four FRs, arranged from amino-terminus to carboxy-terminus in the following order: FR1, CDR1, FR2, CDR2, FR3, CDR3, FR4.

The antibody molecule can be a polyclonal or a monoclonal antibody.

The terms "monoclonal antibody" or "monoclonal antibody composition" as used herein refer to a preparation of antibody molecules of single molecular composition. A monoclonal antibody composition displays a single binding specificity and affinity for a particular epitope. A monoclonal antibody can be made by hybridoma technology or by methods that do not use hybridoma technology (e.g., recombinant methods).

The antibody can be recombinantly produced, e.g., produced by phage display or by combinatorial methods, or by yeast display.

Phage display and combinatorial methods for generating antibodies are known in the art (as described in, e.g., Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology* 9:1370-1372; Hay et al. (1992) *Hum Antibod Hybridomas* 3:81-85; Huse et al. (1989) *Science* 246:1275-1281; Griffths et al. (1993) *EMBO J* 12:725-734; Hawkins et al. (1992) *J Mol Biol* 226:889-896; Clackson et al. (1991) *Nature* 352:624-628; Gram et al. (1992) *PNAS* 89:3576-3580; Garrad et al. (1991) *Bio/Technology* 9:1373-1377; Hoogenboom et al. (1991) *Nuc Acid Res* 19:4133-4137; and Barbas et al. (1991) *PNAS* 88:7978-7982, the contents of all of which are incorporated by reference herein).

The yeast display method for generating or identifying antibodies is known in the art, e.g., as described in Chao et al. (2006) *Nature Protocols* 1(2):755-68, the entire contents of which is incorporated by reference herein.

In one embodiment, the antibody is a fully human antibody (e.g., an antibody made in a mouse which has been genetically engineered to produce an antibody from a human immunoglobulin sequence), or a non-human antibody, e.g., a rodent (mouse or rat), goat, primate (e.g., monkey), camel antibody. Preferably, the non-human antibody is a rodent (mouse or rat antibody). Methods of producing rodent antibodies are known in the art.

Human monoclonal antibodies can be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 *Nature* 368:856-859; Green, L. L. et al. 1994 *Nature Genet.* 7:13-21; Morrison, S. L. et al. 1994 *Proc. Natl. Acad. Sci. USA* 81:6851-6855; Bruggeman et al. 1993 *Year Immunol* 7:33-40; Tuaillon et al. 1993 *PNAS* 90:3720-3724; Bruggeman et al. 1991 *Eur J Immunol* 21:1323-1326).

An antibody molecule can be one in which the variable region, or a portion thereof, e.g., the CDRs, are generated in a non-human organism, e.g., a rat or mouse. Chimeric, CDR-grafted, and humanized antibodies are within the invention. Antibody molecules generated in a non-human organism, e.g., a rat or mouse, and then modified, e.g., in the variable framework or constant region, to decrease antigenicity in a human are within the invention.

An "effectively human" protein is a protein that does substantially not evoke a neutralizing antibody response, e.g., the human anti-murine antibody (HAMA) response. HAMA can be problematic in a number of circumstances, e.g., if the antibody molecule is administered repeatedly, e.g., in treatment of a chronic or recurrent disease condition. A HAMA response can make repeated antibody administration potentially ineffective because of an increased antibody clearance from the serum (see, e.g., Saleh et al., *Cancer Immunol. Immunother.,* 32:180-190 (1990)) and also because of potential allergic reactions (see, e.g., LoBuglio et al., *Hybridoma,* 5:5117-5123 (1986)).

Chimeric antibodies can be produced by recombinant DNA techniques known in the art (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125,023; Better et al. (1988 *Science* 240:1041-1043); Liu et al. (1987) *PNAS* 84:3439-3443; Liu et al., 1987, *J. Immunol.* 139:3521-3526; Sun et al. (1987) *PNAS* 84:214-218; Nishimura et al., 1987, *Canc. Res.* 47:999-1005; Wood et al. (1985) *Nature* 314:446-449; and Shaw et al., 1988, *J. Natl Cancer Inst.* 80:1553-1559).

A humanized or CDR-grafted antibody will have at least one or two but generally all three recipient CDRs (of heavy and or light immuoglobulin chains) replaced with a donor CDR. The antibody may be replaced with at least a portion of a non-human CDR or only some of the CDRs may be replaced with non-human CDRs. It is only necessary to replace the number of CDRs required for binding to the antigen. Preferably, the donor will be a rodent antibody, e.g., a rat or mouse antibody, and the recipient will be a human framework or a human consensus framework. Typically, the immunoglobulin providing the CDRs is called the "donor" and the immunoglobulin providing the framework is called the "acceptor." In one embodiment, the donor immunoglobulin is a non-human (e.g., rodent). The acceptor framework is a naturally-occurring (e.g., a human) framework or a consensus framework, or a sequence about 85% or higher, preferably 90%, 95%, 99% or higher identical thereto.

As used herein, the term "consensus sequence" refers to the sequence formed from the most frequently occurring amino acids (or nucleotides) in a family of related sequences (See e.g., Winnaker, From Genes to Clones (Verlagsgesellschaft, Weinheim, Germany 1987). In a family of proteins, each position in the consensus sequence is occupied by the amino acid occurring most frequently at that position in the family. If two amino acids occur equally frequently, either can be included in the consensus sequence. A "consensus framework" refers to the framework region in the consensus immunoglobulin sequence.

An antibody molecule can be humanized by methods known in the art (see e.g., Morrison, S. L., 1985, *Science* 229:1202-1207, by Oi et al., 1986, *BioTechniques* 4:214, and by Queen et al. U.S. Pat. Nos. 5,585,089, 5,693,761 and 5,693,762, the contents of all of which are hereby incorporated by reference).

Humanized or CDR-grafted antibody molecules can be produced by CDR-grafting or CDR substitution, wherein one, two, or all CDRs of an immunoglobulin chain can be replaced. See e.g., U.S. Pat. No. 5,225,539; Jones et al. 1986 *Nature* 321:552-525; Verhoeyan et al. 1988 *Science* 239:

1534; Beidler et al. 1988 *J. Immunol.* 141:4053-4060; Winter U.S. Pat. No. 5,225,539, the contents of all of which are hereby expressly incorporated by reference. Winter describes a CDR-grafting method which may be used to prepare the humanized antibodies of the present invention (UK Patent Application GB 2188638A, filed on Mar. 26, 1987; Winter U.S. Pat. No. 5,225,539), the contents of which is expressly incorporated by reference.

Also within the scope of the invention are humanized antibody molecules in which specific amino acids have been substituted, deleted or added. Criteria for selecting amino acids from the donor are described in U.S. Pat. No. 5,585,089, e.g., columns 12-16 of U.S. Pat. No. 5,585,089, e.g., columns 12-16 of U.S. Pat. No. 5,585,089, the contents of which are hereby incorporated by reference. Other techniques for humanizing antibodies are described in Padlan et al. EP 519596 A1, published on Dec. 23, 1992.

The antibody molecule can be a single chain antibody. A single-chain antibody (scFV) may be engineered (see, for example, Colcher, D. et al. (1999) *Ann NY Acad Sci* 880: 263-80; and Reiter, Y. (1996) *Clin Cancer Res* 2:245-52). The single chain antibody can be dimerized or multimerized to generate multivalent antibodies having specificities for different epitopes of the same target protein.

In yet other embodiments, the antibody molecule has a heavy chain constant region chosen from, e.g., the heavy chain constant regions of IgG1, IgG2, IgG3, IgG4, IgM, IgA1, IgA2, IgD, and IgE; particularly, chosen from, e.g., the (e.g., human) heavy chain constant regions of IgG1, IgG2, IgG3, and IgG4. In another embodiment, the antibody molecule has a light chain constant region chosen from, e.g., the (e.g., human) light chain constant regions of kappa or lambda. The constant region can be altered, e.g., mutated, to modify the properties of the antibody (e.g., to increase or decrease one or more of: Fc receptor binding, antibody glycosylation, the number of cysteine residues, effector cell function, and/or complement function). In one embodiment the antibody has: effector function; and can fix complement. In other embodiments the antibody does not; recruit effector cells; or fix complement. In another embodiment, the antibody has reduced or no ability to bind an Fc receptor. For example, it is a isotype or subtype, fragment or other mutant, which does not support binding to an Fc receptor, e.g., it has a mutagenized or deleted Fc receptor binding region.

Methods for altering an antibody constant region are known in the art. Antibodies with altered function, e.g. altered affinity for an effector ligand, such as FcR on a cell, or the C1 component of complement can be produced by replacing at least one amino acid residue in the constant portion of the antibody with a different residue (see e.g., EP 388,151 A1, U.S. Pat. Nos. 5,624,821 and 5,648,260, the contents of all of which are hereby incorporated by reference). Similar type of alterations could be described which if applied to the murine, or other species immunoglobulin would reduce or eliminate these functions.

An antibody molecule can be derivatized or linked to another functional molecule (e.g., another peptide or protein). As used herein, a "derivatized" antibody molecule is one that has been modified. Methods of derivatization include but are not limited to the addition of a fluorescent moiety, a radionucleotide, a toxin, an enzyme or an affinity ligand such as biotin. Accordingly, the antibody molecules of the invention are intended to include derivatized and otherwise modified forms of the antibodies described herein, including immunoadhesion molecules. For example, an antibody molecule can be functionally linked (by chemical coupling, genetic fusion, noncovalent association or otherwise) to one or more other molecular entities, such as another antibody (e.g., a bispecific antibody or a diabody), a detectable agent, a cytotoxic agent, a pharmaceutical agent, and/or a protein or peptide that can mediate association of the antibody or antibody portion with another molecule (such as a streptavidin core region or a polyhistidine tag).

One type of derivatized antibody molecule is produced by crosslinking two or more antibodies (of the same type or of different types, e.g., to create bispecific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available from Pierce Chemical Company, Rockford, Ill.

Multispecific or Multifunctional Antibody Molecules

Exemplary structures of multispecific and multifunctional molecules defined herein are described throughout. Exemplary structures are further described in: Weidle U et al. (2013) The Intriguing Options of Multispecific Antibody Formats for Treatment of Cancer. *Cancer Genomics & Proteomics* 10: 1-18 (2013); and Spiess C et al. (2015) Alternative molecular formats and therapeutic applications for bispecific antibodies. *Molecular Immunology* 67: 95-106; the full contents of each of which is incorporated by reference herein).

In embodiments, multispecific antibody molecules can comprise more than one antigen-binding site, where different sites are specific for different antigens. In embodiments, multispecific antibody molecules can bind more than one (e.g., two or more) epitopes on the same antigen. In embodiments, multispecific antibody molecules comprise an antigen-binding site specific for a target cell (e.g., cancer cell) and a different antigen-binding site specific for an immune effector cell. In one embodiment, the multispecific antibody molecule is a bispecific antibody molecule. Bispecific antibody molecules can be classified into five different structural groups: (i) bispecific immunoglobulin G (BsIgG); (ii) IgG appended with an additional antigen-binding moiety; (iii) bispecific antibody fragments; (iv) bispecific fusion proteins; and (v) bispecific antibody conjugates.

BsIgG is a format that is monovalent for each antigen. Exemplary BsIgG formats include but are not limited to crossMab, DAF (two-in-one), DAF (four-in-one), DutaMab, DT-IgG, knobs-in-holes common LC, knobs-in-holes assembly, charge pair, Fab-arm exchange, SEEDbody, triomab, LUZ-Y, Fcab, KA-body, orthogonal Fab. See Spiess et al. Mol. Immunol. 67(2015):95-106. Exemplary BsIgGs include catumaxomab (Fresenius Biotech, Trion Pharma, Neopharm), which contains an anti-CD3 arm and an anti-EpCAM arm; and ertumaxomab (Neovii Biotech, Fresenius Biotech), which targets CD3 and HER2. In some embodiments, BsIgG comprises heavy chains that are engineered for heterodimerization. For example, heavy chains can be engineered for heterodimerization using a "knobs-into-holes" strategy, a SEED platform, a common heavy chain (e.g., in κλ-bodies), and use of heterodimeric Fc regions. See Spiess et al. Mol. Immunol. 67(2015):95-106. Strategies that have been used to avoid heavy chain pairing of homodimers in BsIgG include knobs-in-holes, duobody, azymetric, charge pair, HA-TF, SEEDbody, and differential protein A affinity. See Id. BsIgG can be produced by separate expression of the component antibodies in different host cells and subsequent purification/assembly into a BsIgG. BsIgG can also be produced by expression of the component antibodies in a single host cell. BsIgG can be purified using affinity chromatography, e.g., using protein A and sequential pH elution.

IgG appended with an additional antigen-binding moiety is another format of bispecific antibody molecules. For example, monospecific IgG can be engineered to have bispecificity by appending an additional antigen-binding unit onto the monospecific IgG, e.g., at the N- or C-terminus of either the heavy or light chain. Exemplary additional antigen-binding units include single domain antibodies (e.g., variable heavy chain or variable light chain), engineered protein scaffolds, and paired antibody variable domains (e.g., single chain variable fragments or variable fragments). See Id. Examples of appended IgG formats include dual variable domain IgG (DVD-Ig), IgG(H)-scFv, scFv-(H)IgG, IgG(L)-scFv, scFv-(L)IgG, IgG(L,H)-Fv, IgG(H)-V, V(H)-IgG, IgG(L)-V, V(L)-IgG, KIH IgG-scFab, 2scFv-IgG, IgG-2scFv, scFv4-Ig, zybody, and DVI-IgG (four-in-one). See Spiess et al. Mol. Immunol. 67(2015):95-106. An example of an IgG-scFv is MM-141 (Merrimack Pharmaceuticals), which binds IGF-1R and HER3. Examples of DVD-Ig include ABT-981 (AbbVie), which binds IL-1a and IL-1β; and ABT-122 (AbbVie), which binds TNF and IL-17A.

Bispecific antibody fragments (BsAb) are a format of bispecific antibody molecules that lack some or all of the antibody constant domains. For example, some BsAb lack an Fc region. In embodiments, bispecific antibody fragments include heavy and light chain regions that are connected by a peptide linker that permits efficient expression of the BsAb in a single host cell. Exemplary bispecific antibody fragments include but are not limited to Nanobody® (an antibody derived from heavy-chain-only antibody), Nanobody® (an antibody derived from heavy-chain-only antibody)-HAS, BiTE® (bispecific T cell engager), Diabody, DART® (dual-affinity retargeting antibody), TandAb, scDiabody, scDiabody-CH3, Diabody-CH3, triple body, miniantibody, minibody, TriBi minibody, scFv-CH3 KIH, Fab-scFv, scFv-CH-CL-scFv, F(ab')2, F(ab')2-scFv2, scFv-KIH, Fab-scFv-Fc, tetravalent HCAb, scDiabody-Fc, Diabody-Fc, tandem scFv-Fc, and intrabody. See Id. For example, the BiTE® (bispecific T cell engager) format comprises tandem scFvs, where the component scFvs bind to CD3 on T cells and a surface antigen on cancer cells.

Bispecific fusion proteins include antibody fragments linked to other proteins, e.g., to add additional specificity and/or functionality. An example of a bispecific fusion protein is an immTAC, which comprises an anti-CD3 scFv linked to an affinity-matured T-cell receptor that recognizes HLA-presented peptides. In embodiments, the dock-and-lock (DNL) method can be used to generate bispecific antibody molecules with higher valency. Also, fusions to albumin binding proteins or human serum albumin can be extend the serum half-life of antibody fragments. See Id.

In embodiments, chemical conjugation, e.g., chemical conjugation of antibodies and/or antibody fragments, can be used to create BsAb molecules. See Id. An exemplary bispecific antibody conjugate includes the CovX-body format, in which a low molecular weight drug is conjugated site-specifically to a single reactive lysine in each Fab arm or an antibody or fragment thereof. In embodiments, the conjugation improves the serum half-life of the low molecular weight drug. An exemplary CovX-body is CVX-241 (NCT01004822), which comprises an antibody conjugated to two short peptides inhibiting either VEGF or Ang2. See Id.

The antibody molecules can be produced by recombinant expression, e.g., of at least one or more component, in a host system. Exemplary host systems include eukaryotic cells (e.g., mammalian cells, e.g., CHO cells, or insect cells, e.g., SF9 or S2 cells) and prokaryotic cells (e.g., *E. coli*). Bispecific antibody molecules can be produced by separate expression of the components in different host cells and subsequent purification/assembly. Alternatively, the antibody molecules can be produced by expression of the components in a single host cell. Purification of bispecific antibody molecules can be performed by various methods such as affinity chromatography, e.g., using protein A and sequential pH elution. In other embodiments, affinity tags can be used for purification, e.g., histidine-containing tag, myc tag, or streptavidin tag.

Exemplary Bispecific Molecules

In an aspect, a multispecific molecule disclosed herein comprises a sequence disclosed herein, e.g., a sequence chosen from SEQ ID NOs: 1004-1007, 3275-3277, 3286, or 3287, or a sequence with at least 85%, 90%, 955, 96%, 97%, 98%, 99% or more identity thereto. In some embodiments, a multispecific molecule disclosed herein comprises a leader sequence comprising the amino acid sequence of SEQ ID NO: 3288. In some embodiments, a multispecific molecule disclosed herein does not comprise a leader sequence comprising the amino acid sequence of SEQ ID NO: 3288.

Molecule F: aCD19xaVb6.5

Molecule F comprises a heavy chain comprising the amino acid sequence of SEQ ID NO: 1004 and a light chain comprising the amino acid sequence of SEQ ID NO: 1005.

```
Molecule F.1
(heavy chain) (Tcrvbeta6_5 scFv/anti-CD19
heavy chain)
                                           SEQ ID NO: 1004
METDTLLLWVLLLWVPGSTGQVQLVQSGAEVKKPGSSVKVSCKASGYSFT

TYYIHWVRQAPGQGLEWMGWFFPGSGNIKYNEKFKGRVTITADTSTSTAY

MELSSLRSEDTAVYYCAGSYYSYDVLDYWGQGTTVTVSSGGGGSGGGGSG

GGGSGGGGSDIQMTQSPSFLSASVGDRVTITCKASQNVGINVVWHQQKPG

KAPKALIYSSSHRYSGVPSRFSGSGSGTEFTLTISSLQPEDFATYFCQQF

KSYPLTFGQGTKLEIKGGGGSQVTLRESGPALVKPTQTLTLTCTFSGFSL

STSGMGVGWIRQPPGKALEWLAHIWWDDDKRYNPALKSRLTISKDTSKNQ

VFLTMTNMDPVDTATYYCARMELWSYYFDYWGQGTTVTVSSASTKGPSVF

PLAPSSKSTSGGTAALGCLVKDYFPEPVTVSWNSGALTSGVHTFPAVLQS

SGLYSLSSVVTVPSSSLGTQTYICNVNHKPSNTKVDKKVEPKSCDKTHTC

PPCPAPELLGGPSVFLFPPKPKDTLMISRTPEVTCVVVDVSHEDPEVKFN

WYVDGVEVHNAKTKPREEQYASTYRVVSVLTVLHQDWLNGKEYKCKVSNK

ALPAPIEKTISKAKGQPREPQVYTLPPSREEMTKNQVSLTCLVKGFYPSD

IAVEWESNGQPENNYKTTPPVLDSDGSFFLYSKLTVDKSRWQQGNVFSCS

VMHEALHNHYTQKSLSLSPGK

Molecule F.2
(light chain) (anti-CD19 light chain)
                                           SEQ ID NO: 1005
METPAQLLFLLLLWLPDTTGENVLTQSPATLSLSPGERATLSCSASSSVS

YMHWYQQKPGQAPRLLIYDTSKLASGIPARFSGSGSGTDHTLTISSLEPE
```

-continued

DFAVYYCFQGSVYPFTFGQGTKLEIKRTVAAPSVFIFPPSDEQLKSGTAS

VVCLLNNFYPREAKVQWKVDNALQSGNSQESVTEQDSKDSTYSLSSTLTL

SKADYEKHKVYACEVTHQGLSSPVTKSFNRGEC

Molecule F.2
(light chain) (anti-CD19 light chain)
[]SEQ ID NO: 1005
METPAQLLFLLLLWLPDTTGENVLTQSPATLSLSPGERATLSCSASSSV

SYMHWYQQKPGQAPRLLIYDTSKLASGIPARFSGSGSGTDHTLTISSLE

PEDFAVYYCFQGSVYPFTFGQGTKLEIKRTVAAPSVFIFPPSDEQLKSG

TASVVCLLNNFYPREAKVQWKVDNALQSGNSQESVTEQDSKDSTYSLSS

TLTLSKADYEKHKVYACEVTHQGLSSPVTKSFNRGEC

In an aspect, a multispecific molecule disclosed herein comprises SEQ ID NO: 1004 and/or SEQ ID NO: 1005 or a sequence with at least 85%, 90%, 955, 96%, 97%, 98%, 99% or more identity thereto.

Molecule G: aBCMA×aVb6.5

Molecule G comprises a heavy chain comprising the amino acid sequence of SEQ ID NO: 1006 and a light chain comprising the amino acid sequence of SEQ ID NO: 1007.

Molecule G.1
(heavy chain)
SEQ ID NO: 1006
METDTLLLWVLLLWVPGSTGQVQLVQSGAEVKKPGSSVKVSCKASGYSFT

TYYIHWVRQAPGQGLEWMGWFFPGSGNIKYNEKFKGRVTITADTSTSTAY

MELSSLRSEDTAVYYCAGSYYSYDVLDYWGQGTTVTVSSGGGGSGGGGSG

GGGSGGGGSDIQMTQSPSFLSASVGDRVTITCKASQNVGINVVWHQQKPG

KAPKALIYSSSHRYSGVPSRFSGSGSGTEFTLTISSLQPEDFATYFCQQF

KSYPLTFGQGTKLEIKGGGGSQVQLVESGGGVVQPGRSLRLSCAASGIDF

SRYWMSWVRQAPGKGLEWVGEINPDSSTINYAPSLKDRFTISRDNSKNTL

YLQMSSLRAEDTAVYYCASLYYDYGDAMDYWGQGTTVTVSSASTKGPSVF

PLAPSSKSTSGGTAALGCLVKDYFPEPVTVSWNSGALTSGVHTFPAVLQS

SGLYSLSSVVTVPSSSLGTQTYICNVNHKPSNTKVDKKVEPKSCDKTHTC

PPCPAPELLGGPSVFLFPPKPKDTLMISRTPEVTCVVVDVSHEDPEVKFN

WYVDGVEVHNAKTKPREEQYASTYRVVSVLTVLHQDWLNGKEYKCKVSNK

ALPAPIEKTISKAKGQPREPQVYTLPPSREEMTKNQVSLTCLVKGFYPSD

IAVEWESNGQPENNYKTTPPVLDSDGSFFLYSKLTVDKSRWQQGNVFSCS

VMHEALHNRFTQKSLSLSPGK

Molecule G.2
(light chain)
SEQ ID NO: 1007
METDTLLLWVLLLWVPGSTGDIQMTQSPSSLSASVGDRVTITCKASQSVD

SNVAWYQQKPEKAPKALIFSASLRFSGVPSRFSGSGSGTDFTLTISSLQP

EDFATYFCQQYNNYPLTFGQGTKLEIKRTVAAPSVFIFPPSDEQLKSGTA

SVVCLLNNFYPREAKVQWKVDNALQSGNSQESVTEQDSKDSTYSLSSTLT

LSKADYEKHKVYACEVTHQGLSSPVTKSFNRGEC

In an aspect, a multispecific molecule disclosed herein comprises SEQ ID NO: 1006 and/or SEQ ID NO: 1007 or a sequence with at least 85%, 90%, 955, 96%, 97%, 98%, 99% or more identity thereto.

Molecule H: aBCMA×aTCRvbeta6_5

Molecule H comprises a first heavy chain comprising the amino acid sequence of SEQ ID NO: 3275, a light chain comprising the amino acid sequence of SEQ ID NO: 3277, and a second heavy chain comprising the amino acid sequence of SEQ ID NO: 3276.

Molecule H.1

Molecule H.1
(anti-BCMA heavy chain)
SEQ ID NO: 3275
METDTLLLWVLLLWVPGSTGQVQLVESGGGVVQPGRSLRLSCAASGIDFS

RYWMSWVRQAPGKGLEWVGEINPDSSTINYAPSLKDRFTISRDNSKNTLY

LQMSSLRAEDTAVYYCASLYYDYGDAMDYWGQGTTVTVSSASTKGPSVFP

LAPSSKSTSGGTAALGCLVKDYFPEPVTVSWNSGALTSGVHTFPAVLQSS

GLYSLSSVVTVPSSSLGTQTYICNVNHKPSNTKVDKRVEPKSCDKTHTCP

PCPAPELLGGPSVFLFPPKPKDTLMISRTPEVTCVVVDVSHEDPEVKFNW

YVDGVEVHNAKTKPREEQYNATYRVVSVLTVLHQDWLNGKEYKCKVSNKA

LPAPIEKTISKAKGQPREPQVYTLPPCREEMTKNQVSLWCLVKGFYPSDI

AVEWESNGQPENNYKTTPPVLDSDGSFFLYSKLTVDKSRWQQGNVFSCSV

MHEALHNHYTQKSLSLSPGK

Molecule H.2
(TCRvbeta_6_5 scFv humanized)
SEQ ID NO: 3276
METDTLLLWVLLLWVPGSTGQVQLVQSGAEVKKPGSSVKVSCKASGYSFT

TYYIHWVRQAPGQGLEWMGWFFPGSGNIKYNEKFKGRVTITADTSTSTAY

MELSSLRSEDTAVYYCAGSYYSYDVLDYWGQGTTVTVSSGGGGSGGGGSG

GGGSGGGGSDIQMTQSPSFLSASVGDRVTITCKASQNVGINVVWHQQKPG

KAPKALIYSSSHRYSGVPSRFSGSGSGTEFTLTISSLQPEDFATYFCQQF

KSYPLTFGQGTKLEIKGGGGSGGGGSDKTHTCPPCPAPELLGGPSVFLFP

PKPKDTLMISRTPEVTCVVVDVSHEDPEVKFNWYVDGVEVHNAKTKPREE

QYASTYRVVSVLTVLHQDWLNGKEYKCKVSNKALPAPIEKTISKAKGQPR

EPQVCTLPPSREEMTKNQVSLSCAVKGFYPSDIAVEWESNGQPENNYKTT

PPVLDSDGSFFLVSKLTVDKSRWQQGNVFSCSVMHEALHNHYTQKSLSLS

PGK

Molecule H.3
(anti-BCMA light chain)
SEQ ID NO: 3277
METDTLLLWVLLLWVPGSTGDIQMTQSPSSLSASVGDRVTITCKAS

QSVDSNVAWYQQKPEKAPKALIFSASLRFSGVPSRFSGSGSGTDFTLTIS

SLQPEDFATYFCQQYNNYPLTFGQGTKLEIKRTVAAPSVFIFPPSDEQLK

SGTASVVCLLNNFYPREAKVQWKVDNALQSGNSQESVTEQDSKDSTYSLS

STLTLSKADYEKHKVYACEVTHQGLSSPVTKSFNRGEC

In an aspect, a multispecific molecule disclosed herein comprises SEQ ID NO: 3275, SEQ ID NO: 3276, and/or SEQ ID NO: 3277 or a sequence with at least 85%, 90%, 955, 96%, 97%, 98%, 99% or more identity thereto.

Molecule I: Half Arm BCMA Fab with c-Terminal scFv TCRvbeta

Molecule I comprises a first heavy chain comprising the amino acid sequence of SEQ ID NO: 3286, a light chain comprising the amino acid sequence of SEQ ID NO: 3277, and a second heavy chain comprising the amino acid sequence of SEQ ID NO: 3287.

```
Molecule I.1
(heavy chain 1)
                                            SEQ ID NO: 3286
METDTLLLWVLLLWVPGSTGQVQLVESGGGVVQPGRSLRLSCAASGIDFS

RYWMSWVRQAPGKGLEWVGEINPDSSTINYAPSLKDRFTISRDNSKNTLY

LQMSSLRAEDTAVYYCASLYYDYGDAMDYWGQGTTVTVSSASTKGPSVFP

LAPSSKSTSGGTAALGCLVKDYFPEPVTVSWNSGALTSGVHTFPAVLQSS

GLYSLSSVVTVPSSSLGTQTYICNVNHKPSNTKVDKRVEPKSCDKTHTCP

PCPAPELLGGPSVFLFPPKPKDTLMISRTPEVTCVVVDVSHEDPEVKFNW

YVDGVEVHNAKTKPREEQYNSTYRVVSVLTVLHQDWLNGKEYKCKVSNKA

LPAPIEKTISKAKGQPREPQVYTLPPCREEMTKNQVSLWCLVKGFYPSDI

AVEWESNGQPENNYKTTPPVLDSDGSFFLYSKLTVDKSRWQQGNVFSCSV

MHEALHNHYTQKSLSLSPGKGGGGSGGGGSGGGGSEVQLVESGGGLVQPG

GSLRLSCAASGFTFSTYAMNWVRQAPGKGLEWVSRIRSKYNNYATYYADS

VKDRFTISRDDSKNTLYLQMNSLKTEDTAVYYCVRHGNFGNSYVSWFAYW

GQGTLVTVSSGGGGSGGGGSGGGGSGGGGSQAVVTQEPSLTVSPGGTVTL

TCRSSTGAVTTSNYANWVQQKPGQAPRGLIGGTNKRAPWTPARFSGSLLG

GKAALTLSGAQPEDEAEYYCALWYSNLWVFGGGTKLTVL

Molecule I.2
(light chain)
                                            SEQ ID NO: 3277
METDTLLLWVLLLWVPGSTGDIQMTQSPSSLSASVGDRVTITCKASQSVD

SNVAWYQQKPEKAPKALIFSASLRFSGVPSRFSGSGSGTDFTLTISSLQP

EDFATYFCQQYNNYPLTFGQGTKLEIKRTVAAPSVFIFPPSDEQLKSGTA

SVVCLLNNFYPREAKVQWKVDNALQSGNSQESVTEQDSKDSTYSLSSTLT

LSKADYEKHKVYACEVTHQGLSSPVTKSFNRGEC

Molecule I.3
(heavy chain 2)
                                            SEQ ID NO: 3287
METDTLLLWVLLLWVPGSTGDKTHTCPPCPAPELLGGPSVFLFPPKPKDT

LMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVCT

LPPSREEMTKNQVSLSCAVKGFYPSDIAVEWESNGQPENNYKTTPPVLDS

DGSFFLVSKLTVDKSRWQQGNVFSCSVMHEALHNHYTQKSLSLSPGK
```

In an aspect, a multispecific molecule disclosed herein comprises SEQ ID NO: 3286, SEQ ID NO: 3277, and/or SEQ ID NO: 3287 or a sequence with at least 85%, 90%, 955, 96%, 97%, 98%, 99% or more identity thereto.

Antibody-Like Frameworks or Scaffolds

A wide variety of antibody/immunoglobulin frameworks or scaffolds can be employed in the anti-TCRvb antibody molecules disclosed herein or multifunctional formats thereof so long as the resulting polypeptide includes at least one binding region which specifically binds to the target antigen, e.g., a TCRvb, a tumor antigen, among others. Such frameworks or scaffolds include the 5 main idiotypes of human immunoglobulins, or fragments thereof, and include immunoglobulins of other animal species, preferably having humanized aspects. Novel frameworks, scaffolds and fragments continue to be discovered and developed by those skilled in the art.

In one embodiment, the anti-TCRvb antibody molecules disclosed herein or multifunctional formats thereof include non-immunoglobulin based antibodies using non-immunoglobulin scaffolds onto which CDRs can be grafted. Any non-immunoglobulin frameworks and scaffolds may be employed, as long as they comprise a binding region specific for the target antigen (e.g., TCRvb or a tumor antigen). Exemplary non-immunoglobulin frameworks or scaffolds include, but are not limited to, fibronectin (Compound Therapeutics, Inc., Waltham, MA), ankyrin (Molecular Partners AG, Zurich, Switzerland), domain antibodies (Domantis, Ltd., Cambridge, MA, and Ablynx nv, Zwijnaarde, Belgium), lipocalin (Pieris Proteolab AG, Freising, Germany), small modular immuno-pharmaceuticals (Trubion Pharmaceuticals Inc., Seattle, WA), maxybodies (Avidia, Inc., Mountain View, CA), Protein A (Affibody AG, Sweden), and affilin (gamma-crystallin or ubiquitin) (Scil Proteins GmbH, Halle, Germany).

Fibronectin scaffolds are typically based on fibronectin type III domain (e.g., the tenth module of the fibronectin type III (10 Fn3 domain)). The fibronectin type III domain has 7 or 8 beta strands which are distributed between two beta sheets, which themselves pack against each other to form the core of the protein, and further containing loops (analogous to CDRs) which connect the beta strands to each other and are solvent exposed. There are at least three such loops at each edge of the beta sheet sandwich, where the edge is the boundary of the protein perpendicular to the direction of the beta strands (see U.S. Pat. No. 6,818,418). Because of this structure, the non-immunoglobulin antibody mimics antigen binding properties that are similar in nature and affinity to those of antibodies. These scaffolds can be used in a loop randomization and shuffling strategy in vitro that is similar to the process of affinity maturation of antibodies in vivo. These fibronectin-based molecules can be used as scaffolds where the loop regions of the molecule can be replaced with CDRs of the invention using standard cloning techniques.

The ankyrin technology is based on using proteins with ankyrin derived repeat modules as scaffolds for bearing variable regions which can be used for binding to different targets. The ankyrin repeat module typically is a about 33 amino acid polypeptide consisting of two anti-parallel α-helices and a β-turn. Binding of the variable regions can be optimized by using ribosome display.

Avimers are used by nature for protein-protein interactions and in human over 250 proteins are structurally based on A-domains. Avimers consist of a number of different "A-domain" monomers (2-10) linked via amino acid linkers. Avimers can be created that can bind to the target antigen using the methodology described in, for example, U.S. Patent Application Publication Nos. 20040175756; 20050053973; 20050048512; and 20060008844.

Affibody affinity ligands are small, simple proteins composed of a three-helix bundle based on the scaffold of one of the IgG-binding domains of Protein A. Protein A is a surface protein from the bacterium *Staphylococcus aureus*. This scaffold domain consists of 58 amino acids, 13 of which are randomized to generate affibody libraries with a large number of ligand variants (See e.g., U.S. Pat. No. 5,831,012). Affibody molecules mimic antibodies, they have a molecular weight of 6 kDa, compared to the molecular weight of antibodies, which is 150 kDa. In spite of its small size, the binding site of affibody molecules is similar to that of an antibody.

Anticalins are known commercially, e.g., *Pieris* ProteoLab AG. They are derived from lipocalins, a widespread group of small and robust proteins that are usually involved in the physiological transport or storage of chemically sensitive or insoluble compounds. Several natural lipocalins occur in human tissues or body liquids. The protein architecture is reminiscent of immunoglobulins, with hypervariable loops on top of a rigid framework. However, in contrast with antibodies or their recombinant fragments, lipocalins are composed of a single polypeptide chain with 160 to 180 amino acid residues, being just marginally bigger than a single immunoglobulin domain. The set of four loops, which makes up the binding pocket, shows pronounced structural plasticity and tolerates a variety of side chains. The binding site can thus be reshaped in a proprietary process in order to recognize prescribed target molecules of different shape with high affinity and specificity. One protein of lipocalin family, the bilin-binding protein (BBP) of *Pieris Brassicae* has been used to develop anticalins by mutagenizing the set of four loops. One example of a patent application describing anticalins is in PCT Publication No. WO 199916873.

Affilin molecules are small non-immunoglobulin proteins which are designed for specific affinities towards proteins and small molecules. New affilin molecules can be very quickly selected from two libraries, each of which is based on a different human derived scaffold protein. Affilin molecules do not show any structural homology to immunoglobulin proteins. Currently, two affilin scaffolds are employed, one of which is gamma crystalline, a human structural eye lens protein and the other is "ubiquitin" superfamily proteins. Both human scaffolds are very small, show high temperature stability and are almost resistant to pH changes and denaturing agents. This high stability is mainly due to the expanded beta sheet structure of the proteins. Examples of gamma crystalline derived proteins are described in WO200104144 and examples of "ubiquitin-like" proteins are described in WO2004106368.

Protein epitope mimetics (PEM) are medium-sized, cyclic, peptide-like molecules (MW 1-2 kDa) mimicking beta-hairpin secondary structures of proteins, the major secondary structure involved in protein-protein interactions.

Domain antibodies (dAbs) can be used in the anti-TCRvb antibody molecules disclosed herein or multifunctional formats thereof are small functional binding fragments of antibodies, corresponding to the variable regions of either the heavy or light chains of antibodies. Domain antibodies are well expressed in bacterial, yeast, and mammalian cell systems. Further details of domain antibodies and methods of production thereof are known in the art (see, for example, U.S. Pat. Nos. 6,291,158; 6,582,915; 6,593,081; 6,172,197; 6,696,245; European Patents 0368684 & 0616640; WO05/035572, WO04/101790, WO04/081026, WO04/058821, WO04/003019 and WO03/002609. Nanobodies are derived from the heavy chains of an antibody.

A Nanobody® (an antibody derived from heavy-chain-only antibody) typically comprises a single variable domain and two constant domains (CH2 and CH3) and retains antigen-binding capacity of the original antibody. Nanobodies can be prepared by methods known in the art (See e.g., U.S. Pat. Nos. 6,765,087, 6,838,254, WO 06/079372). Unibodies consist of one light chain and one heavy chain of an IgG4 antibody. Unibodies may be made by the removal of the hinge region of IgG4 antibodies. Further details of unibodies and methods of preparing them may be found in WO2007/059782.

Tumor Antigen Moiety

In an aspect, provided herein is a multispecific molecule, e.g., a bispecific molecule, comprising:

(i) a first moiety (e.g., a first immune cell engager) comprising the anti-TCRβV antibody molecule described herein; and (ii) a second moiety comprising one or more of: a tumor-targeting moiety; a second immune cell engager; a cytokine molecule or a stromal modifying moiety.

In some embodiments of any of the compositions or methods disclosed herein, the tumor-targeting moiety is an antigen, e.g., a cancer antigen. In some embodiments, the cancer antigen is a tumor antigen or stromal antigen, or a hematological antigen.

In some embodiments of any of the compositions or methods disclosed herein, the tumor-targeting moiety, e.g., cancer antigen, is chosen from: BCMA, FcRH5, CD19, CD20, CD22, CD30, CD33, CD38, CD47, CD99, CD123, FcRH5, CLEC12, CD179A, SLAMF7, or NY-ESO1, PDL1, CD47, ganglioside 2 (GD2), prostate stem cell antigen (PSCA), prostate specific membrane antigen (PMSA), prostate-specific antigen (PSA), carcinoembryonic antigen (CEA), Ron Kinase, c-Met, Immature laminin receptor, TAG-72, BING-4, Calcium-activated chloride channel 2, Cyclin-B1, 9D7, Ep-CAM, EphA3, Her2/neu, Telomerase, SAP-1, Survivin, NY-ESO-1/LAGE-1, PRAME, SSX-2, Melan-A/MART-1, Gp100/pmel17, Tyrosinase, TRP-1/-2, MC1R, β-catenin, BRCA1/2, CDK4, CML66, Fibronectin, p53, Ras, TGF-B receptor, AFP, ETA, MAGE, MUC-1, CA-125, BAGE, GAGE, NY-ESO-1, β-catenin, CDK4, CDC27, α actinin-4, TRP1/gp75, TRP2, gp100, Melan-A/MART1, gangliosides, WT1, EphA3, Epidermal growth factor receptor (EGFR), MART-2, MART-1, MUC1, MUC2, MUM1, MUM2, MUM3, NA88-1, NPM, OA1, OGT, RCC, RUI1, RUI2, SAGE, TRG, TRP1, TSTA, Folate receptor alpha, L1-CAM, CAIX, gpA33, GD3, GM2, VEGFR, Integrins (Integrin alphaVbeta3, Integrin alpha5Beta1), Carbohydrates (Le), IGF1R, EPHA3, TRAILR1, TRAILR2, RANKL, (FAP), TGF-beta, hyaluronic acid, collagen, e.g., collagen IV, tenascin C, or tenascin W. In some embodiments, the tumor-targeting moiety, e.g., cancer antigen, is BCMA. In some embodiments, the tumor-targeting moiety, e.g., cancer antigen, is FcRH5.

In some embodiments of any of the compositions or methods disclosed herein, the tumor-targeting moiety, e.g., cancer antigen, is chosen from: CD19, CD123, CD22, CD30, CD171, CS-1, C-type lectin-like molecule-1, CD33, epidermal growth factor receptor variant III (EGFRvIII), ganglioside G2 (GD2), ganglioside GD3, TNF receptor family member B cell maturation (BCMA), Tn antigen ((Tn Ag) or (GalNAca-Ser/Thr)), prostate-specific membrane antigen (PSMA), Receptor tyrosine kinase-like orphan receptor 1 (ROR1), Fms-Like Tyrosine Kinase 3 (FLT3), Tumor-associated glycoprotein 72 (TAG72), CD38, CD44v6, Carcinoembryonic antigen (CEA), Epithelial cell adhesion molecule (EPCAM), B7H3 (CD276), KIT (CD117), Interleukin-13 receptor subunit alpha-2, mesothelin, Interleukin 11 receptor alpha (IL-11Ra), prostate stem cell antigen (PSCA), Protease Serine 21, vascular endothelial growth factor receptor 2 (VEGFR2), Lewis(Y) antigen, CD24, Platelet-derived growth factor receptor beta (PDGFR-beta), Stage-specific embryonic antigen-4 (SSEA-4), CD20, Folate receptor alpha, Receptor tyrosine-protein kinase ERBB2 (Her2/neu), Mucin 1, cell surface associated (MUC1), epidermal growth factor receptor (EGFR), neural cell adhesion molecule (NCAM), Prostase, prostatic acid phosphatase (PAP), elongation factor 2 mutated (ELF2M), Ephrin B2, fibroblast activation protein alpha (FAP), insulin-like growth factor 1 receptor (IGF-I receptor), carbonic anhydrase IX (CAIX), Proteasome (Prosome, Macropain) Subunit, Beta Type, 9 (LMP2), glycoprotein 100 (gp100), oncogene fusion protein consisting of breakpoint cluster region (BCR) and Abelson murine leukemia viral oncogene homolog 1 (Abl) (bcr-abl), tyrosinase, ephrin type-A receptor 2 (EphA2), Fucosyl GM1, sialyl Lewis adhesion molecule (sLe), ganglioside GM3, transglutaminase 5 (TGS5), high molecular weight-melanoma-associated antigen (HMWMAA), o-acetyl-GD2 ganglioside (OAcGD2), Folate receptor beta, tumor endothelial marker 1 (TEM1/CD248), tumor endothelial marker 7-related (TEM7R), claudin 6 (CLDN6), thyroid stimulating hormone receptor (TSHR), G protein-coupled receptor class C group 5, member D (GPRC5D), chromosome X open reading frame 61 (CXORF61), CD97, CD179a, anaplastic lymphoma kinase (ALK), Polysialic acid, placenta-specific 1 (PLAC1), hexasaccharide portion of globoH glycoceramide (GloboH), mammary gland differentiation antigen (NY-BR-1), uroplakin 2 (UPK2), Hepatitis A virus cellular receptor 1 (HAVCR1), adrenoceptor beta 3 (ADRB3), pannexin 3 (PANX3), G protein-coupled receptor 20 (GPR20), lymphocyte antigen 6 complex, locus K 9 (LY6K), Olfactory receptor 51E2 (OR51E2), TCR Gamma Alternate Reading Frame Protein (TARP), Wilms tumor protein (WT1), Cancer/testis antigen 1 (NY-ESO-1), Cancer/testis antigen 2 (LAGE-1a), Melanoma-associated antigen 1 (MAGE-A1), ETS translocation-variant gene 6, located on chromosome 12p (ETV6-AML), sperm protein 17 (SPA17), X Antigen Family, Member 1A (XAGE1), angiopoietin-binding cell surface receptor 2 (Tie 2), melanoma cancer testis antigen-1 (MAD-CT-1), melanoma cancer testis antigen-2 (MAD-CT-2), Fos-related antigen 1, tumor protein p53 (p53), p53 mutant, prostein, surviving, telomerase, prostate carcinoma tumor antigen-1, melanoma antigen recognized by T cells 1, Rat sarcoma (Ras) mutant, human Telomerase reverse transcriptase (hTERT), sarcoma translocation breakpoints, melanoma inhibitor of apoptosis (ML-IAP), ERG (transmembrane protease, serine 2 (TMPRSS2) ETS fusion gene), N-Acetyl glucosaminyl-transferase V (NA17), paired box protein Pax-3 (PAX3), Androgen receptor, Cyclin B1, v-myc avian myelocytomatosis viral oncogene neuroblastoma derived homolog (MYCN), Ras Homolog Family Member C (RhoC), Tyrosinase-related protein 2 (TRP-2), Cytochrome P450 1B1 (CYPIB1), CCCTC-Binding Factor (Zinc Finger Protein)-Like, Squamous Cell Carcinoma Antigen Recognized By T Cells 3 (SART3), Paired box protein Pax-5 (PAX5), proacrosin binding protein sp32 (OY-TES1), lymphocyte-specific protein tyrosine kinase (LCK), A kinase anchor protein 4 (AKAP-4), synovial sarcoma, X breakpoint 2 (SSX2), Receptor for Advanced Glycation Endproducts (RAGE-1), renal ubiquitous 1 (RU1), renal ubiquitous 2 (RU2), legumain, human papilloma virus E6 (HPV E6), human papilloma virus E7 (HPV E7), intestinal carboxyl esterase, heat shock protein 70-2 mutated (mut hsp70-2), CD79a, CD79b, CD72, Leukocyte-associated immunoglobulin-like receptor 1 (LAIRI), Fc fragment of IgA receptor (FCAR or CD89), Leukocyte immunoglobulin-like receptor subfamily A member 2 (LILRA2), CD300 molecule-like family member f (CD300LF), C-type lectin domain family 12 member A (CLEC12A), bone marrow stromal cell antigen 2 (BST2), EGF-like module-containing mucin-like hormone receptor-like 2 (EMR2), lymphocyte antigen 75 (LY75), Glypican-3 (GPC3), Fc receptor-like 5 (FCRL5), or immunoglobulin lambda-like polypeptide 1 (IGLL1).

FcRH5 Targeting Moieties

In some embodiments, the multispecific molecules disclosed herein include a targeting moiety that binds to FcRH5 (e.g., a FcRH5 targeting moiety). The FcRH5 targeting moiety can be chosen from an antibody molecule (e.g., an antigen binding domain as described herein), a receptor or a receptor fragment, or a ligand or a ligand fragment, or a combination thereof. In some embodiments, the FcRH5 targeting moiety associates with, e.g., binds to, a cancer or hematopoietic cell (e.g., a molecule, e.g., antigen, present on the surface of the cancer or hematopoietic cell). In certain embodiments, the FcRH5 targeting moiety targets, e.g., directs the multispecific molecules disclosed herein to a cancer or hematopoietic cell. In some embodiments, the cancer is a hematological cancer, e.g., multiple myeloma.

In some embodiments, the multispecific molecule, e.g., the FcRH5 targeting moiety, binds to a FcRH5 antigen on the surface of a cell, e.g., a cancer or hematopoietic cell. The FcRH5 antigen can be present on a primary tumor cell, or a metastatic lesion thereof. In some embodiments, the cancer is a hematological cancer, e.g., multiple myeloma. For example, the FcRH5 antigen can be present on a tumor, e.g., a tumor of a class typified by having one or more of: limited tumor perfusion, compressed blood vessels, or fibrotic tumor interstitium.

The multispecific molecules described herein includes a FcRH5 targeting moiety that comprises an anti-FcRH5 antibody or antigen-binding fragment thereof described in U.S. Pat. No. 7,999,077, US20150098900, U.S. Pat. Nos. 8,299,220, 7,105,149, 8,362,213, 8,466,260, 8,617,559, US20160368985, US20150166661, and US20080247944, the entire contents of any of the aforesaid publications are herein incorporated by reference.

In some embodiments, the multispecific molecules described herein includes a FcRH5 targeting moiety that comprises an anti-FcRH5 antibody or antigen-binding fragment thereof described in U.S. Pat. No. 7,999,077, the entire contents of which are herein incorporated by reference.

BCMA Targeting Moieties

In certain embodiments, the multispecific molecules disclosed herein include a targeting moiety that binds to BCMA (e.g., a BCMA targeting moiety). The BCMA targeting moiety can be chosen from an antibody molecule (e.g., an antigen binding domain as described herein), a receptor or a receptor fragment, or a ligand or a ligand fragment, or a combination thereof. In some embodiments, the BCMA targeting moiety associates with, e.g., binds to, a cancer or hematopoietic cell (e.g., a molecule, e.g., antigen, present on the surface of the cancer or hematopoietic cell). In certain embodiments, the BCMA targeting moiety targets, e.g., directs the multispecific molecules disclosed herein to a cancer or hematopoietic cell. In some embodiments, the cancer is a hematological cancer, e.g., multiple myeloma.

In some embodiments, the multispecific molecule, e.g., the BCMA targeting moiety, binds to a BCMA antigen on the surface of a cell, e.g., a cancer or hematopoietic cell. The BCMA antigen can be present on a primary tumor cell, or a metastatic lesion thereof. In some embodiments, the cancer is a hematological cancer, e.g., multiple myeloma. For example, the BCMA antigen can be present on a tumor, e.g., a tumor of a class typified by having one or more of: limited tumor perfusion, compressed blood vessels, or fibrotic tumor interstitium.

Exemplar BCMA Targeting Moieties

The multispecific molecules described herein can include a BCMA targeting moiety that comprises an anti-BCMA antibody or antigen-binding fragment thereof described in U.S. Pat. Nos. 8,920,776, 9,243,058, 9,340,621, 8,846,042, 7,083,785, 9,545,086, 7,276,241, 9,034,324, 7,799,902, 9,387,237, 8,821,883, US861745, US20130273055, US20160176973, US20150368351, US20150376287, US20170022284, US20160015749, US20140242077, US20170037128, US20170051068, US20160368988, US20160311915, US20160131654, US20120213768, US20110177093, US20160297885, EP3137500, EP2699259, EP2982694, EP3029068, EP3023437, WO2016090327, WO2017021450, WO2016110584, WO2016118641, WO2016168149, the entire contents of which are incorporated herein by reference.

In one embodiment, the BCMA-targeting moiety includes an antibody molecule (e.g., Fab or scFv) that binds to BCMA. In some embodiments, the antibody molecule to BCMA comprises one, two, or three CDRs from any of the heavy chain variable domain sequences of Table 1, or a closely related CDR, e.g., CDRs which have at least one amino acid alteration, but not more than two, three or four alterations (e.g., substitutions, deletions, or insertions, e.g., conservative substitutions) from any of the CDR sequences of Table 14. In some embodiments, the antibody molecule to BCMA comprises a heavy chain variable domain sequence chosen from any of the amino acid sequences of Table 14, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions)).

Alternatively, or in combination with the heavy chain to BCMA disclosed herein, the antibody molecule to BCMA comprises one, two, or three CDRs from any of the light chain variable domain sequences of Table 14, or a closely related CDR, e.g., CDRs which have at least one amino acid alteration, but not more than two, three or four alterations (e.g., substitutions, deletions, or insertions, e.g., conservative substitutions) from any of the CDR sequences of Table 14. In some embodiments, the antibody molecule to BCMA comprises a light chain variable domain sequence chosen from any of the amino acid sequences of Table 14, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions)).

TABLE 14

Amino acid sequences of exemplary variable regions of anti-BCMA antibodies.

| SEQ ID NO | Description | Sequence |
|---|---|---|
| 3439 | 83A10 VH | EVQLLESGGGLVQPGGSLRLSCAASGFTFSSYAMSWVRQAPGKGL EWVSAISGSGGSTYYADSVKGRFTISRDNSKNTLYLQMNSLRAED TAVYYCAKVLGWFDYWGQGTLVTVSS |
| 3440 | 83A10 VL | EIVLTQSPGTLSLSPGERATLSCRASQSVSSSYLAWYQQKPGQAPR LLIYGASSRATGIPDRFSGSGSGTDFTLTISRLEPEDFAVYYCQQYG YPPDFTFGQGTKVEIK |
| 3441 | 17A5 VH | EVQLLESGGGLVQPGGSLRLSCAASGFTFSSYAMSWVRQAPGKGL EWVSAISGSGGSTYYADSVKGRFTISRDNSKNTLYLQMNSLRAED TAVYYCAKVAPYFAPFDYWGQGTLVTVSS |
| 3442 | 17A5 VL | EIVLTQSPGTLSLSPGERATLSCRASQSVSSSYLAWYQQKPGQAPR LLIYGASSRATGIPDRFSGSGSGTDFTLTISRLEPEDFAVYYCQQYG NPPLYTFGQGTKVEIK |
| 3443 | 13A4 VH | EVQLVQSGAEVKKPGESLKISCKGSGYSFTSYWIGWVRQMPGKGL EWMGIIYPGDSDTRYSPSFQGQVTISADKSISTAYLQWSSLKASDT AMYYCARNGYLGDYWGQGTLVTVSS |
| 3444 | 13A4 VL | DIVMTQSPLSLPVTPGEPASISCRSSQSLLHSNGYNYLDWYLQKPG QSPQLLIYLGSNRASGVPDRFSGSGSGTDFTLKISRVEAEDVGVYY CMQAMQIPTFGQGTKVEIK |
| 3445 | J22.9-xi VH | QVQLQQSGGGLVQPGGSLKLSCAASGIDFSRYWMSWVRRAPGKG LEWIGEINPDSSTINYAPSLKDKFIISRDNAKNTLYLQMSKVRSEDT ALYYCASLYYDYGDAMDYWGQGTSVTVSS |
| 3446 | J22.9-xi VL | DIVMTQSQRFMTTSVGDRVSVTCKASQSVDSNVAWYQQKPRQSP KALIFSASLRFSGVPARFTGSGSGTDFTLTISNLQSEDLAEYFCQQY NNYPLTFGAGTKLELKR |
| 3447 | 2A1 VH | EVQLVESGGGLVKPGGSLRLSCAASGFTFGDYALSWFRQAPGKGL EWVGVSRSKAYGGTTDYAASVKGRFTISRDDSKSTAYLQMNSLKT EDTAVYYCASSGYSSGWTPFDYWGQGTLVTVSS |
| 3448 | 2A1 VL | QSVLTQPPSASGTPGQRVTISCSGSSSNIGSNTVNWYQQLPGTAPKL LIFNYHQRPSGVPDRFSGSKSGSSASLAISGLQSEDEADYYCAAWD DSLNGWVFGGGTKLTVLG |

CDR-Grafted Scaffolds

In embodiments, the antibody molecule is a CDR-grafted scaffold domain. In embodiments, the scaffold domain is based on a fibronectin domain, e.g., fibronectin type III domain. The overall fold of the fibronectin type III (Fn3) domain is closely related to that of the smallest functional antibody fragment, the variable domain of the antibody heavy chain. There are three loops at the end of Fn3; the positions of BC, DE and FG loops approximately correspond to those of CDR1, 2 and 3 of the VH domain of an antibody. Fn3 does not have disulfide bonds; and therefore Fn3 is stable under reducing conditions, unlike antibodies and their fragments (see, e.g., WO 98/56915; WO 01/64942; WO 00/34784). An Fn3 domain can be modified (e.g., using CDRs or hypervariable loops described herein) or varied, e.g., to select domains that bind to an antigen/marker/cell described herein.

In embodiments, a scaffold domain, e.g., a folded domain, is based on an antibody, e.g., a "minibody" scaffold created by deleting three beta strands from a heavy chain variable domain of a monoclonal antibody (see, e.g., Tramontano et al., 1994, J Mol. Recognit. 7:9; and Martin et al., 1994, EMBO J. 13:5303-5309). The "minibody" can be used to present two hypervariable loops. In embodiments, the scaffold domain is a V-like domain (see, e.g., Coia et al. WO 99/45110) or a domain derived from tendamistatin, which is a 74 residue, six-strand beta sheet sandwich held together by two disulfide bonds (see, e.g., McConnell and Hoess, 1995, J Mol. Biol. 250:460). For example, the loops of tendamistatin can be modified (e.g., using CDRs or hypervariable loops) or varied, e.g., to select domains that bind to a marker/antigen/cell described herein. Another exemplary scaffold domain is a beta-sandwich structure derived from the extracellular domain of CTLA-4 (see, e.g., WO 00/60070).

Other exemplary scaffold domains include but are not limited to T-cell receptors; MHC proteins; extracellular domains (e.g., fibronectin Type III repeats, EGF repeats); protease inhibitors (e.g., Kunitz domains, ecotin, BPTI, and so forth); TPR repeats; trifoil structures; zinc finger domains; DNA-binding proteins; particularly monomeric DNA binding proteins; RNA binding proteins; enzymes, e.g., proteases (particularly inactivated proteases), RNase; chaperones, e.g., thioredoxin, and heat shock proteins; and intracellular signaling domains (such as SH2 and SH3 domains). See, e.g., US 20040009530 and U.S. Pat. No. 7,501,121, incorporated herein by reference.

In embodiments, a scaffold domain is evaluated and chosen, e.g., by one or more of the following criteria: (1) amino acid sequence, (2) sequences of several homologous domains, (3) 3-dimensional structure, and/or (4) stability data over a range of pH, temperature, salinity, organic solvent, oxidant concentration. In embodiments, the scaffold domain is a small, stable protein domain, e.g., a protein of less than 100, 70, 50, 40 or 30 amino acids. The domain may include one or more disulfide bonds or may chelate a metal, e.g., zinc.

Antibody-Based Fusions

A variety of formats can be generated which contain additional binding entities attached to the N or C terminus of antibodies. These fusions with single chain or disulfide stabilized Fvs or Fabs result in the generation of tetravalent molecules with bivalent binding specificity for each antigen. Combinations of scFvs and scFabs with IgGs enable the production of molecules which can recognize three or more different antigens.

Antibody-Fab Fusion

Antibody-Fab fusions are bispecific antibodies comprising a traditional antibody to a first target and a Fab to a second target fused to the C terminus of the antibody heavy chain. Commonly the antibody and the Fab will have a common light chain. Antibody fusions can be produced by (1) engineering the DNA sequence of the target fusion, and (2) transfecting the target DNA into a suitable host cell to express the fusion protein. It seems like the antibody-scFv fusion may be linked by a (Gly)-Ser linker between the C-terminus of the CH3 domain and the N-terminus of the scFv, as described by Coloma, J. et al. (1997) *Nature Biotech* 15:159.

Antibody-scFv Fusion

Antibody-scFv Fusions are bispecific antibodies comprising a traditional antibody and a scFv of unique specificity fused to the C terminus of the antibody heavy chain. The scFv can be fused to the C terminus through the Heavy Chain of the scFv either directly or through a linker peptide. Antibody fusions can be produced by (1) engineering the DNA sequence of the target fusion, and (2) transfecting the target DNA into a suitable host cell to express the fusion protein. It seems like the antibody-scFv fusion may be linked by a (Gly)-Ser linker between the C-terminus of the CH3 domain and the N-terminus of the scFv, as described by Coloma, J. et al. (1997) *Nature Biotech* 15:159.

Variable Domain Immunoglobulin DVD

A related format is the dual variable domain immunoglobulin (DVD), which are composed of VH and VL domains of a second specificity place upon the N termini of the V domains by shorter linker sequences.

Other exemplary multispecific antibody formats include, e.g., those described in the following US20160114057A1, US20130243775A1, US20140051833, US20130022601, US20150017187A1, US20120201746A1, US20150133638A1, US20130266568A1, US20160145340A1, WO2015127158A1, US20150203591A1, US20140322221A1, US20130303396A1, US20110293613, US20130017200A1, US20160102135A1, WO2015197598A2, WO2015197582A1, U.S. Pat. No. 9,359,437, US20150018529, WO2016115274A1, WO2016087416A1, US20080069820A1, U.S. Pat. Nos. 9,145,588B, 7,919,257, and US20150232560A1. Exemplary multispecific molecules utilizing a full antibody-Fab/scFab format include those described in the following, U.S. Pat. No. 9,382,323B2, US20140072581A1, US20140308285A1, US20130165638A1, US20130267686A1, US20140377269A1, U.S. Pat. No. 7,741,446B2, and WO1995009917A1. Exemplary multispecific molecules utilizing a domain exchange format include those described in the following, US20150315296A1, WO2016087650A1, US20160075785A1, WO2016016299A1, US20160130347A1, US20150166670, U.S. Pat. No. 8,703,132B2, US20100316645, U.S. Pat. No. 8,227,577B2, US20130078249.

Fc-Containing Entities (Mini-Antibodies)

Fc-containing entities, also known as mini-antibodies, can be generated by fusing scFv to the C-termini of constant heavy region domain 3 (CH3-scFv) and/or to the hinge region (scFv-hinge-Fc) of an antibody with a different specificity. Trivalent entities can also be made which have disulfide stabilized variable domains (without peptide linker) fused to the C-terminus of CH3 domains of IgGs.

Fc-Containing Multispecific Molecules

In some embodiments, the multispecific molecules disclosed herein includes an immunoglobulin constant region (e.g., an Fc region). Exemplary Fc regions can be chosen from the heavy chain constant regions of IgG1, IgG2, IgG3 or IgG4; more particularly, the heavy chain constant region of human IgG1, IgG2, IgG3, or IgG4.

In some embodiments, the immunoglobulin chain constant region (e.g., the Fc region) is altered, e.g., mutated, to increase or decrease one or more of: Fc receptor binding, antibody glycosylation, the number of cysteine residues, effector cell function, or complement function.

In other embodiments, an interface of a first and second immunoglobulin chain constant regions (e.g., a first and a second Fc region) is altered, e.g., mutated, to increase or decrease dimerization, e.g., relative to a non-engineered interface, e.g., a naturally-occurring interface. For example, dimerization of the immunoglobulin chain constant region (e.g., the Fc region) can be enhanced by providing an Fc interface of a first and a second Fc region with one or more of: a paired protuberance-cavity ("knob-in-a hole"), an electrostatic interaction, or a strand-exchange, such that a greater ratio of heteromultimer to homomultimer forms, e.g., relative to a non-engineered interface.

In some embodiments, the multispecific molecules include a paired amino acid substitution at a position chosen from one or more of 347, 349, 350, 351, 366, 368, 370, 392, 394, 395, 397, 398, 399, 405, 407, or 409, e.g., of the Fc region of human IgG1 For example, the immunoglobulin chain constant region (e.g., Fc region) can include a paired an amino acid substitution chosen from: T366S, L368A, or Y407V (e.g., corresponding to a cavity or hole), and T366W (e.g., corresponding to a protuberance or knob).

In other embodiments, the multifunctional molecule includes a half-life extender, e.g., a human serum albumin or an antibody molecule to human serum albumin.

Heterodimerized Antibody Molecules & Methods of Making

Various methods of producing multispecific antibodies have been disclosed to address the problem of incorrect heavy chain pairing. Exemplary methods are described below. Exemplary multispecific antibody formats and methods of making said multispecific antibodies are also disclosed in e.g., Speiss et al. Molecular Immunology 67 (2015) 95-106; and Klein et al mAbs 4:6, 653-663; November/December 2012; the entire contents of each of which are incorporated by reference herein.

Heterodimerized bispecific antibodies are based on the natural IgG structure, wherein the two binding arms recognize different antigens. IgG derived formats that enable defined monovalent (and simultaneous) antigen binding are generated by forced heavy chain heterodimerization, combined with technologies that minimize light chain mispairing (e.g., common light chain). Forced heavy chain heterodimerization can be obtained using, e.g., knob-in-hole OR strand exchange engineered domains (SEED).

Knob-In-Hole

Knob-in-Hole as described in U.S. Pat. Nos. 5,731,116, 7,476,724 and Ridgway, J. et al. (1996) Prot. Engineering 9(7): 617-621, broadly involves: (1) mutating the CH3 domain of one or both antibodies to promote heterodimerization; and (2) combining the mutated antibodies under conditions that promote heterodimerization. "Knobs" or "protuberances" are typically created by replacing a small amino acid in a parental antibody with a larger amino acid (e.g., T366Y or T366W); "Holes" or "cavities" are created by replacing a larger residue in a parental antibody with a smaller amino acid (e.g., Y407T, T366S, L368A and/or Y407V).

For bispecific antibodies including an Fc domain, introduction of specific mutations into the constant region of the heavy chains to promote the correct heterodimerization of the Fc portion can be utilized. Several such techniques are reviewed in Klein et al. (mAbs (2012) 4:6, 1-11), the contents of which are incorporated herein by reference in their entirety. These techniques include the "knobs-into-holes" (KiH) approach which involves the introduction of a bulky residue into one of the CH3 domains of one of the antibody heavy chains. This bulky residue fits into a complementary "hole" in the other CH3 domain of the paired heavy chain so as to promote correct pairing of heavy chains (see e.g., U.S. Pat. No. 7,642,228).

Exemplary KiH mutations include S354C, T366W in the "knob" heavy chain and Y349C, T366S, L368A, Y407V in the "hole" heavy chain. Other exemplary KiH mutations are provided in Table 4, with additional optional stabilizing Fc cysteine mutations.

TABLE 4

Exemplary Fc KiH mutations and optional Cysteine mutations

| Position | Knob Mutation | Hole Mutation |
|---|---|---|
| T366 | T366W | T366S |
| L368 | — | L368A |
| Y407 | — | Y407V |

Additional Cysteine Mutations to form a stabilizing disulfide bridge

| Position | Knob CH3 | Hole CH3 |
|---|---|---|
| S354 | S354C | — |
| Y349 | — | Y349C |

Other Fc mutations are provided by Igawa and Tsunoda who identified 3 negatively charged residues in the CH3 domain of one chain that pair with three positively charged residues in the CH3 domain of the other chain. These specific charged residue pairs are: E356-K439, E357-K370, D399-K409 and vice versa. By introducing at least two of the following three mutations in chain A: E356K, E357K and D399K, as well as K370E, K409D, K439E in chain B, alone or in combination with newly identified disulfide bridges, they were able to favor very efficient heterodimerization while suppressing homodimerization at the same time (Martens T et al. A novel one-armed antic-Met antibody inhibits glioblastoma growth in vivo. Clin Cancer Res 2006; 12:6144-52; PMID:17062691). Xencor defined 41 variant pairs based on combining structural calculations and sequence information that were subsequently screened for maximal heterodimerization, defining the combination of S364H, F405A (HA) on chain A and Y349T, T394F on chain B (TF) (Moore G L et al. A novel bispecific antibody format enables simultaneous bivalent and monovalent co-engagement of distinct target antigens. MAbs 2011; 3:546-57; PMID: 22123055).

Other exemplary Fc mutations to promote heterodimerization of multispecific antibodies include those described in the following references, the contents of each of which is incorporated by reference herein, WO2016071377A1, US20140079689A1, US20160194389A1, US20160257763, WO2016071376A2, WO2015107026A1, WO2015107025A1, WO2015107015A1, US20150353636A1, US20140199294A1, U.S. Pat. No. 7,750,128B2, US20160229915A1, US20150344570A1, U.S. Pat. No. 8,003,774A1, US20150337049A1, US20150175707A1, US20140242075A1, US20130195849A1, US20120149876A1, US20140200331A1, U.S. Pat. No.

9,309,311B2, U.S. Pat. No. 8,586,713, US20140037621A1, US20130178605A1, US20140363426A1, US20140051835A1 and US20110054151A1.

Stabilizing cysteine mutations have also been used in combination with KiH and other Fc heterodimerization promoting variants, see e.g., U.S. Pat. No. 7,183,076. Other exemplary cysteine modifications include, e.g., those disclosed in US20140348839A1, U.S. Pat. No. 7,855,275B2, and U.S. Pat. No. 9,000,130B2.

Strand Exchange Engineered Domains (SEED)

Heterodimeric Fc platform that support the design of bispecific and asymmetric fusion proteins by devising strand-exchange engineered domain (SEED) C(H)3 heterodimers are known. These derivatives of human IgG and IgA C(H)3 domains create complementary human SEED C(H)3 heterodimers that are composed of alternating segments of human IgA and IgG C(H)3 sequences. The resulting pair of SEED C(H)3 domains preferentially associates to form heterodimers when expressed in mammalian cells. SEEDbody (Sb) fusion proteins consist of [IgG1 hinge]-C(H)2-[SEED C(H)3], that may be genetically linked to one or more fusion partners (see e.g., Davis J H et al. SEEDbodies: fusion proteins based on strand exchange engineered domain (SEED) CH3 heterodimers in an Fc analogue platform for asymmetric binders or immunofusions and bispecific antibodies. Protein Eng Des Sel 2010; 23:195-202; PMID:20299542 and U.S. Pat. No. 8,871,912. The contents of each of which are incorporated by reference herein).

Duobody

"Duobody" technology to produce bispecific antibodies with correct heavy chain pairing are known. The DuoBody technology involves three basic steps to generate stable bispecific human IgG1 antibodies in a post-production exchange reaction. In a first step, two IgG1s, each containing single matched mutations in the third constant (CH3) domain, are produced separately using standard mammalian recombinant cell lines. Subsequently, these IgG1 antibodies are purified according to standard processes for recovery and purification. After production and purification (post-production), the two antibodies are recombined under tailored laboratory conditions resulting in a bispecific antibody product with a very high yield (typically >95%) (see e.g., Labrijn et al, PNAS 2013; 110(13):5145-5150 and Labrijn et al. Nature Protocols 2014; 9(10):2450-63, the contents of each of which are incorporated by reference herein).

Electrostatic Interactions

Methods of making multispecific antibodies using CH3 amino acid changes with charged amino acids such that homodimer formation is electrostatically unfavorable are disclosed. EP1870459 and WO 2009089004 describe other strategies for favoring heterodimer formation upon co-expression of different antibody domains in a host cell. In these methods, one or more residues that make up the heavy chain constant domain 3 (CH3), CH3-CH3 interfaces in both CH3 domains are replaced with a charged amino acid such that homodimer formation is electrostatically unfavorable and heterodimerization is electrostatically favorable. Additional methods of making multispecific molecules using electrostatic interactions are described in the following references, the contents of each of which is incorporated by reference herein, include US20100015133, U.S. Pat. No. 8,592,562B2, U.S. Pat. No. 9,200,060B2, US20140154254A1, and U.S. Pat. No. 9,358,286A1.

Common Light Chain

Light chain mispairing needs to be avoided to generate homogenous preparations of bispecific IgGs. One way to achieve this is through the use of the common light chain principle, i.e. combining two binders that share one light chain but still have separate specificities. An exemplary method of enhancing the formation of a desired bispecific antibody from a mixture of monomers is by providing a common variable light chain to interact with each of the heteromeric variable heavy chain regions of the bispecific antibody. Compositions and methods of producing bispecific antibodies with a common light chain as disclosed in, e.g., U.S. Pat. No. 7,183,076B2, US20110177073A1, EP2847231A1, WO2016079081A1, and EP3055329A1, the contents of each of which is incorporated by reference herein.

CrossMab

Another option to reduce light chain mispairing is the CrossMab technology which avoids non-specific L chain mispairing by exchanging CH1 and CL domains in the Fab of one half of the bispecific antibody. Such crossover variants retain binding specificity and affinity, but make the two arms so different that L chain mispairing is prevented. The CrossMab technology (as reviewed in Klein et al. Supra) involves domain swapping between heavy and light chains so as to promote the formation of the correct pairings. Briefly, to construct a bispecific IgG-like CrossMab antibody that could bind to two antigens by using two distinct light chain-heavy chain pairs, a two-step modification process is applied. First, a dimerization interface is engineered into the C-terminus of each heavy chain using a heterodimerization approach, e.g., Knob-into-hole (KiH) technology, to ensure that only a heterodimer of two distinct heavy chains from one antibody (e.g., Antibody A) and a second antibody (e.g., Antibody B) is efficiently formed. Next, the constant heavy 1 (CH1) and constant light (CL) domains of one antibody are exchanged (Antibody A), keeping the variable heavy (VH) and variable light (VL) domains consistent. The exchange of the CH1 and CL domains ensured that the modified antibody (Antibody A) light chain would only efficiently dimerize with the modified antibody (antibody A) heavy chain, while the unmodified antibody (Antibody B) light chain would only efficiently dimerize with the unmodified antibody (Antibody B) heavy chain; and thus only the desired bispecific CrossMab would be efficiently formed (see e.g., Cain, C. SciBX 4(28); doi:10.1038/scibx.2011.783, the contents of which are incorporated by reference herein).

Common Heavy Chain

An exemplary method of enhancing the formation of a desired bispecific antibody from a mixture of monomers is by providing a common variable heavy chain to interact with each of the heteromeric variable light chain regions of the bispecific antibody. Compositions and methods of producing bispecific antibodies with a common heavy chain are disclosed in, e.g., US20120184716, US20130317200, and US20160264685A1, the contents of each of which is incorporated by reference herein.

Amino Acid Modifications

Alternative compositions and methods of producing multispecific antibodies with correct light chain pairing include various amino acid modifications. For example, Zymeworks describes heterodimers with one or more amino acid modifications in the CH1 and/or CL domains, one or more amino acid modifications in the VH and/or VL domains, or a combination thereof, which are part of the interface between the light chain and heavy chain and create preferential pairing between each heavy chain and a desired light chain such that when the two heavy chains and two light chains of the heterodimer pair are co-expressed in a cell, the heavy chain of the first heterodimer preferentially pairs with one of the light chains rather than the other (see e.g., WO2015181805). Other exemplary methods are described in WO2016026943 (Argen-X), US20150211001, US20140072581A1, US20160039947A1, and US20150368352.

Lambda/Kappa Formats

Multispecific molecules (e.g., multispecific antibody molecules) that include the lambda light chain polypeptide and a kappa light chain polypeptides, can be used to allow for heterodimerization. Methods for generating bispecific antibody molecules comprising the lambda light chain polypeptide and a kappa light chain polypeptides are disclosed in PCT/US17/53053 filed on Sep. 22, 2017 and designated publication number WO 2018/057955, incorporated herein by reference in its entirety.

In embodiments, the multispecific molecule includes a multispecific antibody molecule, e.g., an antibody molecule comprising two binding specificities, e.g., a bispecific antibody molecule. The multispecific antibody molecule includes:

a lambda light chain polypeptide 1 (LLCP1) specific for a first epitope;

a heavy chain polypeptide 1 (HCP1) specific for the first epitope;

a kappa light chain polypeptide 2 (KLCP2) specific for a second epitope; and a heavy chain polypeptide 2 (HCP2) specific for the second epitope.

"Lambda light chain polypeptide 1 (LLCP1)", as that term is used herein, refers to a polypeptide comprising sufficient light chain (LC) sequence, such that when combined with a cognate heavy chain variable region, can mediate specific binding to its epitope and complex with an HCP1. In an embodiment it comprises all or a fragment of a CH1 region. In an embodiment, an LLCP1 comprises LC-CDR1, LC-CDR2, LC-CDR3, FR1, FR2, FR3, FR4, and CH1, or sufficient sequence therefrom to mediate specific binding of its epitope and complex with an HCP1. LLCP1, together with its HCP1, provide specificity for a first epitope (while KLCP2, together with its HCP2, provide specificity for a second epitope). As described elsewhere herein, LLCP1 has a higher affinity for HCP1 than for HCP2.

"Kappa light chain polypeptide 2 (KLCP2)", as that term is used herein, refers to a polypeptide comprising sufficient light chain (LC) sequence, such that when combined with a cognate heavy chain variable region, can mediate specific binding to its epitope and complex with an HCP2. In some embodiments, it comprises all or a fragment of a CH1 region. In an embodiment, a KLCP2 comprises LC-CDR1, LC-CDR2, LC-CDR3, FR1, FR2, FR3, FR4, and CH1, or sufficient sequence therefrom to mediate specific binding of its epitope and complex with an HCP2. KLCP2, together with its HCP2, provide specificity for a second epitope (while LLCP1, together with its HCP1, provide specificity for a first epitope).

"Heavy chain polypeptide 1 (HCP1)", as that term is used herein, refers to a polypeptide comprising sufficient heavy chain (HC) sequence, e.g., HC variable region sequence, such that when combined with a cognate LLCP1, can mediate specific binding to its epitope and complex with an HCP1. In some embodiments, it comprises all or a fragment of a CH1 region. In an embodiment, it comprises all or a fragment of a CH2 and/or CH3 region. In an embodiment an HCP1 comprises HC-CDR1, HC-CDR2, HC-CDR3, FR1, FR2, FR3, FR4, CH1, CH2, and CH3, or sufficient sequence therefrom to: (i) mediate specific binding of its epitope and complex with an LLCP1, (ii) to complex preferentially, as described herein to LLCP1 as opposed to KLCP2; and (iii) to complex preferentially, as described herein, to an HCP2, as opposed to another molecule of HCP1. HCP1, together with its LLCP1, provide specificity for a first epitope (while KLCP2, together with its HCP2, provide specificity for a second epitope).

"Heavy chain polypeptide 2 (HCP2)", as that term is used herein, refers to a polypeptide comprising sufficient heavy chain (HC) sequence, e.g., HC variable region sequence, such that when combined with a cognate LLCP1, can mediate specific binding to its epitope and complex with an HCP1. In some embodiments, it comprises all or a fragment of a CH1 region. In some embodiments, it comprises all or a fragment of a CH2 and/or CH3 region. In an embodiment an HCP1 comprises HC-CDR1, HC-CDR2, HC-CDR3, FR1, FR2, FR3, FR4, CH1, CH2, and CH3, or sufficient sequence therefrom to: (i) mediate specific binding of its epitope and complex with an KLCP2, (ii) to complex preferentially, as described herein to KLCP2 as opposed to LLCP1; and (iii) to complex preferentially, as described herein, to an HCP1, as opposed to another molecule of HCP2. HCP2, together with its KLCP2, provide specificity for a second epitope (while LLCP1, together with its HCP1, provide specificity for a first epitope).

In some embodiments of the multispecific antibody molecule disclosed herein:

LLCP1 has a higher affinity for HCP1 than for HCP2; and/or

KLCP2 has a higher affinity for HCP2 than for HCP1.

In embodiments, the affinity of LLCP1 for HCP1 is sufficiently greater than its affinity for HCP2, such that under preselected conditions, e.g., in aqueous buffer, e.g., at pH 7, in saline, e.g., at pH 7, or under physiological conditions, at least 75, 80, 90, 95, 98, 99, 99.5, or 99.9% of the multispecific antibody molecule molecules have a LLCP1 complexed, or interfaced with, a HCP1.

In some embodiments of the multispecific antibody molecule disclosed herein: the HCP1 has a greater affinity for HCP2, than for a second molecule of HCP1; and/or the HCP2 has a greater affinity for HCP1, than for a second molecule of HCP2.

In embodiments, the affinity of HCP1 for HCP2 is sufficiently greater than its affinity for a second molecule of HCP1, such that under preselected conditions, e.g., in aqueous buffer, e.g., at pH 7, in saline, e.g., at pH 7, or under physiological conditions, at least 75%, 80, 90, 95, 98, 99 99.5 or 99.9% of the multispecific antibody molecule molecules have a HCP1 complexed, or interfaced with, a HCP2.

In another aspect, disclosed herein is a method for making, or producing, a multispecific antibody molecule. The method includes:

(i) providing a first heavy chain polypeptide (e.g., a heavy chain polypeptide comprising one, two, three or all of a first heavy chain variable region (first VH), a first CH1, a first heavy chain constant region (e.g., a first CH2, a first CH3, or both));

(ii) providing a second heavy chain polypeptide (e.g., a heavy chain polypeptide comprising one, two, three or all of a second heavy chain variable region (second VH), a second CH1, a second heavy chain constant region (e.g., a second CH2, a second CH3, or both));

(iii) providing a lambda chain polypeptide (e.g., a lambda light variable region (VL), a lambda light constant chain (VL), or both) that preferentially associates with the first heavy chain polypeptide (e.g., the first VH); and (iv) providing a kappa chain polypeptide (e.g., a lambda light variable region (VL), a lambda light constant chain (VL), or both) that preferentially associates with the second heavy chain polypeptide (e.g., the second VH), under conditions where (i)-(iv) associate.

In embodiments, the first and second heavy chain polypeptides form an Fc interface that enhances heterodimerization.

In embodiments, (i)-(iv) (e.g., nucleic acid encoding (i)-(iv)) are introduced in a single cell, e.g., a single mammalian cell, e.g., a CHO cell. In embodiments, (i)-(iv) are expressed in the cell.

In embodiments, (i)-(iv) (e.g., nucleic acid encoding (i)-(iv)) are introduced in different cells, e.g., different mammalian cells, e.g., two or more CHO cell. In embodiments, (i)-(iv) are expressed in the cells.

In embodiments, the method further comprises purifying a cell-expressed antibody molecule, e.g., using a lambda- and/or-kappa-specific purification, e.g., affinity chromatography.

In embodiments, the method further comprises evaluating the cell-expressed multispecific antibody molecule. For example, the purified cell-expressed multispecific antibody molecule can be analyzed by techniques known in the art, include mass spectrometry. In one embodiment, the purified cell-expressed antibody molecule is cleaved, e.g., digested with papain to yield the Fab moieties and evaluated using mass spectrometry.

In embodiments, the method produces correctly paired kappa/lambda multispecific, e.g., bispecific, antibody molecules in a high yield, e.g., at least 75%, 80, 90, 95, 98, 99 99.5 or 99.9%.

In other embodiments, the multispecific, e.g., a bispecific, antibody molecule that includes:

(i) a first heavy chain polypeptide (HCP1) (e.g., a heavy chain polypeptide comprising one, two, three or all of a first heavy chain variable region (first VH), a first CH1, a first heavy chain constant region (e.g., a first CH2, a first CH3, or both)), e.g., wherein the HCP1 binds to a first epitope;

(ii) a second heavy chain polypeptide (HCP2) (e.g., a heavy chain polypeptide comprising one, two, three or all of a second heavy chain variable region (second VH), a second CH1, a second heavy chain constant region (e.g., a second CH2, a second CH3, or both)), e.g., wherein the HCP2 binds to a second epitope;

(iii) a lambda light chain polypeptide (LLCP1) (e.g., a lambda light variable region (VLl), a lambda light constant chain (VLl), or both) that preferentially associates with the first heavy chain polypeptide (e.g., the first VH), e.g., wherein the LLCP1 binds to a first epitope; and (iv) a kappa light chain polypeptide (KLCP2) (e.g., a lambda light variable region (VLk), a lambda light constant chain (VLk), or both) that preferentially associates with the second heavy chain polypeptide (e.g., the second VH), e.g., wherein the KLCP2 binds to a second epitope.

In embodiments, the first and second heavy chain polypeptides form an Fc interface that enhances heterodimerization. In embodiments, the multispecific antibody molecule has a first binding specificity that includes a hybrid VLl-CL1 heterodimerized to a first heavy chain variable region connected to the Fc constant, CH2-CH3 domain (having a knob modification) and a second binding specificity that includes a hybrid VLk-CLk heterodimerized to a second heavy chain variable region connected to the Fc constant, CH2-CH3 domain (having a hole modification).

Cytokine Molecules

Cytokines are generally polypeptides that influence cellular activity, for example, through signal transduction pathways. Accordingly, a cytokine of the multispecific or multifunctional polypeptide is useful and can be associated with receptor-mediated signaling that transmits a signal from outside the cell membrane to modulate a response within the cell. Cytokines are proteinaceous signaling compounds that are mediators of the immune response. They control many different cellular functions including proliferation, differentiation and cell survival/apoptosis; cytokines are also involved in several pathophysiological processes including viral infections and autoimmune diseases. Cytokines are synthesized under various stimuli by a variety of cells of both the innate (monocytes, macrophages, dendritic cells) and adaptive (T- and B-cells) immune systems. Cytokines can be classified into two groups: pro- and anti-inflammatory. Pro-inflammatory cytokines, including IFNγ, IL-1, IL-6 and TNF-alpha, are predominantly derived from the innate immune cells and Th1 cells. Anti-inflammatory cytokines, including IL-10, IL-4, IL-13 and IL-5, are synthesized from Th2 immune cells.

The present disclosure provides, inter alia, multispecific (e.g., bi-, tri-, quad-specific) or multifunctional molecules, that include, e.g., are engineered to contain, one or more cytokine molecules, e.g., immunomodulatory (e.g., proinflammatory) cytokines and variants, e.g., functional variants, thereof. Accordingly, in some embodiments, the cytokine molecule is an interleukin or a variant, e.g., a functional variant thereof. In some embodiments the interleukin is a proinflammatory interleukin. In some embodiments the interleukin is chosen from interleukin-2 (IL-2), interleukin-12 (IL-12), interleukin-15 (IL-15), interleukin-18 (IL-18), interleukin-21 (IL-21), interleukin-7 (IL-7), or interferon gamma. In some embodiments, the cytokine molecule is a proinflammatory cytokine.

In certain embodiments, the cytokine is a single chain cytokine. In certain embodiments, the cytokine is a multichain cytokine (e.g., the cytokine comprises 2 or more (e.g., 2) polypeptide chains. An exemplary multichain cytokine is IL-12.

Examples of useful cytokines include, but are not limited to, GM-CSF, IL-1α, IL-1β, IL-2, IL-3, IL-4, IL-5, IL-6, IL-7, IL-8, IL-10, IL-12, IL-21, IFN-α, IFN-β, IFN-γ, MIP-1α, MIP-1β, TGF-β, TNF-α, and TNFβ. In one embodiment the cytokine of the multispecific or multifunctional polypeptide is a cytokine selected from the group of GM-CSF, IL-2, IL-7, IL-8, IL-10, IL-12, IL-15, IL-21, IFN-α, IFN-γ, MIP-1α, MIP-1β and TGF-β. In one embodiment the cytokine of the i the multispecific or multifunctional polypeptide is a cytokine selected from the group of IL-2, IL-7, IL-10, IL-12, IL-15, IFN-α, and IFN-γ. In certain embodiments the cytokine is mutated to remove N- and/or O-glycosylation sites. Elimination of glycosylation increases homogeneity of the product obtainable in recombinant production.

In one embodiment, the cytokine of the multispecific or multifunctional polypeptide is IL-2. In a specific embodiment, the IL-2 cytokine can elicit one or more of the cellular responses selected from the group consisting of: proliferation in an activated T lymphocyte cell, differentiation in an activated T lymphocyte cell, cytotoxic T cell (CTL) activity, proliferation in an activated B cell, differentiation in an activated B cell, proliferation in a natural killer (NK) cell, differentiation in a NK cell, cytokine secretion by an activated T cell or an NK cell, and NK/lymphocyte activated killer (LAK) antitumor cytotoxicity. In another particular embodiment the IL-2 cytokine is a mutant IL-2 cytokine having reduced binding affinity to the .alpha.-subunit of the IL-2 receptor. Together with the .beta.- and .gamma.-subunits (also known as CD122 and CD132, respectively), the .alpha.-subunit (also known as CD25) forms the heterotrimeric high-affinity IL-2 receptor, while the dimeric receptor consisting only of the β- and γ-subunits is termed the intermediate-affinity IL-2 receptor. As described in PCT patent application number PCT/EP2012/051991, which is incorporated herein by reference in its entirety, a mutant IL-2 polypeptide with reduced binding to the .alpha.-subunit of the IL-2 receptor has a reduced ability to induce IL-2 signaling in regulatory T cells, induces less activation-induced cell death (AICD) in T cells, and has a reduced toxicity profile in vivo, compared to a wild-type IL-2 polypeptide. The use of such an cytokine with reduced toxicity is particularly advantageous in a multispecific or multifunctional polypeptide according to the invention, having a long serum half-life due to the presence of an Fc domain. In one embodiment, the mutant IL-2 cytokine of the multispecific or multifunctional polypeptide according to the invention comprises at least one amino acid mutation that reduces or abolishes the affinity of the mutant IL-2 cytokine to the .alpha.-subunit of the IL-2 receptor (CD25) but preserves the affinity of the mutant IL-2 cytokine to the intermediate-affinity IL-2 receptor (consisting of the β and γ subunits of the IL-2 receptor), compared to the non-mutated IL-2 cytokine. In one embodiment the one or more amino acid mutations are amino acid substitutions. In a specific embodiment, the mutant IL-2 cytokine comprises one, two or three amino acid substitutions at one, two or three position(s) selected from the positions corresponding to residue 42, 45, and 72 of human IL-2. In a more specific embodiment, the mutant IL-2 cytokine comprises three amino acid substitutions at the positions corresponding to residue 42, 45 and 72 of human IL-2. In an even more specific embodiment, the mutant IL-2 cytokine is human IL-2 comprising the amino acid substitutions F42A, Y45A and L72G. In one embodiment the mutant IL-2 cytokine additionally comprises an amino acid mutation at a position corresponding to position 3 of human IL-2, which eliminates the O-glycosylation site of IL-2. Particularly, said additional amino acid mutation is an amino acid substitution replacing a threonine residue by an alanine residue. A particular mutant IL-2 cytokine useful in the invention comprises four amino acid substitutions at positions corresponding to residues 3, 42, 45 and 72 of human IL-2. Specific amino acid substitutions are T3A, F42A, Y45A and L72G. As demonstrated in PCT patent application number PCT/EP2012/051991 and in the appended Examples, said quadruple mutant IL-2 polypeptide (IL-2 qm) exhibits no detectable binding to CD25, reduced ability to induce apoptosis in T cells, reduced ability to induce IL-2 signaling in T.sub.reg cells, and a reduced toxicity profile in vivo. However, it retains ability to activate IL-2 signaling in effector cells, to induce proliferation of effector cells, and to generate IFN-7 as a secondary cytokine by NK cells.

The IL-2 or mutant IL-2 cytokine according to any of the above embodiments may comprise additional mutations that provide further advantages such as increased expression or stability. For example, the cysteine at position 125 may be replaced with a neutral amino acid such as alanine, to avoid the formation of disulfide-bridged IL-2 dimers. Thus, in certain embodiments the IL-2 or mutant IL-2 cytokine of the multispecific or multifunctional polypeptide according to the invention comprises an additional amino acid mutation at a position corresponding to residue 125 of human IL-2. In one embodiment said additional amino acid mutation is the amino acid substitution C125A.

In a specific embodiment the IL-2 cytokine of the multispecific or multifunctional polypeptide comprises the polypeptide sequence of SEQ ID NO: 2270

```
[APTSSSTKKTQLQLEHLLLDLQMILNGINNYKNPKLTRMLTFKFYMPK
KATELKHLQCLEEELKPLEEVLNLAQSKNFHLRPRDLISNINVIVLELK
GSETTFMCEYADETATIVEFLNRWITFAQSIISTLT]].
```

In another specific embodiment the IL-2 cytokine of the multispecific or multifunctional polypeptide comprises the polypeptide sequence of SEQ ID NO: 2280

```
[APASSSTKKTQLQLEHLLLDLQMILNGINNYKNPKLTRMLTAKFAMPKK
ATELKHLQCLEEELKPLEEVLNGAQSKNFHLRPRDLISNINVIVLELKGS
ETTFMCEYADETATIVEFLNRWITFAQSIISTLT].
```

In another embodiment the cytokine of the multispecific or multifunctional polypeptide is IL-12. In a specific embodiment said IL-12 cytokine is a single chain IL-12 cytokine. In an even more specific embodiment the single chain IL-12 cytokine comprises the polypeptide sequence of SEQ ID NO: 2290 [IWELKKDVYVVELDWYP-DAPGEMVVLTCDTPEEDGITWTLDQSSEVLGSGKTL-TIQVKEF GDAGQYTCHKGGEVLSHSLLLLHKKEDG-IWSTDILKDQKEPKNKTFLRCEAKNYSGRFTC WWLTTISTDLTFSVKSSRGSSDPQGVTCGAATL-SAERVRGDNKEYEYSVECQEDSACPAAE ESLPIEVMVDAVHKLKYENYTSSFFIR-DIIKPDPPKNLQLKPLKNSRQVEVSWEYPDTWSTP HSYFSLTFCVQVQGKSKREKKDRVFTDKTSATVI-CRKNASISVRAQDRYYSSSWSEWASVP CSGGGGSGGGGSGGGGSRNLP-VATPDPGMFPCLHHSQNLLRAVSNMLQKAR-QTLEFYPCT SEEIDHEDITKDKTSTVEACLPLELTK-NESCLNSRETSFITNGSCLASRKTSFMMALCLSSIYE DLKMYQVEFKTMNAKLLMDPKRQIFLDQNMLAVI-DELMQALNFNSETVPQKSSLEEPDFY KTKIKLCIL-LHAFRIRAVTIDRVMSYLNAS]. In one embodiment, the IL-12 cytokine can elicit one or more of the cellular responses selected from the group consisting of: proliferation in a NK cell, differentiation in a NK cell, proliferation in a T cell, and differentiation in a T cell.

In another embodiment the cytokine of the multispecific or multifunctional polypeptide is IL-10. In a specific embodiment said IL-10 cytokine is a single chain IL-10 cytokine. In an even more specific embodiment the single chain IL-10 cytokine comprises the polypeptide sequence of

```
                                           SEQ ID NO: 2300
[SPGQGTQSENSCTHFPGNLPNMLRDLRDAFSRVKTFFQMKDQLDNLLLK
ESLLEDFKGYLGCQALSEMIQFYLEEVMPQAENQDPDIKAHVNSLGENLK
TLRLRLRRCHRFLPCENKSKAVEQVKNAFNKLQEKGIYKAMSEFDIFINY
IEAYMTMKIRNGGGGSGGGGSGGGGSGGGGSSPGQGTQSENSCTHFPGNL
PNMLRDLRDAFSRVKTFFQMKDQLDNLLLKESLLEDFKGYLGCQALSEMI
```

-continued

QFYLEEVMPQAENQDPDIKAHVNSLGENLKTLRLRLRRCHRFLPCENKSK

AVEQVKNAFNKLQEKGIYKAMSEFDIFINYIEAYMTMKIRN].

In another specific embodiment the IL-10 cytokine is a monomeric IL-10 cytokine. In a more specific embodiment the monomeric IL-10 cytokine comprises the polypeptide sequence of SEQ ID NO: 2310 [SPGQGTQSEN-SCTHFPGNLPNMLRDLRDAFSRVKTFFQMKDQLDN LLLKESLLEDFKGYL GCQALSEMIQFYLEEVMPQAE-NQDPDIKAHVNSL-GENLKTLRLRLRRCHRFLPCENGGGSG GKSKAVEQVKNAFNKLQEKGIYKAMSEFDI-FINYIEAYMTMKIRN]. In one embodiment, the IL-10 cytokine can elicit one or more of the cellular responses selected from the group consisting of: inhibition of cytokine secretion, inhibition of antigen presentation by antigen presenting cells, reduction of oxygen radical release, and inhibition of T cell proliferation. A multispecific or multifunctional polypeptide according to the invention wherein the cytokine is IL-10 is particularly useful for downregulation of inflammation, e.g. in the treatment of an inflammatory disorder.

In another embodiment, the cytokine of the multispecific or multifunctional polypeptide is IL-15. In a specific embodiment said IL-15 cytokine is a mutant IL-15 cytokine having reduced binding affinity to the α-subunit of the IL-15 receptor. Without wishing to be bound by theory, a mutant IL-15 polypeptide with reduced binding to the .alpha.-subunit of the IL-15 receptor has a reduced ability to bind to fibroblasts throughout the body, resulting in improved pharmacokinetics and toxicity profile, compared to a wild-type IL-15 polypeptide. The use of an cytokine with reduced toxicity, such as the described mutant IL-2 and mutant IL-15 effector moieties, is particularly advantageous in a multispecific or multifunctional polypeptide according to the invention, having a long serum half-life due to the presence of an Fc domain. In one embodiment the mutant IL-15 cytokine of the multispecific or multifunctional polypeptide according to the invention comprises at least one amino acid mutation that reduces or abolishes the affinity of the mutant IL-15 cytokine to the .alpha.-subunit of the IL-15 receptor but preserves the affinity of the mutant IL-15 cytokine to the intermediate-affinity IL-15/IL-2 receptor (consisting of the .beta.- and .gamma.-subunits of the IL-15/IL-2 receptor), compared to the non-mutated IL-15 cytokine. In one embodiment the amino acid mutation is an amino acid substitution. In a specific embodiment, the mutant IL-15 cytokine comprises an amino acid substitution at the position corresponding to residue 53 of human IL-15. In a more specific embodiment, the mutant IL-15 cytokine is human IL-15 comprising the amino acid substitution E53A. In one embodiment the mutant IL-15 cytokine additionally comprises an amino acid mutation at a position corresponding to position 79 of human IL-15, which eliminates the N-glycosylation site of IL-15. Particularly, said additional amino acid mutation is an amino acid substitution replacing an asparagine residue by an alanine residue. In an even more specific embodiment the IL-15 cytokine comprises the polypeptide sequence of SEQ ID NO: 2320 [NWVNVISDLK-KIEDLIQSMHIDATLYTESDVHPSCKVTAMKCFL-LELQVISLASGDASIHDT VENLIILANNSLSSNGAVTESGCKECEELEEKNIKE-FLQSFVHIVQMFINTS]. In one embodiment, the IL-15 cytokine can elicit one or more of the cellular responses selected from the group consisting of: proliferation in an activated T lymphocyte cell, differentiation in an activated T lymphocyte cell, cytotoxic T cell (CTL) activity, proliferation in an activated B cell, differentiation in an activated B cell, proliferation in a natural killer (NK) cell, differentiation in a NK cell, cytokine secretion by an activated T cell or an NK cell, and NK/lymphocyte activated killer (LAK) antitumor cytotoxicity.

Mutant cytokine molecules useful as effector moieties in the multispecific or multifunctional polypeptide can be prepared by deletion, substitution, insertion or modification using genetic or chemical methods well known in the art. Genetic methods may include site-specific mutagenesis of the encoding DNA sequence, PCR, gene synthesis, and the like. The correct nucleotide changes can be verified for example by sequencing. Substitution or insertion may involve natural as well as non-natural amino acid residues. Amino acid modification includes well known methods of chemical modification such as the addition or removal of glycosylation sites or carbohydrate attachments, and the like.

In one embodiment, the cytokine, particularly a single-chain cytokine, of the multispecific or multifunctional polypeptide is GM-CSF. In a specific embodiment, the GM-CSF cytokine can elicit proliferation and/or differentiation in a granulocyte, a monocyte or a dendritic cell. In one embodiment, the cytokine, particularly a single-chain cytokine, of the multispecific or multifunctional polypeptide is IFN-α. In a specific embodiment, the IFN-α cytokine can elicit one or more of the cellular responses selected from the group consisting of: inhibiting viral replication in a virus-infected cell, and upregulating the expression of major histocompatibility complex I (MHC I). In another specific embodiment, the IFN-α cytokine can inhibit proliferation in a tumor cell. In one embodiment the cytokine, particularly a single-chain cytokine, of the multispecific or multifunctional polypeptide is IFNγ. In a specific embodiment, the IFN-γ cytokine can elicit one or more of the cellular responses selected from the group of: increased macrophage activity, increased expression of MHC molecules, and increased NK cell activity. In one embodiment the cytokine, particularly a single-chain cytokine, of the multispecific or multifunctional polypeptide is IL-7. In a specific embodiment, the IL-7 cytokine can elicit proliferation of T and/or B lymphocytes. In one embodiment, the cytokine, particularly a single-chain cytokine, of the multispecific or multifunctional polypeptide is IL-8. In a specific embodiment, the IL-8 cytokine can elicit chemotaxis in neutrophils. In one embodiment, the cytokine, particularly a single-chain cytokine, of the multispecific or multifunctional polypeptide, is MIP-1α. In a specific embodiment, the MIP-1α cytokine can elicit chemotaxis in monocytes and T lymphocyte cells. In one embodiment, the cytokine, particularly a single-chain cytokine, of the multispecific or multifunctional polypeptide is MIP-1β. In a specific embodiment, the MIP-1β cytokine can elicit chemotaxis in monocytes and T lymphocyte cells. In one embodiment, the cytokine, particularly a single-chain cytokine, of the multispecific or multifunctional polypeptide is TGF-β. In a specific embodiment, the TGF-β cytokine can elicit one or more of the cellular responses selected from the group consisting of: chemotaxis in monocytes, chemotaxis in macrophages, upregulation of IL-1 expression in activated macrophages, and upregulation of IgA expression in activated B cells.

In one embodiment, the multispecific or multifunctional polypeptide of the invention binds to an cytokine receptor with a dissociation constant ($K_D$) that is at least about 1, 1.5, 2, 2.5, 3, 3.5, 4, 4.5, 5, 5.5, 6, 6.5, 7, 7.5, 8, 8.5, 9, 9.5 or 10 times greater than that for a control cytokine. In another embodiment, the multispecific or multifunctional polypeptide binds to an cytokine receptor with a $K_D$ that is at least 2, 3, 4, 5, 6, 7, 8, 9, or 10 times greater than that for a corresponding multispecific or multifunctional polypeptide comprising two or more effector moieties. In another embodiment, the multispecific or multifunctional polypeptide binds to an cytokine receptor with a dissociation constant $K_D$ that is about 10 times greater than that for a corresponding the multispecific or multifunctional polypeptide comprising two or more cytokines.

In some embodiments, the multispecific molecules disclosed herein include a cytokine molecule. In embodiments, the cytokine molecule includes a full length, a fragment or a variant of a cytokine; a cytokine receptor domain, e.g., a cytokine receptor dimerizing domain; or an agonist of a cytokine receptor, e.g., an antibody molecule (e.g., an agonistic antibody) to a cytokine receptor.

In some embodiments the cytokine molecule is chosen from IL-2, IL-12, IL-15, IL-18, IL-7, IL-21, or interferon gamma, or a fragment or variant thereof, or a combination of any of the aforesaid cytokines. The cytokine molecule can be a monomer or a dimer. In embodiments, the cytokine molecule can further include a cytokine receptor dimerizing domain.

In other embodiments, the cytokine molecule is an agonist of a cytokine receptor, e.g., an antibody molecule (e.g., an agonistic antibody) to a cytokine receptor chosen from an IL-15Ra or IL-21R.

In one embodiment, the cytokine molecule is IL-15, e.g., human IL-15 (e.g., comprising the amino acid sequence: NWVNVISDLKKIEDLIQSMHIDATLYTESDVHP-SCKVTAMKCFLLELQVISLESGDASIHDT VEN-LIILANNSLSSNGNVTESGCKECEELEEKNIKE-FLQSFVHIVQMFINTS (SEQ ID NO: 2170), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 2170.

In some embodiments, the cytokine molecule comprises a receptor dimerizing domain, e.g., an IL15Ralpha dimerizing domain. In one embodiment, the IL15Ralpha dimerizing domain comprises the amino acid sequence: MAPR-RARGCRTLGLPALLLLLLLRPPATRGITCPPPMSVE-HADIWVKSYSLYSRERYICNSG FKRKAGTSSLTECVL (SEQ ID NO: 2180), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 2180. In some embodiments, the cytokine molecule (e.g., IL-15) and the receptor dimerizing domain (e.g., an IL15Ralpha dimerizing domain) of the multispecific molecule are covalently linked, e.g., via a linker (e.g., a Gly-Ser linker, e.g., a linker comprising the amino acid sequence SGGSGGGGSGGGSGGGGSLQ (SEQ ID NO: 2190). In other embodiments, the cytokine molecule (e.g., IL-15) and the receptor dimerizing domain (e.g., an IL15Ralpha dimerizing domain) of the multispecific molecule are not covalently linked, e.g., are non-covalently associated.

In other embodiments, the cytokine molecule is IL-2, e.g., human IL-2 (e.g., comprising the amino acid sequence: APTSSSTKKTQLQLEHLLLDLQMILNGINNYKNPKL-TRMLTFKFYMPKKATELKHLQCLEE ELKPLEEVLN-LAQSKNFHLRPRDLISNINVIVLELKGSETTFMCEYA-DETATIVEFLNRWITF CQSIISTLT (SEQ ID NO: 2191), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO:2191).

In other embodiments, the cytokine molecule is IL-18, e.g., human IL-18 (e.g., comprising the amino acid sequence: YFGKLESKLSVIRNLNDQVLFIDQGNR-PLFEDMTDSDCRDNAPRTIFIISMYKDSQPRGMAV TISVKCEKISTLSCENKIISFKEMNPPDNIKDTKS-DIIFFQRSVPGHDNKMQFESSSYEGYFLA CEKER-DLFKLILKKEDELGDRSIMFTVQNED (SEQ ID NO: 2192), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 2192).

In other embodiments, the cytokine molecule is IL-21, e.g., human IL-21 (e.g., comprising the amino acid sequence: QGQDRHMIRMRQLIDI-VDQLKNYVNDLVPEFLPAPEDVETNCEWS-AFSCFQKAQLKSANT GNNERIINVSIKKLKRKPPST-NAGRRQKHRLTCPSCDSYEKKPPKEFLERFKSLLQK MIHQH LSSRTHGSEDS (SEQ ID NO: 2193), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 2193).

In yet other embodiments, the cytokine molecule is interferon gamma, e.g., human interferon gamma (e.g., comprising the amino acid sequence: QDPYVKEAE-NLKKYFNAGHSDVADNGTLFLGILKNWKEESDRKIM QSQIVSFYFKLFKNF KDDQSIQKSVE-TIKEDMNVKFFNSNKKKRDDFEKLT-NYSVTDLNVQRKAIHELIQVMAELS PAAKTGKRKR-SQMLFRG (SEQ ID NO: 2194), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 2194).

Immune Cell Engagers

The immune cell engagers, e.g., first and/or second immune cell engager, of the multispecific or multifunctional molecules disclosed herein can mediate binding to, and/or activation of, an immune cell, e.g., an immune effector cell. In some embodiments, the immune cell is chosen from a T cell, an NK cell, a B cell, a dendritic cell, or a macrophage cell engager, or a combination thereof. In some embodiments, the immune cell engager is chosen from one, two, three, or all of a T cell engager, NK cell engager, a B cell engager, a dendritic cell engager, or a macrophage cell engager, or a combination thereof. The immune cell engager can be an agonist of the immune system. In some embodiments, the immune cell engager can be an antibody molecule, a ligand molecule (e.g., a ligand that further comprises an immunoglobulin constant region, e.g., an Fc region), a small molecule, a nucleotide molecule.

Natural Killer Cell Engagers

Natural Killer (NK) cells recognize and destroy tumors and virus-infected cells in an antibody-independent manner.

The regulation of NK cells is mediated by activating and inhibiting receptors on the NK cell surface. One family of activating receptors is the natural cytotoxicity receptors (NCRs) which include NKp30, NKp44 and NKp46. The NCRs initiate tumor targeting by recognition of heparan sulfate on cancer cells. NKG2D is a receptor that provides both stimulatory and costimulatory innate immune responses on activated killer (NK) cells, leading to cytotoxic activity. DNAM1 is a receptor involved in intercellular adhesion, lymphocyte signaling, cytotoxicity and lymphokine secretion mediated by cytotoxic T-lymphocyte (CTL) and NK cell. DAP10 (also known as HCST) is a transmembrane adapter protein which associates with KLRK1 to form an activation receptor KLRK1-HCST in lymphoid and myeloid cells; this receptor plays a major role in triggering cytotoxicity against target cells expressing cell surface ligands such as MHC class I chain-related MICA and MICB, and U (optionally L1)6-binding proteins (ULBPs); it KLRK1-HCST receptor plays a role in immune surveillance against tumors and is required for cytolysis of tumors cells; indeed, melanoma cells that do not express KLRK1 ligands escape from immune surveillance mediated by NK cells. CD16 is a receptor for the Fc region of IgG, which binds complexed or aggregated IgG and also monomeric IgG and thereby mediates antibody-dependent cellular cytotoxicity (ADCC) and other antibody-dependent responses, such as phagocytosis.

In some embodiments, the NK cell engager is a viral hemagglutinin (HA), HA is a glycoprotein found on the surface of influenza viruses. It is responsible for binding the virus to cells with sialic acid on the membranes, such as cells in the upper respiratory tract or erythrocytes. HA has at least 18 different antigens. These subtypes are named H1 through H18. NCRs can recognize viral proteins. NKp46 has been shown to be able to interact with the HA of influenza and the HA-NA of Paramyxovirus, including Sendai virus and Newcastle disease virus. Besides NKp46, NKp44 can also functionally interact with HA of different influenza subtypes.

The present disclosure provides, inter alia, multispecific (e.g., bi-, tri-, quad-specific) or multifunctional molecules, that are engineered to contain one or more NK cell engagers that mediate binding to and/or activation of an NK cell. Accordingly, in some embodiments, the NK cell engager is selected from an antigen binding domain or ligand that binds to (e.g., activates): NKp30, NKp40, NKp44, NKp46, NKG2D, DNAM1, DAP10, CD16 (e.g., CD16a, CD16b, or both), CRTAM, CD27, PSGL1, CD96, CD100 (SEMA4D), NKp80, CD244 (also known as SLAMF4 or 2B4), SLAMF6, SLAMF7, KIR2DS2, KIR2DS4, KIR3DS1, KIR2DS3, KIR2DS5, KIR2DS1, CD94, NKG2C, NKG2E, or CD160.

In one embodiment, the NK cell engager is a ligand of NKp30 is a B7-6, e.g., comprises the amino acid sequence of:

DLKVEMMAGGTQITPLNDNVTIFCNI-FYSQPLNITSMGITWFWKSLTFDKEVKVF EFFGDHQEAFRPGAIVSPWRLKSGDASLRLPGIQLEE-AGEYRCEVVVTPLKAQGTVQLEVV ASPASRLLL-DQVGMKENEDKYMCESSGFYPEAINIT-WEKQTQKFPHPIEISEDVITGPTIKN MDGTFNVTSCLKLNSSQEDPGTVYQCVVRHASLHT PLRSNFTLTAARHSLSETEKTDNFS (SEQ ID NO: 3291), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 3291.

In other embodiments, the NK cell engager is a ligand of NKp44 or NKp46, which is a viral HA. Viral hemagglutinins (HA) are glyco proteins which are on the surface of viruses. HA proteins allow viruses to bind to the membrane of cells via sialic acid sugar moieties which contributes to the fusion of viral membranes with the cell membranes (see e.g., Eur J Immunol. 2001 September; 31(9):2680-9 "Recognition of viral hemagglutinins by NKp44 but not by NKp30"; and Nature. 2001 Feb. 22; 409(6823):1055-60 "Recognition of haemagglutinins on virus-infected cells by NKp46 activates lysis by human NK cells" the contents of each of which are incorporated by reference herein).

In other embodiments, the NK cell engager is a ligand of NKG2D chosen from MICA, MICB, or ULBP1, e.g., wherein:

(i) MICA comprises the amino acid sequence:

```
                                    (SEQ ID NO: 3292)
EPHSLRYNLTVLSWDGSVQSGFLTEVHLDGQPFLRCDRQKCRAKPQGQWA

EDVLGNKTWDRETRDLTGNGKDLRMTLAHIKDQKEGLHSLQEIRVCEIHE

DNSTRSSQHFYYDGELFLSQNLETKEWTMPQSSRAQTLAMNVRNFLKEDA

MKTKTHYHAMHADCLQELRRYLKSGVVLRRTVPPMVNVTRSEASEGNITV

TCRASGFYPWNITLSWRQDGVSLSHDTQQWGDVLPDGNGTYQTWVATRIC

QGEEQRFTCYMEHSGNHSTHPVPSGKVLVLQSHW,
```

a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 3292;

(ii) MICB comprises the amino acid sequence:

```
                                    (SEQ ID NO: 3293)
AEPHSLRYNLMVLSQDESVQSGFLAEGHLDGQPFLRYDRQKRRAKPQGQW

AEDVLGAKTWDTETEDLTENGQDLRRTLTHIKDQKGGLHSLQEIRVCEIH

EDSSTRGSRHFYYDGELFLSQNLETQESTVPQSSRAQTLAMNVTNFWKED

AMKTKTHYRAMQADCLQKLQRYLKSGVAIRRTVPPMVNVTCSEVSEGNIT

VTCRASSFYPRNITLTWRQDGVSLSHNTQQWGDVLPDGNGTYQTWVATRI

RQGEEQRFTCYMEHSGNHGTHPVPSGKVLVLQSQRTD,
```

a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 3293; or (iii) ULBP1 comprises the amino acid sequence: GWVDTHCLCYDFIITPKSRPEPQWCE-VQGLVDERPFLHYDCVNHKAKA-FASLGKKVNVTK TWEEQTETLRDVVD-FLKGQLLDIQVENLIPIEPLTLQARMSCEHEAHG HGRGSWQFLFNGQ KFLLFDSNNRKWTALHP-GAKKMTEKWEKNRDVTMFFQKIS-LGDCKMWLEEFLMYWEQM LDPTKPPSLAPG (SEQ ID NO: 3294), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 3294.

In other embodiments, the NK cell engager is a ligand of DNAM1 chosen from NECTIN2 or NECL5, e.g., wherein:

(i) NECTIN2 comprises the amino acid sequence: QDVRVQVLPEVRGQLGGTVELPCHLLPPVPGLY-ISLVTWQRPDAPANHQNVAAFHPKMGP SFPSPKPGSERLSFVSAKQSTGQDTEAELQDAT-LALHGLTVEDEGNYTCEFATFPKGSVRG MTWLRVIAKPKNQAEAQKVTFSQDPTTVAL-CISKEGRPPARISWLSSLDWEAKETQVSGTL AGTVTVTSRFTLVPSGRADGVTVTCKVEHES-FEEPALIPVTLSVRYPPEVSISGYDDNWYLG RTDATLSCDVRSNPEPTGYDWSTTSGTFPT-SAVAQGSQLVIHAVDSLFNTTFVCTVTNAVG MGRAEQVIFVRETPNTAGAGATGG (SEQ ID NO: 3295), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 3295; or (ii) NECL5 comprises the amino acid sequence: WPPPGTGDVVVQAPTQVPGFLGDSVTLPCYLQ VPNMEVTHVSQLTWARHGESGSMAVFH QTQGPSYSESKRLEFVAARLGAELR-NASLRMFGLRVEDEGNYT-CLFVTFPQGSRSVDIWLR VLAKPQN-TAEVQKVQLTGEPVPMARCVSTGGRPPAQITWH SDLGGMPNTSQVPGFLSGTV TVTSLWIL-VPSSQVDGKNVTCKVEHES-FEKPQLLTVNLTVYYPPEVSIS-GYDNNWYLGQNE ATLTCDARSNPEPTGYNWSTTMGPLPP-FAVAQGAQLLIRPVDKPINTTLICNVTNALGARQ AELTVQVKEGPPSEHSGISRN (SEQ ID NO: 3296), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 3296.

In yet other embodiments, the NK cell engager is a ligand of DAP10, which is an adapter for NKG2D (see e.g., Proc Natl Acad Sci USA. 2005 May 24; 102(21): 7641-7646; and Blood, 15 Sep. 2011 Volume 118, Number 11, the full contents of each of which is incorporated by reference herein).

In other embodiments, the NK cell engager is a ligand of CD16, which is a CD16a/b ligand, e.g., a CD16a/b ligand further comprising an antibody Fc region (see e.g., Front Immunol. 2013; 4: 76 discusses how antibodies use the Fc to trigger NK cells through CD16, the full contents of which are incorporated herein).

In other embodiments, the NK cell engager is a ligand of CRTAM, which is NECL2, e.g., wherein NECL2 comprises the amino acid sequence: QNLFTKDVTVIEGEVA-TISCQVNKSDDSVIQLLNPNRQTIYFRDFR-PLKDSRFQLLNFSSSEL KVSLTNVSISDE-GRYFCQLYTDPPQESYTTITVLVPPRNLMIDIQKDTA VEGEEIEVNCTAM ASKPATTIRWFKGNTELKGK-SEVEEWS-DMYTVTSQLMLKVHKEDDGVPVICQVEHPAVT GNLQTQRYLEVQYKPQVHIQMTYPLQGL-TREGDALELTCEAIGKPQPVMVTWVRVDDEM PQHAVLSGPNLFINNLNKTDNGTYRCEASNIV-GKAHSDYMLYVYDPPTTIPPPTTTITTTT TTTTILT-IITDSRAGEEGSIRAVDH (SEQ ID NO: 3297), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 3297.

In other embodiments, the NK cell engager is a ligand of CD27, which is CD70, e.g., wherein CD70 comprises the amino acid sequence: QRFAQAQQQLPLESLGWDVAEL-QLNHTGPQQDPRLYWQGGPALGRSFLHG-PELDKGQLRI HRDGIYMVHIQVTLAICSSTTAS-RHHPTTLAVGICSPASRSISLLRLSFHQGCTIASQRLTP-LA RGDTLCTNLTGTLLPSRNTDETFFGVQWVRP (SEQ ID NO: 3298), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 3298.

In other embodiments, the NK cell engager is a ligand of PSGL1, which is L-selectin (CD62L), e.g., wherein L-selectin comprises the amino acid sequence:

```
                                          (SEQ ID NO: 3299)
WTYHYSEKPMNWQRARRFCRDNYTDLVAIQNKAEIEYLEKTLPFSRSYYW

IGIRKIGGIWTWVGTNKSLTEEAENWGDGEPNNKKNKEDCVEIYIKRNKD

AGKWNDDACHKLKAALCYTASCQPWSCSGHGECVEIINNYTCNCDVGYYG

PQCQFVIQCEPLEAPELGTMDCTHPLGNFSFSSQCAFSCSEGTNLTGIEE

TTCGPFGNWSSPEPTCQVIQCEPLSAPDLGIMNCSHPLASFSFTSACTFI

CSEGTELIGKKKTICESSGIWSNPSPICQKLDKSFSMIKEGDYN,
```

a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 3299.

In other embodiments, the NK cell engager is a ligand of CD96, which is NECL5, e.g., wherein NECL5 comprises the amino acid sequence: WPPPGTGDVVVQAPTQVPGFLGDSVTLPCYLQVPN-MEVTHVSQLTWARHGESGSMAVFH QTQGPSYS-ESKRLEFVAARLGAELRNASLRMFGLRVEDEGNYT-CLFVTFPQGSRSVDIWLR VLAKPQNTAEVQKVQLTGEPVPMARCVSTGGRP-PAQITWHSDLGGMPNTSQVPGFLSGTV TVTSLWIL-VPSSQVDGKNVTCKVEHES-FEKPQLLTVNLTVYYPPEVSISGYDNNWYLGQNE ATLTCDARSNPEPTGYNWSTTMGPLPPFAVAQGAQL-LIRPVDKPINTTLICNVTNALGARQ AELTVQVKEG-PPSEHSGISRN (SEQ ID NO: 3296), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 3296.

In other embodiments, the NK cell engager is a ligand of CD100 (SEMA4D), which is CD72, e.g., wherein CD72 comprises the amino acid sequence: RYLQVSQQLQQTNRVLEVTNSSLRQQLRLKITQLGQSAEDLQGSRRELAQSQEALQVEQR AHQAAEGQLQACQADRQKTKETLQSEEQQRRALEQKLSNMENRLKPFFTCGSADTCCPSG WIMHQKSCFYISLTSKNWQESQKQCETLSSKLATFSEIYPQSHSYYFLNSLLPNGGSGNSYW TGLSSNKDWKLTDDTQRTRTYAQSSKCNKVHKTWSWWTLESESCRSSLPYICEMTAFRFP D (SEQ ID NO: 3300), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 3300.

In other embodiments, the NK cell engager is a ligand of NKp80, which is CLEC2B (AICL), e.g., wherein CLEC2B (AICL) comprises the amino acid sequence:

KLTRDSQSLCPYDWIGFQNKCYYFSKEEGDWNSSKYNCSTQHADLTIIDNIEEM NFLRRYKCSSDHWIGLKMAKNRTGQWVDGATFTKSFGMRGSEGCAYLSDDGAATARCY TERKWICRKRIH (SEQ ID NO: 3301), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 3301.

In other embodiments, the NK cell engager is a ligand of CD244, which is CD48, e.g., wherein CD48 comprises the amino acid sequence: QGHLVHMTVVSGSNVTLNISESLPENYKQLTWFYTFDQKIVEWDSRKSKYFESKFKGRVR LDPQSGALYISKVQKEDNSTYIMRVLKKTGNEQEWKIKLQVLDPVPKPVIKIEKIEDM DDN CYLKLSCVIPGESVNYTWYGDKRPFPKELQNSVLETTLMPHNYSRCYTCQVSNSVSSKNGT VCLSPPCTLARS (SEQ ID NO: 3302), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 3302.

T Cell Engagers

The present disclosure provides, inter alia, multispecific (e.g., bi-, tri-, quad-specific) or multifunctional molecules, that are engineered to contain one or more T cell engager that mediate binding to and/or activation of a T cell. In some embodiments, the T cell engager is an antigen binding domain that binds to, e.g., activates TCRβ, e.g., a TCRβV region, as described herein. In some embodiments, the T cell engager is selected from an antigen binding domain or ligand that binds to (e.g., and in some embodiments activates) one or more of CD3, TCRα, TCRγ, TCRξ, ICOS, CD28, CD27, HVEM, LIGHT, CD40, 4-1BB, OX40, DR3, GITR, CD30, TIM1, SLAM, CD2, or CD226. In other embodiments, the T cell engager is selected from an antigen binding domain or ligand that binds to and does not activate one or more of CD3, TCRα, TCRγ, TCR, ICOS, CD28, CD27, HVEM, LIGHT, CD40, 4-1BB, OX40, DR3, GITR, CD30, TIM1, SLAM, CD2, or CD226.

B Cell, Macrophage & Dendritic Cell Engagers

Broadly, B cells, also known as B lymphocytes, are a type of white blood cell of the lymphocyte subtype. They function in the humoral immunity component of the adaptive immune system by secreting antibodies. Additionally, B cells present antigen (they are also classified as professional antigen-presenting cells (APCs)) and secrete cytokines. Macrophages are a type of white blood cell that engulfs and digests cellular debris, foreign substances, microbes, cancer cells via phagocytosis. Besides phagocytosis, they play important roles in nonspecific defense (innate immunity) and also help initiate specific defense mechanisms (adaptive immunity) by recruiting other immune cells such as lymphocytes. For example, they are important as antigen presenters to T cells. Beyond increasing inflammation and stimulating the immune system, macrophages also play an important anti-inflammatory role and can decrease immune reactions through the release of cytokines. Dendritic cells (DCs) are antigen-presenting cells that function in processing antigen material and present it on the cell surface to the T cells of the immune system.

The present disclosure provides, inter alia, multispecific (e.g., bi-, tri-, quad-specific) or multifunctional molecules, that include, e.g., are engineered to contain, one or more B cell, macrophage, and/or dendritic cell engager that mediate binding to and/or activation of a B cell, macrophage, and/or dendritic cell.

Accordingly, in some embodiments, the immune cell engager comprises a B cell, macrophage, and/or dendritic cell engager chosen from one or more of CD40 ligand (CD40L) or a CD70 ligand; an antibody molecule that binds to CD40 or CD70; an antibody molecule to OX40; an OX40 ligand (OX40L); an agonist of a Toll-like receptor (e.g., as described herein, e.g., a TLR4, e.g., a constitutively active TLR4 (caTLR4), or a TLR9 agonists); a 41BB; a CD2; a CD47; or a STING agonist, or a combination thereof.

In some embodiments, the B cell engager is a CD40L, an OX40L, or a CD70 ligand, or an antibody molecule that binds to OX40, CD40 or CD70.

In some embodiments, the macrophage engager is a CD2 agonist. In some embodiments, the macrophage engager is an antigen binding domain that binds to: CD40L or antigen binding domain or ligand that binds CD40, a Toll like receptor (TLR) agonist (e.g., as described herein), e.g., a TLR9 or TLR4 (e.g., caTLR4 (constitutively active TLR4), CD47, or a STING agonist. In some embodiments, the STING agonist is a cyclic dinucleotide, e.g., cyclic di-GMP (cdGMP) or cyclic di-AMP (cdAMP). In some embodiments, the STING agonist is biotinylated.

In some embodiments, the dendritic cell engager is a CD2 agonist. In some embodiments, the dendritic cell engager is a ligand, a receptor agonist, or an antibody molecule that binds to one or more of: OX40L, 41BB, a TLR agonist (e.g., as described herein) (e.g., TLR9 agonist, TLR4 (e.g., caTLR4 (constitutively active TLR4)), CD47, or and a STING agonist. In some embodiments, the STING agonist is a cyclic dinucleotide, e.g., cyclic di-GMP (cdGMP) or cyclic di-AMP (cdAMP). In some embodiments, the STING agonist is biotinylated.

In other embodiments, the immune cell engager mediates binding to, or activation of, one or more of a B cell, a macrophage, and/or a dendritic cell. Exemplary B cell, macrophage, and/or dendritic cell engagers can be chosen from one or more of CD40 ligand (CD40L) or a CD70 ligand; an antibody molecule that binds to CD40 or CD70; an antibody molecule to OX40; an OX40 ligand (OX40L); a Toll-like receptor agonist (e.g., a TLR4, e.g., a constitutively active TLR4 (caTLR4) or a TLR9 agonist); a 41BB agonist; a CD2; a CD47; or a STING agonist, or a combination thereof.

In some embodiments, the B cell engager is chosen from one or more of a CD40L, an OX40L, or a CD70 ligand, or an antibody molecule that binds to OX40, CD40 or CD70.

In other embodiments, the macrophage cell engager is chosen from one or more of a CD2 agonist; a CD40L; an OX40L; an antibody molecule that binds to OX40, CD40 or CD70; a Toll-like receptor agonist or a fragment thereof (e.g., a TLR4, e.g., a constitutively active TLR4 (caTLR4)); a CD47 agonist; or a STING agonist.

In other embodiments, the dendritic cell engager is chosen from one or more of a CD2 agonist, an OX40 antibody, an OX40L, 41BB agonist, a Toll-like receptor agonist or a fragment thereof (e.g., a TLR4, e.g., a constitutively active TLR4 (caTLR4)), CD47 agonist, or a STING agonist.

In one embodiment, the OX40L comprises the amino acid sequence: QVSHRYPRIQSIKVQFTEYKKEKGFILT-SQKEDEIMKVQNNSVIINCDGFYLISLKGYFSQEV NISLHYQKDEEP-LFQLKKVRSVNSLMVASLTYKDKVYLNVTTDNT-SLDDFHVNGGELILIH QNPGEFCVL (SEQ ID NO: 3303), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 3303.

In another embodiment, the CD40L comprises the amino acid sequence: MQKGDQNPQIAAHVISEAS-SKTTSVLQWAEKGYYTMSNNLVT-LENGKQLTVKRQGLYYI YAQVTFCSNREASSQAP-FIASLCLKSPGRFERILLRAANTHSSAKPCGQQSIHLG GVFELQPG ASVFVNVTDPSQVSHGTGFTSFGLLKL (SEQ ID NO: 3304), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 3304.

In yet other embodiments, the STING agonist comprises a cyclic dinucleotide, e.g., a cyclic di-GMP (cdGMP), a cyclic di-AMP (cdAMP), or a combination thereof, optionally with 2',5' or 3',5' phosphate linkages.

In one embodiment, the immune cell engager includes 41BB ligand, e.g., comprising the amino acid sequence: ACPWAVSGARASPGSAASPRLREGPELSPDD-PAGLLDLRQGMFAQLVAQNVLLIDGPLSW YSDPGLAGVSLTGGLSYKEDTKELVVAK-AGVYYVFFQLELRRVVAGEGSGSVSLALHLQP LRSAAGAAALALTVDLPPASSEARN-SAFGFQGRLLHLSAGQRLGVHLHTEARARHAWQLT QGATVLGLFRVTPEIPAGLPSPRSE (SEQ ID NO: 3305), a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 3305.

Toll-Like Receptors

Toll-Like Receptors (TLRs) are evolutionarily conserved receptors are homologues of the *Drosophila* Toll protein, and recognize highly conserved structural motifs known as pathogen-associated microbial patterns (PAMPs), which are exclusively expressed by microbial pathogens, or danger-associated molecular patterns (DAMPs) that are endogenous molecules released from necrotic or dying cells. PAMPs include various bacterial cell wall components such as lipopolysaccharide (LPS), peptidoglycan (PGN) and lipopeptides, as well as flagellin, bacterial DNA and viral double-stranded RNA. DAMPs include intracellular proteins such as heat shock proteins as well as protein fragments from the extracellular matrix. Stimulation of TLRs by the corresponding PAMPs or DAMPs initiates signaling cascades leading to the activation of transcription factors, such as AP-1, NF-κB and interferon regulatory factors (IRFs). Signaling by TLRs results in a variety of cellular responses, including the production of interferons (IFNs), pro-inflammatory cytokines and effector cytokines that direct the adaptive immune response. TLRs are implicated in a number of inflammatory and immune disorders and play a role in cancer (Rakoff-Nahoum S. & Medzhitov R., 2009. Toll-like receptors and cancer. Nat Revs Cancer 9:57-63.)

TLRs are type I transmembrane proteins characterized by an extracellular domain containing leucine-rich repeats (LRRs) and a cytoplasmic tail that contains a conserved region called the Toll/IL-1 receptor (TIR) domain. Ten human and twelve murine TLRs have been characterized, TLR1 to TLR10 in humans, and TLR1 to TLR9, TLR11, TLR12 and TLR13 in mice, the homolog of TLR10 being a pseudogene. TLR2 is essential for the recognition of a variety of PAMPs from Gram-positive bacteria, including bacterial lipoproteins, lipomannans and lipoteichoic acids. TLR3 is implicated in virus-derived double-stranded RNA. TLR4 is predominantly activated by lipopolysaccharide. TLR5 detects bacterial flagellin and TLR9 is required for response to unmethylated CpG DNA. Finally, TLR7 and TLR8 recognize small synthetic antiviral molecules, and single-stranded RNA was reported to be their natural ligand. TLR11 has been reported to recognize uropathogenic *E. coli* and a profilin-like protein from *Toxoplasma gondii*. The repertoire of specificities of the TLRs is apparently extended by the ability of TLRs to heterodimerize with one another. For example, dimers of TLR2 and TLR6 are required for responses to diacylated lipoproteins while TLR2 and TLR1 interact to recognize triacylated lipoproteins. Specificities of the TLRs are also influenced by various adapter and accessory molecules, such as MD-2 and CD14 that form a complex with TLR4 in response to LPS.

TLR signaling consists of at least two distinct pathways: a MyD88-dependent pathway that leads to the production of inflammatory cytokines, and a MyD88-independent pathway associated with the stimulation of IFN-β and the maturation of dendritic cells. The MyD88-dependent pathway is common to all TLRs, except TLR3 (Adachi O. et al., 1998. Targeted disruption of the MyD88 gene results in loss of IL-1- and IL-18-mediated function. Immunity. 9(1):143-50). Upon activation by PAMPs or DAMPs, TLRs hetero- or homodimerize inducing the recruitment of adaptor proteins via the cytoplasmic TIR domain. Individual TLRs induce different signaling responses by usage of the different adaptor molecules. TLR4 and TLR2 signaling requires the adaptor TIRAP/Mal, which is involved in the MyD88-dependent pathway. TLR3 triggers the production of IFN-β in response to double-stranded RNA, in a MyD88-independent manner, through the adaptor TRIF/TICAM-1. TRAM/TICAM-2 is another adaptor molecule involved in the MyD88-independent pathway which function is restricted to the TLR4 pathway.

TLR3, TLR7, TLR8 and TLR9 recognize viral nucleic acids and induce type I IFNs. The signaling mechanisms leading to the induction of type I IFNs differ depending on the TLR activated. They involve the interferon regulatory factors, IRFs, a family of transcription factors known to play a critical role in antiviral defense, cell growth and immune regulation. Three IRFs (IRF3, IRF5 and IRF7) function as direct transducers of virus-mediated TLR signaling. TLR3 and TLR4 activate IRF3 and IRF7, while TLR7 and TLR8 activate IRF5 and IRF7 (Doyle S. et al., 2002. IRF3 mediates a TLR3/TLR4-specific antiviral gene program. Immunity. 17(3):251-63). Furthermore, type I IFN production stimulated by TLR9 ligand CpG-A has been shown to be mediated by PI(3)K and mTOR (Costa-Mattioli M. & Sonenberg N. 2008. RAPping production of type I interferon in pDCs through mTOR. Nature Immunol. 9: 1097-1099).

TLR-9

TLR9 recognizes unmethylated CpG sequences in DNA molecules. CpG sites are relatively rare (~1%) on vertebrate genomes in comparison to bacterial genomes or viral DNA. TLR9 is expressed by numerous cells of the immune system such as B lymphocytes, monocytes, natural killer (NK) cells, and plasmacytoid dendritic cells. TLR9 is expressed intracellularly, within the endosomal compartments and functions to alert the immune system of viral and bacterial infections by binding to DNA rich in CpG motifs. TLR9 signals leads to activation of the cells initiating pro-inflammatory reactions that result in the production of cytokines such as type-I interferon and IL-12.

TLR Agonists

A TLR agonist can agonize one or more TLR, e.g., one or more of human TLR-1, 2, 3, 4, 5, 6, 7, 8, 9, or 10. In some embodiments, an adjunctive agent described herein is a TLR agonist. In some embodiments, the TLR agonist specifically agonizes human TLR-9. In some embodiments, the TLR-9 agonist is a CpG moiety. As used herein, a CpG moiety, is a linear dinucleotide having the sequence: 5'-C-phosphate-G-3', that is, cytosine and guanine separated by only one phosphate.

In some embodiments, the CpG moiety comprises at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or more CpG dinucleotides. In some embodiments, the CpG moiety consists of 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 CpG dinucleotides. In some embodiments, the CpG moiety has 1-5, 1-10, 1-20, 1-30, 1-40, 1-50, 5-10, 5-20, 5-30, 10-20, 10-30, 10-40, or 10-50 CpG dinucleotides.

In some embodiments, the TLR-9 agonist is a synthetic ODN (oligodeoxynucleotides). CpG ODNs are short synthetic single-stranded DNA molecules containing unmethylated CpG dinucleotides in particular sequence contexts (CpG motifs). CpG ODNs possess a partially or completely phosphorothioated (PS) backbone, as opposed to the natural phosphodiester (PO) backbone found in genomic bacterial DNA. There are three major classes of CpG ODNs: classes A, B and C, which differ in their immunostimulatory activities. CpG-A ODNs are characterized by a PO central CpG-containing palindromic motif and a PS-modified 3' poly-G string. They induce high IFN-α production from pDCs but are weak stimulators of TLR9-dependent NF-κB signaling and pro-inflammatory cytokine (e.g. IL-6) production. CpG-B ODNs contain a full PS backbone with one or more CpG dinucleotides. They strongly activate B cells and TLR9-dependent NF-κB signaling but weakly stimulate IFN-α secretion. CpG-C ODNs combine features of both classes A and B. They contain a complete PS backbone and a CpG-containing palindromic motif. C-Class CpG ODNs induce strong IFN-α production from pDC as well as B cell stimulation.

Tumor-Targeting Moieties

The present disclosure provides, inter alia, multispecific (e.g., bi-, tri-, tetra-specific) molecules, that include, e.g., are engineered to contain, one or more tumor specific targeting moieties that direct the molecule to a tumor cell.

In certain embodiments, the multispecific molecules disclosed herein include a tumor-targeting moiety. The tumor targeting moiety can be chosen from an antibody molecule (e.g., an antigen binding domain as described herein), a receptor or a receptor fragment, or a ligand or a ligand fragment, or a combination thereof. In some embodiments, the tumor targeting moiety associates with, e.g., binds to, a tumor cell (e.g., a molecule, e.g., antigen, present on the surface of the tumor cell). In certain embodiments, the tumor targeting moiety targets, e.g., directs the multispecific molecules disclosed herein to a cancer (e.g., a cancer or tumor cells). In some embodiments, the cancer is chosen from a hematological cancer, a solid cancer, a metastatic cancer, or a combination thereof.

In some embodiments, the multispecific molecule, e.g., the tumor-targeting moiety, binds to a solid tumor antigen or a stromal antigen. The solid tumor antigen or stromal antigen can be present on a solid tumor, or a metastatic lesion thereof. In some embodiments, the solid tumor is chosen from one or more of pancreatic (e.g., pancreatic adenocarcinoma), breast, colorectal, lung (e.g., small or non-small cell lung cancer), skin, ovarian, or liver cancer. In one embodiment, the solid tumor is a fibrotic or desmoplastic solid tumor. For example, the solid tumor antigen or stromal antigen can be present on a tumor, e.g., a tumor of a class typified by having one or more of: limited tumor perfusion, compressed blood vessels, or fibrotic tumor interstitium.

In certain embodiments, the solid tumor antigen is chosen from one or more of: PDL1, CD47, ganglioside 2 (GD2), prostate stem cell antigen (PSCA), prostate specific membrane antigen (PMSA), prostate-specific antigen (PSA), carcinoembryonic antigen (CEA), Ron Kinase, c-Met, Immature laminin receptor, TAG-72, BING-4, Calcium-activated chloride channel 2, Cyclin-B1, 9D7, Ep-CAM, EphA3, Her2/neu, Telomerase, SAP-1, Survivin, NY-ESO-1/LAGE-1, PRAME, SSX-2, Melan-A/MART-1, Gp100/pmel17, Tyrosinase, TRP-1/-2, MC1R, β-catenin, BRCA1/2, CDK4, CML66, Fibronectin, p53, Ras, TGF-B receptor, AFP, ETA, MAGE, MUC-1, CA-125, BAGE, GAGE, NY-ESO-1, β-catenin, CDK4, CDC27, CD47, α actinin-4, TRP1/gp75, TRP2, gp100, Melan-A/MART1, gangliosides, WT1, EphA3, Epidermal growth factor receptor (EGFR), MART-2, MART-1, MUC1, MUC2, MUM1, MUM2, MUM3, NA88-1, NPM, OA1, OGT, RCC, RUI1, RUI2, SAGE, TRG, TRP1, TSTA, Folate receptor alpha, L1-CAM, CAIX, EGFRvIII, gpA33, GD3, GM2, VEGFR, Intergrins (Integrin alphaVbeta3, Integrin alpha5Beta1), Carbohydrates (Le), IGF1R, EPHA3, TRAILR1, TRAILR2, or RANKL.

In other embodiments, the multispecific molecule, e.g., the tumor-targeting moiety, binds to a molecule, e.g., antigen, present on the surface of a hematological cancer, e.g., a leukemia or a lymphoma. In some embodiments, the hematological cancer is a B-cell or T cell malignancy. In some embodiments, the hematological cancer is chosen from one or more of a Hodgkin's lymphoma, Non-Hodgkin's lymphoma (e.g., B cell lymphoma, diffuse large B cell lymphoma, follicular lymphoma, chronic lymphocytic leukemia, mantle cell lymphoma, marginal zone B-cell lymphoma, Burkitt lymphoma, lymphoplasmacytic lymphoma, hairy cell leukemia), acute myeloid leukemia (AML), chronic myeloid leukemia, myelodysplastic syndrome (MDS), multiple myeloma, or acute lymphocytic leukemia. In embodiments, the cancer is other than acute myeloid leukemia (AML) or myelodysplastic syndrome (MDS). In embodiments, the hematological antigen is chosen from CD47, CD99, CD30, CD38, SLAMF7, or NY-ESO1. In some embodiments, the hematological antigen is chosen from is chosen from one or more of: BCMA, CD19, CD20, CD22, CD33, CD123, FcRH5, CLEC12, or CD179A.

Stromal Modifying Moieties

Solid tumors have a distinct structure that mimics that of normal tissues and comprises two distinct but interdependent compartments: the parenchyma (neoplastic cells) and the stroma that the neoplastic cells induce and in which they are dispersed. All tumors have stroma and require stroma for nutritional support and for the removal of waste products. In the case of tumors which grow as cell suspensions (e.g., leukemias, ascites tumors), the blood plasma serves as stroma (Connolly J L et al. Tumor Structure and Tumor Stroma Generation. In: Kufe D W et al., editors. Holland-Frei *Cancer Medicine.* 6th edition. Hamilton: BC Decker; 2003). The stroma includes a variety of cell types, including fibroblasts/myofibroblasts, glial, epithelial, fat, vascular, smooth muscle, and immune cells along with extracellular matrix (ECM) and extracellular molecules (Li Hanchen et al. Tumor Microenvironment: The Role of the Tumor Stroma in Cancer. *J of Cellular Biochemistry* 101: 805-815 (2007)).

Stromal modifying moieties described herein include moieties (e.g., proteins, e.g., enzymes) capable of degrading a component of the stroma, e.g., an ECM component, e.g., a glycosaminoglycan, e.g., hyaluronan (also known as hyaluronic acid or HA), chondroitin sulfate, chondroitin, dermatan sulfate, heparin sulfate, heparin, entactin, tenascin, aggrecan and keratin sulfate; or an extracellular protein, e.g., collagen, laminin, elastin, fibrinogen, fibronectin, and vitronectin.

Stromal Modifying Enzymes

In some embodiments, the stromal modifying moiety is an enzyme. For example, the stromal modifying moiety can include, but is not limited to a hyaluronidase, a collagenase, a chondroitinase, a matrix metalloproteinase (e.g., macrophage metalloelastase).

Hyaluronidases

Hyaluronidases are a group of neutral- and acid-active enzymes found throughout the animal kingdom. Hyaluronidases vary with respect to substrate specificity, and mechanism of action. There are three general classes of hyaluronidases: (1) Mammalian-type hyaluronidases, (EC 3.2.1.35) which are endo-beta-N-acetylhexosaminidases with tetrasaccharides and hexasaccharides as the major end products. They have both hydrolytic and transglycosidase activities, and can degrade hyaluronan and chondroitin sulfates; (2) Bacterial hyaluronidases (EC 4.2.99.1) degrade hyaluronan and, and to various extents, chondroitin sulfate and dermatan sulfate. They are endo-beta-N-acetylhexosaminidases that operate by a beta elimination reaction that yields primarily disaccharide end products; (3) Hyaluronidases (EC 3.2.1.36) from leeches, other parasites, and crustaceans are endo-beta-glucuronidases that generate tetrasaccharide and hexasaccharide end products through hydrolysis of the beta 1-3 linkage.

Mammalian hyaluronidases can be further divided into two groups: (1) neutral active and (2) acid active enzymes. There are six hyaluronidase-like genes in the human genome, HYAL1, HYAL2, HYAL3 HYAL4 HYALP1 and PH20/SPAM1. HYALP1 is a pseudogene, and HYAL3 has not been shown to possess enzyme activity toward any known substrates. HYAL4 is a chondroitinase and lacks activity towards hyaluronan. HYAL1 is the prototypical acid-active enzyme and PH20 is the prototypical neutral-active enzyme. Acid active hyaluronidases, such as HYAL1 and HYAL2 lack catalytic activity at neutral pH. For example, HYAL1 has no catalytic activity in vitro over pH 4.5 (Frost and Stern, "A Microtiter-Based Assay for Hyaluronidase Activity Not Requiring Specialized Reagents", Analytical Biochemistry, vol. 251, pp. 263-269 (1997). HYAL2 is an acid active enzyme with a very low specific activity in vitro.

In some embodiments the hyaluronidase is a mammalian hyaluronidase. In some embodiments the hyaluronidase is a recombinant human hyaluronidase. In some embodiments, the hyaluronidase is a neutral active hyaluronidase. In some embodiments, the hyaluronidase is a neutral active soluble hyaluronidase. In some embodiments, the hyaluronidase is a recombinant PH20 neutral-active enzyme. In some embodiments, the hyaluronidase is a recombinant PH20 neutral-active soluble enzyme. In some embodiments the hyaluronidase is glycosylated. In some embodiments, the hyaluronidase possesses at least one N-linked glycan. A recombinant hyaluronidase can be produced using conventional methods known to those of skill in the art, e.g., U.S. Pat. No. 7,767,429, the entire contents of which are incorporated by reference herein.

In some embodiments the hyaluronidase is rHuPH20 (also referred to as Hylenex®; presently manufactured by Halozyme; approved by the FDA in 2005 (see e.g., Scodeller P (2014) Hyaluronidase and other Extracellular Matrix Degrading Enzymes for Cancer Therapy: New Uses and Nano-Formulations. J Carcinog Mutage 5:178; U.S. Pat. Nos. 7,767,429; 8,202,517; 7,431,380; 8,450,470; 8,772,246; 8,580,252, the entire contents of each of which is incorporated by reference herein). rHuPH20 is produced by genetically engineered CHO cells containing a DNA plasmid encoding for a soluble fragment of human hyaluronidase PH20. In some embodiments the hyaluronidase is glycosylated. In some embodiments, the hyaluronidase possesses at least one N-linked glycan. A recombinant hyaluronidase can be produced using conventional methods known to those of skill in the art, e.g., U.S. Pat. No. 7,767,429, the entire contents of which are incorporated by reference herein. In some embodiments, rHuPH20 has a sequence at least 95% (e.g., at least 96%, 97%, 98%, 99%, 100%) identical to the amino acid sequence of (SEQ ID NO: 3306)

```
LNFRAPPVIPNVPFLWAWNAPSEFCLGKFDEPLDMSLFSFIGSPRINATG
QGVTIFYVDRLGYYPYIDSITGVTVNGGIPQKISLQDHLDKAKKDITFYM
PVDNLGMAVIDWEEWRPTWARNWKPKDVYKNRSIELVQQQNVQLSLTEAT
EKAKQEFEKAGKDFLVETIKLGKLLRPNHLWGYYLFPDCYNHHYKKPGYN
GSCFNVEIKRNDDLSWLWNESTALYPSIYLNTQQSPVAATLYVRNRVREA
IRVSKIPDAKSPLPVFAYTRIVFTDQVLKFLSQDELVYTFGETVALGASG
IVIWGTLSIMRSMKSCLLLDNYMETILNPYIINVTLAAKMCSQVLCQEQG
VCIRKNWNSSDYLHLNPDNFAIQLEKGGKFTVRGKPTLEDLEQFSEKFYC
SCYSTLSCKEKADVKDTDAVDVCIADGVCIDAFLKPPMETEEPQIFYNAS
PSTLS.
```

In any of the methods provided herein, the anti-hyaluronan agent can be an agent that degrades hyaluronan or can be an agent that inhibits the synthesis of hyaluronan. For example, the anti-hyaluronan agent can be a hyaluronan degrading enzyme. In another example, the anti-hyaluronan agent or is an agent that inhibits hyaluronan synthesis. For example, the anti-hyaluronan agent is an agent that inhibits hyaluronan synthesis such as a sense or antisense nucleic acid molecule against an HA synthase or is a small molecule drug. For example, an anti-hyaluronan agent is 4-methylumbelliferone (MU) or a derivative thereof, or leflunomide or a derivative thereof. Such derivatives include, for example, a derivative of 4-methylumbelliferone (MU) that is 6,7-dihydroxy-4-methyl coumarin or 5,7-dihydroxy-4-methyl coumarin.

In further examples of the methods provided herein, the hyaluronan degrading enzyme is a hyaluronidase. In some examples, the hyaluronan-degrading enzyme is a PH20 hyaluronidase or truncated form thereof to lacking a C-terminal glycosylphosphatidylinositol (GPI) attachment site or a portion of the GPI attachment site. In specific examples, the hyaluronidase is a PH20 selected from a human, monkey, bovine, ovine, rat, mouse or guinea pig PH20. For example, the hyaluronan-degrading enzyme is a human PH20 hyaluronidase that is neutral active and N-glycosylated and is selected from among (a) a hyaluronidase polypeptide that is a full-length PH20 or is a C-terminal truncated form of the PH20, wherein the truncated form includes at least amino acid residues 36-464 of SEQ ID NO: 139, such as 36-481, 36-482, 36-483, where the full-length PH20 has the sequence of amino acids set forth in SEQ ID NO: 139; or (b) a hyaluronidase polypeptide comprising a sequence of amino acids having at least 85%, 86%, 87%, 88%, 89%, 90%, 91%, 92%, 93%, 94%, 95%, 96%, 97%, 98%, 99% or more sequence identity with the polypeptide or truncated form of sequence of amino acids set forth in SEQ ID NO: 139; or (c) a hyaluronidase polypeptide of (a) or (b) comprising amino acid substitutions, whereby the hyaluronidase polypeptide has a sequence of amino acids having at least 85%, 86%, 87%, 88%, 89%, 90%, 91%, 92%, 93%, 94%, 95%, 96%, 97%, 98%, 99% or more sequence identity with the polypeptide set forth in SEQ ID NO: 139 or the with the corresponding truncated forms thereof. In exemplary examples, the hyaluronan-degrading enzyme is a PH20 that comprises a composition designated rHuPH20.

In other examples, the anti-hyaluronan agent is a hyaluronan degrading enzyme that is modified by conjugation to a polymer. The polymer can be a PEG and the anti-hyaluronan agent a PEGylated hyaluronan degrading enzyme. Hence, in some examples of the methods provided herein the hyaluronan-degrading enzyme is modified by conjugation to a polymer. For example, the hyaluronan-degrading enzyme is conjugated to a PEG, thus the hyaluronan degrading enzyme is PEGylated. In an exemplary example, the hyaluronan-degrading enzyme is a PEGylated PH20 enzyme (PEGPH20). In the methods provided herein, the corticosteroid can be a glucocorticoid that is selected from among cortisones, dexamethasones, hydrocortisones, methylprednisolones, prednisolones and prednisones.

Chondroitinases

Chondroitinases are enzymes found throughout the animal kingdom which degrade glycosaminoglycans, specifically chondroitins and chondroitin sulfates, through an endoglycosidase reaction. In some embodiments the chondroitinase is a mammalian chondroitinase. In some embodiments the chondroitinase is a recombinant human chondroitinase. In some embodiments the chondroitinase is HYAL4. Other exemplary chondroitinases include chondroitinase ABC (derived from *Proteus vulgaris*; Japanese Patent Application Laid-open No 6-153947, T. Yamagata et al. J. Biol. Chem., 243, 1523 (1968), S. Suzuki et al, J. Biol. Chem., 243, 1543 (1968)), chondroitinase AC (derived from *Flavobacterium heparinum*; T. Yamagata et al., J. Biol. Chem., 243, 1523 (1968)), chondroitinase AC II (derived from *Arthrobacter aurescens*; K. Hiyama, and S. Okada, J. Biol. Chem., 250, 1824 (1975), K. Hiyama and S. Okada, J. Biochem. (Tokyo), 80, 1201 (1976)), Hyaluronidase ACIII (derived from *Flavobacterium* sp. Hp102; Hirofumi Miyazono et al., Seikagaku, 61, 1023 (1989)), chondroitinase B (derived from *Flavobacterium heparinum*; Y. M. Michelacci and C. P. Dietrich, Biochem. Biophys. Res. Commun., 56, 973 (1974), Y. M. Michelacci and C. P. Dietrich, Biochem. J., 151, 121 (1975), Kenichi Maeyama et al, Seikagaku, 57, 1189 (1985)), chondroitinase C (derived from *Flavobacterium* sp. Hp102; Hirofumi Miyazono et al, Seikagaku, 61, 1023 (1939)), and the like.

Matrix Metalloproteinases

Matrix metalloproteases (MMPs) are zinc-dependent endopeptidases that are the major proteases involved in extracellular matrix (ECM) degradation. MMPs are capable of degrading a wide range of extracellular molecules and a number of bioactive molecules. Twenty-four MMP genes have been identified in humans, which can be organized into six groups based on domain organization and substrate preference: Collagenases (MMP-1, -8 and -13), Gelatinases (MMP-2 and MMP-9), Stromelysins (MMP-3, -10 and -11), Matrilysin (MMP-7 and MMP-26), Membrane-type (MT)-MMPs (MMP-14, -15, -16, -17, -24 and -25) and others (MMP-12, -19, -20, -21, -23, -27 and -28). In some embodiments, the stromal modifying moiety is a human recombinant MMP (e.g., MMP-1, -2, -3, -4, -5, -6, -7, -8, -9, 10, -11, -12, -13, -14, 15, -15, -17, -18, -19, 20, -21, -22, -23, or -24).

Collagenases

The three mammalian collagenases (MMP-1, -8, and -13) are the principal secreted endopeptidases capable of cleaving collagenous extracellular matrix. In addition to fibrillar collagens, collagenases can cleave several other matrix and non-matrix proteins including growth factors. Collagenases are synthesized as inactive pro-forms, and once activated, their activity is inhibited by specific tissue inhibitors of metalloproteinases, TIMPs, as well as by non-specific proteinase inhibitors (Ala-aho R et al. Biochimie. Collagenases in cancer. 2005 March-April; 87(3-4):273-86). In some embodiments, the stromal modifying moiety is a collagenase. In some embodiments, the collagenase is a human recombinant collagenase. In some embodiments, the collagenase is MMP-1. In some embodiments, the collagenase is MMP-8. In some embodiments, the collagenase is MMP-13.

Macrophage Metalloelastase

Macrophage metalloelastase (MME), also known as MMP-12, is a member of the stromelysin subgroup of MMPs and catalyzes the hydrolysis of soluble and insoluble elastin and a broad selection of matrix and nonmatrix substrates including type IV collagen, fibronectin, laminin, vitronectin, entactin, heparan, and chondroitin sulfates (Erja Kerkelă et al. Journal of Investigative Dermatology (2000) 114, 1113-1119; doi:10.1046/j.1523-1747.2000.00993). In some embodiments, the stromal modifying moiety is a MME. In some embodiments, the MME is a human recombinant MME. In some embodiments, the MME is MMP-12.

Additional Stromal Modifying Moieties

In some embodiments, the stromal modifying moiety causes one or more of: decreases the level or production of a stromal or extracellular matrix (ECM) component; decreases tumor fibrosis; increases interstitial tumor transport; improves tumor perfusion; expands the tumor microvasculature; decreases interstitial fluid pressure (IFP) in a tumor; or decreases or enhances penetration or diffusion of an agent, e.g., a cancer therapeutic or a cellular therapy, into a tumor or tumor vasculature.

In some embodiments, the stromal or ECM component decreased is chosen from a glycosaminoglycan or an extracellular protein, or a combination thereof. In some embodiments, the glycosaminoglycan is chosen from hyaluronan (also known as hyaluronic acid or HA), chondroitin sulfate, chondroitin, dermatan sulfate, heparin, heparin sulfate, entactin, tenascin, aggrecan and keratin sulfate. In some embodiments, the extracellular protein is chosen from collagen, laminin, elastin, fibrinogen, fibronectin, or vitronectin. In some embodiments, the stromal modifying moiety includes an enzyme molecule that degrades a tumor stroma or extracellular matrix (ECM). In some embodiments, the enzyme molecule is chosen from a hyaluronidase molecule, a collagenase molecule, a chondroitinase molecule, a matrix metalloproteinase molecule (e.g., macrophage metalloelastase), or a variant (e.g., a fragment) of any of the aforesaid. The term "enzyme molecule" includes a full length, a fragment or a variant of the enzyme, e.g., an enzyme variant that retains at least one functional property of the naturally-occurring enzyme.

In some embodiments, the stromal modifying moiety decreases the level or production of hyaluronic acid. In other embodiments, the stromal modifying moiety comprises a hyaluronan degrading enzyme, an agent that inhibits hyaluronan synthesis, or an antibody molecule against hyaluronic acid.

In some embodiments, the hyaluronan degrading enzyme is a hyaluronidase molecule, e.g., a full length or a variant (e.g., fragment thereof) thereof. In some embodiments, the hyaluronan degrading enzyme is active in neutral or acidic pH, e.g., pH of about 4-5. In some embodiments, the hyaluronidase molecule is a mammalian hyaluronidase molecule, e.g., a recombinant human hyaluronidase molecule, e.g., a full length or a variant (e.g., fragment thereof, e.g., a truncated form) thereof. In some embodiments, the hyaluronidase molecule is chosen from HYAL1, HYAL2, or PH-20/SPAM1, or a variant thereof (e.g., a truncated form thereof). In some embodiments, the truncated form lacks a C-terminal glycosylphosphatidylinositol (GPI) attachment site or a portion of the GPI attachment site. In some embodiments, the hyaluronidase molecule is glycosylated, e.g., comprises at least one N-linked glycan.

In some embodiments, the hyaluronidase molecule comprises the amino acid sequence: LNFRAPPVIPNVPFL-
WAWNAPSEFCLGKFDEPLDMSLFSFIGSPRI-
NATGQGVTIFYVDRLG
YYPYIDSITGVTVNGGIPQKIS-
LQDHLDKAKKDITFYMPVDNLGMAVIDWEEWRPT-
WARN WKPKDVYKNRSIELVQQQNVQLSL-
TEATEKAKQEFEKAGKDFLVETIKLGKLLRPNHLWG
YYLFPDCYNHHYKKPGYNGSCFNVEIKRND-
DLSWLWNESTALYPSIYLNTQQSPVAATLY
VRNRVREAIRVSKIPDAKSPLPVFAY-
TRIVFTDQVLKFLSQDELVYTFGETVALGASGIVIW
GTLSIMRSMKSCLLLDNYMETILNPYIINVT-
LAAKMCSQVLCQEQGVCIRKNWNSSDYLHL NPDN-
FAIQLEKGGKFTVRGKP-
TLEDLEQFSEKFYCSCYSTLSCKEKADVKDTDAVDV
CIAD GVCIDAFLKPPMETEEPQIFYNASPSTLS (SEQ ID NO:3311), or a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 3311.

In some embodiments, the hyaluronidase molecule comprises:

(i) the amino acid sequence of 36-464 of SEQ ID NO: 3311;

(ii) the amino acid sequence of 36-481, 36-482, or 36-483 of PH20, wherein PH20 has the sequence of amino acids set forth in SEQ ID NO: 3311; or (iii) an amino acid sequence having at least 95% to 100% sequence identity to the polypeptide or truncated form of sequence of amino acids set forth in SEQ ID NO: 3311; or (iv) an amino acid sequence having 30, 20, 10, 5 or fewer amino acid substitutions to the amino acid sequence set forth in SEQ ID NO: 3311. In some embodiments, the hyaluronidase molecule comprises an amino acid sequence at least 95% (e.g., at least 95%, 96%, 97%, 98%, 99%, 100%) identical to the amino acid sequence of SEQ ID NO: 3311. In some embodiments, the hyaluronidase molecule is encoded by a nucleotide sequence at least 95% (e.g., at least 96%, 97%, 98%, 99%, 100%) identical to the nucleotide sequence of SEQ ID NO: 3311.

In some embodiments, the hyaluronidase molecule is PH20, e.g., rHuPH20. In some embodiments, the hyaluronidase molecule is HYAL1 and comprises the amino acid sequence: FRGPLLPNRPFTTVWNANTQWCLER-
HGVDVDVSVFDVVANPGQTFRGPDMTIFYSSQGTY
PYYTPTGEPVFGGLPQNASLIAHLARTFQDILAAI-
PAPDFSGLAVIDWEAWRPRWAFNWDT
KDIYRQRSRALVQAQHPDWPAPQVEAV-
AQDQFQGAARAWMAGTLQLGRALRPRGLWGF
YGFPDCYNYDFLSPNYTGQCPSGI-
RAQNDQLGWLWGQSRALYPSIYMPAVLEGTGKSQM
YVQHRVAEAFRVAVAAGDPNLPVLPYVQI-
FYDTTNHFLPLDELEHSLGESAAQGAAGVVL WVS-
WENTRTKESCQAIKEYMDTTLGP-
FILNVTSGALLCSQALCSGHGRCVRRTSHPKALLL
LNPASFSIQLTPGGGPLSLR-
GALSLEDQAQMAVEFKCRCYPGWQAPWCERKSMW
(SEQ ID NO: 3312), or a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 3312.

In some embodiments, the hyaluronan degrading enzyme, e.g., the hyaluronidase molecule, further comprises a polymer, e.g., is conjugated to a polymer, e.g., PEG. In some embodiments, the hyaluronan-degrading enzyme is a PEGylated PH20 enzyme (PEGPH20). In some embodiments, the hyaluronan degrading enzyme, e.g., the hyaluronidase molecule, further comprises an immunoglobulin chain constant region (e.g., Fc region) chosen from, e.g., the heavy chain constant regions of IgG1, IgG2, IgG3, and IgG4, more particularly, the heavy chain constant region of human IgG1, IgG2, IgG3, or IgG4. In some embodiments, the immunoglobulin constant region (e.g., the Fc region) is linked, e.g., covalently linked to, the hyaluronan degrading enzyme, e.g., the hyaluronidase molecule. In some embodiments, the immunoglobulin chain constant region (e.g., Fc region) is altered, e.g., mutated, to increase or decrease one or more of: Fc receptor binding, antibody glycosylation, the number of cysteine residues, effector cell function, or complement function. In some embodiments, the hyaluronan degrading enzyme, e.g., the hyaluronidase molecule forms a dimer.

In some embodiments, the stromal modifying moiety comprises an inhibitor of the synthesis of hyaluronan, e.g., an HA synthase. In some embodiments, the inhibitor comprises a sense or an antisense nucleic acid molecule against an HA synthase or is a small molecule drug. In some embodiments, the inhibitor is 4-methylumbelliferone (MU) or a derivative thereof (e.g., 6,7-dihydroxy-4-methyl coumarin or 5,7-dihydroxy-4-methyl coumarin), or leflunomide or a derivative thereof.

In some embodiments, the stromal modifying moiety comprises antibody molecule against hyaluronic acid.

In some embodiments, the stromal modifying moiety comprises a collagenase molecule, e.g., a mammalian collagenase molecule, or a variant (e.g., fragment) thereof. In some embodiments, the collagenase molecule is collagenase molecule IV, e.g., comprising the amino acid sequence of: YNFFPRKPKWDKNQITYRIIGYTPDLDPETVDDAFARAFQVWSDVTPLRFSRIHDGEADIMI NFGRWEHGDGYPFDGKDGLLAHAFAPGTGVGGDSHFDDDELWTLGEGQVVRVKYGNAD GEYCKFPFLFNGKEYNSCTDTGRSDGFLWCSTTYNFEKDGKYGFCPHEALFTMGGNAEGQ PCKFPFRFQGTSYDSCTTEGRTDGYRWCGTTEDYDRDKKYGFCPETAMSTVGGNSEGAPC VFPFTFLGNKYESCTSAGRSDGKMWCATTANYDDDRKWGFCPDQGYSLFLVAAHEFGHA MGLEHSQDPGALMAPIYTYTKNFRLSQDDIKGIQELYGASPDIDLGTGPTPTLGPVTPEICK QDIVFDGIAQIRGEIFFFKDRFIWRTVTPRDKPMGPLLVATFWPELPEKIDAVYEAPQEEKA VFFAGNEYWIYSASTLERGYPKPLTSLGLPPDVQRVDAAFNWSKNKKTYIFAGDKFWRYN EVKKKMDPGFPKLIADAWNAIPDNLDAVVDLQGGGHSYFFKGAYYLKLENQSLKSVKFG SIKSDWLGC (SEQ ID NO: 3313), or a fragment thereof, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions) to the amino acid sequence of SEQ ID NO: 3313.

Linkers

The multispecific or multifunctional molecule disclosed herein can further include a linker, e.g., a linker between one or more of: the antigen binding domain and the cytokine molecule, the antigen binding domain and the immune cell engager, the antigen binding domain and the stromal modifying moiety, the cytokine molecule and the immune cell engager, the cytokine molecule and the stromal modifying moiety, the immune cell engager and the stromal modifying moiety, the antigen binding domain and the immunoglobulin chain constant region, the cytokine molecule and the immunoglobulin chain constant region, the immune cell engager and the immunoglobulin chain constant region, or the stromal modifying moiety and the immunoglobulin chain constant region. In embodiments, the linker is chosen from: a cleavable linker, a non-cleavable linker, a peptide linker, a flexible linker, a rigid linker, a helical linker, or a non-helical linker, or a combination thereof.

In one embodiment, the multispecific molecule can include one, two, three or four linkers, e.g., a peptide linker. In one embodiment, the peptide linker includes Gly and Ser. In some embodiments, the peptide linker is selected from GGGGS (SEQ ID NO: 3307); GGGGSGGGGS (SEQ ID NO: 3308); GGGGSGGGGSGGGGS (SEQ ID NO: 3309); and DVPSGPGGGGGSGGGGS (SEQ ID NO: 3310). In some embodiments, the peptide linker is a A(EAAAK)nA (SEQ ID NO: 3437) family of linkers (e.g., as described in Protein Eng. (2001) 14 (8): 529-532). These are stiff helical linkers with n ranging from 2-5. In some embodiments, the peptide linker is selected from AEAAAKEAAAKAAA (SEQ ID NO: 3314); AEAAAKEAAAKEAAAKAAA (SEQ ID NO: 3315); AEAAAKEAAAKEAAAKEAAAKAAA (SEQ ID NO: 3316); and AEAAAKEAAAKEAAAKEAAAKEAAAKAAA(SEQ ID NO: 3317).

Nucleic Acids

Nucleic acids encoding the aforementioned antibody molecules, e.g., anti-TCRβV antibody molecules, multispecific or multifunctional molecules are also disclosed.

In certain embodiments, the invention features nucleic acids comprising nucleotide sequences that encode heavy and light chain variable regions and CDRs or hypervariable loops of the antibody molecules, as described herein. For example, the invention features a first and second nucleic acid encoding heavy and light chain variable regions, respectively, of an antibody molecule chosen from one or more of the antibody molecules disclosed herein. The nucleic acid can comprise a nucleotide sequence as set forth in the tables herein, or a sequence substantially identical thereto (e.g., a sequence at least about 85%, 90%, 95%, 99% or more identical thereto, or which differs by no more than 3, 6, 15, 30, or 45 nucleotides from the sequences shown in the tables herein.

In certain embodiments, the nucleic acid can comprise a nucleotide sequence encoding at least one, two, or three CDRs or hypervariable loops from a heavy chain variable region having an amino acid sequence as set forth in the tables herein, or a sequence substantially homologous thereto (e.g., a sequence at least about 85%, 90%, 95%, 99% or more identical thereto, and/or having one or more substitutions, e.g., conserved substitutions). In other embodiments, the nucleic acid can comprise a nucleotide sequence encoding at least one, two, or three CDRs or hypervariable loops from a light chain variable region having an amino acid sequence as set forth in the tables herein, or a sequence substantially homologous thereto (e.g., a sequence at least about 85%, 90%, 95%, 99% or more identical thereto, and/or having one or more substitutions, e.g., conserved substitutions). In yet another embodiment, the nucleic acid can comprise a nucleotide sequence encoding at least one, two, three, four, five, or six CDRs or hypervariable loops from heavy and light chain variable regions having an amino acid sequence as set forth in the tables herein, or a sequence substantially homologous thereto (e.g., a sequence at least about 85%, 90%, 95%, 99% or more identical thereto, and/or having one or more substitutions, e.g., conserved substitutions).

In certain embodiments, the nucleic acid can comprise a nucleotide sequence encoding at least one, two, or three CDRs or hypervariable loops from a heavy chain variable region having the nucleotide sequence as set forth in the tables herein, a sequence substantially homologous thereto (e.g., a sequence at least about 85%, 90%, 95%, 99% or more identical thereto, and/or capable of hybridizing under the stringency conditions described herein). In another embodiment, the nucleic acid can comprise a nucleotide sequence encoding at least one, two, or three CDRs or hypervariable loops from a light chain variable region having the nucleotide sequence as set forth in the tables herein, or a sequence substantially homologous thereto (e.g., a sequence at least about 85%, 90%, 95%, 99% or more identical thereto, and/or capable of hybridizing under the stringency conditions described herein). In yet another embodiment, the nucleic acid can comprise a nucleotide sequence encoding at least one, two, three, four, five, or six CDRs or hypervariable loops from heavy and light chain variable regions having the nucleotide sequence as set forth in the tables herein, or a sequence substantially homologous thereto (e.g., a sequence at least about 85%, 90%, 95%, 99% or more identical thereto, and/or capable of hybridizing under the stringency conditions described herein).

In certain embodiments, the nucleic acid can comprise a nucleotide sequence encoding a cytokine molecule, an immune cell engager, or a stromal modifying moiety disclosed herein.

In another aspect, the application features host cells and vectors containing the nucleic acids described herein. The nucleic acids may be present in a single vector or separate vectors present in the same host cell or separate host cell, as described in more detail hereinbelow.

Vectors

Further provided herein are vectors comprising the nucleotide sequences encoding antibody molecules, e.g., anti-TCRβV antibody molecules, or a multispecific or multifunctional molecule described herein. In one embodiment, the vectors comprise nucleic acid sequences encoding antibody molecules, e.g., anti-TCRβV antibody molecules, or multispecific or multifunctional molecule described herein. In one embodiment, the vectors comprise the nucleotide sequences described herein. The vectors include, but are not limited to, a virus, plasmid, cosmid, lambda phage or a yeast artificial chromosome (YAC).

Numerous vector systems can be employed. For example, one class of vectors utilizes DNA elements which are derived from animal viruses such as, for example, bovine papilloma virus, polyoma virus, adenovirus, vaccinia virus, baculovirus, retroviruses (Rous Sarcoma Virus, MMTV or MOMLV) or SV40 virus. Another class of vectors utilizes RNA elements derived from RNA viruses such as Semliki Forest virus, Eastern Equine Encephalitis virus and Flaviviruses.

Additionally, cells which have stably integrated the DNA into their chromosomes may be selected by introducing one or more markers which allow for the selection of transfected host cells. The marker may provide, for example, prototropy to an auxotrophic host, biocide resistance (e.g., antibiotics), or resistance to heavy metals such as copper, or the like. The selectable marker gene can be either directly linked to the DNA sequences to be expressed, or introduced into the same cell by cotransformation. Additional elements may also be needed for optimal synthesis of mRNA. These elements may include splice signals, as well as transcriptional promoters, enhancers, and termination signals.

Once the expression vector or DNA sequence containing the constructs has been prepared for expression, the expression vectors may be transfected or introduced into an appropriate host cell. Various techniques may be employed to achieve this, such as, for example, protoplast fusion, calcium phosphate precipitation, electroporation, retroviral transduction, viral transfection, gene gun, lipid based transfection or other conventional techniques. In the case of protoplast fusion, the cells are grown in media and screened for the appropriate activity Methods and conditions for culturing the resulting transfected cells and for recovering the antibody molecule produced are known to those skilled in the art, and may be varied or optimized depending upon the specific expression vector and mammalian host cell employed, based upon the present description.

Cells

In another aspect, the application features host cells and vectors containing the nucleic acids described herein. The nucleic acids may be present in a single vector or separate vectors present in the same host cell or separate host cell. The host cell can be a eukaryotic cell, e.g., a mammalian cell, an insect cell, a yeast cell, or a prokaryotic cell, e.g., *E. coli*. For example, the mammalian cell can be a cultured cell or a cell line. Exemplary mammalian cells include lymphocytic cell lines (e.g., NSO), Chinese hamster ovary cells (CHO), COS cells, oocyte cells, and cells from a transgenic animal, e.g., mammary epithelial cell.

The invention also provides host cells comprising a nucleic acid encoding an antibody molecule as described herein.

In one embodiment, the host cells are genetically engineered to comprise nucleic acids encoding the antibody molecule.

In one embodiment, the host cells are genetically engineered by using an expression cassette. The phrase "expression cassette," refers to nucleotide sequences, which are capable of affecting expression of a gene in hosts compatible with such sequences. Such cassettes may include a promoter, an open reading frame with or without introns, and a termination signal. Additional factors necessary or helpful in effecting expression may also be used, such as, for example, an inducible promoter.

The invention also provides host cells comprising the vectors described herein.

The cell can be, but is not limited to, a eukaryotic cell, a bacterial cell, an insect cell, or a human cell. Suitable eukaryotic cells include, but are not limited to, Vero cells, HeLa cells, COS cells, CHO cells, HEK293 cells, BHK cells and MDCKII cells. Suitable insect cells include, but are not limited to, Sf9 cells.

Method of Expanding Cells with Anti-TCRVB Antibodies

Any of the compositions and methods described herein can be used to expand an immune cell population. An immune cell provided herein includes an immune cell derived from a hematopoietic stem cell or an immune cell derived from a non-hematopoietic stem cell, e.g., by differentiation or de-differentiation.

An immune cell includes a hematopoietic stem cell, progeny thereof and/or cells that have differentiated from said HSC, e.g., lymphoid cells or myeloid cells. An immune cell can be an adaptive immune cell or an innate immune cell. Examples of immune cells include T cells, B cells, Natural Killer cells, Natural Killer T cells, neutrophils, dendritic cells, monocytes, macrophages, and granulocytes.

In some embodiments of any of the methods of compositions disclosed herein, an immune cell is a T cell. In some embodiments, a T cell includes a CD4+ T cell, a CD8+ T cell, a TCR alpha-beta T cell, a TCR gamma-delta T cell. In some embodiments, a T cell comprises a memory T cell (e.g., a central memory T cell, or an effector memory T cell (e.g., a TEMRA) or an effector T cell. In some embodiments, a T cell comprises a tumor infiltrating lymphocyte (TIL).

In some embodiments of any of the methods of compositions disclosed herein, an immune cell is an NK cell.

In some embodiments of any of the methods of compositions disclosed herein, an immune cell is a TIL. TILs are immune cells (e.g., T cells, B cells or NK cells) that can be found in a tumor or around a tumor (e.g., in the stroma or tumor microenvironment of a tumor), e.g., a solid tumor, e.g., as described herein. TILs can be obtained from a sample from a subject having cancer, e.g., a biopsy or a surgical sample. In some embodiments, TILs can be expanded using a method disclosed herein. In some embodiments, a population of expanded TILs, e.g., expanded using a method disclosed herein, can be administered to a subject to treat a disease, e.g., a cancer.

In certain aspects of the present disclosure, immune cells, e.g., T cells (e.g., TILs), can be obtained from a unit of blood collected from a subject using any number of techniques known to the skilled artisan, such as Ficoll™ separation. In one aspect, cells from the circulating blood of an individual are obtained by apheresis. The apheresis product typically contains lymphocytes, including T cells, monocytes, granulocytes, B cells, other nucleated white blood cells, red blood cells, and platelets. In one aspect, the cells collected by apheresis may be washed to remove the plasma fraction and, optionally, to place the cells in an appropriate buffer or media for subsequent processing steps. In one embodiment, the cells are washed with phosphate buffered saline (PBS). In an alternative embodiment, the wash solution lacks calcium and may lack magnesium or may lack many if not all divalent cations. The methods described herein can include more than one selection step, e.g., more than one depletion step.

In one embodiment, the methods of the application can utilize culture media conditions comprising DMEM, DMEM F12, RPMI 1640, and/or AIM V media. The media can be supplemented with glutamine, HEPES buffer (e.g., 10 mM), serum (e.g., heat-inactivated serum, e.g., 10%), and/or beta mercaptoethanol (e.g., 55 uM). IN some embodiments, the culture conditions disclosed herein comprise one or more supplements, cytokines, growth factors, or hormones. In some embodiments, the culture condition comprises one or more of IL-2, IL-15, or IL-7, or a combination thereof.

Immune effector cells such as T cells may be activated and expanded generally using methods as described, for example, in U.S. Pat. Nos. 6,352,694; 6,534,055; or 6,905, 680. Generally, a population of immune cells, may be expanded by contact with an agent that stimulates a CD3/TCR complex associated signal and a ligand that stimulates a costimulatory molecule on the surface of the T cells; and/or by contact with a cytokine, e.g., IL-2, IL-15 or IL-7. T cell expansion protocols can also include stimulation, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For example, a population of T cells can be contacted with an anti-CD3 antibody and an anti-CD28 antibody, under conditions appropriate for stimulating proliferation of the T cells. To stimulate proliferation of either CD4+ T cells or CD8+ T cells, an anti-CD3 antibody and an anti-CD28 antibody can be used. Examples of an anti-CD28 antibody include 9.3, B-T3, XR-CD28 (Diaclone, Besançon, France) can be used as can other methods commonly known in the art (Berg et al., Transplant Proc. 30(8):3975-3977, 1998; Haanen et al., J. Exp. Med. 190(9):13191328, 1999; Garland et al., J. Immunol Meth. 227(1-2):53-63, 1999).

A TIL population can also be expanded by methods known in the art. For example, a population of TILs can be expanded as described in Hall et al., *Journal for ImmunoTherapy of Cancer* (2016) 4:61, the entire contents of which are hereby incorporated by reference. Briefly, TILs can be isolated from a sample by mechanical and/or physical digestion. The resultant TIL population can be stimulated with an anti-CD3 antibody in the presence of non-dividing feeder cells. In some embodiments, the TIL population can be cultured, e.g., expanded, in the presence of IL-2, e.g., human IL-2. In some embodiments, the TIL cells can be cultured, e.g., expanded for a period of at least 1-21 days, e.g., at least 1, 2, 3, 4, 5, 6, 7, 8, 9, 10, 11, 12, 13, 14, 15, 16, 17, 18, 19, 20 or 21 days.

As disclosed herein, in some embodiments, an immune cell population (e.g., a T cell (e.g., a TEMRA cell or a TIL population) can be expanded by contacting the immune cell population with an anti-TCRVB antibody, e.g., as described herein.

In some embodiments, the expansion occurs in vivo, e.g., in a subject. In some embodiments, a subject is administered an anti-TCRβV antibody molecule disclosed herein resulting in expansion of immune cells in vivo.

In some embodiments, the expansion occurs ex vivo, e.g., in vitro. In some embodiments, cells from a subject, e.g., T cells, e.g., TIL cells, are expanded in vitro with an anti-TCRβV antibody molecule disclosed herein. In some embodiments, the expanded TILs are administered to the subject to treat a disease or a symptom of a disease.

In some embodiments, a method of expansion disclosed herein results in an expansion of at least 1.1-10 fold, 10-20 fold, or 20-50 fold expansion. In some embodiments, the expansion is at least 1.1, 1.2, 1.3, 1.4, 1.5, 2, 3, 4, 5, 6, 7, 8, 9, 10, 15, 20, 25, 30, 35, 40, 45 or 50 fold expansion.

In some embodiments, a method of expansion disclosed herein comprises culturing, e.g., expanding, the cells for at least about 4 hours, 6 hours, 10 hours, 12 hours, 15 hours, 18 hours, 20 hours, or 22 hours. In some embodiments, a method of expansion disclosed herein comprises culturing, e.g., expanding, the cells for at least 1, 2, 3, 4, 5, 6, 7, 8, 9, 10, 11, 12, 13, 14, 15, 1, 6 17, 18, 19, 20 or 21 days. In some embodiments, a method of expansion disclosed herein comprises culturing, e.g., expanding, the cells for at least about 1 week, 2 weeks, 3 weeks, 4 weeks, 5 weeks, 6 weeks, 7 weeks or 8 weeks.

In some embodiments, a method of expansion disclosed herein is performed on immune cells obtained from a healthy subject.

In some embodiments, a method of expansion disclosed herein is performed on immune cells (e.g., TILs) obtained from a subject having a disease, e.g., a cancer, e.g., a solid tumor as disclosed herein.

In some embodiments, a method of expansion disclosed herein further comprises contacting the population of cells with an agent, that promotes, e.g., increases, immune cell expansion. In some embodiments, the agent comprises an immune checkpoint inhibitor, e.g., a PD-1 inhibitor, a LAG-3 inhibitor, a CTLA4 inhibitor, or a TIM-3 inhibitor. In some embodiments, the agent comprises a 4-1BB agonist, e.g., an anti-4-1BB antibody.

Without wishing to be bound by theory, it is believed that an anti-TCRβV antibody molecule disclosed herein can expand, e.g., selectively or preferentially expand, T cells expressing a T cell receptor (TCR) comprising a TCR alpha and/or TCR beta molecule, e.g., TCR alpha-beta T cells (αβ T cells). In some embodiments, an anti-TCRβV antibody molecule disclosed herein does not expand, or induce proliferation of T cells expressing a TCR comprising a TCR gamma and/or TCR delta molecule, e.g., TCR gamma-delta T cells (γδ T cells). In some embodiments, an anti-TCRβV antibody molecule disclosed herein, selectively or preferentially expands αβ T cells over γδ T cells.

Without wishing to be bound by theory, it is believed that, in some embodiments, γδ T cells are associated with cytokine release syndrome (CRS) and/or neurotoxicity (NT). In some embodiments, an anti-TCRβV antibody molecule disclosed herein results in selective expansion of non-γδ T cells, e.g., expansion of αβ T cells, thus reducing CRS and/or NT.

In some embodiments, any of the compositions or methods disclosed herein result in an immune cell population having a reduction of, e.g., depletion of, γδ T cells. In some embodiments, the immune cell population is contacted with an agent that reduces, e.g., inhibits or depletes, γδ T cells, e.g., an anti-IL-17 antibody or an agent that binds to a TCR gamma and/or TCR delta molecule.

Uses and Combination Therapies

Methods described herein include treating a cancer in a subject by using an anti-TCRβV antibody molecule, a multispecific or multifunctional molecule described herein, e.g., using a pharmaceutical composition described herein. Also provided are methods for reducing or ameliorating a symptom of a cancer in a subject, as well as methods for inhibiting the growth of a cancer and/or killing one or more cancer cells. In embodiments, the methods described herein decrease the size of a tumor and/or decrease the number of cancer cells in a subject administered with a described herein or a pharmaceutical composition described herein.

In embodiments, the cancer is a hematological cancer. In embodiments, the hematological cancer is a leukemia or a lymphoma. As used herein, a "hematologic cancer" refers to a tumor of the hematopoietic or lymphoid tissues, e.g., a tumor that affects blood, bone marrow, or lymph nodes. Exemplary hematologic malignancies include, but are not limited to, leukemia (e.g., acute lymphoblastic leukemia (ALL), acute myeloid leukemia (AML), chronic lymphocytic leukemia (CLL), chronic myelogenous leukemia (CML), hairy cell leukemia, acute monocytic leukemia (AMoL), chronic myelomonocytic leukemia (CMML), juvenile myelomonocytic leukemia (JMML), or large granular lymphocytic leukemia), lymphoma (e.g., AIDS-related lymphoma, cutaneous T-cell lymphoma, Hodgkin lymphoma (e.g., classical Hodgkin lymphoma or nodular lymphocyte-predominant Hodgkin lymphoma), mycosis fungoides, non-Hodgkin lymphoma (e.g., B-cell non-Hodgkin lymphoma (e.g., Burkitt lymphoma, small lymphocytic lymphoma (CLL/SLL), diffuse large B-cell lymphoma, follicular lymphoma, immunoblastic large cell lymphoma, precursor B-lymphoblastic lymphoma, or mantle cell lymphoma) or T-cell non-Hodgkin lymphoma (mycosis fungoides, anaplastic large cell lymphoma, or precursor T-lymphoblastic lymphoma)), primary central nervous system lymphoma, Sezary syndrome, Waldenstrom macroglobulinemia), chronic myeloproliferative neoplasm, Langerhans cell histiocytosis, multiple myeloma/plasma cell neoplasm, myelodysplastic syndrome, or myelodysplastic/myeloproliferative neoplasm.

In embodiments, the cancer is a myeloproliferative neoplasm, e.g., primary or idiopathic myelofibrosis (MF), essential thrombocytosis (ET), polycythemia vera (PV), or chronic myelogenous leukemia (CML). In embodiments, the cancer is myelofibrosis. In embodiments, the subject has myelofibrosis. In embodiments, the subject has a calreticulin mutation, e.g., a calreticulin mutation disclosed herein. In embodiments, the subject does not have the JAK2-V617F mutation. In embodiments, the subject has the JAK2-V617F mutation. In embodiments, the subject has a MPL mutation. In embodiments, the subject does not have a MPL mutation.

In embodiments, the cancer is a solid cancer. Exemplary solid cancers include, but are not limited to, ovarian cancer, rectal cancer, stomach cancer, testicular cancer, cancer of the anal region, uterine cancer, colon cancer, rectal cancer, renal-cell carcinoma, liver cancer, non-small cell carcinoma of the lung, cancer of the small intestine, cancer of the esophagus, melanoma, Kaposi's sarcoma, cancer of the endocrine system, cancer of the thyroid gland, cancer of the parathyroid gland, cancer of the adrenal gland, bone cancer, pancreatic cancer, skin cancer, cancer of the head or neck, cutaneous or intraocular malignant melanoma, uterine cancer, brain stem glioma, pituitary adenoma, epidermoid cancer, carcinoma of the cervix squamous cell cancer, carcinoma of the fallopian tubes, carcinoma of the endometrium, carcinoma of the vagina, sarcoma of soft tissue, cancer of the urethra, carcinoma of the vulva, cancer of the penis, cancer of the bladder, cancer of the kidney or ureter, carcinoma of the renal pelvis, spinal axis tumor, neoplasm of the central nervous system (CNS), primary CNS lymphoma, tumor angiogenesis, metastatic lesions of said cancers, or combinations thereof.

In some embodiments, the cancer is acute lymphoblastic leukemia, acute lymphocytic leukemia, acute myelogenous leukemia, aplastic anemia, chronic myelogenous leukemia, desmoplastic small round cell tumor, Ewing's sarcoma, Hodgkin's disease, multiple myeloma, myelodysplasia, Non-Hodgkin's lymphoma, paroxysmal nocturnal hemoglobinuria, radiation poisoning, chronic lymphocytic leukemia, AL amyloidosis, essential thrombocytosis, polycythemia vera, severe aplastic anemia, neuroblastoma, breast tumors, ovarian tumors, renal cell carcinoma, autoimmune disorders, such as systemic sclerosis, osteopetrosis, inherited metabolic disorders, juvenile chronic arthritis, adrenoleukodystrophy, amegakaryocytic thrombocytopenia, sickle cell disease, severe congenital immunodeficiency, Griscelli syndrome type IL, Hurler syndrome, Kostmann syndrome, Krabbe disease, metachromatic leukodystrophy, thalassemia, hemophagocytic lymphohistiocytosis, and Wiskott-Aldrich syndrome, leukemias, lymphomas, melanomas, neuroendocrine tumors, carcinomas and sarcomas. Exemplary cancers that may be treated with a compound, pharmaceutical composition, or method provided herein include lymphoma, sarcoma, bladder cancer, bone cancer, brain tumor, cervical cancer, colon cancer, esophageal cancer, gastric cancer, head and neck cancer, kidney cancer, myeloma, thyroid cancer, leukemia, prostate cancer, breast cancer (e.g. triple negative, ER positive, ER negative, chemotherapy resistant, herceptin resistant, HER2 positive, doxorubicin resistant, tamoxifen resistant, ductal carcinoma, lobular carcinoma, primary, metastatic), ovarian cancer, pancreatic cancer, liver cancer (e.g., hepatocellular carcinoma), lung cancer (e.g. non-small cell lung carcinoma, squamous cell lung carcinoma, adenocarcinoma, large cell lung carcinoma, small cell lung carcinoma, carcinoid, sarcoma), glioblastoma multiforme, glioma, melanoma, prostate cancer, castration-resistant prostate cancer, breast cancer, triple negative breast cancer, glioblastoma, ovarian cancer, lung cancer, squamous cell carcinoma (e.g., head, neck, or esophagus), colorectal cancer, leukemia, acute myeloid leukemia, lymphoma, B cell lymphoma, or multiple myeloma. Additional examples include, cancer of the thyroid, endocrine system, brain, breast, cervix, colon, head & neck, esophagus, liver, kidney, lung, non-small cell lung, melanoma, mesothelioma, ovary, sarcoma, stomach, uterus or Medulloblastoma, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, Paget's Disease of the Nipple, Phyllodes Tumors, Lobular Carcinoma, Ductal Carcinoma, cancer of the pancreatic stellate cells, cancer of the hepatic stellate cells, or prostate cancer. In some embodiments, the cancer is a solid tumor. In some embodiments, the cancer is hematological.

In embodiments, the anti-TCRβV antibody molecule, multispecific or multifunctional molecules (or pharmaceutical composition) are administered in a manner appropriate to the disease to be treated or prevented. The quantity and frequency of administration will be determined by such factors as the condition of the patient, and the type and severity of the patient's disease. Appropriate dosages may be determined by clinical trials. For example, when "an effective amount" or "a therapeutic amount" is indicated, the precise amount of the pharmaceutical composition (or multispecific or multifunctional molecules) to be administered can be determined by a physician with consideration of individual differences in tumor size, extent of infection or metastasis, age, weight, and condition of the subject. In embodiments, the pharmaceutical composition described herein can be administered at a dosage of $10^4$ to $10^9$ cells/kg body weight, e.g., $10^5$ to $10^6$ cells/kg body weight, including all integer values within those ranges. In embodiments, the pharmaceutical composition described herein can be administered multiple times at these dosages. In embodiments, the pharmaceutical composition described herein can be administered using infusion techniques described in immunotherapy (see, e.g., Rosenberg et al., New Eng. J. of Med. 319:1676, 1988).

In embodiments, the anti-TCRβV antibody molecule, multispecific or multifunctional molecules or pharmaceutical composition is administered to the subject parentally. In embodiments, the cells are administered to the subject intravenously, subcutaneously, intratumorally, intranodally, intramuscularly, intradermally, or intraperitoneally. In embodiments, the cells are administered, e.g., injected, directly into a tumor or lymph node. In embodiments, the cells are administered as an infusion (e.g., as described in Rosenberg et al., New Eng. J. of Med. 319:1676, 1988) or an intravenous push. In embodiments, the cells are administered as an injectable depot formulation.

In embodiments, the subject is a mammal. In embodiments, the subject is a human, monkey, pig, dog, cat, cow, sheep, goat, rabbit, rat, or mouse. In embodiments, the subject is a human. In embodiments, the subject is a pediatric subject, e.g., less than 18 years of age, e.g., less than 17, 16, 15, 14, 13, 12, 11, 10, 9, 8, 7, 6, 5, 4, 3, 2, 1 or less years of age. In embodiments, the subject is an adult, e.g., at least 18 years of age, e.g., at least 19, 20, 21, 22, 23, 24, 25, 25-30, 30-35, 35-40, 40-50, 50-60, 60-70, 70-80, or 80-90 years of age.

Methods of Cancer Treatment

Methods described herein include treating a cancer in a subject by using an anti-TCRBV antibody molecule, e.g., using a pharmaceutical composition described herein. Also provided are methods for reducing or ameliorating a symptom of a cancer in a subject, as well as methods for inhibiting the growth of a cancer and/or killing one or more cancer cells. In embodiments, the methods described herein decrease the size of a tumor and/or decrease the number of cancer cells in a subject administered with a described herein or a pharmaceutical composition described herein.

Disclosed herein are methods of treating a subject having a cancer comprising acquiring a status of one or more TCRBV molecules in a subject. In some embodiments, a higher, e.g., increased, level or activity of one or more TCRBV molecules in a subject, e.g., in a sample from a subject, is indicative of a bias, e.g., a preferential expansion, e.g., clonal expansion, of T cells expressing said one or more TCRBV molecules in the subject.

Without wishing to be bound by theory, it is believed that a biased T cell population, e.g., a T cell population expressing a TCRβV molecule, is antigen-specific for a disease antigen, e.g., a cancer antigen (Wang C Y, et al., *Int J Oncol.* (2016) 48(6):2247-56). In some embodiments, the cancer antigen comprises a cancer associated antigen or a neoantigen. In some embodiments, a subject having a cancer, e.g., as disclosed herein, has a higher, e.g., increased, level or activity of one or more TCRβV molecules associated with the cancer. In some embodiments, the TCRβV molecule is associated with, e.g., recognizes, a cancer antigen, e.g., a cancer associated antigen or a neoantigen.

Accordingly, disclosed herein are methods of expanding an immune effector cell population obtained from a subject, comprising acquiring a status of one or more TCRβV molecules in a sample from the subject, comprising contacting said immune effector cell population with an anti-TCRβV antibody molecule disclosed herein, e.g., an anti-TCRβV antibody molecule that binds to the same TCRβV molecule that is higher, e.g., increased in the immune effector cell population in the sample from the subject. In some embodiments, contacting the population of immune effector cells (e.g., comprising T cells that express one or more TCRβV molecules) with an anti-TCRβV molecule results in expansion of the population of immune effector cells expressing one or more TCRβV molecules. In some embodiments, the expanded population, or a portion thereof, is administered to the subject (e.g., same subject from whom the immune effector cell population was obtained), to treat the cancer. In some embodiments, the expanded population, or a portion thereof, is administered to a different subject (e.g., not the same subject from whom the immune effector cell population was obtained), to treat the cancer.

Also disclosed herein, are methods of treating a subject having a cancer, comprising: acquiring a status of one or more TCRβV molecules in a sample from the subject, and determining whether the one or more TCRβV molecules is higher, e.g., increased, in a sample from the subject compared to a reference value, wherein responsive to said determination, administering to the subject an effective amount of an anti-TCRβV antibody molecule, e.g., an agonistic anti-TCRβV antibody molecule, e.g., as described herein.

In some embodiments of any of the methods or composition for use disclosed herein, the subject has B-CLL. In some embodiments, a subject having B-CLL has a higher, e.g., increased, level or activity of one or more TCRβV molecules, e.g., one or more TCRβV molecules comprising: (i) TCRβ V6 subfamily comprising, e.g., TCRβ V6-4*01, TCRβ V6-4*02, TCRβ V6-9*01, TCRβ V6-8*01, TCRβ V6-5*01, TCRβ V6-6*02, TCRβ V6-6*01, TCRβ V6-2*01, TCRβ V6-3*01 or TCRβ V6-1*01; (ii) TCRβ V5 subfamily comprising TCRβ V5-6*01, TCRβ V5-4*01, or TCRβ V5-8*01; (iii) TCRβ V3 subfamily comprising TCRβ V3-1*01; (iv) TCRβ V2 subfamily comprising TCRβ V2*01; or (v) TCRβ V19 subfamily comprising TCRβ V19*01, or TCRβ V19*02.

In some embodiments, a subject having B-CLL has a higher, e.g., increased, level or activity of a TCRβ V6 subfamily comprising, e.g., TCRβ V6-4*01, TCRβ V6-4*02, TCRβ V6-9*01, TCRβ V6-8*01, TCRβ V6-5*01, TCRβ V6-6*02, TCRβ V6-6*01, TCRβ V6-2*01, TCRβ V6-3*01 or TCRβ V6-1*01. In some embodiments, the subject is administered an anti-TCRβV molecule (e.g., an agonistic anti-TCRβV molecule as described herein) that binds to one or more members of the TCRβ V6 subfamily. In some embodiments, administration of the an anti-TCRβV molecule results in expansion of immune cells expressing one or more members of the TCRβ V6 subfamily.

In some embodiments, a subject having B-CLL has a higher, e.g., increased, level or activity of a TCRβ V5 subfamily comprising TCRβ V5-6*01, TCRβ V5-4*01, or TCRβ V5-8*01. In some embodiments, the subject is administered an anti-TCRβV molecule (e.g., an agonistic anti-TCRβV molecule as described herein) that binds to one or more members of the TCRβ V5 subfamily. In some embodiments, administration of the an anti-TCRβV molecule results in expansion of immune cells expressing one or more members of the TCRβ V5 subfamily.

In some embodiments, a subject having B-CLL has a higher, e.g., increased, level or activity of a TCRβ V3 subfamily comprising TCRβ V3-1*01. In some embodiments, the subject is administered an anti-TCRβV molecule (e.g., an agonistic anti-TCRβV molecule as described herein) that binds to one or more members of the TCRβ V3 subfamily. In some embodiments, administration of the an anti-TCRβV molecule results in expansion of immune cells expressing one or more members of the TCRβ V3 subfamily.

In some embodiments, a subject having B-CLL has a higher, e.g., increased, level or activity of a TCRβ V2 subfamily comprising TCRβ V2*01. In some embodiments, the subject is administered an anti-TCRβV molecule (e.g., an agonistic anti-TCRβV molecule as described herein) that binds to one or more members of the TCRβ V2 subfamily. In some embodiments, administration of the an anti-TCRβV molecule results in expansion of immune cells expressing one or more members of the TCRβ V2 subfamily.

In some embodiments, a subject having B-CLL has a higher, e.g., increased, level or activity of a TCRβ V19 subfamily comprising TCRβ V19*01, or TCRβ V19*02. In some embodiments, the subject is administered an anti-TCRβV molecule (e.g., an agonistic anti-TCRBV molecule as described herein) that binds to one or more members of the TCRβ V19 subfamily. In some embodiments, administration of the an anti-TCRβV molecule results in expansion of immune cells expressing one or more members of the TCRβ V19 subfamily.

In some embodiments of any of the methods or composition for use disclosed herein, the subject has melanoma. In some embodiments, a subject having melanoma has a higher, e.g., increased, level or activity of one or more TCRβV molecules, e.g., one or more TCRβV molecules comprising the TCRβ V6 subfamily comprising, e.g., TCRβ V6-4*01, TCRβ V6-4*02, TCRβ V6-9*01, TCRβ V6-8*01, TCRβ V6-5*01, TCRβ V6-6*02, TCRβ V6-6*01, TCRβ V6-2*01, TCRβ V6-3*01 or TCRβ V6-1*01. In some embodiments, the subject is administered an anti-TCRβV molecule (e.g., an agonistic anti-TCRβV molecule as described herein) that binds to one or more members of the TCRβ V6 subfamily. In some embodiments, administration of the an anti-TCRβV molecule results in expansion of immune cells expressing one or more members of the TCRβ V6 subfamily.

In some embodiments of any of the methods or composition for use disclosed herein, the subject has DLBCL. In some embodiments, a subject having melanoma has a higher, e.g., increased, level or activity of one or more TCRβV molecules, e.g., one or more TCRβV molecules comprising: (i) TCRβ V13 subfamily comprising TCRβ V13*01; (ii) TCRβ V3 subfamily comprising TCRβ V3-1*01; or (iii) TCRβ V23 subfamily.

In some embodiments, a subject having DLBCL has a higher, e.g., increased, level or activity of a TCRβ V13 subfamily comprising TCRβ V13*01. In some embodiments, the subject is administered an anti-TCRβV molecule (e.g., an agonistic anti-TCRβV molecule as described herein) that binds to one or more members of the TCRβ V13 subfamily. In some embodiments, administration of the an anti-TCRβV molecule results in expansion of immune cells expressing one or more members of the TCRβ V13 subfamily.

In some embodiments, a subject having DLBCL has a higher, e.g., increased, level or activity of a TCRβ V3 subfamily comprising TCRβ V3-1*01. In some embodiments, the subject is administered an anti-TCRβV molecule (e.g., an agonistic anti-TCRβV molecule as described herein) that binds to one or more members of the TCRβ V3 subfamily. In some embodiments, administration of the an anti-TCRβV molecule results in expansion of immune cells expressing one or more members of the TCRβ V3 subfamily.

In some embodiments, a subject having DLBCL has a higher, e.g., increased, level or activity of a TCRβ V23 subfamily. In some embodiments, the subject is administered an anti-TCRβV molecule (e.g., an agonistic anti-TCRβV molecule as described herein) that binds to one or more members of the TCRβ V23 subfamily. In some embodiments, administration of the an anti-TCRβV molecule results in expansion of immune cells expressing one or more members of the TCRβ V23 subfamily.

In some embodiments of any of the methods or composition for use disclosed herein, the subject has CRC. In some embodiments, a subject having melanoma has a higher, e.g., increased, level or activity of one or more TCRβV molecules, e.g., one or more TCRβV molecules comprising: (i) TCRβ V19 subfamily comprising TCRβ V19*01, or TCRβ V19*02; (ii) TCRβ V12 subfamily comprising TCRβ V12-4*01, TCRβ V12-3*01, or TCRβ V12-5*01; (iii) TCRβ V16 subfamily comprising TCRβ V16*01; or (iv) TCRβ V21 subfamily.

In some embodiments, a subject having CRC has a higher, e.g., increased, level or activity of a TCRβ V19 subfamily comprising TCRβ V19*01, or TCRβ V19*02. In some embodiments, the subject is administered an anti-TCRβV molecule (e.g., an agonistic anti-TCRβV molecule as described herein) that binds to one or more members of the TCRβ V19 subfamily. In some embodiments, administration of the an anti-TCRβV molecule results in expansion of immune cells expressing one or more members of the TCRβ V19 subfamily.

In some embodiments, a subject having CRC has a higher, e.g., increased, level or activity of a TCRβ V12 subfamily comprising TCRβ V12-4*01, TCRβ V12-3*01, or TCRβ V12-5*01. In some embodiments, the subject is administered an anti-TCRβV molecule (e.g., an agonistic anti-TCRβV molecule as described herein) that binds to one or more members of the TCRβ V12 subfamily. In some embodiments, administration of the an anti-TCRβV molecule results in expansion of immune cells expressing one or more members of the TCRβ V12 subfamily.

In some embodiments, a subject having CRC has a higher, e.g., increased, level or activity of a TCRβ V16 subfamily comprising TCRβ V16*01. In some embodiments, the subject is administered an anti-TCRβV molecule (e.g., an agonistic anti-TCRβV molecule as described herein) that binds to one or more members of the TCRβ V16 subfamily. In some embodiments, administration of the an anti-TCRβV molecule results in expansion of immune cells expressing one or more members of the TCRβ V16 subfamily.

In some embodiments, a subject having CRC has a higher, e.g., increased, level or activity of a TCRβ V21 subfamily. In some embodiments, the subject is administered an anti-TCRβV molecule (e.g., an agonistic anti-TCRβV molecule as described herein) that binds to one or more members of the TCRβ V21 subfamily. In some embodiments, administration of the an anti-TCRβV molecule results in expansion of immune cells expressing one or more members of the TCRβ V21 subfamily.

In some embodiments, acquiring a value for the status, e.g., presence, level and/or activity, of one or more TCRβV molecules comprises acquiring a measure of the T cell receptor (TCR) repertoire of a sample. In some embodiments, the value comprises a measure of the clonotype of a population of T cells in the sample.

In some embodiments, a value for the status of one or more TCRβV molecules is obtained, e.g., measured, using an assay described in Wang C Y, et al., *Int J Oncol.* (2016) 48(6):2247-56, the entire contents of which are hereby incorporated by reference.

In some embodiments, a value for the status of one or more TCRβV molecules is obtained, e.g., measured, using flow cytometry.

Combination Therapies

The anti-TCRβV antibody molecule, multispecific or multifunctional molecules disclosed herein can be used in combination with a second therapeutic agent or procedure.

In embodiments, the anti-TCRβV antibody molecule, multispecific or multifunctional molecule and the second therapeutic agent or procedure are administered/performed after a subject has been diagnosed with a cancer, e.g., before the cancer has been eliminated from the subject. In embodiments, the anti-TCRβV antibody molecule, multispecific or multifunctional molecule and the second therapeutic agent or procedure are administered/performed simultaneously or concurrently. For example, the delivery of one treatment is still occurring when the delivery of the second commences, e.g., there is an overlap in administration of the treatments. In other embodiments, the anti-TCRβV antibody molecule, multispecific or multifunctional molecule and the second therapeutic agent or procedure are administered/performed sequentially. For example, the delivery of one treatment ceases before the delivery of the other treatment begins.

In embodiments, combination therapy can lead to more effective treatment than monotherapy with either agent alone. In embodiments, the combination of the first and second treatment is more effective (e.g., leads to a greater reduction in symptoms and/or cancer cells) than the first or second treatment alone. In embodiments, the combination therapy permits use of a lower dose of the first or the second treatment compared to the dose of the first or second treatment normally required to achieve similar effects when administered as a monotherapy. In embodiments, the combination therapy has a partially additive effect, wholly additive effect, or greater than additive effect.

In one embodiment, the anti-TCRBV antibody, multispecific or multifunctional molecule is administered in combination with a therapy, e.g., a cancer therapy (e.g., one or more of anti-cancer agents, immunotherapy, photodynamic therapy (PDT), surgery and/or radiation). The terms "chemotherapeutic," "chemotherapeutic agent," and "anti-cancer agent" are used interchangeably herein. The administration of the multispecific or multifunctional molecule and the therapy, e.g., the cancer therapy, can be sequential (with or without overlap) or simultaneous. Administration of the anti-TCRBV antibody, multispecific or multifunctional molecule can be continuous or intermittent during the course of therapy (e.g., cancer therapy). Certain therapies described herein can be used to treat cancers and non-cancerous diseases. For example, PDT efficacy can be enhanced in cancerous and non-cancerous conditions (e.g., tuberculosis) using the methods and compositions described herein (reviewed in, e.g., Agostinis, P. et al. (2011) *C A Cancer J. Clin.* 61:250-281).

Anti-Cancer Therapies

In other embodiments, the anti-TCRβV antibody molecule, multispecific or multifunctional molecule is administered in combination with a low or small molecular weight chemotherapeutic agent. Exemplary low or small molecular weight chemotherapeutic agents include, but not limited to, 13-cis-retinoic acid (isotretinoin, ACCUTANE®), 2-CdA (2-chlorodeoxyadenosine, cladribine, LEUSTATIN™), 5-azacitidine (azacitidine, VIDAZA®), 5-fluorouracil (5-FU, fluorouracil, ADRUCIL®), 6-mercaptopurine (6-MP, mercaptopurine, PURINETHOL®), 6-TG (6-thioguanine, thioguanine, THIOGUANINE TABLOID®), abraxane (paclitaxel protein-bound), actinomycin-D (dactinomycin, COSMEGEN®), alitretinoin (PANRETIN®), all-trans-retinoic acid (ATRA, tretinoin, VESANOID®), altretamine (hexamethylmelamine, HMM, HEXALEN®), amethopterin (methotrexate, methotrexate sodium, MTX, TREXALL™, RHEUMATREX®), amifostine (ETHYOL®), arabinosylcytosine (Ara-C, cytarabine, CYTOSAR-U®), arsenic trioxide (TRISENOX®), asparaginase (*Erwinia* L-asparaginase, L-asparaginase, ELSPAR®, KIDROLASE®), BCNU (carmustine, BiCNU®), bendamustine (TREANDA®), bexarotene (TARGRETIN®), bleomycin (BLENOXANE®), busulfan (BUSULFEX®, MYLERAN®), calcium leucovorin (Citrovorum Factor, folinic acid, leucovorin), camptothecin-11 (CPT-11, irinotecan, CAMPTOSAR®), capecitabine (XELODA®), carboplatin (PARAPLATIN®), carmustine wafer (prolifeprospan 20 with carmustine implant, GLIADEL® wafer), CCI-779 (temsirolimus, TORISEL®), CCNU (lomustine, CeeNU), CDDP (cisplatin, PLATINOL®, PLATINOL-AQ®), chlorambucil (leukeran), cyclophosphamide (CYTOXAN®, NEOSAR®), dacarbazine (DIC, DTIC, imidazole carboxamide, DTIC-DOME®), daunomycin (daunorubicin, daunorubicin hydrochloride, rubidomycin hydrochloride, CERUBIDINE®), decitabine (DACOGEN®), dexrazoxane (ZINECARD®), DHAD (mitoxantrone, NOVANTRONE®), docetaxel (TAXOTERE®), doxorubicin (ADRIAMYCIN®, RUBEX®), epirubicin (ELLENCE™), estramustine (EMCYT®), etoposide (VP-16, etoposide phosphate, TOPOSAR®, VEPESID®, ETOPOPHOS®), floxuridine (FUDR®), fludarabine (FLUDARA®), fluorouracil (cream) (CARAC™, EFUDEX®, FLUOROPLEX®), gemcitabine (GEMZAR®), hydroxyurea (HYDREA®, DROXIA™, MYLOCEL™), idarubicin (IDAMYCIN®), ifosfamide (IFEX®), ixabepilone (IXEMPRA™), LCR (leurocristine, vincristine, VCR, ONCOVIN®, VINCASAR PFS®), L-PAM (L-sarcolysin, melphalan, phenylalanine mustard, ALKERAN®), mechlorethamine (mechlorethamine hydrochloride, mustine, nitrogen mustard, MUSTARGEN®), mesna (MESNEX™), mitomycin (mitomycin-C, MTC, MUTAMYCIN®), nelarabine (ARRANON®), oxaliplatin (ELOXATIN™), paclitaxel (TAXOL®, ONXAL™), pegaspargase (PEG-L-asparaginase, ONCOSPAR®), PEMETREXED (ALIMTA®), pentostatin (NIPENT®), procarbazine (MATULANE®), streptozocin (ZANOSAR®), temozolomide (TEMODAR®), teniposide (VM-26, VUMON®), TESPA (thiophosphoamide, thiotepa, TSPA, THIOPLEX®), topotecan (HYCAMTIN®), vinblastine (vinblastine sulfate, vincaleukoblastine, VLB, ALKABAN-AQ®, VELBAN®), vinorelbine (vinorelbine tartrate, NAVELBINE®), and vorinostat (ZOLINZA®).

In another embodiment, the anti-TCRβV antibody molecule, multispecific or multifunctional molecule is administered in conjunction with a biologic. Biologics useful in the treatment of cancers are known in the art and a binding molecule of the invention may be administered, for example, in conjunction with such known biologics. For example, the FDA has approved the following biologics for the treatment of breast cancer: HERCEPTIN® (trastuzumab, Genentech Inc., South San Francisco, Calif.; a humanized monoclonal antibody that has anti-tumor activity in HER2-positive breast cancer); FASLODEX® (fulvestrant, AstraZeneca Pharmaceuticals, LP, Wilmington, Del.; an estrogen-receptor antagonist used to treat breast cancer); ARIMIDEX® (anastrozole, AstraZeneca Pharmaceuticals, LP; a nonsteroidal aromatase inhibitor which blocks aromatase, an enzyme needed to make estrogen); Aromasin® (exemestane, Pfizer Inc., New York, N.Y.; an irreversible, steroidal aromatase inactivator used in the treatment of breast cancer); FEMARA® (letrozole, Novartis Pharmaceuticals, East Hanover, N.J.; a nonsteroidal aromatase inhibitor approved by the FDA to treat breast cancer); and NOLVADEX® (tamoxifen, AstraZeneca Pharmaceuticals, LP; a nonsteroidal antiestrogen approved by the FDA to treat breast cancer). Other biologics with which the binding molecules of the invention may be combined include: AVASTIN® (bevacizumab, Genentech Inc.; the first FDA-approved therapy designed to inhibit angiogenesis); and ZEVALIN® (ibritumomab tiuxetan, Biogen Idec, Cambridge, Mass.; a radiolabeled monoclonal antibody currently approved for the treatment of B-cell lymphomas).

In addition, the FDA has approved the following biologics for the treatment of colorectal cancer: AVASTIN®; ERBITUX® (cetuximab, ImClone Systems Inc., New York, N.Y., and Bristol-Myers Squibb, New York, N.Y.; is a monoclonal antibody directed against the epidermal growth factor receptor (EGFR)); GLEEVEC® (imatinib mesylate; a protein kinase inhibitor); and ERGAMISOL® (levamisole hydrochloride, Janssen Pharmaceutica Products, LP, Titusville, N.J.; an immunomodulator approved by the FDA in 1990 as an adjuvant treatment in combination with 5-fluorouracil after surgical resection in patients with Dukes' Stage C colon cancer).

For the treatment of lung cancer, exemplary biologics include TARCEVA® (erlotinib HCL, OSI Pharmaceuticals Inc., Melville, N.Y.; a small molecule designed to target the human epidermal growth factor receptor 1 (HER1) pathway).

For the treatment of multiple myeloma, exemplary biologics include VELCADE® (bortezomib, Millennium Pharmaceuticals, Cambridge Mass.; a proteasome inhibitor). Additional biologics include THALIDOMID® (thalidomide, Clegene Corporation, Warren, N.J.; an immunomodulatory agent and appears to have multiple actions, including the ability to inhibit the growth and survival of myeloma cells and anti-angiogenesis).

Additional exemplary cancer therapeutic antibodies include, but are not limited to, 3F8, abagovomab, adecatumumab, afutuzumab, alacizumab pegol, alemtuzumab (CAMPATH®, MABCAMPATH®), altumomab pentetate (HYBRI-CEAKER®), anatumomab mafenatox, anrukinzumab (IMA-638), apolizumab, arcitumomab (CEA-SCAN®), bavituximab, bectumomab (LYMPHOSCAN®), belimumab (BENLYSTA®, LYMPHOSTAT-B®), besilesomab (SCINTIMUN®), bevacizumab (AVASTIN®), bivatuzumab mertansine, blinatumomab, brentuximab vedotin, cantuzumab mertansine, capromab pendetide (PROSTASCINT®), catumaxomab (REMOVAB®), CC49, cetuximab (C225, ERBITUX®), citatuzumab bogatox, cixutumumab, clivatuzumab tetraxetan, conatumumab, dacetuzumab, denosumab (PROLIA®), detumomab, ecromeximab, edrecolomab (PANOREX®), elotuzumab, epitumomab cituxetan, epratuzumab, ertumaxomab (REXOMUN®), etaracizumab, farletuzumab, figitumumab, fresolimumab, galiximab, gemtuzumab ozogamicin (MYLOTARG®), girentuximab, glembatumumab vedotin, ibritumomab (ibritumomab tiuxetan, ZEVALIN®), igovomab (INDIMACIS-125®), intetumumab, inotuzumab ozogamicin, ipilimumab, iratumumab, labetuzumab (CEA-CIDE®), lexatumumab, lintuzumab, lucatumumab, lumiliximab, mapatumumab, matuzumab, milatuzumab, minretumomab, mitumomab, nacolomab tafenatox, naptumomab estafenatox, necitumumab, nimotuzumab (THERACIM®, THERALOC®), nofetumomab merpentan (VERLUMA®), ofatumumab (ARZERRA®), olaratumab, oportuzumab monatox, oregovomab (OVAREX®), panitumumab (VECTIBIX®), pemtumomab (THERAGYN®), pertuzumab (OMNITARG®), pintumomab, pritumumab, ramucirumab, ranibizumab (LUCENTIS®), rilotumumab, rituximab (MABTHERA®, RITUXAN®), robatumumab, satumomab pendetide, sibrotuzumab, siltuximab, sontuzumab, tacatuzumab tetraxetan (AFP-CIDE®), taplitumomab paptox, tenatumomab, TGN1412, ticilimumab (tremelimumab), tigatuzumab, TNX-650, tositumomab (BEXXAR®), trastuzumab (HERCEPTIN®), tremelimumab, tucotuzumab celmoleukin, veltuzumab, volociximab, votumumab (HUMASPECT®), zalutumumab (HUMAX-EGFR®), and zanolimumab (HUMAX-CD4®).

In other embodiments, the anti-TCRβV antibody molecule, multispecific or multifunctional molecule is administered in combination with a viral cancer therapeutic agent. Exemplary viral cancer therapeutic agents include, but not limited to, vaccinia virus (vvDD-CDSR), carcinoembryonic antigen-expressing measles virus, recombinant vaccinia virus (TK-deletion plus GM-CSF), Seneca Valley virus-001, Newcastle virus, coxsackie virus A21, GL-ONC1, EBNA1 C-terminal/LMP2 chimeric protein-expressing recombinant modified vaccinia Ankara vaccine, carcinoembryonic antigen-expressing measles virus, G207 oncolytic virus, modified vaccinia virus Ankara vaccine expressing p53, OncoVEX GM-CSF modified herpes-simplex 1 virus, fowlpox virus vaccine vector, recombinant vaccinia prostate-specific antigen vaccine, human papillomavirus 16/18 L1 virus-like particle/AS04 vaccine, MVA-EBNA1/LMP2 Inj. vaccine, quadrivalent HPV vaccine, quadrivalent human papillomavirus (types 6, 11, 16, 18) recombinant vaccine (GARDASIL®), recombinant fowlpox-CEA(6D)/TRICOM vaccine; recombinant vaccinia-CEA(6D)-TRICOM vaccine, recombinant modified vaccinia Ankara-5T4 vaccine, recombinant fowlpox-TRICOM vaccine, oncolytic herpes virus NV1020, HPV L1 VLP vaccine V504, human papillomavirus bivalent (types 16 and 18) vaccine (CERVARIX®), herpes simplex virus HF10, Ad5CMV-p53 gene, recombinant vaccinia DF3/MUC1 vaccine, recombinant vaccinia-MUC-1 vaccine, recombinant vaccinia-TRICOM vaccine, ALVAC MART-1 vaccine, replication-defective herpes simplex virus type I (HSV-1) vector expressing human Preproenkephalin (NP2), wild-type reovirus, reovirus type 3 Dearing (REOLYSIN®), oncolytic virus HSV1716, recombinant modified vaccinia Ankara (MVA)-based vaccine encoding Epstein-Barr virus target antigens, recombinant fowlpox-prostate specific antigen vaccine, recombinant vaccinia prostate-specific antigen vaccine, recombinant vaccinia-B7.1 vaccine, rAd-p53 gene, Ad5-delta24RGD, HPV vaccine 580299, JX-594 (thymidine kinase-deleted vaccinia virus plus GM-CSF), HPV-16/18 L1/AS04, fowlpox virus vaccine vector, vaccinia-tyrosinase vaccine, MEDI-517 HPV-16/18 VLP AS04 vaccine, adenoviral vector containing the thymidine kinase of herpes simplex virus TK99UN, HspE7, FP253/Fludarabine, ALVAC(2) melanoma multi-antigen therapeutic vaccine, ALVAC-hB7.1, canarypox-hIL-12 melanoma vaccine, Ad-REIC/Dkk-3, rAd-IFN SCH 721015, TIL-Ad-INFg, Ad-ISF35, and coxsackievirus A21 (CVA21, CAVATAK®).

In other embodiments, anti-TCRβV antibody molecule, multispecific or multifunctional molecule is administered in combination with a nanopharmaceutical. Exemplary cancer nanopharmaceuticals include, but not limited to, ABRAXANE® (paclitaxel bound albumin nanoparticles), CRLX101 (CPT conjugated to a linear cyclodextrin-based polymer), CRLX288 (conjugating docetaxel to the biodegradable polymer poly (lactic-co-glycolic acid)), cytarabine liposomal (liposomal Ara-C, DEPOCYT™), daunorubicin liposomal (DAUNOXOME®), doxorubicin liposomal (DOXIL®, CAELYX®), encapsulated-daunorubicin citrate liposome (DAUNOXOME®), and PEG anti-VEGF aptamer (MACUGEN®).

In some embodiments, the anti-TCRβV antibody molecule, multispecific or multifunctional molecule is administered in combination with paclitaxel or a paclitaxel formulation, e.g., TAXOL®, protein-bound paclitaxel (e.g., ABRAXANE®). Exemplary paclitaxel formulations include, but are not limited to, nanoparticle albumin-bound paclitaxel (ABRAXANE®, marketed by Abraxis Bioscience), docosahexaenoic acid bound-paclitaxel (DHA-paclitaxel, Taxoprexin, marketed by Protarga), polyglutamate bound-paclitaxel (PG-paclitaxel, paclitaxel poliglumex, CT-2103, XYOTAX, marketed by Cell Therapeutic), the tumor-activated prodrug (TAP), ANG105 (Angiopep-2 bound to three molecules of paclitaxel, marketed by ImmunoGen), paclitaxel-EC-1 (paclitaxel bound to the erbB2-recognizing peptide EC-1; see Li et al., *Biopolymers* (2007) 87:225-230), and glucose-conjugated paclitaxel (e.g., 2'-paclitaxel methyl 2-glucopyranosyl succinate, see Liu et al., *Bioorganic & Medicinal Chemistry Letters* (2007) 17:617-620).

Exemplary RNAi and antisense RNA agents for treating cancer include, but not limited to, CALAA-01, siG12D LODER (Local Drug EluteR), and ALN-VSP02.

Other cancer therapeutic agents include, but not limited to, cytokines (e.g., aldesleukin (IL-2, Interleukin-2, PROLEUKIN®), alpha Interferon (IFN-alpha, Interferon alfa, INTRON® A (Interferon alfa-2b), ROFERON-A® (Interferon alfa-2a)), Epoetin alfa (PROCRIT®), filgrastim (G-CSF, Granulocyte—Colony Stimulating Factor, NEUPOGEN®), GM-CSF (Granulocyte Macrophage Colony Stimulating Factor, sargramostim, LEUKINE™), IL-11 (Interleukin-11, oprelvekin, NEUMEGA®), Interferon alfa-2b (PEG conjugate) (PEG interferon, PEG-INTRON™), and pegfilgrastim (NEULASTA™)), hormone therapy agents (e.g., aminoglutethimide (CYTADREN®), anastrozole (ARIMIDEX®), bicalutamide (CASODEX®), exemestane (AROMASIN®), fluoxymesterone (HALOTESTIN®), flutamide (EULEXIN®), fulvestrant (FASLODEX®), goserelin (ZOLADEX®), letrozole (FEMARA®), leuprolide (ELIGARD™, LUPRON®, LUPRON DEPOT®, VIADUR™), megestrol (megestrol acetate, MEGACE®), nilutamide (ANANDRON®, NILANDRON®), octreotide (octreotide acetate, SANDOSTATIN®, SANDOSTATIN LAR®), raloxifene (EVISTA®), romiplostim (NPLATE®), tamoxifen (NOVALDEX®), and toremifene (FARESTON®)), phospholipase A2 inhibitors (e.g., anagrelide (AGRYLIN®)), biologic response modifiers (e.g., BCG (THERACYS®, TICE®), and Darbepoetin alfa (ARANESP®)), target therapy agents (e.g., bortezomib (VELCADE®), dasatinib (SPRYCEL™), denileukin diftitox (ONTAK®), erlotinib (TARCEVA®), everolimus (AFINITOR®), gefitinib (IRESSA®), imatinib mesylate (STI-571, GLEEVEC™), lapatinib (TYKERB®), sorafenib (NEXAVAR®), and SU11248 (sunitinib, SUTENT®)), immunomodulatory and antiangiogenic agents (e.g., CC-5013 (lenalidomide, REVLIMID®), and thalidomide (THALOMID®)), glucocorticosteroids (e.g., cortisone (hydrocortisone, hydrocortisone sodium phosphate, hydrocortisone sodium succinate, ALA-CORT®, HYDROCORT ACETATE®, hydrocortone phosphate LANACORT®, SOLU-CORTEF®), decadron (dexamethasone, dexamethasone acetate, dexamethasone sodium phosphate, DEXASONE®, DIODEX®, HEXADROL®, MAXIDEX®), methylprednisolone (6-methylprednisolone, methylprednisolone acetate, methylprednisolone sodium succinate, DURALONE®, MEDRALONE®, MEDROL®, M-PREDNISOL®, SOLU-MEDROL®), prednisolone (DELTA-CORTEF®, ORAPRED®, PEDIAPRED®, PRELONE®), and prednisone (DELTASONE®, LIQUID PRED®, METICORTEN®, ORASONE®)), and bisphosphonates (e.g., pamidronate (AREDIA®), and zoledronic acid (ZOMETA®))

In some embodiments, the anti-TCRβV antibody molecule, multispecific or multifunctional molecule is used in combination with a tyrosine kinase inhibitor (e.g., a receptor tyrosine kinase (RTK) inhibitor). Exemplary tyrosine kinase inhibitor include, but are not limited to, an epidermal growth factor (EGF) pathway inhibitor (e.g., an epidermal growth factor receptor (EGFR) inhibitor), a vascular endothelial growth factor (VEGF) pathway inhibitor (e.g., an antibody against VEGF, a VEGF trap, a vascular endothelial growth factor receptor (VEGFR) inhibitor (e.g., a VEGFR-1 inhibitor, a VEGFR-2 inhibitor, a VEGFR-3 inhibitor)), a platelet derived growth factor (PDGF) pathway inhibitor (e.g., a platelet derived growth factor receptor (PDGFR) inhibitor (e.g., a PDGFR-ß inhibitor)), a RAF-1 inhibitor, a KIT inhibitor and a RET inhibitor. In some embodiments, the anti-cancer agent used in combination with the AHCM agent is selected from the group consisting of: axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), alemtuzumab (CAMPATH®), gemtuzumab ozogamicin (MYLOTARG®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, XL228, AEE788, AG-490, AST-6, BMS-599626, CUDC-101, PD153035, pelitinib (EKB-569), vandetanib (zactima), WZ3146, WZ4002, WZ8040, ABT-869 (linifanib), AEE788, AP24534 (ponatinib), AV-951 (tivozanib), axitinib, BAY 73-4506 (regorafenib), brivanib alaninate (BMS-582664), brivanib (BMS-540215), cediranib (AZD2171), CHIR-258 (dovitinib), CP 673451, CYC 116, E7080, Ki8751, masitinib (AB1010), MGCD-265, motesanib diphosphate (AMG-706), MP-470, OSI-930, Pazopanib Hydrochloride, PD173074, Sorafenib Tosylate (Bay 43-9006), SU 5402, TSU-68 (SU6668), vatalanib, XL880 (GSK1363089, EXEL-2880). Selected tyrosine kinase inhibitors are chosen from sunitinib, erlotinib, gefitinib, or sorafenib. In one embodiment, the tyrosine kinase inhibitor is sunitinib.

In one embodiment, the anti-TCRβV antibody molecule, multispecific or multifunctional molecule is administered in combination with one of more of: an anti-angiogenic agent, or a vascular targeting agent or a vascular disrupting agent. Exemplary anti-angiogenic agents include, but are not limited to, VEGF inhibitors (e.g., anti-VEGF antibodies (e.g., bevacizumab); VEGF receptor inhibitors (e.g., itraconazole); inhibitors of cell proliferatin and/or migration of endothelial cells (e.g., carboxyamidotriazole, TNP-470); inhibitors of angiogenesis stimulators (e.g., suramin), among others. A vascular-targeting agent (VTA) or vascular disrupting agent (VDA) is designed to damage the vasculature (blood vessels) of cancer tumors causing central necrosis (reviewed in, e.g., Thorpe, P. E. (2004) *Clin. Cancer Res*. Vol. 10:415-427). VTAs can be small-molecule. Exemplary small-molecule VTAs include, but are not limited to, microtubule destabilizing drugs (e.g., combretastatin A-4 disodium phosphate (CA4P), ZD6126, AVE8062, Oxi 4503); and vadimezan (ASA404).

Immune Checkpoint Inhibitors

In other embodiments, methods described herein comprise use of an immune checkpoint inhibitor in combination with the anti-TCRβV antibody molecule, multispecific or multifunctional molecule. The methods can be used in a therapeutic protocol in vivo.

In embodiments, an immune checkpoint inhibitor inhibits a checkpoint molecule. Exemplary checkpoint molecules include but are not limited to CTLA4, PD1, PD-L1, PD-L2, TIM3, LAG3, CD160, 2B4, CD80, CD86, B7-H3 (CD276), B7-H4 (VTCN1), HVEM (TNFRSF14 or CD270), BTLA, KIR, MHC class I, MHC class IL, GAL9, VISTA, BTLA, TIGIT, LAIR1, and A2aR. See, e.g., Pardoll. Nat. Rev. Cancer 12.4(2012):252-64, incorporated herein by reference.

In embodiments, the immune checkpoint inhibitor is a PD-1 inhibitor, e.g., an anti-PD-1 antibody such as Nivolumab, Pembrolizumab or Pidilizumab. Nivolumab (also called MDX-1106, MDX-1106-04, ONO-4538, or BMS-936558) is a fully human IgG4 monoclonal antibody that specifically inhibits PD1. See, e.g., U.S. Pat. No. 8,008,449 and WO2006/121168. Pembrolizumab (also called Lambrolizumab, MK-3475, MK03475, SCH-900475 or KEYTRUDA®; Merck) is a humanized IgG4 monoclonal antibody that binds to PD-1. See, e.g., Hamid, O. et al. (2013) *New England Journal of Medicine* 369 (2): 134-44, U.S. Pat. No. 8,354,509 and WO2009/114335. Pidilizumab (also called CT-011 or Cure Tech) is a humanized IgGlk monoclonal antibody that binds to PD1. See, e.g., WO2009/101611. In one embodiment, the inhibitor of PD-1 is an antibody molecule having a sequence substantially identical or similar thereto, e.g., a sequence at least 85%, 90%, 95% identical or higher to the sequence of Nivolumab, Pembrolizumab or Pidilizumab. Additional anti-PD1 antibodies, e.g., AMP 514 (Amplimmune), are described, e.g., in U.S. Pat. No. 8,609,089, US 2010028330, and/or US 20120114649.

In some embodiments, the PD-1 inhibitor is an immunoadhesin, e.g., an immunoadhesin comprising an extracellular/PD-1 binding portion of a PD-1 ligand (e.g., PD-L1 or PD-L2) that is fused to a constant region (e.g., an Fc region of an immunoglobulin). In embodiments, the PD-1 inhibitor is AMP-224 (B7-DCIg, e.g., described in WO2011/066342 and WO2010/027827), a PD-L2 Fc fusion soluble receptor that blocks the interaction between B7-H1 and PD-1.

In embodiments, the immune checkpoint inhibitor is a PD-L1 inhibitor, e.g., an antibody molecule. In some embodiments, the PD-L1 inhibitor is YW243.55.S70, MPDL3280A, MEDI-4736, MSB-0010718C, or MDX-1105. In some embodiments, the anti-PD-L1 antibody is MSB0010718C (also called A09-246-2; Merck Serono), which is a monoclonal antibody that binds to PD-L1. Exemplary humanized anti-PD-L1 antibodies are described, e.g., in WO2013/079174. In one embodiment, the PD-L1 inhibitor is an anti-PD-L1 antibody, e.g., YW243.55.S70. The YW243.55.S70 antibody is described, e.g., in WO 2010/077634. In one embodiment, the PD-L1 inhibitor is MDX-1105 (also called BMS-936559), which is described, e.g., in WO2007/005874. In one embodiment, the PD-L1 inhibitor is MDPL3280A (Genentech/Roche), which is a human Fc-optimized IgG1 monoclonal antibody against PD-L1. See, e.g., U.S. Pat. No. 7,943,743 and U.S Publication No.: 20120039906. In one embodiment, the inhibitor of PD-L1 is an antibody molecule having a sequence substantially identical or similar thereto, e.g., a sequence at least 85%, 90%, 95% identical or higher to the sequence of YW243.55.S70, MPDL3280A, MEDI-4736, MSB-0010718C, or MDX-1105.

In embodiments, the immune checkpoint inhibitor is a PD-L2 inhibitor, e.g., AMP-224 (which is a PD-L2 Fc fusion soluble receptor that blocks the interaction between PD1 and B7-H1. See, e.g., WO2010/027827 and WO2011/066342.

In one embodiment, the immune checkpoint inhibitor is a LAG-3 inhibitor, e.g., an anti LAG-3 antibody molecule. In embodiments, the anti-LAG-3 antibody is BMS-986016 (also called BMS986016; Bristol-Myers Squibb). BMS-986016 and other humanized anti-LAG-3 antibodies are described, e.g., in US 2011/0150892, WO2010/019570, and WO2014/008218.

In embodiments, the immune checkpoint inhibitor is a TIM-3 inhibitor, e.g., anti-TIM3 antibody molecule, e.g., described in U.S. Pat. No. 8,552,156, WO 2011/155607, EP 2581113 and U.S Publication No.: 2014/044728.

In embodiments, the immune checkpoint inhibitor is a CTLA-4 inhibitor, e.g., anti-CTLA-4 antibody molecule. Exemplary anti-CTLA4 antibodies include Tremelimumab (IgG2 monoclonal antibody from Pfizer, formerly known as ticilimumab, CP-675,206); and Ipilimumab (also called MDX-010, CAS No. 477202-00-9). Other exemplary anti-CTLA-4 antibodies are described, e.g., in U.S. Pat. No. 5,811,097.

CRS Grading

In some embodiments, CRS can be graded in severity from 1-5 as follows. Grades 1-3 are less than severe CRS. Grades 4-5 are severe CRS. For Grade 1 CRS, only symptomatic treatment is needed (e.g., nausea, fever, fatigue, myalgias, malaise, headache) and symptoms are not life threatening. For Grade 2 CRS, the symptoms require moderate intervention and generally respond to moderate intervention. Subjects having Grade 2 CRS develop hypotension that is responsive to either fluids or one low-dose vasopressor; or they develop grade 2 organ toxicity or mild respiratory symptoms that are responsive to low flow oxygen (<40% oxygen). In Grade 3 CRS subjects, hypotension generally cannot be reversed by fluid therapy or one low-dose vasopressor. These subjects generally require more than low flow oxygen and have grade 3 organ toxicity (e.g., renal or cardiac dysfunction or coagulopathy) and/or grade 4 transaminitis. Grade 3 CRS subjects require more aggressive intervention, e.g., oxygen of 40% or higher, high dose vasopressor(s), and/or multiple vasopressors. Grade 4 CRS subjects suffer from immediately life-threatening symptoms, including grade 4 organ toxicity or a need for mechanical ventilation. Grade 4 CRS subjects generally do not have transaminitis. In Grade 5 CRS subjects, the toxicity causes death. Sets of criteria for grading CRS are provided herein as Table 5, Table 6, and Table 7. Unless otherwise specified, CRS as used herein refers to CRS according to the criteria of Table 6.

In embodiments, CRS is graded according to Table 5:

TABLE 5

| CRS grading | |
|---|---|
| Gr1 | Supportive care only |
| Gr2 | IV therapies +/− hospitalization. |
| Gr3 | Hypotension requiring IV fluids or low-dose vasoactives or hypoxemia requiring oxygen, CPAP, or BIPAP. |
| Gr4 | Hypotension requiring high-dose vasoactives or hypoxemia requiring mechanical ventilation. |
| Gr 5 | Death |

TABLE 6

CTCAE v 4.0 CRS grading scale

| CRS grade | Characteristics |
|---|---|
| Grade 1 | Mild; No infusion interruption; No intervention |
| Grade 2 | Infusion interruption indicated but responds promptly to symptomatic treatment (e.g., antihistamines, NSAIDS, narcotics, IV fluids); prophylactic medications indicated for <=24 hrs |
| Grade 3 | Prolonged (e.g., not rapidly responsive to symptomatic medications and/or brief interruption of infusion); recurrence of symptoms following initial improvement; hospitalization indicated for clinical sequelae (e.g., renal impairment, pulmonary infiltrates) |
| Grade 4 | Life threatening consequences; pressor or ventilator support |

TABLE 7

NCI CRS grading scale

| CRS grade | Characteristics |
|---|---|
| Grade 1 | Symptoms are not life threatening and require symptomatic treatment only; e.g., fever, nausea, fatigue, headache, myalgias, malaise |
| Grade 2 | Symptoms require and respond to moderate intervention; Oxygen requirement <40% or hypotension responsive to fluids or low dose pressors or Grade 2 organ toxicity |
| Grade 3 | Symptoms require and respond to aggressive intervention; Oxygen requirement >=40% or Hypotension requiring high dose or multiple pressors or grade 3 organ toxicity or grade 4 transaminitis |
| Grade 4 | Life threatening symptoms Requirement for ventilator support or Grade 4; organ toxicity (excluding transaminitis) |

EXAMPLES

Example 1. Humanization of α-TRBV6-5 Antibody Clone Antibody A

The germline for the mouse α-TCRβ antibody clone Antibody A VH and VL were assigned using IMGT nomenclature, with CDR regions defined by a combined Kabat and Chothia classification. SEQ ID NO: 1 and SEQ ID NO: 2 are the Antibody A VH and VL sequences respectively where the VH germline is mouse IGHV1S12*01 and the VL germline is mouse IGKV6-15*01. SEQ ID NOs: 3-5 are the Antibody A VH CDR regions 1-3 respectively and SEQ ID NOs: 6-8 correspond to the VL CDR regions 1-3 (as described in Table 1).

Humanization of the Antibody A VH and VL sequences was done separately using similar methodology. Amino acids positions were identified in the framework regions which were important for the success of CDR grafting. Human germline sequences were identified which preserved the necessary residues and contained a high amount of overall identity. When the human germline framework sequence did not contain a matching important amino acid, it was back mutated to match the mouse sequence. CDR regions were grafted onto the human germline unchanged. The Antibody A VH was humanized into human IGHV1-69*01 and the Antibody A VL was humanized into IGKV1-17*01 and IGKV1-27*01. All 3 humanized sequences were confirmed to contain no introduced potential negative post translational modification sites such as NG, DG, NS, NN, DS, NT, NXS, or NXT as a result of the humanization process. SEQ ID NO: 9 is the humanized Antibody A-H.1 VH and SEQ ID NOs: 10 and 11 are the humanized VL IGKV1-17*01 and IGKV1-27*01 germlines respectively (as described in Table 1). FIGS. 1A and 1B show the murine and humanized sequences with annotations depicting the CDR and framework regions (FR).

Example 2: Humanization of α-TRBV12-3 and TRBV12-4 Antibody Clone Antibody B The germline for the mouse α-TCRβ antibody clone Antibody B VH and VL were assigned using IMGT nomenclature, with CDR regions defined by a combined Kabat and Chothia classification. SEQ ID NO: 15 and SEQ ID NO: 16 are the Antibody B VH and VL sequences respectively where the VH germline is mouse IGHV5-17*02 and the VL germline is mouse IGKV4-50*01. SEQ ID NOs: 17-19 are the B-H VH CDR regions 1-3 respectively and SEQ ID NOs: 20-22 are the B-H VL CDR regions 1-3 (as described in Table 2).

The method applied to humanize Antibody A described in Example 1 was used to humanize Antibody B. The Antibody B VH was humanized into human IGHV3-30*01, IGHV3-48*01, and IGHV3-66*01 and the Antibody B VL was humanized into human IGKV1-9*01, IGKV1-39*01, IGKV3-15*01, IGLV1-47*01 and IGLV3-10*01. SEQ ID NOs: 23-25 are the B-H.1A, B-H.1B, and B-H.1C humanized heavy chains and SEQ ID NOs: 26-30 are the B-H.1D, B-H.1E, B-H.1F, B-H.1G and B-H.1H humanized light chains (as described in Table 2). FIGS. 2A and 2B show the murine and humanized sequences with annotations depicting the CDR and framework regions (FR).

Example 3: Characteristics of Anti-TCRβV Antibodies

Introduction

Current bispecific constructs designed to redirect T cells to promote tumor cell lysis for cancer immunotherapy typically utilize single chain variable fragments (scFvs) that are derived from monoclonal antibodies (mAb) directed against the CD3e subunit of the T cell receptor (TCR). However, there are limitations to this approach which may prevent the full realization of the therapeutic potential for such bispecific constructs. Previous studies have shown that, e.g., low "activating" doses of anti-CD3e mAb can cause long-term T cell dysfunction and exert immunosuppressive effects. In addition, anti-CD3e mAbs bind to all T cells and thus activate equally all T cells, which has been associated with the first dose side effects of anti-CD3e mAbs that result from massive T cell activation. These large number of activated T cells secrete substantial amounts of cytokines, the most important of which is Interferon gamma (IFNg). This excess amount of IFNg in turn, e.g., activates macrophages which then can overproduce proinflammatory cytokines such as IL-1, IL-6 and TNF-alpha, causing a "cytokine storm" known as the cytokine release syndrome (CRS). Thus, it might be advantageous to develop antibodies that are capable of binding and activating only a subset of necessary effector T cells to reduce the CRS.

Results

Figure 4A:
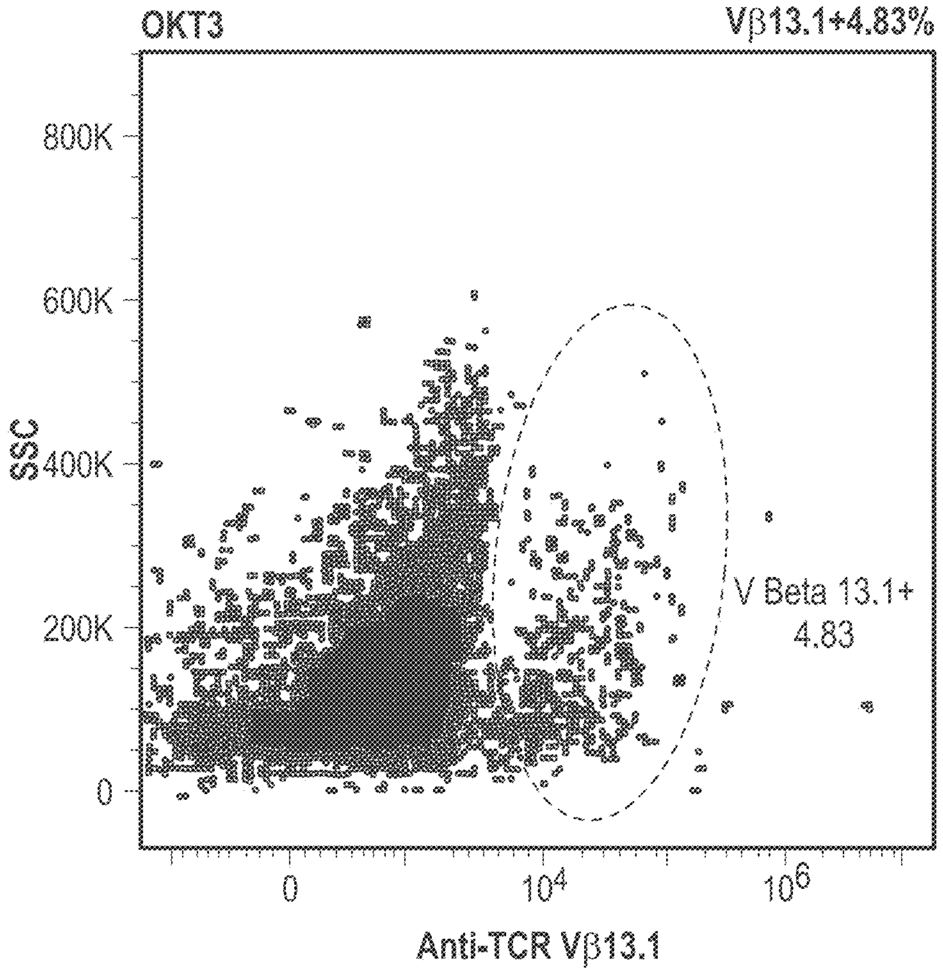
FIGS. 4A-4D show human CD3+ T cells activated by anti-TCR Vβ13.1 antibody (A-H.1) for 6-days. Human CD3+ T cells were isolated using magnetic-bead separation (negative selection) and activated with immobilized (plate-coated) anti-TCR Vβ13.1 (A-H.1) or anti-CD3ϵ (OKT3) antibodies at 100 nM for 6 days.
Figure 4B:
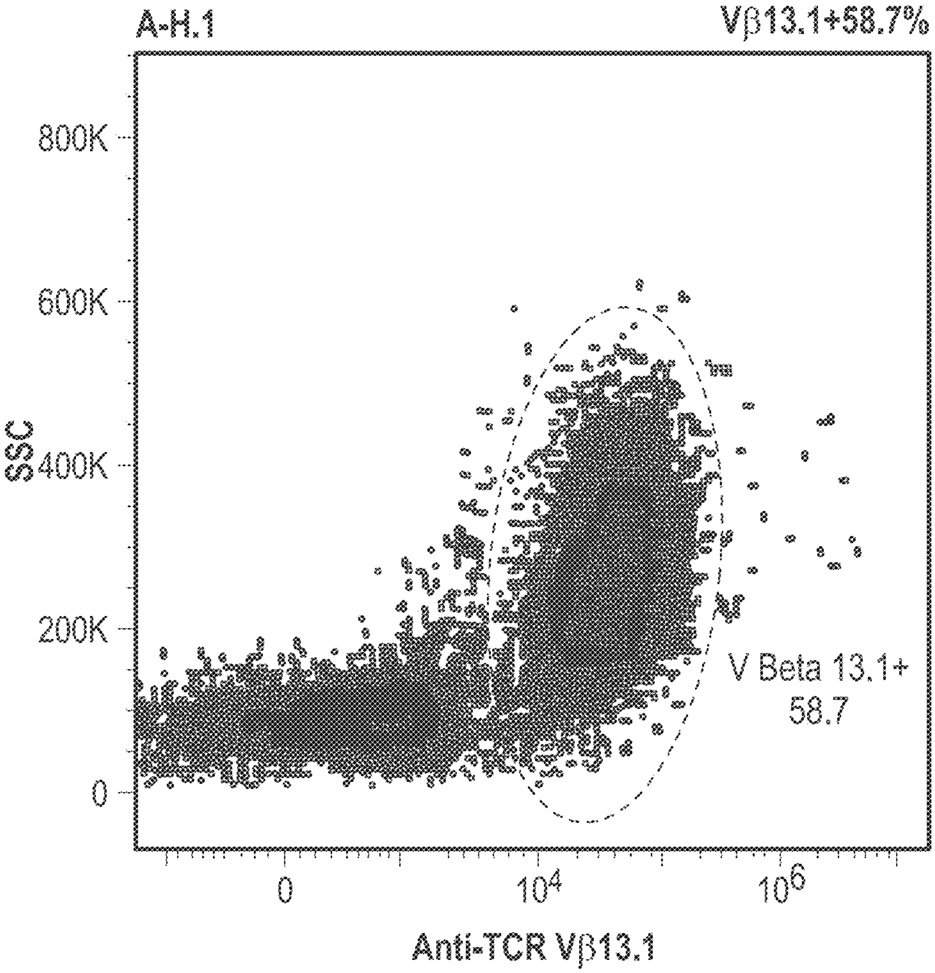
Figure 4C:
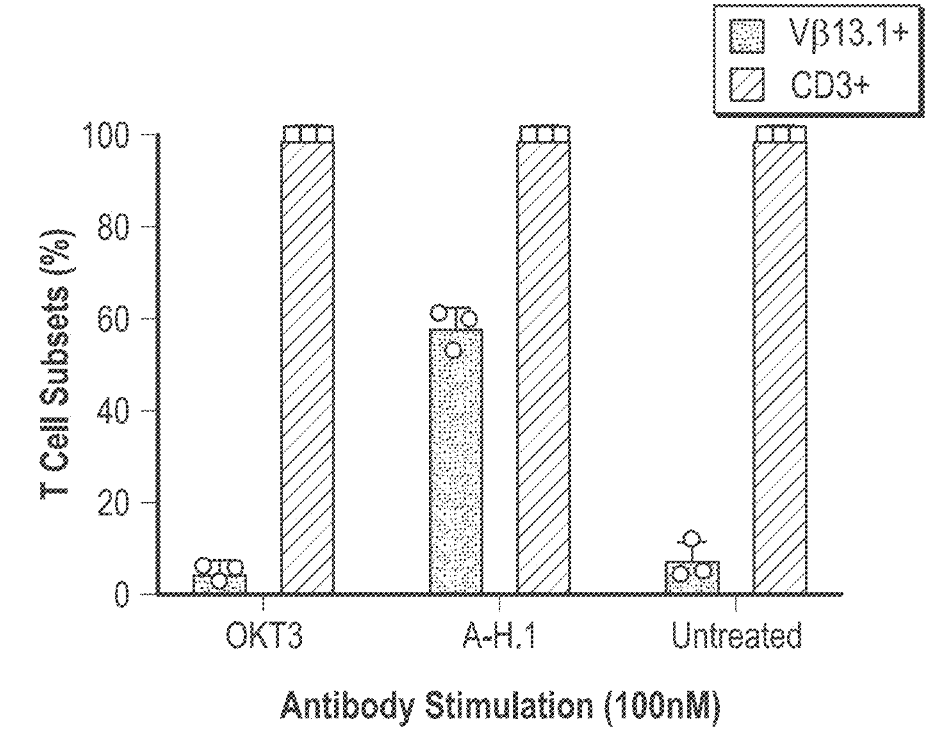
Figure 4D:
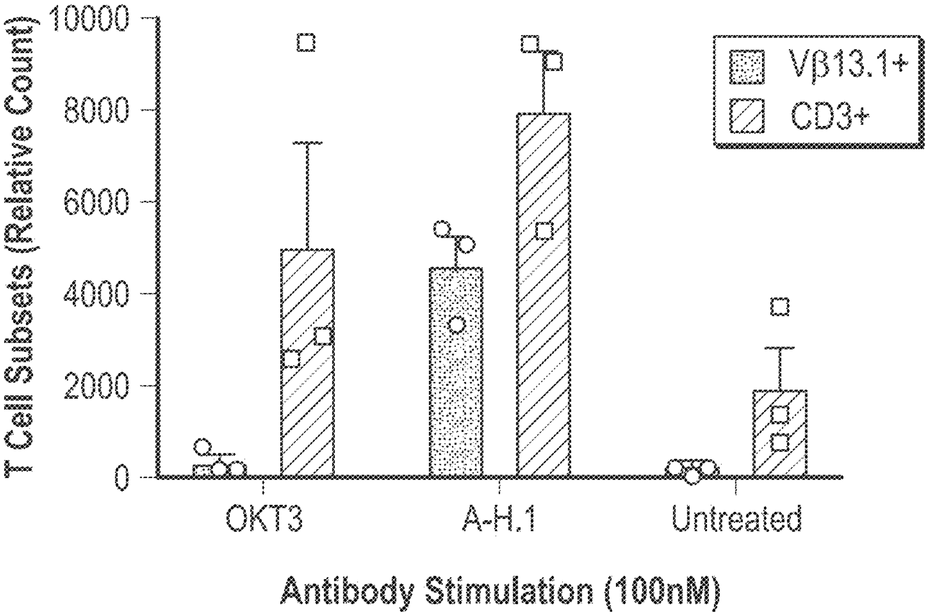
Figure 5A:
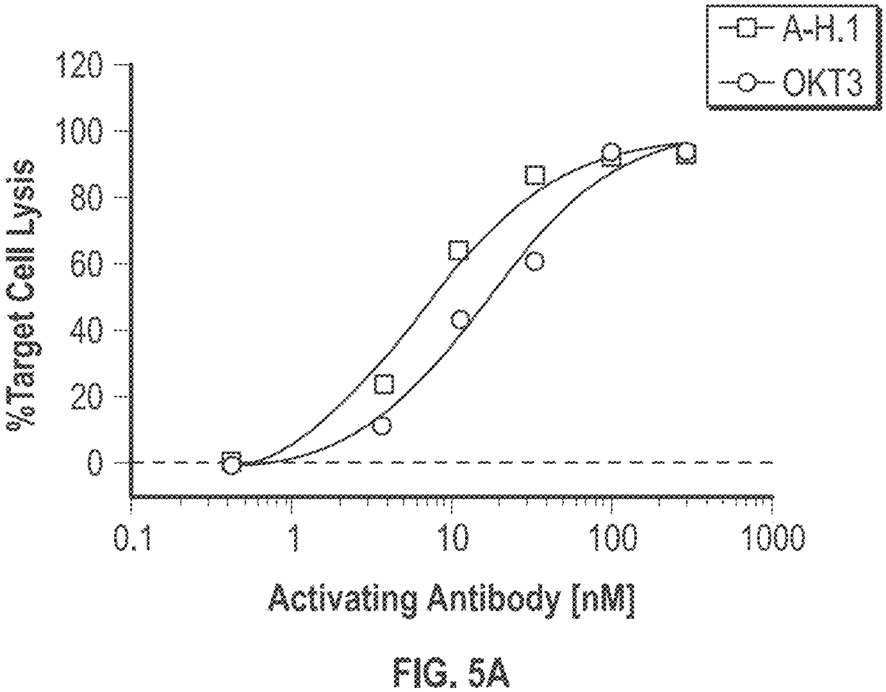
FIGS. 5A-5B show cytolytic activity of human CD3+ T cells activated by anti-TCR Vβ13.1 antibody (A-H.1) against transformed cell line RPMI 8226.
Figure 5B:
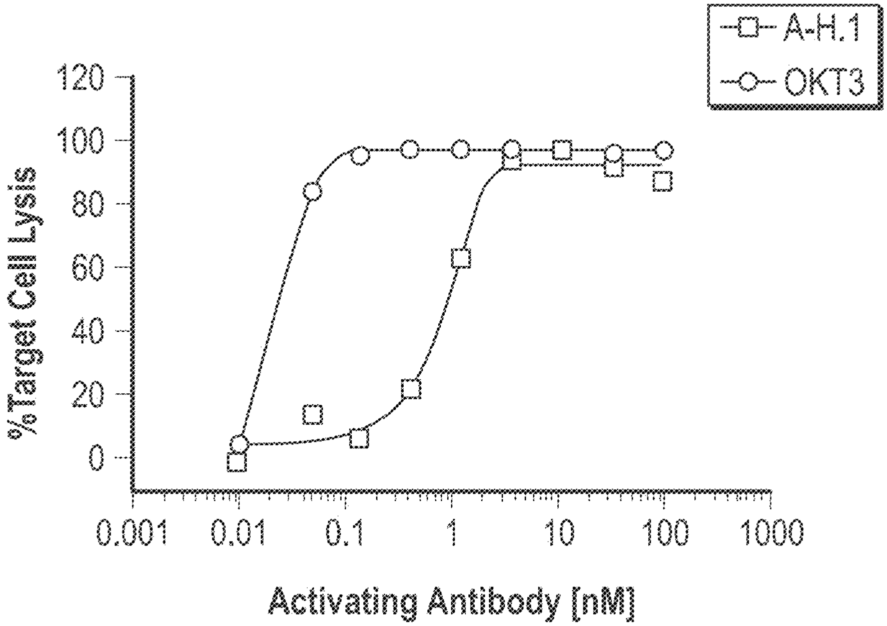

To that end, antibodies directed to the variable chain of the beta subunit of TCR (TCR Vb) were identified. These anti-TCR Vb antibodies bind and activate a subset of T cells, but with, e.g., no or markedly reduced CRS. Using plate-bound anti-TCR Vb13.1 mAbs (A-H.1 and A-H.2) it was shown that a population of T cells, defined by positive staining with A-H.1, can be expanded (from ~5% of T cells on day 0 to almost 60% of total T cells on day 6 of cell culture) (FIGS. 4A-4C). For this experiment, human CD3+ T cells were isolated using magnetic-bead separation (negative selection) and activated with immobilized (plate-coated) A-H.1 or OKT3 (anti-CD3ε) antibodies at 100 nM for 6 days. The expanded Vb13.1+ T cells display cytolytic activity against transformed cell line RPMI-8226 when co-cultured with purified CD3+ T cells (FIGS. 5A-5B).

Next, the ability of PBMCs activated by anti-TCR VB antibodies to produce cytokines was assessed. The cytokine production of PBMCs activated with anti-TCR VB antibodies was compared to the cytokine production of PBMCs activated with: (i) anti-CD3ε antibodies (OKT3 or SP34-2); (ii) anti-TCR V alpha (TCR VA) antibodies including anti-TCR VA 12.1 antibody 6D6.6, anti-TCR VA24JA18 antibody 6B11; (iii) anti-TCR alpha beta antibody T10B9; and/or (iv) isotype control (BGM0109). The anti-TCR VB antibodies tested include: humanized anti-TCRVB 13.1 antibodies (A-H.1, or A-H.2), murine anti-TCR VB5 antibody Antibody E, murine anti-TCR VB8.1 antibody Antibody B, and murine anti-TCR VB12 antibody Antibody D. BGM0109 comprises the amino acid sequence of (SEQ ID NO: 3282)

```
METDTLLLWVLLLWVPGSTGGLNDIFEAQKIEWHEGGGGSEPRTDTDTCP
NPPDPCPTCPTPDLLGGPSVFIFPPKPKDVLMISLTPKITCVVVDVSEEE
PDVQFNWYVNNVEDKTAQTETRQRQYNSTYRVVSVLPIKHQDWMSGKVFK
CKVNNNALPSPIEKTISKPRGQVRVPQIYTFPPPIEQTVKKDVSVTCLVT
GFLPQDIHVEWESNGQPQPEQNYKNTQPVLDSDGSYFLYSKLNVPKSRWD
QGDSFTCSVIHEALHNHHMTKTISRSLGNGGGGS.
```

Figure 6A:
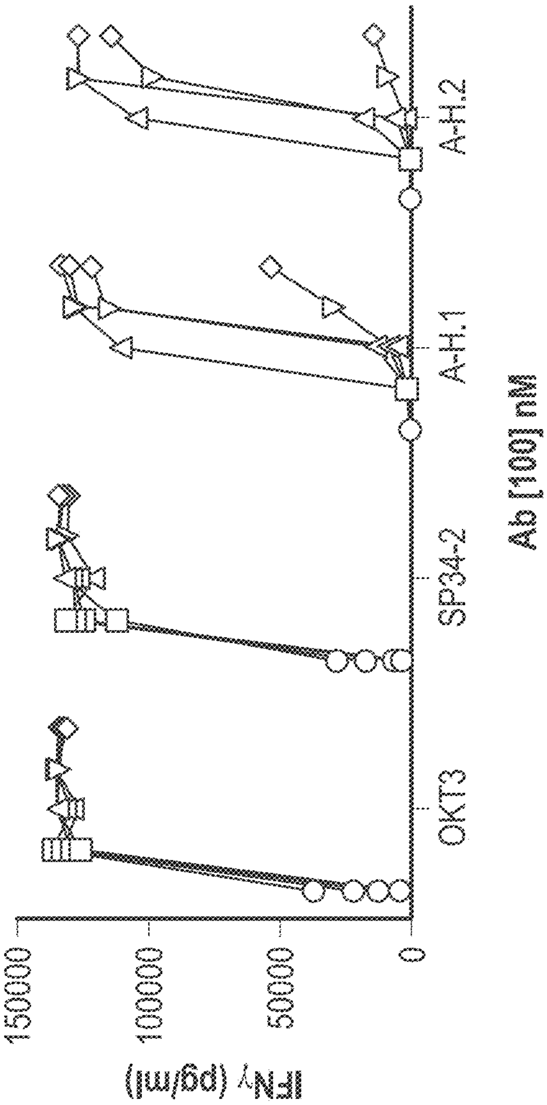
FIGS. 6A-6B show IFNg production by human PBMCs activated with the indicated antibodies. Human PBMCs were isolated from whole blood from the indicated number of donors, followed by solid-phase (plate-coated) stimulation with the indicated antibodies at 100 Nm. Supernatant was collected on Days 1, 2, 3, 5, or 6.
Figure 6B:
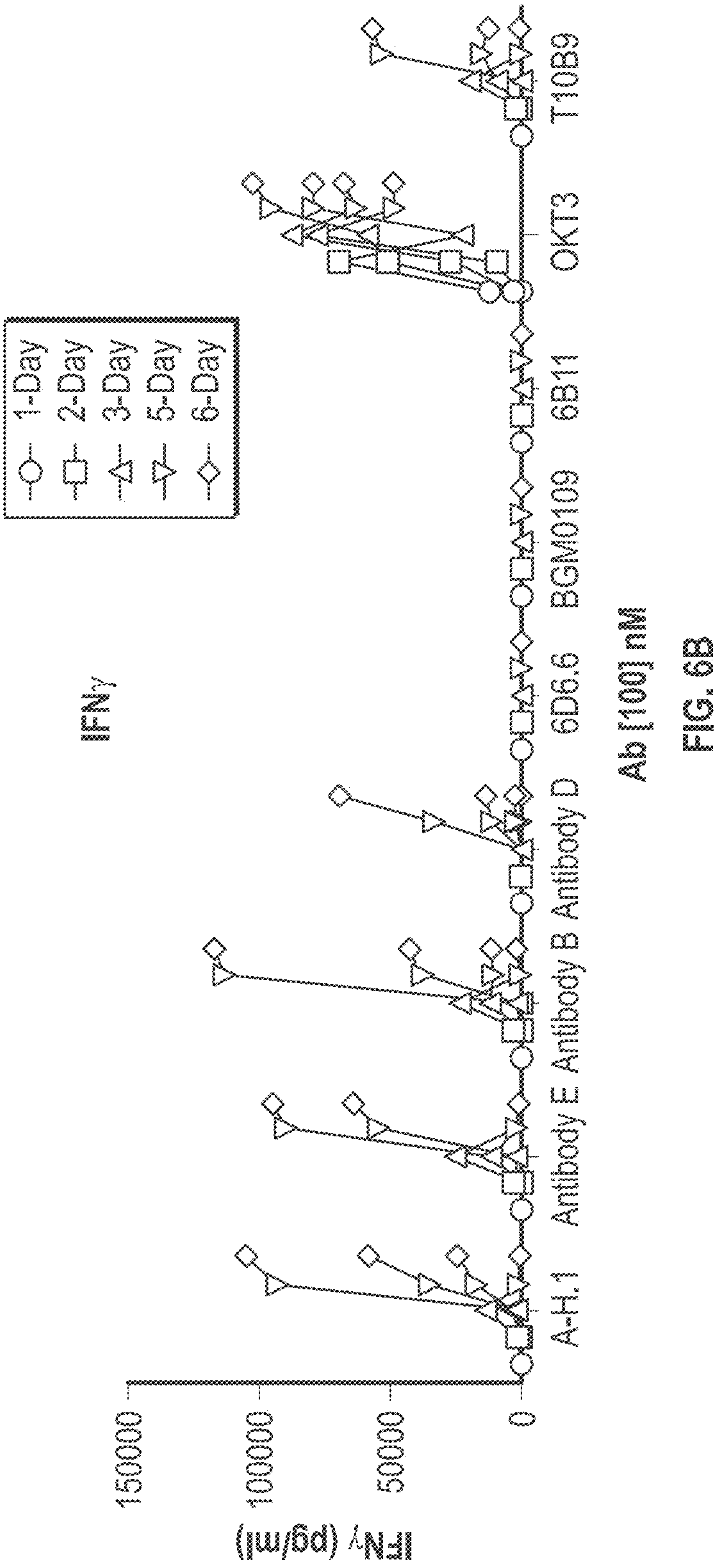

As shown in FIG. 6A, when plate-bound A-H.1 or A-H.2, or anti-CD3e antibodies (OKT3 or SP34-2) were used to activate human PBMCs, the T cell cytokine IFNg was induced (FIG. 6A). All anti-TCR VB antibodies tested had a similar effect on the production of IFNg (FIG. 6B). The anti-TCR VA antibodies did not induce similar IFNg production.

Figure 7A:
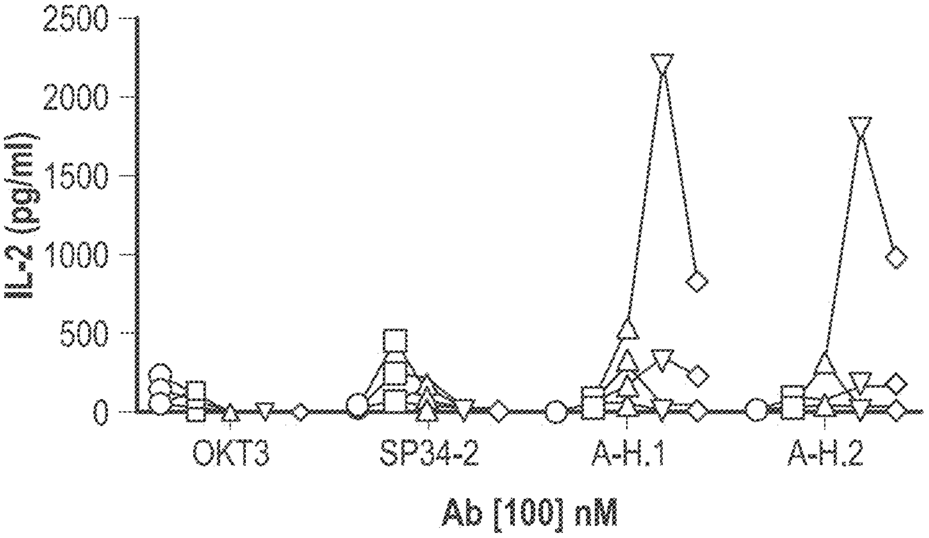
FIGS. 7A-7B show IL-2 production by human PBMCs activated with the indicated antibodies. A similar experimental setup as described for FIGS. 6A-6B was used.
Figure 7B:
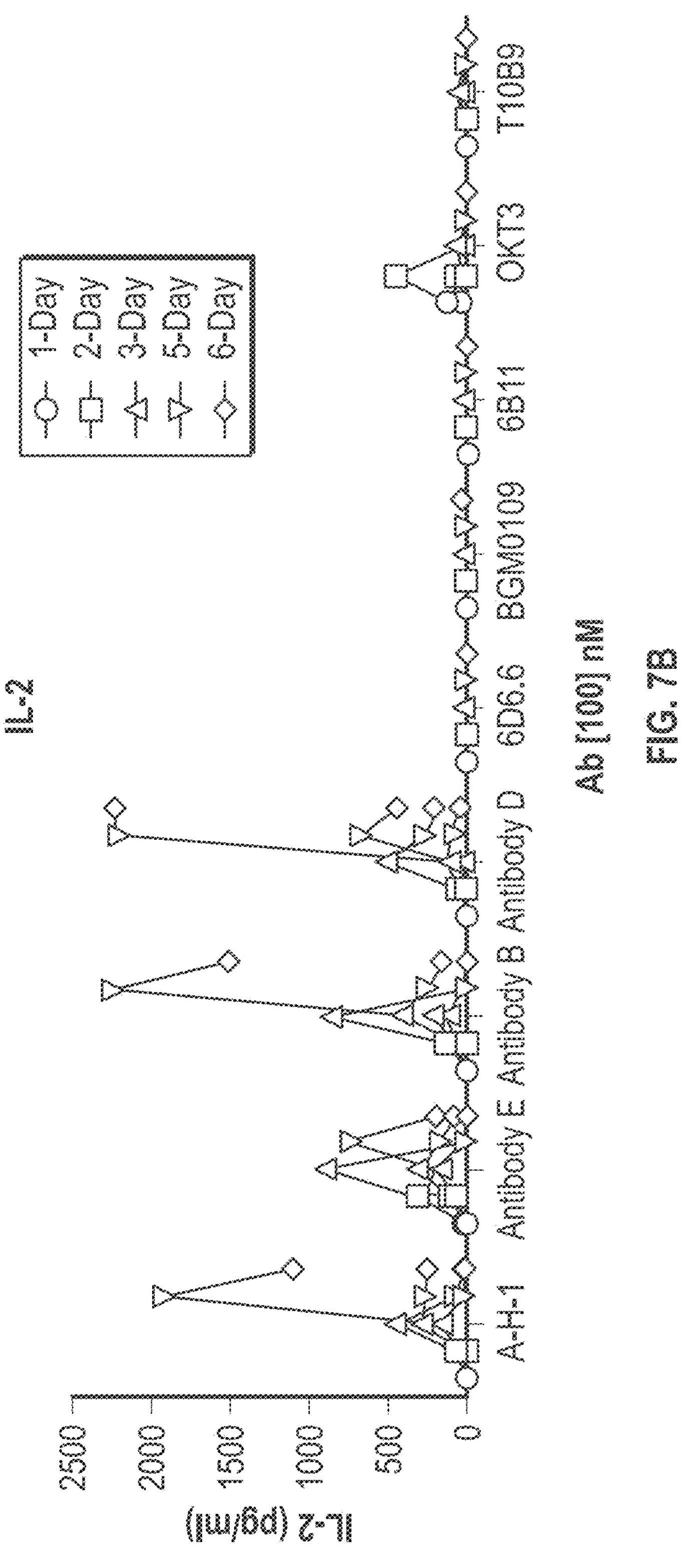

With respect to IL-2 production, PBMCs activated with A-H.1 and A-H.2 resulted in increased IL-2 production (FIG. 7A) with delayed kinetics (FIG. 7B) as compared to PBMCs activated with anti-CD3e antibodies (OKT3 or SP34-2). FIG. 7B shows that anti-TCR VB antibody activated PBMCs demonstrate peak production of IL-2 at Day 5 or Day 6 post-activation (incubation with plate-coated antibodies). In contrast, IL-2 production in PBMCs activated with OKT3 peaked at day 2 post-activation. As with IFNG, the IL-2 effect (e.g., enhanced production of IL-2 and delayed kinetics) was similar across all anti-TCR VB antibodies tested (FIG. 7B).

Figure 8A:
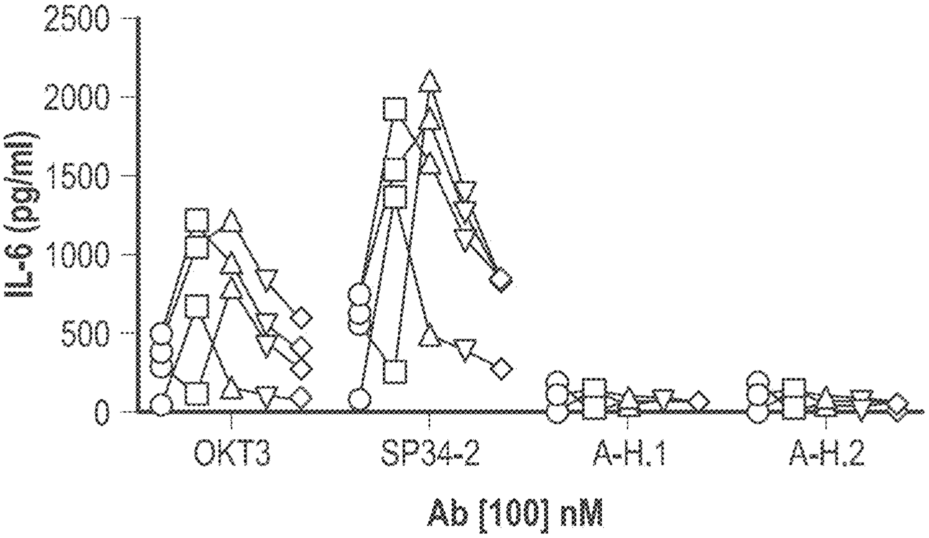
FIGS. 8A-8B show IL-6 production by human PBMCs activated with the indicated antibodies. A similar experimental setup as described for FIGS. 6A-6B was used.
Figure 8B:
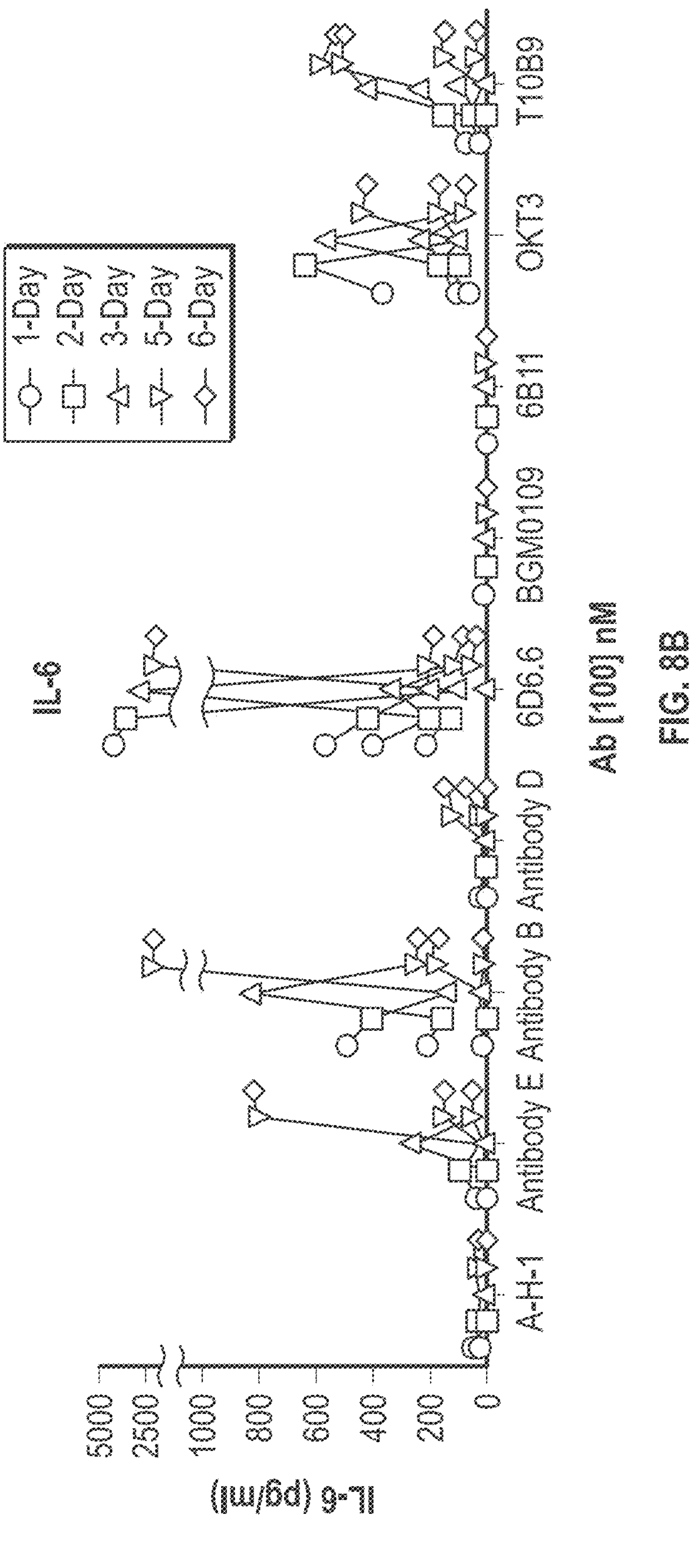
Figure 9A:
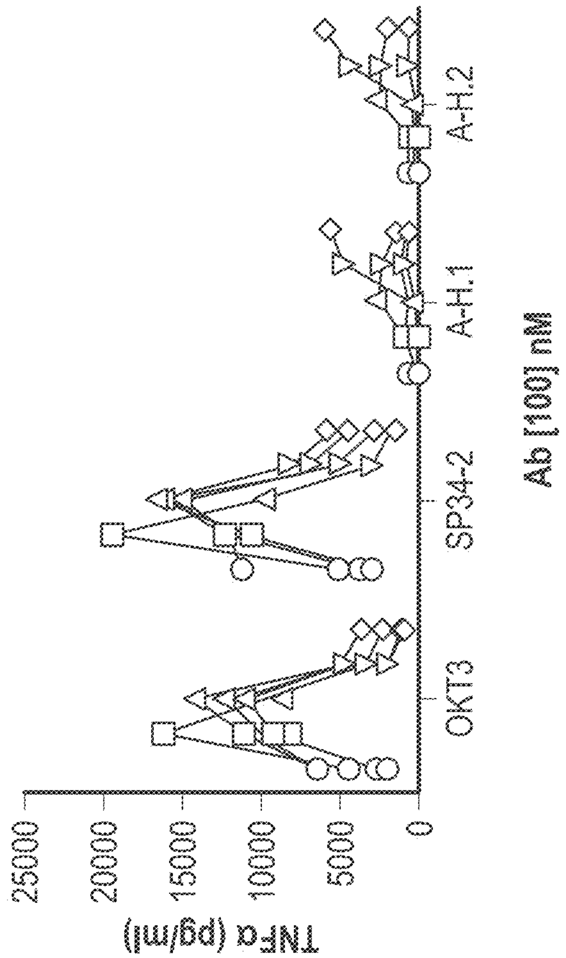
FIGS. 9A-9B show TNF-alpha production by human PBMCs activated with the indicated antibodies. A similar experimental setup as described for FIGS. 6A-6B was used.
Figure 9B:
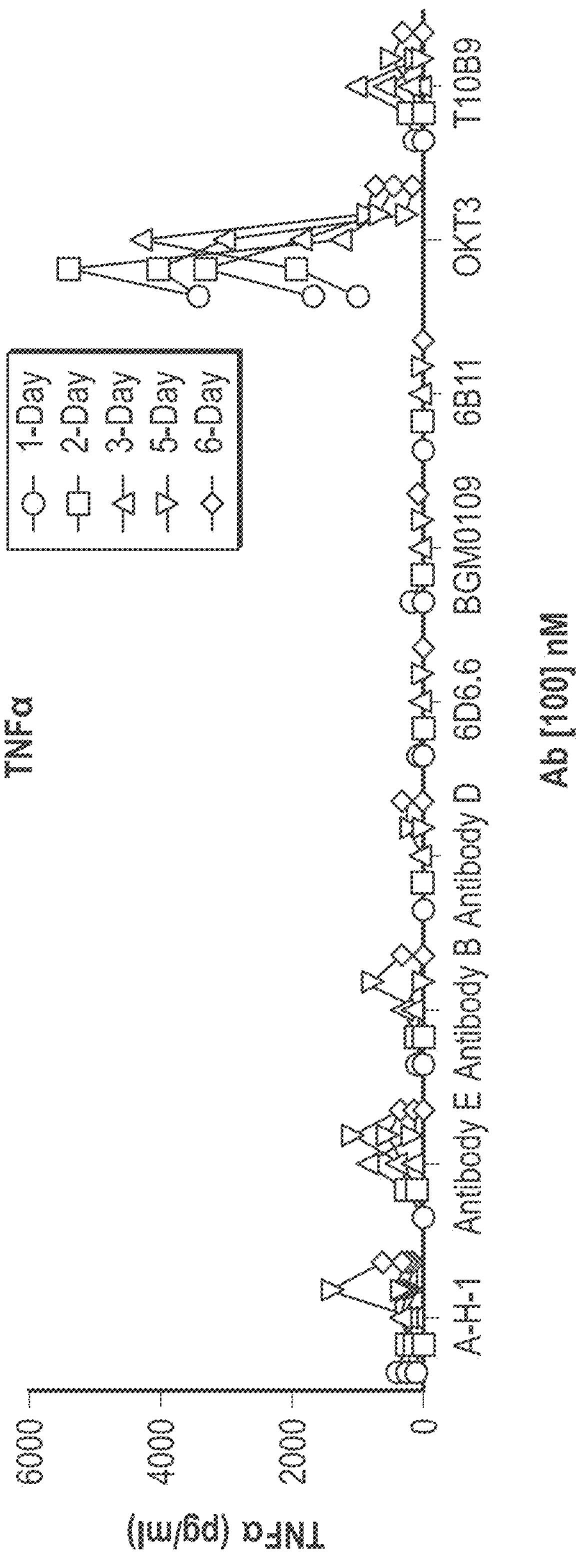
Figure 10A:
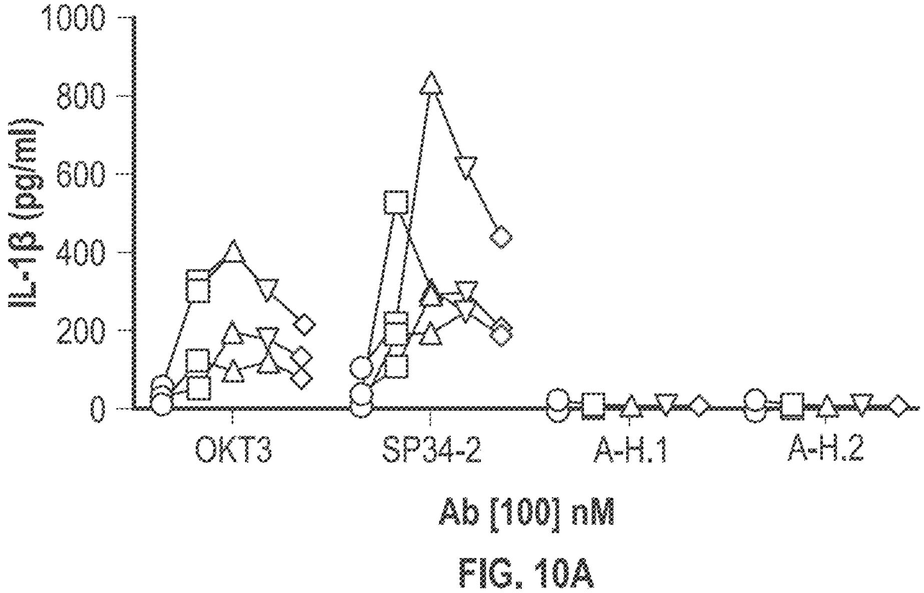
FIGS. 10A-10B show IL-1beta production by human PBMCs activated with the indicated antibodies. A similar experimental setup as described for FIGS. 6A-6B was used.
Figure 10B:
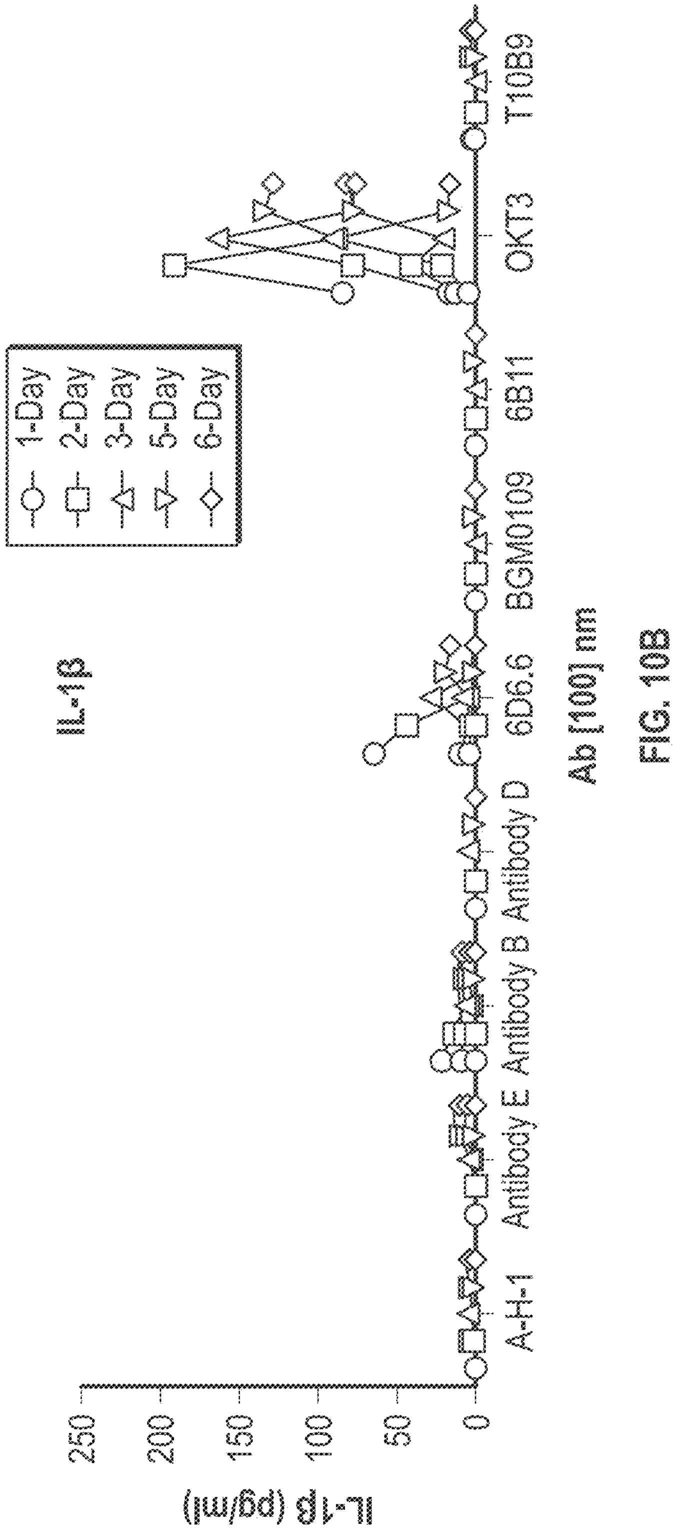

The production of cytokines IL-6, IL-1β and TNF-alpha which are associated with "cytokine storms" (and accordingly CRS) was also assessed under similar conditions. FIGS. 8A, 9A and 10A shows that while PBMCs activated with anti-CD3e antibodies demonstrate production of IL-6 (FIG. 8A), TNF-alpha (FIG. 9A) and IL-1β (FIG. 10A), no or little induction of these cytokines was observed with PBMCs activated with A-H.1 or A-H.2. As shown in FIGS. 9B and 10B, TNF-alpha and IL-1β production was not induced by activation of PBMCs with any of the anti-TCR VB antibodies.

Figure 11A:
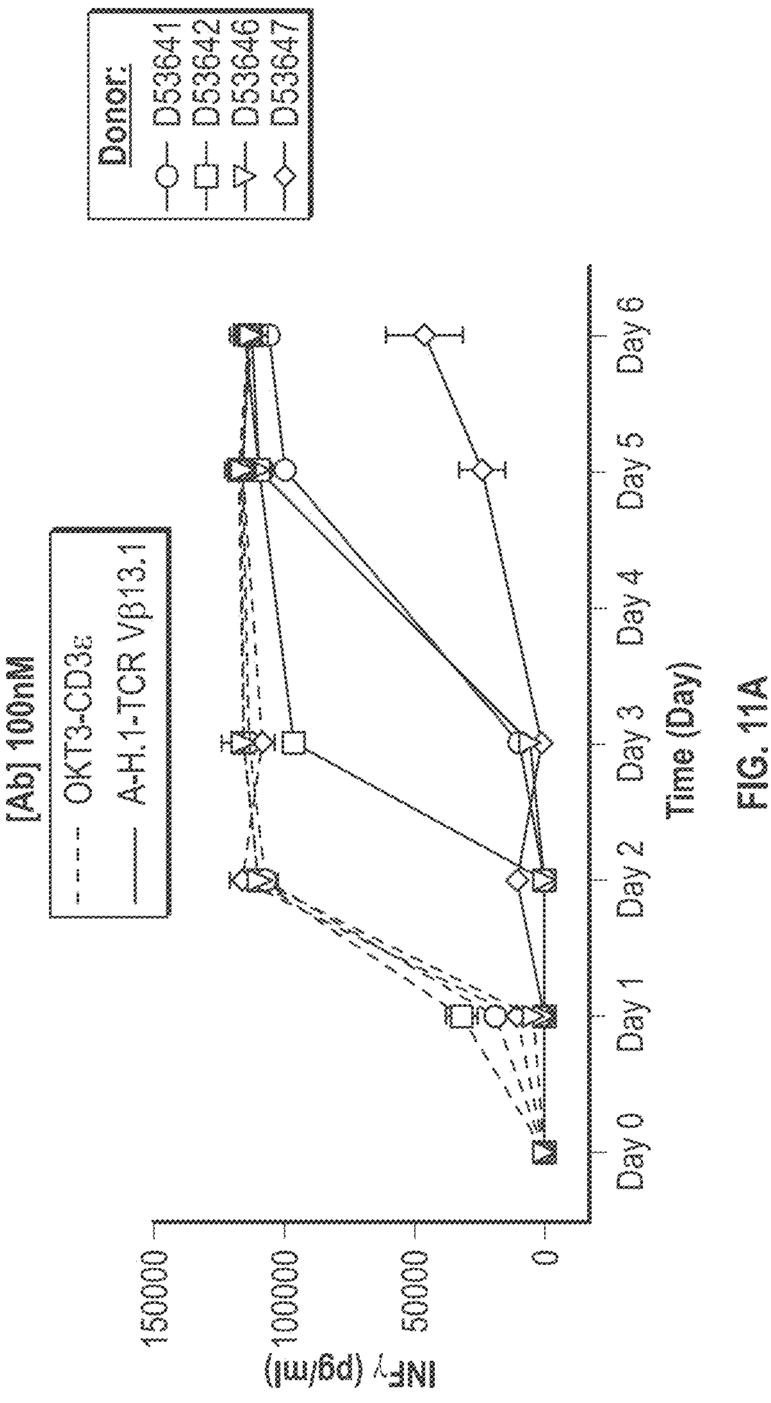
FIGS. 11A-11B are graphs showing delayed kinetics of IFNg secretion in human PMBCs activated by anti-TCR Vβ13.1 antibody A-H.1 when compared to PBMCs activated by anti-CD3e antibody OKT3.
Figure 11B:
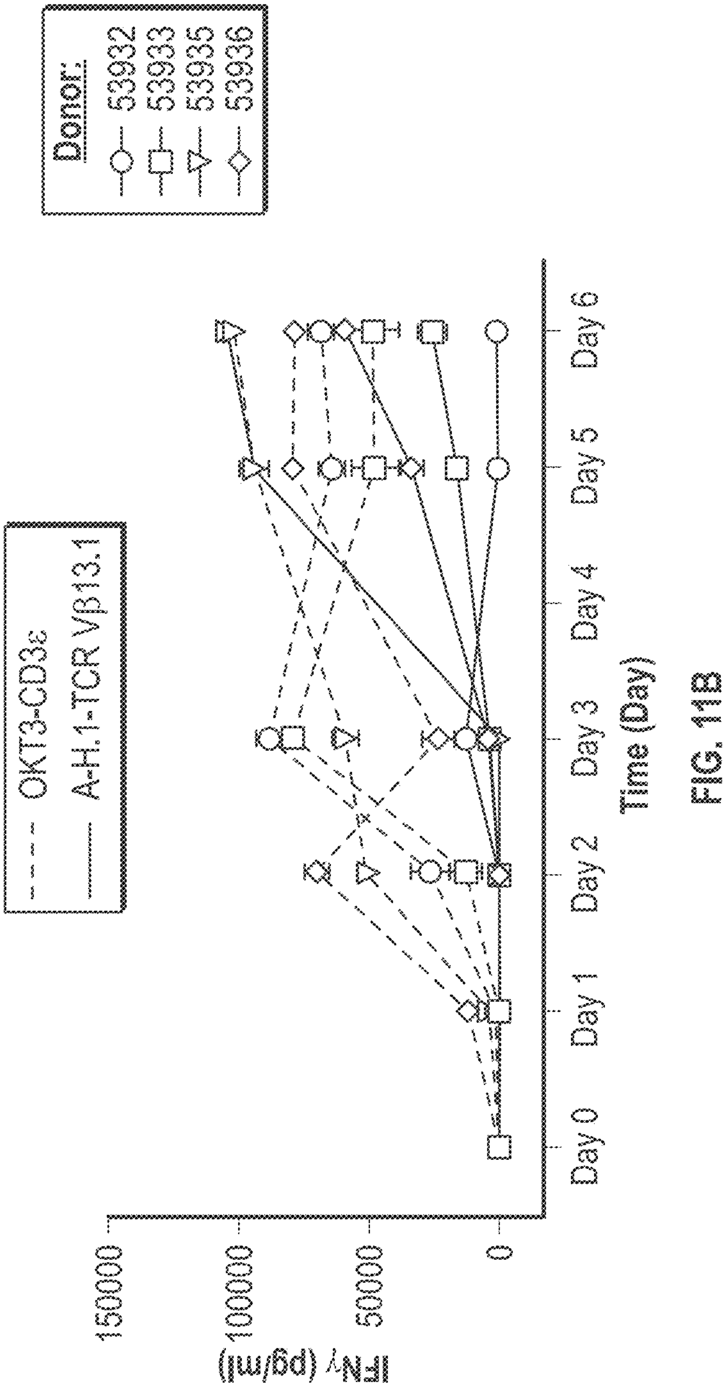

It was further noted that the kinetics of IFNg production by A-H.1-activated CD3+ T cells was delayed relative to those produced by CD3+ T cells activated by anti-CD3ε mAbs (OKT3 and SP34-2) (FIGS. 11A and 11B).

Figure 12:
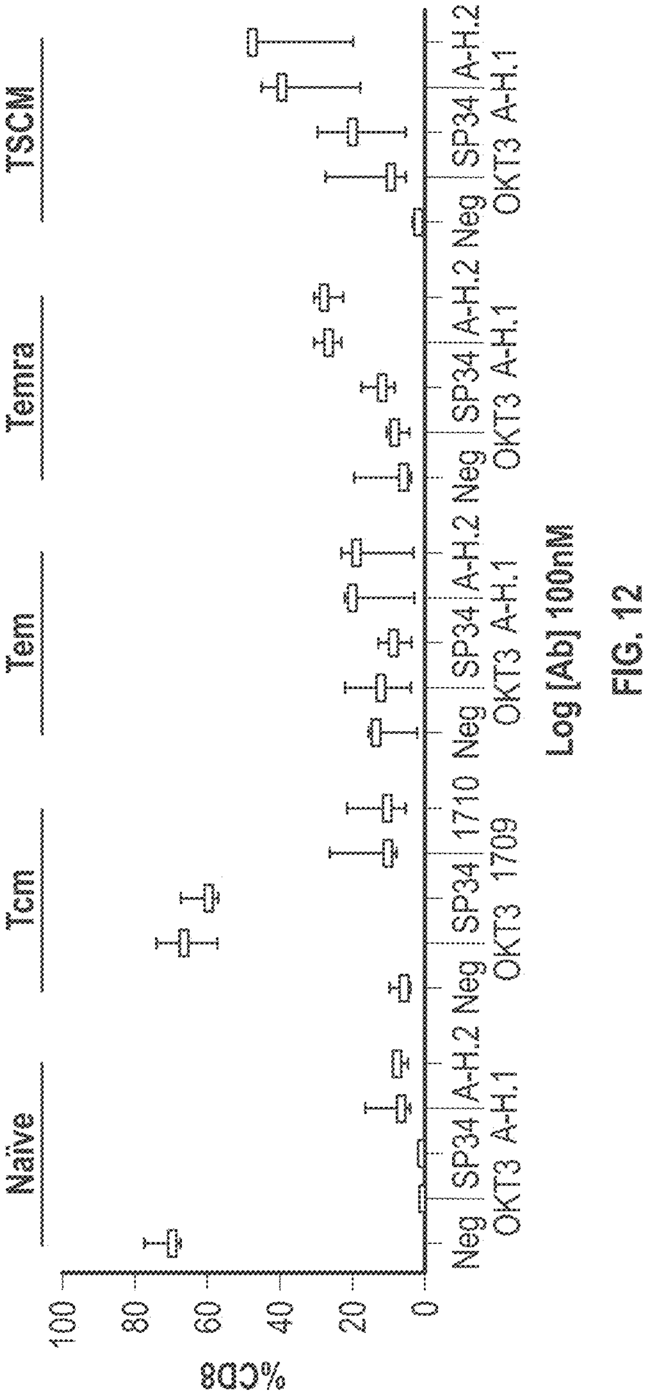
FIG. 12 depicts increased CD8+ TSCM and Temra T cell subsets in human PBMCs activated by anti-TCR Vβ13.1 antibodies (A-H.1 or A-H.2) compared to PBMCs activated by anti-CD3e antibodies (OKT3 or SP34-2).

Finally, it was observed that the subset of memory effector T cells known as TEMRA was preferentially expanded in CD8+ T cells activated by A-H.1 or A-H.2 (FIG. 12). Isolated human PBMCs were activated with immobilized (plate-coated) anti-CD3ε or anti-TCR Vβ13.1 at 100 nM for 6-days. After a 6-day incubation, T-cell subsets were identified by FACS staining for surface markers for Naive T cell (CD8+, CD95−, CD45RA+, CCR7+), T stem cell memory (TSCM; CD8+, CD95+, CD45RA+, CCR7+), T central memory (Tcm; CD8+, CD95+, CD45RA−, CCR7+), T effector memory (Tem; CD8+, CD95+, CD45RA−, CCR7−), and T effector memory re-expressing CD45RA (Temra; CD8+, CD95+, CD45RA+, CCR7−). Human PBMCs activated by anti-TCR VP 13.1 antibodies (A-H.1 or A-H.2) increased CD8+ TSCM and Temra T cell subsets when compared to PBMCs activated by anti-CD3ε antibodies (OKT3 or SP34-2). Similar expansion was observed with CD4+ T cells.

Conclusion

The data provided in this Example show that antibodies directed against TCR Vb can, e.g., preferentially activate a subset of T cells, leading to an expansion of TEMRA, which can, e.g., promote tumor cell lysis but not CRS. Thus, bispecific constructs utilizing either a Fab or scFV or a peptide directed to the TCR Vb can, e.g., be used to activate and redirect T cells to promote tumor cell lysis for cancer immunotherapy, without, e.g., the harmful side-effects of CRS associated with anti-CD3ε targeting.

Example 4: On-Target T Cell Mediated Cytotoxicity of Multiple Myeloma (MM) Cells with a Dual-Targeting Antibody Molecule Against BCMA and a T Cell Engager This example shows on-target T cell mediated cytotoxicity of multiple myeloma (MM) cells with dual-targeting antibody molecules that recognize a T cell engager, e.g., TCRVb, on T cells and BCMA on MM cells.

Figure 13A:
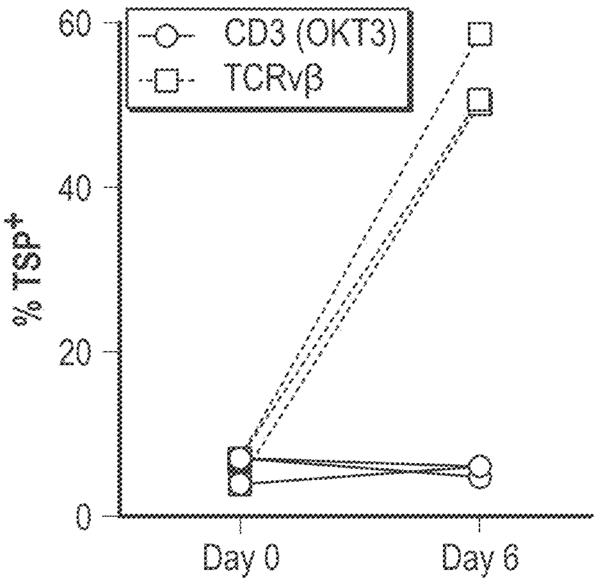
FIGS. 13A-13F show characterization of an anti-TCRVb antibody.
Figure 13B:
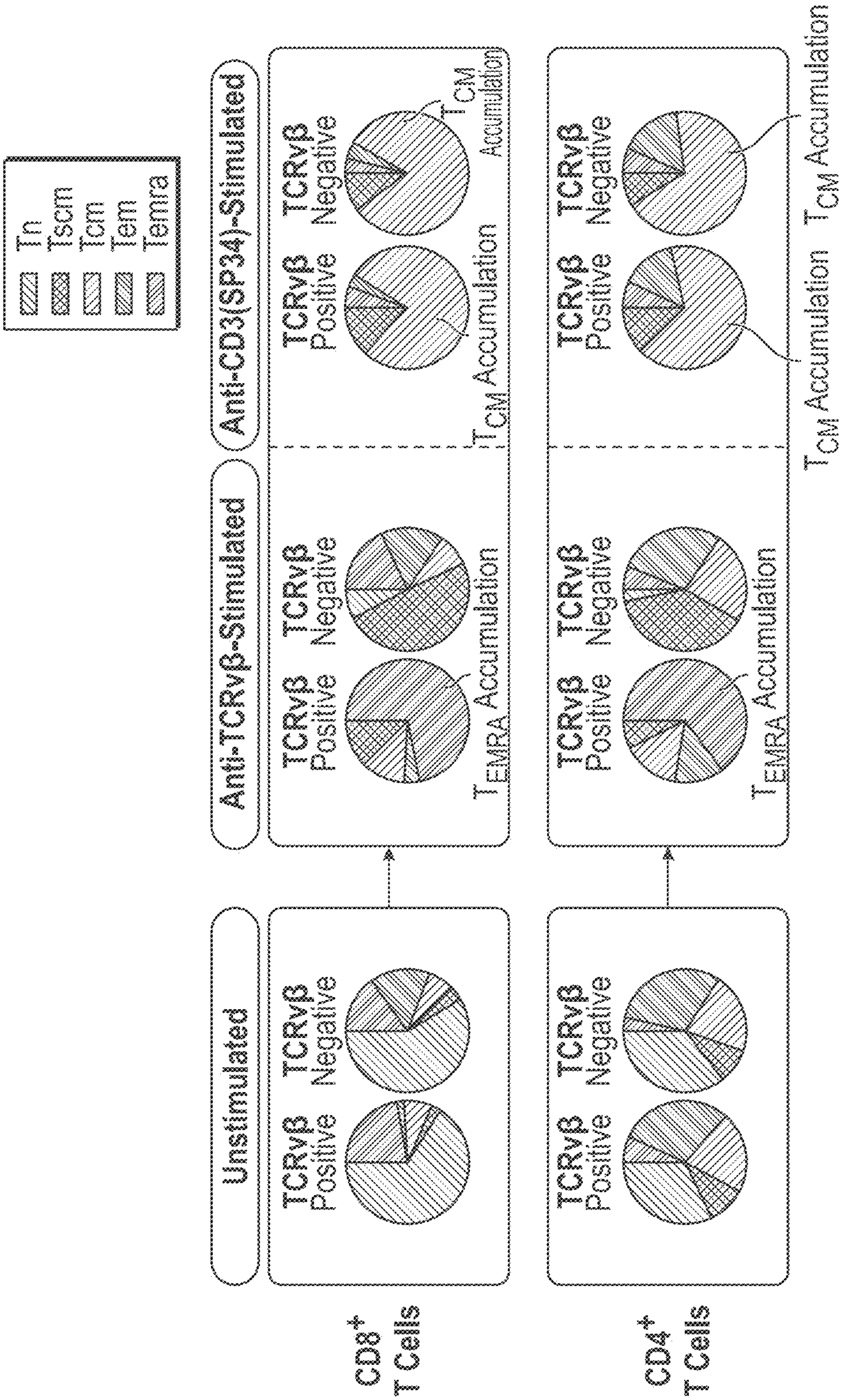
Figure 13C:
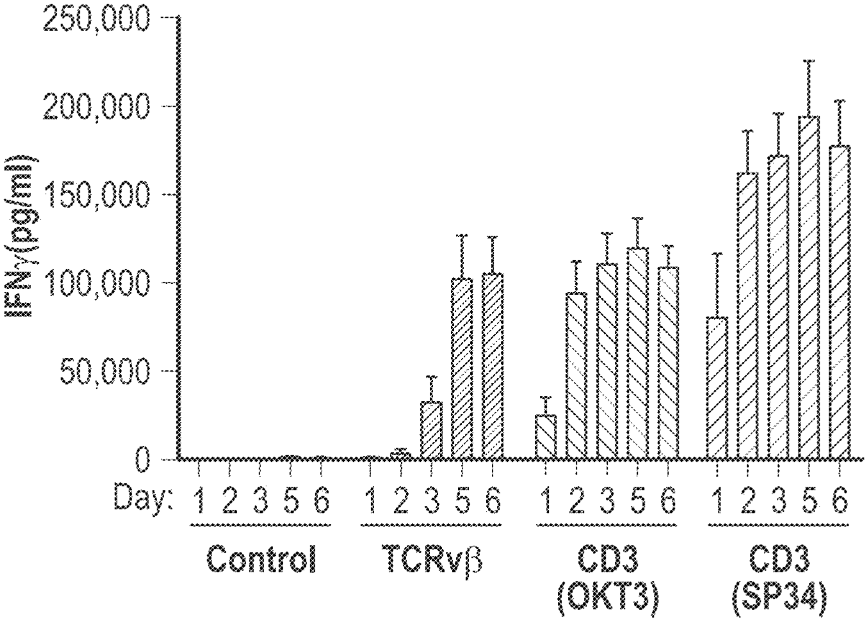
Figure 13D:
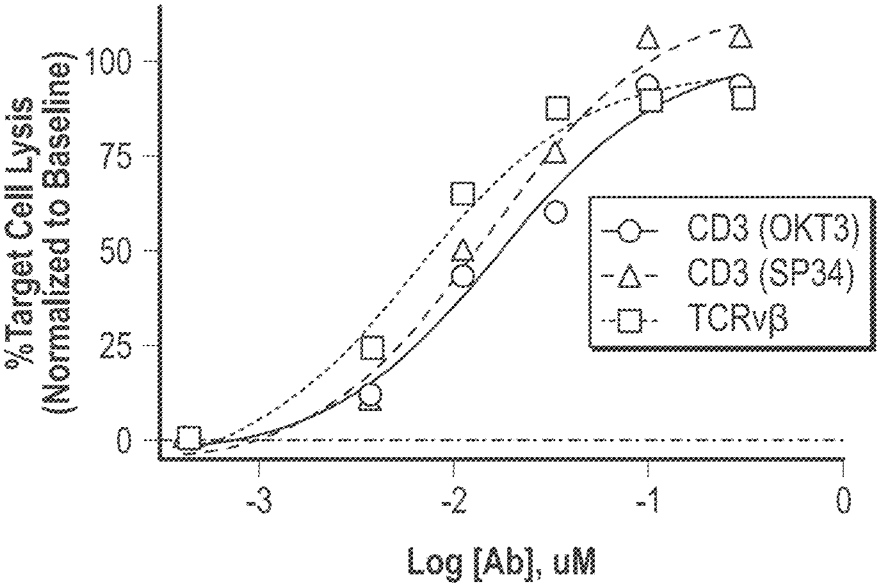
Figure 13E:
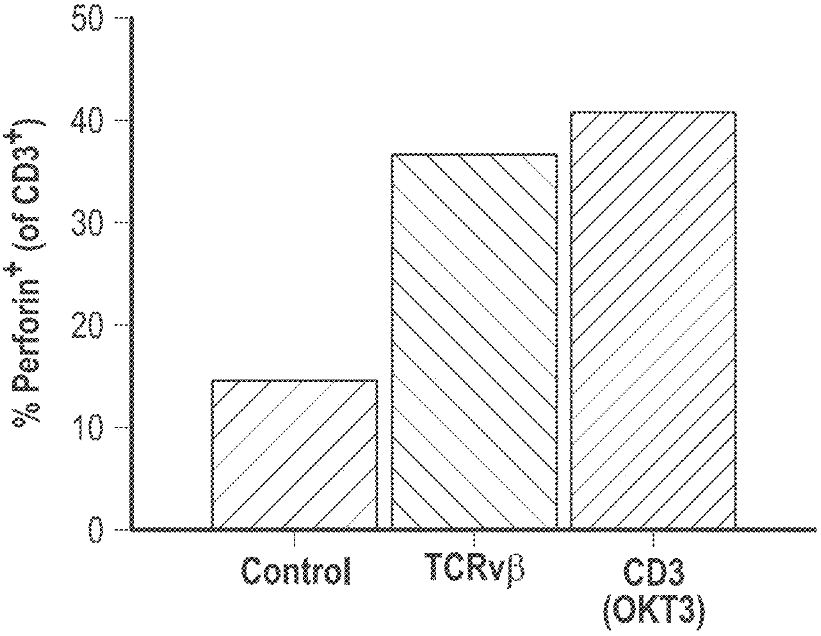
Figure 13F:
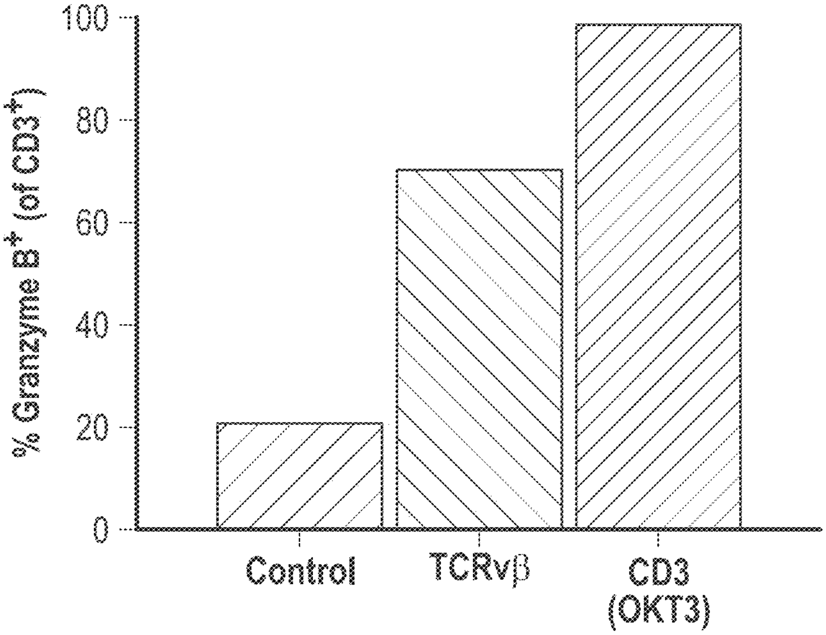

As shown in FIG. 13A, purified human T cells activated with plate-bound anti-TCRVb antibody for 5 days proliferate at a higher rate than purified human T cells activated with plate-bound anti-CD3 (OKT3) antibody. Anti-TCRVb antibody stimulation of T cells resulted in selective expansion of CD45RA+ effector memory CD8+ and CD4+ T cells (TEMRA) cells (FIG. 13B). Both CD8+ and CD4+ Temra cell populations expanded more when stimulated with an anti-TCRVb antibody, compared to unstimulated cells or cells stimulated with an anti-CD3 (SP34) antibody. Anti-TCRVb antibodies resulted in delayed secretion of IFN-g by PBMCs stimulated with an anti-TCRVb antibody compared to PBMCs stimulated with anti-CD3 antibodies (FIG. 13C). Additionally, T cells stimulated with anti-TCRVb antibody or anti-CD3 antibodies resulted in comparable lysis of multiple myeloma target cells, as shown in FIG. 13D. As shown in FIGS. 13E-13F, T cells stimulated for 5 days with 100 ng/ml plate-bound an anti-TCRVb antibody, or an anti-CD3 antibody secreted perforin and Granzyme B.

Figure 14A:
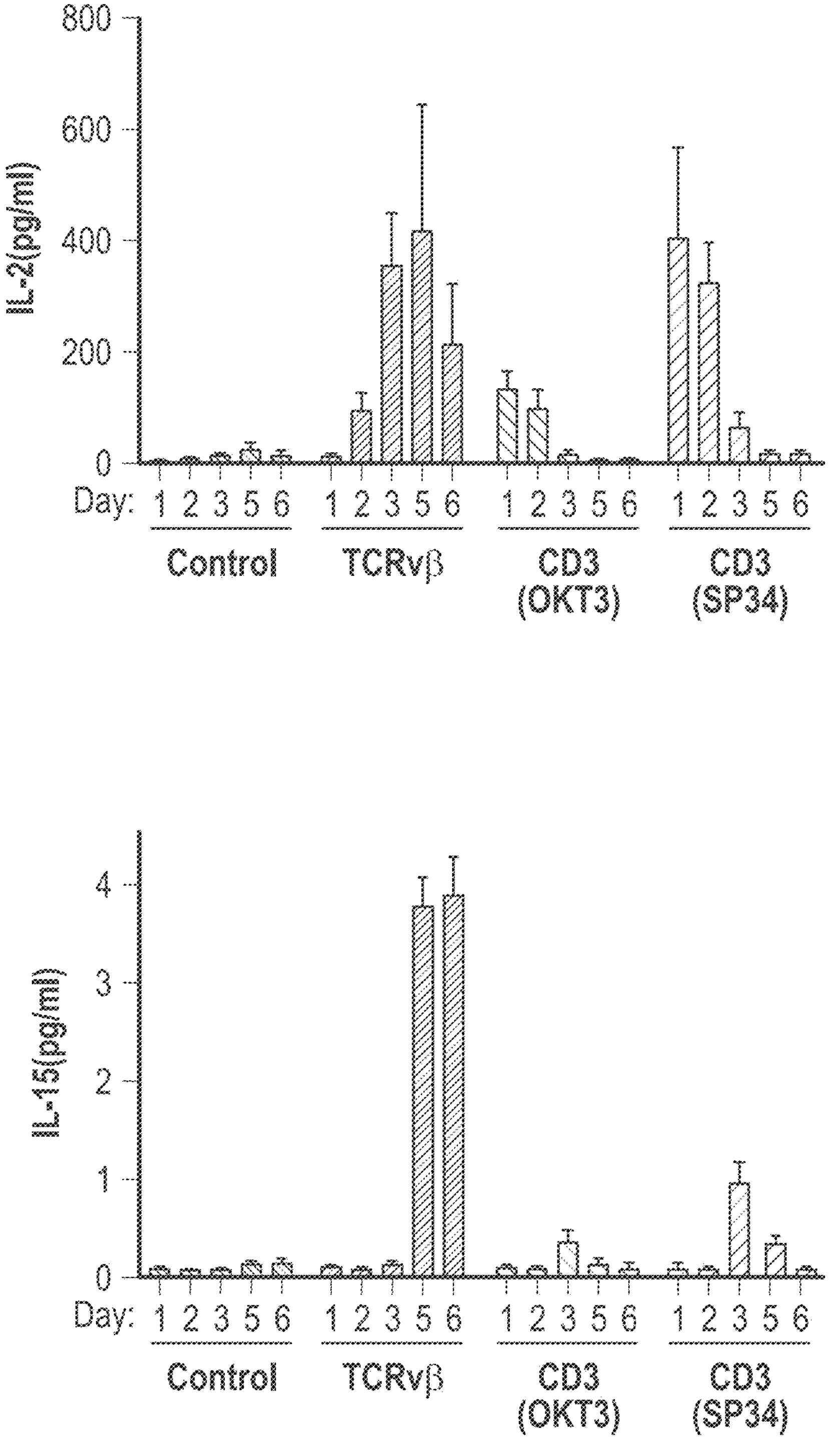
FIGS. 14A-14C show production of IL-2 and IL-15 and expansion of human NK cells by stimulation of PBMCs with anti-TCRVb antibody for 6 days at a dose of 100 nM.
Figure 14B:
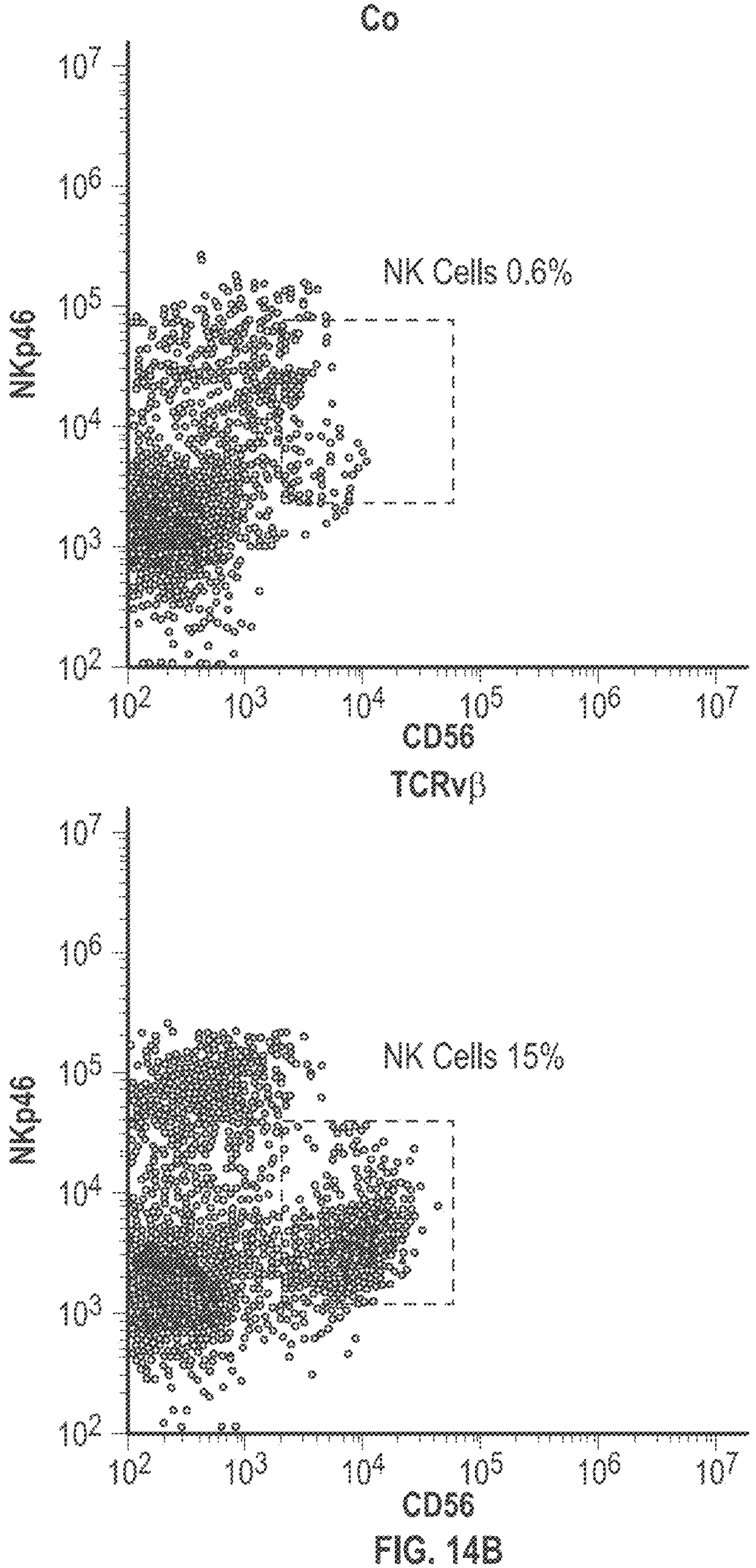
Figure 14C:
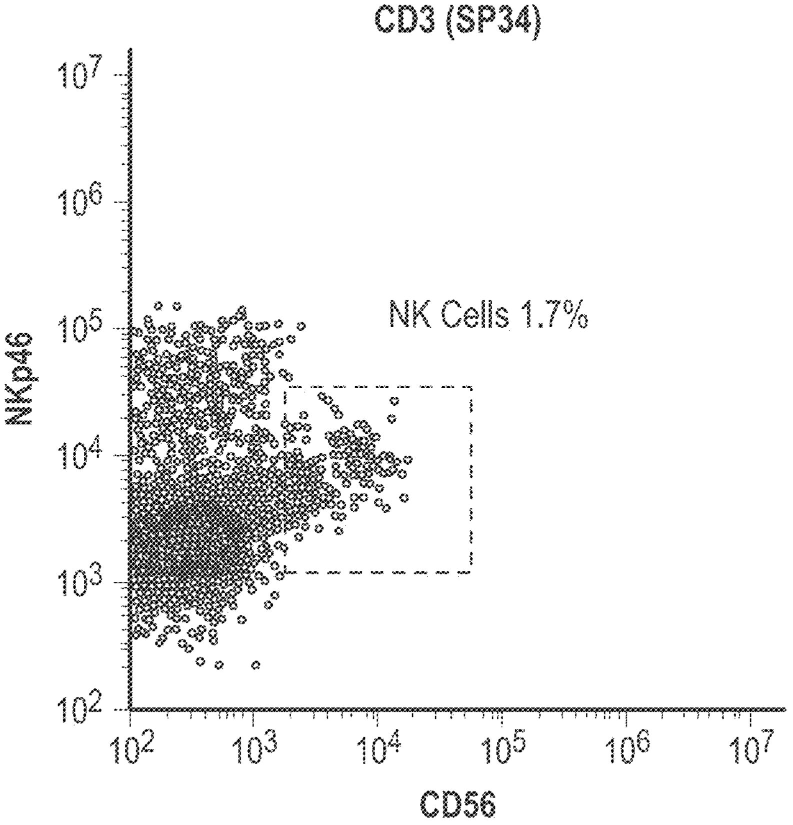
Figure 15A:
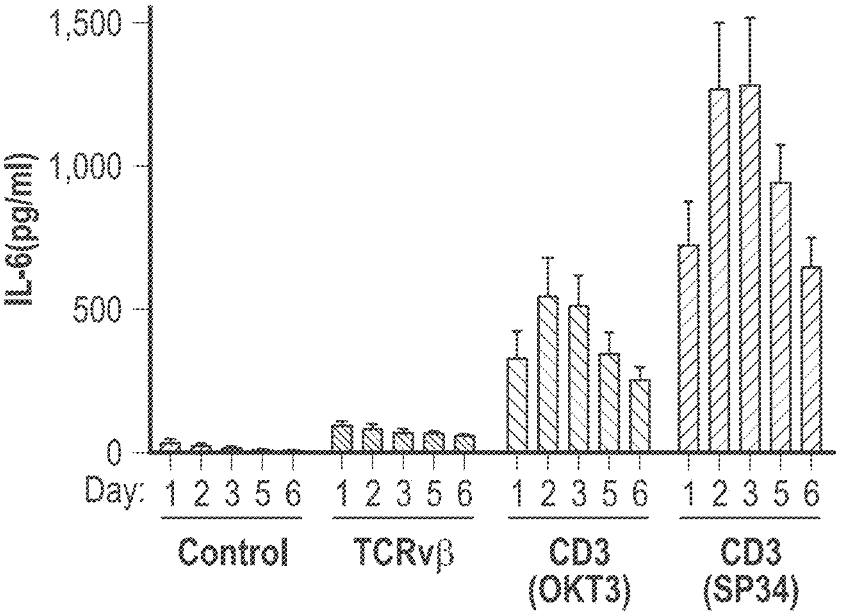
FIGS. 15A-15C show secretion of cytokines in PBMCs stimulated with an anti-TCRVb antibody, or anti-CD3 antibodies.
Figure 15B:
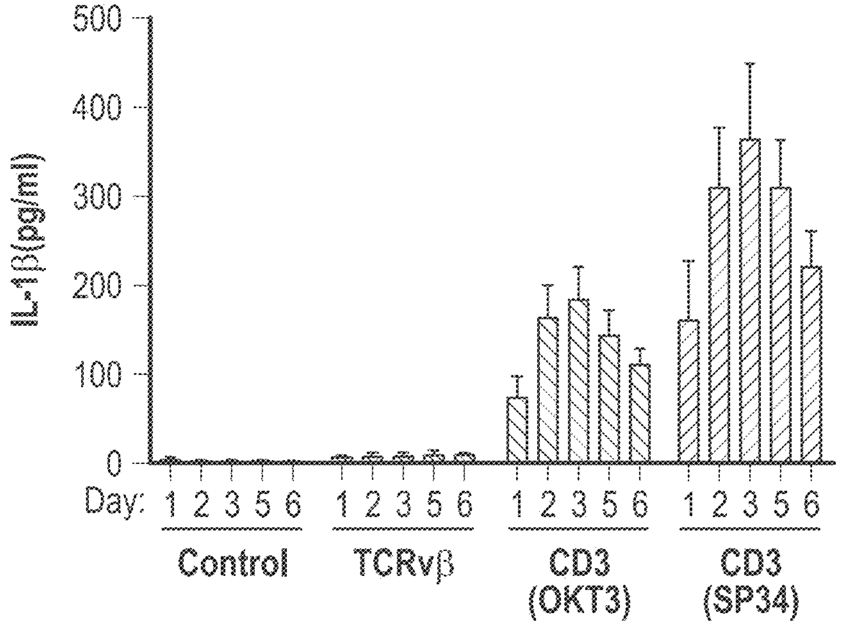
Figure 15C:
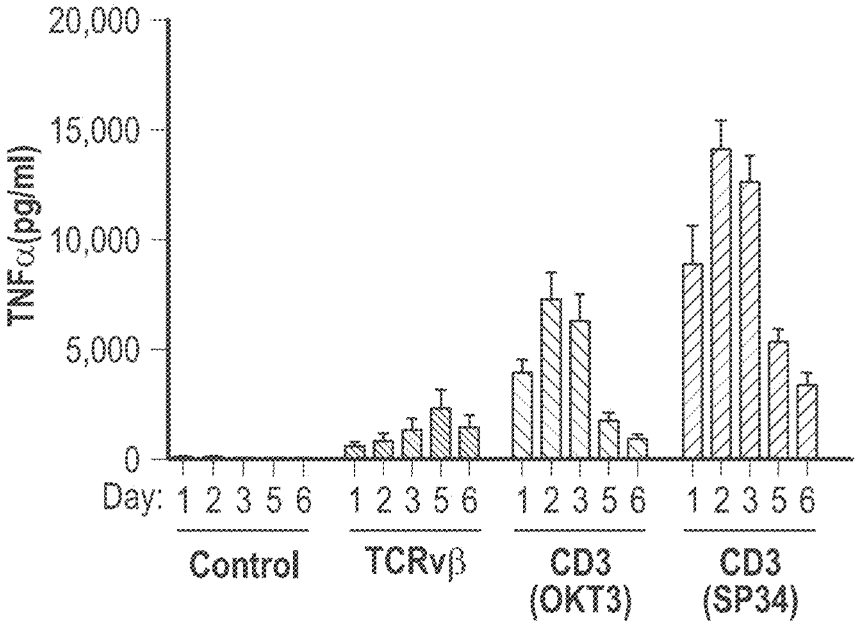

Activation of PBMCs with anti-TCRVb antibody resulted in higher production and/or secretion of IL-2 and/or IL-15 compared to PBMCs activated with an anti-OKT3 antibody (FIG. 14A). Anti-TCRVb antibody activated of PBMCs also resulted in expansion and/or survival, e.g., proliferation of Natural Killer (NK) cells (FIG. 14B). In comparison, PBMCS activated with an anti-OKT3 antibody did not result in NK cell expansion. Further, as described in Example 3, PBMCs activated with an anti-TCRVb antibody did not result in the production of cytokines IL-6, IL-1β and TNF-alpha which are associated with CRS (FIG. 15). These in vitro characterization studies show that in some embodiments, anti-TCRVb antibodies, e.g., activate and/or stimulate, T cells to promote T cell killing as evidenced by target cell lysis, perforin secretion and granzyme B secretion, and secretion of IFN-g with, e.g., delayed kinetics.

Figure 16A:
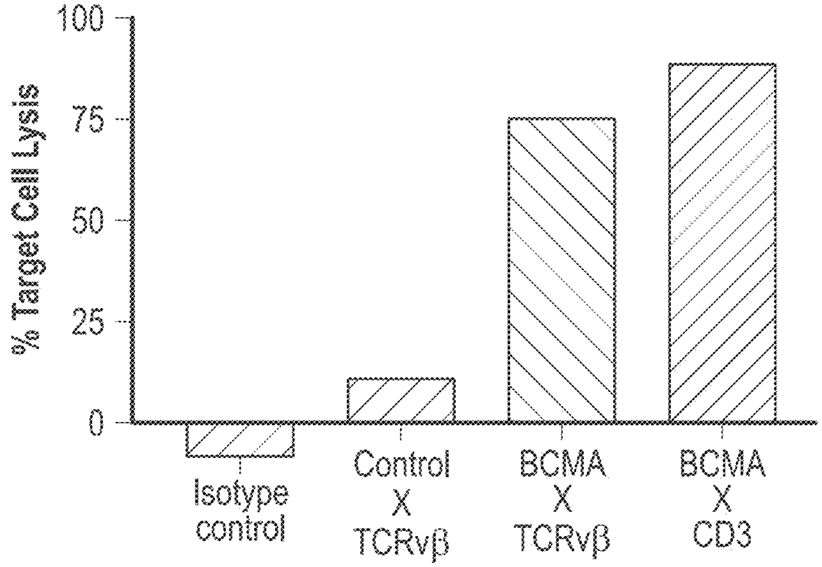
FIGS. 16A-16B show killing of MM cells by dual targeting BCMA-TCRvb antibody molecules.

Next, the ability of a dual-targeting antibody molecule (Molecule I), which targets BCMA on one arm and TCRVb on the other arm, to target and kill multiple myeloma (MM) cells was tested. Healthy donor PBMCs were co-incubated with the RMPI8226 MM cell line and one of the following dual-targeting antibody molecules: BCMA-TCRVb (Molecule I), BCMA-CD3, or Control-TCRVb; or an isotype control Target cell lysis was then assessed using flow cytometry. As shown in FIG. 16A, the dual-targeting BCMA-TCRVb antibody molecule (Molecule I) resulted in killing of MM cells in vitro.

Figure 16B:
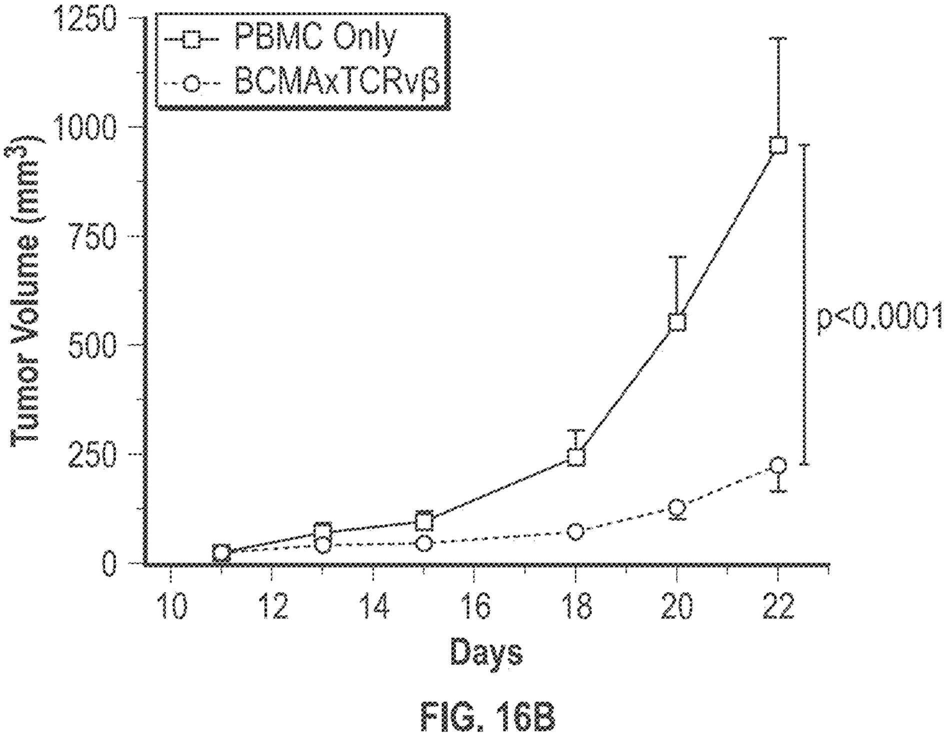

The dual-targeting BCMA-TCRVb antibody molecule (Molecule I) was further tested in vivo for its ability to inhibit MM tumor growth in a MM mouse model. The NCI-H929 cell line was injected in NOD-scid IL2rγnull (NSG) recipient mice on Day 0 followed by delivery of PBMCs on Day 9. On Days 12, 15, 18 and 21, the dual-targeting BCMA-TCRVb antibody molecule (Molecule I) was administered via intraperitoneal injection at a dose of 0.5 mg/kg. FIG. 16B shows prevention, e.g., inhibition, of MM tumor growth in vivo with the dual-targeting BCMA-TCRVb antibody molecule (Molecule I). These results demonstrate that in some embodiments the dual-targeting BCMA-TCRVb antibody molecule, e.g., can kill tumor cells, e.g., MM tumor cells, in vitro and in vivo. Accordingly, in some embodiments, a dual-targeting BCMA-TCRVb antibody molecule can be used, e.g., as a therapy for cancer, e.g., a hematological cancer, e.g., MM.

Figure 17:
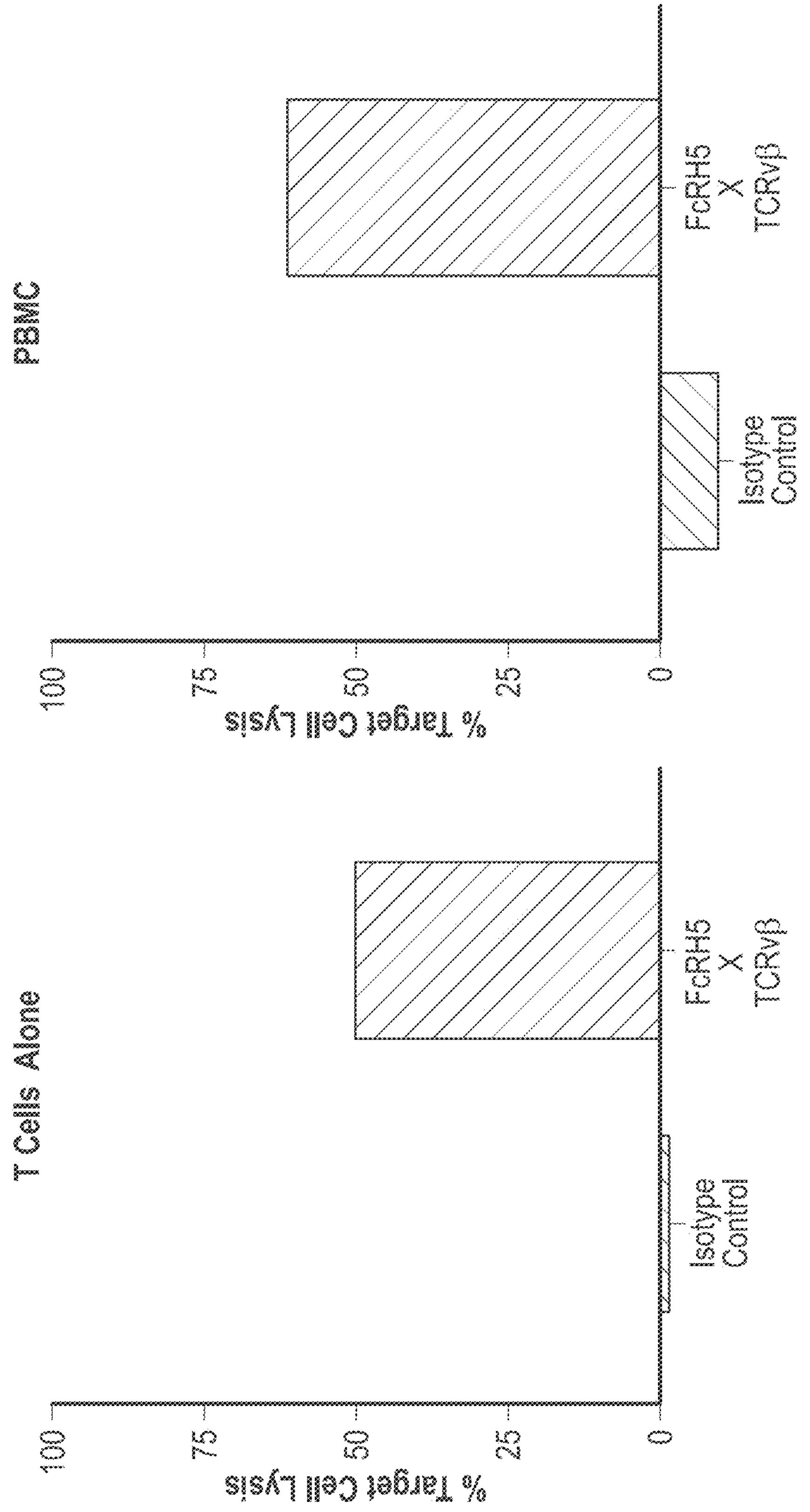
FIG. 17 shows lysis of MM target cells with a dual targeting antibody (Molecule E) which recognized FcRH5 on one arm and TCRVb on the other arm.

Example 5: In Vitro Cytotoxicity of a Dual-Targeting Antibody Molecule Against FcRH5 and a T Cell Engager This example shows in vitro cytotoxicity on multiple myeloma (MM) cells with a dual-targeting antibody molecule that recognizes a T cell engager, e.g., TCRVb, on T cells and FcRH5 on MM cells. Healthy donor PBMCs or purified T cells were co-incubated with the MOL8M MM cell line and a dual-targeting antibody molecule which targets FcRH5 on one arm and TCRVb on the other arm (Molecule E), or with an isotype control antibody. Target cell lysis was then assessed using flow cytometry. As shown in FIG. 17, the dual targeting FcRH5-TCRVb molecule (Molecule E) resulted in killing of MM cells by both purified T cells or PBMCs. This shows that the dual targeting FcRH5-TCRVb molecule can target and promote killing of MM cells by immune cells, e.g., in PBMCs, including T cells.

Example 6: Characteristics of Anti-TCR Vβ8a Antibodies

This Example shows in vitro characterization of anti-TCR Vβ8a antibodies (B-H.1). TCR Vβ8 is also referred to as TCR Vβ12 (as described in Table 8A). Isolated human PBMCs were activated with immobilized (plate-coated) anti-CD3ϵ or anti-TCR Vβ8a at 100 nM, and cell culture supernatants were collected on day 1, 2, 3, 5, 6 and 8 post stimulation. Cytokines (IFNγ, IL-2, TNFα, IL-1β or IL-6) were measured using MSD technology platform (MesoScale Discovery) as described in the manufacturer's protocol.

Figure 18A:
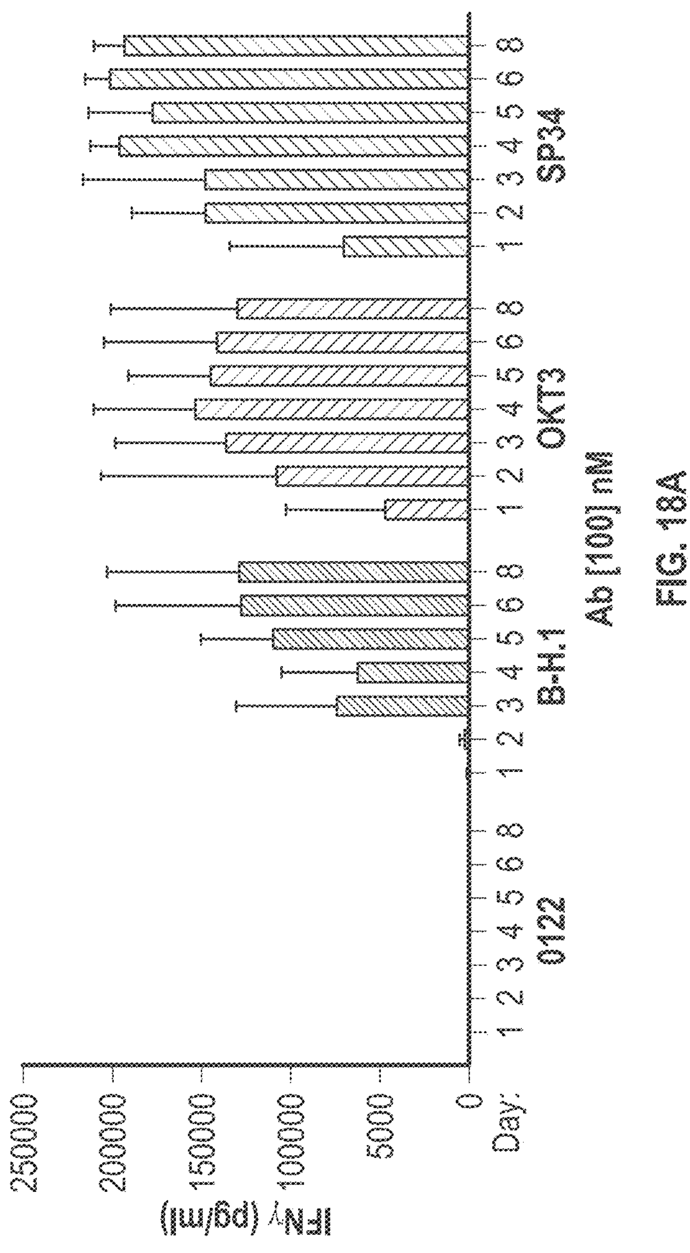
FIGS. 18A-18B demonstrate cytokine production from human PBMCs activated by anti-TCR Vβ8a antibodies (B-H.1) when compared to those activated by anti-CD3ϵ antibodies (OKT3 or SP34-2).
Figure 18B:
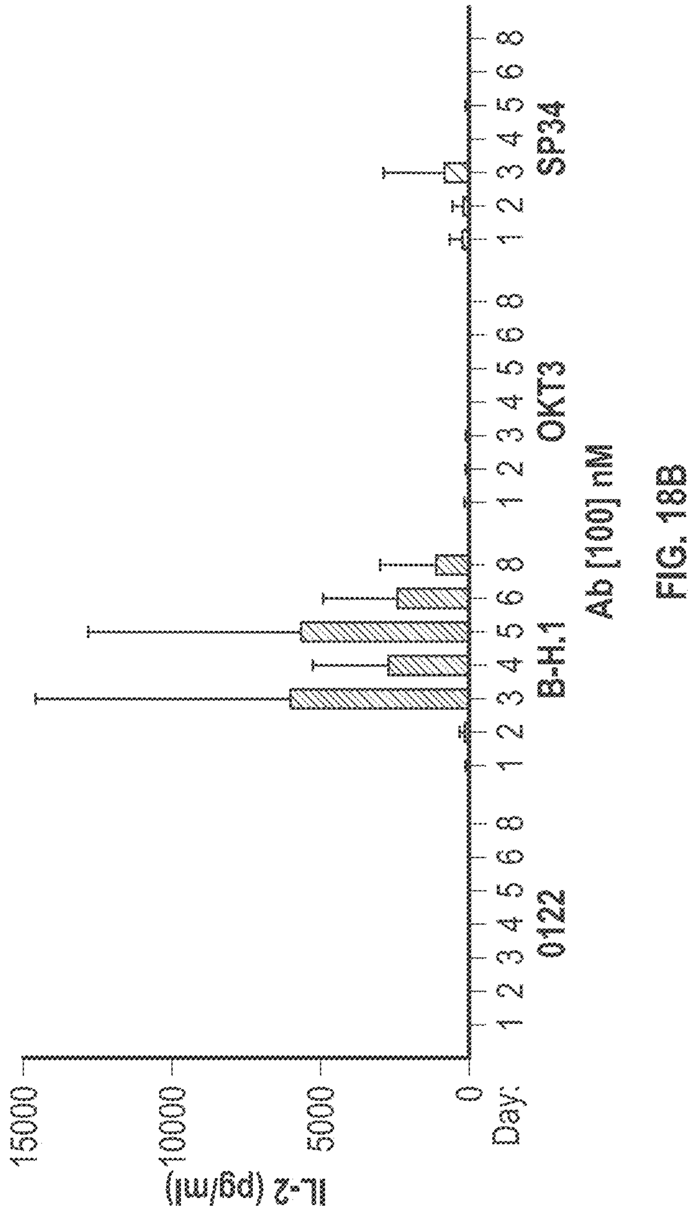

As shown in FIGS. 18A-18B, Human PBMCs activated by anti-TCR Vβ8a antibodies (B-H.1) produce similar or reduced levels of IFNγ (FIG. 18A) and higher levels IL-2 (FIG. 18B) when compared to those activated by anti-CD3ϵ antibodies (OKT3 or SP34-2).

Figure 19A:
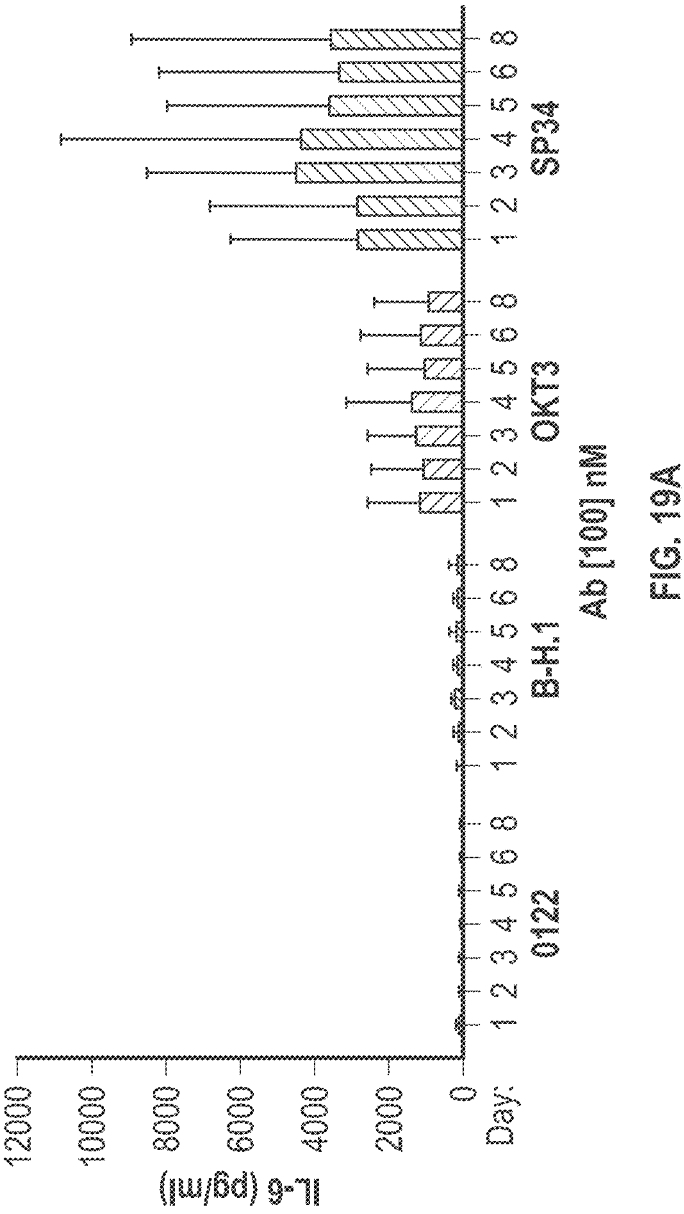
FIGS. 19A-19C demonstrate cytokine production from human PBMCs activated by anti-TCR Vβ8a antibodies (B-H.1). Human PBMCs activated by anti-TCR Vβ8a antibodies (B-H.1) do not significantly produce IL-6 (FIG. 19A), IL1b (FIG. 19B), and less TNFa (FIG. 19C), when compared to PBMCs activated by anti-CD3ϵ antibodies (OKT3 or SP34-2). Data shown is representative of n=6 donors.
Figure 19B:
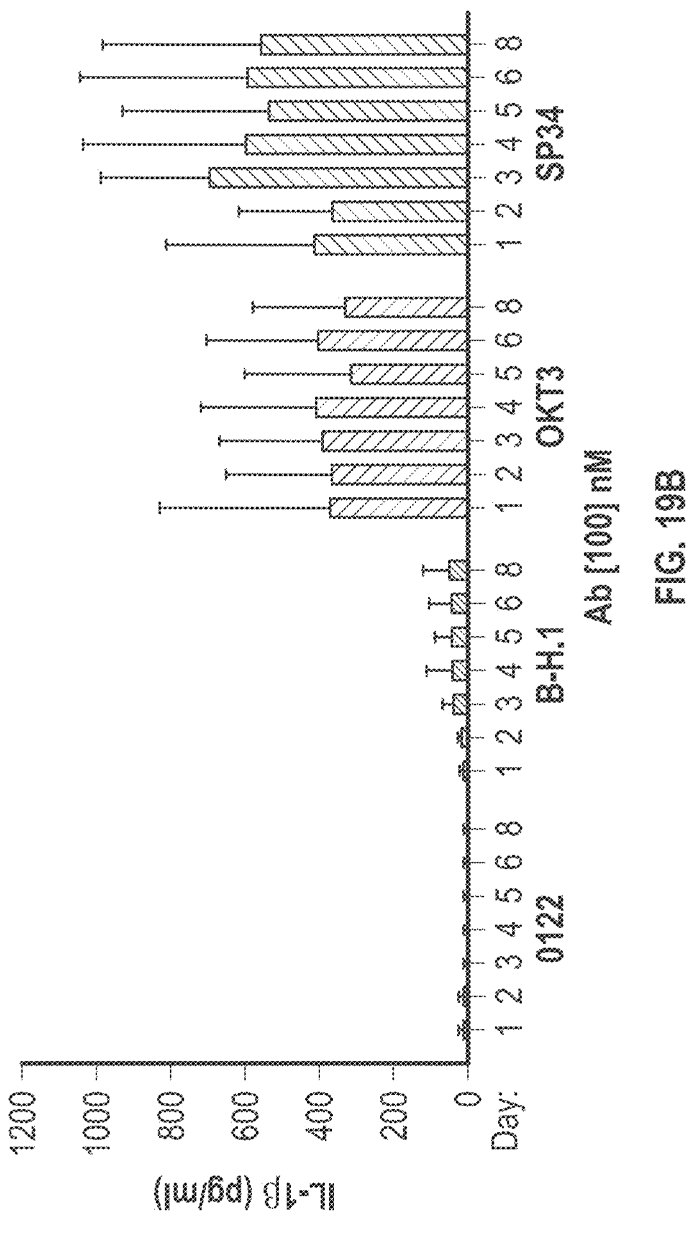
Figure 19C:
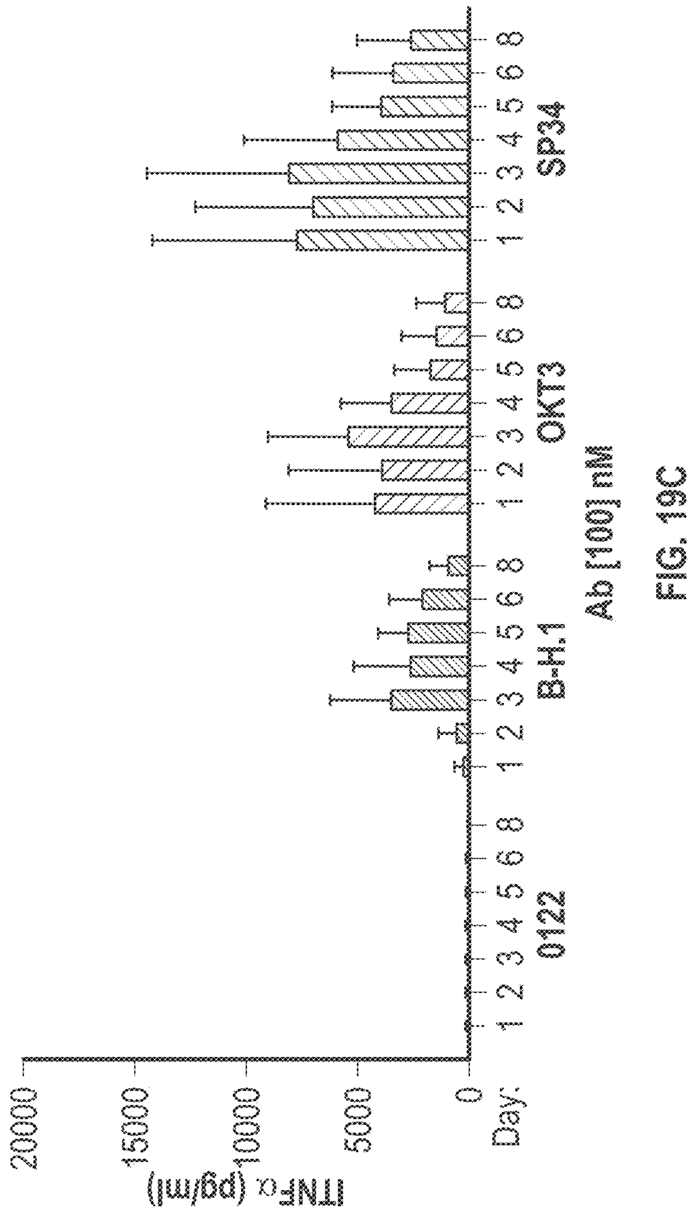

FIGS. 19A-19B show that human PBMCs activated by anti-TCR Vβ8a antibodies (B-H.1) do not produce significant levels of IL-6, or IL1b. Activation of human PBMCs with anti-TCR Vβ8a antibodies (B-H.1) also results in lesser TNFa when compared to PBMCs activated by anti-CD3ϵ antibodies (OKT3 or SP34-2) (see FIG. 19C).

In summary, as shown in Example 3, this Example shows that anti-TCR Vβ8a antibodies can, e.g., preferentially induce expression of T cell cytokines, e.g., IL-2 and IFNg, but not production of cytokines IL-6, IL-1β and TNF-alpha which are associated with "cytokine storms" (and accordingly CRS).

Example 7: Characteristics of Anti-TCRβV Antibody D Antibody

This Example describes characterization of anti-TCRβV antibodies which can bind and activate a subset of T cells, but with, e.g., no or markedly reduced, CRS.

Human PBMCs were isolated from whole blood followed by solid-phase (plate-coated) stimulation with anti-TCR Vβ12 antibody (Antibody D) or anti-CD3e antibodies (OKT3) at 100 nM. Supernatant was collected on Days 1, 2, 3, 5, or 6 followed by multiplex cytokine analysis for IFNg, IL-2, IL-6, IL-1beta, or TNFalpha. The data was quantified using MSD (Meso Scale Discovery) platform, following the manufacturer's protocol.

Figure 20A:
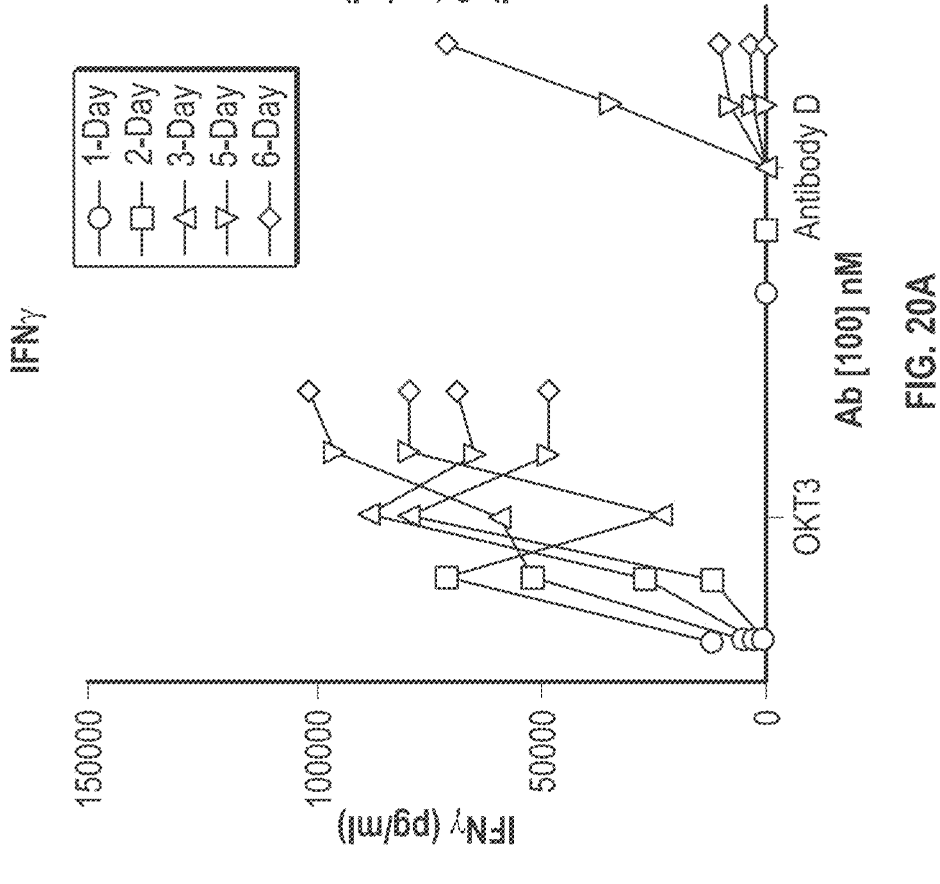
FIGS. 20A-20E demonstrate cytokine production from human PBMCs activated by anti-TCRβV Antibody D antibody compared to control anti-CD3e antibody (OKT3).
Figure 20B:
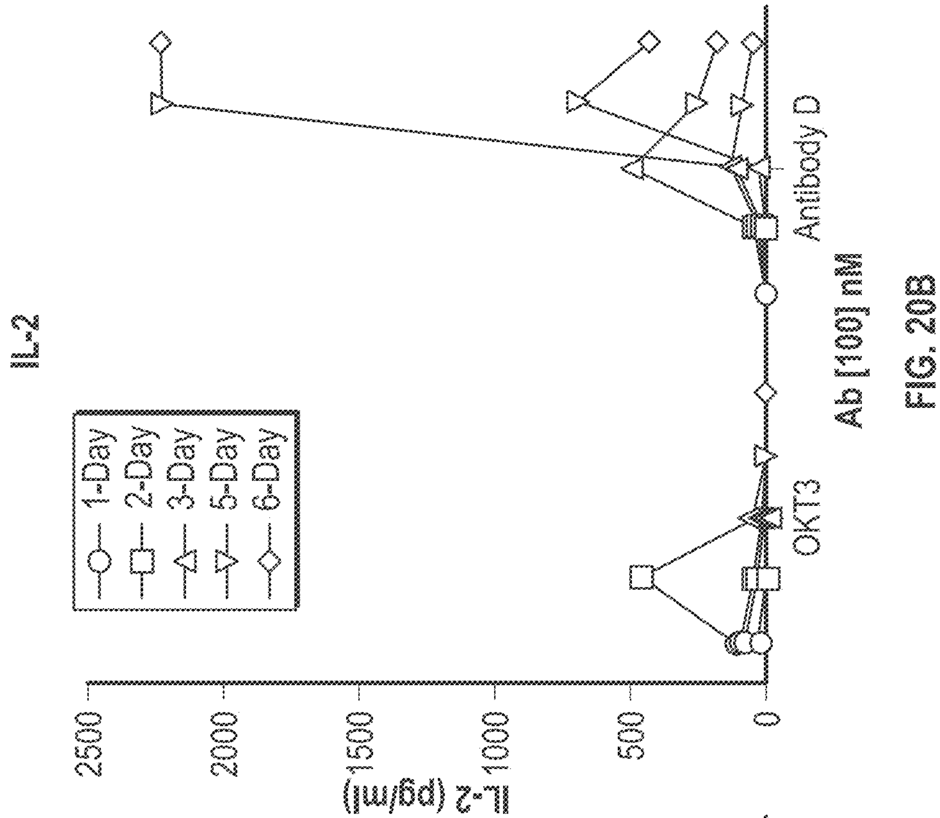

As shown in FIG. 20A, when plate-bound anti-TCR Vβ12 antibody (Antibody D) or anti-CD3e antibodies (OKT3) were used to activate human PBMCs, the T cell cytokine IFNg was induced. With respect to IL-2 production, PBMCs activated with anti-TCR Vβ12 antibody (Antibody D) resulted in increased IL-2 production with delayed kinetics (FIG. 20B) as compared to PBMCs activated with anti-CD3e antibodies (OKT3).

Figure 20D:
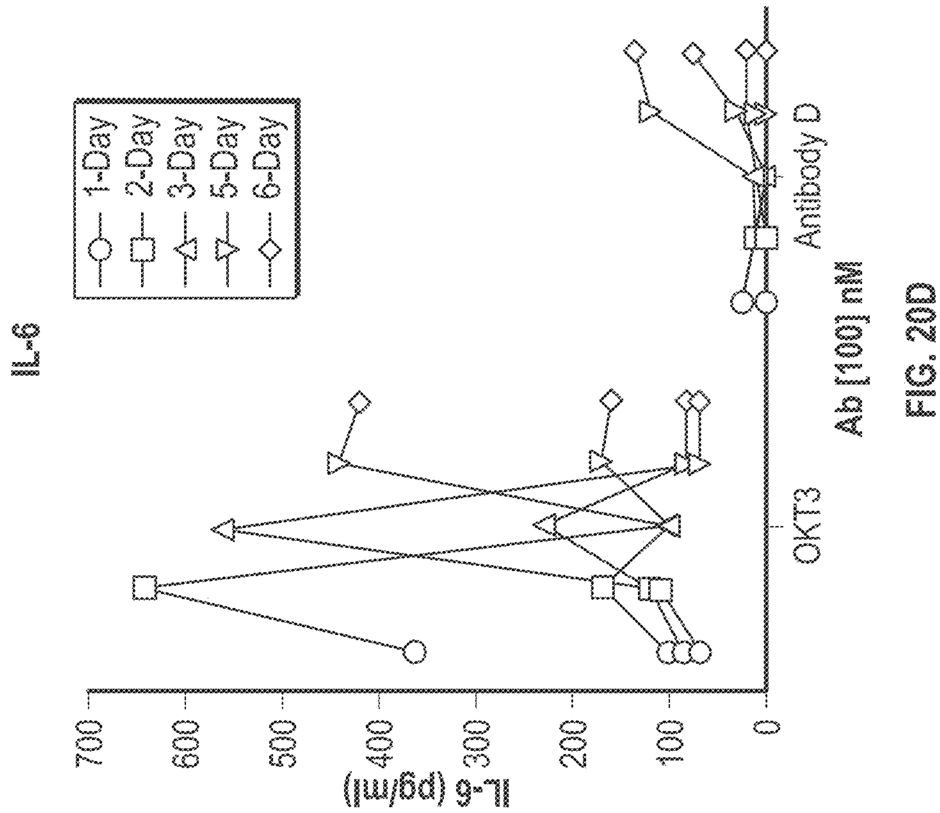
Figure 20C:
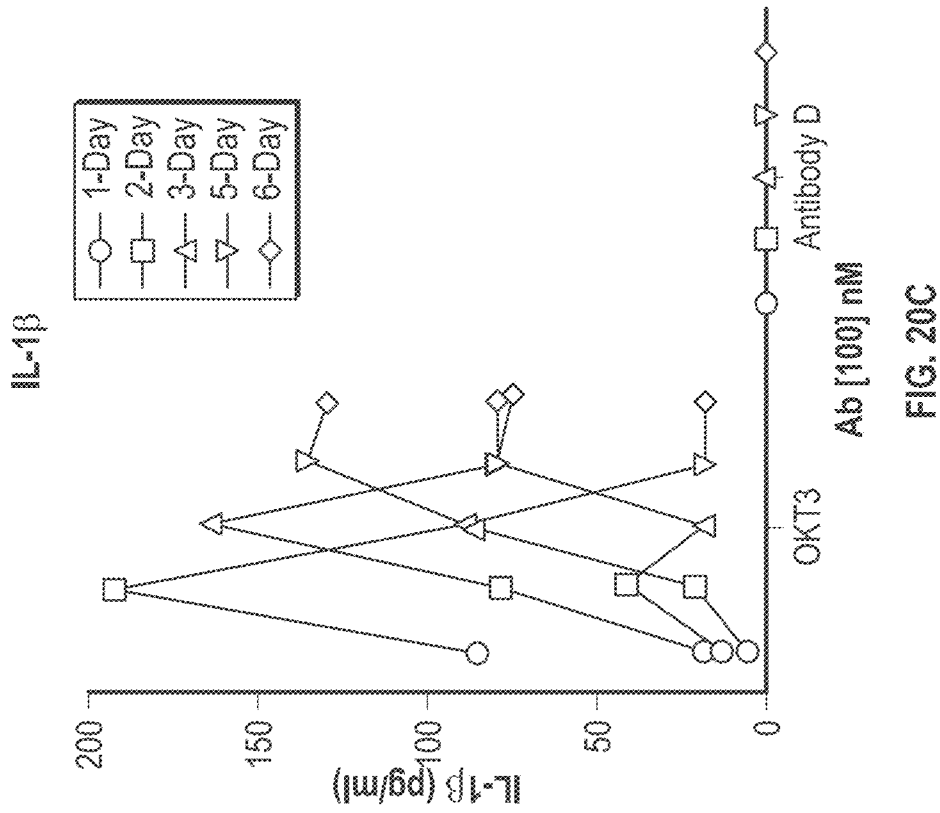
Figure 20E:
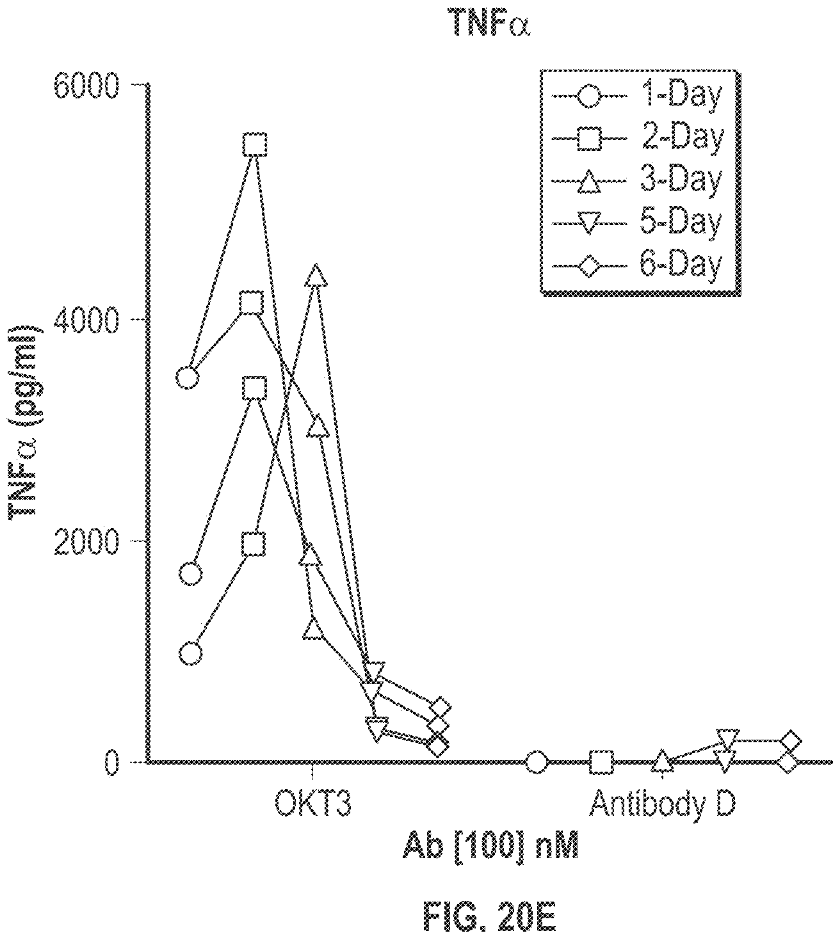

The production of cytokines IL-6, IL-1β and TNF-alpha which are associated with "cytokine storms" (and accordingly CRS) was also assessed under similar conditions. FIGS. 20C-20E show that that while PBMCs activated with anti-CD3e antibodies demonstrate production of IL-6 (FIG. 20D), TNF-alpha (FIG. 20C) and IL-1β (FIG. 20E), no or little induction of these cytokines was observed with PBMCs activated with anti-TCR Vβ12 antibody (Antibody D).

The data provided in this Example show that antibodies directed against TCR Vβ can, e.g., preferentially activate a subset of T cells, and do not results in induction of cytokines associated with cytokine storms or CRS.

Example 8: Characteristics of Anti-TCRβV Antibody E

This Example describes characterization of anti-TCRβV antibodies which can bind and activate a subset of T cells, but with, e.g., no or markedly reduced, CRS.

Human PBMCs were isolated from whole blood followed by solid-phase (plate-coated) stimulation with anti-TCR Vβ5 antibody (Antibody E) or anti-CD3ε antibodies (OKT3 and SP34-2), each at 100 nM. Supernatant was collected on Days 1, 3, 5, or 7 followed by multiplex cytokine analysis for IFNg, IL-2, IL-6, IL-1beta, IL-10 or TNFalpha. The data was quantified using MSD (Meso Scale Discovery) platform, following the manufacturer's protocol.

Figure 21A:
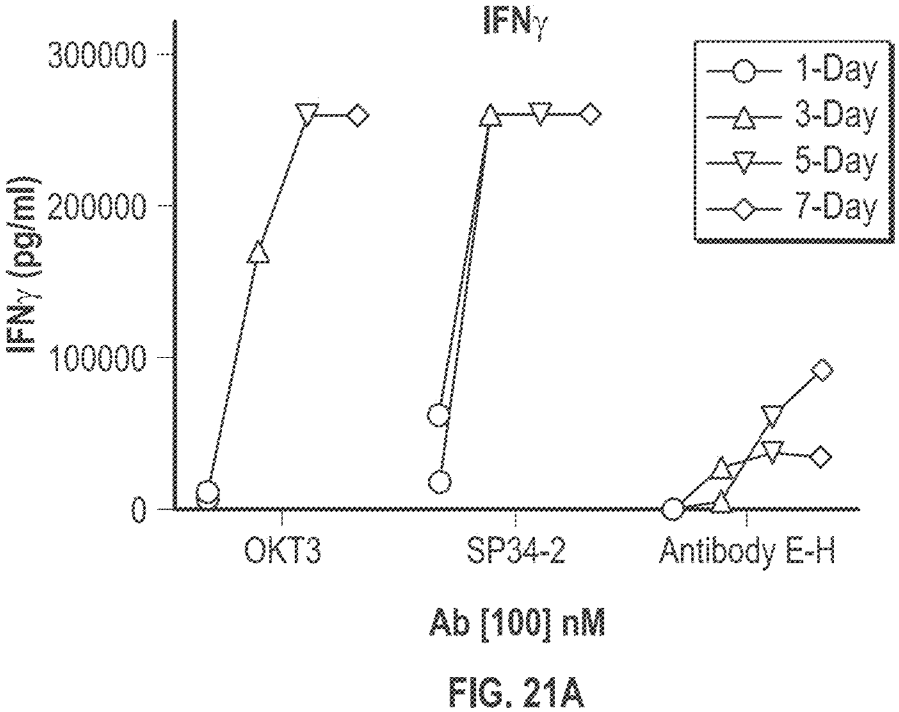
FIGS. 21A-21B demonstrate cytokine production from human PBMCs activated by anti-TCR Vβ5 antibody (Antibody E).
Figure 21B:
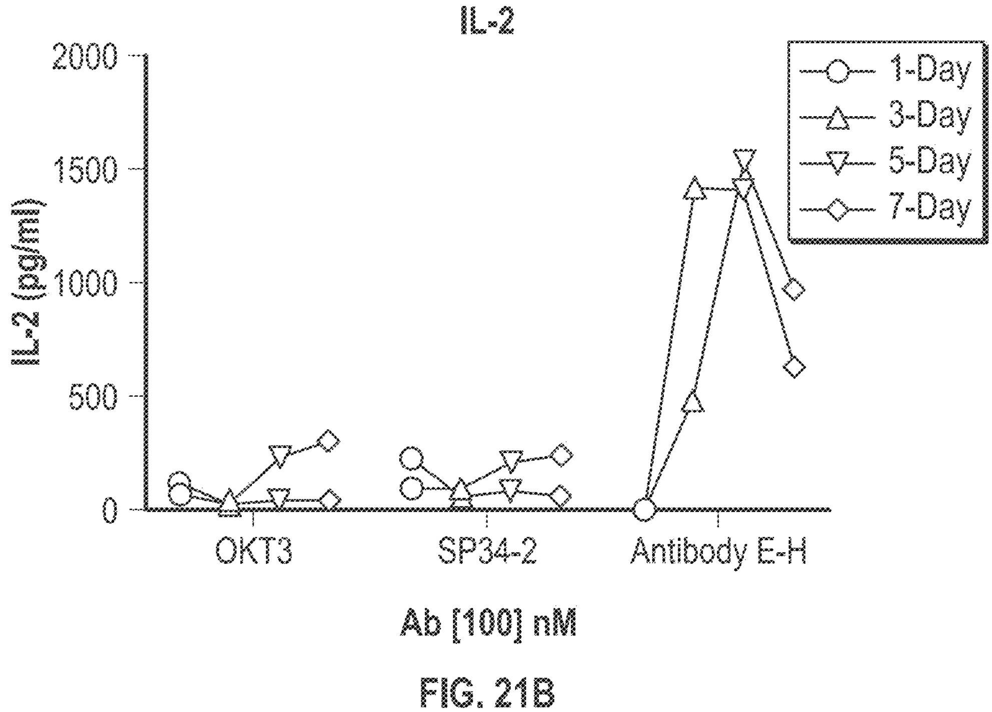
Figure 22A:
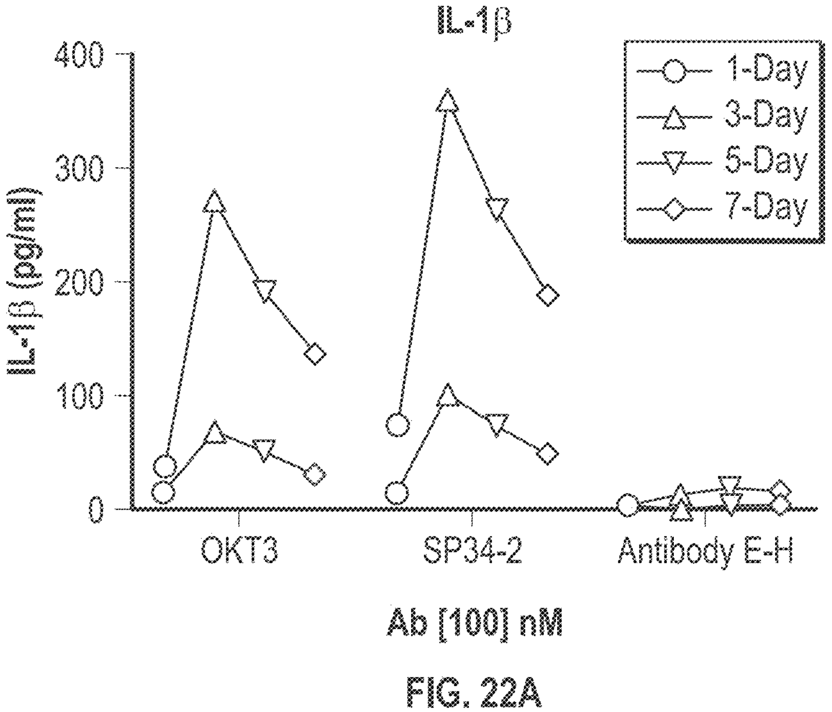
FIGS. 22A-22D demonstrate cytokine production from human PBMCs activated by an anti-TCR Vβ5 antibody (Antibody E). Human PBMCs activated by anti-TCR Vβ5 antibody do not significantly produce IL-1beta (FIG. 22A), IL-6, (FIG. 22B), TNFalpha (FIG. 22C), or IL-10 (FIG. 22D) as compared to PBMCs activated by anti-CD3ϵ antibodies (OKT3 or SP34-2). Data shown is representative of n=4 donors.
Figure 22B:
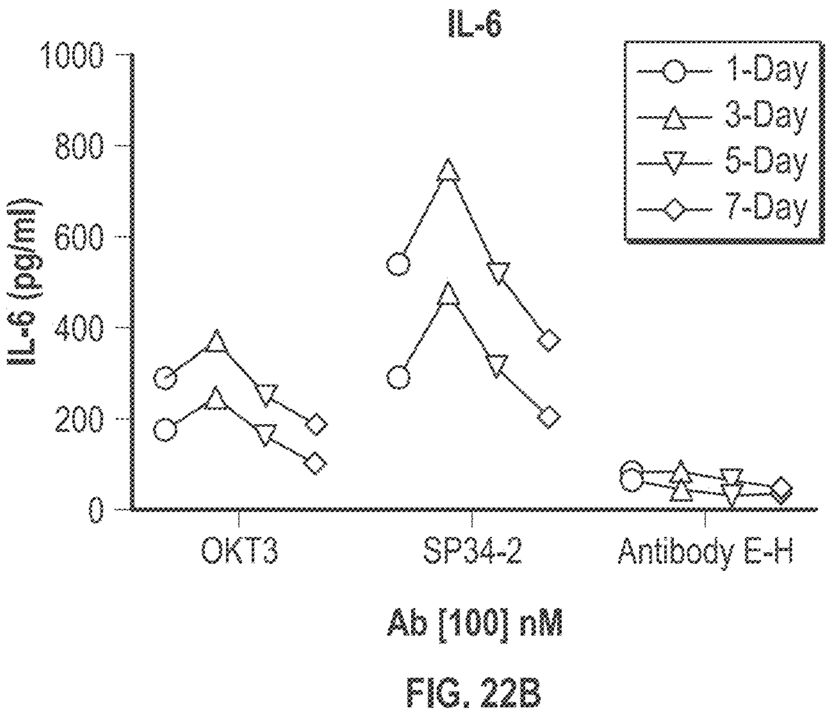
Figure 22C:
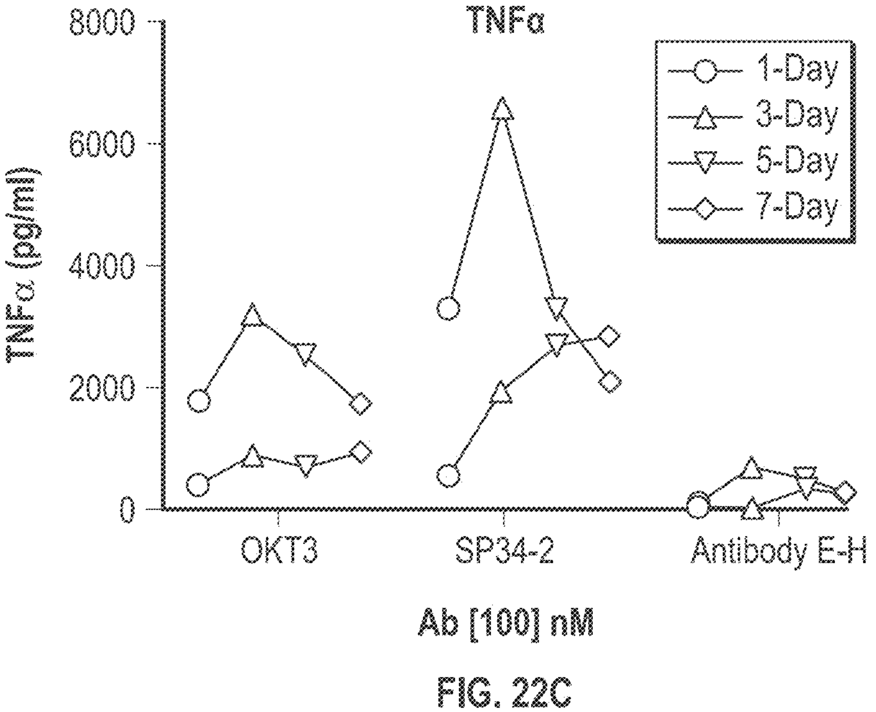
Figure 22D:
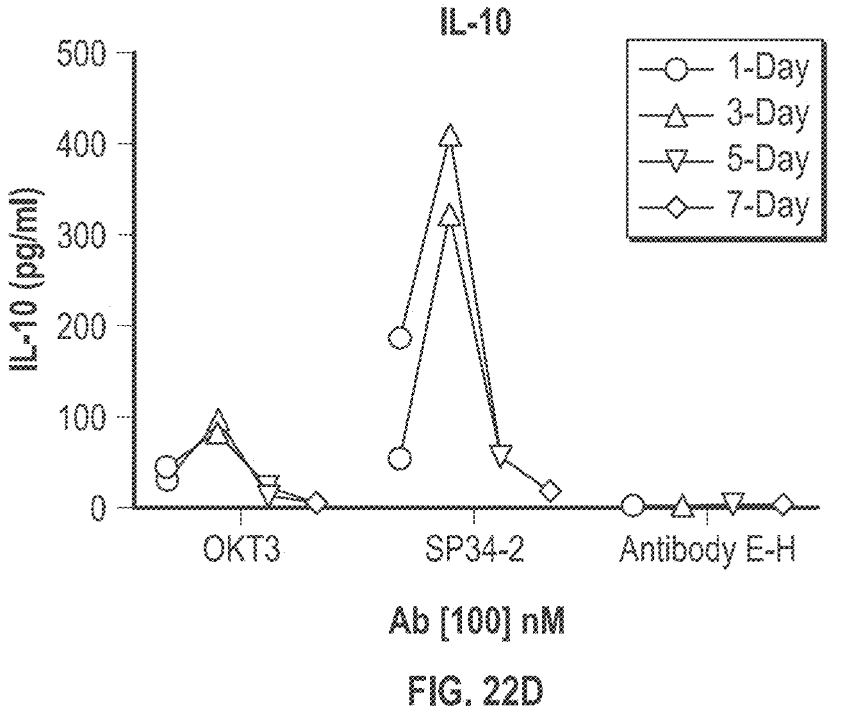

As shown in FIG. 21A, when plate-bound anti-TCR Vβ5 antibody (Antibody E) or anti-CD3e antibodies (OKT3 and SP34-2) were used to activate human PBMCs, the T cell cytokine IFNg was induced. With respect to IL-2 production, PBMCs activated with anti-TCR Vβ5 antibody (Antibody E) resulted in increased IL-2 production with delayed kinetics (FIG. 21B) as compared to PBMCs activated with anti-CD3e antibodies (OKT3 or SP34-2).

The production of cytokines IL-6, IL-1β, IL-10 and TNF-alpha which are associated with "cytokine storms" (and accordingly CRS) was also assessed under similar conditions. FIGS. 22A-22D show that that while PBMCs activated with anti-CD3ε antibodies demonstrate production of IL-1β (FIG. 22A), IL-6 (FIG. 22B), TNF-alpha (FIG. 22C) and IL-10 (FIG. 22D), no or little induction of these cytokines was observed with PBMCs activated with anti-TCR Vβ5 antibody (Antibody E).

The data provided in this Example show that antibodies directed against TCR Vβ can, e.g., preferentially activate a subset of T cells, and do not results in induction of cytokines associated with cytokine storms or CRS.

Example 9: Characteristics of a Dual-Targeting Antibody Molecule Against BCMA and TCRβV This Example describes characterization of a dual targeting antibody (e.g., a bispecific molecule) comprising an anti-TCRβV binding moiety and a BCMA binding moiety (Molecule H) which can bind and activate a subset of T cells, but with, e.g., no or markedly reduced, CRS.

Human PBMCs were isolated from whole blood followed by solid-phase (plate-coated) stimulation with an anti-TCRβV×BCMA bispecific molecule (Molecule H) or anti-CD3e antibodies (OKT3), each at 100 nM. Supernatant was collected on Days 1, 2, 3, or 5 followed by multiplex cytokine analysis for IFNg, IL-2, IL-6, IL-1beta, IL-10 or TNFalpha. The data was quantified using MSD (Meso Scale Discovery) platform, following the manufacturer's protocol.

Figure 23A:
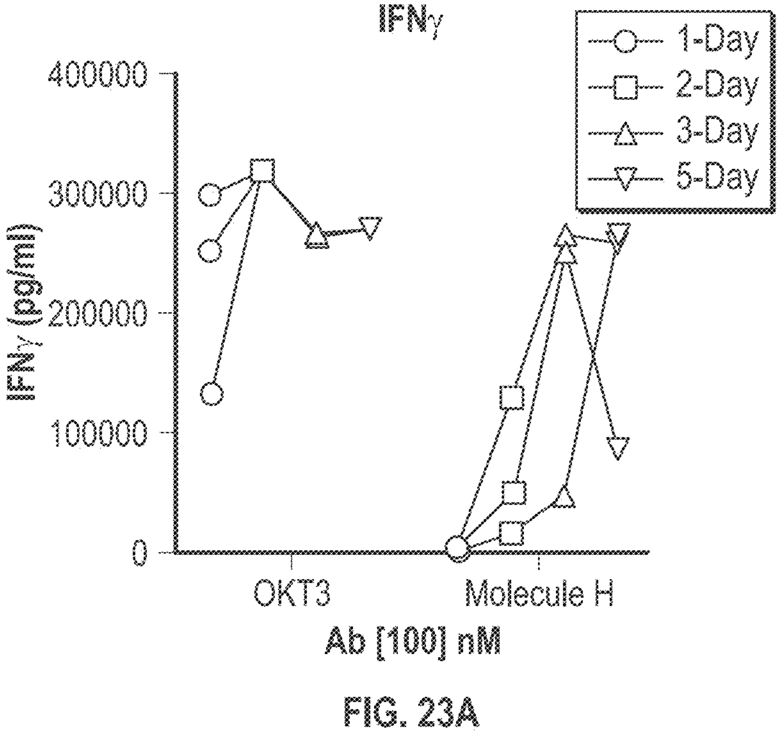
FIGS. 23A-23F demonstrate cytokine production from human PBMCs activated by a dual targeting (bispecific molecule) comprising an anti-TCRβV binding moiety and a BCMA binding moiety.
Figure 23B:
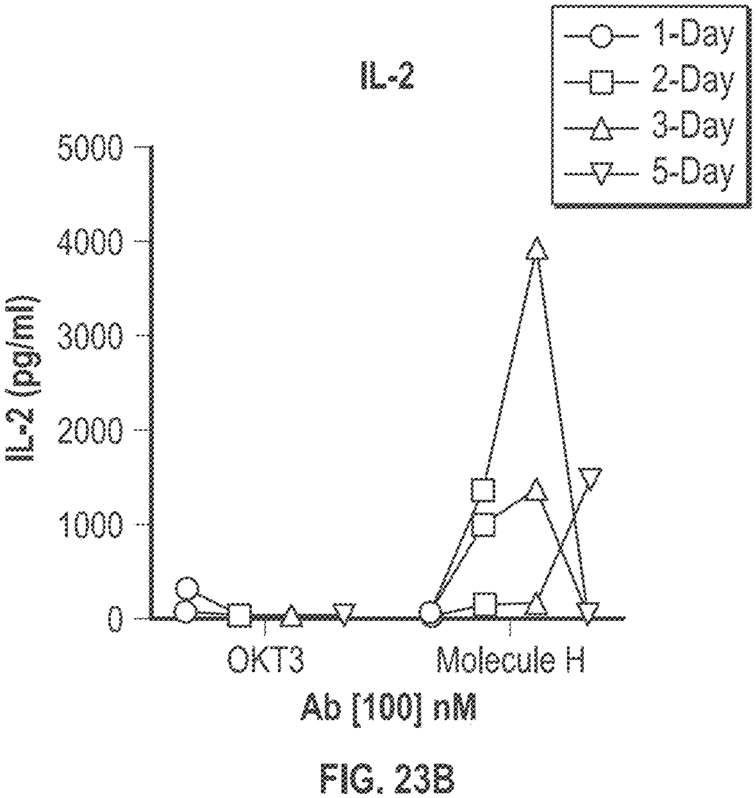

As shown in FIG. 23A, when plate-bound anti-TCRβV×BCMA bispecific molecule (Molecule H) or anti-CD3e antibodies (OKT3) were used to activate human PBMCs, the T cell cytokine IFNg was induced. With respect to IL-2 production, PBMCs activated with anti-TCRβV×BCMA bispecific molecule (Molecule H) resulted in increased IL-2 production (FIG. 23B) as compared to PBMCs activated with anti-CD3e antibodies (OKT3).

Figure 23C:
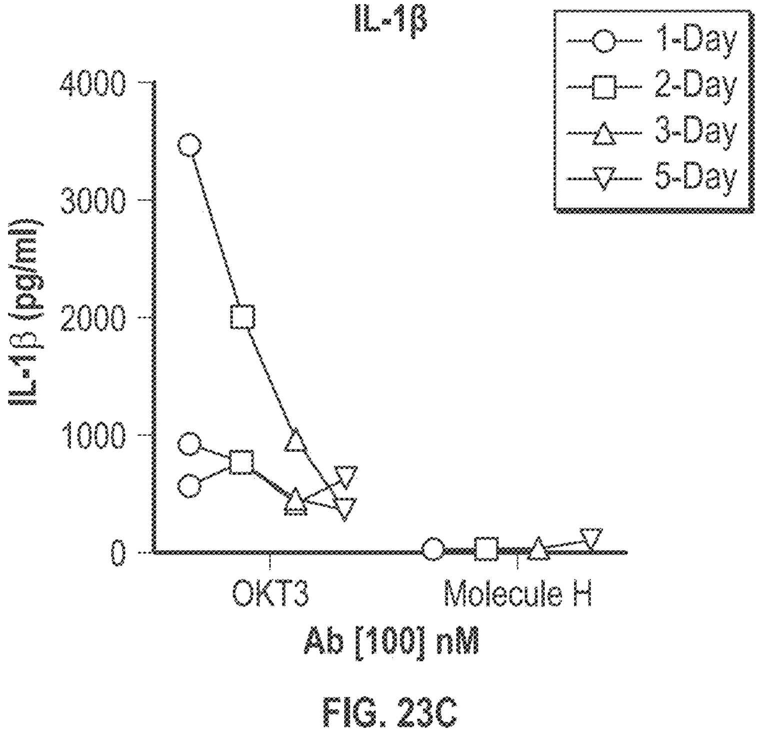
Figure 23D:
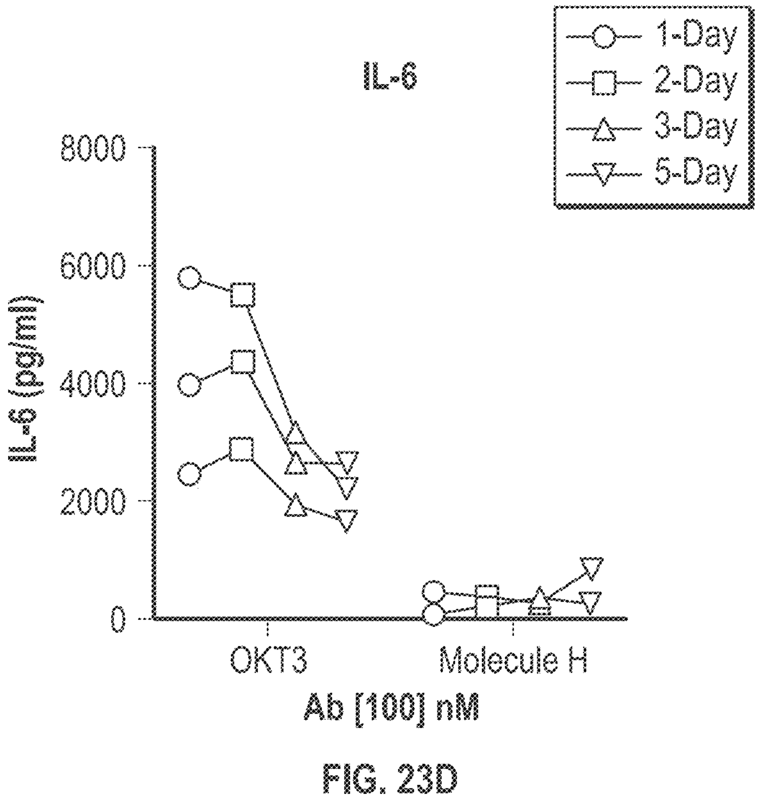
Figure 23E:
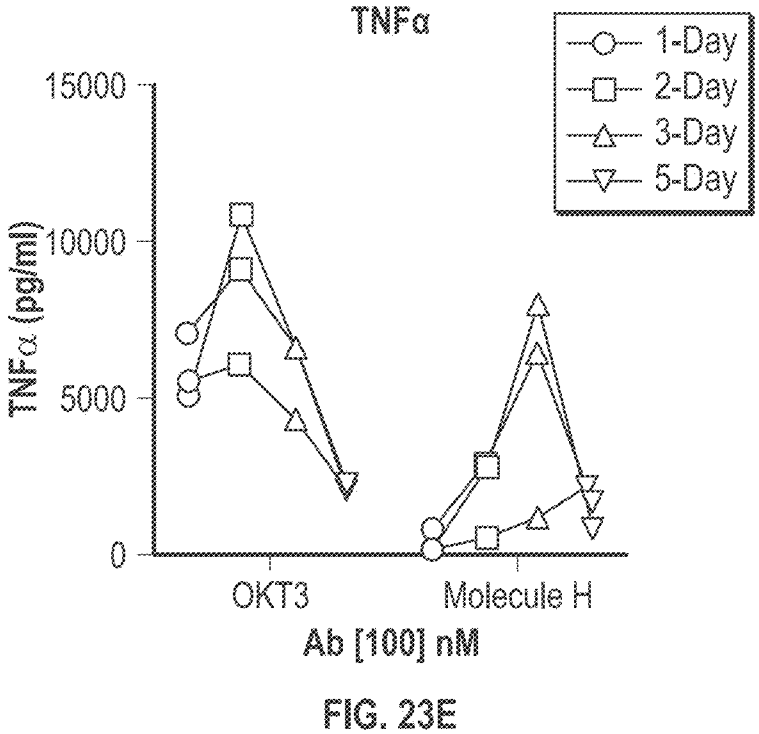
Figure 23F:
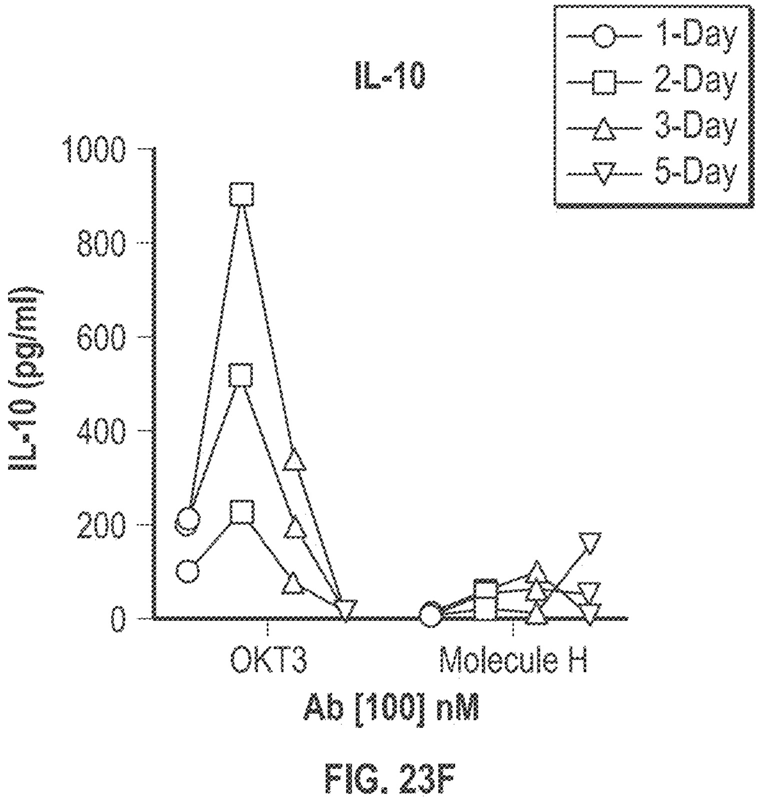

The production of cytokines IL-6, IL-1β, IL-10 and TNF-alpha which are associated with "cytokine storms" (and accordingly CRS) was also assessed under similar conditions. FIGS. 23C-E show that that while PBMCs activated with anti-CD3ε antibodies demonstrate production of IL-1β (FIG. 23C), IL-6 (FIG. 23D), TNF-alpha (FIG. 23D) and IL-10 (FIG. 23E), no or little induction of these cytokines was observed with PBMCs activated with anti-TCRβV×BCMA bispecific molecule (Molecule H).

The data provided in this Example show that antibodies directed against TCR Vβ can, e.g., preferentially activate a subset of T cells, and do not result in induction of cytokines associated with cytokine storm or CRS.

Example 10: Cytokine and Chemokine Profile of Anti-TCRVb Antibodies

This Examples describes cytokines and chemokines secreted by PBMCs following activation by anti-TCR Vβ antibodies.

Human PBMCs were isolated from whole blood followed by solid-phase (plate-coated) stimulation with an anti-TCRβV antibodies (A-H.1, B-H.1), or a bispecific molecule comprising an anti-TCRVb antibody (Molecule H), an isotype control (BGM0122) or an anti-CD3e antibody (SP34), each at 100 nM. Supernatant was collected on Days 1, 2, 3, 4, 5, 6, 7 and 8 followed by multiplex analysis for the indicated cytokines or chemokines. The data was quantified using MSD (Meso Scale Discovery) platform, following the manufacturer's protocol. BGM0122 comprises the amino acid sequence of (SEQ ID NO: 3283)

```
METDTLLLWVLLLWVPGSTGDKTHTCPPCPAPELLGGPSVFLFPPKPKDT

LMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYT
```

-continued

```
LPPSREEMTKNQVSLTCLVKGFYPSDIAVEWESNGQPENNYKTTPPVLDS

DGSFFLYSKLTVDKSRWQQGNVFSCSVMHEALHNHYTQKSLSLSPGKGGG

GSGGGGSGLNDIFEAQKIEWHE.
```

FIGS. 25A-25J, FIGS. 26A-26H, and FIGS. 27A-27L show the levels of cytokine and chemokine from PBMCs activated with the indicated antibodies.

Figure 25A:
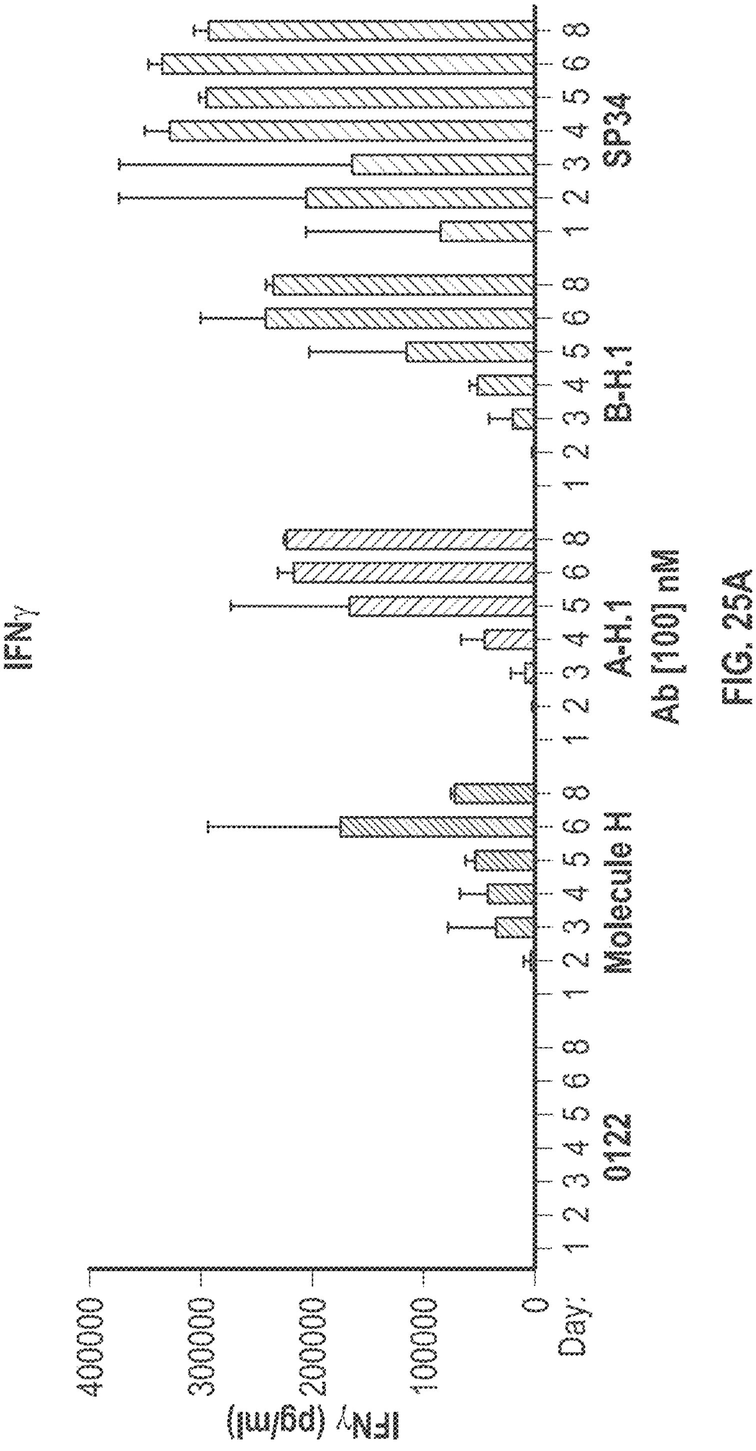
FIGS. 25A-25J show cytokine or chemokine secretion of PBMCs activated with anti-TCRVb antibodies (A-H.1, B-H.1), a bispecific molecule comprising an anti-TCRVb antibody (Molecule H), control isotype (122) or anti-CD3e antibody (OKT3). Data shown is representative of n=2 donors and representative of 2 independent experiments.
Figure 25B:
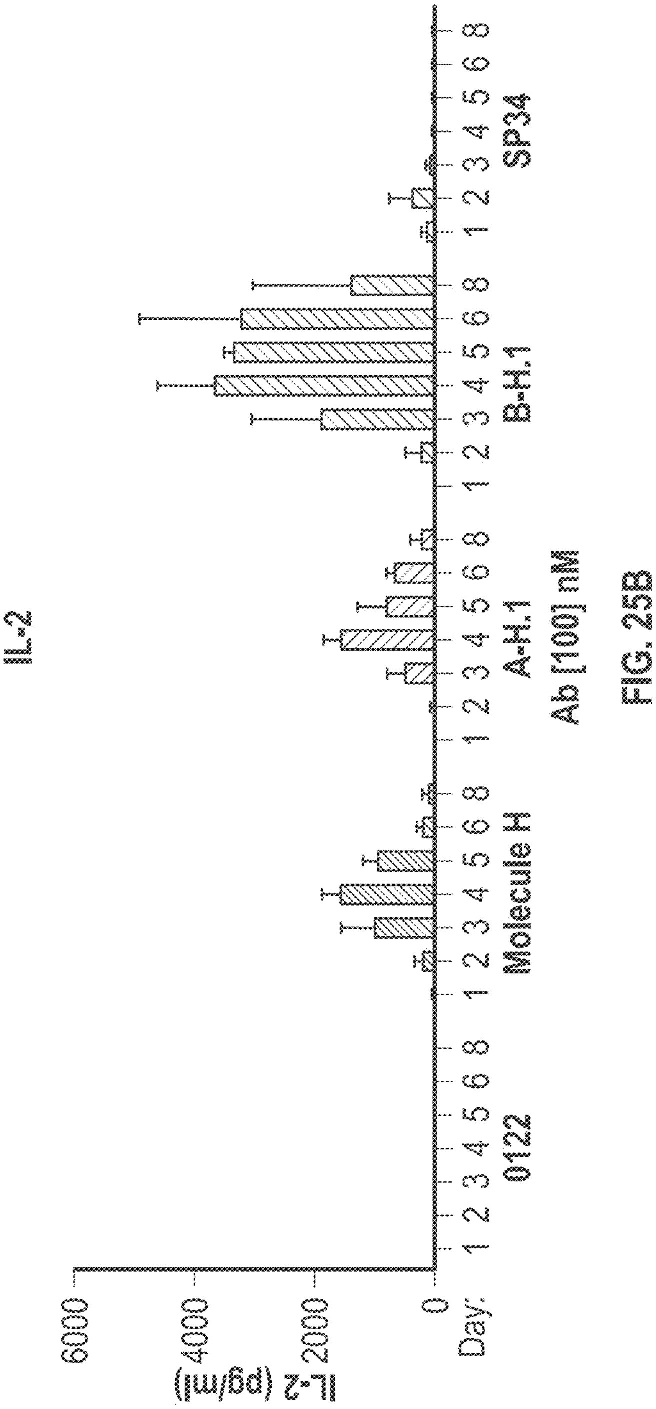
Figure 25C:
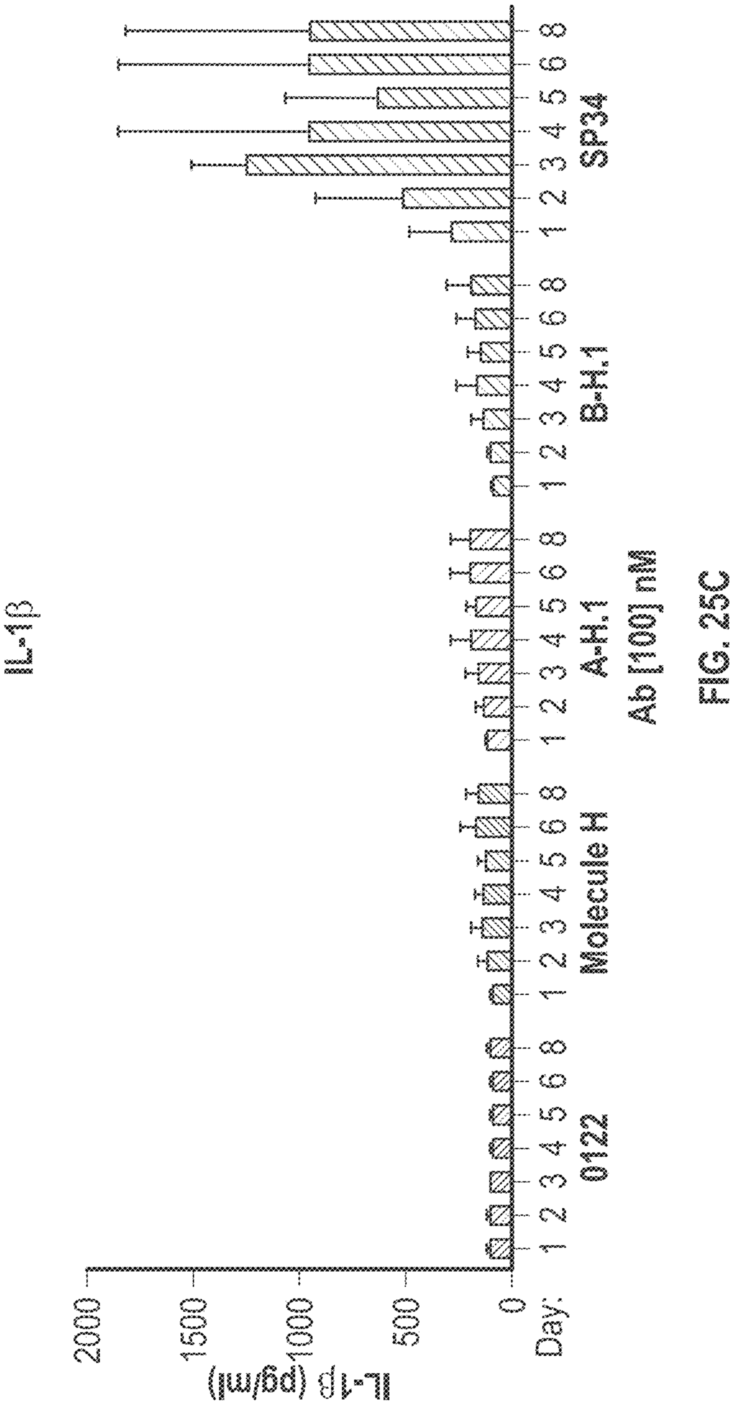
Figure 25D:
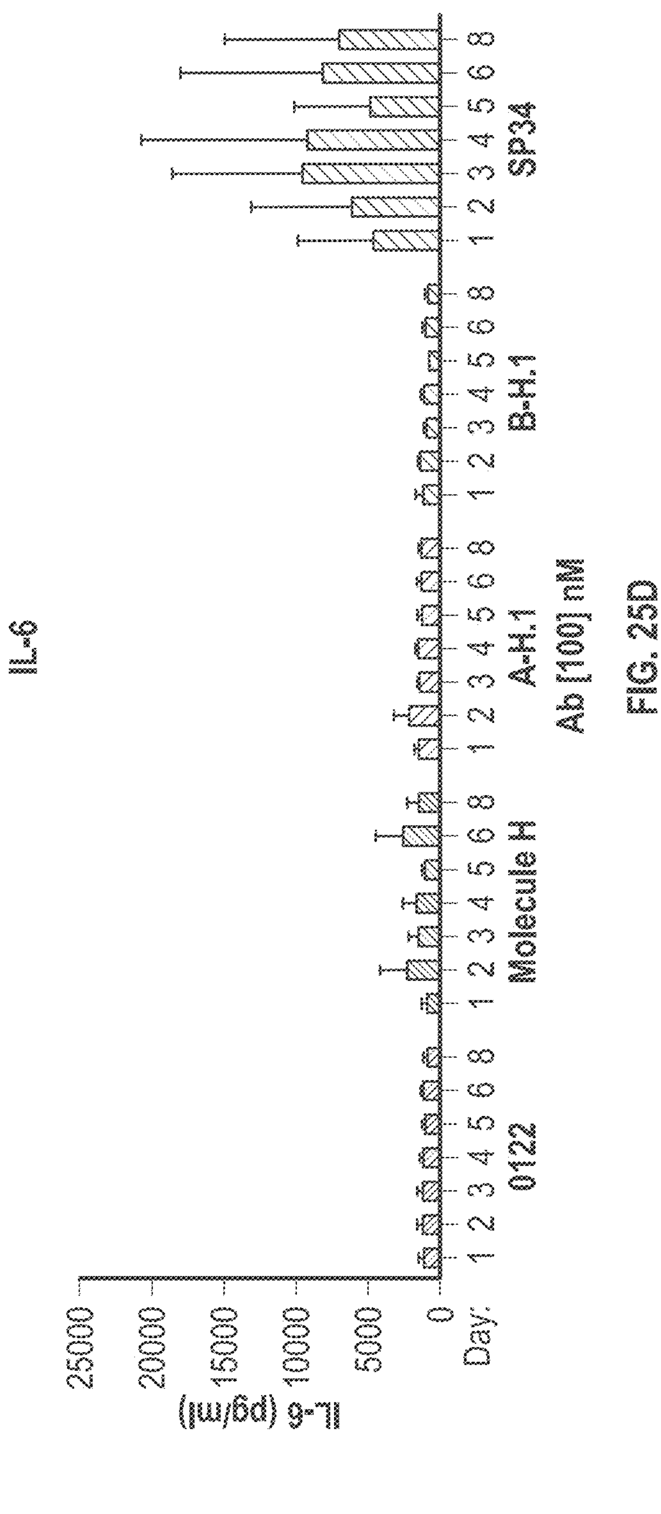
Figure 25E:
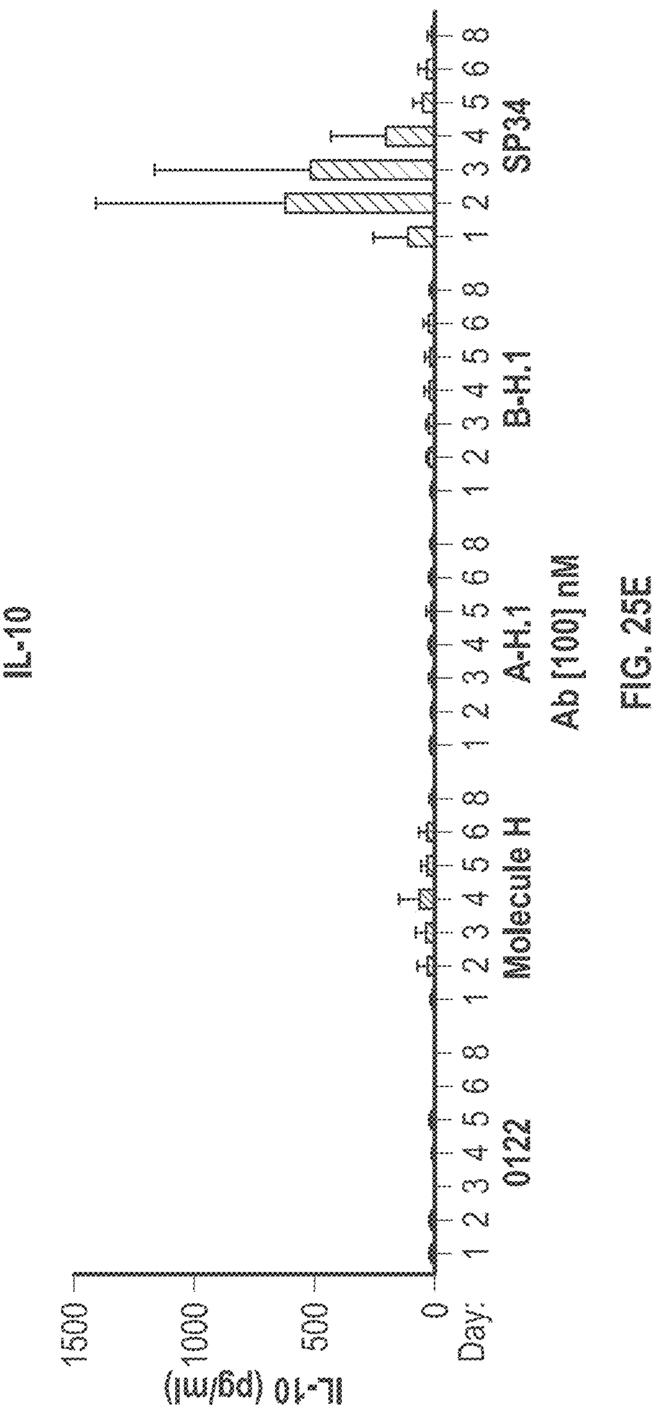
Figure 25F:
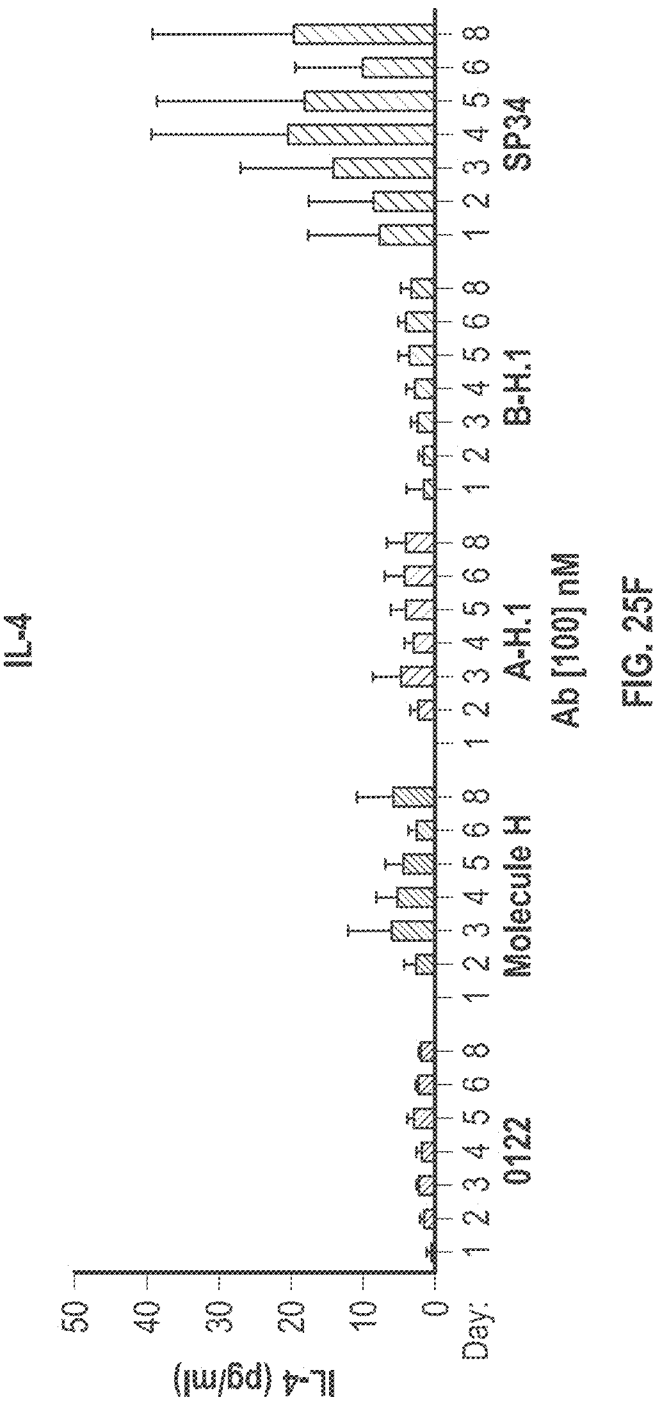
Figure 25G:
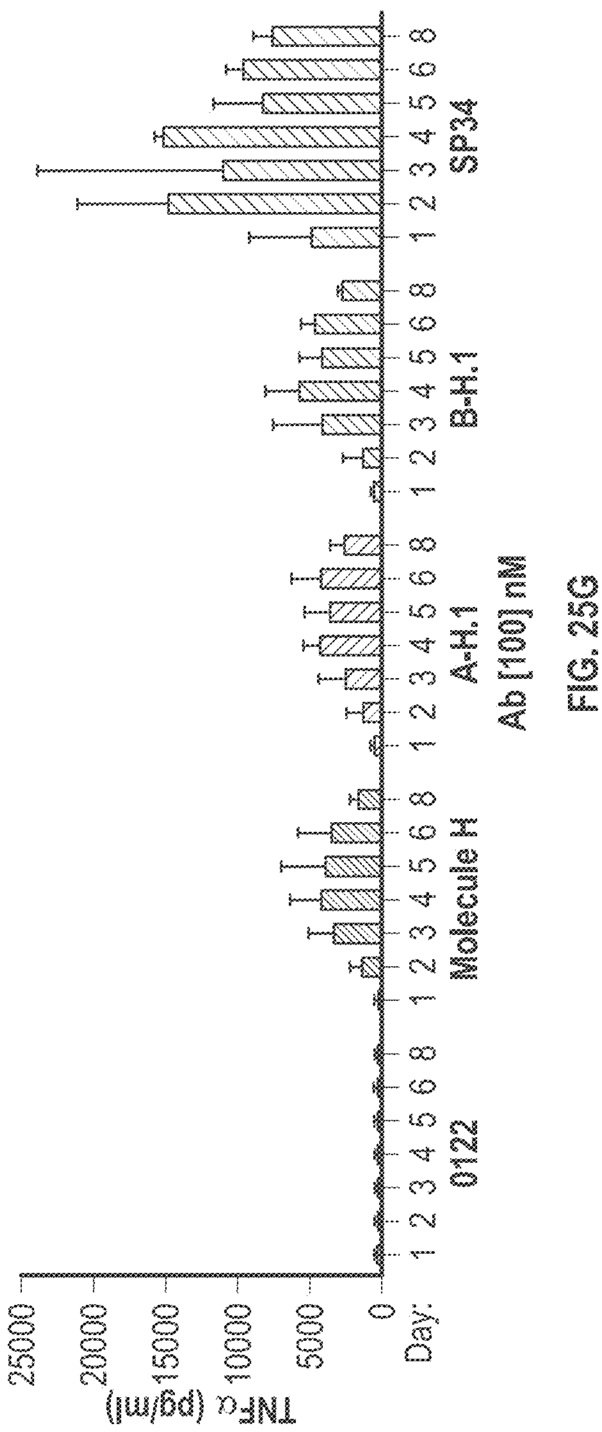
Figure 25H:
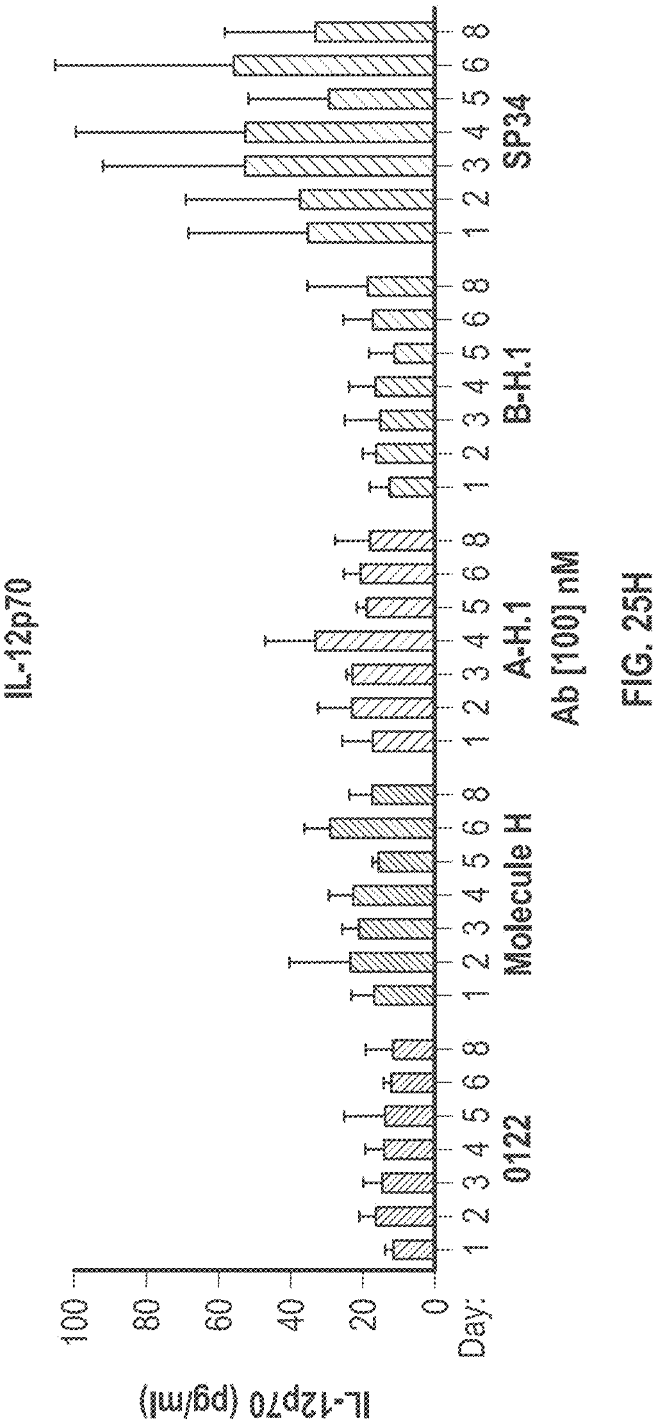
Figure 25I:
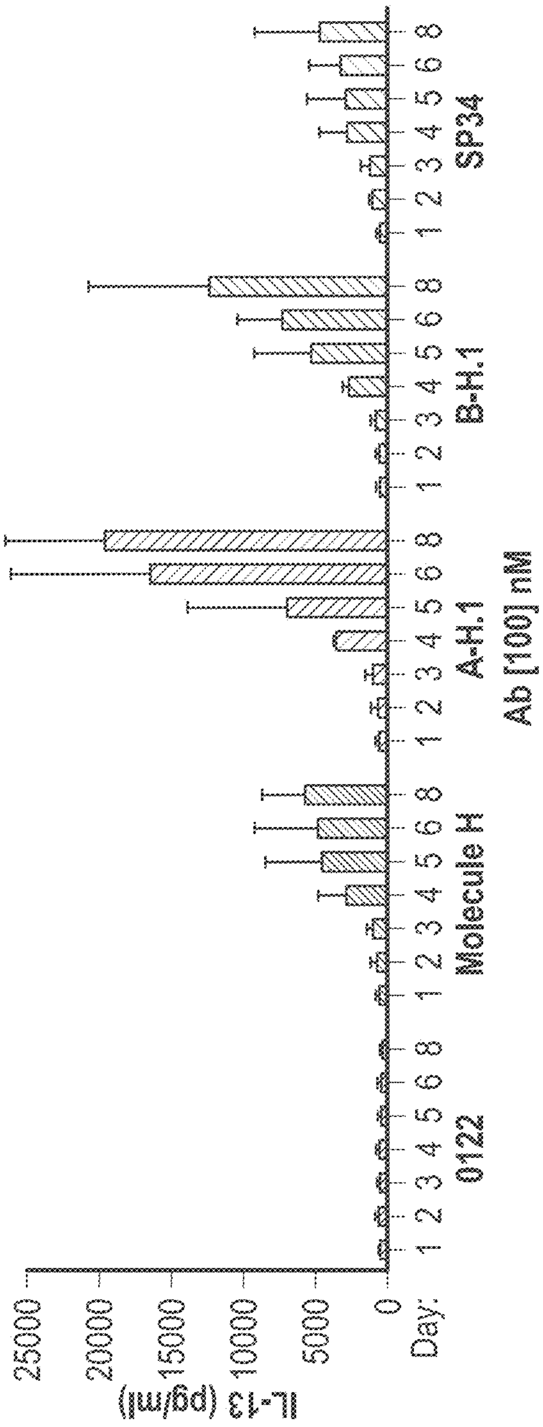
Figure 25J:
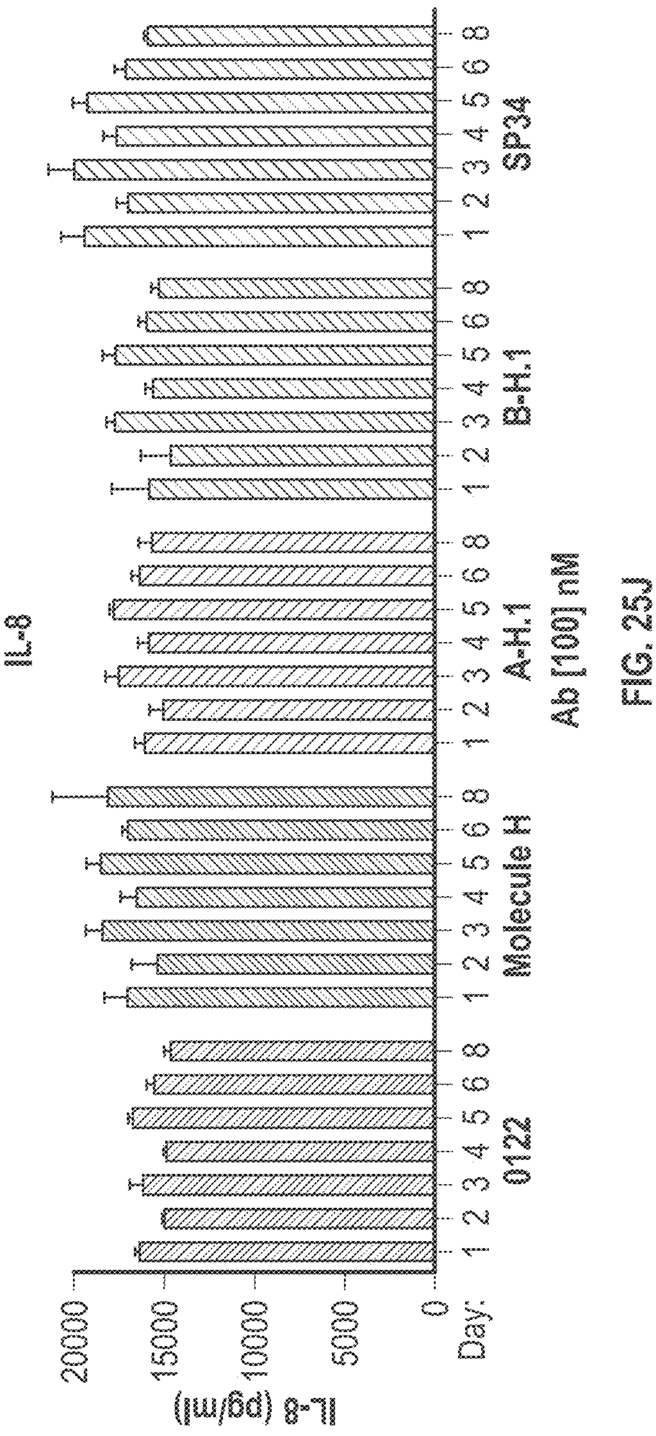
Figure 26A:
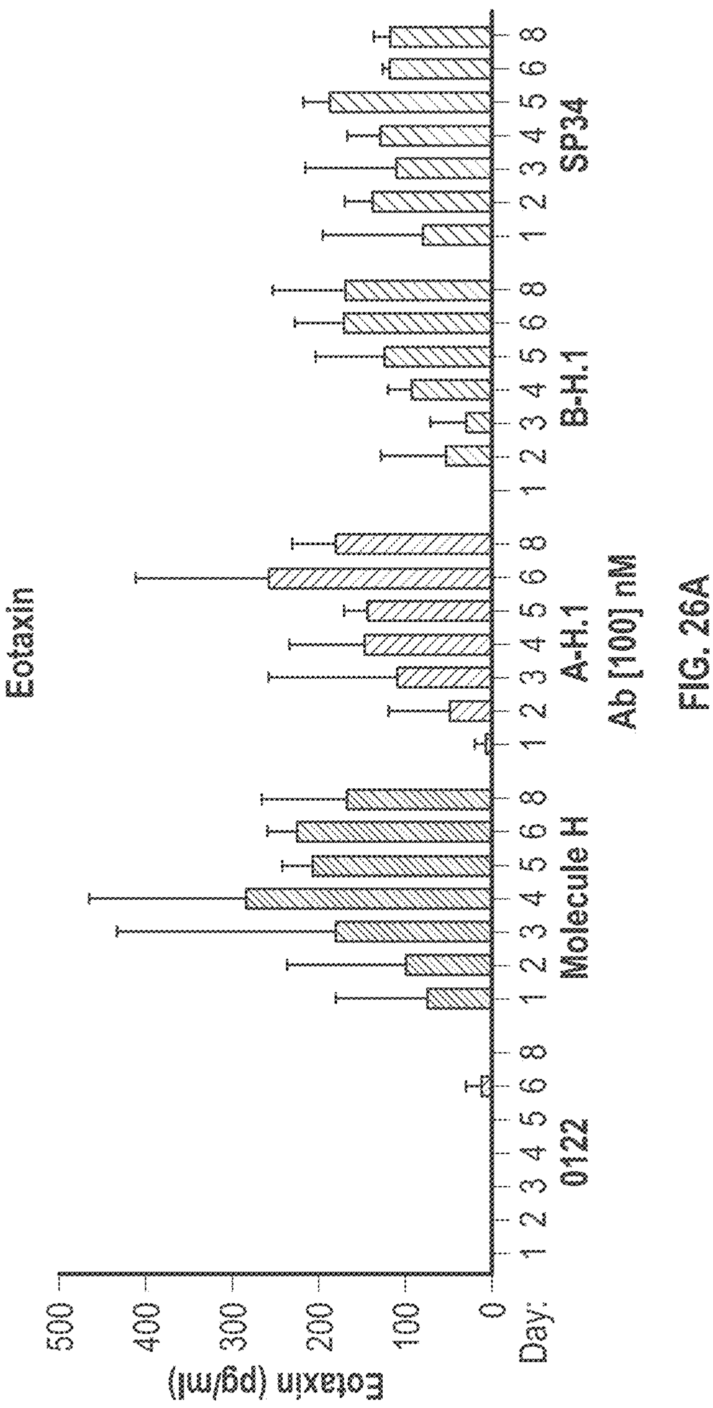
FIGS. 26A-26H show cytokine or chemokine secretion of PBMCs activated with anti-TCRVb antibodies (A-H.1, B-H.1), a bispecific molecule comprising an anti-TCRVb antibody (Molecule H), control isotype (122) or anti-CD3e antibody (OKT3). Data shown is representative of n=2 donors and representative of 2 independent experiments.
Figure 26B:
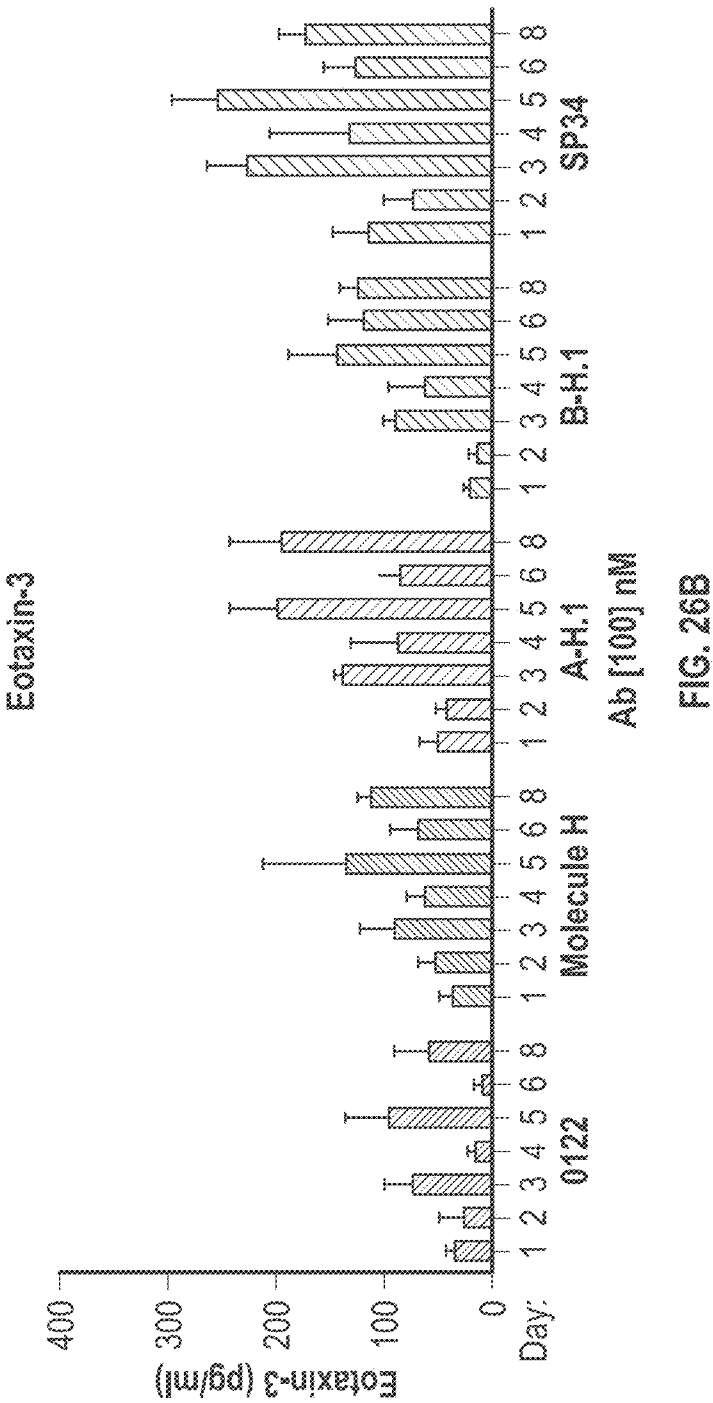
Figure 26C:
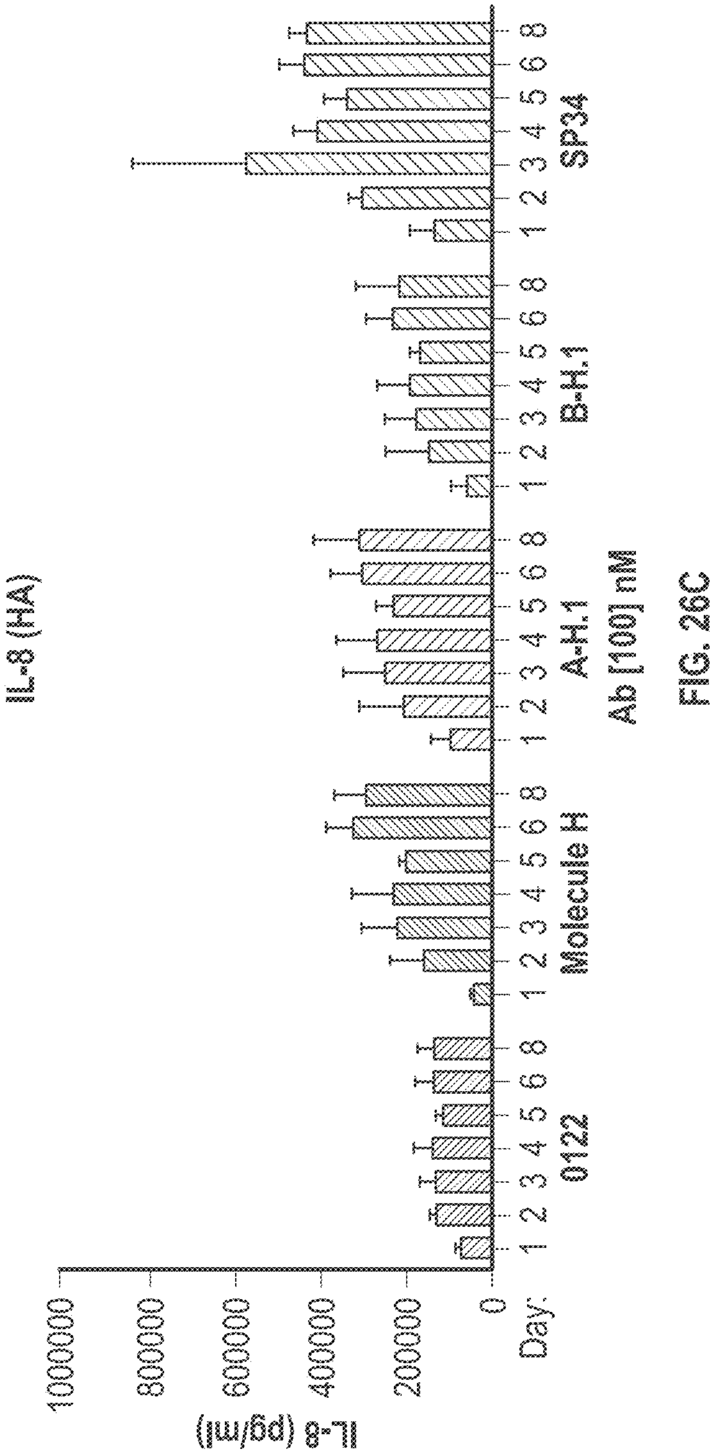
Figure 26D:
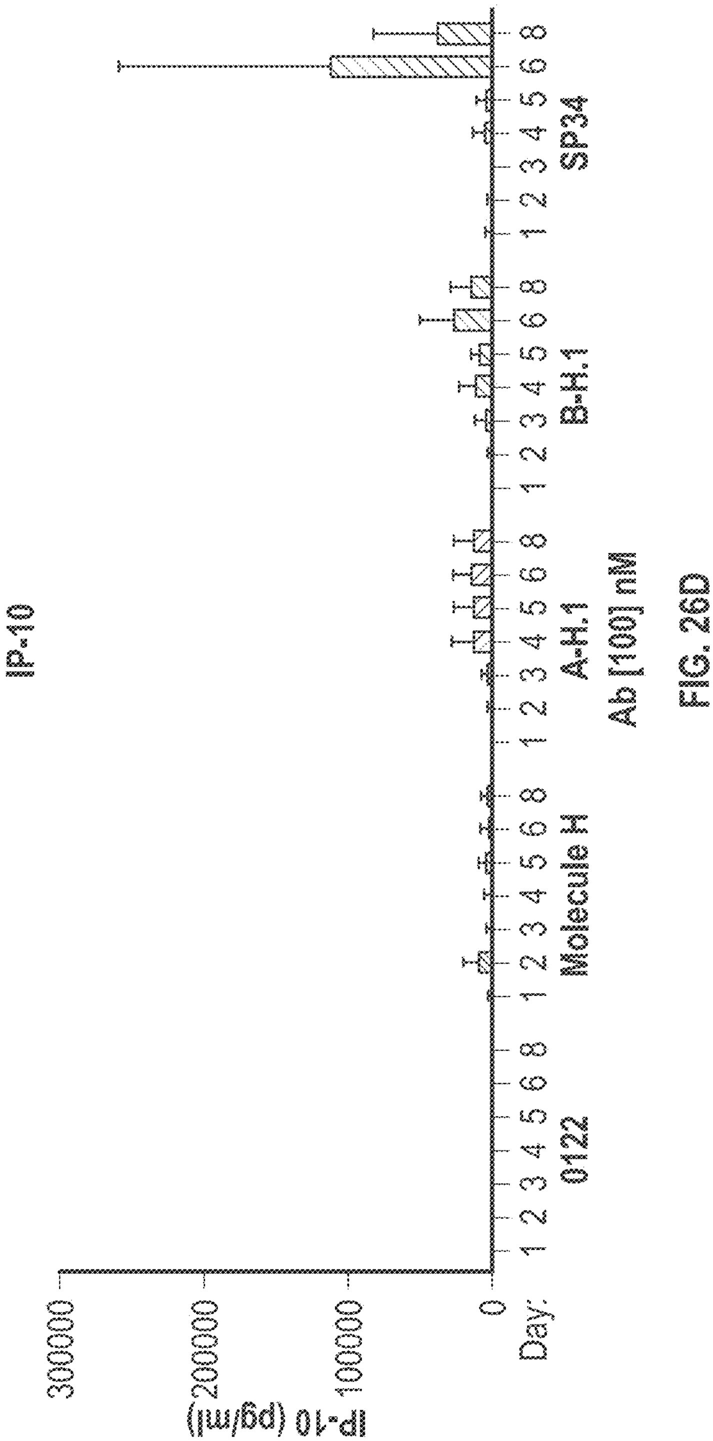
Figure 26E:
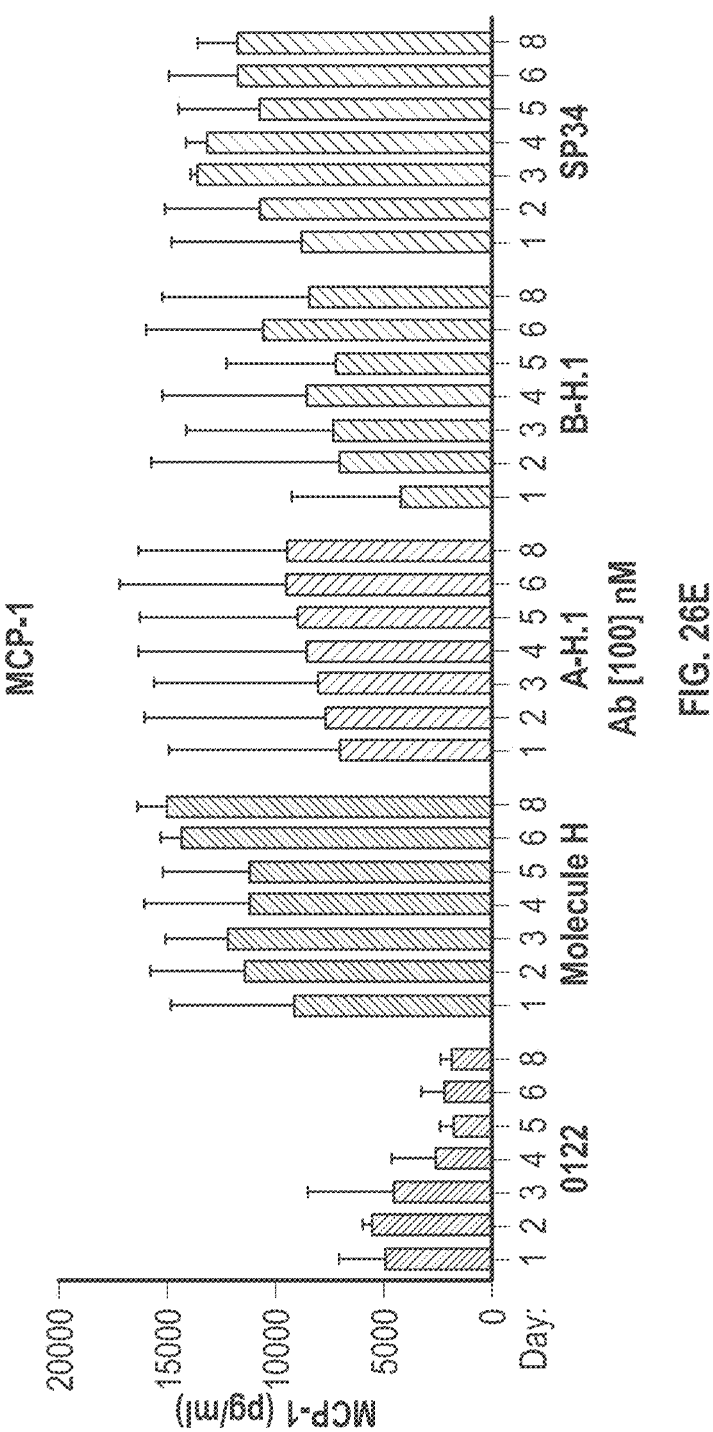
Figure 26F:
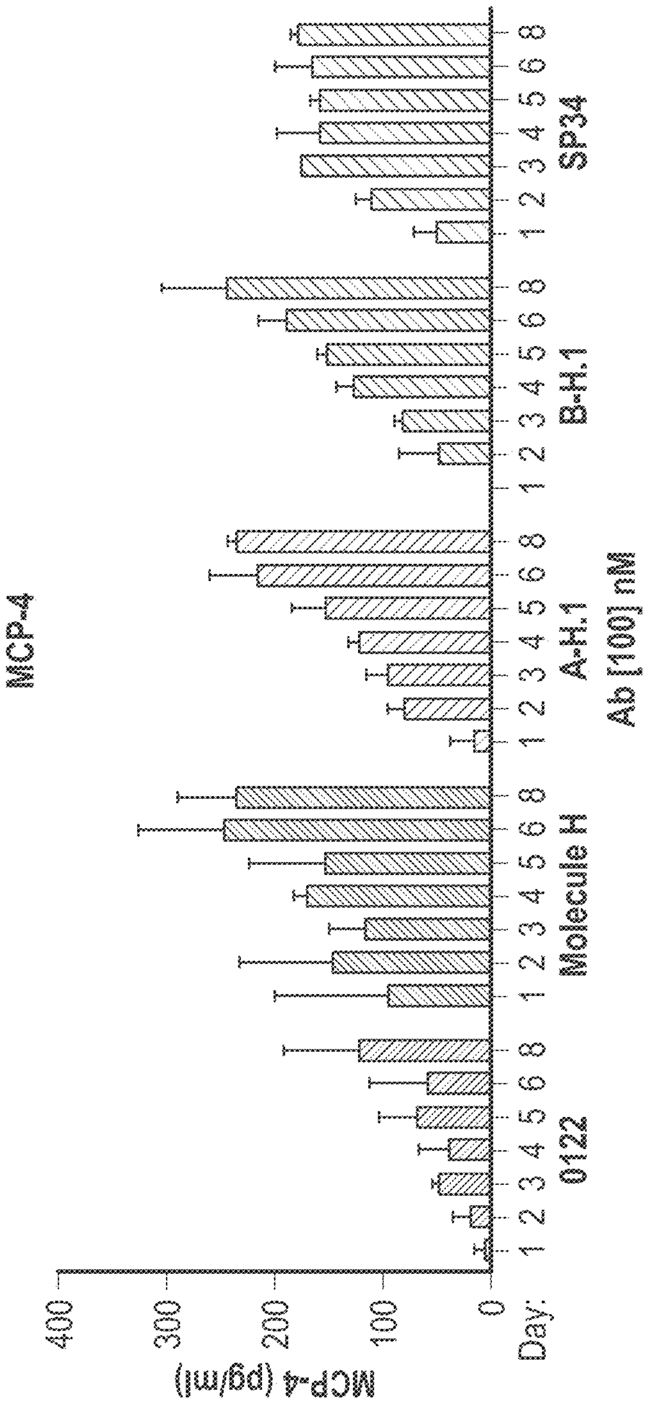
Figure 26G:
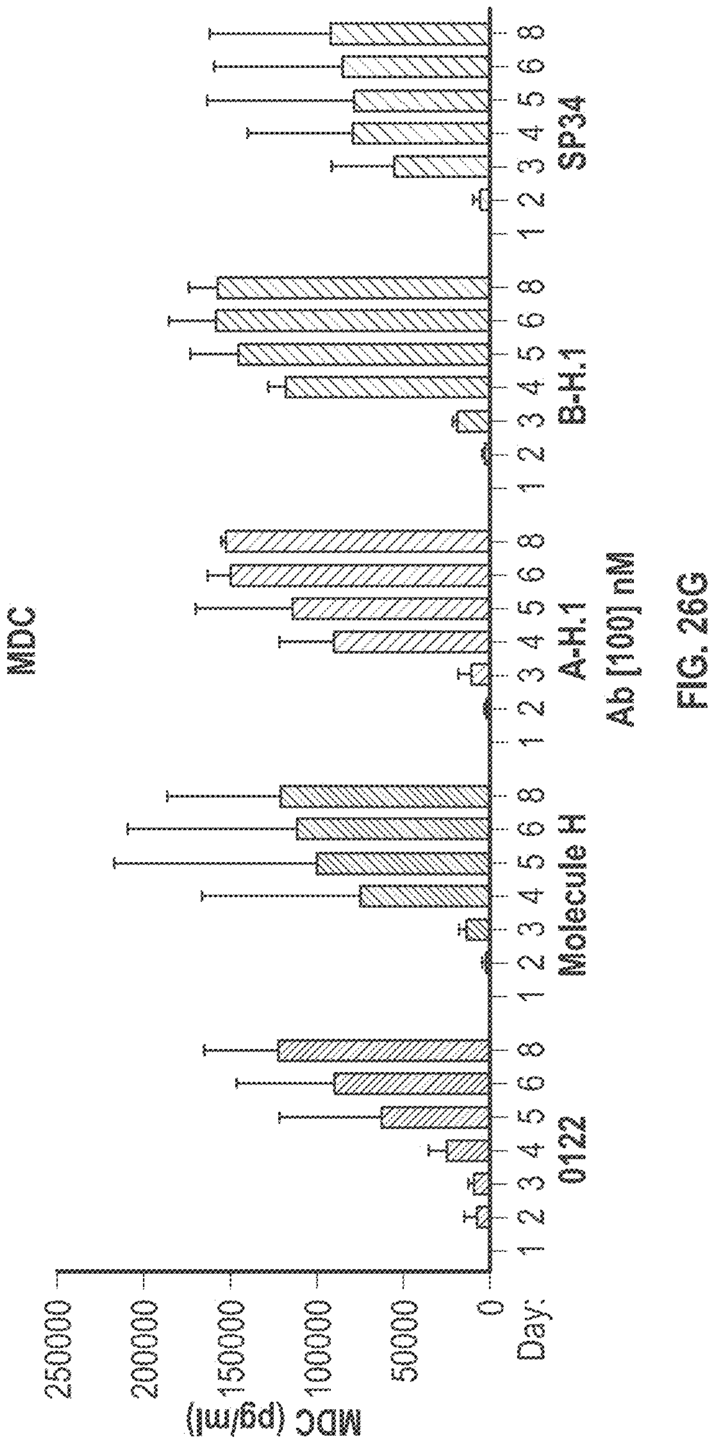
Figure 26H:
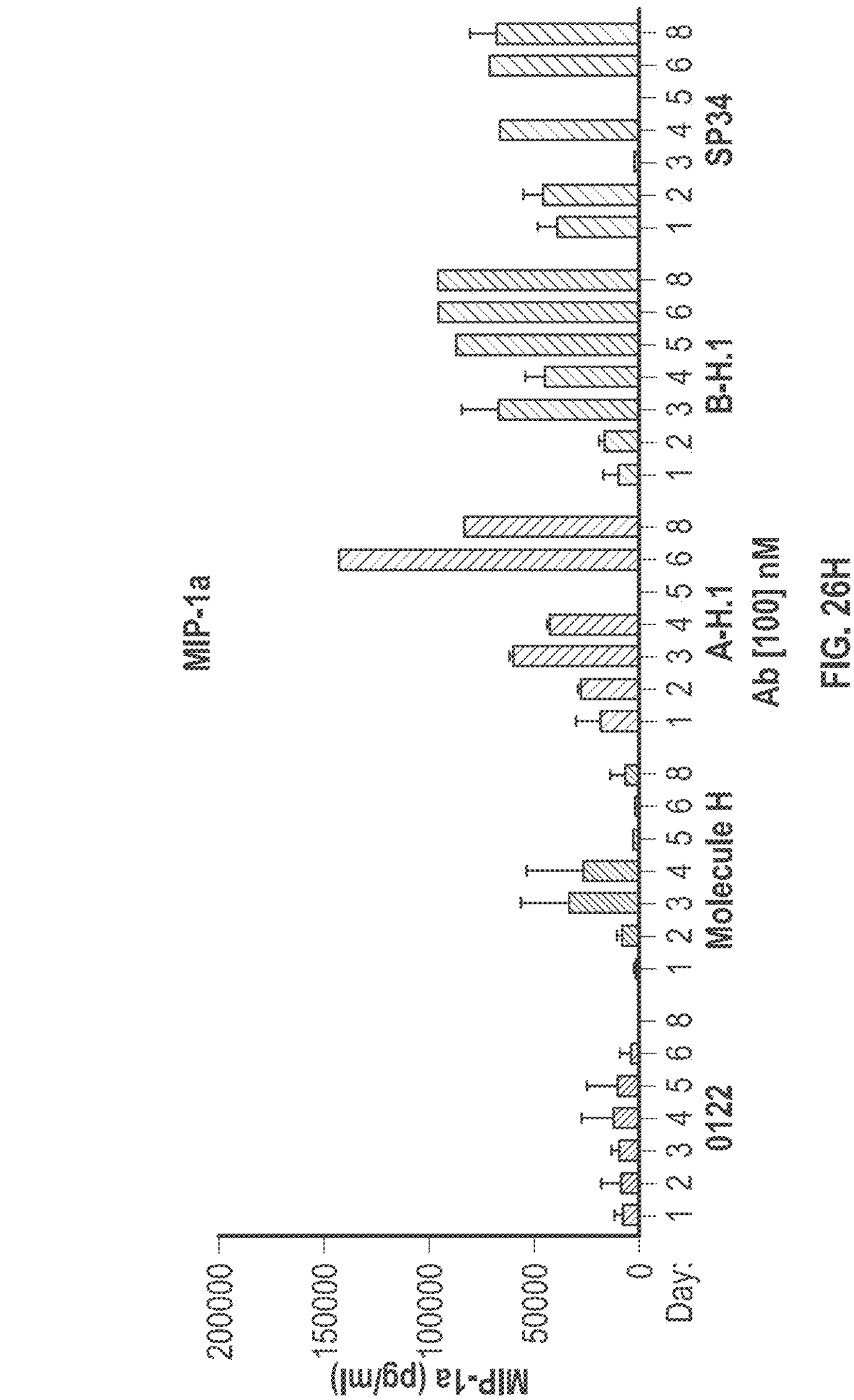

As shown in FIG. 25A, when plate-bound anti-TCR Vβ antibodies or anti-CD3ε antibodies (OKT3) were used to activate human PBMCs, the T cell cytokine IFNg was induced. With respect to IL-2 production, PBMCs activated with anti-TCR Vβ antibodies resulted in increased IL-2 production with delayed kinetics (FIG. 25B) as compared to PBMCs activated with anti-CD3e antibody (OKT3).

While IL-1beta (FIG. 25C), IL-6 (FIG. 25D), IL-10 (FIG. 25E), IL-4 (FIG. 25F), TNFalpha (FIG. 25G), IP-10 (FIG. 26C), IL-12-23p40 (FIG. 27D), IL-17A (FIG. 27G), and IL-1a (FIG. 27H), were induced by anti-CD3ε antibody (OKT3), no or little induction of these cytokines or chemokines was observed with PBMCs activated with anti-TCRVb antibodies.

Figure 27A:
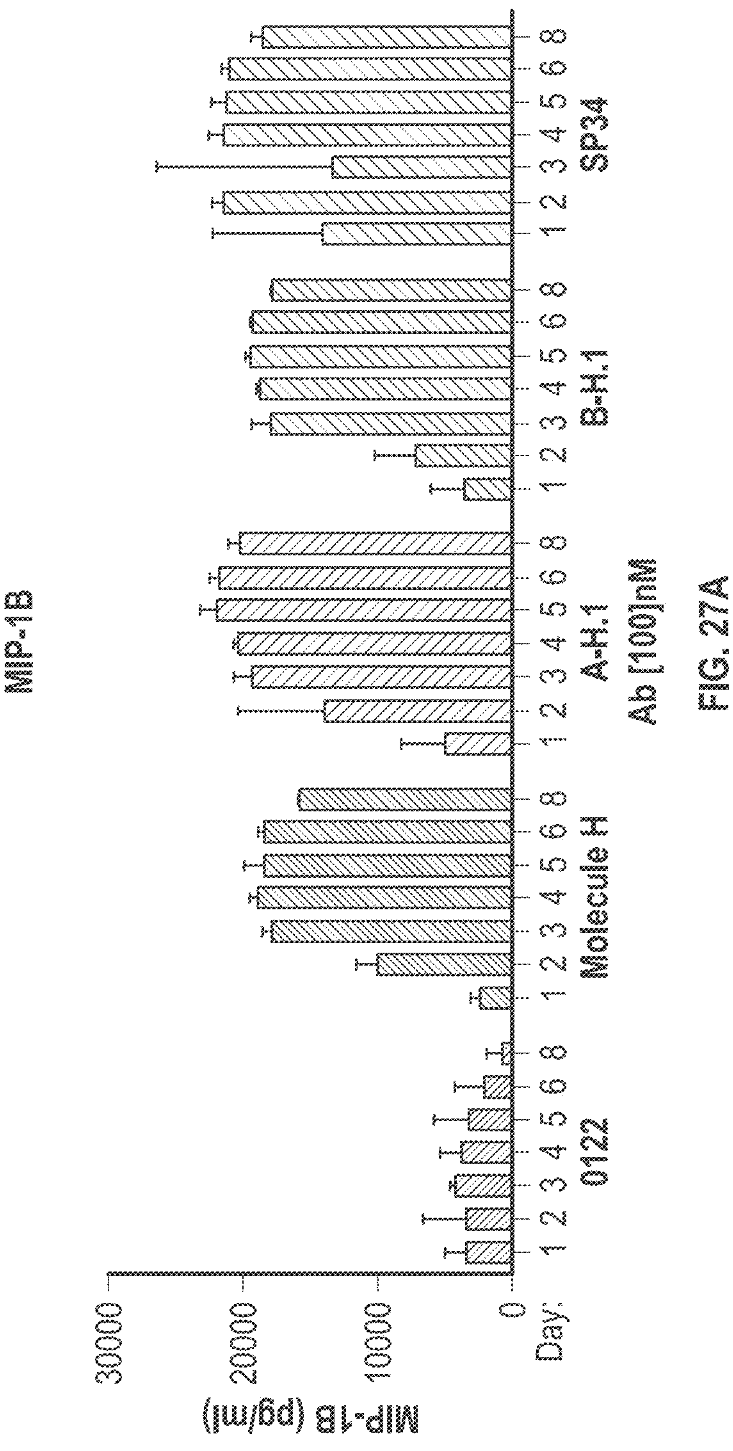
FIGS. 27A-27L show cytokine or chemokine secretion of PBMCs activated with anti-TCRVb antibodies (A-H.1, B-H.1), a bispecific molecule comprising an anti-TCRVb antibody (Molecule H), control isotype (122) or anti-CD3e antibody (OKT3). Data shown is representative of n=2 donors and representative of 2 independent experiments.
Figure 27B:
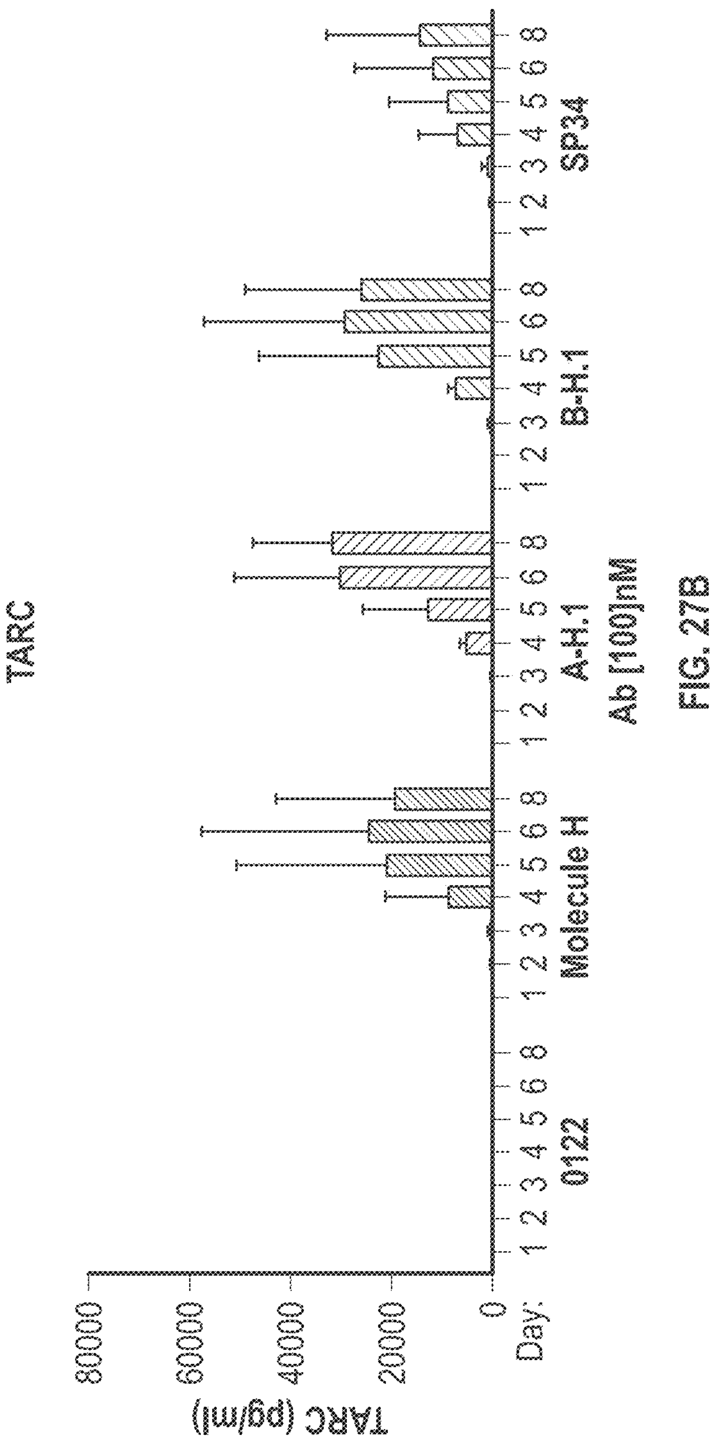
Figure 27C:
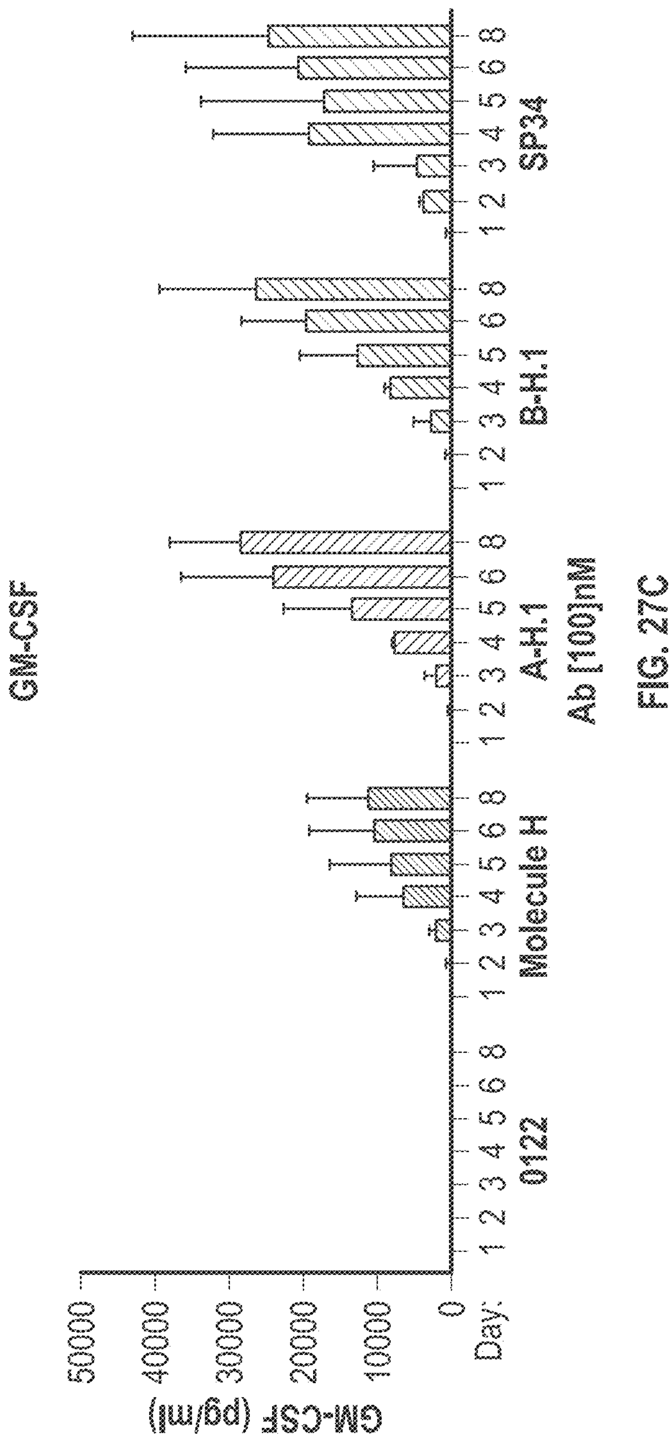
Figure 27D:
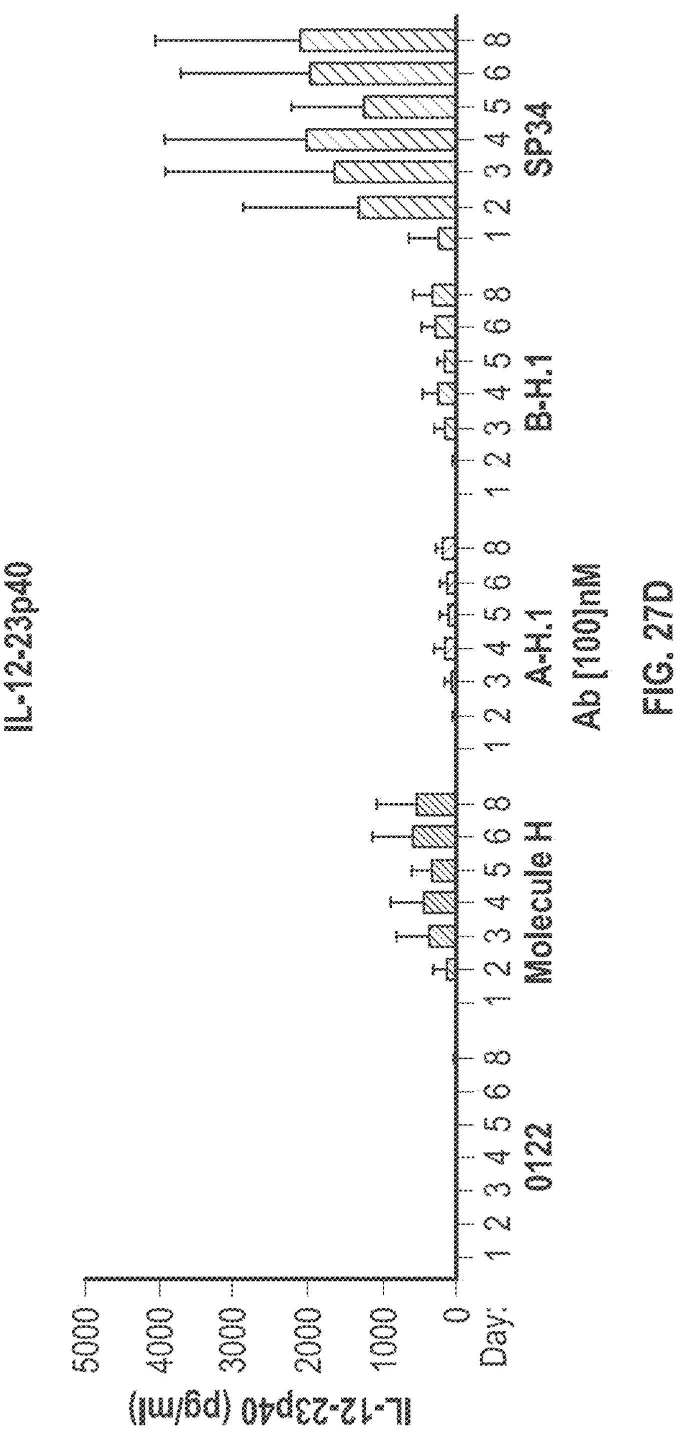
Figure 27E:
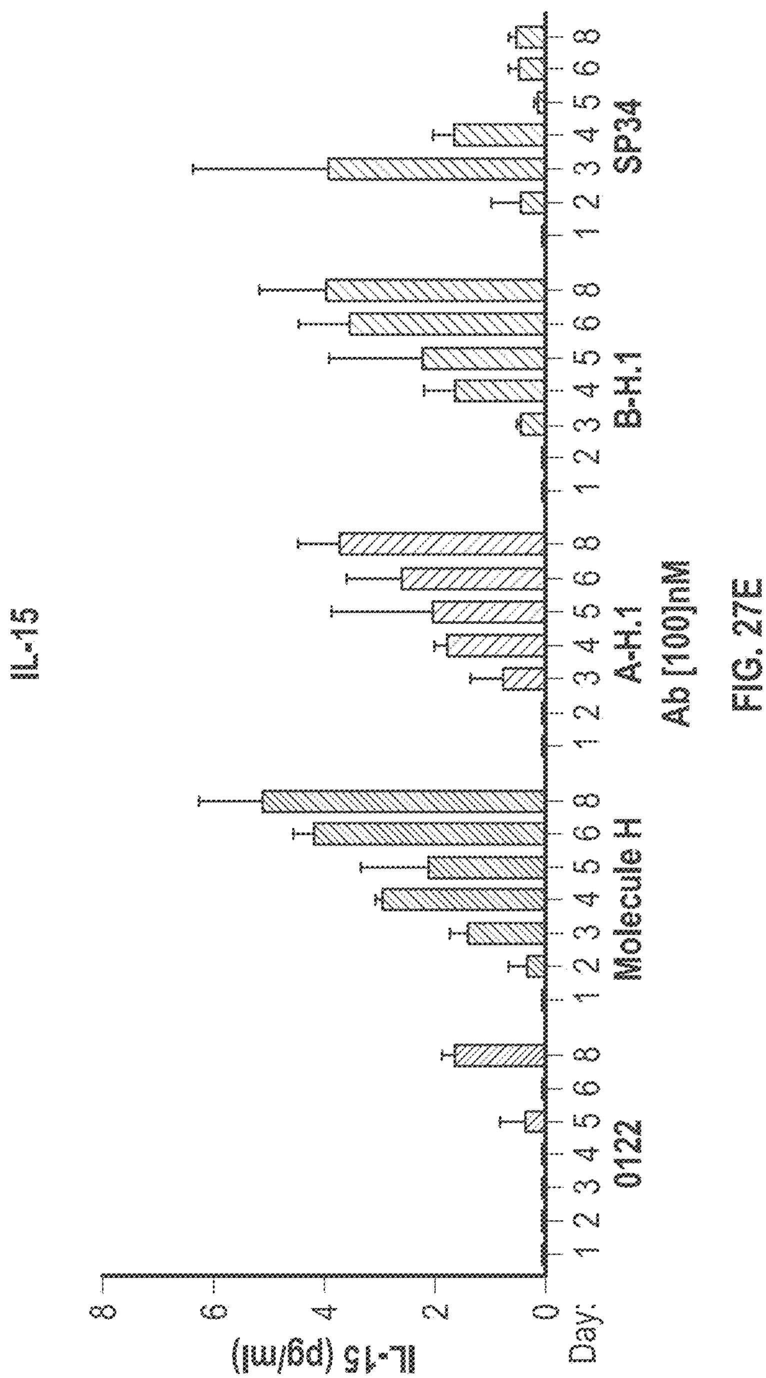
Figure 27F:
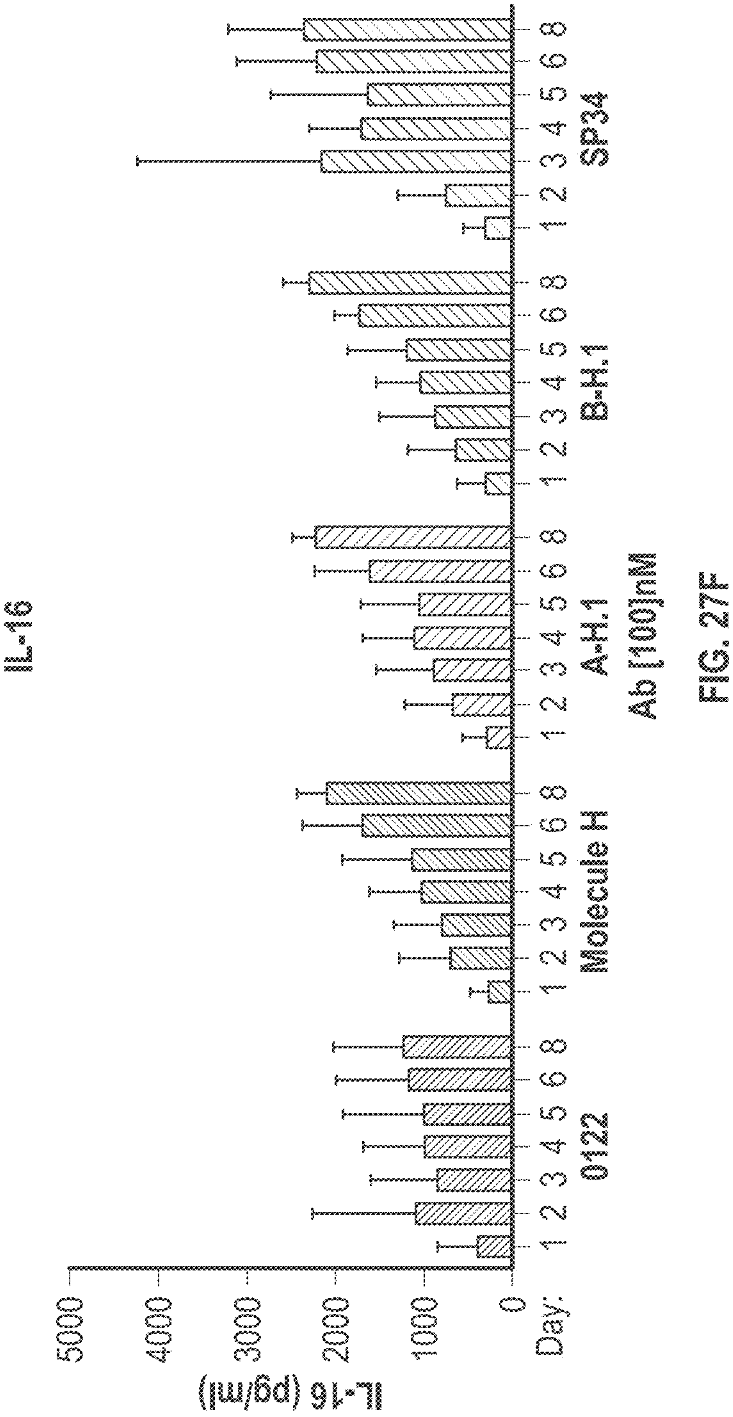
Figure 27G:
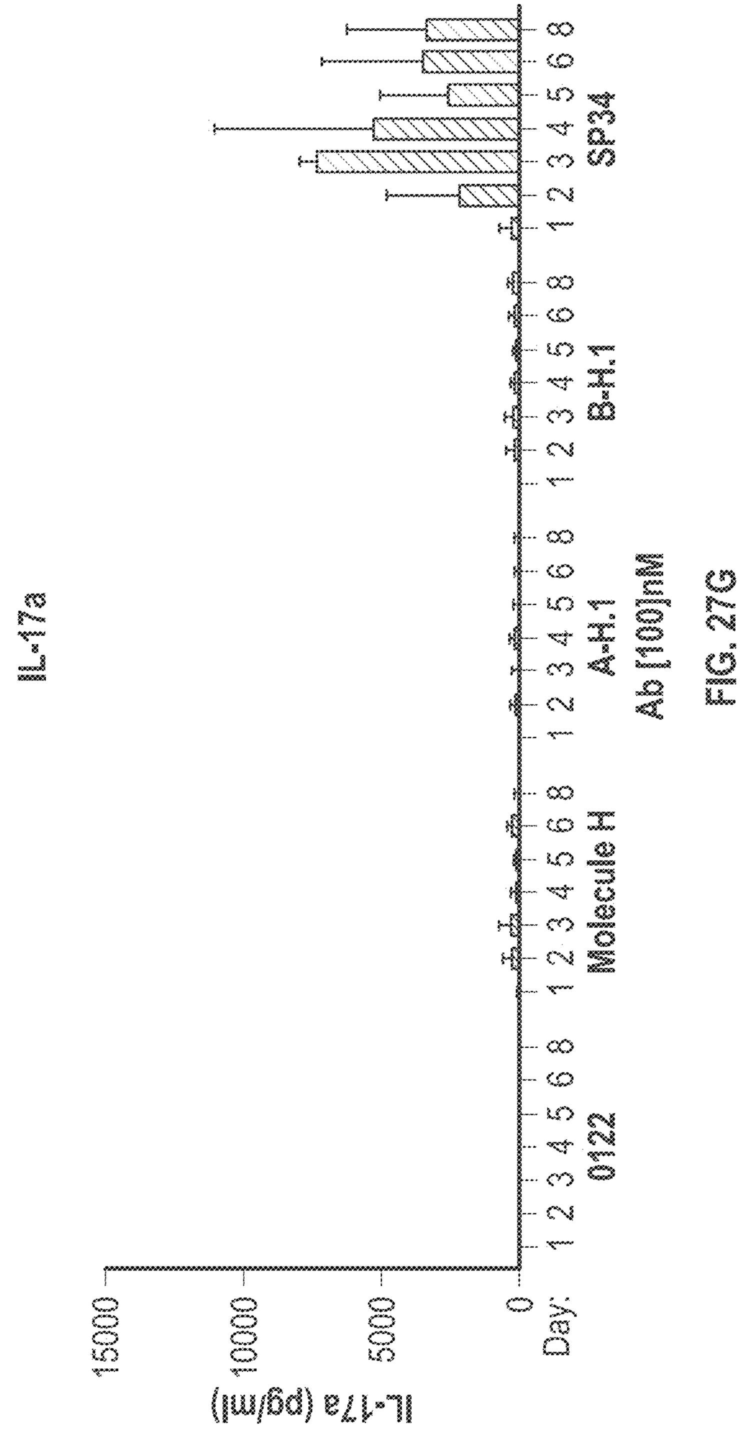
Figure 27H:
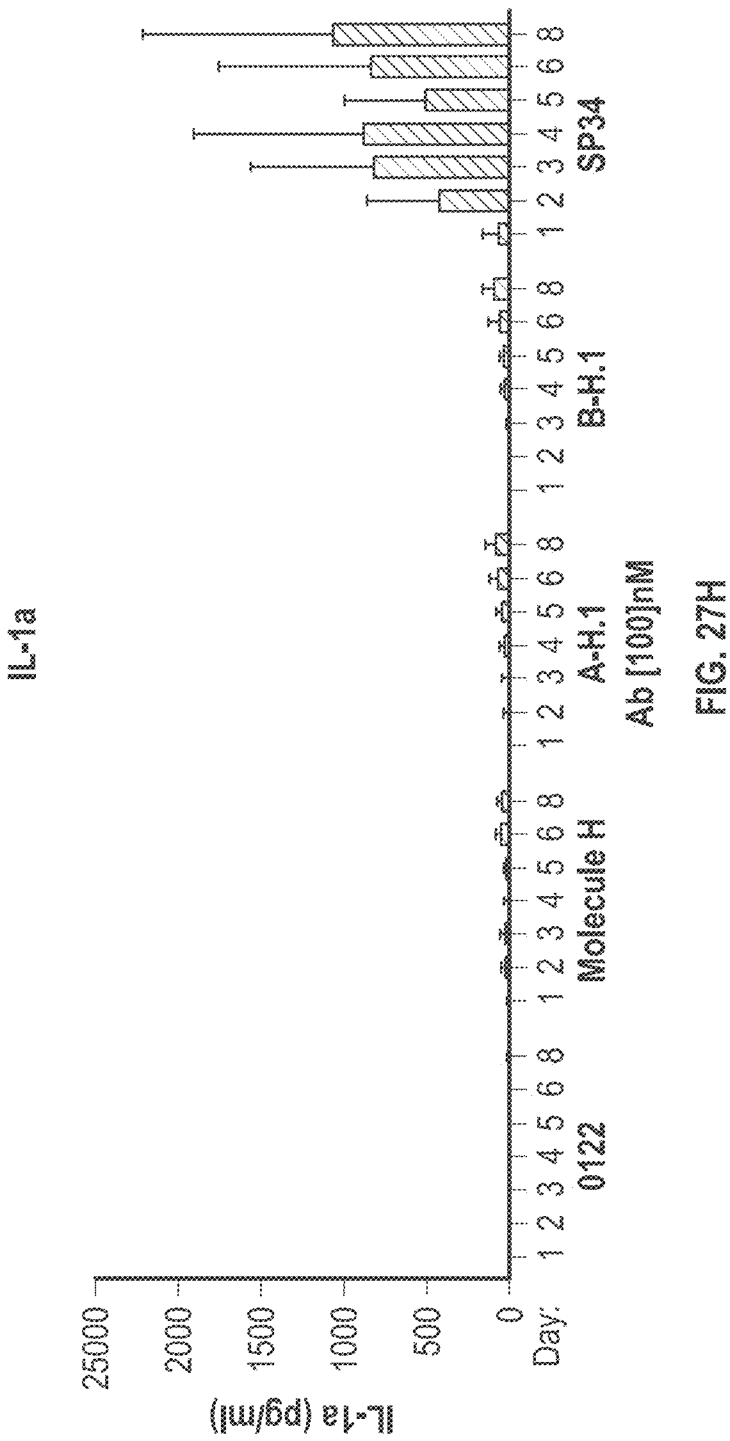
Figure 27I:
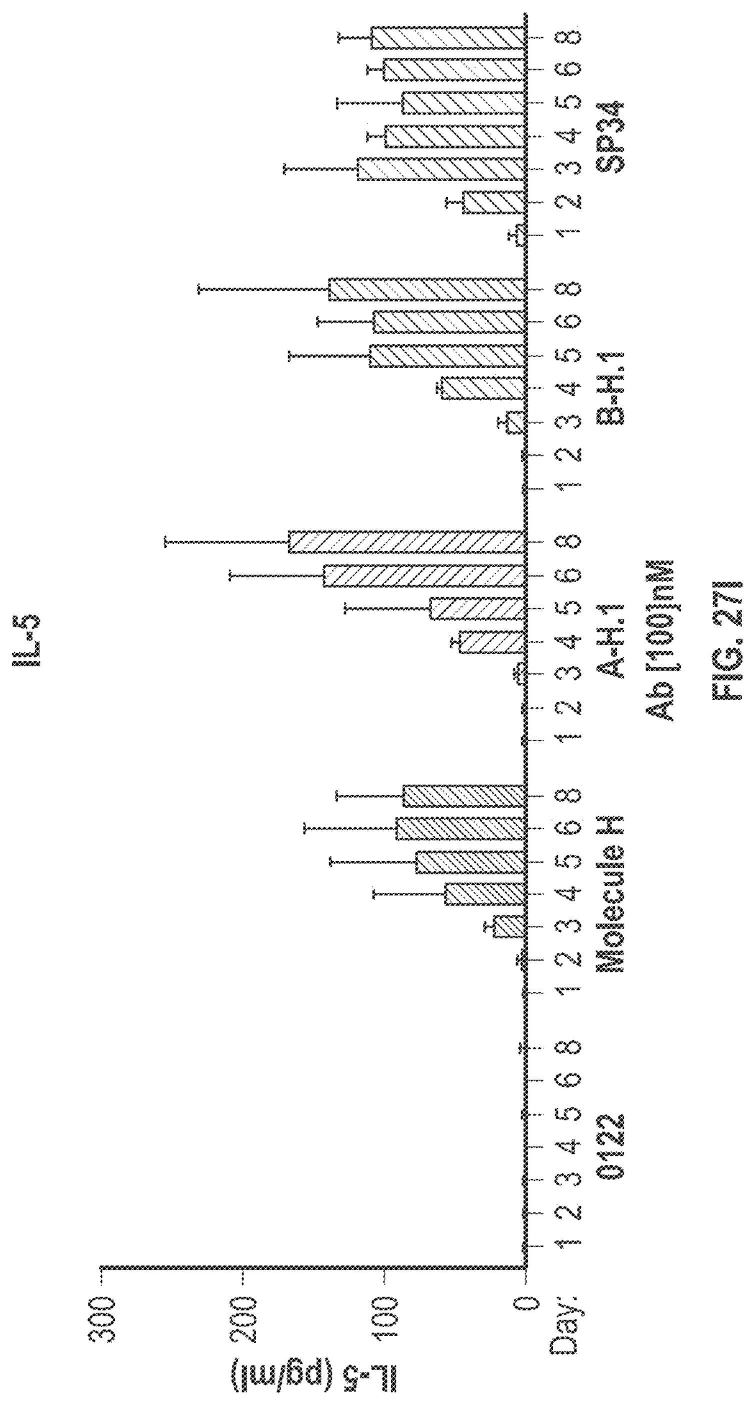
Figure 27J:
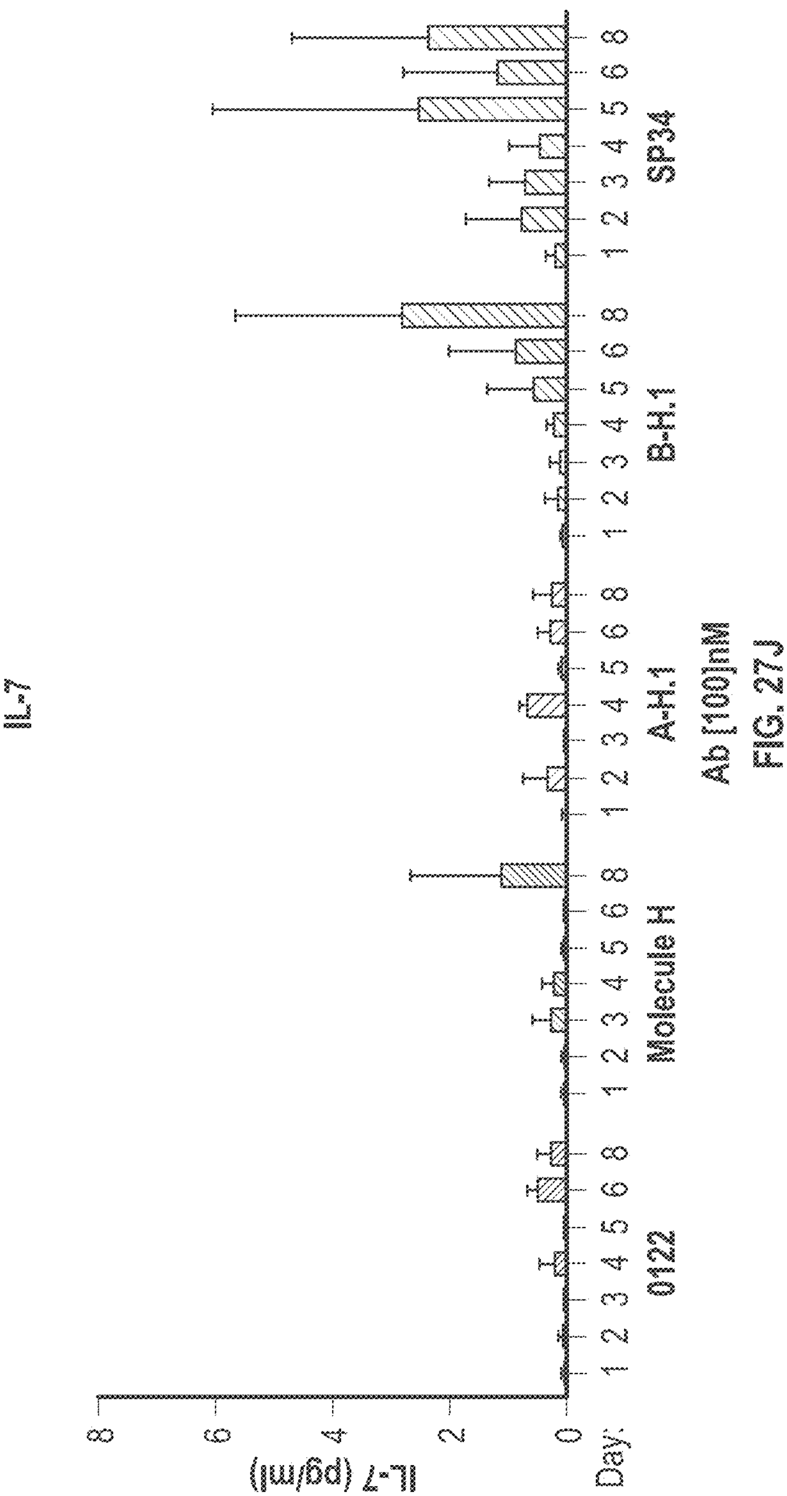
Figure 27K:
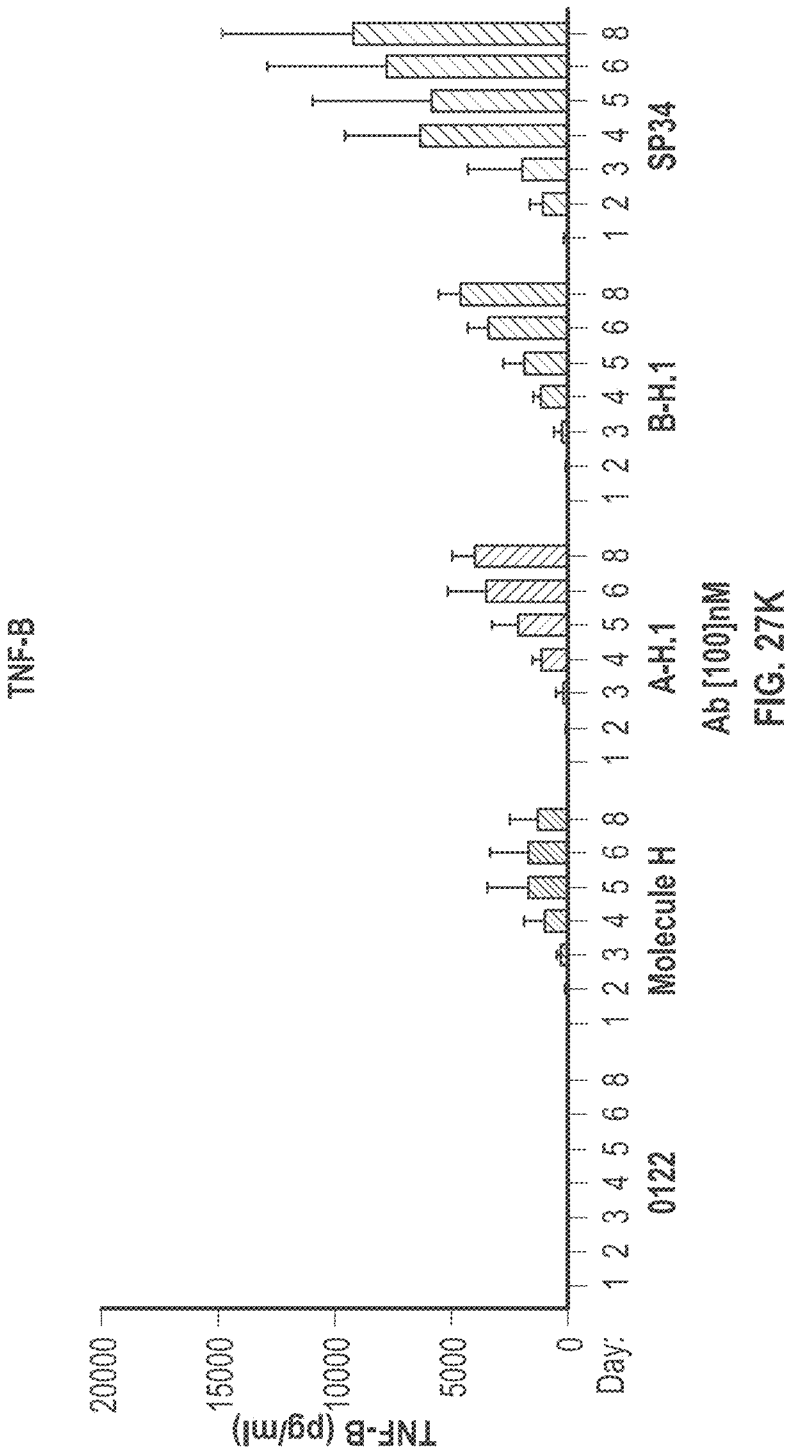
Figure 27L:
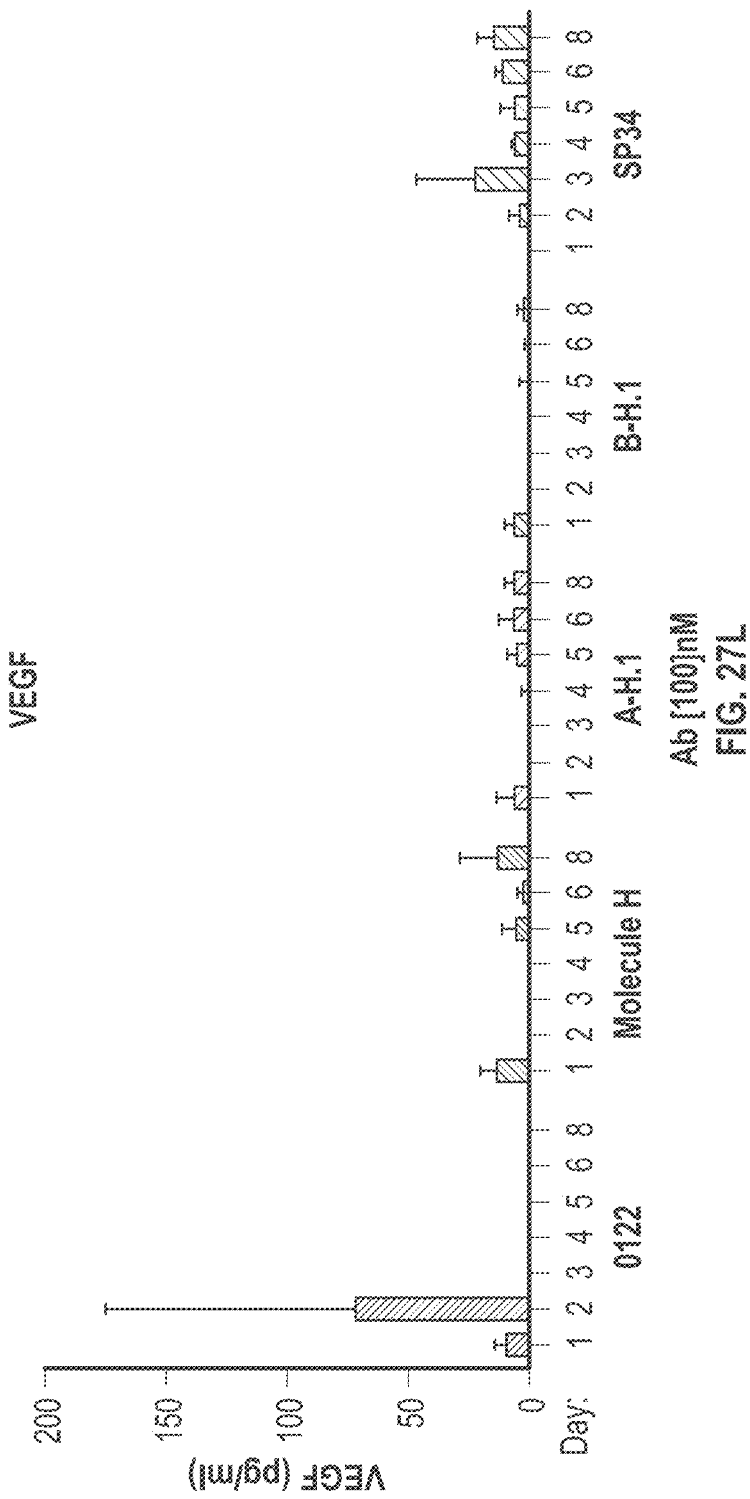

PBMCs activated with anti-TCR Vβ antibodies demonstrated induction of IL-13 (FIG. 25I), IL-8 (FIG. 25J), Eotaxin (FIG. 26A), Eotaxin 3 (FIG. 26B), IL-18 (HA) (FIG. 26C), MCP-1 (FIG. 26E), MCP-4 (FIG. 26F), MDC (FIG. 26G), MIP1a (FIG. 26H), MIP1B (FIG. 27A), TARC (FIG. 27B), GM-CSF (FIG. 27C), IL-15 (FIG. 27E), IL-16 (FIG. 27F), and IL-15 (FIG. 27I), IL-7 (FIG. 27J).

Example 11: Nanostring-Based Gene Expression Profiling of TCR Vb-Activated T Cells This Example describes gene expression profiling of TCR Vβ-activated T cells to, e.g., uncover potential mechanisms or pathways underlying TCR Vβ activation of T cells.

In a first study, the anti-TCR Vβ13.1 antibody A-H.1 was compared with an anti-CD3 antibody OKT3. Briefly, human PBMCs were isolated from whole blood. From isolated PBMCs, human CD3+ T cells were isolated using magnetic-bead separation (negative selection) (Miltenyi biotec) and activated by immobilized (plate-coated) anti-TCR Vβ13.1 antibody (A-H.1) or anti-CD3 antibody (OKT3) at 100 nM for 6 days. Activated T-cells (from plate-coated) were then prepared for gene expression profiling (PanCancer IO 360™ Panel, nanoString), following manufacturer's protocol. Differential gene expression analysis was grouped by anti-TCR Vβ13.1 (A-H.1) vs anti-CD3 (OKT3) activated T-cells using the nSolver Analysis Software (Nanostring). Data shown in Table 15A are mean values from 3 donors. The differentially regulated genes shown in Table 15A have a p-value of 0.05 or less. In the fourth column of Table 15A showing fold changes in gene expression, a positive value indicates genes that are upregulated at the transcriptional level in TCR Vβ-activated T cells compared to OKT3-activated T cells, whereas a negative value indicates genes downregulated at the transcriptional level in TCR Vβ-activated T cells compared to OKT3-activated T cells.

TABLE 15A

Summary of genes whose expression are preferentially regulated in TCR Vβ-activatedT cells compared to OKT3-activated T cells.

| Probe Name | Accession # | NS Probe ID | TCR Vβ13.1 vs OKT3 Fold Change | P value |
|---|---|---|---|---|
| CCR2 | NM_001123041.2 | NM_001123041.2:743 | −3.06 | 0.00019145 |
| LIF | NM_002309.3 | NM_002309.3:1240 | 21.6 | 0.0003319 |
| TCF7 | NM_003202.2 | NM_003202.2:2420 | −8.38 | 0.00037035 |
| PLA2G6 | NM_001004426.1 | NM_001004426.1:1954 | −2.19 | 0.00043564 |
| CD84 | NM_001184879.1 | NM_001184879.1:28 | −3.81 | 0.00062413 |
| ITGB2 | NM_000211.2 | NM_000211.2:520 | −2.11 | 0.0012003 |
| GZMK | NM_002104.2 | NM_002104.2:700 | −11.09 | 0.00135083 |
| HLA-DRB4 | NM_021983.4 | NM_021983.4:194 | −5.75 | 0.00137591 |
| CCR7 | NM_001838.2 | NM_001838.2:1610 | −2.43 | 0.00165716 |
| PDCD1 | NM_005018.1 | NM_005018.1:175 | 7.24 | 0.00195468 |
| CD96 | NM_005816.4 | NM_005816.4:1355 | −6.44 | 0.00221401 |
| SELL | NR_029467.1 | NR_029467.1:1585 | −5 | 0.00227156 |
| NFATC4 | NM_001136022.2 | NM_001136022.2:2296 | −2.75 | 0.0025171 |
| CD8B | NM_004931.3 | NM_004931.3:440 | −3.56 | 0.00302475 |
| NLRC5 | NM_032206.4 | NM_032206.4:860 | −2.27 | 0.00309164 |
| CD1C | NM_001765.2 | NM_001765.2:750 | 8.62 | 0.0035729 |
| HLA-B | NM_005514.6 | NM_005514.6:937 | −1.81 | 0.00363669 |
| NUP107 | NM_020401.2 | NM_020401.2:1002 | 1.64 | 0.00366886 |
| CD3D | NM_000732.4 | NM_000732.4:110 | −2.05 | 0.00401569 |
| HDAC3 | NM_003883.2 | NM_003883.2:1455 | −1.41 | 0.0042794 |
| PRKCE | NM_005400.2 | NM_005400.2:1695 | −1.86 | 0.00429076 |
| HLA-DQB1 | NM_002123.3 | NM_002123.3:384 | −5.71 | 0.00430297 |
| AKT3 | NM_181690.1 | NM_181690.1:755 | −2.98 | 0.00430433 |
| VCAM1 | NM_001078.3 | NM_001078.3:2535 | −23.93 | 0.00464703 |
| CD53 | NM_001040033.1 | NM_001040033.1:835 | −1.7 | 0.00507702 |
| LRP1 | NM_002332.2 | NM_002332.2:4240 | −2.22 | 0.00508974 |
| CD28 | NM_001243078.1 | NM_001243078.1:2065 | −1.73 | 0.00545641 |
| OSM | NM_020530.4 | NM_020530.4:580 | 8.97 | 0.00558554 |
| CLEC4A | NM_194448.2 | NM_194448.2:388 | −1.7 | 0.0056661 |
| MFGE8 | NM_001114614.1 | NM_001114614.1:328 | −2.75 | 0.00633707 |
| IFNAR2 | NM_000874.3 | NM_000874.3:631 | −3.69 | 0.00659279 |
| LTA | NM_000595.2 | NM_000595.2:885 | 6.53 | 0.00727884 |
| ITGAE | NM_002208.4 | NM_002208.4:3405 | −3.42 | 0.00779862 |

TABLE 15A-continued

Summary of genes whose expression are preferentially regulated in TCR Vβ-activatedT cells compared to OKT3-activated T cells.

| Probe Name | Accession # | NS Probe ID | TCR Vβ13.1 vs OKT3 Fold Change | P value |
|---|---|---|---|---|
| CXCR5 | NM_001716.3 | NM_001716.3:2618 | 4.38 | 0.00781195 |
| CD6 | NM_006725.3 | NM_006725.3:1280 | −1.38 | 0.00848703 |
| ICOS | NM_012092.2 | NM_012092.2:640 | 1.74 | 0.00914866 |
| NOS2A | NM_153292.1 | NM_153292.1:546 | −2.29 | 0.0095337 |
| CD1A | NM_001763.2 | NM_001763.2:1815 | 5.12 | 0.00956367 |
| CD27 | NM_001242.4 | NM_001242.4:330 | −3.41 | 0.00984676 |
| KLRD1 | NM_002262.3 | NM_002262.3:542 | −6.43 | 0.00998325 |
| TARP | NM_001003799.1 | NM_001003799.1:560 | −3.71 | 0.00998698 |
| HLA-DPB1 | NM_002121.4 | NM_002121.4:931 | −8.85 | 0.01064161 |
| PTPRC | NM_080921.3 | NM_080921.3:258 | −2.86 | 0.01124117 |
| CD44 | NM_001001392.1 | NM_001001392.1:429 | −2.07 | 0.01138242 |
| SLAMF6 | NM_001184714.1 | NM_001184714.1:1032 | −1.81 | 0.00175123 |
| HLA-DMB | NM_002118.3 | NM_002118.3:20 | −6.39 | 0.01184625 |
| CD276 | NM_001024736.1 | NM_001024736.1:2120 | 6.22 | 0.01207813 |
| MAGEA1 | NM_004988.4 | NM_004988.4:476 | −2.93 | 0.01210408 |
| HLA-DMA | NM_006120.3 | NM_006120.3:380 | −5.75 | 0.1210789 |
| EP300 | NM_001429.2 | NM_001429.2:715 | −1.24 | 0.01228626 |
| ADA | NM_000022.2 | NM_000022.2:1300 | −2.97 | 0.01228787 |
| ICAM1 | NM_000201.2 | NM_000201.2:2253 | 2.52 | 0.01290081 |
| SIGIRR | NM_021805.2 | NM_021805.2:469 | −4.46 | 0.01309473 |
| TNF | NM_000594.2 | NM_000594.2:1010 | 4.6 | 0.01318389 |
| IL1RAP | NM_002182.2 | NM_002182.2:460 | 2.77 | 0.01329693 |
| CSF1 | NM_000757.4 | NM_000757.4:823 | 2.55 | 0.01373637 |
| CD40LG | NM_000074.2 | NM_000074.2:1225 | 11.92 | 0.01376174 |
| CYFIP2 | NM_001037332.2 | NM_001037332.2:4043 | −1.38 | 0.01389707 |
| MUC1 | NM_001018017.1 | NM_001018017.1:725 | 3.12 | 0.01399543 |
| HLA-DRB3 | NM_022555.3 | NM_022555.3:698 | −7.11 | 0.01404049 |
| CD2 | NM_001767.3 | NM_001767.3:687 | −1.53 | 0.01432842 |
| IL2RG | NM_000206.1 | NM_000206.1:595 | −1.82 | 0.01477006 |
| HLA-A | NM_002116.5 | NM_002116.5:1000 | −1.96 | 0.01454336 |
| TXK | NM_003328.1 | NM_003328.1:800 | −2.7 | 0.01590341 |
| ITGA4 | NM_000885.4 | NM_000885.4:975 | −3.59 | 0.01601785 |
| DHX16 | NM_001164239.1 | NM_001164239.1:2490 | 1.41 | 0.0167432 |
| CD3E | NM_000733.2 | NM_000733.2:75 | −1.52 | 0.01736902 |
| MR1 | NM_001531.2 | NM_001531.2:7695 | −2.26 | 0.01744764 |
| SMAD3 | NM_005902.3 | NM_005902.3:4220 | −2.82 | 0.01751245 |
| CCRL2 | NM_003965.4 | NM_003965.4:1110 | −1.87 | 0.01834479 |
| HRAS | NM_005343.2 | NM_005343.2:396 | 1.97 | 0.0187379 |
| IL18R1 | NM_003855.2 | NM_003855.2:2025 | 2.36 | 0.01896204 |
| CMA1 | NM_001836.2 | NM_001836.2:561 | −1.96 | 0.01964938 |
| PSMB7 | NM_002799.2 | NM_002799.2:420 | 1.53 | 0.01980367 |
| BCL10 | NM_003921.2 | NM_003921.2:1250 | −1.38 | 0.01981376 |
| HLA-DRA | NM_019111.3 | NM_019111.3:335 | −7.46 | 0.02026993 |
| CD80 | NM_005191.3 | NM_005191.3:1288 | 4.18 | 0.02055337 |
| PIK3CD | NM_005026.3 | NM_005026.3:2978 | −1.23 | 0.02056576 |
| ETS1 | NM_005238.3 | NM_005238.3:4625 | −1.51 | 0.02083359 |
| CHUK | NM_001278.3 | NM_001278.3:860 | 1.67 | 0.0217326 |
| CCL5 | NM_002985.2 | NM_002985.2:280 | −2.47 | 0.02195802 |
| ITGAL | NM_002209.2 | NM_002209.2:3905 | −3 | 0.02244779 |
| TNFRSF18 | NM_004195.2 | NM_004195.2:445 | −3.76 | 0.02330885 |
| EIF2B4 | NM_172195.3 | NM_172195.3:1390 | 1.28 | 0.02349098 |
| CD79A | NM_001783.3 | NM_001783.3:695 | −4.47 | 0.02361746 |
| ABCF1 | NM_001090.2 | NM_001090.2:850 | 1.31 | 0.02452054 |
| CD37 | NM_001774.2 | NM_001774.2:535 | −2.06 | 0.02476513 |
| STAT5B | NM_012448.3 | NM_012448.3:200 | −1.56 | 0.02495121 |
| CSF2 | NM_000758.2 | NM_000758.2:475 | 11.38 | 0.0256982 |
| STAT3 | NM_139276.2 | NM_139276.2:4535 | −1.47 | 0.02629936 |
| GZMA | NM_006144.2 | NM_006144.2:155 | −2.46 | 0.02646368 |
| C1R | NM_001733.4 | NM_001733.4:760 | −3.1 | 0.02653879 |
| MIF | NM_002415.1 | NM_002415.1:319 | −1.38 | 0.02690018 |
| CD46 | NM_172350.1 | NM_172350.1:365 | −1.36 | 0.02725208 |
| PIK3CG | NM_002649.2 | NM_002649.2:2125 | −2.34 | 0.02762105 |
| CFB | NM_001710.5 | NM_001710.5:2029 | −2.59 | 0.02802998 |
| IL3 | NM_000588.3 | NM_000588.3:130 | 13.37 | 0.02820076 |
| TNFRSF13C | NM_052945.3 | NM_052945.3:789 | −2.2 | 0.02835259 |
| MRPS5 | NM_031902.3 | NM_031902.3:390 | 1.2 | 0.02849936 |
| TUBB | NM_178014.2 | NM_178014.2:320 | 1.06 | 0.02874459 |

TABLE 15A-continued

Summary of genes whose expression are preferentially regulated in TCR Vβ-activatedT cells compared to OKT3-activated T cells.

| Probe Name | Accession # | NS Probe ID | TCR Vβ13.1 vs OKT3 Fold Change | P value |
|---|---|---|---|---|
| PECAM1 | NM_000442.3 | NM_000442.3:1365 | −4.35 | 0.02901845 |
| PVR | NM_006505.3 | NM_006505.3:604 | 2.28 | 0.0299334 |
| AMICA1 | NM_153206.2 | NM_153206.2:620 | −2.38 | 0.03034954 |
| CD74 | NM_001025159.1 | NM_001025159.1:964 | −3.28 | 0.0305419 |
| ENTPD1 | NM_001098175.1 | NM_001098175.1:8830 | −8.02 | 0.03085618 |
| CD97 | NM_078481.2 | NM_078481.2:1370 | −1.56 | 0.03086014 |
| KLRK1 | NM_007360.3 | NM_007360.3:522 | −4.16 | 0.03108504 |
| HLA-DQA1 | NM_002122.3 | NM_002122.3:261 | −5.51 | 0.03126291 |
| CD247 | NM_198053.1 | NM_198053.1:1490 | −1.88 | 0.03182703 |
| IFNG | NM_000619.2 | NM_000619.2:970 | 5.98 | 0.03202586 |
| SAA1 | NM_199161.1 | NM_199161.1:135 | −2.35 | 0.03341258 |
| TBX21 | NM_013351.1 | NM_013351.1:890 | 1.92 | 0.03359165 |
| RORA | NM_134261.2 | NM_134261.2:1715 | −2.57 | 0.03591525 |
| MASP2 | NM_139208.1 | NM_139208.1:330 | −1.65 | 0.03611762 |
| CLU | NM_001831.2 | NM_001831.2:2340 | −1.55 | 0.0369776 |
| KLRB1 | NM_002258.2 | NM_002258.2:85 | −7.43 | 0.03705134 |
| RELA | NM_021975.2 | NM_021975.2:360 | −1.26 | 0.03765981 |
| SLAMF1 | NM_003037.2 | NM_003037.2:580 | 1.82 | 0.03768168 |
| CD8A | NM_001768.5 | NM_001768.5:1320 | −4.49 | 0.0380276 |
| IL11RA | NM_147162.1 | NM_147162.1:400 | −3.54 | 0.03855863 |
| CD3G | NM_000073.2 | NM_000073.2:404 | −1.44 | 0.03877635 |
| JAK1 | NM_002227.1 | NM_002227.1:285 | −1.84 | 0.4001383 |
| SPN | NM_003123.3 | NM_003123.3:2345 | −1.72 | 0.04035383 |
| CXCR4 | NM_003467.2 | NM_003467.2:1335 | −3.03 | 0.04122601 |
| FAS | NM_000043.3 | NM_000043.3:90 | −2.37 | 0.04150638 |
| IL2 | NM_000586.2 | NM_000586.2:300 | 10.9 | 0.04175377 |
| ITGA1 | NM_181501.1 | NM_181501.1:1875 | −2.75 | 0.04213304 |
| IGF1R | NM_000875.2 | NM_000875.2:455 | −1.94 | 0.0424234 |
| CLEC6A | NM_001007033.1 | NM_001007033.1:342 | −2.83 | 0.04299769 |
| RPS6 | NM_001010.2 | NM_001010.2:171 | −1.36 | 0.04334091 |
| MAPK11 | NM_002751.5 | NM_002751.5:1310 | −1.98 | 0.04344288 |
| REL | NM_002908.2 | NM_002908.2:225 | −2.37 | 0.04382344 |
| EOMES | NM_005442.2 | NM_005442.2:1670 | −6.49 | 0.04442535 |
| KLRG1 | NM_005810.3 | NM_005810.3:65 | −3.52 | 0.04487411 |
| IL2RA | NM_000417.1 | NM_000417.1:1000 | 3.4 | 0.0457568 |
| IFNA17 | NM_021268.2 | NM_021268.2:291 | −3.13 | 0.04595868 |
| SH2D1B | NM_053282.4 | NM_053282.4:545 | −1.44 | 0.04640447 |
| CCL2 | NM_002982.3 | NM_002982.3:123 | 4.01 | 0.04660539 |
| TXNIP | NM_006472.1 | NM_006472.1:255 | −4.07 | 0.04695375 |
| CXCL13 | NM_006419.2 | NM_006419.2:210 | −65.05 | 0.04708191 |
| CASP8 | NM_001228.4 | NM_001228.4:301 | −1.42 | 0.04720592 |
| MTMR14 | NM_022485.3 | NM_022485.3:720 | −1.25 | 0.04798024 |
| MAP3K5 | NM_005923.3 | NM_005923.3:1760 | −1.62 | 0.04838454 |
| ADORA2A | NM_000675.3 | NM_000675.3:1095 | 1.3 | 0.04872028 |
| CCR5 | NM_000579.1 | NM_000579.1:2730 | −4.01 | 0.04885927 |

In a second study, the multispecific anti-TCR Vβ13.1/anti-BCMA antibody Molecule H was compared with the anti-CD3 antibody OKT3. Purified T cells were stimulated with solid-phase anti-TCR Vβ antibody over 6 days with the anti-TCR Vβ antibody Molecule H or anti-CD3e antibody (OKT3) at 100 nM. Expanded T cells were collected by centrifugation followed by RNA extraction. Seven hundred and seventy eight (778) immunology-related genes were counted using the nCounter Technology (Nanostring) followed by gene expression analysis using nSolver analysis tools. The data described in this Example is representative of 3 donors.

Based on this analysis, a panel of genes were identified as being differentially regulated in TCR Vβ-activated T cells compared to OKT3-activated T cells (Table 15B). The differentially regulated genes shown in Table 15B have a p-value of 0.05 or less. For example, LIF, CD40LG, PDCD1, CXCR5, LTA, and CD80 are all upregulated at the transcriptional level in TCR Vβ-activated T cells compared to OKT3-activated T cells. GZMK, ENTPD1 (CD39), TCF7, CD396, HLA-DRB4, SIGIRR and SELL are down-regulated at the transcriptional level in TCR Vβ-activated T cells compared to OKT3-activated T cells. TCR Vβ-activated T cells also expressed high levels of cytolytic effectors (e.g., IFNg, Granzyme B and perforin).

TABLE 15B

Summary of genes whose expression are preferentially regulated in TCR Vβ-activated T cells compared to OKT3-activated T cells.

| Gene | Description | $Log_2$ Fold Change | P-Value |
|---|---|---|---|
| LIF | LIF Interleukin 6 Family Cytokine | 4.65 | 0.0119 |
| GZMK | Granzyme K | −3.65 | 0.0468 |
| CD40LG | CD40 Ligand | 3.56 | 0.0082 |
| ENTPD1 (CD39) | Ectonucleoside Triphosphate Diphosphohydrolase 1 | −3.53 | 0.0541 |
| PDCD1 | Programmed Cell Death 1 | 3.19 | 0.0257 |
| TCF7 | Transcription Factor 7 | −3.1 | 0.00634 |
| CXCR5 | Chemokine receptor for CXCL13 | 3.05 | 0.0337 |
| CD96 | Transmembrane glycoprotein Ig superfamily receptor, interacts with nectin and nectin-like proteins, including CD155/polio virus receptor (PVR) | −2.75 | 0.007 |
| LTA | Lymphotoxin Alpha | 2.67 | 0.0082 |
| HLA-DRB4 | Major Histocompatibility Complex, Class 11, DR Beta 4 | −2.66 | 0.0377 |
| CD80 | T cell costimulatory molecule | 2.58 | 0.0425 |
| SIGIRR | Single Ig And TIR Domain Containing | −2.37 | 0.0227 |
| SELL | Selection L | −2.3 | 0.00634 |

Example 12: Binding Affinity of Affinity Matured Humanized Antibody A-H Antibodies This Example describes the evaluation of binding affinity of affinity matured humanized Antibody A-H antibodies to recombinant protein TCRVB 6-5.

Antibody A-H humanized antibodies were affinity matured. The resulting affinity matured antibodies were tested for their binding affinity to TCRVB 6-5 as described below.

TCRVB 6-5 at 5 μg/mL was immobilized on a Biotin CAP Series S Sensor Chip to 60 RU. BJM0277 was diluted to 200 nM and then serially diluted two fold. Association was 120 seconds, and dissociation was 300 seconds. This assay was run in 1×HBS-EP+ Buffer pH 7.4 and 25 C. The data was fit using a 1:1 binding model.

TCRVB 6-5 at 5 μg/mL was immobilized on a Biotin CAP Series S Sensor Chip to 60 RU. A-H.45 was diluted to 50 nM and then serially diluted two fold. Association was 120 seconds, and dissociation was 300 seconds. This assay was run in 1×HBS-EP+ Buffer pH 7.4 and 25 C. The data was fit using a 1:1 binding model. A-H.45 is an improved yeast clone (TCRvB/CD19 bispecific) and contains a mutation (G to V) at the last residue in framework 3, just before HCDR3. The affinity is 35-fold greater than the BJM0277 (Table 16).

TCRVB 6-5 at 5 μg/mL was immobilized on a Biotin CAP Series S Sensor Chip to 60 RU. A-H.52 was diluted to 50 nM and then serially diluted two fold. Association was 120 seconds, dissociation was 300 seconds. This assay was run in 1×HBS-EP+ Buffer pH 7.4 and 25 C. The data was fit using a 1:1 binding model. A-H.52 is a phage clones and is a monovalent scFv. A-H.52 has two mutations on CDRH1. The affinity of A-H.52 is 20-fold greater than BJM0277 (Table 16).

TCRVB 6-5 at 5 ug/mL was immobilized on a Biotin CAP Series S Sensor Chip to 60 RU. A-H.53 was diluted to 50 nM and then serially diluted two fold. Association was 120 seconds, dissociation was 300 seconds. This assay was run in 1×HBS-EP+ Buffer pH 7.4 and 25 C. The data was fit using a 1:1 binding model. A-H.53 (phage clone) affinity is in the pM range (Table 16). The affinity of A-H.53 is 200-fold greater than BJM0277 (Table 16).

TCRVB 6-5 at 5 ug/mL was immobilized on a Biotin CAP Series S Sensor Chip to 60 RU. A-H.54 was diluted to 50 nM and then serially diluted two fold. Association was 120 seconds, dissociation was 300 seconds. This assay was run in 1×HBS-EP+ Buffer pH 7.4 and 25 C. The data was fit using a 1:1 binding model. A-H.54 (phage clone) affinity is 17-fold greater than BJM0277 (Table 16).

TABLE 16

Summary of affinity maturation of anti-TCRVb antibodies

| Construct | Target: TCRVβ 6-5 |
|---|---|
| BJM0277 | 35 nM |
| A-H.45 | 1.08 Nm |
| A-H.52 | 1.76 nM |
| A-H.53 | 165 pM |
| A-H.54 | 2.22 nM |

Example 13: Therapeutic Efficacy of CD19/TCRvB Bispecific Molecules in Subcutaneous Human Tumor Xenograft Models This Example demonstrates the in vivo efficacy of a CD19/TCRvB Bispecific molecule in a subcutaneous human tumor animal model.

On day 1 of the study $1\times10^6$ cells of the human cancer cell line Raji, stably expressing firefly luciferase (Raji-luc) were subcutaneously injected in the right dorsal flank of female NOD/SCID/IL-2Rγnull (NSG) mice. On day 3, $10\times10^6$ human PBMCs were transplanted into mice by injection into the peritoneal cavity.

Antibody treatment started at day 10, when tumors had reached a mean tumor volume (TV) of 80 $mm^3$. Mean TV of each group was not statistically different from any other group at start of treatment. Mice were treated with 0.2 mg/kg, 1 mg/kg and 5 mg/kg of CD19/TCRvB bispecific molecule every three days for a total of 7 doses by intravenous bolus injection.

Tumor volume (TV) was measured every 3 days by calipers and progress evaluated by intergroup comparison of TV. Tumor growth inhibition T/C [%] was calculated as T/C[%]=100×(mean TV of analyzed group)/(mean TV of vehicle group).

Figure 28:
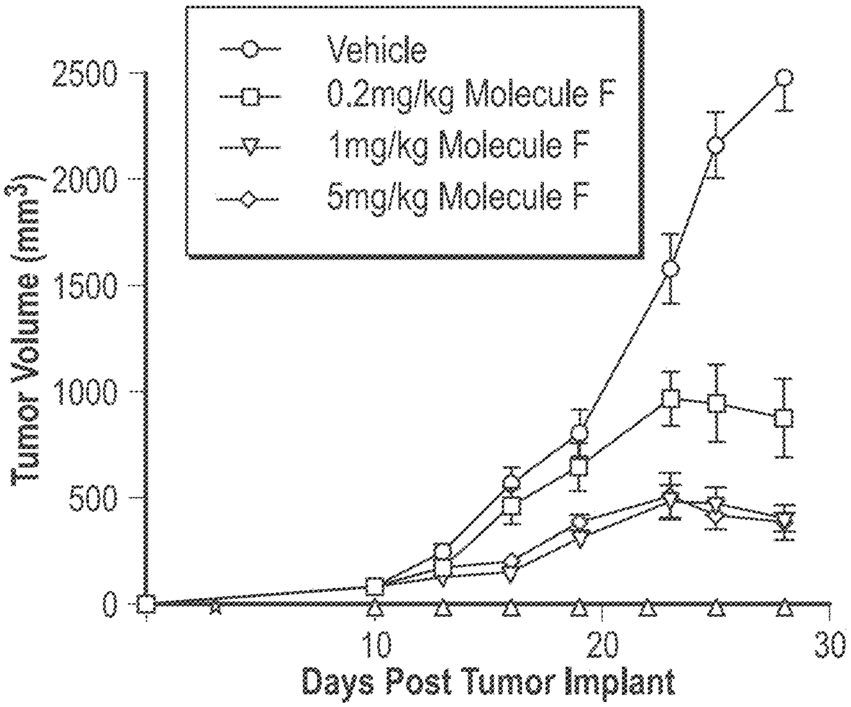
FIG. 28 is a graph depicting mean tumor volume in NOD/SCID/IL-2Rγnull (NSG) mice engrafted with Raji-luc cells at days 10 to 28. The Star denotes PBMC implantation. Open triangles denote antibody treatment with the indicated antibodies.

Results are shown in Table 17 and FIG. 28. Treatment with the CD19/TCRvB Bispecific molecule inhibited tumor growth compared to vehicle control treatment (FIG. 28). The results demonstrate that the CD19/TCRvB bispecific molecule inhibits tumor growth and has anti-tumor activity.

TABLE 17

Mean tumor volume and tumor growth inhibition (T/C) at days 10 to 28.

| Dose group | Data | D10 | D13 | D16 | D19 | D23 | D25 | D28 |
|---|---|---|---|---|---|---|---|---|
| Vehicle | TV ($mm^3$) | 84 | 241 | 566 | 802 | 1577 | 2161 | 2478 |
| | T/C[%] | 100 | 100 | 100 | 100 | 100 | 100 | 100 |
| 0.2 mg/kg CD19/TCRvB | TV ($mm^3$) | 82 | 169 | 460 | 643 | 967 | 946 | 875 |
| | T/C[%] | 98 | 70 | 81 | 80 | 61 | 44 | 35 |
| 1 mg/kg CD19/TCRvB | TV ($mm^3$) | 82 | 122 | 147 | 307 | 482 | 469 | 406 |
| | T/C[%] | 98 | 51 | 26 | 38 | 31 | 22 | 16 |
| 5 mg/kg CD19/TCRvB | TV ($mm^3$) | 79 | 160 | 200 | 381 | 510 | 409 | 382 |
| | | 94 | 66 | 35 | 48 | 32 | 19 | 15 |

Example 14: Therapeutic Efficacy of CD19/TCRvB Bispecific Molecules in Human Tumor Xenograft Models This Example demonstrates the in vivo efficacy of a CD19/TCRvB Bispecific molecules in a xenograft animal model.

On day 1 of the study $10\times10^6$ human PBMCs were transplanted into NOD/SCID/IL-2Rγnull (NSG) mice by injection into the peritoneal cavity.

On day 7, $1\times10^6$ cells of the human cancer cell line Raji, stably expressing firefly luciferase (Raji-luc) were intravenously injected into NOD/SCID/IL-2Rγnull (NSG) mice. Control animals were injected with $10\times10^6$ cells of the CD19 negative human cancer cell line K562 stably expressing firefly luciferase (K562-luc). These animals were used to assess specific killing ability of CD19/TCRvB molecules. Antibody treatment started at day 16, when tumor engraftment had reached a mean bioluminescence flux level of $4\times10^7$ photons/s. Mean Flux level of each group was not statistically different from any other group at start of treatment. Mice were treated with 1 mg/kg and 5 mg/kg of CD19/TCRvB bispecific molecule every three days for a total of 6 doses by intravenous bolus injection.

Tumor burden was measured weekly by bioluminescence imaging and progress evaluated by intergroup comparison of total bioluminescence flux (Total Flux). Tumor growth inhibition T/C [%] was calculated as T/C[%]=100×(mean Total Flux of analyzed group)/(mean Total Flux of vehicle group).

Figure 29A:
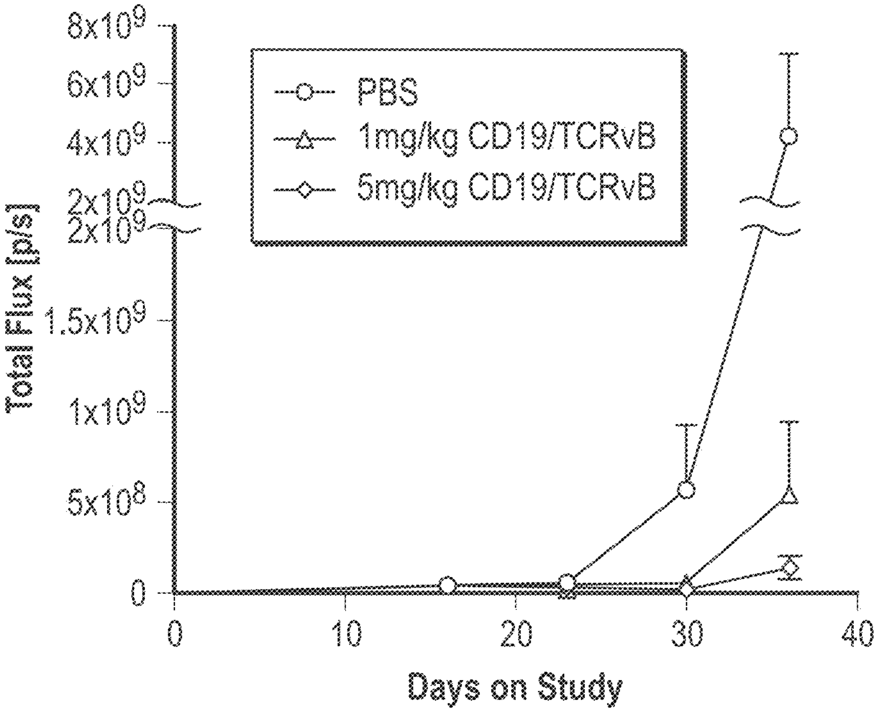
FIGS. 29A-29B depicting Mean tumor burden (Total Flux) in NOD/SCID/IL-2Rγnull (NSG) mice engrafted with cancer cells and treated with the indicated antibody. NSG mice were implanted with PBMCs on Day 1 followed by injection with cancer cells on Day 7 (Raji-luc in FIG. 29A; K562-Luc control in FIG. 29B). Antibody treatment with the indicated antibodies began on Day 16.
Figure 29B:
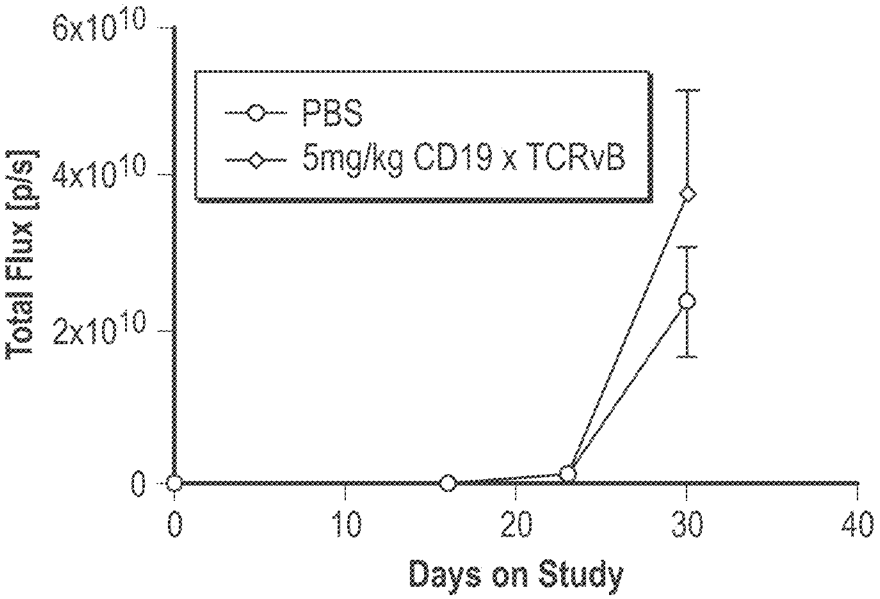

The results for Raji-luc engrafted animals are shown in Table 18 and FIG. 29A and results for K562-luc engrafted animals are shown in Table 19 and FIG. 29B. The results demonstrate that the CD19/TCRvB bispecific molecule inhibits tumor growth and has anti-tumor activity (FIG. 29A and Table 18).

TABLE 18

Mean tumor burden (Total Flux) and tumor growth inhibition (T/C) at days 16 to 37 in animals engrafted with Raji-luc cells

| Dose group | Data | D16 | D23 | D30 | D37 |
|---|---|---|---|---|---|
| Vehicle | Total Flux (p/s) | 4.26E+07 | 5.92E+07 | 5.77E+08 | 4.23E+09 |
| | T/C [%] | 100 | 100 | 100 | 100 |
| 1 mg/kg CD19/TCRvB | Total Flux (p/s) | 4.05E+07 | 2.66E+07 | 5.03E+07 | 5.42E+08 |
| | T/C [%] | 95.0 | 44.9 | 8.7 | 12.8 |
| 5 mg/kg CD19/TCRvB | Total Flux (p/s) | 4.18E+07 | 3.10E+07 | 2.37E+07 | 1.44E+08 |
| | T/C [%] | 98.0 | 52.3 | 4.1 | 3.4 |

TABLE 19

| Mean tumor burden (Total Flux) and tumor growth inhibition (T/C) at days 16 to 30 in animals engrafted with K562-luc cells | | | | |
|---|---|---|---|---|
| Dose group | Data | D16 | D23 | D30 |
| Vehicle | Total Flux (p/s) | 2.98E+07 | 9.94E+08 | 2.40E+10 |
| | T/C [%] | 100 | 100 | 100 |
| 5 mg/kg CD19/TCRvB | Total Flux (p/s) | 2.00E+07 | 1.22E+09 | 3.82E+10 |
| | T/C [%] | 67.0 | 122.4 | 159.4 |

Example 15: Therapeutic Efficacy of BCMA/TCRvB Bispecific Molecules in Human Tumor Xenograft Models This Example demonstrates the in vivo efficacy of a BCMA/TCRvB Bispecific molecule in a xenograft animal model.

On day 1, $20\times10^6$ cells of the human cancer cell line RPMI-8226, stably expressing firefly luciferase (RPMI-8226-luc) were intravenously injected into NOD/SCID/IL-2Rγnull (NSG) mice. On day 11, $10\times10^6$ human PBMCs were transplanted into mice by injection into the peritoneal cavity. Antibody treatment started at day 17, when tumor engraftment had reached a mean bioluminescence flux level of $4\times10^7$ photons/s. Mice were treated with 0.5 mg/kg of a molecule bivalent for both BCMA and TCRvB (2×2 molecule) and 0.5 mg/kg of a molecule bivalent for BCMA and monovalent for TCRvB (2×1 molecule) once a week for a total of 2 doses by intravenous bolus injection.

Tumor burden was measured weekly by bioluminescence imaging and progress evaluated by intergroup comparison of total bioluminescence flux (Total Flux). Tumor growth inhibition T/C [%] was calculated as T/C[%]=100×(mean Total Flux of analyzed group)/(mean Total Flux of vehicle group).

Figure 30:
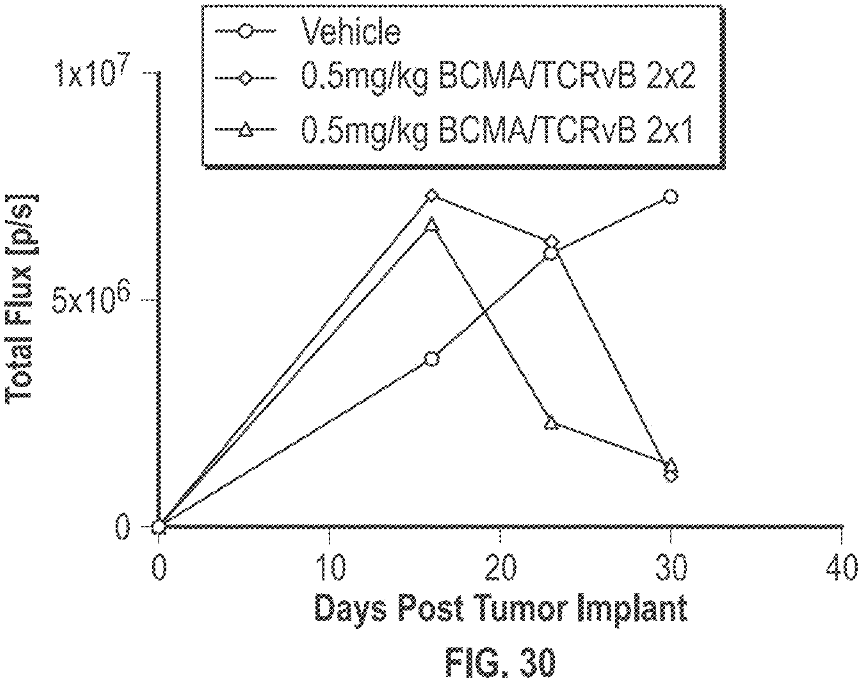
FIG. 30 is a graph depicting Mean tumor burden (Total Flux) mean tumor volume in NOD/SCID/IL-2Rγnull (NSG) mice engrafted with RPMI-8226 cells. The RPMI-8226 cells were engrafted on Day 1. On Day 11, PBMCs were implanted into the mice and antibody treatment began on Day 17.

Results of these studies are shown in Table 20 and FIG. 30. Treatment with the BCMA/TCRvB Bispecific molecule inhibited tumor growth compared to vehicle control treatment (FIG. 29). The results demonstrate that the BCMA/TCRvB bispecific molecule inhibits tumor growth and has anti-tumor activity.

TABLE 20

| Mean tumor burden (Total Flux) and tumor growth inhibition (T/C) at days 16 to 30. | | | | |
|---|---|---|---|---|
| Dose group | Data | D16 | D23 | D30 |
| Vehicle | Total Flux (p/s) | 3.71E+06 | 6.04E+06 | 7.29E+06 |
| | T/C [%] | 100 | 100 | 100 |
| 0.5 mg/kg BCMA/TCRvB 2 × 2 | Total Flux (p/s) | 7.33E+06 | 6.30E+06 | 1.13E+06 |
| | T/C [%] | 197.7 | 104.3 | 15.5 |
| 0.5 mg/kg BCMA/TCRvB 2 × 1 | Total Flux (p/s) | 3.66E+06 | 3.15E+06 | 5.65E+05 |
| | T/C [%] | 98.8 | 52.1 | 7.8 |

Example 16: Expression and Purification of Antibody Constructs

Construction of the Plasmids

The DNA encoding the protein sequences was optimized for expression in *Cricetulus griseus*, synthesized, and cloned into the pcDNA3.4-TOPO (Life Technologies A14697) using Gateway cloning. All constructs contained an Ig Kappa leader sequence METDTLLLWVLLLWVPGSTG (SEQ ID NO: 3288).

Expression and Purification

The plasmids were co-transfected into either Expi293™ cells (293 cell line) (Life Technologies A14527) or ExpiCHO™ cells (a subclone of Chinese hamster ovary cells) (Life Technologies A29127). Transfections were performed using 1 mg of total DNA for a multispecific construct with a 1:1 heavy chain ratio and 3:2 light chain to heavy chain ratio if applicable. Transfection in Expi293™ cells (293 cell line) was done using linear 25,000 Da polyethylenimine (PEI, Polysciences Inc 23966) in a 3:1 ratio with the total DNA. The DNA and PEI were each added to 50 mL of OptiMem™ cells (an improved Minimal Essential Medium) (Life Technologies 31985088) medium and sterile filtered. The DNA and PEI were combined for 10 minutes and added to the Expi293™ cells (293 cell line) with a cell density of $1.8\text{-}2.8\times10^6$ cells/mL and a viability of at least 95%. The ExpiCHO™ (a subclone of Chinese hamster ovary cells) transfection was performed according to the manufacturer's instructions. Expi293™ cells (293 cell line) were grown in a humidified incubator at 37° C. with 8% $CO_2$ for 5-7 days after transfection and ExpiCHO™ cells (a subclone of Chinese hamster ovary cells) were grown for 14 days at 32° C. with 5% $CO_2$. The cells were pelleted by centrifugation at 4500×g and the supernatant was filtered through a 0.2 μm membrane. Protein A resin (GE 17-1279-03) was added to the filtered supernatant and incubated for 1-3 hours at room temperature. The resin was packed into a column, washed with 3×10 column volumes of Dulbecco's phosphate-buffered saline (DPBS, Life Technologies 14190-144). The bound protein was eluted from the column with 20 mM citrate, 100 mM NaCl, pH 2.9. When necessary, the proteins were further purified using ligand affinity and/or size exclusion chromatography on a Superdex 200® (chromatography resin with a composite matrix of dextran and agarose) column with a running buffer of DPBS.

Example 17: Humanization of Anti-TRBV5-5 Antibody Clone Antibody C

The germline for the mouse anti-TCRvbeta antibody clone Antibody C VH and VL were assigned using IMGT nomenclature, with CDR regions defined by a combined Kabat and Chothia classification. SEQ ID NO: 232 and SEQ ID NO: 233 are the Antibody C VH and VL sequences respectively where the VH germline is mouse IGHV2-6-7*01 and the VL germline is mouse IGKV10-94*02. The method applied to humanize Antibody A described in Example 1 was used to humanize Antibody C. The Antibody C VH was humanized into human IGHV2-26*01, IGHV2-70*04, IGHV4-4*02, IGHV2-5*09, IGHV2-5*08, IGHV4-34*09, IGHV4-59*01, IGHV4-59*07, IGHV4-61*02, IGHV4-38-2*01, IGHV4-31*01, IGHV3-49*04, IGHV3-49*02, IGHV4-4*07, IGHV3-49*05, IGHV4-34*10, IGHV4-28*04, IGHV3-72*01, IGHV3-15*07, IGHV6-1*01, IGHV3-7*01, IGHV4-34*01, IGHV3-33*02, IGHV3-48*02, IGHV3-23*03, IGHV3-21*01, IGHV3-73*01, IGHV3-30*02, IGHV3-7*01, IGHV3-43*01, and IGHV3-53*03 and the Antibody C VL was humanized into human IGKV1D-43*01, IGKV1-27*01, IGKV1-17*02, IGKV1-17*01, IGKV1-5*01, IGKV4-1*01, IGKV3-7*02, IGKV3-7*01, IGKV2-29*02, IGKV6D-41*01, IGKV2-28*01, IGKV2-40*01, IGKV3-15*01, IGKV2-24*01, IGKV6-21*01, IGKV2D-26*01, and IGKV2D-26*03.

SEQ ID NOs: 3040-3089 are the Antibody C humanized heavy chains and SEQ ID NOs: 3000-3039 are the Antibody C humanized light chains (as described in Table 10).

Example 18: Humanization of TRBV10-1, TRBV10-2, and TRBV10-3 Antibody Clone Antibody D The germline for the mouse anti-TCRvbeta antibody clone Antibody D VH and VL were assigned using IMGT nomenclature, with CDR regions defined by a combined Kabat and Chothia classification. SEQ ID NO: 3183 and SEQ ID NO: 3184 are the Antibody D VH and VL sequences respectively where the VH germline is mouse IGHV5-6*01 and the VL germline is mouse IGKV4-59*01.

The method applied to humanize Antibody A described in Example 1 was used to humanize Antibody D. The Antibody D VH was humanized into human IGHV3-30*03, IGHV3-30*02, IGHV3-7*01, IGHV3-21*01, IGHV3-23*04, IGHV3-30*15, IGHV3-48*02, IGHV3-53*04, IGHV3-23*03, IGHV3-53*03, IGHV3-53*01, IGHV3-9*01, IGHV3-30*13, IGHV3-20*01, IGHV3-43D*03, IGHV3-43*02, IGHV3-43*01, IGHV3-53*02, IGHV3-13*01, IGHV3-38-3*01, IGHV3-9*03, IGHV3-64D*06, IGHV3-33*02, IGHV3-11*03, IGHV3-64*02, IGHV3-64*01, IGHV3-64*03, IGHV3-7*01, IGHV3-35*01, IGHV3-13*02, IGHV3-38*02, and IGHV3-38*01 and the Antibody D VL was humanized into human IGKV3-11*01, IGKV1-13*02, IGKV1-9*01, IGKV6-21*01, IGKV1D-43*01, IGKV3-11*01, IGKV3D-11*02, IGKV1-17*03, IGKV3D-20*01, IGKV3-20*01, IGKV1D-16*01, IGKV4-1*01, IGKV2-28*01, IGKV2-40*01, IGKV2-29*02, IGKV2-29*01, IGKV1D-42*01, IGKV2-24*01, and IGKV5-2*01. SEQ ID NOs: 3225-3274 are the Antibody D humanized heavy chains and SEQ ID NOs: 3185-3224 are the Antibody D humanized light chains (as described in Table 12).

Example 19: Humanization of TRBV5-5 and TRBV5-6 Antibody Clone Antibody E

The germline for the mouse anti-TCRβ antibody clone Antibody E VH and VL were assigned using IMGT nomenclature, with CDR regions defined by a combined Kabat and Chothia classification. SEQ ID NO: 3091 and SEQ ID NO: 3092 are the Antibody E VH and VL sequences respectively where the VH germline is mouse IGHV1-82*01 and the VL germline is mouse IGKV3-5*01.

The method applied to humanize Antibody A described in Example 1 was used to humanize Antibody E. The Antibody E VH was humanized into human IGHV1-69*08, IGHV1-3*02, IGHV1-18*03, IGHV1-3*01, IGHV1-18*01, IGHV1-2*06, IGHV1-2*01, IGHV1-2*06, IGHV1-8*01, IGHV7-4-1*02, IGHV1-58*02, IGHV5-51*01, IGHV7-4-1*04, IGHV7-81*01, IGHV5-51*04, IGHV5-51*01, IGHV1-45*03, IGHV3-49*04, IGHV3-49*02, IGHV3-49*05, IGHV4-4*02, IGHV3-49*05, IGHV3-73*01, IGHV4-4*02, IGHV3-15*07, IGHV3-15*02, IGHV3-72*01, IGHV4-59*07, IGHV4-31*01, IGHV4-31*02, IGHV3-30*15, IGHV3-21*01, IGHV3-7*01, IGHV4-28*01, IGHV4-28*02, IGHV3-30*08, IGHV3-30*05, and IGHV3-30*01 and the Antibody E VL was humanized into human IGKV4-1*01, IGKV3-11*01, IGKV3-20*02, IGKV3-11*01, IGKV1-13*02, IGKV3D-11*01, IGKV3D-20*02, IGKV1-13*02, IGKV3D-20*01, IGKV1-9*01, IGKV3D-15*03, IGKV3-15*01, IGKV1-5*01, IGKV2D-29*01, IGKV3-7*02, IGKV1-9*01, IGKV2-28*01, IGKV2-40*01, IGKV2D-29*02, IGKV3-7*01, IGKV2-30*01, IGKV2-24*01, IGKV6D-41*01, IGKV1D-42*01, IGKV2D-26*01, IGKV2D-26*03, and IGKV5-2*01. SEQ ID NOs: 3133-3182 are the Antibody E humanized heavy chains and SEQ ID NOs: 3093-3132 are the Antibody E humanized light chains (as described in Table 11).

Example 20: In Vitro Cytotoxicity of an Anti-TCRVb/CD19 Antibody Molecule and an Anti-TCRVb/BCMA Antibody Molecule Anti-TCR/Anti-CD19 Dual Targeting Antibody Molecule Human PBMCs were isolated from whole blood. From isolated PBMCs, human CD3+ T cells were isolated using magnetic-bead separation (negative selection) (Miltenyi biotec) and activated by immobilized (plate-coated) anti-TCR Vβ13.1 (A-H.1) at 100 nM for 6 days. Activated T-cells (from plate-coated) were then transferred and expanded in tissue culture flask in the presence of human IL-2 at a concentration of 50 U/ml for two additional days. Expanded TCR Vβ13.1+ cells were washed and co-cultured in the presence of CD19-expressing Raji cells (target cells) at an E:T ratio of 5:1 and serial diluted concentrations of T-cell engager bispecific antibodies including, anti-TCR Vβ13.1/CD19 (Molecule F), anti-CD3/CD19, and anti-TCR Vβ13.1 (A-H.1, serving as control) for 24 hours. Post 24 hours, cell co-culture supernatants were collected and quantified for specific target cell death. Target cells (Raji cells) are a KILR-retroparticles reporter cell assay (DiscoverX). KILR-Raji target cells are engineered to stably express a protein tagged with enhanced ProLabel (ePL), a β-gal reporter fragment, using the KILR Retroparticles, and when the membrane of the target cells is compromised due to cell death, the target cells will release the tagged protein into the media. This KILR reporter protein can be detected in the media/supernatant by the addition of detection reagents containing the enzyme acceptor (EA) fragment of the β-gal reporter. This leads to the formation of the active β-gal enzyme which hydrolyzes the substrate to give a chemiluminescent output (RLU). Percentage (%) of target cell death is calculated using the following formula:

$$(RLU_{Treatment}-RLU_{No\ Treatment})/(RLU_{Maximum\ Lysis}-RLU_{No\ Treatment})\times 100$$

Figure 31A:
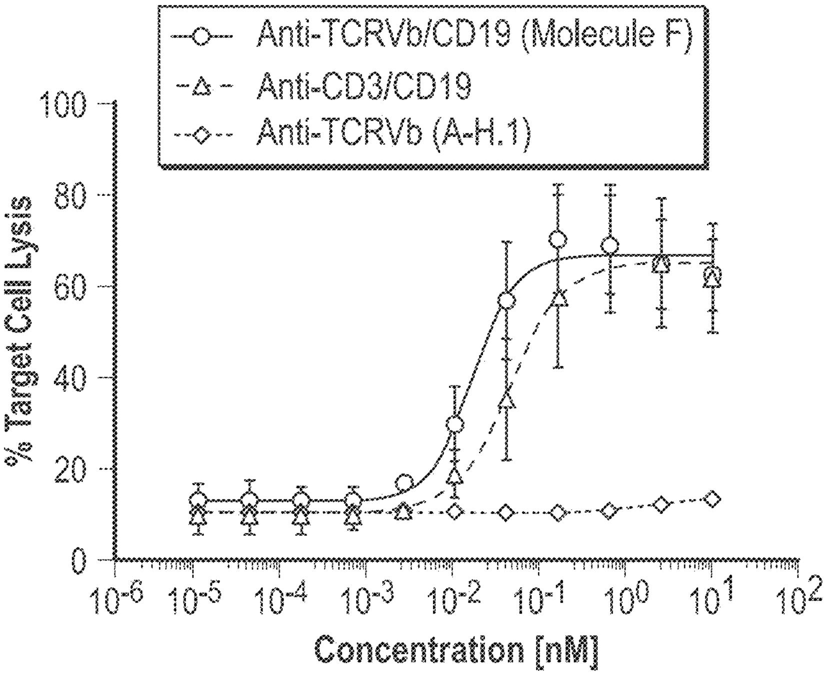
FIGS. 31A-31B are graphs showing % target cell lysis at different antibody concentrations.

Data shown in FIG. 31A are mean values from 4 donors.

Anti-TCR/Anti-BCMA Dual Targeting Antibody Molecule

Figure 31B:
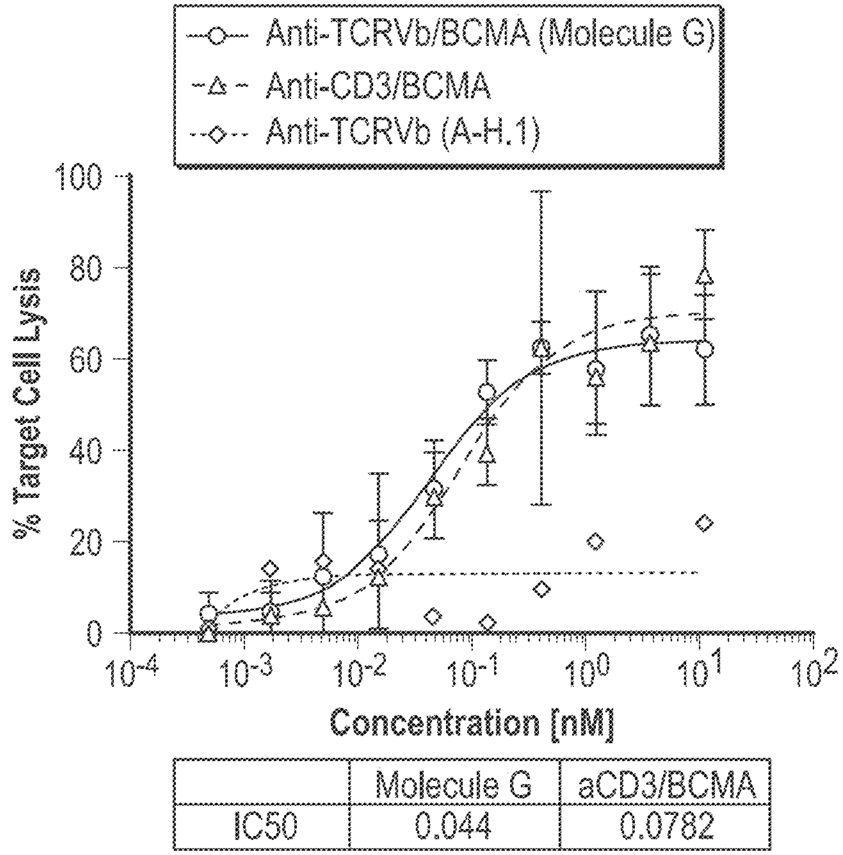
Figure 32A:
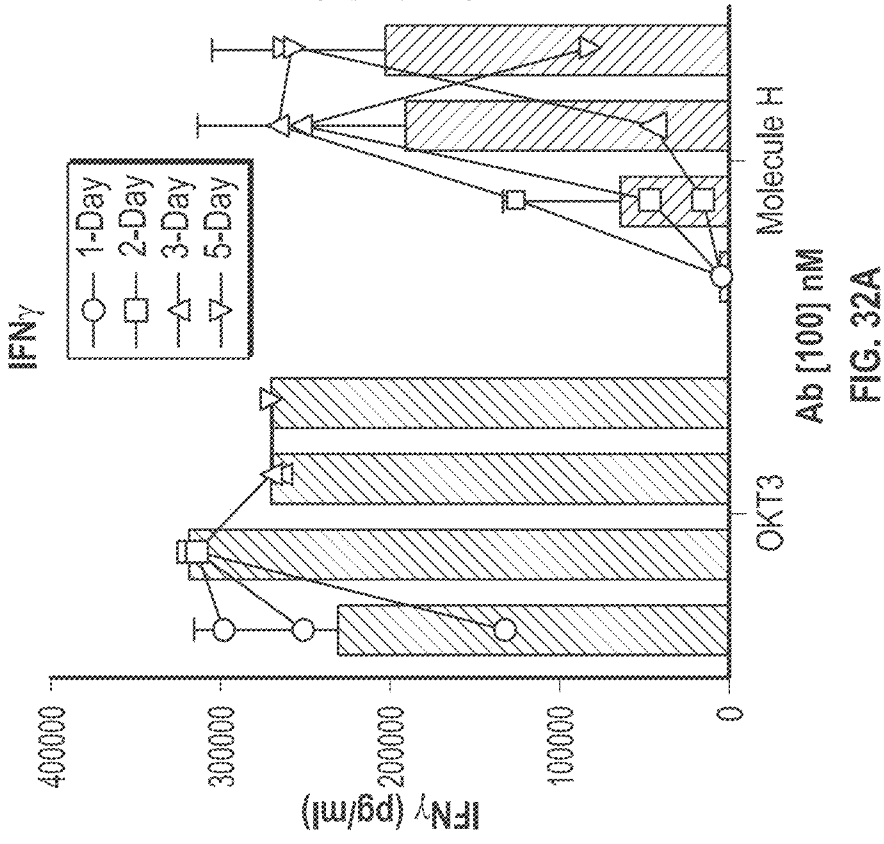
FIGS. 32A-32F are graphs showing cytokine secretion stimulated by anti-TCR Vβ/anti-BCMA (Molecule H) or anti-CD3 (OKT3) at Days 1, 2, 3, and 5. Cytokines examined include: IFNγ (FIG. 32A), IL-2 (FIG. 32B), IL-1β (FIG. 32C), IL-6 (FIG. 32D), IL-10 (FIG. 32E), and TNFα (FIG. 32F).
Figure 32B:
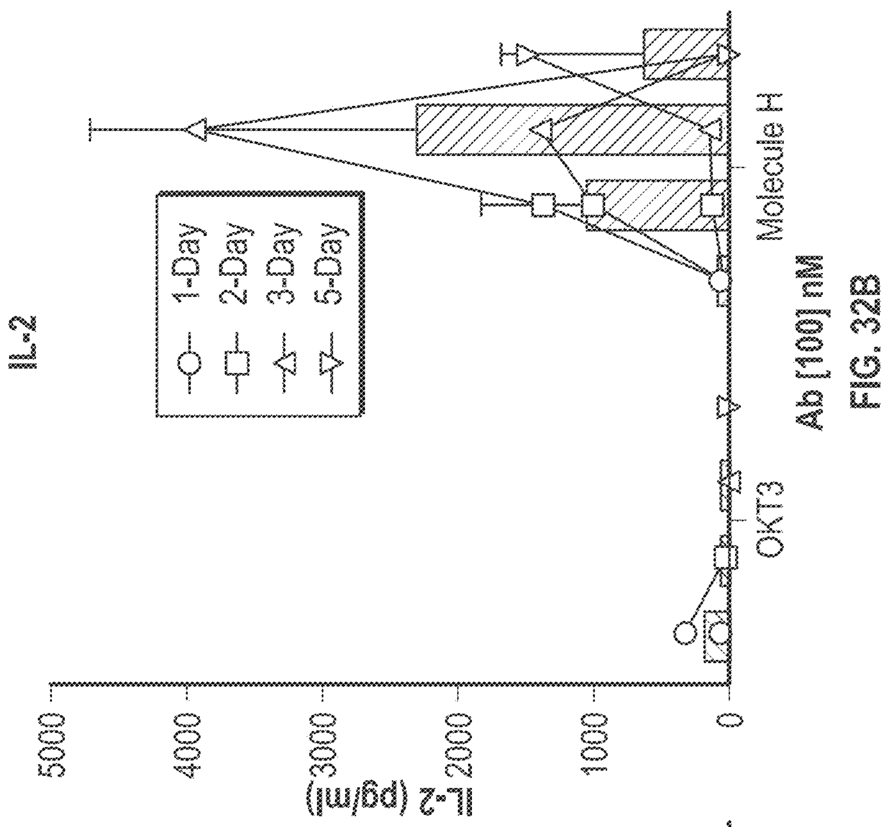
Figure 32D:
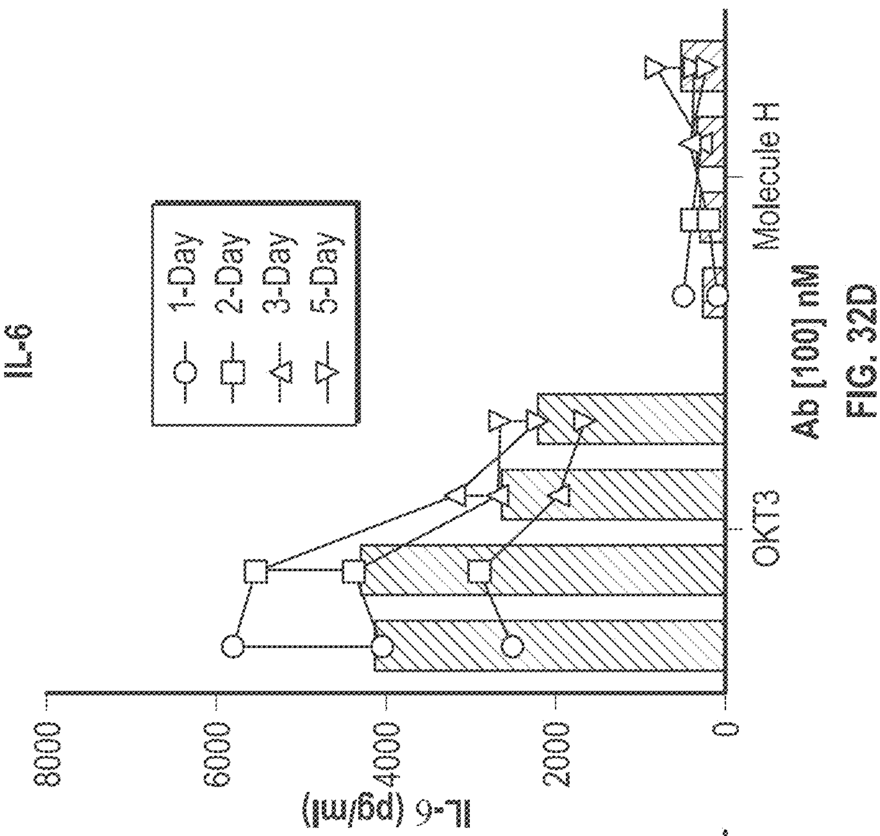
Figure 32C:
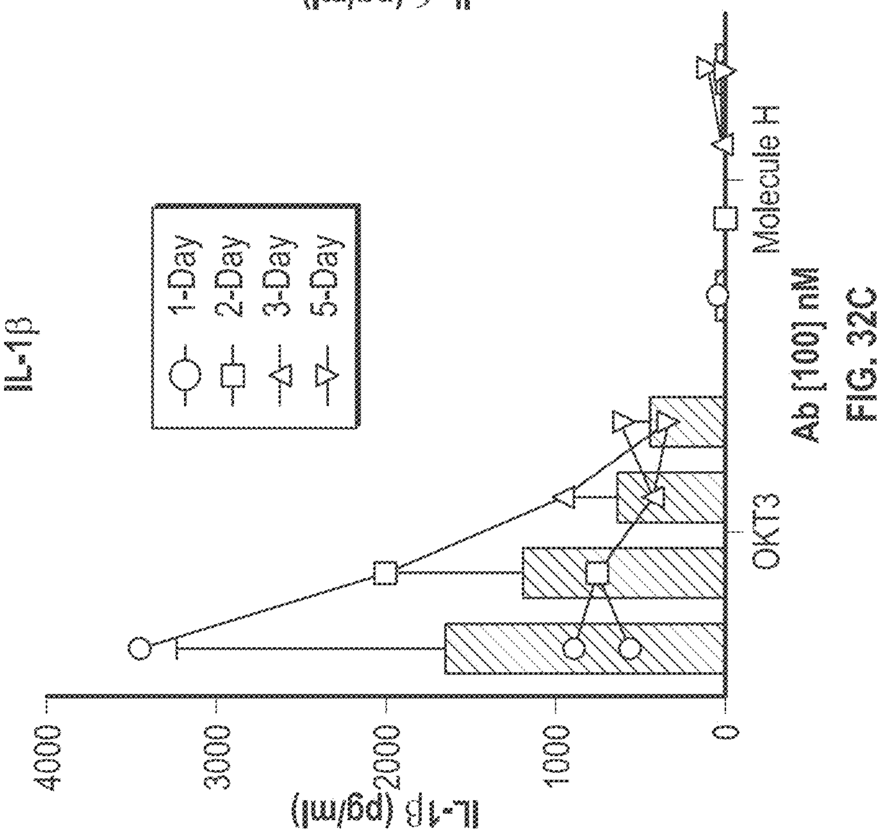
Figure 32E:
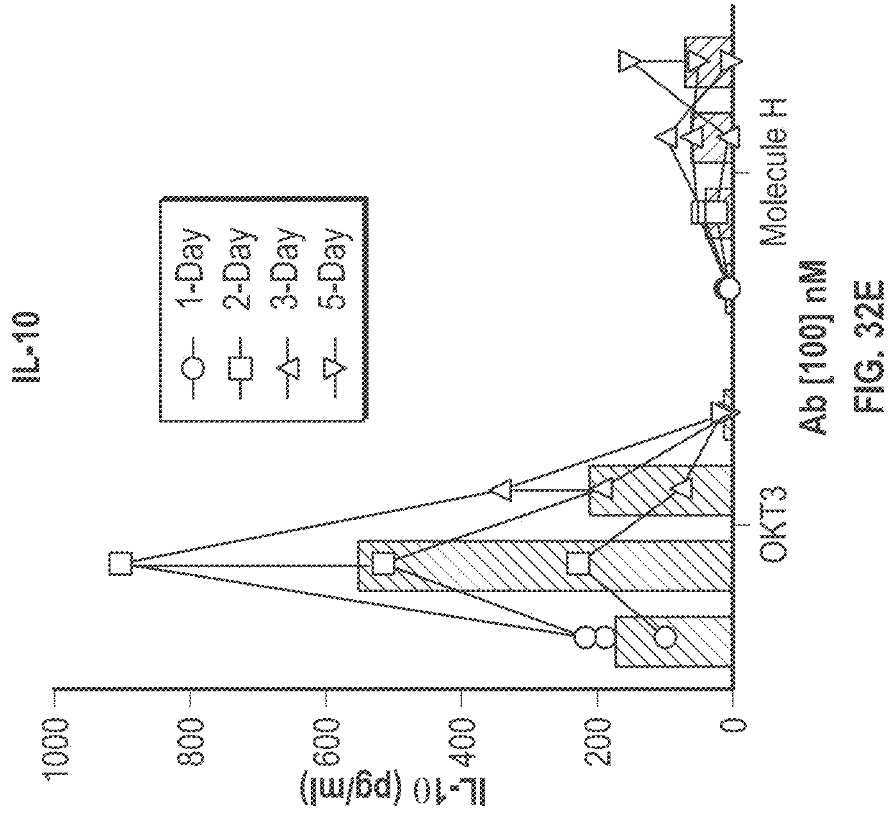
Figure 32F:
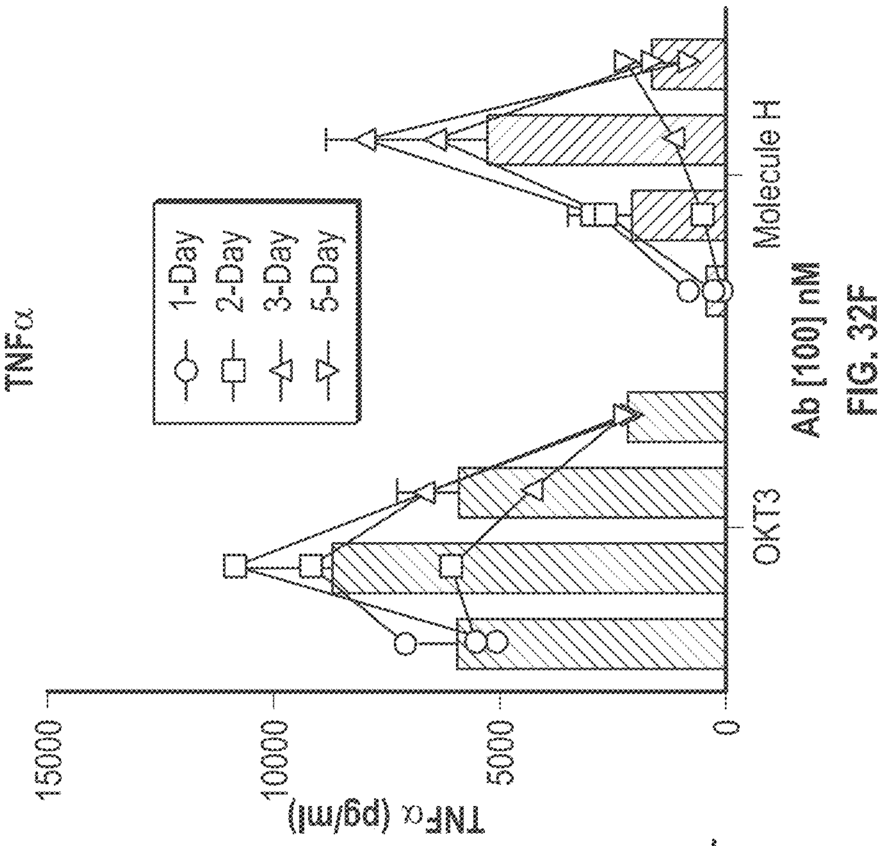
Figure 33A:
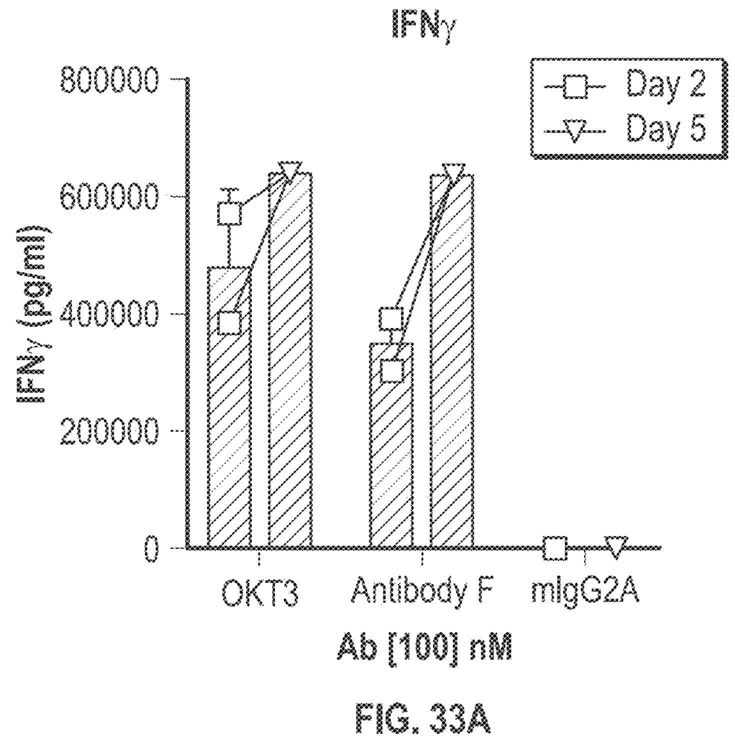
FIGS. 33A-33F are graphs showing cytokine secretion stimulated by anti-TRBC1 (Antibody F) or anti-CD3 (OKT3) at Days 2 and 5. Cytokines examined include: IFNγ (FIG. 33A), IL-2 (FIG. 33B), IL-1β (FIG. 33C), IL-6 (FIG. 33D), IL-10 (FIG. 33E), and TNFα (FIG. 33F).
Figure 33B:
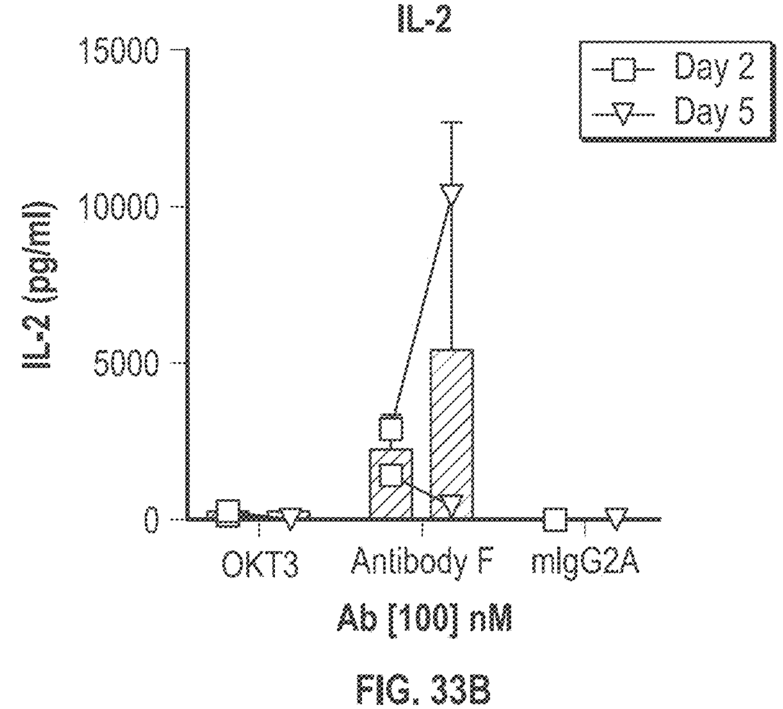
Figure 33C:
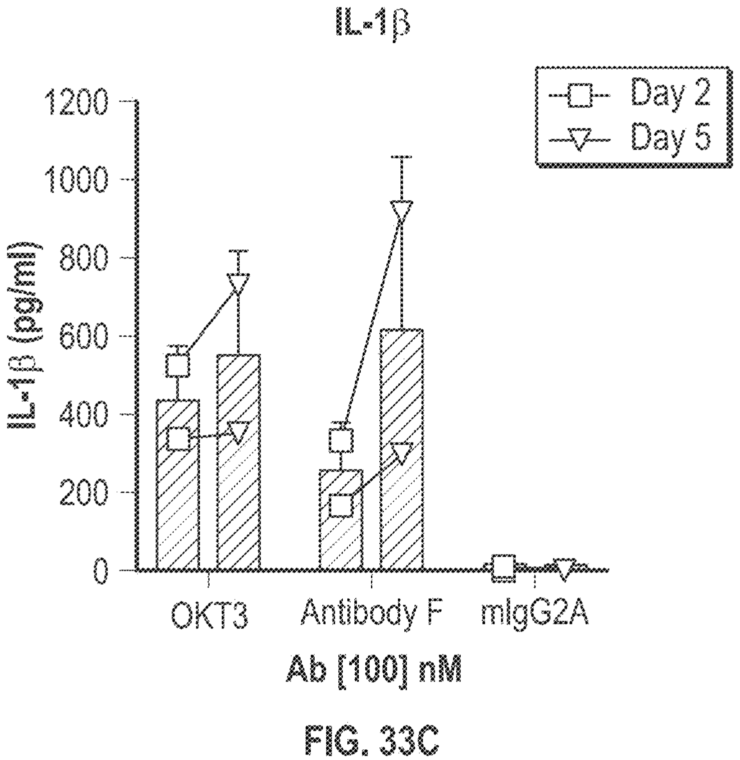
Figure 33D:
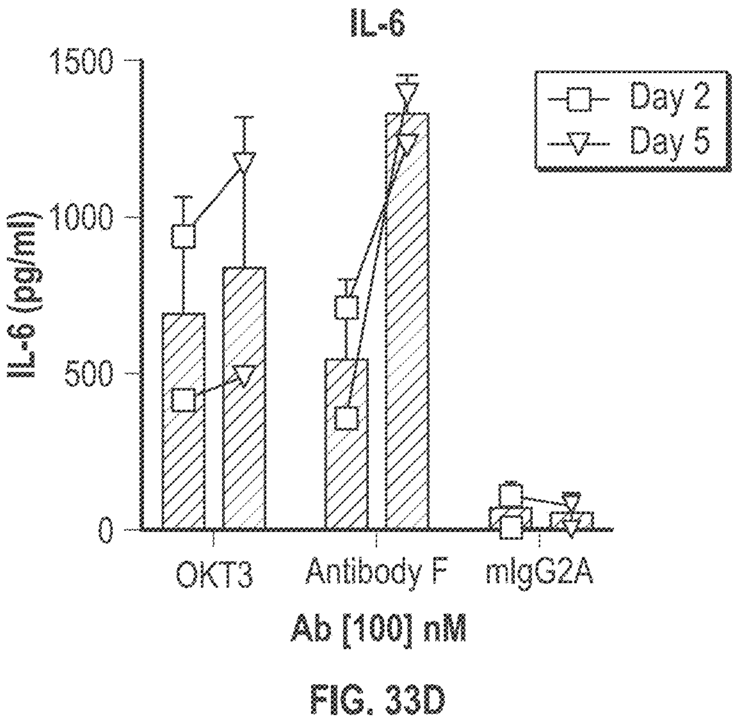
Figure 33E:
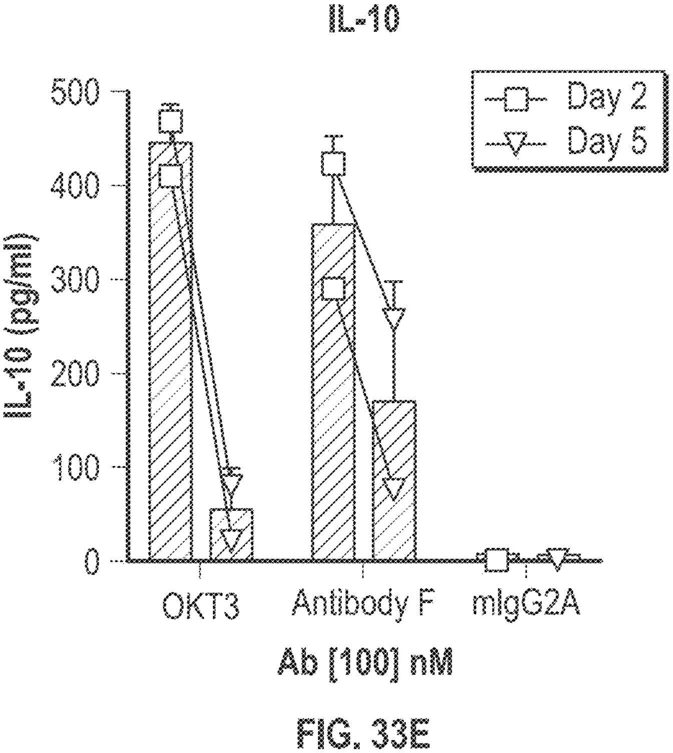
Figure 33F:
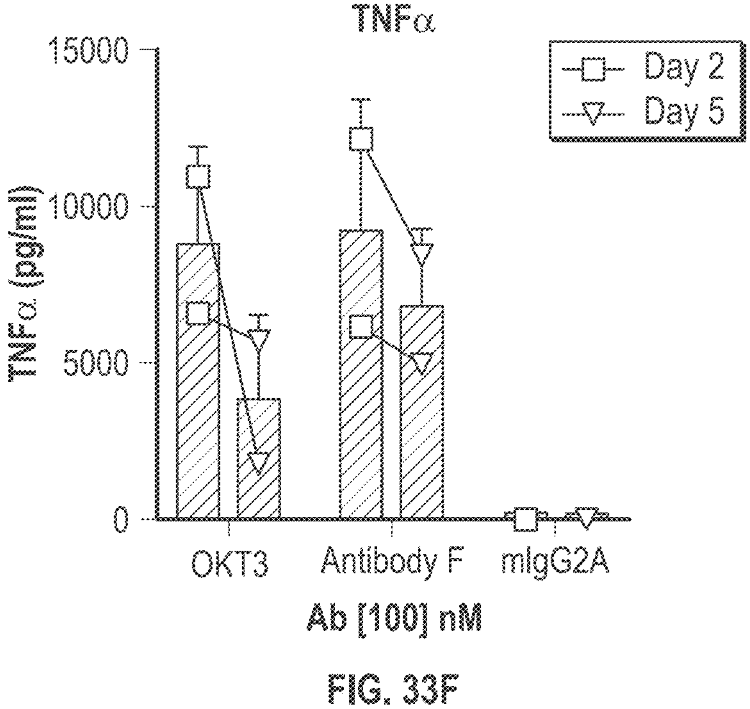

Human PBMCs were isolated from whole blood. From isolated PBMCs, human CD3+ T cells were isolated using magnetic-bead separation (negative selection) (Miltenyi biotec) and activated by immobilized (plate-coated) anti-TCR Vβ13.1 (A-H.1) at 100 nM for 6 days. Activated T-cells (from plate-coated) were then transferred and expanded in tissue culture flask in the presence of human IL-2 at a concentration of 50 U/ml for two additional days. Expanded TCR Vβ13.1+ cells were washed and co-cultured in the presence of BCMA-expressing RPMI8226 cells (target cells) at an E:T ratio of 5:1 and serial diluted concentrations of T-cell engager bispecific antibodies including, anti-TCR Vβ13.1/BCMA (Molecule G), anti-CD3/BCMA, and anti-TCR Vβ13.1 (A-H.1, serving as control) for 24 hours. Post 24 hours, cell co-culture supernatants were collected and quantified for specific target cell death. Target cells (RPMI8226 cells) are a KILR-retroparticles reporter cell assay (DiscoverX). KILR-RPMI8226 target cells are engineered to stably express a protein tagged with enhanced ProLabel (ePL), a β-gal reporter fragment, using the KILR Retroparticles, and when the membrane of the target cells is compromised due to cell death, the target cells will release the tagged protein into the media. This KILR reporter protein was detected and percentage (%) of target cell death was calculated as described above. Data shown in FIG. 31B are mean values from 4 donors.

Example 21: Cytokine Profile of an Anti-TCRVb/BCMA Antibody Molecule

This Example describes cytokines secreted by PBMCs following activation by the anti-TCR Vβ/anti-BCMA antibody Molecule H. For comparison, activation by an anti-TCR beta constant 1 (TRBC1) antibody Antibody F was also analyzed.

Briefly, human PBMCs were isolated from whole blood followed by solid-phase (plate-coated) stimulation with Molecule H or Antibody F at 100 nM. Supernatant was collected on Days 1, 2, 3, and 5 (for Molecule H) or Days 2 and 5 (for Antibody F) followed by multiplex cytokine analysis for IFNγ, IL-2, IL-1β, IL-6, IL-10, and TNFα, quantified using MSD (Meso Scale Discovery) platform, following the manufacturer's protocol.

As shown in FIGS. 32A-32F and 33A-33F, the cytokine profile of the anti-TCR Vβ/anti-BCMA antibody Molecule H is different from that of the anti-CD3 antibody OKT3 or the anti-TRBC1 Antibody F.

Example 22: Kinetics of T Cell Expansion Following TCRβV 6-5 Stimulation

To assess the kinetics and absolute count of anti-TCRβv 6-5 expanded T cells—either PBMCs or purified T cells were stimulated with plate-immobilized anti-TCRvb 6-5 antibody over 8 days with a T cell-activating antibody at 100 nM. T cell activating antibodies tested included: i) anti-TCRvb 6-5 v1 antibody; ii) anti-TCRvb 6-5 v2; iii) OKT3 (anti-CD3ε antibody); iv) SP34-2 (anti-CD3ε antibody); and v) IgG1 N297A (isotype control). Cell pellets were collected each day and stained for CD3, CD4, CD8 and TCRvb 6-5 for flow analysis.

Figure 34A:
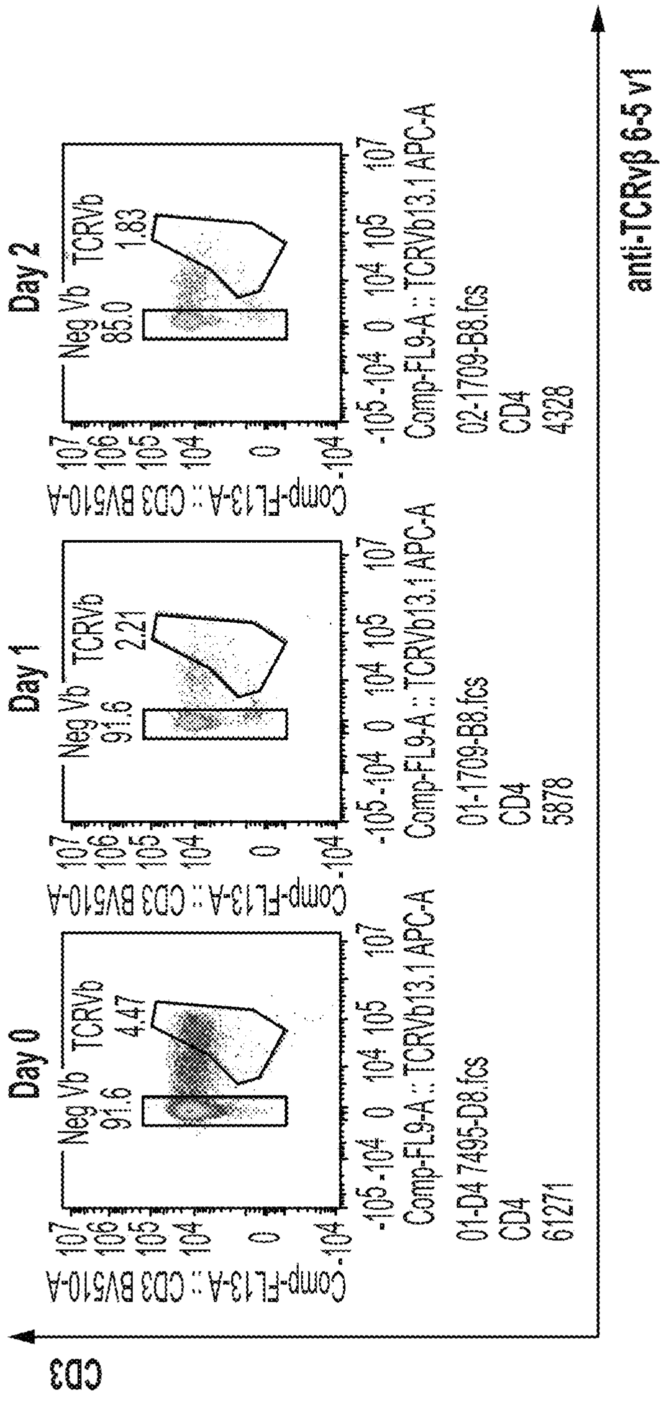
FIGS. 34A-34B are FACS plots showing the expansion of TCRvb 6-5+ T cells over 8 days using anti-TCRvb 6-5 v1.
Figure 34B:
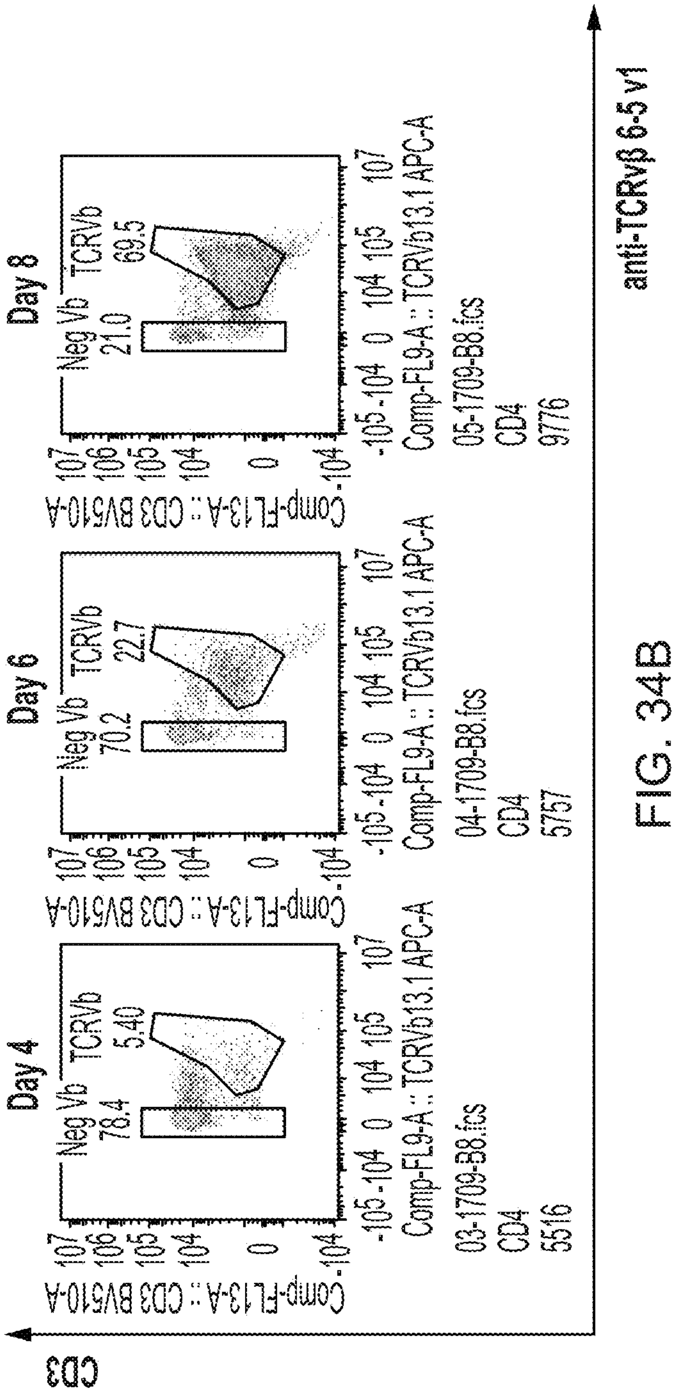
Figure 35:
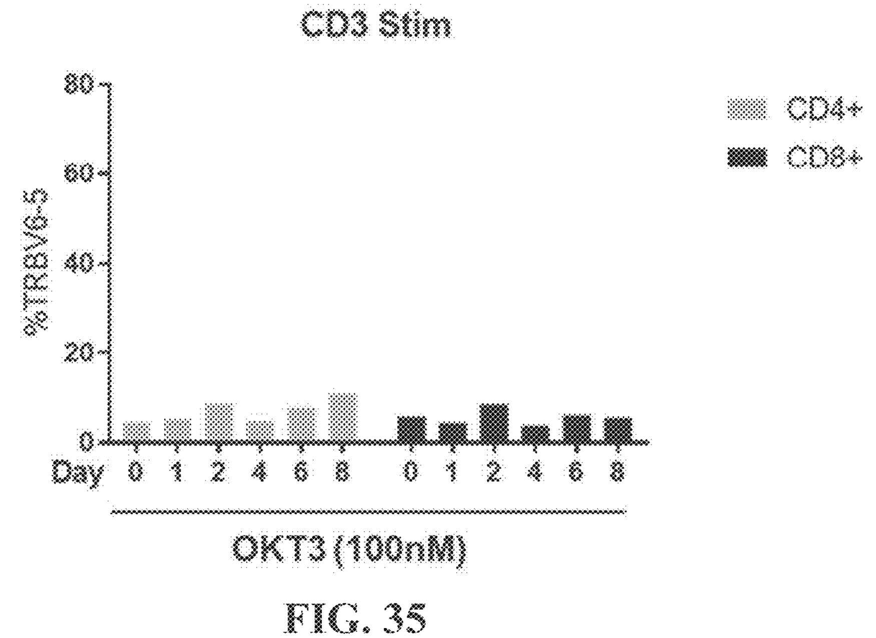
FIG. 35 is a bar graph showing the expansion of TCRvb 6-5+ CD4+ T cells and TCRvb 6-5+ CD8+ T cells over 8 days using the anti-CD3ε antibody OKT3 (100 nM).
Figure 36:
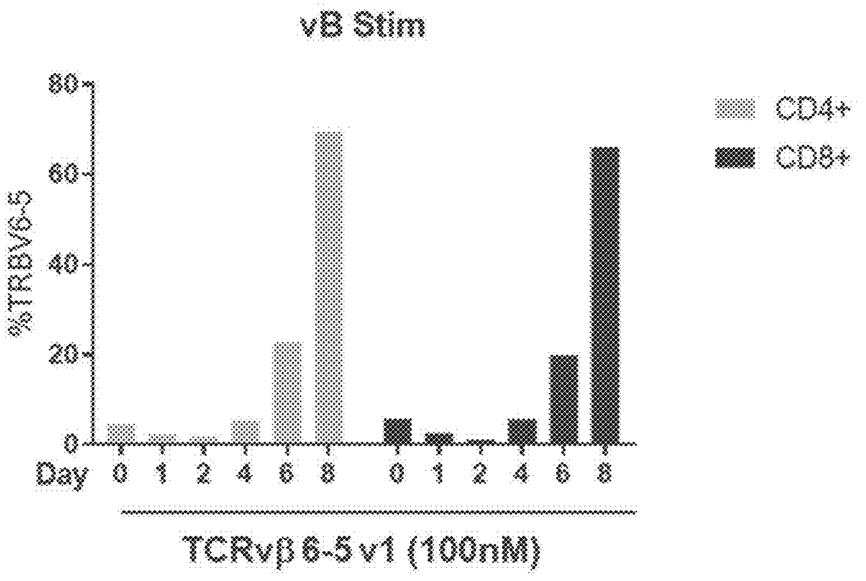
FIG. 36 is a bar graph showing the expansion of TCRvb 6-5+ CD4+ T cells and TCRvb 6-5+ CD8+ T cells over 8 days using the anti-TCRvb 6-5 v1 antibody (100 nM).
Figure 37:
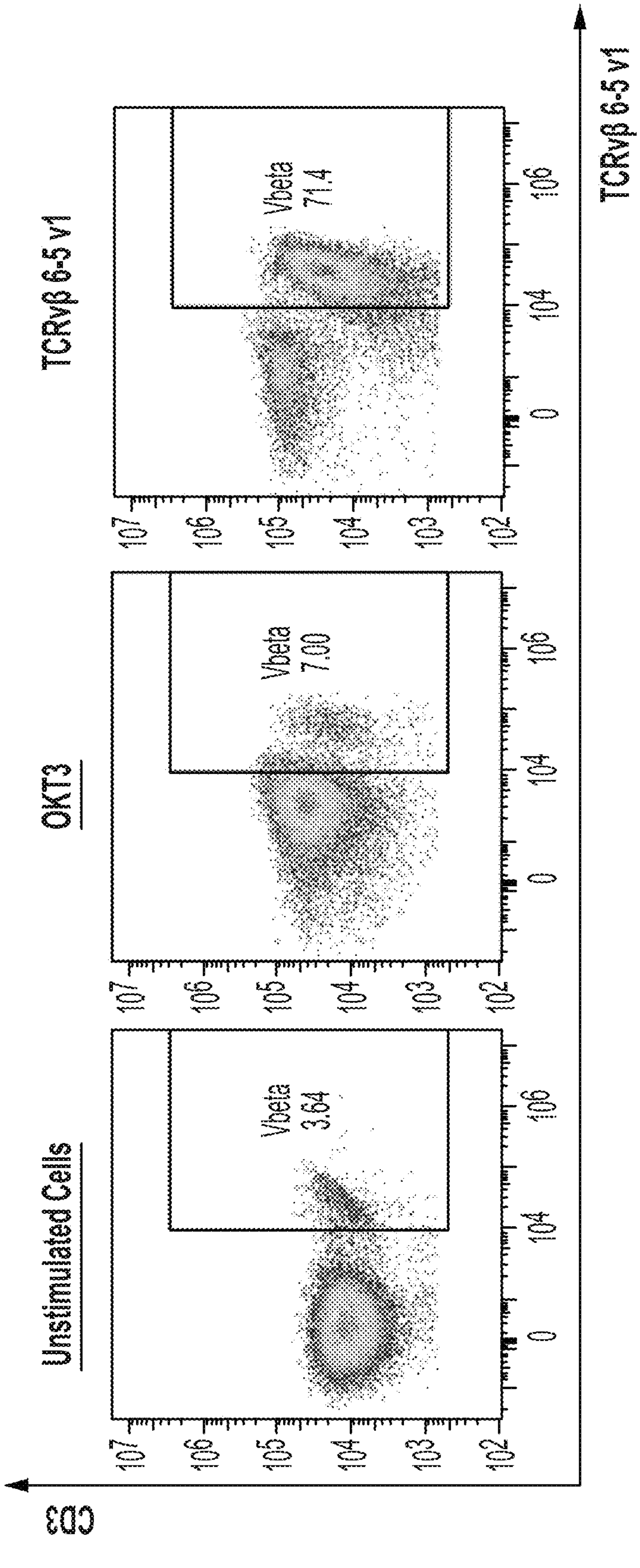
FIG. 37 is a FACS plot showing the showing the expansion of TCRvb 6-5+ T cells over 8 days using anti-TCRvb 6-5 v1 or the anti-CD3ε antibody OKT3.

TCRvb 6-5+ T cell expansion over 8 days using anti-TCRvb 6-5 v1 is shown in FIG. 34, as assessed by flow cytometry. The data is for a single representative donor; and similar results were seen with PBMCs from two other independent donors. FIG. 36 further shows the specific expansion of TCRvb 6-5+ CD4+ T cells and TCRvb 6-5+ CD8+ T cells by TCRvb 6-5 v1. In contrast, there was no specific TCRvb 6-5+ T-cell expansion by OKT3 (FIG. 35; FIG. 37).

Figure 38A:
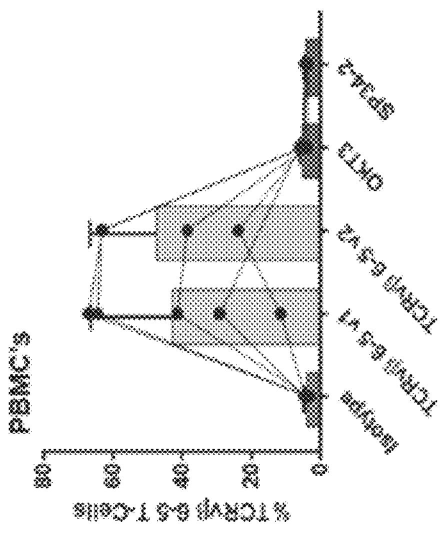
FIG. 38A is a bar graph showing the percentage of TCRβV 6-5+ T cells in PBMC cultures after 8 days of culture with the indicated antibody. Data for 5 replicates are shown.
Figure 38B:
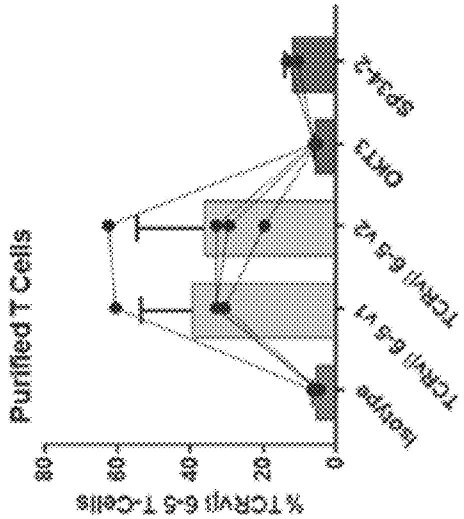
FIG. 38B is a bar graph showing the percentage of TCRβV 6-5+ T cells in purified T cell cultures after 8 days of culture with the indicated antibody. Data for 5 replicates are shown.
Figure 39A:
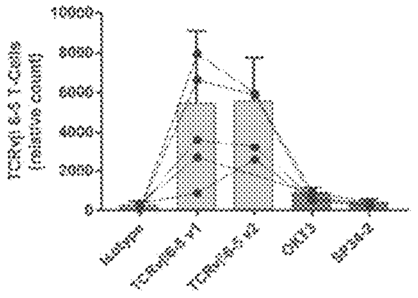
FIG. 39A is a bar graph showing the relative count of TCRβV 6-5+ T cells in PBMC culture after 8 days of culture with the indicated antibody.
Figure 39B:
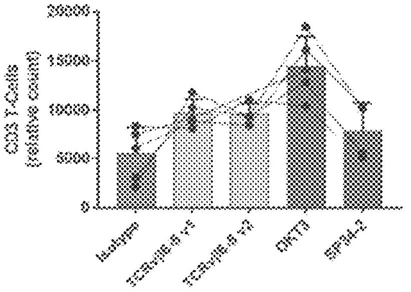
FIG. 39B is a bar graph showing the relative count of TCRβV 6-5+ T cells in PBMC culture after 8 days of culture with the indicated antibody.
Figure 40A:
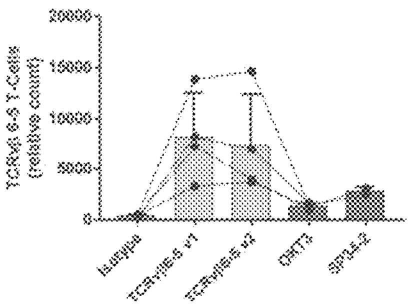
FIG. 40A is a bar graph showing the relative count of TCRβV 6-5+ T cells in a purified T cell culture after 8 days of culture with the indicated antibody.
Figure 40B:
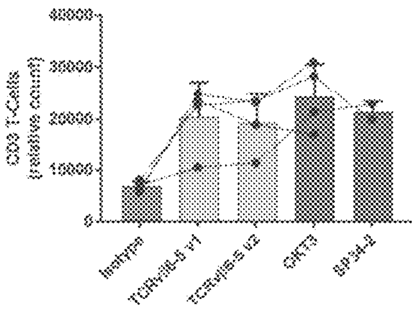
FIG. 40B is a bar graph showing the relative count of TCRβV 6-5+ T cells in a purified T cell culture after 8 days of culture with the indicated antibody.
Figure 41:
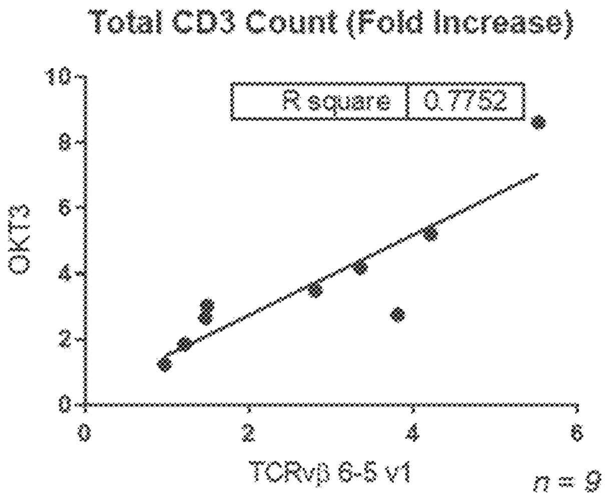
FIG. 41 is a line graph showing the total CD3+ T cell count (fold increase) after 8 days of T cell culture with either the anti-CD3ε antibody OKT3 or the anti-TCRvb 6-5 v1 antibody.

FIGS. 38A and 38B show selective expansion of TCRβV 6-5+ T cells in human PBMCs (FIG. 38A) and purified T cells (FIG. 38B).

FIGS. 39A-41 shows that anti-TCRβV and anti-CD3ε antibodies expand T cells in a PBMC culture (FIGS. 39A and 39B) or a purified T cell culture (FIGS. 40A and 40B)) to comparable levels after 8 days, as measured by both relative count of TCRVB 6-5+ T cells (FIGS. 39A-40B) and relative count of total CD3+ T cells (FIGS. 39A-41).

Example 23: Activated TCRvb 6-5+ T Cells Exert Cytolytic Function

Figure 42:
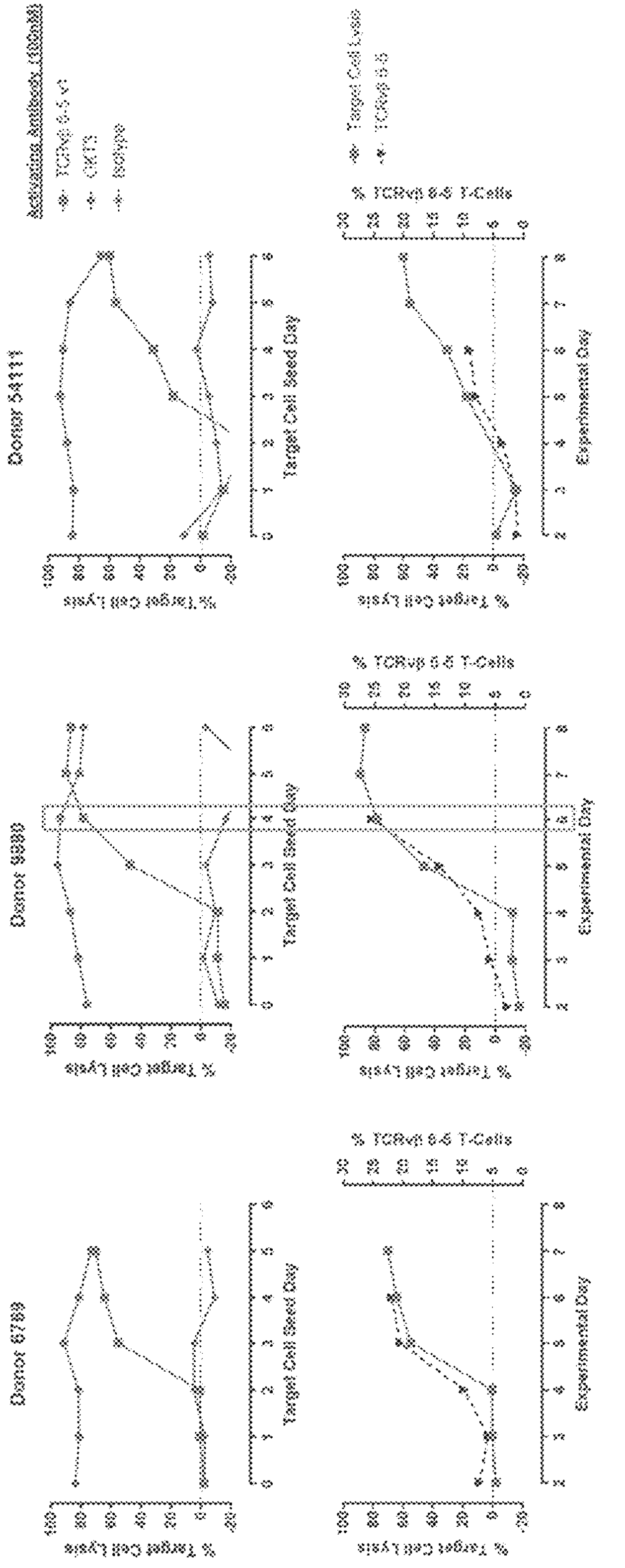
FIG. 42 is a series of line graphs showing the kinetics of target cells by TCRβV 6-5 v1 activated T cells or anti-CD3ε (OKT3) activated T cells. T cells from three different donors were utilized (donor 6769, donor 9880, donor 5411).

To assess the ability of T cells activated/expanded with anti-TCRVβ to mediate tumor cell lysis—purified T cells were stimulated over 6 days with an immobilized T cell-activating antibody at 100 nM. T cell activating antibodies tested included: i) TCRvb 6-5 v1 antibody; ii) OKT3 (anti-CD3ε antibody); or iii) IgG1 N297A (isotype control). Target cells (RPMI-8226 cells) were added on each day and incubated with the activated T cells at an initial effector T cell:target (E:T) cell ratio of 5:1 for 48 hours. Quantification of target cell lysis was measured using CFSE/CD138 and DRAQ7 FACS staining. Three different T cell donors were used (donor 6769, donor 9880, donor 54111). The data shows that the kinetics of target cell lysis by TCRVb 6-5 v1 activated T cells correlates with the expansion of TCRvb 6-5+ T cells (FIG. 42).

Figure 43A:
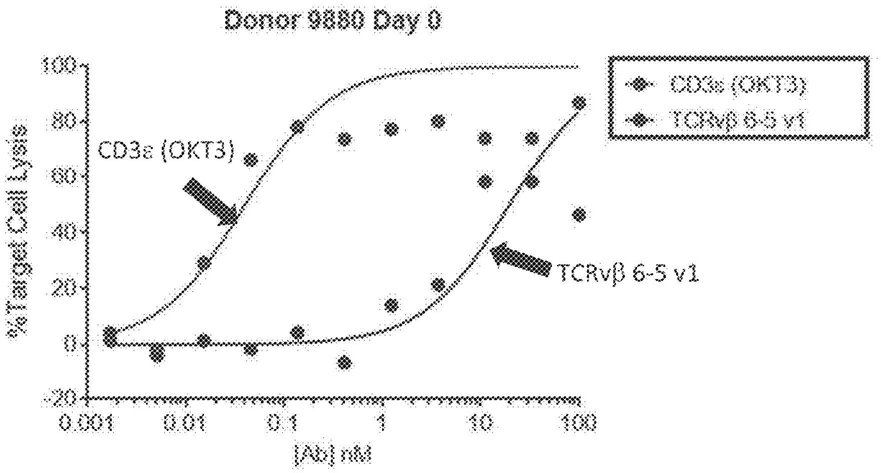
FIG. 43A is a scatter plot showing the percent of target cell lysis by T cells by TCRβV 6-5 v1 activated T cells or anti-CD3ε (OKT3) activated T cells without T cell pre activation. The data is presented at day 6 of co-culture between target cells and effector T cells.
Figure 43B:
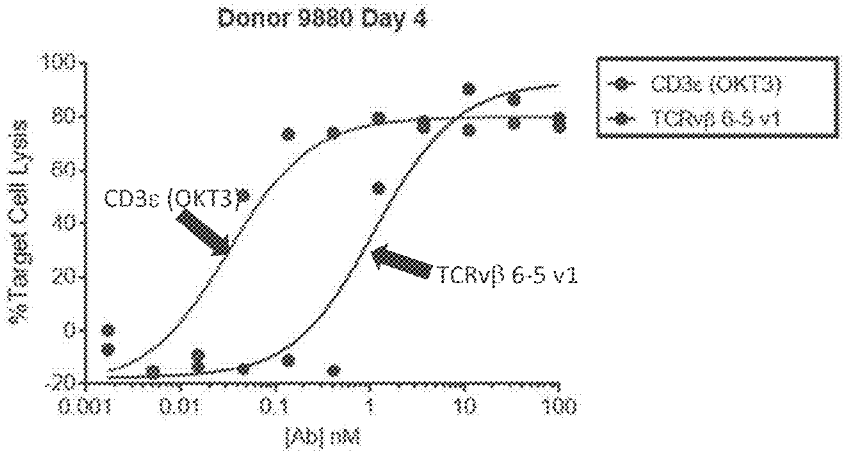
FIG. 43B is a scatter plot showing the percent of target cell lysis by T cells by TCRβV 6-5 v1 activated T cells or anti-CD3ε (OKT3) activated T cells with 4 days of T cell pre activation. The data is presented at day 2 of co-culture between target cells and effector T cells (after 4 days of T cell pre-activation).
Figure 44:
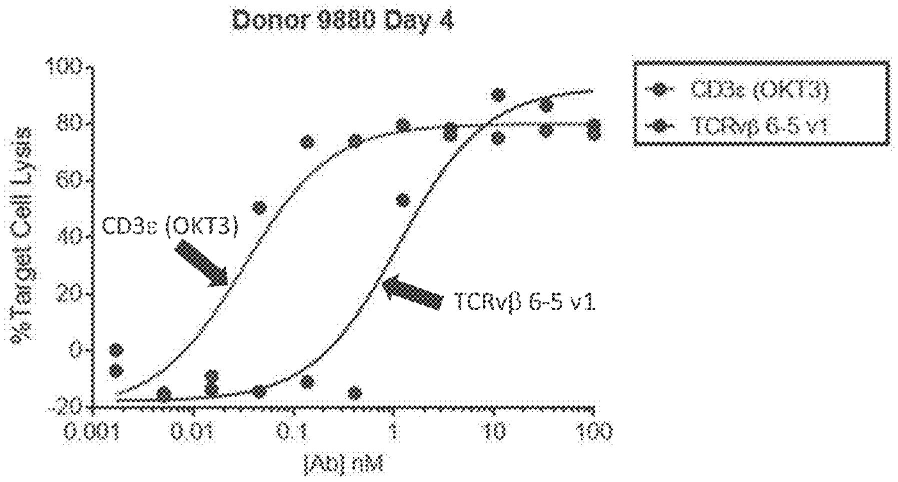
FIG. 44 is a scatter plot showing the percent of target cell lysis by T cells by TCRβV 6-5 v1 activated T cells or anti-CD3ε (OKT3) activated T cells with 4 days of T cell pre activation. The data is presented at day 2 of co-culture between target cells and effector T cells (after 4 days of T cell pre-activation).
Figure 45:
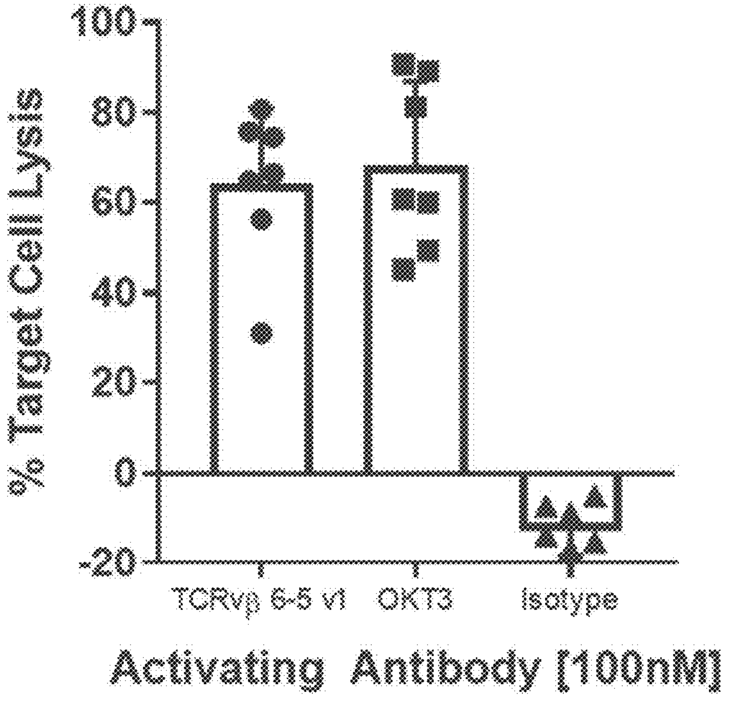
FIG. 45 is a bar graph showing target cell lysis by T cells by TCRβV 6-5 v1 activated T cells or anti-CD3ε (OKT3) activated T cells (100 nM each antibody). The data includes seven replicates of each experimental condition.

To further assess target cell lysis OKT3 or TCRvb 6-5 v1 antibodies were immobilized (plate-coated) with a %2 log serial dilution from a top dose concentration of 100 nM for purified T-cell (pan CD3 isolated) activation. The purified T-cells were stimulated with the activation plate for 0 (i.e. without antibody preactivation) to 4 (i.e. with antibody preactivation) days prior to addition of the target cells. Target cells (RPMI8226) were added to the activation plate (at an initial E:T cell ratio, 5:1) for up to 6-days (i.e. for plate 0, E:T coculture for 6-days, and for plate 4, E:T coculture for 2-days) followed by target cell lysis quantification via CFSE/CD138 and DRAQ7 FACS staining. The data shows that without T-cell preactivation, approximately 3% of Vb cells were able to kill target cells at day 6 (at higher concentration) (FIG. 43A); and with T-cell preactivation, approximately 25% of Vb cells were able to kill target cells at day 6 (the killing curve is shifted to the left) (FIG. 43B). TCRvb 6-5 v1 activated T cells exhibit comparable maximal target cell lysis when compared to anti-CD3ε when T cells are preactivated for 4 days (FIG. 44). At 100 nM, TCRvb 6-5 v1 activation shows comparable killing of target cells to anti-CD3ε activation (FIG. 45) (preactivation between 4-6 days depending on the donor and the cultures cultured for 48 h in presence of target cells).

Example 24: Assessing TCRvb Downregulation/Internalization by Anti-TCRvb 6-5 Antibody To assess the effect anti-TCRvb 6-5 mediated T cell activation has on cell surface expression of TCRvb-purified T cells were stimulated over 8 days with the indicated T cell-activating antibody at 100 nM (plate bound). T cell activating antibodies included: i) anti-TCRvb 6-5 v1 antibody; or ii) SP34-2 (anti-CD3ε antibody). Cell pellets were collected each day and stained for CD3, CD4, CD8 and TCRβV 6-5 for flow cytometry analysis. A total of three donors were tested, each showing similar results.

Figure 46:
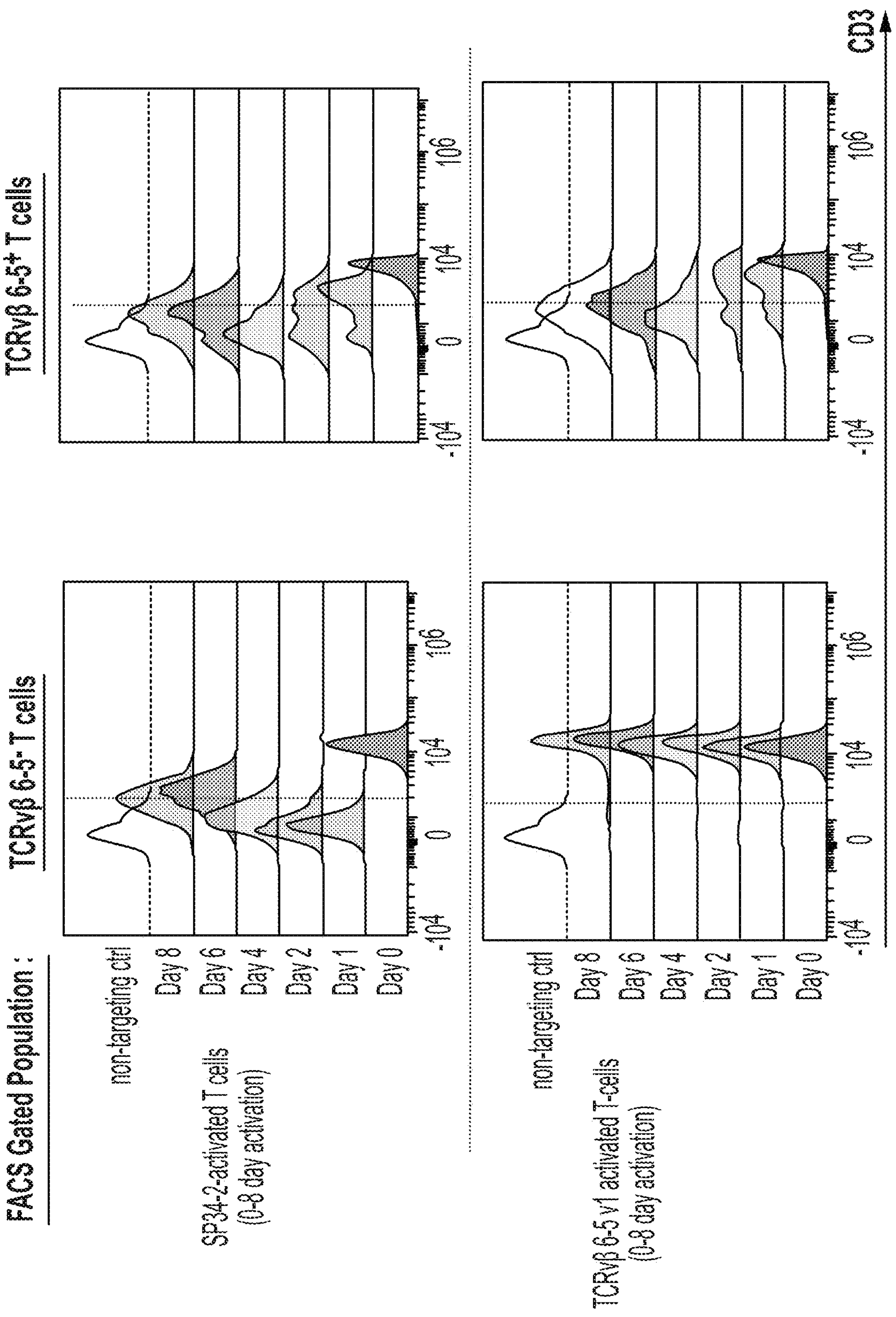
FIG. 46 is a series of FACS plots that show the cell surface expression of CD3ε on CD4+ TCRβV $6\text{-}5^{-}$ or CD4+ TCRβV 6-5+ T cells activated with either SP34-2 (anti-CD3ε antibody) or anti-TCRβV 6-5 v1 (anti-TCRβV 6-5 antibody) at days 0, 1, 2, 4, 6, or 8 post antibody activation.
Figure 47:
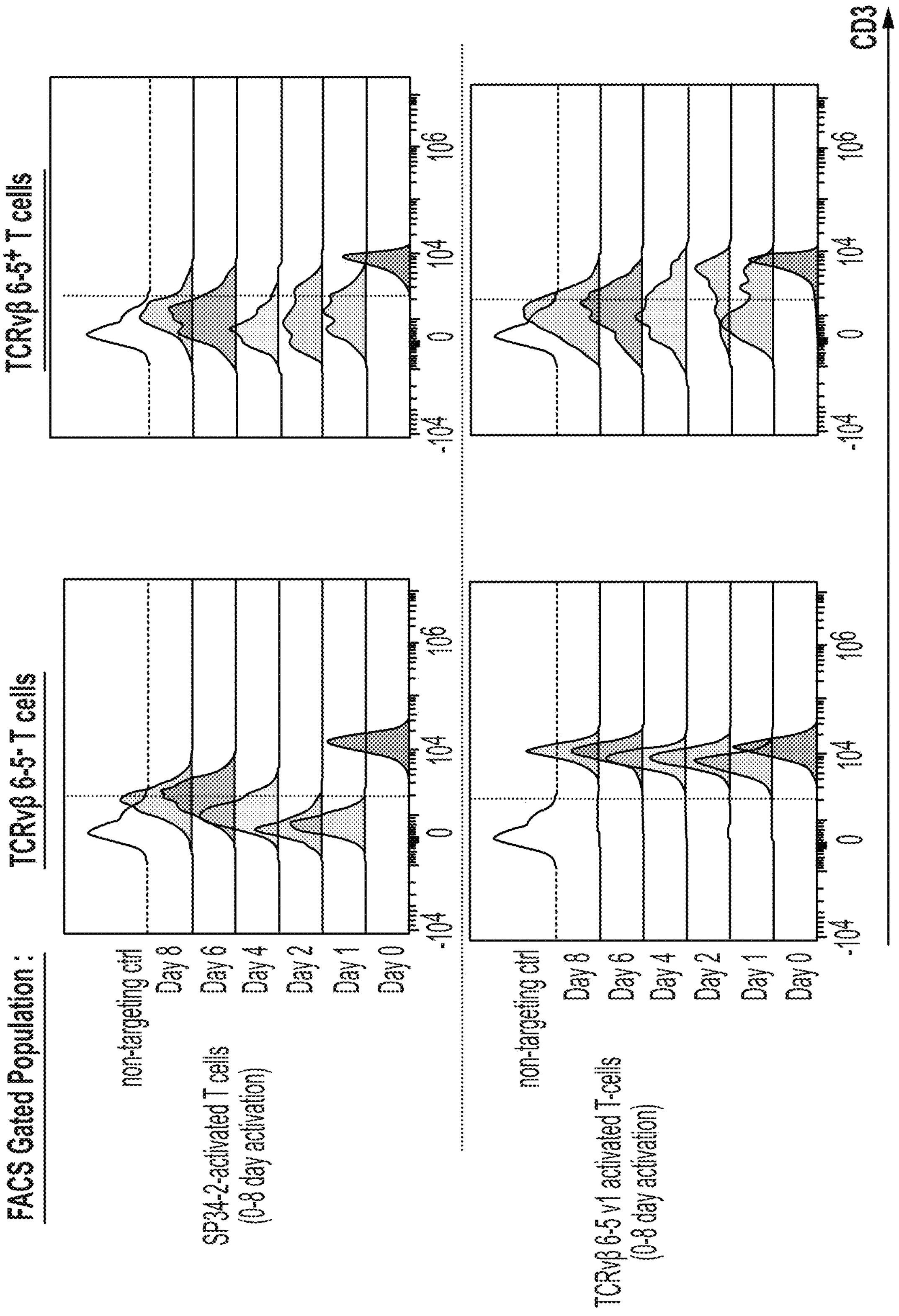
FIG. 47 is a series of FACS plots that show the cell surface expression of CD3ε on CD8+ TCRβV 6-5⁻ or CD8+ TCRβV 6-5+ T cells activated with either SP34-2 (anti-CD3ε antibody) or anti-TCRβV 6-5 v1 (anti-TCRβV 6-5 antibody) at days 0, 1, 2, 4, 6, or 8 post antibody activation.
Figure 48:
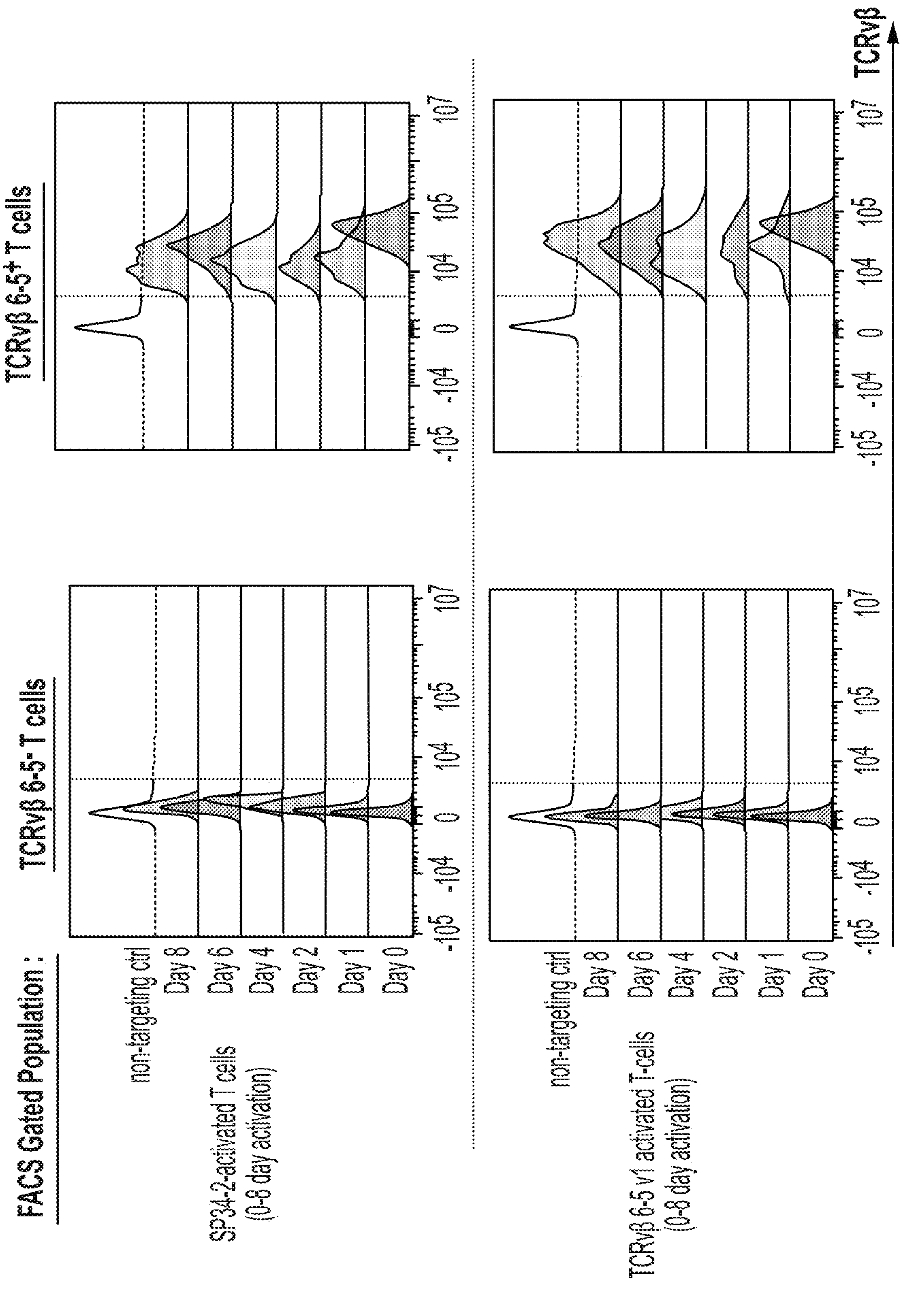
FIG. 48 is a series of FACS plots that show the cell surface expression of TCRβV on CD4+ TCRβV $6\text{-}5^-$ or CD4+ TCRβV 6-5+ T cells activated with either SP34-2 (anti-CD3ε antibody) or anti-TCRβV 6-5 v1 (anti-TCRβV 6-5 antibody) at days 0, 1, 2, 4, 6, or 8 post antibody activation.
Figure 49:
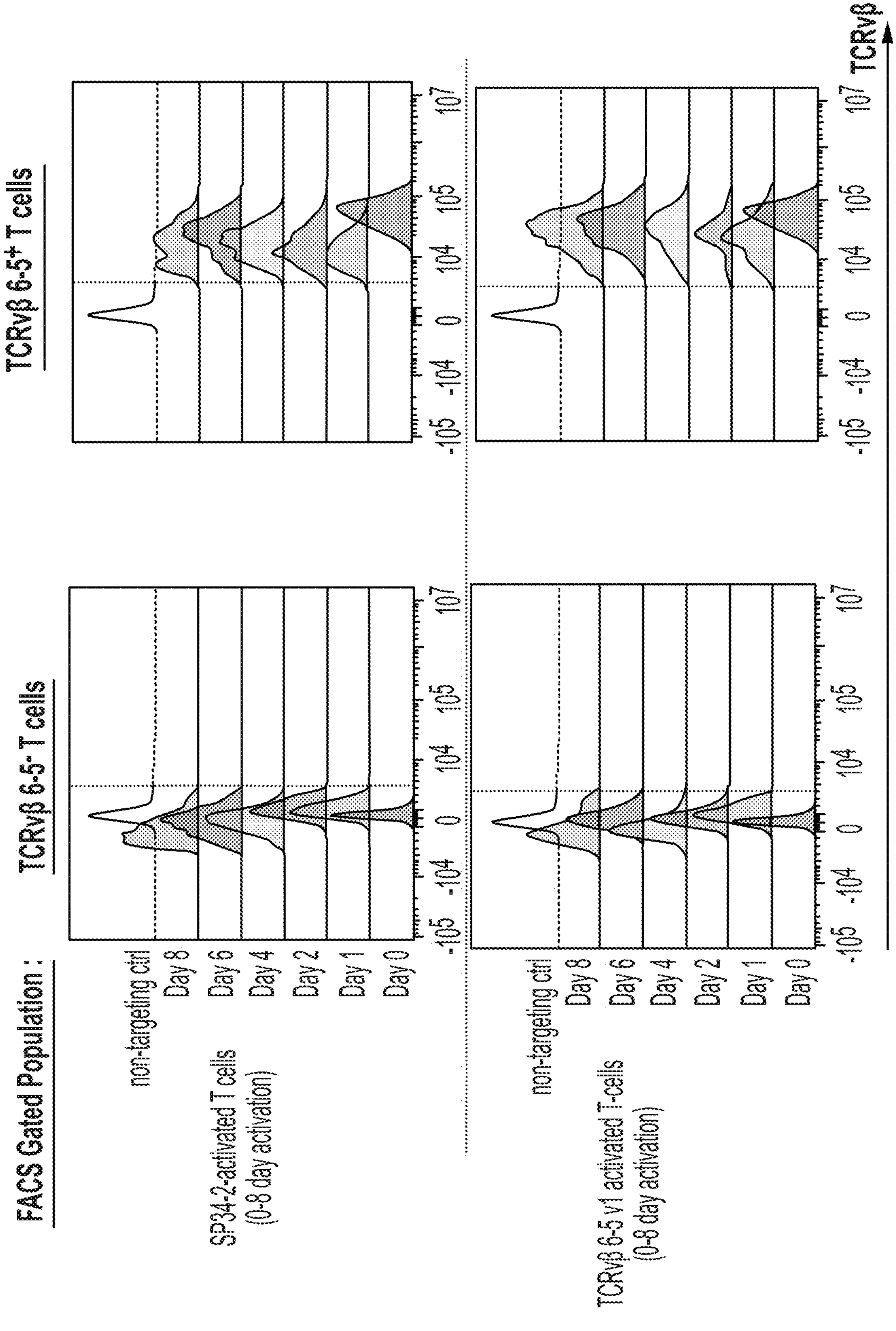
FIG. 49 is a series of FACS plots that show the cell surface expression of TCRβV on CD8+ TCRβV $6\text{-}5^-$ or CD8+ TCRβV $6\text{-}5^+$ T cells activated with either SP34-2 (anti-CD3ε antibody) or anti-TCRβV 6-5 v1 (anti-TCRβV 6-5 antibody) at days 0, 1, 2, 4, 6, or 8 post antibody activation.

The results show that both anti-CD3ε and anti-TCRvb antibodies activated CD4+ T cells (FIG. 46) and activated CD8+ T cells (FIG. 47) display reduced CD3ε cell surface expression; whereas, TCRvb 6-5 cell surface expression on CD4+ T cells (FIG. 48) and CD8+ T cells (FIG. 49) remains detectable post T cell activation. The results show that the CD3ε subunit is downregulated/internalized in T cells activated by either anti-CD3ε or anti-TCRvb antibodies; while TCRvb 6-5 remains detectable post T cell activation. Additionally, CD4 and CD8 staining did not show any signs of downmodulation of these receptors by either antibody.

Example 25: Cynomolgus Cross Reactivity of Anti-TCRβV Antibodies

Figure 50A:
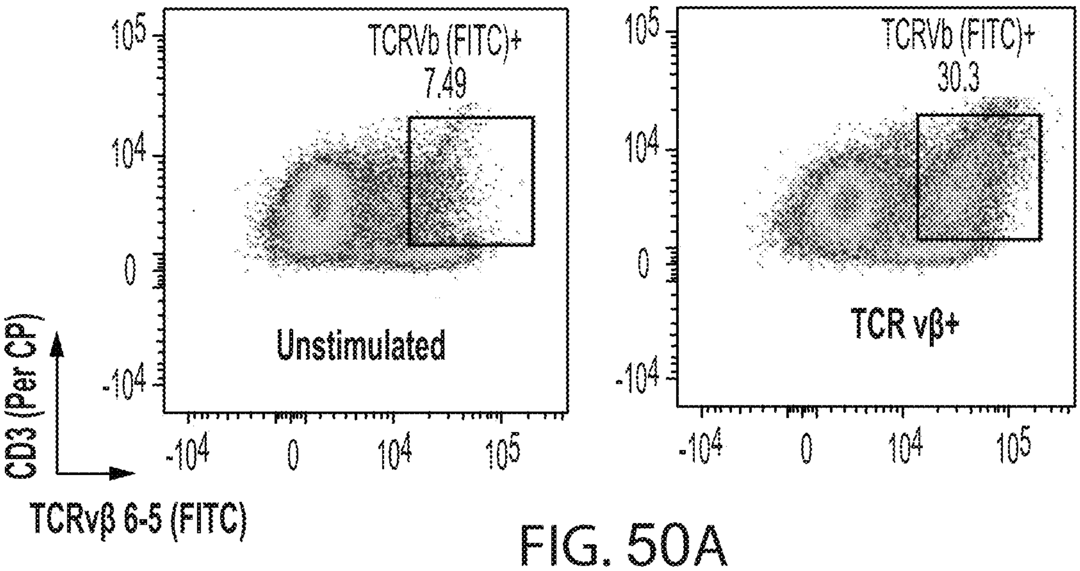
FIG. 50A shows FACS plot of TCRβV $6\text{-}5^+$ cynomolgus T cell expansion either unstimulated (left) or stimulated with anti-TCRβV 6-5 v1 (right) 7 days post activation of cynomolgus PBMCs. PBMCs from Donor DW8N (fresh PBMC sample, male, age 8, weight 7.9 kgs) were used.
Figure 50B:
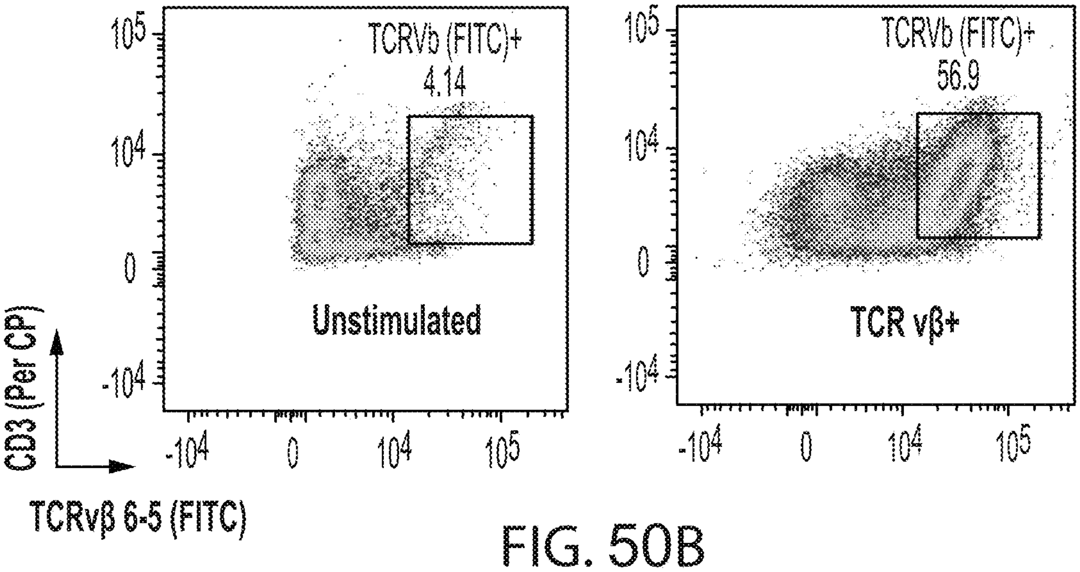
FIG. 50B shows FACS plot of TCRβV $6\text{-}5^+$ cynomolgus T cell expansion either unstimulated (left) or stimulated with anti-TCRβV 6-5 v1 (right) 7 days post activation of cynomolgus PBMCs. PBMCs from Donor G709 (cryopreserved sample, male, age 6, weight 4.7 kgs) were used.
Figure 51:
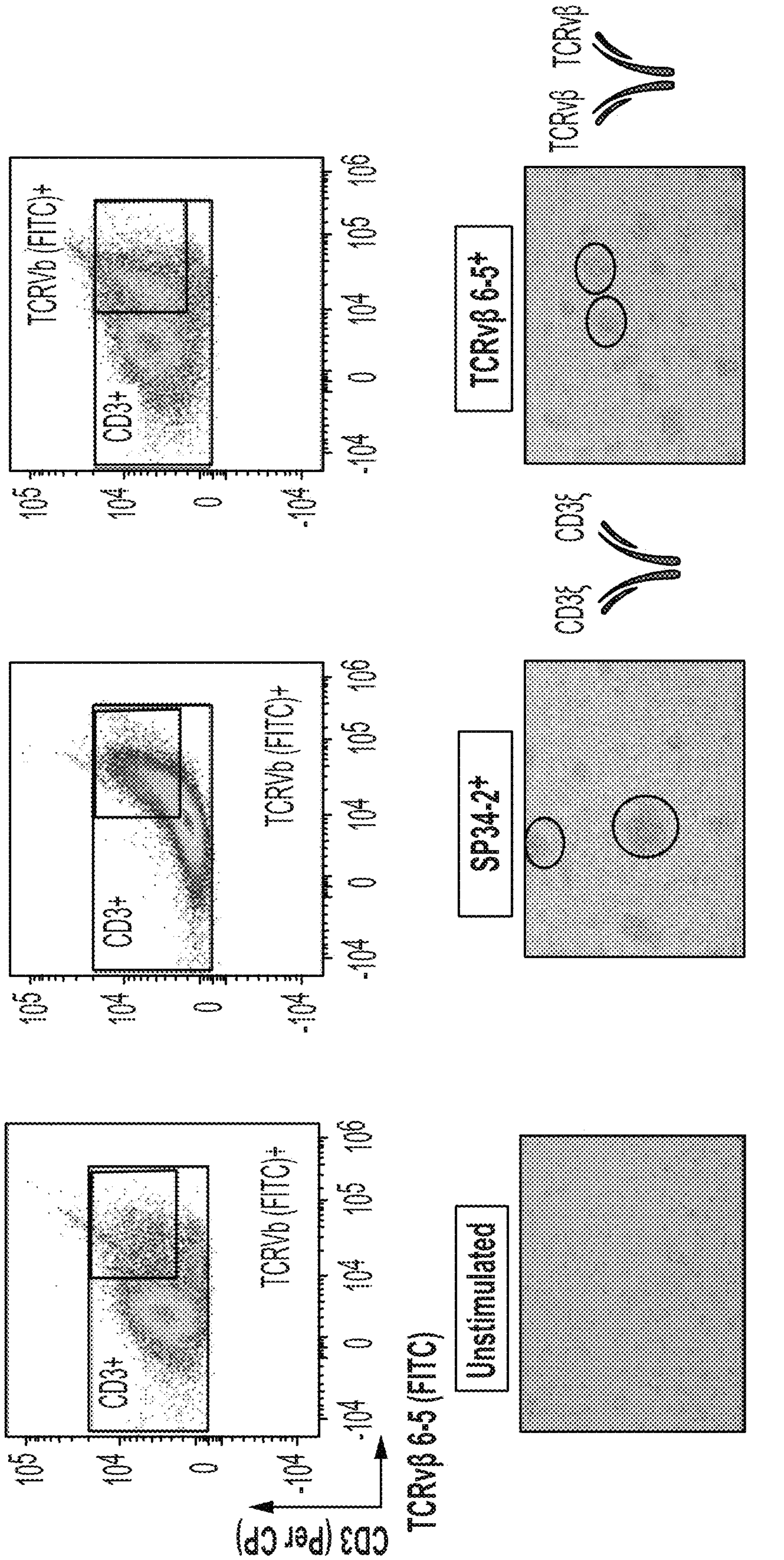
FIG. 51 shows FACS plot and corresponding microscopy images of TCRβV $6\text{-}5^+$ cynomolgus T cell expansion either unstimulated (left), stimulated with SP34-2 (anti-CD3ε antibody) (middle); or stimulated with anti-TCRβV 6-5 v1 (right) post activation of cryopreserved donor DW8N cynomolgus PBMCs. The microscopy images show the cell cluster formation (indicated by circles).

To assess the cross reactivity of anti-TCRβV antibodies for cynomolgus TCRβV clonotype—fresh and cryopreserved cynomolgus PBMCs were cultured in complete media (RPMI with 10% FBS) in tissue culture treated flat bottom 96 well plates precoated with anti-TCRβV 6-5 v1 or anti-CD3ξ antibodies at 100 nM concentration. Negative control or unstimulated wells received PBS alone. TCRβV 6-5 expression was evaluated after 6 days in culture using CytoFlex flow cytometer (Beckmann Coulter) and imaged. Two donors samples were used: Donor DW8N—fresh PBMC sample, male, age 8, weight 7.9 kgs (data presented in FIG. 50A); Donor G709-cryopreserved sample, male, age 6, weight 4.7 kgs (data presented in FIG. 50B). The data show that cynomolgus T cells were activated and expanded by the anti-TCRβV 6-5 v1 (FIG. 50A and FIG. 50B). Fresh cynomolgus PBMCs from donor DW8N that had shown TCRvb 6-5 expansion were cryopreserved and after a week in cryopreservation, the cells were thawed and stimulated using anti-CD3ξ and anti-TCRvb 6-5 v1 for seven days. Cluster formation and expansion were both reproducible as shown in FIG. 51.

Example 26: No Activation of γδ T Cells by Anti-TCRβV Antibodies

Figure 52:
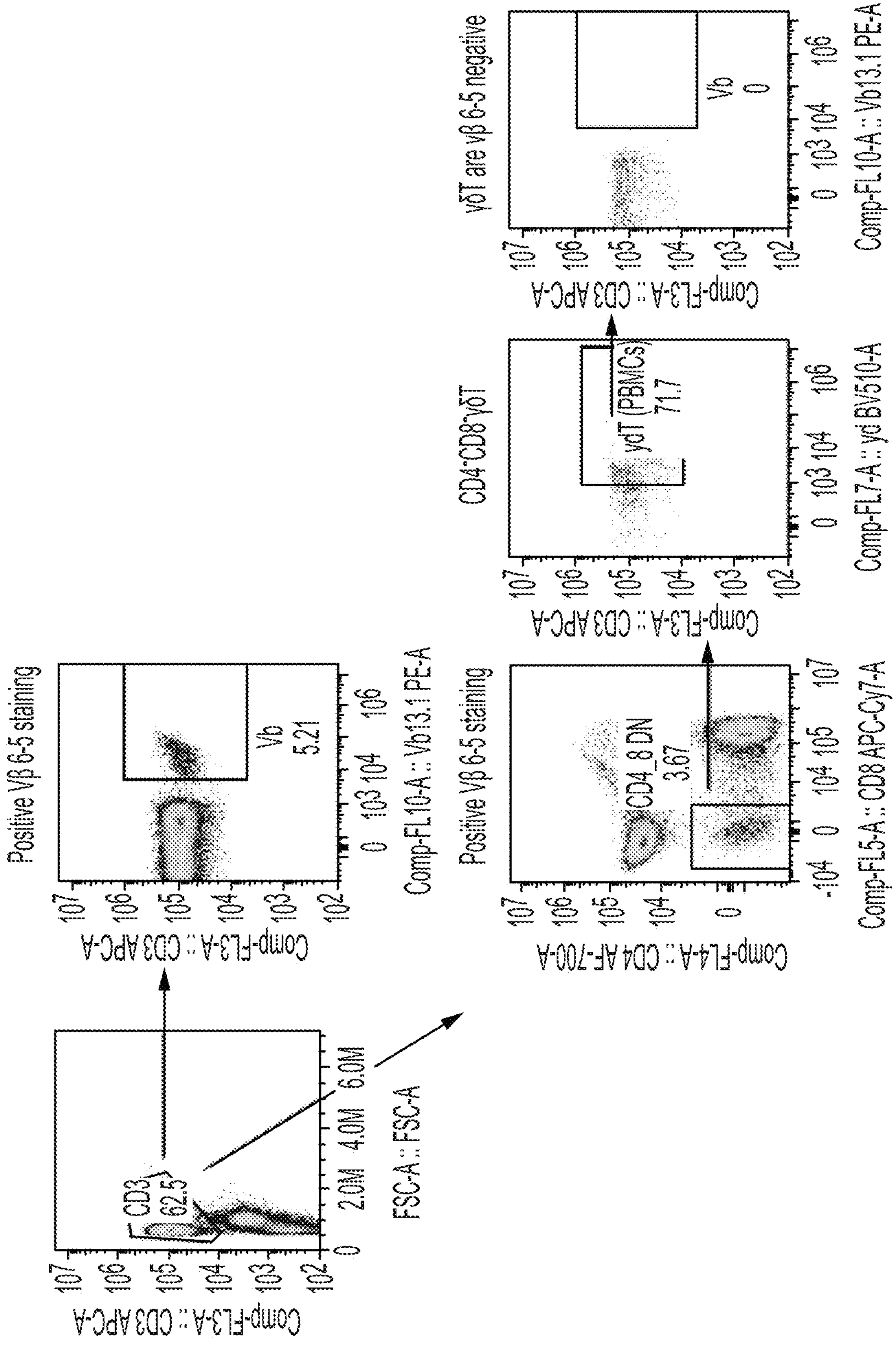
FIG. 52 shows a schematic of FACS plot showing the FACS gating/staining of PBMCs prior γδ T cell purification.
Figure 53:
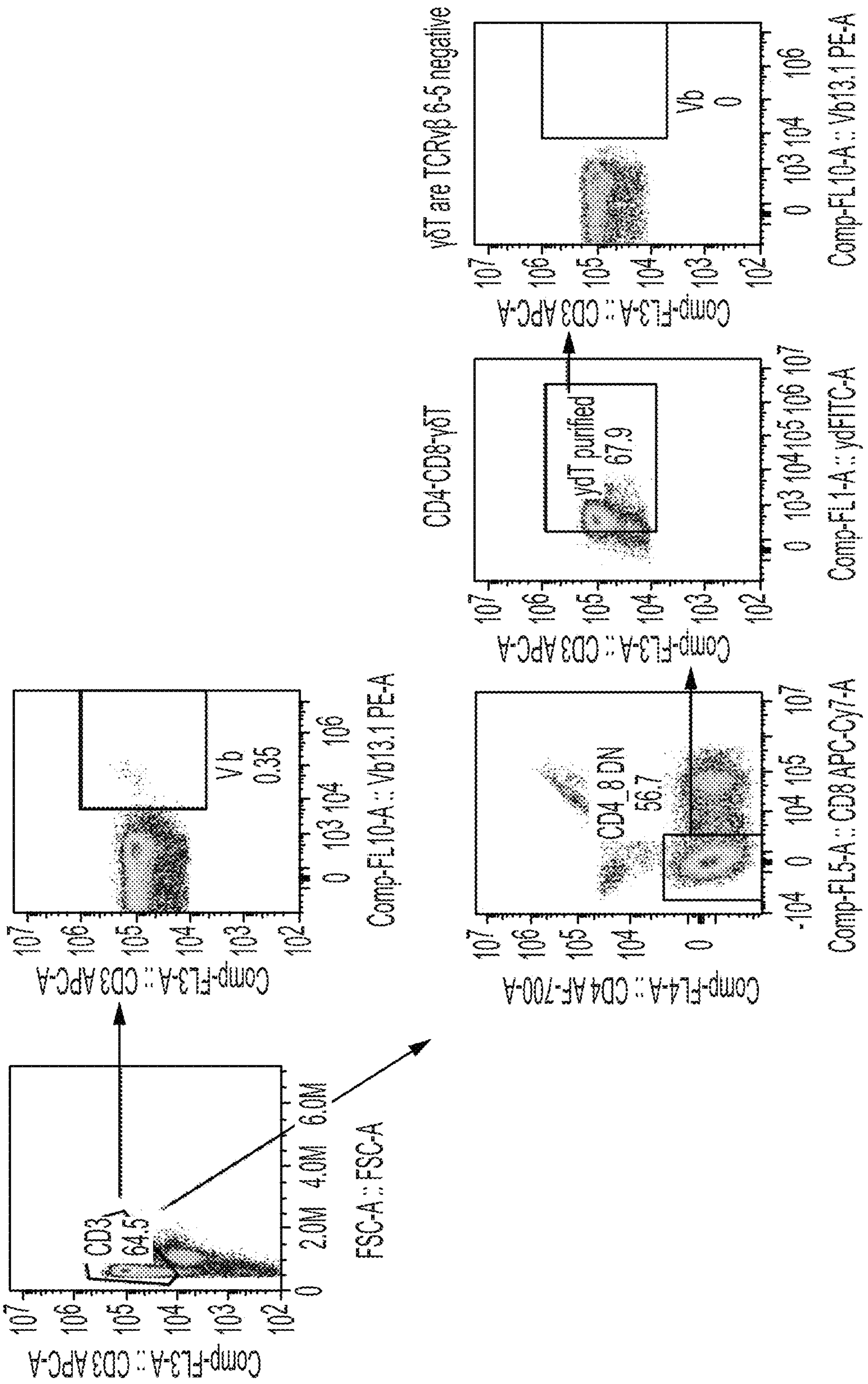
FIG. 53 shows a schematic of FACS plot showing the FACS gating/staining of purified γδ T cell population.
Figure 54A:
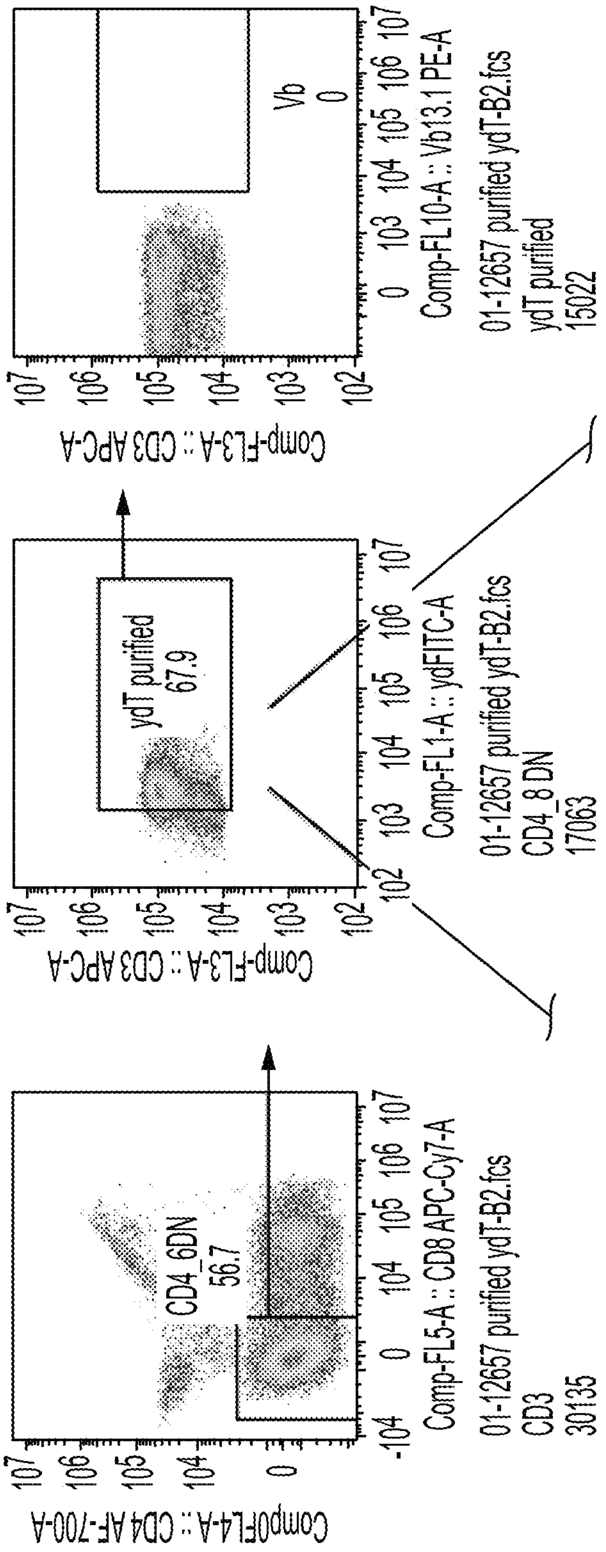
FIG. 54A show activation of purified γδ T cell population with anti-CD3ε antibody (SP34-2) (left) or anti-TCRβV antibody (anti-TCRβV 6-5 v1) (right).
Figure 54B:
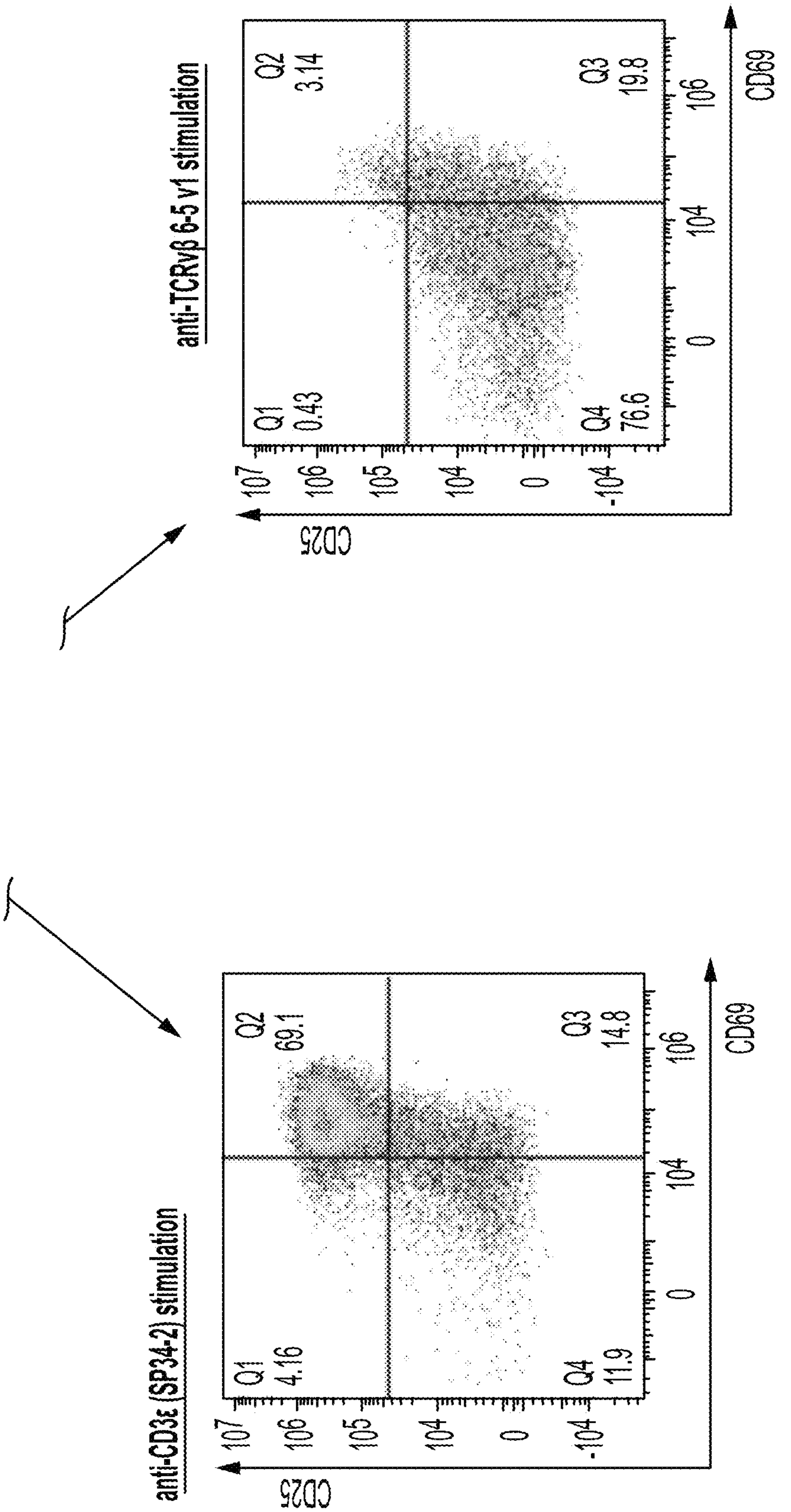
FIG. 54B show activation of purified γδ T cell population with anti-CD3ε antibody (SP34-2) (left) or anti-TCRβV antibody (anti-TCRβV 6-5 v1) (right), continued from FIG. 54A.
Figure 55A:
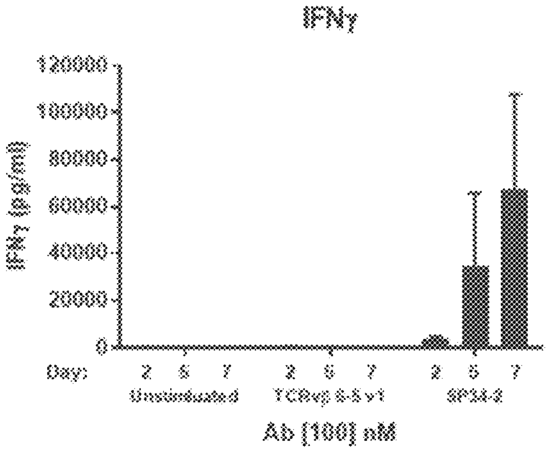
FIG. 55A shows the release of IFNγ from purified γδ T cell populations activated with anti-CD3ε antibody (SP34-2), anti-TCRβV antibody (anti-TCRβV 6-5 v1), or unstimulated.
Figure 55B:
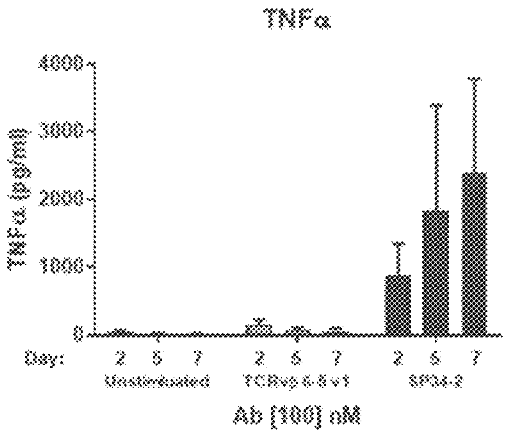
FIG. 55B shows the release of TNFα from purified γδ T cell populations activated with anti-CD3ε antibody (SP34-2), anti-TCRβV antibody (anti-TCRβV 6-5 v1), or unstimulated.
Figure 55C:
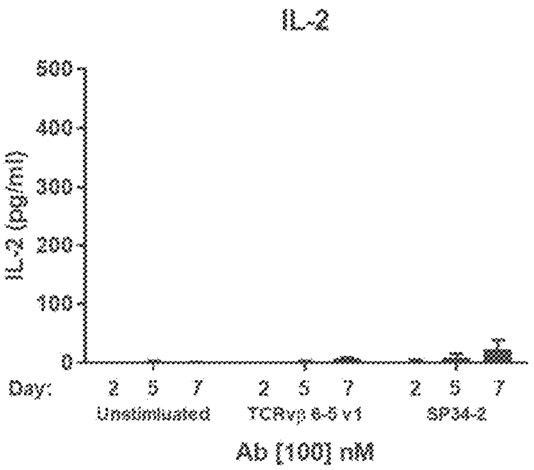
FIG. 55C shows the release of IL-2 from purified γδ T cell populations activated with anti-CD3ε antibody (SP34-2), anti-TCRβV antibody (anti-TCRβV 6-5 v1), or unstimulated.
Figure 55D:
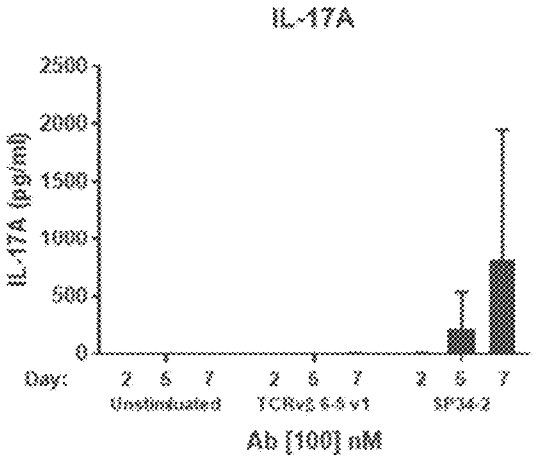
FIG. 55D shows the release of IL-17A from purified γδ T cell populations activated with anti-CD3ε antibody (SP34-2), anti-TCRβV antibody (anti-TCRβV 6-5 v1), or unstimulated.
Figure 55E:
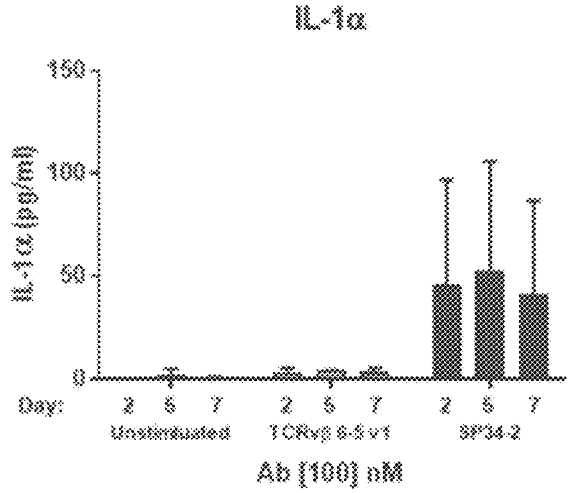
FIG. 55E shows the release of IL-1a from purified γδ T cell populations activated with anti-CD3ε antibody (SP34-2), anti-TCRβV antibody (anti-TCRβV 6-5 v1), or unstimulated.
Figure 55F:
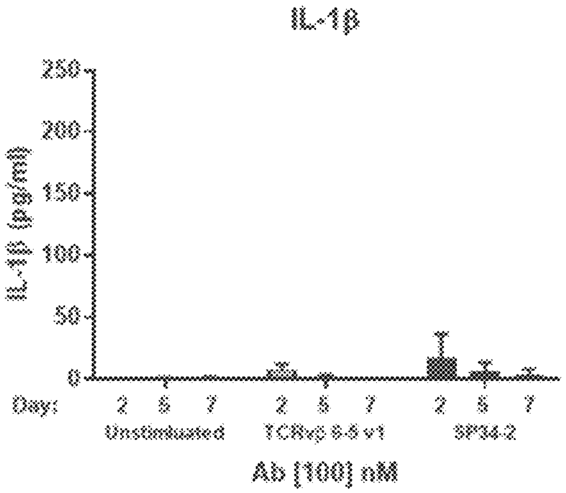
FIG. 55F shows the release of IL-1β from purified γδ T cell populations activated with anti-CD3ε antibody (SP34-2), anti-TCRβV antibody (anti-TCRβV 6-5 v1), or unstimulated.
Figure 55G:
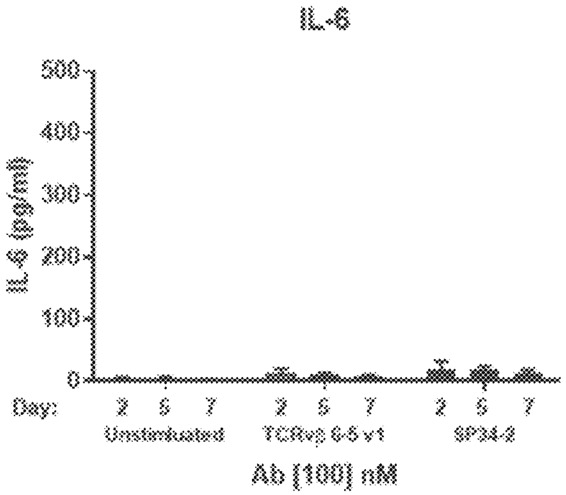
FIG. 55G shows the release of IL-6 from purified γδ T cell populations activated with anti-CD3ε antibody (SP34-2), anti-TCRβV antibody (anti-TCRβV 6-5 v1), or unstimulated.
Figure 55H:
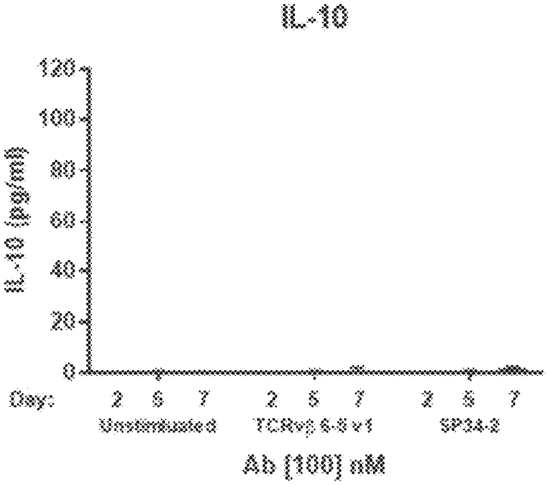
FIG. 55H shows the release of IL-10 from purified γδ T cell populations activated with anti-CD3ε antibody (SP34-2), anti-TCRβV antibody (anti-TCRβV 6-5 v1), or unstimulated.

To determine if anti-TCRvb antibodies are able to activate γδ T cells—γδ T cells were purified from human PBMCs via magnetic bead separation. γδ T cells were immobilized on plate-coated anti-CD3ε (SP34-2) or anti-TCRvb 6-5 (anti-TCRvb 6-5 v1) antibodies for 24 hours and analyzed for CD69 and CD25 expression by flow cytometry. Supernatants were collected post activation 2, 5, and 7 days, and analyzed for cytokines using Meso Scale Discovery (MSD) assay. FACS gating/staining on PBMCs was conducted prior to γδ T cell purification showing that γδ T cells are vβ 6-5 negative (Donor 12657—gating for γδ T and TCRvβ 6-5 based on FMO) (FIG. 52). FACS gating/staining on purified γδ T cell was conducted showing that purified γδ T cells are vβ 6-5 negative (Donor 12657—gating for γδ T and TCRvβ 6-5 based on FMO) (FIG. 53). As shown in FIG. 54, the anti-TCR Vβ 6-5 antibody (anti-TCRvb 6-5 v1) did not activate γδ T cells; while the anti-CD3ε antibody (SP34-2) did. The cytokine analysis showed that anti-TCRβV 6-5 v1 does not induce cytokine release by γδ T cells, cytokines analyzed include IFNγ, TNFα, IL1-2, IL-17A, IL-1α, IL-1β, IL-6, and IL-10 (FIG. 55A-55H).

Example 27: Polyclonal T Cell Expansion by Anti-TCRVβ Antibodies

Figure 56A:
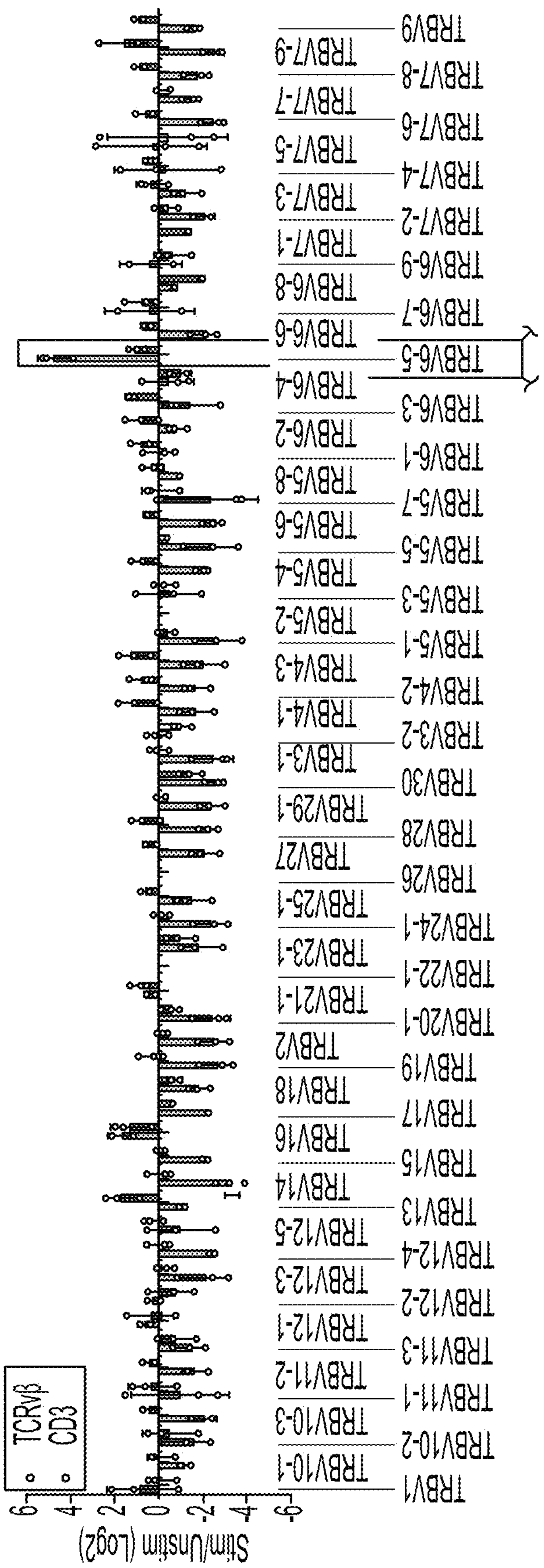
FIG. 56A shows the relative representations of all TCR alpha V segments (TRAV group of genes) and their variants (top), all TCR beta V segment 6-5 variants (TRBV6-5 gene) (bottom left), and all TCR beta V segments and variants excluding 6-5 (bottom right).
Figure 56B:
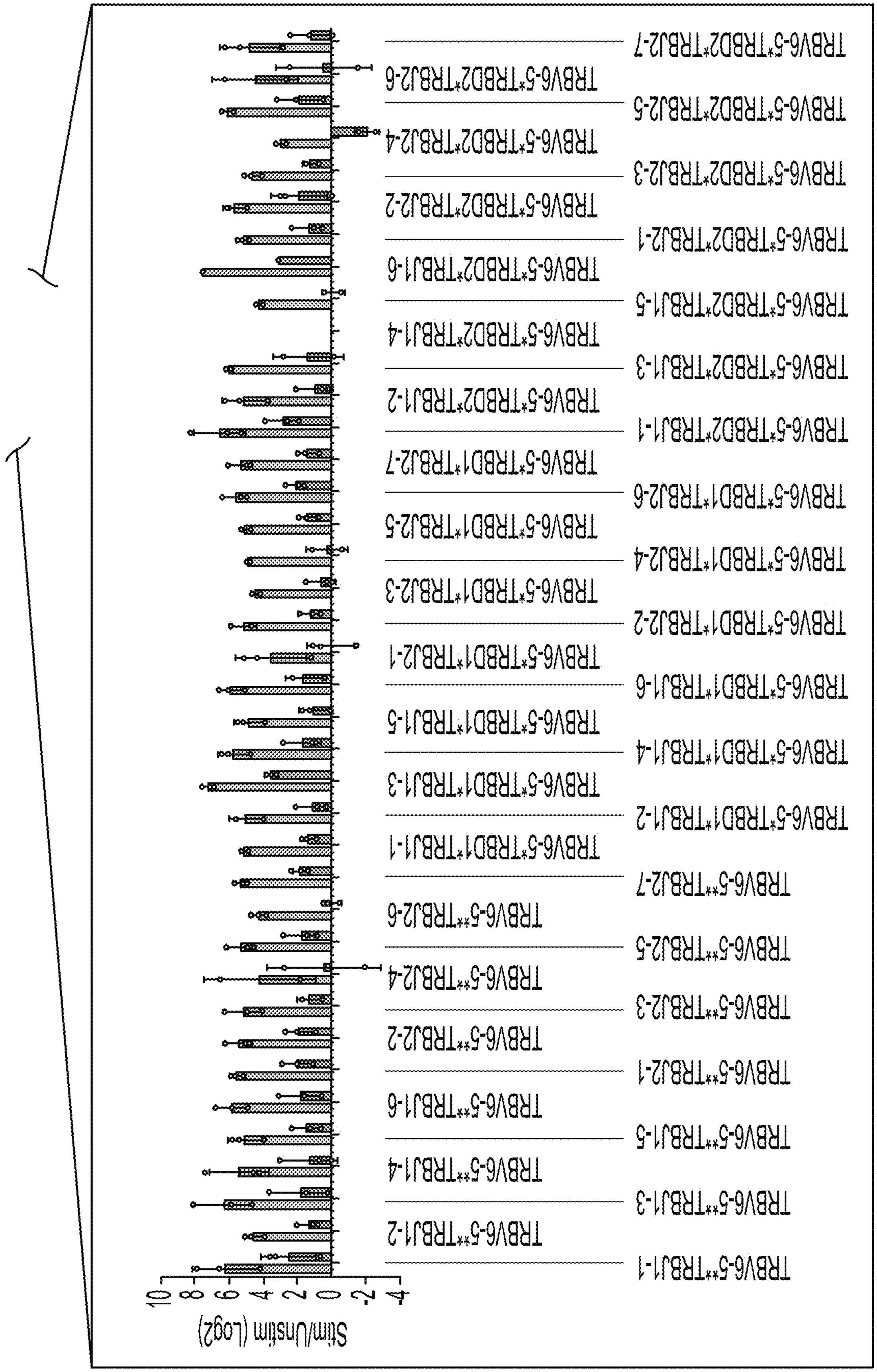
FIG. 56B shows the relative representations of all TCR alpha V segments (TRAV group of genes) and their variants (top), all TCR beta V segment 6-5 variants (TRBV6-5 gene) (bottom left), and all TCR beta V segments and variants excluding 6-5 (bottom right), continued from FIG. 56A.

To assess the ability of anti-TCRVβ antibodies to induce polyclonal T cell expansion—human CD3+ T cells were isolated using magnetic-bead separation (negative selection) and activated with immobilized (plate-coated) anti-TCRβV 6-5 v1 at 100 nM for 6 days. The expanded T cell population was washed and lysed using Takara single cell lysis buffer for SMART(er) TCR cDNA synthesis and sequencing. TCR sequencing was carried out and absolute counts and relative representation of the different TCR alpha V and J segments and TCR beta V, D, and J segments were determined, as well as the different variants of each of them that arise from Artemis/TdT activity during the V(D)J recombination, and that correspond to unique clones of T cells. FIG. 56 shows the relative representations of all TCR alpha V segments (TRAV group of genes) and their variants (top), all TCR beta V segment 6-5 variants (TRBV6-5 gene) (bottom left), and all TCR beta V segments and variants excluding 6-5 (bottom right). The data show that the anti-TCRVβ antibody stimulation does not induce proliferation of specific T cell clones within the TRBV6-5 positive population, as the relative difference in clonal representation in that population is comparable to the TRBV6-5 negative population as well as total TRAV usage.

Example 28: T Cells Expanded by Anti-TCRβV Represent a Novel Subset of Recently Activated Effector T Cells To assess the phenotype of anti-TCRβV expanded T cells—purified T cells were stimulated with solid-phase anti-TCRβV antibody over 8 days with the indicated T cell-activating antibody at 100 nM: i) anti-TCRvb 6-5 v1 antibody; ii) anti-TCRvb 6-5 v2; iii) OKT3 (anti-CD3ε antibody); or iv) IgG1 N297A (isotype control). T-cell subsets were identified by FACS staining for specific surface markers for: Naive T cell (CD4/CD8+, CD45RA+, CCR7+); T stem cell memory (TSCM; CD4/CD8+, CD95+, CD45RA+, CCR7+); T central memory (TCM; CD4/CD8+, CD95+, CD45RA−, CCR7+); T effector memory (TEM; CD4/CD8+, CD95+, CD45RA−, CCR7−); T effector memory re-expressing CD45RA (TEMRA; CD4/CD8+, CD95+, CD45RA+, CCR7−); and CD27, CD28, 4-1BB, OX40, and ICOS. Data is representative of more than 5 independent experiments.

Figure 57A:
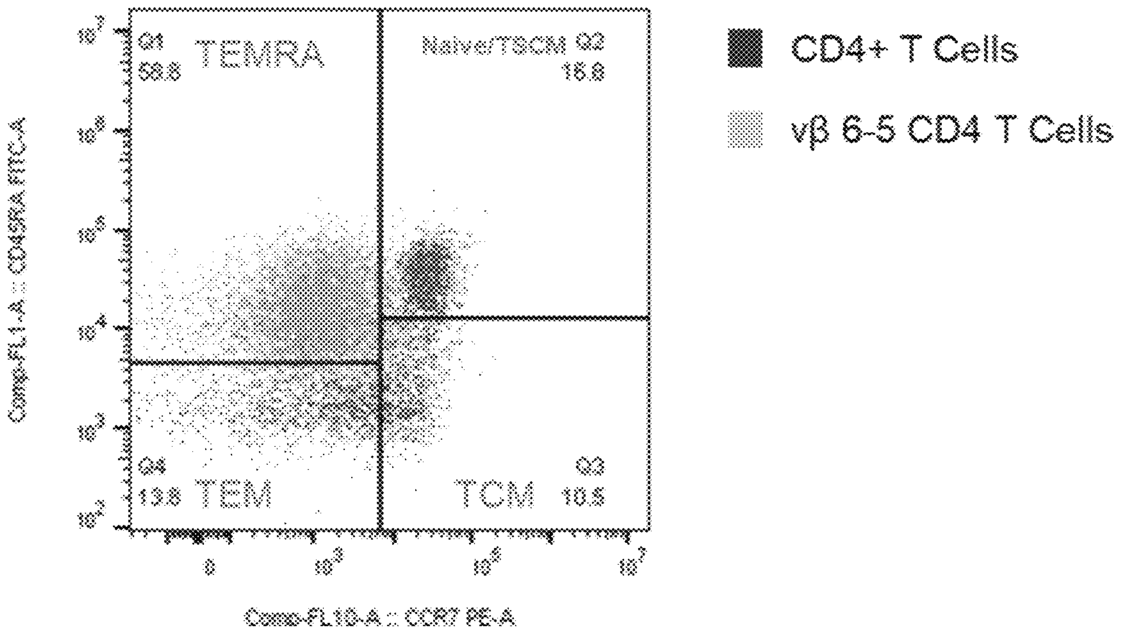
FIG. 57A is a FACS plot showing phenotypic markers of CD4+ T cells expanded with anti-TCRβV antibody (anti-TCRβV 6-5 v1). Defined phenotypes include TEMRA (top left), Naïve/TSCM (top right), TEM (bottom left), and TCM (bottom right).
Figure 57B:
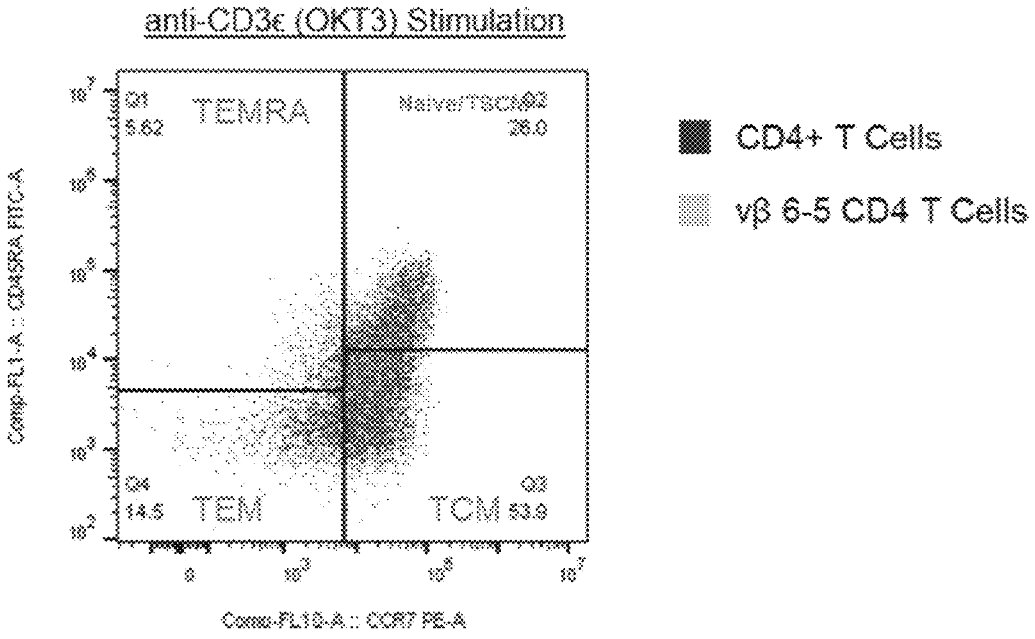
FIG. 57B is a FACS plot showing phenotypic markers of CD4+ T cells expanded with anti-CD3ε antibody (OKT3). Defined phenotypes include TEMRA (top left), Naïve/TSCM (top right), TEM (bottom left), and TCM (bottom right).
Figure 58A:
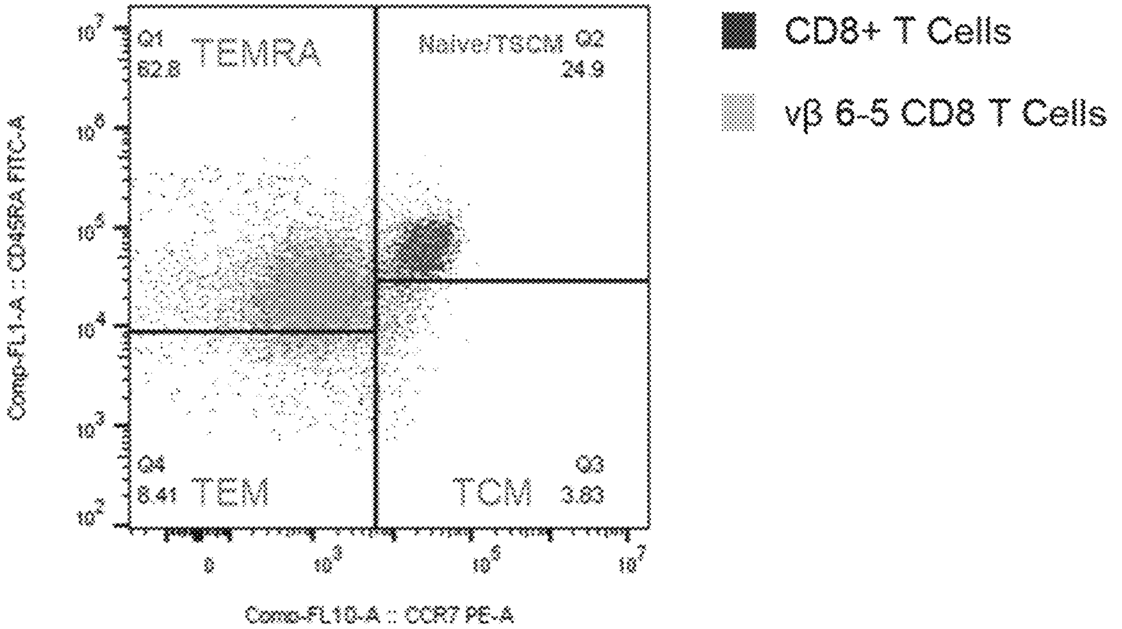
FIG. 58A is a FACS plot showing phenotypic markers of CD8+ T cells expanded with anti-TCRβV antibody (anti-TCRβV 6-5 v1). Defined phenotypes include TEMRA (top left), Naïve/TSCM (top right), TEM (bottom left), and TCM (bottom right).
Figure 58B:
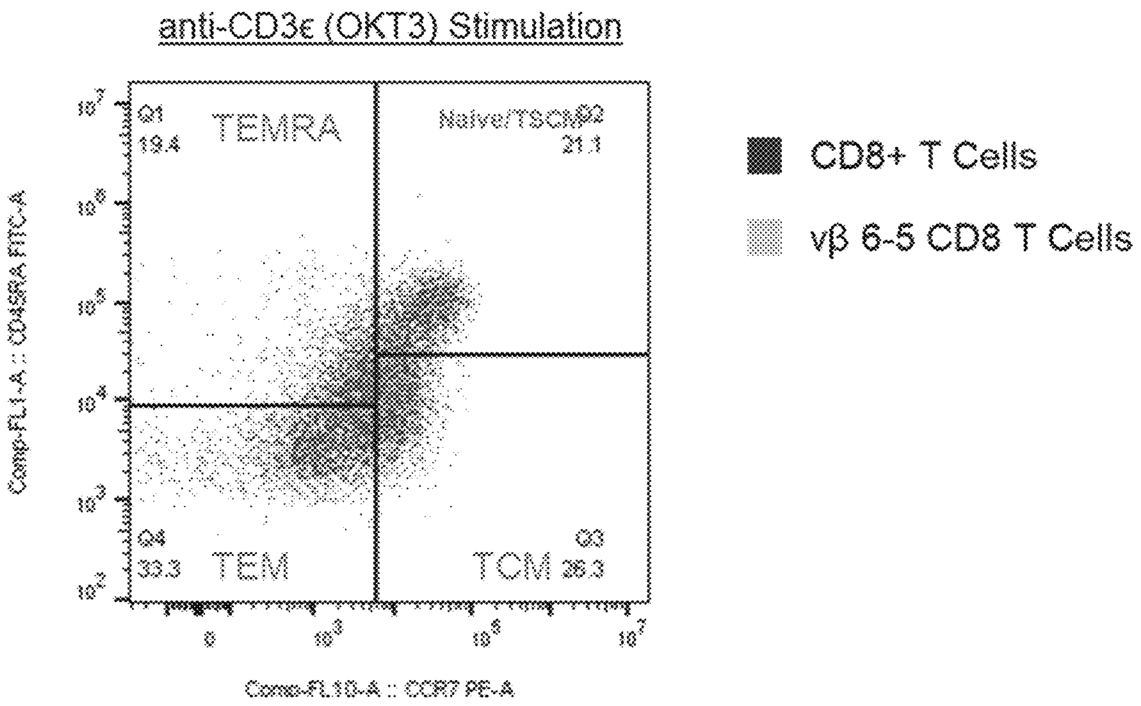
FIG. 58B is a FACS plot showing phenotypic markers of CD8+ T cells expanded with anti-CD3ε antibody (OKT3). Defined phenotypes include TEMRA (top left), Naïve/TSCM (top right), TEM (bottom left), and TCM (bottom right).
Figure 59A:
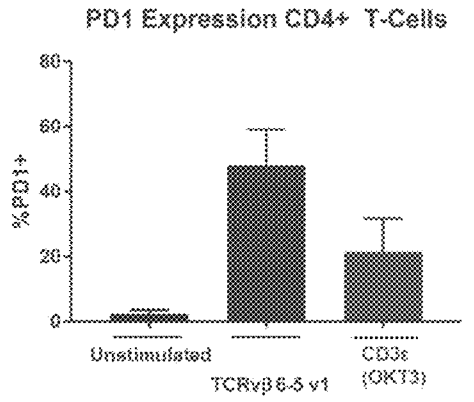
FIG. 59A is a bar graph showing the percentage of PD1 expressing CD4+ T cells from T cell cultures activated with anti-TCRβV antibody (anti-TCRβV 6-5 v1), anti-CD3ε antibody (OKT3), or unstimulated.
Figure 59B:
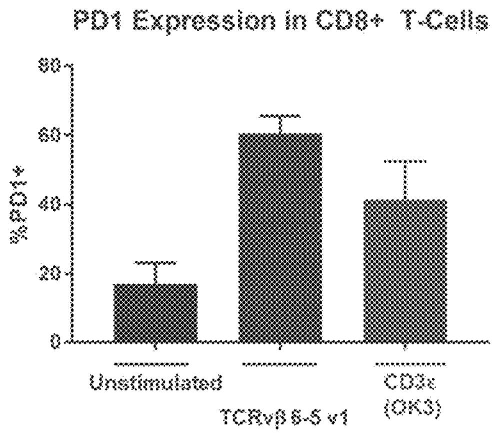
FIG. 59B is a bar graph showing the percentage of PD1 expressing CD8+ T cells from T cell cultures activated with anti-TCRβV antibody (anti-TCRβV 6-5 v1), anti-CD3ε antibody (OKT3), or unstimulated.
Figure 60A:
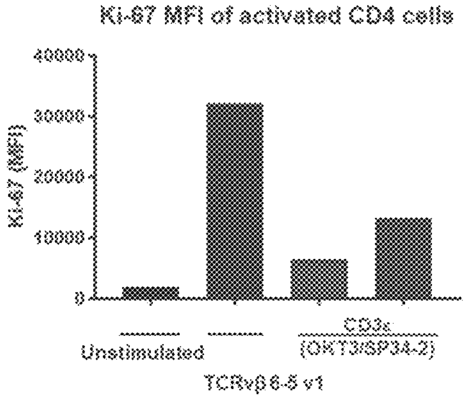
FIG. 60A is a bar graph showing the expression of Ki-67 by CD4+ T cells from T cell cultures activated with anti-TCRβV antibody (anti-TCRβV 6-5 v1), anti-CD3ε antibody (OKT3), or unstimulated.
Figure 60B:
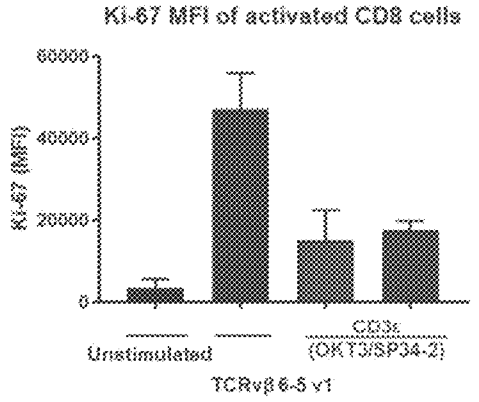
FIG. 60B is a bar graph showing the expression of Ki-67 by CD8+ T cells from T cell cultures activated with anti-TCRβV antibody (anti-TCRβV 6-5 v1), anti-CD3ε antibody (OKT3), or unstimulated.

The data shows that CD4+ T cells expanded by anti-TCR Vβ antibody (FIG. 57A), but not OKT3 (FIG. 57B), share phenotypic markers with the TEMRA subset. Likewise, the data shows that CD4+ T cells expanded by anti-TCR Vβ antibody (FIG. 58A), but not OKT3 (FIG. 58B), share phenotypic markers with the TEMRA subset. Further analysis of PD1 expression showed anti-TCR Vβ activated CD4+ T cells (FIG. 59A) and CD8+ T cells (FIG. 59B) display increased PD1 expression relative to anti-CD3ε activated CD4+ T cells (FIG. 59A) and CD8+ T cells (FIG. 59B). These anti-TCR Vβ activated CD4+ T cells (FIG. 60A) (PD-1+ TEMRA phenotype) and anti-TCR VP activated CD8+ T cells (FIG. 60B) (PD-1+ TEMRA phenotype) show Ki-67 enriched phenotype relative to anti-CD3ε activated CD4+ T cells (FIG. 60A) and CD8+ T cells (FIG. 60B).

Figure 61A:
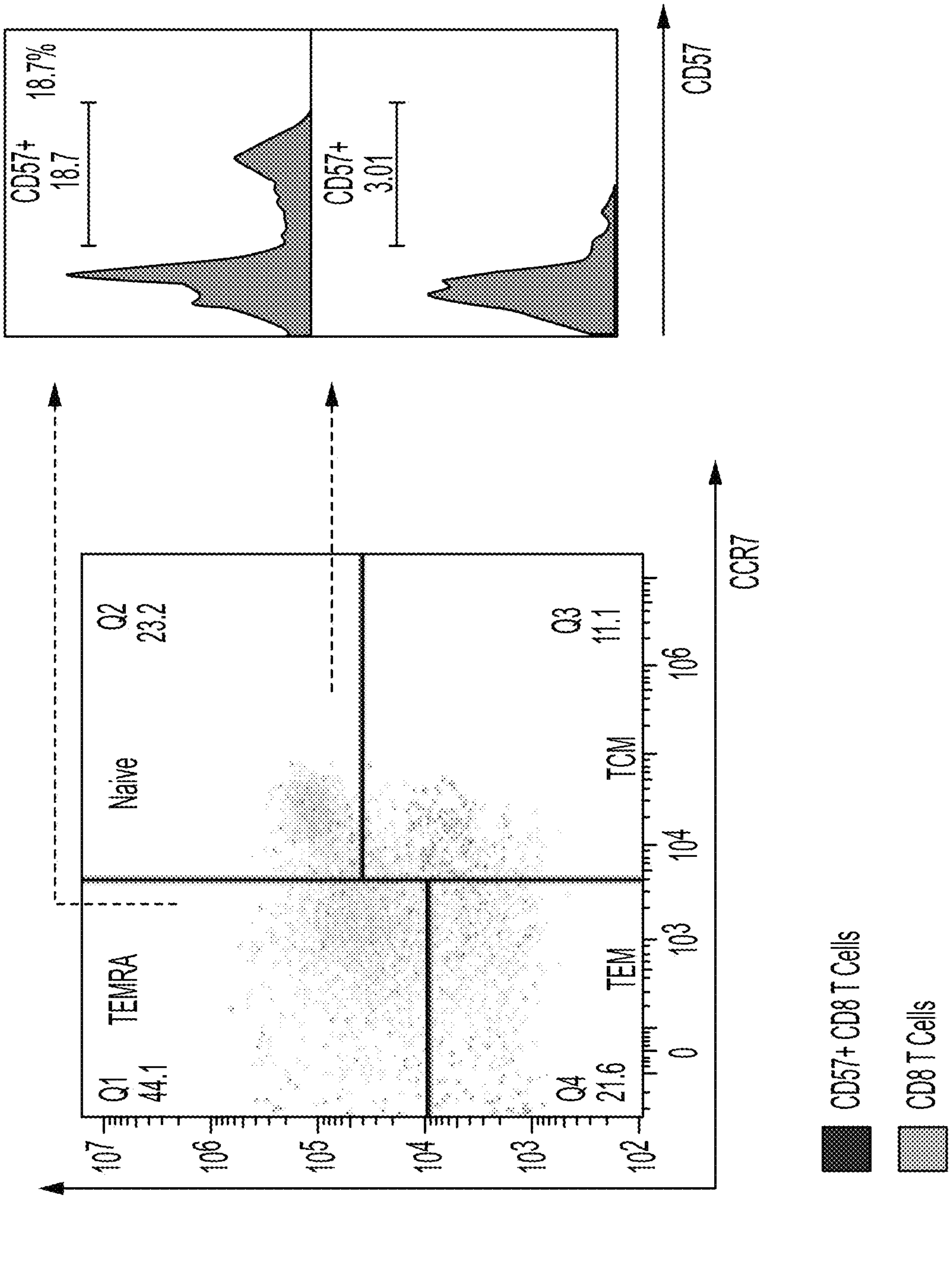
FIG. 61A is a FACS plot showing the percentage of TEMRA-like CD8+ T cells activated using anti-TCRβV antibody (anti-TCRβV 6-5 v1) that express CD57 (18.7%).
Figure 61B:
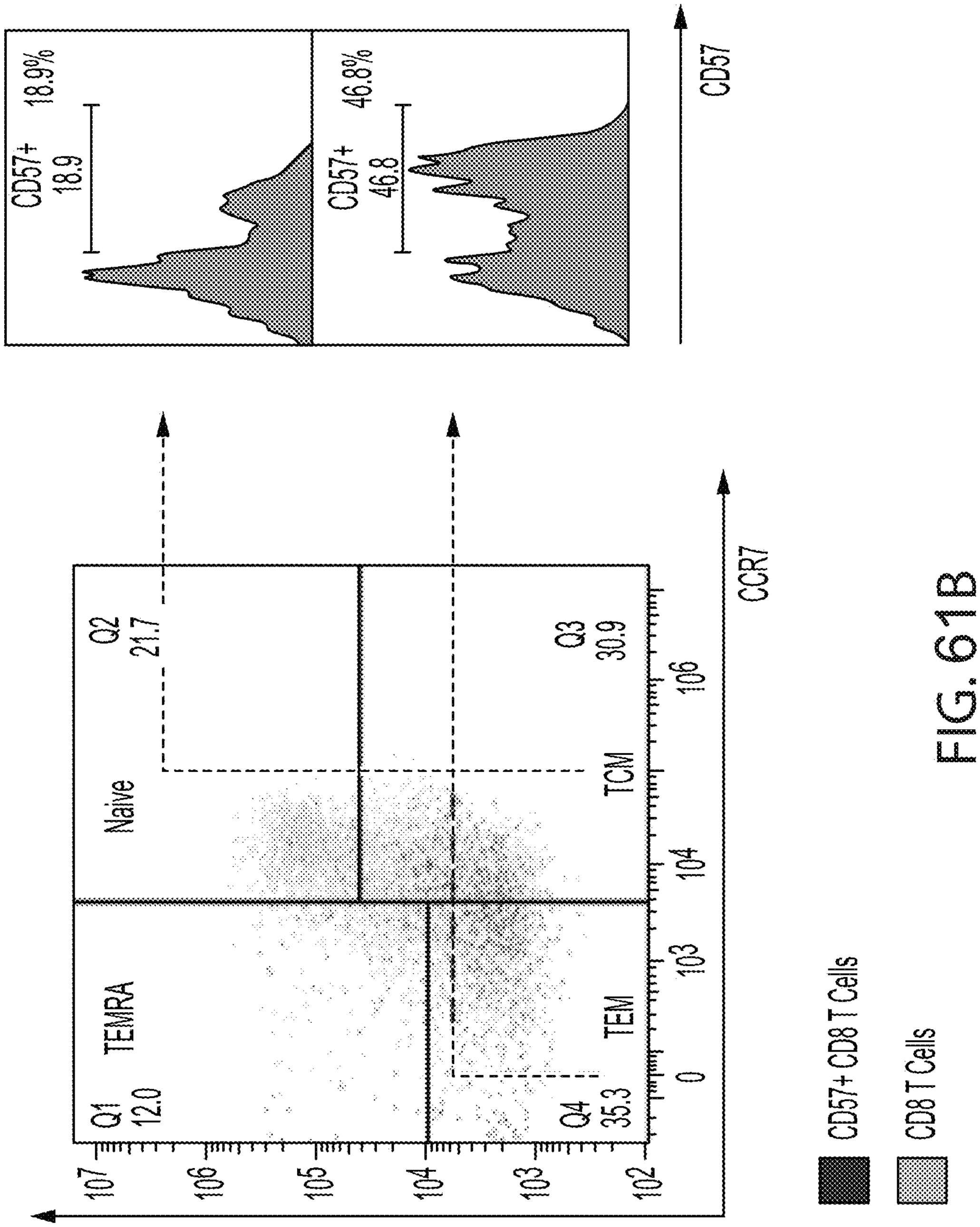
FIG. 61B is a FACS plot showing the percentage of TEM-like CD8+ T cells activated using anti-CD3ε antibody (OKT3) that express CD57 (46.8%) and the percentage of TCM-like CD8+ T cells activated using anti-CD3ε antibody (OKT3) that express CD57 (18.9%).
Figure 62:
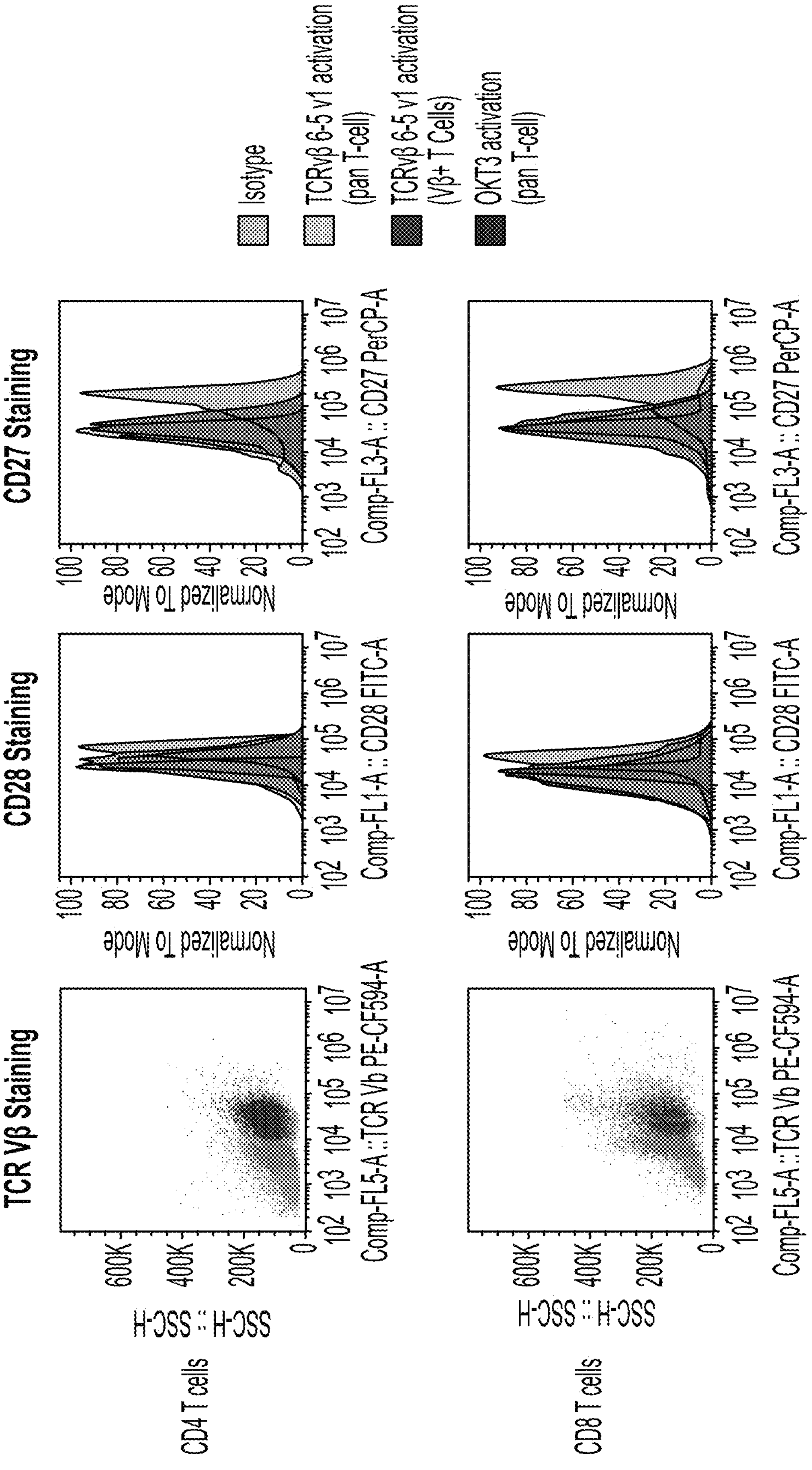
FIG. 62 shows a series of FACS plots showing the expression of expression of CD27 and by CD4+ (top) or CD8+ (bottom) T cells from T cell cultures activated with anti-TCRβV antibody (anti-TCRβV 6-5 v1), anti-CD3ε antibody (OKT3), or unstimulated.

Further analysis of CD57 expression showed anti-TCR Vβ activated CD8+ T cells (FIG. 61A) do not display increased CD57 expression relative to anti-CD3ε activated CD8+ T cells (FIG. 61B). Likewise, analysis of CD27 and CD28 expression showed anti-TCR Vβ activated CD4+ T cells (FIG. 62 top) and anti-TCR Vβ activated CD8+ T cells (FIG. 62 bottom) do not display increased CD27 and CD28 expression relative to anti-CD3ε activated CD8+ T cells (FIG. 62).

Figure 63:
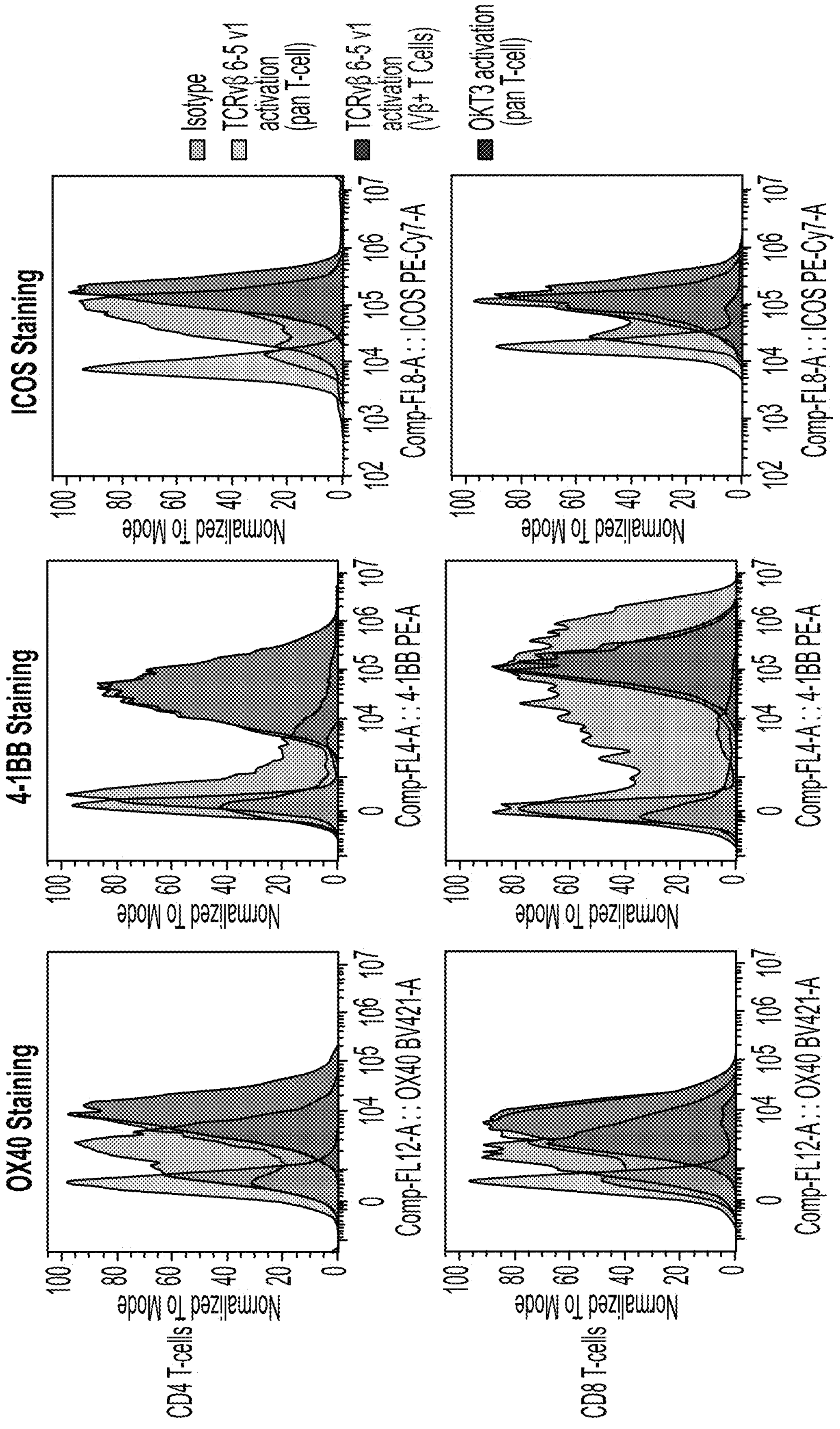
FIG. 63 shows a series of FACS plots showing the expression of expression of OX40, 41BB, and ICOS by CD4+(top) or CD8+(bottom) T cells from T cell cultures activated with anti-TCRβV antibody (anti-TCRβV 6-5 v1), anti-CD3ε antibody (OKT3), or unstimulated.

Further analysis of OX40, 41BB, and ICOS expression showed anti-TCR Vβ activated CD4+ T cells (FIG. 63 top) and anti-TCR Vβ activated CD8+ T cells (FIG. 63 bottom) display increased OX40, 41BB, and ICOS expression relative to anti-CD3ε activated CD8+ T cells (FIG. 63).

The TEMRA like phenotype of anti-TCR Vβ antibody expanded T cells was further analyzed using time lapse flow cytometry to evaluate expression of CD45RA and CCR7 at different time points post activation. Isolated human T-cells were activated with immobilized (plate-coated) anti-CD3ε or anti-TCR Vβ at 100 nM for between 1-8-days. After each (1, 2, 3, 4, 5, 6, 8-) day activation, T-cell subsets were identified by FACS staining for surface markers for Naïve/TSCM T cell (CD4+/CD8+, CD45RA+, CCR7+), T central memory (TCM; CD4+/CD8+, CD95+, CD45RA−, CCR7+), T effector memory (TEM; CD4+/CD8+, CD95+, CD45RA−, CCR7−), and T effector memory re-expressing CD45RA (TEMRA; CD4+/CD8+, CD95+, CD45RA+, CCR7−). TCRβV+ T-cells are identified by TCR Vβ+ staining. FACS stained samples were analyzed by flow cytometry analysis. Data shown a representative for CD4+ T-cells from 1 of 3 donors.

Figure 64A:
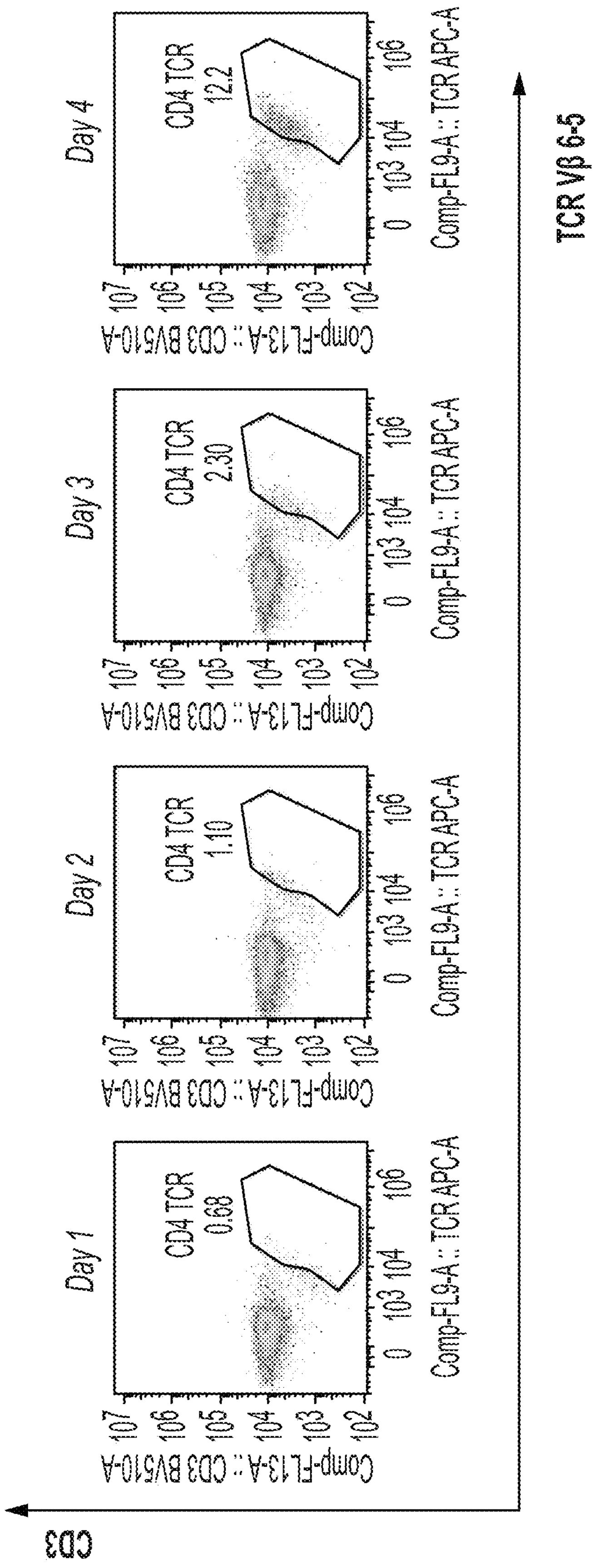
FIG. 64A shows a series of FACS plots showing the percentage of CD3+(CD4 gated) TCRβV 6-5+ T cells 1, 2, 3, 4, 5, 6, and 8 days port activation with BCMA and the anti-TCR Vβ antibody anti-TCR Vβ 6-5 v1.
Figure 64B:
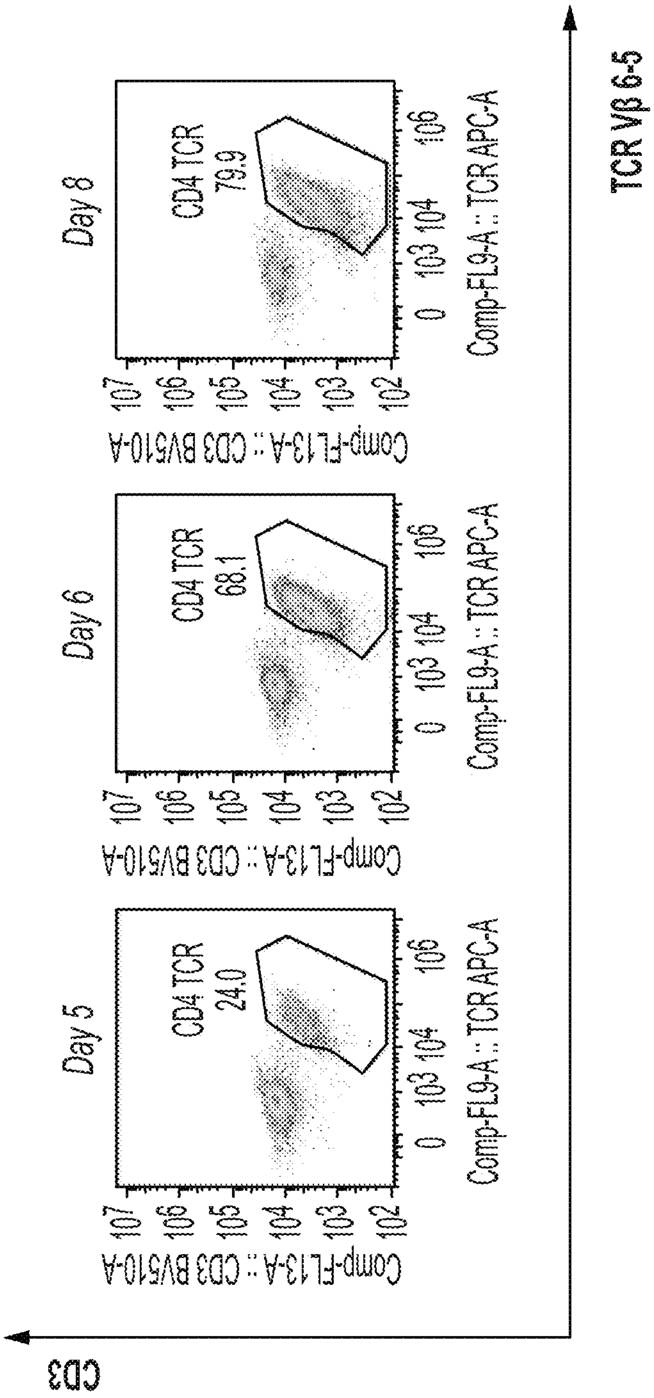
FIG. 64B shows a series of FACS plots showing the percentage of CD3+ (CD4 gated) TCRβV 6-5+ T cells 1, 2, 3, 4, 5, 6, and 8 days port activation with BCMA and the anti-TCR Vβ antibody anti-TCR Vβ 6-5 v1, continued from FIG. 64A.
Figure 65A:
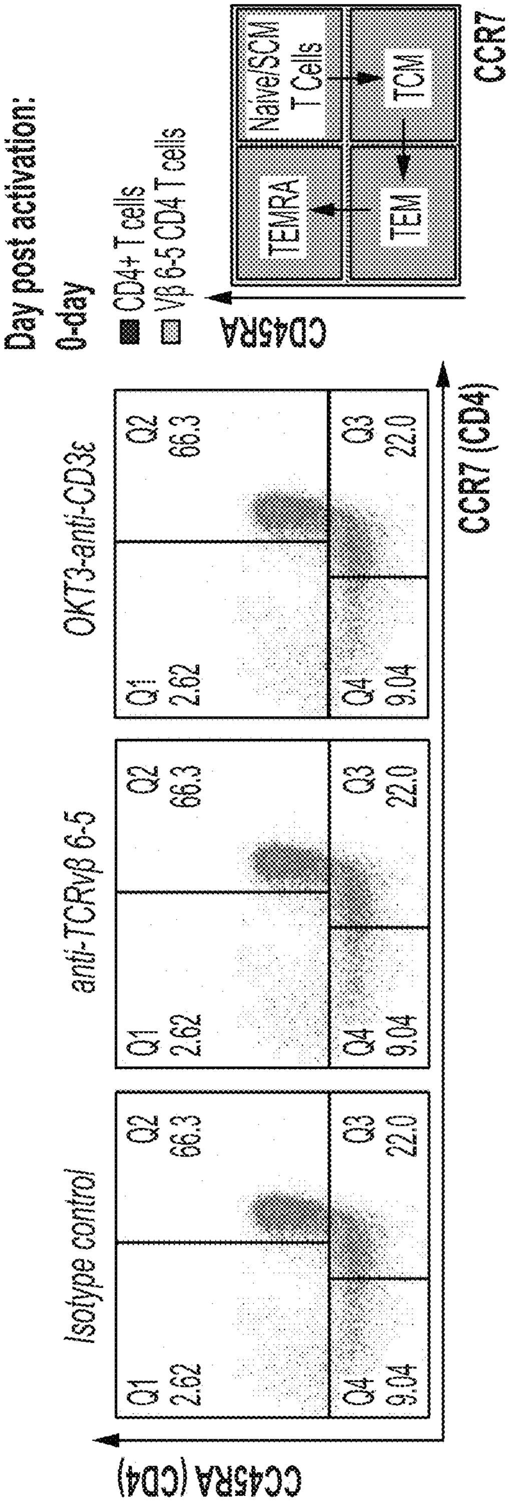
FIG. 65A shows a series of FACS plots showing the percentage of CD4+ T cells expanded using isotype control (IgG1 N297A), anti-TCRβV (anti-TCR Vβ 6-5 v1), or anti-CD3ε (OKT3) antibodies on day 0 post activation.
Figure 65B:
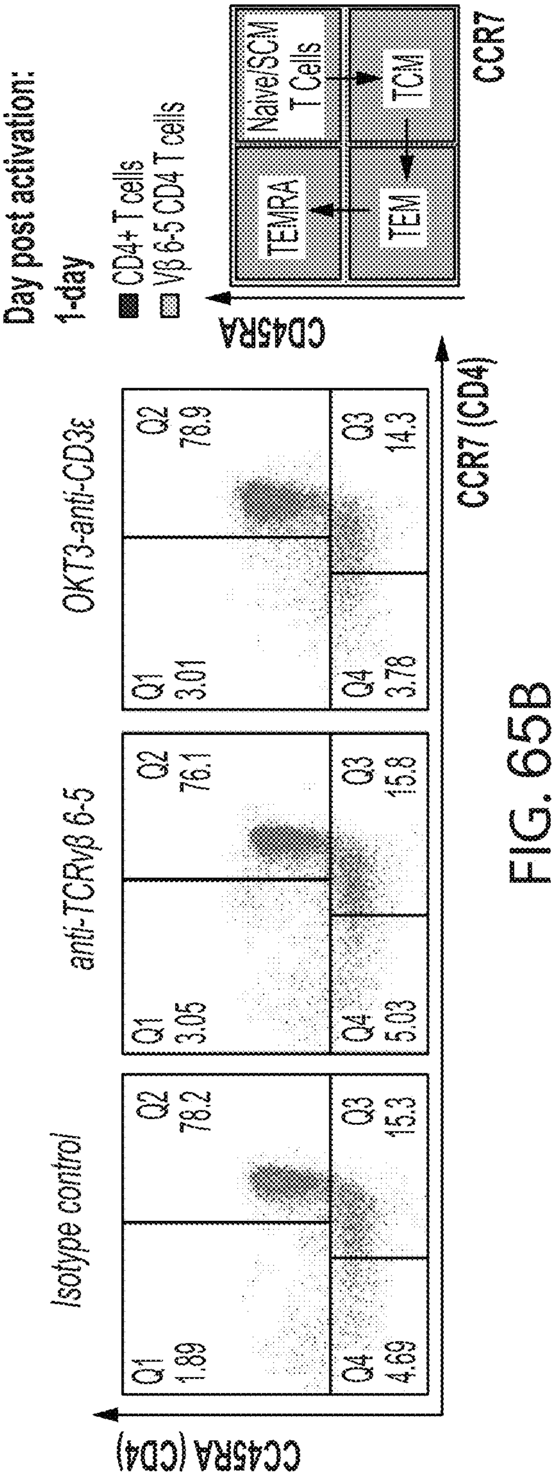
FIG. 65B shows a series of FACS plots showing the percentage of CD4+ T cells expanded using isotype control (IgG1 N297A), anti-TCRβV (anti-TCR Vβ 6-5 v1), or anti-CD3ε (OKT3) antibodies on day 1 post activation.
Figure 65C:
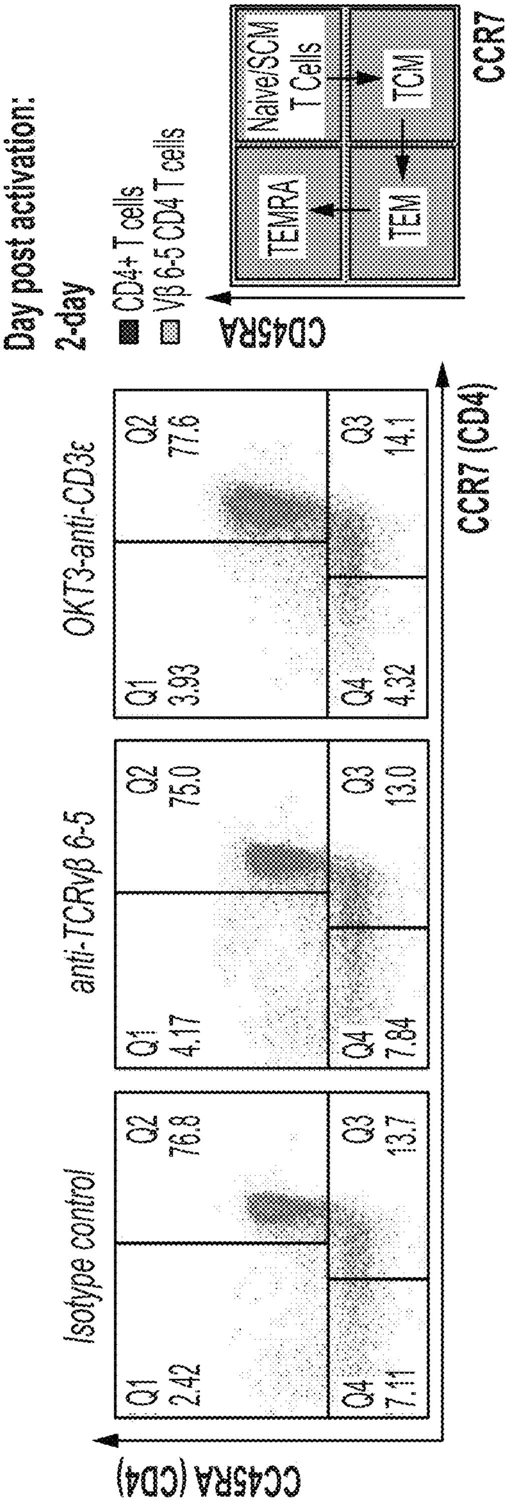
FIG. 65C shows a series of FACS plots showing the percentage of CD4+ T cells expanded using isotype control (IgG1 N297A), anti-TCRβV (anti-TCR Vβ 6-5 v1), or anti-CD3ε (OKT3) antibodies on day 2 post activation.
Figure 65D:
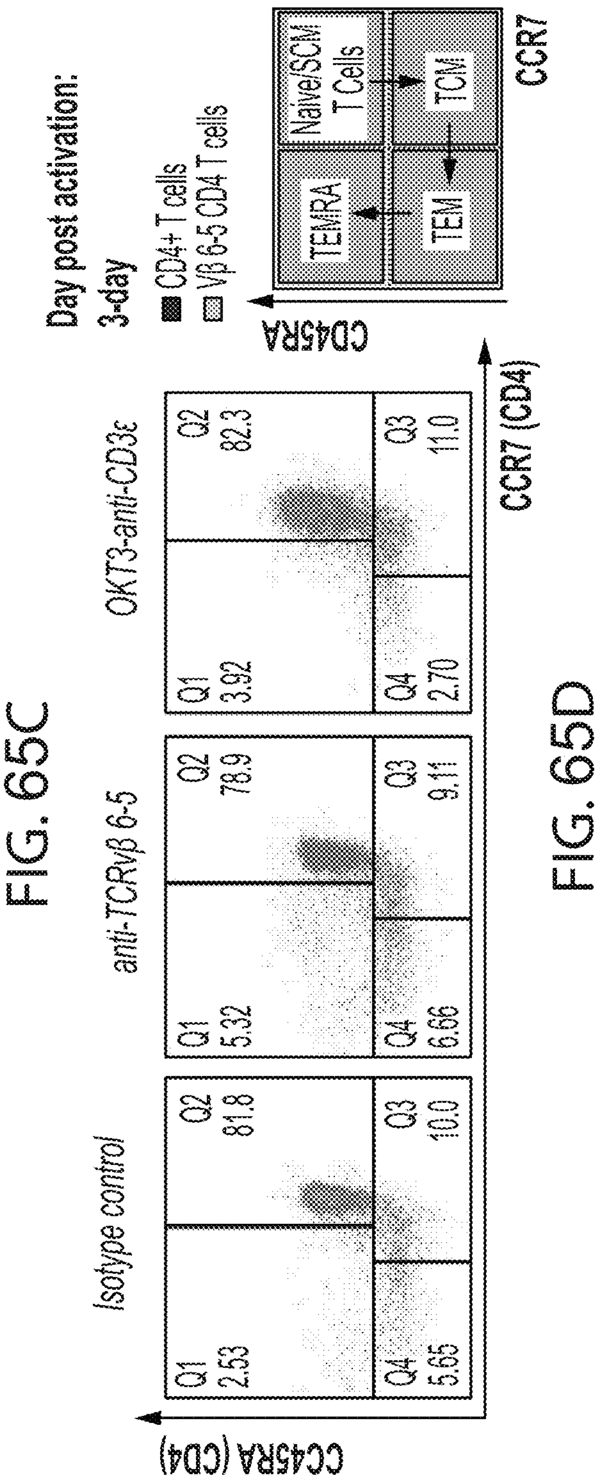
FIG. 65D shows a series of FACS plots showing the percentage of CD4+ T cells expanded using isotype control (IgG1 N297A), anti-TCRβV (anti-TCR Vβ 6-5 v1), or anti-CD3ε (OKT3) antibodies on day 3 post activation.
Figure 65E:
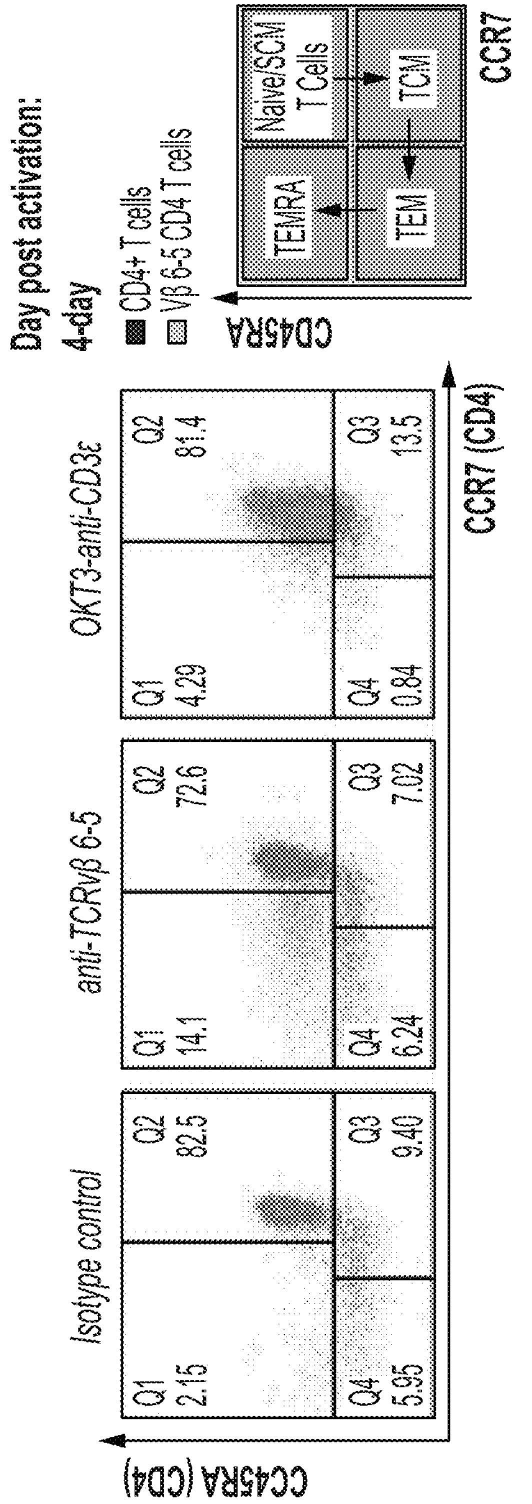
FIG. 65E shows a series of FACS plots showing the percentage of CD4+ T cells expanded using isotype control (IgG1 N297A), anti-TCRβV (anti-TCR Vβ 6-5 v1), or anti-CD3ε (OKT3) antibodies on day 4 post activation.
Figure 65F:
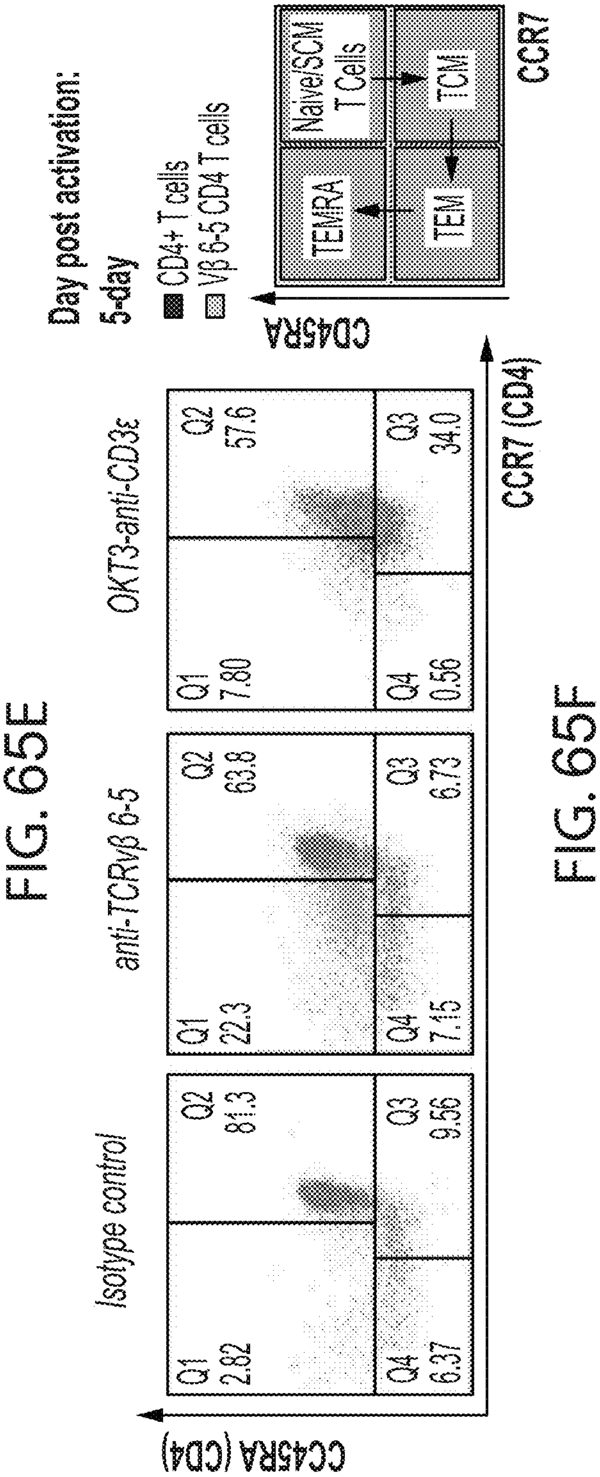
FIG. 65F shows a series of FACS plots showing the percentage of CD4+ T cells expanded using isotype control (IgG1 N297A), anti-TCRβV (anti-TCR Vβ 6-5 v1), or anti-CD3ε (OKT3) antibodies on day 5 post activation.
Figure 65G:
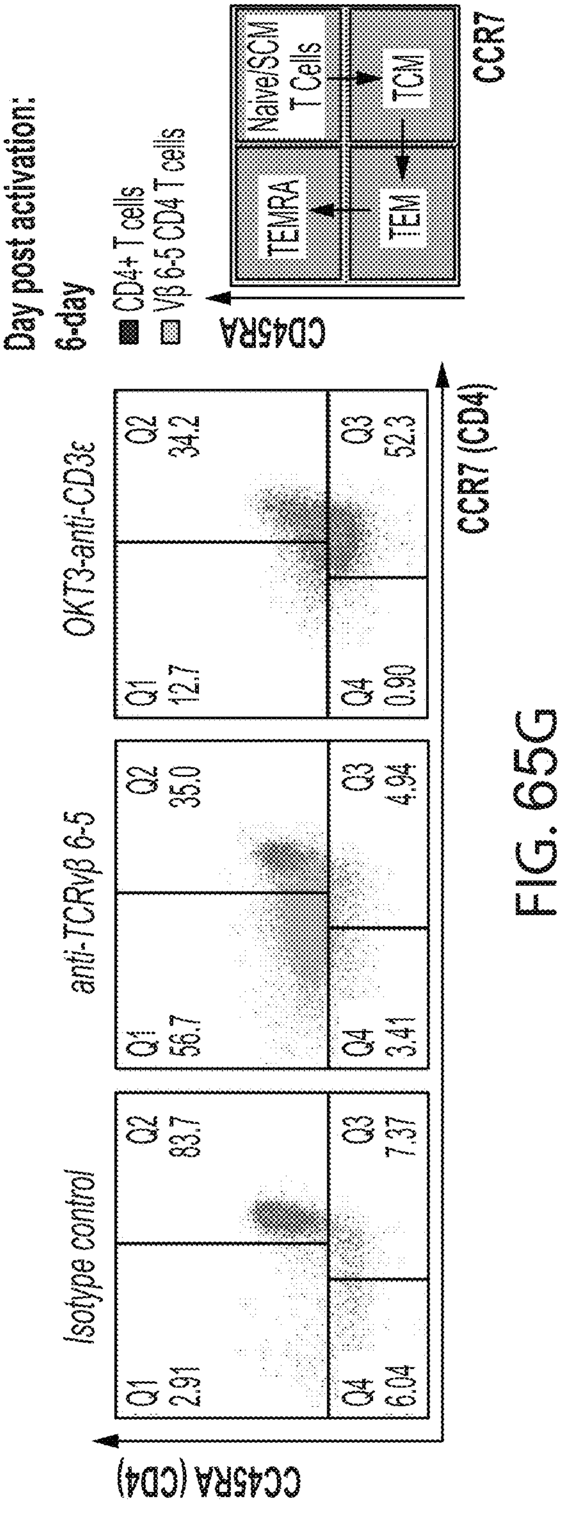
FIG. 65G shows a series of FACS plots showing the percentage of CD4+ T cells expanded using isotype control (IgG1 N297A), anti-TCRβV (anti-TCR Vβ 6-5 v1), or anti-CD3ε (OKT3) antibodies on day 6 post activation.
Figure 65H:
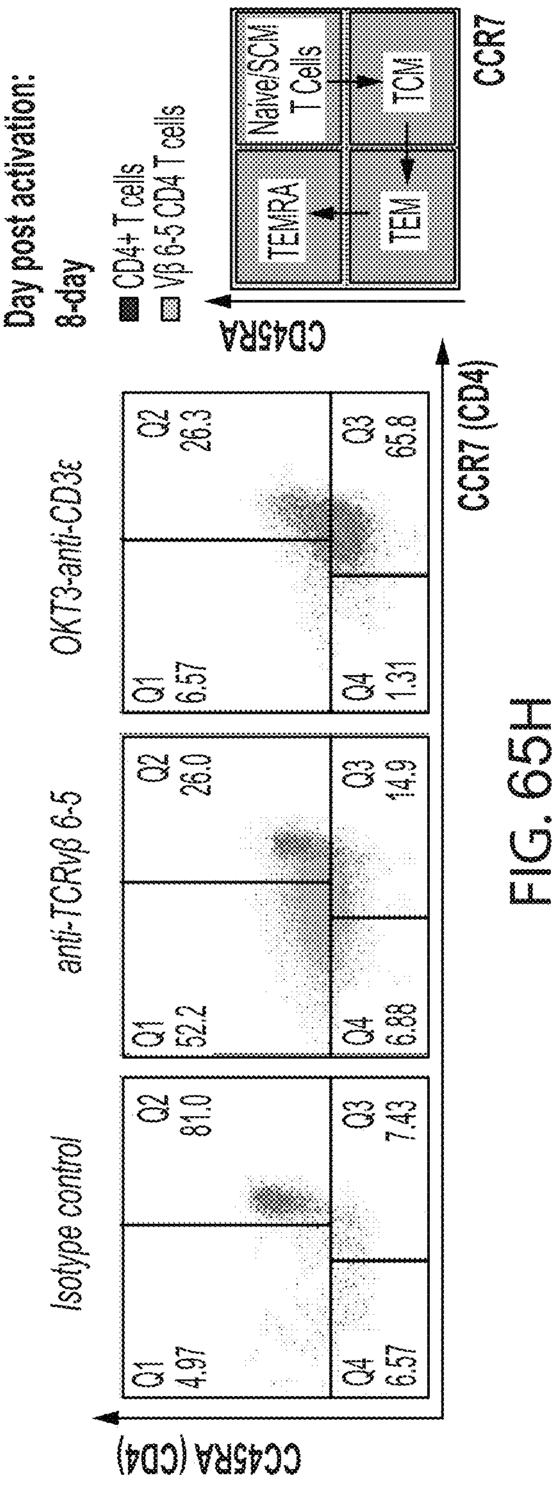
FIG. 65H shows a series of FACS plots showing the percentage of CD4+ T cells expanded using isotype control (IgG1 N297A), anti-TCRβV (anti-TCR Vβ 6-5 v1), or anti-CD3ε (OKT3) antibodies on day 8 post activation.

FIG. 64 shows a series of FACS plots showing the percentage of CD3+(CD4 gated) TCRβV 6-5+ T cells 1, 2, 3, 4, 5, 6, and 8 days port activation with BCMA and the anti-TCR Vβ antibody anti-TCR Vβ 6-5 v1. Analysis of the percentage of CD4+ T cells expanded using isotype control (IgG1 N297A), anti-TCRβV (anti-TCR Vβ 6-5 v1), or anti-CD3ε (OKT3) antibodies on day 0 post activation (FIG. 65A), day 1 post activation (FIG. 65B), day 2 post activation (FIG. 65C), day 3 post activation (FIG. 65D), day 4 post activation (FIG. 65E), day 5 post activation (FIG. 65F), day 6 post activation (FIG. 65G), and day 8 post activation (FIG. 65H). The percentage of TEMRA like T cells expressing both CD45RA and CCR7 shows an increase in the population of TEMRA like cells in the CD4+ TCR Vβ 6-5+ T cell cultures expanded with the anti-TCR Vβ 6-5 v1 antibody compared to those expanded with the OKT3 antibody. Similar results were seen with CD8+ T cells. The results further show that purified human T-cells activated by anti-TCRβV 6-5 directly differentiates to TEMRA subsets and proliferate when compared to purified T-cells activated by anti-CD3ε (OKT3).

In summary, the data shows anti-TCRβV antibodies activated and expanded T cells represent a novel subset of recently activated effector T cells which share phenotypic markers with $T_{EMRA}$. This is in contrast to anti-CD3ε-expanded T cells which differentiated into $T_{CM}$ and $T_{EM}$. TCRβV expanded T cells are highly proliferative and do not upregulate the senescent marker CD57 OX40, 4-1BB, and ICOS are upregulated on anti-TCRβV activated T cells.

Example 29: Metabolic State of αTCRβV Activated T Cells

Figure 66A:
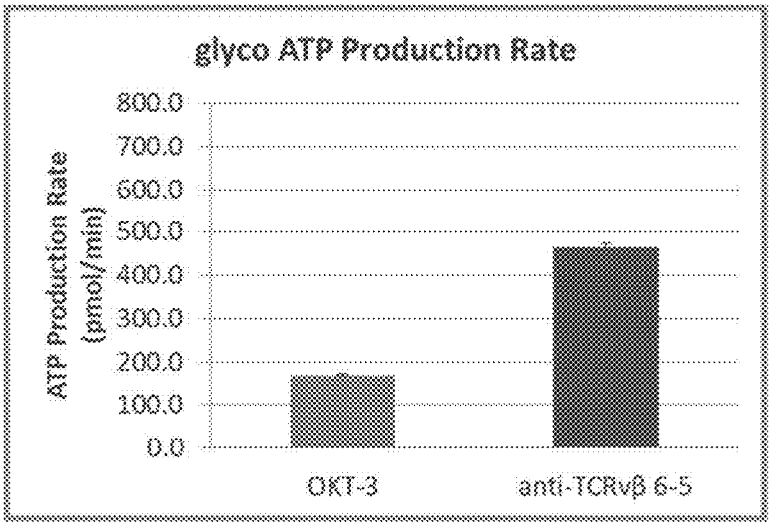
FIG. 66A is a bar graph showing ATP production from glycolysis of T cell cultures activated with the indicated antibodies.
Figure 66B:
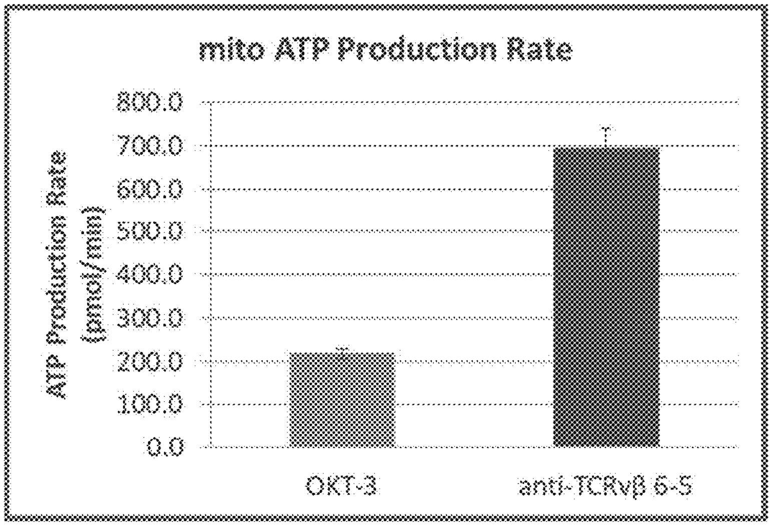
FIG. 66B is a bar graph showing ATP production from oxidative phosphorylation of T cell cultures activated with the indicated antibodies.

To evaluate the metabolic phenotype of T cells activated with αTCRβV antibodies—naïve T cells from PBMCs were stimulated and expanded for 5 days with plate-bound anti-CD3 antibody (OKT3) or anti-TCRβV antibody (anti-TCRβV 6-5 v1 antibody). Activated T cells were then rested in IL-2 containing media for 2 days, before they were cryopreserved. Prior to assay setup, cells were thawed and re-stimulated for 3 days with plate-bound anti-CD3 Ab (clone OKT3) or anti-TCRβV antibody (anti-TCRβV 6-5 v1 antibody), respectively. Equal numbers of live cells were plated on a Seahorse cartridge, and the Real-Time ATP Rate Assay was performed according to manufacturer's instructions. The data showed that ATP production from glycolysis (FIG. 66A) oxidative phosphorylation (FIG. 66B) in T cells from 3 donors (representative results from a single donor presented in FIG. 66A-66B) activated with the anti-TCRβV 6-5 v1 antibody increased compared to T cells activated with the OKT3 antibody (3-fold increase in ATP production was observed on average); and one donor showed equal levels of ATP production in anti-TCRβV 6-5 v1 and OKT3 Ab stimulated cells (data not shown).

Figure 67:
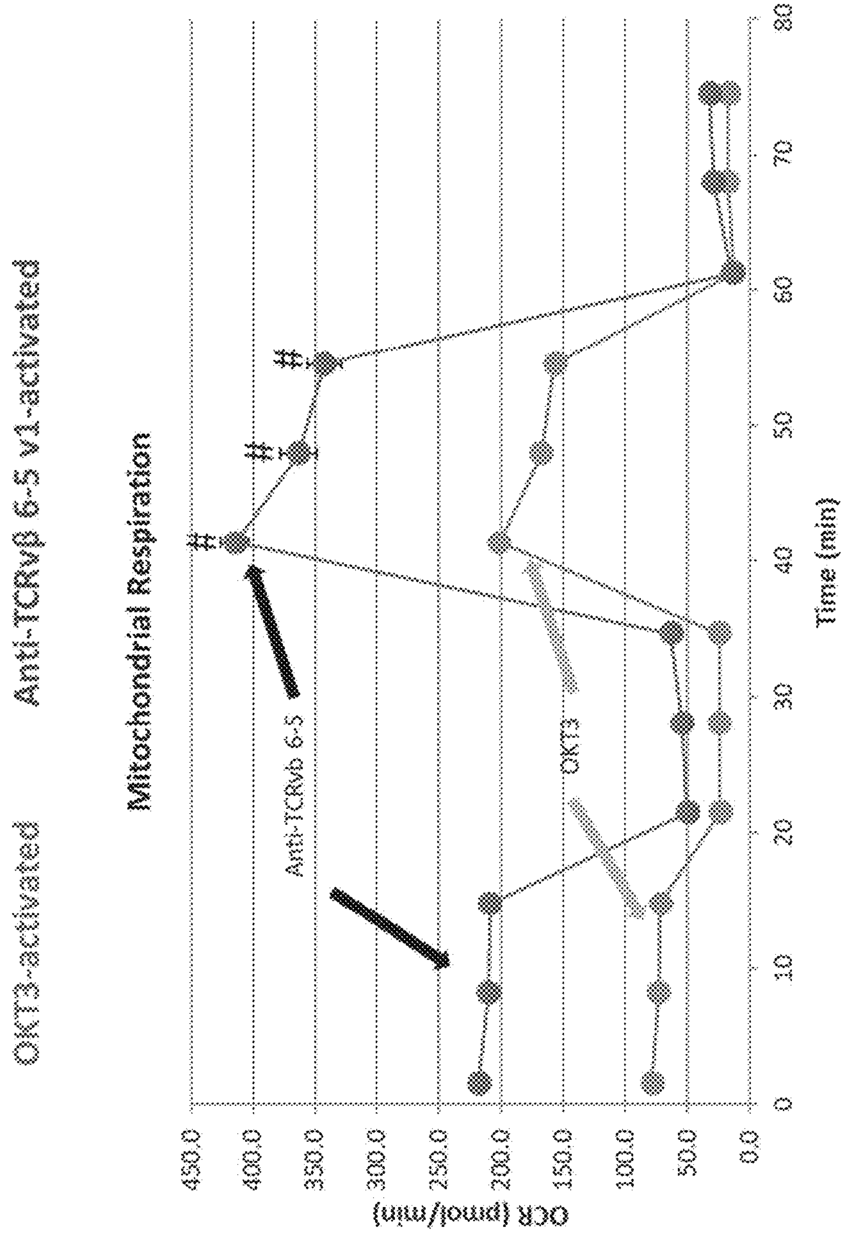
FIG. 67 is a line graph showing the oxygen consumption rate (OCR) of T cells from about 0 to 75 minutes activated with the indicated antibody.
Figure 68A:
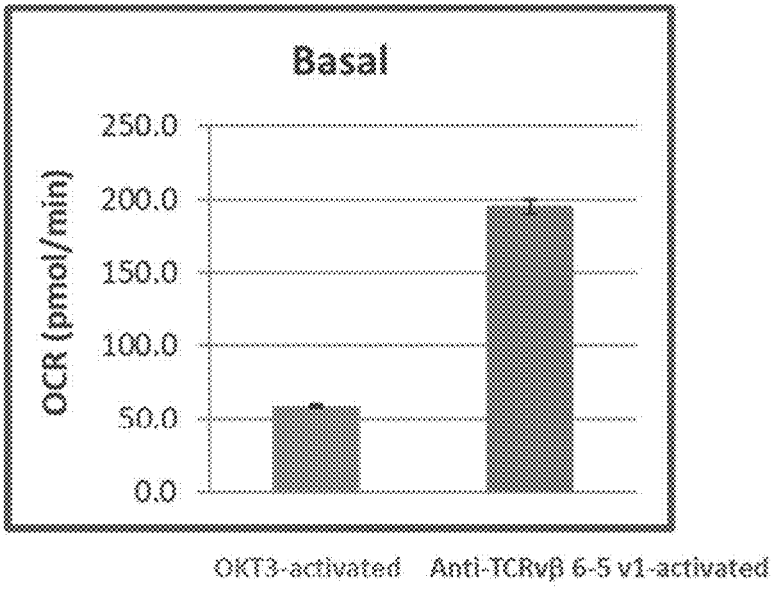
FIG. 68A shows the oxygen consumption rate (OCR) of T cells activated with the indicated antibody during basal respiration.
Figure 68B:
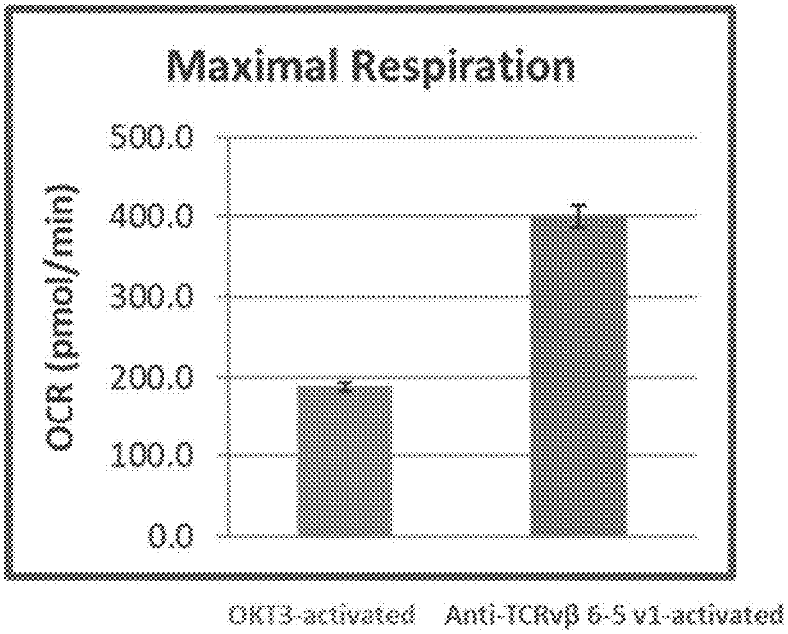
FIG. 68B shows the oxygen consumption rate (OCR) of T cells activated with the indicated antibody during maximal respiration.
Figure 68C:
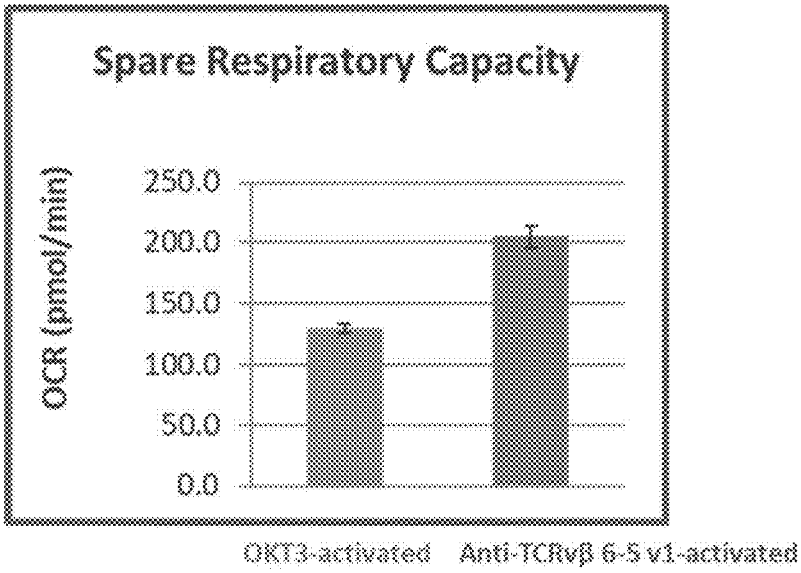
FIG. 68C shows the oxygen consumption rate (OCR) of T cells activated with the indicated antibody during spare respiratory capacity.
Figure 68D:
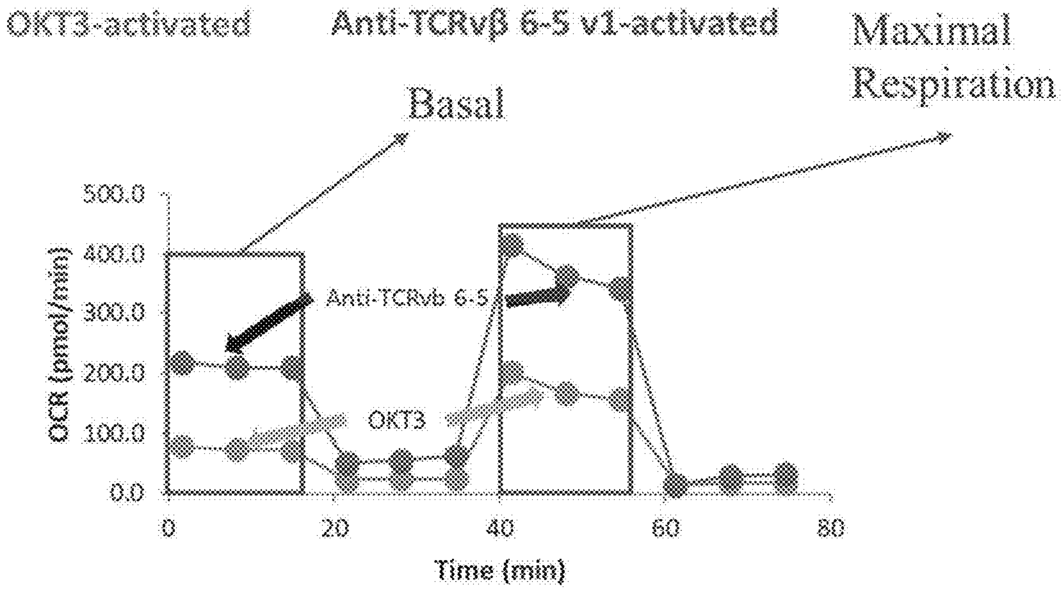
FIG. 68D is a line graph indicates the areas of basal respiration and maximal respiration as shown in FIG. 68A and FIG. 68B, respectively.

The increased mitochondrial respiration in T cells activated with anti-TCRβV 6-5 v1 antibody compared to T cells activated with the OKT3 antibody is further shown in FIG. 67, which shows the oxygen consumption rate (OCR) of T cells from about 0 to 75 minutes activated with the indicated antibody. Data in FIG. 66 is from a single donor; a second donor tested showed equal levels of ATP production in anti-TCRβV 6-5 v1 and OKT3 Ab stimulated cells (data not shown). FIGS. 68A-68C show the oxygen consumption rate (OCR) of T cells activated with the indicated antibody during basal respiration (FIG. 68A), maximal respiration (FIG. 68B), and spare respiratory capacity (FIG. 68C). Cells were plated in media containing glucose and glutamine to measure basal OCR. FCCP (ETC accelerator) was added to the cell culture medium to determine maximum respiratory capacity/max OCR. Antimycin A & Rotenone (ETC inhibitor) were added to the cell culture medium to determine spare respiratory capacity and non-mitochondrial oxygen consumption. The data presented in FIGS. 68A-68C α-TCRβV 6-5 v1 activated T cells had significantly increased basal respiration, maximal respiration, and spare respiratory capacity compared to α-CD3 (OKT3) activated T cells (data from a single donor). A second donor was tested which showed equal levels of ATP production in anti-TCRβV 6-5 v1 and OKT3 Ab stimulated cells (data not shown). FIG. 68D indicates the areas of basal respiration and maximal respiration as shown in FIG. 67A and FIG. 67B, respectively.

In order to determine if the observed increase in metabolism due to differences in T cell stimulation, or is it intrinsic to the differentiation stage of T cells activated with anti-TCRβV antibodies TCRβV 6-5+ T cells were expanded for 5 days with plate-bound anti-TCRβV 6-5 v1 Ab. Cells were then rested in IL-2 containing media for 2 days and cryopreserved. Upon thawing, cells were re-stimulated with anti-TCRβV 6-5 v1 for 3 days. Cells were then counted and equal numbers of live cells were re-seeded and stimulated with plate-bound anti-CD3 Ab (clone OKT3) or anti-TCRβV 6-5 v1, respectively, for 24 hours. Equal numbers of live cells were plated on the Seahorse cartridge and the Real-Time ATP Rate Assay was performed.

Figure 69A:
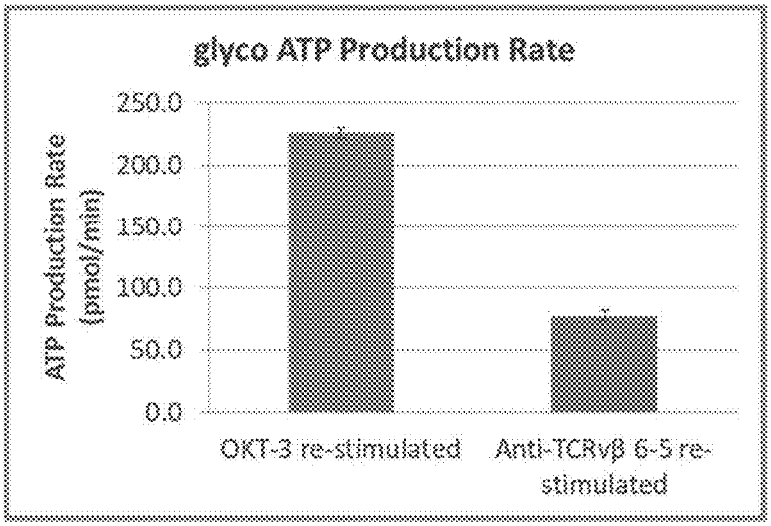
FIG. 69A is a bar graph showing ATP production from glycolysis of T cell cultures activated with anti-TCRβV 6-5 v1 and re-stimulated with the indicated antibody.
Figure 69B:
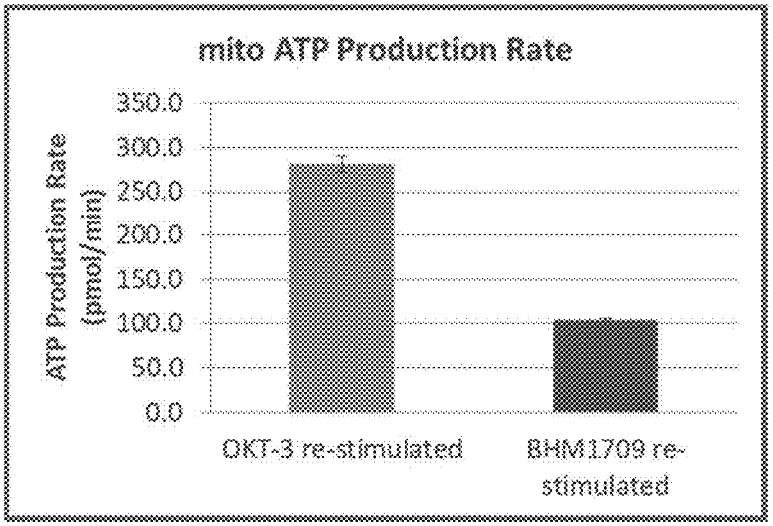
FIG. 69B is a bar graph showing ATP production from oxidative phosphorylation of T cell cultures activated with anti-TCRβV 6-5 v1 and re-stimulated with the indicated antibody.
Figure 70A:
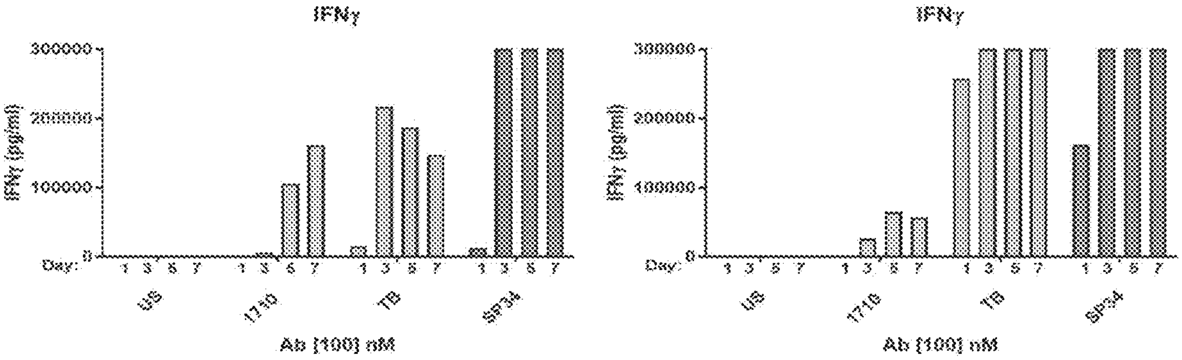
FIGS. 70A-70G are graphs showing expression of IFNg (FIG. 70A), TNFa (FIG. 70E), IL-1a (FIG. 70B), IL-1b (FIG. 70C), IL-6 (FIG. 70D), IL-10 (FIG. 70F), IL-17A (FIG. 70G) (CRS and neurotoxicity associated cytokines) with BHM1710 (anti TCRVB), a reduced affinity anti CD3 antibody (TB) and the SP34 anti CD3ε antibody.
Figure 70B:
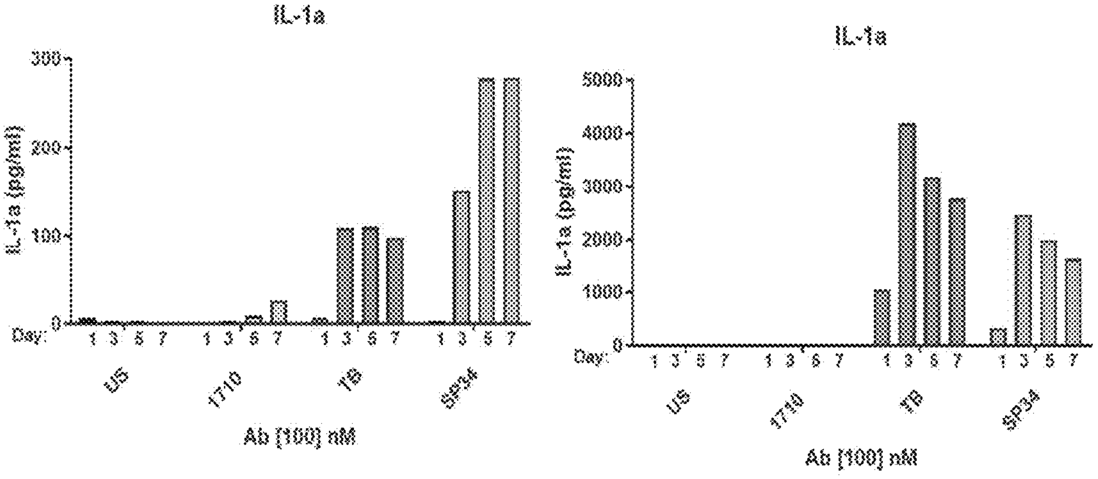
Figure 70C:
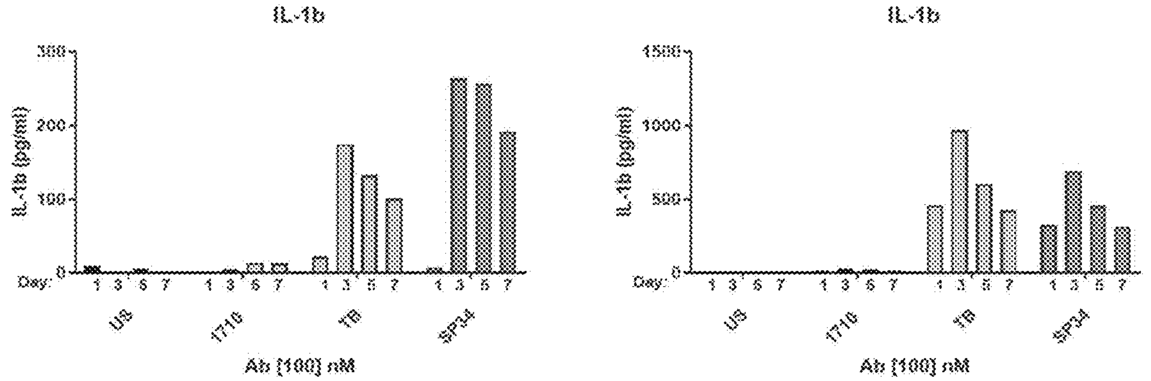
Figure 70D:
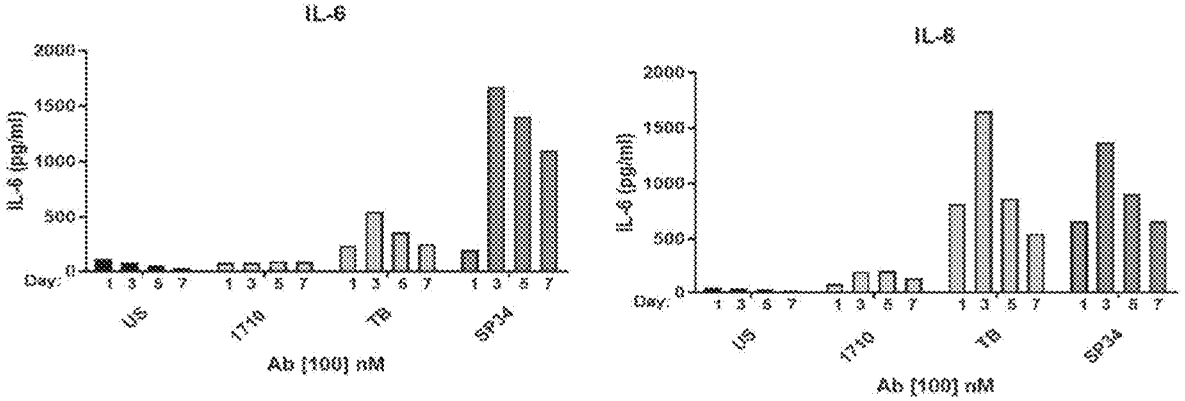
Figure 70E:
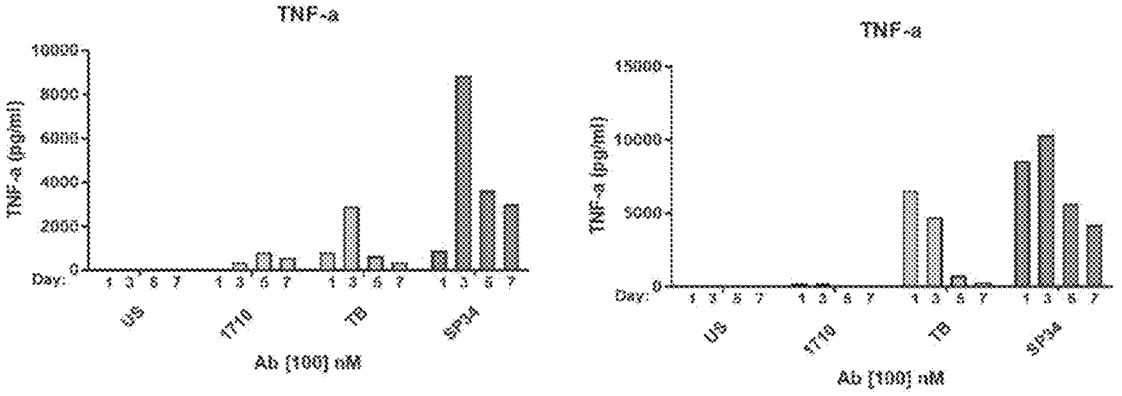
Figure 70F:
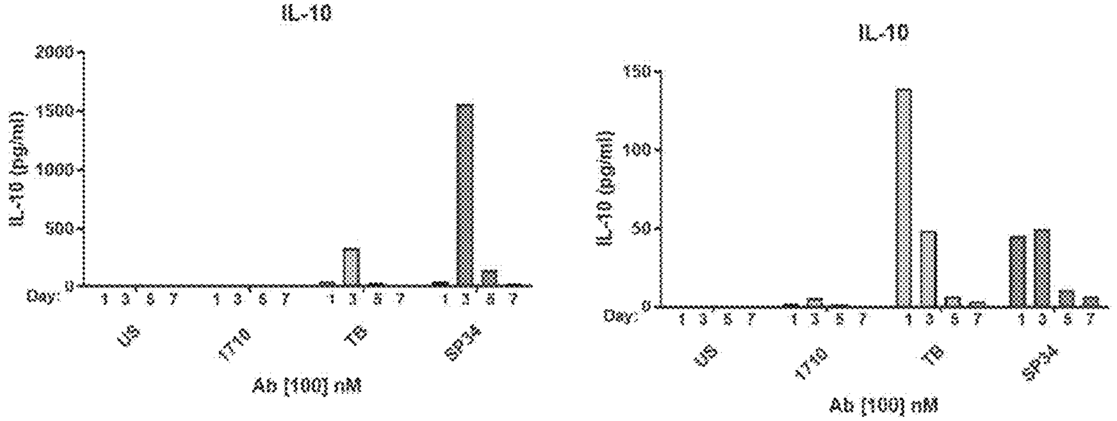
Figure 70G:
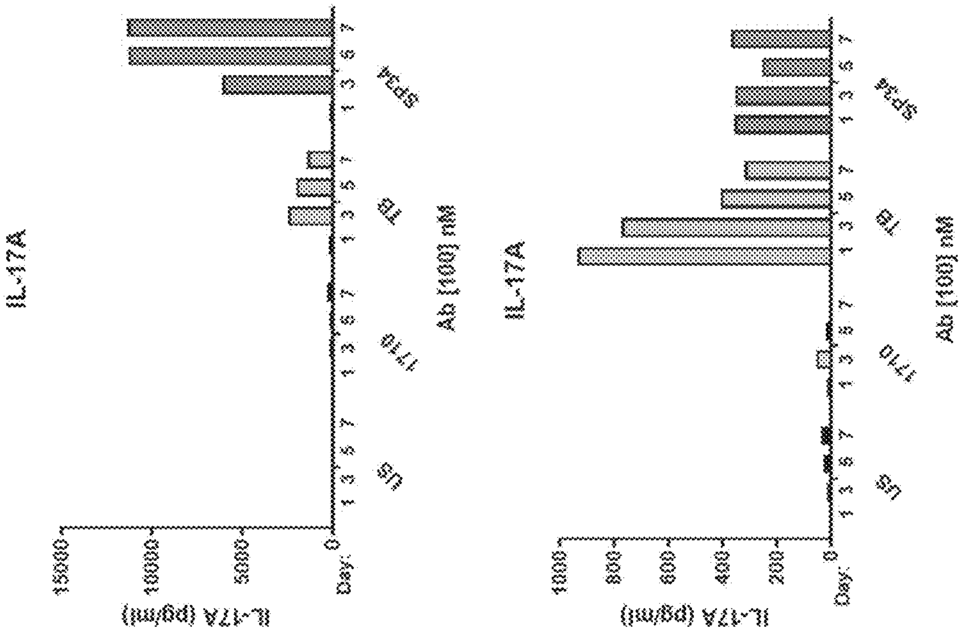

The results show that ATP production by glycolysis (FIG. 69A) and oxidative phosphorylation (FIG. 69B) by T cells activated with anti-TCRβV 6-5 v1 is significantly increased upon re-stimulation with α-CD3 antibody OKT3 versus α-TCRβV 6-5 v1 antibody. The observed increase in metabolism of T cells activated with anti-TCRβV 6-5 v1 appears to be due to intrinsic differences upon differentiation into these cells. T cells activated with anti-TCRβV 6-5 v1 have an increased metabolism compared to CD3-activated T cells, which can be further enhanced with strong T cell stimulation via OKT3.

In summary, the results show that T cells activated with anti-TCRβV antibodies have a metabolic memory phenotype. The cells are not metabolically exhausted, because exhausted T cells have a decreased metabolism. α-TCRβV 6-5 v1-stimulation induces a T cell differentiation stage, which is highly metabolically active, indicative of an effector memory phenotype. This metabolic phenotype is maintained when these cells are re-stimulated with other T cell engagers (OKT3).

Example 30: Assessment of CRS with Anti-CD3ε Antibody Compared to Anti-TCRβV Antibody To determine CRS effect of a low affinity (Teneobio) anti-CD3e antibody, a cytokine release assay (CRA) with PBMCs was used. Briefly, PBMCs from two donors were stimulated with plate-coated antibodies: anti-TCRvb6-5 v2, anti-CD3e (SP34) or Teneobio's anti-CD3e antibody. T cell activating antibodies were tested at 100 nM, the highest concentration previously shown not to induce CRS cytokines in this assay. Supernatants were collected at day 1, 3, 5 and 7. Cytokine secretion measurement (IFN-g, IL-10, IL-15, IL-17A, IL-1a, IL-1b, IL-2, IL-4, IL-6 and TNF-a) was detected using MSD analysis. The data show results from two donors.

FIGS. 70A-70F show that a reduced affinity anti CD3ε antibody (TeneoBio) induces expression of IFNg, TNFa, IL-1a, IL-1b, IL-6 (CRS and neurotoxicity associated cytokines) similar to the SP34-2 anti CD3e antibody. In contrast, the anti-TCRvb6-5 v2 of the present invention does not induce CRS or neurotoxicity associated cytokines.

In summary the data shows that Tenebio's anti-CD3e antibody induces cytokines associated with CRS and neurotoxicty in this highly sensitive PBMC CRA. Thus, Tenebio's anti-CD3e antibody has potential to induce CRS and NT as seen with SP34-based T cell-redirecting bispecific molecules. The anti-TCRvb6-5 disclosed herein does not induce CRS- and NT-associated cytokines in this assay, suggesting that in some embodiments, TCRvb6-5 based antibodies may be amenable to administration at higher doses and avoid MABEL (minimum anticipated biologic effect level) dosing regimen required for current CD3ε-based bispecific molecules.

Example 31: Anti-TCRβV Stimulated PBMC Mediated Stimulation of NK Cell Expansion To assess whether anti-TCRβV stimulated PBMCs mediate expansion of NK cells in vitro—human PBMCs were stimulated with 100 nM of plate-coated anti-TCRβV 6-5 v1 anti-CD3ε (OKT3 and SP34-2) for up to 7 days. NK cells were identified via FACS staining for CD3-/CD56+/CD16+/NKp46+ populations. NK cell count was determined by a constant μl sample (presented as relative count for each donor). NK cell-mediated target cell lysis was determined 6-days post stimulation, in which PBMCs were harvested and co-cultured with K562 target cells for 4 hours to determine cell killing, via DRAQ7 viability FACS staining.

Figure 71:
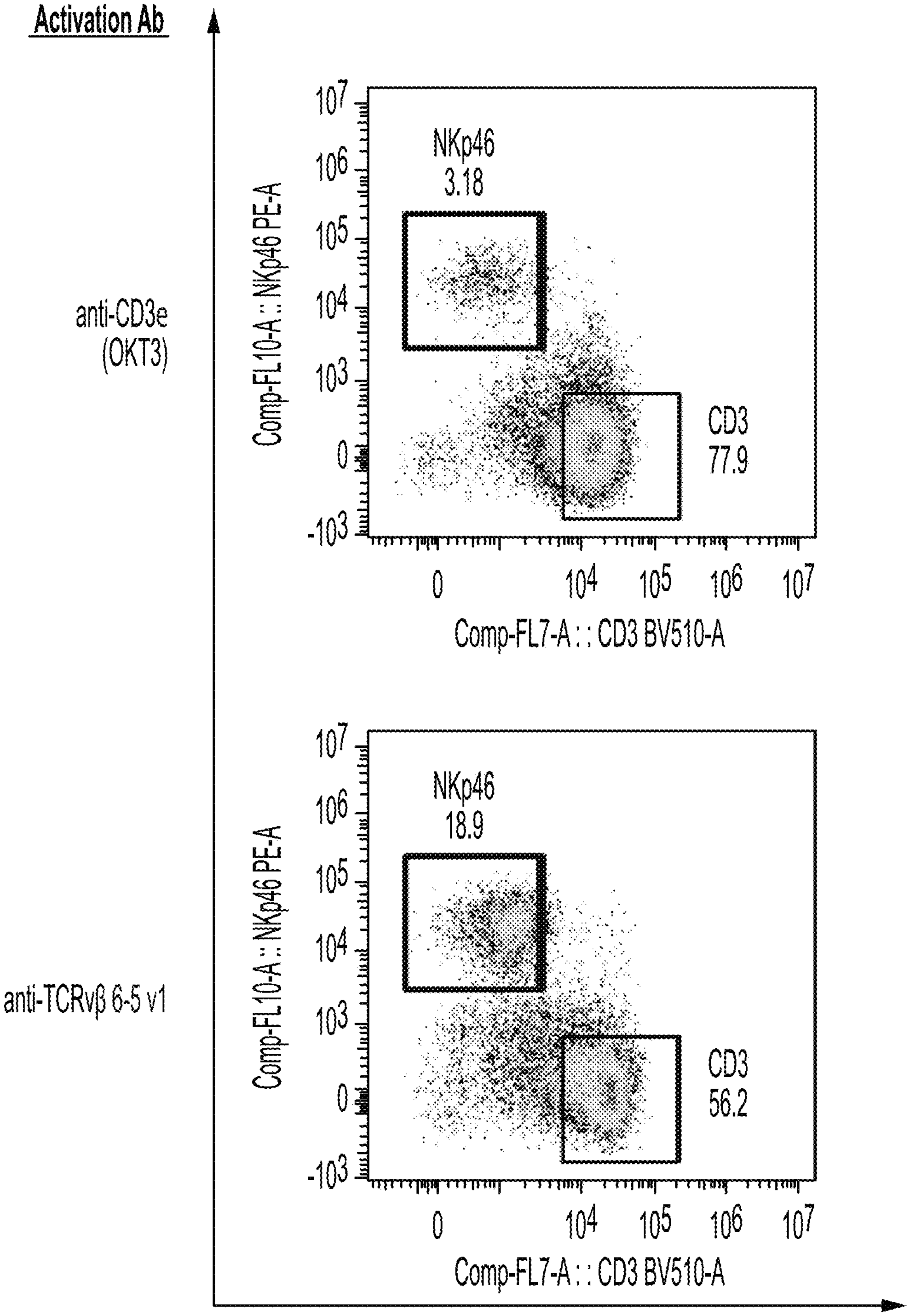
FIG. 71 is a FACS plot showing the percentage of NK cells expanded from T cell cultures activated with the indicated antibody.
Figure 72:
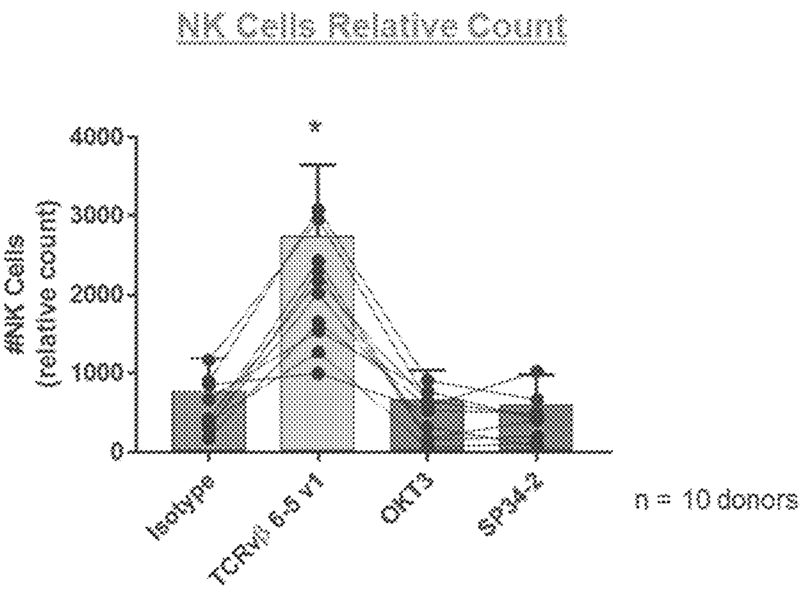
FIG. 72 is a bar graph showing the number of NK cells expanded from T cell cultures activated with the indicated antibody.
Figure 73:
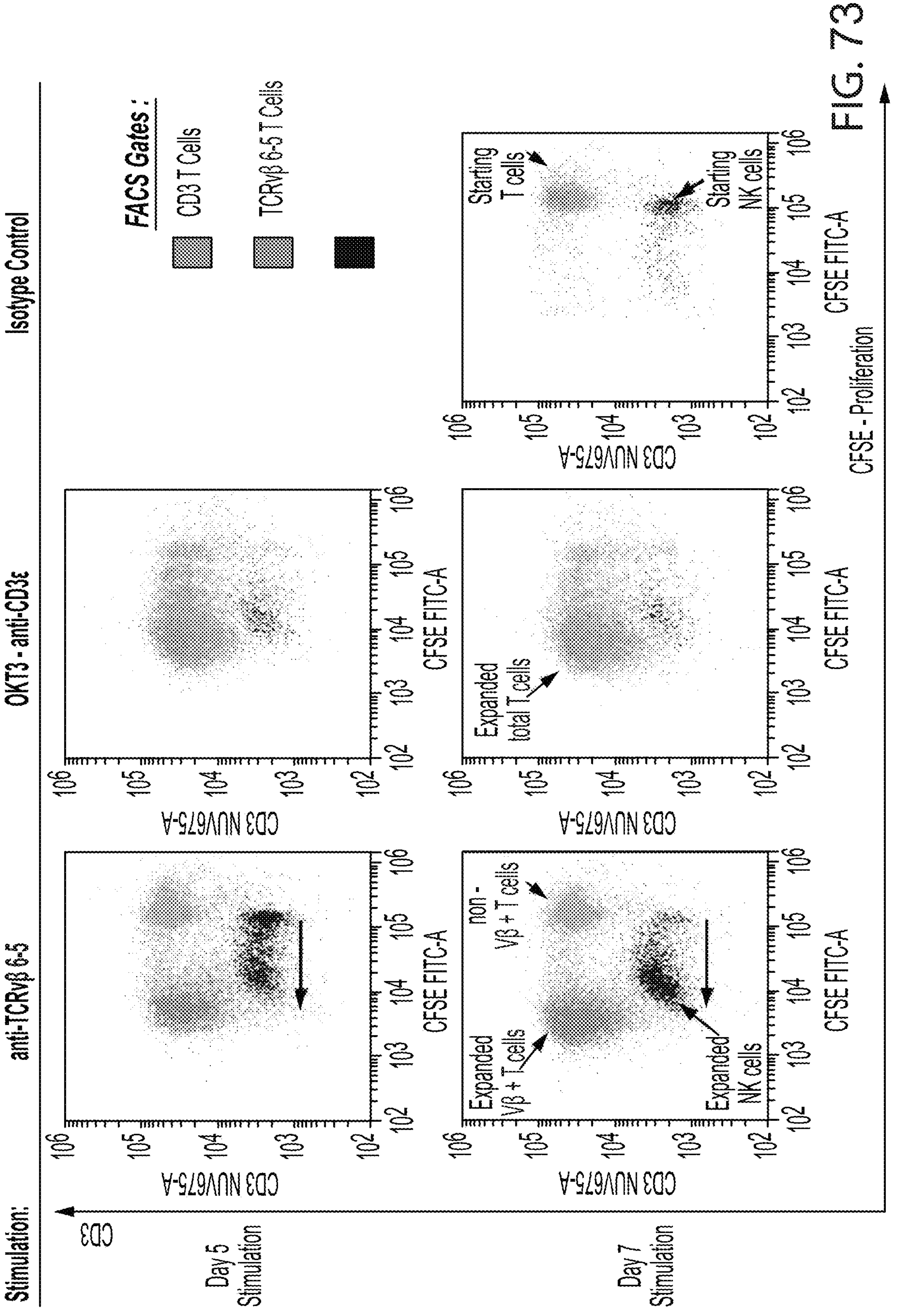
FIG. 73 shows a series of FACS plots showing NK cell proliferation induced by T cell cultures activated with the indicated antibody.
Figure 74:
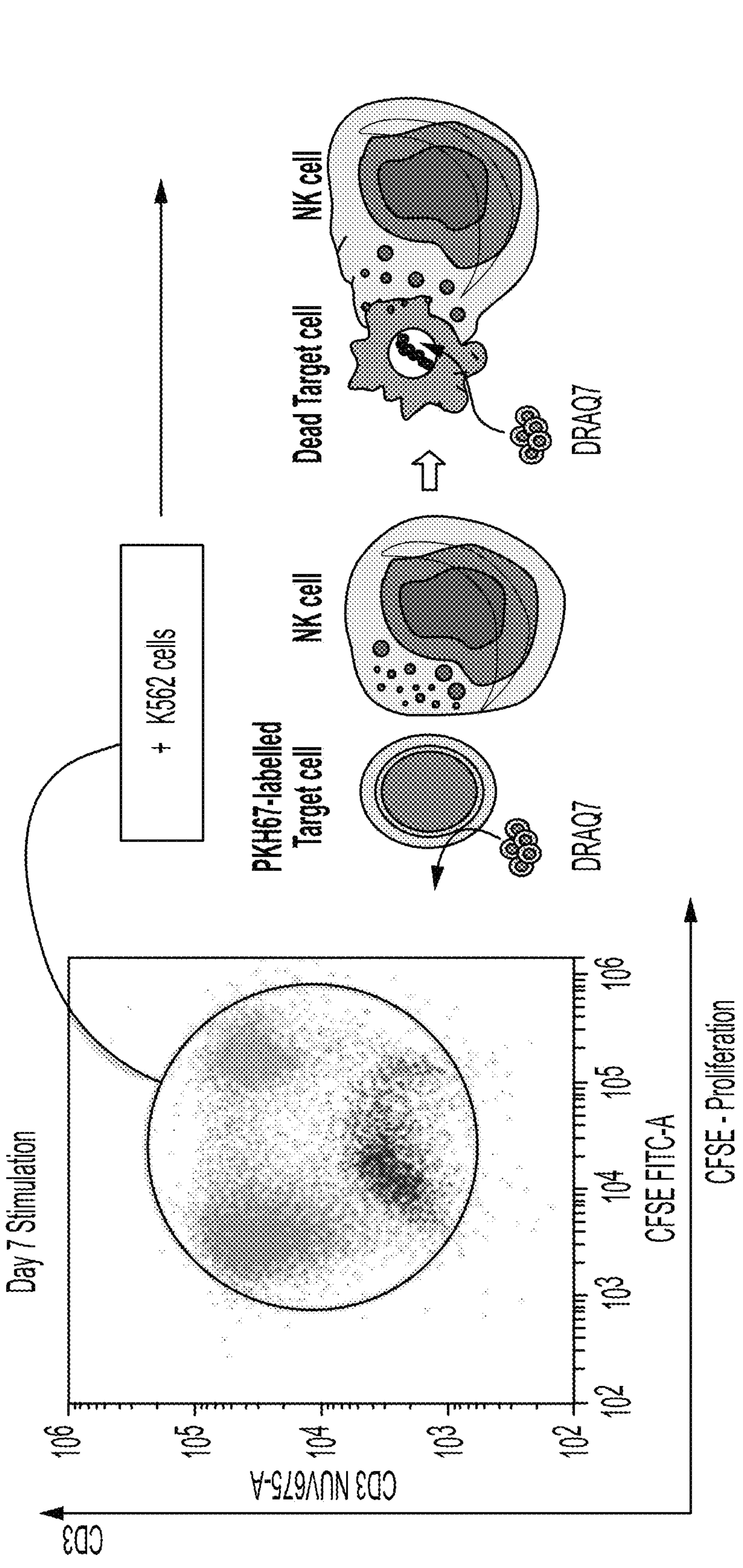
FIG. 74 is a schematic showing an assay described in Example for determining NK cell mediated lysis of target K562 cells.
Figure 75:
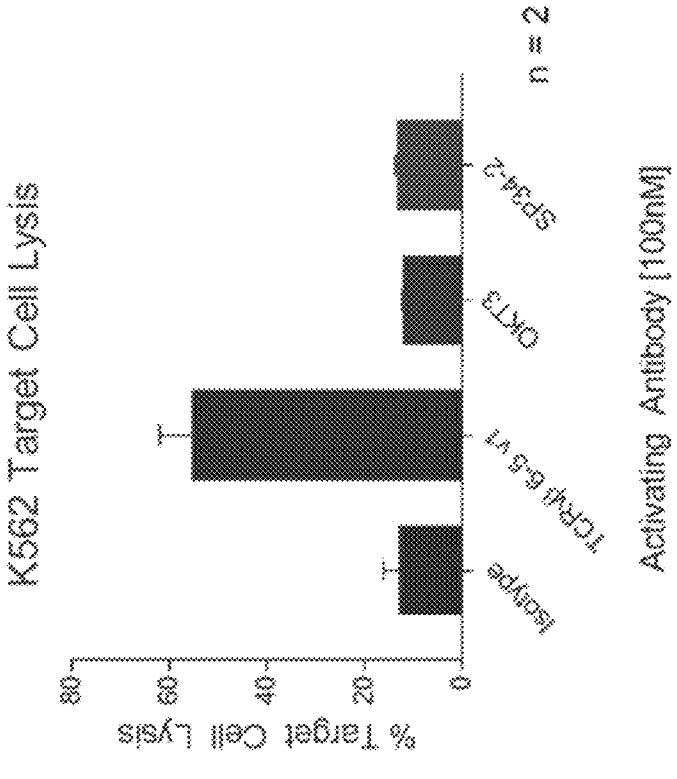
FIG. 75 is a bar graph showing the percent target cell lysis mediated by NK cells activated by PBMCs activated with the indicated antibody.

The results show that anti-TCRβV stimulation increases NK cell numbers compared to OKT3 stimulation (FIG. 71; FIG. 72). FACS CFSE staining further shows NK cell proliferation (FIG. 73). FIG. 74 and FIG. 75 show NK cell mediated lysis of target K562 cells. In summary, anti-TCRβV 6-5 antibody induces expansion of NK cells in PBMC; and this effect is unlikely to be mediated through the FcR on NK cells as anti-CD3ε antibodies did not expand NK cells. Expanded NK cells by anti-TCRβV 6-5 v1 mediate potent target cell (K562) lysis in vitro.

In addition to the experiments conducted above using the anti-TCRβV 6-5 v1 antibody, similar experiments were carried out using anti-TCRβV antibodies that recognize different clonotypes. In one experiment, the anti-TCRβV 12 antibodies: anti-TCRvβ 12-3/4 v1, anti-TCRvβ 12-3/4 v2, and anti-TCRvβ 12-3/4 v3 were used to activate/expand PBMCs using solid-phase stimulated (plate-coated) with the indicated T cell-activating antibody at 100 nM for 6 days as described above. Flow analysis was performed for NK cells using NKp46 and CD56 (CD3 negative). Data was generated from 3 donors and representative of 1 independent experiments.

Figure 76A:
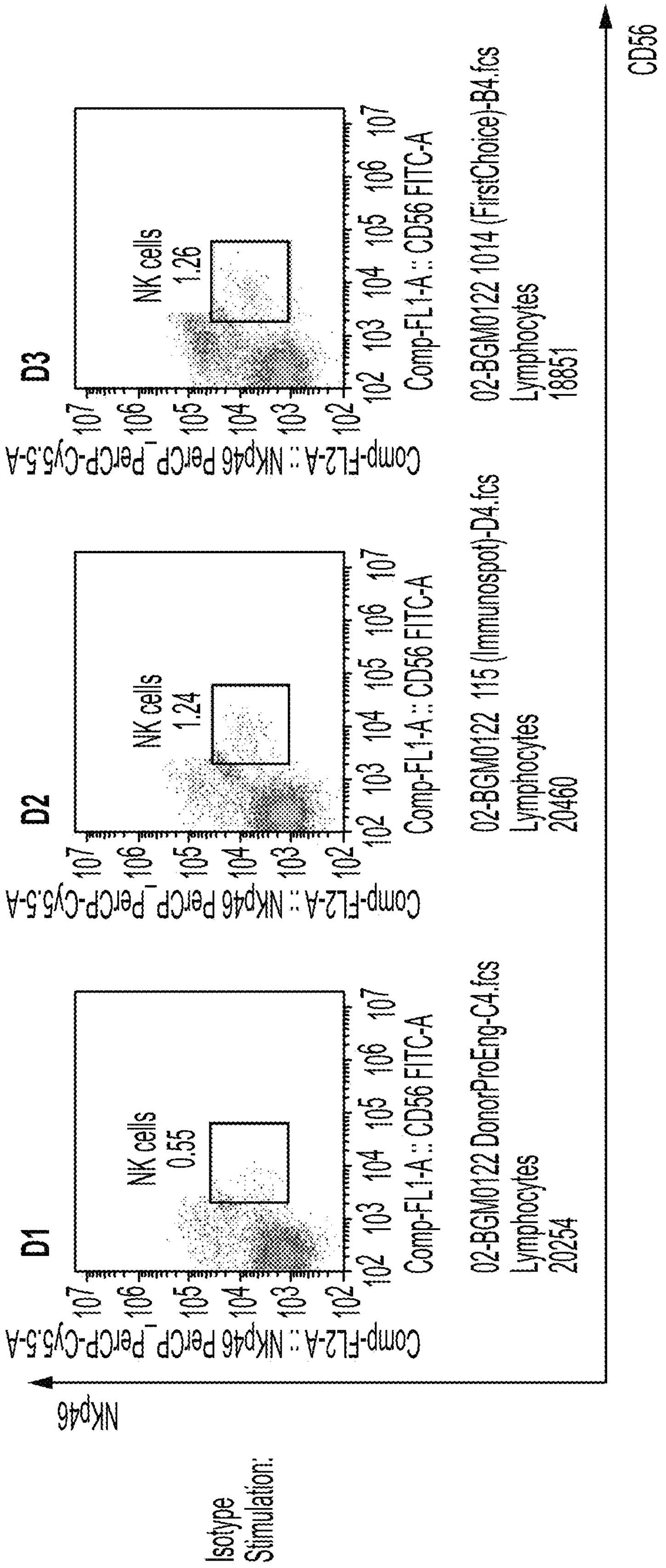
FIG. 76A shows a series of FACS plots showing the proliferation of NK cells from PBMC cultures activated/expanded with the indicated antibody (isotype control or OKT3). PBMCs from three donors (D1, D2, and D3) were analyzed.
Figure 76B:
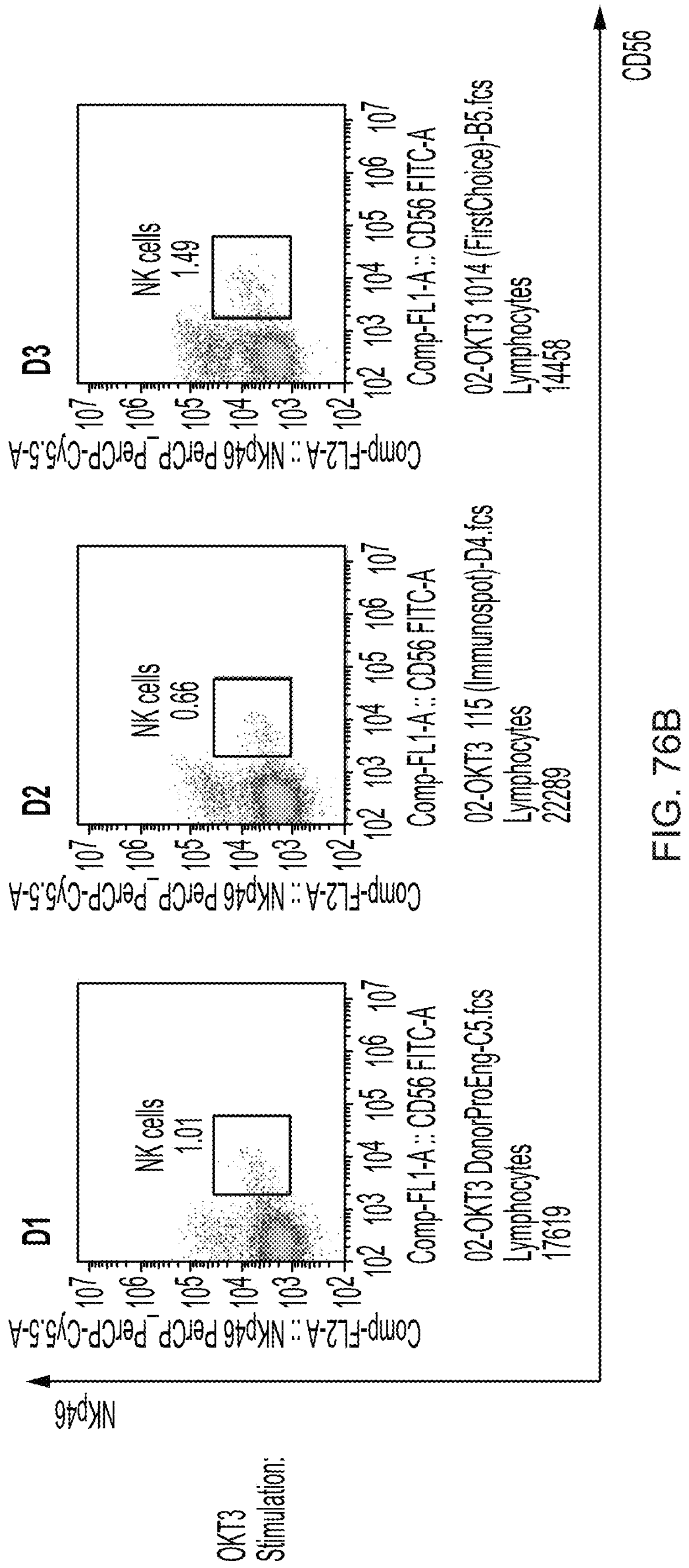
FIG. 76B shows a series of FACS plots showing the proliferation of NK cells from PBMC cultures activated/expanded with the indicated antibody (isotype control or OKT3). PBMCs from three donors (D1, D2, and D3) were analyzed, continued from FIG. 76A.
Figure 77A:
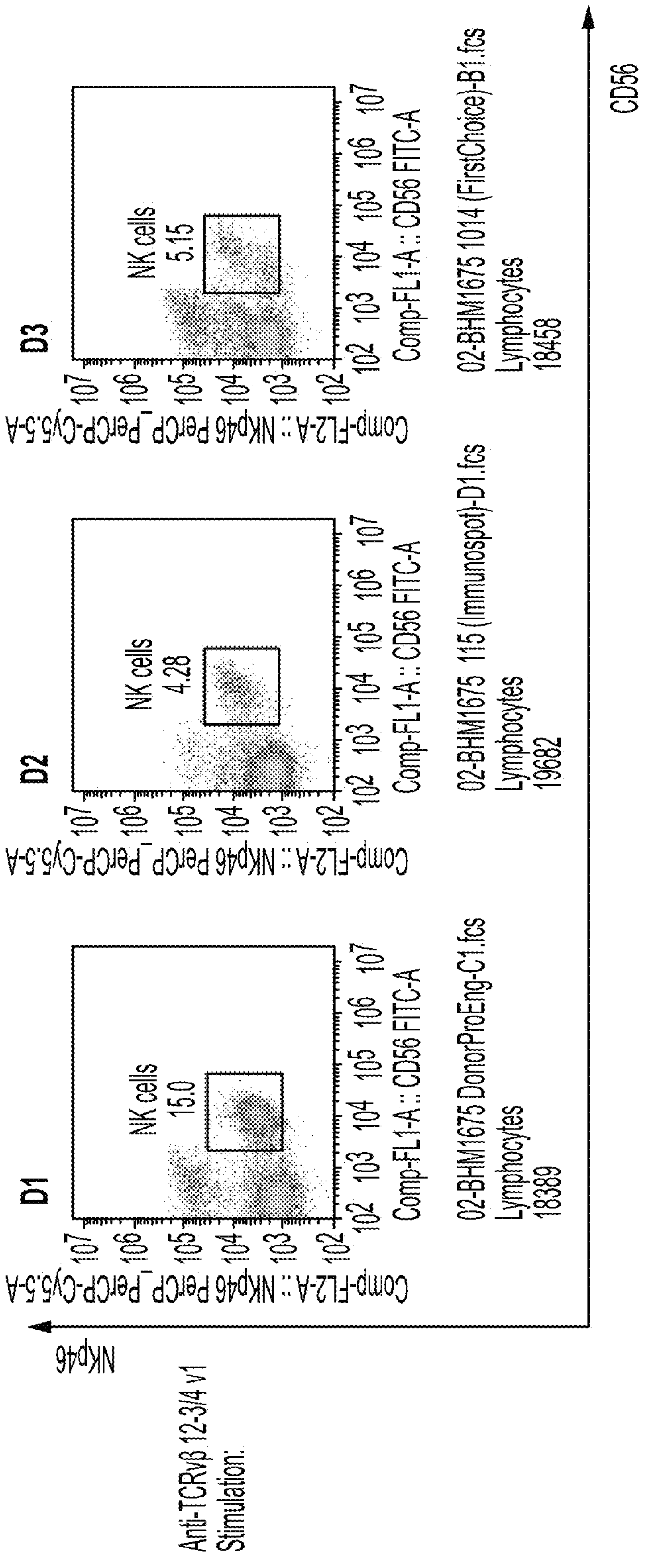
FIG. 77A shows a series of FACS plots showing the proliferation of NK cells from PBMC cultures activated/expanded with the indicated antibody (anti-TCRvβ 12-3/4 v1 or anti-TCRvβ 12-3/4 v2). PBMCs from three donors (D1, D2, and D3) were analyzed.
Figure 77B:
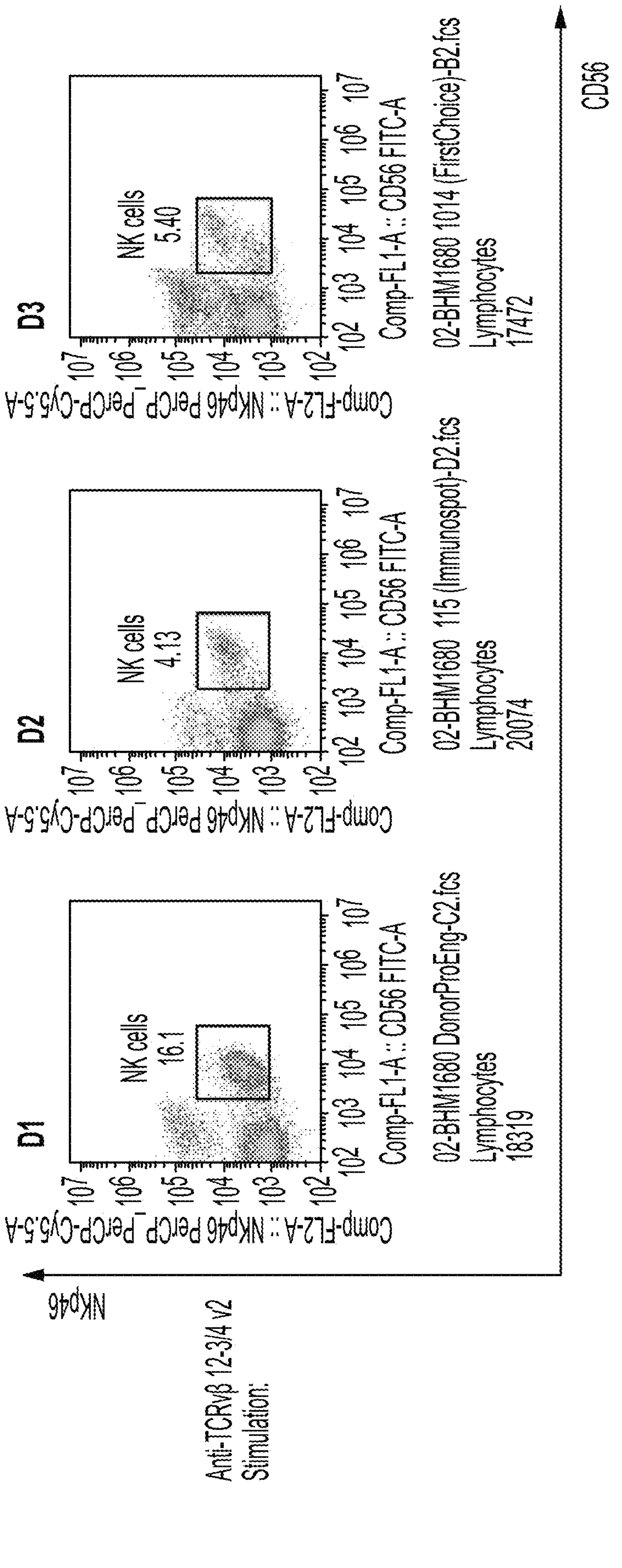
FIG. 77B shows a series of FACS plots showing the proliferation of NK cells from PBMC cultures activated/expanded with the indicated antibody (anti-TCRvβ 12-3/4 v1 or anti-TCRvβ 12-3/4 v2). PBMCs from three donors (D1, D2, and D3) were analyzed, continued from FIG. 77A.
Figure 78A:
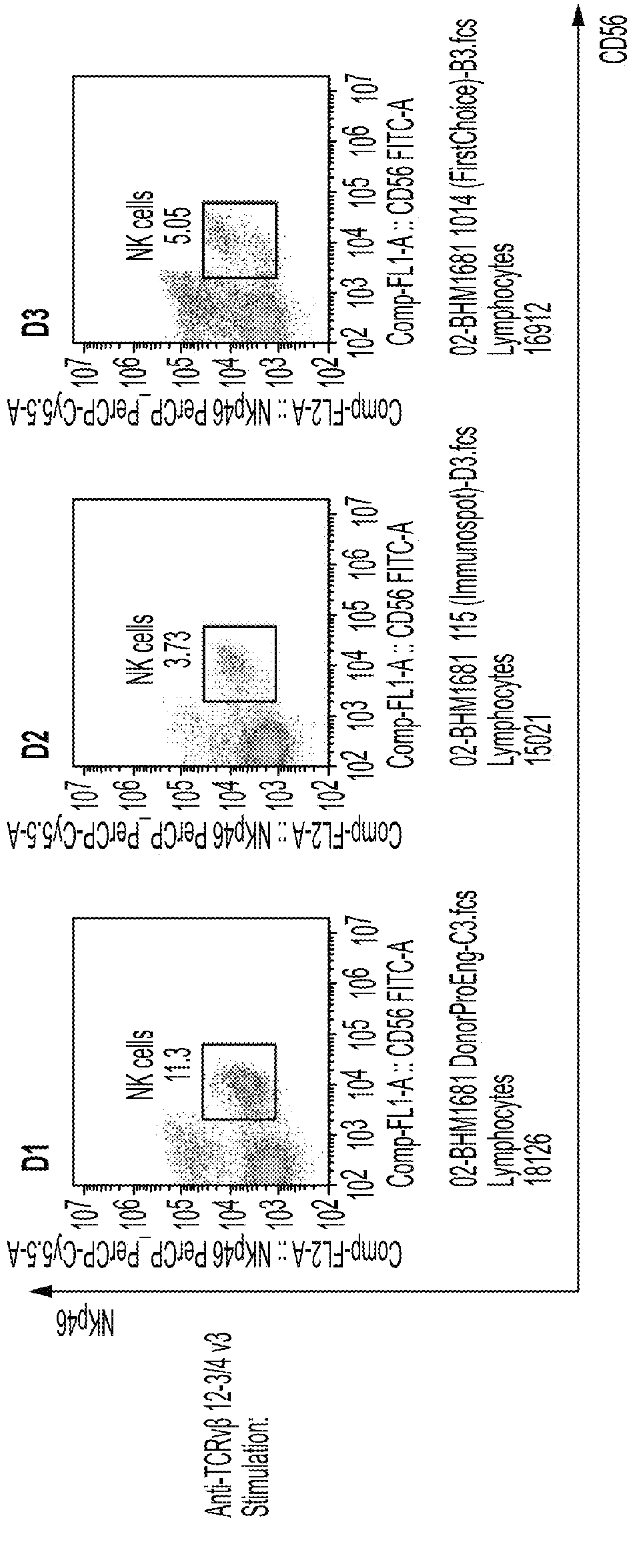
FIG. 78A shows a series of FACS plots showing the proliferation of NK cells from PBMC cultures activated/expanded with the indicated antibody (anti-TCRvβ 12-3/4 v3 or SP34-2). PBMCs from three donors (D1, D2, and D3) were analyzed.
Figure 78B:
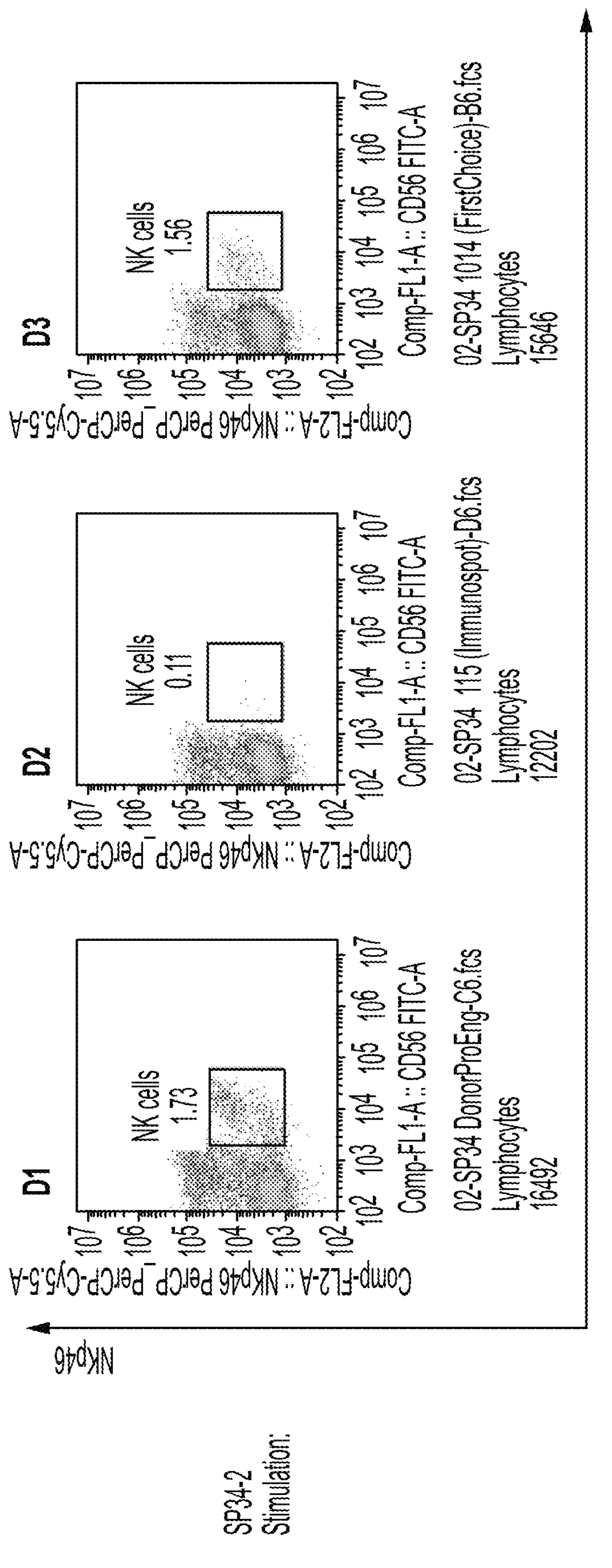
FIG. 78B shows a series of FACS plots showing the proliferation of NK cells from PBMC cultures activated/expanded with the indicated antibody (anti-TCRvβ 12-3/4 v3 or SP34-2). PBMCs from three donors (D1, D2, and D3) were analyzed, continued from FIG. 78A.

Activation/expansion of the PBMCs with isotype control or the anti-CD3ε antibody OKT3 or SP34-2 did not induce expansion of NK cells (FIG. 76; FIG. 78). However, activation/expansion of PBMCs with anti-TCRvβ 12-3/4 v1 (FIG. 77), anti-TCRvβ 12-3/4 v2 (FIG. 77), and anti-TCRvβ 12-3/4 v3 (FIG. 78) all induced NK cell expansion. In summary, the data shows that anti-TCRvb 12 antibodies are able to induce indirect expansion of NK cells from PBMC cultures in vitro.

Example 32: Concentration Response to Anti-TCRβV Stimulation In Vitro

Figure 79:
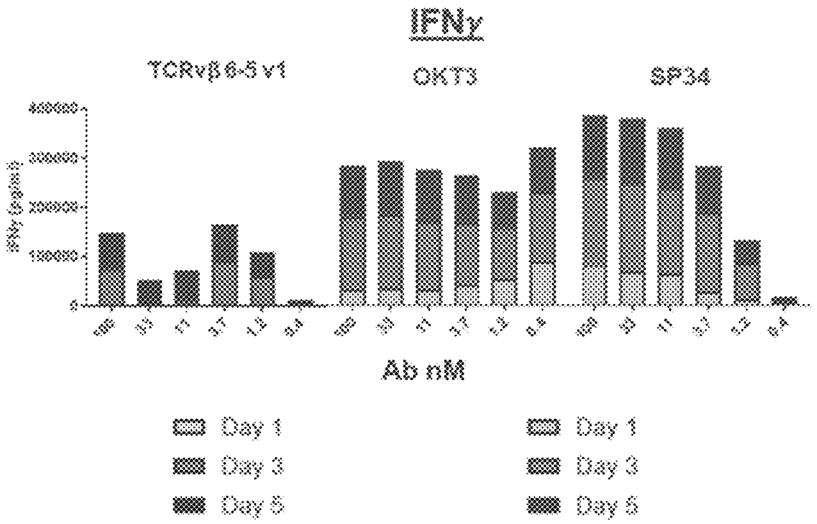
FIG. 79 is a bar graph showing the level of secreted IFNγ by T cells activated/expanded with the indicated antibody (anti-TCRβV 6-5 v1, OKT3, or SP34) and cultured with said antibody for the indicated number of days (1, 3, or 5).
Figure 80:
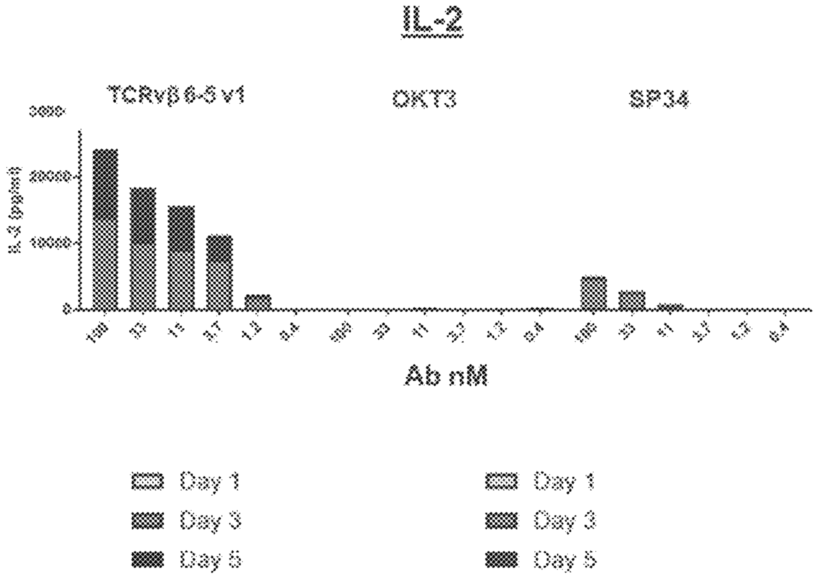
FIG. 80 is a bar graph showing the level of secreted IL-2 by T cells activated/expanded with the indicated antibody (anti-TCRβV 6-5 v1, OKT3, or SP34) and cultured with said antibody for the indicated number of days (1, 3, or 5).
Figure 81:
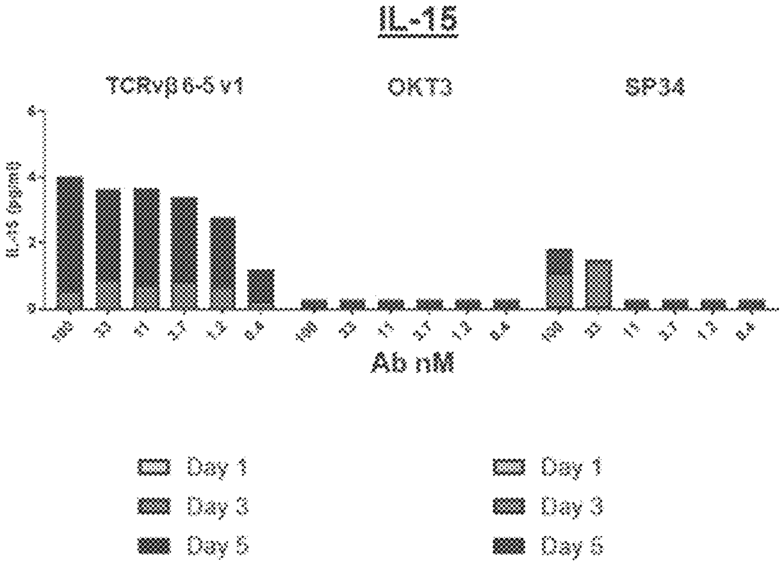
FIG. 81 is a bar graph showing the level of secreted IL-15 by T cells activated/expanded with the indicated antibody (anti-TCRβV 6-5 v1, OKT3, or SP34) and cultured with said antibody for the indicated number of days (1, 3, or 5).
Figure 82:
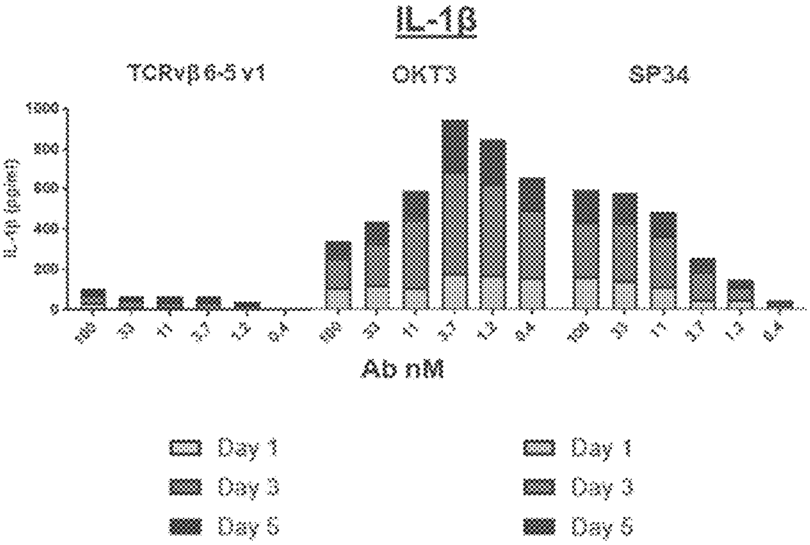
FIG. 82 is a bar graph showing the level of secreted IL-1β by T cells activated/expanded with the indicated antibody (anti-TCRβV 6-5 v1, OKT3, or SP34) and cultured with said antibody for the indicated number of days (1, 3, or 5).
Figure 83:
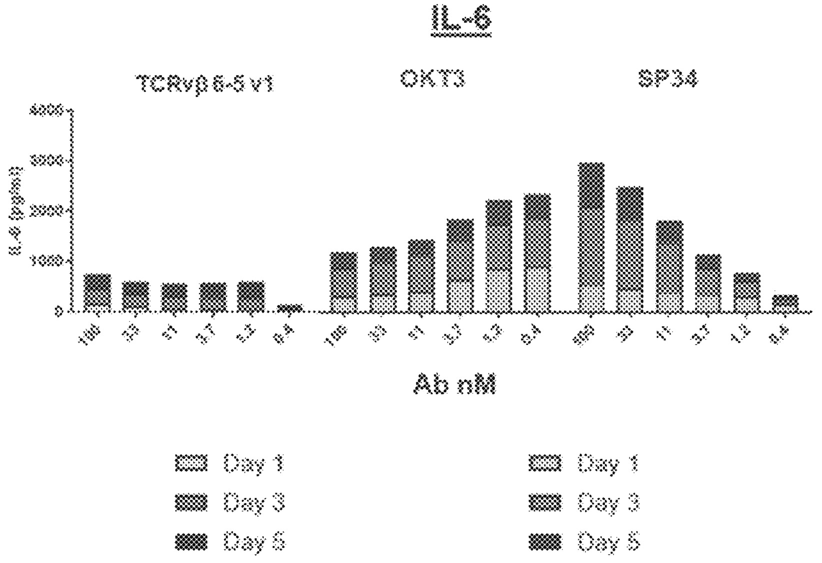
FIG. 83 is a bar graph showing the level of secreted IL-6 by T cells activated/expanded with the indicated antibody (anti-TCRβV 6-5 v1, OKT3, or SP34) and cultured with said antibody for the indicated number of days (1, 3, or 5).
Figure 84:
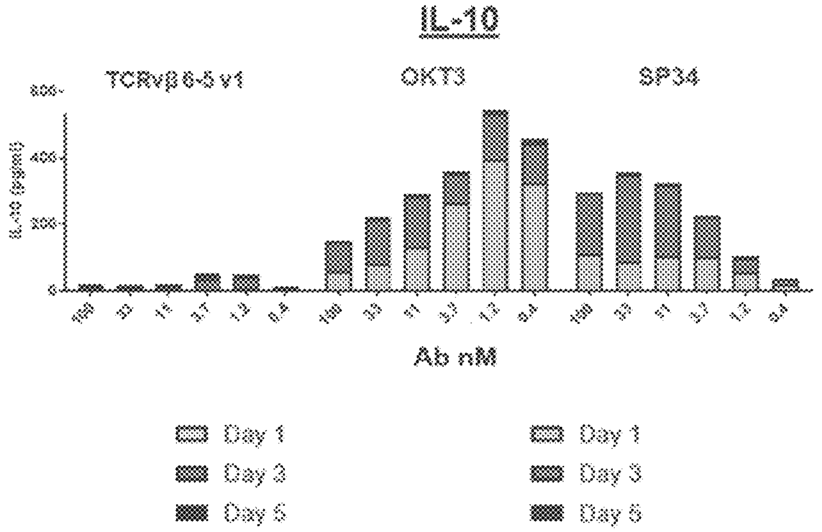
FIG. 84 is a bar graph showing the level of secreted IL-10 by T cells activated/expanded with the indicated antibody (anti-TCRβV 6-5 v1, OKT3, or SP34) and cultured with said antibody for the indicated number of days (1, 3, or 5).

Human PBMCs were solid-phase stimulated (plate-coated) with the indicated T cell-activating antibody at the indicated different concentrations: i) anti-TCRvb 6-5 v1 antibody; ii) OKT3 (anti-CD3ε antibody); or iii) SP34-2 (anti-CD3ε antibody). Supernatant were collected on day 1, day 3 and day 5 and cytokines quantified by using Meso Scale Discovery (MSD) assay. The production of cytokines IFNγ (FIG. 79), IL-2 (FIG. 80), IL-15 (FIG. 81), IL-1β (FIG. 82), IL-6 (FIG. 83), and IL-10 (FIG. 84) was analyzed. The results indicate that the lack of CRS associated cytokine induction by T cells activated with an anti-TCRvb is not a result of inhibition or toxicity due to high antibody concentrations.

Example 33: T Cells Activated by Anti-TCRβV Antibodies have a Distinct Cytokine Release Profile Compared to T Cell Activated with Anti-CD3ε Antibodies To assess the cytokine release profile of T cells activated/expanded using anti-TCRβV antibodies as compared to anti-CD3ε antibodies—PBMCs were cultured in cell culture plates coated with the immobilized anti-TCRβV antibody anti-TCRβV 6-5 v1 or an anti-CD3ε antibody, either OKT3 or SP37-2. The cells were cultured for 1-8 days, the supernatant collected, and cytokines analyzed using Meso Scale Discovery (MSD) assay. T cells samples from numerous different human donors were tested.

Figure 85:
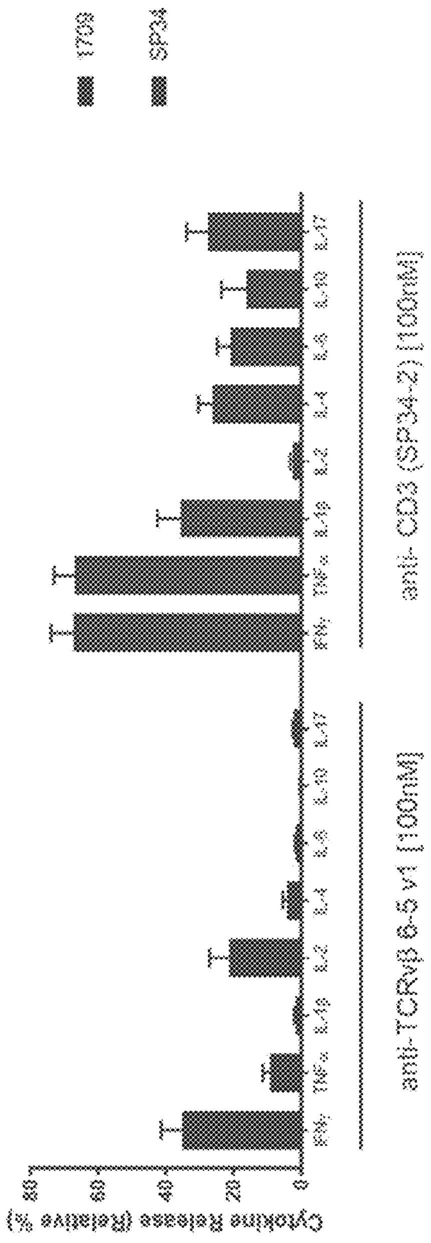
FIG. 85 is a bar graph showing the level of the indicated cytokine secreted by T cells activated/expanded with the indicated antibody (anti-TCRβV 6-5 v1 or SP34). The data includes use of 17 individual PBMC donors.

FIG. 85 shows a summary of data from 17 donors. The highest overall cytokine secretion from time points (day 3 and beyond) was used for further analysis. Each data point was normalized against the highest secretion for each donor and showed as relative % of highest (at a confidence interval of 0.95 percentile). The data shows that T cells activated/expanded with an anti-TCRβV antibody as compared to anti-CD3ε antibody release less IFNγ, TNFα, IL-1β, IL-4, IL-6, IL10, and IL-17; while releasing an increased amount of IL-2 (FIG. 85).

Figure 86A:
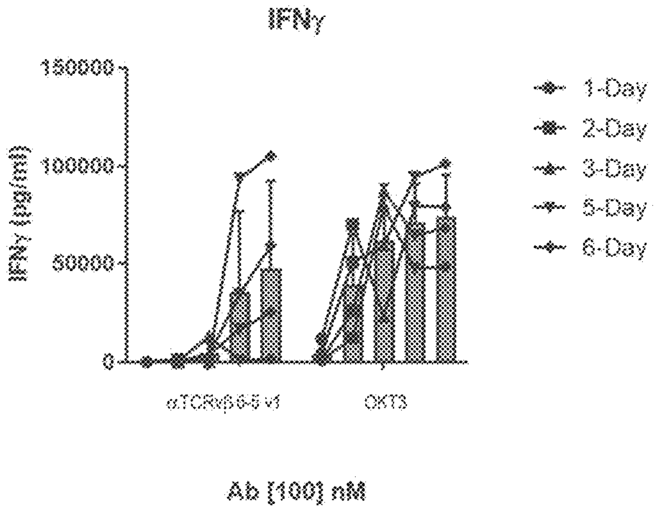
FIG. 86A is a bar graph showing the level of secreted IFNγ by T cells activated/expanded with the indicated antibody (anti-TCRβV 6-5 v1 or OKT3) and cultured with said antibody for the indicated number of days (1, 2, 3, 5, or 6).
Figure 86B:
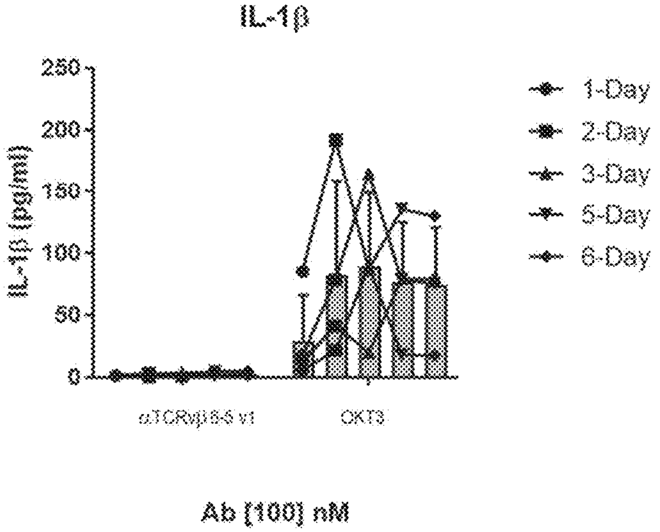
FIG. 86B is a bar graph showing the level of secreted IL-1β by T cells activated/expanded with the indicated antibody (anti-TCRβV 6-5 v1 or OKT3) and cultured with said antibody for the indicated number of days (1, 2, 3, 5, or 6).
Figure 86C:
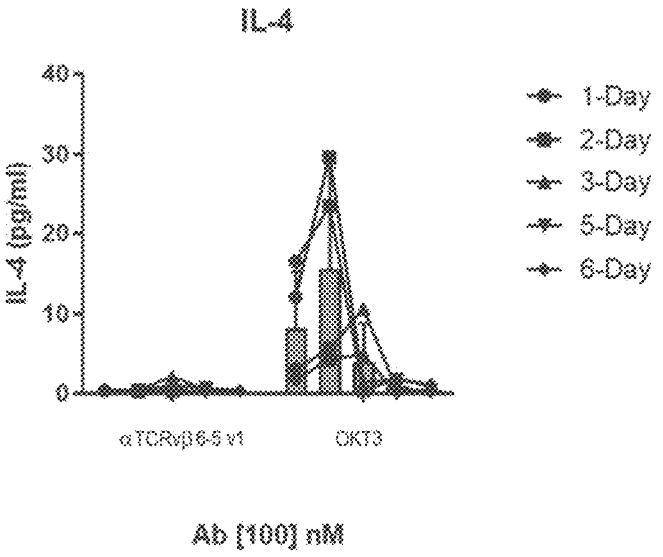
FIG. 86C is a bar graph showing the level of secreted IL-4 by T cells activated/expanded with the indicated antibody (anti-TCRβV 6-5 v1 or OKT3) and cultured with said antibody for the indicated number of days (1, 2, 3, 5, or 6).
Figure 86D:
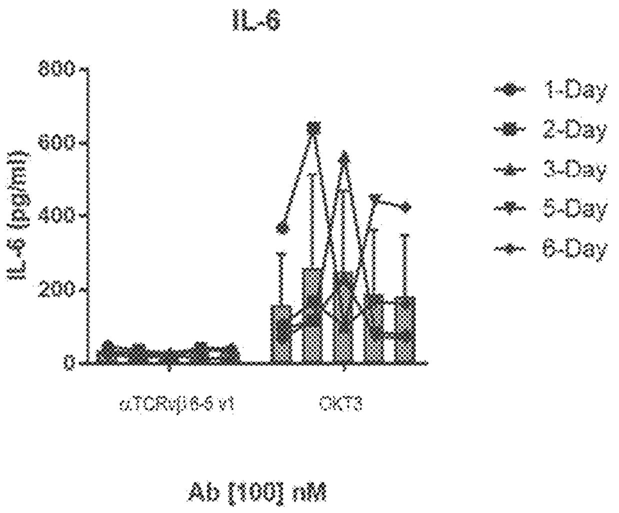
FIG. 86D is a bar graph showing the level of secreted IL-6 by T cells activated/expanded with the indicated antibody (anti-TCRβV 6-5 v1 or OKT3) and cultured with said antibody for the indicated number of days (1, 2, 3, 5, or 6).
Figure 86E:
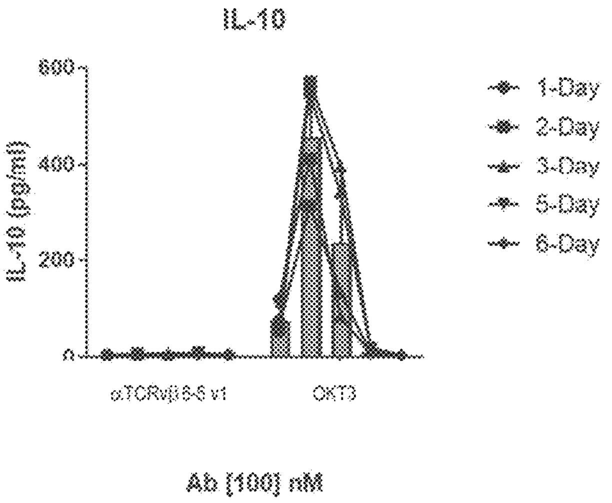
FIG. 86E is a bar graph showing the level of secreted IL-10 by T cells activated/expanded with the indicated antibody (anti-TCRβV 6-5 v1 or OKT3) and cultured with said antibody for the indicated number of days (1, 2, 3, 5, or 6).
Figure 86F:
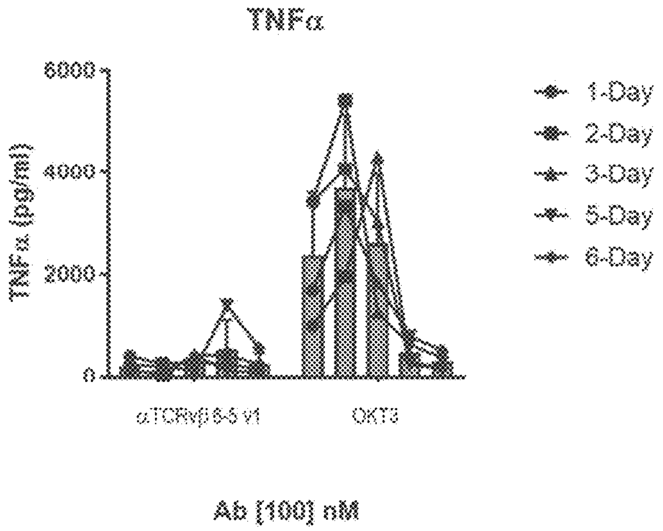
FIG. 86F is a bar graph showing the level of secreted TNFα by T cells activated/expanded with the indicated antibody (anti-TCRβV 6-5 v1 or OKT3) and cultured with said antibody for the indicated number of days (1, 2, 3, 5, or 6).
Figure 86G:
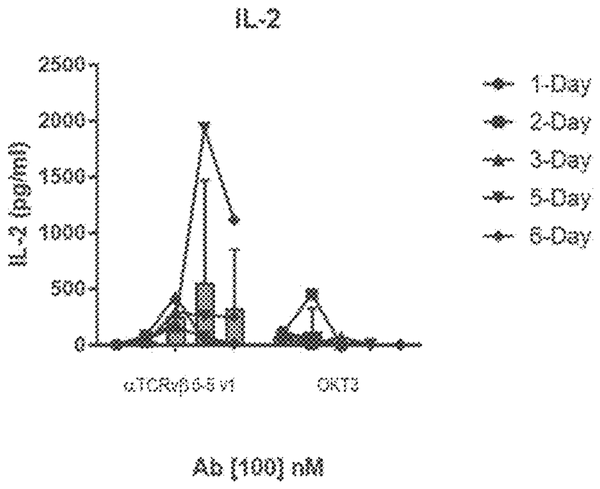
FIG. 86G is a bar graph showing the level of secreted IL-2 by T cells activated/expanded with the indicated antibody (anti-TCRβV 6-5 v1 or OKT3) and cultured with said antibody for the indicated number of days (1, 2, 3, 5, or 6).

A series of experiments using the methods previously described, but varying the culture period were conducted with PBMCs from different donors. In one experiment, PBMCs from four different donors were cultured in plates coated with immobilized anti-TCRβV antibody anti-TCRβV 6-5 v1 or an anti-CD3ε antibody, either OKT3 or SP37-2 for 1-6 days. The data confirms that T cells activated/expanded with an anti-TCRβV antibody as compared to anti-CD3ε antibody release lower levels of IFNγ (FIG. 86A), IL-1β (FIG. 86B), IL-4 (FIG. 86C), IL-6 (FIG. 86D), IL10 (FIG. 86E), and TNFα (FIG. 86F); and higher levels of IL-2 (FIG. 86G).

Figure 87A:
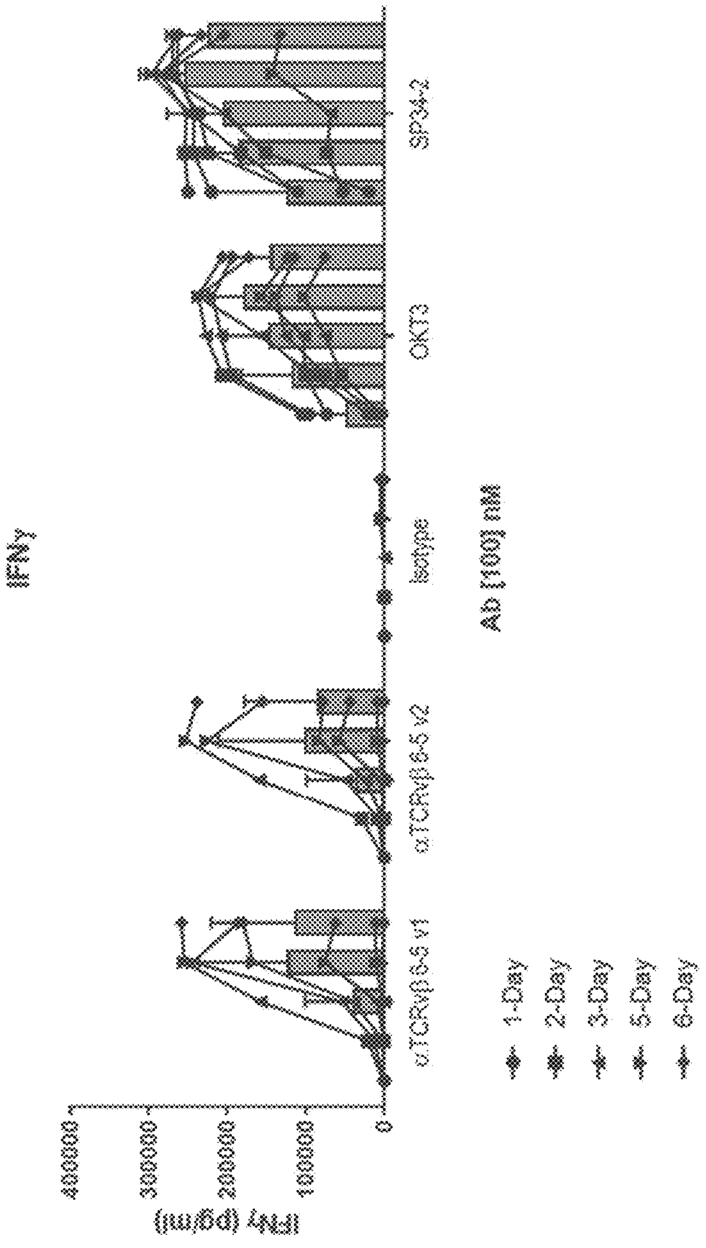
FIG. 87A is a bar graph showing the level of secreted IFNγ by T cells activated/expanded with the indicated antibody (anti-TCRβV 6-5 v1, anti-TCRβV 6-5 v1, OKT3, SP34-2, or isotype control) and cultured with said antibody for the indicated number of days (1, 2, 3, 5, or 6).
Figure 87B:
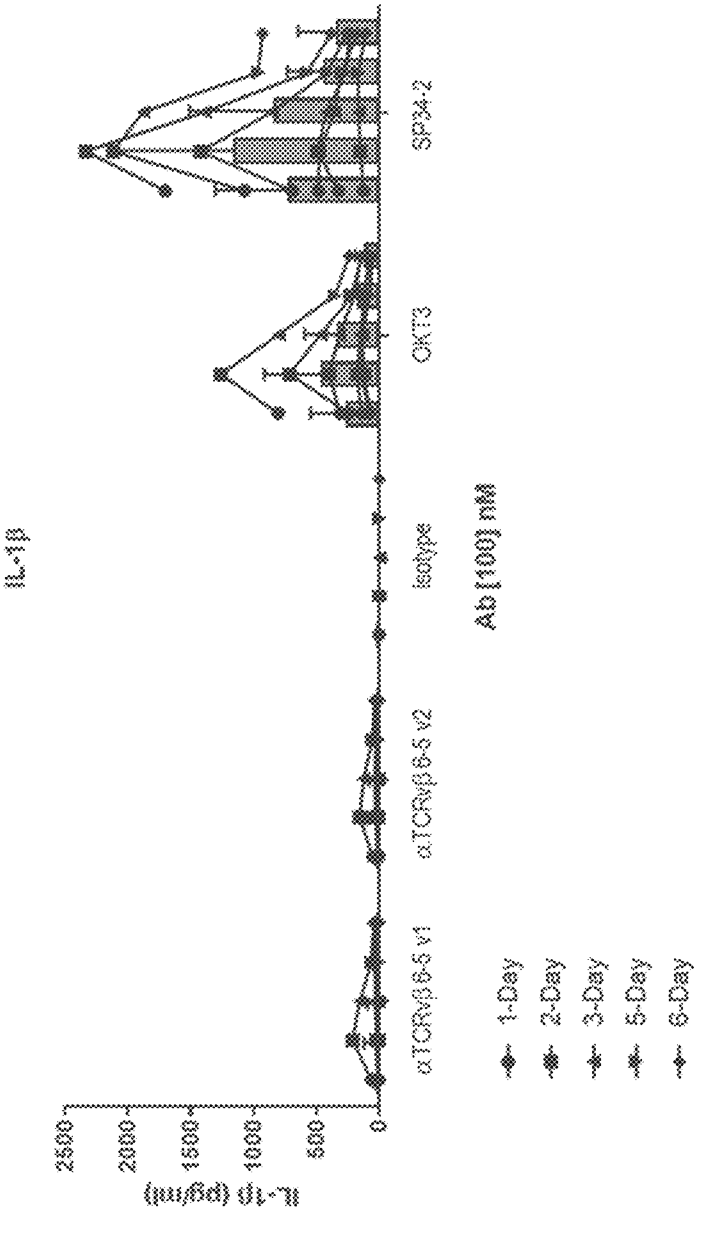
FIG. 87B is a bar graph showing the level of secreted IL-1β by T cells activated/expanded with the indicated antibody (anti-TCRβV 6-5 v1, anti-TCRβV 6-5 v1, OKT3, SP34-2, or isotype control) and cultured with said antibody for the indicated number of days (1, 2, 3, 5, or 6).
Figure 87C:
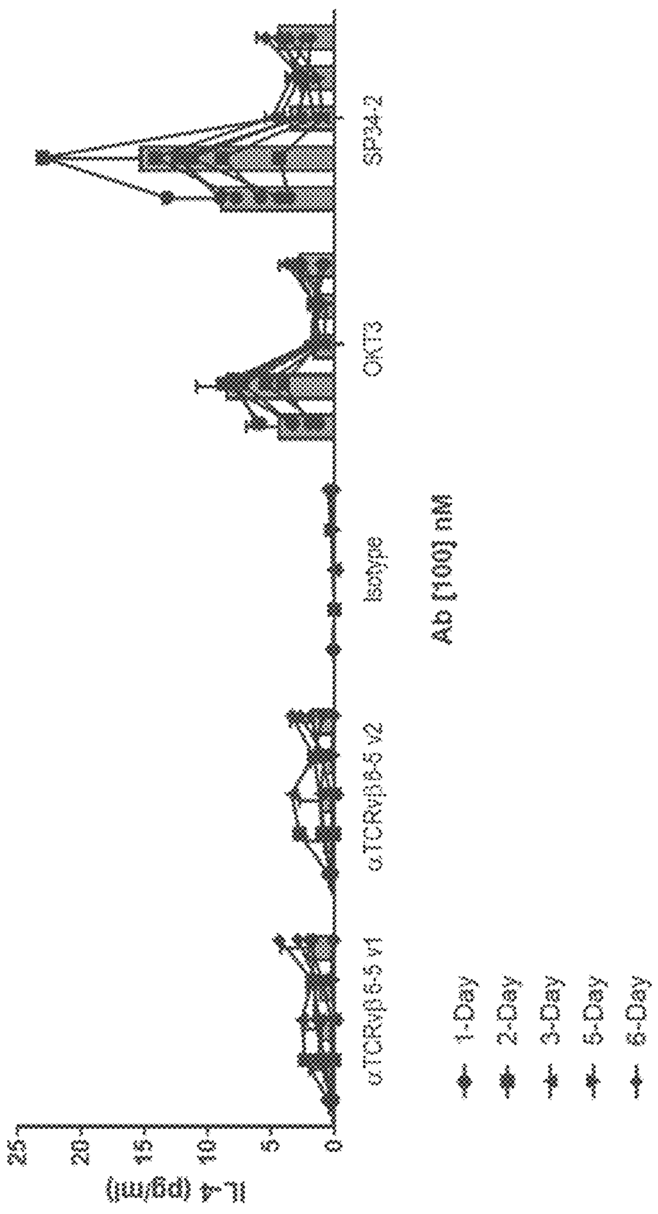
FIG. 87C is a bar graph showing the level of secreted IL-4 by T cells activated/expanded with the indicated antibody (anti-TCRβV 6-5 v1, anti-TCRβV 6-5 v1, OKT3, SP34-2, or isotype control) and cultured with said antibody for the indicated number of days (1, 2, 3, 5, or 6).
Figure 87D:
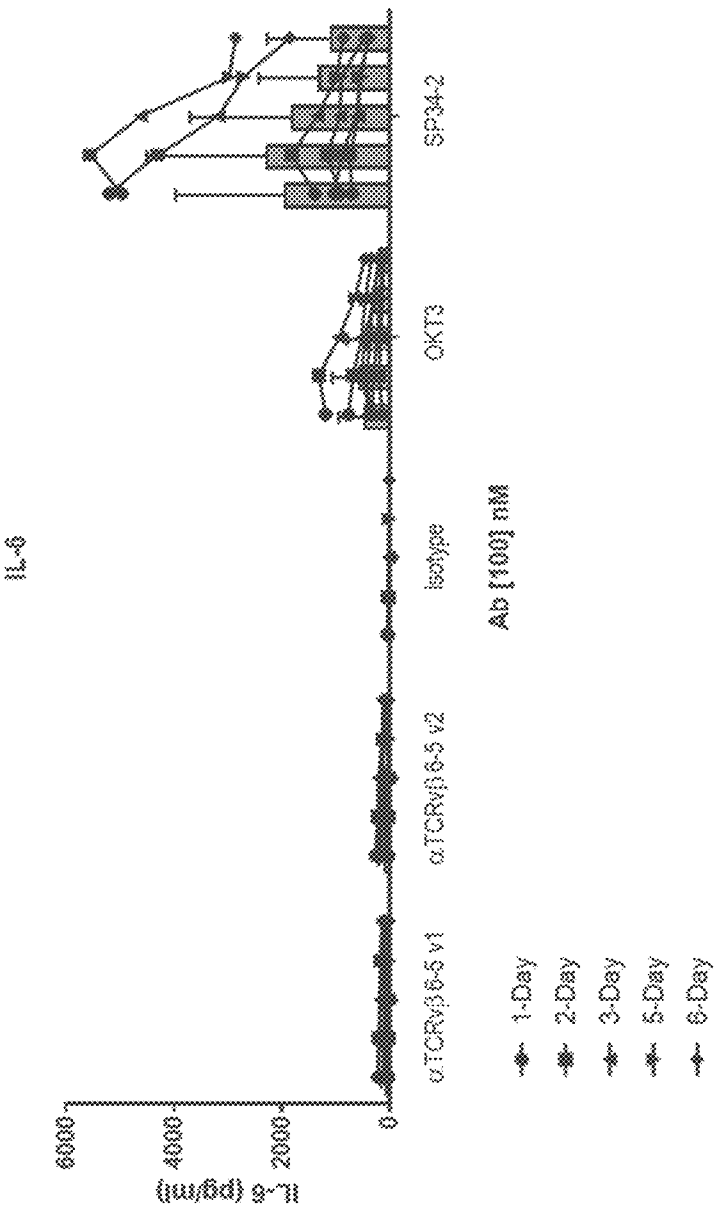
FIG. 87D is a bar graph showing the level of secreted IL-6 by T cells activated/expanded with the indicated antibody (anti-TCRβV 6-5 v1, anti-TCRβV 6-5 v1, OKT3, SP34-2, or isotype control) and cultured with said antibody for the indicated number of days (1, 2, 3, 5, or 6).
Figure 87E:
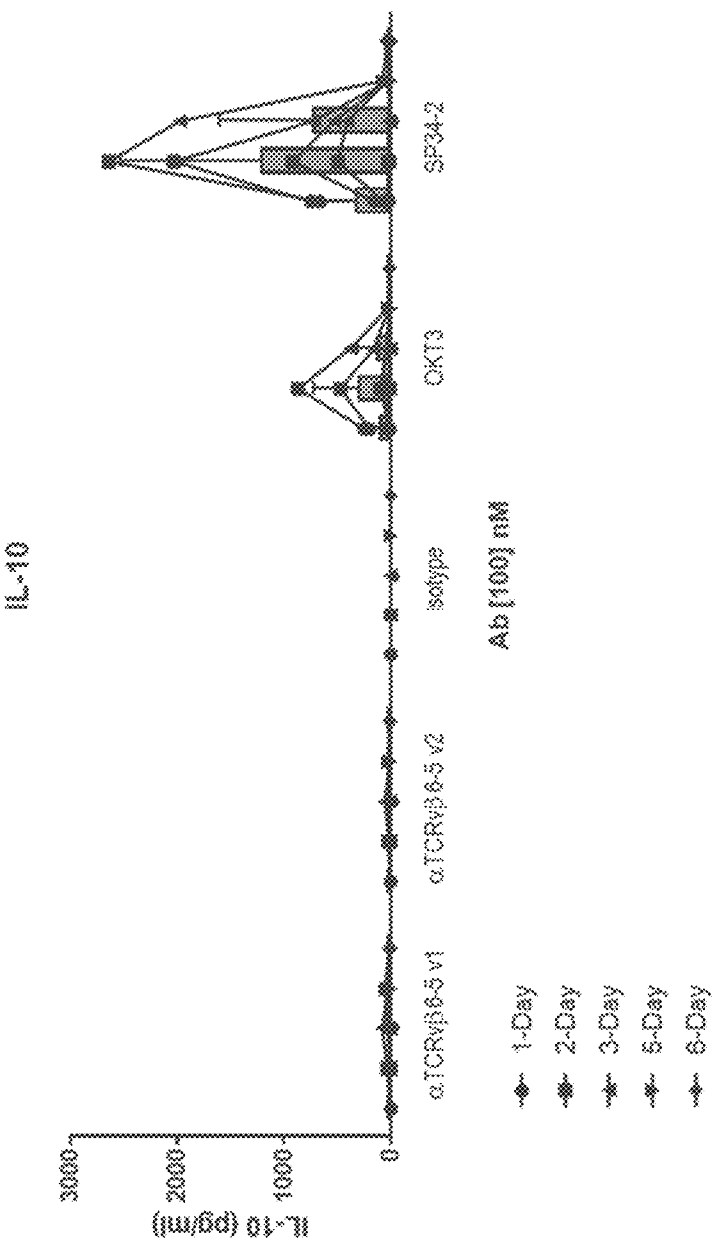
FIG. 87E is a bar graph showing the level of secreted IL-10 by T cells activated/expanded with the indicated antibody (anti-TCRβV 6-5 v1, anti-TCRβV 6-5 v1, OKT3, SP34-2, or isotype control) and cultured with said antibody for the indicated number of days (1, 2, 3, 5, or 6).
Figure 87F:
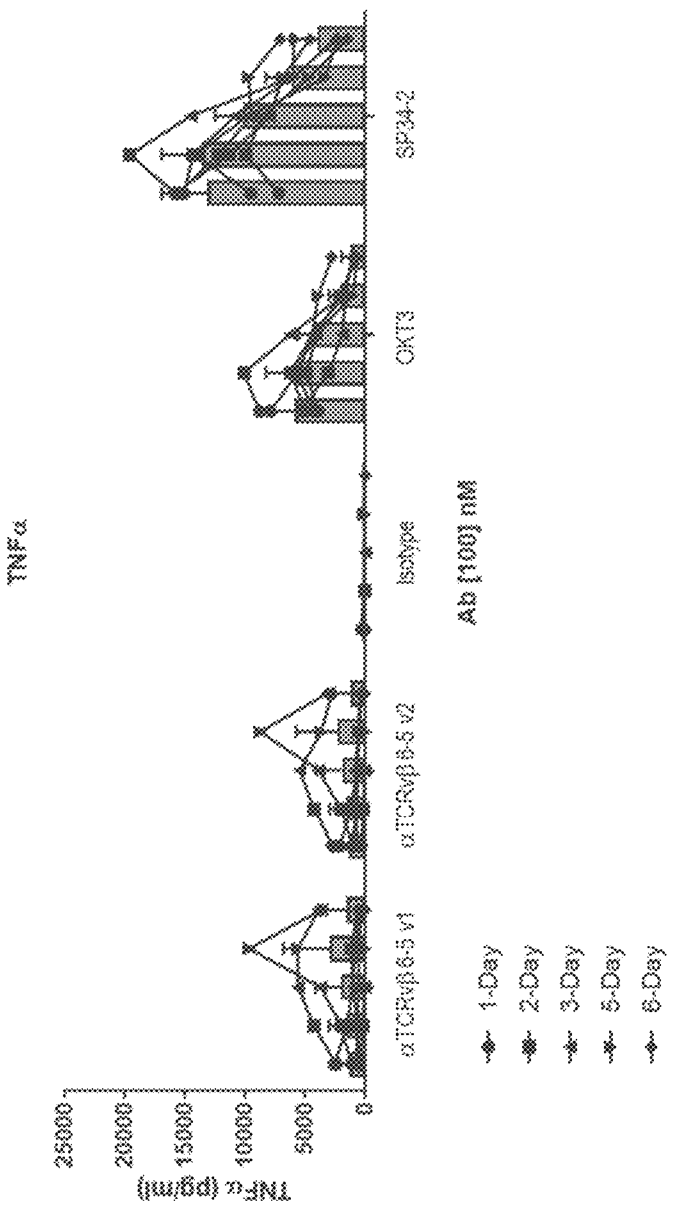
FIG. 87F is a bar graph showing the level of secreted TNFα by T cells activated/expanded with the indicated antibody (anti-TCRβV 6-5 v1, anti-TCRβV 6-5 v1, OKT3, SP34-2, or isotype control) and cultured with said antibody for the indicated number of days (1, 2, 3, 5, or 6).
Figure 87G:
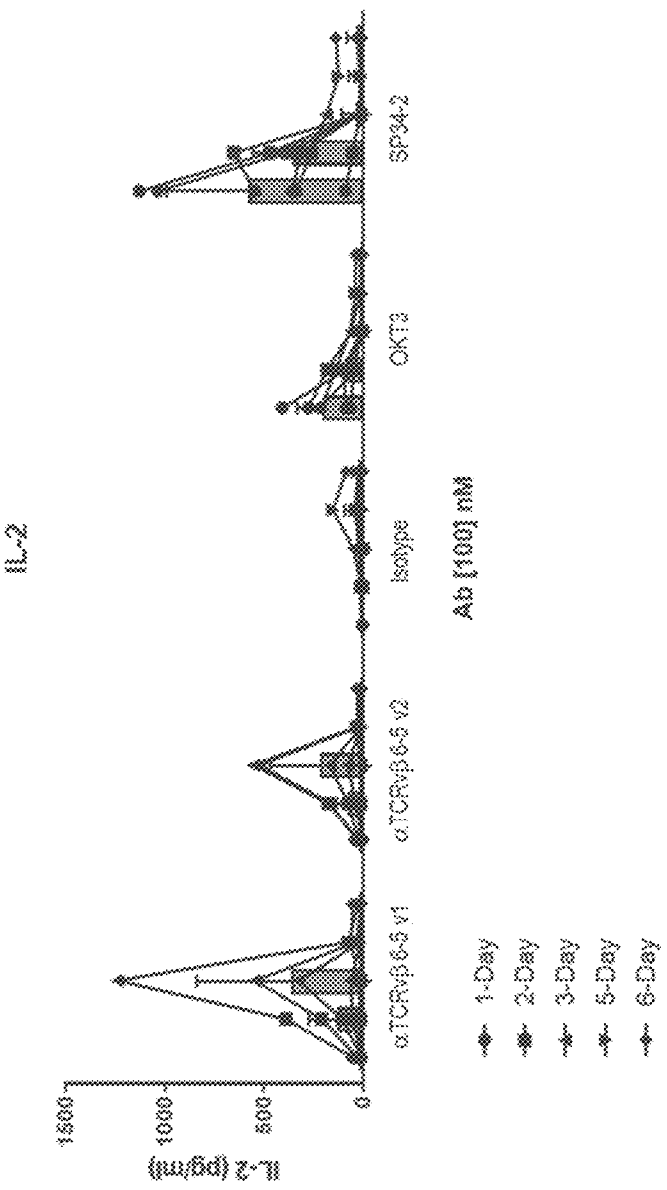
FIG. 87G is a bar graph showing the level of secreted IL-2 by T cells activated/expanded with the indicated antibody (anti-TCRβV 6-5 v1, anti-TCRβV 6-5 v1, OKT3, SP34-2, or isotype control) and cultured with said antibody for the indicated number of days (1, 2, 3, 5, or 6).

In a second experiment, PBMCs from six different donors were cultured in plates coated with immobilized anti-TCRβV antibody, either anti-TCRβV 6-5 v1 or anti-TCRβV 6-5 v1; or an anti-CD3ε antibody, either OKT3 or SP37-2 for 1-6 days, or isotype control. The data confirms that T cells activated/expanded with an anti-TCRβV antibody as compared to anti-CD3ε antibody release lower levels of IFNγ (FIG. 87A), IL-1β (FIG. 87B), IL-4 (FIG. 87C), I1-6 (FIG. 87D), IL10 (FIG. 87E), and TNFα (FIG. 87F); and higher levels of IL-2 (FIG. 87G).

Figure 88A:
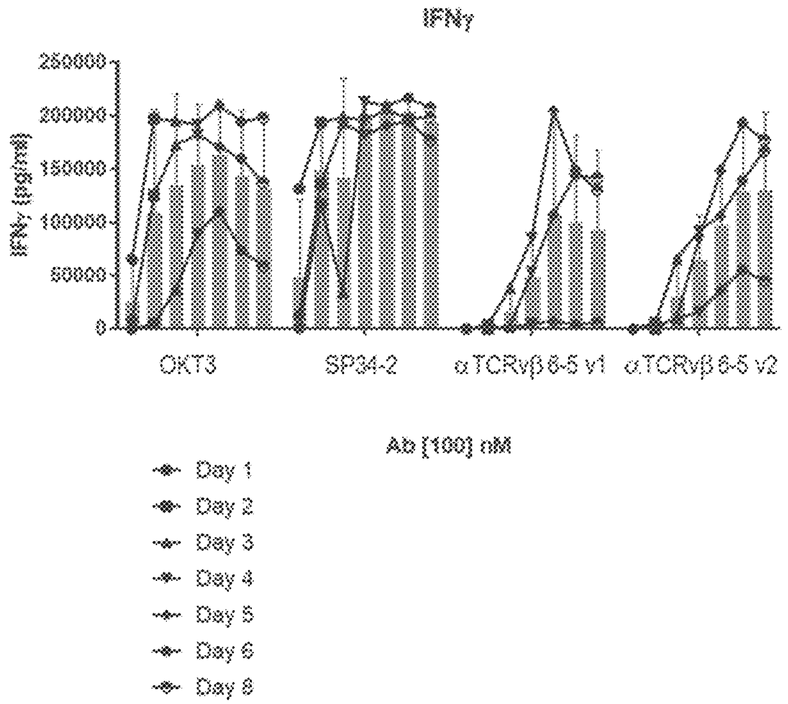
FIG. 88A is a bar graph showing the level of secreted IFNγ by T cells activated/expanded with the indicated antibody (anti-TCRβV 6-5 v1, anti-TCRβV 6-5 v1, OKT3, or SP34-2) and cultured with said antibody for the indicated number of days (1, 2, 3, 4, 5, 6, or 8).
Figure 88B:
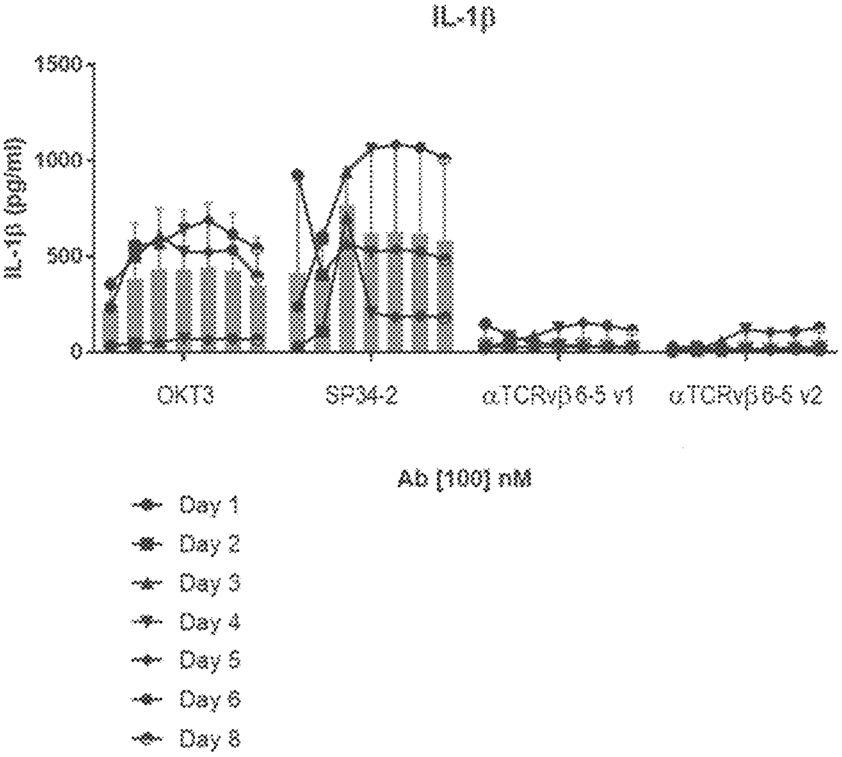
FIG. 88B is a bar graph showing the level of secreted IL-1β by T cells activated/expanded with the indicated antibody (anti-TCRβV 6-5 v1, anti-TCRβV 6-5 v1, OKT3, or SP34-2) and cultured with said antibody for the indicated number of days (1, 2, 3, 4, 5, 6, or 8).
Figure 88C:
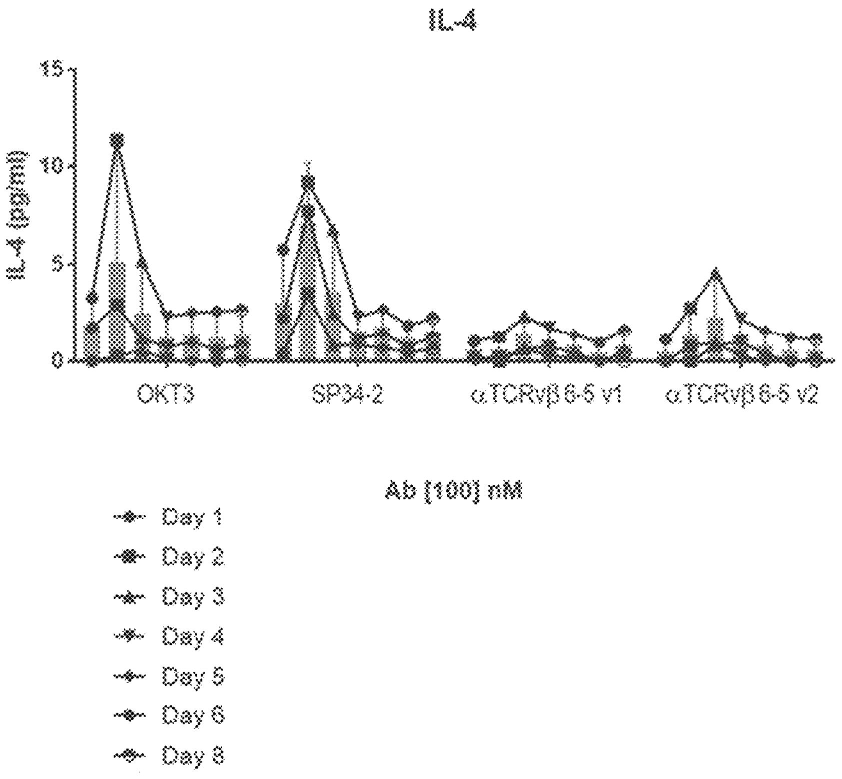
FIG. 88C is a bar graph showing the level of secreted IL-4 by T cells activated/expanded with the indicated antibody (anti-TCRβV 6-5 v1, anti-TCRβV 6-5 v1, OKT3, or SP34-2) and cultured with said antibody for the indicated number of days (1, 2, 3, 4, 5, 6, or 8).

In a third experiments, PBMCs from three different donors were cultured in plates coated with immobilized anti-TCRβV antibody, either anti-TCRβV 6-5 v1 or anti-TCRβV 6-5 v1; or an anti-CD3ε antibody, either OKT3 or SP37-2 for 1-8 days, or isotype control. The data confirms that T cells activated/expanded with an anti-TCRβV antibody as compared to anti-CD3ε antibody release lower levels of IFNγ (FIG. 88A), IL-1β (FIG. 88B), IL-4 (FIG.

Figure 88D:
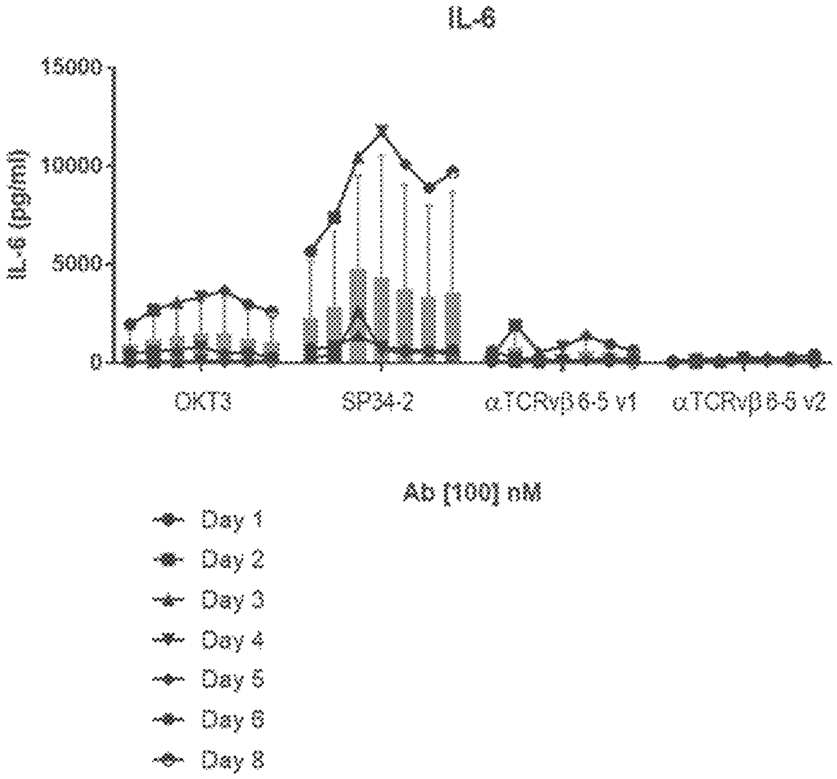
FIG. 88D is a bar graph showing the level of secreted IL-6 by T cells activated/expanded with the indicated antibody (anti-TCRβV 6-5 v1, anti-TCRβV 6-5 v1, OKT3, or SP34-2) and cultured with said antibody for the indicated number of days (1, 2, 3, 4, 5, 6, or 8).
Figure 88E:
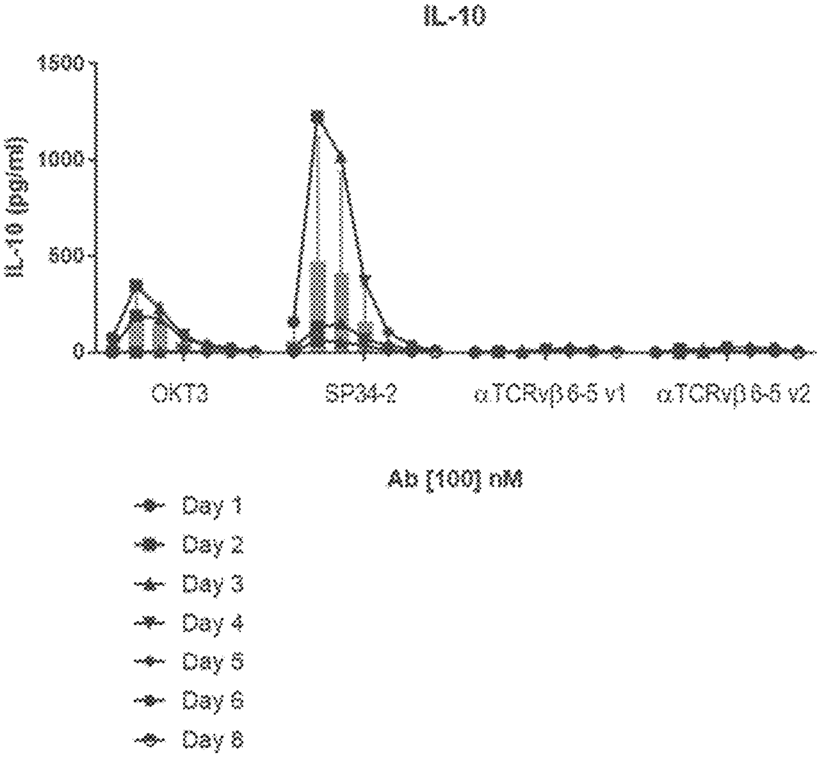
FIG. 88E is a bar graph showing the level of secreted IL-10 by T cells activated/expanded with the indicated antibody (anti-TCRβV 6-5 v1, anti-TCRβV 6-5 v1, OKT3, or SP34-2) and cultured with said antibody for the indicated number of days (1, 2, 3, 4, 5, 6, or 8).
Figure 88F:
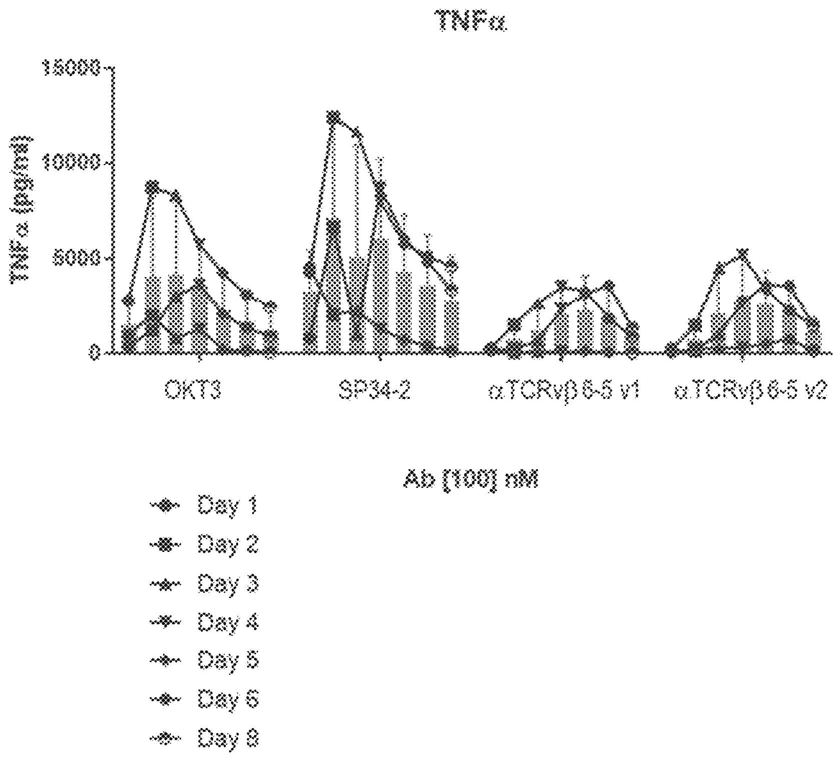
FIG. 88F is a bar graph showing the level of secreted TNFα by T cells activated/expanded with the indicated antibody (anti-TCRβV 6-5 v1, anti-TCRβV 6-5 v1, OKT3, or SP34-2) and cultured with said antibody for the indicated number of days (1, 2, 3, 4, 5, 6, or 8).
Figure 88G:
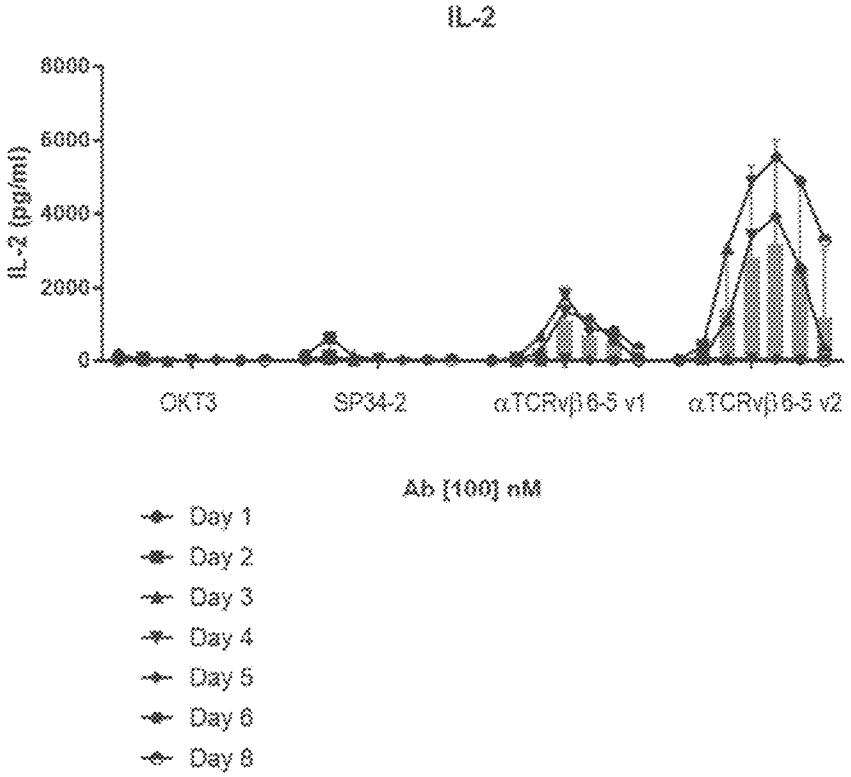
FIG. 88G is a bar graph showing the level of secreted IL-2 by T cells activated/expanded with the indicated antibody (anti-TCRβV 6-5 v1, anti-TCRβV 6-5 v1, OKT3, or SP34-2) and cultured with said antibody for the indicated number of days (1, 2, 3, 4, 5, 6, or 8).

88C), IL-6 (FIG. 88D), IL10 (FIG. 88E), and TNFα (FIG. 88F); and higher levels of IL-2 (FIG. 88G).

Figure 89A:
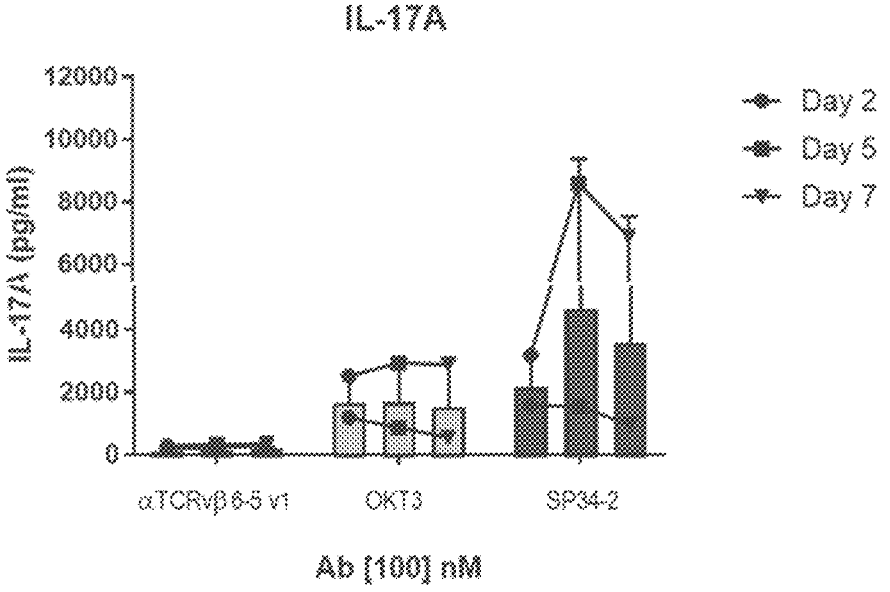
FIG. 89A is a bar graph showing the level of secreted IL-17A by T cells activated/expanded with the indicated antibody (anti-TCRβV 6-5 v1, OKT3, or SP34-2) and cultured with said antibody for the indicated number of days (2, 5, or 7).
Figure 89B:
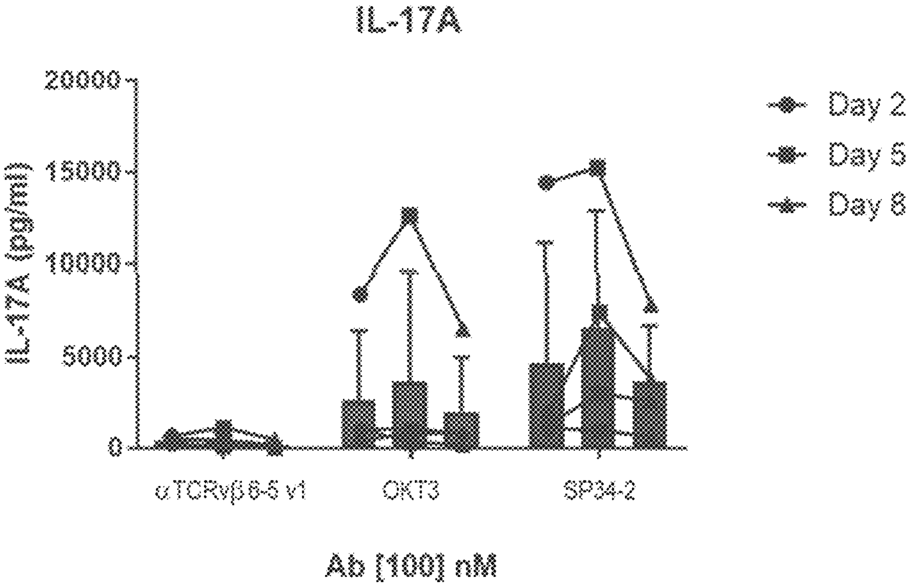
FIG. 89B is a bar graph showing the level of secreted IL-17A by T cells activated/expanded with the indicated antibody (anti-TCRβV 6-5 v1, OKT3, or SP34-2) and cultured with said antibody for the indicated number of days (2, 5, or 8).
Figure 89C:
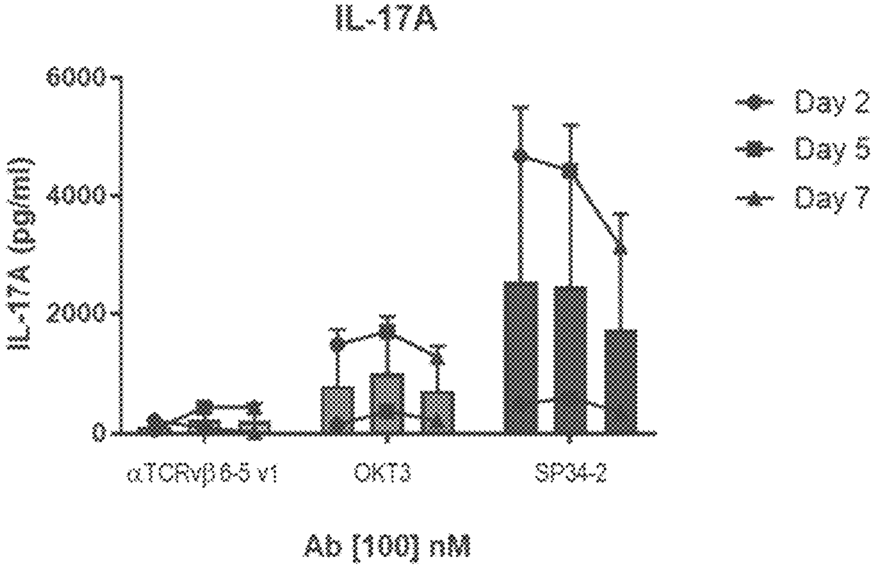
FIG. 89C is a bar graph showing the level of secreted IL-17A by T cells activated/expanded with the indicated antibody (anti-TCRβV 6-5 v1, OKT3, or SP34-2) and cultured with said antibody for the indicated number of days (2, 5, or 7).
Figure 89D:
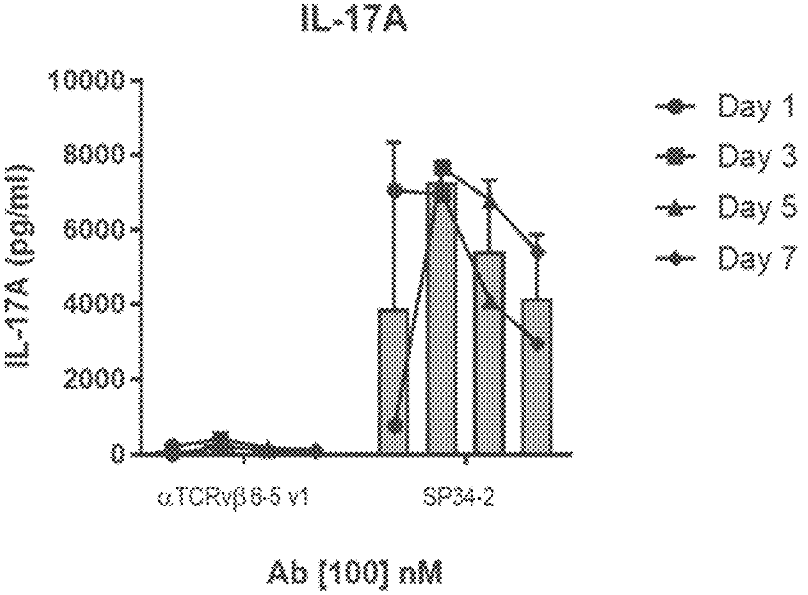
FIG. 89D is a bar graph showing the level of secreted IL-17A by T cells activated/expanded with the indicated antibody (anti-TCRβV 6-5 v1 or SP34-2) and cultured with said antibody for the indicated number of days (1, 3, 5, or 7).

In a fourth experiments, PBMCs from two different donors were cultured in plates coated with immobilized anti-TCRβV antibody, either anti-TCRβV 6-5 v1 or anti-TCRβV 6-5 v1; or an anti-CD3ε antibody, either OKT3 or SP37-2 for 2-7 days, or isotype control. The data confirms that T cells activated/expanded with an anti-TCRβV antibody as compared to anti-CD3ε antibody release lower levels of IL-17A (FIG. 89A). In a fifth experiments, PBMCs from four different donors were cultured in plates coated with immobilized anti-TCRβV antibody, either anti-TCRβV 6-5 v1 or anti-TCRβV 6-5 v1; or an anti-CD3ε antibody, either OKT3 or SP37-2 for 2-8 days, or isotype control. The data confirms that T cells activated/expanded with an anti-TCRβV antibody as compared to anti-CD3ε antibody release lower levels of IL-17A (FIG. 89B). In a sixth experiments, PBMCs from two different donors were cultured in plates coated with immobilized anti-TCRβV antibody, either anti-TCRβV 6-5 v1 or anti-TCRβV 6-5 v1; or an anti-CD3ε antibody, either OKT3 or SP37-2 for 2-7 days, or isotype control. The data confirms that T cells activated/expanded with an anti-TCRβV antibody as compared to anti-CD3ε antibody release lower levels of IL-17A (FIG. 89C). In a seventh experiments, PBMCs from two different donors were cultured in plates coated with immobilized anti-TCRβV antibody, either anti-TCRβV 6-5 v1 or anti-TCRβV 6-5 v1; or an anti-CD3ε antibody, either OKT3 or SP37-2 for 2-7 days, or isotype control. The data confirms that T cells activated/expanded with an anti-TCRβV antibody as compared to anti-CD3ε antibody release lower levels of IL-17A (FIG. 89D).

A series of similar experiments were conducted using the TCRβV antibody anti-TCRβV 6-5 v1 or anti-TCRvb 12-3/4 v1 to further assess the cytokine release profile of T cells activated/expanded using anti-TCRβV antibodies as compared to anti-CD3ε antibodies. As described above, PBMCs were cultured in cell culture plates coated with the immobilized anti-TCRβV antibody, anti-TCRβV 6-5 v1 or anti-TCRvb 12-3/4 v1; or an anti-CD3ε antibody, either OKT3 or SP37-2; isotype control; or anti-TCRβV 6-5 v1 in combination with. The cells were cultured for 1-8 days, the supernatant collected, and cytokines analyzed using Meso Scale Discovery (MSD) assay. Data generated from 2 donors and representative of 2 independent experiments.

Figure 90A:
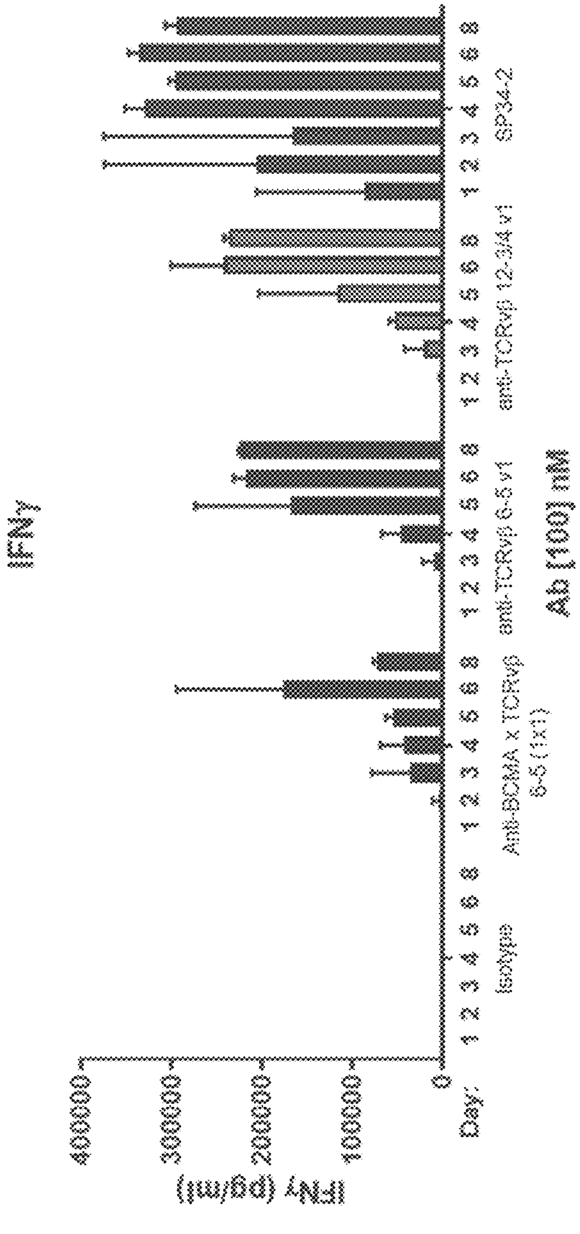
FIG. 90A is a bar graph showing the level of secreted IFNγ by T cells activated/expanded with the indicated antibody (isotype control; anti-TCRβV 6-5 v1 with anti-BCMA antibody; anti-TCRβV 6-5 v1; anti-TCRβV 123/4 v1, or SP34-2) and cultured with said antibody for the indicated number of days (1, 2, 3, 4, 5, 6, or 8).
Figure 90B:
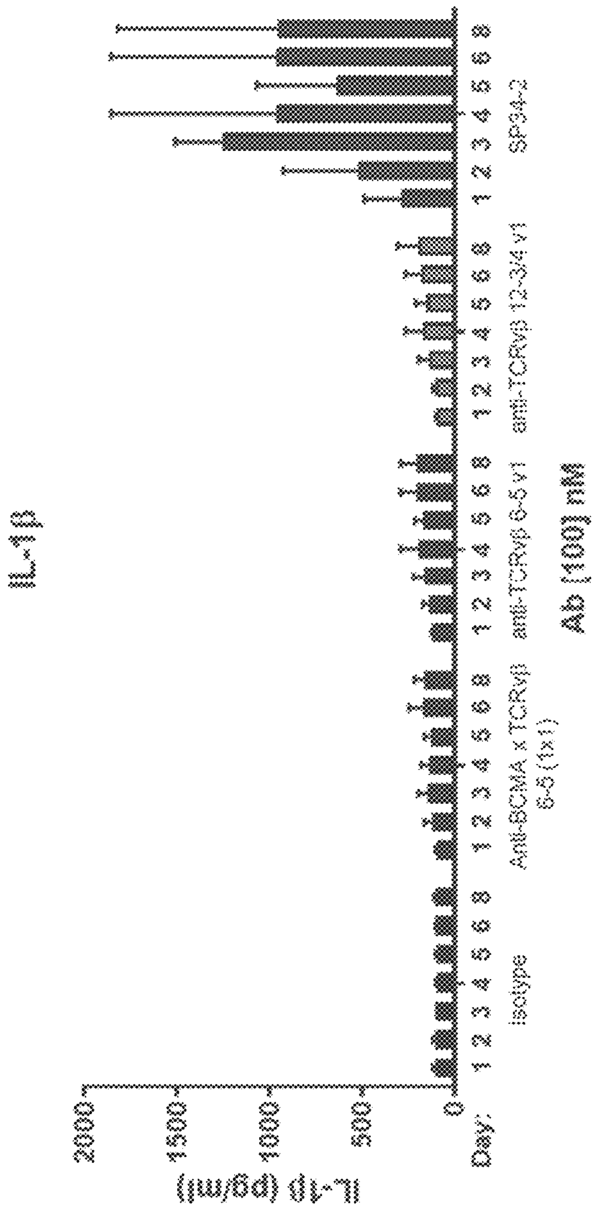
FIG. 90B is a bar graph showing the level of secreted IL-1β by T cells activated/expanded with the indicated antibody (isotype control; anti-TCRβV 6-5 v1 with anti-BCMA antibody; anti-TCRβV 6-5 v1; anti-TCRβV 123/4 v1, or SP34-2) and cultured with said antibody for the indicated number of days (1, 2, 3, 4, 5, 6, or 8).
Figure 90C:
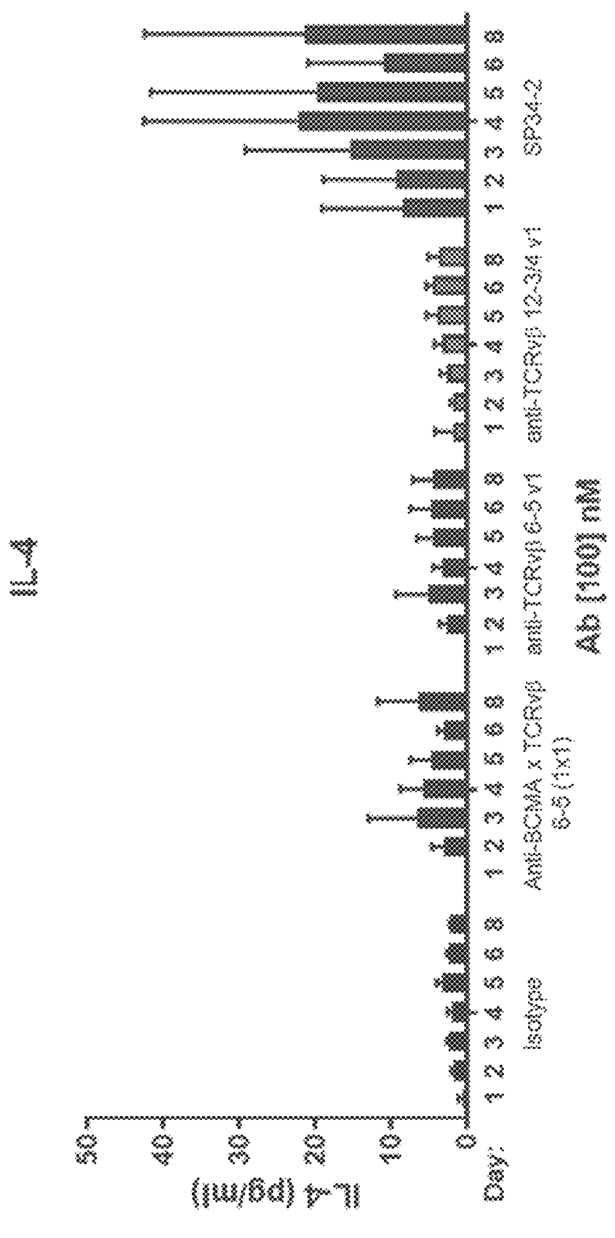
FIG. 90C is a bar graph showing the level of secreted IL-4 by T cells activated/expanded with the indicated antibody (isotype control; anti-TCRβV 6-5 v1 with anti-BCMA antibody; anti-TCRβV 6-5 v1; anti-TCRβV 123/4 v1, or SP34-2) and cultured with said antibody for the indicated number of days (1, 2, 3, 4, 5, 6, or 8).
Figure 90D:
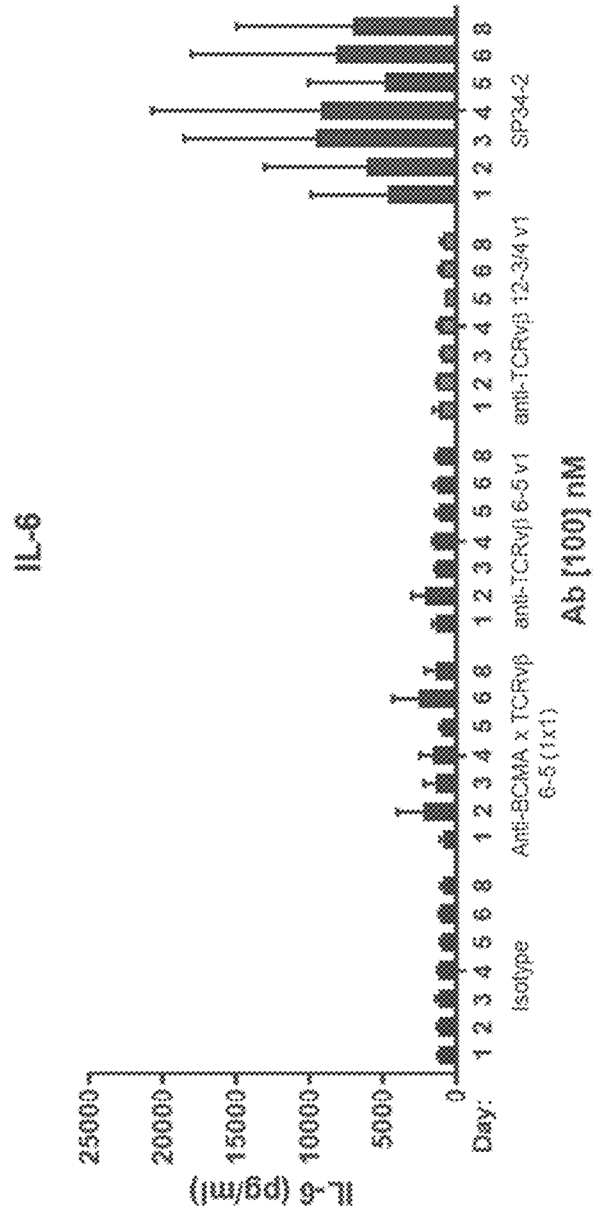
FIG. 90D is a bar graph showing the level of secreted IL-6 by T cells activated/expanded with the indicated antibody (isotype control; anti-TCRβV 6-5 v1 with anti-BCMA antibody; anti-TCRβV 6-5 v1; anti-TCRβV 123/4 v1, or SP34-2) and cultured with said antibody for the indicated number of days (1, 2, 3, 4, 5, 6, or 8).
Figure 90E:
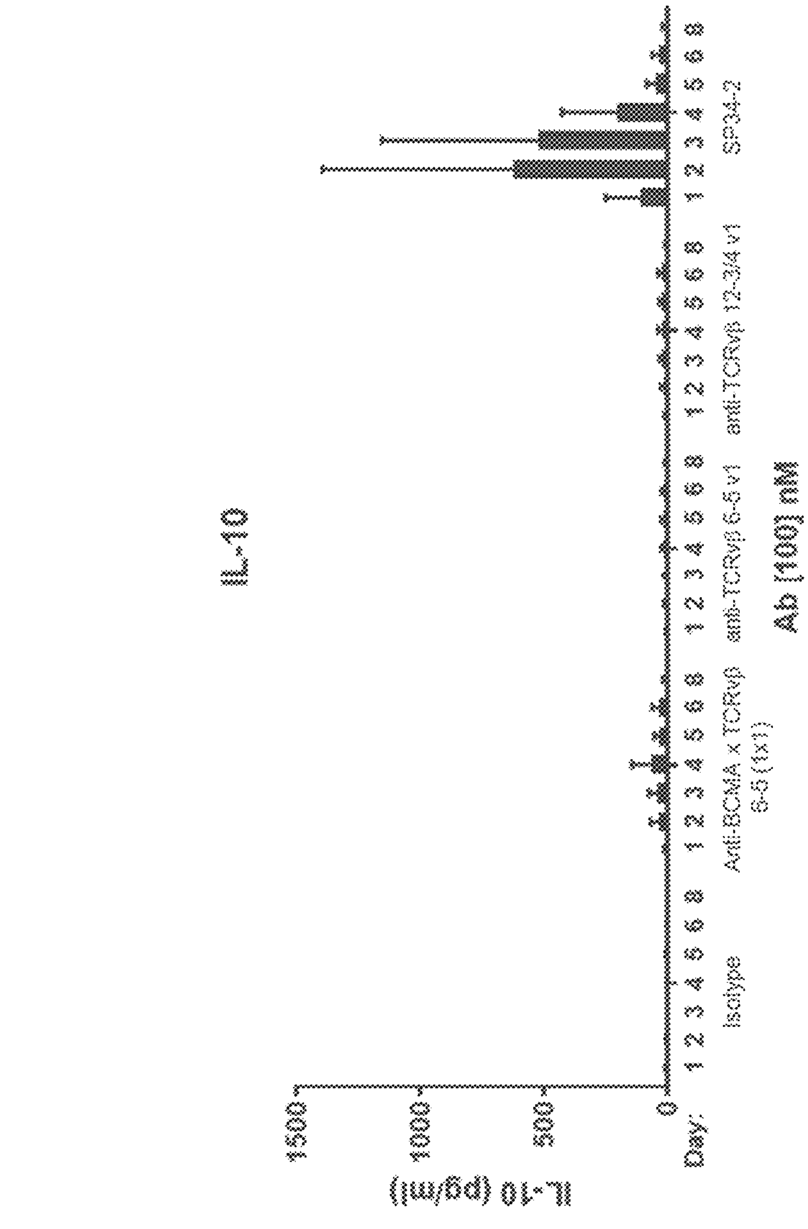
FIG. 90E is a bar graph showing the level of secreted IL-10 by T cells activated/expanded with the indicated antibody (isotype control; anti-TCRβV 6-5 v1 with anti-BCMA antibody; anti-TCRβV 6-5 v1; anti-TCRβV 123/4 v1, or SP34-2) and cultured with said antibody for the indicated number of days (1, 2, 3, 4, 5, 6, or 8).
Figure 90F:
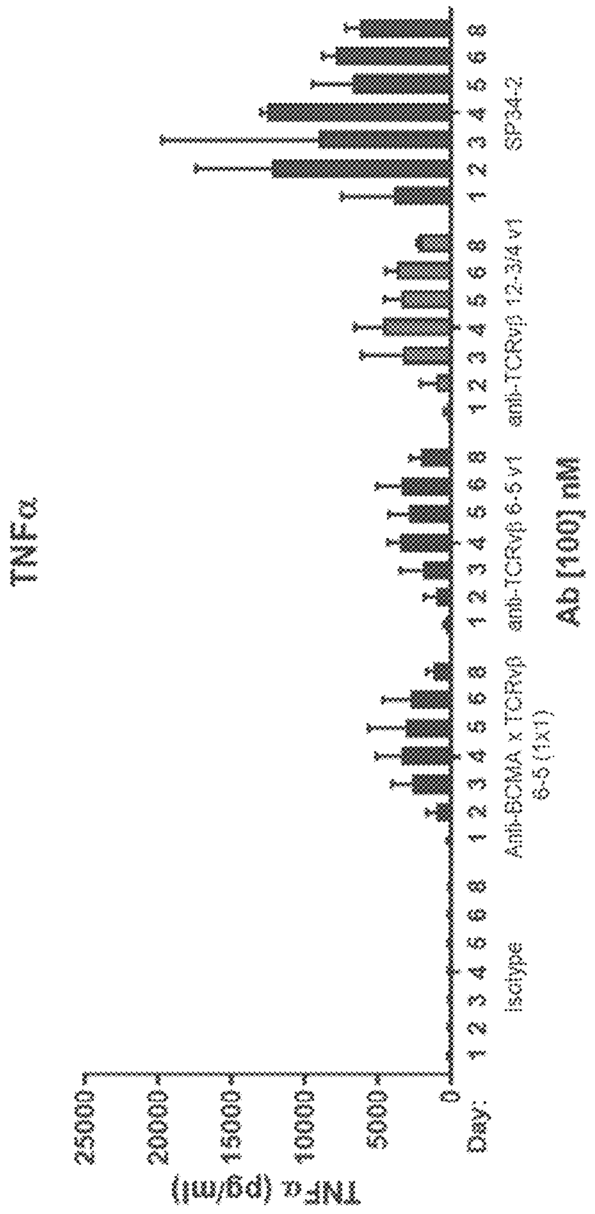
FIG. 90F is a bar graph showing the level of secreted TNFα by T cells activated/expanded with the indicated antibody (isotype control; anti-TCRβV 6-5 v1 with anti-BCMA antibody; anti-TCRβV 6-5 v1; anti-TCRβV 123/4 v1, or SP34-2) and cultured with said antibody for the indicated number of days (1, 2, 3, 4, 5, 6, or 8).
Figure 90G:
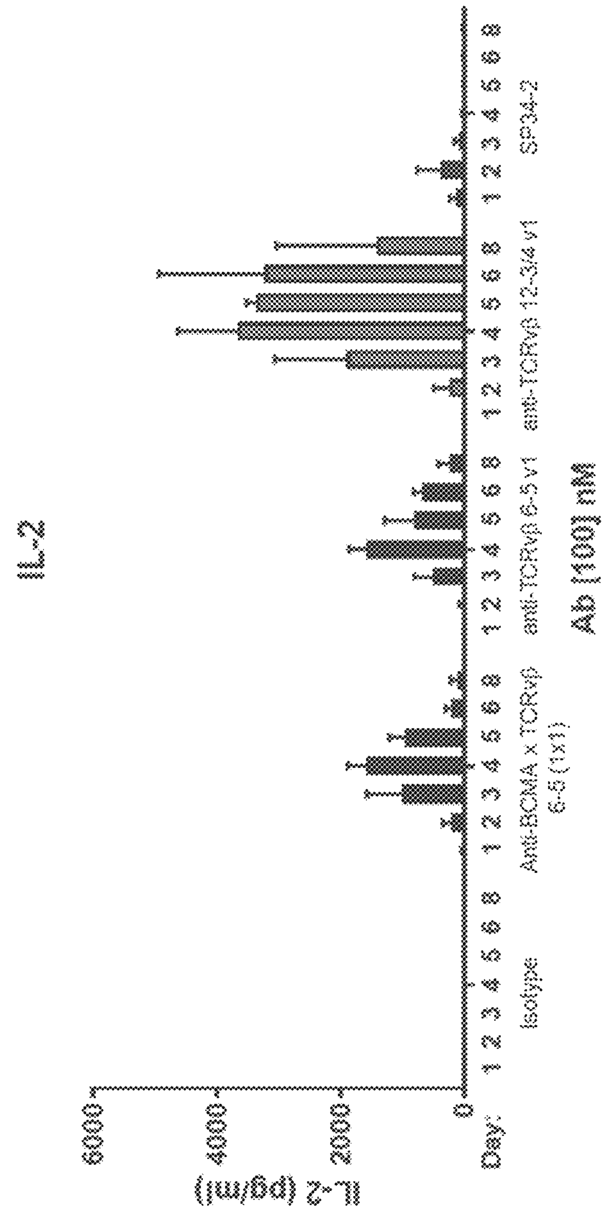
FIG. 90G is a bar graph showing the level of secreted IL-2 by T cells activated/expanded with the indicated antibody (isotype control; anti-TCRβV 6-5 v1 with anti-BCMA antibody; anti-TCRβV 6-5 v1; anti-TCRβV 123/4 v1, or SP34-2) and cultured with said antibody for the indicated number of days (1, 2, 3, 4, 5, 6, or 8).
Figure 90H:
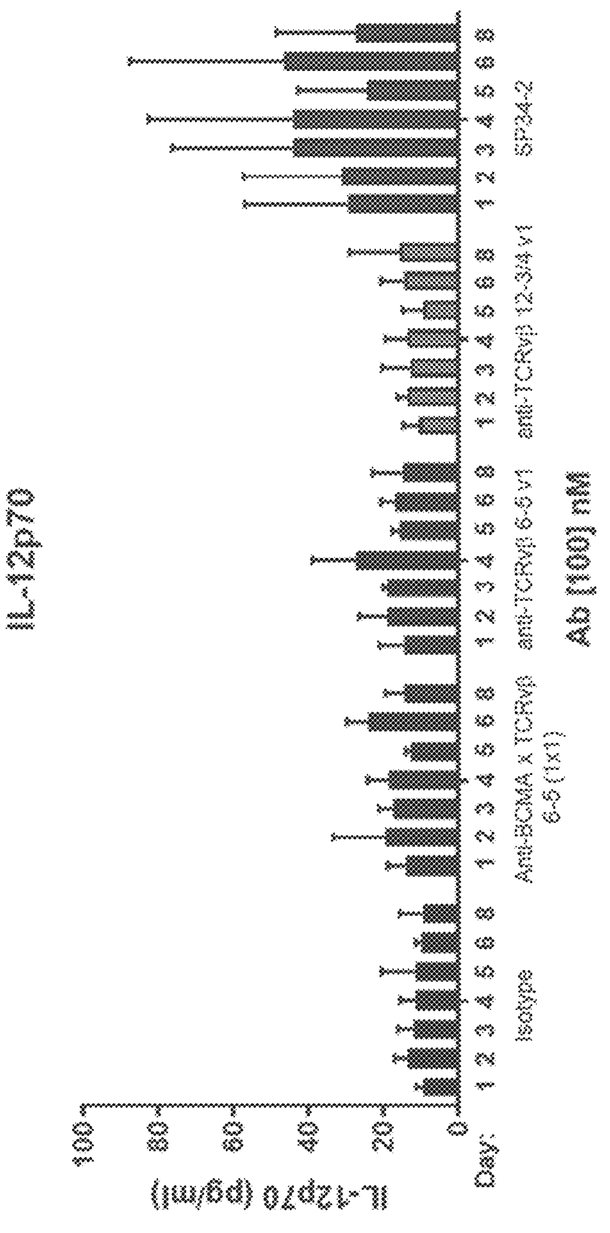
FIG. 90H is a bar graph showing the level of secreted IL-12p70 by T cells activated/expanded with the indicated antibody (isotype control; anti-TCRβV 6-5 v1 with anti-BCMA antibody; anti-TCRβV 6-5 v1; anti-TCRβV 123/4 v1, or SP34-2) and cultured with said antibody for the indicated number of days (1, 2, 3, 4, 5, 6, or 8).
Figure 90I:
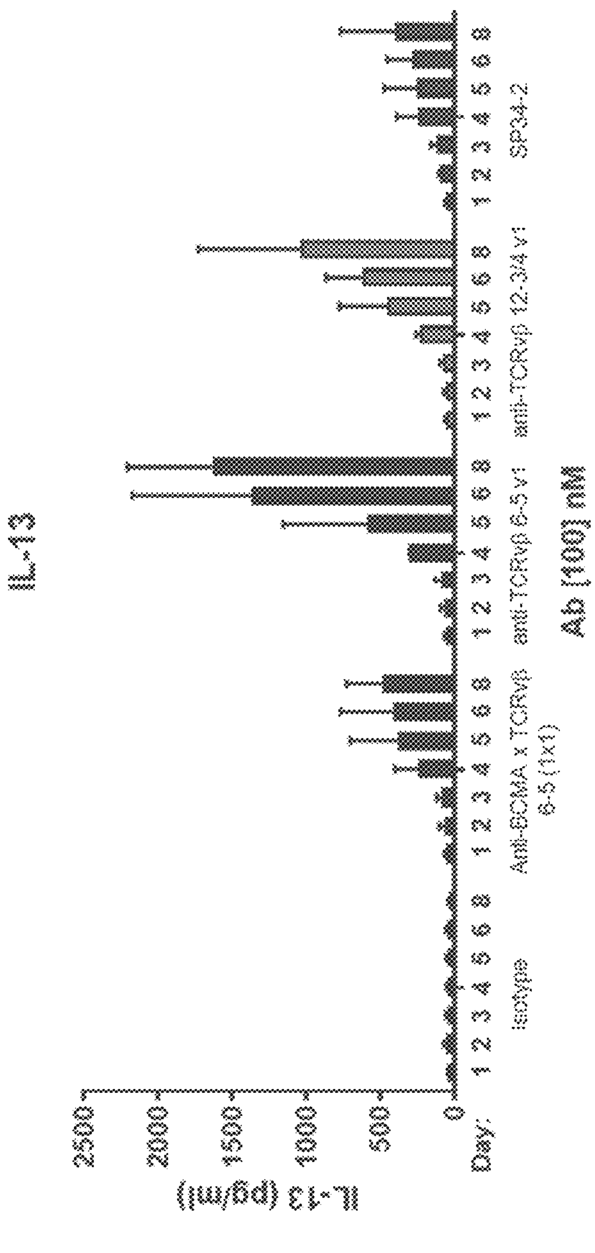
FIG. 90I is a bar graph showing the level of secreted IL-13 by T cells activated/expanded with the indicated antibody (isotype control; anti-TCRβV 6-5 v1 with anti-BCMA antibody; anti-TCRβV 6-5 v1; anti-TCRβV 123/4 v1, or SP34-2) and cultured with said antibody for the indicated number of days (1, 2, 3, 4, 5, 6, or 8).
Figure 90J:
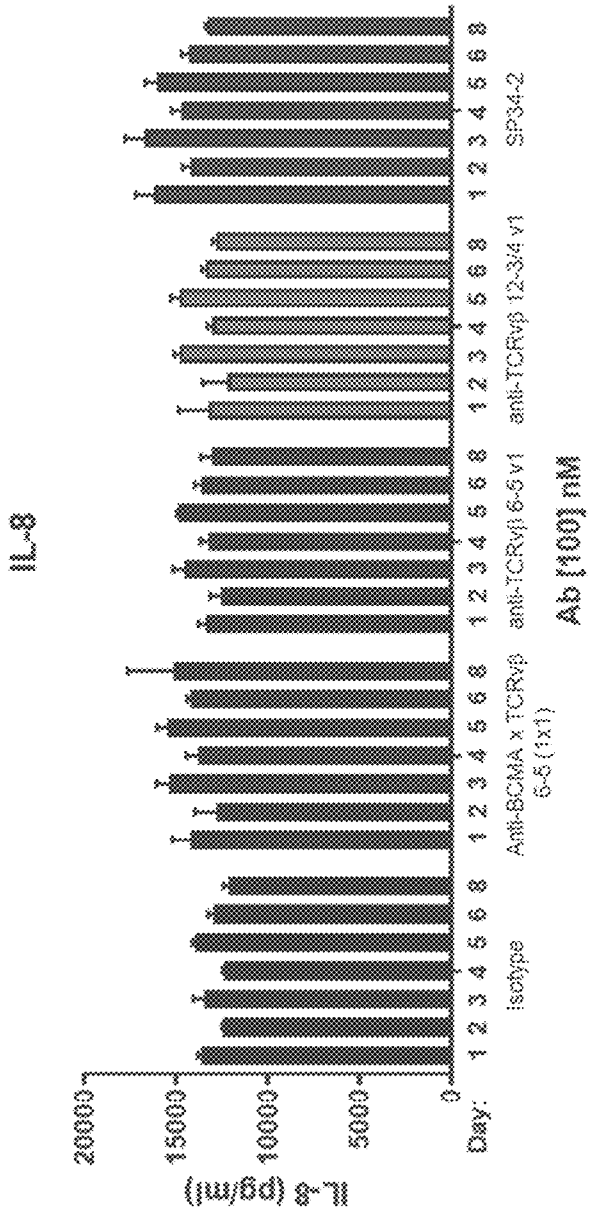
FIG. 90J is a bar graph showing the level of secreted IL-8 by T cells activated/expanded with the indicated antibody (isotype control; anti-TCRβV 6-5 v1 with anti-BCMA antibody; anti-TCRβV 6-5 v1; anti-TCRβV 123/4 v1, or SP34-2) and cultured with said antibody for the indicated number of days (1, 2, 3, 4, 5, 6, or 8).
Figure 90K:
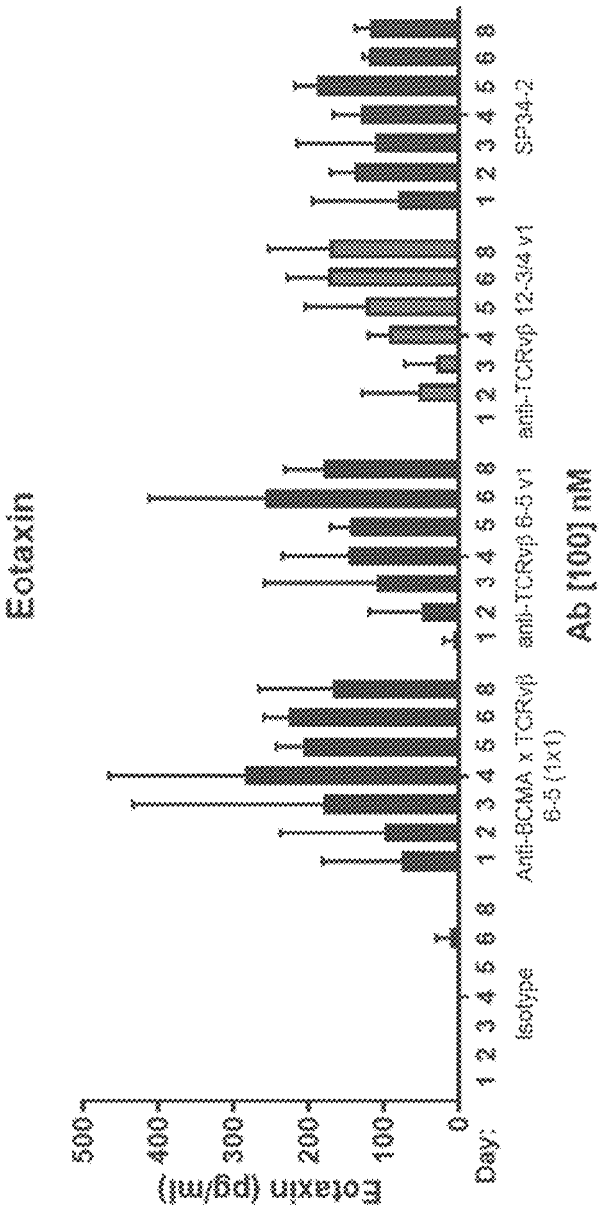
FIG. 90K is a bar graph showing the level of secreted exotaxin by T cells activated/expanded with the indicated antibody (isotype control; anti-TCRβV 6-5 v1 with anti-BCMA antibody; anti-TCRβV 6-5 v1; anti-TCRβV 123/4 v1, or SP34-2) and cultured with said antibody for the indicated number of days (1, 2, 3, 4, 5, 6, or 8).
Figure 90L:
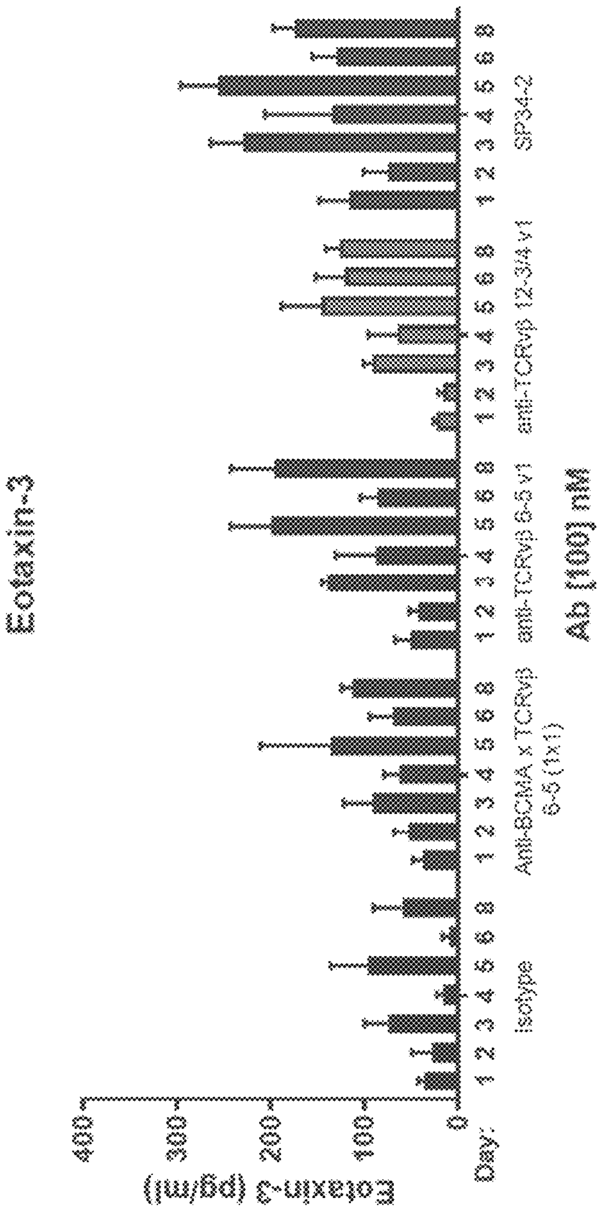
FIG. 90L is a bar graph showing the level of secreted exotoxin-3 by T cells activated/expanded with the indicated antibody (isotype control; anti-TCRβV 6-5 v1 with anti-BCMA antibody; anti-TCRβV 6-5 v1; anti-TCRβV 123/4 v1, or SP34-2) and cultured with said antibody for the indicated number of days (1, 2, 3, 4, 5, 6, or 8).
Figure 90M:
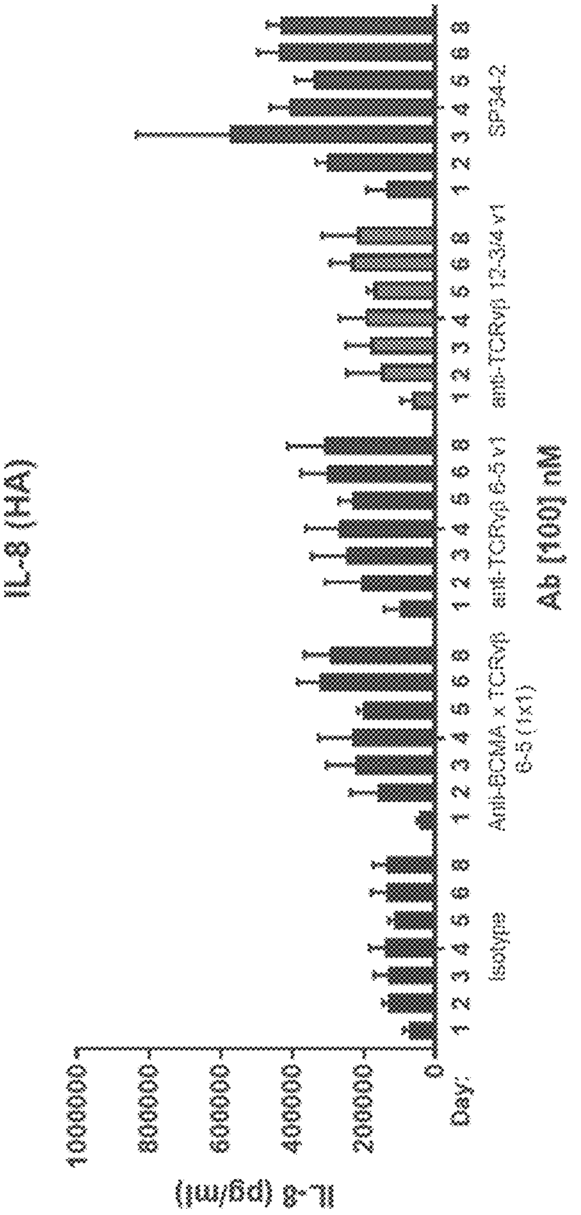
FIG. 90M is a bar graph showing the level of secreted IL-8 by T cells activated/expanded with the indicated antibody (isotype control; anti-TCRβV 6-5 v1 with anti-BCMA antibody; anti-TCRβV 6-5 v1; anti-TCRβV 123/4 v1, or SP34-2) and cultured with said antibody for the indicated number of days (1, 2, 3, 4, 5, 6, or 8).
Figure 90N:
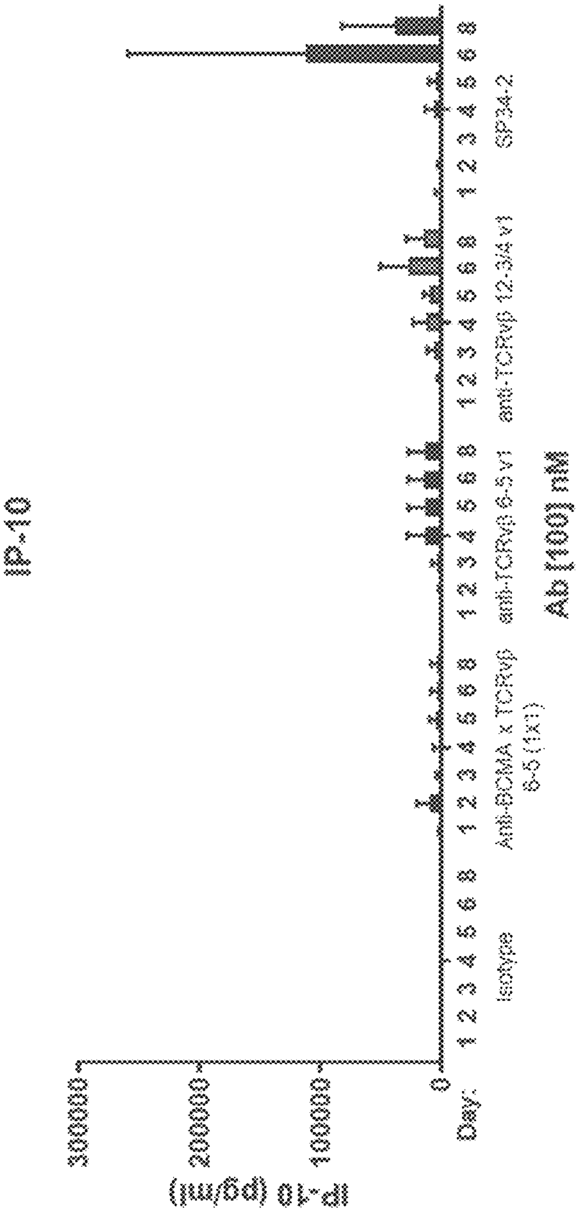
FIG. 90N is a bar graph showing the level of secreted IP-10 by T cells activated/expanded with the indicated antibody (isotype control; anti-TCRβV 6-5 v1 with anti-BCMA antibody; anti-TCRβV 6-5 v1; anti-TCRβV 123/4 v1, or SP34-2) and cultured with said antibody for the indicated number of days (1, 2, 3, 4, 5, 6, or 8).
Figure 90O:
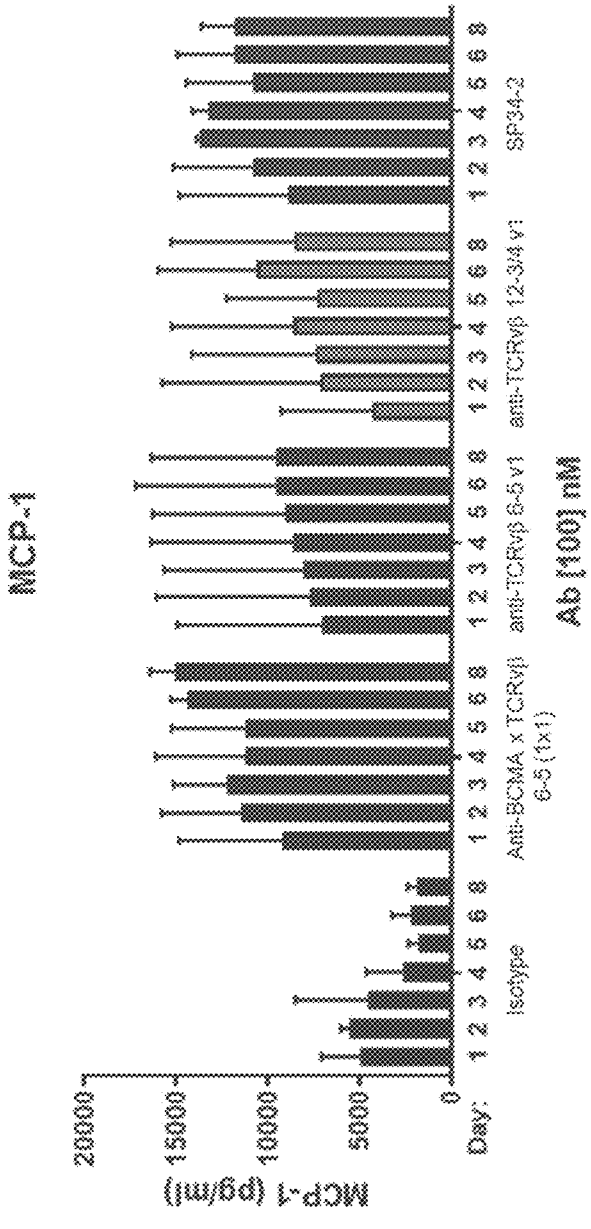
FIG. 90O is a bar graph showing the level of secreted MCP-1 by T cells activated/expanded with the indicated antibody (isotype control; anti-TCRβV 6-5 v1 with anti-BCMA antibody; anti-TCRβV 6-5 v1; anti-TCRβV 123/4 v1, or SP34-2) and cultured with said antibody for the indicated number of days (1, 2, 3, 4, 5, 6, or 8).
Figure 90P:
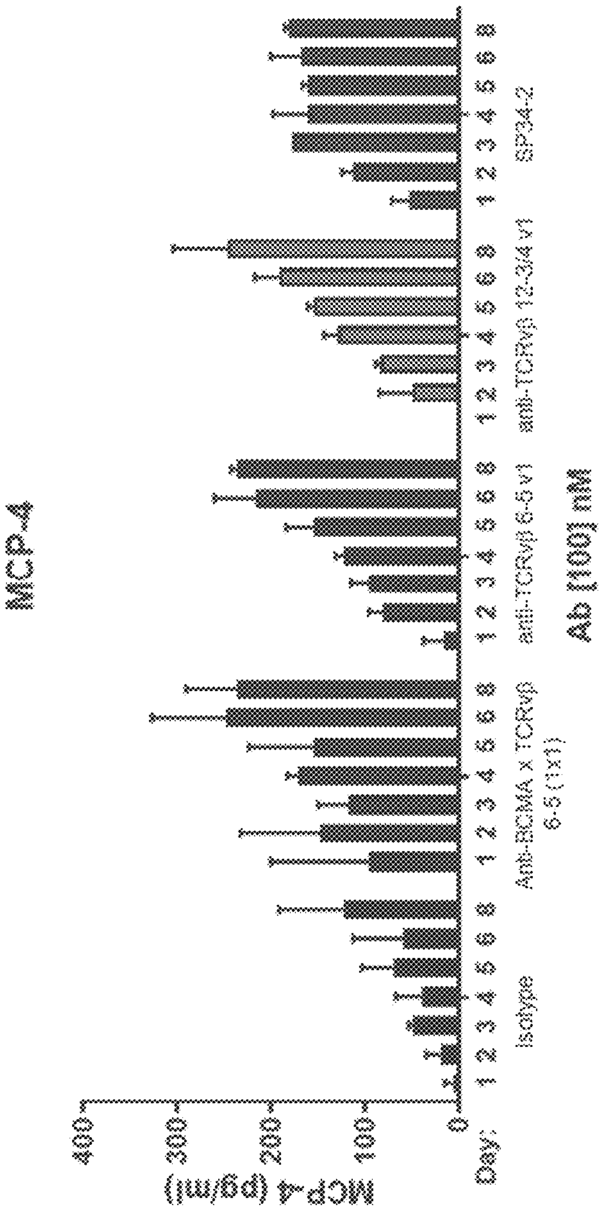
FIG. 90P is a bar graph showing the level of secreted MCP-4 by T cells activated/expanded with the indicated antibody (isotype control; anti-TCRβV 6-5 v1 with anti-BCMA antibody; anti-TCRβV 6-5 v1; anti-TCRβV 123/4 v1, or SP34-2) and cultured with said antibody for the indicated number of days (1, 2, 3, 4, 5, 6, or 8).
Figure 90Q:
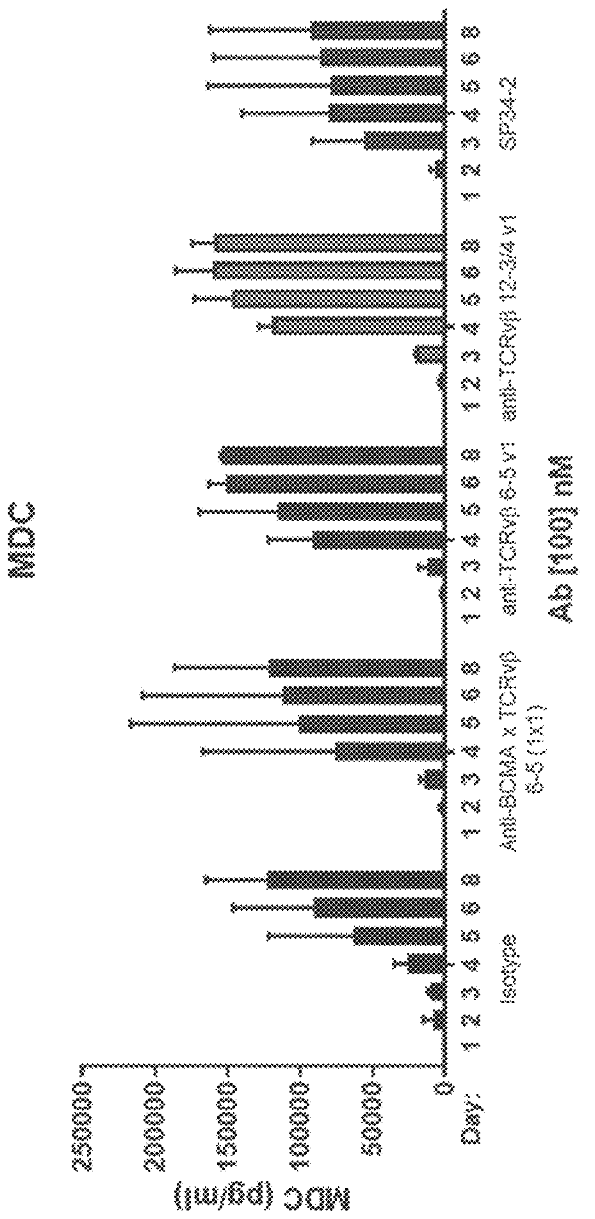
FIG. 90Q is a bar graph showing the level of secreted MDC by T cells activated/expanded with the indicated antibody (isotype control; anti-TCRβV 6-5 v1 with anti-BCMA antibody; anti-TCRβV 6-5 v1; anti-TCRβV 123/4 v1, or SP34-2) and cultured with said antibody for the indicated number of days (1, 2, 3, 4, 5, 6, or 8).
Figure 90R:
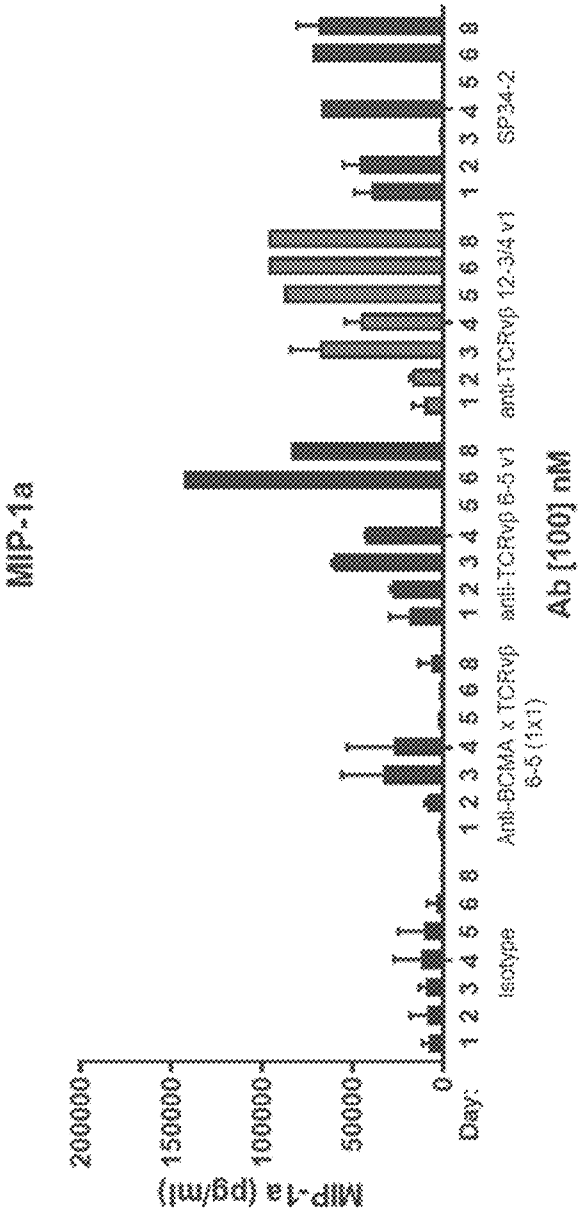
FIG. 90R is a bar graph showing the level of secreted MIP-1a by T cells activated/expanded with the indicated antibody (isotype control; anti-TCRβV 6-5 v1 with anti-BCMA antibody; anti-TCRβV 6-5 v1; anti-TCRβV 123/4 v1, or SP34-2) and cultured with said antibody for the indicated number of days (1, 2, 3, 4, 5, 6, or 8).
Figure 90S:
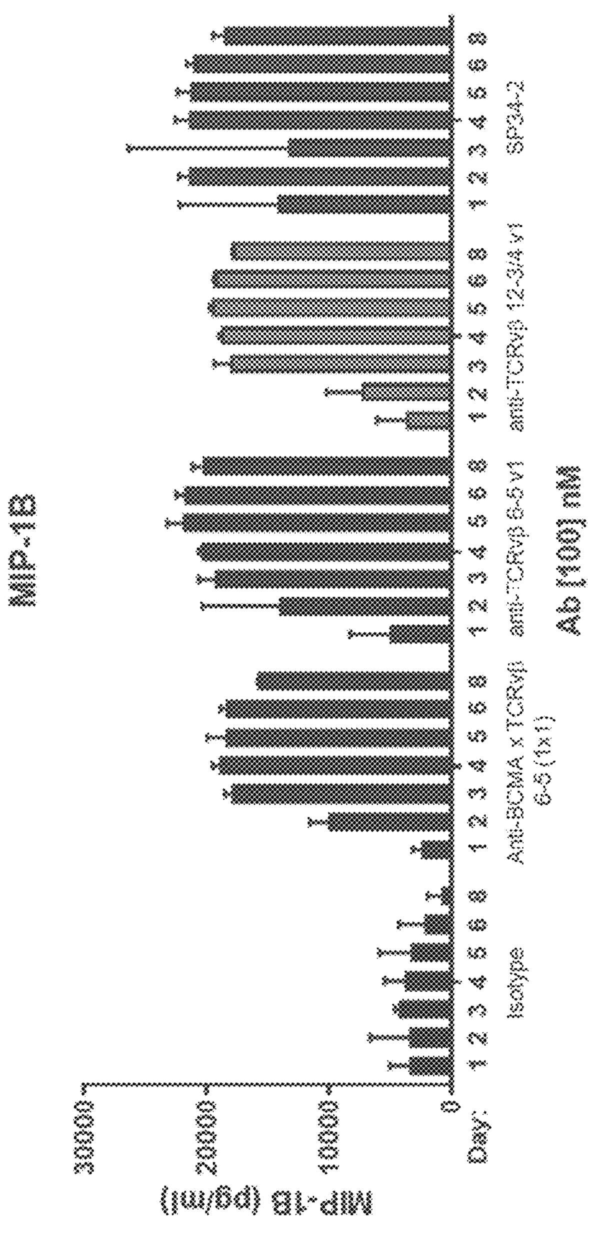
FIG. 90S is a bar graph showing the level of secreted MIP-1b by T cells activated/expanded with the indicated antibody (isotype control; anti-TCRβV 6-5 v1 with anti-BCMA antibody; anti-TCRβV 6-5 v1; anti-TCRβV 123/4 v1, or SP34-2) and cultured with said antibody for the indicated number of days (1, 2, 3, 4, 5, 6, or 8).
Figure 90T:
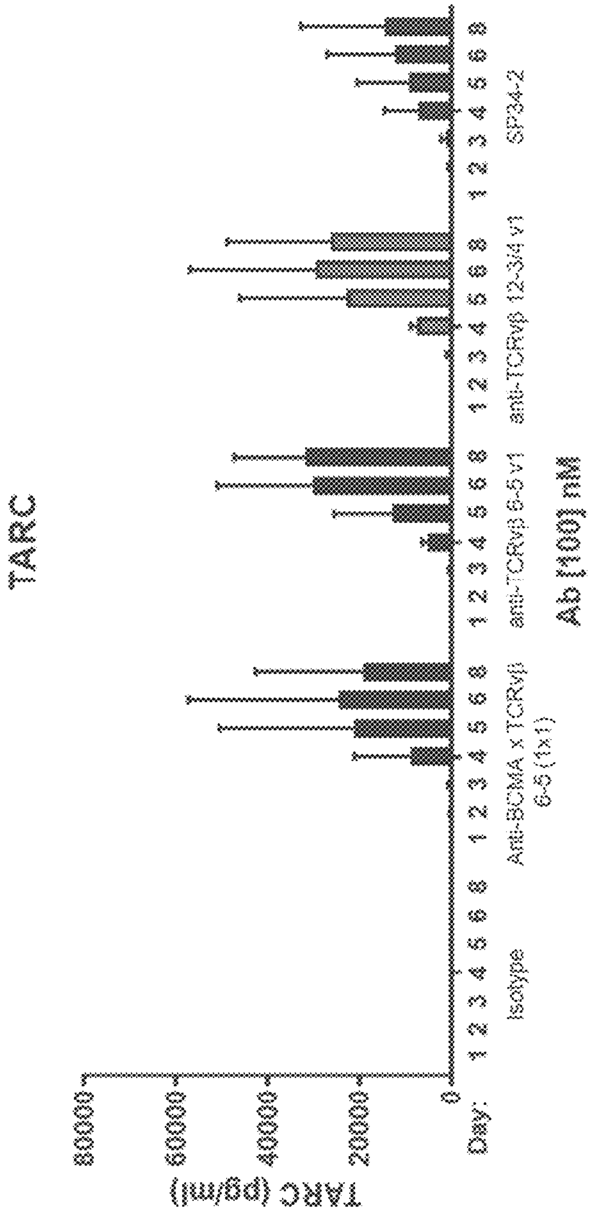
FIG. 90T is a bar graph showing the level of secreted TARC by T cells activated/expanded with the indicated antibody (isotype control; anti-TCRβV 6-5 v1 with anti-BCMA antibody; anti-TCRβV 6-5 v1; anti-TCRβV 123/4 v1, or SP34-2) and cultured with said antibody for the indicated number of days (1, 2, 3, 4, 5, 6, or 8).
Figure 90U:
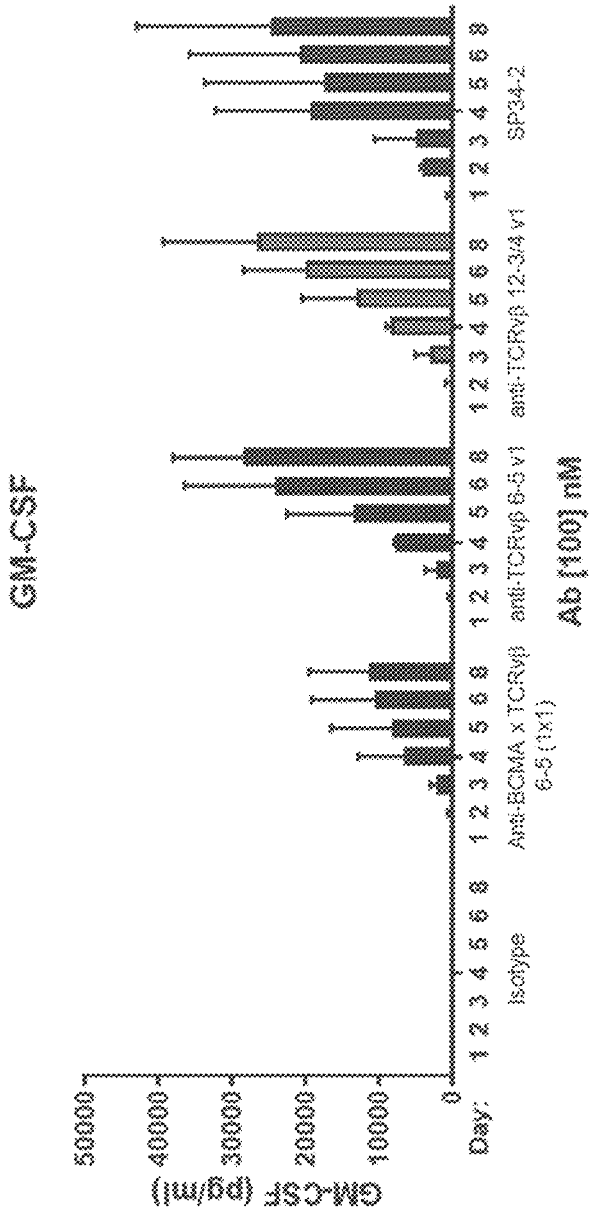
FIG. 90U is a bar graph showing the level of secreted GMCSF by T cells activated/expanded with the indicated antibody (isotype control; anti-TCRβV 6-5 v1 with anti-BCMA antibody; anti-TCRβV 6-5 v1; anti-TCRβV 123/4 v1, or SP34-2) and cultured with said antibody for the indicated number of days (1, 2, 3, 4, 5, 6, or 8).
Figure 90V:
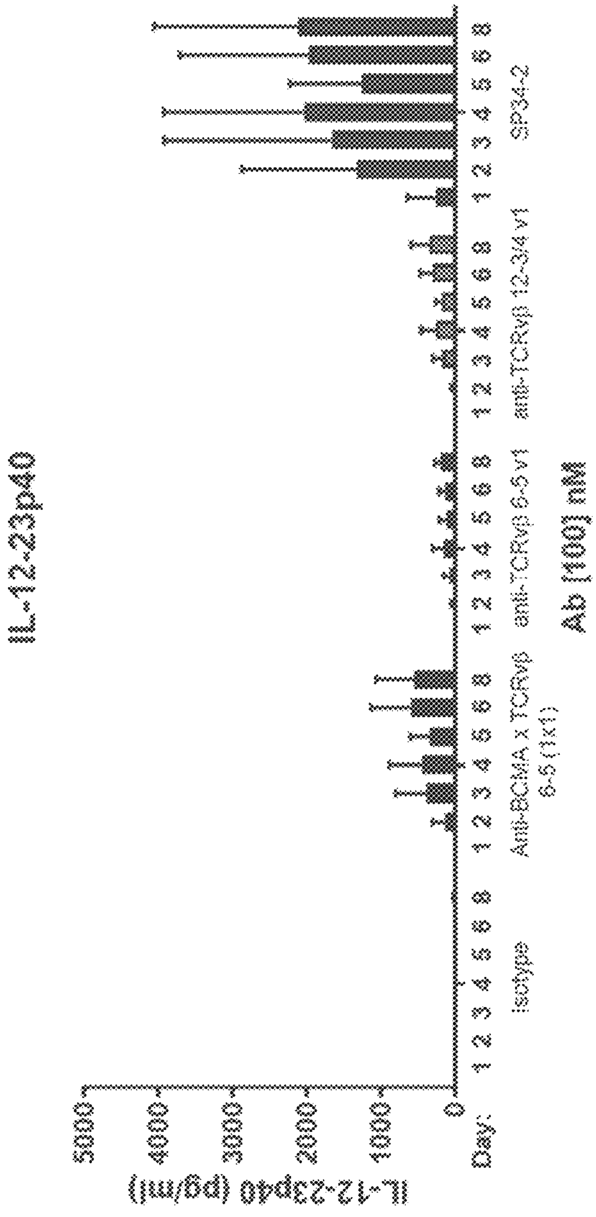
FIG. 90V is a bar graph showing the level of secreted IL-12-23p40 by T cells activated/expanded with the indicated antibody (isotype control; anti-TCRβV 6-5 v1 with anti-BCMA antibody; anti-TCRβV 6-5 v1; anti-TCRβV 123/4 v1, or SP34-2) and cultured with said antibody for the indicated number of days (1, 2, 3, 4, 5, 6, or 8).
Figure 90W:
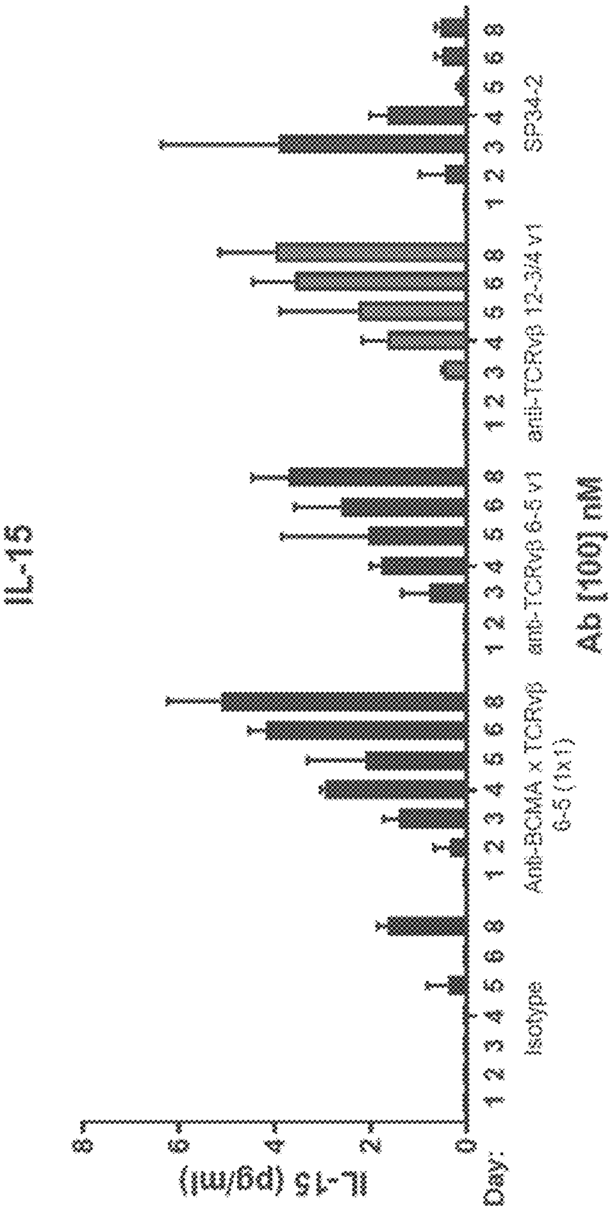
FIG. 90W is a bar graph showing the level of secreted IL-15 by T cells activated/expanded with the indicated antibody (isotype control; anti-TCRβV 6-5 v1 with anti-BCMA antibody; anti-TCRβV 6-5 v1; anti-TCRβV 123/4 v1, or SP34-2) and cultured with said antibody for the indicated number of days (1, 2, 3, 4, 5, 6, or 8).
Figure 90X:
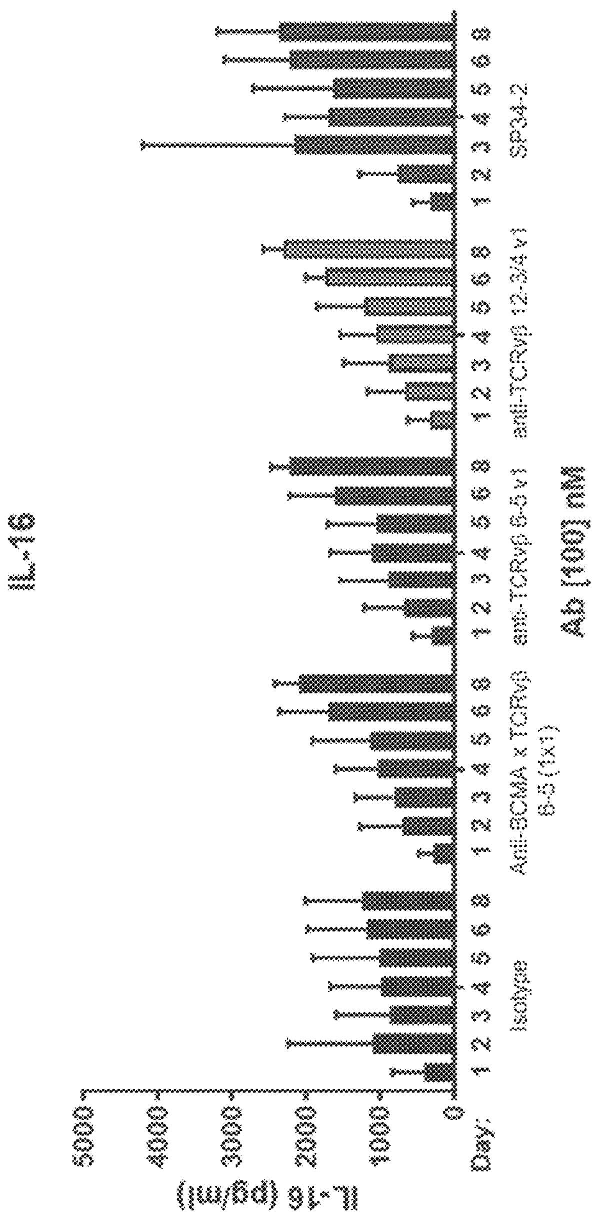
FIG. 90X is a bar graph showing the level of secreted IL-16 by T cells activated/expanded with the indicated antibody (isotype control; anti-TCRβV 6-5 v1 with anti-BCMA antibody; anti-TCRβV 6-5 v1; anti-TCRβV 123/4 v1, or SP34-2) and cultured with said antibody for the indicated number of days (1, 2, 3, 4, 5, 6, or 8).
Figure 90Y:
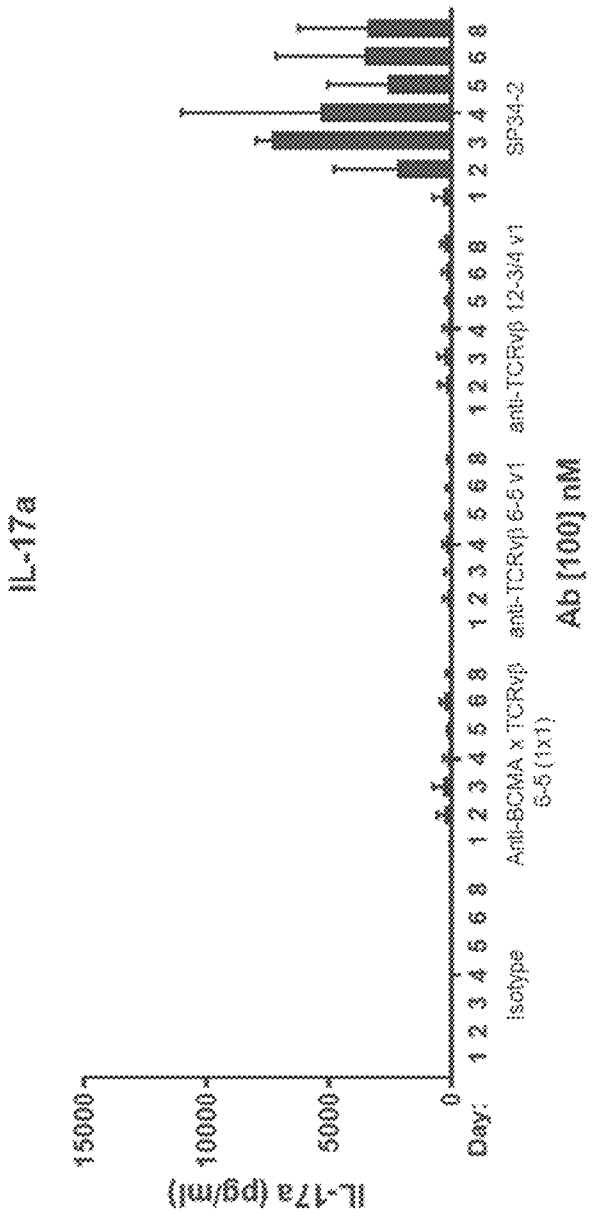
FIG. 90Y is a bar graph showing the level of secreted IL-17a by T cells activated/expanded with the indicated antibody (isotype control; anti-TCRβV 6-5 v1 with anti-BCMA antibody; anti-TCRβV 6-5 v1; anti-TCRβV 123/4 v1, or SP34-2) and cultured with said antibody for the indicated number of days (1, 2, 3, 4, 5, 6, or 8).
Figure 90Z:
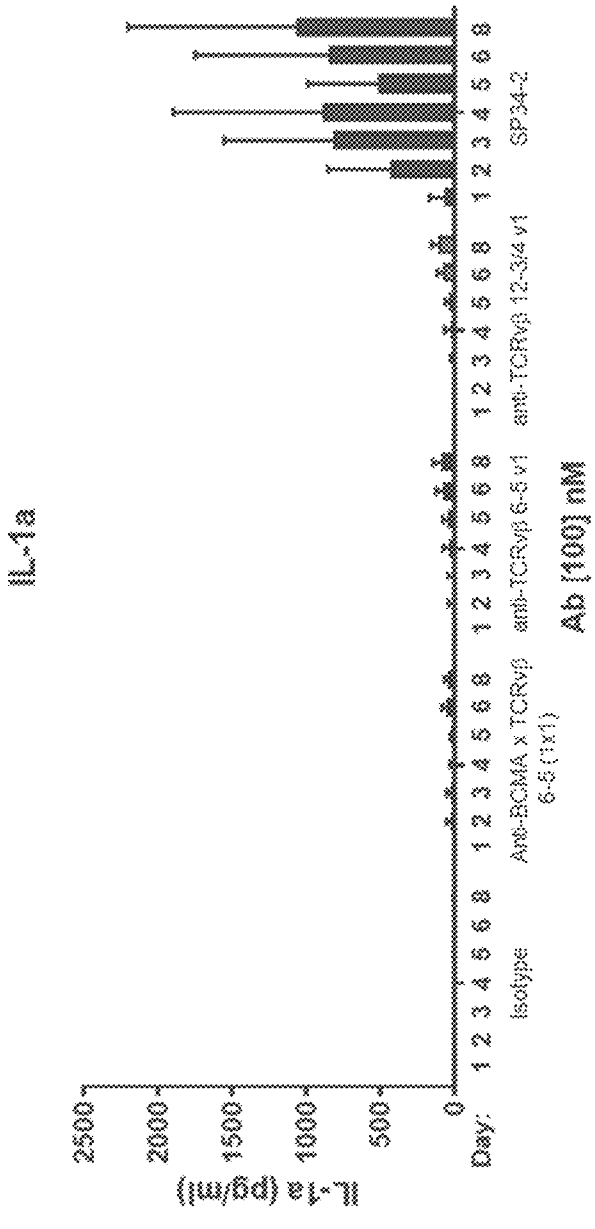
FIG. 90Z is a bar graph showing the level of secreted IL-1a by T cells activated/expanded with the indicated antibody (isotype control; anti-TCRβV 6-5 v1 with anti-BCMA antibody; anti-TCRβV 6-5 v1; anti-TCRβV 123/4 v1, or SP34-2) and cultured with said antibody for the indicated number of days (1, 2, 3, 4, 5, 6, or 8).
Figure 90A:
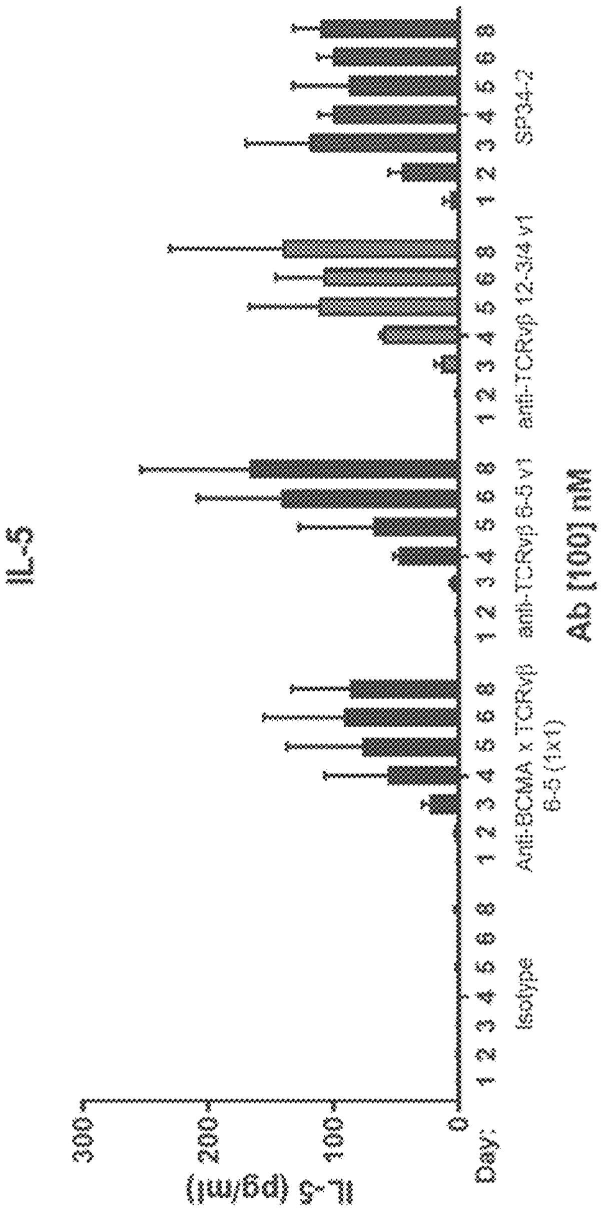
Figure 90B:
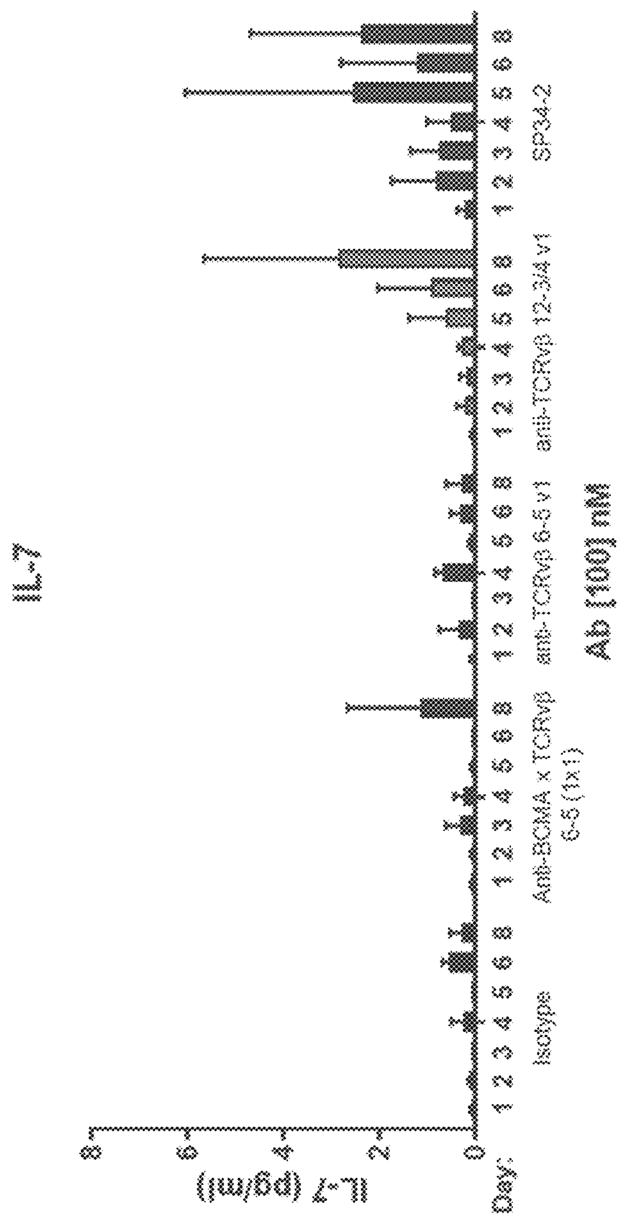
Figure 90C:
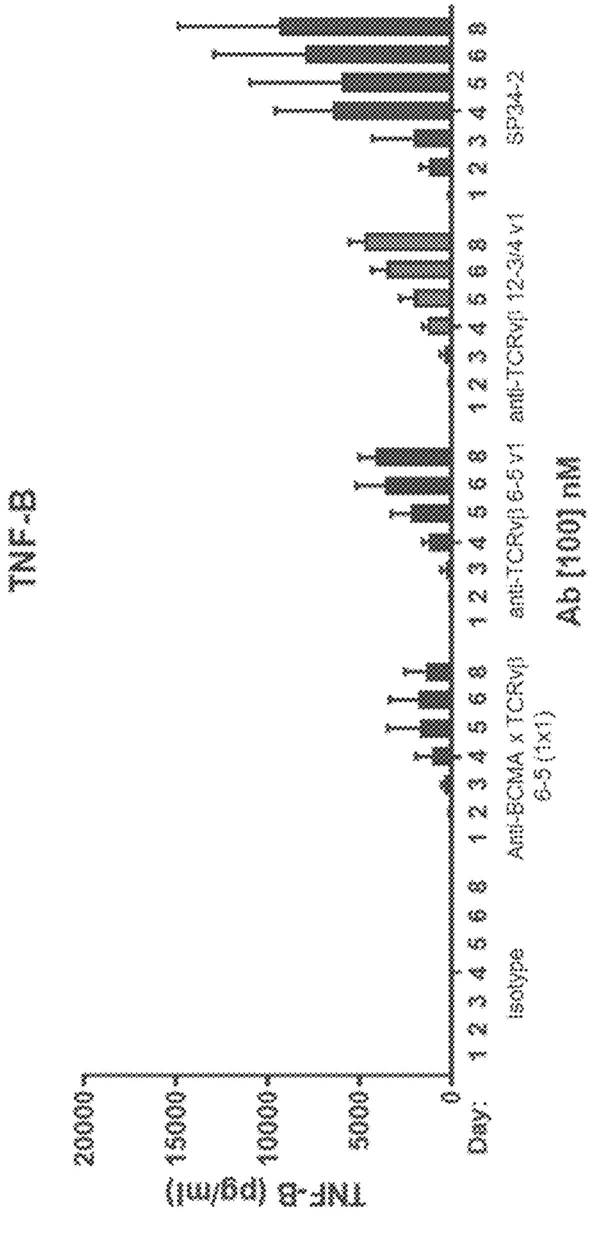
Figure 90D:
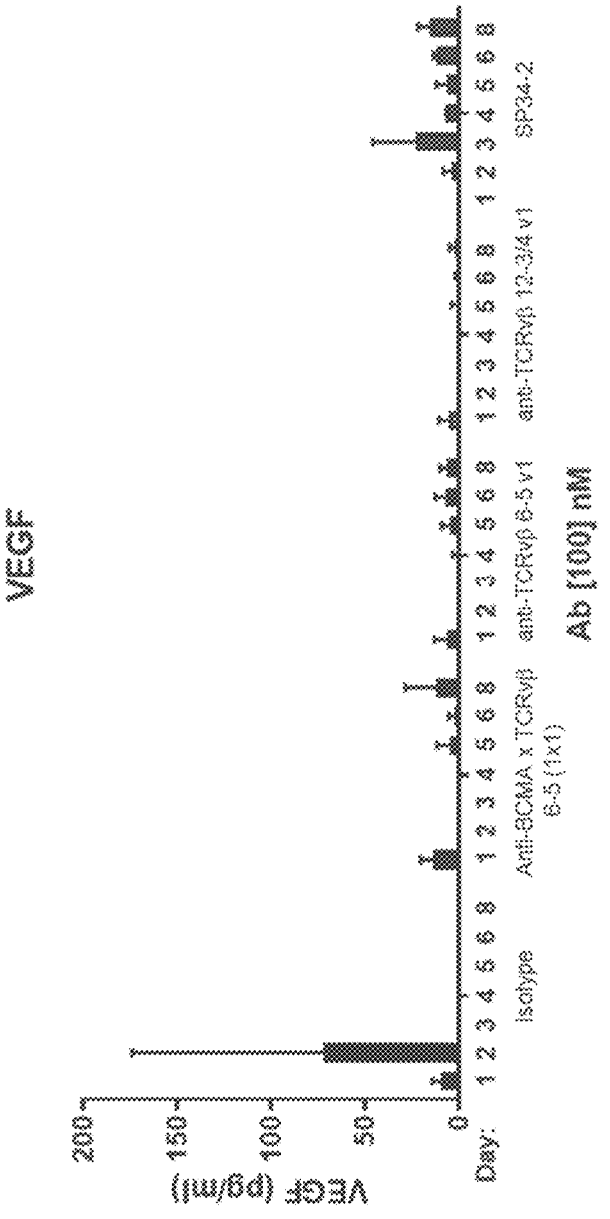
Figure 91:
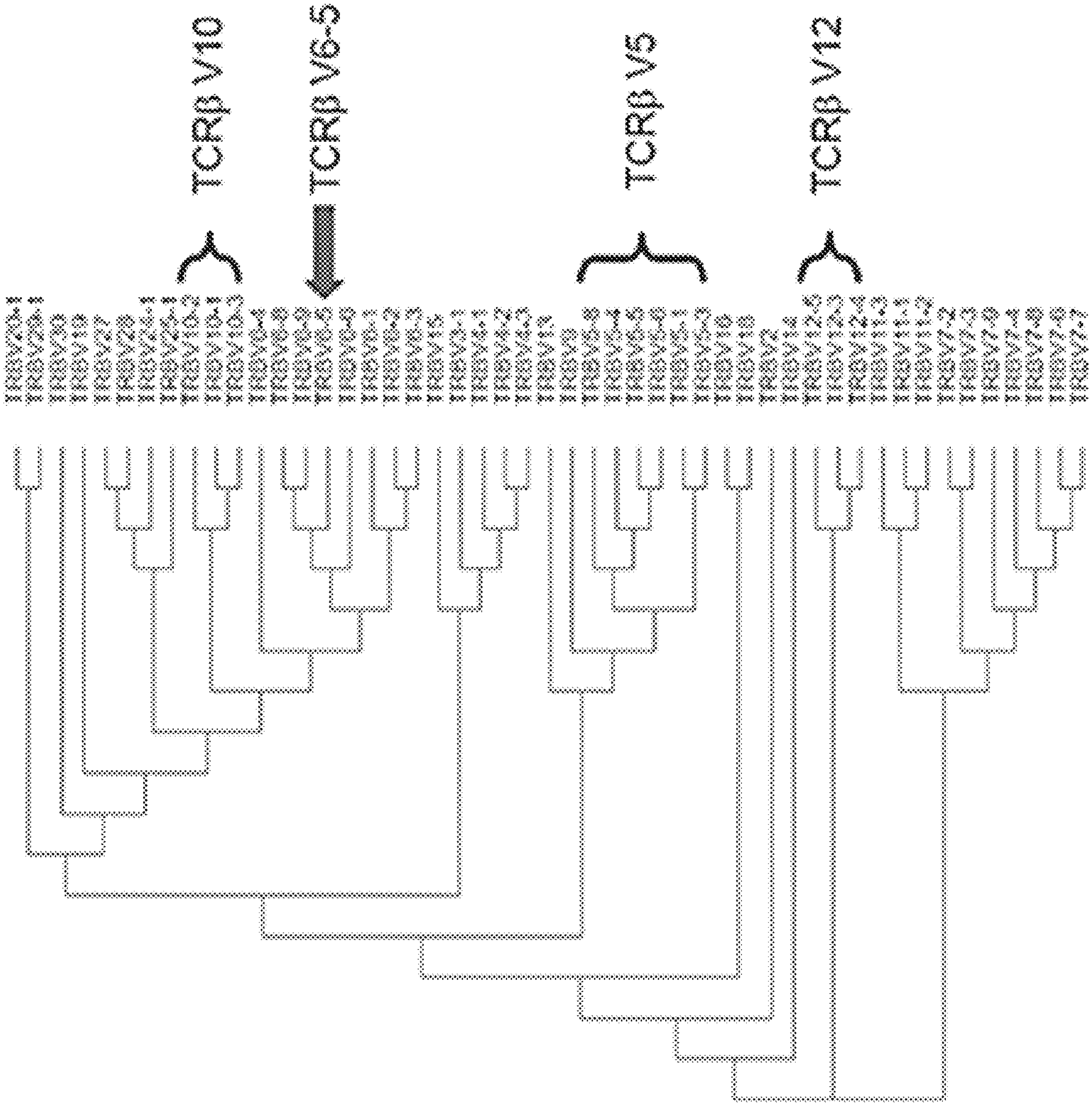
FIG. 91 shows a graphical representation of the relation of sequences between different TCRVB clonotype subfamilies.

The data confirmed that T cells activated/expanded by either anti-TCRβV antibody, anti-TCRβV 6-5 v1 or anti-TCRvb 12-3/4 v1, as compared to either anti-CD3ε antibody (OKT3 or SP37-2) secreted a lower level of IFNγ (FIG. 90A), IL-1β (FIG. 90B), IL-4 (FIG. 90C), IL-6 (FIG. 90D), IL10 (FIG. 90E), TNFα (FIG. 90F); and higher levels of IL-2 (FIG. 90G). Secretion of IL-12p70 (FIG. 90H), IL-13 (FIG. 90I), IL-8 (FIG. 90J), Exotaxin (FIG. 90K), Exotaxin-3 (FIG. 90L), IL-8 (FIG. 90M), IP-10 (FIG. 90N), MCP-1 (FIG. 90O), MCP-4 (FIG. 90P), MDC (FIG. 90), MIP-1α(FIG. 90R), MIP-1b (FIG. 90S), TARC (FIG. 90T), GMCSF (FIG. 90U), IL-12-23p40 (FIG. 90V), IL-15 (FIG. 90W), IL-16 (FIG. 90X), IL-17a (FIG. 90Y), IL-1a (FIG. 90Z), IL-5 (FIG. 90AA), IL-7 (FIG. 90BB), TNF-β (FIG. 90CC), and VEGF (FIG. 90DD), were also tested.

In addition to determining the cytokine profile of T cells activated with the αTCRβV antibodies αTCRβV 6-5 v1 and αTCRβV 6-5 v2 (described above); the assays were conducted with additional αTCRβV antibodies recognizing different clonotypes.

Figure 92A:
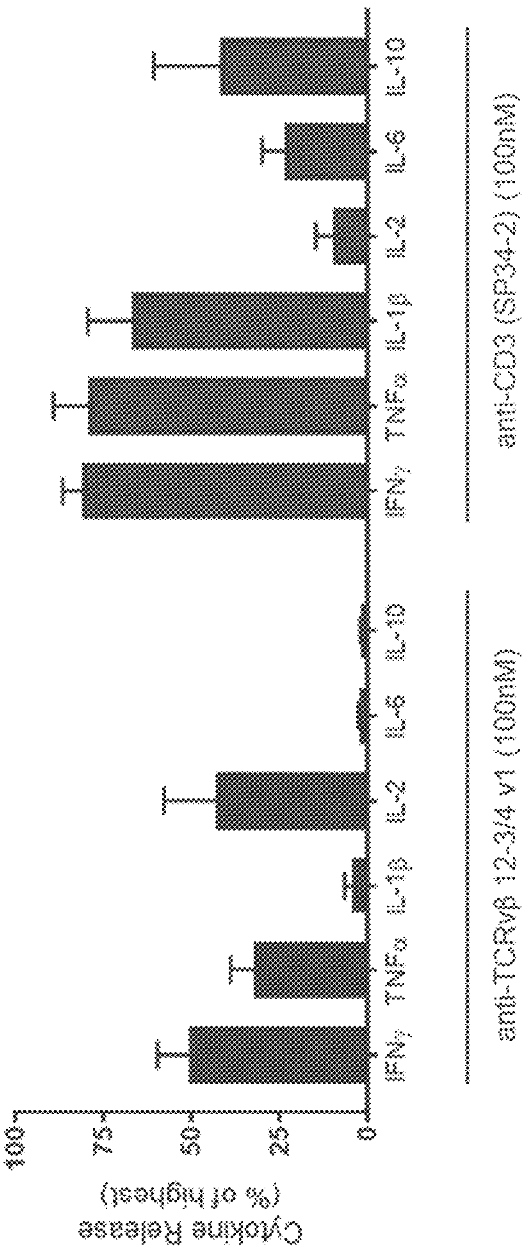
FIG. 92A is a bar graph showing the percentage of cytokine release from PBMCs activated/expanded for eight days using the indicated antibody (anti-TCRβV 12-3/4 v1 or SP34-2).
Figure 92B:
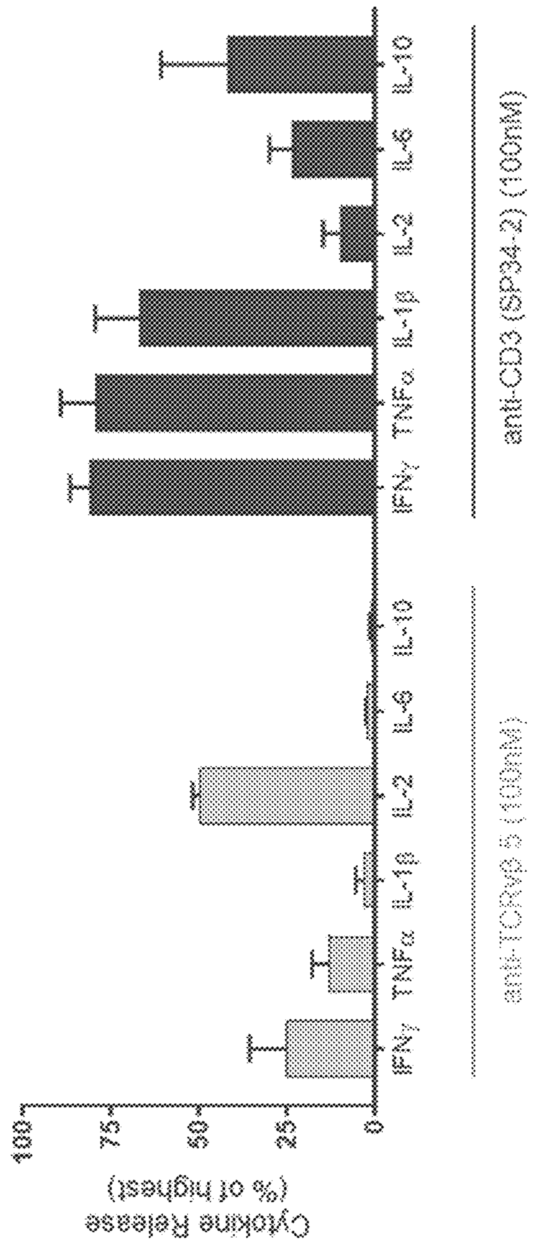
FIG. 92B is a bar graph showing the percentage of cytokine release from PBMCs activated/expanded for eight days using the indicated antibody (anti-TCRβV 5 or SP34-2).
Figure 92C:
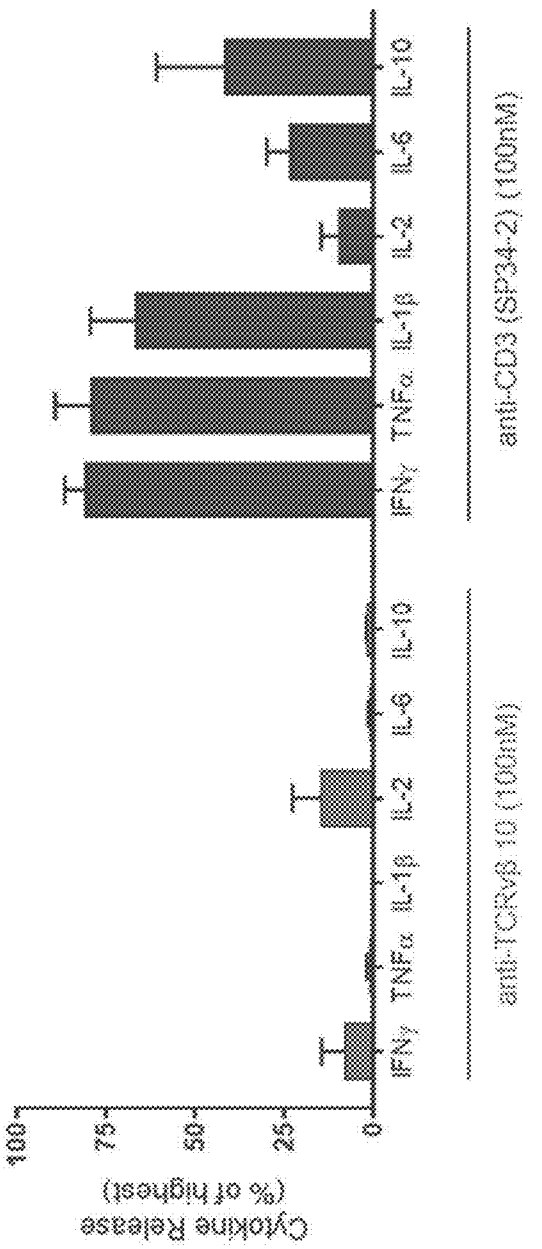
FIG. 92C is a bar graph showing the percentage of cytokine release from PBMCs activated/expanded for eight days using the indicated antibody (anti-TCRβV 10 or SP34-2).

In one series of experiments antibodies tested included anti-TCRvb 12-3/4 v1, anti-TCRvb 10, and anti-TCRvb 5. Per the protocol described above, human PBMCs were solid-phase stimulated (plate-coated) with the indicated T cell-activating antibody (anti-TCRvb 12-3/4 v1, anti-TCRvb 10, anti-TCRvb 5, or the anti-CD3ε antibody SP34) at 100 nM. Supernatant were collected on day 1 to day 8; and cytokines were quantified using Meso Scale Discovery (MSD) assay. 91 provides a graphical representation of sequences between the different clonotypes, highlighting the four subfamilies tested in this series of experiments. PBMCs activated/expanded with the anti-TCRvb 12-3/4 v1 antibody (FIG. 92A), anti-TCRvb 10 antibody (FIG. 92B), or anti-TCRvb antibody (FIG. 92C) exhibited lower levels of secretion of cytokines associated with cytokine release syndrome, including IFNγ, TNFα, IL-1β, IL-2, IL-6, and IL-10, as compared to PBMCs activated/expanded with the anti-CD3ε antibody SP34-2.

Figure 93A:
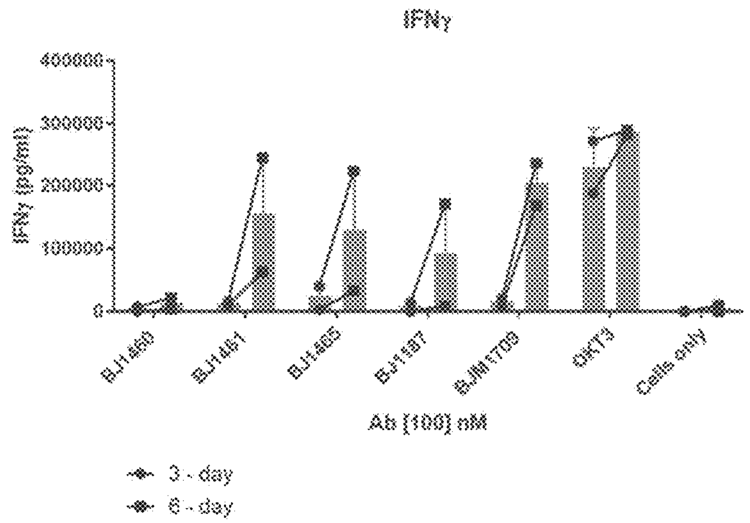
FIG. 93A a bar graph showing the level of secreted IFNγ by T cells activated/expanded with the indicated antibody for the indicated number of days (3 or 6).
Figure 93B:
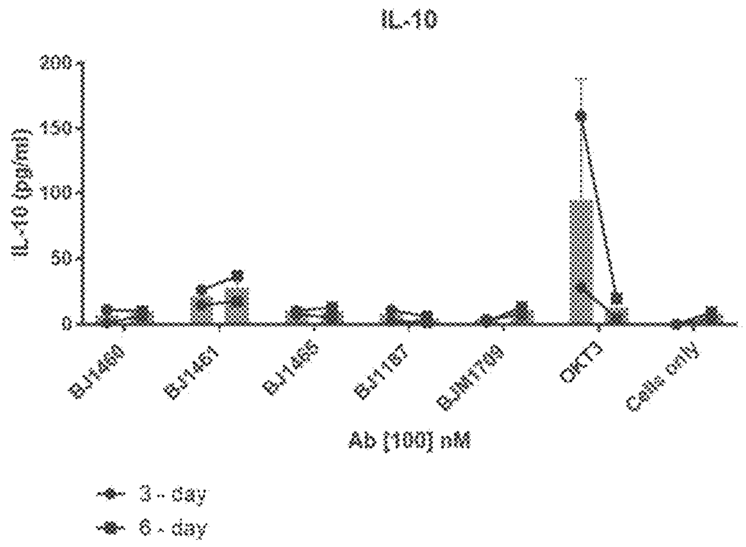
FIG. 93B a bar graph showing the level of secreted IL-10 by T cells activated/expanded with the indicated antibody for the indicated number of days (3 or 6).
Figure 93C:
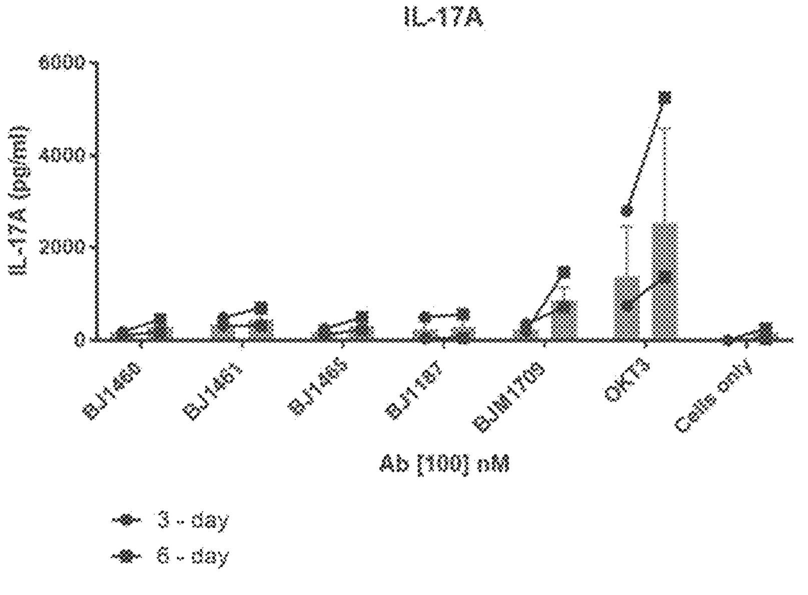
FIG. 93C a bar graph showing the level of secreted IL-17A by T cells activated/expanded with the indicated antibody for the indicated number of days (3 or 6).
Figure 93D:
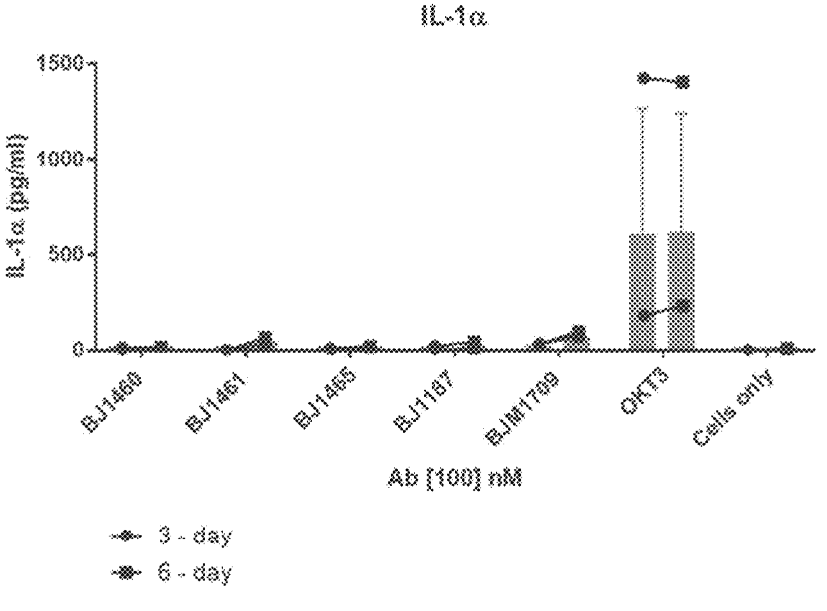
FIG. 93D a bar graph showing the level of secreted IL-1a by T cells activated/expanded with the indicated antibody for the indicated number of days (3 or 6).
Figure 93E:
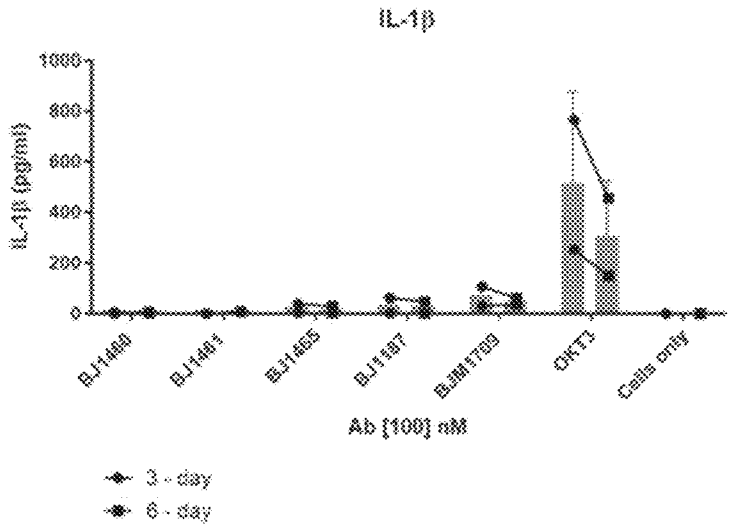
FIG. 93E a bar graph showing the level of secreted IL-1β by T cells activated/expanded with the indicated antibody for the indicated number of days (3 or 6).
Figure 93F:
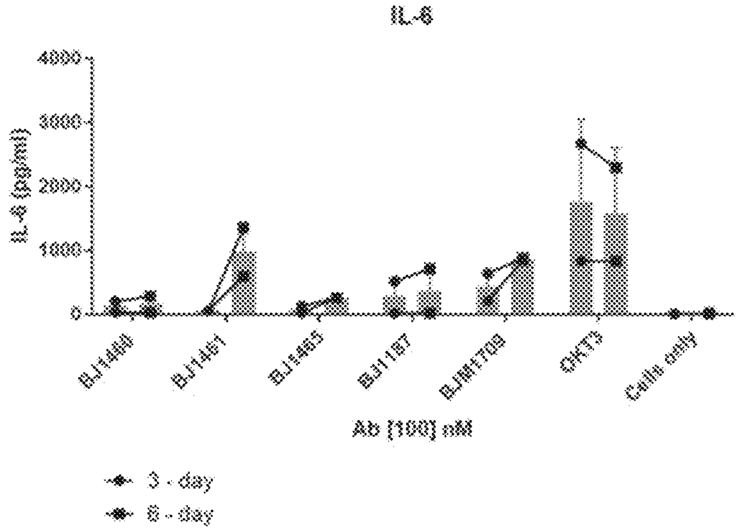
FIG. 93F a bar graph showing the level of secreted IL-6 by T cells activated/expanded with the indicated antibody for the indicated number of days (3 or 6).
Figure 93G:
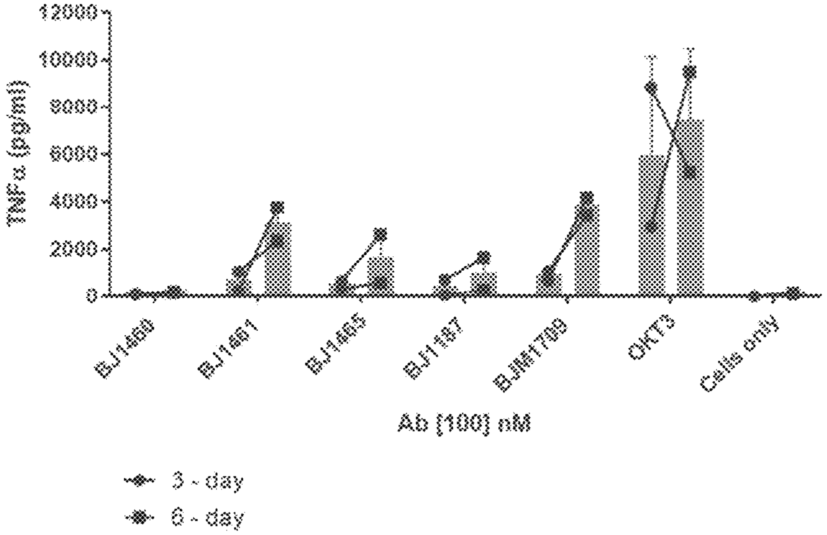
FIG. 93G a bar graph showing the level of secreted TNFα by T cells activated/expanded with the indicated antibody for the indicated number of days (3 or 6).
Figure 93H:
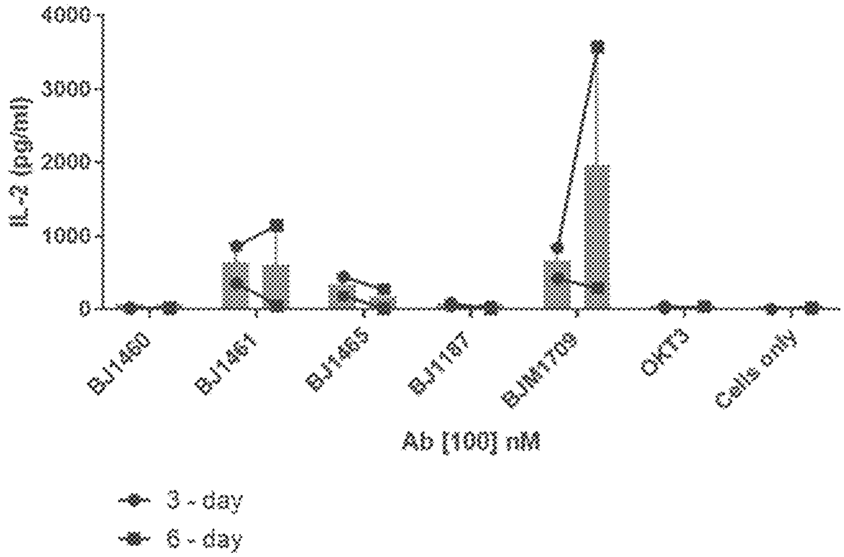
FIG. 93H a bar graph showing the level of secreted IL-2 by T cells activated/expanded with the indicated antibody for the indicated number of days (3 or 6).
Figure 94:
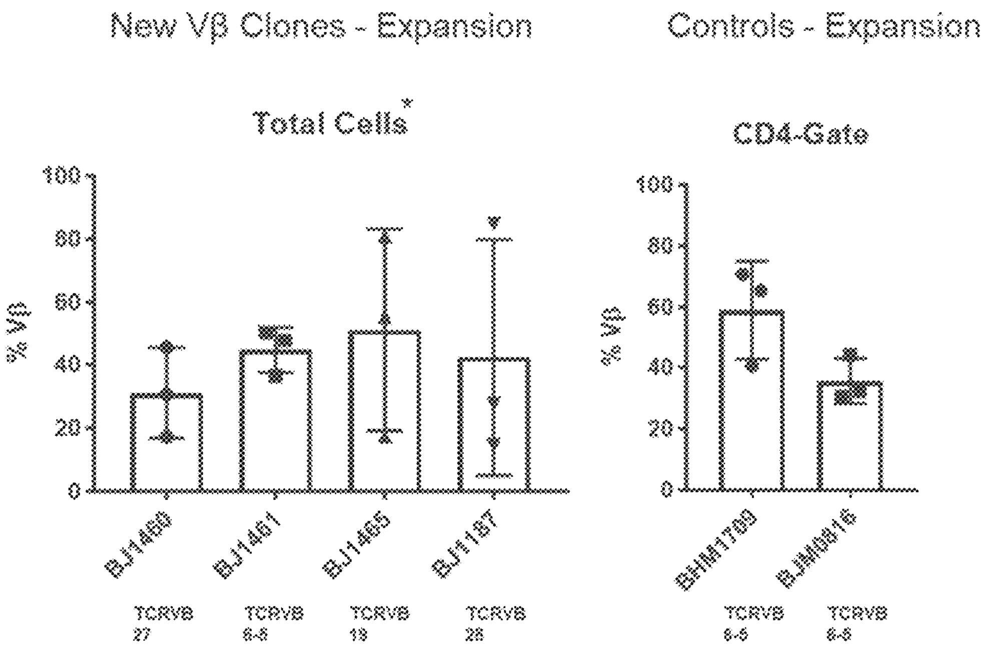
FIG. 94 is a bar graph summarizing data from FACS analysis of PBMCs activated/expanded for 6 days using the indicated anti-TCRVβ antibody.

In a second series of experiments, antibodies tested included the anti-TCRVβ antibodies: BJ1460, BJ1461, BJ1465, BJ1187, BJM1709; the anti-CD3ε antibody OKT3, and a cell only control. At Day-0 PBMCs from donor 10749 were thawed and counted along with PBMCs from two fresh donors (13836 and 14828). 200,000 PBMCs in 180 uL of X-vivo media/well (1×10e6 cells/mL) was added to a round bottom 96 well plate—one donor for 3 of the plate. 20 uL of 10×TCRVβ antibodies at 100 nM or 15 μg/mL were added to the wells of the plate and one triplicate of wells was added with cells only. The pate was kept in a 37° C. incubator with 5% $CO_2$. The cells were stimulated for 3 days with a selected antibody and 50 μL of supernatant harvested from the plate and stored at −20° C. 50 μL of media was added back to each well and the plate kept in a 37° C. incubator with 5% $CO_2$. On Day-6 50 uL of supernatant was harvested from each well of the plate and stored at −20° C. The cells from two wells out of the triplicate were combined and media replenished with huIL-2 was added the cell suspension for each donor was transferred into a 12-well plate. The cells were incubated overnight to allow for rest and expansion in IL-2. The cells were subsequently stained for specific Vβ-clones for detection of specific Vβ-clone expansion by FACS analysis. The concentration of cytokines (including IFNγ, IL-10, IL-17A, IL-1α, IL-1β, IL-2, IL-6, and TNFα) in the media were analyzed in the Day-3 and Day-6 supernatant samples using Meso Scale Discovery (MSD) assay. The data confirmed that PBMCs cells activated/expanded using any of the anti-TCRβV antibodies—BJ1460, BJ1461, BJ1465, BJ1187, BJM1709—secreted lower levels of IFNγ (FIG. 93A), IL-10 (FIG. 93B), IL-17A (FIG. 93C), IL-1α (FIG. 93D), IL-1β (FIG. 93E), IL-6 (FIG. 93F), TNFα (FIG. 93G); and higher levels of IL-2 (FIG. 93H). FACS analysis further showed expansion of T cells expressing the indicated TCRVβ clones (FIG. 94).

Figure 95A:
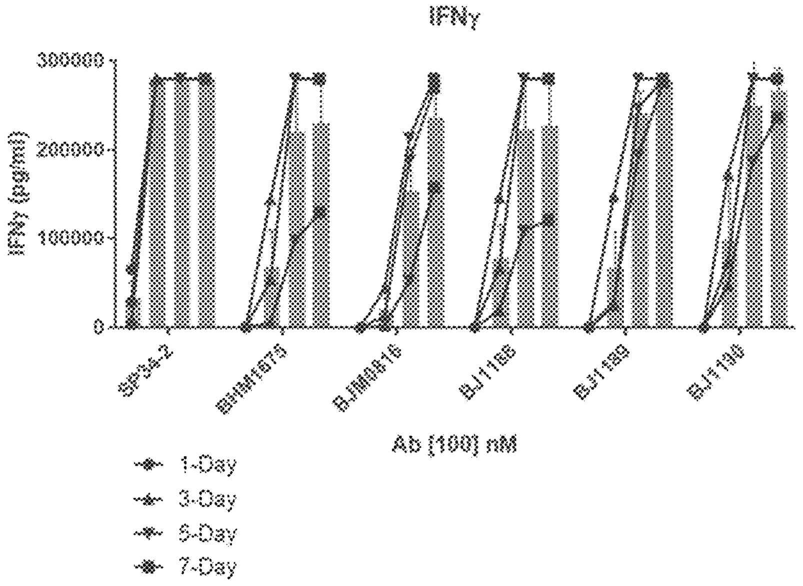
FIG. 95A a bar graph showing the level of secreted IFNγ by T cells activated/expanded with the indicated antibody for the indicated number of days (1, 3, 5, or 7).
Figure 95B:
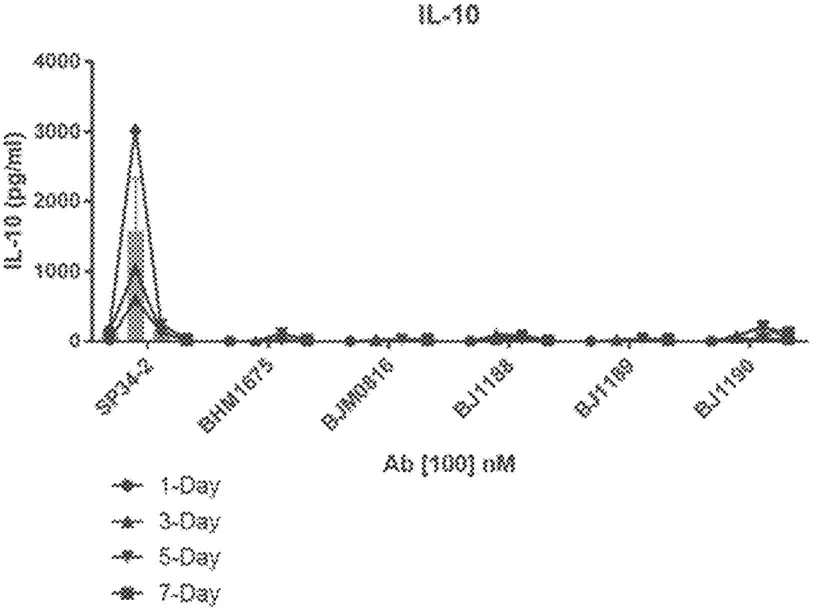
FIG. 95B a bar graph showing the level of secreted IL-10 by T cells activated/expanded with the indicated antibody for the indicated number of days (1, 3, 5, or 7).
Figure 95C:
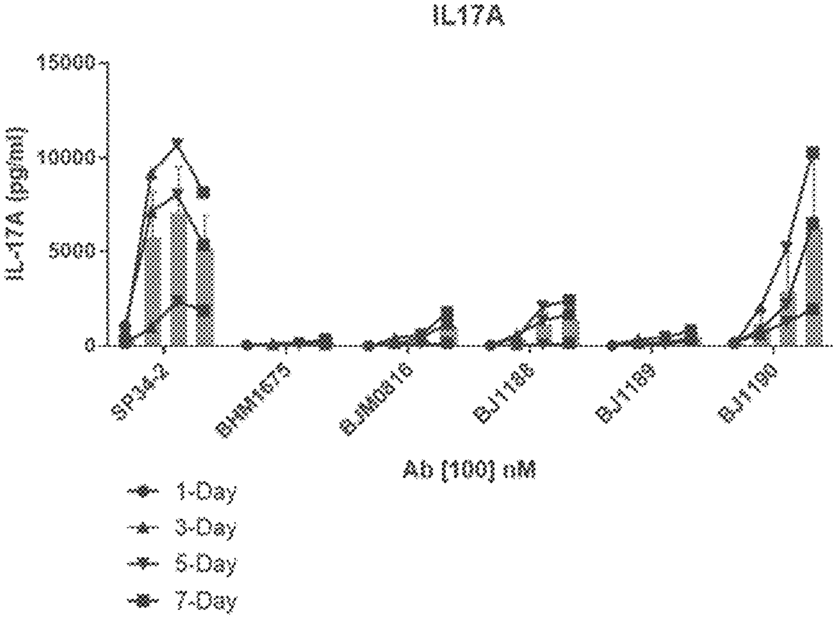
FIG. 95C a bar graph showing the level of secreted IL-17A by T cells activated/expanded with the indicated antibody for the indicated number of days (1, 3, 5, or 7).
Figure 95D:
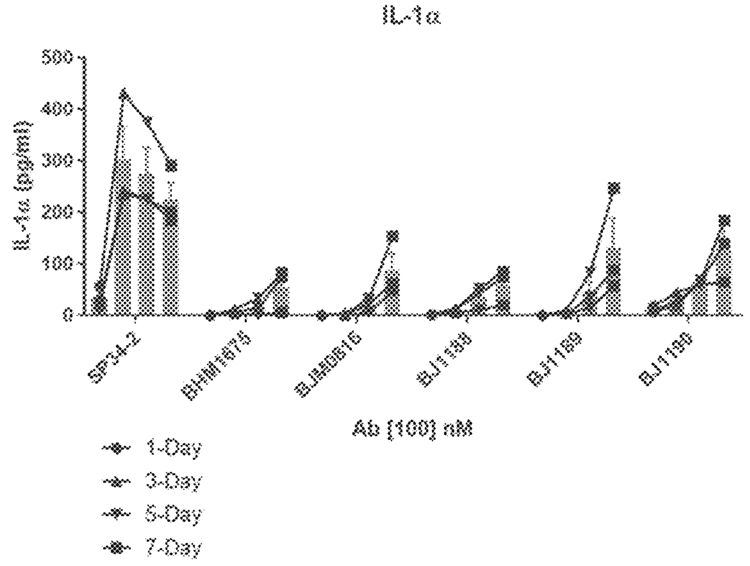
FIG. 95D a bar graph showing the level of secreted IL-1a by T cells activated/expanded with the indicated antibody for the indicated number of days (1, 3, 5, or 7).
Figure 95E:
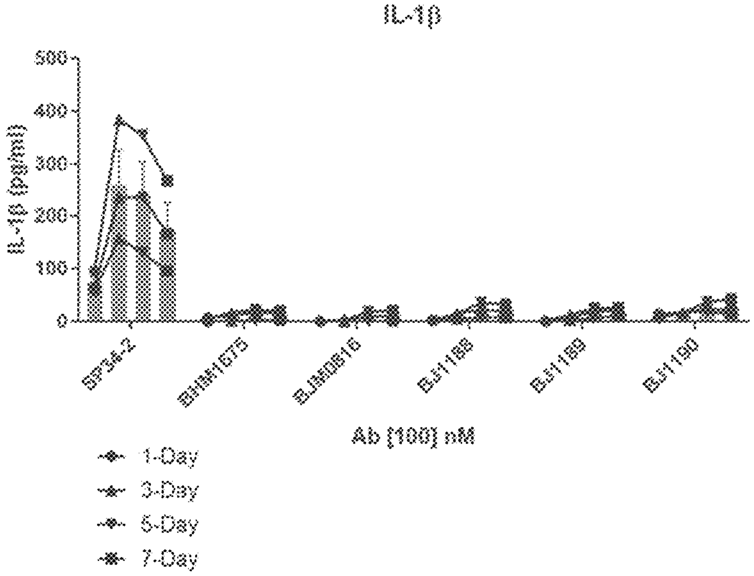
FIG. 95E a bar graph showing the level of secreted IL-1β by T cells activated/expanded with the indicated antibody for the indicated number of days (1, 3, 5, or 7).
Figure 95F:
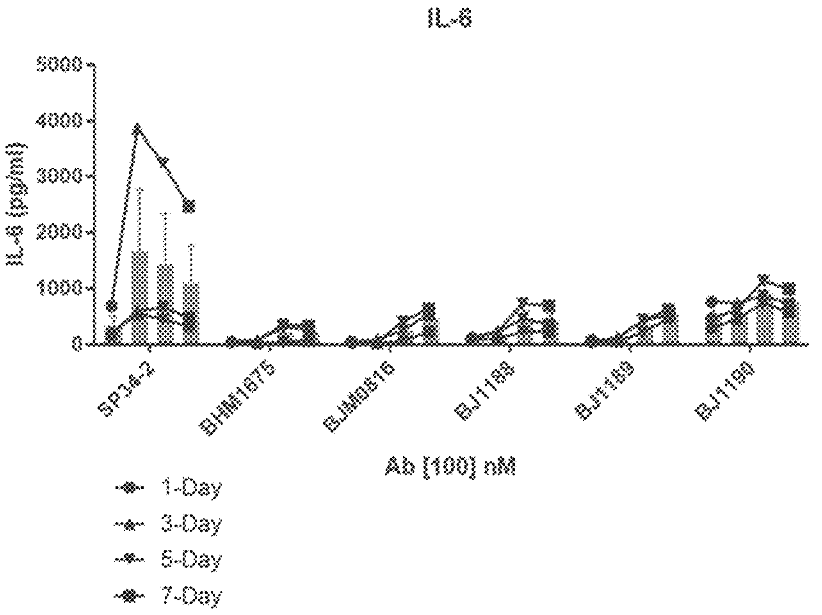
FIG. 95F a bar graph showing the level of secreted IL-6 by T cells activated/expanded with the indicated antibody for the indicated number of days (1, 3, 5, or 7).
Figure 95G:
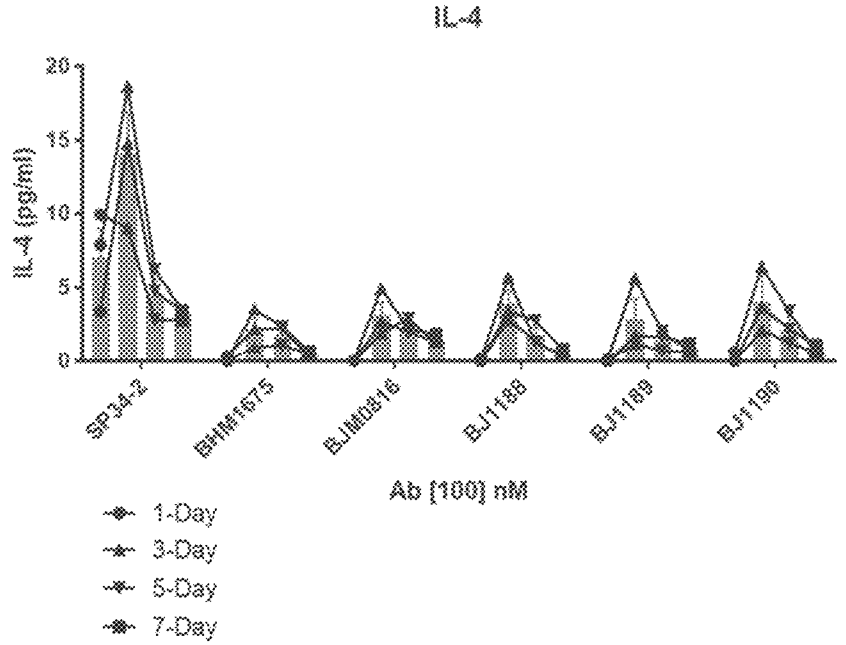
FIG. 95G a bar graph showing the level of secreted IL-4 by T cells activated/expanded with the indicated antibody for the indicated number of days (1, 3, 5, or 7).
Figure 95H:
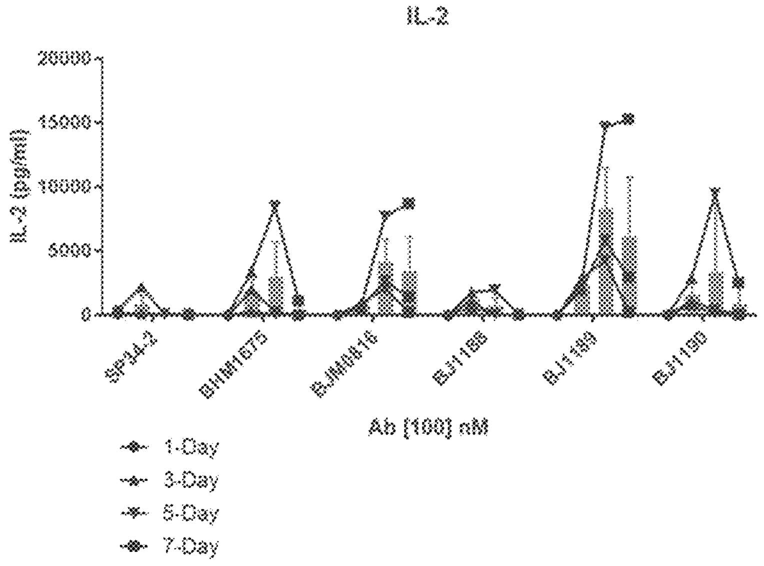
FIG. 95H a bar graph showing the level of secreted IL-2 by T cells activated/expanded with the indicated antibody for the indicated number of days (1, 3, 5, or 7).
Figure 96:
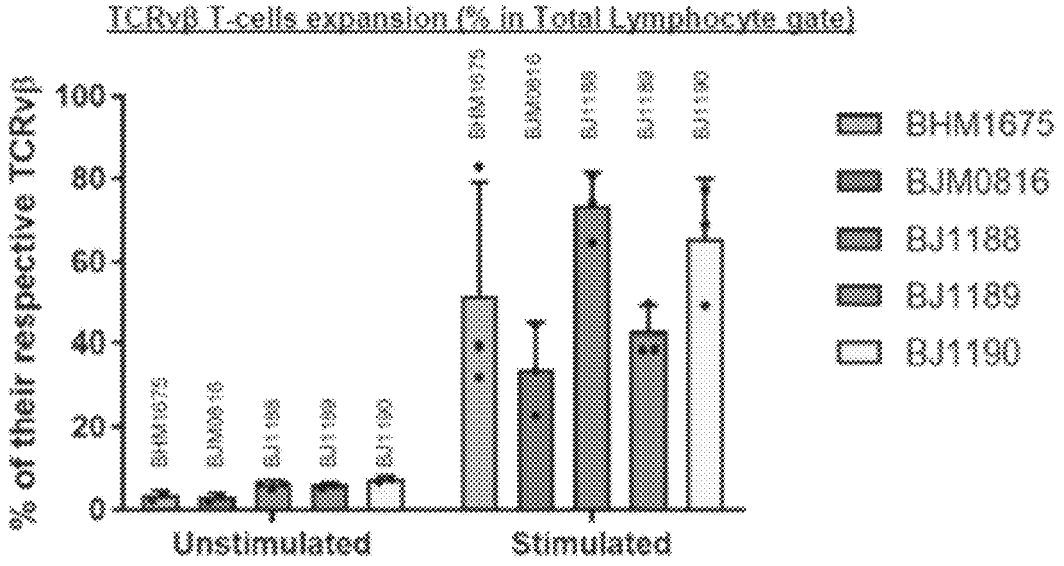
FIG. 96 is a bar graph summarizing data from FACS analysis of PBMCs activated/expanded for 7 days using the indicated anti-TCRVβ antibody.

In a third series of experiments, antibodies tested included the anti-TCRVβ antibodies: BHM1675, BJM0816, BJ1188, BJ1189, BJ1190; and the anti-CD3ε antibody SP34-2. The indicated antibodies were coated into a 96-well round bottom plate at concentration of 100 nM or 15 μg/mL at 200 μl/well in PBS at 4° C. overnight or at 37° C. for a minimum of 2 hours. The plate was washed the next day with 200 μL of PBS and 0.2×10^6 PBMCs/well from donors: CTL_123, CTL_323 and CTL_392. Supernatant samples were collected on days 1, 3, 5, and 7. A 10-plex Meso Scale Discovery (MSD) assay was run on the supernatants to determine the concentration of cytokines (including IFNγ, IL-10, IL-17A, IL-1α, IL-1β, IL-6, IL-4, and IL-2). After day 7, cells were pelleted and added to culture medium supplemented with IL-2 for one additional day to allow for expansion. Expansion of T cells expressing TCRVβ clones was analyzed by FACS staining using the same activating antibody followed by a secondary anti-human/mouse FITC antibody. Live/Dead, CD4+ and CD8+ T cells were also stained for using BHM1675, BJM0816, BJ1189 and BJ1190 antibodies. The data confirmed that PBMCs cells activated/expanded using any of the anti-TCRβV antibodies—BHM1675, BJM0816, BJ1188, BJ1189, BJ1190—secreted lower levels of IFNγ (FIG. 95A), IL-10 (FIG. 95B), IL-17A (FIG. 95C), IL-1α (FIG. 95D), IL-1β (FIG. 95E), IL-6 (FIG. 95F), IL-4 (FIG. 95G); and higher levels of IL-2 (FIG. 95H). FACS analysis further showed that TCRVβ sub-clone T-cells are expanded by their respective activation antibody (FIG. 96).

Figure 97A:
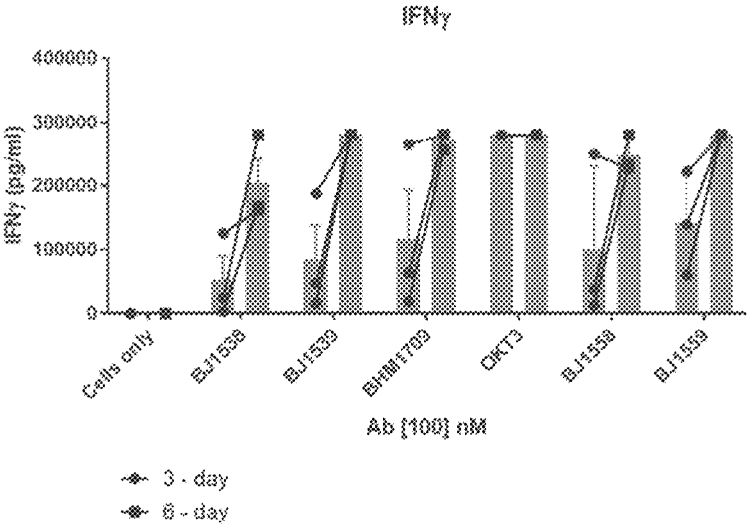
FIG. 97A is a bar graph showing the level of secreted IFNγ by T cells activated/expanded with the indicated antibody for the indicated number of days (3 or 6).
Figure 97B:
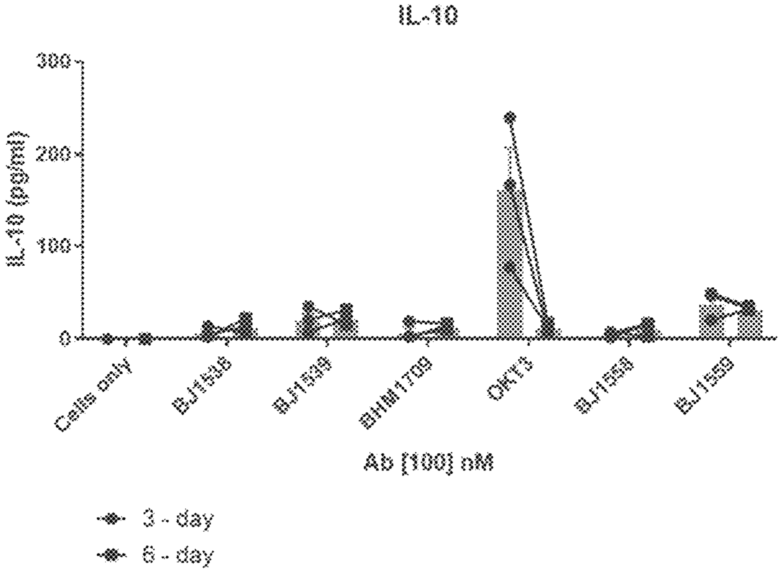
FIG. 97B a bar graph showing the level of secreted IL-10 by T cells activated/expanded with the indicated antibody for the indicated number of days (3 or 6).
Figure 97C:
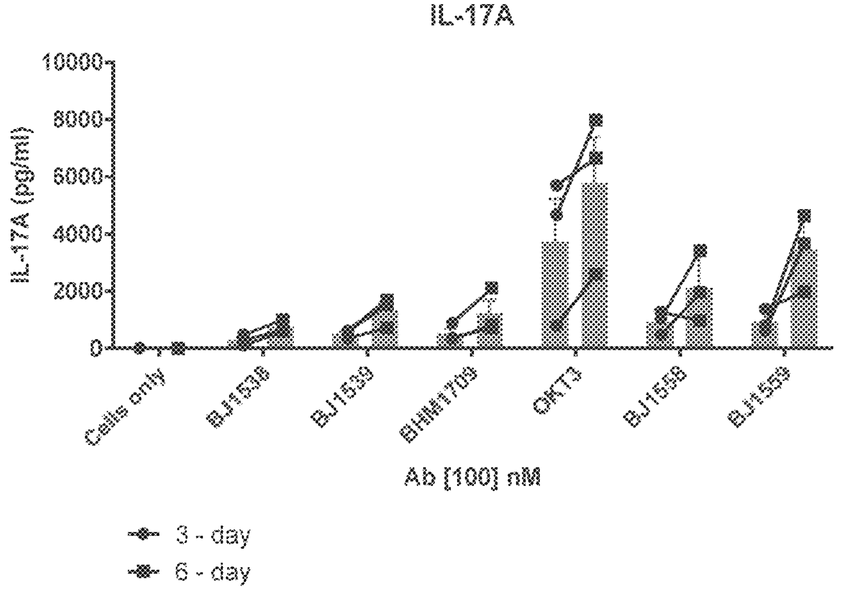
FIG. 97C a bar graph showing the level of secreted IL-17A by T cells activated/expanded with the indicated antibody for the indicated number of days (3 or 6).
Figure 97D:
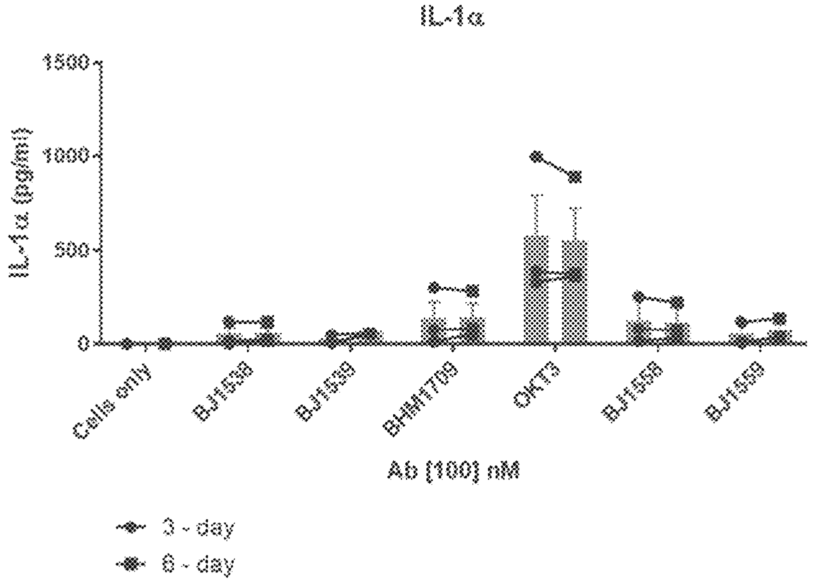
FIG. 97D a bar graph showing the level of secreted IL-1a by T cells activated/expanded with the indicated antibody for the indicated number of days (3 or 6).
Figure 97E:
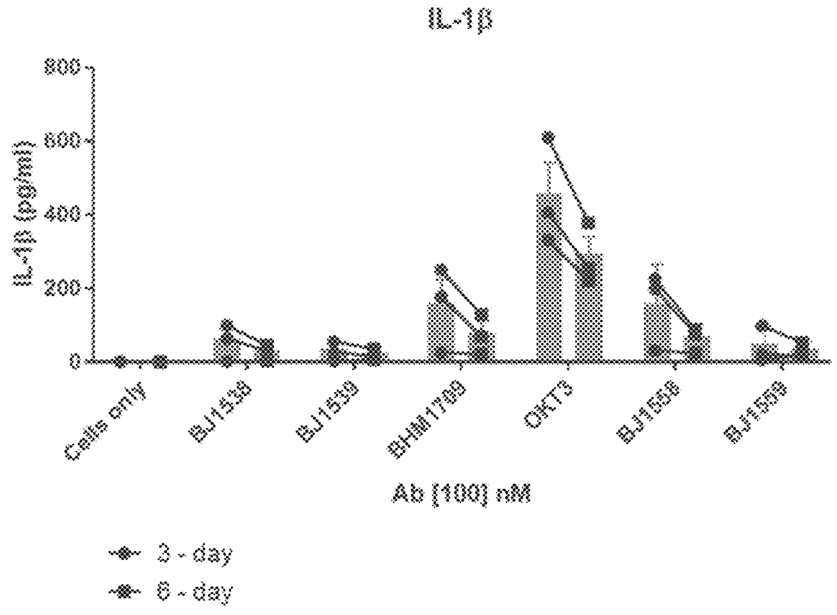
FIG. 97E a bar graph showing the level of secreted IL-1β by T cells activated/expanded with the indicated antibody for the indicated number of days (3 or 6).
Figure 97F:
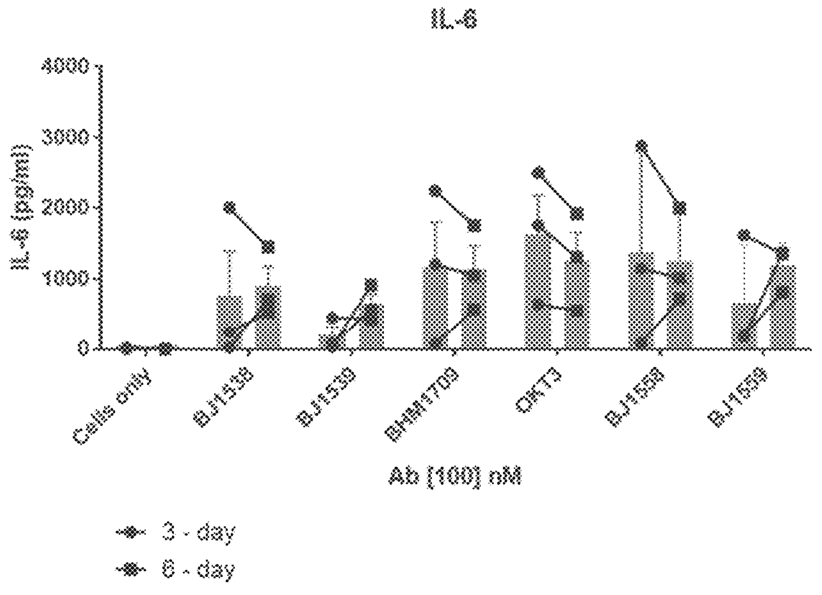
FIG. 97F a bar graph showing the level of secreted IL-6 by T cells activated/expanded with the indicated antibody for the indicated number of days (3 or 6).
Figure 97G:
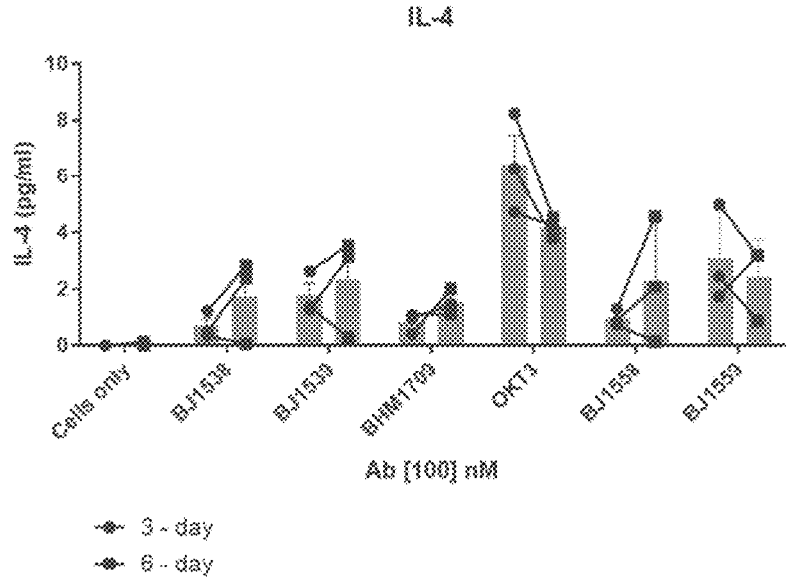
FIG. 97G a bar graph showing the level of secreted IL-4 by T cells activated/expanded with the indicated antibody for the indicated number of days (3 or 6).
Figure 97H:
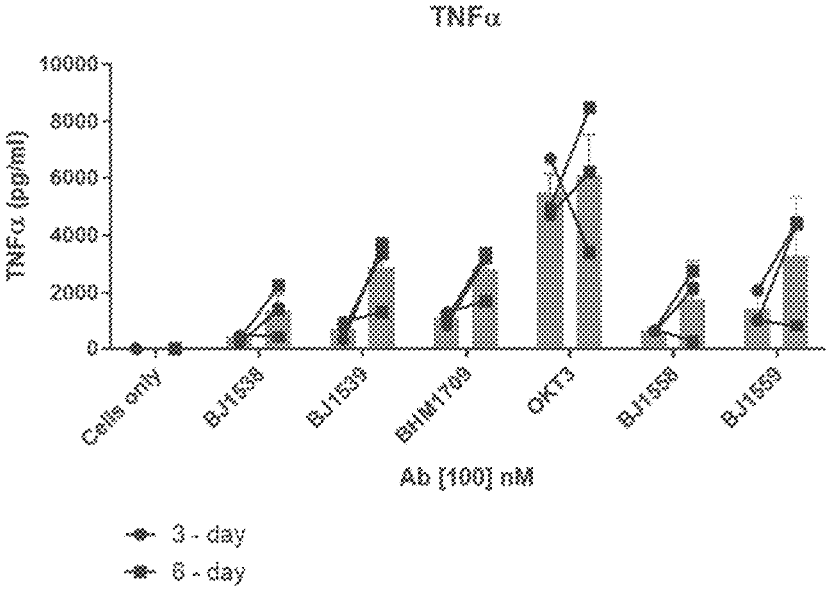
FIG. 97H a bar graph showing the level of secreted TNFα by T cells activated/expanded with the indicated antibody for the indicated number of days (3 or 6).
Figure 97I:
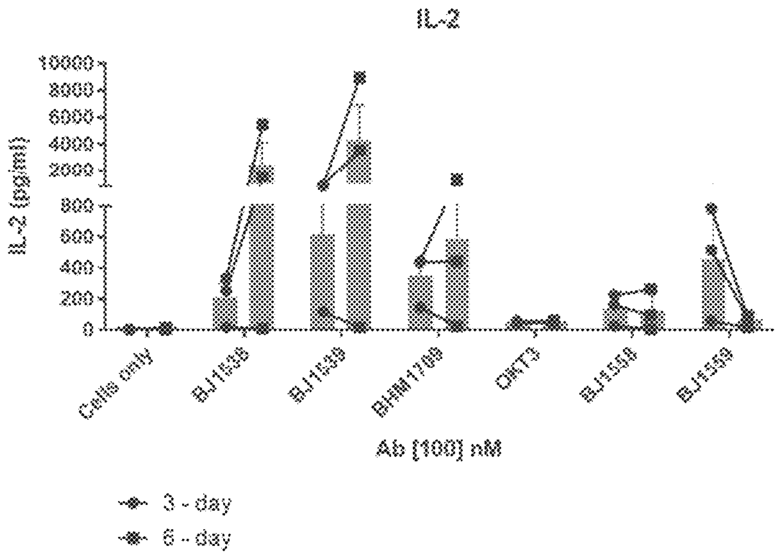
FIG. 97I a bar graph showing the level of secreted IL-2 by T cells activated/expanded with the indicated antibody for the indicated number of days (3 or 6).

In a fourth series of experiments, antibodies tested included the anti-TCRVβ antibodies: BJ1538, BJ1539, BJ1558, BJ1559, BHM1709; and the anti-CD3ε antibody OKT3. The indicated antibodies were coated into a 96-well round bottom plate at concentration of 100 nM or 15 μg/mL at 200 μl/well in PBS at 4° C. overnight or at 37° C. for a minimum of 2 hours. The plate was washed the next day with 200 μL of PBS and 0.2×10^6 PBMCs/well from donors: 10749, 5078 and 15562 (frozen and thawed samples). Supernatant samples were collected on days 3 and 6. A 10-plex Meso Scale Discovery (MSD) assay was run on the supernatants to determine the concentration of cytokines (including IFNγ, IL-10, IL-17A, IL-1α, IL-1β, IL-6, IL-4, TNFα, and IL-2). The data confirmed that PBMCs cells activated/expanded using any of the anti-TCRβV antibodies—BJ1538, BJ1539, BJ1558, BJ1559, BHM1709—secreted lower levels of IFNγ (FIG. 97A), IL-10 (FIG. 97B), IL-17A (FIG. 97C), IL-1a (FIG. 97D), IL-1β (FIG. 97E), IL-6 (FIG. 97F), IL-4 (FIG. 97G) TNFα (FIG. 97H); and higher levels of IL-2 (FIG. 97I).

In summary, the data shows that anti-TCRvb antibodies recognizing different TCRvb subfamilies (or subtypes) have a similar cytokine profile and do not induce cytokines associated with CRS.

Example 34: Anti-TCRvb does not Activate T Cells without Cross-Linking

To assess whether bivalent anti-TCRvb antibodies activate T cells without cross-linking-purified T cells from 2 donors were stimulated with anti-TCRvb (TCRvb 6-5 v1) or anti-CD3e (SP34), either plate-coated or in solution. Supernatants were collected at day 1, 3, 5 and 7 post activation. Cytokine secretion was detected using MSD 10 plex kit (IFN-g, IL-10, IL-15, IL-17A, IL-1a, IL-1b, IL-2, IL-4, IL-6 and TNF-α).

Figure 98A:
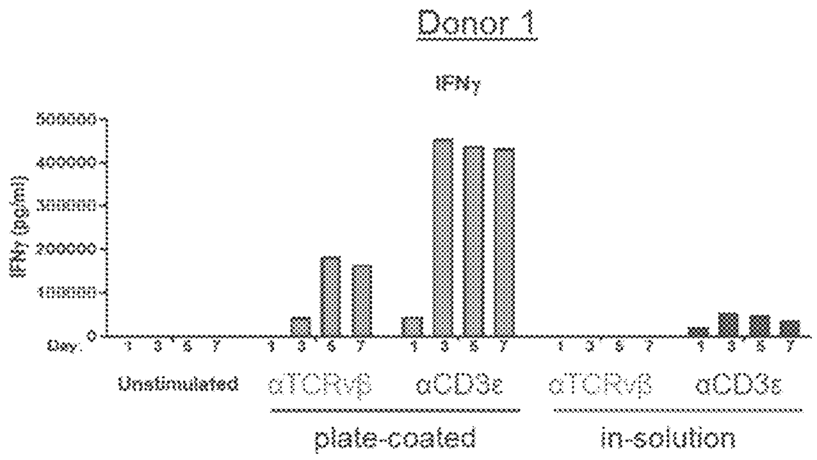
FIG. 98A is a bar graph showing the level of secreted IFN-γ by T cells activated/expanded with the indicated antibody (anti-TCRβV 6-5 v1 (plate coated), anti-CD3ε (plate coated), anti-TCRβV 6-5 v1 (in solution), or anti-CD3ε (in solution) and cultured with said antibody for the indicated number of days (1, 3, 5, or 7).
Figure 98B:
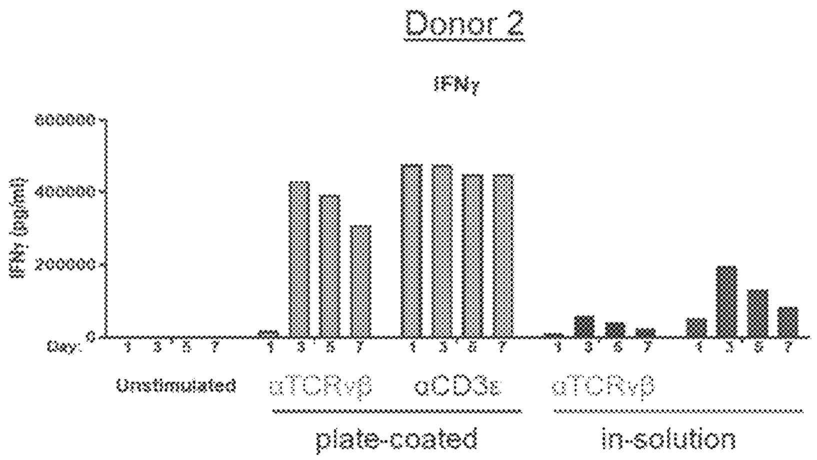
FIG. 98B is a bar graph showing the level of secreted IFN-γ by T cells activated/expanded with the indicated antibody (anti-TCRβV 6-5 v1 (plate coated), anti-CD3ε (plate coated), anti-TCRβV 6-5 v1 (in solution), or anti-CD3ε (in solution) and cultured with said antibody for the indicated number of days (1, 3, 5, or 7).
Figure 98C:
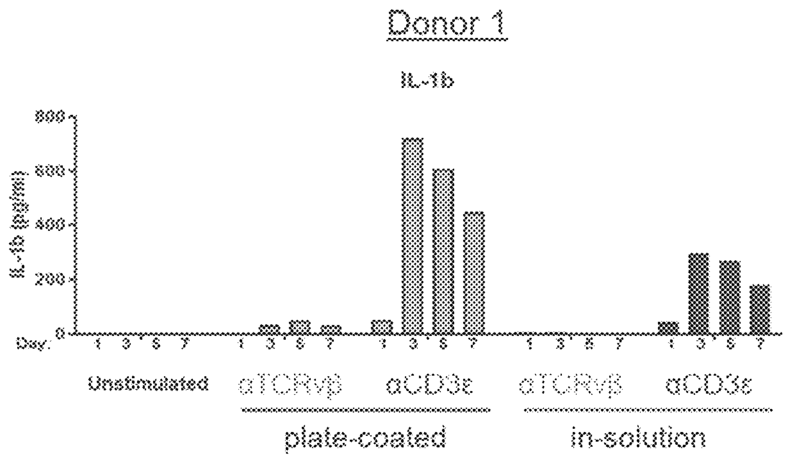
FIG. 98C is a bar graph showing the level of secreted IL-1b by T cells activated/expanded with the indicated antibody (anti-TCRβV 6-5 v1 (plate coated), anti-CD3ε (plate coated), anti-TCRβV 6-5 v1 (in solution), or anti-CD3ε (in solution) and cultured with said antibody for the indicated number of days (1, 3, 5, or 7).
Figure 98D:
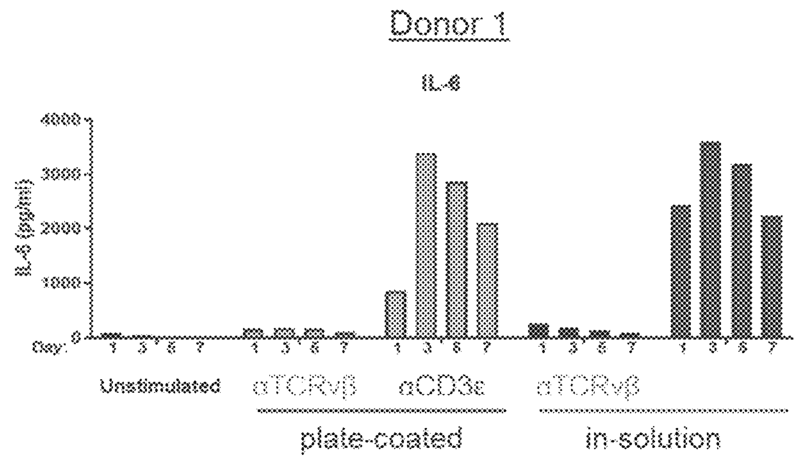
FIG. 98D is a bar graph showing the level of secreted IL-6 by T cells activated/expanded with the indicated antibody (anti-TCRβV 6-5 v1 (plate coated), anti-CD3ε (plate coated), anti-TCRβV 6-5 v1 (in solution), or anti-CD3ε (in solution) and cultured with said antibody for the indicated number of days (1, 3, 5, or 7).
Figure 98E:
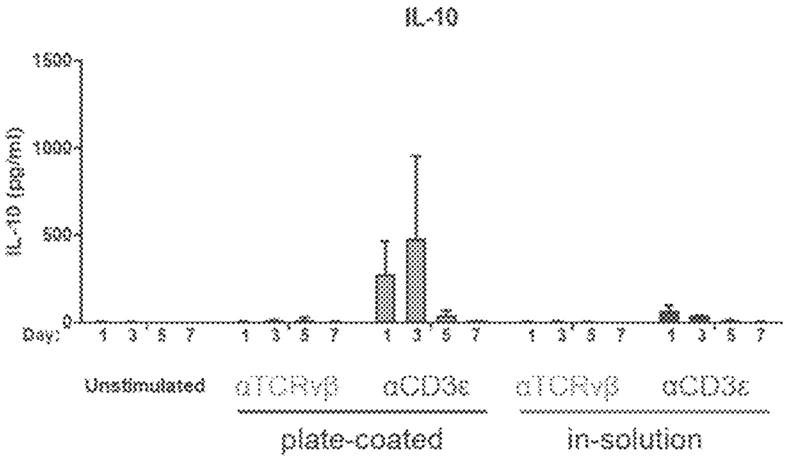
FIG. 98E is a bar graph showing the level of secreted IL-10 by T cells activated/expanded with the indicated antibody (anti-TCRβV 6-5 v1 (plate coated), anti-CD3ε (plate coated), anti-TCRβV 6-5 v1 (in solution), or anti-CD3ε (in solution) and cultured with said antibody for the indicated number of days (1, 3, 5, or 7).
Figure 98F:
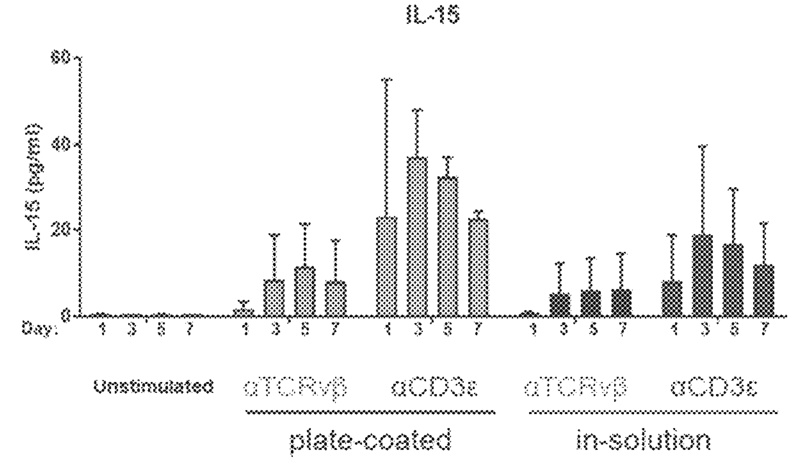
FIG. 98F is a bar graph showing the level of secreted IL-15 by T cells activated/expanded with the indicated antibody (anti-TCRβV 6-5 v1 (plate coated), anti-CD3ε (plate coated), anti-TCRβV 6-5 v1 (in solution), or anti-CD3ε (in solution) and cultured with said antibody for the indicated number of days (1, 3, 5, or 7).
Figure 98G:
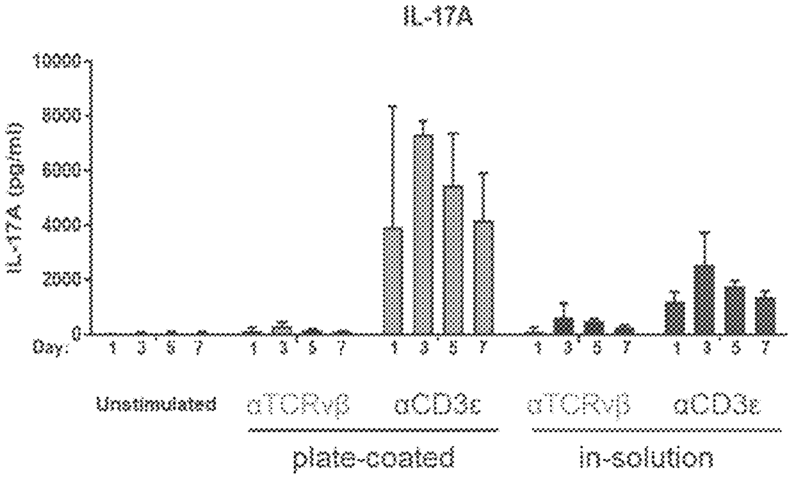
FIG. 98G is a bar graph showing the level of secreted IL-17A by T cells activated/expanded with the indicated antibody (anti-TCRβV 6-5 v1 (plate coated), anti-CD3ε (plate coated), anti-TCRβV 6-5 v1 (in solution), or anti-CD3ε (in solution) and cultured with said antibody for the indicated number of days (1, 3, 5, or 7).
Figure 98H:
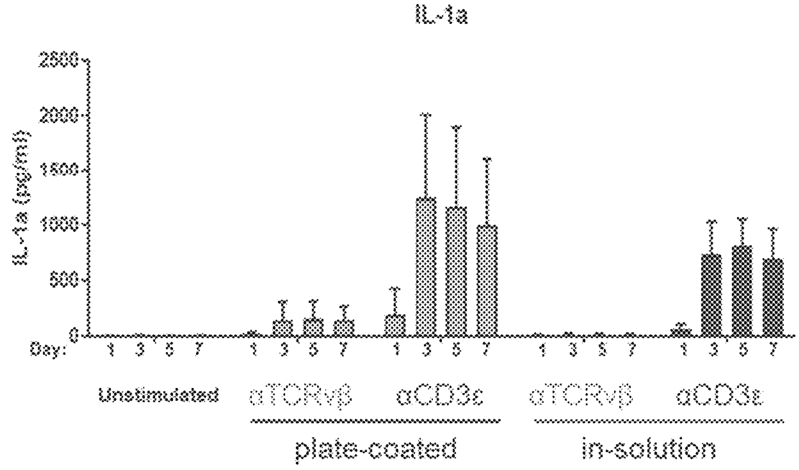
FIG. 98H is a bar graph showing the level of secreted IL-1a by T cells activated/expanded with the indicated antibody (anti-TCRβV 6-5 v1 (plate coated), anti-CD3ε (plate coated), anti-TCRβV 6-5 v1 (in solution), or anti-CD3ε (in solution) and cultured with said antibody for the indicated number of days (1, 3, 5, or 7).
Figure 98I:
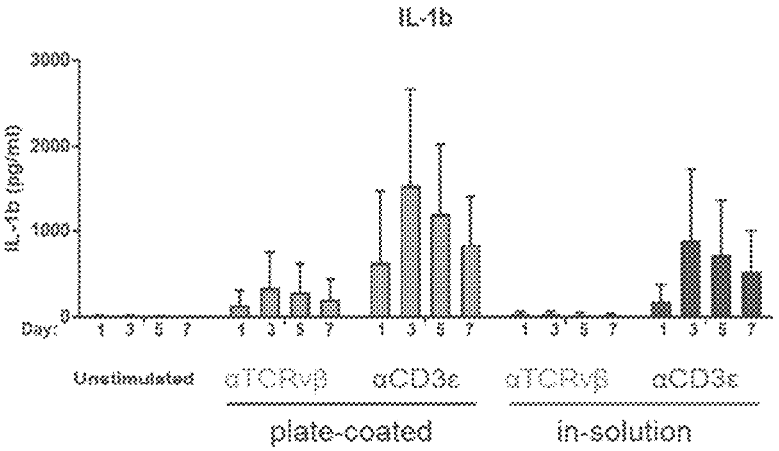
FIG. 98I is a bar graph showing the level of secreted IL-1b by T cells activated/expanded with the indicated antibody (anti-TCRβV 6-5 v1 (plate coated), anti-CD3ε (plate coated), anti-TCRβV 6-5 v1 (in solution), or anti-CD3ε (in solution) and cultured with said antibody for the indicated number of days (1, 3, 5, or 7).
Figure 98J:
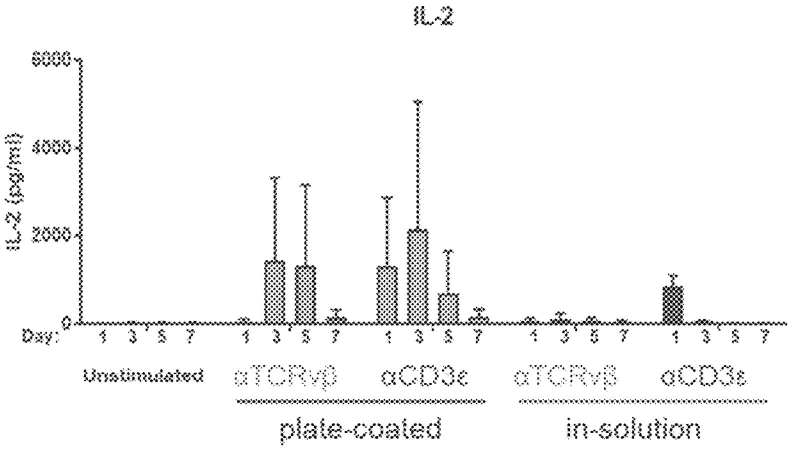
FIG. 98J is a bar graph showing the level of secreted IL-2 by T cells activated/expanded with the indicated antibody (anti-TCRβV 6-5 v1 (plate coated), anti-CD3ε (plate coated), anti-TCRβV 6-5 v1 (in solution), or anti-CD3ε (in solution) and cultured with said antibody for the indicated number of days (1, 3, 5, or 7).
Figure 98K:
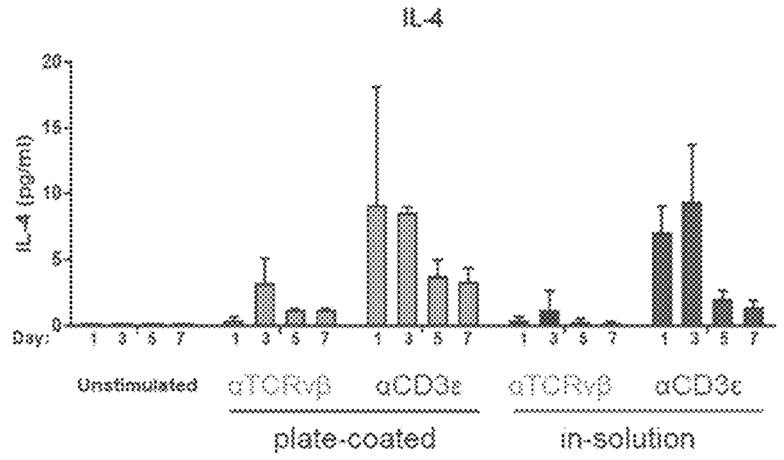
FIG. 98K is a bar graph showing the level of secreted IL-4 by T cells activated/expanded with the indicated antibody (anti-TCRβV 6-5 v1 (plate coated), anti-CD3ε (plate coated), anti-TCRβV 6-5 v1 (in solution), or anti-CD3ε (in solution) and cultured with said antibody for the indicated number of days (1, 3, 5, or 7).
Figure 98L:
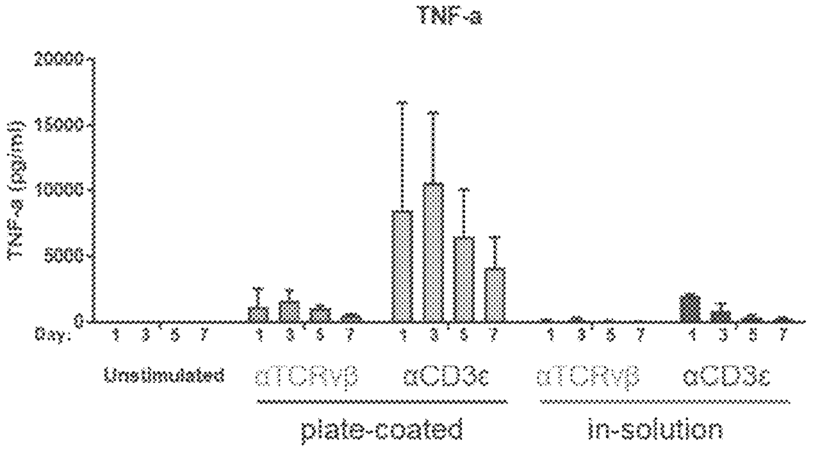
FIG. 98L is a bar graph showing the level of secreted TNF-a by T cells activated/expanded with the indicated antibody (anti-TCRβV 6-5 v1 (plate coated), anti-CD3ε (plate coated), anti-TCRβV 6-5 v1 (in solution), or anti-CD3ε (in solution) and cultured with said antibody for the indicated number of days (1, 3, 5, or 7).

The results show the PBMCs activated/expanded with anti-TCRvb 6-5 v1 antibody in solution do no induce very little IFNγ secretion as compared to PBMCs activated/expanded with anti-TCRvb 6-5 v1 antibody in immobilized (allowing for crosslinking) (FIG. 98A and FIG. 98B). The results show the PBMCs activated/expanded with anti-TCRvb 6-5 v1 antibody in solution do no induce very little or no IL-1b (FIG. 98C), IL-10 (FIG. 98E), IL-15 (FIG. 98F), IL-17A (FIG. 98G), IL-1a (FIG. 98H), IL-1b (FIG. 98I), IL-2 (FIG. 98J), IL-4 (FIG. 98K), IL-6 (FIG. 98D), and TNF-a (FIG. 98L) secretion. In summary, the data shows that anti-CD3ε activates T cells in solution (without cross-linking); while the anti-TCRvb antibodies does not activate T-cells in solution.

Example 35: Competition of Binding to TCRVB by Two Anti-TCRVβ 5-5,5-6 Antibodies with Distinct Sequences This Example describes epitope competition of two anti-TCRVβ 5-5,5-6 antibodies for binding to their shared TCRVB antigen. The TM23 and MH3-2 antibodies both bind to TCRVβ 5-5,5-6. However, the TM23 and MH3-2 antibodies do not share substantial sequence homology. As shown in FIG. 24A-B, anti-TCRβV antibody molecules disclosed herein recognize a structurally conserved domain on the TCRBV protein (as denoted by the circled area in FIG. 24A), but have low sequence similarity among themselves. To test whether two anti-TCRVβ 5-5,5-6 antibodies which do not share substantial sequence homology, can compete for binding to the TCRBV antigen, a competition assay was carried out.

Purified MH3-2 antibody was conjugated to AF647. T cells from two donors were preincubated with 500 nM of the TM23 antibody or left untreated. The T cells were then stained with the MH3-2 antibody conjugated to AF647.

Figure 99:
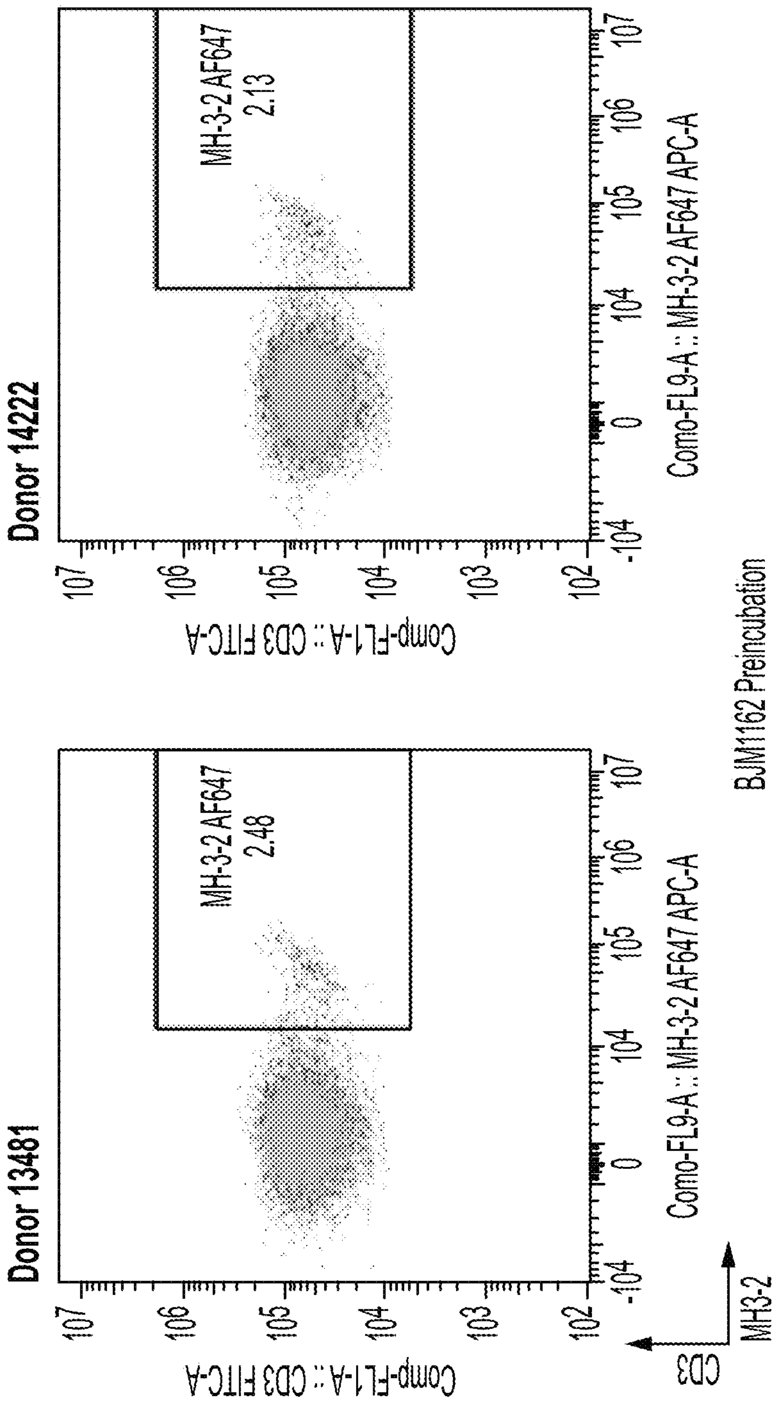
FIG. 99 is a FACS plot showing the showing the ability of MH3-2 to bind PBMCs from one of two donors when the PBMCs are either preincubated with TM23 or not (MH3-2 Alone).
Figure 100A:
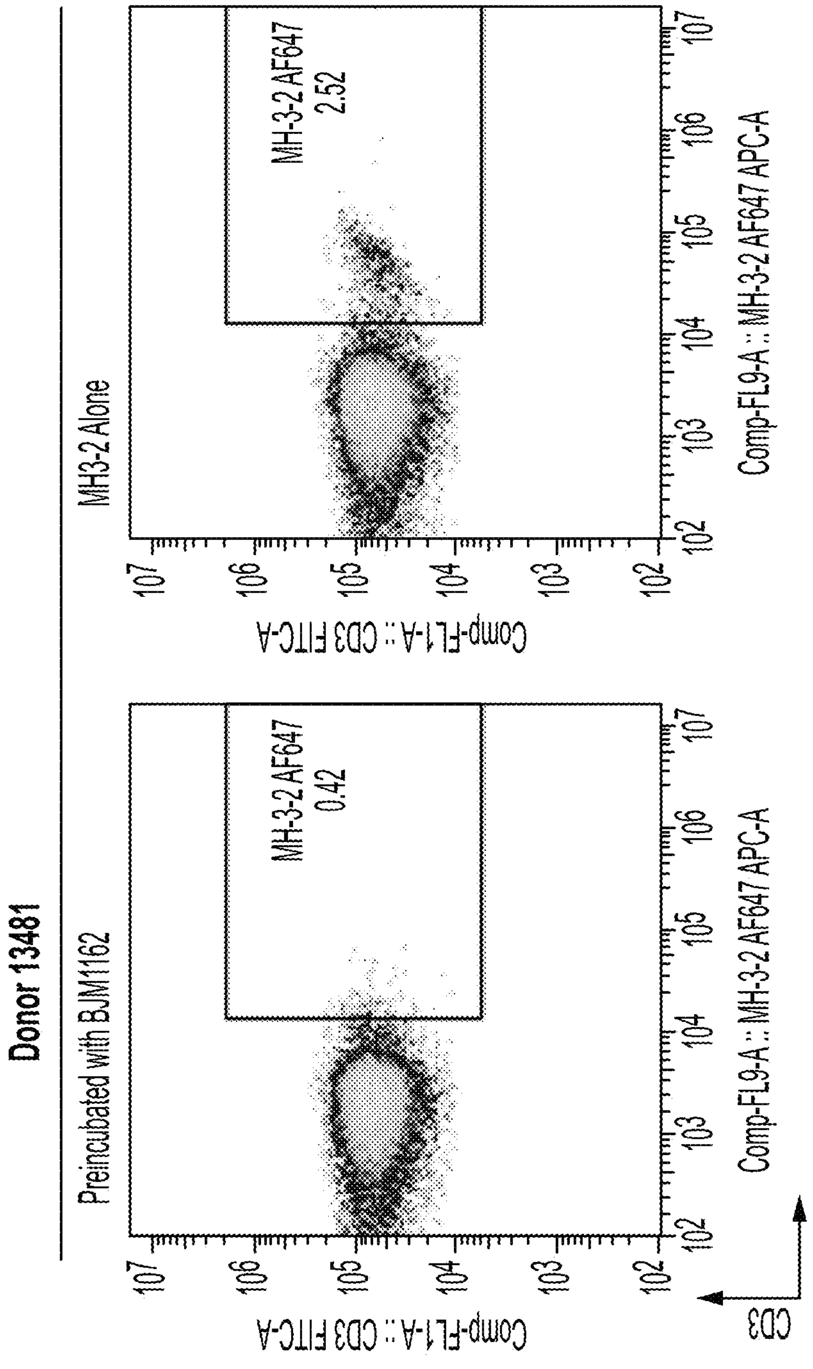
FIG. 100A is a FACS plot showing the ability of MH3-2 to bind PBMCs from one of two donors when the PBMCs are either preincubated with TM23 or not (MH3-2 Alone).
Figure 100B:
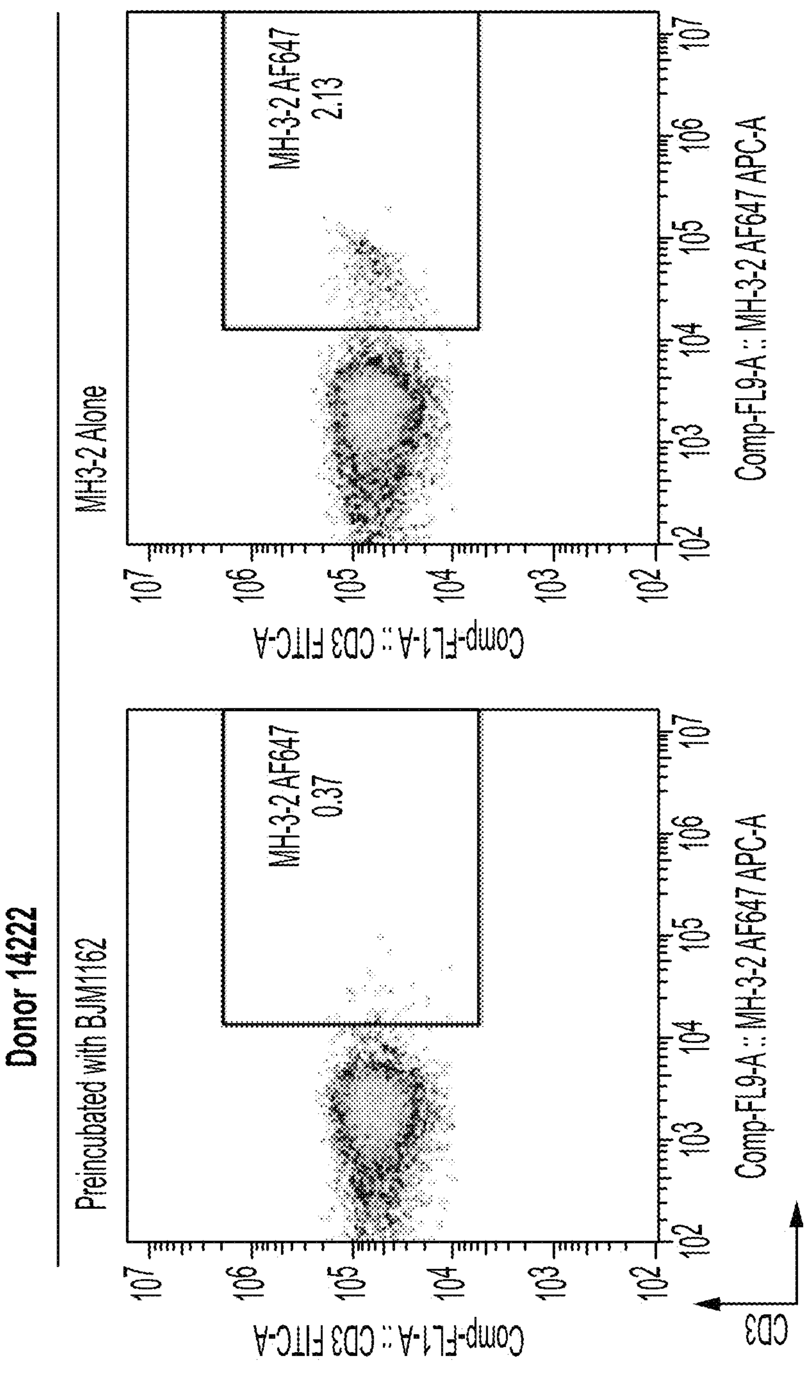
FIG. 100B is a FACS plot showing the ability of MH3-2 to bind PBMCs from one of two donors when the PBMCs are either preincubated with TM23 or not (MH3-2 Alone), continued from FIG. 100A.

The results show that preincubation of T cells with the TM23 antibody blocks binding of MH3-2 (FIG. 99 and FIG. 100). The data shows that the TM23 antibody competes for binding with the same epitope as the MH3-2 antibody, despite both antibodies having diverse sequences. This data confirms the observation that anti-TCRβV antibody molecules which have low sequence similarities among themselves, bind and recognize a structurally conserved epitope on the TCRBV protein.

Figure 101A:
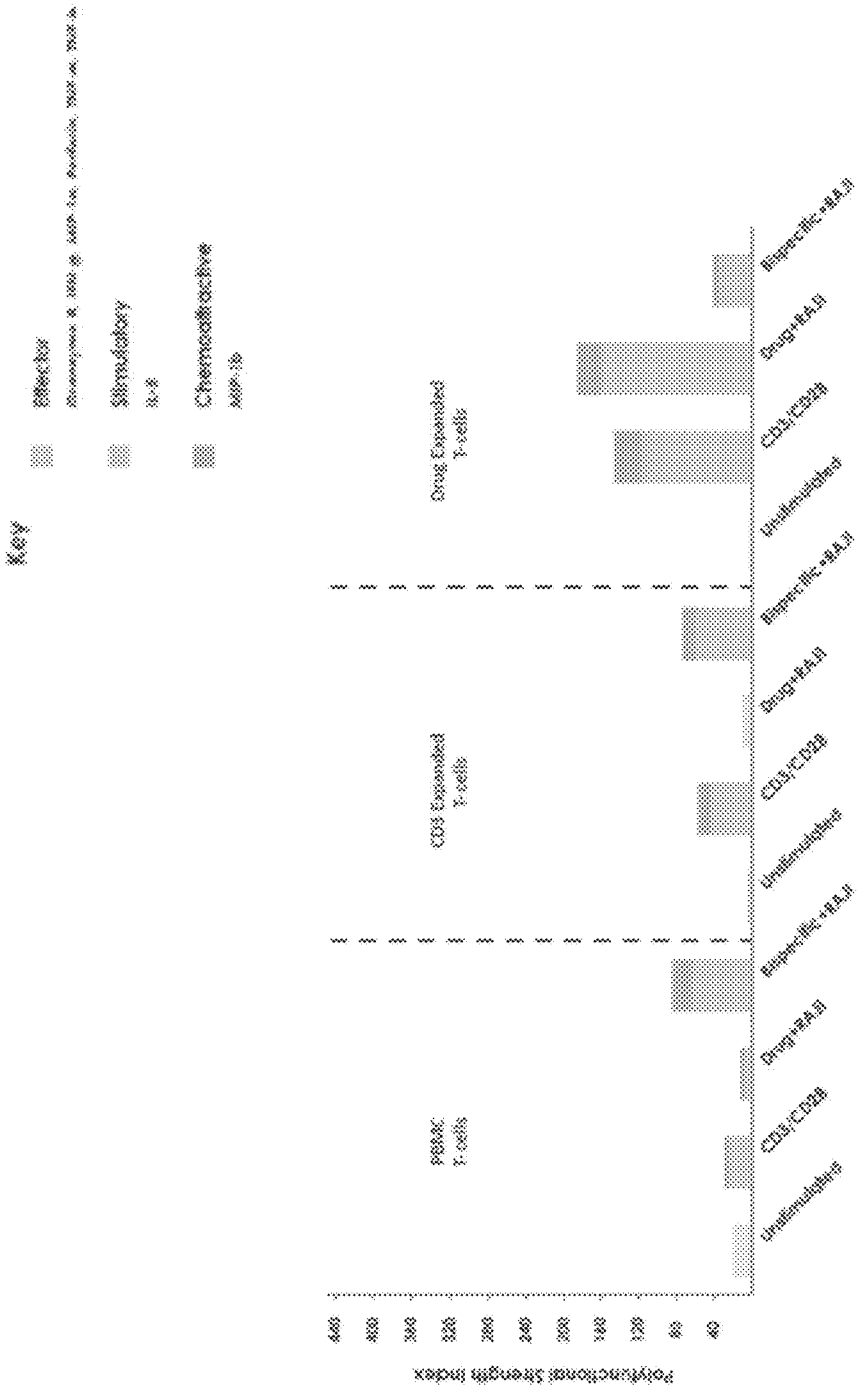
FIG. 101A is a bar graph showing the polyfunctional strength index (PSI) of PBMC CD4+ T cells, CD4+ T cells expanded with anti-CD3 antibody, (CD3 Expanded T cells), and CD4+ T cells expanded with anti-TCRVβ 6-5 antibody (Drug Expanded T cells). The Effector mediators are Granzyme B, IFNγ, MIP-1α, perforin, TNFα, and TNFβ. The Stimulatory mediators are IL-5. The Chemoattractive mediators are MIP-1b.
Figure 101B:
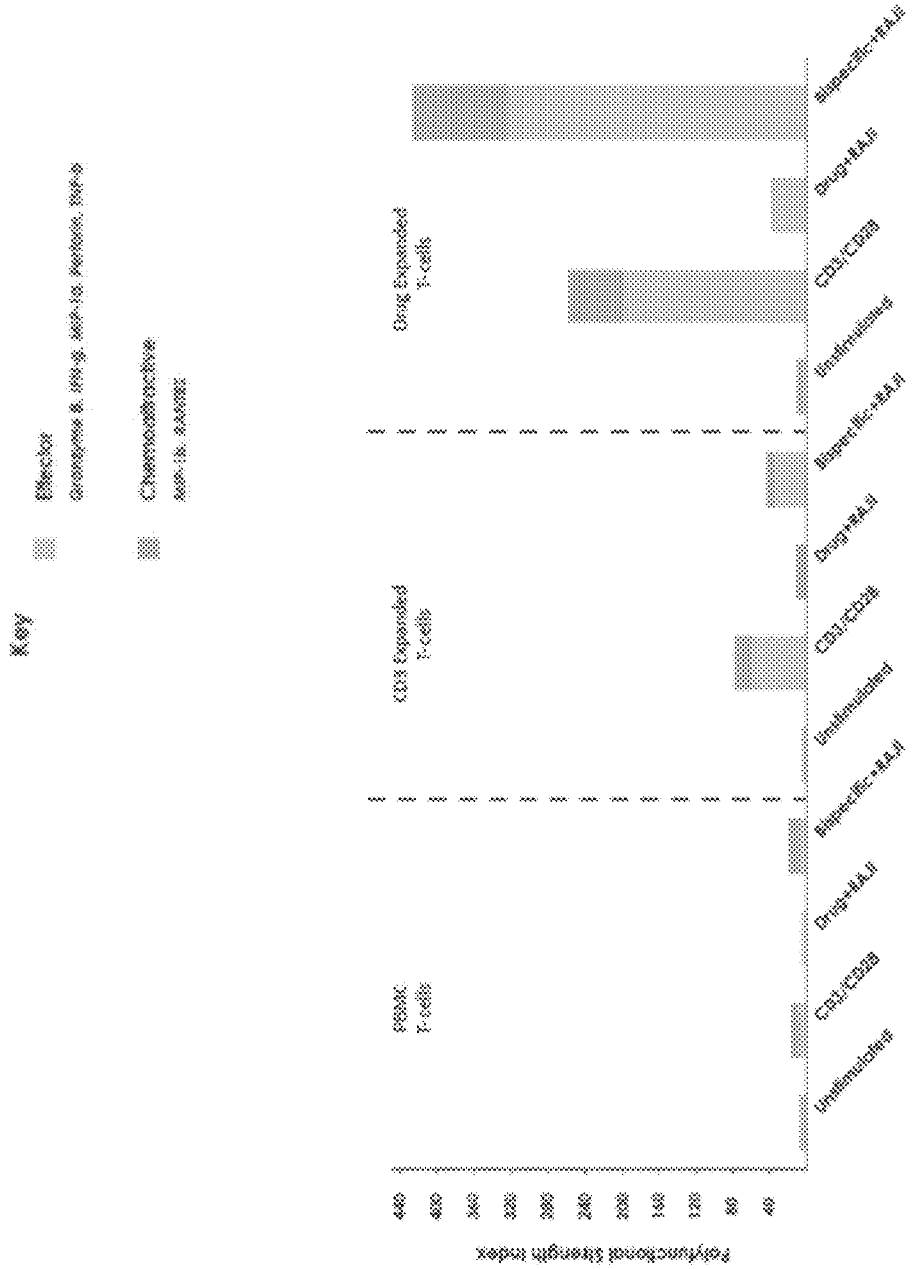
FIG. 101B is a bar graph showing the polyfunctional strength index (PSI) of PBMC CD8+ T cells, CD8+ T cells expanded with anti-CD3 antibody, (CD3 Expanded T cells), and CD8+ T cells expanded with anti-TCRVβ 6-5 antibody (Drug Expanded T cells). The Effector mediators are Granzyme B, IFNγ, MIP-1α, perforin, and TNFβ. The Chemoattractive mediators are MIP-1b and RANTES.

Example 36. Polyfunctional Strength Index of Anti-TCRVβ 6-5 Antibody Expanded T Cells The polyfunctional strength index (PSI) of PBMCs were compared to anti-CD3ε antibody expanded CD4+ T cell (FIG. 101A) and CD8+ T cells (FIG. 101B) and anti-TCRVβ 6-5 antibody expanded (Drug Expanded T cells) CD4+ T cells (FIG. 101A) and CD8+ T cells (FIG. 101B). PSI is defined as the percentage of polyfunctional cells in the sample, multiplied by the intensities of the secreted cytokines. The data shows that there is a greater upregulation of PSI in the CD4+ T cells (FIG. 101A) and CD8+ T cells (FIG. 101B) across the groups expanded with anti-TCRVβ 6-5 antibody.

Example 37: Binding of TCRVB/CD19 Bispecific to Soluble TCR and Jurkat Cells Expressing TCR In this Example, the binding affinity of a TCRVB/CD19 bispecific (FIG. 102A) for the TCR was tested.

Jurkat cells expressing TRBV6-5 were stained with increasing concentrations of bispecific molecule CD19×TCRvb6-5 (2×2) or control antibody TCRvb6-5 v1 at 4 Celsius for 30 min. Subsequently, the cells were washed with PBS buffer and antibodies bound to the surface of the cells detected by PE-labeled anti-human Fc antibody. The percentage of the positive stained cells were blotted against the concentration. FIG. 102B shows the binding of a TCRVB/CD19 bispecific to soluble TCR. The bispecific molecule binds soluble TCR with a Kd of 12 nM.

Bispecific CD19×TCRvb6-5 (2×2) antibody was immobilized on a CM5 Series S Sensor Chip via Anti-human Fc antibody to 50 RU. Soluble TRBV6-5 antigen was diluted to 500 nM and then serially diluted two-fold. Association was 180 seconds, dissociation was 300 seconds. This assay was run in 1×HBS-EP+ Buffer pH 7.4 and at 25 C. The data was fit using a 1:1 binding model. FIG. 102C shows the binding of a TCRVB/CD19 bispecific or the anti-TCRVB 6-5 v1 antibody to TCR expressed on Jurkat cells. The EC50 for the anti-TCRVB 6-5 v1 antibody was 0.6486 and the EC50 for the bispecific molecule was 1.720.

Example 38: In Vitro and In Vivo Characterization of a Murine Anti-TCRVB Antibody This Examples describes the characterization of a murine anti-TCRVB antibody. Similar to the human clonotypes (subfamilies), the TCRb variable chain locus in mice consists of 31 different families with a total of 35 subfamilies of which 23 are functionally expressed. A surrogate TCRvb clonotypical antibody for mice strain C57BL/6 has been identified which shares similar characteristics with the human TCRvb antibodies. This anti-mouse TCRvb antibody binds specifically to TCRvb 13-2 and 13-3 in C57BL/6 mice which are expressed on approximately 15% of all T cells. Similar to the human TCRvb specific antibodies, this murine TCRvb specific antibody (TCRvb 13-2/3) induces murine T cell proliferation and a similar cytokine profile in vitro. The discovery of TCRvb 13-2/3 will enable the evaluation of TCRvb-mediated T cell activation and re-directed cell killing in fully immuno-competent mice models, as well as to assess memory anti-tumor response in vivo.

Figure 103A:
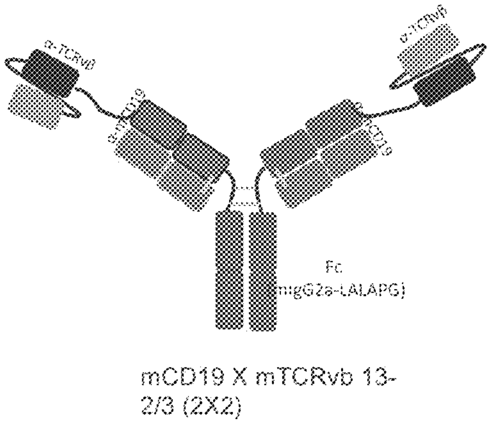
FIGS. 103A-103D show the characterization of a murine CD19×TCRvβ 13-2/3 (2×2) bispecific molecule.

FIG. 103A shows the schematic of a bispecific molecule which was used in the following experiments. The bispecific molecule recognizes murine CD19 and murine TCRVB 13-2, 13-3 (also referred to as mCD19×mTCRvb 13-2/3). The bispecific molecule did not bind to mouse Fc gamma receptors.

First, the in vitro functional activity of the murine bispecific molecule was tested. Splenic mononuclear cells were freshly isolated from C57BL6 mice, treated with mCD19×mTCRvb 13-2/3 (2×2). The isolated cells were assessed for B cell depletion, TCRvβ+ T cell binding, expansion and activation. Cells were treated with 0.0008-200 nM doses (4-fold dilutions) of mCD19xmTCRvb 13-2/3 (2×2) in RPMI-1640 with 10% FBS, or medium alone, for 6 days. On day 3 and 6, cells were analyzed by flow cytometry using the antibodies shown below:

TABLE 23

| Antibodies | |
|---|---|
| Primary Ab | Secondary Ab |
| eFLuor780 | Viability |
| CD20 | A647 |
| CD3 | BV421 |
| TCRVβ 13-2/3 | PE |
| CD25 | FITC |

Figure 103B:
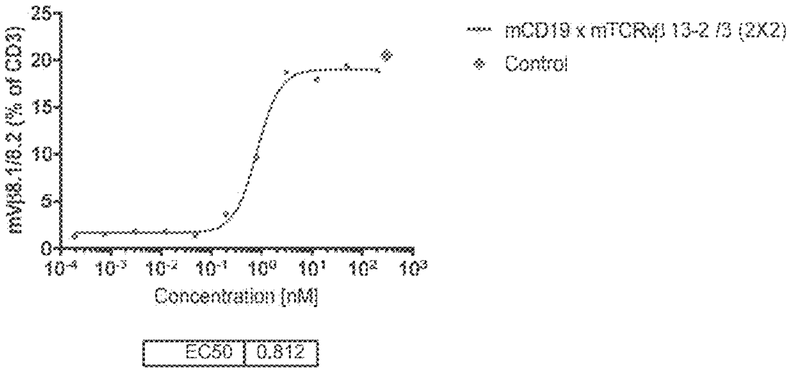
Figure 103C:
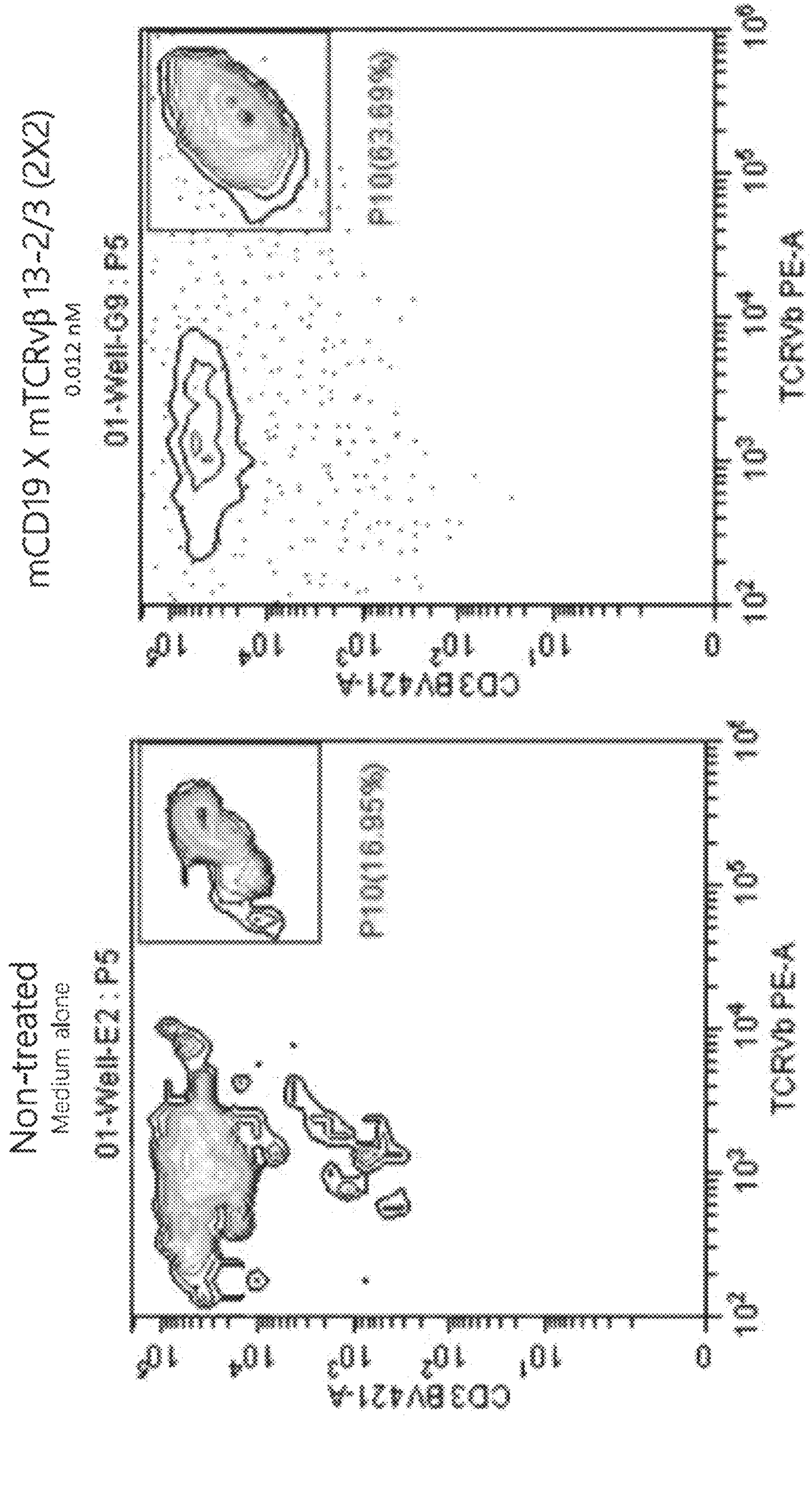
Figure 103D:
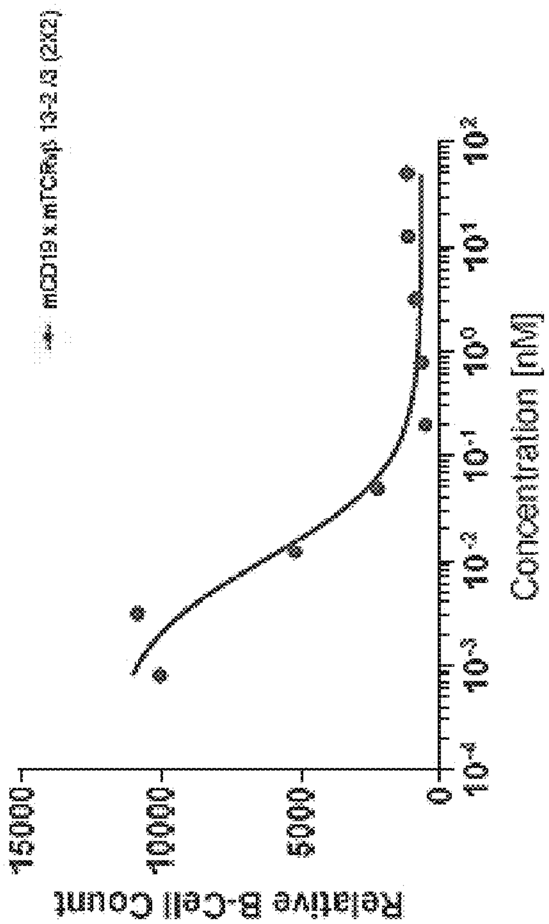

FIG. 103B shows that the mCD19×mTCRvb 13-2/3 (2×2) bispecific antibody bound specifically to splenic T cells from C57BL6 mice. Activation and expansion of mTCRvβ+ T cells was observed at day 3 and 6, respectively (FIG. 103C). Following 6 days of treatment, mCD19×mTCRvb 13-2/3 (2×2) induced efficient murine B cell depletion in C57BL6 splenocytes in vitro (FIG. 103D). Taken together, the in vitro characterization shows that mCD19×mTCRvb 13-2/3 (2×2) could serve as a surrogate tool for syngeneic tumor model studies.

Next, in vivo experiments were performed with the murine bispecific molecule. On day 0, 8 week old female C57BL/6 mice were randomized in to three arms (n=5/arm) based on body weight. Mice were intravenously injected once either with PBS, 0.1 mg/kg and 1 mg/kg mCD19×mTCRvb 13-2/3 (2×2). On Day 3 mice were sacrificed and harvested for whole blood and spleen. Tissues were subjected to Flow cytometry and checked for B-cells, NK cells, TCRvb+ cells and CD3+ cells.

Figure 104:
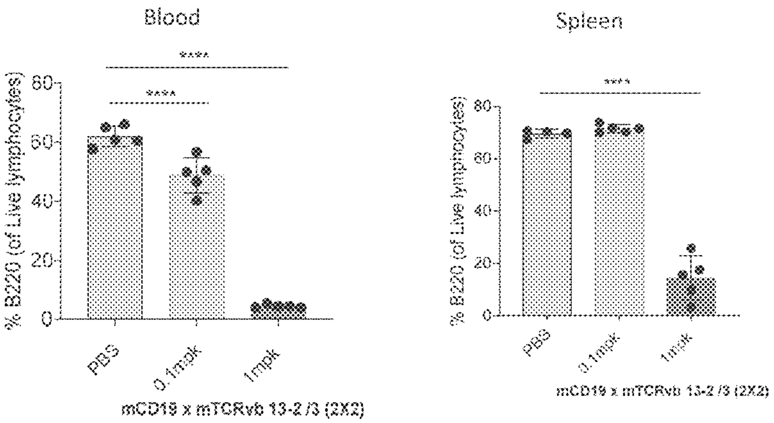
FIG. 104 are graphs showing the level of B cells in the blood or spleen of animals treated with 0.1 mg per kg or 1 mg per kg of a murine CD19×TCRvβ 13-2/3 bispecific antibody.
Figure 105A:
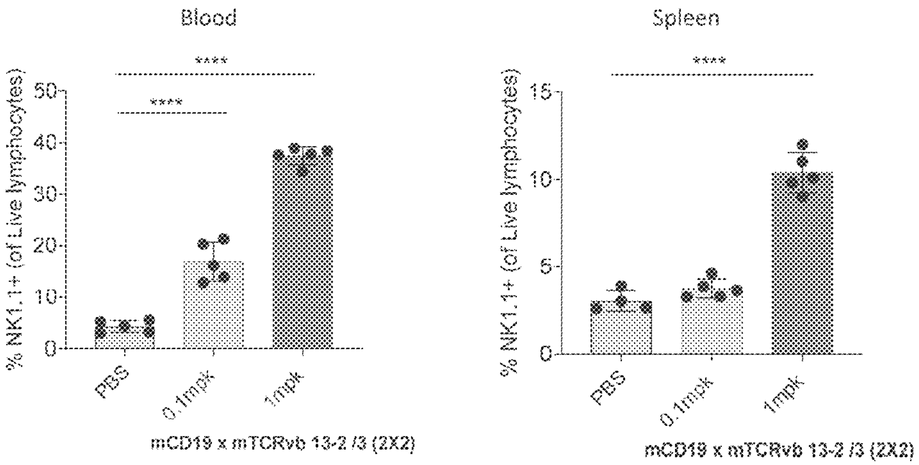
FIGS. 105A-105B are graphs showing the level of NK cells (FIG. 105A) or T cells (FIG. 105B) in the blood or spleen of animals treated with 0.1 mg per kg or 1 mg per kg of a murine CD19×TCRvβ 13-2/3 bispecific antibody.
Figure 105B:
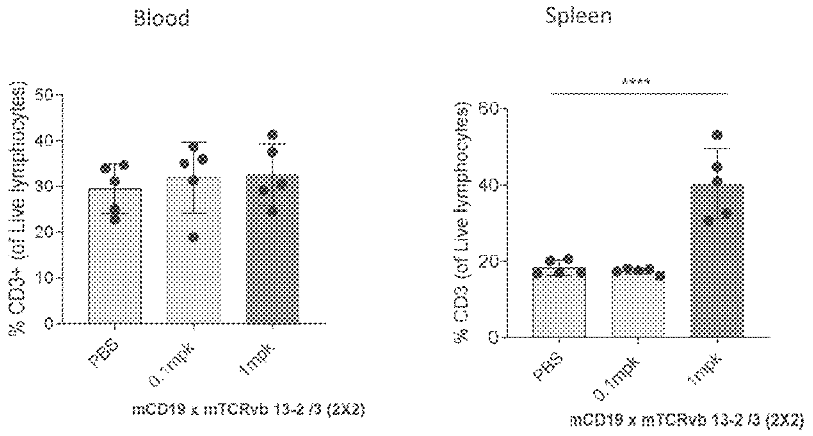

The results show that the murine mCD19×mTCRvb 13-2/3 bispecific molecule depletes B cells in the blood and spleen of animals (FIG. 104). The murine bispecific molecule also expands mouse NK cells in vivo, in the blood and spleen (FIG. 105). The study also demonstrated that mCD19×mTCRvb 13-2/3 (2×2) is well tolerated at the indicated doses and duration of study.

Example 39: Target Cell Lysis and Cytokine Profile of CD19×TCRvβ Bispecific Molecule This Example describes potent lysis of target cells and reduced CRS associated cytokine secretion with a CD19×TCRvβ bispecific molecule.

To test target cell killing, αTCRvβ 6-5 v1 pre-expanded T cells were incubated with Raji target cells in the presence of an CD19×TCRvβ bispecific molecule, CD19×CD3 bispecific molecule or αTCRvβ 6-5 v1 antibody (non-targeted) for 24 hours. Target cell lysis was assessed by a KILR Cytotoxicity and Cytokine Quantification as follows. Human PBMCs were isolated from whole blood. From isolated PBMC's, human CD3+ T cells were isolated using magnetic-bead separation (negative selection) (Miltenyi biotec) and activated by immobilized (plate-coated) anti-TCR Vβ13.1 (BHM1709) at 100 nM for 6 days. Activated T-cells (from plate-coated) were then transferred and expanded in tissue culture flask in the presence of human IL-2 at a concentration of 50 U/ml for an additional 2 days. Expanded TCR Vβ13.1 were washed and co-cultured in the presence of CD19-expressing Raji Cells (target cells) at a E:T ratio of 5:1 and serial diluted concentration of T-cell engager bispecific antibodies including, anti-TCR Vβ13.1/CD19 (BJM0093), anti-CD3/CD19 (BJM0030) and anti-TCR Vβ13.1 (BHM1709, serving as control) for 24 hours. Post 24 hours, cell co-culture supernatants were collected and quantified for specific target cell death. Target cells (Raji cells) is a KILR-retroparticles reporter cell assay (DiscoverX).

Figure 106A:
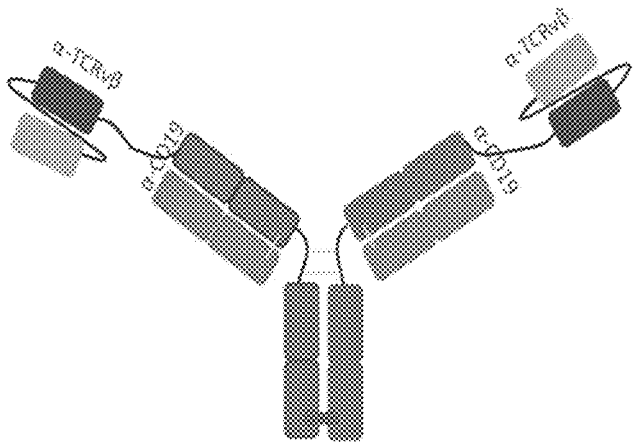
FIGS. 106A-106F show expansion of TCRVB+ T cells and lysis of target cells with a CD19×TCRvβ bispecific molecule.
Figure 106B:
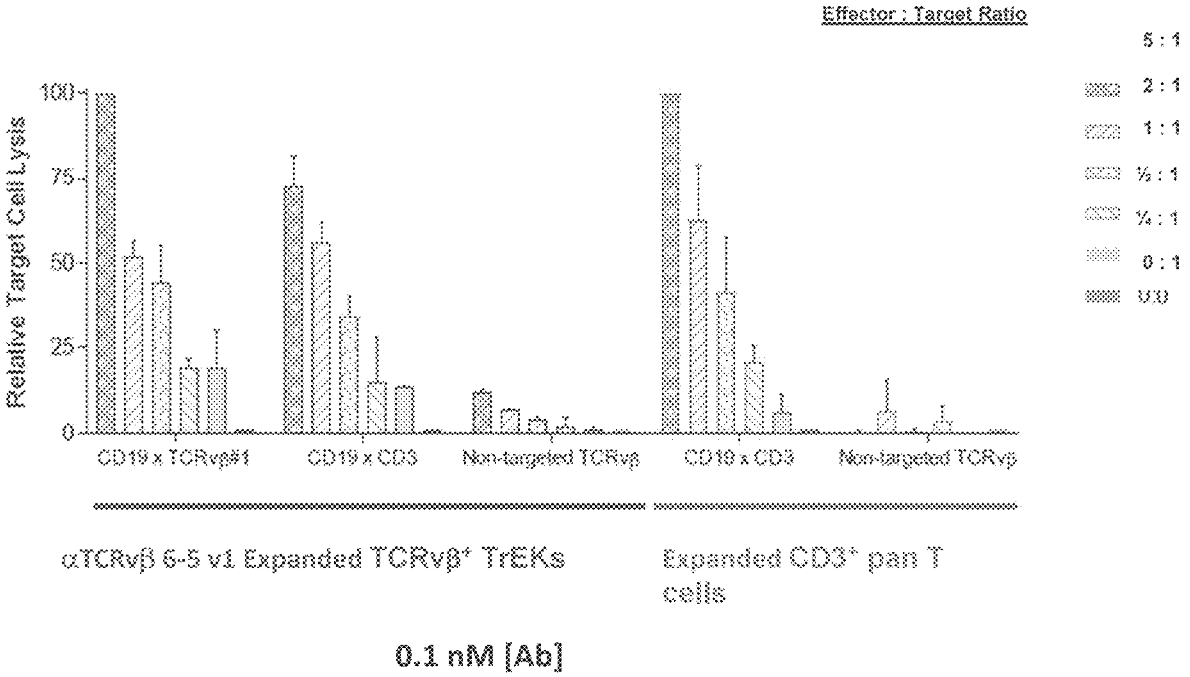

KILR-Raji Target cells are engineered to stably express a protein tagged with enhanced ProLabel (ePL), a β-gal reporter fragment, using the KILR Retroparticles, and when its membrane is compromised due to cell death, it will release the tagged protein into the media. The KILR reporter protein is detected in the media/supernatant by the addition of detection reagents containing the enzyme acceptor (EA) fragment of the β-gal reporter. This leads to the formation of the active β-gal enzyme which hydrolyzes the substrate to give a chemiluminescent output (RLU). Percentage (%) of target cell death is calculated using the following formula: (RLU Treatment—RLU No Treatment). FIG. 106B shows the results of this assay. αTCRvβ 6-5 v1 pre-expanded T cells (TrEKs) demonstrate efficient killing of Raji target cell at low effector to target ratios of 0.25:1.

Figure 106C:
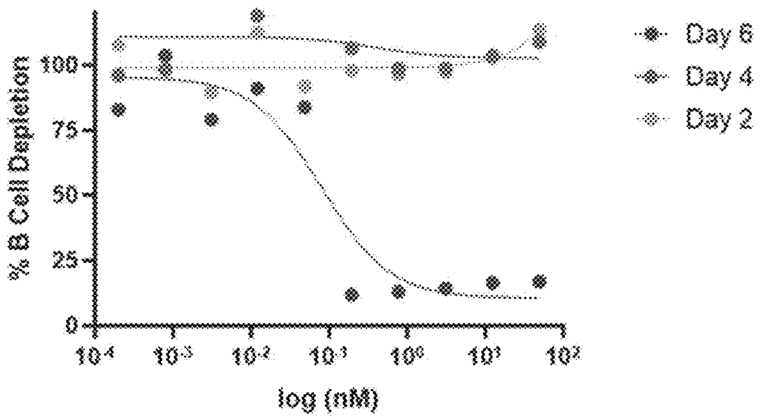
Figure 106D:
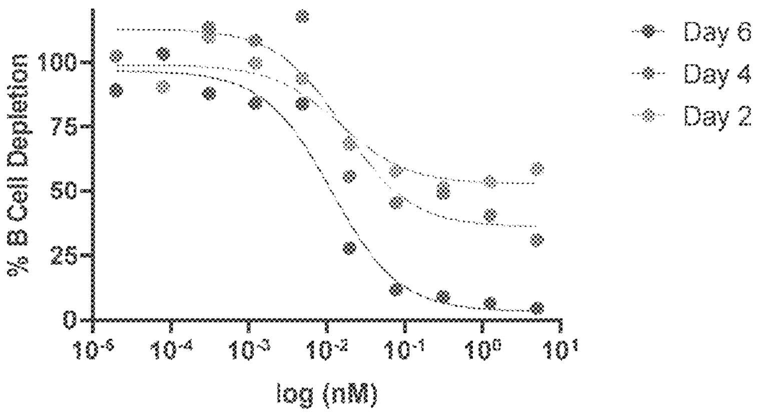
Figure 106E:
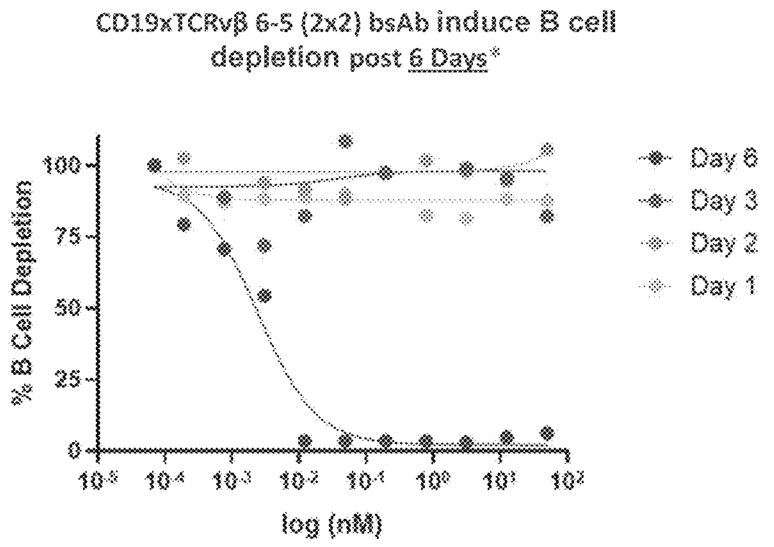
Figure 106F:
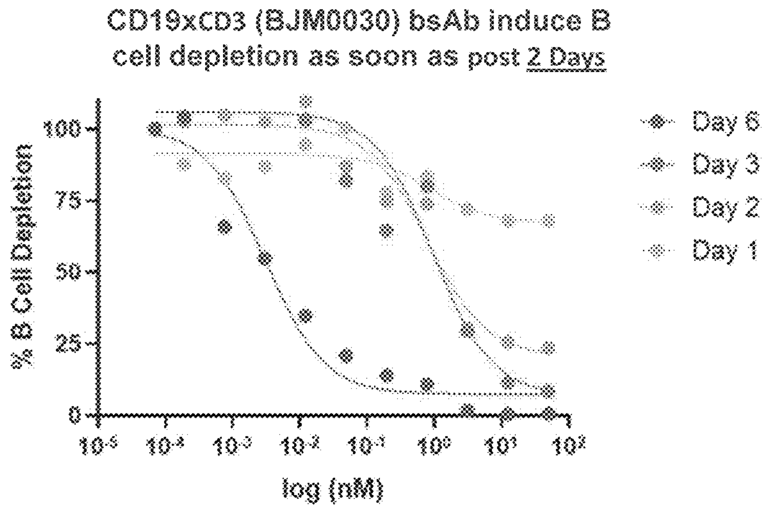

Next, B cell depletion with the CD19×TCRvβ bispecific molecule was tested. Purified T-cells and purified B-cells from the same donor were treated with anti-TCRvβ/CD19 bispecific or Amgen's Blincyto for 2-6 days. B-cell depletion was measured by anti-CD20 staining via FACS analysis. As shown in FIG. 106C-D, CD19×TCRvβ 6-5 (2×2) bispecific concept molecule induces B cell depletion 6 days after co-incubation with target cells. A similar result was observed when PBMC's were treated with the anti-TCRvβ/CD19 bispecific or anti-CD3/CD19 bispecific for 1-6 days followed by measurement of B-cell depletion by anti-CD20 staining via FACS analysis (FIG. 106D-E). This data shows that the anti-TCRvβ/CD19 bispecific requires time for differentiation and expansion of TCRvβ+ T cells.

To determine if the lack of CRS associated cytokine induction by immobilized anti-TCR Vb antibodies can be recapitulated by the bispecific molecule targeting CD19, human PBMCs were incubated in the presence of T cell-activating antibody bispecific molecules at 3 nM. Compounds tested/compared were: CD19×TCRvb and CD19×CD3ε. Supernatant were collected on day 1 to day 6, and cytokines were quantified by using MSD.

Figure 107A:
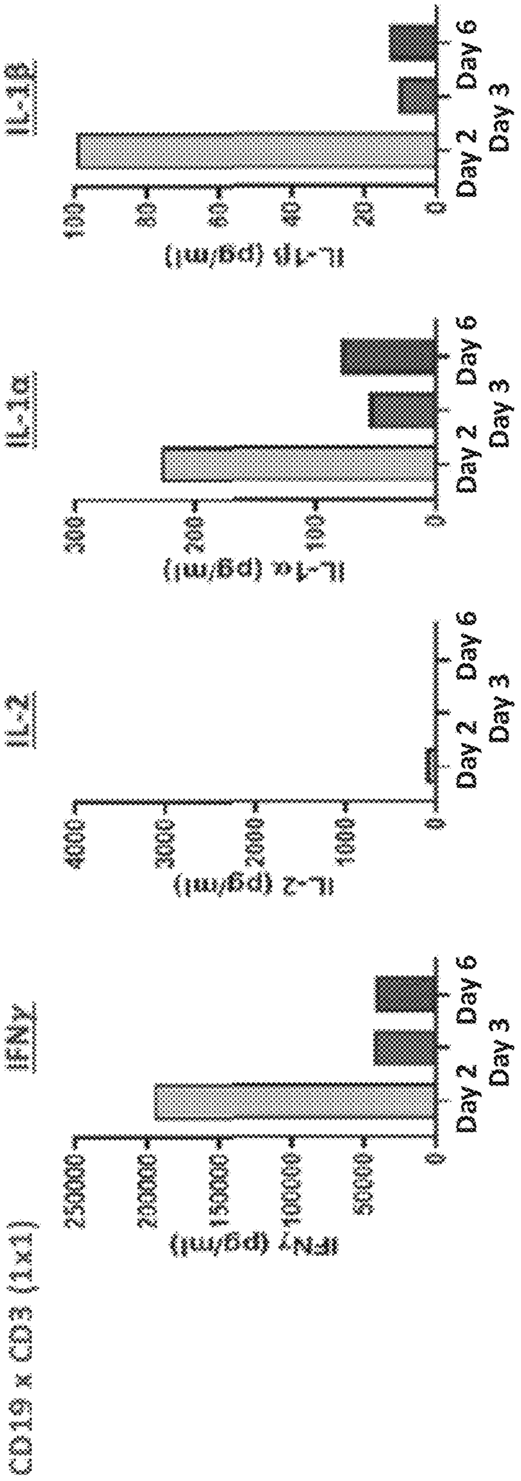
FIGS. 107A-107D are graphs showing the expression of various cytokines from PBMCs treated with a CD19×CD3 bispecific molecule (FIGS. 107A and 107C (continued from FIG. 107A)) or a CD19×TCRVB 6-5 bispecific molecule (FIGS. 107B and 107D (continued from FIG. 107B)).
Figure 107B:
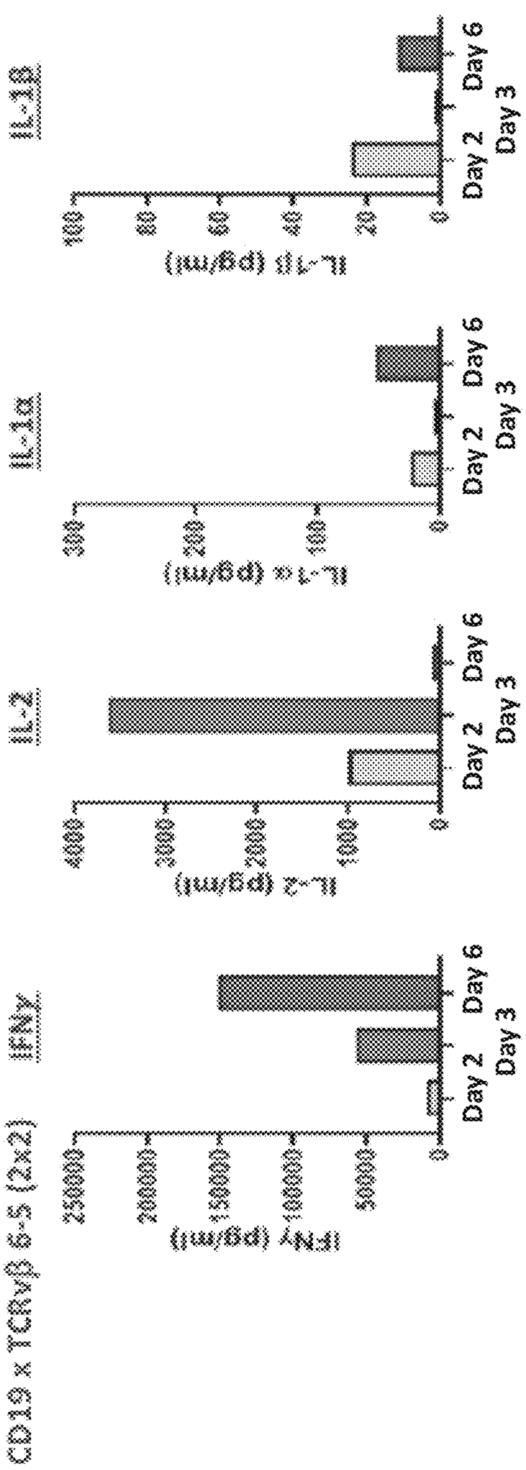
Figure 107C:
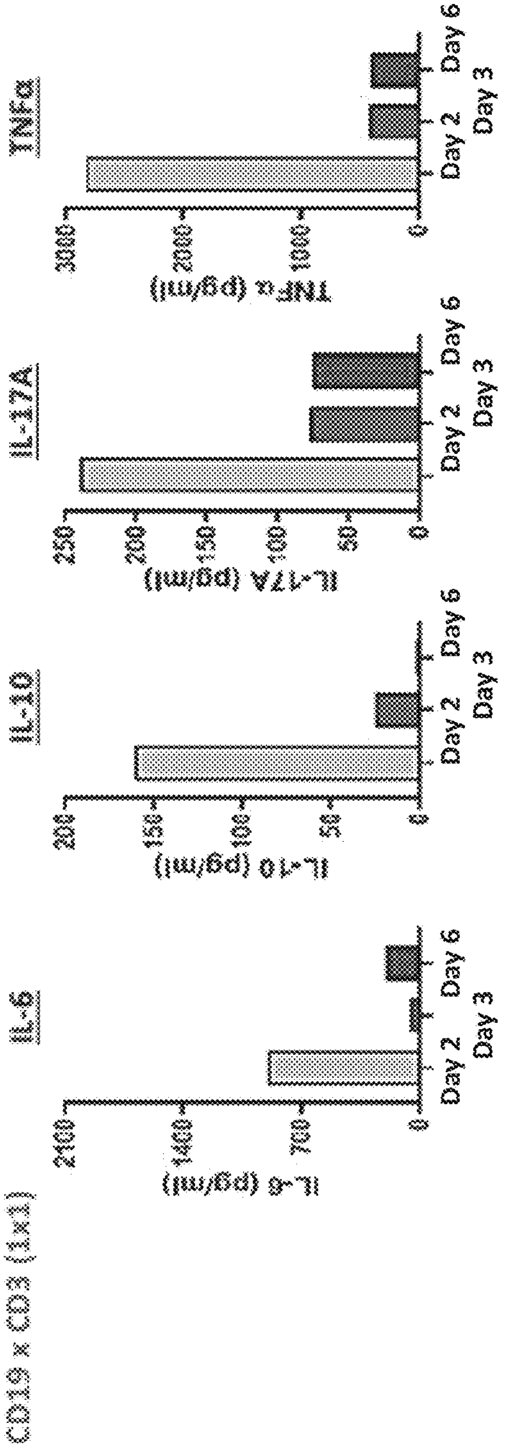
Figure 107D:
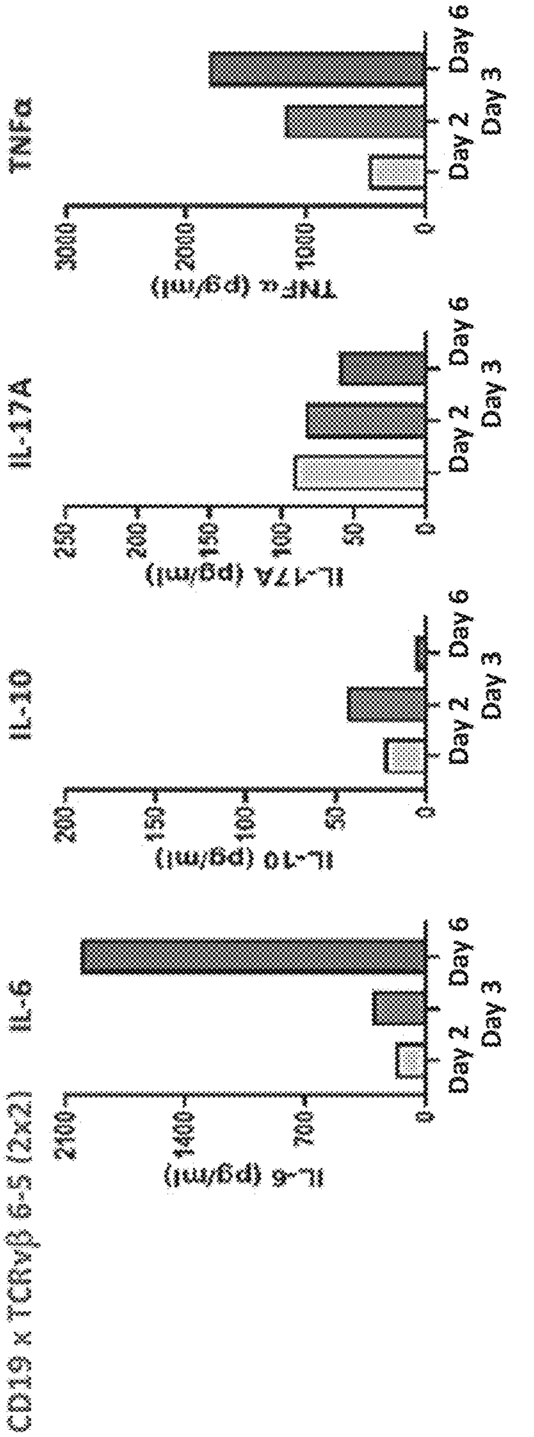

FIG. 107A-B show that the CD19×TCRvβ (2×2) bispecific molecule shows increased IL-2 production against a backdrop of delayed and reduced levels of CRS-related cytokines compared to the CD19×CD3ε bispecific molecule.

Example 40: Pharmacokinetic (PK) Profile of CD19×TCRvβ 6-5 (2×2) in Mice

Figure 108A:
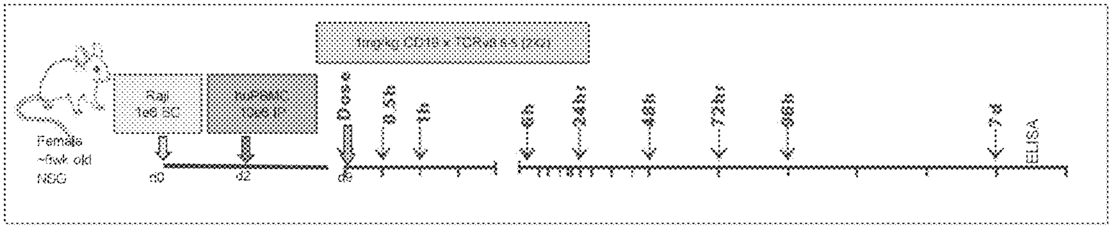
FIGS. 108A-108C show a CD19×TCRvβ 6-5 (2×2) pharmacokinetic (PK) profile and dosing strategy.

This Example describes the pharmacokinetic (PK) profile of CD19×TCRvβ 6-5 (2×2) in mice to guide the dosing and/or schedule treatment decision for the efficacy study. The study design is shown in FIG. 108A. Briefly, on day 0, 6-8 week old female NSG mice were implanted subcutaneously with 1×10(6) Raji leukemia cells. On day 2, mice were humanized by injecting 10×10(6) human PBMCs via the peritoneal cavity. On day 9, mice were treated with a single dose of CD19×TCRvβ 6-5 (2×2) intravenously. Serum was harvested from animals by submandibular bleed at 0, 0.5, 1, 6, 24, 48, 72, 96, 148 hours (n=3 per time point). Serum drug concentration was measured by Sandwich ELISA.

Figure 108B:
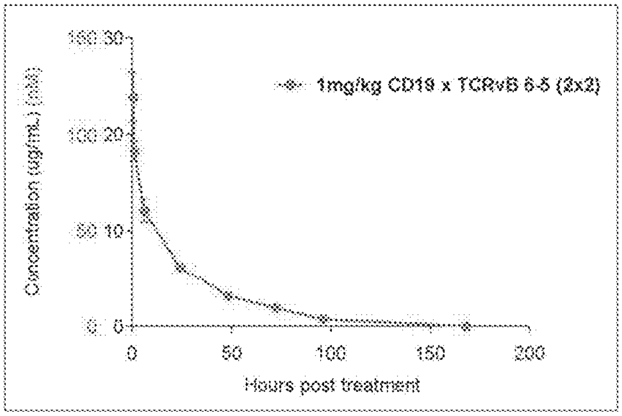
Figure 108C:
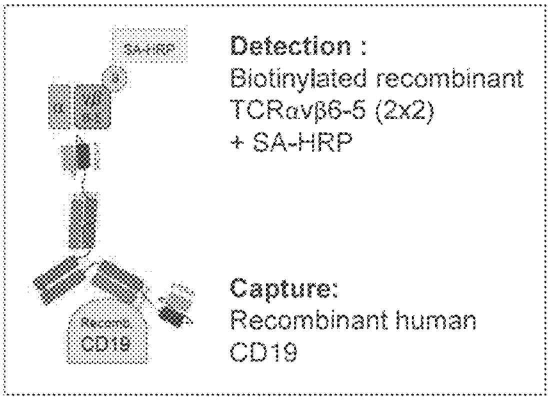

As shown in FIG. 108B and Table 22 below, the serum half-life of CD19×TCRvβ 6-5 (2×2) in tumor bearing humanized NSG animals is approximately 24 hours following a single dose of 1 mg/kg via iv route. This data allowed dose and schedule determination for efficacy studies. Exposures at this dose allow coverage above cellular EC90 beyond 100 hours.

TABLE 22

CD19 × TCRvβ 6-5 PK profile

| Parameter | Value |
|---|---|
| T(½) | 23.89 h |
| Tmax | 0.5 h |
| Cmax | 123 nM |
| AUC0-t | 2436.6 nmol/*h |

Example 41. Optimization of α-TRBV6-5 Antibody

The anti TRBV6-5 antibody was optimized to improve affinity for the human and cyno antigen, improve thermal stability, and remove sequence motifs that might pose chemical stability liabilities. ScFv libraries were built using random mutagenesis (Caldwell et al. (1992) Randomization of genes by PCR mutagenesis. PCR Meth. Appl. 2:28) or a modified version of Kunkel mutagenesis (Kunkel T A. (1985) Rapid and efficient site-specific mutagenesis without phenotypic selection. PNAS 82(2): 488-92). For affinity improvement, library selections vs human and cyno antigens were performed using standard phage display (Lee, C M et al. (2007) Selection of human antibody fragments by phage display. Nature protocols 2, 3001) and yeast display techniques (Chao G, et al. (2006) Isolating and engineering human antibodies using yeast surface display. Nature Protocols. 1(2):755-69). Thermal challenge of phage or yeast populations was used to select for clones with improved thermal stability. Selections were followed by standard screening methods such as ELISA and flow cytometry to identify individual clones with improved properties. Following hit sequencing and analysis of mutation-activity correlation, second-generation libraries were constructed using the same methods above. Library selections and individual clone screening were repeated as above with the modification that more stringent conditions were applied to select for clones with maximized activity. Following hit sequencing, scFv genes were reformatted into the biologically relevant antibody format for expression, purification, and triaging.

Exemplary Embodiments

Disclosed herein are, inter alia, antibody molecules directed to the variable chain of the beta subunit of TCR (TCRβV) which bind and, e.g., activate or expand, T cells, e.g., a subset of T cells ("anti-TCRβV antibody molecules"). In some embodiments, the anti-TCRβV antibody molecules disclosed herein result in a cytokine profile, e.g., a cytokine secretion profile, that differs from that of a T cell engager that binds to a receptor or molecule other than a TCRβV region ("a non-TCRβV-binding T cell engager"). In some embodiments, the anti-TCRβV antibody molecules disclosed herein result in lesser, minimal, or no production of cytokines associated with cytokine release syndrome (CRS), e.g., IL-6, IL-1beta, IL-10 and TNF alpha; and enhanced and/or delayed production of IL-2 and IFN-gamma. In some embodiments, the anti-TCRβV antibodies disclosed herein result in expansion of an immune cell, e.g., a T cell, a tumor infiltrating lymphocyte (TIL), an NK cell, or other immune cells (e.g., as described herein). Also provided herein are methods of making said anti-TCRβV antibody molecules, and methods of using said anti-TCRβV antibody molecules including, methods of using an anti-TCRβV antibody molecule for expanding an immune cell or an immune cell population, and method of using an anti-TCRβV antibody molecule for treating cancer, including the use as combination therapy with TIL and immune checkpoint therapeutics. This disclosure further provides multispecific molecules, e.g., bispecific molecules, comprising said anti-TCRβV antibody molecules. In some embodiments, compositions comprising anti-TCRβV antibody molecules of the present disclosure, can be used, e.g., to activate and/or redirect T cells to promote tumor cell lysis for cancer immunotherapy. In some embodiments, compositions comprising anti-TCRβV antibody molecules as disclosed herein limit the unwanted side-effects of CRS and/or NT, e.g., CRS and/or NT associated with anti-CD3e targeting.

In some embodiments, the anti-TCRβV antibody molecules disclosed herein result in lesser, minimal, or no production of cytokines associated with cytokine release syndrome (CRS), e.g., IL-6, IL-1beta, IL-10 and TNF alpha; and enhanced and/or delayed production of IL-2 and IFN-gamma, compared with an anti-CD3 antibody molecule (e.g., a low affinity anti-CD3 antibody molecule). In some embodiments, administration of the anti-TCRβV antibody molecules disclosed herein in a subject results in reduced cytokine release syndrome (CRS) (e.g., lesser duration of CRS or no CRS), a reduced severity of CRS (e.g., absence of severe CRS, e.g., CRS grade 4 or 5), reduced neurotoxicity (NT), or a reduced severity of NT, compared with similar administration of an anti-CD3 antibody molecule (e.g., a low affinity anti-CD3 antibody molecule).

Accordingly, provided herein are, anti-TCRβV antibody molecules, multispecific or multifunctional molecules (e.g., multispecific or multifunctional antibody molecules) (also referred to herein as a "composition") that comprise anti-TCRβV antibody molecules, nucleic acids encoding the same, methods of producing the aforesaid molecules, pharmaceutical compositions comprising aforesaid molecules, and methods of treating a disease or disorder, e.g., cancer, using the aforesaid molecules. The antibody molecules and pharmaceutical compositions disclosed herein can be used (alone or in combination with other agents or therapeutic modalities) to treat, prevent and/or diagnose disorders and conditions, e.g., cancer, e.g., as described herein.

In one aspect, the disclosure provides an antibody molecule, e.g., a non-murine, e.g., a human-like (e.g., a human, or humanized antibody molecule), which binds, e.g., specifically binds, to a T cell receptor beta variable (TCRβV) region.

In some embodiments, the anti-TCRBV antibody molecule comprises an antigen binding domain of an antibody disclosed in any of Tables 1-2, or 10-13, or a sequence with at least 85%, 90%, 95%, 96%, 97%, 98%, or 99% identity thereto. In some embodiments, the anti-TCRBV antibody molecule comprises a leader sequence comprising the amino acid sequence of SEQ ID NO: 3288. In some embodiments, the anti-TCRBV antibody molecule does not comprise a leader sequence comprising the amino acid sequence of SEQ ID NO: 3288.

In some embodiments, binding of the anti-TCRβV antibody molecule to a TCRβV region results in a cytokine profile, e.g., a cytokine secretion profile, (e.g., comprising one or more cytokines and/or one or more chemokines), that differs from that of a T cell engager that binds to a receptor or molecule other than a TCRβV region ("a non-TCRβV-binding T cell engager").

In some embodiments, the cytokine profile, e.g., cytokine secretion profile, comprises one, two, three, four, five, six, seven, or all of the following:

(i) increased level, e.g., expression level, and/or activity of IL-2;

(ii) reduced level, e.g., expression level, and/or activity of IL-1β;

(iii) reduced level, e.g., expression level, and/or activity of IL-6;

(iv) reduced level, e.g., expression level, and/or activity of TNFα;

(v) reduced level, e.g., expression level, and/or activity of IL-10;

(vi) a delay, e.g., at least 1, 2, 3, 4, 5, 6, 7, 8, 9, 10 or more hours delay, in increased level, e.g., expression level, and/or activity of IL-2;

(vii) a delay, e.g., at least 1, 2, 3, 4, 5, 6, 7, 8, 9, 10 hours delay, in increased level, e.g., expression level, and/or activity of IFN-gamma; or (viii) increased level, e.g., expression level, and/or activity of IL-15, e.g., wherein (i)-(viii) are relative to the cytokine profile, e.g., cytokine secretion profile, of the non-TCRβV-binding T cell engager.

In some embodiments, binding of the anti-TCRBV antibody to a TCRβV region results in reduced cytokine storm, e.g., reduced cytokine release syndrome (CRS) and/or neurotoxicity (NT), as measured by an assay of Example 3, e.g., relative to the cytokine storm induced by the non-TCRβV-binding T cell engager.

In some embodiments, binding of the anti-TCRBV antibody to a TCRβV region results in one, two, three or all of:

(ix) reduced T cell proliferation kinetics;

(x) cell killing, e.g., target cell killing, e.g. cancer cell killing, e.g., as measured by an assay of Example 4;

(xi) increased Natural Killer (NK) cell proliferation, e.g., expansion; or (xii) expansion, e.g., at least about 1.1-10 fold expansion (e.g., at least about 1.1, 1.2, 1.3, 1.4, 1.5, 2, 3, 4, 5, 6, 7, 8, 9, or 10 fold expansion), of a population of T cells having a memory-like phenotype, e.g., as described herein, e.g., wherein (ix)-(xii) are relative to the non-TCRβV-binding T cell engager.

In some embodiments, an anti-TCRβV antibody molecule disclosed herein recognizes (e.g., binds to), a structurally conserved domain on the TCRβV protein (e.g., as denoted by the circled area in FIG. 24A).

In some embodiments, an anti-TCRVβ antibody disclosed herein comprises an Fc region, e.g., as described herein. In some embodiments, the Fc region is a wildtype Fc region, e.g., a wildtype human Fc region. In some embodiments, the Fc region comprises a variant, e.g., an Fc region comprising an addition, substitution, or deletion of at least one amino acid residue in the Fc region which results in, e.g., reduced affinity for and/or binding to, at least one Fc receptor. In some embodiments, the reduced affinity is compared to an otherwise similar antibody with a wildtype Fc region.

In some embodiments, an anti-TCRVβ antibody comprising a variant Fc region has one or more of the following properties: (1) reduced effector function (e.g., reduced ADCC, ADCP and/or CDC); (2) reduced binding to one or more Fc receptors; and/or (3) reduced binding to C1q complement. In some embodiments, the reduction in any one, or all of properties (1)-(3) is compared to an otherwise similar antibody with a wildtype Fc region.

In some embodiments, an anti-TCRVβ antibody comprising a variant Fc region has reduced affinity to a human Fc receptor, e.g., FcγR I, FcγR II and/or FcγR III. In some embodiments, the anti-TCRVβ antibody comprising a variant Fc region comprises a human IgG1 region or a human IgG4 region.

In some embodiments, an anti-TCRVβ antibody disclosed herein comprises any one or all, or any combination of Fc region variants, e.g., mutations, disclosed in Table 21. In some embodiments, an anti-TCRVβ antibody disclosed herein comprise an Asn297Ala (N297A) mutation. In some embodiments, an anti-TCRVβ antibody disclosed herein comprise a Leu234Ala/Leu235Ala (LALA) mutation.

In some embodiments, an anti-TCRβV antibody molecule disclosed herein does not recognize, e.g., bind to, an interface of a TCRβV:TCRalpha complex.

In some embodiments, an anti-TCRβV antibody molecule disclosed herein does not recognize, e.g., bind to, a constant region of a TCRβV protein. An exemplary antibody that binds to a constant region of a TCRBV region is JOVI.1 as described in Viney et al., (*Hybridoma*. 1992 December; 11(6):701-13).

In some embodiments, an anti-TCRβV antibody molecule disclosed herein does not recognize, e.g., bind to, one or more (e.g., all) of a complementarity determining region (e.g., CDR1, CDR2 and/or CDR3) of a TCRβV protein.

In some embodiments, binding of the anti-TCRβV antibody molecule to a TCRβV region results in one, two, three, four, five, six, seven, eight, nine, ten or more (e.g., all) of the following:

(i) reduced level, e.g., expression level, and/or activity of IL-1β;

(ii) reduced level, e.g., expression level, and/or activity of IL-6;

(iii) reduced level, e.g., expression level, and/or activity of TNFα;

(iv) increased level, e.g., expression level, and/or activity of IL-2;

(v) a delay, e.g., at least 1, 2, 3, 4, 5, 6, 7, 8, 9, 10 or more hours delay, in increased level, e.g., expression level, and/or activity of IL-2;

(vi) a delay, e.g., at least 1, 2, 3, 4, 5, 6, 7, 8, 9, 10 hours delay, in increased level, e.g., expression level, and/or activity of IFN-gamma;

(vii) reduced T cell proliferation kinetics;

(viii) reduced cytokine storm, e.g., cytokine release syndrome (CRS) and/or neurotoxicity (NT), e.g., as measured by an assay of Example 3;

(ix) cell killing, e.g., target cell killing, e.g. cancer cell killing, e.g., as measured by an assay of Example 4;

(x) increased level, e.g., expression level, and/or activity of IL-15; or (xi) increased Natural Killer (NK) cell proliferation, e.g., expansion.

In some embodiments, any one or all of (i)-(xi) or any combination thereof resulting from an anti-TCRβV antibody molecule disclosed herein is compared to an antibody that binds to: a CD3 molecule, e.g., CD3 epsilon (CD3e) molecule; or a TCR alpha (TCRα) molecule.

In some embodiments, binding of the anti-TCRβV antibody molecule to a TCRβV region results in secretion, e.g., production of perforin and/or Granzyme B.

In an aspect, the disclosure provides an antibody molecule which binds, e.g., specifically binds, to a T cell receptor beta variable chain (TCRβV) region, wherein the anti-TCRβV antibody molecule comprises an antigen binding domain comprising:

(a) a light chain variable region (VL) comprising:

(i) one, two or all of (e.g., three) a light chain complementarity determining region 1 (LC CDR1), a light chain complementarity determining region 2 (LC CDR2), and a light chain complementarity determining region 3 (LC CDR3) of SEQ ID NO: 10 or SEQ ID NO: 11; and (ii) a framework region (FR) having at least 95% identity with one, two, three, or all of (e.g., four) a non-murine germline framework 1 (FR1), a non-murine germline framework region 2 (FR2), a non-murine germline framework region 3 (FR3), and a non-murine germline framework region 4 (FR4); and/or (b) a heavy chain variable region (VH) comprising:

(i) one, two or all of (e.g., three) a heavy chain complementarity determining region 1 (HC CDR1), a heavy chain complementarity determining region 2 (HC CDR2) and a heavy chain complementarity determining region 3 (HC CDR3) of SEQ ID NO: 9; and (ii) a framework region (FR) having at least 95% identity with one, two, three, or all of (e.g., four) a non-murine germline framework 1 (FR1), a non-murine germline framework region 2 (FR2), a non-murine germline framework region 3 (FR3), and a non-murine germline framework region 4 (FR4).

In some embodiments, the VL comprises a sequence having a consensus sequence of SEQ ID NO: 230 or 3289.

In some embodiments, the VH comprises a sequence having a consensus sequence of SEQ ID NO: 231 or 3290.

In some embodiments, the anti-TCRβV antibody molecule binds to TCRβ V6, e.g., one or more of TCRβ V6-4*01, TCRβ V6-4*02, TCRβ V6-9*01, TCRβ V6-8*01, TCRβ V6-5*01, TCRβ V6-6*02, TCRβ V6-6*01, TCRβ V6-2*01, TCRβ V6-3*01 or TCRβ V6-1*01, or a variant thereof.

In some embodiment, the anti-TCRβV antibody molecule comprises an antigen binding domain comprising:

(i) a HC CDR1, a HC CDR2 and a HC CDR3 of SEQ ID NO: 1 or SEQ ID NO: 9, or an amino acid sequence listed in Table 1; or (ii) a LC CDR1, a LC CDR2, and a LC CDR3 of SEQ ID NO: 2, SEQ ID NO: 10 or SEQ ID NO: 11, or an amino acid sequence listed in Table 1.

In some embodiments, the anti-TCRβV antibody molecule comprises an antigen binding domain comprising a light chain variable region (VL) comprising one, two or all (e.g., three) of a LC CDR1, a LC CDR2 and a LC CDR3 of SEQ ID NO: 2, SEQ ID NO: 10 or SEQ ID NO: 11, or an amino acid sequence listed in Table 1.

In some embodiments, the anti-TCRβV antibody molecule comprises an antigen binding domain comprising a heavy chain variable region (VH) comprising one, two or all (e.g., three) of a HC CDR1, a HC CDR2 and a HC CDR3 of SEQ ID NO:1 or SEQ ID NO: 9, or an amino acid sequence listed in Table 1.

In some embodiments, the anti-TCRβV antibody molecule comprises an antigen binding domain comprising:

(i) a VL comprising: a LC CDR1 amino acid sequence of SEQ ID NO: 6 (or an amino acid sequence with not more than 1, 2, 3 or 4 modifications, e.g., substitutions, additions or deletions thereof), a LC CDR2 amino acid sequence of SEQ ID NO:7 (or an amino acid sequence with not more than 1, 2, 3 or 4 modifications, e.g., substitutions, additions or deletions thereof), and/or a LC CDR3 amino acid sequence of SEQ ID NO:8 (or an amino acid sequence with not more than 1, 2, 3 or 4 modifications, e.g., substitutions, additions or deletions thereof); and/or (ii) a VH comprising: a HC CDR1 amino acid sequence of SEQ ID NO: 3 (or an amino acid sequence with not more than 1, 2, 3 or 4 modifications, e.g., substitutions, additions or deletions thereof), a HC CDR2 amino acid sequence of SEQ ID NO:4 (or an amino acid sequence with not more than 1, 2, 3 or 4 modifications, e.g., substitutions, additions or deletions thereof), and/or a HC CDR3 amino acid sequence of SEQ ID NO:5 (or an amino acid sequence with not more than 1, 2, 3 or 4 modifications, e.g., substitutions, additions or deletions thereof).

In some embodiments, the anti-TCRβV antibody molecule comprises an antigen binding domain comprising:

a variable heavy chain (VH) of an amino acid sequence listed in Table 1, e.g., SEQ ID NO: 9, or a sequence having at least about 85%, 90%, 95%, or 99% sequence identity to an amino acid sequence listed in Table 1, e.g., SEQ ID NO: 9 or SEQ ID NO: 1312; and/or a variable light chain (VL) of an amino acid sequence listed in Table 1, e.g., SEQ ID NO: 10 or SEQ ID NO: 11, or a sequence having at least about 85%, 90%, 95%, or 99% sequence identity to an amino acid sequence listed in Table 1, e.g., SEQ ID NO: 10 or SEQ ID NO: 11 or SEQ ID NO: 1314.

In some embodiments, the anti-TCRβV antibody molecule comprises an antigen binding domain comprising:

(i) the VH amino acid sequence of SEQ ID NO: 9 or SEQ ID NO: 1312;

(ii) an amino acid sequence having at least about 85%, 90%, 95%, or 99% sequence identity to the amino acid sequence of SEQ ID NO: 9 or SEQ ID NO: 1312;

(iii) the VL amino acid sequence of SEQ ID NO: 10 or SEQ ID NO: 1314; and/or (iv) an amino acid sequence having at least about 85%, 90%, 95%, or 99% sequence identity to the amino acid sequence of SEQ ID NO: 10 or SEQ ID NO: 1314.

In an aspect, provided herein is an antibody molecule which binds, e.g., specifically binds, to a T cell receptor beta variable chain (TCRβV) region, wherein the anti-TCRβV antibody molecule comprises an antigen binding domain comprising:

(a) a light chain variable region (VL) comprising:

(i) one, two or all of (e.g., three) a light chain complementarity determining region 1 (LC CDR1), a light chain complementarity determining region 2 (LC CDR2), and a light chain complementarity determining region 3 (LC CDR3) of a humanized B-H light chain (LC) of Table 2; and (ii) a framework region (FR) having at least 95% identity with one, two, three or all (e.g., four) of a framework region 1 (FR1), a framework region 2 (FR2), a framework region 3 (FR3), and a framework region 4 (FR4) of a humanized B-H LC of Table 2; and/or (b) a heavy chain variable region (VH) comprising:

(i) one, two or all of (e.g., three) a heavy chain complementarity determining region 1 (HC CDR1), a heavy chain complementarity determining region 2 (HC CDR2) and a heavy chain complementarity determining region 3 (HC CDR3) of a humanized B-H heavy chain (HC) of Table 2; and (ii) a framework region (FR) having at least 95% identity with one, two, three or all (e.g., four) of a framework region 1 (FR1), a framework region 2 (FR2), a framework region 3 (FR3), and a framework region 4 (FR4) of a humanized B-H HC of Table 2.

In some embodiments, the anti-TCRBV binds to TCRβ V12, e.g., TCRβ V12-4*01, TCRβ V12-3*01, or TCRβ V12-5*01, or a variant thereof.

In some embodiment, the anti-TCRβV antibody molecule comprises an antigen binding domain comprising:

(i) a HC CDR1, a HC CDR2 and a HC CDR3 of Antibody B listed in Table 2; or (ii) a LC CDR1, a LC CDR2, and a LC CDR3 of Antibody B listed in Table 2.

In some embodiments, the anti-TCRβV antibody molecule comprises an antigen binding domain comprising a light chain variable region (VL) comprising one, two or all (e.g., three) of a LC CDR1, a LC CDR2 and a LC CDR3 of a humanized B-H antibody listed in Table 2.

In some embodiments, the anti-TCRβV antibody molecule comprises an antigen binding domain comprising a heavy chain variable region (VH) comprising one, two or all (e.g., three) of a HC CDR1, a HC CDR2 and a HC CDR3 of a humanized B-H antibody listed in Table 2.

In some embodiments, the anti-TCRβV antibody molecule comprises an antigen binding domain comprising a light chain variable region (VL) comprising one, two or all (e.g., three) of a LC CDR1, a LC CDR2 and a LC CDR3 of a humanized B-H antibody listed in Table 2.

In some embodiments, the anti-TCRβV antibody molecule comprises:

a VH sequence of a humanized B-H antibody listed in Table 2, or a sequence having at least about 85%, 90%, 95%, or 99% sequence identity to a VH of a humanized B-H antibody listed in Table 2; and/or a VL sequence of a humanized B-H antibody listed in Table 2, or a sequence having at least about 85%, 90%, 95%, or 99% sequence identity to a VL of a humanized B-H antibody listed in Table 2.

In some embodiments, the anti-TCRβV antibody molecule comprises a framework region (FR) having at least 95% identity with one of: a FR1, a FR2, a FR3, and a FR4 of a humanized B-H LC of Table 2.

In some embodiments, the anti-TCRβV antibody molecule comprises a framework region (FR) having at least 95% identity with any two of: a FR1, a FR2, a FR3, and a FR4 of a humanized B-H LC of Table 2.

In some embodiments, the anti-TCRβV antibody molecule comprises a framework region (FR) having at least 95% identity with any three of: a FR1, a FR2, a FR3, and a FR4 of a humanized B-H LC of Table 2.

In some embodiments, the anti-TCRβV antibody molecule comprises a framework region (FR) having at least 95% identity with all of: a FR1, a FR2, a FR3, and a FR4 of a humanized B-H LC of Table 2.

In some embodiments, the anti-TCRβV antibody molecule comprises a framework region (FR) having at least 95% identity with one of: a FR1, a FR2, a FR3, and a FR4 of a humanized B-H HC of Table 2.

In some embodiments, the anti-TCRβV antibody molecule comprises a framework region (FR) having at least 95% identity with any two of: a FRI, a FR2, a FR3, and a FR4 of a humanized B-H HC of Table 2.

In some embodiments, the anti-TCRβV antibody molecule comprises a framework region (FR) having at least 95% identity with any three of: a FR1, a FR2, a FR3, and a FR4 of a humanized B-H HC of Table 2.

In some embodiments, the anti-TCRβV antibody molecule comprises a framework region (FR) having at least 95% identity with all of: a FR1, a FR2, a FR3, and a FR4 of a humanized B-H HC of Table 2.

In some embodiment, the anti-TCRβV antibody molecule comprises an antigen binding domain comprising:

(i) a HC CDR1, a HC CDR2 and a HC CDR3 of Antibody C listed in Table 10; or (ii) a LC CDR1, a LC CDR2, and a LC CDR3 of Antibody C listed in Table 10.

In some embodiments, the anti-TCRβV antibody molecule comprises an antigen binding domain comprising a heavy chain variable region (VH) comprising one, two or all (e.g., three) of a HC CDR1, a HC CDR2 and a HC CDR3 of antibody C or humanized C-H antibody listed in Table 10.

In some embodiments, the anti-TCRβV antibody molecule comprises an antigen binding domain comprising a light chain variable region (VL) comprising one, two or all (e.g., three) of a LC CDR1, a LC CDR2 and a LC CDR3 of antibody C or humanized C-H antibody listed in Table 10.

In some embodiments, the anti-TCRβV antibody molecule comprises:

a VH sequence of a humanized C-H antibody listed in Table 10, or a sequence having at least about 85%, 90%, 95%, or 99% sequence identity to a VH of a humanized C-H antibody listed in Table 10; and/or a VL sequence of a humanized C-H antibody listed in Table 10, or a sequence having at least about 85%, 90%, 95%, or 99% sequence identity to a VL of a humanized C-H antibody listed in Table 10.

In some embodiment, the anti-TCRβV antibody molecule comprises an antigen binding domain comprising:

(i) a HC CDR1, a HC CDR2 and a HC CDR3 of Antibody E listed in Table 11; or (ii) a LC CDR1, a LC CDR2, and a LC CDR3 of Antibody E listed in Table 11.

In some embodiments, the anti-TCRβV antibody molecule comprises an antigen binding domain comprising a heavy chain variable region (VH) comprising one, two or all (e.g., three) of a HC CDR1, a HC CDR2 and a HC CDR3 of antibody E or humanized E-H antibody listed in Table 11.

In some embodiments, the anti-TCRβV antibody molecule comprises an antigen binding domain comprising a light chain variable region (VL) comprising one, two or all (e.g., three) of a LC CDR1, a LC CDR2 and a LC CDR3 of antibody E or humanized E-H antibody listed in Table 11.

In some embodiments, the anti-TCRβV antibody molecule comprises:

a VH sequence of a humanized E-H antibody listed in Table 11, or a sequence having at least about 85%, 90%, 95%, or 99% sequence identity to a VH of a humanized E-H antibody listed in Table 11; and/or a VL sequence of a humanized E-H antibody listed in Table 11, or a sequence having at least about 85%, 90%, 95%, or 99% sequence identity to a VL of a humanized E-H antibody listed in Table 11.

In some embodiment, the anti-TCRβV antibody molecule comprises an antigen binding domain comprising:

(i) a HC CDR1, a HC CDR2 and a HC CDR3 of Antibody D listed in Table 12; or (ii) a LC CDR1, a LC CDR2, and a LC CDR3 of Antibody D listed in Table 12.

In some embodiments, the anti-TCRβV antibody molecule comprises an antigen binding domain comprising a heavy chain variable region (VH) comprising one, two or all (e.g., three) of a HC CDR1, a HC CDR2 and a HC CDR3 of antibody D or humanized D-H antibody listed in Table 12.

In some embodiments, the anti-TCRβV antibody molecule comprises an antigen binding domain comprising a light chain variable region (VL) comprising one, two or all (e.g., three) of a LC CDR1, a LC CDR2 and a LC CDR3 of antibody D or humanized D-H antibody listed in Table 12.

In some embodiments, the anti-TCRβV antibody molecule comprises:

a VH sequence of a humanized D-H antibody listed in Table 12, or a sequence having at least about 85%, 90%, 95%, or 99% sequence identity to a VH of a humanized D-H antibody listed in Table 12; and/or a VL sequence of a humanized D-H antibody listed in Table 12, or a sequence having at least about 85%, 90%, 95%, or 99% sequence identity to a VL of a humanized D-H antibody listed in Table 12.

In some embodiment, the anti-TCRβV antibody molecule comprises an antigen binding domain comprising:

(i) a HC CDR1, a HC CDR2 and a HC CDR3 of Antibody G listed in Table 13; or (ii) a LC CDR1, a LC CDR2, and a LC CDR3 of Antibody G listed in Table 13.

In some embodiments, the anti-TCRβV antibody molecule comprises an antigen binding domain comprising a heavy chain variable region (VH) comprising one, two or all (e.g., three) of a HC CDR1, a HC CDR2 and a HC CDR3 of antibody G or humanized G-H antibody listed in Table 13.

In some embodiments, the anti-TCRβV antibody molecule comprises an antigen binding domain comprising a light chain variable region (VL) comprising one, two or all (e.g., three) of a LC CDR1, a LC CDR2 and a LC CDR3 of antibody G or humanized G-H antibody listed in Table 13.

In some embodiments, the anti-TCRβV antibody molecule comprises:

a VH sequence of a humanized G-H antibody listed in Table 13, or a sequence having at least about 85%, 90%, 95%, or 99% sequence identity to a VH of a humanized G-H antibody listed in Table 13; and/or a VL sequence of a humanized G-H antibody listed in Table 13, or a sequence having at least about 85%, 90%, 95%, or 99% sequence identity to a VL of a humanized G-H antibody listed in Table 13.

In some embodiment, the anti-TCRβV antibody molecule comprises an antigen binding domain comprising:

(i) a HC CDR1, a HC CDR2 and a HC CDR3 of Antibody H listed in Table 13; or (ii) a LC CDR1, a LC CDR2, and a LC CDR3 of Antibody H listed in Table 13.

In some embodiments, the anti-TCRβV antibody molecule comprises an antigen binding domain comprising a heavy chain variable region (VH) comprising one, two or all (e.g., three) of a HC CDR1, a HC CDR2 and a HC CDR3 of antibody H or humanized H-H antibody listed in Table 13.

In some embodiments, the anti-TCRβV antibody molecule comprises an antigen binding domain comprising a light chain variable region (VL) comprising one, two or all (e.g., three) of a LC CDR1, a LC CDR2 and a LC CDR3 of antibody H or humanized H-H antibody listed in Table 13.

In some embodiments, the anti-TCRβV antibody molecule comprises:

a VH sequence of a humanized H-H antibody listed in Table 13, or a sequence having at least about 85%, 90%, 95%, or 99% sequence identity to a VH of a humanized H-H antibody listed in Table 13; and/or a VL sequence of a humanized H-H antibody listed in Table 13, or a sequence having at least about 85%, 90%, 95%, or 99% sequence identity to a VL of a humanized H-H antibody listed in Table 13.

In some embodiment, the anti-TCRβV antibody molecule comprises an antigen binding domain comprising:

(i) a HC CDR1, a HC CDR2 and a HC CDR3 of Antibody I listed in Table 13; or (ii) a LC CDR1, a LC CDR2, and a LC CDR3 of Antibody I listed in Table 13.

In some embodiments, the anti-TCRβV antibody molecule comprises an antigen binding domain comprising a heavy chain variable region (VH) comprising one, two or all (e.g., three) of a HC CDR1, a HC CDR2 and a HC CDR3 of antibody I or humanized I-H antibody listed in Table 13.

In some embodiments, the anti-TCRβV antibody molecule comprises an antigen binding domain comprising a light chain variable region (VL) comprising one, two or all (e.g., three) of a LC CDR1, a LC CDR2 and a LC CDR3 of antibody I or humanized I-H antibody listed in Table 13.

In some embodiments, the anti-TCRβV antibody molecule comprises:

a VH sequence of a humanized I-H antibody listed in Table 13, or a sequence having at least about 85%, 90%, 95%, or 99% sequence identity to a VH of a humanized I-H antibody listed in Table 13; and/or a VL sequence of a humanized I-H antibody listed in Table 13, or a sequence having at least about 85%, 90%, 95%, or 99% sequence identity to a VL of a humanized I-H antibody listed in Table 13.

In some embodiment, the anti-TCRβV antibody molecule comprises an antigen binding domain comprising:

(i) a HC CDR1, a HC CDR2 and a HC CDR3 of Antibody J listed in Table 13; or (ii) a LC CDR1, a LC CDR2, and a LC CDR3 of Antibody J listed in Table 13.

In some embodiments, the anti-TCRβV antibody molecule comprises an antigen binding domain comprising a heavy chain variable region (VH) comprising one, two or all (e.g., three) of a HC CDR1, a HC CDR2 and a HC CDR3 of antibody J or humanized J-H antibody listed in Table 13.

In some embodiments, the anti-TCRβV antibody molecule comprises an antigen binding domain comprising a light chain variable region (VL) comprising one, two or all (e.g., three) of a LC CDR1, a LC CDR2 and a LC CDR3 of antibody J or humanized J-H antibody listed in Table 13.

In some embodiments, the anti-TCRβV antibody molecule comprises:

a VH sequence of a humanized J-H antibody listed in Table 13, or a sequence having at least about 85%, 90%, 95%, or 99% sequence identity to a VH of a humanized J-H antibody listed in Table 13; and/or a VL sequence of a humanized J-H antibody listed in Table 13, or a sequence having at least about 85%, 90%, 95%, or 99% sequence identity to a VL of a humanized J-H antibody listed in Table 13.

In some embodiment, the anti-TCRβV antibody molecule comprises an antigen binding domain comprising:

(i) a HC CDR1, a HC CDR2 and a HC CDR3 of Antibody K listed in Table 13; or (ii) a LC CDR1, a LC CDR2, and a LC CDR3 of Antibody K listed in Table 13.

In some embodiments, the anti-TCRβV antibody molecule comprises an antigen binding domain comprising a heavy chain variable region (VH) comprising one, two or all (e.g., three) of a HC CDR1, a HC CDR2 and a HC CDR3 of antibody K or humanized K-H antibody listed in Table 13.

In some embodiments, the anti-TCRβV antibody molecule comprises an antigen binding domain comprising a light chain variable region (VL) comprising one, two or all (e.g., three) of a LC CDR1, a LC CDR2 and a LC CDR3 of antibody K or humanized K-H antibody listed in Table 13.

In some embodiments, the anti-TCRβV antibody molecule comprises:

a VH sequence of a humanized G-H antibody listed in Table 13, or a sequence having at least about 85%, 90%, 95%, or 99% sequence identity to a VH of a humanized K-H antibody listed in Table 13; and/or a VL sequence of a humanized G-H antibody listed in Table 13, or a sequence having at least about 85%, 90%, 95%, or 99% sequence identity to a VL of a humanized K-H antibody listed in Table 13.

In some embodiment, the anti-TCRβV antibody molecule comprises an antigen binding domain comprising:

(i) a HC CDR1, a HC CDR2 and a HC CDR3 of Antibody L listed in Table 13; or (ii) a LC CDR1, a LC CDR2, and a LC CDR3 of Antibody L listed in Table 13.

In some embodiments, the anti-TCRβV antibody molecule comprises an antigen binding domain comprising a heavy chain variable region (VH) comprising one, two or all (e.g., three) of a HC CDR1, a HC CDR2 and a HC CDR3 of antibody L or humanized L-H antibody listed in Table 13.

In some embodiments, the anti-TCRβV antibody molecule comprises an antigen binding domain comprising a light chain variable region (VL) comprising one, two or all (e.g., three) of a LC CDR1, a LC CDR2 and a LC CDR3 of antibody L or humanized L-H antibody listed in Table 13.

In some embodiments, the anti-TCRβV antibody molecule comprises:

a VH sequence of a humanized L-H antibody listed in Table 13, or a sequence having at least about 85%, 90%, 95%, or 99% sequence identity to a VH of a humanized L-H antibody listed in Table 13; and/or a VL sequence of a humanized L-H antibody listed in Table 13, or a sequence having at least about 85%, 90%, 95%, or 99% sequence identity to a VL of a humanized L-H antibody listed in Table 13.

In some embodiment, the anti-TCRβV antibody molecule comprises an antigen binding domain comprising:

(i) a HC CDR1, a HC CDR2 and a HC CDR3 of Antibody M listed in Table 13; or (ii) a LC CDR1, a LC CDR2, and a LC CDR3 of Antibody M listed in Table 13.

In some embodiments, the anti-TCRβV antibody molecule comprises an antigen binding domain comprising a heavy chain variable region (VH) comprising one, two or all (e.g., three) of a HC CDR1, a HC CDR2 and a HC CDR3 of antibody M or humanized M-H antibody listed in Table 13.

In some embodiments, the anti-TCRβV antibody molecule comprises an antigen binding domain comprising a light chain variable region (VL) comprising one, two or all (e.g., three) of a LC CDR1, a LC CDR2 and a LC CDR3 of antibody M or humanized M-H antibody listed in Table 13.

In some embodiments, the anti-TCRβV antibody molecule comprises:

a VH sequence of a humanized M-H antibody listed in Table 13, or a sequence having at least about 85%, 90%, 95%, or 99% sequence identity to a VH of a humanized M-H antibody listed in Table 13; and/or a VL sequence of a humanized M-H antibody listed in Table 13, or a sequence having at least about 85%, 90%, 95%, or 99% sequence identity to a VL of a humanized M-H antibody listed in Table 13.

In some embodiment, the anti-TCRβV antibody molecule comprises an antigen binding domain comprising:

(i) a HC CDR1, a HC CDR2 and a HC CDR3 of Antibody N listed in Table 13; or (ii) a LC CDR1, a LC CDR2, and a LC CDR3 of Antibody N listed in Table 13.

In some embodiments, the anti-TCRβV antibody molecule comprises an antigen binding domain comprising a heavy chain variable region (VH) comprising one, two or all (e.g., three) of a HC CDR1, a HC CDR2 and a HC CDR3 of antibody N or humanized N-H antibody listed in Table 13.

In some embodiments, the anti-TCRβV antibody molecule comprises an antigen binding domain comprising a light chain variable region (VL) comprising one, two or all (e.g., three) of a LC CDR1, a LC CDR2 and a LC CDR3 of antibody N or humanized N-H antibody listed in Table 13.

In some embodiments, the anti-TCRβV antibody molecule comprises:

a VH sequence of a humanized N-H antibody listed in Table 13, or a sequence having at least about 85%, 90%, 95%, or 99% sequence identity to a VH of a humanized N-H antibody listed in Table 13; and/or a VL sequence of a humanized N-H antibody listed in Table 13, or a sequence having at least about 85%, 90%, 95%, or 99% sequence identity to a VL of a humanized N-H antibody listed in Table 13.

In some embodiment, the anti-TCRβV antibody molecule comprises an antigen binding domain comprising:

(i) a HC CDR1, a HC CDR2 and a HC CDR3 of Antibody O listed in Table 13; or (ii) a LC CDR1, a LC CDR2, and a LC CDR3 of Antibody O listed in Table 13.

In some embodiments, the anti-TCRβV antibody molecule comprises an antigen binding domain comprising a heavy chain variable region (VH) comprising one, two or all (e.g., three) of a HC CDR1, a HC CDR2 and a HC CDR3 of antibody O or humanized O-H antibody listed in Table 13.

In some embodiments, the anti-TCRβV antibody molecule comprises an antigen binding domain comprising a light chain variable region (VL) comprising one, two or all (e.g., three) of a LC CDR1, a LC CDR2 and a LC CDR3 of antibody O or humanized O-H antibody listed in Table 13.

In some embodiments, the anti-TCRβV antibody molecule comprises:

a VH sequence of a humanized O-H antibody listed in Table 13, or a sequence having at least about 85%, 90%, 95%, or 99% sequence identity to a VH of a humanized O-H antibody listed in Table 13; and/or a VL sequence of a humanized O-H antibody listed in Table 13, or a sequence having at least about 85%, 90%, 95%, or 99% sequence identity to a VL of a humanized O-H antibody listed in Table 13.

In another aspect, the disclosure provides a non-murine, e.g., a human-like antibody molecule (e.g., a human or humanized antibody molecule), which binds, e.g., specifically binds, to a T cell receptor beta variable (TCRβV) region. In some embodiments, binding of the anti-TCRβV antibody molecule results in expansion, e.g., at least about 1.1-50 fold expansion (e.g., at least about 1.5-40 fold, 2-35 fold, 3-30 fold, 5-25 fold, 8-20 fold, or 10-15 fold expansion), of a population of T cells, e.g., a population of T cells having a memory-like phenotype, e.g., CD45RA+ CCR7− T cells. In some embodiments, the population of T cells having a memory-like phenotype comprises CD4+ and/or CD8+ T cells. In some embodiments, the population of T cells having a memory-like phenotype comprises a population of memory T cells, e.g., T effector memory ($T_{EM}$) cells, e.g., $T_{EM}$ cells expressing CD45RA ($T_{EMRA}$) cells, e.g., CD4+ or CD8+ $T_{EMRA}$ cells. In some embodiments, the population of T cells having a memory-like phenotype does not express a senescent marker, e.g., CD57. In some embodiments, the population of T cells having a memory-like phenotype does not express an inhibitory receptor, e.g., OX40, 4-1BB, and/or ICOS.

In some embodiments, the population of T cells having a memory-like phenotype is a population of T cells with CD45RA+ CCR7− CD57−. In some embodiments, the population of T cells having a memory-like phenotype does not express an inhibitory receptor, e.g., OX40, 4-1BB, and/or ICOS.

In some embodiments, the population of T cells having a memory-like phenotype, e.g., as described herein, has increased proliferative capacity, e.g., as compared to a reference cell population, e.g., an otherwise similar population of cells that has not been contacted with an anti-TCRβV antibody.

In some embodiments, the expansion is at least about 1.1-10 fold expansion (e.g., at least about 1.1, 1.2, 1.3, 1.4, 1.5, 2, 3, 4, 5, 6, 7, 8, 9, or 10 fold expansion).

In some embodiments, expansion of the population of T cells having a memory-like phenotype, e.g., memory effector T cells, e.g., $T_{EM}$ cells, e.g., $T_{EMRA}$ cells, e.g., CD4+ or CD8+ $T_{EMRA}$ cells, is compared to expansion of a similar population of cells with an antibody that binds to: a CD3 molecule, e.g., CD3 epsilon (CD3e) molecule; or a TCR alpha (TCRα) molecule.

In some embodiments, the population of expanded T cells having a memory-like phenotype, e.g., T effector memory cells, comprises cells T cells, e.g., CD3+, CD8+ or CD4+ T cells. In some embodiments, the population of expanded T cells having a memory-like phenotype, T effector memory cells, comprises CD3+ and CD8+ T cells. In some embodiments, the population of expanded T cells having a memory-like phenotype, e.g., T effector memory cells comprises CD3+ and CD4+ T cells.

In some embodiments, the population of expanded T cells having a memory-like phenotype, T effector memory ($T_{EM}$) cells, comprises cells T cells, e.g., CD3+, CD8+ or CD4+ T cells, which express or re-express, CD45RA, e.g., CD45RA+. In some embodiments, the population comprises $T_{EM}$ cells expressing CD45RA, e.g., $T_{EMRA}$ cells. In some embodiments, expression of CD45RA on $T_{EMRA}$ cells, e.g., CD4+ or CD8+ $T_{EMRA}$ cells, can be detected by a method disclosed herein, e.g., flow cytometry.

In some embodiments, the population of T cells having a memory-like phenotype, e.g., $T_{EMRA}$ cells have low or no expression of CCR7, e.g., CCR7- or CCR7 low. In some embodiments, expression of CCR7 on $T_{EMRA}$ cells cannot be detected by a method disclosed herein, e.g., flow cytometry.

In some embodiments, the population of T cells having a memory-like phenotype, e.g., $T_{EMRA}$ cells express CD95, e.g., CD95+. In some embodiments, expression of CD95 on $T_{EMRA}$ cells can be detected by a method disclosed herein, e.g., flow cytometry.

In some embodiments, the population of T cells having a memory-like phenotype, e.g., $T_{EMRA}$ cells express CD45RA, e.g., CD45RA+, have low or no expression of CCR7, e.g., CCR7− or CCR7 low, and express CD95, e.g., CD95+. In some embodiments, the population of T cells having a memory-like phenotype, e.g., $T_{EMRA}$ cells can be identified as CD45RA+, CCR7− and CD95+ cells. In some embodiments, the population of T cells having a memory-like phenotype, e.g., $T_{EMRA}$ cells comprise CD3+, CD4+ or CD8+ T cells (e.g., CD3+ T cells, CD3+CD8+ T cells, or CD3+CD4+ T cells).

In some embodiments, the population of T cells having a memory-like phenotype does not express a senescent marker, e.g., CD57.

In some embodiments, the population of T cells having a memory-like phenotype does not express an inhibitory receptor, e.g., OX40, 4-1BB, and/or ICOS.

In some embodiments, binding of the anti-TCRβV antibody molecule results in expansion, e.g., at least about 1.1-50 fold expansion (e.g., at least about 1.5-40 fold, 2-35 fold, 3-30 fold, 5-25 fold, 8-20 fold, or 10-15 fold expansion), of a subpopulation of T cells. In some embodiments, the anti-TCRβV antibody molecule-activated (e.g., expanded) subpopulation of T cells resemble $T_{EMRA}$ cells in high expression of CD45RA and/or low expression of CCR7. In some embodiments, the anti-TCRβV antibody molecule-activated (e.g., expanded) subpopulation of T cells do not display upregulation of the senescence markers CD57 and/or KLRG1. In some embodiments, the anti-TCRβV antibody molecule-activated (e.g., expanded) subpopulation of T cells do not display upregulation of co-stimulatory molecules CD27 and/or CD28. In some embodiments, the anti-TCRβV antibody molecule-activated (e.g., expanded) subpopulation of T cells are highly proliferative. In some embodiments, the anti-TCRβV antibody molecule-activated (e.g., expanded) subpopulation of T cells secrete IL-2. In some embodiments, expression of surface markers on T cells can be detected by a method disclosed herein, e.g., flow cytometry. In some embodiments, the proliferative capability of T cells can be detected by a method disclosed herein, e.g., a method described in Example 4. In some embodiments, cytokine expression of T cells can be detected by a method disclosed herein, e.g., a method described in Examples 10 and 21. In some embodiments, the expansion is at least about 1.1-10 fold expansion (e.g., at least about 1.1, 1.2, 1.3, 1.4, 1.5, 2, 3, 4, 5, 6, 7, 8, 9, or 10 fold expansion). In some embodiments, the expansion is compared to expansion of a similar population of cells with an antibody that binds to a CD3 molecule, e.g., CD3 epsilon (CD3ε) molecule; or a TCR alpha (TCRα) molecule.

In some embodiments, binding of the anti-TCRβV antibody molecule to a TCRβV region results in one, two, three, four, five, six, seven, eight, nine, ten or more (e.g., all) of the following:

(i) reduced level, e.g., expression level, and/or activity of IL-1β;

(ii) reduced level, e.g., expression level, and/or activity of IL-6;

(iii) reduced level, e.g., expression level, and/or activity of TNFα;

(iv) increased level, e.g., expression level, and/or activity of IL-2;

(v) a delay, e.g., at least 1, 2, 3, 4, 5, 6, 7, 8, 9, 10 or more hours delay, in increased level, e.g., expression level, and/or activity of IL-2;

(vi) a delay, e.g., at least 1, 2, 3, 4, 5, 6, 7, 8, 9, 10 hours delay, in increased level, e.g., expression level, and/or activity of IFNg;

(vii) reduced T cell proliferation kinetics;

(viii) reduced cytokine storm, e.g., cytokine release syndrome (CRS) and/or neurotoxicity (NT), e.g., as measured by an assay of Example 3;

(ix) cell killing, e.g., target cell killing, e.g. cancer cell killing, e.g., as measured by an assay of Example 4;

(x) increased level, e.g., expression level, and/or activity of IL-15; or (xi) increased Natural Killer (NK) cell proliferation, e.g., expansion, compared to an antibody that binds to: a CD3 molecule, e.g., CD3 epsilon (CD3ε) molecule; or a TCR alpha (TCRα) molecule.

In some embodiments of any of the compositions disclosed herein, binding of the anti-TCRβV antibody molecule to a TCRβV region results in a reduction of at least 2, 5, 10, 20, 50, 100, or 200 fold, or at least 2-200 fold (e.g., 5-150, 10-100, 20-50 fold) in the expression level and or activity of IL-1β as measured by an assay of Example 3.

In some embodiments of any of the compositions disclosed herein, binding of the anti-TCRβV antibody molecule to a TCRβV region results in a reduction of at least 2, 5, 10, 20, 50, 100, 200, 300, 400, 500, 600, 700, 800, 900, or 1000 fold, or at least 2-1000 fold (e.g., 5-900, 10-800, 20-700, 50-600, 100-500, or 200-400 fold) in the expression level and or activity of IL-6 as measured by an assay of Example 3.

In some embodiments of any of the compositions disclosed herein, binding of the anti-TCRβV antibody molecule to a TCRβV region results in a reduction of at least 2, 5, 10, 20, 50, 100, 200, 300, 400, 500, 600, 700, 800, 900, 1000, or 2000 fold, or at least 2-2000 fold (e.g., 5-1000, 10-900, 20-800, 50-700, 100-600, 200-500, or 300-400 fold) in the expression level and or activity of TNFα as measured by an assay of Example 3.

In some embodiments of any of the compositions disclosed herein, binding of the anti-TCRβV antibody molecule to a TCRβV region results in an increase of at least 2, 5, 10, 20, 50, 100, 200, 300, 400, 500, 600, 700, 800, 900, 1000, or 2000 fold, or at least 2-2000 fold (e.g., 5-1000, 10-900, 20-800, 50-700, 100-600, 200-500, or 300-400 fold) in the expression level and or activity of IL-2 as measured by an assay of Example 3.

In some embodiments of any of the compositions disclosed herein, binding of the anti-TCRβV antibody molecule to a TCRβV region results in an increase of at least 2, 5, 10, 20, 50, 100, 200, 300, 400, 500, 600, 700, 800, 900, 1000, or 2000 fold, or at least 2-2000 fold (e.g., 5-1000, 10-900, 20-800, 50-700, 100-600, 200-500, or 300-400 fold) in the expression level and or activity of IL-15 as measured by an assay of Example 4.

In some embodiments of any of the compositions disclosed herein, binding of the anti-TCRβV antibody molecule results in proliferation, e.g., expansion, e.g., at least about 1.1-50 fold expansion (e.g., at least about 1.5-40 fold, 2-35 fold, 3-30 fold, 5-25 fold, 8-20 fold, or 10-15 fold expansion), of a population of Natural Killer (NK) cells. In some embodiments, the expansion of NK cells is at least about 1.1-30 fold expansion (e.g., at least about 1.1, 1.2, 1.3, 1.4, 1.5, 2, 3, 4, 5, 6, 7, 8, 9, 10, 15, 20, 25, or at least about 1.1-5, 5-10, 10-15, 15-20, 20-25, or 25-30 fold expansion). In some embodiments, the expansion of NK cells is measure by an assay of Example 4. In some embodiments, the expansion of NK cells by, e.g., binding of, the anti-TCRβV antibody molecule is compared to expansion of an otherwise similar population not contacted with the anti-TCRβV antibody molecule.

In some embodiments of any of the compositions disclosed herein, binding of the anti-TCRβV antibody molecule results in cell killing, e.g., target cell killing, e.g. cancer cell killing. In some embodiments, the cancer cell is a hematological cancer cell or a solid tumor cell. In some embodiments, the cancer cell is a multiple myeloma cell. In some embodiments, binding of the anti-TCRβV antibody molecule results in cell killing in vitro or in vivo. In some embodiments, cell killing is measured by an assay of Example 4.

In some embodiments of any of the compositions disclosed herein, binding of the anti-TCRβV antibody molecule to a TCRβV region results in an increase or decrease of at least 2, 5, 10, 20, 50, 100, 200, 300, 400, 500, 600, 700, 800, 900, 1000, or 2000 fold, or at least 2-2000 fold (e.g., 5-1000, 10-900, 20-800, 50-700, 100-600, 200-500, or 300-400 fold) of any of the activities described herein compared the activity of 16G8 or TM23 murine antibody, or a humanized version thereof as described in U.S. Pat. No. 5,861,155.

In an aspect, provided herein is an antibody molecule which binds, e.g., specifically binds, to a T cell receptor beta variable chain (TCRβV) region (an anti-TCRβV antibody molecule), wherein the anti-TCRβV antibody molecule:

(i) binds specifically to an epitope on TCRβV, e.g., the same or similar epitope as the epitope recognized by an anti-TCRβV antibody molecule as described herein, e.g., a second anti-TCRβV antibody molecule;

(ii) shows the same or similar binding affinity or specificity, or both, as an anti-TCRβV antibody molecule as described herein, e.g., a second anti-TCRβV antibody molecule;

(iii) inhibits, e.g., competitively inhibits, the binding of an anti-TCRβV antibody molecule as described herein, e.g., a second anti-TCRβV antibody molecule;

(iv) binds the same or an overlapping epitope with an anti-TCRβV antibody molecule as described herein, e.g., a second anti-TCRβV antibody molecule; or (v) competes for binding, and/or binds the same epitope, with an anti-TCRβV antibody molecule as described herein, e.g., a second anti-TCRβV antibody molecule, In some embodiments, the second anti-TCRβV antibody molecule comprises an antigen binding domain chosen from Table 1 or Table 2, or a sequence substantially identical thereto. In some embodiments, the second anti-TCRβV antibody molecule comprises an antigen binding domain, comprising:

a heavy chain complementarity determining region 1 (HC CDR1), a heavy chain complementarity determining region 2 (HC CDR2) and/or a heavy chain complementarity determining region 3 (HC CDR3) of SEQ ID NO: 1 or SEQ ID NO: 9; and/or a light chain complementarity determining region 1 (LC CDR1), a light chain complementarity determining region 2 (LC CDR2), and/or a light chain complementarity determining region 3 (LC CDR3) of SEQ ID NO: 2, SEQ ID NO: 10 or SEQ ID NO: 11.

In some embodiments of any of the compositions disclosed herein, binding of the anti-TCRβV antibody molecule to a TCRβV region results in a change in any (e.g., one, two, three, four or all) of (i)-(v) that is different, e.g., an increase or decrease, of at least 2, 5, 10, 20, 50, 100-fold, compared the activity of 16G8 or TM23 murine antibody or a humanized version thereof as described in U.S. Pat. No. 5,861,155.

In some embodiments of any of the compositions disclosed herein, the anti-TCRβV antibody molecule binds to a TCRBV family (e.g., gene family), e.g., a TCRBV gene family comprising subfamilies, e.g., as described herein. In some embodiments, the TCRBV family, e.g., gene family, comprises: a TCRβ V6 subfamily, a TCRβ V10 subfamily, a TCRβ V12 subfamily, a TCRβ V5 subfamily, a TCRβ V7 subfamily, a TCRβ VII subfamily, a TCRβ V14 subfamily, a TCRβ V16 subfamily, a TCRβ V18 subfamily, a TCRβ V9 subfamily, a TCRβ V13 subfamily, a TCRβ V4 subfamily, a TCRβ V3 subfamily, a TCRβ V2 subfamily, a TCRβ V15 v, a TCRβ V30 subfamily, a TCRβ V19 subfamily, a TCRβ V27 subfamily, a TCRβ V28 subfamily, a TCRβ V24 subfamily, a TCRβ V20 subfamily, TCRβ V25 subfamily, a TCRβ V29 subfamily, a TCRβ V23 subfamily, a TCRβ V21 subfamily, a TCRβ V1 subfamily, a TCRβ V17 subfamily, or a TCRβ V26 subfamily.

In some embodiments, the anti-TCRβV antibody binds to a TCRβ V6 subfamily chosen from: TCRβ V6-4*01, TCRβ V6-4*02, TCRβ V6-9*01, TCRβ V6-8*01, TCRβ V6-5*01, TCRβ V6-6*02, TCRβ V6-6*01, TCRβ V6-2*01, TCRβ V6-3*01 or TCRβ V6-1*01. In some embodiments the TCRβ V6 subfamily comprises TCRβ V6-5*01.

In some embodiments, the anti-TCRβV antibody binds to a TCRβ V10 subfamily chosen from: TCRβ V10-1*01, TCRβ V10-1*02, TCRβ V10-3*01 or TCRβ V10-2*01.

In some embodiments, the anti-TCRβV antibody binds to a TCRβ V12 subfamily chosen from: TCRβ V12-4*01, TCRβ V12-3*01 or TCRβ V12-5*01.

In some embodiments of any of the compositions disclosed herein, the anti-TCRβV antibody molecule does not bind to TCRβ V12, or binds to TCRβ V12 with an affinity and/or binding specificity that is less than (e.g., less than about 10%, 20%, 30%, 40%, 50%, 60%, 70%, 80%, 90% or about 2-, 5-, or 10-fold) the affinity and/or binding specificity of the 16G8 murine antibody or a humanized version thereof as described in U.S. Pat. No. 5,861,155.

In some embodiments of any of the compositions disclosed herein, the anti-TCRβV antibody molecule binds to TCRβ V12 with an affinity and/or binding specificity that is greater than (e.g., greater than about 10%, 20%, 30%, 40%, 50%, 60%, 70%, 80%, 90% or about 2-, 5-, or 10-fold) the affinity and/or binding specificity of the 16G8 murine antibody or a humanized version thereof as described in U.S. Pat. No. 5,861,155.

In some embodiments of any of the compositions disclosed herein, the anti-TCRβV antibody molecule binds to a TCRβV region other than TCRβ V12 (e.g., TCRβV region as described herein, e.g., TCRβ V6 subfamily (e.g., TCRβ V6-5*01) with an affinity and/or binding specificity that is greater than (e.g., greater than about 10%, 20%, 30%, 40%, 50%, 60%, 70%, 80%, 90% or about 2-, 5-, or 10-fold) the affinity and/or binding specificity of the 16G8 murine antibody or a humanized version thereof as described in U.S. Pat. No. 5,861,155.

In some embodiments of any of the compositions disclosed herein, the anti-TCRβV antibody molecule does not comprise at least one CDR of Antibody B. In some embodiments of any of the compositions disclosed herein, the anti-TCRβV antibody molecule does not comprise the CDRs of Antibody B.

In some embodiments of any of the compositions disclosed herein, the anti-TCRβV antibody binds to a TCRβ V5 subfamily chosen from: TCRβ V5-5*01, TCRβ V5-6*01, TCRβ V5-4*01, TCRβ V5-8*01, TCRβ V5-1*01.

In some embodiments of any of the compositions disclosed herein, the anti-TCRβV antibody binds to a TCRβ V5 subfamily chosen from: TCRβ V5-5*01, TCRβ V5-6*01, TCRβ V5-4*01, TCRβ V5-8*01, TCRβ V5-1*01.

In some embodiments of any of the compositions disclosed herein, the anti-TCRβV antibody molecule does not bind to TCRβ V5-5*01 or TCRβ V5-1*01, or binds to TCRβ V5-5*01 or TCRβ V5-1*01 with an affinity and/or binding specificity that is less than (e.g., less than about 10%, 20%, 30%, 40%, 50%, 60%, 70%, 80%, 90% or about 2-, 5-, or 10-fold) the affinity and/or binding specificity of the TM23 murine antibody or a humanized version thereof as described in U.S. Pat. No. 5,861,155.

In some embodiments of any of the compositions disclosed herein, the anti-TCRβV antibody molecule binds to TCRβ V5-5*01 or TCRβ V5-1*01 with an affinity and/or binding specificity that is greater than (e.g., greater than about 10%, 20%, 30%, 40%, 50%, 60%, 70%, 80%, 90% or about 2-, 5-, or 10-fold) the affinity and/or binding specificity of the TM23 murine antibody or a humanized version thereof as described in U.S. Pat. No. 5,861,155.

In some embodiments of any of the compositions disclosed herein, the anti-TCRβV antibody molecule binds to a TCRβV region other than TCRβ V5-5*01 or TCRβ V5-1*01 (e.g., TCRβV region as described herein, e.g., TCRβ V6 subfamily (e.g., TCRβ V6-5*01) with an affinity and/or binding specificity that is greater than (e.g., greater than about 10%, 20%, 30%, 40%, 50%, 60%, 70%, 80%, 90% or about 2-, 5-, or 10-fold) the affinity and/or binding specificity of the TM23 murine antibody or a humanized version thereof as described in U.S. Pat. No. 5,861,155.

In some embodiments of any of the compositions disclosed herein, the anti-TCRβV antibody molecule does not comprise at least one CDR of the TM23 murine antibody. In some embodiments of any of the compositions disclosed herein, the anti-TCRβV antibody molecule does not comprise the CDRs of the TM23 murine antibody.

In some embodiments of any of the compositions disclosed herein, an anti-TCRβV antibody molecule disclosed herein does not comprise the sequence of a murine anti-rat TCR antibody R73, e.g., as disclosed in J Exp Med. 1989 Jan. 1; 169(1): 73-86, herein incorporated by reference in its entirety. In some embodiments of any of the compositions disclosed herein, a multispecific antibody molecule disclosed herein does not comprise the sequence of a murine anti-rat TCR antibody R73, e.g., as disclosed in J Immunol. 1993 Mar. 15; 150(6):2305-15, herein incorporated by reference in its entirety.

In some embodiments of any of the compositions disclosed herein, an anti-TCRβV antibody molecule disclosed herein does not comprise a viral peptide-MHC complex, e.g., as disclosed in Oncoimmunology. 2016; 5(1): e1052930, herein incorporated by reference in its entirety. In some embodiments of any of the compositions disclosed herein, a multispecific antibody molecule disclosed herein does not comprise a viral peptide-MHC complex, e.g., as disclosed in Oncoimmunology. 2016; 5(1): e1052930, herein incorporated by reference in its entirety.

In some embodiments of any of the compositions disclosed herein, the anti-TCRβV antibody molecule binds to one or more (e.g., all) of the following TCRβV subfamilies:

(i) TCRβ V6 subfamily comprising, e.g., one or more of TCRβ V6-4*01, TCRβ V6-4*02, TCRβ V6-9*01, TCRβ V6-8*01, TCRβ V6-5*01, TCRβ V6-6*02, TCRβ V6-6*01, TCRβ V6-2*01, TCRβ V6-3*01 or TCRβ V6-1*01;
(ii) TCRβ V10 subfamily comprising, e.g., one or more of TCRβ V10-1*01, TCRβ V10-1*02, TCRβ V10-3*01 or TCRβ V10-2*01;
(iii) TCRβ V5 subfamily comprising, e.g., one or more of TCRβ V5-6*01, TCRβ V5-4*01, or TCRβ V5-8*01;
(iv) TCRβ V12 subfamily comprising e.g., one or more of TCRβ V12-4*01, TCRβ V12-3*01, or TCRβ V12-5*01;
(v) TCRβ V7 subfamily comprising e.g., one or more of TCRβ V7-7*01, TCRβ V7-6*01, TCRβ V7-8*02, TCRβ V7-4*01, TCRβ V7-2*02, TCRβ V7-2*03, TCRβ V7-2*01, TCRβ V7-3*01, TCRβ V7-9*03, or TCRβ V7-9*01;
(vi) TCRβ V11 subfamily comprising e.g., one or more of TCRβ V11-1*01, TCRβ V11-2*01 or TCRβ V11-3*01;
(vii) TCRβ V14 subfamily comprising TCRβ V14*01;
(viii) TCRβ V16 subfamily comprising TCRβ V16*01;
(ix) TCRβ V18 subfamily comprising TCRβ V18*01;
(x) TCRβ V9 subfamily comprising T e.g., one or more of CRO V9*01 or TCRβ V9*02;
(xi) TCRβ V13 subfamily comprising TCRβ V13*01;
(xii) TCRβ V4 subfamily comprising e.g., one or more of e.g., one or more of TCRβ V4-2*01, TCRβ V4-3*01, or TCRβ V4-1*01;
(xiii) TCRβ V3 subfamily comprising TCRβ V3-1*01;
(xiv) TCRβ V2 subfamily comprising TCRβ V2*01;
(xv) TCRβ V15 subfamily comprising TCRβ V15*01;
(xvi) TCRβ V30 subfamily comprising e.g., one or more of TCRβ V30*01, or TCRβ V30*02;
(xvii) TCRβ V19 subfamily comprising e.g., one or more of TCRβ V19*01, or TCRβ V19*02;
(xviii) TCRβ V27 subfamily comprising TCRβ V27*01;
(xix) TCRβ V28 subfamily comprising TCRβ V28*01;
(xx) TCRβ V24 subfamily comprising TCRβ V24-1*01;
(xxi) TCRβ V20 subfamily comprising e.g., one or more of TCRβ V20-1*01, or TCRβ V20-1*02;
(xxii) TCRβ V25 subfamily comprising TCRβ V25-1*01; or
(xxiii) TCRβ V29 subfamily comprising TCRβ V29-1*01;
(xxiv) TCRβ V21 subfamily;
(xxv) TCRβ V1 subfamily;
(xxvi) TCRβ V17 subfamily;
(xvii) TCRβ V23 subfamily; or
(xviii) TCRβ V26 subfamily.

In some embodiments of any of the compositions disclosed herein, the anti-TCRβV antibody molecule binds to one or more (e.g., all) of the following TCRβV subfamilies:

(i) TCRβ V6, e.g., one or more of TCRβ V6-4*01, TCRβ V6-4*02, TCRβ V6-9*01, TCRβ V6-8*01, TCRβ V6-5*01, TCRβ V6-6*02, TCRβ V6-6*01, TCRβ V6-2*01, TCRβ V6-3*01 or TCRβ V6-1*01;
(ii) TCRβ V10, e.g., one or more of TCRβ V10-1*01, TCRβ V10-1*02, TCRβ V10-3*01 or TCRβ V10-2*01;
(iii) TCRβ V12, e.g., one or more of TCRβ V12-4*01, TCRβ V12-3*01, or TCRβ V12-5*01; or
(iv) TCRβ V5, e.g., one or more of TCRβ V5-5*01, TCRβ V5-6*01, TCRβ V5-4*01, TCRβ V5-8*01, TCRβ V5-1*01.

In some embodiments, the anti-TCRβV antibody molecule binds to TCRβ V6, e.g., one or more of TCRβ V6-4*01, TCRβ V6-4*02, TCRβ V6-9*01, TCRβ V6-8*01, TCRβ V6-5*01, TCRβ V6-6*02, TCRβ V6-6*01, TCRβ V6-2*01, TCRβ V6-3*01 or TCRβ V6-1*01. In some embodiments, the anti-TCRβV antibody molecule binds to TCRβ V6-5*01.

In some embodiments, the anti-TCRβV antibody molecule does not bind to TCRβ V12.

In some embodiments, the anti-TCRβV antibody molecule does not bind to TCRβ V5-5*01 or TCRβ V5-1*01.

In an aspect, provided herein is a multispecific molecule (e.g., a bispecific molecule), comprising a first moiety (e.g., a first immune cell engager) comprising an antibody molecule which binds (e.g., specifically binds) to a T cell receptor beta variable region (TCRβV) ("anti-TCRβV antibody molecule").

In some embodiments, the multispecific molecule comprises a second moiety which comprises one or more of: a tumor-targeting moiety, a cytokine molecule, a stromal modifying moiety, or an anti-TCRβV antibody molecule other than the first moiety.

In some embodiments, binding of the first moiety to the TCRβV region results in a cytokine profile, e.g., cytokine secretion profile, that differs from that of a T cell engager that binds to a receptor or molecule other than a TCRβV region ("a non-TCRβV-binding T cell engager").

In another aspect, the disclosure provides a multispecific molecule, e.g., a bispecific molecule, comprising the anti-TCRβV antibody molecule disclosed herein.

In some embodiments, the multispecific molecule further comprises: a tumor-targeting moiety, a cytokine molecule, an immune cell engager, e.g., a second immune cell engager, and/or a stromal modifying moiety.

In yet another aspect, disclosed herein is a multispecific molecule, e.g., a bispecific molecule, comprising:

(i) a first moiety comprising a first immune cell engager comprising an anti-TCRβV antibody molecule disclosed herein; and
(ii) a second moiety comprising one or more of: a tumor-targeting moiety; a second immune cell engager; a cytokine molecule or a stromal modifying moiety.

In another aspect, the disclosure provides an isolated nucleic acid molecule comprising a nucleotide sequence encoding an anti-TCRβV antibody molecule disclosed herein, or a nucleotide sequence having at least 75%, 80%, 85%, 90%, 95%, or 99% identity thereto.

In another aspect, the disclosure provides an isolated nucleic acid molecule comprising a nucleotide sequence encoding a multispecific molecule disclosed herein, or a nucleotide sequence having at least 75%, 80%, 85%, 90%, 95%, or 99% identity thereto.

In yet another aspect, the disclosure provides a vector, e.g., an expression vector, comprising a nucleotide sequence encoding an anti-TCRβV antibody molecule disclosed herein, or a nucleotide sequence having at least 75%, 80%, 85%, 90%, 95%, or 99% identity thereto.

In another aspect, the disclosure provides a vector, e.g., an expression vector, comprising a nucleotide sequence encoding a multispecific molecule disclosed herein, or a nucleotide sequence having at least 75%, 80%, 85%, 90%, 95%, or 99% identity thereto.

In one aspect, the disclosure provides a cell, e.g., host cell, e.g., a population of cells, comprising a nucleic acid molecule encoding an anti-TCRβV antibody molecule disclosed herein, or a nucleotide sequence having at least 75%, 80%, 85%, 90%, 95%, or 99% identity thereto. In some embodiments, the cell or population of cells comprising a nucleic acid molecule encoding anti-TCRβV antibody molecule, comprises: (i) a heavy chain comprising: a variable region (VH), e.g., a VH listed in Tables 1-2 or 10-13, or a sequence having at least 75%, 80%, 85%, 90%, 95%, or 99% identity thereto; and one or more heavy chain constant regions, e.g., as described herein; and/or (ii) a light chain comprising: a variable region (VL) e.g., a VL listed in Tables 1-2 or 10-13, or a sequence having at least 75%, 80%, 85%, 90%, 95%, or 99% identity thereto; and a light chain constant region, e.g., as described herein, e.g., a kappa chain constant region comprising the sequence of SEQ ID NO: 39, or a sequence with at least 85%, 90%, 95%, or 99% sequence identity thereto. In some embodiments, the cell or population of cells further comprises an IgJ heavy chain constant region or a fragment thereof. In some embodiments, the SeqJ heavy chain constant region comprises the sequence of SEQ ID NO: 76 or a sequence with at least 85%, 90%, 95%, or 99% sequence identity thereto. In some embodiments, the IgJ is comprised in, e.g., expressed in, the same cell or population of cells comprising, e.g., expressing, the anti-TCRβV antibody molecule, e.g., the heavy chain and/or the light chain of the anti-TCRβV antibody molecule. In some embodiments, the IgJ is expressed in a different cell or population of cells than the cell or population of cells comprising, e.g., expressing, the anti-TCRβV antibody molecule, e.g., the heavy chain and/or the light chain of the anti-TCRβV antibody molecule.

In one aspect, the disclosure provides a cell, e.g., host cell, e.g., a population of cells, comprising a nucleic acid molecule encoding a multispecific molecule disclosed herein, or a nucleotide sequence having at least 75%, 80%, 85%, 90%, 95%, or 99% identity thereto.

In one aspect, disclosed herein is an anti-TCRβV antibody molecule for use in the manufacture of a medicament for treating a disease, e.g., cancer, in a subject.

In one aspect, disclosed herein is a multispecific molecule comprising an anti-TCRβV antibody molecule for use in the manufacture of a medicament for treating a disease, e.g., cancer, in a subject.

In another aspect, the disclosure provides a method of making, e.g., producing, an anti-TCRβV antibody molecule, a multispecific molecule described herein, comprising culturing a host cell described herein, under suitable conditions. In some embodiments of a method of making a multispecific molecule, the conditions comprise, e.g., conditions suitable for gene expression and/or homo- or heterodimerization.

In another aspect, the disclosure provides a pharmaceutical composition comprising an anti-TCRβV antibody molecule, or a multispecific molecule described herein, and a pharmaceutically acceptable carrier, excipient, or stabilizer.

In an aspect, the disclosure provides a method of modulating, e.g., enhancing, an immune response in a subject comprising administering to the subject an effective amount of an antibody molecule which binds (e.g., specifically binds) to a T cell receptor beta variable region (TCRβV) ("anti-TCRβV antibody molecule").

In an aspect, the disclosure provides a method of modulating, e.g., enhancing, an immune response in a subject comprising administering to the subject an effective amount of a multispecific molecule disclosed herein.

In some embodiments, the method comprises expanding, e.g., increasing the number of, an immune cell population in the subject.

In an aspect, the disclosure provides a method of expanding, e.g., increasing the number of, an immune cell population comprising, contacting the immune cell population with an effective amount of an antibody molecule which binds (e.g., specifically binds) to a T cell receptor beta variable region (TCRβV) ("anti-TCRβV antibody molecule").

In an aspect, the disclosure provides a method of expanding, e.g., increasing the number of, an immune cell population comprising, contacting the immune cell population with an effective amount of a multispecific molecule disclosed herein.

In some embodiments, the expansion occurs in vivo or ex vivo (e.g., in vitro).

In some embodiments, the immune cell population comprises a TCRβV expressing cell, e.g., a TCRβV+ cell.

In some embodiments, the TCRβV expressing cell is a T cell, e.g., a CD8+ T cell, a CD3+ T cell or a CD4+ T cell.

In some embodiments, the immune cell population comprises a T cell (e.g., a CD4 T cell, or a CD8 T cell). In some embodiments, the immune cell population comprises a T cell having a memory-like phenotype, e.g., CD45RA+ CCR7−. In some embodiments, the immune cell population comprises an effector T cell or a memory T cell (e.g., a memory effector T cell (e.g., TEM cell, e.g., TEMRA cell), or a tumor infiltrating lymphocyte (TIL)).

In some embodiments, the immune cell population comprises a T cell, a Natural Killer cell, a B cell, or a myeloid cell.

In some embodiments, the immune cell population is obtained from a healthy subject.

In an aspect, provided herein is a method of treating a disease e.g., cancer, in a subject comprising administering to the subject an effective amount, e.g., a therapeutically effective amount, of an anti-TCRβV antibody molecule or a multispecific molecule comprising an anti-TCRβV antibody molecule disclosed herein, thereby treating the disease.

In a related aspect, provided herein is a composition comprising an anti-TCRβV antibody molecule or a multispecific molecule comprising an anti-TCRβV antibody molecule disclosed herein, for use in the treatment of a disease, e.g., cancer, in a subject.

In some embodiments, the disease is a cancer, e.g., a solid tumor or a hematological cancer, or a metastatic lesion.

In some embodiments, the method further comprises administering a second agent, e.g., therapeutic agent, e.g., as described herein. In some embodiments, second agent comprises a therapeutic agent (e.g., a chemotherapeutic agent, a biologic agent, hormonal therapy), radiation, or surgery. In some embodiments, therapeutic agent is selected from: a chemotherapeutic agent, or a biologic agent.

In another aspect, provided herein is a method of targeting, e.g., directing or re-directing, a therapy, e.g., treatment, to a T cell, e.g., in a subject, e.g., having a disease, e.g., cancer, comprising administering an effective amount of: (i) an anti-TCRβV antibody disclosed herein; and (ii) the therapy, e.g., a tumor targeting therapy (e.g., an antibody that binds to a cancer antigen), e.g., as described herein, thereby targeting the T cell.

In some embodiments, (i) and (ii) are conjugated, e.g., linked.

In some embodiments, (i) and (ii) are administered simultaneously or concurrently.

In some embodiments, the method results in: reduced cytokine release syndrome (CRS) (e.g., lesser duration of CRS or no CRS), or a reduced severity of CRS (e.g., absence of severe CRS, e.g., CRS grade 4 or 5) compared to administration of (ii) alone. In some embodiments, CRS is assessed by an assay of Example 3. In some embodiments, the method results in: reduced neurotoxicity (NT) (e.g., lesser duration of NT or no NT), or a reduced severity of NT (e.g., absence of severe NT) compared to administration of (ii) alone.

In yet another aspect, the disclosure provides, a method of targeting a T cell, e.g., in a subject having a disease, e.g., cancer, with an anti-TCRβV antibody disclosed herein or a multispecific molecule comprising an anti-TCRβV antibody disclosed herein.

In another aspect, the disclosure provides a method of treating, e.g., preventing or reducing, cytokine release syndrome (CRS) and/or neurotoxicity (NT) in a subject, e.g., CRS and/or NT associated with a treatment, e.g., a previously administered treatment, comprising administering to the subject an effective amount of an anti-TCRβV antibody disclosed herein or a multispecific molecule comprising an anti-TCRβV antibody disclosed herein, wherein, the subject has a disease, e.g., a cancer, thereby treating, e.g., preventing or reducing, CRS and/or NT in the subject.

In a related aspect, the disclosure provides a composition comprising an anti-TCRβV antibody disclosed herein or a multispecific molecule comprising an anti-TCRβV antibody disclosed herein, for use in the treatment, e.g., prevention or reduction, of cytokine release syndrome (CRS) and/or neurotoxicity (NT) in a subject, e.g., CRS and/or NT associated with a treatment, e.g., a previously administered treatment, comprising administering to the subject an effective amount of the anti-TCRβV antibody, wherein the subject has a disease, e.g., a cancer.

In some embodiments of a method or composition for use disclosed herein, the anti-TCRβV antibody is administered concurrently with or after the administration of the treatment associated with CRS and/or NT.

In another aspect, provided herein is a method of expanding, e.g., increasing the number of, an immune cell population comprising, contacting the immune cell population with an antibody molecule, e.g., humanized antibody molecule, which binds, e.g., specifically binds, to a T cell receptor beta variable chain (TCRβV) region (e.g., anti-TCRβV antibody molecule described herein or a multispecific molecule comprising an anti-TCRβV antibody molecule described herein), thereby expanding the immune cell population.

In some embodiments, the expansion occurs in vivo or ex vivo (e.g., in vitro).

In an aspect, provided herein is a method of evaluating a subject having a cancer, comprising acquiring a value of the status of a TCRβV molecule for the subject, wherein said value comprises a measure of the presence of, e.g., level or activity of, a TCRβV molecule in a sample from the subject, wherein the value of the status of a TCRβV molecule is higher, e.g., increased, in a sample from the subject compared to a reference value, e.g., a value from a healthy subject, e.g., a subject that does not have cancer.

In another aspect, the disclosure provides a method of treating a subject having a cancer, the method comprising (i) acquiring a value of the status of a TCRβV molecule for the subject, wherein said value comprises a measure of the presence of, e.g., level or activity of, a TCRβV molecule in a sample from the subject, and (ii) responsive to said value, administering an effective amount of an anti-TCRβV antibody molecule described herein (e.g., a TCRβV agonist) to the subject, thereby treating the cancer.

In some embodiments, the value is higher, e.g., increased, in a sample from the subject compared to a reference value, e.g., a value from a healthy subject, e.g., a subject that does not have cancer.

In a related aspect, the disclosure provides a composition comprising an anti-TCRβV antibody molecule for use in the treatment of a subject having a cancer, comprising (i) acquiring a value of the status of a TCRβV molecule for the subject, wherein said value comprises a measure of the presence of, e.g., level or activity of, a TCRβV molecule in a sample from the subject, and (ii) responsive to said value, administering an effective amount of an anti-TCRβV antibody molecule described herein (e.g., a TCRβV agonist) to the subject.

In an aspect, provided herein is method of evaluating a subject for the presence of a cancer, the method comprising:

(i) acquiring a value of the status of one or more TCRβV molecules for the subject, e.g., in a biological sample from the subject, wherein said value comprises a measure of the presence of, e.g., level or activity of, a TCRβV molecule in a sample from the subject, and (ii) determining whether the value for the one or more TCRβV molecules is higher, e.g., increased, in a sample from the subject compared to a reference value, e.g., a value from a healthy subject, e.g., a subject that does not have cancer, wherein a value that is higher, e.g., increased, in the subject relative to the reference, e.g., healthy subject, is indicative of the presence of cancer in the subject.

In another aspect, the disclosure provides, a method of treating a subject having cancer, the method comprising:

(i) acquiring a value of the status of one or more TCRβV molecules for the subject, e.g., in a biological sample from the subject, wherein said value comprises a measure of the presence of, e.g., level or activity of, a TCRβV molecule in a sample from the subject;

(ii) determining whether the value for the one or more TCRβV molecules is higher, e.g., increased, in a sample from the subject compared to a reference value, e.g., a value from a healthy subject, e.g., a subject that does not have cancer, and (iii) if a value that is higher, e.g., increased, in the subject relative to the reference value is determined, administering an effective amount of an anti-TCRβV antibody molecule, e.g., as described herein (e.g., a TCRβV agonist), to the subject, thereby treating the cancer.

In a related aspect, provided herein is a composition comprising anti-TCRβV antibody molecule for use in a method of treating a subject having a cancer, comprising (i) acquiring a value of the status of one or more TCRβV molecules for the subject, e.g., in a biological sample from the subject, wherein said value comprises a measure of the presence of, e.g., level or activity of, a TCRβV molecule in a sample from the subject;

(ii) determining whether the value for the one or more TCRβV molecules is higher, e.g., increased, in a sample from the subject compared to a reference value, e.g., a value from a healthy subject, e.g., a subject that does not have cancer, and (iii) if a value that is higher, e.g., increased, in the subject relative to the reference value is determined, administering an effective amount of an anti-TCRβV antibody molecule, e.g., as described herein (e.g., a TCRβV agonist), to the subject.

In some embodiments of any of the methods of treatment, or composition for use disclosed herein, the status is indicative of the subject having cancer, or a symptom thereof.

In some embodiments of any of the methods of treatment or composition for use disclosed herein, the status is indicative of responsiveness to a therapy, e.g., a therapy comprising an anti-TCRβV antibody molecule, e.g., as described herein.

In some embodiments of any of the methods of treatment or composition for use disclosed herein, the value of the status is determined, e.g., measured, by an assay described herein.

In yet another aspect, provided herein is a method of treating a subject having a cancer, comprising administering to the subject an effective amount of an anti-TCRBV antibody molecule described herein, wherein the subject has a higher, e.g., increased, level or activity of one or more TCRBV molecules, e.g., as described herein, compared to a reference level or activity of one or more TCRBV molecules, e.g., in a healthy subject, e.g., a subject not having a cancer In an aspect, the disclosure provides, method of treating a subject having a cancer, comprising

- (i) isolating a biological sample from the subject; e.g., a peripheral blood sample, biopsy sample, or bone marrow sample; and
- (ii) acquiring a value of the status of one or more TCRBV molecules for the subject, e.g., in the biological sample from the subject, wherein said value comprises a measure of the presence of, e.g., level or activity of, a TCRβV molecule in a sample from the subject compared to a reference value, e.g., a sample from a health subject, wherein a value that is higher, e.g., increased, in the subject relative to the reference, e.g., healthy subject, is indicative of the presence of cancer in the subject,

- (iii) contacting the biological sample with an anti-TCRβV antibody molecule, e.g., in vitro; and
- (iv) administering the biological sample or a portion thereof from step (iii) to the subject.

In another aspect, provided herein is method of expanding a population of immune effector cells from a subject having a cancer, the method comprising:

- (i) isolating a biological sample comprising a population of immune effector cells from the subject; e.g., a peripheral blood sample, biopsy sample, or bone marrow sample;
- (ii) acquiring a value of the status of one or more TCRβV molecules for the subject, e.g., in the biological sample from the subject, wherein said value comprises a measure of the presence of, e.g., level or activity of, a TCRβV molecule in a sample from the subject compared to a reference value, e.g., a sample from a health subject, wherein a value that is higher, e.g., increased, in the subject relative to the reference, e.g., healthy subject, is indicative of the presence of cancer in the subject, and

- (iii) contacting the biological sample comprising a population of immune effector cells with an anti-TCRβV antibody molecule.

In some embodiments, the method further comprises administering the population of immune effector cells contacted with the anti-TCRβV antibody molecule to the subject.

In some embodiments, a method of expansion, or method of treatment, or composition for use disclosed herein comprises measuring T cell function (e.g., cytotoxic activity, cytokine secretion, or degranulation) in the population of immune effector cells, e.g., compared to a reference population, e.g., an otherwise similar population not contacted with the anti-TCRβV antibody molecule or a population of immune effector cells obtained from a healthy subject (e.g., a subject that does not have a cancer).

In some embodiments of any of the methods or composition for use disclosed herein, the biological sample comprising the population of immune effector cells is contacted with an anti-TCRβV antibody molecule that binds to the one or more TCRβV molecules (e.g., the same TCRβV molecule) identified as being higher, e.g., increased, in the biological sample.

In some embodiments of any of the methods or composition for use disclosed herein, the biological sample comprising the population of immune effector cells is contacted with an anti-TCRβV antibody molecule that does not bind to the one or more TCRβV molecules (e.g., a different TCRβV molecule) identified as being higher, e.g., increased, in the biological sample.

In another aspect, provided herein is a method of identifying one or more TCRβV molecules associated with a cancer, the method comprising:

- (i) acquiring a status for a plurality of TCRβV molecules in a biological sample from a first subject having the disease and in a biological sample from a second subject not having the disease; and
- (ii) determining whether the level or activity of one or more of the TCRβV molecules is higher, e.g., increased, in the first subject relative to the second subject;

thereby identifying one or more TCRβV molecules associated with the cancer.

In some embodiments of any of the methods or composition for use disclosed herein, the one or more of the TCRβV molecules comprises one or more, (e.g., all) of the following TCRβV subfamilies:

- (i) TCRβ V6 subfamily comprising, e.g., one or more of TCRβ V6-4*01, TCRβ V6-4*02, TCRβ V6-9*01, TCRβ V6-8*01, TCRβ V6-5*01, TCRβ V6-6*02, TCRβ V6-6*01, TCRβ V6-2*01, TCRβ V6-3*01 or TCRβ V6-1*01;
- (ii) TCRβ V10 subfamily comprising, e.g., one or more of TCRβ V10-1*01, TCRβ V10-1*02, TCRβ V10-3*01 or TCRβ V10-2*01;
- (iii) TCRβ V5 subfamily comprising, e.g., one or more of TCRβ V5-6*01, TCRβ V5-4*01, or TCRβ V5-8*01;
- (iv) TCRβ V12 subfamily comprising e.g., one or more of TCRβ V12-4*01, TCRβ V12-3*01, or TCRβ V12-5*01;
- (v) TCRβ V7 subfamily comprising e.g., one or more of TCRβ V7-7*01, TCRβ V7-6*01, TCRβ V7-8*02, TCRβ V7-4*01, TCRβ V7-2*02, TCRβ V7-2*03, TCRβ V7-2*01, TCRβ V7-3*01, TCRβ V7-9*03, or TCRβ V7-9*01;
- (vi) TCRβ V11 subfamily comprising e.g., one or more of TCRβ V11-1*01, TCRβ V11-2*01 or TCRβ V11-3*01;
- (vii) TCRβ V14 subfamily comprising TCRβ V14*01;
- (viii) TCRβ V16 subfamily comprising TCRβ V16*01;
- (ix) TCRβ V18 subfamily comprising TCRβ V18*01;
- (x) TCRβ V9 subfamily comprising T e.g., one or more of CRO V9*01 or TCRβ V9*02;
- (xi) TCRβ V13 subfamily comprising TCRβ V13*01;

(xii) TCRβ V4 subfamily comprising e.g., one or more of e.g., one or more of TCRβ V4-2*01, TCRβ V4-3*01, or TCRβ V4-1*01;

(xiii) TCRβ V3 subfamily comprising TCRβ V3-1*01;

(xiv) TCRβ V2 subfamily comprising TCRβ V2*01;

(xv) TCRβ V15 subfamily comprising TCRβ V15*01;

(xvi) TCRβ V30 subfamily comprising e.g., one or more of TCRβ V30*01, or TCRβ V30*02;

(xvii) TCRβ V19 subfamily comprising e.g., one or more of TCRβ V19*01, or TCRβ V19*02;

(xviii) TCRβ V27 subfamily comprising TCRβ V27*01;

(xix) TCRβ V28 subfamily comprising TCRβ V28*01;

(xx) TCRβ V24 subfamily comprising TCRβ V24-1*01;

(xxi) TCRβ V20 subfamily comprising e.g., one or more of TCRβ V20-1*01, or TCRβ V20-1*02;

(xxii) TCRβ V25 subfamily comprising TCRβ V25-1*01; or (xxiii) TCRβ V29 subfamily comprising TCRβ V29-1*01;

(xxiv) TCRβ V21 subfamily;

(xxv) TCRβ V1 subfamily;

(xxvi) TCRβ V17 subfamily;

(xvii) TCRβ V23 subfamily; or (xviii) TCRβ V26 subfamily.

In some embodiments of any of the methods or composition for use disclosed herein, the cancer is a solid tumor including but not limited to: melanoma, pancreatic (e.g., pancreatic adenocarcinoma) cancer, breast cancer, colorectal cancer (CRC), lung cancer (e.g., small or non-small cell lung cancer), skin cancer, ovarian cancer, or liver cancer.

In some embodiments of any of the methods or composition for use disclosed herein, the cancer is a hematological cancer including, but not limited to: a B-cell or T cell malignancy, e.g., Hodgkin's lymphoma, Non-Hodgkin's lymphoma (e.g., B cell lymphoma, diffuse large B cell lymphoma (DLBCL), follicular lymphoma, chronic lymphocytic leukemia (B-CLL), mantle cell lymphoma, marginal zone B-cell lymphoma, Burkitt lymphoma, lymphoplasmacytic lymphoma, hairy cell leukemia), acute myeloid leukemia (AML), chronic myeloid leukemia, myelodysplastic syndrome, multiple myeloma, and acute lymphocytic leukemia.

In some embodiments of a method of expansion, or method of treatment, or composition for use disclosed herein, a higher, e.g., increased, level or activity of one or more TCRβV molecules in a subject, e.g., in a sample from a subject, is indicative of a bias, e.g., a preferential expansion, e.g., clonal expansion, of T cells expressing said one or more TCRβV molecules in the subject.

In some embodiments, a subject having a cancer, e.g., as disclosed herein, has a higher, e.g., increased, level or activity of one or more TCRβV molecules associated with the cancer. In some embodiments, the TCRβV molecule is associated with, e.g., recognizes, a cancer antigen, e.g., a cancer associated antigen or a neoantigen.

In some embodiments of any of the methods or composition for use disclosed herein, the subject has B-CLL. In some embodiments, a subject having B-CLL has a higher, e.g., increased, level or activity of one or more TCRβV molecules, e.g., one or more TCRβV molecules comprising: (i) TCRβ V6 subfamily comprising, e.g., TCRβ V6-4*01, TCRβ V6-4*02, TCRβ V6-9*01, TCRβ V6-8*01, TCRβ V6-5*01, TCRβ V6-6*02, TCRβ V6-6*01, TCRβ V6-2*01, TCRβ V6-3*01 or TCRβ V6-1*01; (ii) TCRβ V5 subfamily comprising TCRβ V5-6*01, TCRβ V5-4*01, or TCRβ V5-8*01; (iii) TCRβ V3 subfamily comprising TCRβ V3-1*01; (iv) TCRβ V2 subfamily comprising TCRβ V2*01; or (v) TCRβ V19 subfamily comprising TCRβ V19*01, or TCRβ V19*02.

In some embodiments, a subject having B-CLL has a higher, e.g., increased, level or activity of a TCRβ V6 subfamily comprising, e.g., TCRβ V6-4*01, TCRβ V6-4*02, TCRβ V6-9*01, TCRβ V6-8*01, TCRβ V6-5*01, TCRβ V6-6*02, TCRβ V6-6*01, TCRβ V6-2*01, TCRβ V6-3*01 or TCRβ V6-1*01. In some embodiments, the subject is administered an anti-TCRβV molecule (e.g., an agonistic anti-TCRβV molecule as described herein) that binds to one or more members of the TCRβ V6 subfamily. In some embodiments, administration of the an anti-TCRβV molecule results in expansion of immune cells expressing one or more members of the TCRβ V6 subfamily.

In some embodiments, a subject having B-CLL has a higher, e.g., increased, level or activity of a TCRβ V5 subfamily comprising TCRβ V5-6*01, TCRβ V5-4*01, or TCRβ V5-8*01. In some embodiments, the subject is administered an anti-TCRβV molecule (e.g., an agonistic anti-TCRβV molecule as described herein) that binds to one or more members of the TCRβ V5 subfamily. In some embodiments, administration of the an anti-TCRβV molecule results in expansion of immune cells expressing one or more members of the TCRβ V5 subfamily.

In some embodiments, a subject having B-CLL has a higher, e.g., increased, level or activity of a TCRβ V3 subfamily comprising TCRβ V3-1*01. In some embodiments, the subject is administered an anti-TCRβV molecule (e.g., an agonistic anti-TCRβV molecule as described herein) that binds to one or more members of the TCRβ V3 subfamily. In some embodiments, administration of an anti-TCRβV molecule results in expansion of immune cells expressing one or more members of the TCRβ V3 subfamily.

In some embodiments, a subject having B-CLL has a higher, e.g., increased, level or activity of a TCRβ V2 subfamily comprising TCRβ V2*01. In some embodiments, the subject is administered an anti-TCRβV molecule (e.g., an agonistic anti-TCRβV molecule as described herein) that binds to one or more members of the TCRβ V2 subfamily. In some embodiments, administration of an anti-TCRβV molecule results in expansion of immune cells expressing one or more members of the TCRβ V2 subfamily.

In some embodiments, a subject having B-CLL has a higher, e.g., increased, level or activity of a TCRβ V19 subfamily comprising TCRβ V19*01, or TCRβ V19*02. In some embodiments, the subject is administered an anti-TCRβV molecule (e.g., an agonistic anti-TCRBV molecule as described herein) that binds to one or more members of the TCRβ V19 subfamily. In some embodiments, administration of an anti-TCRβV molecule results in expansion of immune cells expressing one or more members of the TCRβ V19 subfamily.

In some embodiments of any of the methods or composition for use disclosed herein, the subject has melanoma. In some embodiments, a subject having melanoma has a higher, e.g., increased, level or activity of one or more TCRβV molecules, e.g., one or more TCRβV molecules comprising the TCRβ V6 subfamily comprising, e.g., TCRβ V6-4*01, TCRβ V6-4*02, TCRβ V6-9*01, TCRβ V6-8*01, TCRβ V6-5*01, TCRβ V6-6*02, TCRβ V6-6*01, TCRβ V6-2*01, TCRβ V6-3*01 or TCRβ V6-1*01. In some embodiments, the subject is administered an anti-TCRβV molecule (e.g., an agonistic anti-TCRβV molecule as described herein) that binds to one or more members of the TCRβ V6 subfamily. In some embodiments, administration of an anti-TCRβV molecule results in expansion of immune cells expressing one or more members of the TCRβ V6 subfamily.

In some embodiments of any of the methods or composition for use disclosed herein, the subject has DLBCL. In some embodiments, a subject having melanoma has a higher, e.g., increased, level or activity of one or more TCRβV molecules, e.g., one or more TCRβV molecules comprising: (i) TCRβ V13 subfamily comprising TCRβ V13*01; (ii) TCRβ V3 subfamily comprising TCRβ V3-1*01; or (iii) TCRβ V23 subfamily.

In some embodiments, a subject having DLBCL has a higher, e.g., increased, level or activity of a TCRβ V13 subfamily comprising TCRβ V13*01. In some embodiments, the subject is administered an anti-TCRβV molecule (e.g., an agonistic anti-TCRβV molecule as described herein) that binds to one or more members of the TCRβ V13 subfamily. In some embodiments, administration of an anti-TCRβV molecule results in expansion of immune cells expressing one or more members of the TCRβ V13 subfamily.

In some embodiments, a subject having DLBCL has a higher, e.g., increased, level or activity of a TCRβ V3 subfamily comprising TCRβ V3-1*01. In some embodiments, the subject is administered an anti-TCRβV molecule (e.g., an agonistic anti-TCRβV molecule as described herein) that binds to one or more members of the TCRβ V3 subfamily. In some embodiments, administration of an anti-TCRβV molecule results in expansion of immune cells expressing one or more members of the TCRβ V3 subfamily.

In some embodiments, a subject having DLBCL has a higher, e.g., increased, level or activity of a TCRβ V23 subfamily. In some embodiments, the subject is administered an anti-TCRβV molecule (e.g., an agonistic anti-TCRβV molecule as described herein) that binds to one or more members of the TCRβ V23 subfamily. In some embodiments, administration of an anti-TCRβV molecule results in expansion of immune cells expressing one or more members of the TCRβ V23 subfamily.

In some embodiments of any of the methods or composition for use disclosed herein, the subject has CRC. In some embodiments, a subject having melanoma has a higher, e.g., increased, level or activity of one or more TCRβV molecules, e.g., one or more TCRβV molecules comprising: (i) TCRβ V19 subfamily comprising TCRβ V19*01, or TCRβ V19*02; (ii) TCRβ V12 subfamily comprising TCRβ V12-4*01, TCRβ V12-3*01, or TCRβ V12-5*01; (iii) TCRβ V16 subfamily comprising TCRβ V16*01; or (iv) TCRβ V21 subfamily.

In some embodiments, a subject having CRC has a higher, e.g., increased, level or activity of a TCRβ V19 subfamily comprising TCRβ V19*01, or TCRβ V19*02. In some embodiments, the subject is administered an anti-TCRβV molecule (e.g., an agonistic anti-TCRβV molecule as described herein) that binds to one or more members of the TCRβ V19 subfamily. In some embodiments, administration of an anti-TCRβV molecule results in expansion of immune cells expressing one or more members of the TCRβ V19 subfamily.

In some embodiments, a subject having CRC has a higher, e.g., increased, level or activity of a TCRβ V12 subfamily comprising TCRβ V12-4*01, TCRβ V12-3*01, or TCRβ V12-5*01. In some embodiments, the subject is administered an anti-TCRβV molecule (e.g., an agonistic anti-TCRβV molecule as described herein) that binds to one or more members of the TCRβ V12 subfamily. In some embodiments, administration of an anti-TCRβV molecule results in expansion of immune cells expressing one or more members of the TCRβ V12 subfamily.

In some embodiments, a subject having CRC has a higher, e.g., increased, level or activity of a TCRβ V16 subfamily comprising TCRβ V16*01. In some embodiments, the subject is administered an anti-TCRβV molecule (e.g., an agonistic anti-TCRβV molecule as described herein) that binds to one or more members of the TCRβ V16 subfamily. In some embodiments, administration of an anti-TCRβV molecule results in expansion of immune cells expressing one or more members of the TCRβ V16 subfamily.

In some embodiments, a subject having CRC has a higher, e.g., increased, level or activity of a TCRβ V21 subfamily. In some embodiments, the subject is administered an anti-TCRβV molecule (e.g., an agonistic anti-TCRβV molecule as described herein) that binds to one or more members of the TCRβ V21 subfamily. In some embodiments, administration of an anti-TCRβV molecule results in expansion of immune cells expressing one or more members of the TCRβ V21 subfamily.

Alternatively or in combination with any of the embodiments disclosed herein, provided herein is an anti-TCRβV antibody molecule which:

(i) binds specifically to an epitope on TCRβV, e.g., the same or similar epitope as the epitope recognized by an anti-TCRβV antibody molecule as described herein, e.g., a second anti-TCRβV antibody molecule;
(ii) shows the same or similar binding affinity or specificity, or both, as an anti-TCRβV antibody molecule as described herein, e.g., a second anti-TCRβV antibody molecule;
(iii) inhibits, e.g., competitively inhibits, the binding of an anti-TCRβV antibody molecule as described herein, e.g., a second anti-TCRβV antibody molecule;
(iv) binds the same or an overlapping epitope with an anti-TCRβV antibody molecule as described herein, e.g., a second anti-TCRβV antibody molecule; or
(v) competes for binding, and/or binds the same epitope, with an anti-TCRβV antibody molecule as described herein, e.g., a second anti-TCRβV antibody molecule, In some embodiments, the second anti-TCRβV antibody molecule comprises an antigen binding domain chosen from Table 1 or Table 2, or a sequence substantially identical thereto. In some embodiments, the second anti-TCRβV antibody molecule comprises an antigen binding domain, comprising:

a heavy chain complementarity determining region 1 (HC CDR1), a heavy chain complementarity determining region 2 (HC CDR2) and/or a heavy chain complementarity determining region 3 (HC CDR3) of SEQ ID NO: 1 or SEQ ID NO: 9; and/or a light chain complementarity determining region 1 (LC CDR1), a light chain complementarity determining region 2 (LC CDR2), and/or a light chain complementarity determining region 3 (LC CDR3) of SEQ ID NO: 2, SEQ ID NO: 10 or SEQ ID NO: 11.

In some embodiments of any of the compositions or methods disclosed herein, the anti-TCRβV antibody molecule comprises an antigen binding domain comprising:

(i) a heavy chain complementarity determining region 1 (HC CDR1), a heavy chain complementarity determining region 2 (HC CDR2) and/or a heavy chain complementarity determining region 3 (HC CDR3) of SEQ ID NO: 1 or SEQ ID NO: 9, or a sequence disclosed in Table 1; or
(ii) a light chain complementarity determining region 1 (LC CDR1), a light chain complementarity determining region 2 (LC CDR2), and/or a light chain complementarity determining region 3 (LC CDR3) of SEQ ID NO: 2, SEQ ID NO: 10 or SEQ ID NO: 11, or a sequence disclosed in Table 1.

In some embodiments of any of the compositions or methods disclosed herein, the anti-TCRβV antibody molecule comprises an antigen binding domain comprising a light chain variable region (VL) comprising one, two or all (e.g., three) of a LC CDR1, a LC CDR2 and a LC CDR3 of SEQ ID NO: 2, SEQ ID NO: 10 or SEQ ID NO: 11.

In some embodiments of any of the compositions or methods disclosed herein, the anti-TCRβV antibody molecule comprises an antigen binding domain comprising a heavy chain variable region (VH) comprising one, two or all (e.g., three) of a HC CDR1, a HC CDR2 and a HC CDR3 of SEQ ID NO:1 or SEQ ID NO: 9.

In some embodiments of any of the compositions or methods disclosed herein, the anti-TCRβV antibody molecule comprises an antigen binding domain comprising:

(i) a VL comprising: a LC CDR1 amino acid sequence of SEQ ID NO: 6 (or an amino acid sequence with not more than 1, 2, 3 or 4 modifications, e.g., substitutions, additions or deletions thereof), a LC CDR2 amino acid sequence of SEQ ID NO:7 (or an amino acid sequence with not more than 1, 2, 3 or 4 modifications, e.g., substitutions, additions or deletions thereof), and/or a LC CDR3 amino acid sequence of SEQ ID NO:8 (or an amino acid sequence with not more than 1, 2, 3 or 4 modifications, e.g., substitutions, additions or deletions thereof); and/or (ii) a VH comprising: a HC CDR1 amino acid sequence of SEQ ID NO: 3 (or an amino acid sequence with not more than 1, 2, 3 or 4 modifications, e.g., substitutions, additions or deletions thereof), a HC CDR2 amino acid sequence of SEQ ID NO:4 (or an amino acid sequence with not more than 1, 2, 3 or 4 modifications, e.g., substitutions, additions or deletions thereof), and/or a HC CDR3 amino acid sequence of SEQ ID NO:5 (or an amino acid sequence with not more than 1, 2, 3 or 4 modifications, e.g., substitutions, additions or deletions thereof).

In some embodiments of any of the compositions or methods disclosed herein, the anti-TCRβV antibody molecule comprises an antigen binding domain comprising: a variable heavy chain (VH) of SEQ ID NO: 9 or SEQ ID NO: 1312, or a sequence having at least about 75%, 80%, 85%, 90%, 95%, or 99% sequence identity thereto; and/or a variable light chain (VL) of SEQ ID NO: 10 or SEQ ID NO: 11 or SEQ ID NO: 1314, or a sequence having at least about 75%, 80%, 85%, 90%, 95%, or 99% sequence identity thereto.

In some embodiments of any of the compositions or methods disclosed herein, the anti-TCRβV antibody molecule comprises an antigen binding domain comprising the VH amino acid sequence of SEQ ID NO: 9 and the VL amino acid sequence of SEQ ID NO: 10.

In some embodiments of any of the compositions or methods disclosed herein, the anti-TCRβV antibody molecule comprises an antigen binding domain comprising the VH amino acid sequence of SEQ ID NO: 9 and the VL amino acid sequence of SEQ ID NO: 11.

In some embodiments of any of the compositions or methods disclosed herein, the anti-TCRβV antibody molecule comprises an antigen binding domain comprising the VH amino acid sequence of SEQ ID NO: 1312 and the VL amino acid sequence of SEQ ID NO: 1314.

In some embodiments of any of the compositions or methods disclosed herein, the anti-TCRβV antibody molecule comprises an antigen binding domain comprising the amino acid sequence of SEQ ID NO: 1337, or a sequence with at least 85%, 90%, 95%, 96%, 97%, 98% or 99% identity thereto.

In some embodiments of any of the compositions or methods disclosed herein, the anti-TCRβV antibody molecule comprises an antigen binding domain comprising the amino acid sequence of SEQ ID NO: 1500, or a sequence with at least 85%, 90%, 95%, 96%, 97%, 98% or 99% identity thereto.

In some embodiments of any of the compositions or methods disclosed herein, the anti-TCRβV antibody molecule comprises a heavy chain comprising a framework region, e.g., framework region 3 (FR3), comprising one or both of: (i) a Threonine at position 73, e.g., a substitution at position 73 according to Kabat numbering, e.g., a Glutamic Acid to Threonine substitution; or (ii) a Glycine at position, e.g., a substitution at position 94 according to Kabat numbering, e.g., a Arginine to Glycine substitution. In some embodiments, the substitution is relative to a human germline heavy chain framework region sequence.

In some embodiments of any of the compositions or methods disclosed herein, the anti-TCRβV antibody molecule comprises a light chain comprising a framework region, e.g., framework region 1 (FR1), comprising a Phenylalanine at position 10, e.g., a substitution at position 10 according to Kabat numbering, e.g., a Serine to Phenyalanine substitution. In some embodiments, the substitution is relative to a human germline light chain framework region sequence.

In some embodiments of any of the compositions or methods disclosed herein, the anti-TCRβV antibody molecule comprises a light chain comprising a framework region, e.g., framework region 2 (FR2), comprising one or both of: (i) a Histidine at position 36, e.g., a substitution at position 36 according to Kabat numbering, e.g., a Tyrosine to Histidine substitution; or (ii) an Alanine at position 46, e.g., a substitution at position 46 according to Kabat numbering, e.g., a Arginine to Alanine substitution. In some embodiments, the substitution is relative to a human germline light chain framework region sequence.

In some embodiments of any of the compositions or methods disclosed herein, the anti-TCRβV antibody molecule comprises a light chain comprising a framework region, e.g., framework region 3 (FR3), comprising a Phenylalanine at position 87, e.g., a substitution at position 87 according to Kabat numbering, e.g., a Tyrosine to Phenyalanine substitution. In some embodiments, the substitution is relative to a human germline light chain framework region sequence.

In some embodiments of any of the compositions or methods disclosed herein, the anti-TCRβV antibody molecule binds to TCRβ V6, e.g., TCRβ V6-4*01, TCRβ V6-4*02, TCRβ V6-9*01, TCRβ V6-8*01, TCRβ V6-5*01, TCRβ V6-6*02, TCRβ V6-6*01, TCRβ V6-2*01, TCRβ V6-3*01 or TCRβ V6-1*01. In some embodiments the anti-TCRβV antibody molecule binds to TCRβ V6-5*01.

In some embodiments, TCRβ V6, e.g., TCRβ V6-4*01, TCRβ V6-4*02, TCRβ V6-9*01, TCRβ V6-8*01, TCRβ V6-5*01, TCRβ V6-6*02, TCRβ V6-6*01, TCRβ V6-2*01, TCRβ V6-3*01 or TCRβ V6-1*01, is recognized, e.g., bound, by SEQ ID NO: 1 and/or SEQ ID NO: 2. In some embodiments, TCRβ V6, e.g., TCRβ V6-4*01, TCRβ V6-4*02, TCRβ V6-9*01, TCRβ V6-8*01, TCRβ V6-5*01, TCRβ V6-6*02, TCRβ V6-6*01, TCRβ V6-2*01, TCRβ

V6-3*01 or TCRβ V6-1*01, is recognized, e.g., bound, by SEQ ID NO: 9 and/or SEQ ID NO: 10. In some embodiments, TCRβ V6, e.g., TCRβ V6-4*01, TCRβ V6-4*02, TCRβ V6-9*01, TCRβ V6-8*01, TCRβ V6-5*01, TCRβ V6-6*02, TCRβ V6-6*01, TCRβ V6-2*01, TCRβ V6-3*01 or TCRβ V6-1*01, is recognized, e.g., bound, by SEQ ID NO: 9 and/or SEQ ID NO: 11. In some embodiments, TCRβ V6-5*01 is recognized, e.g., bound by SEQ ID NO: 9 and/or SEQ ID NO: 10, or a sequence having at least about 75%, 80%, 85%, 90%, 95%, or 99% sequence identity thereto. In some embodiments, TCRβ V6-5*01 is recognized, e.g., bound by SEQ ID NO: 9 and/or SEQ ID NO: 11, or a sequence having at least about 75%, 80%, 85%, 90%, 95%, or 99% sequence identity thereto.

In some embodiments of any of the compositions or methods disclosed herein, the anti-TCRβV antibody molecule comprises an antigen binding domain comprising:

(i) a heavy chain complementarity determining region (HC CDR1), a HC CDR2 and/or a HC CDR3 of SEQ ID NO: 15, SEQ ID NO: 23, SEQ ID NO: 24 or SEQ ID NO: 25, or a sequence disclosed in Table 2; and/or (ii) a light chain complementarity determining region 1 (LC CDR1), a LC CDR2, and/or a LC CDR3 of SEQ ID NO: 16, SEQ ID NO: 26, SEQ ID NO: 27, SEQ ID NO: 28, SEQ ID NO: 29 or SEQ ID NO:30, or a sequence disclosed in Table 2.

In some embodiments of any of the compositions or methods disclosed herein, the anti-TCRβV antibody molecule comprises an antigen binding domain comprising a light chain variable region (VL) comprising one, two or all of a LC CDR1, a LC CDR2 and a LC CDR3 of SEQ ID NO: 16, SEQ ID NO: 26, SEQ ID NO: 27, SEQ ID NO: 28, SEQ ID NO: 29 or SEQ ID NO:30.

In some embodiments of any of the compositions or methods disclosed herein, the anti-TCRβV antibody molecule comprises an antigen binding domain comprising a heavy chain variable region (VH) comprising one, two or all of a HC CDR1, a HC CDR2 and a HC CDR3 of SEQ ID NO: 15, SEQ ID NO: 23, SEQ ID NO: 24 or SEQ ID NO: 25.

In some embodiments of any of the compositions or methods disclosed herein, the anti-TCRβV antibody molecule comprises an antigen binding domain comprising:

(i) a VL comprising: a LC CDR1 amino acid sequence of SEQ ID NO: 20 (or an amino acid sequence with not more than 1, 2, 3 or 4 modifications, e.g., substitutions, additions or deletions thereof), a LC CDR2 amino acid sequence of SEQ ID NO:21 (or an amino acid sequence with not more than 1, 2, 3 or 4 modifications, e.g., substitutions, additions or deletions thereof), and/or a LC CDR3 amino acid sequence of SEQ ID NO:22 (or an amino acid sequence with not more than 1, 2, 3 or 4 modifications, e.g., substitutions, additions or deletions thereof); and/or (ii) a VH comprising: a HC CDR1 amino acid sequence of SEQ ID NO: 17 (or an amino acid sequence with not more than 1, 2, 3 or 4 modifications, e.g., substitutions, additions or deletions thereof), a HC CDR2 amino acid sequence of SEQ ID NO:18 (or an amino acid sequence with not more than 1, 2, 3 or 4 modifications, e.g., substitutions, additions or deletions thereof), and/or a HC CDR3 amino acid sequence of SEQ ID NO:19 (or an amino acid sequence with not more than 1, 2, 3 or 4 modifications, e.g., substitutions, additions or deletions thereof).

In some embodiments of any of the compositions or methods disclosed herein, the anti-TCRβV antibody molecule comprises an antigen binding domain comprising: a variable heavy chain (VH) of SEQ ID NO: 23, SEQ ID NO: 24 or SEQ ID NO: 25, or a sequence having at least about 75%, 80%, 85%, 90%, 95%, or 99% sequence identity thereto; and/or a variable light chain (VL) of SEQ ID NO: 26, SEQ ID NO: 27, SEQ ID NO: 28, SEQ ID NO: 29 or SEQ ID NO:30, or a sequence having at least about 75%, 80%, 85%, 90%, 95%, or 99% sequence identity thereto.

In some embodiments of any of the compositions or methods disclosed herein, the anti-TCRβV antibody molecule comprises a light chain comprising a framework region, e.g., framework region 1 (FR1), comprising one, two or all (e.g., three) of: (i) an Aspartic Acid at position 1, e.g., a substitution at position 1 according to Kabat numbering, e.g., a Alanine to Aspartic Acid substitution; or (ii) an Asparagine at position 2, e.g., a substitution at position 2 according to Kabat numbering, e.g., a Isoleucine to Asparagine substitution, a Serine to Asparagine substitution, or a Tyrosine to Asparagine substitution; or (iii) a Leucine at position 4, e.g., a substitution at position 4 according to Kabat numbering, e.g., a Methionine to Leucine substitution. In some embodiments, the substitution is relative to a human germline light chain framework region sequence.

In some embodiments of any of the compositions or methods disclosed herein, the anti-TCRβV antibody molecule comprises a light chain comprising a framework region, e.g., framework region 3 (FR3), comprising one, two or all (e.g., three) of: (i) a Glycine as position 66, e.g., a substitution at position 66 according to Kabat numbering, e.g., a Lysine to Glycine substitution, or a Serine to Glycine substitution; or (ii) an Asparagine at position 69, e.g., a substitution at position 69 according to Kabat numbering, e.g., a Threonine to Asparagine substitution; or (iii) a Tyrosine at position 71, e.g., a substitution at position 71 according to Kabat numbering, e.g., a Phenylalanine to Tyrosine substitution, or an Alanine to Tyrosine substitution. In some embodiments, the substitution is relative to a human germline light chain framework region sequence.

In some embodiments of any of the compositions or methods disclosed herein, the anti-TCRβV antibody molecule binds to TCRβ V12, e.g., TCRβ V12-4*01, TCRβ V12-3*01, or TCRβ V12-5*01. In some embodiments the anti-TCRβV antibody molecule binds to TCRβ V12-4*01 or TCRβ V12-3*01.

In some embodiments, TCRβ V12, e.g., TCRβ V12-4*01, TCRβ V12-3*01, or TCRβ V12-5*01 is recognized, e.g., bound, by SEQ ID NO: 15 and/or SEQ ID NO: 16. In some embodiments, TCRβ V12, e.g., TCRβ V12-4*01, TCRβ V12-3*01, or TCRβ V12-5*01, is recognized, e.g., bound, by any one of SEQ ID NOs 23-25, and/or any one of SEQ ID NO: 26-30, or an amino acid sequence having at least about 75%, 80%, 85%, 90%, 95%, or 99% sequence identity thereto. In some embodiments TCRβ V12-4*01 is recognized, e.g., bound, by any one of SEQ ID NOs 23-25, and/or any one of SEQ ID NO: 26-30, or an amino acid sequence having at least about 75%, 80%, 85%, 90%, 95%, or 99% sequence identity thereto. In some embodiments TCRβ V12-3*01 is recognized, e.g., bound, by any one of SEQ ID NOs 23-25, and/or any one of SEQ ID NO: 26-30, or an amino acid sequence having at least about 75%, 80%, 85%, 90%, 95%, or 99% sequence identity thereto.

In some embodiments of any of the compositions or methods disclosed herein, the anti-TCRβV antibody molecule comprises the anti-TCRβV antibody molecule comprises an antigen binding domain comprising a single chain Fv (scFv) or a Fab.

In some embodiments of any of the compositions or methods disclosed herein, the anti-TCRβV antibody molecule comprises binds to a conformational or a linear epitope on the T cell.

In some embodiments of any of the compositions or methods disclosed herein, the tumor comprises an antigen, e.g., a tumor antigen, e.g., a tumor associated antigen or a neoantigen. In some embodiments, the anti-TCRβV antibody molecule recognize, e.g., bind to, the tumor antigen.

In some embodiments of any of the compositions or methods disclosed herein, the anti-TCRβV antibody molecule is a full antibody (e.g., an antibody that includes at least one, and preferably two, complete heavy chains, and at least one, and preferably two, complete light chains), or an antigen-binding fragment (e.g., a Fab, $F(ab')_2$, Fv, a single chain Fv fragment, a single domain antibody, a diabody (dAb), a bivalent antibody, or bispecific antibody or fragment thereof, a single domain variant thereof, a camelid antibody, or a rat-derived VH.

In some embodiments of any of the compositions or methods disclosed herein, the anti-TCRβV antibody molecule comprises the anti-TCRβV antibody molecule comprises one or more heavy chain constant regions chosen from IgG1, IgG2, IgG3, IgGA1, IgGA2, IgM, IgJ or IgG4, or a fragment thereof, e.g., as disclosed in Table 3.

In some embodiments of any of the compositions or methods disclosed herein, the anti-TCRβV antibody molecule comprises a heavy chain constant region of an IgM or a fragment thereof, optionally wherein the IgM heavy chain constant region comprises the sequence of SEQ ID NO: 73, or a sequence with at least 85%, 90%, 95%, or 99% sequence identity thereto. In some embodiments of any of the compositions or methods disclosed herein, the anti-TCRβV antibody molecule comprising an IgM constant region, further comprises a heavy chain constant region of an IgJ or a fragment thereof, optionally wherein the IgJ heavy chain constant region comprises the sequence of SEQ ID NO: 76 or a sequence with at least 85%, 90%, 95%, or 99% sequence identity thereto.

In some embodiments of any of the compositions or methods disclosed herein, the anti-TCRβV antibody molecule comprises a heavy chain constant region of an IgJ or a fragment thereof, optionally wherein the IgJ heavy chain constant region comprises the sequence of SEQ ID NO: 76 or a sequence with at least 85%, 90%, 95%, or 99% sequence identity thereto.

In some embodiments of any of the compositions or methods disclosed herein, the anti-TCRβV antibody molecule comprises a heavy chain constant region of an IgGA1, or a fragment thereof, optionally wherein the IgGA1 heavy chain constant region comprises the sequence of SEQ ID NO: 74, or a sequence with at least 85%, 90%, 95%, or 99% sequence identity thereto.

In some embodiments of any of the compositions or methods disclosed herein, the anti-TCRβV antibody molecule comprises a heavy chain constant region of an IgGA2, or a fragment thereof, optionally wherein the IgGA2 heavy chain constant region comprises a sequence listed in Table 3, e.g., SEQ ID NO: 75, or a sequence with at least 85%, 90%, 95%, or 99% sequence identity thereto.

In some embodiments of any of the compositions or methods disclosed herein, binding of the anti-TCRβV antibody molecule to a TCRβV region results in a cytokine profile, e.g., a cytokine secretion profile, (e.g., comprising one or more cytokines and/or one or more chemokines), that differs from that of a T cell engager that binds to a receptor or molecule other than a TCRβV region ("a non-TCRβV-binding T cell engager").

In some embodiments, the cytokine profile, e.g., cytokine secretion profile, comprises the level and/or activity of one or more cytokines and/or one or more chemokines (e.g., as described herein). In an embodiment, a cytokine profile, e.g., a cytokine secretion profile, comprises the level and/or activity of one or more of: IL-2 (e.g., full length, a variant, or a fragment thereof); IL-1beta (e.g., full length, a variant, or a fragment thereof); IL-6 (e.g., full length, a variant, or a fragment thereof); TNFα (e.g., full length, a variant, or a fragment thereof); IFNg (e.g., full length, a variant, or a fragment thereof) IL-10 (e.g., full length, a variant, or a fragment thereof); IL-4 (e.g., full length, a variant, or a fragment thereof); TNF alpha (e.g., full length, a variant, or a fragment thereof); IL-12p70 (e.g., full length, a variant, or a fragment thereof); IL-13 (e.g., full length, a variant, or a fragment thereof); IL-8 (e.g., full length, a variant, or a fragment thereof); Eotaxin (e.g., full length, a variant, or a fragment thereof); Eotaxin-3 (e.g., full length, a variant, or a fragment thereof); IL-8 (HA) (e.g., full length, a variant, or a fragment thereof); IP-10 (e.g., full length, a variant, or a fragment thereof); MCP-1 (e.g., full length, a variant, or a fragment thereof); MCP-4 (e.g., full length, a variant, or a fragment thereof); MDC (e.g., full length, a variant, or a fragment thereof); MIP-1α(e.g., full length, a variant, or a fragment thereof); MIP-1b (e.g., full length, a variant, or a fragment thereof); TARC (e.g., full length, a variant, or a fragment thereof); GM-CSF (e.g., full length, a variant, or a fragment thereof); IL-12 23p40 (e.g., full length, a variant, or a fragment thereof); IL-15 (e.g., full length, a variant, or a fragment thereof); IL-16 (e.g., full length, a variant, or a fragment thereof); IL-17a (e.g., full length, a variant, or a fragment thereof); IL-1a (e.g., full length, a variant, or a fragment thereof); IL-5 (e.g., full length, a variant, or a fragment thereof); IL-7 (e.g., full length, a variant, or a fragment thereof); TNF-beta (e.g., full length, a variant, or a fragment thereof); or VEGF (e.g., full length, a variant, or a fragment thereof).

In some embodiments, the cytokine profile, e.g., cytokine secretion profile, comprises one, two, three, four, five, six, seven, or all of the following:

(i) increased level, e.g., expression level, and/or activity of IL-2;

(ii) reduced level, e.g., expression level, and/or activity of IL-1β;

(iii) reduced level, e.g., expression level, and/or activity of IL-6;

(iv) reduced level, e.g., expression level, and/or activity of TNFα;

(v) reduced level, e.g., expression level, and/or activity of IL-10;

(vi) a delay, e.g., at least 1, 2, 3, 4, 5, 6, 7, 8, 9, 10 or more hours delay, in increased level, e.g., expression level, and/or activity of IL-2;

(vii) a delay, e.g., at least 1, 2, 3, 4, 5, 6, 7, 8, 9, 10 hours delay, in increased level, e.g., expression level, and/or activity of IFNg; or (viii) increased level, e.g., expression level, and/or activity of IL-15, e.g., wherein (i)-(viii) are relative to the cytokine profile, e.g., cytokine secretion profile, of the non-TCRβV-binding T cell engager.

In some embodiments, binding of the anti-TCRBV antibody to a TCRβV region results in reduced cytokine storm, e.g., reduced cytokine release syndrome (CRS) and/or neurotoxicity (NT), as measured by an assay of Example 3, e.g., relative to the cytokine storm induced by the non-TCRβV-binding T cell engager.

In some embodiments, binding of the anti-TCRBV antibody to a TCRβV region results in one, two, three or all of:

(ix) reduced T cell proliferation kinetics;

(x) cell killing, e.g., target cell killing, e.g. cancer cell killing, e.g., as measured by an assay of Example 4;

(xi) increased Natural Killer (NK) cell proliferation, e.g., expansion; or (xii) expansion, e.g., at least about 1.1-10 fold expansion (e.g., at least about 1.1, 1.2, 1.3, 1.4, 1.5, 2, 3, 4, 5, 6, 7, 8, 9, or 10 fold expansion), of a population of T cells having a memory-like phenotype, e.g., wherein (ix)-(xii) are relative to the non-TCRβV-binding T cell engager.

In some embodiments, an anti-TCRβV antibody molecule disclosed herein recognizes (e.g., binds to), a structurally conserved domain on the TCRβV protein (e.g., as denoted by the circled area in FIG. 24A).

In some embodiments, an anti-TCRβV antibody molecule disclosed herein does not recognize, e.g., bind to, an interface of a TCRβV:TCRalpha complex.

In some embodiments, an anti-TCRβV antibody molecule disclosed herein does not recognize, e.g., bind to, a constant region of a TCRβV protein. An exemplary antibody that binds to a constant region of a TCRBV region is JOVI.1 as described in Viney et al., (*Hybridoma*. 1992 December; 11(6):701-13).

In some embodiments, an anti-TCRβV antibody molecule disclosed herein does not recognize, e.g., bind to, one or more (e.g., all) of a complementarity determining region (e.g., CDR1, CDR2 and/or CDR3) of a TCRβV protein.

In some embodiments of any of the compositions or methods disclosed herein, the anti-TCRβV antibody molecule comprises a light chain constant region chosen from the light chain constant regions of kappa or lambda, or a fragment thereof, e.g., as disclosed in Table 3.

In some embodiments of any of the compositions or methods disclosed herein, the anti-TCRβV antibody molecule comprises a light chain constant region of a kappa chain, or a fragment thereof, optionally wherein the kappa chain constant region comprises the sequence of SEQ ID NO: 39, or a sequence with at least 85%, 90%, 95%, or 99% sequence identity thereto In some embodiments of any of the compositions or methods disclosed herein, the anti-TCRβV antibody molecule comprises:

(i) one or more heavy chain constant regions comprising a heavy chain constant region chosen from IgG1, IgG2, IgG3, IgGA1, IgGA2, IgG4, IgJ, IgM, IgD, or IgE, or a fragment thereof, e.g., as described in Table 3; and (ii) a light chain constant region comprising a light chain constant region chosen from the light chain constant regions of kappa or lambda, or a fragment thereof, e.g., as described in Table 3.

In some embodiments of any of the compositions or methods disclosed herein, the anti-TCRβV antibody molecule comprises or a cell comprising an anti-TCRβV antibody molecule comprises:

(i) a heavy chain comprising a variable region (VH), e.g., a VH of an antibody disclosed herein; and/or one or more heavy chain constant regions, e.g., as disclosed herein; and/or (ii) a light chain comprising a variable light (VL), e.g., a VL of an antibody disclosed herein; and/or one or more light chain constant regions, e.g., as disclosed herein.

In some embodiments of any of the compositions or methods disclosed herein, the anti-TCRβV antibody molecule comprises, or a cell comprising an anti-TCRβV antibody molecule comprises:

(i) a heavy chain comprising a heavy chain constant region comprising:

(a) an IgM heavy chain constant region or a fragment thereof, comprising the sequence of SEQ ID NO: 73, or a sequence with at least 85%, 90%, 95%, or 99% sequence identity thereto;

(b) an IgGA1 heavy chain constant region or a fragment thereof, comprising the sequence of SEQ ID NO: 74, or a sequence with at least 85%, 90%, 95%, or 99% sequence identity thereto; or (c) an IgGA2 heavy chain constant region or a fragment thereof, comprising the sequence of SEQ ID NO: 75, or a sequence with at least 85%, 90%, 95%, or 99% sequence identity thereto; and (ii) a light chain comprising a light chain constant region comprising a kappa chain constant region comprising the sequence of SEQ ID NO: 39, or a sequence with at least 85%, 90%, 95%, or 99% sequence identity thereto, optionally wherein, the anti-TCRβV antibody molecule further comprises an IgJ heavy chain constant region or a fragment thereof, wherein the IgJ heavy chain constant region comprises the sequence of SEQ ID NO: 76 or a sequence with at least 85%, 90%, 95%, or 99% sequence identity thereto.

In some embodiments of any of the compositions or methods disclosed herein, the anti-TCRβV antibody molecule comprises, or a cell comprising an anti-TCRβV antibody molecule comprises:

(i) a heavy chain comprising: a VH chosen from a VH of Tables 1-2 or 10-13, or a sequence with at least 85%, 90%, 95%, or 99% sequence identity thereto; and a heavy chain constant region comprising:

(a) an IgM heavy chain constant region or a fragment thereof, comprising the sequence of SEQ ID NO: 73, or a sequence with at least 85%, 90%, 95%, or 99% sequence identity thereto;

(b) an IgGA1 heavy chain constant region or a fragment thereof, comprising the sequence of SEQ ID NO: 74, or a sequence with at least 85%, 90%, 95%, or 99% sequence identity thereto; or (c) an IgGA2 heavy chain constant region or a fragment thereof, comprising the sequence of SEQ ID NO: 75, or a sequence with at least 85%, 90%, 95%, or 99% sequence identity thereto; and (ii) a light chain comprising: a VL chosen from a VL of Tables 1-2 or 10-13, or a sequence with at least 85%, 90%, 95%, or 99% sequence identity thereto; and a light chain constant region comprising a kappa chain constant region comprising the sequence of SEQ ID NO: 39, or a sequence with at least 85%, 90%, 95%, or 99% sequence identity thereto, optionally wherein, the anti-TCRβV antibody molecule further comprises an IgJ heavy chain constant region or a fragment thereof, wherein the IgJ heavy chain constant region comprises the sequence of SEQ ID NO: 76 or a sequence with at least 85%, 90%, 95%, or 99% sequence identity thereto.

In some embodiments of any of the methods disclosed herein, the anti-TCRβV antibody molecule binds to one or more (e.g., all) of the following TCRβV subfamilies:

(i) TCRβ V6 subfamily comprising, e.g., one or more of TCRβ V6-4*01, TCRβ V6-4*02, TCRβ V6-9*01, TCRβ V6-8*01, TCRβ V6-5*01, TCRβ V6-6*02, TCRβ V6-6*01, TCRβ V6-2*01, TCRβ V6-3*01 or TCRβ V6-1*01;

(ii) TCRβ V10 subfamily comprising, e.g., one or more of TCRβ V10-1*01, TCRβ V10-1*02, TCRβ V10-3*01 or TCRβ V10-2*01;

(iii) TCRβ V5 subfamily comprising, e.g., one or more of TCRβ V5-6*01, TCRβ V5-4*01, or TCRβ V5-8*01;

(iv) TCRβ V12 subfamily comprising e.g., one or more of TCRβ V12-4*01, TCRβ V12-3*01, or TCRβ V12-5*01;

(v) TCRβ V7 subfamily comprising e.g., one or more of TCRβ V7-7*01, TCRβ V7-6*01, TCRβ V7-8*02, TCRβ V7-4*01, TCRβ V7-2*02, TCRβ V7-2*03, TCRβ V7-2*01, TCRβ V7-3*01, TCRβ V7-9*03, or TCRβ V7-9*01;

(vi) TCRβ V11 subfamily comprising e.g., one or more of TCRβ V11-1*01, TCRβ V11-2*01 or TCRβ V11-3*01;

(vii) TCRβ V14 subfamily comprising TCRβ V14*01;

(viii) TCRβ V16 subfamily comprising TCRβ V16*01;

(ix) TCRβ V18 subfamily comprising TCRβ V18*01;

(x) TCRβ V9 subfamily comprising T e.g., one or more of CRO V9*01 or TCRβ V9*02;

(xi) TCRβ V13 subfamily comprising TCRβ V13*01;

(xii) TCRβ V4 subfamily comprising e.g., one or more of e.g., one or more of TCRβ V4-2*01, TCRβ V4-3*01, or TCRβ V4-1*01;

(xiii) TCRβ V3 subfamily comprising TCRβ V3-1*01;

(xiv) TCRβ V2 subfamily comprising TCRβ V2*01;

(xv) TCRβ V15 subfamily comprising TCRβ V15*01;

(xvi) TCRβ V30 subfamily comprising e.g., one or more of TCRβ V30*01, or TCRβ V30*02;

(xvii) TCRβ V19 subfamily comprising e.g., one or more of TCRβ V19*01, or TCRβ V19*02;

(xviii) TCRβ V27 subfamily comprising TCRβ V27*01;

(xix) TCRβ V28 subfamily comprising TCRβ V28*01;

(xx) TCRβ V24 subfamily comprising TCRβ V24-1*01;

(xxi) TCRβ V20 subfamily comprising e.g., one or more of TCRβ V20-1*01, or TCRβ V20-1*02;

(xxii) TCRβ V25 subfamily comprising TCRβ V25-1*01; or (xxiii) TCRβ V29 subfamily comprising TCRβ V29-1*01;

(xxiv) TCRβ V21 subfamily;

(xxv) TCRβ V1 subfamily;

(xxvi) TCRβ V17 subfamily;

(xvii) TCRβ V23 subfamily; or (xviii) TCRβ V26 subfamily.

In some embodiments of any of the methods disclosed herein, the anti-TCRβV antibody molecule binds to one or more (e.g., all) of the following TCRβV subfamilies:

(i) TCRβ V6, e.g., TCRβ V6-4*01, TCRβ V6-4*02, TCRβ V6-9*01, TCRβ V6-8*01, TCRβ V6-5*01, TCRβ V6-6*02, TCRβ V6-6*01, TCRβ V6-2*01, TCRβ V6-3*01 or TCRβ V6-1*01;

(ii) TCRβ V10, e.g., TCRβ V10-1*01, TCRβ V10-1*02, TCRβ V10-3*01 or TCRβ V10-2*01;

(iii) TCRβ V12, e.g., TCRβ V12-4*01, TCRβ V12-3*01, or TCRβ V12-5*01; or (iv) TCRβ V5, e.g., TCRβ V5-5*01, TCRβ V5-6*01, TCRβ V5-4*01, TCRβ V5-8*01, TCRβ V5-1*01.

In some embodiments, the anti-TCRβV antibody molecule binds to TCRβ V6, e.g., TCRβ V6-4*01, TCRβ V6-4*02, TCRβ V6-9*01, TCRβ V6-8*01, TCRβ V6-5*01, TCRβ V6-6*02, TCRβ V6-6*01, TCRβ V6-2*01, TCRβ V6-3*01 or TCRβ V6-1*01. In some embodiments, the anti-TCRβV antibody molecule binds to TCRβ V6-5*01.

In some embodiments, the anti-TCRβV antibody molecule does not bind to TCRβ V12.

In some embodiments, the anti-TCRβV antibody molecule does not bind to TCRβ V5-5*01 or TCRβ V5-1*01.

In some embodiments of any of the methods disclosed herein, the anti-TCRβV antibody molecule does not bind to TCRβ V12, or binds to TCRβ V12 with an affinity and/or binding specificity that is less than (e.g., less than about 10%, 20%, 30%, 40%, 50%, 60%, 70%, 80%, 90% or about 2-, 5-, or 10-fold) the affinity and/or binding specificity of the 16G8 murine antibody or a humanized version thereof as described in U.S. Pat. No. 5,861,155.

In some embodiments of any of the methods disclosed herein, the anti-TCRβV antibody molecule binds to TCRβ V12 with an affinity and/or binding specificity that is greater than (e.g., greater than about 10%, 20%, 30%, 40%, 50%, 60%, 70%, 80%, 90% or about 2-, 5-, or 10-fold) the affinity and/or binding specificity of the 16G8 murine antibody or a humanized version thereof as described in U.S. Pat. No. 5,861,155.

In some embodiments of any of the methods disclosed herein, the anti-TCRβV antibody molecule binds to a TCRβV region other than TCRβ V12 (e.g., TCRβV region as described herein, e.g., TCRβ V6 subfamily (e.g., TCRβ V6-5*01) with an affinity and/or binding specificity that is greater than (e.g., greater than about 10%, 20%, 30%, 40%, 50%, 60%, 70%, 80%, 90% or about 2-, 5-, or 10-fold) the affinity and/or binding specificity of the 16G8 murine antibody or a humanized version thereof as described in U.S. Pat. No. 5,861,155.

In some embodiments of any of the methods disclosed herein, the anti-TCRβV antibody molecule does not comprise at least one CDR of Antibody B. In some embodiments of any of the methods disclosed herein, the anti-TCRβV antibody molecule does not comprise the CDRs of Antibody B.

In some embodiments of any of the methods disclosed herein, the anti-TCRβV antibody molecule does not bind to TCRβ V5-5*01 or TCRβ V5-1*01, or binds to TCRβ V5-5*01 or TCRβ V5-1*01 with an affinity and/or binding specificity that is less than (e.g., less than about 10%, 20%, 30%, 40%, 50%, 60%, 70%, 80%, 90% or about 2-, 5-, or 10-fold) the affinity and/or binding specificity of the TM23 murine antibody or a humanized version thereof as described in U.S. Pat. No. 5,861,155.

In some embodiments of any of the methods disclosed herein, the anti-TCRβV antibody molecule binds to TCRβ V5-5*01 or TCRβ V5-1*01 with an affinity and/or binding specificity that is greater than (e.g., greater than about 10%, 20%, 30%, 40%, 50%, 60%, 70%, 80%, 90% or about 2-, 5-, or 10-fold) the affinity and/or binding specificity of the TM23 murine antibody or a humanized version thereof as described in U.S. Pat. No. 5,861,155.

In some embodiments of any of the methods disclosed herein, the anti-TCRβV antibody molecule binds to a TCRβV region other than TCRβ V5-5*01 or TCRβ V5-1*01 (e.g., TCRβV region as described herein, e.g., TCRβ V6 subfamily (e.g., TCRβ V6-5*01) with an affinity and/or binding specificity that is greater than (e.g., greater than about 10%, 20%, 30%, 40%, 50%, 60%, 70%, 80%, 90% or about 2-, 5-, or 10-fold) the affinity and/or binding specificity of the TM23 murine antibody or a humanized version thereof as described in U.S. Pat. No. 5,861,155.

In some embodiments of any of the methods disclosed herein, the anti-TCRβV antibody molecule does not comprise at least one CDR of the TM23 murine antibody. In some embodiments of any of the methods disclosed herein, the anti-TCRβV antibody molecule does not comprise the CDRs of the TM23 murine antibody.

In some embodiments of any of the methods disclosed herein, an anti-TCRβV antibody molecule disclosed herein does not comprise the sequence of a murine anti-rat TCR antibody R73, e.g., as disclosed in J Exp Med. 1989 Jan. 1; 169(1): 73-86, herein incorporated by reference in its entirety. In some embodiments of any of the methods disclosed herein, a multispecific antibody molecule disclosed herein does not comprise the sequence of a murine anti-rat TCR antibody R73, e.g., as disclosed in J Immunol. 1993 Mar. 15; 150(6):2305-15, herein incorporated by reference in its entirety.

In some embodiments of any of the methods disclosed herein, an anti-TCRβV antibody molecule disclosed herein does not comprise a viral peptide-MHC complex, e.g., as disclosed in Oncoimmunology. 2016; 5(1): e1052930, herein incorporated by reference in its entirety. In some embodiments of any of the methods disclosed herein, a multispecific antibody molecule disclosed herein does not comprise a viral peptide-MHC complex, e.g., as disclosed in Oncoimmunology. 2016; 5(1): e1052930, herein incorporated by reference in its entirety.

In some embodiments of a method disclosed herein, the immune cell population comprises a T cell, a Natural Killer cell, a B cell, an antigen presenting cell, or a myeloid cell (e.g., a monocyte, a macrophage, a neutrophil or a granulocyte).

In some embodiments of a method disclosed herein, the immune cell population comprises a T cell, e.g., a CD4+ T cell, a CD8+ T cell, a TCR alpha-beta T cell, or a TCR gamma-delta T cell. In some embodiments, a T cell comprises a memory T cell (e.g., a central memory T cell, or an effector memory T cell (e.g., a $T_{EMRA}$) or an effector T cell. In some embodiments, a T cell comprises a tumor infiltrating lymphocyte (TIL).

In some embodiments of a method disclosed herein, the immune cell population is obtained from a healthy subject.

In some embodiments of a method disclosed herein, the immune cell population is obtained from a subject (e.g., from an apheresis sample from the subject) having a disease, e.g., a cancer, e.g., as described herein. In some embodiments, the immune cell population obtained from a subject having a disease, e.g., a cancer, comprises a tumor infiltrating lymphocyte (TIL).

In some embodiments of a method disclosed herein, the method results in an expansion of at least 1.1-10 fold (e.g., at least 1.1, 1.2, 1.3, 1.4, 1.5, 2, 3, 4, 5, 6, 7, 8, 9, or 10 fold expansion).

In some embodiments of a method disclosed herein, the method further comprises contacting the population of cells with an agent that promotes, e.g., increases, immune cell expansion. In some embodiments, the agent includes an immune checkpoint inhibitor, e.g., as described herein. In some embodiments, the agent includes a 4-1BB (CD127) agonist, e.g., an anti-4-1BB antibody.

In some embodiments of a method disclosed herein, the method further comprises comprising contacting the population of cells with a non-dividing population of cells, e.g., feeder cells, e.g., irradiated allogenic human PBMCs.

In some embodiments of a method disclosed herein, an expansion method described herein comprises expanding the cells for a period of at least about 4 hours, 6 hours, 10 hours, 12 hours, 15 hours, 18 hours, 20 hours, or 22 hours, or for at least 1, 2, 3, 4, 5, 6, 7, 8, 9, 10, 11, 12, 13, 14, 15, 1, 6 17, 18, 19, 20 or 21 days, or for at least about 1 week, 2 weeks, 3 weeks, 4 weeks, 5 weeks, 6 weeks, 7 weeks or 8 weeks.

In some embodiments of a method disclosed herein, expansion of the population of immune cells, is compared to expansion of a similar population of cells with an antibody that binds to: a CD3 molecule, e.g., CD3 epsilon (CD3ε) molecule; or a TCR alpha (TCRα) molecule.

In some embodiments of a method disclosed herein, expansion of the population of immune cells, is compared to expansion of a similar population of cells not contacted with the anti-TCRβV antibody molecule.

In some embodiments of a method disclosed herein, expansion of the population of memory effector T cells, e.g., $T_{EM}$ cells, e.g., $T_{EMRA}$ cells, is compared to expansion of a similar population of cells with an antibody that binds to: a CD3 molecule, e.g., CD3 epsilon (CD3ε) molecule; or a TCR alpha (TCRα) molecule.

In some embodiments of a method disclosed herein, the method results in expansion of, e.g., selective or preferential expansion of, T cells expressing a T cell receptor (TCR) comprising a TCR alpha and/or TCR beta molecule, e.g., TCR alpha-beta T cells (αβ T cells).

In some embodiments of a method disclosed herein, the method results in expansion of αβT cells over expansion of T cells expressing a TCR comprising a TCR gamma and/or TCR delta molecule, e.g., TCR gamma-delta T cells (γδ T cells). In some embodiments, expansion of αβT cells over γδ T cells results in reduced production of cytokines associated with CRS. In some embodiments, expansion of αβT cells over γδ T cells results in immune cells that have reduced capacity to, e.g., are less prone to, induce CRS upon administration into a subject.

In some embodiments of a method disclosed herein, an immune cell population (e.g., T cells (e.g., $T_{EMRA}$ cells or TILs) or NK cells) cultured in the presence of, e.g., expanded with, an anti-TCRβV antibody disclosed herein does not induce CRS and/or NT when administered into a subject, e.g., a subject having a disease or condition as described herein.

In some embodiments, the anti-TCRβV antibody molecule in a multispecific molecule disclosed herein is a first immune cell engager moiety. In some embodiments, the anti-TCRβV antibody molecule does not bind to TCRβ V12, or binds to TCRβ V12 with an affinity and/or binding specificity that is less than (e.g., less than about 10%, 20%, 30%, 40%, 50%, 60%, 70%, 80%, 90% or about 2-, 5-, or 10-fold) the affinity and/or binding specificity of the 16G8 murine antibody or a humanized version thereof as described in U.S. Pat. No. 5,861,155. In some embodiments, the anti-TCRβV antibody molecule binds to TCRβ V12 with an affinity and/or binding specificity that is greater than (e.g., greater than about 10%, 20%, 30%, 40%, 50%, 60%, 70%, 80%, 90% or about 2-, 5-, or 10-fold) the affinity and/or binding specificity of the 16G8 murine antibody or a humanized version thereof as described in U.S. Pat. No. 5,861,155. In some embodiments, the anti-TCRβV antibody molecule binds to a TCRβV region other than TCRβ V12 (e.g., TCRβV region as described herein, e.g., TCRβ V6 subfamily (e.g., TCRβ V6-5*01) with an affinity and/or binding specificity that is greater than (e.g., greater than about 10%, 20%, 30%, 40%, 50%, 60%, 70%, 80%, 90% or about 2-, 5-, or 10-fold) the affinity and/or binding specificity of the 16G8 murine antibody or a humanized version thereof as described in U.S. Pat. No. 5,861,155. In some embodiments, the anti-TCRβV antibody molecule does not comprise the CDRs of the Antibody B murine antibody.

In some embodiments, the anti-TCRβV antibody molecule in a multispecific molecule disclosed herein is a first immune cell engager moiety. In some embodiments, the anti-TCRβV antibody molecule does not bind to TCRβ V5-5*01 or TCRβ V5-1*01, or binds to TCRβ V5-5*01 or TCRβ V5-1*01 with an affinity and/or binding specificity that is less than (e.g., less than about 10%, 20%, 30%, 40%, 50%, 60%, 70%, 80%, 90% or about 2-, 5-, or 10-fold) the affinity and/or binding specificity of the TM23 murine antibody or a humanized version thereof as described in U.S. Pat. No. 5,861,155. In some embodiments, the anti-TCRβV antibody molecule binds to TCRβ V5-5*01 or TCRβ V5-1*01 with an affinity and/or binding specificity that is greater than (e.g., greater than about 10%, 20%, 30%, 40%, 50%, 60%, 70%, 80%, 90% or about 2-, 5-, or 10-fold) the affinity and/or binding specificity of the TM23 murine antibody or a humanized version thereof as described in U.S. Pat. No. 5,861,155. In some embodiments, the anti-TCRβV antibody molecule binds to a TCRβV region other than TCRβ V5-5*01 or TCRβ V5-1*01 (e.g., TCRβV region as described herein, e.g., TCRβ V6 subfamily (e.g., TCRβ V6-5*01) with an affinity and/or binding specificity that is greater than (e.g., greater than about 10%, 20%, 30%, 40%, 50%, 60%, 70%, 80%, 90% or about 2-, 5-, or 10-fold) the affinity and/or binding specificity of the TM23 murine antibody or a humanized version thereof as described in U.S. Pat. No. 5,861,155. In some embodiments, the anti-TCRβV antibody molecule does not comprise the CDRs of the TM23 murine antibody.

In some embodiments, the multispecific molecule further comprises a second immune cell engager moiety. In some embodiments, the first and/or second immune cell engager binds to and activates an immune cell, e.g., an effector cell. In some embodiments, the first and/or second immune cell engager binds to, but does not activate, an immune cell, e.g., an effector cell. In some embodiments, the second immune cell engager is chosen from an NK cell engager, a T cell engager, a B cell engager, a dendritic cell engager, or a macrophage cell engager, or a combination thereof. In some embodiments, the second immune cell engager comprises a T cell engager which binds to CD3, TCRα, TCRγ, TCRζ ICOS, CD28, CD27, HVEM, LIGHT, CD40, 4-1BB, OX40, DR3, GITR, CD30, TIM1, SLAM, CD2, or CD226.

In some embodiments, a multispecific molecule disclosed herein comprises a tumor targeting moiety. In some embodiment, the tumor-targeting moiety comprises an antibody molecule (e.g., Fab or scFv), a receptor molecule (e.g., a receptor, a receptor fragment or functional variant thereof), or a ligand molecule (e.g., a ligand, a ligand fragment or functional variant thereof), or a combination thereof, that binds to a cancer antigen. In some embodiments, the tumor-targeting moiety binds to a cancer antigen present on a cancer, e.g., a hematological cancer, a solid tumor, a metastatic cancer, soft tissue tumor, metastatic lesion, or a combination thereof. In some embodiments, the tumor-targeting moiety binds to a cancer antigen, e.g., BCMA or FcRH5.

In some embodiments, the tumor-targeting antibody molecule binds to a conformational or a linear epitope on the tumor antigen.

In some embodiments of any of the compositions or methods disclosed herein, the tumor-targeting moiety is an antigen, e.g., a cancer antigen. In some embodiments, the cancer antigen is a tumor antigen or stromal antigen, or a hematological antigen.

In some embodiments of any of the compositions or methods disclosed herein, the tumor-targeting moiety binds to a cancer antigen chosen from: BCMA, FcRH5, CD19, CD20, CD22, CD30, CD33, CD38, CD47, CD99, CD123, FcRH5, CLEC12, CD179A, SLAMF7, or NY-ESO1, PDL1, CD47, gangloside 2 (GD2), prostate stem cell antigen (PSCA), prostate specific membrane antigen (PMSA), prostate-specific antigen (PSA), carcinoembryonic antigen (CEA), Ron Kinase, c-Met, Immature laminin receptor, TAG-72, BING-4, Calcium-activated chloride channel 2, Cyclin-B1, 9D7, Ep-CAM, EphA3, Her2/neu, Telomerase, SAP-1, Survivin, NY-ESO-1/LAGE-1, PRAME, SSX-2, Melan-A/MART-1, Gp100/pmel17, Tyrosinase, TRP-1/-2, MC1R, β-catenin, BRCA1/2, CDK4, CML66, Fibronectin, p53, Ras, TGF-B receptor, AFP, ETA, MAGE, MUC-1, CA-125, BAGE, GAGE, NY-ESO-1, β-catenin, CDK4, CDC27, α actinin-4, TRP1/gp75, TRP2, gp100, Melan-A/MART1, gangliosides, WT1, EphA3, Epidermal growth factor receptor (EGFR), MART-2, MART-1, MUC1, MUC2, MUM1, MUM2, MUM3, NA88-1, NPM, OA1, OGT, RCC, RUI1, RUI2, SAGE, TRG, TRP1, TSTA, Folate receptor alpha, L1-CAM, CAIX, gpA33, GD3, GM2, VEGFR, Integrins (Integrin alphaVbeta3, Integrin alpha5Beta1), Carbohydrates (Le), IGF1R, EPHA3, TRAILR1, TRAILR2, RANKL, (FAP), TGF-beta, hyaluronic acid, collagen, e.g., collagen IV, tenascin C, or tenascin W.

In some embodiments of any of the compositions or methods disclosed herein, the cancer is a solid tumor including but not limited to: pancreatic (e.g., pancreatic adenocarcinoma) cancer, breast cancer, colorectal cancer, lung cancer (e.g., small or non-small cell lung cancer), skin cancer, ovarian cancer, or liver cancer.

In some embodiments of any of the compositions or methods disclosed herein, the cancer antigen or tumor antigen is a hematological antigen. In some embodiments, the cancer or tumor antigen is chosen from one or more of: BCMA, FcRH5, CD19, CD20, CD22, CD30, CD33, CD38, CD47, CD99, CD123, FcRH5, CLEC12, CD179A, SLAMF7, or NY-ESO1. In some embodiments, the tumor-targeting moiety binds to one or both of BCMA or FcRH5.

In some embodiments, the tumor-targeting moiety binds to BCMA. In embodiments, the tumor-targeting moiety comprises a BCMA targeting moiety. In some embodiments, the tumor-targeting moiety comprising a BCMA targeting moiety binds to a BCMA antigen on the surface of a cell, e.g., a cancer or hematopoietic cell. The BCMA antigen can be present on a primary tumor cell, or a metastatic lesion thereof. In some embodiments, the cancer is a hematological cancer, e.g., multiple myeloma. For example, the BCMA antigen can be present on a tumor, e.g., a tumor of a class typified by having one or more of: limited tumor perfusion, compressed blood vessels, or fibrotic tumor interstitium. In some embodiments, the tumor targeting moiety comprising a BCMA targeting moiety comprises an anti-BCMA antibody or antigen-binding fragment thereof described in U.S. Pat. Nos. 8,920,776, 9,243,058, 9,340,621, 8,846,042, 7,083,785, 9,545,086, 7,276,241, 9,034,324, 7,799,902, 9,387,237, 8,821,883, US861745, US20130273055, US20160176973, US20150368351, US20150376287, US20170022284, US20160015749, US20140242077, US20170037128, US20170051068, US20160368988, US20160311915, US20160131654, US20120213768, US20110177093, US20160297885, EP3137500, EP2699259, EP2982694, EP3029068, EP3023437, WO2016090327, WO2017021450, WO2016110584, WO2016118641, WO2016168149, the entire contents of which are incorporated herein by reference.

In some embodiments, the BCMA-targeting moiety includes an antibody molecule (e.g., Fab or scFv) that binds to BCMA. In some embodiments, the antibody molecule to BCMA comprises one, two, or three CDRs from any of the heavy chain variable domain sequences of Table 14, or a closely related CDR, e.g., CDRs which have at least one amino acid alteration, but not more than two, three or four alterations (e.g., substitutions, deletions, or insertions, e.g., conservative substitutions) from any of the CDR sequences of Table 14. In some embodiments, the antibody molecule to BCMA comprises a heavy chain variable domain sequence chosen from any of the amino acid sequences of Table 14, or an amino acid sequence substantially identical thereto (e.g., 95% to 99.9% identical thereto, or having at least one amino acid alteration, but not more than five, ten or fifteen alterations (e.g., substitutions, deletions, or insertions, e.g., conservative substitutions)).

In some embodiments, the tumor-targeting moiety binds to FcRH5. In embodiments, the tumor-targeting moiety comprises a FcRH5 targeting moiety. In some embodiments, the tumor-targeting moiety comprising a FcRH5 targeting moiety binds to a FcRH5 antigen on the surface of a cell, e.g., a cancer or hematopoietic cell. The FcRH5 antigen can be present on a primary tumor cell, or a metastatic lesion thereof. In some embodiments, the cancer is a hematological cancer, e.g., multiple myeloma. For example, the FcRH5 antigen can be present on a tumor, e.g., a tumor of a class typified by having one or more of: limited tumor perfusion, compressed blood vessels, or fibrotic tumor interstitium. In some embodiments, the tumor targeting moiety comprising a FcRH5 targeting moiety comprises an anti-FcRH5 antibody or antigen-binding fragment thereof described in U.S. Pat. No. 7,999,077 the entire contents of which are incorporated herein by reference.

In some embodiments of any of the compositions or methods disclosed herein, the cancer is a hematological cancer including, but not limited to: a B-cell or T cell malignancy, e.g., Hodgkin's lymphoma, Non-Hodgkin's lymphoma (e.g., B cell lymphoma, diffuse large B cell lymphoma, follicular lymphoma, chronic lymphocytic leukemia, mantle cell lymphoma, marginal zone B-cell lymphoma, Burkitt lymphoma, lymphoplasmacytic lymphoma, hairy cell leukemia), acute myeloid leukemia (AML), chronic myeloid leukemia, myelodysplastic syndrome, multiple myeloma, and acute lymphocytic leukemia. In some embodiments, the hematological cancer is multiple myeloma.

In some embodiments, a multispecific molecule disclosed herein further comprises a cytokine molecule, e.g., one or two cytokine molecules. In some embodiments, the cytokine molecule is chosen from interleukin-2 (IL-2), interleukin-7 (IL-7), interleukin-12 (IL-12), interleukin-15 (IL-15), interleukin-18 (IL-18), interleukin-21 (IL-21), or interferon gamma, or a fragment, variant or combination thereof. In some embodiments, is a monomer or a dimer. In some embodiments, the cytokine molecule further comprises a receptor dimerizing domain, e.g., an IL15Ralpha dimerizing domain. In some embodiments, the cytokine molecule (e.g., IL-15) and the receptor dimerizing domain (e.g., an IL5Ralpha dimerizing domain) are not covalently linked, e.g., are non-covalently associated.

In some embodiments, a multispecific molecule disclosed herein comprises:

(i) an anti-TCRβV antibody molecule (e.g., an anti-TCRβV antibody molecule as described herein); and (ii) a tumor-targeting antibody molecule (e.g., an antibody molecule that binds to a hematological antigen as described herein, e.g., chosen from one or more of BCMA, FcRH5, CD19, CD22, CD33, CD123, FcRH5, CD179a, or CLEC12).

In some embodiments, the multispecific molecule disclosed herein comprises the anti-TCRβV antibody molecule of (i), the tumor-targeting antibody molecule of (ii) and a cytokine molecule as described herein, e.g., an IL-12 cytokine molecule.

In some embodiments, the multispecific molecule comprises an anti-TCRβV antibody molecule as described herein; and a tumor-targeting antibody molecule that binds to one or both of BCMA or FcRH5. In some embodiments, the multispecific molecule further comprises an IL-12 cytokine molecule. The multispecific molecule can be used to treat a BCMA- or FcRH5-expressing hematological cancer, e.g., multiple myeloma.

In some embodiments, the multispecific molecule comprises an anti-TCRβV antibody molecule as described herein; and a tumor-targeting antibody molecule that binds one or more of CD19, CD22, or CD123. In some embodiments, the multispecific molecule further comprises an IL-12 cytokine molecule. The multispecific molecule can be used to treat a CD19-, CD22-, or CD123-expressing hematological cancer, e.g., leukemia or lymphoma. In some embodiments, the CD19-, CD22-, or CD123-expressing hematological cancer is chosen from a B-cell or T cell malignancy, e.g., Hodgkin's lymphoma, Non-Hodgkin's lymphoma (e.g., B cell lymphoma, diffuse large B cell lymphoma, follicular lymphoma, chronic lymphocytic leukemia, mantle cell lymphoma, marginal zone B-cell lymphoma, Burkitt lymphoma, lymphoplasmacytic lymphoma, hairy cell leukemia), acute myeloid leukemia (AML), chronic myeloid leukemia, myelodysplastic syndrome, multiple myeloma, and acute lymphocytic leukemia. In some embodiments, the hematological cancer is multiple myeloma.

In some embodiments, a multispecific molecule disclosed herein further comprises an immunoglobulin constant region (e.g., Fc region) chosen from the heavy chain constant regions of IgG1, IgG2, and IgG4, more particularly, the heavy chain constant region of human IgG1, IgG2 or IgG4. In some embodiments, the immunoglobulin constant region (e.g., an Fc region) is linked, e.g., covalently linked to, one or more of tumor-targeting moiety, the immune cell engager, the cytokine molecule, or the stromal modifying moiety. In some embodiments, an interface of a first and second immunoglobulin chain constant regions (e.g., Fc region) is altered, e.g., mutated, to increase or decrease dimerization, e.g., relative to a non-engineered interface. In some embodiments, the dimerization of the immunoglobulin chain constant region (e.g., Fc region) is enhanced by providing an Fc interface of a first and a second Fc region with one or more of: a paired cavity-protuberance ("knob-in-a hole"), an electrostatic interaction, or a strand-exchange, such that a greater ratio of heteromultimer:homomultimer forms, e.g., relative to a non-engineered interface. In some embodiments, In some embodiments, a multispecific molecule disclosed herein further comprises a linker, e.g., a linker described herein, optionally wherein the linker is selected from: a cleavable linker, a non-cleavable linker, a peptide linker, a flexible linker, a rigid linker, a helical linker, or a non-helical linker.

In some embodiments, the multispecific molecule comprises at least two non-contiguous polypeptide chains.

In some embodiments, the multispecific molecule comprises the following configuration:

A, B-[dimerization module]-C,-D wherein:

(1) the dimerization module comprises an immunoglobulin constant domain, e.g., a heavy chain constant domain (e.g., a homodimeric or heterodimeric heavy chain constant region, e.g., an Fc region), or a constant domain of an immunoglobulin variable region (e.g., a Fab region); and (2) A, B, C, and D are independently absent; (i) an antigen binding domain that preferentially binds to a first immune cell engager comprising an anti-TCRβV antibody molecule disclosed herein; (ii) a tumor targeting moiety (e.g., a tumor-targeting antibody molecule as described herein), (iii) a second immune cell engager chosen from a T cell engager, an NK cell engager, a B cell engager, a dendritic cell engager, or a macrophage cell engager; (iv) a cytokine molecule; or (v) a stromal modifying moiety, provided that:

at least one, two, or three of A, B, C, and D comprises an antigen binding domain that preferentially binds to a TCRβV region disclosed herein, and any of the remaining A, B, C, and D is absent or comprises one of a tumor targeting moiety, a second immune cell engager, a cytokine molecule, or a stromal modifying moiety.

In some embodiments, the dimerization module comprises one or more immunoglobulin chain constant regions (e.g., Fc regions) comprising one or more of: a paired cavity-protuberance ("knob-in-a hole"), an electrostatic interaction, or a strand-exchange. In some embodiments, the one or more immunoglobulin chain constant regions (e.g., Fc regions) comprise an amino acid substitution at a position chosen from one or more of 347, 349, 350, 351, 366, 368, 370, 392, 394, 395, 397, 398, 399, 405, 407, or 409, e.g., of the Fc region of human IgG1. In some embodiments, the one or more immunoglobulin chain constant regions (e.g., Fc regions) comprise an amino acid substitution chosen from: T366S, L368A, or Y407V (e.g., corresponding to a cavity or hole), or T366W (e.g., corresponding to a protuberance or knob), or a combination thereof.

In some embodiments, the multispecific molecule further comprises a linker, e.g., a linker between one or more of: the antigen binding domain of an anti-TCRβV antibody molecule disclosed herein and the tumor targeting moiety; the antigen binding domain of an anti-TCRβV antibody molecule disclosed herein and the second immune cell engager, the antigen binding domain of an anti-TCRβV antibody molecule disclosed herein and the cytokine molecule, the antigen binding domain of an anti-TCRβV antibody molecule disclosed herein and the stromal modifying moiety, the second immune cell engager and the cytokine molecule, the second immune cell engager and the stromal modifying moiety, the cytokine molecule and the stromal modifying moiety, the antigen binding domain of an anti-TCRβV antibody molecule disclosed herein and the dimerization module, the second immune cell engager and the dimerization module, the cytokine molecule and the dimerization module, the stromal modifying moiety and the dimerization module, the tumor targeting moiety and the dimerization module, the tumor targeting moiety and the cytokine molecule, the tumor targeting moiety and the second immune cell engager, or the tumor targeting moiety and the antigen binding domain of an anti-TCRβV antibody molecule disclosed herein. In some embodiments, the linker is chosen from: a cleavable linker, a non-cleavable linker, a peptide linker, a flexible linker, a rigid linker, a helical linker, or a non-helical linker. In some embodiments, the linker is a peptide linker. In some embodiments, the peptide linker comprises Gly and Ser. In some embodiments, the peptide linker comprises an amino acid sequence chosen from SEQ ID NOs: 142-145 or 175-178.

In some embodiments of a method or composition for use disclosed herein, the disease is a cancer chosen from: a hematological cancer, a solid tumor, a metastatic cancer, soft tissue tumor, metastatic lesion, or a combination thereof.

In some embodiments of a method or composition for use disclosed herein, the cancer is a solid tumor chosen from: a melanoma, a pancreatic cancer (e.g., pancreatic adenocarcinoma), a breast cancer, a colorectal cancer (CRC), a lung cancer (e.g., small or non-small cell lung cancer), a skin cancer, an ovarian cancer, or a liver cancer. In some embodiments, the cancer is melanoma or CRC.

In some embodiments of a method or composition for use disclosed herein the cancer is a hematological cancer chosen from: a B-cell or T cell malignancy, e.g., Hodgkin's lymphoma, Non-Hodgkin's lymphoma (e.g., B cell lymphoma, diffuse large B cell lymphoma, follicular lymphoma, chronic lymphocytic leukemia, mantle cell lymphoma, marginal zone B-cell lymphoma, Burkitt lymphoma, lymphoplasmacytic lymphoma, hairy cell leukemia), acute myeloid leukemia (AML), chronic myeloid leukemia, myelodysplastic syndrome, multiple myeloma, or acute lymphocytic leukemia. In some embodiments, the hematological cancer is multiple myeloma. In some embodiments, the hematological cancer is CLL or DLBCL.

In some embodiments of a method or composition for use disclosed herein the sample from the subject comprises a blood sample, e.g., a peripheral blood sample, a biopsy, e.g., a tumor biopsy, or a bone marrow sample. In some embodiments, the sample comprises a biological sample comprising immune effector cells, e.g., T cells, or NK cells. In some embodiments, T cells comprise a CD4 T cell, a CD8 T cell, (e.g., an effector T cell or a memory T cell (e.g., a memory effector T cell (e.g., $T_{EM}$ cell, e.g., $T_{EMRA}$ cell), or a tumor infiltrating lymphocyte (TIL).

In some aspects, provided herein is, inter alia, a multispecific molecule (e.g., a bispecific molecule), comprising a first moiety (e.g., a first immune cell engager) comprising an antibody molecule which binds (e.g., specifically binds) to a T cell receptor beta variable region (TCRβV) ("anti-TCRβV antibody molecule"), wherein binding of the first moiety to the TCRβV region results in a cytokine profile that differs from a cytokine profile of a T cell engager that binds to a receptor or molecule other than a TCRβV region ("a non-TCRβV-binding T cell engager").

In some embodiments, the multispecific molecule as provided herein comprises a second moiety which comprises one or more of: a tumor-targeting moiety, a cytokine molecule, a stromal modifying moiety, or an anti-TCRβV antibody molecule other than the first moiety.

In some embodiments, the first moiety comprising the anti-TCRβV antibody molecule comprises an Fc region comprising a variant, e.g., an Fc variant described in Table 21, e.g., an Asn297Ala (N297A) mutation or a Leu234Ala/Leu235Ala (LALA) mutation.

In some embodiments, the non-TCRβV-binding T cell engager comprises an antibody that binds to a CD3 molecule (e.g., CD3 epsilon (CD3ε) molecule); or a TCR alpha (TCRα) molecule.

In some embodiments, the cytokine profile of the first moiety comprises, one, two, three, four, five, six, seven, or all of the following:

(i) increased level, e.g., expression level, and/or activity of IL-2;
(ii) reduced level, e.g., expression level, and/or activity of IL-1β;
(iii) reduced level, e.g., expression level, and/or activity of IL-6;
(iv) reduced level, e.g., expression level, and/or activity of TNFα;
(v) reduced level, e.g., expression level, and/or activity of IL-10;
(vi) a delay, e.g., at least 1, 2, 3, 4, 5, 6, 7, 8, 9, 10 or more hours delay, in increased level, e.g., expression level, and/or activity of IL-2;
(vii) a delay, e.g., at least 1, 2, 3, 4, 5, 6, 7, 8, 9, 10 hours delay, in increased level, e.g., expression level, and/or activity of IFNg; or
(viii) increased level, e.g., expression level, and/or activity of IL-15, e.g., wherein (i)-(viii) are relative to the cytokine profile of the non-TCRβV-binding T cell engager.

In some embodiments, binding of the first moiety to the TCRβV region results in reduced cytokine storm, e.g., reduced cytokine release syndrome (CRS), as measured by an assay of Example 3, e.g., relative to the cytokine storm induced by the non-TCRβV-binding T cell engager.

In some embodiments, binding of the first moiety to the TCRβV region results in one, two, three or all of:
(ix) reduced T cell proliferation kinetics;
(x) cell killing, e.g., target cell killing, e.g. cancer cell killing, e.g., as measured by an assay of Example 4;
(xi) increased Natural Killer (NK) cell proliferation, e.g., expansion; or
(xii) expansion, e.g., at least about 1.1-10 fold expansion (e.g., at least about 1.1, 1.2, 1.3, 1.4, 1.5, 2, 3, 4, 5, 6, 7, 8, 9, or 10 fold expansion), of a population of T cells having a memory-like phenotype,
e.g., wherein (ix)-(xii) are relative to the non-TCRβV-binding T cell engager.

In some embodiments, the population of T cells having a memory-like phenotype comprises CD45RA+ CCR7− T cells, e.g., CD4+ and/or CD8+ T cells.

In some embodiments, the first moiety binds to one or more of a TCRβV subfamily chosen from:
(i) TCRβ V6 subfamily comprising, e.g., one or more of TCRβ V6-4*01, TCRβ V6-4*02, TCRβ V6-9*01, TCRβ V6-8*01, TCRβ V6-5*01, TCRβ V6-6*02, TCRβ V6-6*01, TCRβ V6-2*01, TCRβ V6-3*01 or TCRβ V6-1*01;
(ii) TCRβ V10 subfamily comprising, e.g., one or more of TCRβ V10-1*01, TCRβ V10-1*02, TCRβ V10-3*01 or TCRβ V10-2*01;
(iii) TCRβ V5 subfamily comprising, e.g., one or more of TCRβ V5-6*01, TCRβ V5-4*01, TCRβ V5-1*01 or TCRβ V5-8*01;
(iv) TCRβ V12 subfamily comprising, e.g., one or more of TCRβ V12-4*01, TCRβ V12-3*01, or TCRβ V12-5*01;
(v) TCRβ V27 subfamily;
(vi) TCRβ V28 subfamily;
(vii) TCRβ V4 subfamily comprising, e.g., one or more of TCRβ V4-1, TCRβ V4-2 or TCRβ V4-3;
(viii) TCRβ V19 subfamily;
(ix) TCRβ V9 subfamily; or
(x) TCRβ V11 subfamily comprising, e.g., TCRβ V11-2.

In some embodiments, the anti-TCRβV antibody molecule:
(i) binds specifically to an epitope on TCRβV, e.g., the same or similar epitope as the epitope recognized by an anti-TCRβV antibody molecule as described herein, e.g., a second anti-TCRβV antibody molecule;
(ii) shows the same or similar binding affinity or specificity, or both, as an anti-TCRβV antibody molecule as described herein, e.g., a second anti-TCRβV antibody molecule;
(iii) inhibits, e.g., competitively inhibits, the binding of an anti-TCRβV antibody molecule as described herein, e.g., a second anti-TCRβV antibody molecule;
(vi) binds the same or an overlapping epitope with an anti-TCRβV antibody molecule as described herein, e.g., a second anti-TCRβV antibody molecule; or
(v) competes for binding, and/or binds the same epitope, with an anti-TCRβV antibody molecule as described herein, e.g., a second anti-TCRβV antibody molecule,
wherein the second anti-TCRβV antibody molecule comprises an antigen binding domain comprising a heavy chain complementarity determining region 1 (HC CDR1), a heavy chain complementarity determining region 2 (HC CDR2) and/or a heavy chain complementarity determining region 3 (HC CDR3) of SEQ ID NO: 1 or SEQ ID NO: 9; and/or a light chain complementarity determining region 1 (LC CDR1), a light chain complementarity determining region 2 (LC CDR2), and/or a light chain complementarity determining region 3 (LC CDR3) of SEQ ID NO: 2, SEQ ID NO: 10 or SEQ ID NO: 11.

In some embodiments, the anti-TCRβV antibody molecule comprises an antigen binding domain comprising:
(a) a HC CDR1, a HC CDR2 and/or a HC CDR3 of SEQ ID NO: 15, SEQ ID NO: 23, SEQ ID NO: 24 or SEQ ID NO: 25; and/or (b) a LC CDR1, a LC CDR2, and/or a LC CDR3 of SEQ ID NO: 16, SEQ ID NO: 26, SEQ ID NO: 27, SEQ ID NO: 28, SEQ ID NO: 29 or SEQ ID NO:30; or (a) a LC CDR1, a LC CDR2 and/or a LC CDR3 of SEQ ID NO: 2, SEQ ID NO: 10 or SEQ ID NO: 11; and/or (b) a HC CDR1, a HC CDR2 and/or a HC CDR2 of SEQ ID NO: 1 or SEQ ID NO: 9.

In some embodiments, the anti-TCRβV antibody molecule binds the same or different TCRβV subfamily members.

In some embodiments, the multispecific molecule as provided herein comprises an antibody molecule chosen from a bispecific antibody molecule, a bivalent antibody molecule, or a biparatopic antibody molecule.

In some embodiments, the multispecific molecule as provided herein comprises a bispecific antibody molecule that binds to two different TCRβV subfamily members.

In some embodiments, the anti-TCRβV antibody molecule binds:
one or more of a TCRβ V6 subfamily member and one or more of a TCRβ V10 subfamily member;
one or more of a TCRβ V6 subfamily member and one or more of a TCRβ V5 subfamily member;
one or more of a TCRβ V6 subfamily member and one or more of a TCRβ V12 subfamily member;
one or more of a TCRβ V10 subfamily member and one or more of a TCRβ V5 subfamily member;
one or more of a TCRβ V10 subfamily member and one or more of a TCRβ V12 subfamily member; or
one or more of a TCRβ V5 subfamily member and one or more of a TCRβ V12 subfamily member.

In another aspect, provided herein is a multispecific molecule, e.g., a bispecific molecule, comprising the anti-TCRβV antibody molecule as provided herein.

In another aspect, provided herein is an antibody molecule which binds, e.g., specifically binds, to a T cell receptor beta variable chain (TCRβV) region, wherein the anti-TCRβV antibody molecule comprises an antigen binding domain comprising:

(a) a light chain variable region (VL) comprising:

(i) one, two or all of (e.g., three) a light chain complementarity determining region 1 (LC CDR1), a light chain complementarity determining region 2 (LC CDR2), and a light chain complementarity determining region 3 (LC CDR3) of SEQ ID NO: 10 or SEQ ID NO: 11; and (ii) a framework region (FR) having at least 95% identity with one, two, three, or all of (e.g., four) a non-murine germline framework 1 (FR1), a non-murine germline framework region 2 (FR2), a non-murine germline framework region 3 (FR3), and a non-murine germline framework region 4 (FR4); and/or (b) a heavy chain variable region (VH) comprising:

(i) one, two or all of (e.g., three) a heavy chain complementarity determining region 1 (HC CDR1), a heavy chain complementarity determining region 2 (HC CDR2) and a heavy chain complementarity determining region 3 (HC CDR3) of SEQ ID NO: 9; and (ii) a framework region (FR) having at least 95% identity with one, two, three, or all of (e.g., four) a non-murine germline framework 1 (FR1), a non-murine germline framework region 2 (FR2), a non-murine germline framework region 3 (FR3), and a non-murine germline framework region 4 (FR4).

In some embodiments, the VL comprises an amino acid sequence having a consensus sequence of SEQ ID NO: 230.

In some embodiments, the VH comprises an amino acid sequence having a consensus sequence of SEQ ID NO: 231.

In some embodiments, the anti-TCRβV antibody molecule as provided herein binds to TCRβ V6, e.g., one or more of TCRβ V6-4*01, TCRβ V6-4*02, TCRβ V6-9*01, TCRβ V6-8*01, TCRβ V6-5*01, TCRβ V6-6*02, TCRβ V6-6*01, TCRβ V6-2*01, TCRβ V6-3*01 or TCRβ V6-1*01, or a variant thereof.

In some embodiments, the anti-TCRβV antibody molecule comprises an antigen binding domain comprising:

(i) a HC CDR1, a HC CDR2 and a HC CDR3 of SEQ ID NO: 1 or SEQ ID NO: 9, or an amino acid sequence listed in Table 1; or (ii) a LC CDR1, a LC CDR2, and a LC CDR3 of SEQ ID NO: 2, SEQ ID NO: 10 or SEQ ID NO: 11, or an amino acid sequence listed in Table 1.

In some embodiments, the anti-TCRβV antibody molecule comprises an antigen binding domain comprising a light chain variable region (VL) comprising one, two or all (e.g., three) of a LC CDR1, a LC CDR2 and a LC CDR3 of SEQ ID NO: 2, SEQ ID NO: 10 or SEQ ID NO: 11, or an amino acid sequence listed in Table 1.

In some embodiments, the anti-TCRβV antibody molecule comprises an antigen binding domain comprising a heavy chain variable region (VH) comprising one, two or all (e.g., three) of a HC CDR1, a HC CDR2 and a HC CDR3 of SEQ ID NO:1 or SEQ ID NO: 9, or an amino acid sequence listed in Table 1.

In some embodiments, the anti-TCRβV antibody molecule comprises an antigen binding domain comprising:

(i) a VL comprising: a LC CDR1 amino acid sequence of SEQ ID NO: 6 (or an amino acid sequence with not more than 1, 2, 3 or 4 modifications, e.g., substitutions, additions or deletions thereof), a LC CDR2 amino acid sequence of SEQ ID NO:7 (or an amino acid sequence with not more than 1, 2, 3 or 4 modifications, e.g., substitutions, additions or deletions thereof), and/or a LC CDR3 amino acid sequence of SEQ ID NO:8 (or an amino acid sequence with not more than 1, 2, 3 or 4 modifications, e.g., substitutions, additions or deletions thereof); and/or (ii) a VH comprising: a HC CDR1 amino acid sequence of SEQ ID NO: 3 (or an amino acid sequence with not more than 1, 2, 3 or 4 modifications, e.g., substitutions, additions or deletions thereof), a HC CDR2 amino acid sequence of SEQ ID NO:4 (or an amino acid sequence with not more than 1, 2, 3 or 4 modifications, e.g., substitutions, additions or deletions thereof), and/or a HC CDR3 amino acid sequence of SEQ ID NO:5 (or an amino acid sequence with not more than 1, 2, 3 or 4 modifications, e.g., substitutions, additions or deletions thereof).

In some embodiments, the anti-TCRβV antibody molecule comprises an antigen binding domain comprising:

a variable heavy chain (VH) of an amino acid sequence listed in Table 1, e.g., SEQ ID NO: 9 or SEQ ID NO: 1312, or a sequence having at least about 85%, 90%, 95%, or 99% sequence identity to an amino acid sequence listed in Table 1, e.g., SEQ ID NO: 9 or SEQ ID NO: 1312; and/or a variable light chain (VL) of an amino acid sequence listed in Table 1, e.g., SEQ ID NO: 10 or SEQ ID NO: 11 or SEQ ID NO: 1314, or a sequence having at least about 85%, 90%, 95%, or 99% sequence identity to an amino acid sequence listed in Table 1, e.g., SEQ ID NO: 10 or SEQ ID NO: 11 or SEQ ID NO: 1314.

In some embodiments, the anti-TCRβV antibody molecule comprises an antigen binding domain comprising:

(i) the VH amino acid sequence of SEQ ID NO: 9 or SEQ ID NO: 1312;

(ii) an amino acid sequence having at least about 85%, 90%, 95%, or 99% sequence identity to the amino acid sequence of SEQ ID NO: 9 or SEQ ID NO: 1312;

(iii) the VL amino acid sequence of SEQ ID NO: 10 or SEQ ID NO: 1314; and/or (iv) an amino acid sequence having at least about 85%, 90%, 95%, or 99% sequence identity to the amino acid sequence of SEQ ID NO: 10 or SEQ ID NO: 1314.

In some embodiments, the anti-TCRβV antibody molecule comprises an antigen binding domain comprising:

(i) the VH amino acid sequence of SEQ ID NO: 9 or SEQ ID NO: 1312;

(ii) an amino acid sequence having at least about 85%, 90%, 95%, or 99% sequence identity to the amino acid sequence of SEQ ID NO: 9 or SEQ ID NO: 1312;

(iii) the VL amino acid sequence of SEQ ID NO: 11 or SEQ ID NO: 1314; and/or (iv) an amino acid sequence having at least about 85%, 90%, 95%, or 99% sequence identity to the amino acid sequence of SEQ ID NO: 11 or SEQ ID NO: 1314.

In some embodiments, the anti-TCRβV antibody molecule comprises a heavy chain comprising a framework region, e.g., framework region 3 (FR3), comprising one or both of:

(i) a Threonine at position 73, e.g., a substitution at position 73 according to Kabat numbering, e.g., a Glutamic Acid to Threonine substitution; or (ii) a Glycine a position 94, e.g., a substitution at position 94 according to Kabat numbering, e.g., a Arginine to Glycine substitution;

wherein the substitution is relative to a human germline heavy chain framework region sequence.

In some embodiments, the anti-TCRβV antibody molecule comprises a light chain comprising a framework region, e.g., framework region 1 (FR1), comprising a Phenyalanine at position 10, e.g., a substitution at position 10 according to Kabat numbering, e.g., a Serine to Phenyalanine substitution, wherein the substitution is relative to a human germline light chain framework region sequence.

In some embodiments, the anti-TCRβV antibody molecule comprises a light chain comprising a framework region, e.g., framework region 2 (FR2), comprising one or both of:

(i) a Histidine at position 36, e.g., a substitution at position 36 according to Kabat numbering, e.g., a Tyrosine to Histidine substitution; or (ii) an Alanine at position 46, e.g., a substitution at position 46 according to Kabat numbering, e.g., a Arginine to Alanine substitution;

wherein the substitution is relative to a human germline light chain framework region sequence.

In some embodiments, the anti-TCRβV antibody molecule comprises a light chain comprising a framework region, e.g., framework region 3 (FR3), comprising a Phenyalanine at position 87, e.g., a substitution at position 87 according to Kabat numbering, e.g., a Tyrosine to Phenyalanine substitution, wherein the substitution is relative to a human germline light chain framework region sequence.

In another aspect, provided herein is an antibody molecule which binds, e.g., specifically binds, to a T cell receptor beta variable chain (TCRβV) region, wherein the anti-TCRβV antibody molecule comprises an antigen binding domain comprising:

(a) a light chain variable region (VL) comprising:

(i) one, two or all of (e.g., three) a light chain complementarity determining region 1 (LC CDR1), a light chain complementarity determining region 2 (LC CDR2), and a light chain complementarity determining region 3 (LC CDR3) of a humanized B-H light chain (LC) of Table 2; and (ii) a framework region (FR) having at least 95% identity with one, two, three or all (e.g., four) of a framework region 1 (FR1), a framework region 2 (FR2), a framework region 3 (FR3), and a framework region 4 (FR4) of a humanized B-H LC of Table 2; and/or (b) a heavy chain variable region (VH) comprising:

(i) one, two or all of (e.g., three) a heavy chain complementarity determining region 1 (HC CDR1), a heavy chain complementarity determining region 2 (HC CDR2) and a heavy chain complementarity determining region 3 (HC CDR3) of a humanized B-H heavy chain (HC) of Table 2; and (ii) a framework region (FR) having at least 95% identity with one, two, three or all (e.g., four) of a framework region 1 (FR1), a framework region 2 (FR2), a framework region 3 (FR3), and a framework region 4 (FR4) of a humanized B-H HC of Table 2.

In some embodiments, the anti-TCRβV antibody molecule as provided herein binds to TCRβ V12, e.g., TCRβ V12-4*01, TCRβ V12-3*01, or TCRβ V12-5*01, or a variant thereof.

In some embodiments, the anti-TCRβV antibody molecule comprises an antigen binding domain comprising:

(i) a HC CDR1, a HC CDR2 and a HC CDR3 of Antibody B-H listed in Table 2; or (ii) a LC CDR1, a LC CDR2, and a LC CDR3 of Antibody B-H listed in Table 2.

In some embodiments, the anti-TCRβV antibody molecule comprises an antigen binding domain comprising a light chain variable region (VL) comprising one, two or all (e.g., three) of a LC CDR1, a LC CDR2 and a LC CDR3 of SEQ ID NO: 2, SEQ ID NO: 10 or SEQ ID NO: 11, or an amino acid sequence listed in Table 1.

In some embodiments, the anti-TCRβV antibody molecule comprises an antigen binding domain comprising a heavy chain variable region (VH) comprising one, two or all (e.g., three) of a HC CDR1, a HC CDR2 and a HC CDR3 of a humanized Antibody B-H listed in Table 2.

In some embodiments, the anti-TCRβV antibody molecule comprises an antigen binding domain comprising a light chain variable region (VL) comprising one, two or all (e.g., three) of a LC CDR1, a LC CDR2 and a LC CDR3 of a humanized Antibody B-H listed in Table 2.

In some embodiments, the anti-TCRβV antibody molecule comprises:

a VH sequence of a humanized Antibody B-H listed in Table 2, or a sequence having at least about 85%, 90%, 95%, or 99% sequence identity to a VH of a humanized Antibody B-H listed in Table 2; and/or a VL sequence of a humanized Antibody B-H listed in Table 2, or a sequence having at least about 85%, 90%, 95%, or 99% sequence identity to a VL of a humanized Antibody B-H listed in Table 2.

In some embodiments, the anti-TCRβV antibody molecule comprises a framework region (FR) having at least 95% identity with one of: a FR1, a FR2, a FR3, and a FR4 of a humanized B-H LC of Table 2.

In some embodiments, the anti-TCRβV antibody molecule comprises a framework region (FR) having at least 95% identity with any two of: a FR1, a FR2, a FR3, and a FR4 of a humanized B-H LC of Table 2.

In some embodiments, the anti-TCRβV antibody molecule comprises a framework region (FR) having at least 95% identity with any three of: a FR1, a FR2, a FR3, and a FR4 of a humanized B-H LC of Table 2.

In some embodiments, the anti-TCRβV antibody molecule comprises a framework region (FR) having at least 95% identity with all of: a FR1, a FR2, a FR3, and a FR4 of a humanized B-H LC of Table 2.

In some embodiments, the anti-TCRβV antibody molecule comprises a framework region (FR) having at least 95% identity with one of: a FR1, a FR2, a FR3, and a FR4 of a humanized B-H HC of Table 2.

In some embodiments, the anti-TCRβV antibody molecule comprises a framework region (FR) having at least 95% identity with any two of: a FRI, a FR2, a FR3, and a FR4 of a humanized B-H HC of Table 2.

In some embodiments, the anti-TCRβV antibody molecule comprises a framework region (FR) having at least 95% identity with any three of: a FR1, a FR2, a FR3, and a FR4 of a humanized B-H HC of Table 2.

In some embodiments, the anti-TCRβV antibody molecule comprises a framework region (FR) having at least 95% identity with all of: a FR1, a FR2, a FR3, and a FR4 of a humanized B-H HC of Table 2.

In some embodiments, binding of the anti-TCRβV antibody molecule to the TCRβV region results in a cytokine profile that differs from a cytokine profile of a T cell engager that binds to a receptor or molecule other than a TCRβV region ("a non-TCRβV-binding T cell engager").

In some embodiments, the non-TCRβV-binding T cell engager comprises an antibody that binds to a CD3 molecule (e.g., CD3 epsilon (CD3ε) molecule); or a TCR alpha (TCRa) molecule.

In some embodiments, the cytokine profile of the first moiety comprises, one, two, three, four, five, six, seven, or all of the following:

(i) increased level, e.g., expression level, and/or activity of IL-2;

(ii) reduced level, e.g., expression level, and/or activity of IL-1β;

(iii) reduced level, e.g., expression level, and/or activity of IL-6;

(iv) reduced level, e.g., expression level, and/or activity of TNFα;

(v) reduced level, e.g., expression level, and/or activity of IL-10;

(vi) a delay, e.g., at least 1, 2, 3, 4, 5, 6, 7, 8, 9, 10 or more hours delay, in increased level, e.g., expression level, and/or activity of IL-2;

(vii) a delay, e.g., at least 1, 2, 3, 4, 5, 6, 7, 8, 9, 10 hours delay, in increased level, e.g., expression level, and/or activity of IFNg; or (viii) increased level, e.g., expression level, and/or activity of IL-15, e.g., wherein (i)-(vii) are relative to the cytokine profile of the non-TCRβV-binding T cell engager.

In some embodiments, binding of the anti-TCRβV antibody molecule to the TCRβV region results in reduced cytokine storm, e.g., reduced cytokine release syndrome (CRS), as measured by an assay of Example 3, e.g., relative to the cytokine storm induced by the non-TCRβV-binding T cell engager.

In some embodiments, binding of the anti-TCRβV antibody molecule to the TCRβV region results in one, two, three or all of:

(ix) reduced T cell proliferation kinetics;

(x) cell killing, e.g., target cell killing, e.g. cancer cell killing, e.g., as measured by an assay of Example 4;

(xi) increased Natural Killer (NK) cell proliferation, e.g., expansion; or (xii) expansion, e.g., at least about 1.1-10 fold expansion (e.g., at least about 1.1, 1.2, 1.3, 1.4, 1.5, 2, 3, 4, 5, 6, 7, 8, 9, or 10 fold expansion), of a population of T cells having a memory-like phenotype, e.g., relative to the non-TCRβV-binding T cell engager.

In some embodiments, the population of T cells having a memory-like phenotype comprises CD45RA+ CCR7− T cells, e.g., CD4+ and/or CD8+ T cells.

In some embodiments, binding of the anti-TCRβV antibody molecule to a TCRβV region results in a reduction of at least 2, 5, 10, 20, 50, 100, or 200 fold, or at least 2-200 fold (e.g., 5-150, 10-100, 20-50 fold) in the expression level and or activity of IL-1β as measured by an assay of Example 3.

In some embodiments, binding of the anti-TCRβV antibody molecule to a TCRβV region results in a reduction of at least 2, 5, 10, 20, 50, 100, 200, 300, 400, 500, 600, 700, 800, 900, or 1000 fold, or at least 2-1000 fold (e.g., 5-900, 10-800, 20-700, 50-600, 100-500, or 200-400 fold) in the expression level and or activity of IL-6 as measured by an assay of Example 3.

In some embodiments, binding of the anti-TCRβV antibody molecule to a TCRβV region results in a reduction of at least 2, 5, 10, 20, 50, 100, 200, 300, 400, 500, 600, 700, 800, 900, 1000, or 2000 fold, or at least 2-2000 fold (e.g., 5-1000, 10-900, 20-800, 50-700, 100-600, 200-500, or 300-400 fold) in the expression level and or activity of TNFα as measured by an assay of Example 3.

In some embodiments, binding of the anti-TCRβV antibody molecule to a TCRβV region results in an increase of at least 2, 5, 10, 20, 50, 100, 200, 300, 400, 500, 600, 700, 800, 900, 1000, or 2000 fold, or at least 2-2000 fold (e.g., 5-1000, 10-900, 20-800, 50-700, 100-600, 200-500, or 300-400 fold) in the expression level and or activity of IL-2 as measured by an assay of Example 3.

In some embodiments, the anti-TCRβV antibody molecule comprises an antigen binding domain comprising a single chain Fv (scFv) or a Fab.

In some embodiments, the anti-TCRβV antibody molecule binds to a conformational or a linear epitope on the T cell.

In some embodiments, the anti-TCRβV antibody molecule is a full antibody (e.g., an antibody that includes at least one, and preferably two, complete heavy chains, and at least one, and preferably two, complete light chains), or an antigen-binding fragment (e.g., a Fab, F(ab')2, Fv, a single chain Fv fragment, a single domain antibody, a diabody (dAb), a bivalent antibody, or bispecific antibody or fragment thereof, a single domain variant thereof, or a camelid antibody).

In some embodiments, the anti-TCRβV antibody molecule comprises one or more heavy chain constant regions chosen from IgG1, IgG2, IgG3, IgGA1, IgGA2, IgG4, IgJ, IgM, IgD, or IgE, or a fragment thereof, e.g., as described in Table 3.

In some embodiments, the anti-TCRβV antibody molecule comprises a heavy chain constant region of an IgM or a fragment thereof, optionally wherein the IgM heavy chain constant region comprises the sequence of SEQ ID NO: 73, or a sequence with at least 85%, 90%, 95%, or 99% sequence identity thereto.

In some embodiments, the anti-TCRβV antibody molecule comprises a heavy chain constant region of an IgJ or a fragment thereof, optionally wherein the IgJ heavy chain constant region comprises the sequence of SEQ ID NO: 76 or a sequence with at least 85%, 90%, 95%, or 99% sequence identity thereto.

In some embodiments, the anti-TCRβV antibody molecule comprises a heavy chain constant region of an IgGA1, or a fragment thereof, optionally wherein the IgGA1 heavy chain constant region comprises the sequence of SEQ ID NO: 74, or a sequence with at least 85%, 90%, 95%, or 99% sequence identity thereto.

In some embodiments, the anti-TCRβV antibody molecule comprises a heavy chain constant region of an IgGA2, or a fragment thereof, optionally wherein the IgGA2 heavy chain constant region comprises a sequence listed in Table 3, e.g., SEQ ID NO: 75, or a sequence with at least 85%, 90%, 95%, or 99% sequence identity thereto.

In some embodiments, the anti-TCRβV antibody molecule comprises a light chain constant region chosen from the light chain constant regions of kappa or lambda, or a fragment thereof, e.g., as described in Table 3.

In some embodiments, the anti-TCRβV antibody molecule comprises a light chain constant region of a kappa chain, or a fragment thereof, optionally wherein the kappa chain constant region comprises the sequence of SEQ ID NO: 39, or a sequence with at least 85%, 90%, 95%, or 99% sequence identity thereto.

In some embodiments, the anti-TCRβV antibody molecule comprises:

(i) one or more heavy chain constant regions comprising a heavy chain constant region chosen from IgG1, IgG2, IgG3, IgGA1, IgGA2, IgG4, IgJ, IgM, IgD, or IgE, or a fragment thereof, e.g., as described in Table 3; and (ii) a light chain constant region comprising a light chain constant region chosen from the light chain constant regions of kappa or lambda, or a fragment thereof, e.g., as described in Table 3.

In some embodiments, the anti-TCRβV antibody molecule comprises:

(i) a heavy chain constant region comprising:

(a) an IgM heavy chain constant region or a fragment thereof, comprising the sequence of SEQ ID NO: 73, or a sequence with at least 85%, 90%, 95%, or 99% sequence identity thereto;

(b) an IgGA1 heavy chain constant region or a fragment thereof, comprising the sequence of SEQ ID NO: 74, or a sequence with at least 85%, 90%, 95%, or 99% sequence identity thereto; or (c) an IgGA2 heavy chain constant region or a fragment thereof, comprising the sequence of SEQ ID NO: 75, or a sequence with at least 85%, 90%, 95%, or 99% sequence identity thereto; and (ii) a light chain constant region comprising a kappa chain constant region comprising the sequence of SEQ ID NO: 39, or a sequence with at least 85%, 90%, 95%, or 99% sequence identity thereto, optionally wherein, the anti-TCRβV antibody molecule further comprises an IgJ heavy chain constant region or a fragment thereof, wherein the IgJ heavy chain constant region comprises the sequence of SEQ ID NO: 76 or a sequence with at least 85%, 90%, 95%, or 99% sequence identity thereto.

In some embodiments, the second moiety is a tumor-targeting moiety.

In some embodiments, the second moiety is a cytokine molecule.

In some embodiments, the second moiety is a stromal modifying moiety.

In some embodiments, the second moiety is an anti-TCRβV antibody molecule other than the first moiety.

In some embodiments, the first and/or second moiety binds to and activates an immune cell, e.g., an effector cell.

In some embodiments, the first and/or second moiety binds to, but does not activate an immune cell, e.g., an effector cell.

In some embodiments, the second moiety is chosen from an NK cell engager, a T cell engager other than an anti-TCRβV antibody molecule, a B cell engager, a dendritic cell engager, or a macrophage cell engager, or a combination thereof.

In some embodiments, the tumor-targeting moiety comprises an antibody molecule (e.g., Fab or scFv), a receptor molecule (e.g., a receptor, a receptor fragment or functional variant thereof), or a ligand molecule (e.g., a ligand, a ligand fragment or functional variant thereof), or a combination thereof, that binds to a cancer antigen.

In some embodiments, the tumor-targeting moiety binds to a cancer antigen present on a cancer, e.g., a hematological cancer, a solid tumor, a metastatic cancer, soft tissue tumor, metastatic lesion, or a combination thereof.

In some embodiments, the cancer antigen is a tumor antigen or stromal antigen, or a hematological antigen.

In some embodiments, the cancer antigen is chosen from: BCMA, CD19, CD20, CD22, FcRH5, PDL1, CD47, ganglioside 2 (GD2), prostate stem cell antigen (PSCA), prostate specific membrane antigen (PMSA), prostate-specific antigen (PSA), carcinoembryonic antigen (CEA), Ron Kinase, c-Met, Immature laminin receptor, TAG-72, BING-4, Calcium-activated chloride channel 2, Cyclin-B1, 9D7, Ep-CAM, EphA3, Her2/neu, Telomerase, SAP-1, Survivin, NY-ESO-1/LAGE-1, PRAME, SSX-2, Melan-A/MART-1, Gp100/pmel17, Tyrosinase, TRP-1/-2, MC1R, β-catenin, BRCA1/2, CDK4, CML66, Fibronectin, p53, Ras, TGF-B receptor, AFP, ETA, MAGE, MUC-1, CA-125, BAGE, GAGE, NY-ESO-1, 0-catenin, CDK4, CDC27, α actinin-4, TRP1/gp75, TRP2, gp100, Melan-A/MART1, gangliosides, WT1, EphA3, Epidermal growth factor receptor (EGFR), MART-2, MART-1, MUC1, MUC2, MUM1, MUM2, MUM3, NA88-1, NPM, OA1, OGT, RCC, RUI1, RUI2, SAGE, TRG, TRP1, TSTA, Folate receptor alpha, L1-CAM, CAIX, gpA33, GD3, GM2, VEGFR, Integrins (Integrin alphaVbeta3, Integrin alpha5Beta1), Carbohydrates (Le), IGF1R, EPHA3, TRAILR1, TRAILR2, RANKL, (FAP), TGF-beta, hyaluronic acid, collagen, e.g., collagen IV, tenascin C, or tenascin W.

In some embodiments, the tumor-targeting moiety is a BCMA targeting moiety or a FcRH5 targeting moiety.

In some embodiments, the cancer is a solid tumor including but not limited to: pancreatic (e.g., pancreatic adenocarcinoma) cancer, breast cancer, colorectal cancer, lung cancer (e.g., small or non-small cell lung cancer), skin cancer, ovarian cancer, or liver cancer.

In some embodiments, the cancer is a hematological cancer including, but not limited to: a B-cell or T cell malignancy, e.g., Hodgkin's lymphoma, Non-Hodgkin's lymphoma (e.g., B cell lymphoma, diffuse large B cell lymphoma, follicular lymphoma, chronic lymphocytic leukemia, mantle cell lymphoma, marginal zone B-cell lymphoma, Burkitt lymphoma, lymphoplasmacytic lymphoma, hairy cell leukemia), acute myeloid leukemia (AML), chronic myeloid leukemia, myelodysplastic syndrome, multiple myeloma, and acute lymphocytic leukemia.

In some embodiments, the cytokine molecule is chosen from interleukin-2 (IL-2), interleukin-7 (IL-7), interleukin-12 (IL-12), interleukin-15 (IL-15), interleukin-18 (IL-18), interleukin-21 (IL-21), or interferon gamma, or a fragment, variant or combination thereof.

In some embodiments, the cytokine molecule is a monomer or a dimer.

In some embodiments, the cytokine molecule further comprises a receptor dimerizing domain, e.g., an IL15Ralpha dimerizing domain.

In some embodiments, the cytokine molecule (e.g., IL-15) and the receptor dimerizing domain (e.g., an IL15Ralpha dimerizing domain) are not covalently linked, e.g., are non-covalently associated.

In some embodiments, the multispecific molecule as provided herein further comprises an immunoglobulin constant region (e.g., Fc region) chosen from the heavy chain constant regions of IgG1, IgG2, IgG3, IgGA1, IgGA2, IgG4, IgJ, IgM, IgD, or IgE, or a fragment thereof, optionally wherein, the heavy chain constant region comprises the heavy chain constant region of human IgG1, IgG2 or IgG4.

In some embodiments, the immunoglobulin constant region (e.g., an Fc region) is linked, e.g., covalently linked to, one or more of tumor-targeting moiety, the cytokine molecule, or the stromal modifying moiety.

In some embodiments, an interface of a first and second immunoglobulin chain constant regions (e.g., Fc region) is altered, e.g., mutated, to increase or decrease dimerization, e.g., relative to a non-engineered interface.

In some embodiments, the dimerization of the immunoglobulin chain constant region (e.g., Fc region) is enhanced by providing an Fc interface of a first and a second Fc region with one or more of: a paired cavity-protuberance ("knob-in-a hole"), an electrostatic interaction, or a strand-exchange, such that a greater ratio of heteromultimer:homomultimer forms, e.g., relative to a non-engineered interface.

In some embodiments, the multispecific molecule as provided herein further comprises a linker, e.g., a linker described herein, optionally wherein the linker is selected from: a cleavable linker, a non-cleavable linker, a peptide linker, a flexible linker, a rigid linker, a helical linker, or a non-helical linker.

In another aspect, provided herein is an isolated nucleic acid molecule comprising a nucleotide sequence encoding the anti-TCRβV antibody molecule as provided herein, or a nucleotide sequence having at least 75%, 80%, 85%, 90%, 95%, or 99% identity thereto.

In another aspect, provided herein is an isolated nucleic acid molecule comprising a nucleotide sequence encoding the multispecific molecule as provided herein, or a nucleotide sequence having at least 75%, 80%, 85%, 90%, 95%, or 99% identity thereto.

In another aspect, provided herein is a vector, e.g., an expression vector, comprising one or more of the nucleic acid molecules as provided herein.

In another aspect, provided herein is a cell, e.g., host cell, comprising the nucleic acid molecule as provided herein, or the vector as provided herein.

In another aspect, provided herein is a method of making, e.g., producing or manufacturing, the anti-TCRβV antibody molecule as provided herein, or the multispecific molecule as provided herein, comprising culturing the host cell as provided herein, under suitable conditions, e.g., conditions suitable expression of the anti-TCRβV antibody molecule or the multispecific molecule.

In another aspect, provided herein is a pharmaceutical composition comprising the anti-TCRβV antibody molecule as provided herein, or the multispecific molecule as provided herein, and a pharmaceutically acceptable carrier, excipient, or stabilizer.

In another aspect, provided herein is a method of modulating, e.g., enhancing, an immune response in a subject comprising administering to the subject an effective amount of an antibody molecule which binds (e.g., specifically binds) to a T cell receptor beta variable region (TCRβV) ("anti-TCRβV antibody molecule").

In another aspect, provided herein is a method of modulating, e.g., enhancing, an immune response in a subject comprising administering to the subject an effective amount of the multispecific molecule as provided herein.

In some embodiments, the method comprises expanding, e.g., increasing the number of, an immune cell population in the subject.

In another aspect, provided herein is a method of expanding, e.g., increasing the number of, an immune cell population comprising, contacting the immune cell population with an effective amount of an antibody molecule which binds (e.g., specifically binds) to a T cell receptor beta variable region (TCRβV) ("anti-TCRβV antibody molecule").

In another aspect, provided herein is a method of expanding, e.g., increasing the number of, an immune cell population comprising, contacting the immune cell population with an effective amount of the multispecific molecule as provided herein.

In some embodiments, the expansion occurs in vivo or ex vivo (e.g., in vitro).

In some embodiments, the immune cell population comprises a TCRβV expressing cell, e.g., a TCRβV+ cell.

In some embodiments, the TCRβV expressing cell is a T cell, e.g., a CD8+ T cell, a CD3+ T cell or a CD4+ T cell.

In some embodiments, the immune cell population comprises a T cell (e.g., a CD4 T cell, a CD8 T cell (e.g., an effector T cell, a T cell having a memory-like phenotype or a memory T cell (e.g., a memory effector T cell (e.g., TEM cell, e.g., TEMRA cell), or a tumor infiltrating lymphocyte (TIL).

In some embodiments, the immune cell population comprises a T cell, a Natural Killer cell, a B cell, or a myeloid cell.

In some embodiments, the immune cell population is obtained from a healthy subject.

In some embodiments, the immune cell population is obtained from a subject (e.g., from an apheresis sample from the subject) having a disease, e.g., a cancer, e.g., as described herein, optionally wherein the immune cell population comprises a tumor infiltrating lymphocyte (TIL).

In some embodiments, the method results in an expansion of at least 1.1-10 fold (e.g., at least 1.1, 1.2, 1.3, 1.4, 1.5, 2, 3, 4, 5, 6, 7, 8, 9, or 10 fold expansion).

In some embodiments, the method as provided herein further comprises contacting the population of cells with an agent that promotes, e.g., increases, immune cell expansion.

In some embodiments, the method as provided herein further comprises contacting the population of cells with an immune checkpoint inhibitor, e.g., a PD-1 inhibitor.

In some embodiments, the method as provided herein further comprises contacting the population of cells with a 4-1BB (CD127) agonist, e.g., an anti-4-1BB antibody.

In some embodiments, the method as provided herein further comprises contacting the population of cells with a non-dividing population of cells, e.g., feeder cells, e.g., irradiated allogenic human PBMCs.

In some embodiments, the population of cells is expanded in an appropriate media (e.g., media described herein) that includes one or more cytokines, e.g., IL-2, IL-7, IL-15, or a combination thereof.

In some embodiments, the population of cells is expanded for a period of at least about 4 hours, 6 hours, 10 hours, 12 hours, 15 hours, 18 hours, 20 hours, or 22 hours, or for at least 1, 2, 3, 4, 5, 6, 7, 8, 9, 10, 11, 12, 13, 14, 15, 1, 6 17, 18, 19, 20 or 21 days, or for at least about 1 week, 2 weeks, 3 weeks, 4 weeks, 5 weeks, 6 weeks, 7 weeks or 8 weeks.

In some embodiments, expansion of the population of immune cells, is compared to expansion of a similar population of cells with an antibody that binds to: a CD3 molecule, e.g., CD3 epsilon (CD3ε) molecule; or a TCR alpha (TCRα) molecule.

In some embodiments, expansion of the population of immune cells, is compared to expansion of a similar population of cells not contacted with the anti-TCRβV antibody molecule, or multispecific molecule comprising the anti-TCRβV antibody molecule.

In some embodiments, expansion of the population of T cells having a memory-like phenotype, e.g., CD45RA+ CCR7− cells (e.g., memory effector T cells, e.g., TEM cells, e.g., TEMRA cells), is compared to expansion of a similar population of cells with an antibody that binds to: a CD3 molecule, e.g., CD3 epsilon (CD3e) molecule; or a TCR alpha (TCRα) molecule.

In some embodiments, the population of expanded T cells having a memory-like phenotype, e.g., effector memory cells, comprises cells which:

(i) have a detectable level of CD45RA, e.g., express or re-express CD45RA;

(ii) have low or no expression of CCR7; and/or (iii) have a detectable level of CD95, e.g., express CD95, e.g., a population of CD45RA+, CCR7−, CD95+ T cells, optionally wherein the T cells comprise CD3+, CD4+ or CD8+ T cells.

In some embodiments, the method results in expansion of, e.g., selective or preferential expansion of, T cells expressing a T cell receptor (TCR) comprising a TCR alpha and/or TCR beta molecule, e.g., TCR alpha-beta T cells (αβ T cells).

In some embodiments, the method results in expansion of αβT cells over expansion of T cells expressing a TCR comprising a TCR gamma and/or TCR delta molecule, e.g., TCR gamma-delta T cells (γδ T cells).

In another aspect, provided herein is a method of treating a disease, e.g., cancer, in a subject comprising administering to the subject an effective amount of an antibody molecule which binds (e.g., specifically binds) to a T cell receptor beta variable region (TCRβV) ("anti-TCRβV antibody molecule"), thereby treating the cancer.

In another aspect, provided herein is a composition comprising an antibody molecule which binds (e.g., specifically binds) to a T cell receptor beta variable region (TCRβV) ("anti-TCRβV antibody molecule"), for use in treating a disease, e.g., cancer, in a subject.

In another aspect, provided herein is a composition comprising an antibody molecule which binds (e.g., specifically binds) to a T cell receptor beta variable region (TCRβV) ("anti-TCRβV antibody molecule"), for use in the manufacture of a medicament for treating a disease, e.g., cancer, in a subject.

In another aspect, provided herein is a method of treating a disease, e.g., cancer, in a subject comprising administering to the subject an effective amount of the multispecific molecule as provided herein, thereby treating the cancer.

In another aspect, provided herein is a composition comprising the multispecific molecule as provided herein, for use in treating a disease, e.g., cancer, in a subject.

In another aspect, provided herein is a composition comprising the multispecific molecule as provided herein, for use in the manufacture of a medicament for treating a disease, e.g., cancer, in a subject.

In another aspect, provided herein is a method of treating, e.g., preventing or reducing, cytokine release syndrome (CRS) and/or neurotoxicity (NT) in a subject, e.g., CRS and/or NT associated with a treatment, e.g., a previously administered treatment, comprising administering to the subject an effective amount of an antibody molecule which binds (e.g., specifically binds) to a T cell receptor beta variable region (TCRβV) ("anti-TCRβV antibody molecule"), thereby preventing CRS and/or NT in the subject.

In another aspect, provided herein is a method of treating, e.g., preventing or reducing, cytokine release syndrome (CRS) and/or neurotoxicity (NT) in a subject, e.g., CRS and/or NT associated with a treatment, e.g., a previously administered treatment, comprising administering to the subject an effective amount the multispecific molecule as provided herein, thereby preventing CRS and/or NT in the subject.

In another aspect, provided herein is a method of targeting a therapy, e.g., treatment, to a T cell in a subject having a disease, e.g., cancer, comprising administering an effective amount of:

(i) an antibody molecule which binds (e.g., specifically binds) to a T cell receptor beta variable region (TCRβV) ("anti-TCRβV antibody molecule"); and (ii) the therapy, e.g., a tumor targeting therapy (e.g., an antibody that binds to a cancer antigen), e.g., as described herein, thereby targeting the therapy to the T cell in the subject.

In another aspect, provided herein is a method of targeting a therapy, e.g., treatment, to a T cell in a subject having a disease, e.g., cancer, comprising administering an effective amount of:

(i) the multispecific molecule as provided herein; and (ii) the therapy, e.g., a tumor targeting therapy (e.g., an antibody that binds to a cancer antigen), e.g., as described herein, thereby targeting the therapy to the T cell in the subject.

In some embodiments, the method results in: reduced cytokine release syndrome (CRS) (e.g., lesser duration of CRS or no CRS), or a reduced severity of CRS (e.g., absence of severe CRS, e.g., CRS grade 4 or 5) compared to administration of (ii) alone.

In some embodiments, the anti-TCRβV antibody or the multispecific molecule is administered concurrently with or after the administration of the treatment associated with CRS.

In another aspect, provided herein is a method of treating a subject having a cancer, the method comprising:

acquiring a value of the status of a TCRβV subfamily for the subject, wherein said value comprises a measure of the presence of, e.g., level or activity of, a TCRβV molecule in a sample from the subject, and administering an effective amount of an antibody molecule which binds (e.g., specifically binds) to a T cell receptor beta variable region (TCRβV) ("anti-TCRβV antibody molecule"); to the subject, thereby treating the subject.

In another aspect, provided herein is a method of treating a subject having a cancer, the method comprising:

acquiring a value of the status of a TCRβV subfamily for the subject, wherein said value comprises a measure of the presence of, e.g., level or activity of, a TCRβV molecule in a sample from the subject, and administering an effective amount of the multispecific molecule as provided herein to the subject, thereby treating the subject.

In another aspect, provided herein is a method of treating a subject having a cancer, the method comprising administering an effective amount of an antibody molecule which binds (e.g., specifically binds) to a T cell receptor beta variable region (TCRβV) ("anti-TCRβV antibody molecule") to the subject, wherein the subject has a higher, e.g., increased, level or activity of one or more TCRβV subfamilies, e.g., as described herein, compared to a reference level or activity of one or more TCRβV subfamilies, e.g., in a healthy subject, e.g., a subject not having a cancer.

In another aspect, provided herein is a method of treating a subject having a cancer, the method comprising administering an effective amount of the multispecific molecule as provided herein to the subject, wherein the subject has a higher, e.g., increased, level or activity of one or more TCRβV subfamilies, e.g., as described herein, compared to a reference level or activity of one or more TCRβV subfamilies, e.g., in a healthy subject, e.g., a subject not having a cancer.

In another aspect, provided herein is a method of expanding a population of immune effector cells from a subject having a cancer, the method comprising:

(i) isolating a biological sample comprising a population of immune effector cells from the subject; e.g., a peripheral blood sample, biopsy sample, or bone marrow sample;

(ii) acquiring a value of the status of one or more TCRβV subfamilies for the subject, e.g., in the biological sample from the subject, wherein said value comprises a measure of the presence of, e.g., level or activity of, a TCRβV subfamily in a sample from the subject compared to a reference value, e.g., a sample from a health subject, wherein a value that is higher, e.g., increased, in the subject relative to the reference, e.g., healthy subject, is indicative of the presence of cancer in the subject, and (iii) contacting the biological sample comprising a population of immune effector cells with an anti-TCRβV antibody molecule, e.g., as described herein.

In some embodiments, the method as provided herein further comprises administering the population of immune effector cells contacted with the anti-TCRβV antibody molecule to the subject.

In another aspect, provided herein is a method of expanding a population of immune effector cells from a subject having a cancer, the method comprising:

(i) isolating a biological sample comprising a population of immune effector cells from the subject; e.g., a peripheral blood sample, biopsy sample, or bone marrow sample;

(ii) acquiring a value of the status of one or more TCRβV subfamilies for the subject, e.g., in the biological sample from the subject, wherein said value comprises a measure of the presence of, e.g., level or activity of, a TCRβV subfamily in a sample from the subject compared to a reference value, e.g., a sample from a health subject, wherein a value that is higher, e.g., increased, in the subject relative to the reference, e.g., healthy subject, is indicative of the presence of cancer in the subject, and (iii) contacting the biological sample comprising a population of immune effector cells with the multispecific molecule as provided herein.

In some embodiments, the method as provided herein further comprises administering the population of immune effector cells contacted with the multispecific molecule to the subject.

In some embodiments, the method as provided herein comprises measuring T cell function (e.g., cytotoxic activity, cytokine secretion, or degranulation) in the population of immune effector cells, e.g., compared to a reference population, e.g., an otherwise similar population not contacted with the anti-TCRβV antibody molecule or a population of immune effector cells obtained from a healthy subject (e.g., a subject that does not have a cancer).

In some embodiments, the biological sample comprising the population of immune effector cells is contacted with an anti-TCRβV antibody molecule or a multispecific molecule that binds to the one or more TCRβV subfamilies (e.g., the same TCRβV subfamily) identified as being higher, e.g., increased, in the biological sample.

In some embodiments, the biological sample comprising the population of immune effector cells is contacted with an anti-TCRβV antibody molecule or a multispecific molecule that does not bind to the one or more TCRβV subfamilies (e.g., a different TCRβV subfamily) identified as being higher, e.g., increased, in the biological sample.

In some embodiments, the cancer is a solid tumor including but not limited to: melanoma, pancreatic (e.g., pancreatic adenocarcinoma) cancer, breast cancer, colorectal cancer (CRC), lung cancer (e.g., small or non-small cell lung cancer), skin cancer, ovarian cancer, or liver cancer.

In some embodiments, the cancer is a hematological cancer including, but not limited to: a B-cell or T cell malignancy, e.g., Hodgkin's lymphoma, Non-Hodgkin's lymphoma (e.g., B cell lymphoma, diffuse large B cell lymphoma (DLBCL), follicular lymphoma, chronic lymphocytic leukemia (B-CLL), mantle cell lymphoma, marginal zone B-cell lymphoma, Burkitt lymphoma, lymphoplasmacytic lymphoma, hairy cell leukemia), acute myeloid leukemia (AML), chronic myeloid leukemia, myelodysplastic syndrome, multiple myeloma, and acute lymphocytic leukemia.

In some embodiments, the cancer is B-CLL and the TCRβV molecule comprises:

(i) TCRβ V6 subfamily comprising, e.g., TCRβ V6-4*01, TCRβ V6-4*02, TCRβ V6-9*01, TCRβ V6-8*01, TCRβ V6-5*01, TCRβ V6-6*02, TCRβ V6-6*01, TCRβ V6-2*01, TCRβ V6-3*01 or TCRβ V6-1*01;

(ii) TCRβ V5 subfamily comprising TCRβ V5-6*01, TCRβ V5-4*01, or TCRβ V5-8*01;

(iii) TCRβ V3 subfamily comprising TCRβ V3-1*01;

(iv) TCRβ V2 subfamily comprising TCRβ V2*01; or (v) TCRβ V19 subfamily comprising TCRβ V19*01, or TCRβ V19*02.

In some embodiments, the cancer is melanoma and the TCRβV molecule comprises the TCRβ V6 subfamily comprising, e.g., TCRβ V6-4*01, TCRβ V6-4*02, TCRβ V6-9*01, TCRβ V6-8*01, TCRβ V6-5*01, TCRβ V6-6*02, TCRβ V6-6*01, TCRβ V6-2*01, TCRβ V6-3*01 or TCRβ V6-1*01.

In some embodiments, the cancer is DLBCL and the TCRβV molecule comprises:

(i) TCRβ V13 subfamily comprising TCRβ V13*01;

(ii) TCRβ V3 subfamily comprising TCRβ V3-1*01; or (iii) TCRβ V23 subfamily.

In some embodiments, the cancer is CRC and the TCRβV molecule comprises:

(i) TCRβ V19 subfamily comprising TCRβ V19*01, or TCRβ V19*02

(ii) TCRβ V12 subfamily comprising TCRβ V12-4*01, TCRβ V12-3*01, or TCRβ V12-5*01

(iii) TCRβ V16 subfamily comprising TCRβ V16*01; or (iv) TCRβ V21 subfamily.

In some embodiments, the tumor comprises an antigen, e.g., a tumor antigen, e.g., a tumor associated antigen or a neoantigen; and/or the one or more TCRβV subfamilies recognize, e.g., bind to, the tumor antigen.

In some embodiments, the sample comprises a blood sample, e.g., a peripheral blood sample, a biopsy, e.g., a tumor biopsy, or a bone marrow sample.

In some embodiments, the sample comprises a biological sample comprising immune cells, e.g., TCRBV expressing cells (e.g., TCRBV+ cells), T cells, or NK cells.

In some embodiments, the T cells comprise a CD4 T cell, a CD8 T cell, (e.g., an effector T cell or a memory T cell (e.g., a memory effector T cell (e.g., $T_{EM}$ cell, e.g., $T_{EMRA}$ cell), or a tumor infiltrating lymphocyte (TIL).

In some embodiments, the method results in an expansion, e.g., in vivo or ex vivo expansion, of at least 1.1-1000 fold, e.g., 1.1-10, 10-100, 100-200, 200-300, 300-400, 400-500, 500-600, 600-700, 700-800, 800-900, or 900-1000 fold expansion of an immune effector cell population comprising a TCRVB expressing immune effector cell, e.g., T cell.

In some embodiments, the population of cells is expanded in an appropriate media (e.g., media described herein) that includes one or more cytokines, e.g., IL-2, IL-7, IL-15, or a combination thereof.

In some embodiments, the population of cells is expanded for a period of at least about 4 hours, 6 hours, 10 hours, 12 hours, 15 hours, 18 hours, 20 hours, or 22 hours, or for at least 1, 2, 3, 4, 5, 6, 7, 8, 9, 10, 11, 12, 13, 14, 15, 1, 6 17, 18, 19, 20 or 21 days, or for at least about 1 week, 2 weeks, 3 weeks, 4 weeks, 5 weeks, 6 weeks, 7 weeks or 8 weeks.

In some embodiments, expansion of the population of immune cells, is compared to expansion of a similar population of cells with an antibody that binds to: a CD3 molecule, e.g., CD3 epsilon (CD3e) molecule; or a TCR alpha (TCRα) molecule.

In some embodiments, expansion of the population of immune cells, is compared to expansion of a similar population of cells not contacted with the anti-TCRβV antibody molecule.

In some embodiments, expansion of the population of T cells having a memory-like phenotype, e.g., memory effector T cells, e.g., TEM cells, e.g., TEMRA cells, is compared to expansion of a similar population of cells with an antibody that binds to: a CD3 molecule, e.g., CD3 epsilon (CD3e) molecule; or a TCR alpha (TCRα) molecule.

In some embodiments, the population of expanded T cells having a memory-like phenotype, e.g., effector memory cells, comprises cells which:

(i) have a detectable level of CD45RA, e.g., express or re-express CD45RA;
(ii) have low or no expression of CCR7; and/or
(iii) have a detectable level of CD95, e.g., express CD95, e.g., a population of CD45RA+, CCR7−, CD95+ T cells, optionally wherein the T cells comprise CD3+, CD4+ or CD8+ T cells.

In some embodiments, the method results in expansion of, e.g., selective or preferential expansion of, T cells expressing a T cell receptor (TCR) comprising a TCR alpha and/or TCR beta molecule, e.g., TCR alpha-beta T cells (αβ T cells).

In some embodiments, the method results in expansion of αβT cells over expansion of T cells expressing a TCR comprising a TCR gamma and/or TCR delta molecule, e.g., TCR gamma-delta T cells (γδ T cells).

In some embodiments, the anti-TCRβV antibody molecule comprises an antigen binding domain comprising a light chain variable region (VL) comprising one, two or all of a LC CDR1, a LC CDR2 and a LC CDR3 of a VL disclosed in Tables 1, 2, 10, 11, 12 or 13, e.g., SEQ ID NO: 1314, SEQ ID NO: 2, SEQ ID NO: 10, SEQ ID NO: 11, SEQ ID NO: 16, SEQ ID NO: 26, SEQ ID NO: 27, SEQ ID NO: 28, SEQ ID NO: 29 or SEQ ID NO:30

In some embodiments, the anti-TCRβV antibody molecule comprises an antigen binding domain comprising a heavy chain variable region (VH) comprising one, two or all of a HC CDR1, a HC CDR2 and a HC CDR3 of a VH disclosed in Tables 1, 2, 10, 11, 12 or 13, e.g., SEQ ID NO: 1312, SEQ ID NO:1, SEQ ID NO: 9, SEQ ID NO: 15, SEQ ID NO: 23, SEQ ID NO: 24 or SEQ ID NO: 25.

In some embodiments, the anti-TCRβV antibody molecule comprises an antigen binding domain comprising:

(i) a VL comprising: a LC CDR1 amino acid sequence of SEQ ID NO: 20 (or an amino acid sequence with not more than 1, 2, 3 or 4 modifications, e.g., substitutions, additions or deletions thereof), a LC CDR2 amino acid sequence of SEQ ID NO:21 (or an amino acid sequence with not more than 1, 2, 3 or 4 modifications, e.g., substitutions, additions or deletions thereof), and/or a LC CDR3 amino acid sequence of SEQ ID NO:22 (or an amino acid sequence with not more than 1, 2, 3 or 4 modifications, e.g., substitutions, additions or deletions thereof); and/or
(ii) a VH comprising: a HC CDR1 amino acid sequence of SEQ ID NO: 17 (or an amino acid sequence with not more than 1, 2, 3 or 4 modifications, e.g., substitutions, additions or deletions thereof), a HC CDR2 amino acid sequence of SEQ ID NO:18 (or an amino acid sequence with not more than 1, 2, 3 or 4 modifications, e.g., substitutions, additions or deletions thereof), and/or a HC CDR3 amino acid sequence of SEQ ID NO:19 (or an amino acid sequence with not more than 1, 2, 3 or 4 modifications, e.g., substitutions, additions or deletions thereof).

In some embodiments, the anti-TCRβV antibody molecule comprises an antigen binding domain comprising:

a variable heavy chain (VH) of SEQ ID NO: 23, SEQ ID NO: 24 or SEQ ID NO: 25, or a sequence having at least about 85%, 90%, 95%, or 99% sequence identity thereto; and/or
a variable light chain (VL) of SEQ ID NO: 26, SEQ ID NO: 27, SEQ ID NO: 28, SEQ ID NO: 29 or SEQ ID NO:30, or a sequence having at least about 85%, 90%, 95%, or 99% sequence identity thereto.

In some embodiments, the anti-TCRβV antibody molecule comprises an antigen binding domain comprising (i) a VL comprising: a LC CDR1 amino acid sequence of SEQ ID NO: 6 (or an amino acid sequence with not more than 1, 2, 3 or 4 modifications, e.g., substitutions, additions or deletions thereof), a LC CDR2 amino acid sequence of SEQ ID NO:7 (or an amino acid sequence with not more than 1, 2, 3 or 4 modifications, e.g., substitutions, additions or deletions thereof), and/or a LC CDR3 amino acid sequence of SEQ ID NO: 8 (or an amino acid sequence with not more than 1, 2, 3 or 4 modifications, e.g., substitutions, additions or deletions thereof); and/or
(ii) a VH comprising: a HC CDR1 amino acid sequence of SEQ ID NO: 3 (or an amino acid sequence with not more than 1, 2, 3 or 4 modifications, e.g., substitutions, additions or deletions thereof), a HC CDR2 amino acid sequence of SEQ ID NO:4 (or an amino acid sequence with not more than 1, 2, 3 or 4 modifications, e.g., substitutions, additions or deletions thereof), and/or a HC CDR3 amino acid sequence of SEQ ID NO:5 (or an amino acid sequence with not more than 1, 2, 3 or 4 modifications, e.g., substitutions, additions or deletions thereof).

In some embodiments, the anti-TCRβV antibody molecule comprises an antigen binding domain comprising:

a variable heavy chain (VH) of SEQ ID NO: 1 or SEQ ID NO: 9 or SEQ ID NO: 1312, or a sequence having at least about 85%, 90%, 95%, or 99% sequence identity thereto; and/or
a variable light chain (VL) of SEQ ID NO: 2, SEQ ID NO: 10 or SEQ ID NO:11 or SEQ ID NO: 1314, or a sequence having at least about 85%, 90%, 95%, or 99% sequence identity thereto.

In some embodiments, the anti-TCRβV antibody molecule comprises a light chain comprising a framework region, e.g., framework region 1 (FR1), comprising one, two or all (e.g., three) of:

(i) an Aspartic Acid at position 1, e.g., a substitution at position 1 according to Kabat numbering, e.g., a Alanine to Aspartic Acid substitution; or (ii) an Asparagine at position 2, e.g., a substitution at position 2 according to Kabat numbering, e.g., a Isoleucine to Asparagine, a Serine to Asparagine, or a Tyrosine to Asparagine substitution; or (iii) a Leucine at position 4, e.g., a substitution at position 4 according to Kabat numbering, e.g., a Methionine to Leucine substitution, wherein the substitution is relative to a human germline light chain framework region sequence.

In some embodiments, the anti-TCRβV antibody molecule comprises a light chain comprising a framework region, e.g., framework region 3 (FR3), comprising one, two or all (e.g., three) of:

(i) a Glycine at position 66, e.g., a substitution at position 66 according to Kabat numbering, e.g., a Lysine to Glycine, or a Serine to Glycine substitution; or (ii) an Asparagine at position 69, e.g., a substitution at position 69 according to Kabat numbering, e.g., a Threonine to Asparagine substitution; or (iii) a Tyrosine at position 71, e.g., a substitution at position 71 according to Kabat numbering, e.g., a Phenylalanine to Tyrosine, or Alanine to Tyrosine substitution, wherein the substitution is relative to a human germline light chain framework region sequence.

In some embodiments, binding of the anti-TCRβV antibody molecule to the TCRβV region results in a cytokine profile that differs from a cytokine profile of a T cell engager that binds to a receptor or molecule other than a TCRβV region ("a non-TCRβV-binding T cell engager").

In some embodiments, the non-TCRβV-binding T cell engager comprises an antibody that binds to a CD3 molecule (e.g., CD3 epsilon (CD3ε) molecule); or a TCR alpha (TCRα) molecule.

In some embodiments, the cytokine profile of the first moiety comprises, one, two, three, four, five, six, seven, or all of the following:

(i) increased level, e.g., expression level, and/or activity of IL-2;

(ii) reduced level, e.g., expression level, and/or activity of IL-1β;

(iii) reduced level, e.g., expression level, and/or activity of IL-6;

(iv) reduced level, e.g., expression level, and/or activity of TNFα;

(v) reduced level, e.g., expression level, and/or activity of IL-10;

(vi) a delay, e.g., at least 1, 2, 3, 4, 5, 6, 7, 8, 9, 10 or more hours delay, in increased level, e.g., expression level, and/or activity of IL-2;

(vii) a delay, e.g., at least 1, 2, 3, 4, 5, 6, 7, 8, 9, 10 hours delay, in increased level, e.g., expression level, and/or activity of IFNg; or (viii) increased level, e.g., expression level, and/or activity of IL-15, e.g., wherein (i)-(vii) are relative to the cytokine profile of the non-TCRβV-binding T cell engager.

In some embodiments, binding of the anti-TCRβV antibody molecule to the TCRβV region results in reduced cytokine storm, e.g., reduced cytokine release syndrome (CRS), as measured by an assay of Example 3, e.g., relative to the cytokine storm induced by the non-TCRβV-binding T cell engager.

In some embodiments, binding of the anti-TCRβV antibody molecule to the TCRβV region results in one, two, three or all of:

(ix) reduced T cell proliferation kinetics;

(x) cell killing, e.g., target cell killing, e.g. cancer cell killing, e.g., as measured by an assay of Example 4;

(xi) increased Natural Killer (NK) cell proliferation, e.g., expansion; or (xii) expansion, e.g., at least about 1.1-10 fold expansion (e.g., at least about 1.1, 1.2, 1.3, 1.4, 1.5, 2, 3, 4, 5, 6, 7, 8, 9, or 10 fold expansion), of a population of T cells having a memory-like phenotype, e.g., relative to the non-TCRβV-binding T cell engager.

In some embodiments, the anti-TCRβV antibody molecule binds to an outward facing region (e.g., epitope) on a TCRβV protein, e.g., as depicted by the circled area in FIG. 24A.

In some embodiments, the outward facing region on the TCRβV protein comprises a structurally conserved region of TCRβV, e.g., a region of TCRβV having a similar structure across one or more TCRβV subfamilies.

In some embodiments, the method further comprises administering (e.g., sequentially, simultaneously or concurrently) a second agent, e.g., therapeutic agent, e.g., as described herein.

In some embodiments, the second agent, e.g., therapeutic agent, comprises a chemotherapeutic agent, a biologic agent, hormonal therapy), radiation, or surgery.

In some embodiments, the disease is a cancer, e.g., a solid tumor or a hematological cancer, or a metastatic lesion.

In some embodiments, the cancer antigen is BCMA or FcRH5.

In some aspects, provided herein is, inter alia, a multispecific molecule, optionally a bispecific molecule, comprising a first moiety, optionally a first immune cell engager, comprising an antibody molecule which binds, optionally specifically binds, to a T cell receptor beta variable region (TCRβV) ("anti-TCRβV antibody molecule"), wherein binding of the first moiety to the TCRβV region results in a cytokine profile that differs from a cytokine profile of a T cell engager that binds to a receptor or molecule other than a TCRβV region ("a non-TCRβV-binding T cell engager").

In some embodiments, the multispecific molecule as provided herein comprises a second moiety which comprises one or more of: a tumor-targeting moiety, a cytokine molecule, a stromal modifying moiety, or an anti-TCRβV antibody molecule other than the first moiety.

In some embodiments, the first moiety comprising the anti-TCRβV antibody molecule comprises an Fc region comprising a variant, optionally an Fc variant described in Table 21, optionally an Asn297Ala (N297A) mutation or a Leu234Ala/Leu235Ala (LALA) mutation.

In some embodiments, the non-TCRβV-binding T cell engager comprises an antibody that binds to a CD3 molecule, optionally CD3 epsilon (CD3ε) molecule, or a TCR alpha (TCRα) molecule.

In some embodiments, the cytokine profile of the first moiety comprises, one, two, three, four, five, six, seven, or all of the following:

(i) increased level, optionally expression level, and/or activity of IL-2;

(ii) reduced level, optionally expression level, and/or activity of IL-1β;

(iii) reduced level, optionally expression level, and/or activity of IL-6;

(iv) reduced level, optionally expression level, and/or activity of TNFα;

(v) reduced level, optionally expression level, and/or activity of IL-10;

(vi) a delay, optionally at least 1, 2, 3, 4, 5, 6, 7, 8, 9, 10 or more hours delay, in increased level, optionally expression level, and/or activity of IL-2;

(vii) a delay, optionally at least 1, 2, 3, 4, 5, 6, 7, 8, 9, 10 hours delay, in increased level, optionally expression level, and/or activity of IFNg; or (viii) increased level, optionally expression level, and/or activity of IL-15, optionally wherein (i)-(viii) are relative to the cytokine profile of the non-TCRβV-binding T cell engager.

In some embodiments, binding of the first moiety to the TCRβV region results in reduced cytokine storm, optionally reduced cytokine release syndrome (CRS), as measured by an assay of Example 3, optionally relative to the cytokine storm induced by the non-TCRβV-binding T cell engager.

In some embodiments, binding of the first moiety to the TCRβV region results in one, two, three or all of:

(ix) reduced T cell proliferation kinetics;

(x) cell killing, optionally target cell killing, optionally cancer cell killing, optionally as measured by an assay of Example 4;

(xi) increased Natural Killer (NK) cell proliferation, optionally expansion; or (xii) expansion, optionally at least about 1.1-10 fold expansion, optionally at least about 1.1, 1.2, 1.3, 1.4, 1.5, 2, 3, 4, 5, 6, 7, 8, 9, or 10 fold expansion, of a population of T cells having a memory-like phenotype, optionally wherein (ix)-(xii) are relative to the non-TCRβV-binding T cell engager.

In some embodiments, the population of T cells having a memory-like phenotype comprises CD45RA+ CCR7− T cells, optionally CD4+ and/or CD8+ T cells.

In some embodiments, the first moiety binds to one or more of a TCRβV subfamily chosen from:

(i) TCRβ V6 subfamily comprising, optionally one or more of TCRβ V6-4*01, TCRβ V6-4*02, TCRβ V6-9*01, TCRβ V6-8*01, TCRβ V6-5*01, TCRβ V6-6*02, TCRβ V6-6*01, TCRβ V6-2*01, TCRβ V6-3*01 or TCRβ V6-1*01;

(ii) TCRβ V10 subfamily comprising, optionally one or more of TCRβ V10-1*01, TCRβ V10-1*02, TCRβ V10-3*01 or TCRβ V10-2*01;

(iii) TCRβ V5 subfamily comprising, optionally one or more of TCRβ V5-6*01, TCRβ V5-4*01, TCRβ V5-1*01 or TCRβ V5-8*01;

(iv) TCRβ V12 subfamily comprising, optionally one or more of TCRβ V12-4*01, TCRβ V12-3*01, or TCRβ V12-5*01;

(v) TCRβ V27 subfamily;

(vi) TCRβ V28 subfamily;

(vii) TCRβ V4 subfamily comprising, optionally one or more of TCRβ V4-1, TCRβ V4-2 or TCRβ V4-3;

(viii) TCRβ V19 subfamily;

(ix) TCRβ V9 subfamily; or (x) TCRβ V11 subfamily comprising, optionally TCRβ V11-2.

In some embodiments, the anti-TCRβV antibody molecule:

(i) binds specifically to an epitope on TCRβV, optionally the same or similar epitope as the epitope recognized by an anti-TCRβV antibody molecule as described herein, optionally a second anti-TCRβV antibody molecule;

(ii) shows the same or similar binding affinity or specificity, or both, as an anti-TCRβV antibody molecule as described herein, optionally a second anti-TCRβV antibody molecule;

(iii) inhibits, optionally competitively inhibits, the binding of an anti-TCRβV antibody molecule as described herein, optionally a second anti-TCRβV antibody molecule;

(iv) binds the same or an overlapping epitope with an anti-TCRβV antibody molecule as described herein, optionally a second anti-TCRβV antibody molecule; or (v) competes for binding, and/or binds the same epitope, with an anti-TCRβV antibody molecule as described herein, optionally a second anti-TCRβV antibody molecule, wherein the second anti-TCRβV antibody molecule comprises an antigen binding domain comprising a heavy chain complementarity determining region 1 (HC CDR1), a heavy chain complementarity determining region 2 (HC CDR2) and/or a heavy chain complementarity determining region 3 (HC CDR3) of SEQ ID NO: 1 or SEQ ID NO: 9; and/or a light chain complementarity determining region 1 (LC CDR1), a light chain complementarity determining region 2 (LC CDR2), and/or a light chain complementarity determining region 3 (LC CDR3) of SEQ ID NO: 2, SEQ ID NO: 10 or SEQ ID NO: 11.

In some embodiments, the anti-TCRβV antibody molecule comprises an antigen binding domain comprising:

(a) a HC CDR1, a HC CDR2 and/or a HC CDR3 of SEQ ID NO: 15, SEQ ID NO: 23, SEQ ID NO: 24 or SEQ ID NO: 25; and/or (b) a LC CDR1, a LC CDR2, and/or a LC CDR3 of SEQ ID NO: 16, SEQ ID NO: 26, SEQ ID NO: 27, SEQ ID NO: 28, SEQ ID NO: 29 or SEQ ID NO:30; or (a) a LC CDR1, a LC CDR2 and/or a LC CDR3 of SEQ ID NO: 2, SEQ ID NO: 10 or SEQ ID NO: 11; and/or (b) a HC CDR1, a HC CDR2 and/or a HC CDR2 of SEQ ID NO: 1 or SEQ ID NO: 9.

In some embodiments, the anti-TCRβV antibody molecule binds the same or different TCRβV subfamily members.

In some embodiments, the multispecific molecule as provided herein comprises an antibody molecule chosen from a bispecific antibody molecule, a bivalent antibody molecule, or a biparatopic antibody molecule.

In some embodiments, the multispecific molecule as provided herein comprises a bispecific antibody molecule that binds to two different TCRβV subfamily members.

In some embodiments, the anti-TCRβV antibody molecule binds:

one or more of a TCRβ V6 subfamily member and one or more of a TCRβ V10 subfamily member;

one or more of a TCRβ V6 subfamily member and one or more of a TCRβ V5 subfamily member;

one or more of a TCRβ V6 subfamily member and one or more of a TCRβ V12 subfamily member;

one or more of a TCRβ V10 subfamily member and one or more of a TCRβ V5 subfamily member;

one or more of a TCRβ V10 subfamily member and one or more of a TCRβ V12 subfamily member; or one or more of a TCRβ V5 subfamily member and one or more of a TCRβ V12 subfamily member.

In another aspect, provided herein is a multispecific molecule, optionally a bispecific molecule, comprising the anti-TCRβV antibody molecule as provided herein.

In another aspect, provided herein is an antibody molecule which binds, optionally specifically binds, to a T cell receptor beta variable chain (TCRβV) region, wherein the anti-TCRβV antibody molecule comprises an antigen binding domain comprising:

(a) a light chain variable region (VL) comprising:

(i) one, two or all of, optionally three, a light chain complementarity determining region 1 (LC CDR1), a light chain complementarity determining region 2 (LC CDR2), and a light chain complementarity determining region 3 (LC CDR3) of SEQ ID NO: 10 or SEQ ID NO: 11; and (ii) a framework region (FR) having at least 95% identity with one, two, three, or all of, optionally four, a non-murine germline framework 1 (FR1), a non-murine germline framework region 2 (FR2), a non-murine germline framework region 3 (FR3), and a non-murine germline framework region 4 (FR4); and/or (b) a heavy chain variable region (VH) comprising:

(i) one, two or all of, optionally three, a heavy chain complementarity determining region 1 (HC CDR1), a heavy chain complementarity determining region 2 (HC CDR2) and a heavy chain complementarity determining region 3 (HC CDR3) of SEQ ID NO: 9; and (ii) a framework region (FR) having at least 95% identity with one, two, three, or all of, optionally four, a non-murine germline framework 1 (FR1), a non-murine germline framework region 2 (FR2), a non-murine germline framework region 3 (FR3), and a non-murine germline framework region 4 (FR4).

In some embodiments, the VL comprises an amino acid sequence having a consensus sequence of SEQ ID NO: 230.

In some embodiments, the VH comprises an amino acid sequence having a consensus sequence of SEQ ID NO: 231.

In some embodiments, the anti-TCRβV antibody molecule as provided herein binds to TCRβ V6, optionally one or more of TCRβ V6-4*01, TCRβ V6-4*02, TCRβ V6-9*01, TCRβ V6-8*01, TCRβ V6-5*01, TCRβ V6-6*02, TCRβ V6-6*01, TCRβ V6-2*01, TCRβ V6-3*01 or TCRβ V6-1*01, or a variant thereof.

In some embodiments, the anti-TCRβV antibody molecule comprises an antigen binding domain comprising:

(i) a HC CDR1, a HC CDR2 and a HC CDR3 of SEQ ID NO: 1 or SEQ ID NO: 9, or an amino acid sequence listed in Table 1; or (ii) a LC CDR1, a LC CDR2, and a LC CDR3 of SEQ ID NO: 2, SEQ ID NO: 10 or SEQ ID NO: 11, or an amino acid sequence listed in Table 1.

In some embodiments, the anti-TCRβV antibody molecule comprises an antigen binding domain comprising a light chain variable region (VL) comprising one, two or all, optionally three, of a LC CDR1, a LC CDR2 and a LC CDR3 of SEQ ID NO: 2, SEQ ID NO: 10 or SEQ ID NO: 11, or an amino acid sequence listed in Table 1.

In some embodiments, the anti-TCRβV antibody molecule comprises an antigen binding domain comprising a heavy chain variable region (VH) comprising one, two or all, optionally three, of a HC CDR1, a HC CDR2 and a HC CDR3 of SEQ ID NO:1 or SEQ ID NO: 9, or an amino acid sequence listed in Table 1.

In some embodiments, the anti-TCRβV antibody molecule comprises an antigen binding domain comprising:

(i) a VL comprising: a LC CDR1 amino acid sequence of SEQ ID NO: 6 or an amino acid sequence with not more than 1, 2, 3 or 4 modifications, optionally substitutions, additions or deletions thereof, a LC CDR2 amino acid sequence of SEQ ID NO:7 or an amino acid sequence with not more than 1, 2, 3 or 4 modifications, optionally substitutions, additions or deletions thereof, and/or a LC CDR3 amino acid sequence of SEQ ID NO:8 or an amino acid sequence with not more than 1, 2, 3 or 4 modifications, optionally substitutions, additions or deletions thereof, and/or (ii) a VH comprising: a HC CDR1 amino acid sequence of SEQ ID NO: 3 or an amino acid sequence with not more than 1, 2, 3 or 4 modifications, optionally substitutions, additions or deletions thereof, a HC CDR2 amino acid sequence of SEQ ID NO:4 or an amino acid sequence with not more than 1, 2, 3 or 4 modifications, optionally substitutions, additions or deletions thereof, and/or a HC CDR3 amino acid sequence of SEQ ID NO:5 or an amino acid sequence with not more than 1, 2, 3 or 4 modifications, optionally substitutions, additions or deletions thereof.

In some embodiments, the anti-TCRβV antibody molecule comprises an antigen binding domain comprising:

a variable heavy chain (VH) of an amino acid sequence listed in Table 1, optionally SEQ ID NO: 9 or SEQ ID NO: 1312, or a sequence having at least about 85%, 90%, 95%, or 99% sequence identity to an amino acid sequence listed in Table 1, optionally SEQ ID NO: 9 or SEQ ID NO: 1312; and/or a variable light chain (VL) of an amino acid sequence listed in Table 1, optionally SEQ ID NO: 10 or SEQ ID NO: 11 or SEQ ID NO: 1314, or a sequence having at least about 85%, 90%, 95%, or 99% sequence identity to an amino acid sequence listed in Table 1, optionally SEQ ID NO: 10 or SEQ ID NO: 11 or SEQ ID NO: 1314.

In some embodiments, the anti-TCRβV antibody molecule comprises an antigen binding domain comprising:

(i) the VH amino acid sequence of SEQ ID NO: 9 or SEQ ID NO: 1312;

(ii) an amino acid sequence having at least about 85%, 90%, 95%, or 99% sequence identity to the amino acid sequence of SEQ ID NO: 9 or SEQ ID NO: 1312;

(iii) the VL amino acid sequence of SEQ ID NO: 10 or SEQ ID NO: 1314; and/or (iv) an amino acid sequence having at least about 85%, 90%, 95%, or 99% sequence identity to the amino acid sequence of SEQ ID NO: 10 or SEQ ID NO: 1314.

In some embodiments, the anti-TCRβV antibody molecule comprises an antigen binding domain comprising:

(i) the VH amino acid sequence of SEQ ID NO: 9 or SEQ ID NO: 1312;

(ii) an amino acid sequence having at least about 85%, 90%, 95%, or 99% sequence identity to the amino acid sequence of SEQ ID NO: 9 or SEQ ID NO: 1312;

(iii) the VL amino acid sequence of SEQ ID NO: 11 or SEQ ID NO: 1314; and/or (iv) an amino acid sequence having at least about 85%, 90%, 95%, or 99% sequence identity to the amino acid sequence of SEQ ID NO: 11 or SEQ ID NO: 1314.

In some embodiments, the anti-TCRβV antibody molecule comprises a heavy chain comprising a framework region, optionally framework region 3 (FR3), comprising one or both of:

(i) a Threonine at position 73, optionally a substitution at position 73 according to Kabat numbering, optionally a Glutamic Acid to Threonine substitution; or (ii) a Glycine a position 94, optionally a substitution at position 94 according to Kabat numbering, optionally a Arginine to Glycine substitution;

wherein the substitution is relative to a human germline heavy chain framework region sequence.

In some embodiments, the anti-TCRβV antibody molecule comprises a light chain comprising a framework region, optionally framework region 1 (FR1), comprising a Phenyalanine at position 10, optionally a substitution at position 10 according to Kabat numbering, optionally a Serine to Phenyalanine substitution, wherein the substitution is relative to a human germline light chain framework region sequence.

In some embodiments, the anti-TCRβV antibody molecule comprises a light chain comprising a framework region, optionally framework region 2 (FR2), comprising one or both of:

(i) a Histidine at position 36, optionally a substitution at position 36 according to Kabat numbering, optionally a Tyrosine to Histidine substitution; or (ii) an Alanine at position 46, optionally a substitution at position 46 according to Kabat numbering, optionally a Arginine to Alanine substitution;

wherein the substitution is relative to a human germline light chain framework region sequence.

In some embodiments, the anti-TCRβV antibody molecule comprises a light chain comprising a framework region, optionally framework region 3 (FR3), comprising a Phenyalanine at position 87, optionally a substitution at position 87 according to Kabat numbering, optionally a Tyrosine to Phenyalanine substitution, wherein the substitution is relative to a human germline light chain framework region sequence.

In another aspect, provided herein is an antibody molecule which binds, optionally specifically binds, to a T cell receptor beta variable chain (TCRβV) region, wherein the anti-TCRβV antibody molecule comprises an antigen binding domain comprising:

(a) a light chain variable region (VL) comprising:

(i) one, two or all of, optionally three, a light chain complementarity determining region 1 (LC CDR1), a light chain complementarity determining region 2 (LC CDR2), and a light chain complementarity determining region 3 (LC CDR3) of a humanized B-H light chain (LC) of Table 2; and (ii) a framework region (FR) having at least 95% identity with one, two, three or all, optionally four, of a framework region 1 (FR1), a framework region 2 (FR2), a framework region 3 (FR3), and a framework region 4 (FR4) of a humanized B-H LC of Table 2; and/or (b) a heavy chain variable region (VH) comprising:

(i) one, two or all of, optionally three, a heavy chain complementarity determining region 1 (HC CDR1), a heavy chain complementarity determining region 2 (HC CDR2) and a heavy chain complementarity determining region 3 (HC CDR3) of a humanized B-H heavy chain (HC) of Table 2; and (ii) a framework region (FR) having at least 95% identity with one, two, three or all, optionally four, of a framework region 1 (FR1), a framework region 2 (FR2), a framework region 3 (FR3), and a framework region 4 (FR4) of a humanized B-H HC of Table 2.

In some embodiments, the anti-TCRβV antibody molecule as provided herein binds to TCRβ V12, optionally TCRβ V12-4*01, TCRβ V12-3*01, or TCRβ V12-5*01, or a variant thereof.

In some embodiments, the anti-TCRβV antibody molecule comprises an antigen binding domain comprising:

(i) a HC CDR1, a HC CDR2 and a HC CDR3 of Antibody B-H listed in Table 2; or (ii) a LC CDR1, a LC CDR2, and a LC CDR3 of Antibody B-H listed in Table 2.

In some embodiments, the anti-TCRβV antibody molecule comprises an antigen binding domain comprising a light chain variable region (VL) comprising one, two or all, optionally three, of a LC CDR1, a LC CDR2 and a LC CDR3 of SEQ ID NO: 2, SEQ ID NO: 10 or SEQ ID NO: 11, or an amino acid sequence listed in Table 1.

In some embodiments, the anti-TCRβV antibody molecule comprises an antigen binding domain comprising a heavy chain variable region (VH) comprising one, two or all, optionally three, of a HC CDR1, a HC CDR2 and a HC CDR3 of a humanized Antibody B-H listed in Table 2.

In some embodiments, the anti-TCRβV antibody molecule comprises an antigen binding domain comprising a light chain variable region (VL) comprising one, two or all, optionally three, of a LC CDR1, a LC CDR2 and a LC CDR3 of a humanized Antibody B-H listed in Table 2.

In some embodiments, the anti-TCRβV antibody molecule comprises:

a VH sequence of a humanized Antibody B-H listed in Table 2, or a sequence having at least about 85%, 90%, 95%, or 99% sequence identity to a VH of a humanized Antibody B-H listed in Table 2; and/or a VL sequence of a humanized Antibody B-H listed in Table 2, or a sequence having at least about 85%, 90%, 95%, or 99% sequence identity to a VL of a humanized Antibody B-H listed in Table 2.

In some embodiments, the anti-TCRβV antibody molecule comprises a framework region (FR) having at least 95% identity with one of: a FR1, a FR2, a FR3, and a FR4 of a humanized B-H LC of Table 2.

In some embodiments, the anti-TCRβV antibody molecule comprises a framework region (FR) having at least 95% identity with any two of: a FRI, a FR2, a FR3, and a FR4 of a humanized B-H LC of Table 2.

In some embodiments, the anti-TCRβV antibody molecule comprises a framework region (FR) having at least 95% identity with any three of: a FR1, a FR2, a FR3, and a FR4 of a humanized B-H LC of Table 2.

In some embodiments, the anti-TCRβV antibody molecule comprises a framework region (FR) having at least 95% identity with all of: a FR1, a FR2, a FR3, and a FR4 of a humanized B-H LC of Table 2.

In some embodiments, the anti-TCRβV antibody molecule comprises a framework region (FR) having at least 95% identity with one of: a FR1, a FR2, a FR3, and a FR4 of a humanized B-H HC of Table 2.

In some embodiments, the anti-TCRβV antibody molecule comprises a framework region (FR) having at least 95% identity with any two of: a FR1, a FR2, a FR3, and a FR4 of a humanized B-H HC of Table 2.

In some embodiments, the anti-TCRβV antibody molecule comprises a framework region (FR) having at least 95% identity with any three of: a FR1, a FR2, a FR3, and a FR4 of a humanized B-H HC of Table 2.

In some embodiments, the anti-TCRβV antibody molecule comprises a framework region (FR) having at least 95% identity with all of: a FR1, a FR2, a FR3, and a FR4 of a humanized B-H HC of Table 2.

In some embodiments, binding of the anti-TCRβV antibody molecule to the TCRβV region results in a cytokine profile that differs from a cytokine profile of a T cell engager that binds to a receptor or molecule other than a TCRβV region ("a non-TCRβV-binding T cell engager").

In some embodiments, the non-TCRβV-binding T cell engager comprises an antibody that binds to a CD3 molecule, optionally CD3 epsilon (CD3ε) molecule, or a TCR alpha (TCRa) molecule.

In some embodiments, the cytokine profile of the first moiety comprises, one, two, three, four, five, six, seven, or all of the following:

(i) increased level, optionally expression level, and/or activity of IL-2;
(ii) reduced level, optionally expression level, and/or activity of IL-1β;
(iii) reduced level, optionally expression level, and/or activity of IL-6;
(iv) reduced level, optionally expression level, and/or activity of TNFα;
(v) reduced level, optionally expression level, and/or activity of IL-10;
(vi) a delay, optionally at least 1, 2, 3, 4, 5, 6, 7, 8, 9, 10 or more hours delay, in increased level, optionally expression level, and/or activity of IL-2;
(vii) a delay, optionally at least 1, 2, 3, 4, 5, 6, 7, 8, 9, 10 hours delay, in increased level, optionally expression level, and/or activity of IFNg; or
(viii) increased level, optionally expression level, and/or activity of IL-15, optionally wherein (i)-(vii) are relative to the cytokine profile of the non-TCRβV-binding T cell engager.

In some embodiments, binding of the anti-TCRβV antibody molecule to the TCRβV region results in reduced cytokine storm, optionally reduced cytokine release syndrome (CRS), as measured by an assay of Example 3, optionally relative to the cytokine storm induced by the non-TCRβV-binding T cell engager.

In some embodiments, binding of the anti-TCRβV antibody molecule to the TCRβV region results in one, two, three or all of:

(ix) reduced T cell proliferation kinetics;
(x) cell killing, optionally target cell killing, optionally cancer cell killing, optionally as measured by an assay of Example 4;
(xi) increased Natural Killer (NK) cell proliferation, optionally expansion; or
(xii) expansion, optionally at least about 1.1-10 fold expansion, optionally at least about 1.1, 1.2, 1.3, 1.4, 1.5, 2, 3, 4, 5, 6, 7, 8, 9, or 10 fold expansion, of a population of T cells having a memory-like phenotype, optionally relative to the non-TCRβV-binding T cell engager.

In some embodiments, the population of T cells having a memory-like phenotype comprises CD45RA+ CCR7− T cells, optionally CD4+ and/or CD8+ T cells.

In some embodiments, binding of the anti-TCRβV antibody molecule to a TCRβV region results in a reduction of at least 2, 5, 10, 20, 50, 100, or 200 fold, or at least 2-200 fold, optionally 5-150, 10-100, 20-50 fold, in the expression level and or activity of IL-1β as measured by an assay of Example 3.

In some embodiments, binding of the anti-TCRβV antibody molecule to a TCRβV region results in a reduction of at least 2, 5, 10, 20, 50, 100, 200, 300, 400, 500, 600, 700, 800, 900, or 1000 fold, or at least 2-1000 fold, optionally 5-900, 10-800, 20-700, 50-600, 100-500, or 200-400 fold, in the expression level and or activity of IL-6 as measured by an assay of Example 3.

In some embodiments, binding of the anti-TCRβV antibody molecule to a TCRβV region results in a reduction of at least 2, 5, 10, 20, 50, 100, 200, 300, 400, 500, 600, 700, 800, 900, 1000, or 2000 fold, or at least 2-2000 fold, optionally 5-1000, 10-900, 20-800, 50-700, 100-600, 200-500, or 300-400 fold, in the expression level and or activity of TNFα as measured by an assay of Example 3.

In some embodiments, binding of the anti-TCRβV antibody molecule to a TCRβV region results in an increase of at least 2, 5, 10, 20, 50, 100, 200, 300, 400, 500, 600, 700, 800, 900, 1000, or 2000 fold, or at least 2-2000 fold, optionally 5-1000, 10-900, 20-800, 50-700, 100-600, 200-500, or 300-400 fold, in the expression level and or activity of IL-2 as measured by an assay of Example 3.

In some embodiments, the anti-TCRβV antibody molecule comprises an antigen binding domain comprising a single chain Fv (scFv) or a Fab.

In some embodiments, the anti-TCRβV antibody molecule binds to a conformational or a linear epitope on the T cell.

In some embodiments, the anti-TCRβV antibody molecule is a full antibody, optionally an antibody that includes at least one, and preferably two, complete heavy chains, and at least one, and preferably two, complete light chains, or an antigen-binding fragment, optionally a Fab, $F(ab')_2$, Fv, a single chain Fv fragment, a single domain antibody, a diabody (dAb), a bivalent antibody, or bispecific antibody or fragment thereof, a single domain variant thereof, or a camelid antibody.

In some embodiments, the anti-TCRβV antibody molecule comprises one or more heavy chain constant regions chosen from IgG1, IgG2, IgG3, IgGA1, IgGA2, IgG4, IgJ, IgM, IgD, or IgE, or a fragment thereof, optionally as described in Table 3.

In some embodiments, the anti-TCRβV antibody molecule comprises a heavy chain constant region of an IgM or a fragment thereof, optionally wherein the IgM heavy chain constant region comprises the sequence of SEQ ID NO: 73, or a sequence with at least 85%, 90%, 95%, or 99% sequence identity thereto.

In some embodiments, the anti-TCRβV antibody molecule comprises a heavy chain constant region of an IgJ or a fragment thereof, optionally wherein the IgJ heavy chain constant region comprises the sequence of SEQ ID NO: 76 or a sequence with at least 85%, 90%, 95%, or 99% sequence identity thereto.

In some embodiments, the anti-TCRβV antibody molecule comprises a heavy chain constant region of an IgGA1, or a fragment thereof, optionally wherein the IgGA1 heavy chain constant region comprises the sequence of SEQ ID NO: 74, or a sequence with at least 85%, 90%, 95%, or 99% sequence identity thereto.

In some embodiments, the anti-TCRβV antibody molecule comprises a heavy chain constant region of an IgGA2, or a fragment thereof, optionally wherein the IgGA2 heavy chain constant region comprises a sequence listed in Table 3, optionally SEQ ID NO: 75, or a sequence with at least 85%, 90%, 95%, or 99% sequence identity thereto.

In some embodiments, the anti-TCRβV antibody molecule comprises a light chain constant region chosen from the light chain constant regions of kappa or lambda, or a fragment thereof, optionally as described in Table 3.

In some embodiments, the anti-TCRβV antibody molecule comprises a light chain constant region of a kappa chain, or a fragment thereof, optionally wherein the kappa chain constant region comprises the sequence of SEQ ID NO: 39, or a sequence with at least 85%, 90%, 95%, or 99% sequence identity thereto.

In some embodiments, the anti-TCRβV antibody molecule comprises:

(i) one or more heavy chain constant regions comprising a heavy chain constant region chosen from IgG1, IgG2, IgG3, IgGA1, IgGA2, IgG4, IgJ, IgM, IgD, or IgE, or a fragment thereof, optionally as described in Table 3; and
(ii) a light chain constant region comprising a light chain constant region chosen from the light chain constant regions of kappa or lambda, or a fragment thereof, optionally as described in Table 3.

In some embodiments, the anti-TCRβV antibody molecule comprises:

(i) a heavy chain constant region comprising:

(a) an IgM heavy chain constant region or a fragment thereof, comprising the sequence of SEQ ID NO: 73, or a sequence with at least 85%, 90%, 95%, or 99% sequence identity thereto;

(b) an IgGA1 heavy chain constant region or a fragment thereof, comprising the sequence of SEQ ID NO: 74, or a sequence with at least 85%, 90%, 95%, or 99% sequence identity thereto; or (c) an IgGA2 heavy chain constant region or a fragment thereof, comprising the sequence of SEQ ID NO: 75, or a sequence with at least 85%, 90%, 95%, or 99% sequence identity thereto; and (ii) a light chain constant region comprising a kappa chain constant region comprising the sequence of SEQ ID NO: 39, or a sequence with at least 85%, 90%, 95%, or 99% sequence identity thereto, optionally wherein, the anti-TCRβV antibody molecule further comprises an IgJ heavy chain constant region or a fragment thereof, wherein the IgJ heavy chain constant region comprises the sequence of SEQ ID NO: 76 or a sequence with at least 85%, 90%, 95%, or 99% sequence identity thereto.

In some embodiments, the second moiety is a tumor-targeting moiety.

In some embodiments, the second moiety is a cytokine molecule.

In some embodiments, the second moiety is a stromal modifying moiety.

In some embodiments, the second moiety is an anti-TCRβV antibody molecule other than the first moiety.

In some embodiments, the first and/or second moiety binds to and activates an immune cell, optionally an effector cell.

In some embodiments, the first and/or second moiety binds to, but does not activate an immune cell, optionally an effector cell.

In some embodiments, the second moiety is chosen from an NK cell engager, a T cell engager other than an anti-TCRβV antibody molecule, a B cell engager, a dendritic cell engager, or a macrophage cell engager, or a combination thereof.

In some embodiments, the tumor-targeting moiety comprises an antibody molecule, optionally Fab or scFv, a receptor molecule, optionally a receptor, a receptor fragment or functional variant thereof, or a ligand molecule, optionally a ligand, a ligand fragment or functional variant thereof, or a combination thereof, that binds to a cancer antigen.

In some embodiments, the tumor-targeting moiety binds to a cancer antigen present on a cancer, optionally a hematological cancer, a solid tumor, a metastatic cancer, soft tissue tumor, metastatic lesion, or a combination thereof.

In some embodiments, the cancer antigen is a tumor antigen or stromal antigen, or a hematological antigen.

In some embodiments, the cancer antigen is chosen from: BCMA, CD19, CD20, CD22, FcRH5, PDL1, CD47, ganglioside 2 (GD2), prostate stem cell antigen (PSCA), prostate specific membrane antigen (PMSA), prostate-specific antigen (PSA), carcinoembryonic antigen (CEA), Ron Kinase, c-Met, Immature laminin receptor, TAG-72, BING-4, Calcium-activated chloride channel 2, Cyclin-B1, 9D7, Ep-CAM, EphA3, Her2/neu, Telomerase, SAP-1, Survivin, NY-ESO-1/LAGE-1, PRAME, SSX-2, Melan-A/MART-1, Gp100/pmel17, Tyrosinase, TRP-1/-2, MC1R, β-catenin, BRCA1/2, CDK4, CML66, Fibronectin, p53, Ras, TGF-B receptor, AFP, ETA, MAGE, MUC-1, CA-125, BAGE, GAGE, NY-ESO-1, β-catenin, CDK4, CDC27, α actinin-4, TRP1/gp75, TRP2, gp100, Melan-A/MART1, gangliosides, WT1, EphA3, Epidermal growth factor receptor (EGFR), MART-2, MART-1, MUC1, MUC2, MUM1, MUM2, MUM3, NA88-1, NPM, OA1, OGT, RCC, RUI1, RUI2, SAGE, TRG, TRP1, TSTA, Folate receptor alpha, L1-CAM, CAIX, gpA33, GD3, GM2, VEGFR, Integrins (Integrin alphaVbeta3, Integrin alpha5Beta1), Carbohydrates (Le), IGF1R, EPHA3, TRAILR1, TRAILR2, RANKL, (FAP), TGF-beta, hyaluronic acid, collagen, optionally collagen IV, tenascin C, or tenascin W.

In some embodiments, the tumor-targeting moiety is a BCMA targeting moiety or a FcRH5 targeting moiety.

In some embodiments, the cancer is a solid tumor including but not limited to: pancreatic, optionally pancreatic adenocarcinoma, cancer, breast cancer, colorectal cancer, lung cancer, optionally small or non-small cell lung cancer, skin cancer, ovarian cancer, or liver cancer.

In some embodiments, the cancer is a hematological cancer including, but not limited to: a B-cell or T cell malignancy, optionally Hodgkin's lymphoma, Non-Hodgkin's lymphoma, optionally B cell lymphoma, diffuse large B cell lymphoma, follicular lymphoma, chronic lymphocytic leukemia, mantle cell lymphoma, marginal zone B-cell lymphoma, Burkitt lymphoma, lymphoplasmacytic lymphoma, hairy cell leukemia, acute myeloid leukemia (AML), chronic myeloid leukemia, myelodysplastic syndrome, multiple myeloma, and acute lymphocytic leukemia.

In some embodiments, the cytokine molecule is chosen from interleukin-2 (IL-2), interleukin-7 (IL-7), interleukin-12 (IL-12), interleukin-15 (IL-15), interleukin-18 (IL-18), interleukin-21 (IL-21), or interferon gamma, or a fragment, variant or combination thereof.

In some embodiments, the cytokine molecule is a monomer or a dimer.

In some embodiments, the cytokine molecule further comprises a receptor dimerizing domain, optionally an IL15Ralpha dimerizing domain.

In some embodiments, the cytokine molecule, optionally IL-15) and the receptor dimerizing domain, optionally an IL15Ralpha dimerizing domain, are not covalently linked, optionally are non-covalently associated.

In some embodiments, the multispecific molecule as provided herein further comprises an immunoglobulin constant region, optionally Fc region, chosen from the heavy chain constant regions of IgG1, IgG2, IgG3, IgGA1, IgGA2, IgG4, IgJ, IgM, IgD, or IgE, or a fragment thereof, optionally wherein, the heavy chain constant region comprises the heavy chain constant region of human IgG1, IgG2 or IgG4.

In some embodiments, the immunoglobulin constant region, optionally an Fc region, is linked, optionally covalently linked to, one or more of tumor-targeting moiety, the cytokine molecule, or the stromal modifying moiety.

In some embodiments, an interface of a first and second immunoglobulin chain constant regions, optionally Fc region, is altered, optionally mutated, to increase or decrease dimerization, optionally relative to a non-engineered interface.

In some embodiments, the dimerization of the immunoglobulin chain constant region, optionally Fc region, is enhanced by providing an Fc interface of a first and a second Fc region with one or more of: a paired cavity-protuberance ("knob-in-a hole"), an electrostatic interaction, or a strand-exchange, such that a greater ratio of heteromultimer:homomultimer forms, optionally relative to a non-engineered interface.

In some embodiments, the multispecific molecule as provided herein further comprises a linker, optionally a linker described herein, optionally wherein the linker is selected from: a cleavable linker, a non-cleavable linker, a peptide linker, a flexible linker, a rigid linker, a helical linker, or a non-helical linker.

In another aspect, provided herein is an isolated nucleic acid molecule comprising a nucleotide sequence encoding the anti-TCRβV antibody molecule as provided herein, or a nucleotide sequence having at least 75%, 80%, 85%, 90%, 95%, or 99% identity thereto.

In another aspect, provided herein is an isolated nucleic acid molecule comprising a nucleotide sequence encoding the multispecific molecule as provided herein, or a nucleotide sequence having at least 75%, 80%, 85%, 90%, 95%, or 99% identity thereto.

In another aspect, provided herein is a vector, optionally an expression vector, comprising one or more of the nucleic acid molecules as provided herein.

In another aspect, provided herein is a cell, optionally host cell, comprising the nucleic acid molecule as provided herein, or the vector as provided herein.

In another aspect, provided herein is a method of making, optionally producing or manufacturing, the anti-TCRβV antibody molecule as provided herein, or the multispecific molecule as provided herein, comprising culturing the host cell as provided herein, under suitable conditions, optionally conditions suitable expression of the anti-TCRβV antibody molecule or the multispecific molecule.

In another aspect, provided herein is a pharmaceutical composition comprising the anti-TCRβV antibody molecule as provided herein, or the multispecific molecule as provided herein, and a pharmaceutically acceptable carrier, excipient, or stabilizer.

In another aspect, provided herein is a method of modulating, optionally enhancing, an immune response in a subject comprising administering to the subject an effective amount of an antibody molecule which binds, optionally specifically binds, to a T cell receptor beta variable region (TCRβV) ("anti-TCRβV antibody molecule").

In another aspect, provided herein is a method of modulating, optionally enhancing, an immune response in a subject comprising administering to the subject an effective amount of the multispecific molecule as provided herein.

In some embodiments, the method comprises expanding, optionally increasing the number of, an immune cell population in the subject.

In another aspect, provided herein is a method of expanding, optionally increasing the number of, an immune cell population comprising, contacting the immune cell population with an effective amount of an antibody molecule which binds, optionally specifically binds, to a T cell receptor beta variable region (TCRβV) ("anti-TCRβV antibody molecule").

In another aspect, provided herein is a method of expanding, optionally increasing the number of, an immune cell population comprising, contacting the immune cell population with an effective amount of the multispecific molecule as provided herein.

In some embodiments, the expansion occurs in vivo or ex vivo, optionally in vitro.

In some embodiments, the immune cell population comprises a TCRβV expressing cell, optionally a TCRβV+ cell.

In some embodiments, the TCRβV expressing cell is a T cell, optionally a CD8+ T cell, a CD3+ T cell or a CD4+ T cell.

In some embodiments, the immune cell population comprises a T cell, optionally a CD4 T cell, a CD8 T cell, optionally an effector T cell, a T cell having a memory-like phenotype or a memory T cell, optionally a memory effector T cell, optionally TEM cell, optionally TEMRA cell, or a tumor infiltrating lymphocyte (TIL).

In some embodiments, the immune cell population comprises a T cell, a Natural Killer cell, a B cell, or a myeloid cell.

In some embodiments, the immune cell population is obtained from a healthy subject.

In some embodiments, the immune cell population is obtained from a subject, optionally from an apheresis sample from the subject, having a disease, optionally a cancer, optionally as described herein, optionally wherein the immune cell population comprises a tumor infiltrating lymphocyte (TIL).

In some embodiments, the method results in an expansion of at least 1.1-10 fold, optionally at least 1.1, 1.2, 1.3, 1.4, 1.5, 2, 3, 4, 5, 6, 7, 8, 9, or 10 fold expansion.

In some embodiments, the method as provided herein further comprises contacting the population of cells with an agent that promotes, optionally increases, immune cell expansion.

In some embodiments, the method as provided herein further comprises contacting the population of cells with an immune checkpoint inhibitor, optionally a PD-1 inhibitor.

In some embodiments, the method as provided herein further comprises contacting the population of cells with a 4-1BB (CD127) agonist, optionally an anti-4-1BB antibody.

In some embodiments, the method as provided herein further comprises contacting the population of cells with a non-dividing population of cells, optionally feeder cells, optionally irradiated allogenic human PBMCs.

In some embodiments, the population of cells is expanded in an appropriate media, optionally media described herein, that includes one or more cytokines, optionally IL-2, IL-7, IL-15, or a combination thereof.

In some embodiments, the population of cells is expanded for a period of at least about 4 hours, 6 hours, 10 hours, 12 hours, 15 hours, 18 hours, 20 hours, or 22 hours, or for at least 1, 2, 3, 4, 5, 6, 7, 8, 9, 10, 11, 12, 13, 14, 15, 1, 6 17, 18, 19, 20 or 21 days, or for at least about 1 week, 2 weeks, 3 weeks, 4 weeks, 5 weeks, 6 weeks, 7 weeks or 8 weeks.

In some embodiments, expansion of the population of immune cells, is compared to expansion of a similar population of cells with an antibody that binds to: a CD3 molecule, optionally CD3 epsilon (CD3ε) molecule; or a TCR alpha (TCRα) molecule.

In some embodiments, expansion of the population of immune cells, is compared to expansion of a similar population of cells not contacted with the anti-TCRβV antibody molecule, or multispecific molecule comprising the anti-TCRβV antibody molecule.

In some embodiments, expansion of the population of T cells having a memory-like phenotype, optionally CD45RA+ CCR7− cells, optionally memory effector T cells, optionally TEM cells, optionally TEMRA cells, is compared to expansion of a similar population of cells with an antibody that binds to: a CD3 molecule, optionally CD3 epsilon (CD3ε) molecule; or a TCR alpha (TCRα) molecule.

In some embodiments, the population of expanded T cells having a memory-like phenotype, optionally effector memory cells, comprises cells which:

(i) have a detectable level of CD45RA, optionally express or re-express CD45RA;
(ii) have low or no expression of CCR7; and/or
(iii) have a detectable level of CD95, optionally express CD95,
optionally a population of CD45RA+, CCR7−, CD95+ T cells, optionally wherein the T cells comprise CD3+, CD4+ or CD8+ T cells.

In some embodiments, the method results in expansion of, optionally selective or preferential expansion of, T cells expressing a T cell receptor (TCR) comprising a TCR alpha and/or TCR beta molecule, optionally TCR alpha-beta T cells (αβ T cells).

In some embodiments, the method results in expansion of αβT cells over expansion of T cells expressing a TCR comprising a TCR gamma and/or TCR delta molecule, optionally TCR gamma-delta T cells (γδ T cells).

In another aspect, provided herein is a method of treating a disease, optionally cancer, in a subject comprising administering to the subject an effective amount of an antibody molecule which binds, optionally specifically binds, to a T cell receptor beta variable region (TCRβV) ("anti-TCRβV antibody molecule"), thereby treating the cancer.

In another aspect, provided herein is a composition comprising an antibody molecule which binds, optionally specifically binds, to a T cell receptor beta variable region (TCRβV) ("anti-TCRβV antibody molecule"), for use in treating a disease, optionally cancer, in a subject.

In another aspect, provided herein is a composition comprising an antibody molecule which binds, optionally specifically binds, to a T cell receptor beta variable region (TCRβV) ("anti-TCRβV antibody molecule"), for use in the manufacture of a medicament for treating a disease, optionally cancer, in a subject.

In another aspect, provided herein is a method of treating a disease, optionally cancer, in a subject comprising administering to the subject an effective amount of the multispecific molecule as provided herein, thereby treating the cancer.

In another aspect, provided herein is a composition comprising the multispecific molecule as provided herein, for use in treating a disease, optionally cancer, in a subject.

In another aspect, provided herein is a composition comprising the multispecific molecule as provided herein, for use in the manufacture of a medicament for treating a disease, optionally cancer, in a subject.

In another aspect, provided herein is a method of treating, optionally preventing or reducing, cytokine release syndrome (CRS) and/or neurotoxicity (NT) in a subject, optionally CRS and/or NT associated with a treatment, optionally a previously administered treatment, comprising administering to the subject an effective amount of an antibody molecule which binds, optionally specifically binds, to a T cell receptor beta variable region (TCRβV) ("anti-TCRβV antibody molecule"), thereby preventing CRS and/or NT in the subject.

In another aspect, provided herein is a method of treating, optionally preventing or reducing, cytokine release syndrome (CRS) and/or neurotoxicity (NT) in a subject, optionally CRS and/or NT associated with a treatment, optionally a previously administered treatment, comprising administering to the subject an effective amount the multispecific molecule as provided herein, thereby preventing CRS and/or NT in the subject.

In another aspect, provided herein is a method of targeting a therapy, optionally treatment, to a T cell in a subject having a disease, optionally cancer, comprising administering an effective amount of:
(i) an antibody molecule which binds, optionally specifically binds, to a T cell receptor beta variable region (TCRβV) ("anti-TCRβV antibody molecule"); and
(ii) the therapy, optionally a tumor targeting therapy, optionally an antibody that binds to a cancer antigen, optionally as described herein,
thereby targeting the therapy to the T cell in the subject.

In another aspect, provided herein is a method of targeting a therapy, optionally treatment, to a T cell in a subject having a disease, optionally cancer, comprising administering an effective amount of:
(i) the multispecific molecule as provided herein; and
(ii) the therapy, optionally a tumor targeting therapy, optionally an antibody that binds to a cancer antigen, optionally as described herein,
thereby targeting the therapy to the T cell in the subject.

In some embodiments, the method results in: reduced cytokine release syndrome (CRS), optionally lesser duration of CRS or no CRS, or a reduced severity of CRS, optionally absence of severe CRS, optionally CRS grade 4 or 5, compared to administration of (ii) alone.

In some embodiments, the anti-TCRβV antibody or the multispecific molecule is administered concurrently with or after the administration of the treatment associated with CRS.

In another aspect, provided herein is a method of treating a subject having a cancer, the method comprising:
acquiring a value of the status of a TCRβV subfamily for the subject, wherein said value comprises a measure of the presence of, optionally level or activity of, a TCRβV molecule in a sample from the subject, and
administering an effective amount of an antibody molecule which binds, optionally specifically binds, to a T cell receptor beta variable region (TCRβV) ("anti-TCRβV antibody molecule"); to the subject,
thereby treating the subject.

In another aspect, provided herein is a method of treating a subject having a cancer, the method comprising:
acquiring a value of the status of a TCRβV subfamily for the subject, wherein said value comprises a measure of the presence of, optionally level or activity of, a TCRβV molecule in a sample from the subject, and
administering an effective amount of the multispecific molecule as provided herein to the subject, thereby treating the subject.

In another aspect, provided herein is a method of treating a subject having a cancer, the method comprising administering an effective amount of an antibody molecule which binds, optionally specifically binds, to a T cell receptor beta variable region (TCRβV) ("anti-TCRβV antibody molecule") to the subject, wherein the subject has a higher, optionally increased, level or activity of one or more TCRβV subfamilies, optionally as described herein, compared to a reference level or activity of one or more TCRβV subfamilies, optionally in a healthy subject, optionally a subject not having a cancer.

In another aspect, provided herein is a method of treating a subject having a cancer, the method comprising administering an effective amount of the multispecific molecule as provided herein to the subject, wherein the subject has a higher, optionally increased, level or activity of one or more TCRβV subfamilies, optionally as described herein, compared to a reference level or activity of one or more TCRβV subfamilies, optionally in a healthy subject, optionally a subject not having a cancer.

In another aspect, provided herein is a method of expanding a population of immune effector cells from a subject having a cancer, the method comprising:

(i) isolating a biological sample comprising a population of immune effector cells from the subject; optionally a peripheral blood sample, biopsy sample, or bone marrow sample;

(ii) acquiring a value of the status of one or more TCRβV subfamilies for the subject, optionally in the biological sample from the subject, wherein said value comprises a measure of the presence of, optionally level or activity of, a TCRβV subfamily in a sample from the subject compared to a reference value, optionally a sample from a health subject, wherein a value that is higher, optionally increased, in the subject relative to the reference, optionally healthy subject, is indicative of the presence of cancer in the subject, and (iii) contacting the biological sample comprising a population of immune effector cells with an anti-TCRβV antibody molecule, optionally as described herein.

In some embodiments, the method as provided herein further comprises administering the population of immune effector cells contacted with the anti-TCRβV antibody molecule to the subject.

In another aspect, provided herein is a method of expanding a population of immune effector cells from a subject having a cancer, the method comprising:

(i) isolating a biological sample comprising a population of immune effector cells from the subject; optionally a peripheral blood sample, biopsy sample, or bone marrow sample;

(ii) acquiring a value of the status of one or more TCRβV subfamilies for the subject, optionally in the biological sample from the subject, wherein said value comprises a measure of the presence of, optionally level or activity of, a TCRβV subfamily in a sample from the subject compared to a reference value, optionally a sample from a health subject, wherein a value that is higher, optionally increased, in the subject relative to the reference, optionally healthy subject, is indicative of the presence of cancer in the subject, and (iii) contacting the biological sample comprising a population of immune effector cells with the multispecific molecule as provided herein.

In some embodiments, the method as provided herein further comprises administering the population of immune effector cells contacted with the multispecific molecule to the subject.

In some embodiments, the method as provided herein comprises measuring T cell function, optionally cytotoxic activity, cytokine secretion, or degranulation, in the population of immune effector cells, optionally compared to a reference population, optionally an otherwise similar population not contacted with the anti-TCRβV antibody molecule or a population of immune effector cells obtained from a healthy subject, optionally a subject that does not have a cancer.

In some embodiments, the biological sample comprising the population of immune effector cells is contacted with an anti-TCRβV antibody molecule or a multispecific molecule that binds to the one or more TCRβV subfamilies, optionally the same TCRβV subfamily, identified as being higher, optionally increased, in the biological sample.

In some embodiments, the biological sample comprising the population of immune effector cells is contacted with an anti-TCRβV antibody molecule or a multispecific molecule that does not bind to the one or more TCRβV subfamilies, optionally a different TCRβV subfamily, identified as being higher, optionally increased, in the biological sample.

In some embodiments, the cancer is a solid tumor including but not limited to: melanoma, pancreatic, optionally pancreatic adenocarcinoma, cancer, breast cancer, colorectal cancer (CRC), lung cancer, optionally small or non-small cell lung cancer, skin cancer, ovarian cancer, or liver cancer.

In some embodiments, the cancer is a hematological cancer including, but not limited to: a B-cell or T cell malignancy, optionally Hodgkin's lymphoma, Non-Hodgkin's lymphoma, optionally B cell lymphoma, diffuse large B cell lymphoma (DLBCL), follicular lymphoma, chronic lymphocytic leukemia (B-CLL), mantle cell lymphoma, marginal zone B-cell lymphoma, Burkitt lymphoma, lymphoplasmacytic lymphoma, or hairy cell leukemia, acute myeloid leukemia (AML), chronic myeloid leukemia, myelodysplastic syndrome, multiple myeloma, and acute lymphocytic leukemia.

In some embodiments, the cancer is B-CLL and the TCRβV molecule comprises:

(i) TCRβ V6 subfamily comprising, optionally TCRβ V6-4*01, TCRβ V6-4*02, TCRβ V6-9*01, TCRβ V6-8*01, TCRβ V6-5*01, TCRβ V6-6*02, TCRβ V6-6*01, TCRβ V6-2*01, TCRβ V6-3*01 or TCRβ V6-1*01;

(ii) TCRβ V5 subfamily comprising TCRβ V5-6*01, TCRβ V5-4*01, or TCRβ V5-8*01;

(iii) TCRβ V3 subfamily comprising TCRβ V3-1*01;

(iv) TCRβ V2 subfamily comprising TCRβ V2*01; or (v) TCRβ V19 subfamily comprising TCRβ V19*01, or TCRβ V19*02.

In some embodiments, the cancer is melanoma and the TCRβV molecule comprises the TCRβ V6 subfamily comprising, optionally TCRβ V6-4*01, TCRβ V6-4*02, TCRβ V6-9*01, TCRβ V6-8*01, TCRβ V6-5*01, TCRβ V6-6*02, TCRβ V6-6*01, TCRβ V6-2*01, TCRβ V6-3*01 or TCRβ V6-1*01.

In some embodiments, the cancer is DLBCL and the TCRβV molecule comprises:

(i) TCRβ V13 subfamily comprising TCRβ V13*01;

(ii) TCRβ V3 subfamily comprising TCRβ V3-1*01; or (iii) TCRβ V23 subfamily.

In some embodiments, the cancer is CRC and the TCRβV molecule comprises:

(i) TCRβ V19 subfamily comprising TCRβ V19*01, or TCRβ V19*02

(ii) TCRβ V12 subfamily comprising TCRβ V12-4*01, TCRβ V12-3*01, or TCRβ V12-5*01

(iii) TCRβ V16 subfamily comprising TCRβ V16*01; or (iv) TCRβ V21 subfamily.

In some embodiments, the tumor comprises an antigen, optionally a tumor antigen, optionally a tumor associated antigen or a neoantigen; and/or the one or more TCRβV subfamilies recognize, optionally bind to, the tumor antigen.

In some embodiments, the sample comprises a blood sample, optionally a peripheral blood sample, a biopsy, optionally a tumor biopsy, or a bone marrow sample.

In some embodiments, the sample comprises a biological sample comprising immune cells, optionally TCRBV expressing cells, optionally TCRBV+ cells, T cells, or NK cells.

In some embodiments, the T cells comprise a CD4 T cell, a CD8 T cell, optionally an effector T cell or a memory T cell, optionally a memory effector T cell, optionally $T_{EM}$ cell, optionally $T_{EMRA}$ cell, or a tumor infiltrating lymphocyte (TIL).

In some embodiments, the method results in an expansion, optionally in vivo or ex vivo expansion, of at least 1.1-1000 fold, optionally 1.1-10, 10-100, 100-200, 200-300, 300-400, 400-500, 500-600, 600-700, 700-800, 800-900, or 900-1000 fold expansion of an immune effector cell population comprising a TCRVB expressing immune effector cell, optionally T cell.

In some embodiments, the population of cells is expanded in an appropriate media, optionally media described herein, that includes one or more cytokines, optionally IL-2, IL-7, IL-15, or a combination thereof.

In some embodiments, the population of cells is expanded for a period of at least about 4 hours, 6 hours, 10 hours, 12 hours, 15 hours, 18 hours, 20 hours, or 22 hours, or for at least 1, 2, 3, 4, 5, 6, 7, 8, 9, 10, 11, 12, 13, 14, 15, 1, 6 17, 18, 19, 20 or 21 days, or for at least about 1 week, 2 weeks, 3 weeks, 4 weeks, 5 weeks, 6 weeks, 7 weeks or 8 weeks.

In some embodiments, expansion of the population of immune cells, is compared to expansion of a similar population of cells with an antibody that binds to: a CD3 molecule, optionally CD3 epsilon (CD3ε) molecule; or a TCR alpha (TCRα) molecule.

In some embodiments, expansion of the population of immune cells, is compared to expansion of a similar population of cells not contacted with the anti-TCRβV antibody molecule.

In some embodiments, expansion of the population of T cells having a memory-like phenotype, optionally memory effector T cells, optionally TEM cells, optionally TEMRA cells, is compared to expansion of a similar population of cells with an antibody that binds to: a CD3 molecule, optionally CD3 epsilon (CD3e) molecule; or a TCR alpha (TCRα) molecule.

In some embodiments, the population of expanded T cells having a memory-like phenotype, optionally effector memory cells, comprises cells which:

(i) have a detectable level of CD45RA, optionally express or re-express CD45RA;

(ii) have low or no expression of CCR7; and/or (iii) have a detectable level of CD95, optionally express CD95, optionally a population of CD45RA+, CCR7−, CD95+ T cells, optionally wherein the T cells comprise CD3+, CD4+ or CD8+ T cells.

In some embodiments, the method results in expansion of, optionally selective or preferential expansion of, T cells expressing a T cell receptor (TCR) comprising a TCR alpha and/or TCR beta molecule, optionally TCR alpha-beta T cells (αβ T cells).

In some embodiments, the method results in expansion of αβT cells over expansion of T cells expressing a TCR comprising a TCR gamma and/or TCR delta molecule, optionally TCR gamma-delta T cells (γδ T cells).

In some embodiments, the anti-TCRβV antibody molecule comprises an antigen binding domain comprising a light chain variable region (VL) comprising one, two or all of a LC CDR1, a LC CDR2 and a LC CDR3 of a VL disclosed in Tables 1, 2, 10, 11, 12 or 13, optionally SEQ ID NO: 1314, SEQ ID NO: 2, SEQ ID NO: 10, SEQ ID NO: 11, SEQ ID NO: 16, SEQ ID NO: 26, SEQ ID NO: 27, SEQ ID NO: 28, SEQ ID NO: 29 or SEQ ID NO:30

In some embodiments, the anti-TCRβV antibody molecule comprises an antigen binding domain comprising a heavy chain variable region (VH) comprising one, two or all of a HC CDR1, a HC CDR2 and a HC CDR3 of a VH disclosed in Tables 1, 2, 10, 11, 12 or 13, optionally SEQ ID NO: 1312, SEQ ID NO:1, SEQ ID NO: 9, SEQ ID NO: 15, SEQ ID NO: 23, SEQ ID NO: 24 or SEQ ID NO: 25.

In some embodiments, the anti-TCRβV antibody molecule comprises an antigen binding domain comprising:

(i) a VL comprising: a LC CDR1 amino acid sequence of SEQ ID NO: 20 or an amino acid sequence with not more than 1, 2, 3 or 4 modifications, optionally substitutions, additions or deletions thereof, a LC CDR2 amino acid sequence of SEQ ID NO:21 or an amino acid sequence with not more than 1, 2, 3 or 4 modifications, optionally substitutions, additions or deletions thereof, and/or a LC CDR3 amino acid sequence of SEQ ID NO:22 or an amino acid sequence with not more than 1, 2, 3 or 4 modifications, optionally substitutions, additions or deletions thereof; and/or (ii) a VH comprising: a HC CDR1 amino acid sequence of SEQ ID NO: 17 or an amino acid sequence with not more than 1, 2, 3 or 4 modifications, optionally substitutions, additions or deletions thereof, a HC CDR2 amino acid sequence of SEQ ID NO:18 or an amino acid sequence with not more than 1, 2, 3 or 4 modifications, optionally substitutions, additions or deletions thereof, and/or a HC CDR3 amino acid sequence of SEQ ID NO:19 or an amino acid sequence with not more than 1, 2, 3 or 4 modifications, optionally substitutions, additions or deletions thereof.

In some embodiments, the anti-TCRβV antibody molecule comprises an antigen binding domain comprising:

a variable heavy chain (VH) of SEQ ID NO: 23, SEQ ID NO: 24 or SEQ ID NO: 25, or a sequence having at least about 85%, 90%, 95%, or 99% sequence identity thereto; and/or a variable light chain (VL) of SEQ ID NO: 26, SEQ ID NO: 27, SEQ ID NO: 28, SEQ ID NO: 29 or SEQ ID NO:30, or a sequence having at least about 85%, 90%, 95%, or 99% sequence identity thereto.

In some embodiments, the anti-TCRβV antibody molecule comprises an antigen binding domain comprising (i) a VL comprising: a LC CDR1 amino acid sequence of SEQ ID NO: 6 or an amino acid sequence with not more than 1, 2, 3 or 4 modifications, optionally substitutions, additions or deletions thereof, a LC CDR2 amino acid sequence of SEQ ID NO:7 or an amino acid sequence with not more than 1, 2, 3 or 4 modifications, optionally substitutions, additions or deletions thereof, and/or a LC CDR3 amino acid sequence of SEQ ID NO: 8 or an amino acid sequence with not more than 1, 2, 3 or 4 modifications, optionally substitutions, additions or deletions thereof, and/or (ii) a VH comprising: a HC CDR1 amino acid sequence of SEQ ID NO: 3 or an amino acid sequence with not more than 1, 2, 3 or 4 modifications, optionally substitutions, additions or deletions thereof, a HC CDR2 amino acid sequence of SEQ ID NO:4 or an amino acid sequence with not more than 1, 2, 3 or 4 modifications, optionally substitutions, additions or deletions thereof, and/or a HC CDR3 amino acid sequence of SEQ ID NO:5 or an amino acid sequence with not more than 1, 2, 3 or 4 modifications, optionally substitutions, additions or deletions thereof.

In some embodiments, the anti-TCRβV antibody molecule comprises an antigen binding domain comprising:

a variable heavy chain (VH) of SEQ ID NO: 1 or SEQ ID NO: 9 or SEQ ID NO: 1312, or a sequence having at least about 85%, 90%, 95%, or 99% sequence identity thereto; and/or a variable light chain (VL) of SEQ ID NO: 2, SEQ ID NO: 10 or SEQ ID NO:11 or SEQ ID NO: 1314, or a sequence having at least about 85%, 90%, 95%, or 99% sequence identity thereto.

In some embodiments, the anti-TCRβV antibody molecule comprises a light chain comprising a framework region, optionally framework region 1 (FR1), comprising one, two or all, optionally three, of:

(i) an Aspartic Acid at position 1, optionally a substitution at position 1 according to Kabat numbering, optionally a Alanine to Aspartic Acid substitution; or (ii) an Asparagine at position 2, optionally a substitution at position 2 according to Kabat numbering, optionally a Isoleucine to Asparagine, a Serine to Asparagine, or a Tyrosine to Asparagine substitution; or (iii) a Leucine at position 4, optionally a substitution at position 4 according to Kabat numbering, optionally a Methionine to Leucine substitution, wherein the substitution is relative to a human germline light chain framework region sequence.

In some embodiments, the anti-TCRβV antibody molecule comprises a light chain comprising a framework region, optionally framework region 3 (FR3), comprising one, two or all, optionally three, of:

(i) a Glycine at position 66, optionally a substitution at position 66 according to Kabat numbering, optionally a Lysine to Glycine, or a Serine to Glycine substitution; or (ii) an Asparagine at position 69, optionally a substitution at position 69 according to Kabat numbering, optionally a Threonine to Asparagine substitution; or (iii) a Tyrosine at position 71, optionally a substitution at position 71 according to Kabat numbering, optionally a Phenylalanine to Tyrosine, or Alanine to Tyrosine substitution, wherein the substitution is relative to a human germline light chain framework region sequence.

In some embodiments, binding of the anti-TCRβV antibody molecule to the TCRβV region results in a cytokine profile that differs from a cytokine profile of a T cell engager that binds to a receptor or molecule other than a TCRβV region ("a non-TCRβV-binding T cell engager").

In some embodiments, the non-TCRβV-binding T cell engager comprises an antibody that binds to a CD3 molecule, optionally CD3 epsilon (CD3ε) molecule; or a TCR alpha (TCRa) molecule.

In some embodiments, the cytokine profile of the first moiety comprises, one, two, three, four, five, six, seven, or all of the following:

(i) increased level, optionally expression level, and/or activity of IL-2;

(ii) reduced level, optionally expression level, and/or activity of IL-1β;

(iii) reduced level, optionally expression level, and/or activity of IL-6;

(iv) reduced level, optionally expression level, and/or activity of TNFα;

(v) reduced level, optionally expression level, and/or activity of IL-10;

(vi) a delay, optionally at least 1, 2, 3, 4, 5, 6, 7, 8, 9, 10 or more hours delay, in increased level, optionally expression level, and/or activity of IL-2;

(vii) a delay, optionally at least 1, 2, 3, 4, 5, 6, 7, 8, 9, 10 hours delay, in increased level, optionally expression level, and/or activity of IFNg; or (viii) increased level, optionally expression level, and/or activity of IL-15, optionally wherein (i)-(vii) are relative to the cytokine profile of the non-TCRβV-binding T cell engager.

In some embodiments, binding of the anti-TCRβV antibody molecule to the TCRβV region results in reduced cytokine storm, optionally reduced cytokine release syndrome (CRS), as measured by an assay of Example 3, optionally relative to the cytokine storm induced by the non-TCRβV-binding T cell engager.

In some embodiments, binding of the anti-TCRβV antibody molecule to the TCRβV region results in one, two, three or all of:

(ix) reduced T cell proliferation kinetics;

(x) cell killing, optionally target cell killing, optionally cancer cell killing, optionally as measured by an assay of Example 4;

(xi) increased Natural Killer (NK) cell proliferation, optionally expansion; or (xii) expansion, optionally at least about 1.1-10 fold expansion, optionally at least about 1.1, 1.2, 1.3, 1.4, 1.5, 2, 3, 4, 5, 6, 7, 8, 9, or 10 fold expansion, of a population of T cells having a memory-like phenotype, optionally relative to the non-TCRβV-binding T cell engager.

In some embodiments, the anti-TCRβV antibody molecule binds to an outward facing region, optionally epitope, on a TCRβV protein, optionally as depicted by the circled area in FIG. 24A.

In some embodiments, the outward facing region on the TCRβV protein comprises a structurally conserved region of TCRβV, optionally a region of TCRβV having a similar structure across one or more TCRβV subfamilies.

In some embodiments, the method further comprises administering, optionally sequentially, simultaneously or concurrently, a second agent, optionally therapeutic agent, optionally as described herein.

In some embodiments, the second agent, optionally therapeutic agent, comprises a chemotherapeutic agent, a biologic agent, hormonal therapy, radiation, or surgery.

In some embodiments, the disease is a cancer, optionally a solid tumor or a hematological cancer, or a metastatic lesion.

In some embodiments, the cancer antigen is BCMA or FcRH5.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and are not intended to be limiting.

Other features and advantages of the invention will be apparent from the following detailed description and claims.

INCORPORATION BY REFERENCE

All publications and patents mentioned herein are hereby incorporated by reference in their entirety as if each individual publication or patent was specifically and individually indicated to be incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

SEQUENCE LISTING

```
Sequence total quantity: 3642
SEQ ID NO: 1            moltype = AA  length = 119
FEATURE                 Location/Qualifiers
source                  1..119
                        mol_type = protein
                        organism = synthetic construct
SEQUENCE: 1
QVQLQQSGPE LVKPGTSVKI SCKASGYSFT TYYIHWVKQR PGQGLEWIGW FFPGSGNIKY  60
NEKFKGKATL TADTSSSTAY MQLSSLTSEE SAVYFCAGSY YSYDVLDYWG HGTTLTVSS   119

SEQ ID NO: 2            moltype = AA  length = 107
FEATURE                 Location/Qualifiers
source                  1..107
                        mol_type = protein
                        organism = synthetic construct
SEQUENCE: 2
DILMTQSQKF MSTSLGDRVS VSCKASQNVG INVVWHQQKP GQSPKALIYS SSHRYSGVPD  60
RFTGSGSGTD FTLTINNVQS EDLAEYFCQQ FKSYPLTFGA GTKLELK                107

SEQ ID NO: 3            moltype = AA  length = 10
FEATURE                 Location/Qualifiers
source                  1..10
                        mol_type = protein
                        organism = synthetic construct
SEQUENCE: 3
GYSFTTYYIH                                                         10

SEQ ID NO: 4            moltype = AA  length = 17
FEATURE                 Location/Qualifiers
source                  1..17
                        mol_type = protein
                        organism = synthetic construct
SEQUENCE: 4
WFFPGSGNIK YNEKFKG                                                 17

SEQ ID NO: 5            moltype = AA  length = 10
FEATURE                 Location/Qualifiers
source                  1..10
                        mol_type = protein
                        organism = synthetic construct
SEQUENCE: 5
SYYSYDVLDY                                                         10

SEQ ID NO: 6            moltype = AA  length = 11
FEATURE                 Location/Qualifiers
source                  1..11
                        mol_type = protein
                        organism = synthetic construct
SEQUENCE: 6
KASQNVGINV V                                                       11

SEQ ID NO: 7            moltype = AA  length = 7
FEATURE                 Location/Qualifiers
source                  1..7
                        mol_type = protein
                        organism = synthetic construct
SEQUENCE: 7
SSSHRYS                                                            7

SEQ ID NO: 8            moltype = AA  length = 9
FEATURE                 Location/Qualifiers
source                  1..9
                        mol_type = protein
                        organism = synthetic construct
SEQUENCE: 8
QQFKSYPLT                                                          9

SEQ ID NO: 9            moltype = AA  length = 119
FEATURE                 Location/Qualifiers
source                  1..119
                        mol_type = protein
                        organism = synthetic construct
SEQUENCE: 9
QVQLVQSGAE VKKPGSSVKV SCKASGYSFT TYYIHWVRQA PGQGLEWMGW FFPGSGNIKY  60
NEKFKGRVTI TADTSTSTAY MELSSLRSED TAVYYCAGSY YSYDVLDYWG QGTTVTVSS   119

SEQ ID NO: 10           moltype = AA  length = 107
FEATURE                 Location/Qualifiers
```

```
source                  1..107
                        mol_type = protein
                        organism = synthetic construct
SEQUENCE: 10
DIQMTQSPSF LSASVGDRVT ITCKASQNVG INVVWHQQKP GKAPKALIYS SSHRYSGVPS  60
RFSGSGSGTE FTLTISSLQP EDFATYFCQQ FKSYPLTFGQ GTKLEIK                107

SEQ ID NO: 11           moltype = AA  length = 107
FEATURE                 Location/Qualifiers
source                  1..107
                        mol_type = protein
                        organism = synthetic construct
SEQUENCE: 11
DIQMTQSPSS LSASVGDRVT ITCKASQNVG INVVWHQQKP GKVPKALIYS SSHRYSGVPS  60
RFSGSGSGTD FTLTISSLQP EDVATYFCQQ FKSYPLTFGQ GTKLEIK                107

SEQ ID NO: 12           moltype = DNA  length = 357
FEATURE                 Location/Qualifiers
source                  1..357
                        mol_type = other DNA
                        organism = synthetic construct
SEQUENCE: 12
caggtgcagc tggttcagtc tggcgccgaa gtgaagaaac ctggctcctc cgtgaaggtg  60
tcctgcaagg cttccggcta ctccttcacc acctactaca tccactgggt ccgacaggcc  120
cctggacaag gattggaatg gatgggctgg ttcttccccg gctccggcaa catcaagtac  180
aacgagaagt tcaagggccg cgtgaccatc accgccgaca cctctacctc taccgcctac  240
atggaactgt ccagcctgag atctgaggac accgccgtgt actactgcgc cggctcctac  300
tactcttacg acgtgctgga ttactggggc cagggcacca cagtgacagt gtcctct     357

SEQ ID NO: 13           moltype = DNA  length = 321
FEATURE                 Location/Qualifiers
source                  1..321
                        mol_type = other DNA
                        organism = synthetic construct
SEQUENCE: 13
gacatccaga tgacccagtc tccatccttc ctgtccgcct ctgtgggcga cagagtgacc  60
atcacatgca aggcctctca gaacgtgggc atcaacgtcg tgtggcacca gcagaagcct  120
ggcaaggctc ctaaggctct gatctactcc tccagccacc ggtactctgg cgtgccctct  180
agattttccg gctctggctc tggcaccgag tttaccctga caatctccag cctgcagcct  240
gaggacttcg ccacctactt ttgccagcag ttcaagagct accctctgac ctttggccag  300
ggcaccaagc tggaaatcaa g                                            321

SEQ ID NO: 14           moltype = DNA  length = 321
FEATURE                 Location/Qualifiers
source                  1..321
                        mol_type = other DNA
                        organism = synthetic construct
SEQUENCE: 14
gacatccaga tgacccagtc tccatcctct ctgtccgcct ctgtgggcga cagagtgacc  60
atcacatgca aggcctctca gaacgtgggc atcaacgtcg tgtggcacca gcagaaacct  120
ggcaaggtgc ccaaggctct gatctactcc tccagccaca gatactccgg cgtgccctct  180
agattctccg gctctggctc tggcaccgac tttaccctga caatctccag cctgcagcct  240
gaggacgtgg ccacctactt ttgccagcag ttcaagagct accctctgac ctttggccag  300
ggcaccaagc tggaaatcaa g                                            321

SEQ ID NO: 15           moltype = AA  length = 117
FEATURE                 Location/Qualifiers
source                  1..117
                        mol_type = protein
                        organism = synthetic construct
SEQUENCE: 15
DVQLVESGGG LVQPGGSRKL SCAASGFTFS NFGMHWVRQA PDKGLEWVAY ISSGSSTIYY  60
ADTLKGRFTI SRDNPKNTLF LQMTSLRSED TAMYYCARRG EGAMDYWGQG TSVTVSS     117

SEQ ID NO: 16           moltype = AA  length = 106
FEATURE                 Location/Qualifiers
source                  1..106
                        mol_type = protein
                        organism = synthetic construct
SEQUENCE: 16
ENVLTQSPAI MSASLGEKVT MSCRASSSVN YIYWYQQKSD ASPKLWIYYT SNLAPGVPTR  60
FSGSGSGNSY SLTISSMEGE DAATYYCQQF TSSPFTFGSG TKLEIK                 106

SEQ ID NO: 17           moltype = AA  length = 10
FEATURE                 Location/Qualifiers
source                  1..10
                        mol_type = protein
                        organism = synthetic construct
SEQUENCE: 17
```

```
GFTFSNFGMH                                                        10

SEQ ID NO: 18          moltype = AA  length = 17
FEATURE                Location/Qualifiers
source                 1..17
                       mol_type = protein
                       organism = synthetic construct
SEQUENCE: 18
YISSGSSTIY YADTLKG                                                17

SEQ ID NO: 19          moltype = AA  length = 8
FEATURE                Location/Qualifiers
source                 1..8
                       mol_type = protein
                       organism = synthetic construct
SEQUENCE: 19
RGEGAMDY                                                          8

SEQ ID NO: 20          moltype = AA  length = 10
FEATURE                Location/Qualifiers
source                 1..10
                       mol_type = protein
                       organism = synthetic construct
SEQUENCE: 20
RASSSVNYIY                                                        10

SEQ ID NO: 21          moltype = AA  length = 7
FEATURE                Location/Qualifiers
source                 1..7
                       mol_type = protein
                       organism = synthetic construct
SEQUENCE: 21
YTSNLAP                                                           7

SEQ ID NO: 22          moltype = AA  length = 9
FEATURE                Location/Qualifiers
source                 1..9
                       mol_type = protein
                       organism = synthetic construct
SEQUENCE: 22
QQFTSSPFT                                                         9

SEQ ID NO: 23          moltype = AA  length = 117
FEATURE                Location/Qualifiers
source                 1..117
                       mol_type = protein
                       organism = synthetic construct
SEQUENCE: 23
QVQLVESGGG VVQPGRSLRL SCAASGFTFS NFGMHWVRQA PGKGLEWVAY ISSGSSTIYY  60
ADTLKGRFTI SRDNSKNTLY LQMNSLRAED TAVYYCARRG EGAMDYWGQG TTVTVSS     117

SEQ ID NO: 24          moltype = AA  length = 117
FEATURE                Location/Qualifiers
source                 1..117
                       mol_type = protein
                       organism = synthetic construct
SEQUENCE: 24
EVQLVESGGG LVQPGGSLRL SCAASGFTFS NFGMHWVRQA PGKGLEWVSY ISSGSSTIYY  60
ADTLKGRFTI SRDNAKNSLY LQMNSLRAED TAVYYCARRG EGAMDYWGQG TTVTVSS     117

SEQ ID NO: 25          moltype = AA  length = 117
FEATURE                Location/Qualifiers
source                 1..117
                       mol_type = protein
                       organism = synthetic construct
SEQUENCE: 25
EVQLVESGGG LVQPGGSLRL SCAASGFTFS NFGMHWVRQA PGKGLEWVSY ISSGSSTIYY  60
ADTLKGRFTI SRDNSKNTLY LQMNSLRAED TAVYYCARRG EGAMDYWGQG TTVTVSS     117

SEQ ID NO: 26          moltype = AA  length = 106
FEATURE                Location/Qualifiers
source                 1..106
                       mol_type = protein
                       organism = synthetic construct
SEQUENCE: 26
DNQLTQSPSF LSASVGDRVT ITCRASSSVN YIYWYQQKPG KAPKLLIYYT SNLAPGVPSR  60
FSGSGSGNEY TLTISSLQPE DFATYYCQQF TSSPFTFGQG TKLEIK                 106

SEQ ID NO: 27          moltype = AA  length = 106
```

```
FEATURE                Location/Qualifiers
source                 1..106
                       mol_type = protein
                       organism = synthetic construct
SEQUENCE: 27
DNQLTQSPSS LSASVGDRVT ITCRASSSVN YIYWYQQKPG KAPKLLIYYT SNLAPGVPSR  60
FSGSGSGNDY TLTISSLQPE DFATYYCQQF TSSPFTFGQG TKLEIK                106

SEQ ID NO: 28          moltype = AA  length = 106
FEATURE                Location/Qualifiers
source                 1..106
                       mol_type = protein
                       organism = synthetic construct
SEQUENCE: 28
ENVLTQSPAT LSVSPGERAT LSCRASSSVN YIYWYQQKPG QAPRLLIYYT SNLAPGIPAR  60
FSGSGSGNEY TLTISSLQSE DFAVYYCQQF TSSPFTFGQG TKLEIK                106

SEQ ID NO: 29          moltype = AA  length = 105
FEATURE                Location/Qualifiers
source                 1..105
                       mol_type = protein
                       organism = synthetic construct
SEQUENCE: 29
QNVLTQPPSA SGTPGQRVTI SCRASSSVNY IYWYQQLPGT APKLLIYYTS NLAPGVPDRF  60
SGSGSGNSYS LAISGLRSED EADYYCQQFT SSPFTFGTGT KVTVL                 105

SEQ ID NO: 30          moltype = AA  length = 105
FEATURE                Location/Qualifiers
source                 1..105
                       mol_type = protein
                       organism = synthetic construct
SEQUENCE: 30
SNELTQPPSV SVSPGQTARI TCRASSSVNY IYWYQQKSGQ APVLVIYYTS NLAPGIPERF  60
SGSGSGNMYT LTISGAQVED EADYYCQQFT SSPFTFGTGT KVTVL                 105

SEQ ID NO: 31          moltype = DNA  length = 351
FEATURE                Location/Qualifiers
source                 1..351
                       mol_type = other DNA
                       organism = synthetic construct
SEQUENCE: 31
gaggtgcagc tggttgaatc tggcggagga ttggttcagc ctggcggctc tctgagactg  60
tcttgtgccg cttctggctt caccttctcc aacttcggca tgcactgggt ccgacaggcc  120
cctggaaaag gactggaatg ggtgtcctac atctcctccg gctcctccac catctactac  180
gctgacaccc tgaagggcag attcaccatc tctcgggaca acgccaagaa ctccctgtac  240
ctgcagatga acagcctgag agccgaggac accgccgtgt actactgtgc tagaagaggc  300
gagggcgcca tggattattg gggccaggga accacagtga ccgtgtctag c          351

SEQ ID NO: 32          moltype = DNA  length = 351
FEATURE                Location/Qualifiers
source                 1..351
                       mol_type = other DNA
                       organism = synthetic construct
SEQUENCE: 32
gaggtgcagc tggttgaatc tggcggagga ttggttcagc ctggcggctc tctgagactg  60
tcttgtgccg cttctggctt caccttctcc aacttcggca tgcactgggt ccgacaggcc  120
cctggaaaag gactggaatg ggtgtcctac atctcctccg gctcctccac catctactac  180
gctgacaccc tgaagggcag attcaccatc agccgggaca actccaagaa caccctgtac  240
ctgcagatga actccctgag agccgaggac accgccgtgt actactgtgc tagaagaggc  300
gagggcgcca tggattattg gggccaggga accacagtga ccgtgtctag c          351

SEQ ID NO: 33          moltype = DNA  length = 351
FEATURE                Location/Qualifiers
source                 1..351
                       mol_type = other DNA
                       organism = synthetic construct
SEQUENCE: 33
caggtgcagc tggtggaatc tggtggcgga gttgtgcagc ctggcagatc cctgagactg  60
tcttgtgccg cctctggctt caccttctcc aacttcggca tgcactgggt ccgacaggcc  120
cctggaaaag gattggagtg ggtcgcctac atctcctccg gctcctccac catctactac  180
gctgacaccc tgaagggcag attcaccatc agccgggaca actccaagaa caccctgtac  240
ctgcagatga actccctgag agccgaggac accgccgtgt actactgtgc tagaagaggc  300
gagggcgcca tggattattg gggccaggga accacagtga ccgtgtctag c          351

SEQ ID NO: 34          moltype = DNA  length = 318
FEATURE                Location/Qualifiers
source                 1..318
                       mol_type = other DNA
                       organism = synthetic construct
```

```
SEQUENCE: 34
gataaccagc tgacccagtc tcctagcttc ctgtctgcct ctgtgggcga cagagtgaca  60
attacctgcc gggcctcctc ctccgtgaac tacatctact ggtatcagca gaagcccggc  120
aaggccccta agctgctgat ctactacacc tccaatctgg cccctggcgt gccctctaga  180
ttttccggat ctggctccgg caacgagtat accctgacaa tctccagcct gcagcctgag  240
gacttcgcca cctactactg ccagcagttc acctcctctc cattcacctt tggccagggc  300
accaagctgg aaatcaaa                                                318

SEQ ID NO: 35          moltype = DNA  length = 317
FEATURE                Location/Qualifiers
source                 1..317
                       mol_type = other DNA
                       organism = synthetic construct
SEQUENCE: 35
ataaccagct gacccagtct ccttccagcc tgtctgcttc tgtgggcgac agagtgacaa  60
ttacctgccg ggcctcctcc tccgtgaact acatctactg gtatcagcag aagcccggca  120
aggcccctaa gctgctgatc tactacacct ccaatctggc ccctggcgtg ccctctagat  180
tttccggatc tggctccggc aacgactata ccctgacaat ctccagcctg cagcctgagg  240
acttcgccac ctactactgc cagcagttca cctcctctcc attcaccttt ggccagggca  300
ccaagctgga aatcaaa                                                 317

SEQ ID NO: 36          moltype = DNA  length = 318
FEATURE                Location/Qualifiers
source                 1..318
                       mol_type = other DNA
                       organism = synthetic construct
SEQUENCE: 36
gagaatgtgc tgacccagtc tcctgccaca ctgtctgtta gccctggcga gagagctacc  60
ctgagctgca gagcctcttc ctccgtgaac tacatctact ggtatcagca gaagcccggc  120
caggctccta gactgctgat ctactacacc tccaatctgg cccctggcat ccctgccaga  180
ttttccggat ctggctccgg caacgagtat accctgacca tctccagcct gcagtccgag  240
gactttgctg tgtactattg ccagcagttc acaagcagcc ctttcacctt tggccagggc  300
accaagctgg aaatcaaa                                                318

SEQ ID NO: 37          moltype = DNA  length = 315
FEATURE                Location/Qualifiers
source                 1..315
                       mol_type = other DNA
                       organism = synthetic construct
SEQUENCE: 37
cagaatgtgc tgacccaacc tccttccgcc tctggcacac ctggacagag agtgacaatc  60
tcctgccggg cctcctcctc cgtgaactac atctactggt atcagcagct gcccggcacc  120
gctcctaaac tgctgatcta ctacacctcc aatctggccc ctggcgtgcc cgatagattt  180
tccggatctg gctccggcaa ctcctacagc ctggctatct ctggcctgag atctgaggac  240
gaggccgact actactgcca gcagttcacc tcctctccat tcacctttgg caccggcacc  300
aaagtgacag ttctt                                                   315

SEQ ID NO: 38          moltype = DNA  length = 315
FEATURE                Location/Qualifiers
source                 1..315
                       mol_type = other DNA
                       organism = synthetic construct
SEQUENCE: 38
tctaatgagc tgacccagcc tccttccgtg tccgtgtctc ctggacagac cgccagaatt  60
acctgccggg cctcctcctc cgtgaactac atctactggt atcagcagaa gtccggccag  120
gctcctgtgc tcgtgatcta ctacacctcc aatctggccc ctggcatccc tgagagattc  180
tccggatctg gctccggcaa catgtacacc ctgaccatct ctggcgccca ggtggaagat  240
gaggccgact actactgcca gcagttcacc tcctctccat tcacctttgg caccggcacc  300
aaagtgacag ttctt                                                   315

SEQ ID NO: 39          moltype = AA  length = 107
FEATURE                Location/Qualifiers
source                 1..107
                       mol_type = protein
                       organism = Homo sapiens
SEQUENCE: 39
RTVAAPSVFI FPPSDEQLKS GTASVVCLLN NFYPREAKVQ WKVDNALQSG NSQESVTEQD  60
SKDSTYSLSS TLTLSKADYE KHKVYACEVT HQGLSSPVTK SFNRGEC               107

SEQ ID NO: 40          moltype = AA  length = 326
FEATURE                Location/Qualifiers
source                 1..326
                       mol_type = protein
                       organism = synthetic construct
SEQUENCE: 40
ASTKGPSVFP LAPCSRSTSE STAALGCLVK DYFPEPVTVS WNSGALTSGV HTFPAVLQSS  60
GLYSLSSVVT VPSSSLGTKT YTCNVDHKPS NTKVDKRVES KYGPPCPPCP APEFLGGPSV  120
FLFPPKPKDT LMISRTPEVT CVVVDVSQED PEVQFNWYVD GVEVHNAKTK PREEQFNSTY  180
RVVSVLTVLH QDWLNGKEYK CKVSNKGLPS SIEKTISKAK GQPREPQVYT LPPSQEEMTK  240
```

```
NQVSLTCLVK GFYPSDIAVE WESNGQPENN YKTTPPVLDS DGSFFLYSRL TVDKSRWQEG  300
NVFSCSVMHE ALHNHYTQKS LSLSLG                                      326

SEQ ID NO: 41          moltype = AA  length = 330
FEATURE                Location/Qualifiers
source                 1..330
                       mol_type = protein
                       organism = Homo sapiens
SEQUENCE: 41
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKRVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                  330

SEQ ID NO: 42          moltype = AA  length = 330
FEATURE                Location/Qualifiers
source                 1..330
                       mol_type = protein
                       organism = synthetic construct
SEQUENCE: 42
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKRVEP KSCDKTHTCP PCPAPELLGG  120
PSVFLFPPKP KDTLMISRTP EVTCVVVDVS HEDPEVKFNW YVDGVEVHNA KTKPREEQYA  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPGK                                  330

SEQ ID NO: 43          moltype = DNA  length = 344
FEATURE                Location/Qualifiers
source                 1..344
                       mol_type = other DNA
                       organism = synthetic construct
SEQUENCE: 43
atgagcatcg gcctcctgtg ctgtgcagcc ttgtctctcc tgtgggcagg tccagtgaat  60
gctggtgtca ctcagacccc aaaattccag gtcctgaaga caggacagag catgacactg  120
cagtgtgccc aggatatgaa ccatgaatac atgtcctggt atcgacaaga cccaggcatg  180
gggctgaggc tgattcatta ctcagttggt gctggtatca ctgaccaagg agaagtcccc  240
aatggctaca atgtctccag atcaaccaca gaggatttcc cgctcaggct gctgtcggct  300
gctccctccc agacatctgt gtacttctgt gccagcagtt actc                  344

SEQ ID NO: 44          moltype = AA  length = 114
FEATURE                Location/Qualifiers
source                 1..114
                       mol_type = protein
                       organism = synthetic construct
SEQUENCE: 44
MSIGLLCCAA LSLLWAGPVN AGVTQTPKFQ VLKTGQSMTL QCAQDMNHEY MSWYRQDPGM  60
GLRLIHYSVG AGITDQGEVP NGYNVSRSTT EDFPLRLLSA APSQTSVYFC ASSY        114

SEQ ID NO: 45          moltype = AA  length = 5
FEATURE                Location/Qualifiers
source                 1..5
                       mol_type = protein
                       organism = synthetic construct
SEQUENCE: 45
TYYIH                                                             5

SEQ ID NO: 46          moltype = AA  length = 17
FEATURE                Location/Qualifiers
source                 1..17
                       mol_type = protein
                       organism = synthetic construct
SEQUENCE: 46
WFFPGSGNIK YNEKFKG                                                17

SEQ ID NO: 47          moltype = AA  length = 10
FEATURE                Location/Qualifiers
source                 1..10
                       mol_type = protein
                       organism = synthetic construct
SEQUENCE: 47
SYYSYDVLDY                                                        10

SEQ ID NO: 48          moltype = AA  length = 7
FEATURE                Location/Qualifiers
source                 1..7
                       mol_type = protein
```

```
                        organism = synthetic construct
SEQUENCE: 48
GYSFTTY                                                                    7

SEQ ID NO: 49           moltype = AA  length = 6
FEATURE                 Location/Qualifiers
source                  1..6
                        mol_type = protein
                        organism = synthetic construct
SEQUENCE: 49
FPGSGN                                                                     6

SEQ ID NO: 50           moltype = AA  length = 10
FEATURE                 Location/Qualifiers
source                  1..10
                        mol_type = protein
                        organism = synthetic construct
SEQUENCE: 50
SYYSYDVLDY                                                                 10

SEQ ID NO: 51           moltype = AA  length = 11
FEATURE                 Location/Qualifiers
source                  1..11
                        mol_type = protein
                        organism = synthetic construct
SEQUENCE: 51
KASQNVGINV V                                                               11

SEQ ID NO: 52           moltype = AA  length = 7
FEATURE                 Location/Qualifiers
source                  1..7
                        mol_type = protein
                        organism = synthetic construct
SEQUENCE: 52
SSSHRYS                                                                    7

SEQ ID NO: 53           moltype = AA  length = 9
FEATURE                 Location/Qualifiers
source                  1..9
                        mol_type = protein
                        organism = synthetic construct
SEQUENCE: 53
QQFKSYPLT                                                                  9

SEQ ID NO: 54           moltype = AA  length = 11
FEATURE                 Location/Qualifiers
source                  1..11
                        mol_type = protein
                        organism = synthetic construct
SEQUENCE: 54
KASQNVGINV V                                                               11

SEQ ID NO: 55           moltype = AA  length = 7
FEATURE                 Location/Qualifiers
source                  1..7
                        mol_type = protein
                        organism = synthetic construct
SEQUENCE: 55
SSSHRYS                                                                    7

SEQ ID NO: 56           moltype = AA  length = 9
FEATURE                 Location/Qualifiers
source                  1..9
                        mol_type = protein
                        organism = synthetic construct
SEQUENCE: 56
QQFKSYPLT                                                                  9

SEQ ID NO: 57           moltype = AA  length = 5
FEATURE                 Location/Qualifiers
source                  1..5
                        mol_type = protein
                        organism = synthetic construct
SEQUENCE: 57
NFGMH                                                                      5

SEQ ID NO: 58           moltype = AA  length = 17
FEATURE                 Location/Qualifiers
source                  1..17
```

```
                        mol_type = protein
                        organism = synthetic construct
SEQUENCE: 58
YISSGSSTIY YADTLKG                                            17

SEQ ID NO: 59           moltype = AA  length = 8
FEATURE                 Location/Qualifiers
source                  1..8
                        mol_type = protein
                        organism = synthetic construct
SEQUENCE: 59
RGEGAMDY                                                      8

SEQ ID NO: 60           moltype = AA  length = 7
FEATURE                 Location/Qualifiers
source                  1..7
                        mol_type = protein
                        organism = synthetic construct
SEQUENCE: 60
GFTFSNF                                                       7

SEQ ID NO: 61           moltype = AA  length = 6
FEATURE                 Location/Qualifiers
source                  1..6
                        mol_type = protein
                        organism = synthetic construct
SEQUENCE: 61
SSGSST                                                        6

SEQ ID NO: 62           moltype = AA  length = 8
FEATURE                 Location/Qualifiers
source                  1..8
                        mol_type = protein
                        organism = synthetic construct
SEQUENCE: 62
RGEGAMDY                                                      8

SEQ ID NO: 63           moltype = AA  length = 10
FEATURE                 Location/Qualifiers
source                  1..10
                        mol_type = protein
                        organism = synthetic construct
SEQUENCE: 63
RASSSVNYIY                                                    10

SEQ ID NO: 64           moltype = AA  length = 7
FEATURE                 Location/Qualifiers
source                  1..7
                        mol_type = protein
                        organism = synthetic construct
SEQUENCE: 64
YTSNLAP                                                       7

SEQ ID NO: 65           moltype = AA  length = 9
FEATURE                 Location/Qualifiers
source                  1..9
                        mol_type = protein
                        organism = synthetic construct
SEQUENCE: 65
QQFTSSPFT                                                     9

SEQ ID NO: 66           moltype = AA  length = 10
FEATURE                 Location/Qualifiers
source                  1..10
                        mol_type = protein
                        organism = synthetic construct
SEQUENCE: 66
RASSSVNYIY                                                    10

SEQ ID NO: 67           moltype = AA  length = 7
FEATURE                 Location/Qualifiers
source                  1..7
                        mol_type = protein
                        organism = synthetic construct
SEQUENCE: 67
YTSNLAP                                                       7

SEQ ID NO: 68           moltype = AA  length = 9
FEATURE                 Location/Qualifiers
```

```
source                 1..9
                       mol_type = protein
                       organism = synthetic construct
SEQUENCE: 68
QQFTSSPFT                                                        9

SEQ ID NO: 69          moltype = AA  length = 592
FEATURE                Location/Qualifiers
source                 1..592
                       mol_type = protein
                       organism = synthetic construct
SEQUENCE: 69
METDTLLLWV LLLWVPGSTG QVQLVQSGAE VKKPGSSVKV SCKASGYSFT TYYIHWVRQA  60
PGQGLEWMGW FFPGSGNIKY NEKFKGRVTI TADTSTSTAY MELSSLRSED TAVYYCAGSY  120
YSYDVLDYWG QGTTVTVSSG SASAPTLFPL VSCENSPSDT SSVAVGCLAQ DFLPDSITFS  180
WKYKNNSDIS STRGFPSVLR GGKYAATSQV LLPSKDVMQG TDEHVVCKVQ HPNGNKEKNV  240
PLPVIAELPP KVSVFVPPRD GFFGNPRKSK LICQATGFSP RQIQVSWLRE GKQVGSGVTT  300
DQVQAEAKES GPTTYKVTST LTIKESDWLG QSMFTCRVDH RGLTFQQNAS SMCVPDQDTA  360
IRVFAIPPSF ASIFLTKSTK LTCLVTDLTT YDSVTISWTR QNGEAVKTHT NISESHPNAT  420
FSAVGEASIC EDDWNSGERF TCTVTHTDLA SSLKQTISRP KGVALHRPDV YLLPPAREQL  480
NLRESATITC LVTGFSPADV FVQWMQRGQP LSPEKYVTSA PMPEPQAPGR YFAHSILTVS  540
EEEWNTGETY TCVVAHEALP NRVTERTVDK STGKPTLYNV SLVMSDTAGT CY          592

SEQ ID NO: 70          moltype = AA  length = 492
FEATURE                Location/Qualifiers
source                 1..492
                       mol_type = protein
                       organism = synthetic construct
SEQUENCE: 70
METDTLLLWV LLLWVPGSTG QVQLVQSGAE VKKPGSSVKV SCKASGYSFT TYYIHWVRQA  60
PGQGLEWMGW FFPGSGNIKY NEKFKGRVTI TADTSTSTAY MELSSLRSED TAVYYCAGSY  120
YSYDVLDYWG QGTTVTVSSA SPTSPKVFPL SLCSTQPDGN VVIACLVQGF FPQEPLSVTW  180
SESGQGVTAR NFPPSQDASG DLYTTSSQLT LPATQCLAGK SVTCHVKHYT NPSQDVTVPC  240
PVPSTPPTPS PSTPPTPSPS CCHPRLSLHR PALEDLLLGS EANLTCTLTG LRDASGVTFT  300
WTPSSGKSAV QGPPERDLCG CYSVSSVLPG CAEPWNHGKT FTCTAAYPES KTPLTATLSK  360
SGNTFRPEVH LLPPPSEELA LNELVTLTCL ARGFSPKDVL VRWLQGSQEL PREKYLTWAS  420
RQEPSQGTTT FAVTSILRVA AEDWKKGDTF SCMVGHEALP LAFTQKTIDR LAGKPTHVNV  480
SVVMAEVDGT CY                                                    492

SEQ ID NO: 71          moltype = AA  length = 479
FEATURE                Location/Qualifiers
source                 1..479
                       mol_type = protein
                       organism = synthetic construct
SEQUENCE: 71
METDTLLLWV LLLWVPGSTG QVQLVQSGAE VKKPGSSVKV SCKASGYSFT TYYIHWVRQA  60
PGQGLEWMGW FFPGSGNIKY NEKFKGRVTI TADTSTSTAY MELSSLRSED TAVYYCAGSY  120
YSYDVLDYWG QGTTVTVSSA SPTSPKVFPL SLDSTPQDGN VVVACLVQGF FPQEPLSVTW  180
SESGQNVTAR NFPPSQDASG DLYTTSSQLT LPATQCPDGK SVTCHVKHYT NSSQDVTVPC  240
RVPPPPPCCH PRLSLHRPAL EDLLLGSEAN LTCTLTGLRD ASGATFTWTP SSGKSAVQGP  300
PERDLCGCYS VSSVLPGCAQ PWNHGETFTC TAAHPELKTP LTANITKSGN TFRPEVHLLP  360
PPSEELALNE LVTLTCLARG FSPKDVLVRW LQGSQELPRE KYLTWASRQE PSQGTTTYAV  420
TSILRVAAED WKKGETFSCM VGHEALPLAF TQKTIDRMAG KPTHINVSVV MAEADGTCY   479

SEQ ID NO: 72          moltype = AA  length = 234
FEATURE                Location/Qualifiers
source                 1..234
                       mol_type = protein
                       organism = synthetic construct
SEQUENCE: 72
METDTLLLWV LLLWVPGSTG DIQMTQSPSF LSASVGDRVT ITCKASQNVG INVVWHQQKP  60
GKAPKALIYS SSHRYSGVPS RFSGSGSGTE FTLTISSLQP EDFATYFCQQ FKSYPLTFGQ  120
GTKLEIKRTV AAPSVFIFPP SDEQLKSGTA SVVCLLNNFY PREAKVQWKV DNALQSGNSQ  180
ESVTEQDSKD STYSLSSTLT LSKADYEKHK VYACEVTHQG LSSPVTKSFN RGEC        234

SEQ ID NO: 73          moltype = AA  length = 453
FEATURE                Location/Qualifiers
source                 1..453
                       mol_type = protein
                       organism = synthetic construct
SEQUENCE: 73
GSASAPTLFP LVSCENSPSD TSSVAVGCLA QDFLPDSITF SWKYKNNSDI SSTRGFPSVL  60
RGGKYAATSQ VLLPSKDVMQ GTDEHVVCKV QHPNGNKEKN VPLPVIAELP PKVSVFVPPR  120
DGFFGNPRKS KLICQATGFS PRQIQVSWLR EGKQVGSGVT TDQVQAEAKE SGPTTYKVTS  180
TLTIKESDWL GQSMFTCRVD HRGLTFQQNA SSMCVPDQDT AIRVFAIPPS FASIFLTKST  240
KLTCLVTDLT TYDSVTISWT RQNGEAVKTH TNISESHPNA TFSAVGEASI CEDDWNSGER  300
FTCTVTHTDL ASSLKQTISR PKGVALHRPD VYLLPPAREQ LNLRESATIT CLVTGFSPAD  360
VFVQWMQRGQ PLSPEKYVTS APMPEPQAPG RYFAHSILTV SEEEWNTGET YTCVVAHEAL  420
PNRVTERTVD KSTGKPTLYN VSLVMSDTAG TCY                             453
```

```
SEQ ID NO: 74          moltype = AA  length = 353
FEATURE                Location/Qualifiers
source                 1..353
                       mol_type = protein
                       organism = Homo sapiens
SEQUENCE: 74
ASPTSPKVFP LSLCSTQPDG NVVIACLVQG FFPQEPLSVT WSESGQGVTA RNFPPSQDAS  60
GDLYTTSSQL TLPATQCLAG KSVTCHVKHY TNPSQDVTVP CPVPSTPPTP SPSTPPTPSP  120
SCCHPRLSLH RPALEDLLLG SEANLTCTLT GLRDASGVTF TWTPSSGKSA VQGPPERDLC  180
GCYSVSSVLP GCAEPWNHGK TFTCTAAYPE SKTPLTATLS KSGNTFRPEV HLLPPPSEEL  240
ALNELVTLTC LARGFSPKDV LVRWLQGSQE LPREKYLTWA SRQEPSQGTT TFAVTSILRV  300
AAEDWKKGDT FSCMVGHEAL PLAFTQKTID RLAGKPTHVN VSVVMAEVDG TCY         353

SEQ ID NO: 75          moltype = AA  length = 340
FEATURE                Location/Qualifiers
source                 1..340
                       mol_type = protein
                       organism = Homo sapiens
SEQUENCE: 75
ASPTSPKVFP LSLDSTPQDG NVVVACLVQG FFPQEPLSVT WSESGQNVTA RNFPPSQDAS  60
GDLYTTSSQL TLPATQCPDG KSVTCHVKHY TNSSQDVTVP CRVPPPPPCC HPRLSLHRPA  120
LEDLLLGSEA NLTCTLTGLR DASGATFTWT PSSGKSAVQG PPERDLCGCY SVSSVLPGCA  180
QPWNHGETFT CTAAHPELKT PLTANITKSG NTFRPEVHLL PPPSEELALN ELVTLTCLAR  240
GFSPKDVLVR WLQGSQELPR EKYLTWASRQ EPSQGTTTYA VTSILRVAAE DWKKGETFSC  300
MVGHEALPLA FTQKTIDRMA GKPTHINVSV VMAEADGTCY                        340

SEQ ID NO: 76          moltype = AA  length = 159
FEATURE                Location/Qualifiers
source                 1..159
                       mol_type = protein
                       organism = Homo sapiens
SEQUENCE: 76
MKNHLLFWGV LAVFIKAVHV KAQEDERIVL VDNKCKCARI TSRIIRSSED PNEDIVERNI  60
RIIVPLNNRE NISDPTSPLR TRFVYHLSDL CKKCDPTEVE LDNQIVTATQ SNICDEDSAT  120
ETCYTYDRNK CYTAVVPLVY GGETKMVETA LTPDACYPD                         159

SEQ ID NO: 77          moltype =   length =
SEQUENCE: 77
000

SEQ ID NO: 78          moltype =   length =
SEQUENCE: 78
000

SEQ ID NO: 79          moltype =   length =
SEQUENCE: 79
000

SEQ ID NO: 80          moltype = AA  length = 246
FEATURE                Location/Qualifiers
source                 1..246
                       mol_type = protein
                       organism = synthetic construct
SEQUENCE: 80
QVQLVQSGAE VKKPGSSVKV SCKASGTDFK LTYIHWVRQA PGQGLEWMGR VSPGSGNTKY  60
NEKFKGRVTI TADTSTSTAY MELSSLRSED TAVYYCAGSY YSYDVLDYWG QGTTVTVSSG  120
GGGSGGGGSG GGGSGGGGSD IQMTQSPSFL SASVGDRVTI TCKASQNVED RVAWYQQKPG  180
KAPKALIYSS SHRYKGVPSR FSGSGSGTEF TLTISSLQPE DFATYFCQQF KSYPLTFGQG  240
TKLEIK                                                             246

SEQ ID NO: 81          moltype = AA  length = 107
FEATURE                Location/Qualifiers
source                 1..107
                       mol_type = protein
                       organism = synthetic construct
SEQUENCE: 81
DIQMTQSPSF LSASVGDRVT ITCKASQNVE DRVAWYQQKP GKAPKALIYS SSHRYKGVPS  60
RFSGSGSGTE FTLTISSLQP EDFATYFCQQ FKSYPLTFGQ GTKLEIK                107

SEQ ID NO: 82          moltype = AA  length = 119
FEATURE                Location/Qualifiers
source                 1..119
                       mol_type = protein
                       organism = synthetic construct
SEQUENCE: 82
QVQLVQSGAE VKKPGSSVKV SCKASGTDFK LTYIHWVRQA PGQGLEWMGR VSPGSGNTKY  60
NEKFKGRVTI TADTSTSTAY MELSSLRSED TAVYYCAGSY YSYDVLDYWG QGTTVTVSS   119
```

-continued

```
SEQ ID NO: 83          moltype = AA  length = 246
FEATURE                Location/Qualifiers
source                 1..246
                       mol_type = protein
                       organism = synthetic construct
SEQUENCE: 83
QVQLVQSGAE VKKPGSSVKV SCKASGTDFD KIYIHWVRQA PGQGLEWMGR ISAGSGNVKY  60
NEKFKGRVTI TADTSTSTAY MELSSLRSED TAVYYCAGSY YSYDVLDYWG QGTTVTVSSG  120
GGGSGGGGSG GGGSGGGGSD IQMTQSPSFL SASVGDRVTI TCKASQNVED RVAWYQQKPG  180
KAPKALIYSS SHRYKGVPSR FSGSGSGTEF TLTISSLQPE DFATYFCQQF KSYPLTFGQG  240
TKLEIK                                                            246

SEQ ID NO: 84          moltype = AA  length = 107
FEATURE                Location/Qualifiers
source                 1..107
                       mol_type = protein
                       organism = synthetic construct
SEQUENCE: 84
DIQMTQSPSF LSASVGDRVT ITCKASQNVE DRVAWYQQKP GKAPKALIYS SSHRYKGVPS  60
RFSGSGSGTE FTLTISSLQP EDFATYFCQQ FKSYPLTFGQ GTKLEIK               107

SEQ ID NO: 85          moltype = AA  length = 119
FEATURE                Location/Qualifiers
source                 1..119
                       mol_type = protein
                       organism = synthetic construct
SEQUENCE: 85
QVQLVQSGAE VKKPGSSVKV SCKASGTDFD KIYIHWVRQA PGQGLEWMGR ISAGSGNVKY  60
NEKFKGRVTI TADTSTSTAY MELSSLRSED TAVYYCAGSY YSYDVLDYWG QGTTVTVSS   119

SEQ ID NO: 86          moltype = AA  length = 246
FEATURE                Location/Qualifiers
source                 1..246
                       mol_type = protein
                       organism = synthetic construct
SEQUENCE: 86
QVQLVQSGAE VKKPGSSVKV SCKASGHDFR DFYIHWVRQA PGQGLEWMGR VYPGSGSYRY  60
NEKFKGRVTI TADTSTSTAY MELSSLRSED TAVYYCAGSY YSYDVLDYWG QGTTVTVSSG  120
GGGSGGGGSG GGGSGGGGSD IQMTQSPSFL SASVGDRVTI TCKASQNVDD RVAWYQQKPG  180
KAPKALIYSS SHRYKGVPSR FSGSGSGTEF TLTISSLQPE DFATYFCQQF KSYPLTFGQG  240
TKLEIK                                                            246

SEQ ID NO: 87          moltype = AA  length = 107
FEATURE                Location/Qualifiers
source                 1..107
                       mol_type = protein
                       organism = synthetic construct
SEQUENCE: 87
DIQMTQSPSF LSASVGDRVT ITCKASQNVD DRVAWYQQKP GKAPKALIYS SSHRYKGVPS  60
RFSGSGSGTE FTLTISSLQP EDFATYFCQQ FKSYPLTFGQ GTKLEIK               107

SEQ ID NO: 88          moltype = AA  length = 119
FEATURE                Location/Qualifiers
source                 1..119
                       mol_type = protein
                       organism = synthetic construct
SEQUENCE: 88
QVQLVQSGAE VKKPGSSVKV SCKASGHDFR DFYIHWVRQA PGQGLEWMGR VYPGSGSYRY  60
NEKFKGRVTI TADTSTSTAY MELSSLRSED TAVYYCAGSY YSYDVLDYWG QGTTVTVSS   119

SEQ ID NO: 89          moltype = AA  length = 246
FEATURE                Location/Qualifiers
source                 1..246
                       mol_type = protein
                       organism = synthetic construct
SEQUENCE: 89
QVQLVQSGAE VKKPGSSVKV SCKASGHDFK LTYIHWVRQA PGQGLEWMGR ISAGSGNVKY  60
NEKFKGRVTI TADTSTSTAY MELSSLRSED TAVYYCAGSY YSYDVLDYWG QGTTVTVSSG  120
GGGSGGGGSG GGGSGGGGSD IQMTQSPSFL SASVGDRVTI TCKASQNVDN RVAWYQQKPG  180
KAPKALIYSS SHRYKGVPSR FSGSGSGTEF TLTISSLQPE DFATYFCQQF KSYPLTFGQG  240
TKLEIK                                                            246

SEQ ID NO: 90          moltype = AA  length = 107
FEATURE                Location/Qualifiers
source                 1..107
                       mol_type = protein
                       organism = synthetic construct
SEQUENCE: 90
DIQMTQSPSF LSASVGDRVT ITCKASQNVD NRVAWYQQKP GKAPKALIYS SSHRYKGVPS  60
```

```
RFSGSGSGTE FTLTISSLQP EDFATYFCQQ FKSYPLTFGQ GTKLEIK               107

SEQ ID NO: 91          moltype = AA  length = 119
FEATURE                Location/Qualifiers
source                 1..119
                       mol_type = protein
                       organism = synthetic construct
SEQUENCE: 91
QVQLVQSGAE VKKPGSSVKV SCKASGHDFK LTYIHWVRQA PGQGLEWMGR ISAGSGNVKY  60
NEKFKGRVTI TADTSTSTAY MELSSLRSED TAVYYCAGSY YSYDVLDYWG QGTTVTVSS   119

SEQ ID NO: 92          moltype = AA  length = 246
FEATURE                Location/Qualifiers
source                 1..246
                       mol_type = protein
                       organism = synthetic construct
SEQUENCE: 92
QVQLVQSGAE VKKPGSSVKV SCKASGTDFK LTYIHWVRQA PGQGLEWMGR IFPGSGNVKY  60
NEKFKGRVTI TADTSTSTAY MELSSLRSED TAVYYCAGSY YSYDVLDYWG QGTTVTVSSG  120
GGGSGGGGSG GGGSGGGGSD IQMTQSPSFL SASVGDRVTI TCKASQNVEN KVAWHQQKPG  180
KAPKALIYSS SHRYKGVPSR FSGSGSGTEF TLTISSLQPE DFATYFCQQF KSYPLTFGQG  240
TKLEIK                                                            246

SEQ ID NO: 93          moltype = AA  length = 107
FEATURE                Location/Qualifiers
source                 1..107
                       mol_type = protein
                       organism = synthetic construct
SEQUENCE: 93
DIQMTQSPSF LSASVGDRVT ITCKASQNVE NKVAWHQQKP GKAPKALIYS SSHRYKGVPS  60
RFSGSGSGTE FTLTISSLQP EDFATYFCQQ FKSYPLTFGQ GTKLEIK               107

SEQ ID NO: 94          moltype = AA  length = 119
FEATURE                Location/Qualifiers
source                 1..119
                       mol_type = protein
                       organism = synthetic construct
SEQUENCE: 94
QVQLVQSGAE VKKPGSSVKV SCKASGTDFK LTYIHWVRQA PGQGLEWMGR IFPGSGNVKY  60
NEKFKGRVTI TADTSTSTAY MELSSLRSED TAVYYCAGSY YSYDVLDYWG QGTTVTVSS   119

SEQ ID NO: 95          moltype = AA  length = 246
FEATURE                Location/Qualifiers
source                 1..246
                       mol_type = protein
                       organism = synthetic construct
SEQUENCE: 95
QVQLVQSGAE VKKPGSSVKV SCKASGTDFD KIYIHWVRQA PGQGLEWMGR IFAGSGNTKY  60
NEKFKGRVTI TADTSTSTAY MELSSLRSED TAVYYCAGSY YSYDVLDYWG QGTTVTVSSG  120
GGGSGGGGSG GGGSGGGGSD IQMTQSPSFL SASVGDRVTI TCKASQNVDD RVAWYQQKPG  180
KAPKALIYSS SHRYKGVPSR FSGSGSGTEF TLTISSLQPE DFATYFCQQF KSYPLTFGQG  240
TKLEIK                                                            246

SEQ ID NO: 96          moltype = AA  length = 107
FEATURE                Location/Qualifiers
source                 1..107
                       mol_type = protein
                       organism = synthetic construct
SEQUENCE: 96
DIQMTQSPSF LSASVGDRVT ITCKASQNVD DRVAWYQQKP GKAPKALIYS SSHRYKGVPS  60
RFSGSGSGTE FTLTISSLQP EDFATYFCQQ FKSYPLTFGQ GTKLEIK               107

SEQ ID NO: 97          moltype = AA  length = 119
FEATURE                Location/Qualifiers
source                 1..119
                       mol_type = protein
                       organism = synthetic construct
SEQUENCE: 97
QVQLVQSGAE VKKPGSSVKV SCKASGTDFD KIYIHWVRQA PGQGLEWMGR IFAGSGNTKY  60
NEKFKGRVTI TADTSTSTAY MELSSLRSED TAVYYCAGSY YSYDVLDYWG QGTTVTVSS   119

SEQ ID NO: 98          moltype = AA  length = 246
FEATURE                Location/Qualifiers
source                 1..246
                       mol_type = protein
                       organism = synthetic construct
SEQUENCE: 98
QVQLVQSGAE VKKPGSSVKV SCKASGHDFD KFYIHWVRQA PGQGLEWMGR VSAGSGNVKY  60
NEKFKGRVTI TADTSTSTAY MELSSLRSED TAVYYCAGSY YSYDVLDYWG QGTTVTVSSG  120
```

```
GGGSGGGGSG GGGSGGGGSD IQMTQSPSFL SASVGDRVTI TCKASQNVGN RVAWYQQKPG  180
KAPKALIYSS SHRYSGVPSR FSGSGSGTEF TLTISSLQPE DFATYFCQQF KSYPLTFGQG  240
TKLEIK                                                             246

SEQ ID NO: 99          moltype = AA  length = 107
FEATURE                Location/Qualifiers
source                 1..107
                       mol_type = protein
                       organism = synthetic construct
SEQUENCE: 99
DIQMTQSPSF LSASVGDRVT ITCKASQNVG NRVAWYQQKP GKAPKALIYS SSHRYSGVPS  60
RFSGSGSGTE FTLTISSLQP EDFATYFCQQ FKSYPLTFGQ GTKLEIK                107

SEQ ID NO: 100         moltype = AA  length = 119
FEATURE                Location/Qualifiers
source                 1..119
                       mol_type = protein
                       organism = synthetic construct
SEQUENCE: 100
QVQLVQSGAE VKKPGSSVKV SCKASGHDFD KFYIHWVRQA PGQGLEWMGR VSAGSGNVKY  60
NEKFKGRVTI TADTSTSTAY MELSSLRSED TAVYYCAGSY YSYDVLDYWG QGTTVTVSS   119

SEQ ID NO: 101         moltype = AA  length = 247
FEATURE                Location/Qualifiers
source                 1..247
                       mol_type = protein
                       organism = synthetic construct
SEQUENCE: 101
QVQLVQSGAE VKKPGSSVKV SCKASGHDFD KFYIHWVRQA PGQGLEWMGR IFAGSGNVKY  60
NEKFKGRVTI TADTSTSTAY MELSSLRSED TAVYYCAGSY YSYDVLDYWG QGTTVTVSSG  120
GGGSGGGGSG GGGSGGGGSD IQMTQSPSFL SASVGDRVTI TCKASQNVGD RVAWYQQKPG  180
KAPKALIYSS SHRYKGVPSR FSGSGSGTEF TLTISSLQPE DFATYFCQQF KSYPLTFGQG  240
TKLEIKS                                                            247

SEQ ID NO: 102         moltype = AA  length = 107
FEATURE                Location/Qualifiers
source                 1..107
                       mol_type = protein
                       organism = synthetic construct
SEQUENCE: 102
DIQMTQSPSF LSASVGDRVT ITCKASQNVG DRVAWYQQKP GKAPKALIYS SSHRYKGVPS  60
RFSGSGSGTE FTLTISSLQP EDFATYFCQQ FKSYPLTFGQ GTKLEIK                107

SEQ ID NO: 103         moltype = AA  length = 119
FEATURE                Location/Qualifiers
source                 1..119
                       mol_type = protein
                       organism = synthetic construct
SEQUENCE: 103
QVQLVQSGAE VKKPGSSVKV SCKASGHDFD KFYIHWVRQA PGQGLEWMGR IFAGSGNVKY  60
NEKFKGRVTI TADTSTSTAY MELSSLRSED TAVYYCAGSY YSYDVLDYWG QGTTVTVSS   119

SEQ ID NO: 104         moltype = AA  length = 246
FEATURE                Location/Qualifiers
source                 1..246
                       mol_type = protein
                       organism = synthetic construct
SEQUENCE: 104
QVQLVQSGAE VKKPGSSVKV SCKASGTDFK LTYIHWVRQA PGQGLEWMGR VSPGSGNVKY  60
NEKFKGRVTI TADTSTSTAY MELSSLRSED TAVYYCAGSY YSYDVLDYWG QGTTVTVSSG  120
GGGSGGGGSG GGGSGGGGSD IQMTQSPSFL SASVGDRVTI TCKASQNVGD RVAWYQQKPG  180
KAPKALIYSS SHRYKGVPSR FSGSGSGTEF TLTISSLQPE DFATYFCQQF KSYPLTFGQG  240
TKLEIK                                                             246

SEQ ID NO: 105         moltype = AA  length = 107
FEATURE                Location/Qualifiers
source                 1..107
                       mol_type = protein
                       organism = synthetic construct
SEQUENCE: 105
DIQMTQSPSF LSASVGDRVT ITCKASQNVG DRVAWYQQKP GKAPKALIYS SSHRYKGVPS  60
RFSGSGSGTE FTLTISSLQP EDFATYFCQQ FKSYPLTFGQ GTKLEIK                107

SEQ ID NO: 106         moltype = AA  length = 119
FEATURE                Location/Qualifiers
source                 1..119
                       mol_type = protein
                       organism = synthetic construct
SEQUENCE: 106
```

-continued

```
QVQLVQSGAE VKKPGSSVKV SCKASGTDFK LTYIHWVRQA PGQGLEWMGR VSPGSGNVKY  60
NEKFKGRVTI TADTSTSTAY MELSSLRSED TAVYYCAGSY YSYDVLDYWG QGTTVTVSS   119

SEQ ID NO: 107          moltype = AA  length = 246
FEATURE                 Location/Qualifiers
source                  1..246
                        mol_type = protein
                        organism = synthetic construct
SEQUENCE: 107
QVQLVQSGAE VKKPGSSVKV SCKASGTDFD KIYIHWVRQA PGQGLEWMGR VSAGSGNTKY  60
NEKFKGRVTI TADTSTSTAY MELSSLRSED TAVYYCAGSY YSYDVLDYWG QGTTVTVSSG  120
GGGSGGGGSG GGGSGGGGSD IQMTQSPSFL SASVGDRVTI TCKASQNVGN RVAWYQQKPG  180
KAPKALIYSS SHRYKGVPSR FSGSGSGTEF TLTISSLQPE DFATYFCQQF KSYPLTFGQG  240
TKLEIK                                                             246

SEQ ID NO: 108          moltype = AA  length = 107
FEATURE                 Location/Qualifiers
source                  1..107
                        mol_type = protein
                        organism = synthetic construct
SEQUENCE: 108
DIQMTQSPSF LSASVGDRVT ITCKASQNVG NRVAWYQQKP GKAPKALIYS SSHRYKGVPS  60
RFSGSGSGTE FTLTISSLQP EDFATYFCQQ FKSYPLTFGQ GTKLEIK                107

SEQ ID NO: 109          moltype = AA  length = 119
FEATURE                 Location/Qualifiers
source                  1..119
                        mol_type = protein
                        organism = synthetic construct
SEQUENCE: 109
QVQLVQSGAE VKKPGSSVKV SCKASGTDFD KIYIHWVRQA PGQGLEWMGR VSAGSGNTKY  60
NEKFKGRVTI TADTSTSTAY MELSSLRSED TAVYYCAGSY YSYDVLDYWG QGTTVTVSS   119

SEQ ID NO: 110          moltype = AA  length = 246
FEATURE                 Location/Qualifiers
source                  1..246
                        mol_type = protein
                        organism = synthetic construct
SEQUENCE: 110
QVQLVQSGAE VKKPGSSVKV SCKASGTDFK LTYIHWVRQA PGQGLEWMGR IFPGSGNVKY  60
NEKFKGRVTI TADTSTSTAY MELSSLRSED TAVYYCAGSY YSYDVLDYWG QGTTVTVSSG  120
GGGSGGGGSG GGGSGGGGSD IQMTQSPSFL SASVGDRVTI TCKASQNVDN RVAWYQQKPG  180
KAPKALIYSS SHRYKGVPSR FSGSGSGTEF TLTISSLQPE DFATYFCQQF KSYPLTFGQG  240
TKLEIK                                                             246

SEQ ID NO: 111          moltype = AA  length = 107
FEATURE                 Location/Qualifiers
source                  1..107
                        mol_type = protein
                        organism = synthetic construct
SEQUENCE: 111
DIQMTQSPSF LSASVGDRVT ITCKASQNVD NRVAWYQQKP GKAPKALIYS SSHRYKGVPS  60
RFSGSGSGTE FTLTISSLQP EDFATYFCQQ FKSYPLTFGQ GTKLEIK                107

SEQ ID NO: 112          moltype = AA  length = 119
FEATURE                 Location/Qualifiers
source                  1..119
                        mol_type = protein
                        organism = synthetic construct
SEQUENCE: 112
QVQLVQSGAE VKKPGSSVKV SCKASGTDFK LTYIHWVRQA PGQGLEWMGR IFPGSGNVKY  60
NEKFKGRVTI TADTSTSTAY MELSSLRSED TAVYYCAGSY YSYDVLDYWG QGTTVTVSS   119

SEQ ID NO: 113          moltype = AA  length = 246
FEATURE                 Location/Qualifiers
source                  1..246
                        mol_type = protein
                        organism = synthetic construct
SEQUENCE: 113
QVQLVQSGAE VKKPGSSVKV SCKASGTDFD KIYIHWVRQA PGQGLEWMGR ISAGSGNTKY  60
NEKFKGRVTI TADTSTSTAY MELSSLRSED TAVYYCAGSY YSYDVLDYWG QGTTVTVSSG  120
GGGSGGGGSG GGGSGGGGSD IQMTQSPSFL SASVGDRVTI TCKASQNVDD RVAWYQQKPG  180
KAPKALIYSS SHRYKGVPSR FSGSGSGTEF TLTISSLQPE DFATYFCQQF KSYPLTFGQG  240
TKLEIK                                                             246

SEQ ID NO: 114          moltype = AA  length = 107
FEATURE                 Location/Qualifiers
source                  1..107
                        mol_type = protein
```

```
                        organism = synthetic construct
SEQUENCE: 114
DIQMTQSPSF LSASVGDRVT ITCKASQNVD DRVAWYQQKP GKAPKALIYS SSHRYKGVPS  60
RFSGSGSGTE FTLTISSLQP EDFATYFCQQ FKSYPLTFGQ GTKLEIK               107

SEQ ID NO: 115          moltype = AA  length = 119
FEATURE                 Location/Qualifiers
source                  1..119
                        mol_type = protein
                        organism = synthetic construct
SEQUENCE: 115
QVQLVQSGAE VKKPGSSVKV SCKASGTDFD KIYIHWVRQA PGQGLEWMGR ISAGSGNTKY  60
NEKFKGRVTI TADTSTSTAY MELSSLRSED TAVYYCAGSY YSYDVLDYWG QGTTVTVSS   119

SEQ ID NO: 116          moltype = AA  length = 246
FEATURE                 Location/Qualifiers
source                  1..246
                        mol_type = protein
                        organism = synthetic construct
SEQUENCE: 116
QVQLVQSGAE VKKPGSSVKV SCKASGTDFR LTYIHWVRQA PGQGLEWMGR VSPGSGNTKY  60
NEKFKGRVTI TADTSTSTAY MELSSLRSED TAVYYCAGSY YSYDVLDYWG QGTTVTVSSG  120
GGGSGGGGSG GGGSGGGGSD IQMTQSPSFL SASVGDRVTI TCKASQNVDN KVAWHQQKPG  180
KAPKALIYSS SHRYKGVPSR FSGSGSGTEF TLTISSLQPE DFATYFCQQF KSYPLTFGQG  240
TKLEIK                                                            246

SEQ ID NO: 117          moltype = AA  length = 107
FEATURE                 Location/Qualifiers
source                  1..107
                        mol_type = protein
                        organism = synthetic construct
SEQUENCE: 117
DIQMTQSPSF LSASVGDRVT ITCKASQNVD NKVAWHQQKP GKAPKALIYS SSHRYKGVPS  60
RFSGSGSGTE FTLTISSLQP EDFATYFCQQ FKSYPLTFGQ GTKLEIK               107

SEQ ID NO: 118          moltype = AA  length = 119
FEATURE                 Location/Qualifiers
source                  1..119
                        mol_type = protein
                        organism = synthetic construct
SEQUENCE: 118
QVQLVQSGAE VKKPGSSVKV SCKASGTDFR LTYIHWVRQA PGQGLEWMGR VSPGSGNTKY  60
NEKFKGRVTI TADTSTSTAY MELSSLRSED TAVYYCAGSY YSYDVLDYWG QGTTVTVSS   119

SEQ ID NO: 119          moltype = AA  length = 246
FEATURE                 Location/Qualifiers
source                  1..246
                        mol_type = protein
                        organism = synthetic construct
SEQUENCE: 119
QVQLVQSGAE VKKPGSSVKV SCKASGGTFR LTYIHWVRQA PGQGLEWMGR VYPGSGNTKY  60
NEKFKGRVTI TADTSTSTAY MELSSLRSED TAVYYCAGSY YSYDVLDYWG QGTTVTVSSG  120
GGGSGGGGSG GGGSGGGGSD IQMTQSPSFL SASVGDRVTI TCKASQNVDD RVAWYQQKPG  180
KAPKALIYSS SHRYKGVPSR FSGSGSGTEF TLTISSLQPE DFATYFCQQF KSYPLTFGQG  240
TKLEIK                                                            246

SEQ ID NO: 120          moltype = AA  length = 107
FEATURE                 Location/Qualifiers
source                  1..107
                        mol_type = protein
                        organism = synthetic construct
SEQUENCE: 120
DIQMTQSPSF LSASVGDRVT ITCKASQNVD DRVAWYQQKP GKAPKALIYS SSHRYKGVPS  60
RFSGSGSGTE FTLTISSLQP EDFATYFCQQ FKSYPLTFGQ GTKLEIK               107

SEQ ID NO: 121          moltype = AA  length = 119
FEATURE                 Location/Qualifiers
source                  1..119
                        mol_type = protein
                        organism = synthetic construct
SEQUENCE: 121
QVQLVQSGAE VKKPGSSVKV SCKASGGTFR LTYIHWVRQA PGQGLEWMGR VYPGSGNTKY  60
NEKFKGRVTI TADTSTSTAY MELSSLRSED TAVYYCAGSY YSYDVLDYWG QGTTVTVSS   119

SEQ ID NO: 122          moltype = AA  length = 246
FEATURE                 Location/Qualifiers
source                  1..246
                        mol_type = protein
                        organism = synthetic construct
```

```
SEQUENCE: 122
QVQLVQSGAE VKKPGSSVKV SCKASGTDFR LTYIHWVRQA PGQGLEWMGR IFPGSGNTKY  60
NEKFKGRVTI TADTSTSTAY MELSSLRSED TAVYYCAGSY YSYDVLDYWG QGTTVTVSSG  120
GGGSGGGGSG GGGSGGGGSD IQMTQSPSFL SASVGDRVTI TCKASQNVDD RVAWYQQKPG  180
KAPKALIYSS SHRYKGVPSR FSGSGSGTEF TLTISSLQPE DFATYFCQQF KSYPLTFGQG  240
TKLEIK                                                            246

SEQ ID NO: 123         moltype = AA  length = 107
FEATURE                Location/Qualifiers
source                 1..107
                       mol_type = protein
                       organism = synthetic construct
SEQUENCE: 123
DIQMTQSPSF LSASVGDRVT ITCKASQNVD DRVAWYQQKP GKAPKALIYS SSHRYKGVPS  60
RFSGSGSGTE FTLTISSLQP EDFATYFCQQ FKSYPLTFGQ GTKLEIK                107

SEQ ID NO: 124         moltype = AA  length = 119
FEATURE                Location/Qualifiers
source                 1..119
                       mol_type = protein
                       organism = synthetic construct
SEQUENCE: 124
QVQLVQSGAE VKKPGSSVKV SCKASGTDFR LTYIHWVRQA PGQGLEWMGR IFPGSGNTKY  60
NEKFKGRVTI TADTSTSTAY MELSSLRSED TAVYYCAGSY YSYDVLDYWG QGTTVTVSS   119

SEQ ID NO: 125         moltype = AA  length = 246
FEATURE                Location/Qualifiers
source                 1..246
                       mol_type = protein
                       organism = synthetic construct
SEQUENCE: 125
QVQLVQSGAE VKKPGSSVKV SCKASGTDFK LTYIHWVRQA PGQGLEWMGR IFPGSGNVKY  60
NEKFKGRVTI TADTSTSTAY MELSSLRSED TAVYYCAGSY YSYDVLDYWG QGTTVTVSSG  120
GGGSGGGGSG GGGSGGGGSD IQMTQSPSFL SASVGDRVTI TCKASQNVED RVAWYQQKPG  180
KAPKALIYSS SHRYKGVPSR FSGSGSGTEF TLTISSLQPE DFATYFCQQF KSYPLTFGQG  240
TKLEIK                                                            246

SEQ ID NO: 126         moltype = AA  length = 107
FEATURE                Location/Qualifiers
source                 1..107
                       mol_type = protein
                       organism = synthetic construct
SEQUENCE: 126
DIQMTQSPSF LSASVGDRVT ITCKASQNVE DRVAWYQQKP GKAPKALIYS SSHRYKGVPS  60
RFSGSGSGTE FTLTISSLQP EDFATYFCQQ FKSYPLTFGQ GTKLEIK                107

SEQ ID NO: 127         moltype = AA  length = 119
FEATURE                Location/Qualifiers
source                 1..119
                       mol_type = protein
                       organism = synthetic construct
SEQUENCE: 127
QVQLVQSGAE VKKPGSSVKV SCKASGTDFK LTYIHWVRQA PGQGLEWMGR IFPGSGNVKY  60
NEKFKGRVTI TADTSTSTAY MELSSLRSED TAVYYCAGSY YSYDVLDYWG QGTTVTVSS   119

SEQ ID NO: 128         moltype = AA  length = 246
FEATURE                Location/Qualifiers
source                 1..246
                       mol_type = protein
                       organism = synthetic construct
SEQUENCE: 128
QVQLVQSGAE VKKPGSSVKV SCKASGGTFR LTYIHWVRQA PGQGLEWMGR ISAGSGNVKY  60
NEKFKGRVTI TADTSTSTAY MELSSLRSED TAVYYCAGSY YSYDVLDYWG QGTTVTVSSG  120
GGGSGGGGSG GGGSGGGGSD IQMTQSPSFL SASVGDRVTI TCKASQNVGD RVAWYQQKPG  180
KAPKALIYSS SHRYKGVPSR FSGSGSGTEF TLTISSLQPE DFATYFCQQF KSYPLTFGQG  240
TKLEIK                                                            246

SEQ ID NO: 129         moltype = AA  length = 107
FEATURE                Location/Qualifiers
source                 1..107
                       mol_type = protein
                       organism = synthetic construct
SEQUENCE: 129
DIQMTQSPSF LSASVGDRVT ITCKASQNVG DRVAWYQQKP GKAPKALIYS SSHRYKGVPS  60
RFSGSGSGTE FTLTISSLQP EDFATYFCQQ FKSYPLTFGQ GTKLEIK                107

SEQ ID NO: 130         moltype = AA  length = 119
FEATURE                Location/Qualifiers
source                 1..119
```

```
                        mol_type = protein
                        organism = synthetic construct
SEQUENCE: 130
QVQLVQSGAE VKKPGSSVKV SCKASGGTFR LTYIHWVRQA PGQGLEWMGR ISAGSGNVKY  60
NEKFKGRVTI TADTSTSTAY MELSSLRSED TAVYYCAGSY YSYDVLDYWG QGTTVTVSS   119

SEQ ID NO: 131          moltype = AA  length = 246
FEATURE                 Location/Qualifiers
source                  1..246
                        mol_type = protein
                        organism = synthetic construct
SEQUENCE: 131
QVQLVQSGAE VKKPGSSVKV SCKASGGTFD KTYIHWVRQA PGQGLEWMGR ISAGSGNTKY  60
NEKFKGRVTI TADTSTSTAY MELSSLRSED TAVYYCAGSY YSYDVLDYWG QGTTVTVSSG  120
GGGSGGGGSG GGGSGGGGSD IQMTQSPSFL SASVGDRVTI TCKASQNVDD RVAWYQQKPG  180
KAPKALIYSS SHRYKGVPSR FSGSGSGTEF TLTISSLQPE DFATYFCQQF KSYPLTFGQG  240
TKLEIK                                                             246

SEQ ID NO: 132          moltype = AA  length = 107
FEATURE                 Location/Qualifiers
source                  1..107
                        mol_type = protein
                        organism = synthetic construct
SEQUENCE: 132
DIQMTQSPSF LSASVGDRVT ITCKASQNVD DRVAWYQQKP GKAPKALIYS SSHRYKGVPS  60
RFSGSGSGTE FTLTISSLQP EDFATYFCQQ FKSYPLTFGQ GTKLEIK                107

SEQ ID NO: 133          moltype = AA  length = 119
FEATURE                 Location/Qualifiers
source                  1..119
                        mol_type = protein
                        organism = synthetic construct
SEQUENCE: 133
QVQLVQSGAE VKKPGSSVKV SCKASGGTFD KTYIHWVRQA PGQGLEWMGR ISAGSGNTKY  60
NEKFKGRVTI TADTSTSTAY MELSSLRSED TAVYYCAGSY YSYDVLDYWG QGTTVTVSS   119

SEQ ID NO: 134          moltype = AA  length = 246
FEATURE                 Location/Qualifiers
source                  1..246
                        mol_type = protein
                        organism = synthetic construct
SEQUENCE: 134
QVQLVQSGAE VKKPGSSVKV SCKASGHDFD KFYIHWVRQA PGQGLEWMGR ISAGSGNTKY  60
NEKFKGRVTI TADTSTSTAY MELSSLRSED TAVYYCAGSY YSYDVLDYWG QGTTVTVSSG  120
GGGSGGGGSG GGGSGGGGSD IQMTQSPSFL SASVGDRVTI TCKASQNVDD RVAWYQQKPG  180
KAPKALIYSS SHRYKGVPSR FSGSGSGTEF TLTISSLQPE DFATYFCQQF KSYPLTFGQG  240
TKLEIK                                                             246

SEQ ID NO: 135          moltype = AA  length = 107
FEATURE                 Location/Qualifiers
source                  1..107
                        mol_type = protein
                        organism = synthetic construct
SEQUENCE: 135
DIQMTQSPSF LSASVGDRVT ITCKASQNVD DRVAWYQQKP GKAPKALIYS SSHRYKGVPS  60
RFSGSGSGTE FTLTISSLQP EDFATYFCQQ FKSYPLTFGQ GTKLEIK                107

SEQ ID NO: 136          moltype = AA  length = 119
FEATURE                 Location/Qualifiers
source                  1..119
                        mol_type = protein
                        organism = synthetic construct
SEQUENCE: 136
QVQLVQSGAE VKKPGSSVKV SCKASGHDFD KFYIHWVRQA PGQGLEWMGR ISAGSGNTKY  60
NEKFKGRVTI TADTSTSTAY MELSSLRSED TAVYYCAGSY YSYDVLDYWG QGTTVTVSS   119

SEQ ID NO: 137          moltype = AA  length = 246
FEATURE                 Location/Qualifiers
source                  1..246
                        mol_type = protein
                        organism = synthetic construct
SEQUENCE: 137
QVQLVQSGAE VKKPGSSVKV SCKASGTDFK LTYIHWVRQA PGQGLEWMGR ISAGSGNVKY  60
NEKFKGRVTI TADTSTSTAY MELSSLRSED TAVYYCAGSY YSYDVLDYWG QGTTVTVSSG  120
GGGSGGGGSG GGGSGGGGSD IQMTQSPSFL SASVGDRVTI TCKASQNVDN KVAWHQQKPG  180
KAPKALIYSS SHRYKGVPSR FSGSGSGTEF TLTISSLQPE DFATYFCQQF KSYPLTFGQG  240
TKLEIK                                                             246

SEQ ID NO: 138          moltype = AA  length = 107
```

```
FEATURE                Location/Qualifiers
source                 1..107
                       mol_type = protein
                       organism = synthetic construct
SEQUENCE: 138
DIQMTQSPSF LSASVGDRVT ITCKASQNVD NKVAWHQQKP GKAPKALIYS SSHRYKGVPS  60
RFSGSGSGTE FTLTISSLQP EDFATYFCQQ FKSYPLTFGQ GTKLEIK               107

SEQ ID NO: 139         moltype = AA  length = 119
FEATURE                Location/Qualifiers
source                 1..119
                       mol_type = protein
                       organism = synthetic construct
SEQUENCE: 139
QVQLVQSGAE VKKPGSSVKV SCKASGTDFK LTYIHWVRQA PGQGLEWMGR ISAGSGNVKY  60
NEKFKGRVTI TADTSTSTAY MELSSLRSED TAVYYCAGSY YSYDVLDYWG QGTTVTVSS   119

SEQ ID NO: 140         moltype = AA  length = 246
FEATURE                Location/Qualifiers
source                 1..246
                       mol_type = protein
                       organism = synthetic construct
SEQUENCE: 140
QVQLVQSGAE VKKPGSSVKV SCKASGHDFR LTYIHWVRQA PGQGLEWMGR ISAGSGNVKY  60
NEKFKGRVTI TADTSTSTAY MELSSLRSED TAVYYCAGSY YSYDVLDYWG QGTTVTVSSG  120
GGGSGGGGSG GGGSGGGGSD IQMTQSPSFL SASVGDRVTI TCKASQNVAD RVAWYQQKPG  180
KAPKALIYSS SHRYKGVPSR FSGSGSGTEF TLTISSLQPE DFATYFCQQF KSYPLTFGQG  240
TKLEIK                                                            246

SEQ ID NO: 141         moltype = AA  length = 107
FEATURE                Location/Qualifiers
source                 1..107
                       mol_type = protein
                       organism = synthetic construct
SEQUENCE: 141
DIQMTQSPSF LSASVGDRVT ITCKASQNVA DRVAWYQQKP GKAPKALIYS SSHRYKGVPS  60
RFSGSGSGTE FTLTISSLQP EDFATYFCQQ FKSYPLTFGQ GTKLEIK               107

SEQ ID NO: 142         moltype = AA  length = 119
FEATURE                Location/Qualifiers
source                 1..119
                       mol_type = protein
                       organism = synthetic construct
SEQUENCE: 142
QVQLVQSGAE VKKPGSSVKV SCKASGHDFR LTYIHWVRQA PGQGLEWMGR ISAGSGNVKY  60
NEKFKGRVTI TADTSTSTAY MELSSLRSED TAVYYCAGSY YSYDVLDYWG QGTTVTVSS   119

SEQ ID NO: 143         moltype = AA  length = 246
FEATURE                Location/Qualifiers
source                 1..246
                       mol_type = protein
                       organism = synthetic construct
SEQUENCE: 143
QVQLVQSGAE VKKPGSSVKV SCKASGHDFH LWYIHWVRQA PGQGLEWMGR VSAGSGNVKY  60
NEKFKGRVTI TADTSTSTAY MELSSLRSED TAVYYCAGSY YSYDVLDYWG QGTTVTVSSG  120
GGGSGGGGSG GGGSGGGGSD IQMTQSPSFL SASVGDRVTI TCKASQNVDN KVAWHQQKPG  180
KAPKALIYSS SHRYKGVPSR FSGSGSGTEF TLTISSLQPE DFATYFCQQF KSYPLTFGQG  240
TKLEIK                                                            246

SEQ ID NO: 144         moltype = AA  length = 107
FEATURE                Location/Qualifiers
source                 1..107
                       mol_type = protein
                       organism = synthetic construct
SEQUENCE: 144
DIQMTQSPSF LSASVGDRVT ITCKASQNVD NKVAWHQQKP GKAPKALIYS SSHRYKGVPS  60
RFSGSGSGTE FTLTISSLQP EDFATYFCQQ FKSYPLTFGQ GTKLEIK               107

SEQ ID NO: 145         moltype = AA  length = 119
FEATURE                Location/Qualifiers
source                 1..119
                       mol_type = protein
                       organism = synthetic construct
SEQUENCE: 145
QVQLVQSGAE VKKPGSSVKV SCKASGHDFH LWYIHWVRQA PGQGLEWMGR VSAGSGNVKY  60
NEKFKGRVTI TADTSTSTAY MELSSLRSED TAVYYCAGSY YSYDVLDYWG QGTTVTVSS   119

SEQ ID NO: 146         moltype = AA  length = 246
FEATURE                Location/Qualifiers
```

```
source                  1..246
                        mol_type = protein
                        organism = synthetic construct
SEQUENCE: 146
QVQLVQSGAE VKKPGSSVKV SCKASGHDFH LWYIHWVRQA PGQGLEWMGR VFAGSGNTKY  60
NEKFKGRVTI TADTSTSTAY MELSSLRSED TAVYYCAGSY YSYDVLDYWG QGTTVTVSSG  120
GGGSGGGGSG GGGSGGGGSD IQMTQSPSFL SASVGDRVTI TCKASQNVED KVAWYQQKPG  180
KAPKALIYSS SHRYKGVPSR FSGSGSGTEF TLTISSLQPE DFATYFCQQF KSYPLTFGQG  240
TKLEIK                                                            246

SEQ ID NO: 147          moltype = AA  length = 107
FEATURE                 Location/Qualifiers
source                  1..107
                        mol_type = protein
                        organism = synthetic construct
SEQUENCE: 147
DIQMTQSPSF LSASVGDRVT ITCKASQNVE DKVAWYQQKP GKAPKALIYS SSHRYKGVPS  60
RFSGSGSGTE FTLTISSLQP EDFATYFCQQ FKSYPLTFGQ GTKLEIK               107

SEQ ID NO: 148          moltype = AA  length = 119
FEATURE                 Location/Qualifiers
source                  1..119
                        mol_type = protein
                        organism = synthetic construct
SEQUENCE: 148
QVQLVQSGAE VKKPGSSVKV SCKASGHDFH LWYIHWVRQA PGQGLEWMGR VFAGSGNTKY  60
NEKFKGRVTI TADTSTSTAY MELSSLRSED TAVYYCAGSY YSYDVLDYWG QGTTVTVSS   119

SEQ ID NO: 149          moltype = AA  length = 246
FEATURE                 Location/Qualifiers
source                  1..246
                        mol_type = protein
                        organism = synthetic construct
SEQUENCE: 149
QVQLVQSGAE VKKPGSSVKV SCKASGTDFK LTYIHWVRQA PGQGLEWMGR IFPGSGNTKY  60
NEKFKGRVTI TADTSTSTAY MELSSLRSED TAVYYCAGSY YSYDVLDYWG QGTTVTVSSG  120
GGGSGGGGSG GGGSGGGGSD IQMTQSPSFL SASVGDRVTI TCKASQNVDD RVAWYQQKPG  180
KAPKALIYSS SHRYKGVPSR FSGSGSGTEF TLTISSLQPE DFATYFCQQF KSYPLTFGQG  240
TKLEIK                                                            246

SEQ ID NO: 150          moltype = AA  length = 107
FEATURE                 Location/Qualifiers
source                  1..107
                        mol_type = protein
                        organism = synthetic construct
SEQUENCE: 150
DIQMTQSPSF LSASVGDRVT ITCKASQNVD DRVAWYQQKP GKAPKALIYS SSHRYKGVPS  60
RFSGSGSGTE FTLTISSLQP EDFATYFCQQ FKSYPLTFGQ GTKLEIK               107

SEQ ID NO: 151          moltype = AA  length = 119
FEATURE                 Location/Qualifiers
source                  1..119
                        mol_type = protein
                        organism = synthetic construct
SEQUENCE: 151
QVQLVQSGAE VKKPGSSVKV SCKASGTDFK LTYIHWVRQA PGQGLEWMGR IFPGSGNTKY  60
NEKFKGRVTI TADTSTSTAY MELSSLRSED TAVYYCAGSY YSYDVLDYWG QGTTVTVSS   119

SEQ ID NO: 152          moltype =   length =
SEQUENCE: 152
000

SEQ ID NO: 153          moltype = AA  length = 246
FEATURE                 Location/Qualifiers
source                  1..246
                        mol_type = protein
                        organism = synthetic construct
SEQUENCE: 153
QVQLVQSGAE VKKPGSSVKV SCKASGTDFK LTYIHWVRQA PGQGLEWMGR VSAGSGNVKY  60
NEKFKGRVTI TADTSTSTAY MELSSLRSED TAVYYCAGSY YSYDVLDYWG QGTTVTVSSG  120
GGGSGGGGSG GGGSGGGGSD IQMTQSPSFL SASVGDRVTI TCKASQNVGN RVAWYQQKPG  180
KAPKALIYSS SHRYKGVPSR FSGSGSGTEF TLTISSLQPE DFATYFCQQF KSYPLTFGQG  240
TKLEIK                                                            246

SEQ ID NO: 154          moltype = AA  length = 107
FEATURE                 Location/Qualifiers
source                  1..107
                        mol_type = protein
                        organism = synthetic construct
```

```
SEQUENCE: 154
DIQMTQSPSF LSASVGDRVT ITCKASQNVG NRVAWYQQKP GKAPKALIYS SSHRYKGVPS  60
RFSGSGSGTE FTLTISSLQP EDFATYFCQQ FKSYPLTFGQ GTKLEIK               107

SEQ ID NO: 155          moltype = AA  length = 119
FEATURE                 Location/Qualifiers
source                  1..119
                        mol_type = protein
                        organism = synthetic construct
SEQUENCE: 155
QVQLVQSGAE VKKPGSSVKV SCKASGTDFK LTYIHWVRQA PGQGLEWMGR VSAGSGNVKY  60
NEKFKGRVTI TADTSTSTAY MELSSLRSED TAVYYCAGSY YSYDVLDYWG QGTTVTVSS   119

SEQ ID NO: 156          moltype = AA  length = 246
FEATURE                 Location/Qualifiers
source                  1..246
                        mol_type = protein
                        organism = synthetic construct
SEQUENCE: 156
QVQLVQSGAE VKKPGSSVKV SCKASGTDFK LTYIHWVRQA PGQGLEWMGR ISPGSGNTKY  60
NEKFKGRVTI TADTSTSTAY MELSSLRSED TAVYYCAGSY YSYDVLDYWG QGTTVTVSSG  120
GGGSGGGGSG GGGSGGGGSD IQMTQSPSFL SASVGDRVTI TCKASQNVGD RVAWYQQKPG  180
KAPKALIYSS SHRYKGVPSR FSGSGSGTEF TLTISSLQPE DFATYFCQQF KSYPLTFGQG  240
TKLEIK                                                            246

SEQ ID NO: 157          moltype = AA  length = 107
FEATURE                 Location/Qualifiers
source                  1..107
                        mol_type = protein
                        organism = synthetic construct
SEQUENCE: 157
DIQMTQSPSF LSASVGDRVT ITCKASQNVG DRVAWYQQKP GKAPKALIYS SSHRYKGVPS  60
RFSGSGSGTE FTLTISSLQP EDFATYFCQQ FKSYPLTFGQ GTKLEIK               107

SEQ ID NO: 158          moltype = AA  length = 119
FEATURE                 Location/Qualifiers
source                  1..119
                        mol_type = protein
                        organism = synthetic construct
SEQUENCE: 158
QVQLVQSGAE VKKPGSSVKV SCKASGTDFK LTYIHWVRQA PGQGLEWMGR ISPGSGNTKY  60
NEKFKGRVTI TADTSTSTAY MELSSLRSED TAVYYCAGSY YSYDVLDYWG QGTTVTVSS   119

SEQ ID NO: 159          moltype = AA  length = 246
FEATURE                 Location/Qualifiers
source                  1..246
                        mol_type = protein
                        organism = synthetic construct
SEQUENCE: 159
QVQLVQSGAE VKKPGSSVKV SCKASGHDFH LWYIHWVRQA PGQGLEWMGR ISPGSGNVKY  60
NEKFKGRVTI TADTSTSTAY MELSSLRSED TAVYYCAGSY YSYDVLDYWG QGTTVTVSSG  120
GGGSGGGGSG GGGSGGGGSD IQMTQSPSFL SASVGDRVTI TCKASQNVGD RVAWHQQKPG  180
KAPKALIYSS SHRYKGVPSR FSGSGSGTEF TLTISSLQPE DFATYFCQQF KSYPLTFGQG  240
TKLEIK                                                            246

SEQ ID NO: 160          moltype = AA  length = 107
FEATURE                 Location/Qualifiers
source                  1..107
                        mol_type = protein
                        organism = synthetic construct
SEQUENCE: 160
DIQMTQSPSF LSASVGDRVT ITCKASQNVG DRVAWHQQKP GKAPKALIYS SSHRYKGVPS  60
RFSGSGSGTE FTLTISSLQP EDFATYFCQQ FKSYPLTFGQ GTKLEIK               107

SEQ ID NO: 161          moltype = AA  length = 119
FEATURE                 Location/Qualifiers
source                  1..119
                        mol_type = protein
                        organism = synthetic construct
SEQUENCE: 161
QVQLVQSGAE VKKPGSSVKV SCKASGHDFH LWYIHWVRQA PGQGLEWMGR ISPGSGNVKY  60
NEKFKGRVTI TADTSTSTAY MELSSLRSED TAVYYCAGSY YSYDVLDYWG QGTTVTVSS   119

SEQ ID NO: 162          moltype = AA  length = 246
FEATURE                 Location/Qualifiers
source                  1..246
                        mol_type = protein
                        organism = synthetic construct
SEQUENCE: 162
```

```
QVQLVQSGAE VKKPGSSVKV SCKASGHDFK LTYIHWVRQA PGQGLEWMGR ISAGSGNVKY  60
NEKFKGRVTI TADTSTSTAY MELSSLRSED TAVYYCAGSY YSYDVLDYWG QGTTVTVSSG  120
GGGSGGGGSG GGGSGGGGSD IQMTQSPSFL SASVGDRVTI TCKASQNVDD RVAWYQQKPG  180
KAPKALIYSS SHRYKGVPSR FSGSGSGTEF TLTISSLQPE DFATYFCQQF KSYPLTFGQG  240
TKLEIK                                                             246

SEQ ID NO: 163          moltype = AA  length = 107
FEATURE                 Location/Qualifiers
source                  1..107
                        mol_type = protein
                        organism = synthetic construct
SEQUENCE: 163
DIQMTQSPSF LSASVGDRVT ITCKASQNVD DRVAWYQQKP GKAPKALIYS SSHRYKGVPS  60
RFSGSGSGTE FTLTISSLQP EDFATYFCQQ FKSYPLTFGQ GTKLEIK                107

SEQ ID NO: 164          moltype = AA  length = 119
FEATURE                 Location/Qualifiers
source                  1..119
                        mol_type = protein
                        organism = synthetic construct
SEQUENCE: 164
QVQLVQSGAE VKKPGSSVKV SCKASGHDFK LTYIHWVRQA PGQGLEWMGR ISAGSGNVKY  60
NEKFKGRVTI TADTSTSTAY MELSSLRSED TAVYYCAGSY YSYDVLDYWG QGTTVTVSS   119

SEQ ID NO: 165          moltype = AA  length = 246
FEATURE                 Location/Qualifiers
source                  1..246
                        mol_type = protein
                        organism = synthetic construct
SEQUENCE: 165
QVQLVQSGAE VKKPGSSVKV SCKASGTDFH LWYIHWVRQA PGQGLEWMGR VFAGSGSYRY  60
NEKFKGRVTI TADTSTSTAY MELSSLRSED TAVYYCAGSY YSYDVLDYWG QGTTVTVSSG  120
GGGSGGGGSG GGGSGGGGSD IQMTQSPSFL SASVGDRVTI TCKASQNVDD RVAWYQQKPG  180
KAPKALIYSS SHRYKGVPSR FSGSGSGTEF TLTISSLQPE DFATYFCQQF KSYPLTFGQG  240
TKLEIK                                                             246

SEQ ID NO: 166          moltype = AA  length = 107
FEATURE                 Location/Qualifiers
source                  1..107
                        mol_type = protein
                        organism = synthetic construct
SEQUENCE: 166
DIQMTQSPSF LSASVGDRVT ITCKASQNVD DRVAWYQQKP GKAPKALIYS SSHRYKGVPS  60
RFSGSGSGTE FTLTISSLQP EDFATYFCQQ FKSYPLTFGQ GTKLEIK                107

SEQ ID NO: 167          moltype = AA  length = 119
FEATURE                 Location/Qualifiers
source                  1..119
                        mol_type = protein
                        organism = synthetic construct
SEQUENCE: 167
QVQLVQSGAE VKKPGSSVKV SCKASGTDFH LWYIHWVRQA PGQGLEWMGR VFAGSGSYRY  60
NEKFKGRVTI TADTSTSTAY MELSSLRSED TAVYYCAGSY YSYDVLDYWG QGTTVTVSS   119

SEQ ID NO: 168          moltype = AA  length = 246
FEATURE                 Location/Qualifiers
source                  1..246
                        mol_type = protein
                        organism = synthetic construct
SEQUENCE: 168
QVQLVQSGAE VKKPGSSVKV SCKASGTDFD KIYIHWVRQA PGQGLEWMGR ISAGSGNTKY  60
NEKFKGRVTI TADTSTSTAY MELSSLRSED TAVYYCAGSY YSYDVLDYWG QGTTVTVSSG  120
GGGSGGGGSG GGGSGGGGSD IQMTQSPSFL SASVGDRVTI TCKASQNVAD RVAWYQQKPG  180
KAPKALIYSS SHRYKGVPSR FSGSGSGTEF TLTISSLQPE DFATYFCQQF KSYPLTFGQG  240
TKLEIK                                                             246

SEQ ID NO: 169          moltype = AA  length = 107
FEATURE                 Location/Qualifiers
source                  1..107
                        mol_type = protein
                        organism = synthetic construct
SEQUENCE: 169
DIQMTQSPSF LSASVGDRVT ITCKASQNVA DRVAWYQQKP GKAPKALIYS SSHRYKGVPS  60
RFSGSGSGTE FTLTISSLQP EDFATYFCQQ FKSYPLTFGQ GTKLEIK                107

SEQ ID NO: 170          moltype = AA  length = 119
FEATURE                 Location/Qualifiers
source                  1..119
                        mol_type = protein
```

```
                         organism = synthetic construct
SEQUENCE: 170
QVQLVQSGAE VKKPGSSVKV SCKASGTDFD KIYIHWVRQA PGQGLEWMGR ISAGSGNTKY  60
NEKFKGRVTI TADTSTSTAY MELSSLRSED TAVYYCAGSY YSYDVLDYWG QGTTVTVSS   119

SEQ ID NO: 171           moltype = AA  length = 246
FEATURE                  Location/Qualifiers
source                   1..246
                         mol_type = protein
                         organism = synthetic construct
SEQUENCE: 171
QVQLVQSGAE VKKPGSSVKV SCKASGTDFK LTYIHWVRQA PGQGLEWMGR ISAGSGNTKY  60
NEKFKGRVTI TADTSTSTAY MELSSLRSED TAVYYCAGSY YSYDVLDYWG QGTTVTVSSG  120
GGGSGGGGSG GGGSGGGGSD IQMTQSPSFL SASVGDRVTI TCKASQNVED RVAWYQQKPG  180
KAPKALIYSS SHRYKGVPSR FSGSGSGTEF TLTISSLQPE DFATYFCQQF KSYPLTFGQG  240
TKLEIK                                                             246

SEQ ID NO: 172           moltype = AA  length = 107
FEATURE                  Location/Qualifiers
source                   1..107
                         mol_type = protein
                         organism = synthetic construct
SEQUENCE: 172
DIQMTQSPSF LSASVGDRVT ITCKASQNVE DRVAWYQQKP GKAPKALIYS SSHRYKGVPS  60
RFSGSGSGTE FTLTISSLQP EDFATYFCQQ FKSYPLTFGQ GTKLEIK                107

SEQ ID NO: 173           moltype = AA  length = 119
FEATURE                  Location/Qualifiers
source                   1..119
                         mol_type = protein
                         organism = synthetic construct
SEQUENCE: 173
QVQLVQSGAE VKKPGSSVKV SCKASGTDFK LTYIHWVRQA PGQGLEWMGR ISAGSGNTKY  60
NEKFKGRVTI TADTSTSTAY MELSSLRSED TAVYYCAGSY YSYDVLDYWG QGTTVTVSS   119

SEQ ID NO: 174           moltype = AA  length = 246
FEATURE                  Location/Qualifiers
source                   1..246
                         mol_type = protein
                         organism = synthetic construct
SEQUENCE: 174
QVQLVQSGAE VKKPGSSVKV SCKASGTDFR LTYIHWVRQA PGQGLEWMGR ISPGSGNTKY  60
NEKFKGRVTI TADTSTSTAY MELSSLRSED TAVYYCAGSY YSYDVLDYWG QGTTVTVSSG  120
GGGSGGGGSG GGGSGGGGSD IQMTQSPSFL SASVGDRVTI TCKASQNVGN RVAWYQQKPG  180
KAPKALIYSS SHRYKGVPSR FSGSGSGTEF TLTISSLQPE DFATYFCQQF KSYPLTFGQG  240
TKLEIK                                                             246

SEQ ID NO: 175           moltype = AA  length = 107
FEATURE                  Location/Qualifiers
source                   1..107
                         mol_type = protein
                         organism = synthetic construct
SEQUENCE: 175
DIQMTQSPSF LSASVGDRVT ITCKASQNVG NRVAWYQQKP GKAPKALIYS SSHRYKGVPS  60
RFSGSGSGTE FTLTISSLQP EDFATYFCQQ FKSYPLTFGQ GTKLEIK                107

SEQ ID NO: 176           moltype = AA  length = 119
FEATURE                  Location/Qualifiers
source                   1..119
                         mol_type = protein
                         organism = synthetic construct
SEQUENCE: 176
QVQLVQSGAE VKKPGSSVKV SCKASGTDFR LTYIHWVRQA PGQGLEWMGR ISPGSGNTKY  60
NEKFKGRVTI TADTSTSTAY MELSSLRSED TAVYYCAGSY YSYDVLDYWG QGTTVTVSS   119

SEQ ID NO: 177           moltype = AA  length = 246
FEATURE                  Location/Qualifiers
source                   1..246
                         mol_type = protein
                         organism = synthetic construct
SEQUENCE: 177
QVQLVQSGAE VKKPGSSVKV SCKASGHDFD KTYIHWVRQA PGQGLEWMGR VSAGSGNVKY  60
NEKFKGRVTI TADTSTSTAY MELSSLRSED TAVYYCAGSY YSYDVLDYWG QGTTVTVSSG  120
GGGSGGGGSG GGGSGGGGSD IQMTQSPSFL SASVGDRVTI TCKASQNVED RVAWYQQKPG  180
KAPKALIYSS SHRYKGVPSR FSGSGSGTEF TLTISSLQPE DFATYFCQQF KSYPLTFGQG  240
TKLEIK                                                             246

SEQ ID NO: 178           moltype = AA  length = 107
FEATURE                  Location/Qualifiers
```

```
source                  1..107
                        mol_type = protein
                        organism = synthetic construct
SEQUENCE: 178
DIQMTQSPSF LSASVGDRVT ITCKASQNVE DRVAWYQQKP GKAPKALIYS SSHRYKGVPS  60
RFSGSGSGTE FTLTISSLQP EDFATYFCQQ FKSYPLTFGQ GTKLEIK               107

SEQ ID NO: 179          moltype = AA  length = 119
FEATURE                 Location/Qualifiers
source                  1..119
                        mol_type = protein
                        organism = synthetic construct
SEQUENCE: 179
QVQLVQSGAE VKKPGSSVKV SCKASGHDFD KTYIHWVRQA PGQGLEWMGR VSAGSGNVKY  60
NEKFKGRVTI TADTSTSTAY MELSSLRSED TAVYYCAGSY YSYDVLDYWG QGTTVTVSS   119

SEQ ID NO: 180          moltype = AA  length = 246
FEATURE                 Location/Qualifiers
source                  1..246
                        mol_type = protein
                        organism = synthetic construct
SEQUENCE: 180
QVQLVQSGAE VKKPGSSVKV SCKASGHDFK LTYIHWVRQA PGQGLEWMGR VSPGSGNTKY  60
NEKFKGRVTI TADTSTSTAY MELSSLRSED TAVYYCAGSY YSYDVLDYWG QGTTVTVSSG  120
GGGSGGGGSG GGGSGGGGSD IQMTQSPSFL SASVGDRVTI TCKASQNVED RVAWHQQKPG  180
KAPKALIYSS SHRYKGVPSR FSGSGSGTEF TLTISSLQPE DFATYFCQQF KSYPLTFGQG  240
TKLEIK                                                            246

SEQ ID NO: 181          moltype = AA  length = 107
FEATURE                 Location/Qualifiers
source                  1..107
                        mol_type = protein
                        organism = synthetic construct
SEQUENCE: 181
DIQMTQSPSF LSASVGDRVT ITCKASQNVE DRVAWHQQKP GKAPKALIYS SSHRYKGVPS  60
RFSGSGSGTE FTLTISSLQP EDFATYFCQQ FKSYPLTFGQ GTKLEIK               107

SEQ ID NO: 182          moltype = AA  length = 119
FEATURE                 Location/Qualifiers
source                  1..119
                        mol_type = protein
                        organism = synthetic construct
SEQUENCE: 182
QVQLVQSGAE VKKPGSSVKV SCKASGHDFK LTYIHWVRQA PGQGLEWMGR VSPGSGNTKY  60
NEKFKGRVTI TADTSTSTAY MELSSLRSED TAVYYCAGSY YSYDVLDYWG QGTTVTVSS   119

SEQ ID NO: 183          moltype = AA  length = 246
FEATURE                 Location/Qualifiers
source                  1..246
                        mol_type = protein
                        organism = synthetic construct
SEQUENCE: 183
QVQLVQSGAE VKKPGSSVKV SCKASGHDFD KTYIHWVRQA PGQGLEWMGR IYPGSGNVKY  60
NEKFKGRVTI TADTSTSTAY MELSSLRSED TAVYYCAGSY YSYDVLDYWG QGTTVTVSSG  120
GGGSGGGGSG GGGSGGGGSD IQMTQSPSFL SASVGDRVTI TCKASQNVAD RVAWYQQKPG  180
KAPKALIYSS SHRYKGVPSR FSGSGSGTEF TLTISSLQPE DFATYFCQQF KSYPLTFGQG  240
TKLEIK                                                            246

SEQ ID NO: 184          moltype = AA  length = 107
FEATURE                 Location/Qualifiers
source                  1..107
                        mol_type = protein
                        organism = synthetic construct
SEQUENCE: 184
DIQMTQSPSF LSASVGDRVT ITCKASQNVA DRVAWYQQKP GKAPKALIYS SSHRYKGVPS  60
RFSGSGSGTE FTLTISSLQP EDFATYFCQQ FKSYPLTFGQ GTKLEIK               107

SEQ ID NO: 185          moltype = AA  length = 119
FEATURE                 Location/Qualifiers
source                  1..119
                        mol_type = protein
                        organism = synthetic construct
SEQUENCE: 185
QVQLVQSGAE VKKPGSSVKV SCKASGHDFD KTYIHWVRQA PGQGLEWMGR IYPGSGNVKY  60
NEKFKGRVTI TADTSTSTAY MELSSLRSED TAVYYCAGSY YSYDVLDYWG QGTTVTVSS   119

SEQ ID NO: 186          moltype = AA  length = 246
FEATURE                 Location/Qualifiers
source                  1..246
```

```
                         mol_type = protein
                         organism = synthetic construct
SEQUENCE: 186
QVQLVQSGAE VKKPGSSVKV SCKASGTDFD KTYIHWVRQA PGQGLEWMGR ISAGSGNVKY  60
NEKFKGRVTI TADTSTSTAY MELSSLRSED TAVYYCAGSY YSYDVLDYWG QGTTVTVSSG  120
GGGSGGGGSG GGGSGGGGSD IQMTQSPSFL SASVGDRVTI TCKASQNVDD RVAWYQQKPG  180
KAPKALIYSS SHRYKGVPSR FSGSGSGTEF TLTISSLQPE DFATYFCQQF KSYPLTFGQG  240
TKLEIK                                                             246

SEQ ID NO: 187           moltype = AA  length = 107
FEATURE                  Location/Qualifiers
source                   1..107
                         mol_type = protein
                         organism = synthetic construct
SEQUENCE: 187
DIQMTQSPSF LSASVGDRVT ITCKASQNVD DRVAWYQQKP GKAPKALIYS SSHRYKGVPS  60
RFSGSGSGTE FTLTISSLQP EDFATYFCQQ FKSYPLTFGQ GTKLEIK                107

SEQ ID NO: 188           moltype = AA  length = 119
FEATURE                  Location/Qualifiers
source                   1..119
                         mol_type = protein
                         organism = synthetic construct
SEQUENCE: 188
QVQLVQSGAE VKKPGSSVKV SCKASGTDFD KTYIHWVRQA PGQGLEWMGR ISAGSGNVKY  60
NEKFKGRVTI TADTSTSTAY MELSSLRSED TAVYYCAGSY YSYDVLDYWG QGTTVTVSS   119

SEQ ID NO: 189           moltype = AA  length = 246
FEATURE                  Location/Qualifiers
source                   1..246
                         mol_type = protein
                         organism = synthetic construct
SEQUENCE: 189
QVQLVQSGAE VKKPGSSVKV SCKASGTDFD KIYIHWVRQA PGQGLEWMGR ISAGSGNIKY  60
NEKFKGRVTI TADTSTSTAY MELSSLRSED TAVYYCAGSY YSYDVLDYWG QGTTVTVSSG  120
GGGSGGGGSG GGGSGGGGSD IQMTQSPSFL SASVGDRVTI TCKASQNVDD RVAWYQQKPG  180
KAPKALIYSS SHRYKGVPSR FSGSGSGTEF TLTISSLQPE DFATYFCQQF KSYPLTFGQG  240
TKLEIK                                                             246

SEQ ID NO: 190           moltype = AA  length = 107
FEATURE                  Location/Qualifiers
source                   1..107
                         mol_type = protein
                         organism = synthetic construct
SEQUENCE: 190
DIQMTQSPSF LSASVGDRVT ITCKASQNVD DRVAWYQQKP GKAPKALIYS SSHRYKGVPS  60
RFSGSGSGTE FTLTISSLQP EDFATYFCQQ FKSYPLTFGQ GTKLEIK                107

SEQ ID NO: 191           moltype = AA  length = 119
FEATURE                  Location/Qualifiers
source                   1..119
                         mol_type = protein
                         organism = synthetic construct
SEQUENCE: 191
QVQLVQSGAE VKKPGSSVKV SCKASGTDFD KIYIHWVRQA PGQGLEWMGR ISAGSGNIKY  60
NEKFKGRVTI TADTSTSTAY MELSSLRSED TAVYYCAGSY YSYDVLDYWG QGTTVTVSS   119

SEQ ID NO: 192           moltype = AA  length = 246
FEATURE                  Location/Qualifiers
source                   1..246
                         mol_type = protein
                         organism = synthetic construct
SEQUENCE: 192
QVQLVQSGAE VKKPGSSVKV SCKASGTDFD KIYIHWVRQA PGQGLEWMGR ISAGSGNVKY  60
NEKFKGRVTI TADTSTSTAY MELSSLRSED TAVYYCAGSY YSYDVLDYWG QGTTVTVSSG  120
GGGSGGGGSG GGGSGGGGSD IQMTQSPSFL SASVGDRVTI TCKASQNVGD RVAWYQQKPG  180
KAPKALIYSS SHRYKGVPSR FSGSGSGTEF TLTISSLQPE DFATYFCQQF KSYPLTFGQG  240
TKLEIK                                                             246

SEQ ID NO: 193           moltype = AA  length = 107
FEATURE                  Location/Qualifiers
source                   1..107
                         mol_type = protein
                         organism = synthetic construct
SEQUENCE: 193
DIQMTQSPSF LSASVGDRVT ITCKASQNVG DRVAWYQQKP GKAPKALIYS SSHRYKGVPS  60
RFSGSGSGTE FTLTISSLQP EDFATYFCQQ FKSYPLTFGQ GTKLEIK                107

SEQ ID NO: 194           moltype = AA  length = 119
```

```
FEATURE                Location/Qualifiers
source                 1..119
                       mol_type = protein
                       organism = synthetic construct
SEQUENCE: 194
QVQLVQSGAE VKKPGSSVKV SCKASGTDFD KIYIHWVRQA PGQGLEWMGR ISAGSGNVKY  60
NEKFKGRVTI TADTSTSTAY MELSSLRSED TAVYYCAGSY YSYDVLDYWG QGTTVTVSS   119

SEQ ID NO: 195         moltype = AA  length = 246
FEATURE                Location/Qualifiers
source                 1..246
                       mol_type = protein
                       organism = synthetic construct
SEQUENCE: 195
QVQLVQSGAE VKKPGSSVKV SCKASGGTFK LTYIHWVRQA PGQGLEWMGR VSAGSGNVKY  60
NEKFKGRVTI TADTSTSTAY MELSSLRSED TAVYYCAGSY YSYDVLDYWG QGTTVTVSSG  120
GGGSGGGGSG GGGSGGGGSD IQMTQSPSFL SASVGDRVTI TCKASQNVDD RVAWYQQKPG  180
KAPKALIYSS SHRYKGVPSR FSGSGSGTEF TLTISSLQPE DFATYFCQQF KSYPLTFGQG  240
TKLEIK                                                            246

SEQ ID NO: 196         moltype = AA  length = 107
FEATURE                Location/Qualifiers
source                 1..107
                       mol_type = protein
                       organism = synthetic construct
SEQUENCE: 196
DIQMTQSPSF LSASVGDRVT ITCKASQNVD DRVAWYQQKP GKAPKALIYS SSHRYKGVPS  60
RFSGSGSGTE FTLTISSLQP EDFATYFCQQ FKSYPLTFGQ GTKLEIK               107

SEQ ID NO: 197         moltype = AA  length = 119
FEATURE                Location/Qualifiers
source                 1..119
                       mol_type = protein
                       organism = synthetic construct
SEQUENCE: 197
QVQLVQSGAE VKKPGSSVKV SCKASGGTFK LTYIHWVRQA PGQGLEWMGR VSAGSGNVKY  60
NEKFKGRVTI TADTSTSTAY MELSSLRSED TAVYYCAGSY YSYDVLDYWG QGTTVTVSS   119

SEQ ID NO: 198         moltype = AA  length = 246
FEATURE                Location/Qualifiers
source                 1..246
                       mol_type = protein
                       organism = synthetic construct
SEQUENCE: 198
QVQLVQSGAE VKKPGSSVKV SCKASGTDFK LTYIHWVRQA PGQGLEWMGR ISPGSGNVKY  60
NEKFKGRVTI TADTSTSTAY MELSSLRSED TAVYYCAGSY YSYDVLDYWG QGTTVTVSSG  120
GGGSGGGGSG GGGSGGGGSD IQMTQSPSFL SASVGDRVTI TCKASQNVDN RVAWHQQKPG  180
KAPKALIYSS SHRYKGVPSR FSGSGSGTEF TLTISSLQPE DFATYFCQQF KSYPLTFGQG  240
TKLEIK                                                            246

SEQ ID NO: 199         moltype = AA  length = 107
FEATURE                Location/Qualifiers
source                 1..107
                       mol_type = protein
                       organism = synthetic construct
SEQUENCE: 199
DIQMTQSPSF LSASVGDRVT ITCKASQNVD NRVAWHQQKP GKAPKALIYS SSHRYKGVPS  60
RFSGSGSGTE FTLTISSLQP EDFATYFCQQ FKSYPLTFGQ GTKLEIK               107

SEQ ID NO: 200         moltype = AA  length = 119
FEATURE                Location/Qualifiers
source                 1..119
                       mol_type = protein
                       organism = synthetic construct
SEQUENCE: 200
QVQLVQSGAE VKKPGSSVKV SCKASGTDFK LTYIHWVRQA PGQGLEWMGR ISPGSGNVKY  60
NEKFKGRVTI TADTSTSTAY MELSSLRSED TAVYYCAGSY YSYDVLDYWG QGTTVTVSS   119

SEQ ID NO: 201         moltype = AA  length = 246
FEATURE                Location/Qualifiers
source                 1..246
                       mol_type = protein
                       organism = synthetic construct
SEQUENCE: 201
QVQLVQSGAE VKKPGSSVKV SCKASGHDFD KFYIHWVRQA PGQGLEWMGR VSAGSGNTKY  60
NEKFKGRVTI TADTSTSTAY MELSSLRSED TAVYYCAGSY YSYDVLDYWG QGTTVTVSSG  120
GGGSGGGGSG GGGSGGGGSD IQMTQSPSFL SASVGDRVTI TCKASQNVDN RVAWYQQKPG  180
KAPKALIYSS SHRYKGVPSR FSGSGSGTEF TLTISSLQPE DFATYFCQQF KSYPLTFGQG  240
TKLEIK                                                            246
```

```
SEQ ID NO: 202         moltype = AA  length = 107
FEATURE                Location/Qualifiers
source                 1..107
                       mol_type = protein
                       organism = synthetic construct
SEQUENCE: 202
DIQMTQSPSF LSASVGDRVT ITCKASQNVD NRVAWYQQKP GKAPKALIYS SSHRYKGVPS  60
RFSGSGSGTE FTLTISSLQP EDFATYFCQQ FKSYPLTFGQ GTKLEIK                107

SEQ ID NO: 203         moltype = AA  length = 119
FEATURE                Location/Qualifiers
source                 1..119
                       mol_type = protein
                       organism = synthetic construct
SEQUENCE: 203
QVQLVQSGAE VKKPGSSVKV SCKASGHDFD KFYIHWVRQA PGQGLEWMGR VSAGSGNTKY  60
NEKFKGRVTI TADTSTSTAY MELSSLRSED TAVYYCAGSY YSYDVLDYWG QGTTVTVSS   119

SEQ ID NO: 204         moltype = AA  length = 246
FEATURE                Location/Qualifiers
source                 1..246
                       mol_type = protein
                       organism = synthetic construct
SEQUENCE: 204
QVQLVQSGAE VKKPGSSVKV SCKASGTDFD KFYIHWVRQA PGQGLEWMGR VSAGSGNVKY  60
NEKFKGRVTI TADTSTSTAY MELSSLRSED TAVYYCAGSY YSYDVLDYWG QGTTVTVSSG  120
GGGSGGGGSG GGGSGGGGSD IQMTQSPSFL SASVGDRVTI TCKASQNVGD RVVWYQQKPG  180
KAPKALIYSS SHRYKGVPSR FSGSGSGTEF TLTISSLQPE DFATYFCQQF KSYPLTFGQG  240
TKLEIK                                                             246

SEQ ID NO: 205         moltype = AA  length = 119
FEATURE                Location/Qualifiers
source                 1..119
                       mol_type = protein
                       organism = synthetic construct
SEQUENCE: 205
QVQLVQSGAE VKKPGSSVKV SCKASGTDFD KFYIHWVRQA PGQGLEWMGR VSAGSGNVKY  60
NEKFKGRVTI TADTSTSTAY MELSSLRSED TAVYYCAGSY YSYDVLDYWG QGTTVTVSS   119

SEQ ID NO: 206         moltype = AA  length = 246
FEATURE                Location/Qualifiers
source                 1..246
                       mol_type = protein
                       organism = synthetic construct
SEQUENCE: 206
QVQLVQSGAE VKKPGSSVKV SCKASGYSFT TYYIHWVRQA PGQGLEWMGW FSAGSGNTKY  60
NEKFKGRVTI TADTSTSTAY MELSSLRSED TAVYYCAVSY YSYDVLDYWG QGTTVTVSSG  120
GGGSGGGGSG GGGSGGGGSD IQMTQSPSFL SASVGDRVTI TCKASQNVGI NVVWHQQKPG  180
KAPKALIYSS SHRYSGVPSR FSGSGSGTEF TLTISSLQPE DFATYFCQQF KSYPLTFGQG  240
TKLEIK                                                             246

SEQ ID NO: 207         moltype = AA  length = 119
FEATURE                Location/Qualifiers
source                 1..119
                       mol_type = protein
                       organism = synthetic construct
SEQUENCE: 207
QVQLVQSGAE VKKPGSSVKV SCKASGYSFT TYYIHWVRQA PGQGLEWMGW FSAGSGNTKY  60
NEKFKGRVTI TADTSTSTAY MELSSLRSED TAVYYCAVSY YSYDVLDYWG QGTTVTVSS   119

SEQ ID NO: 208         moltype = AA  length = 246
FEATURE                Location/Qualifiers
source                 1..246
                       mol_type = protein
                       organism = synthetic construct
SEQUENCE: 208
QVQLVQSGAE VKKPGSSVKV SCKASGYSFT TYYIHWVRQA PGQGLEWMGW FSAGSGNTKY  60
NEKFKGRVTI TADTSTSTAY MELSSLRSED TAVYYCAGSY YSYDVLDYWG QGTTVTVSSG  120
GGGSGGGGSG GGGSGGGGSD IQMTQSPSFL SASVGDRVTI TCKASQNVGI NVVWHQQKPG  180
KAPKALIYSS SHRYSGVPSR FSGSGSGTEF TLTISSLQPE DFATYFCQQF KSYPLTFGQG  240
TKLEIK                                                             246

SEQ ID NO: 209         moltype = AA  length = 119
FEATURE                Location/Qualifiers
source                 1..119
                       mol_type = protein
                       organism = synthetic construct
SEQUENCE: 209
```

```
QVQLVQSGAE VKKPGSSVKV SCKASGYSFT TYYIHWVRQA PGQGLEWMGW FSAGSGNTKY  60
NEKFKGRVTI TADTSTSTAY MELSSLRSED TAVYYCAGSY YSYDVLDYWG QGTTVTVSS   119

SEQ ID NO: 210         moltype = AA  length = 246
FEATURE                Location/Qualifiers
source                 1..246
                       mol_type = protein
                       organism = synthetic construct
SEQUENCE: 210
QVQLVQSGAE VKKPGSSVKV SCKASGYSFT TYYIHWVRQA PGQGLEWMGW FFPGSGNTKY  60
NEKFKGRVTI TADTSTSTAY MELSSLRSED TAVYYCAGSY YSYDVLDYWG QGTTVTVSSG  120
GGGSGGGGSG GGGSGGGGSD IQMTQSPSFL SASVGDRVTI TCKASQNVGI NVVWHQQKPG  180
KAPKALIYSS SHRYSGVPSR FSGSGSGTEF TLTISSLQPE DFATYFCQQF KSYPLTFGQG  240
TKLEIK                                                             246

SEQ ID NO: 211         moltype = AA  length = 119
FEATURE                Location/Qualifiers
source                 1..119
                       mol_type = protein
                       organism = synthetic construct
SEQUENCE: 211
QVQLVQSGAE VKKPGSSVKV SCKASGYSFT TYYIHWVRQA PGQGLEWMGW FFPGSGNTKY  60
NEKFKGRVTI TADTSTSTAY MELSSLRSED TAVYYCAGSY YSYDVLDYWG QGTTVTVSS   119

SEQ ID NO: 212         moltype = AA  length = 246
FEATURE                Location/Qualifiers
source                 1..246
                       mol_type = protein
                       organism = synthetic construct
SEQUENCE: 212
QVQLVQSGAE VKKPGSSVKV SCKASGYSFT TYYIHWVRQA PGQGLEWMGW FSPGSGNTKY  60
NEKFKGRVTI TADTSTSTAY MELSSLRSED TAVYYCAVSY YSYDVLDYWG QGTTVTVSSG  120
GGGSGGGGSG GGGSGGGGSD IQMTQSPSFL SASVGDRVTI TCKASQNVGI NVVWHQQKPG  180
KAPKALIYSS SHRYSGVPSR FSGSGSGTEF TLTISSLQPE DFATYFCQQF KSYPLTFGQG  240
TKLEIK                                                             246

SEQ ID NO: 213         moltype = AA  length = 119
FEATURE                Location/Qualifiers
source                 1..119
                       mol_type = protein
                       organism = synthetic construct
SEQUENCE: 213
QVQLVQSGAE VKKPGSSVKV SCKASGYSFT TYYIHWVRQA PGQGLEWMGW FSPGSGNTKY  60
NEKFKGRVTI TADTSTSTAY MELSSLRSED TAVYYCAVSY YSYDVLDYWG QGTTVTVSS   119

SEQ ID NO: 214         moltype = AA  length = 246
FEATURE                Location/Qualifiers
source                 1..246
                       mol_type = protein
                       organism = synthetic construct
SEQUENCE: 214
QVQLVQSGAE VKKPGSSVKV SCKASGYSFT TYYIHWVRQA PGQGLEWMGW FSPGSGNTKY  60
NEKFKGRVTI TADTSTSTAY MELSSLRSED TAVYYCAGSY YSYDVLDYWG QGTTVTVSSG  120
GGGSGGGGSG GGGSGGGGSD IQMTQSPSFL SASVGDRVTI TCKASQNVGI NVVWHQQKPG  180
KAPKALIYSS SHRYSGVPSR FSGSGSGTEF TLTISSLQPE DFATYFCQQF KSYPLTFGQG  240
TKLEIK                                                             246

SEQ ID NO: 215         moltype = AA  length = 119
FEATURE                Location/Qualifiers
source                 1..119
                       mol_type = protein
                       organism = synthetic construct
SEQUENCE: 215
QVQLVQSGAE VKKPGSSVKV SCKASGYSFT TYYIHWVRQA PGQGLEWMGW FSPGSGNTKY  60
NEKFKGRVTI TADTSTSTAY MELSSLRSED TAVYYCAGSY YSYDVLDYWG QGTTVTVSS   119

SEQ ID NO: 216         moltype = AA  length = 246
FEATURE                Location/Qualifiers
source                 1..246
                       mol_type = protein
                       organism = synthetic construct
SEQUENCE: 216
QVQLVQSGAE VKKPGSSVKV SCKASGYSFT TYYIHWVRQA PGQGLEWMGR IFPGSGNIKY  60
NEKFKGRVTI TADTSTSTAY MELSSLRSED TAVYYCAGSY YSYDVLDYWG QGTTVTVSSG  120
GGGSGGGGSG GGGSGGGGSD IQMTQSPSFL SASVGDRVTI TCKASQNVGI NVVWHQQKPG  180
KAPKALIYSS SHRYSGVPSR FSGSGSGTEF TLTISSLQPE DFATYFCQQF KSYPLTFGQG  240
TKLEIK                                                             246

SEQ ID NO: 217         moltype = AA  length = 119
```

```
FEATURE                 Location/Qualifiers
source                  1..119
                        mol_type = protein
                        organism = synthetic construct
SEQUENCE: 217
QVQLVQSGAE VKKPGSSVKV SCKASGYSFT TYYIHWVRQA PGQGLEWMGR IFPGSGNIKY  60
NEKFKGRVTI TADTSTSTAY MELSSLRSED TAVYYCAGSY YSYDVLDYWG QGTTVTVSS   119

SEQ ID NO: 218          moltype = AA  length = 246
FEATURE                 Location/Qualifiers
source                  1..246
                        mol_type = protein
                        organism = synthetic construct
SEQUENCE: 218
QVQLVQSGAE VKKPGSSVKV SCKASGYSFT TYYIHWVRQA PGQGLEWMGW FFPGSGNIKY  60
NEKFKGRVTI TADTSTSTAY MELSSLRSED TAVYYCAGSI YSAGVLDYWG QGTTVTVSSG  120
GGGSGGGGSG GGGSGGGGSD IQMTQSPSFL SASVGDRVTI TCKASQNVGI NVVWHQQKPG  180
KAPKALIYSS SHRYSGVPSR FSGSGSGTEF TLTISSLQPE DFATYFCQQF KSYPLTFGQG  240
TKLEIK                                                             246

SEQ ID NO: 219          moltype = AA  length = 119
FEATURE                 Location/Qualifiers
source                  1..119
                        mol_type = protein
                        organism = synthetic construct
SEQUENCE: 219
QVQLVQSGAE VKKPGSSVKV SCKASGYSFT TYYIHWVRQA PGQGLEWMGW FFPGSGNIKY  60
NEKFKGRVTI TADTSTSTAY MELSSLRSED TAVYYCAGSI YSAGVLDYWG QGTTVTVSS   119

SEQ ID NO: 220          moltype = AA  length = 246
FEATURE                 Location/Qualifiers
source                  1..246
                        mol_type = protein
                        organism = synthetic construct
SEQUENCE: 220
QVQLVQSGAE VKKPGSSVKV SCKASGYSFT LGYIHWVRQA PGQGLEWMGW FFPGSGNIKY  60
NEKFKGRVTI TADTSTSTAY MELSSLRSED TAVYYCAGSY YSYDVLDYWG QGTTVTVSSG  120
GGGSGGGGSG GGGSGGGGSD IQMTQSPSFL SASVGDRVTI TCKASQNVGI NVVWHQQKPG  180
KAPKALIYSS SHRYSGVPSR FSGSGSGTEF TLTISSLQPE DFATYFCQQF KSYPLTFGQG  240
TKLEIK                                                             246

SEQ ID NO: 221          moltype = AA  length = 119
FEATURE                 Location/Qualifiers
source                  1..119
                        mol_type = protein
                        organism = synthetic construct
SEQUENCE: 221
QVQLVQSGAE VKKPGSSVKV SCKASGYSFT LGYIHWVRQA PGQGLEWMGW FFPGSGNIKY  60
NEKFKGRVTI TADTSTSTAY MELSSLRSED TAVYYCAGSY YSYDVLDYWG QGTTVTVSS   119

SEQ ID NO: 222          moltype = AA  length = 246
FEATURE                 Location/Qualifiers
source                  1..246
                        mol_type = protein
                        organism = synthetic construct
SEQUENCE: 222
QVQLVQSGAE VKKPGSSVKV SCKASGYSFR LTYIHWVRQA PGQGLEWMGW FFPGSGNIKY  60
NEKFKGRVTI TADTSTSTAY MELSSLRSED TAVYYCAGSY YSYDVLDYWG QGTTVTVSSG  120
GGGSGGGGSG GGGSGGGGSD IQMTQSPSFL SASVGDRVTI TCKASQNVGI NVVWHQQKPG  180
KAPKALIYSS SHRYSGVPSR FSGSGSGTEF TLTISSLQPE DFATYFCQQF KSYPLTFGQG  240
TKLEIK                                                             246

SEQ ID NO: 223          moltype = AA  length = 119
FEATURE                 Location/Qualifiers
source                  1..119
                        mol_type = protein
                        organism = synthetic construct
SEQUENCE: 223
QVQLVQSGAE VKKPGSSVKV SCKASGYSFR LTYIHWVRQA PGQGLEWMGW FFPGSGNIKY  60
NEKFKGRVTI TADTSTSTAY MELSSLRSED TAVYYCAGSY YSYDVLDYWG QGTTVTVSS   119

SEQ ID NO: 224          moltype = AA  length = 246
FEATURE                 Location/Qualifiers
source                  1..246
                        mol_type = protein
                        organism = synthetic construct
SEQUENCE: 224
QVQLVQSGAE VKKPGSSVKV SCKASGYSFH NWYIHWVRQA PGQGLEWMGW FFPGSGNIKY  60
NEKFKGRVTI TADTSTSTAY MELSSLRSED TAVYYCAGSY YSYDVLDYWG QGTTVTVSSG  120
```

```
GGGSGGGGSG GGGSGGGGSD IQMTQSPSFL SASVGDRVTI TCKASQNVGI NVVWHQQKPG  180
KAPKALIYSS SHRYSGVPSR FSGSGSGTEF TLTISSLQPE DFATYFCQQF KSYPLTFGQG  240
TKLEIK                                                             246

SEQ ID NO: 225          moltype = AA  length = 119
FEATURE                 Location/Qualifiers
source                  1..119
                        mol_type = protein
                        organism = synthetic construct
SEQUENCE: 225
QVQLVQSGAE VKKPGSSVKV SCKASGYSFH NWYIHWVRQA PGQGLEWMGW FFPGSGNIKY  60
NEKFKGRVTI TADTSTSTAY MELSSLRSED TAVYYCAGSY YSYDVLDYWG QGTTVTVSS   119

SEQ ID NO: 226          moltype =   length =
SEQUENCE: 226
000

SEQ ID NO: 227          moltype =   length =
SEQUENCE: 227
000

SEQ ID NO: 228          moltype =   length =
SEQUENCE: 228
000

SEQ ID NO: 229          moltype =   length =
SEQUENCE: 229
000

SEQ ID NO: 230          moltype = AA  length = 107
FEATURE                 Location/Qualifiers
VARIANT                 30
                        note = G, E, A, or D
VARIANT                 31
                        note = N or D
VARIANT                 32
                        note = R or K
VARIANT                 36
                        note = Y or H
VARIANT                 56
                        note = K or S
source                  1..107
                        mol_type = protein
                        organism = synthetic construct
SEQUENCE: 230
DIQMTQSPSF LSASVGDRVT ITCKASQNVX XXVAWXQQKP GKAPKALIYS SSHRYXGVPS  60
RFSGSGSGTE FTLTISSLQP EDFATYFCQQ FKSYPLTFGQ GTKLEIK                107

SEQ ID NO: 231          moltype = AA  length = 119
FEATURE                 Location/Qualifiers
VARIANT                 27
                        note = H, T, G, or Y
VARIANT                 28
                        note = D, T, or S
VARIANT                 30
                        note = H, R, D, K, or T
VARIANT                 31
                        note = L, D, K, T, or N
VARIANT                 32
                        note = W, F, T, I, Y, or G
VARIANT                 50
                        note = R or W
VARIANT                 51
                        note = V, I, or F
VARIANT                 52
                        note = F, S, or Y
VARIANT                 53
                        note = A or P
VARIANT                 57
                        note = N or S
VARIANT                 58
                        note = T, V, Y, or I
VARIANT                 59
                        note = K or R
VARIANT                 98
                        note = G or V
VARIANT                 100
                        note = Y or I
VARIANT                 103
```

```
                         note = Y or A
VARIANT                  104
                         note = D or G
source                   1..119
                         mol_type = protein
                         organism = synthetic construct
SEQUENCE: 231
QVQLVQSGAE VKKPGSSVKV SCKASGXXFX XXYIHWVRQA PGQGLEWMGX XXXGSGXXXY  60
NEKFKGRVTI TADTSTSTAY MELSSLRSED TAVYYCAXSX YSXXVLDYWG QGTTVTVSS   119

SEQ ID NO: 232           moltype = AA  length = 107
FEATURE                  Location/Qualifiers
source                   1..107
                         mol_type = protein
                         organism = synthetic construct
SEQUENCE: 232
DIQMTQTTSS LSASLGDRVT ISCSASQGIS NYLNWYQQKP DGTVKLLIYY TSSLHSGVPS  60
RFSGSGSGTD YSLTISNLEP EDIATYYCQQ YSKLPRTFGG GTKVEIK                107

SEQ ID NO: 233           moltype = AA  length = 120
FEATURE                  Location/Qualifiers
source                   1..120
                         mol_type = protein
                         organism = synthetic construct
SEQUENCE: 233
QVQLKESGPG LVAPSQSLSI TCTVSGFSLT AYGVNWVRQP PGKGLEWLGM IWGDGNTDYN  60
SALKSRLSIS KDNSKSQVFL KMNSLQTDDT ARYYCARDRV TATLYAMDYW GQGTSVTVSS  120

SEQ ID NO: 234           moltype =   length =
SEQUENCE: 234
000

SEQ ID NO: 235           moltype =   length =
SEQUENCE: 235
000

SEQ ID NO: 236           moltype =   length =
SEQUENCE: 236
000

SEQ ID NO: 237           moltype =   length =
SEQUENCE: 237
000

SEQ ID NO: 238           moltype =   length =
SEQUENCE: 238
000

SEQ ID NO: 239           moltype =   length =
SEQUENCE: 239
000

SEQ ID NO: 240           moltype =   length =
SEQUENCE: 240
000

SEQ ID NO: 241           moltype =   length =
SEQUENCE: 241
000

SEQ ID NO: 242           moltype =   length =
SEQUENCE: 242
000

SEQ ID NO: 243           moltype =   length =
SEQUENCE: 243
000

SEQ ID NO: 244           moltype =   length =
SEQUENCE: 244
000

SEQ ID NO: 245           moltype =   length =
SEQUENCE: 245
000

SEQ ID NO: 246           moltype =   length =
SEQUENCE: 246
000
```

SEQ ID NO: 247 moltype = length =
SEQUENCE: 247
000

SEQ ID NO: 248 moltype = length =
SEQUENCE: 248
000

SEQ ID NO: 249 moltype = length =
SEQUENCE: 249
000

SEQ ID NO: 250 moltype = length =
SEQUENCE: 250
000

SEQ ID NO: 251 moltype = length =
SEQUENCE: 251
000

SEQ ID NO: 252 moltype = length =
SEQUENCE: 252
000

SEQ ID NO: 253 moltype = length =
SEQUENCE: 253
000

SEQ ID NO: 254 moltype = length =
SEQUENCE: 254
000

SEQ ID NO: 255 moltype = length =
SEQUENCE: 255
000

SEQ ID NO: 256 moltype = length =
SEQUENCE: 256
000

SEQ ID NO: 257 moltype = length =
SEQUENCE: 257
000

SEQ ID NO: 258 moltype = length =
SEQUENCE: 258
000

SEQ ID NO: 259 moltype = length =
SEQUENCE: 259
000

SEQ ID NO: 260 moltype = length =
SEQUENCE: 260
000

SEQ ID NO: 261 moltype = length =
SEQUENCE: 261
000

SEQ ID NO: 262 moltype = length =
SEQUENCE: 262
000

SEQ ID NO: 263 moltype = length =
SEQUENCE: 263
000

SEQ ID NO: 264 moltype = length =
SEQUENCE: 264
000

SEQ ID NO: 265 moltype = length =
SEQUENCE: 265
000

SEQ ID NO: 266 moltype = length =
SEQUENCE: 266

000

SEQ ID NO: 267 moltype = length =
SEQUENCE: 267
000

SEQ ID NO: 268 moltype = length =
SEQUENCE: 268
000

SEQ ID NO: 269 moltype = length =
SEQUENCE: 269
000

SEQ ID NO: 270 moltype = length =
SEQUENCE: 270
000

SEQ ID NO: 271 moltype = length =
SEQUENCE: 271
000

SEQ ID NO: 272 moltype = length =
SEQUENCE: 272
000

SEQ ID NO: 273 moltype = length =
SEQUENCE: 273
000

SEQ ID NO: 274 moltype = length =
SEQUENCE: 274
000

SEQ ID NO: 275 moltype = length =
SEQUENCE: 275
000

SEQ ID NO: 276 moltype = length =
SEQUENCE: 276
000

SEQ ID NO: 277 moltype = length =
SEQUENCE: 277
000

SEQ ID NO: 278 moltype = length =
SEQUENCE: 278
000

SEQ ID NO: 279 moltype = length =
SEQUENCE: 279
000

SEQ ID NO: 280 moltype = length =
SEQUENCE: 280
000

SEQ ID NO: 281 moltype = length =
SEQUENCE: 281
000

SEQ ID NO: 282 moltype = length =
SEQUENCE: 282
000

SEQ ID NO: 283 moltype = length =
SEQUENCE: 283
000

SEQ ID NO: 284 moltype = length =
SEQUENCE: 284
000

SEQ ID NO: 285 moltype = length =
SEQUENCE: 285
000

SEQ ID NO: 286 moltype = length =

SEQUENCE: 286
000

SEQ ID NO: 287 moltype = length =
SEQUENCE: 287
000

SEQ ID NO: 288 moltype = length =
SEQUENCE: 288
000

SEQ ID NO: 289 moltype = length =
SEQUENCE: 289
000

SEQ ID NO: 290 moltype = length =
SEQUENCE: 290
000

SEQ ID NO: 291 moltype = length =
SEQUENCE: 291
000

SEQ ID NO: 292 moltype = length =
SEQUENCE: 292
000

SEQ ID NO: 293 moltype = length =
SEQUENCE: 293
000

SEQ ID NO: 294 moltype = length =
SEQUENCE: 294
000

SEQ ID NO: 295 moltype = length =
SEQUENCE: 295
000

SEQ ID NO: 296 moltype = length =
SEQUENCE: 296
000

SEQ ID NO: 297 moltype = length =
SEQUENCE: 297
000

SEQ ID NO: 298 moltype = length =
SEQUENCE: 298
000

SEQ ID NO: 299 moltype = length =
SEQUENCE: 299
000

SEQ ID NO: 300 moltype = length =
SEQUENCE: 300
000

SEQ ID NO: 301 moltype = length =
SEQUENCE: 301
000

SEQ ID NO: 302 moltype = length =
SEQUENCE: 302
000

SEQ ID NO: 303 moltype = length =
SEQUENCE: 303
000

SEQ ID NO: 304 moltype = length =
SEQUENCE: 304
000

SEQ ID NO: 305 moltype = length =
SEQUENCE: 305
000

SEQ ID NO: 306 moltype = length =
SEQUENCE: 306
000

SEQ ID NO: 307 moltype = length =
SEQUENCE: 307
000

SEQ ID NO: 308 moltype = length =
SEQUENCE: 308
000

SEQ ID NO: 309 moltype = length =
SEQUENCE: 309
000

SEQ ID NO: 310 moltype = length =
SEQUENCE: 310
000

SEQ ID NO: 311 moltype = length =
SEQUENCE: 311
000

SEQ ID NO: 312 moltype = length =
SEQUENCE: 312
000

SEQ ID NO: 313 moltype = length =
SEQUENCE: 313
000

SEQ ID NO: 314 moltype = length =
SEQUENCE: 314
000

SEQ ID NO: 315 moltype = length =
SEQUENCE: 315
000

SEQ ID NO: 316 moltype = length =
SEQUENCE: 316
000

SEQ ID NO: 317 moltype = length =
SEQUENCE: 317
000

SEQ ID NO: 318 moltype = length =
SEQUENCE: 318
000

SEQ ID NO: 319 moltype = length =
SEQUENCE: 319
000

SEQ ID NO: 320 moltype = length =
SEQUENCE: 320
000

SEQ ID NO: 321 moltype = length =
SEQUENCE: 321
000

SEQ ID NO: 322 moltype = length =
SEQUENCE: 322
000

SEQ ID NO: 323 moltype = length =
SEQUENCE: 323
000

SEQ ID NO: 324 moltype = length =
SEQUENCE: 324
000

SEQ ID NO: 325 moltype = length =
SEQUENCE: 325
000

SEQ ID NO: 326 moltype = length =
SEQUENCE: 326
000

SEQ ID NO: 327 moltype = length =
SEQUENCE: 327
000

SEQ ID NO: 328 moltype = length =
SEQUENCE: 328
000

SEQ ID NO: 329 moltype = length =
SEQUENCE: 329
000

SEQ ID NO: 330 moltype = length =
SEQUENCE: 330
000

SEQ ID NO: 331 moltype = length =
SEQUENCE: 331
000

SEQ ID NO: 332 moltype = length =
SEQUENCE: 332
000

SEQ ID NO: 333 moltype = length =
SEQUENCE: 333
000

SEQ ID NO: 334 moltype = length =
SEQUENCE: 334
000

SEQ ID NO: 335 moltype = length =
SEQUENCE: 335
000

SEQ ID NO: 336 moltype = length =
SEQUENCE: 336
000

SEQ ID NO: 337 moltype = length =
SEQUENCE: 337
000

SEQ ID NO: 338 moltype = length =
SEQUENCE: 338
000

SEQ ID NO: 339 moltype = length =
SEQUENCE: 339
000

SEQ ID NO: 340 moltype = length =
SEQUENCE: 340
000

SEQ ID NO: 341 moltype = length =
SEQUENCE: 341
000

SEQ ID NO: 342 moltype = length =
SEQUENCE: 342
000

SEQ ID NO: 343 moltype = length =
SEQUENCE: 343
000

SEQ ID NO: 344 moltype = length =
SEQUENCE: 344
000

SEQ ID NO: 345 moltype = length =
SEQUENCE: 345

000

SEQ ID NO: 346 moltype = length =
SEQUENCE: 346
000

SEQ ID NO: 347 moltype = length =
SEQUENCE: 347
000

SEQ ID NO: 348 moltype = length =
SEQUENCE: 348
000

SEQ ID NO: 349 moltype = length =
SEQUENCE: 349
000

SEQ ID NO: 350 moltype = length =
SEQUENCE: 350
000

SEQ ID NO: 351 moltype = length =
SEQUENCE: 351
000

SEQ ID NO: 352 moltype = length =
SEQUENCE: 352
000

SEQ ID NO: 353 moltype = length =
SEQUENCE: 353
000

SEQ ID NO: 354 moltype = length =
SEQUENCE: 354
000

SEQ ID NO: 355 moltype = length =
SEQUENCE: 355
000

SEQ ID NO: 356 moltype = length =
SEQUENCE: 356
000

SEQ ID NO: 357 moltype = length =
SEQUENCE: 357
000

SEQ ID NO: 358 moltype = length =
SEQUENCE: 358
000

SEQ ID NO: 359 moltype = length =
SEQUENCE: 359
000

SEQ ID NO: 360 moltype = length =
SEQUENCE: 360
000

SEQ ID NO: 361 moltype = length =
SEQUENCE: 361
000

SEQ ID NO: 362 moltype = length =
SEQUENCE: 362
000

SEQ ID NO: 363 moltype = length =
SEQUENCE: 363
000

SEQ ID NO: 364 moltype = length =
SEQUENCE: 364
000

SEQ ID NO: 365 moltype = length =

SEQUENCE: 365
000

SEQ ID NO: 366 moltype = length =
SEQUENCE: 366
000

SEQ ID NO: 367 moltype = length =
SEQUENCE: 367
000

SEQ ID NO: 368 moltype = length =
SEQUENCE: 368
000

SEQ ID NO: 369 moltype = length =
SEQUENCE: 369
000

SEQ ID NO: 370 moltype = length =
SEQUENCE: 370
000

SEQ ID NO: 371 moltype = length =
SEQUENCE: 371
000

SEQ ID NO: 372 moltype = length =
SEQUENCE: 372
000

SEQ ID NO: 373 moltype = length =
SEQUENCE: 373
000

SEQ ID NO: 374 moltype = length =
SEQUENCE: 374
000

SEQ ID NO: 375 moltype = length =
SEQUENCE: 375
000

SEQ ID NO: 376 moltype = length =
SEQUENCE: 376
000

SEQ ID NO: 377 moltype = length =
SEQUENCE: 377
000

SEQ ID NO: 378 moltype = length =
SEQUENCE: 378
000

SEQ ID NO: 379 moltype = length =
SEQUENCE: 379
000

SEQ ID NO: 380 moltype = length =
SEQUENCE: 380
000

SEQ ID NO: 381 moltype = length =
SEQUENCE: 381
000

SEQ ID NO: 382 moltype = length =
SEQUENCE: 382
000

SEQ ID NO: 383 moltype = length =
SEQUENCE: 383
000

SEQ ID NO: 384 moltype = length =
SEQUENCE: 384
000

SEQ ID NO: 385 moltype = length =
SEQUENCE: 385
000

SEQ ID NO: 386 moltype = length =
SEQUENCE: 386
000

SEQ ID NO: 387 moltype = length =
SEQUENCE: 387
000

SEQ ID NO: 388 moltype = length =
SEQUENCE: 388
000

SEQ ID NO: 389 moltype = length =
SEQUENCE: 389
000

SEQ ID NO: 390 moltype = length =
SEQUENCE: 390
000

SEQ ID NO: 391 moltype = length =
SEQUENCE: 391
000

SEQ ID NO: 392 moltype = length =
SEQUENCE: 392
000

SEQ ID NO: 393 moltype = length =
SEQUENCE: 393
000

SEQ ID NO: 394 moltype = length =
SEQUENCE: 394
000

SEQ ID NO: 395 moltype = length =
SEQUENCE: 395
000

SEQ ID NO: 396 moltype = length =
SEQUENCE: 396
000

SEQ ID NO: 397 moltype = length =
SEQUENCE: 397
000

SEQ ID NO: 398 moltype = length =
SEQUENCE: 398
000

SEQ ID NO: 399 moltype = length =
SEQUENCE: 399
000

SEQ ID NO: 400 moltype = length =
SEQUENCE: 400
000

SEQ ID NO: 401 moltype = length =
SEQUENCE: 401
000

SEQ ID NO: 402 moltype = length =
SEQUENCE: 402
000

SEQ ID NO: 403 moltype = length =
SEQUENCE: 403
000

SEQ ID NO: 404 moltype = length =
SEQUENCE: 404
000

SEQ ID NO: 405 moltype = length =
SEQUENCE: 405
000

SEQ ID NO: 406 moltype = length =
SEQUENCE: 406
000

SEQ ID NO: 407 moltype = length =
SEQUENCE: 407
000

SEQ ID NO: 408 moltype = length =
SEQUENCE: 408
000

SEQ ID NO: 409 moltype = length =
SEQUENCE: 409
000

SEQ ID NO: 410 moltype = length =
SEQUENCE: 410
000

SEQ ID NO: 411 moltype = length =
SEQUENCE: 411
000

SEQ ID NO: 412 moltype = length =
SEQUENCE: 412
000

SEQ ID NO: 413 moltype = length =
SEQUENCE: 413
000

SEQ ID NO: 414 moltype = length =
SEQUENCE: 414
000

SEQ ID NO: 415 moltype = length =
SEQUENCE: 415
000

SEQ ID NO: 416 moltype = length =
SEQUENCE: 416
000

SEQ ID NO: 417 moltype = length =
SEQUENCE: 417
000

SEQ ID NO: 418 moltype = length =
SEQUENCE: 418
000

SEQ ID NO: 419 moltype = length =
SEQUENCE: 419
000

SEQ ID NO: 420 moltype = length =
SEQUENCE: 420
000

SEQ ID NO: 421 moltype = length =
SEQUENCE: 421
000

SEQ ID NO: 422 moltype = length =
SEQUENCE: 422
000

SEQ ID NO: 423 moltype = length =
SEQUENCE: 423
000

SEQ ID NO: 424 moltype = length =
SEQUENCE: 424

000

SEQ ID NO: 425 moltype = length =
SEQUENCE: 425
000

SEQ ID NO: 426 moltype = length =
SEQUENCE: 426
000

SEQ ID NO: 427 moltype = length =
SEQUENCE: 427
000

SEQ ID NO: 428 moltype = length =
SEQUENCE: 428
000

SEQ ID NO: 429 moltype = length =
SEQUENCE: 429
000

SEQ ID NO: 430 moltype = length =
SEQUENCE: 430
000

SEQ ID NO: 431 moltype = length =
SEQUENCE: 431
000

SEQ ID NO: 432 moltype = length =
SEQUENCE: 432
000

SEQ ID NO: 433 moltype = length =
SEQUENCE: 433
000

SEQ ID NO: 434 moltype = length =
SEQUENCE: 434
000

SEQ ID NO: 435 moltype = length =
SEQUENCE: 435
000

SEQ ID NO: 436 moltype = length =
SEQUENCE: 436
000

SEQ ID NO: 437 moltype = length =
SEQUENCE: 437
000

SEQ ID NO: 438 moltype = length =
SEQUENCE: 438
000

SEQ ID NO: 439 moltype = length =
SEQUENCE: 439
000

SEQ ID NO: 440 moltype = length =
SEQUENCE: 440
000

SEQ ID NO: 441 moltype = length =
SEQUENCE: 441
000

SEQ ID NO: 442 moltype = length =
SEQUENCE: 442
000

SEQ ID NO: 443 moltype = length =
SEQUENCE: 443
000

SEQ ID NO: 444 moltype = length =

SEQUENCE: 444
000

SEQ ID NO: 445 moltype = length =
SEQUENCE: 445
000

SEQ ID NO: 446 moltype = length =
SEQUENCE: 446
000

SEQ ID NO: 447 moltype = length =
SEQUENCE: 447
000

SEQ ID NO: 448 moltype = length =
SEQUENCE: 448
000

SEQ ID NO: 449 moltype = length =
SEQUENCE: 449
000

SEQ ID NO: 450 moltype = length =
SEQUENCE: 450
000

SEQ ID NO: 451 moltype = length =
SEQUENCE: 451
000

SEQ ID NO: 452 moltype = length =
SEQUENCE: 452
000

SEQ ID NO: 453 moltype = length =
SEQUENCE: 453
000

SEQ ID NO: 454 moltype = length =
SEQUENCE: 454
000

SEQ ID NO: 455 moltype = length =
SEQUENCE: 455
000

SEQ ID NO: 456 moltype = length =
SEQUENCE: 456
000

SEQ ID NO: 457 moltype = length =
SEQUENCE: 457
000

SEQ ID NO: 458 moltype = length =
SEQUENCE: 458
000

SEQ ID NO: 459 moltype = length =
SEQUENCE: 459
000

SEQ ID NO: 460 moltype = length =
SEQUENCE: 460
000

SEQ ID NO: 461 moltype = length =
SEQUENCE: 461
000

SEQ ID NO: 462 moltype = length =
SEQUENCE: 462
000

SEQ ID NO: 463 moltype = length =
SEQUENCE: 463
000

SEQ ID NO: 464 moltype = length =
SEQUENCE: 464
000

SEQ ID NO: 465 moltype = length =
SEQUENCE: 465
000

SEQ ID NO: 466 moltype = length =
SEQUENCE: 466
000

SEQ ID NO: 467 moltype = length =
SEQUENCE: 467
000

SEQ ID NO: 468 moltype = length =
SEQUENCE: 468
000

SEQ ID NO: 469 moltype = length =
SEQUENCE: 469
000

SEQ ID NO: 470 moltype = length =
SEQUENCE: 470
000

SEQ ID NO: 471 moltype = length =
SEQUENCE: 471
000

SEQ ID NO: 472 moltype = length =
SEQUENCE: 472
000

SEQ ID NO: 473 moltype = length =
SEQUENCE: 473
000

SEQ ID NO: 474 moltype = length =
SEQUENCE: 474
000

SEQ ID NO: 475 moltype = length =
SEQUENCE: 475
000

SEQ ID NO: 476 moltype = length =
SEQUENCE: 476
000

SEQ ID NO: 477 moltype = length =
SEQUENCE: 477
000

SEQ ID NO: 478 moltype = length =
SEQUENCE: 478
000

SEQ ID NO: 479 moltype = length =
SEQUENCE: 479
000

SEQ ID NO: 480 moltype = length =
SEQUENCE: 480
000

SEQ ID NO: 481 moltype = length =
SEQUENCE: 481
000

SEQ ID NO: 482 moltype = length =
SEQUENCE: 482
000

SEQ ID NO: 483 moltype = length =
SEQUENCE: 483
000

SEQ ID NO: 484 moltype = length =
SEQUENCE: 484
000

SEQ ID NO: 485 moltype = length =
SEQUENCE: 485
000

SEQ ID NO: 486 moltype = length =
SEQUENCE: 486
000

SEQ ID NO: 487 moltype = length =
SEQUENCE: 487
000

SEQ ID NO: 488 moltype = length =
SEQUENCE: 488
000

SEQ ID NO: 489 moltype = length =
SEQUENCE: 489
000

SEQ ID NO: 490 moltype = length =
SEQUENCE: 490
000

SEQ ID NO: 491 moltype = length =
SEQUENCE: 491
000

SEQ ID NO: 492 moltype = length =
SEQUENCE: 492
000

SEQ ID NO: 493 moltype = length =
SEQUENCE: 493
000

SEQ ID NO: 494 moltype = length =
SEQUENCE: 494
000

SEQ ID NO: 495 moltype = length =
SEQUENCE: 495
000

SEQ ID NO: 496 moltype = length =
SEQUENCE: 496
000

SEQ ID NO: 497 moltype = length =
SEQUENCE: 497
000

SEQ ID NO: 498 moltype = length =
SEQUENCE: 498
000

SEQ ID NO: 499 moltype = length =
SEQUENCE: 499
000

SEQ ID NO: 500 moltype = length =
SEQUENCE: 500
000

SEQ ID NO: 501 moltype = length =
SEQUENCE: 501
000

SEQ ID NO: 502 moltype = length =
SEQUENCE: 502
000

SEQ ID NO: 503 moltype = length =
SEQUENCE: 503

000

SEQ ID NO: 504 moltype = length =
SEQUENCE: 504
000

SEQ ID NO: 505 moltype = length =
SEQUENCE: 505
000

SEQ ID NO: 506 moltype = length =
SEQUENCE: 506
000

SEQ ID NO: 507 moltype = length =
SEQUENCE: 507
000

SEQ ID NO: 508 moltype = length =
SEQUENCE: 508
000

SEQ ID NO: 509 moltype = length =
SEQUENCE: 509
000

SEQ ID NO: 510 moltype = length =
SEQUENCE: 510
000

SEQ ID NO: 511 moltype = length =
SEQUENCE: 511
000

SEQ ID NO: 512 moltype = length =
SEQUENCE: 512
000

SEQ ID NO: 513 moltype = length =
SEQUENCE: 513
000

SEQ ID NO: 514 moltype = length =
SEQUENCE: 514
000

SEQ ID NO: 515 moltype = length =
SEQUENCE: 515
000

SEQ ID NO: 516 moltype = length =
SEQUENCE: 516
000

SEQ ID NO: 517 moltype = length =
SEQUENCE: 517
000

SEQ ID NO: 518 moltype = length =
SEQUENCE: 518
000

SEQ ID NO: 519 moltype = length =
SEQUENCE: 519
000

SEQ ID NO: 520 moltype = length =
SEQUENCE: 520
000

SEQ ID NO: 521 moltype = length =
SEQUENCE: 521
000

SEQ ID NO: 522 moltype = length =
SEQUENCE: 522
000

SEQ ID NO: 523 moltype = length =

SEQUENCE: 523
000

SEQ ID NO: 524 moltype = length =
SEQUENCE: 524
000

SEQ ID NO: 525 moltype = length =
SEQUENCE: 525
000

SEQ ID NO: 526 moltype = length =
SEQUENCE: 526
000

SEQ ID NO: 527 moltype = length =
SEQUENCE: 527
000

SEQ ID NO: 528 moltype = length =
SEQUENCE: 528
000

SEQ ID NO: 529 moltype = length =
SEQUENCE: 529
000

SEQ ID NO: 530 moltype = length =
SEQUENCE: 530
000

SEQ ID NO: 531 moltype = length =
SEQUENCE: 531
000

SEQ ID NO: 532 moltype = length =
SEQUENCE: 532
000

SEQ ID NO: 533 moltype = length =
SEQUENCE: 533
000

SEQ ID NO: 534 moltype = length =
SEQUENCE: 534
000

SEQ ID NO: 535 moltype = length =
SEQUENCE: 535
000

SEQ ID NO: 536 moltype = length =
SEQUENCE: 536
000

SEQ ID NO: 537 moltype = length =
SEQUENCE: 537
000

SEQ ID NO: 538 moltype = length =
SEQUENCE: 538
000

SEQ ID NO: 539 moltype = length =
SEQUENCE: 539
000

SEQ ID NO: 540 moltype = length =
SEQUENCE: 540
000

SEQ ID NO: 541 moltype = length =
SEQUENCE: 541
000

SEQ ID NO: 542 moltype = length =
SEQUENCE: 542
000

-continued

SEQ ID NO: 543 moltype = length =
SEQUENCE: 543
000

SEQ ID NO: 544 moltype = length =
SEQUENCE: 544
000

SEQ ID NO: 545 moltype = length =
SEQUENCE: 545
000

SEQ ID NO: 546 moltype = length =
SEQUENCE: 546
000

SEQ ID NO: 547 moltype = length =
SEQUENCE: 547
000

SEQ ID NO: 548 moltype = length =
SEQUENCE: 548
000

SEQ ID NO: 549 moltype = length =
SEQUENCE: 549
000

SEQ ID NO: 550 moltype = length =
SEQUENCE: 550
000

SEQ ID NO: 551 moltype = length =
SEQUENCE: 551
000

SEQ ID NO: 552 moltype = length =
SEQUENCE: 552
000

SEQ ID NO: 553 moltype = length =
SEQUENCE: 553
000

SEQ ID NO: 554 moltype = length =
SEQUENCE: 554
000

SEQ ID NO: 555 moltype = length =
SEQUENCE: 555
000

SEQ ID NO: 556 moltype = length =
SEQUENCE: 556
000

SEQ ID NO: 557 moltype = length =
SEQUENCE: 557
000

SEQ ID NO: 558 moltype = length =
SEQUENCE: 558
000

SEQ ID NO: 559 moltype = length =
SEQUENCE: 559
000

SEQ ID NO: 560 moltype = length =
SEQUENCE: 560
000

SEQ ID NO: 561 moltype = length =
SEQUENCE: 561
000

SEQ ID NO: 562 moltype = length =
SEQUENCE: 562
000

SEQ ID NO: 563 moltype = length =
SEQUENCE: 563
000

SEQ ID NO: 564 moltype = length =
SEQUENCE: 564
000

SEQ ID NO: 565 moltype = length =
SEQUENCE: 565
000

SEQ ID NO: 566 moltype = length =
SEQUENCE: 566
000

SEQ ID NO: 567 moltype = length =
SEQUENCE: 567
000

SEQ ID NO: 568 moltype = length =
SEQUENCE: 568
000

SEQ ID NO: 569 moltype = length =
SEQUENCE: 569
000

SEQ ID NO: 570 moltype = length =
SEQUENCE: 570
000

SEQ ID NO: 571 moltype = length =
SEQUENCE: 571
000

SEQ ID NO: 572 moltype = length =
SEQUENCE: 572
000

SEQ ID NO: 573 moltype = length =
SEQUENCE: 573
000

SEQ ID NO: 574 moltype = length =
SEQUENCE: 574
000

SEQ ID NO: 575 moltype = length =
SEQUENCE: 575
000

SEQ ID NO: 576 moltype = length =
SEQUENCE: 576
000

SEQ ID NO: 577 moltype = length =
SEQUENCE: 577
000

SEQ ID NO: 578 moltype = length =
SEQUENCE: 578
000

SEQ ID NO: 579 moltype = length =
SEQUENCE: 579
000

SEQ ID NO: 580 moltype = length =
SEQUENCE: 580
000

SEQ ID NO: 581 moltype = length =
SEQUENCE: 581
000

SEQ ID NO: 582 moltype = length =
SEQUENCE: 582

000

SEQ ID NO: 583 moltype = length =
SEQUENCE: 583
000

SEQ ID NO: 584 moltype = length =
SEQUENCE: 584
000

SEQ ID NO: 585 moltype = length =
SEQUENCE: 585
000

SEQ ID NO: 586 moltype = length =
SEQUENCE: 586
000

SEQ ID NO: 587 moltype = length =
SEQUENCE: 587
000

SEQ ID NO: 588 moltype = length =
SEQUENCE: 588
000

SEQ ID NO: 589 moltype = length =
SEQUENCE: 589
000

SEQ ID NO: 590 moltype = length =
SEQUENCE: 590
000

SEQ ID NO: 591 moltype = length =
SEQUENCE: 591
000

SEQ ID NO: 592 moltype = length =
SEQUENCE: 592
000

SEQ ID NO: 593 moltype = length =
SEQUENCE: 593
000

SEQ ID NO: 594 moltype = length =
SEQUENCE: 594
000

SEQ ID NO: 595 moltype = length =
SEQUENCE: 595
000

SEQ ID NO: 596 moltype = length =
SEQUENCE: 596
000

SEQ ID NO: 597 moltype = length =
SEQUENCE: 597
000

SEQ ID NO: 598 moltype = length =
SEQUENCE: 598
000

SEQ ID NO: 599 moltype = length =
SEQUENCE: 599
000

SEQ ID NO: 600 moltype = length =
SEQUENCE: 600
000

SEQ ID NO: 601 moltype = length =
SEQUENCE: 601
000

SEQ ID NO: 602 moltype = length =

SEQUENCE: 602
000

SEQ ID NO: 603 moltype = length =
SEQUENCE: 603
000

SEQ ID NO: 604 moltype = length =
SEQUENCE: 604
000

SEQ ID NO: 605 moltype = length =
SEQUENCE: 605
000

SEQ ID NO: 606 moltype = length =
SEQUENCE: 606
000

SEQ ID NO: 607 moltype = length =
SEQUENCE: 607
000

SEQ ID NO: 608 moltype = length =
SEQUENCE: 608
000

SEQ ID NO: 609 moltype = length =
SEQUENCE: 609
000

SEQ ID NO: 610 moltype = length =
SEQUENCE: 610
000

SEQ ID NO: 611 moltype = length =
SEQUENCE: 611
000

SEQ ID NO: 612 moltype = length =
SEQUENCE: 612
000

SEQ ID NO: 613 moltype = length =
SEQUENCE: 613
000

SEQ ID NO: 614 moltype = length =
SEQUENCE: 614
000

SEQ ID NO: 615 moltype = length =
SEQUENCE: 615
000

SEQ ID NO: 616 moltype = length =
SEQUENCE: 616
000

SEQ ID NO: 617 moltype = length =
SEQUENCE: 617
000

SEQ ID NO: 618 moltype = length =
SEQUENCE: 618
000

SEQ ID NO: 619 moltype = length =
SEQUENCE: 619
000

SEQ ID NO: 620 moltype = length =
SEQUENCE: 620
000

SEQ ID NO: 621 moltype = length =
SEQUENCE: 621
000

SEQ ID NO: 622 moltype = length =
SEQUENCE: 622
000

SEQ ID NO: 623 moltype = length =
SEQUENCE: 623
000

SEQ ID NO: 624 moltype = length =
SEQUENCE: 624
000

SEQ ID NO: 625 moltype = length =
SEQUENCE: 625
000

SEQ ID NO: 626 moltype = length =
SEQUENCE: 626
000

SEQ ID NO: 627 moltype = length =
SEQUENCE: 627
000

SEQ ID NO: 628 moltype = length =
SEQUENCE: 628
000

SEQ ID NO: 629 moltype = length =
SEQUENCE: 629
000

SEQ ID NO: 630 moltype = length =
SEQUENCE: 630
000

SEQ ID NO: 631 moltype = length =
SEQUENCE: 631
000

SEQ ID NO: 632 moltype = length =
SEQUENCE: 632
000

SEQ ID NO: 633 moltype = length =
SEQUENCE: 633
000

SEQ ID NO: 634 moltype = length =
SEQUENCE: 634
000

SEQ ID NO: 635 moltype = length =
SEQUENCE: 635
000

SEQ ID NO: 636 moltype = length =
SEQUENCE: 636
000

SEQ ID NO: 637 moltype = length =
SEQUENCE: 637
000

SEQ ID NO: 638 moltype = length =
SEQUENCE: 638
000

SEQ ID NO: 639 moltype = length =
SEQUENCE: 639
000

SEQ ID NO: 640 moltype = length =
SEQUENCE: 640
000

SEQ ID NO: 641 moltype = length =
SEQUENCE: 641
000

SEQ ID NO: 642 moltype = length =
SEQUENCE: 642
000

SEQ ID NO: 643 moltype = length =
SEQUENCE: 643
000

SEQ ID NO: 644 moltype = length =
SEQUENCE: 644
000

SEQ ID NO: 645 moltype = length =
SEQUENCE: 645
000

SEQ ID NO: 646 moltype = length =
SEQUENCE: 646
000

SEQ ID NO: 647 moltype = length =
SEQUENCE: 647
000

SEQ ID NO: 648 moltype = length =
SEQUENCE: 648
000

SEQ ID NO: 649 moltype = length =
SEQUENCE: 649
000

SEQ ID NO: 650 moltype = length =
SEQUENCE: 650
000

SEQ ID NO: 651 moltype = length =
SEQUENCE: 651
000

SEQ ID NO: 652 moltype = length =
SEQUENCE: 652
000

SEQ ID NO: 653 moltype = length =
SEQUENCE: 653
000

SEQ ID NO: 654 moltype = length =
SEQUENCE: 654
000

SEQ ID NO: 655 moltype = length =
SEQUENCE: 655
000

SEQ ID NO: 656 moltype = length =
SEQUENCE: 656
000

SEQ ID NO: 657 moltype = length =
SEQUENCE: 657
000

SEQ ID NO: 658 moltype = length =
SEQUENCE: 658
000

SEQ ID NO: 659 moltype = length =
SEQUENCE: 659
000

SEQ ID NO: 660 moltype = length =
SEQUENCE: 660
000

SEQ ID NO: 661 moltype = length =
SEQUENCE: 661

000

SEQ ID NO: 662 moltype = length =
SEQUENCE: 662
000

SEQ ID NO: 663 moltype = length =
SEQUENCE: 663
000

SEQ ID NO: 664 moltype = length =
SEQUENCE: 664
000

SEQ ID NO: 665 moltype = length =
SEQUENCE: 665
000

SEQ ID NO: 666 moltype = length =
SEQUENCE: 666
000

SEQ ID NO: 667 moltype = length =
SEQUENCE: 667
000

SEQ ID NO: 668 moltype = length =
SEQUENCE: 668
000

SEQ ID NO: 669 moltype = length =
SEQUENCE: 669
000

SEQ ID NO: 670 moltype = length =
SEQUENCE: 670
000

SEQ ID NO: 671 moltype = length =
SEQUENCE: 671
000

SEQ ID NO: 672 moltype = length =
SEQUENCE: 672
000

SEQ ID NO: 673 moltype = length =
SEQUENCE: 673
000

SEQ ID NO: 674 moltype = length =
SEQUENCE: 674
000

SEQ ID NO: 675 moltype = length =
SEQUENCE: 675
000

SEQ ID NO: 676 moltype = length =
SEQUENCE: 676
000

SEQ ID NO: 677 moltype = length =
SEQUENCE: 677
000

SEQ ID NO: 678 moltype = length =
SEQUENCE: 678
000

SEQ ID NO: 679 moltype = length =
SEQUENCE: 679
000

SEQ ID NO: 680 moltype = length =
SEQUENCE: 680
000

SEQ ID NO: 681 moltype = length =

SEQUENCE: 681
000

SEQ ID NO: 682 moltype = length =
SEQUENCE: 682
000

SEQ ID NO: 683 moltype = length =
SEQUENCE: 683
000

SEQ ID NO: 684 moltype = length =
SEQUENCE: 684
000

SEQ ID NO: 685 moltype = length =
SEQUENCE: 685
000

SEQ ID NO: 686 moltype = length =
SEQUENCE: 686
000

SEQ ID NO: 687 moltype = length =
SEQUENCE: 687
000

SEQ ID NO: 688 moltype = length =
SEQUENCE: 688
000

SEQ ID NO: 689 moltype = length =
SEQUENCE: 689
000

SEQ ID NO: 690 moltype = length =
SEQUENCE: 690
000

SEQ ID NO: 691 moltype = length =
SEQUENCE: 691
000

SEQ ID NO: 692 moltype = length =
SEQUENCE: 692
000

SEQ ID NO: 693 moltype = length =
SEQUENCE: 693
000

SEQ ID NO: 694 moltype = length =
SEQUENCE: 694
000

SEQ ID NO: 695 moltype = length =
SEQUENCE: 695
000

SEQ ID NO: 696 moltype = length =
SEQUENCE: 696
000

SEQ ID NO: 697 moltype = length =
SEQUENCE: 697
000

SEQ ID NO: 698 moltype = length =
SEQUENCE: 698
000

SEQ ID NO: 699 moltype = length =
SEQUENCE: 699
000

SEQ ID NO: 700 moltype = length =
SEQUENCE: 700
000

SEQ ID NO: 701 moltype = length =
SEQUENCE: 701
000

SEQ ID NO: 702 moltype = length =
SEQUENCE: 702
000

SEQ ID NO: 703 moltype = length =
SEQUENCE: 703
000

SEQ ID NO: 704 moltype = length =
SEQUENCE: 704
000

SEQ ID NO: 705 moltype = length =
SEQUENCE: 705
000

SEQ ID NO: 706 moltype = length =
SEQUENCE: 706
000

SEQ ID NO: 707 moltype = length =
SEQUENCE: 707
000

SEQ ID NO: 708 moltype = length =
SEQUENCE: 708
000

SEQ ID NO: 709 moltype = length =
SEQUENCE: 709
000

SEQ ID NO: 710 moltype = length =
SEQUENCE: 710
000

SEQ ID NO: 711 moltype = length =
SEQUENCE: 711
000

SEQ ID NO: 712 moltype = length =
SEQUENCE: 712
000

SEQ ID NO: 713 moltype = length =
SEQUENCE: 713
000

SEQ ID NO: 714 moltype = length =
SEQUENCE: 714
000

SEQ ID NO: 715 moltype = length =
SEQUENCE: 715
000

SEQ ID NO: 716 moltype = length =
SEQUENCE: 716
000

SEQ ID NO: 717 moltype = length =
SEQUENCE: 717
000

SEQ ID NO: 718 moltype = length =
SEQUENCE: 718
000

SEQ ID NO: 719 moltype = length =
SEQUENCE: 719
000

SEQ ID NO: 720 moltype = length =
SEQUENCE: 720
000

SEQ ID NO: 721 moltype = length =
SEQUENCE: 721
000

SEQ ID NO: 722 moltype = length =
SEQUENCE: 722
000

SEQ ID NO: 723 moltype = length =
SEQUENCE: 723
000

SEQ ID NO: 724 moltype = length =
SEQUENCE: 724
000

SEQ ID NO: 725 moltype = length =
SEQUENCE: 725
000

SEQ ID NO: 726 moltype = length =
SEQUENCE: 726
000

SEQ ID NO: 727 moltype = length =
SEQUENCE: 727
000

SEQ ID NO: 728 moltype = length =
SEQUENCE: 728
000

SEQ ID NO: 729 moltype = length =
SEQUENCE: 729
000

SEQ ID NO: 730 moltype = length =
SEQUENCE: 730
000

SEQ ID NO: 731 moltype = length =
SEQUENCE: 731
000

SEQ ID NO: 732 moltype = length =
SEQUENCE: 732
000

SEQ ID NO: 733 moltype = length =
SEQUENCE: 733
000

SEQ ID NO: 734 moltype = length =
SEQUENCE: 734
000

SEQ ID NO: 735 moltype = length =
SEQUENCE: 735
000

SEQ ID NO: 736 moltype = length =
SEQUENCE: 736
000

SEQ ID NO: 737 moltype = length =
SEQUENCE: 737
000

SEQ ID NO: 738 moltype = length =
SEQUENCE: 738
000

SEQ ID NO: 739 moltype = length =
SEQUENCE: 739
000

SEQ ID NO: 740 moltype = length =
SEQUENCE: 740

000

SEQ ID NO: 741 moltype = length =
SEQUENCE: 741
000

SEQ ID NO: 742 moltype = length =
SEQUENCE: 742
000

SEQ ID NO: 743 moltype = length =
SEQUENCE: 743
000

SEQ ID NO: 744 moltype = length =
SEQUENCE: 744
000

SEQ ID NO: 745 moltype = length =
SEQUENCE: 745
000

SEQ ID NO: 746 moltype = length =
SEQUENCE: 746
000

SEQ ID NO: 747 moltype = length =
SEQUENCE: 747
000

SEQ ID NO: 748 moltype = length =
SEQUENCE: 748
000

SEQ ID NO: 749 moltype = length =
SEQUENCE: 749
000

SEQ ID NO: 750 moltype = length =
SEQUENCE: 750
000

SEQ ID NO: 751 moltype = length =
SEQUENCE: 751
000

SEQ ID NO: 752 moltype = length =
SEQUENCE: 752
000

SEQ ID NO: 753 moltype = length =
SEQUENCE: 753
000

SEQ ID NO: 754 moltype = length =
SEQUENCE: 754
000

SEQ ID NO: 755 moltype = length =
SEQUENCE: 755
000

SEQ ID NO: 756 moltype = length =
SEQUENCE: 756
000

SEQ ID NO: 757 moltype = length =
SEQUENCE: 757
000

SEQ ID NO: 758 moltype = length =
SEQUENCE: 758
000

SEQ ID NO: 759 moltype = length =
SEQUENCE: 759
000

SEQ ID NO: 760 moltype = length =

SEQUENCE: 760
000

SEQ ID NO: 761 moltype = length =
SEQUENCE: 761
000

SEQ ID NO: 762 moltype = length =
SEQUENCE: 762
000

SEQ ID NO: 763 moltype = length =
SEQUENCE: 763
000

SEQ ID NO: 764 moltype = length =
SEQUENCE: 764
000

SEQ ID NO: 765 moltype = length =
SEQUENCE: 765
000

SEQ ID NO: 766 moltype = length =
SEQUENCE: 766
000

SEQ ID NO: 767 moltype = length =
SEQUENCE: 767
000

SEQ ID NO: 768 moltype = length =
SEQUENCE: 768
000

SEQ ID NO: 769 moltype = length =
SEQUENCE: 769
000

SEQ ID NO: 770 moltype = length =
SEQUENCE: 770
000

SEQ ID NO: 771 moltype = length =
SEQUENCE: 771
000

SEQ ID NO: 772 moltype = length =
SEQUENCE: 772
000

SEQ ID NO: 773 moltype = length =
SEQUENCE: 773
000

SEQ ID NO: 774 moltype = length =
SEQUENCE: 774
000

SEQ ID NO: 775 moltype = length =
SEQUENCE: 775
000

SEQ ID NO: 776 moltype = length =
SEQUENCE: 776
000

SEQ ID NO: 777 moltype = length =
SEQUENCE: 777
000

SEQ ID NO: 778 moltype = length =
SEQUENCE: 778
000

SEQ ID NO: 779 moltype = length =
SEQUENCE: 779
000

SEQ ID NO: 780 moltype = length =
SEQUENCE: 780
000

SEQ ID NO: 781 moltype = length =
SEQUENCE: 781
000

SEQ ID NO: 782 moltype = length =
SEQUENCE: 782
000

SEQ ID NO: 783 moltype = length =
SEQUENCE: 783
000

SEQ ID NO: 784 moltype = length =
SEQUENCE: 784
000

SEQ ID NO: 785 moltype = length =
SEQUENCE: 785
000

SEQ ID NO: 786 moltype = length =
SEQUENCE: 786
000

SEQ ID NO: 787 moltype = length =
SEQUENCE: 787
000

SEQ ID NO: 788 moltype = length =
SEQUENCE: 788
000

SEQ ID NO: 789 moltype = length =
SEQUENCE: 789
000

SEQ ID NO: 790 moltype = length =
SEQUENCE: 790
000

SEQ ID NO: 791 moltype = length =
SEQUENCE: 791
000

SEQ ID NO: 792 moltype = length =
SEQUENCE: 792
000

SEQ ID NO: 793 moltype = length =
SEQUENCE: 793
000

SEQ ID NO: 794 moltype = length =
SEQUENCE: 794
000

SEQ ID NO: 795 moltype = length =
SEQUENCE: 795
000

SEQ ID NO: 796 moltype = length =
SEQUENCE: 796
000

SEQ ID NO: 797 moltype = length =
SEQUENCE: 797
000

SEQ ID NO: 798 moltype = length =
SEQUENCE: 798
000

SEQ ID NO: 799 moltype = length =
SEQUENCE: 799
000

SEQ ID NO: 800 moltype = length =
SEQUENCE: 800
000

SEQ ID NO: 801 moltype = length =
SEQUENCE: 801
000

SEQ ID NO: 802 moltype = length =
SEQUENCE: 802
000

SEQ ID NO: 803 moltype = length =
SEQUENCE: 803
000

SEQ ID NO: 804 moltype = length =
SEQUENCE: 804
000

SEQ ID NO: 805 moltype = length =
SEQUENCE: 805
000

SEQ ID NO: 806 moltype = length =
SEQUENCE: 806
000

SEQ ID NO: 807 moltype = length =
SEQUENCE: 807
000

SEQ ID NO: 808 moltype = length =
SEQUENCE: 808
000

SEQ ID NO: 809 moltype = length =
SEQUENCE: 809
000

SEQ ID NO: 810 moltype = length =
SEQUENCE: 810
000

SEQ ID NO: 811 moltype = length =
SEQUENCE: 811
000

SEQ ID NO: 812 moltype = length =
SEQUENCE: 812
000

SEQ ID NO: 813 moltype = length =
SEQUENCE: 813
000

SEQ ID NO: 814 moltype = length =
SEQUENCE: 814
000

SEQ ID NO: 815 moltype = length =
SEQUENCE: 815
000

SEQ ID NO: 816 moltype = length =
SEQUENCE: 816
000

SEQ ID NO: 817 moltype = length =
SEQUENCE: 817
000

SEQ ID NO: 818 moltype = length =
SEQUENCE: 818
000

SEQ ID NO: 819 moltype = length =
SEQUENCE: 819

000

SEQ ID NO: 820 moltype = length =
SEQUENCE: 820
000

SEQ ID NO: 821 moltype = length =
SEQUENCE: 821
000

SEQ ID NO: 822 moltype = length =
SEQUENCE: 822
000

SEQ ID NO: 823 moltype = length =
SEQUENCE: 823
000

SEQ ID NO: 824 moltype = length =
SEQUENCE: 824
000

SEQ ID NO: 825 moltype = length =
SEQUENCE: 825
000

SEQ ID NO: 826 moltype = length =
SEQUENCE: 826
000

SEQ ID NO: 827 moltype = length =
SEQUENCE: 827
000

SEQ ID NO: 828 moltype = length =
SEQUENCE: 828
000

SEQ ID NO: 829 moltype = length =
SEQUENCE: 829
000

SEQ ID NO: 830 moltype = length =
SEQUENCE: 830
000

SEQ ID NO: 831 moltype = length =
SEQUENCE: 831
000

SEQ ID NO: 832 moltype = length =
SEQUENCE: 832
000

SEQ ID NO: 833 moltype = length =
SEQUENCE: 833
000

SEQ ID NO: 834 moltype = length =
SEQUENCE: 834
000

SEQ ID NO: 835 moltype = length =
SEQUENCE: 835
000

SEQ ID NO: 836 moltype = length =
SEQUENCE: 836
000

SEQ ID NO: 837 moltype = length =
SEQUENCE: 837
000

SEQ ID NO: 838 moltype = length =
SEQUENCE: 838
000

SEQ ID NO: 839 moltype = length =

SEQUENCE: 839
000

SEQ ID NO: 840 moltype = length =
SEQUENCE: 840
000

SEQ ID NO: 841 moltype = length =
SEQUENCE: 841
000

SEQ ID NO: 842 moltype = length =
SEQUENCE: 842
000

SEQ ID NO: 843 moltype = length =
SEQUENCE: 843
000

SEQ ID NO: 844 moltype = length =
SEQUENCE: 844
000

SEQ ID NO: 845 moltype = length =
SEQUENCE: 845
000

SEQ ID NO: 846 moltype = length =
SEQUENCE: 846
000

SEQ ID NO: 847 moltype = length =
SEQUENCE: 847
000

SEQ ID NO: 848 moltype = length =
SEQUENCE: 848
000

SEQ ID NO: 849 moltype = length =
SEQUENCE: 849
000

SEQ ID NO: 850 moltype = length =
SEQUENCE: 850
000

SEQ ID NO: 851 moltype = length =
SEQUENCE: 851
000

SEQ ID NO: 852 moltype = length =
SEQUENCE: 852
000

SEQ ID NO: 853 moltype = length =
SEQUENCE: 853
000

SEQ ID NO: 854 moltype = length =
SEQUENCE: 854
000

SEQ ID NO: 855 moltype = length =
SEQUENCE: 855
000

SEQ ID NO: 856 moltype = length =
SEQUENCE: 856
000

SEQ ID NO: 857 moltype = length =
SEQUENCE: 857
000

SEQ ID NO: 858 moltype = length =
SEQUENCE: 858
000

SEQ ID NO: 859 moltype = length =
SEQUENCE: 859
000

SEQ ID NO: 860 moltype = length =
SEQUENCE: 860
000

SEQ ID NO: 861 moltype = length =
SEQUENCE: 861
000

SEQ ID NO: 862 moltype = length =
SEQUENCE: 862
000

SEQ ID NO: 863 moltype = length =
SEQUENCE: 863
000

SEQ ID NO: 864 moltype = length =
SEQUENCE: 864
000

SEQ ID NO: 865 moltype = length =
SEQUENCE: 865
000

SEQ ID NO: 866 moltype = length =
SEQUENCE: 866
000

SEQ ID NO: 867 moltype = length =
SEQUENCE: 867
000

SEQ ID NO: 868 moltype = length =
SEQUENCE: 868
000

SEQ ID NO: 869 moltype = length =
SEQUENCE: 869
000

SEQ ID NO: 870 moltype = length =
SEQUENCE: 870
000

SEQ ID NO: 871 moltype = length =
SEQUENCE: 871
000

SEQ ID NO: 872 moltype = length =
SEQUENCE: 872
000

SEQ ID NO: 873 moltype = length =
SEQUENCE: 873
000

SEQ ID NO: 874 moltype = length =
SEQUENCE: 874
000

SEQ ID NO: 875 moltype = length =
SEQUENCE: 875
000

SEQ ID NO: 876 moltype = length =
SEQUENCE: 876
000

SEQ ID NO: 877 moltype = length =
SEQUENCE: 877
000

SEQ ID NO: 878 moltype = length =
SEQUENCE: 878
000

SEQ ID NO: 879 moltype = length =
SEQUENCE: 879
000

SEQ ID NO: 880 moltype = length =
SEQUENCE: 880
000

SEQ ID NO: 881 moltype = length =
SEQUENCE: 881
000

SEQ ID NO: 882 moltype = length =
SEQUENCE: 882
000

SEQ ID NO: 883 moltype = length =
SEQUENCE: 883
000

SEQ ID NO: 884 moltype = length =
SEQUENCE: 884
000

SEQ ID NO: 885 moltype = length =
SEQUENCE: 885
000

SEQ ID NO: 886 moltype = length =
SEQUENCE: 886
000

SEQ ID NO: 887 moltype = length =
SEQUENCE: 887
000

SEQ ID NO: 888 moltype = length =
SEQUENCE: 888
000

SEQ ID NO: 889 moltype = length =
SEQUENCE: 889
000

SEQ ID NO: 890 moltype = length =
SEQUENCE: 890
000

SEQ ID NO: 891 moltype = length =
SEQUENCE: 891
000

SEQ ID NO: 892 moltype = length =
SEQUENCE: 892
000

SEQ ID NO: 893 moltype = length =
SEQUENCE: 893
000

SEQ ID NO: 894 moltype = length =
SEQUENCE: 894
000

SEQ ID NO: 895 moltype = length =
SEQUENCE: 895
000

SEQ ID NO: 896 moltype = length =
SEQUENCE: 896
000

SEQ ID NO: 897 moltype = length =
SEQUENCE: 897
000

SEQ ID NO: 898 moltype = length =
SEQUENCE: 898

000

SEQ ID NO: 899 moltype = length =
SEQUENCE: 899
000

SEQ ID NO: 900 moltype = length =
SEQUENCE: 900
000

SEQ ID NO: 901 moltype = length =
SEQUENCE: 901
000

SEQ ID NO: 902 moltype = length =
SEQUENCE: 902
000

SEQ ID NO: 903 moltype = length =
SEQUENCE: 903
000

SEQ ID NO: 904 moltype = length =
SEQUENCE: 904
000

SEQ ID NO: 905 moltype = length =
SEQUENCE: 905
000

SEQ ID NO: 906 moltype = length =
SEQUENCE: 906
000

SEQ ID NO: 907 moltype = length =
SEQUENCE: 907
000

SEQ ID NO: 908 moltype = length =
SEQUENCE: 908
000

SEQ ID NO: 909 moltype = length =
SEQUENCE: 909
000

SEQ ID NO: 910 moltype = length =
SEQUENCE: 910
000

SEQ ID NO: 911 moltype = length =
SEQUENCE: 911
000

SEQ ID NO: 912 moltype = length =
SEQUENCE: 912
000

SEQ ID NO: 913 moltype = length =
SEQUENCE: 913
000

SEQ ID NO: 914 moltype = length =
SEQUENCE: 914
000

SEQ ID NO: 915 moltype = length =
SEQUENCE: 915
000

SEQ ID NO: 916 moltype = length =
SEQUENCE: 916
000

SEQ ID NO: 917 moltype = length =
SEQUENCE: 917
000

SEQ ID NO: 918 moltype = length =

SEQUENCE: 918
000

SEQ ID NO: 919 moltype = length =
SEQUENCE: 919
000

SEQ ID NO: 920 moltype = length =
SEQUENCE: 920
000

SEQ ID NO: 921 moltype = length =
SEQUENCE: 921
000

SEQ ID NO: 922 moltype = length =
SEQUENCE: 922
000

SEQ ID NO: 923 moltype = length =
SEQUENCE: 923
000

SEQ ID NO: 924 moltype = length =
SEQUENCE: 924
000

SEQ ID NO: 925 moltype = length =
SEQUENCE: 925
000

SEQ ID NO: 926 moltype = length =
SEQUENCE: 926
000

SEQ ID NO: 927 moltype = length =
SEQUENCE: 927
000

SEQ ID NO: 928 moltype = length =
SEQUENCE: 928
000

SEQ ID NO: 929 moltype = length =
SEQUENCE: 929
000

SEQ ID NO: 930 moltype = length =
SEQUENCE: 930
000

SEQ ID NO: 931 moltype = length =
SEQUENCE: 931
000

SEQ ID NO: 932 moltype = length =
SEQUENCE: 932
000

SEQ ID NO: 933 moltype = length =
SEQUENCE: 933
000

SEQ ID NO: 934 moltype = length =
SEQUENCE: 934
000

SEQ ID NO: 935 moltype = length =
SEQUENCE: 935
000

SEQ ID NO: 936 moltype = length =
SEQUENCE: 936
000

SEQ ID NO: 937 moltype = length =
SEQUENCE: 937
000

SEQ ID NO: 938 moltype = length =
SEQUENCE: 938
000

SEQ ID NO: 939 moltype = length =
SEQUENCE: 939
000

SEQ ID NO: 940 moltype = length =
SEQUENCE: 940
000

SEQ ID NO: 941 moltype = length =
SEQUENCE: 941
000

SEQ ID NO: 942 moltype = length =
SEQUENCE: 942
000

SEQ ID NO: 943 moltype = length =
SEQUENCE: 943
000

SEQ ID NO: 944 moltype = length =
SEQUENCE: 944
000

SEQ ID NO: 945 moltype = length =
SEQUENCE: 945
000

SEQ ID NO: 946 moltype = length =
SEQUENCE: 946
000

SEQ ID NO: 947 moltype = length =
SEQUENCE: 947
000

SEQ ID NO: 948 moltype = length =
SEQUENCE: 948
000

SEQ ID NO: 949 moltype = length =
SEQUENCE: 949
000

SEQ ID NO: 950 moltype = length =
SEQUENCE: 950
000

SEQ ID NO: 951 moltype = length =
SEQUENCE: 951
000

SEQ ID NO: 952 moltype = length =
SEQUENCE: 952
000

SEQ ID NO: 953 moltype = length =
SEQUENCE: 953
000

SEQ ID NO: 954 moltype = length =
SEQUENCE: 954
000

SEQ ID NO: 955 moltype = length =
SEQUENCE: 955
000

SEQ ID NO: 956 moltype = length =
SEQUENCE: 956
000

SEQ ID NO: 957 moltype = length =
SEQUENCE: 957
000

SEQ ID NO: 958 moltype = length =
SEQUENCE: 958
000

SEQ ID NO: 959 moltype = length =
SEQUENCE: 959
000

SEQ ID NO: 960 moltype = length =
SEQUENCE: 960
000

SEQ ID NO: 961 moltype = length =
SEQUENCE: 961
000

SEQ ID NO: 962 moltype = length =
SEQUENCE: 962
000

SEQ ID NO: 963 moltype = length =
SEQUENCE: 963
000

SEQ ID NO: 964 moltype = length =
SEQUENCE: 964
000

SEQ ID NO: 965 moltype = length =
SEQUENCE: 965
000

SEQ ID NO: 966 moltype = length =
SEQUENCE: 966
000

SEQ ID NO: 967 moltype = length =
SEQUENCE: 967
000

SEQ ID NO: 968 moltype = length =
SEQUENCE: 968
000

SEQ ID NO: 969 moltype = length =
SEQUENCE: 969
000

SEQ ID NO: 970 moltype = length =
SEQUENCE: 970
000

SEQ ID NO: 971 moltype = length =
SEQUENCE: 971
000

SEQ ID NO: 972 moltype = length =
SEQUENCE: 972
000

SEQ ID NO: 973 moltype = length =
SEQUENCE: 973
000

SEQ ID NO: 974 moltype = length =
SEQUENCE: 974
000

SEQ ID NO: 975 moltype = length =
SEQUENCE: 975
000

SEQ ID NO: 976 moltype = length =
SEQUENCE: 976
000

SEQ ID NO: 977 moltype = length =
SEQUENCE: 977

000

SEQ ID NO: 978 moltype = length =
SEQUENCE: 978
000

SEQ ID NO: 979 moltype = length =
SEQUENCE: 979
000

SEQ ID NO: 980 moltype = length =
SEQUENCE: 980
000

SEQ ID NO: 981 moltype = length =
SEQUENCE: 981
000

SEQ ID NO: 982 moltype = length =
SEQUENCE: 982
000

SEQ ID NO: 983 moltype = length =
SEQUENCE: 983
000

SEQ ID NO: 984 moltype = length =
SEQUENCE: 984
000

SEQ ID NO: 985 moltype = length =
SEQUENCE: 985
000

SEQ ID NO: 986 moltype = length =
SEQUENCE: 986
000

SEQ ID NO: 987 moltype = length =
SEQUENCE: 987
000

SEQ ID NO: 988 moltype = length =
SEQUENCE: 988
000

SEQ ID NO: 989 moltype = length =
SEQUENCE: 989
000

SEQ ID NO: 990 moltype = length =
SEQUENCE: 990
000

SEQ ID NO: 991 moltype = length =
SEQUENCE: 991
000

SEQ ID NO: 992 moltype = length =
SEQUENCE: 992
000

SEQ ID NO: 993 moltype = length =
SEQUENCE: 993
000

SEQ ID NO: 994 moltype = length =
SEQUENCE: 994
000

SEQ ID NO: 995 moltype = length =
SEQUENCE: 995
000

SEQ ID NO: 996 moltype = length =
SEQUENCE: 996
000

SEQ ID NO: 997 moltype = length =

```
SEQUENCE: 997
000

SEQ ID NO: 998         moltype =   length =
SEQUENCE: 998
000

SEQ ID NO: 999         moltype =   length =
SEQUENCE: 999
000

SEQ ID NO: 1000        moltype =   length =
SEQUENCE: 1000
000

SEQ ID NO: 1001        moltype =   length =
SEQUENCE: 1001
000

SEQ ID NO: 1002        moltype =   length =
SEQUENCE: 1002
000

SEQ ID NO: 1003        moltype =   length =
SEQUENCE: 1003
000

SEQ ID NO: 1004        moltype = AA  length = 721
FEATURE                Location/Qualifiers
source                 1..721
                       mol_type = protein
                       organism = synthetic construct
SEQUENCE: 1004
METDTLLLWV LLLWVPGSTG QVQLVQSGAE VKKPGSSVKV SCKASGYSFT TYYIHWVRQA  60
PGQGLEWMGW FFPGSGNIKY NEKFKGRVTI TADTSTSTAY MELSSLRSED TAVYYCAGSY  120
YSYDVLDYWG QGTTVTVSSG GGGSGGGGSG GGGSGGGGSD IQMTQSPSFL SASVGDRVTI  180
TCKASQNVGI NVVWHQQKPG KAPKALIYSS SHRYSGVPSR FSGSGSGTEF TLTISSLQPE  240
DFATYFCQQF KSYPLTFGQG TKLEIKGGGG SQVTLRESGP ALVKPTQTLT LTCTFSGFSL  300
STSGMGVGWI RQPPGKALEW LAHIWWDDDK RYNPALKSRL TISKDTSKNQ VFLTMTNMDP  360
VDTATYYCAR MELWSYYFDY WGQGTTVTVS SASTKGPSVF PLAPSSKSTS GGTAALGCLV  420
KDYFPEPVTV SWNSGALTSG VHTFPAVLQS SGLYSLSSVV TVPSSSLGTQ TYICNVNHKP  480
SNTKVDKKVE PKSCDKTHTC PPCPAPELLG GPSVFLFPPK PKDTLMISRT PEVTCVVVDV  540
SHEDPEVKFN WYVDGVEVHN AKTKPREEQY ASTYRVVSVL TVLHQDWLNG KEYKCKVSNK  600
ALPAPIEKTI SKAKGQPREP QVYTLPPSRE EMTKNQVSLT CLVKGFYPSD IAVEWESNGQ  660
PENNYKTTPP VLDSDGSFFL YSKLTVDKSR WQQGNVFSCS VMHEALHNHY TQKSLSLSPG  720
K                                                                 721

SEQ ID NO: 1005        moltype = AA  length = 233
FEATURE                Location/Qualifiers
source                 1..233
                       mol_type = protein
                       organism = synthetic construct
SEQUENCE: 1005
METPAQLLFL LLLWLPDTTG ENVLTQSPAT LSLSPGERAT LSCSASSSVS YMHWYQQKPG  60
QAPRLLIYDT SKLASGIPAR FSGSGSGTDH TLTISSLEPE DFAVYYCFQG SVYPFTFGQG  120
TKLEIKRTVA APSVFIFPPS DEQLKSGTAS VVCLLNNFYP REAKVQWKVD NALQSGNSQE  180
SVTEQDSKDS TYSLSSTLTL SKADYEKHKV YACEVTHQGL SSPVTKSFNR GEC         233

SEQ ID NO: 1006        moltype = AA  length = 721
FEATURE                Location/Qualifiers
source                 1..721
                       mol_type = protein
                       organism = synthetic construct
SEQUENCE: 1006
METDTLLLWV LLLWVPGSTG QVQLVQSGAE VKKPGSSVKV SCKASGYSFT TYYIHWVRQA  60
PGQGLEWMGW FFPGSGNIKY NEKFKGRVTI TADTSTSTAY MELSSLRSED TAVYYCAGSY  120
YSYDVLDYWG QGTTVTVSSG GGGSGGGGSG GGGSGGGGSD IQMTQSPSFL SASVGDRVTI  180
TCKASQNVGI NVVWHQQKPG KAPKALIYSS SHRYSGVPSR FSGSGSGTEF TLTISSLQPE  240
DFATYFCQQF KSYPLTFGQG TKLEIKGGGG SQVQLVESGG GVVQPGRSLR LSCAASGIDF  300
SRYWMSWVRQ APGKGLEWVG EINPDSSTIN YAPSLKDRFT ISRDNSKNTL YLQMSSLRAE  360
DTAVYYCASL YYDYGDAMDY WGQGTTVTVS SASTKGPSVF PLAPSSKSTS GGTAALGCLV  420
KDYFPEPVTV SWNSGALTSG VHTFPAVLQS SGLYSLSSVV TVPSSSLGTQ TYICNVNHKP  480
SNTKVDKKVE PKSCDKTHTC PPCPAPELLG GPSVFLFPPK PKDTLMISRT PEVTCVVVDV  540
SHEDPEVKFN WYVDGVEVHN AKTKPREEQY ASTYRVVSVL TVLHQDWLNG KEYKCKVSNK  600
ALPAPIEKTI SKAKGQPREP QVYTLPPSRE EMTKNQVSLT CLVKGFYPSD IAVEWESNGQ  660
PENNYKTTPP VLDSDGSFFL YSKLTVDKSR WQQGNVFSCS VMHEALHNRF TQKSLSLSPG  720
K                                                                 721

SEQ ID NO: 1007        moltype = AA  length = 234
```

```
FEATURE                Location/Qualifiers
source                 1..234
                       mol_type = protein
                       organism = synthetic construct
SEQUENCE: 1007
METDTLLLWV LLLWVPGSTG DIQMTQSPSS LSASVGDRVT ITCKASQSVD SNVAWYQQKP  60
EKAPKALIFS ASLRFSGVPS RFSGSGSGTD FTLTISSLQP EDFATYFCQQ YNNYPLTFGQ  120
GTKLEIKRTV AAPSVFIFPP SDEQLKSGTA SVVCLLNNFY PREAKVQWKV DNALQSGNSQ  180
ESVTEQDSKD STYSLSSTLT LSKADYEKHK VYACEVTHQG LSSPVTKSFN RGEC        234

SEQ ID NO: 1008        moltype =   length =
SEQUENCE: 1008
000

SEQ ID NO: 1009        moltype =   length =
SEQUENCE: 1009
000

SEQ ID NO: 1010        moltype =   length =
SEQUENCE: 1010
000

SEQ ID NO: 1011        moltype =   length =
SEQUENCE: 1011
000

SEQ ID NO: 1012        moltype =   length =
SEQUENCE: 1012
000

SEQ ID NO: 1013        moltype =   length =
SEQUENCE: 1013
000

SEQ ID NO: 1014        moltype =   length =
SEQUENCE: 1014
000

SEQ ID NO: 1015        moltype =   length =
SEQUENCE: 1015
000

SEQ ID NO: 1016        moltype =   length =
SEQUENCE: 1016
000

SEQ ID NO: 1017        moltype =   length =
SEQUENCE: 1017
000

SEQ ID NO: 1018        moltype =   length =
SEQUENCE: 1018
000

SEQ ID NO: 1019        moltype =   length =
SEQUENCE: 1019
000

SEQ ID NO: 1020        moltype =   length =
SEQUENCE: 1020
000

SEQ ID NO: 1021        moltype =   length =
SEQUENCE: 1021
000

SEQ ID NO: 1022        moltype =   length =
SEQUENCE: 1022
000

SEQ ID NO: 1023        moltype =   length =
SEQUENCE: 1023
000

SEQ ID NO: 1024        moltype =   length =
SEQUENCE: 1024
000

SEQ ID NO: 1025        moltype =   length =
```

SEQUENCE: 1025
000

SEQ ID NO: 1026 moltype = length =
SEQUENCE: 1026
000

SEQ ID NO: 1027 moltype = length =
SEQUENCE: 1027
000

SEQ ID NO: 1028 moltype = length =
SEQUENCE: 1028
000

SEQ ID NO: 1029 moltype = length =
SEQUENCE: 1029
000

SEQ ID NO: 1030 moltype = length =
SEQUENCE: 1030
000

SEQ ID NO: 1031 moltype = length =
SEQUENCE: 1031
000

SEQ ID NO: 1032 moltype = length =
SEQUENCE: 1032
000

SEQ ID NO: 1033 moltype = length =
SEQUENCE: 1033
000

SEQ ID NO: 1034 moltype = length =
SEQUENCE: 1034
000

SEQ ID NO: 1035 moltype = length =
SEQUENCE: 1035
000

SEQ ID NO: 1036 moltype = length =
SEQUENCE: 1036
000

SEQ ID NO: 1037 moltype = length =
SEQUENCE: 1037
000

SEQ ID NO: 1038 moltype = length =
SEQUENCE: 1038
000

SEQ ID NO: 1039 moltype = length =
SEQUENCE: 1039
000

SEQ ID NO: 1040 moltype = length =
SEQUENCE: 1040
000

SEQ ID NO: 1041 moltype = length =
SEQUENCE: 1041
000

SEQ ID NO: 1042 moltype = length =
SEQUENCE: 1042
000

SEQ ID NO: 1043 moltype = length =
SEQUENCE: 1043
000

SEQ ID NO: 1044 moltype = length =
SEQUENCE: 1044
000

SEQ ID NO: 1045 moltype = length =
SEQUENCE: 1045
000

SEQ ID NO: 1046 moltype = length =
SEQUENCE: 1046
000

SEQ ID NO: 1047 moltype = length =
SEQUENCE: 1047
000

SEQ ID NO: 1048 moltype = length =
SEQUENCE: 1048
000

SEQ ID NO: 1049 moltype = length =
SEQUENCE: 1049
000

SEQ ID NO: 1050 moltype = length =
SEQUENCE: 1050
000

SEQ ID NO: 1051 moltype = length =
SEQUENCE: 1051
000

SEQ ID NO: 1052 moltype = length =
SEQUENCE: 1052
000

SEQ ID NO: 1053 moltype = length =
SEQUENCE: 1053
000

SEQ ID NO: 1054 moltype = length =
SEQUENCE: 1054
000

SEQ ID NO: 1055 moltype = length =
SEQUENCE: 1055
000

SEQ ID NO: 1056 moltype = length =
SEQUENCE: 1056
000

SEQ ID NO: 1057 moltype = length =
SEQUENCE: 1057
000

SEQ ID NO: 1058 moltype = length =
SEQUENCE: 1058
000

SEQ ID NO: 1059 moltype = length =
SEQUENCE: 1059
000

SEQ ID NO: 1060 moltype = length =
SEQUENCE: 1060
000

SEQ ID NO: 1061 moltype = length =
SEQUENCE: 1061
000

SEQ ID NO: 1062 moltype = length =
SEQUENCE: 1062
000

SEQ ID NO: 1063 moltype = length =
SEQUENCE: 1063
000

SEQ ID NO: 1064 moltype = length =
SEQUENCE: 1064
000

SEQ ID NO: 1065 moltype = length =
SEQUENCE: 1065
000

SEQ ID NO: 1066 moltype = length =
SEQUENCE: 1066
000

SEQ ID NO: 1067 moltype = length =
SEQUENCE: 1067
000

SEQ ID NO: 1068 moltype = length =
SEQUENCE: 1068
000

SEQ ID NO: 1069 moltype = length =
SEQUENCE: 1069
000

SEQ ID NO: 1070 moltype = length =
SEQUENCE: 1070
000

SEQ ID NO: 1071 moltype = length =
SEQUENCE: 1071
000

SEQ ID NO: 1072 moltype = length =
SEQUENCE: 1072
000

SEQ ID NO: 1073 moltype = length =
SEQUENCE: 1073
000

SEQ ID NO: 1074 moltype = length =
SEQUENCE: 1074
000

SEQ ID NO: 1075 moltype = length =
SEQUENCE: 1075
000

SEQ ID NO: 1076 moltype = length =
SEQUENCE: 1076
000

SEQ ID NO: 1077 moltype = length =
SEQUENCE: 1077
000

SEQ ID NO: 1078 moltype = length =
SEQUENCE: 1078
000

SEQ ID NO: 1079 moltype = length =
SEQUENCE: 1079
000

SEQ ID NO: 1080 moltype = length =
SEQUENCE: 1080
000

SEQ ID NO: 1081 moltype = length =
SEQUENCE: 1081
000

SEQ ID NO: 1082 moltype = length =
SEQUENCE: 1082
000

SEQ ID NO: 1083 moltype = length =
SEQUENCE: 1083
000

SEQ ID NO: 1084 moltype = length =
SEQUENCE: 1084

000

SEQ ID NO: 1085 moltype = length =
SEQUENCE: 1085
000

SEQ ID NO: 1086 moltype = length =
SEQUENCE: 1086
000

SEQ ID NO: 1087 moltype = length =
SEQUENCE: 1087
000

SEQ ID NO: 1088 moltype = length =
SEQUENCE: 1088
000

SEQ ID NO: 1089 moltype = length =
SEQUENCE: 1089
000

SEQ ID NO: 1090 moltype = length =
SEQUENCE: 1090
000

SEQ ID NO: 1091 moltype = length =
SEQUENCE: 1091
000

SEQ ID NO: 1092 moltype = length =
SEQUENCE: 1092
000

SEQ ID NO: 1093 moltype = length =
SEQUENCE: 1093
000

SEQ ID NO: 1094 moltype = length =
SEQUENCE: 1094
000

SEQ ID NO: 1095 moltype = length =
SEQUENCE: 1095
000

SEQ ID NO: 1096 moltype = length =
SEQUENCE: 1096
000

SEQ ID NO: 1097 moltype = length =
SEQUENCE: 1097
000

SEQ ID NO: 1098 moltype = length =
SEQUENCE: 1098
000

SEQ ID NO: 1099 moltype = length =
SEQUENCE: 1099
000

SEQ ID NO: 1100 moltype = AA length = 119
FEATURE Location/Qualifiers
source 1..119
mol_type = protein
organism = synthetic construct
SEQUENCE: 1100
QVQLVQSGAE VKKPGSSVKV SCKASGYSFT TYYIHWVRQA PGQGLEWMGW FFPGSGNIKY 60
NEKFKGRVTI TADTSTSTAY MELSSLRSED TAVYYCAGSY YSYDVLDYWG QGTTVTVSS 119

SEQ ID NO: 1101 moltype = AA length = 106
FEATURE Location/Qualifiers
source 1..106
mol_type = protein
organism = synthetic construct
SEQUENCE: 1101
QSVLTQPPSV SEAPRQRVTI SCKASQNVGI NVVWHQQLPG KAPKALIYSS SHRYSGVSDR 60
FSGSGSGTSF SLAISGLQSE DEADYFCQQF KSYPLTFGTG TKVTVL 106

```
SEQ ID NO: 1102         moltype = AA  length = 5
FEATURE                 Location/Qualifiers
source                  1..5
                        mol_type = protein
                        organism = synthetic construct
SEQUENCE: 1102
SAYMH                                                                       5

SEQ ID NO: 1103         moltype = AA  length = 17
FEATURE                 Location/Qualifiers
source                  1..17
                        mol_type = protein
                        organism = synthetic construct
SEQUENCE: 1103
RIDPATGKTK YAPKFQA                                                          17

SEQ ID NO: 1104         moltype = AA  length = 10
FEATURE                 Location/Qualifiers
source                  1..10
                        mol_type = protein
                        organism = synthetic construct
SEQUENCE: 1104
SLNWDYGLDY                                                                  10

SEQ ID NO: 1105         moltype = AA  length = 7
FEATURE                 Location/Qualifiers
source                  1..7
                        mol_type = protein
                        organism = synthetic construct
SEQUENCE: 1105
GFNIKSA                                                                     7

SEQ ID NO: 1106         moltype = AA  length = 6
FEATURE                 Location/Qualifiers
source                  1..6
                        mol_type = protein
                        organism = synthetic construct
SEQUENCE: 1106
DPATGK                                                                      6

SEQ ID NO: 1107         moltype = AA  length = 15
FEATURE                 Location/Qualifiers
source                  1..15
                        mol_type = protein
                        organism = synthetic construct
SEQUENCE: 1107
RASKSVSILG THLIH                                                            15

SEQ ID NO: 1108         moltype = AA  length = 7
FEATURE                 Location/Qualifiers
source                  1..7
                        mol_type = protein
                        organism = synthetic construct
SEQUENCE: 1108
AASNLES                                                                     7

SEQ ID NO: 1109         moltype = AA  length = 9
FEATURE                 Location/Qualifiers
source                  1..9
                        mol_type = protein
                        organism = synthetic construct
SEQUENCE: 1109
QQSIEDPWT                                                                   9

SEQ ID NO: 1110         moltype = AA  length = 11
FEATURE                 Location/Qualifiers
source                  1..11
                        mol_type = protein
                        organism = synthetic construct
SEQUENCE: 1110
SKSVSILGTH L                                                                11

SEQ ID NO: 1111         moltype = AA  length = 111
FEATURE                 Location/Qualifiers
source                  1..111
                        mol_type = protein
                        organism = synthetic construct
SEQUENCE: 1111
```

```
DIVLTQSPAS LAVSLGQRAT ISCRASKSVS ILGTHLIHWY QQKPGQPPKL LIYAASNLES  60
GVPARFSGSG SETVFTLNIH PVEEEDAATY FCQQSIEDPW TFGGGTKLGI K          111

SEQ ID NO: 1112        moltype = AA  length = 119
FEATURE                Location/Qualifiers
source                 1..119
                       mol_type = protein
                       organism = synthetic construct
SEQUENCE: 1112
EVQLQQSVAD LVRPGASLKL SCTASGFNIK SAYMHWVIQR PDQGPECLGR IDPATGKTKY  60
APKFQAKATI TADTSSNTAY LQLSSLTSED TAIYYCTRSL NWDYGLDYWG QGTSVTVSS   119

SEQ ID NO: 1113        moltype = AA  length = 119
FEATURE                Location/Qualifiers
source                 1..119
                       mol_type = protein
                       organism = synthetic construct
SEQUENCE: 1113
QVQLVQSGAE VKKPGASVKV SCKASGFNIK SAYMHWVRQA PGQGLEWMGR IDPATGKTKY  60
APKFQARVTM TADTSTNTAY MELSSLRSED TAVYYCARSL NWDYGLDYWG QGTLVTVSS   119

SEQ ID NO: 1114        moltype = AA  length = 119
FEATURE                Location/Qualifiers
source                 1..119
                       mol_type = protein
                       organism = synthetic construct
SEQUENCE: 1114
QVQLVQSGAE VKKPGASVKV SCKASGFNIK SAYMHWVRQA PGQEPGCMGR IDPATGKTKY  60
APKFQARVTM TADTSINTAY TELSSLRSED TATYYCARSL NWDYGLDYWG QGTLVTVSS   119

SEQ ID NO: 1115        moltype = AA  length = 119
FEATURE                Location/Qualifiers
source                 1..119
                       mol_type = protein
                       organism = synthetic construct
SEQUENCE: 1115
QVQLVQSGAE VKKPGSSVKV SCKASGFNIK SAYMHWVRQA PGQGLEWMGR IDPATGKTKY  60
APKFQARVTI TADTSTNTAY MELSSLRSED TAVYYCARSL NWDYGLDYWG QGTLVTVSS   119

SEQ ID NO: 1116        moltype = AA  length = 119
FEATURE                Location/Qualifiers
source                 1..119
                       mol_type = protein
                       organism = synthetic construct
SEQUENCE: 1116
QVQLVQSGAE VKKPGASVKV SCKASGFNIK SAYMHWVRQA PGQRLEWMGR IDPATGKTKY  60
APKFQARVTI TADTSANTAY MELSSLRSED TAVYYCARSL NWDYGLDYWG QGTLVTVSS   119

SEQ ID NO: 1117        moltype = AA  length = 109
FEATURE                Location/Qualifiers
source                 1..109
                       mol_type = protein
                       organism = synthetic construct
SEQUENCE: 1117
EIVLTQSPAT LSLSPGERAT LSCRASKSVS ILGTHLIHWY QQKPGQAPRL LIYAASNLES  60
GIPARFSGSG SETDFTLTIS SLEPEDFAVY FCQQSIEDPF GGGTKVEIK             109

SEQ ID NO: 1118        moltype = AA  length = 109
FEATURE                Location/Qualifiers
source                 1..109
                       mol_type = protein
                       organism = synthetic construct
SEQUENCE: 1118
EIVLTQSPAT LSLSPGERAT LSCRASKSVS ILGTHLIHWY QQKPGLAPRL LIYAASNLES  60
GIPDRFSGSG SETDFTLTIS RLEPEDFAVY FCQQSIEDPF GGGTKVEIK             109

SEQ ID NO: 1119        moltype = AA  length = 109
FEATURE                Location/Qualifiers
source                 1..109
                       mol_type = protein
                       organism = synthetic construct
SEQUENCE: 1119
EIVLTQSPGT LSLSPGERAT LSCRASKSVS ILGTHLIHWY QQKPGQAPRL LIYAASNLES  60
GIPDRFSGSG SETDFTLTIS RLEPEDFAVY FCQQSIEDPF GGGTKVEIK             109

SEQ ID NO: 1120        moltype = AA  length = 5
FEATURE                Location/Qualifiers
source                 1..5
                       mol_type = protein
```

```
                        organism = synthetic construct
SEQUENCE: 1120
DTYMY                                                                  5

SEQ ID NO: 1121         moltype = AA  length = 17
FEATURE                 Location/Qualifiers
source                  1..17
                        mol_type = protein
                        organism = synthetic construct
SEQUENCE: 1121
RIDPANGNTK YDPKFQD                                                     17

SEQ ID NO: 1122         moltype = AA  length = 9
FEATURE                 Location/Qualifiers
source                  1..9
                        mol_type = protein
                        organism = synthetic construct
SEQUENCE: 1122
GSYYYAMDY                                                              9

SEQ ID NO: 1123         moltype = AA  length = 7
FEATURE                 Location/Qualifiers
source                  1..7
                        mol_type = protein
                        organism = synthetic construct
SEQUENCE: 1123
GFKTEDT                                                                7

SEQ ID NO: 1124         moltype = AA  length = 6
FEATURE                 Location/Qualifiers
source                  1..6
                        mol_type = protein
                        organism = synthetic construct
SEQUENCE: 1124
DPANGN                                                                 6

SEQ ID NO: 1125         moltype = AA  length = 10
FEATURE                 Location/Qualifiers
source                  1..10
                        mol_type = protein
                        organism = synthetic construct
SEQUENCE: 1125
GFKTEDTYMY                                                             10

SEQ ID NO: 1126         moltype = AA  length = 15
FEATURE                 Location/Qualifiers
source                  1..15
                        mol_type = protein
                        organism = synthetic construct
SEQUENCE: 1126
RASESVDSYG NSFMH                                                       15

SEQ ID NO: 1127         moltype = AA  length = 7
FEATURE                 Location/Qualifiers
source                  1..7
                        mol_type = protein
                        organism = synthetic construct
SEQUENCE: 1127
RASNLES                                                                7

SEQ ID NO: 1128         moltype = AA  length = 9
FEATURE                 Location/Qualifiers
source                  1..9
                        mol_type = protein
                        organism = synthetic construct
SEQUENCE: 1128
QQSNEDPYT                                                              9

SEQ ID NO: 1129         moltype = AA  length = 111
FEATURE                 Location/Qualifiers
source                  1..111
                        mol_type = protein
                        organism = synthetic construct
SEQUENCE: 1129
DIVLTQSPAS LAVSLGQRAT ISCRASESVD SYGNSFMHWY QQKPGQPPKL LIYRASNLES  60
GIPARFSGSG SRTDFTLTIN PVEADDVATY YCQQSNEDPY TFGGGTKLEI K           111

SEQ ID NO: 1130         moltype = AA  length = 118
FEATURE                 Location/Qualifiers
```

```
source                  1..118
                        mol_type = protein
                        organism = synthetic construct
SEQUENCE: 1130
EVQLQQSGAE LVKPGASVKL SCTASGFKTE DTYMYWVKQR PEQGLEWIGR IDPANGNTKY  60
DPKFQDKATI TADSSSNTAY LQLSSLPSED TAVYYCARGS YYYAMDYWGQ GTSVTVSS    118

SEQ ID NO: 1131         moltype = AA  length = 118
FEATURE                 Location/Qualifiers
source                  1..118
                        mol_type = protein
                        organism = synthetic construct
SEQUENCE: 1131
QVQLVQSGAE VKKPGSSVKV SCKASGFKTE DTYMYWVRQA PGQGLEWIGR IDPANGNTKY  60
DPKFQDRATI TADSSTNTAY MELSSLRSED TAVYYCARGS YYYAMDYWGQ GTLVTVSS    118

SEQ ID NO: 1132         moltype = AA  length = 118
FEATURE                 Location/Qualifiers
source                  1..118
                        mol_type = protein
                        organism = synthetic construct
SEQUENCE: 1132
QVQLVQSGAE VKKPGASVKV SCKASGFKTE DTYMYWVRQA PGQRLEWIGR IDPANGNTKY  60
DPKFQDRATI TADSSANTAY MELSSLRSED TAVYYCARGS YYYAMDYWGQ GTLVTVSS    118

SEQ ID NO: 1133         moltype = AA  length = 118
FEATURE                 Location/Qualifiers
source                  1..118
                        mol_type = protein
                        organism = synthetic construct
SEQUENCE: 1133
EVQLVESGGG LVQPGGSLKL SCAASGFKTE DTYMYWVRQA SGKGLEWIGR IDPANGNTKY  60
DPKFQDRATI SADSSKNTAY LQMNSLKTED TAVYYCARGS YYYAMDYWGQ GTLVTVSS    118

SEQ ID NO: 1134         moltype = AA  length = 118
FEATURE                 Location/Qualifiers
source                  1..118
                        mol_type = protein
                        organism = synthetic construct
SEQUENCE: 1134
EVQLVQSGAE VKKPGESLRI SCKASGFKTE DTYMYWVRQM PGKGLEWIGR IDPANGNTKY  60
DPKFQDQATI SADSSINTAY LQWSSLKASD TAMYYCARGS YYYAMDYWGQ GTLVTVSS    118

SEQ ID NO: 1135         moltype = AA  length = 118
FEATURE                 Location/Qualifiers
source                  1..118
                        mol_type = protein
                        organism = synthetic construct
SEQUENCE: 1135
QVQLVQSGSE LKKPGASVKV SCKASGFKTE DTYMYWVRQA PGQGLEWIGR IDPANGNTKY  60
DPKFQDRAVI SADSSVNTAY LQISSLKAED TAVYYCARGS YYYAMDYWGQ GTLVTVSS    118

SEQ ID NO: 1136         moltype = AA  length = 111
FEATURE                 Location/Qualifiers
source                  1..111
                        mol_type = protein
                        organism = synthetic construct
SEQUENCE: 1136
DIVLTQSPDS LAVSLGERAT INCRASESVD SYGNSFMHWY QQKPGQPPKL LIYRASNLES  60
GVPDRFSGSG SRTDFTLTIS SLQAEDVAVY YCQQSNEDPY TFGQGTKLEI K           111

SEQ ID NO: 1137         moltype = AA  length = 111
FEATURE                 Location/Qualifiers
source                  1..111
                        mol_type = protein
                        organism = synthetic construct
SEQUENCE: 1137
EIVLTQSPAT LSLSPGERAT LSCRASESVD SYGNSFMHWY QQKPGQAPKL LIYRASNLES  60
GIPARFSGSG SRTDFTLTIS RLEPEDFAVY YCQQSNEDPY TFGQGTKLEI K           111

SEQ ID NO: 1138         moltype = AA  length = 111
FEATURE                 Location/Qualifiers
source                  1..111
                        mol_type = protein
                        organism = synthetic construct
SEQUENCE: 1138
DIQLTQSPSS LSASVGDRVT ITCRASESVD SYGNSFMHWY QQKPGQAPKL LIYRASNLES  60
GVPSRFSGSG SRTDFTLTIS SLQPEDVATY YCQQSNEDPY TFGQGTKLEI K           111
```

```
SEQ ID NO: 1139        moltype = AA  length = 111
FEATURE                Location/Qualifiers
source                 1..111
                       mol_type = protein
                       organism = synthetic construct
SEQUENCE: 1139
AIQLTQSPSS LSASVGDRVT ITCRASESVD SYGNSFMHWY QQKPGKAPKL LIYRASNLES  60
GVPSRFSGSG SRTDFTLTIS SLQPEDFATY YCQQSNEDPY TFGQGTKLEI K           111

SEQ ID NO: 1140        moltype = AA  length = 111
FEATURE                Location/Qualifiers
source                 1..111
                       mol_type = protein
                       organism = synthetic construct
SEQUENCE: 1140
EIVLTQSPDF QSVTPKEKVT ITCRASESVD SYGNSFMHWY QQKPDQSPKL LIYRASNLES  60
GVPSRFSGSG SRTDFTLTIN SLEAEDAATY YCQQSNEDPY TFGQGTKLEI K           111

SEQ ID NO: 1141        moltype = AA  length = 5
FEATURE                Location/Qualifiers
source                 1..5
                       mol_type = protein
                       organism = synthetic construct
SEQUENCE: 1141
SYAMS                                                              5

SEQ ID NO: 1142        moltype = AA  length = 17
FEATURE                Location/Qualifiers
source                 1..17
                       mol_type = protein
                       organism = synthetic construct
SEQUENCE: 1142
HISNGGDYIY YADTVKG                                                 17

SEQ ID NO: 1143        moltype = AA  length = 12
FEATURE                Location/Qualifiers
source                 1..12
                       mol_type = protein
                       organism = synthetic construct
SEQUENCE: 1143
PSYYSDPWFF DV                                                      12

SEQ ID NO: 1144        moltype = AA  length = 7
FEATURE                Location/Qualifiers
source                 1..7
                       mol_type = protein
                       organism = synthetic construct
SEQUENCE: 1144
GFTFRSY                                                            7

SEQ ID NO: 1145        moltype = AA  length = 6
FEATURE                Location/Qualifiers
source                 1..6
                       mol_type = protein
                       organism = synthetic construct
SEQUENCE: 1145
SNGGDY                                                             6

SEQ ID NO: 1146        moltype = AA  length = 10
FEATURE                Location/Qualifiers
source                 1..10
                       mol_type = protein
                       organism = synthetic construct
SEQUENCE: 1146
GFTFRSYAMS                                                         10

SEQ ID NO: 1147        moltype = AA  length = 10
FEATURE                Location/Qualifiers
source                 1..10
                       mol_type = protein
                       organism = synthetic construct
SEQUENCE: 1147
SAGSSVSFMH                                                         10

SEQ ID NO: 1148        moltype = AA  length = 7
FEATURE                Location/Qualifiers
source                 1..7
                       mol_type = protein
                       organism = synthetic construct
```

```
SEQUENCE: 1148
DTSKLAS                                                           7

SEQ ID NO: 1149        moltype = AA  length = 9
FEATURE                Location/Qualifiers
source                 1..9
                       mol_type = protein
                       organism = synthetic construct
SEQUENCE: 1149
LQGSGFPLT                                                         9

SEQ ID NO: 1150        moltype = AA  length = 6
FEATURE                Location/Qualifiers
source                 1..6
                       mol_type = protein
                       organism = synthetic construct
SEQUENCE: 1150
GSSVSF                                                            6

SEQ ID NO: 1151        moltype = AA  length = 106
FEATURE                Location/Qualifiers
source                 1..106
                       mol_type = protein
                       organism = synthetic construct
SEQUENCE: 1151
ENVLTQSPAI MSASPGEKVT MTCSAGSSVS FMHWYQQKSS TSPKLWIYDT SKLASGVPGR  60
FSGSGSGNSF SLTISSMEAE DVAIYYCLQG SGFPLTFGSG TKLEIK                106

SEQ ID NO: 1152        moltype = AA  length = 121
FEATURE                Location/Qualifiers
source                 1..121
                       mol_type = protein
                       organism = synthetic construct
SEQUENCE: 1152
DVKLVESGEG LVKPGGSLKL SCAASGFTFR SYAMSWVRQT PEKRLEWVAH ISNGGDYIYY  60
ADTVKGRFTI SRDNARNTLY LQMSSLKSED TAMYYCTRPS YYSDPWFFDV WGTGTTVTVS  120
S                                                                 121

SEQ ID NO: 1153        moltype = AA  length = 121
FEATURE                Location/Qualifiers
source                 1..121
                       mol_type = protein
                       organism = synthetic construct
SEQUENCE: 1153
EVQLVESGGG LVQPGGSLRL SCAASGFTFR SYAMSWVRQA PGKGLEWVAH ISNGGDYIYY  60
ADTVKGRFTI SRDNAKNSLY LQMNSLRAED TAVYYCTRPS YYSDPWFFDV WGQGTTVTVS  120
S                                                                 121

SEQ ID NO: 1154        moltype = AA  length = 121
FEATURE                Location/Qualifiers
source                 1..121
                       mol_type = protein
                       organism = synthetic construct
SEQUENCE: 1154
QVQLVESGGG VVQPGRSLRL SCAASGFTFR SYAMSWVRQA PGKGLEWVAH ISNGGDYIYY  60
ADTVKGRFTI SRDNSKNTLY LQMSSLRAED TAVYYCTRPS YYSDPWFFDV WGQGTTVTVS  120
S                                                                 121

SEQ ID NO: 1155        moltype = AA  length = 121
FEATURE                Location/Qualifiers
source                 1..121
                       mol_type = protein
                       organism = synthetic construct
SEQUENCE: 1155
EVQLVESGGG LVQPGGSLRL SCAASGFTFR SYAMSWVRQA PGKGLEWVAH ISNGGDYIYY  60
ADTVKGRFTI SRDNSKNTLY LQMNSLRAED TAVYYCTRPS YYSDPWFFDV WGQGTTVTVS  120
S                                                                 121

SEQ ID NO: 1156        moltype = AA  length = 121
FEATURE                Location/Qualifiers
source                 1..121
                       mol_type = protein
                       organism = synthetic construct
SEQUENCE: 1156
QVQLVQSGSE LKKPGASVKV SCKASGFTFR SYAMSWVRQA PGQGLEWVAH ISNGGDYIYY  60
ADTVKGRFVI SRDNSVNTLY LQISSLKAED TAVYYCTRPS YYSDPWFFDV WGQGTTVTVS  120
S                                                                 121

SEQ ID NO: 1157        moltype = AA  length = 121
```

```
FEATURE                Location/Qualifiers
source                 1..121
                       mol_type = protein
                       organism = synthetic construct
SEQUENCE: 1157
QVQLVQSGAE VKKPGASVKV SCKASGFTFR SYAMSWVRQA PGQRLEWVAH ISNGGDYIYY  60
ADTVKGRFTI TRDNSANTLY MELSSLRSED TAVYYCTRPS YYSDPWFFDV WGQGTTVTVS  120
S                                                                 121

SEQ ID NO: 1158        moltype = AA  length = 106
FEATURE                Location/Qualifiers
source                 1..106
                       mol_type = protein
                       organism = synthetic construct
SEQUENCE: 1158
ENVLTQSPAT LSLSPGERAT LSCSAGSSVS FMHWYQQKPG QAPKLLIYDT SKLASGIPAR  60
FSGSGSGNDF TLTISSLEPE DFAVYYCLQG SGFPLTFGQG TKLEIK                106

SEQ ID NO: 1159        moltype = AA  length = 106
FEATURE                Location/Qualifiers
source                 1..106
                       mol_type = protein
                       organism = synthetic construct
SEQUENCE: 1159
ENVLTQSPDF QSVTPKEKVT ITCSAGSSVS FMHWYQQKPD QSPKLLIYDT SKLASGVPSR  60
FSGSGSGNDF TLTINSLEAE DAATYYCLQG SGFPLTFGQG TKLEIK                106

SEQ ID NO: 1160        moltype = AA  length = 106
FEATURE                Location/Qualifiers
source                 1..106
                       mol_type = protein
                       organism = synthetic construct
SEQUENCE: 1160
DNQLTQSPSS LSASVGDRVT ITCSAGSSVS FMHWYQQKPG KVPKLLIYDT SKLASGVPSR  60
FSGSGSGNDF TLTISSLQPE DVATYYCLQG SGFPLTFGQG TKLEIK                106

SEQ ID NO: 1161        moltype = AA  length = 106
FEATURE                Location/Qualifiers
source                 1..106
                       mol_type = protein
                       organism = synthetic construct
SEQUENCE: 1161
ANQLTQSPSS LSASVGDRVT ITCSAGSSVS FMHWYQQKPG KAPKLLIYDT SKLASGVPSR  60
FSGSGSGNDF TLTISSLQPE DFATYYCLQG SGFPLTFGQG TKLEIK                106

SEQ ID NO: 1162        moltype = AA  length = 106
FEATURE                Location/Qualifiers
source                 1..106
                       mol_type = protein
                       organism = synthetic construct
SEQUENCE: 1162
DNVLTQSPDS LAVSLGERAT INCSAGSSVS FMHWYQQKPG QPPKLLIYDT SKLASGVPDR  60
FSGSGSGNDF TLTISSLQAE DVAVYYCLQG SGFPLTFGQG TKLEIK                106

SEQ ID NO: 1163        moltype = AA  length = 5
FEATURE                Location/Qualifiers
source                 1..5
                       mol_type = protein
                       organism = synthetic construct
SEQUENCE: 1163
DYNIH                                                             5

SEQ ID NO: 1164        moltype = AA  length = 17
FEATURE                Location/Qualifiers
source                 1..17
                       mol_type = protein
                       organism = synthetic construct
SEQUENCE: 1164
YINPYNGRTG YNQKFKA                                                17

SEQ ID NO: 1165        moltype = AA  length = 9
FEATURE                Location/Qualifiers
source                 1..9
                       mol_type = protein
                       organism = synthetic construct
SEQUENCE: 1165
WDGSSYFDY                                                         9

SEQ ID NO: 1166        moltype = AA  length = 10
```

```
FEATURE                Location/Qualifiers
source                 1..10
                       mol_type = protein
                       organism = synthetic construct
SEQUENCE: 1166
GYTFTDYNIH                                                 10

SEQ ID NO: 1167        moltype = AA  length = 6
FEATURE                Location/Qualifiers
source                 1..6
                       mol_type = protein
                       organism = synthetic construct
SEQUENCE: 1167
NPYNGR                                                     6

SEQ ID NO: 1168        moltype = AA  length = 10
FEATURE                Location/Qualifiers
source                 1..10
                       mol_type = protein
                       organism = synthetic construct
SEQUENCE: 1168
SASSSVSYMH                                                 10

SEQ ID NO: 1169        moltype = AA  length = 7
FEATURE                Location/Qualifiers
source                 1..7
                       mol_type = protein
                       organism = synthetic construct
SEQUENCE: 1169
EISKLAS                                                    7

SEQ ID NO: 1170        moltype = AA  length = 9
FEATURE                Location/Qualifiers
source                 1..9
                       mol_type = protein
                       organism = synthetic construct
SEQUENCE: 1170
QQWNYPLLT                                                  9

SEQ ID NO: 1171        moltype = AA  length = 106
FEATURE                Location/Qualifiers
source                 1..106
                       mol_type = protein
                       organism = synthetic construct
SEQUENCE: 1171
EIVLTQSPAI TAASLGQKVT ITCSASSSVS YMHWYQQKSG TSPKPWIYEI SKLASGVPAR  60
FSGSGSGTSY SLTISSMEAE DAAIYYCQQW NYPLLTFGAG TKLELK             106

SEQ ID NO: 1172        moltype = AA  length = 118
FEATURE                Location/Qualifiers
source                 1..118
                       mol_type = protein
                       organism = synthetic construct
SEQUENCE: 1172
EVQLQQSGPV LVKPGASVRM SCKASGYTFT DYNIHWVKQS HGRSLEWVGY INPYNGRTGY  60
NQKFKAKATL TVDKSSSTAY MDLRSLTSED SAVYYCARWD GSSYFDYWGQ GTTLTVSS   118

SEQ ID NO: 1173        moltype = AA  length = 118
FEATURE                Location/Qualifiers
source                 1..118
                       mol_type = protein
                       organism = synthetic construct
SEQUENCE: 1173
QVQLVQSGAE VKKPGSSVKV SCKASGYTFT DYNIHWVRQA PGQGLEWVGY INPYNGRTGY  60
NQKFKARATL TVDKSTSTAY MELSSLRSED TAVYYCARWD GSSYFDYWGQ GTTVTVSS   118

SEQ ID NO: 1174        moltype = AA  length = 118
FEATURE                Location/Qualifiers
source                 1..118
                       mol_type = protein
                       organism = synthetic construct
SEQUENCE: 1174
QVQLVQSGAE VKKPGASVKV SCKASGYTFT DYNIHWVRQA PGQGLEWVGY INPYNGRTGY  60
NQKFKARATL TVDKSTSTAY MELRSLRSDD MAVYYCARWD GSSYFDYWGQ GTTVTVSS   118

SEQ ID NO: 1175        moltype = AA  length = 118
FEATURE                Location/Qualifiers
source                 1..118
                       mol_type = protein
```

```
                        organism = synthetic construct
SEQUENCE: 1175
QVQLVQSGAE VKKPGASVKV SCKASGYTFT DYNIHWVRQA TGQGLEWVGY INPYNGRTGY  60
NQKFKARATL TVNKSISTAY MELSSLRSED TAVYYCARWD GSSYFDYWGQ GTTVTVSS    118

SEQ ID NO: 1176         moltype = AA  length = 118
FEATURE                 Location/Qualifiers
source                  1..118
                        mol_type = protein
                        organism = synthetic construct
SEQUENCE: 1176
EVQLVESGGG LVQPGRSLRL SCTASGYTFT DYNIHWVRQA PGKGLEWVGY INPYNGRTGY  60
NQKFKARATL SVDKSKSIAY LQMNSLKTED TAVYYCARWD GSSYFDYWGQ GTTVTVSS    118

SEQ ID NO: 1177         moltype = AA  length = 118
FEATURE                 Location/Qualifiers
source                  1..118
                        mol_type = protein
                        organism = synthetic construct
SEQUENCE: 1177
QVQLVQSGSE LKKPGASVKV SCKASGYTFT DYNIHWVRQA PGQGLEWVGY INPYNGRTGY  60
NQKFKARAVL SVDKSVSTAY LQISSLKAED TAVYYCARWD GSSYFDYWGQ GTTVTVSS    118

SEQ ID NO: 1178         moltype = AA  length = 106
FEATURE                 Location/Qualifiers
source                  1..106
                        mol_type = protein
                        organism = synthetic construct
SEQUENCE: 1178
EIVLTQSPAT LSLSPGERAT LSCSASSSVS YMHWYQQKPG QAPKLLIYEI SKLASGIPAR  60
FSGSGSGTDY TLTISSLEPE DFAVYYCQQW NYPLLTFGQG TKLEIK                106

SEQ ID NO: 1179         moltype = AA  length = 106
FEATURE                 Location/Qualifiers
source                  1..106
                        mol_type = protein
                        organism = synthetic construct
SEQUENCE: 1179
EIVLTQSPAT LSLSPGERAT LSCSASSSVS YMHWYQQKPG QAPKLLIYEI SKLASGIPAR  60
FSGSGSGTDY TLTISRLEPE DFAVYYCQQW NYPLLTFGQG TKLEIK                106

SEQ ID NO: 1180         moltype = AA  length = 106
FEATURE                 Location/Qualifiers
source                  1..106
                        mol_type = protein
                        organism = synthetic construct
SEQUENCE: 1180
EIVLTQSPDF QSVTPKEKVT ITCSASSSVS YMHWYQQKPD QSPKLLIYEI SKLASGVPSR  60
FSGSGSGTDY TLTINSLEAE DAATYYCQQW NYPLLTFGQG TKLEIK                106

SEQ ID NO: 1181         moltype = AA  length = 106
FEATURE                 Location/Qualifiers
source                  1..106
                        mol_type = protein
                        organism = synthetic construct
SEQUENCE: 1181
DIQLTQSPSF LSASVGDRVT ITCSASSSVS YMHWYQQKPG KAPKLLIYEI SKLASGVPSR  60
FSGSGSGTEY TLTISSLQPE DFATYYCQQW NYPLLTFGQG TKLEIK                106

SEQ ID NO: 1182         moltype = AA  length = 106
FEATURE                 Location/Qualifiers
source                  1..106
                        mol_type = protein
                        organism = synthetic construct
SEQUENCE: 1182
AIQLTQSPSS LSASVGDRVT ITCSASSSVS YMHWYQQKPG KAPKLLIYEI SKLASGVPSR  60
FSGSGSGTDY TLTISSLQPE DFATYYCQQW NYPLLTFGQG TKLEIK                106

SEQ ID NO: 1183         moltype = AA  length = 106
FEATURE                 Location/Qualifiers
source                  1..106
                        mol_type = protein
                        organism = synthetic construct
SEQUENCE: 1183
AIRLTQSPFS LSASVGDRVT ITCSASSSVS YMHWYQQKPA KAPKLFIYEI SKLASGVPSR  60
FSGSGSGTDY TLTISSLQPE DFATYYCQQW NYPLLTFGQG TKLEIK                106

SEQ ID NO: 1184         moltype = AA  length = 106
FEATURE                 Location/Qualifiers
```

```
source                  1..106
                        mol_type = protein
                        organism = synthetic construct
SEQUENCE: 1184
DIVLTQSPDS LAVSLGERAT INCSASSSVS YMHWYQQKPG QPPKLLIYEI SKLASGVPDR  60
FSGSGSGTDY TLTISSLQAE DVAVYYCQQW NYPLLTFGQG TKLEIK                 106

SEQ ID NO: 1185         moltype = AA  length = 5
FEATURE                 Location/Qualifiers
source                  1..5
                        mol_type = protein
                        organism = synthetic construct
SEQUENCE: 1185
GSWMN                                                              5

SEQ ID NO: 1186         moltype = AA  length = 17
FEATURE                 Location/Qualifiers
source                  1..17
                        mol_type = protein
                        organism = synthetic construct
SEQUENCE: 1186
RIYPGDGDTD YSGKFKG                                                 17

SEQ ID NO: 1187         moltype = AA  length = 12
FEATURE                 Location/Qualifiers
source                  1..12
                        mol_type = protein
                        organism = synthetic construct
SEQUENCE: 1187
SGYFNYVPVF DY                                                      12

SEQ ID NO: 1188         moltype = AA  length = 7
FEATURE                 Location/Qualifiers
source                  1..7
                        mol_type = protein
                        organism = synthetic construct
SEQUENCE: 1188
GYTFSGS                                                            7

SEQ ID NO: 1189         moltype = AA  length = 6
FEATURE                 Location/Qualifiers
source                  1..6
                        mol_type = protein
                        organism = synthetic construct
SEQUENCE: 1189
YPGDGD                                                             6

SEQ ID NO: 1190         moltype = AA  length = 10
FEATURE                 Location/Qualifiers
source                  1..10
                        mol_type = protein
                        organism = synthetic construct
SEQUENCE: 1190
GYTFSGSWMN                                                         10

SEQ ID NO: 1191         moltype = AA  length = 10
FEATURE                 Location/Qualifiers
source                  1..10
                        mol_type = protein
                        organism = synthetic construct
SEQUENCE: 1191
SANSTVGYIH                                                         10

SEQ ID NO: 1192         moltype = AA  length = 7
FEATURE                 Location/Qualifiers
source                  1..7
                        mol_type = protein
                        organism = synthetic construct
SEQUENCE: 1192
TTSNLAS                                                            7

SEQ ID NO: 1193         moltype = AA  length = 8
FEATURE                 Location/Qualifiers
source                  1..8
                        mol_type = protein
                        organism = synthetic construct
SEQUENCE: 1193
HQWSFYPT                                                           8
```

```
SEQ ID NO: 1194         moltype = AA  length = 6
FEATURE                 Location/Qualifiers
source                  1..6
                        mol_type = protein
                        organism = synthetic construct
SEQUENCE: 1194
NSTVGY                                                            6

SEQ ID NO: 1195         moltype = AA  length = 105
FEATURE                 Location/Qualifiers
source                  1..105
                        mol_type = protein
                        organism = synthetic construct
SEQUENCE: 1195
QIVLTQSPAI MSASLGEEIA LTCSANSTVG YIHWYQQKSG TSPKLLIYTT SNLASGVPSR  60
FSGSGSGTFY SLTISSVEAE DAADYFCHQW SFYPTFGGGT KLEIK                 105

SEQ ID NO: 1196         moltype = AA  length = 121
FEATURE                 Location/Qualifiers
source                  1..121
                        mol_type = protein
                        organism = synthetic construct
SEQUENCE: 1196
QIQLQQSGPE VVKPGASVQI SCKASGYTFS GSWMNWVKQR PGKGLEWIGR IYPGDGDTDY  60
SGKFKGRATL TADKSSSTAY MRLSSLTSED SAVYFCARSG YFNYVPVFDY WGQGTTLSVS  120
S                                                                 121

SEQ ID NO: 1197         moltype = AA  length = 121
FEATURE                 Location/Qualifiers
source                  1..121
                        mol_type = protein
                        organism = synthetic construct
SEQUENCE: 1197
QIQLVQSGAE VKKPGASVKV SCKASGYTFS GSWMNWVRQA PGQGLEWIGR IYPGDGDTDY  60
SGKFKGRATL TADKSTSTAY MELSSLRSED TAVYYCARSG YFNYVPVFDY WGQGTTVTVS  120
S                                                                 121

SEQ ID NO: 1198         moltype = AA  length = 121
FEATURE                 Location/Qualifiers
source                  1..121
                        mol_type = protein
                        organism = synthetic construct
SEQUENCE: 1198
QIQLVQSGAE VKKPGSSVKV SCKASGYTFS GSWMNWVRQA PGQGLEWIGR IYPGDGDTDY  60
SGKFKGRATL TADKSTSTAY MELSSLRSED TAVYYCARSG YFNYVPVFDY WGQGTTVTVS  120
S                                                                 121

SEQ ID NO: 1199         moltype = AA  length = 121
FEATURE                 Location/Qualifiers
source                  1..121
                        mol_type = protein
                        organism = synthetic construct
SEQUENCE: 1199
EIQLVQSGAE VKKPGESLKI SCKASGYTFS GSWMNWVRQM PGKGLEWIGR IYPGDGDTDY  60
SGKFKGQATL SADKSISTAY LQWSSLKASD TAMYYCARSG YFNYVPVFDY WGQGTTVTVS  120
S                                                                 121

SEQ ID NO: 1200         moltype = AA  length = 121
FEATURE                 Location/Qualifiers
source                  1..121
                        mol_type = protein
                        organism = synthetic construct
SEQUENCE: 1200
QIQLVQSGSE LKKPGASVKV SCKASGYTFS GSWMNWVRQA PGQGLEWIGR IYPGDGDTDY  60
SGKFKGRAVL SADKSVSTAY LQISSLKAED TAVYYCARSG YFNYVPVFDY WGQGTTVTVS  120
S                                                                 121

SEQ ID NO: 1201         moltype = AA  length = 121
FEATURE                 Location/Qualifiers
source                  1..121
                        mol_type = protein
                        organism = synthetic construct
SEQUENCE: 1201
QIQLVQSGSE LKKPGASVKV SCKASGYTFS GSWMNWVRQA PGQGLEWIGR IYPGDGDTDY  60
SGKFKGRAVL SADKSVSMAY LQISSLKAED TAVYYCARSG YFNYVPVFDY WGQGTTVTVS  120
S                                                                 121

SEQ ID NO: 1202         moltype = AA  length = 121
FEATURE                 Location/Qualifiers
```

```
source                  1..121
                        mol_type = protein
                        organism = synthetic construct
SEQUENCE: 1202
EIQLVESGGG LVQPGRSLRL SCTASGYTFS GSWMNWVRQA PGKGLEWIGR IYPGDGDTDY  60
SGKFKGRATL SADKSKSIAY LQMNSLKTED TAVYYCARSG YFNYVPVFDY WGQGTTVTVS  120
S                                                                  121

SEQ ID NO: 1203         moltype = AA  length = 105
FEATURE                 Location/Qualifiers
source                  1..105
                        mol_type = protein
                        organism = synthetic construct
SEQUENCE: 1203
EIVLTQSPAT LSLSPGERAT LSCSANSTVG YIHWYQQKPG QAPKLLIYTT SNLASGIPAR  60
FSGSGSGTDY TLTISSLEPE DFAVYFCHQW SFYPTFGQGT KLEIK                 105

SEQ ID NO: 1204         moltype = AA  length = 105
FEATURE                 Location/Qualifiers
source                  1..105
                        mol_type = protein
                        organism = synthetic construct
SEQUENCE: 1204
DIQLTQSPSF LSASVGDRVT ITCSANSTVG YIHWYQQKPG KAPKLLIYTT SNLASGVPSR  60
FSGSGSGTEY TLTISSLQPE DFATYFCHQW SFYPTFGQGT KLEIK                 105

SEQ ID NO: 1205         moltype = AA  length = 105
FEATURE                 Location/Qualifiers
source                  1..105
                        mol_type = protein
                        organism = synthetic construct
SEQUENCE: 1205
EIVLTQSPAT LSLSPGERAT LSCSANSTVG YIHWYQQKPG QAPKLLIYTT SNLASGIPAR  60
FSGSGPGTDY TLTISSLEPE DFAVYFCHQW SFYPTFGQGT KLEIK                 105

SEQ ID NO: 1206         moltype = AA  length = 105
FEATURE                 Location/Qualifiers
source                  1..105
                        mol_type = protein
                        organism = synthetic construct
SEQUENCE: 1206
DIVLTQSPDS LAVSLGERAT INCSANSTVG YIHWYQQKPG QPPKLLIYTT SNLASGVPDR  60
FSGSGSGTDY TLTISSLQAE DVAVYFCHQW SFYPTFGQGT KLEIK                 105

SEQ ID NO: 1207         moltype = AA  length = 105
FEATURE                 Location/Qualifiers
source                  1..105
                        mol_type = protein
                        organism = synthetic construct
SEQUENCE: 1207
EIVLTQSPDF QSVTPKEKVT ITCSANSTVG YIHWYQQKPD QSPKLLIYTT SNLASGVPSR  60
FSGSGSGTDY TLTINSLEAE DAATYFCHQW SFYPTFGQGT KLEIK                 105

SEQ ID NO: 1208         moltype = AA  length = 5
FEATURE                 Location/Qualifiers
source                  1..5
                        mol_type = protein
                        organism = synthetic construct
SEQUENCE: 1208
DYYMY                                                             5

SEQ ID NO: 1209         moltype = AA  length = 17
FEATURE                 Location/Qualifiers
source                  1..17
                        mol_type = protein
                        organism = synthetic construct
SEQUENCE: 1209
TISGGGSYTY SPDSVKG                                                17

SEQ ID NO: 1210         moltype = AA  length = 14
FEATURE                 Location/Qualifiers
source                  1..14
                        mol_type = protein
                        organism = synthetic construct
SEQUENCE: 1210
ERDIYYGNFN AMVY                                                   14

SEQ ID NO: 1211         moltype = AA  length = 7
FEATURE                 Location/Qualifiers
```

```
source                  1..7
                        mol_type = protein
                        organism = synthetic construct
SEQUENCE: 1211
GFTFSDY                                                                  7

SEQ ID NO: 1212         moltype = AA  length = 6
FEATURE                 Location/Qualifiers
source                  1..6
                        mol_type = protein
                        organism = synthetic construct
SEQUENCE: 1212
SGGGSY                                                                   6

SEQ ID NO: 1213         moltype = AA  length = 10
FEATURE                 Location/Qualifiers
source                  1..10
                        mol_type = protein
                        organism = synthetic construct
SEQUENCE: 1213
GFTFSDYYMY                                                               10

SEQ ID NO: 1214         moltype = AA  length = 15
FEATURE                 Location/Qualifiers
source                  1..15
                        mol_type = protein
                        organism = synthetic construct
SEQUENCE: 1214
RASKSVSTSG YSYMH                                                         15

SEQ ID NO: 1215         moltype = AA  length = 7
FEATURE                 Location/Qualifiers
source                  1..7
                        mol_type = protein
                        organism = synthetic construct
SEQUENCE: 1215
LASNLES                                                                  7

SEQ ID NO: 1216         moltype = AA  length = 9
FEATURE                 Location/Qualifiers
source                  1..9
                        mol_type = protein
                        organism = synthetic construct
SEQUENCE: 1216
QHSRDLPWT                                                                9

SEQ ID NO: 1217         moltype = AA  length = 11
FEATURE                 Location/Qualifiers
source                  1..11
                        mol_type = protein
                        organism = synthetic construct
SEQUENCE: 1217
SKSVSTSGYS Y                                                             11

SEQ ID NO: 1218         moltype = AA  length = 111
FEATURE                 Location/Qualifiers
source                  1..111
                        mol_type = protein
                        organism = synthetic construct
SEQUENCE: 1218
DIVLTQSPVS LTVSLGQRAT ISCRASKSVS TSGYSYMHWY QQKPGQPPKL LIYLASNLES  60
GVPARFSGSG SGTDFTLNIH PVEEEDAATY YCQHSRDLPW TFGGGTKLEI K           111

SEQ ID NO: 1219         moltype = AA  length = 123
FEATURE                 Location/Qualifiers
source                  1..123
                        mol_type = protein
                        organism = synthetic construct
SEQUENCE: 1219
EVQLVESGGG LVKPGGSLKL SCAASGFTFS DYYMYWVRQT PEKRLEWVAT ISGGGSYTYS  60
PDSVKGRFTI SRDNAKNNLY LQMSSLRSED TAMYFCARER DIYYGNFNAM VYWGRGTSVT  120
VSS                                                                123

SEQ ID NO: 1220         moltype = AA  length = 123
FEATURE                 Location/Qualifiers
source                  1..123
                        mol_type = protein
                        organism = synthetic construct
SEQUENCE: 1220
```

```
EVQLLESGGG LVQPGGSLRL SCAASGFTFS DYYMYWVRQA PGKGLEWVAT ISGGGSYTYS  60
PDSVKGRFTI SRDNSKNTLY LQMNSLRAED TAVYYCARER DIYYGNFNAM VYWGRGTLVT  120
VSS                                                                123

SEQ ID NO: 1221        moltype = AA  length = 123
FEATURE                Location/Qualifiers
source                 1..123
                       mol_type = protein
                       organism = synthetic construct
SEQUENCE: 1221
EVQLVESGGG LVQPGGSLRL SCAASGFTFS DYYMYWVRQA PGKGLEWVAT ISGGGSYTYS  60
PDSVKGRFTI SRDNAKNSLY LQMNSLRAED TAVYYCARER DIYYGNFNAM VYWGRGTLVT  120
VSS                                                                123

SEQ ID NO: 1222        moltype = AA  length = 123
FEATURE                Location/Qualifiers
source                 1..123
                       mol_type = protein
                       organism = synthetic construct
SEQUENCE: 1222
QVQLVESGGG VVQPGRSLRL SCAASGFTFS DYYMYWVRQA PGKGLEWVAT ISGGGSYTYS  60
PDSVKGRFTI SRDNSKNTLY LQMNSLRAED TAVYYCARER DIYYGNFNAM VYWGRGTLVT  120
VSS                                                                123

SEQ ID NO: 1223        moltype = AA  length = 123
FEATURE                Location/Qualifiers
source                 1..123
                       mol_type = protein
                       organism = synthetic construct
SEQUENCE: 1223
QVQLVESGGG LVKPGGSLRL SCAASGFTFS DYYMYWIRQA PGKGLEWVAT ISGGGSYTYS  60
PDSVKGRFTI SRDNAKNSLY LQMNSLRAED TAVYYCARER DIYYGNFNAM VYWGRGTLVT  120
VSS                                                                123

SEQ ID NO: 1224        moltype = AA  length = 111
FEATURE                Location/Qualifiers
source                 1..111
                       mol_type = protein
                       organism = synthetic construct
SEQUENCE: 1224
EIVLTQSPGT LSLSPGERAT LSCRASKSVS TSGYSYMHWY QQKPGQAPRL LIYLASNLES  60
GIPDRFSGSG SGTDFTLTIS RLEPEDFAVY YCQHSRDLPW TFGGGTKVEI K           111

SEQ ID NO: 1225        moltype = AA  length = 111
FEATURE                Location/Qualifiers
source                 1..111
                       mol_type = protein
                       organism = synthetic construct
SEQUENCE: 1225
EIVLTQSPAT LSLSPGERAT LSCRASKSVS TSGYSYMHWY QQKPGQAPRL LIYLASNLES  60
GIPARFSGSG SGTDFTLTIS SLEPEDFAVY YCQHSRDLPW TFGGGTKVEI K           111

SEQ ID NO: 1226        moltype = AA  length = 111
FEATURE                Location/Qualifiers
source                 1..111
                       mol_type = protein
                       organism = synthetic construct
SEQUENCE: 1226
DIQLTQSPST LSASVGDRVT ITCRASKSVS TSGYSYMHWY QQKPGKAPKL LIYLASNLES  60
GVPSRFSGSG SGTEFTLTIS SLQPDDFATY YCQHSRDLPW TFGGGTKVEI K           111

SEQ ID NO: 1227        moltype = AA  length = 111
FEATURE                Location/Qualifiers
source                 1..111
                       mol_type = protein
                       organism = synthetic construct
SEQUENCE: 1227
AIQLTQSPSS LSASVGDRVT ITCRASKSVS TSGYSYMHWY QQKPGKAPKL LIYLASNLES  60
GVPSRFSGSG SGTDFTLTIS SLQPEDFATY YCQHSRDLPW TFGGGTKVEI K           111

SEQ ID NO: 1228        moltype =   length =
SEQUENCE: 1228
000

SEQ ID NO: 1229        moltype = AA  length = 5
FEATURE                Location/Qualifiers
source                 1..5
                       mol_type = protein
                       organism = synthetic construct
```

```
SEQUENCE: 1229
GYFWN                                                                   5

SEQ ID NO: 1230        moltype = AA  length = 16
FEATURE                Location/Qualifiers
source                 1..16
                       mol_type = protein
                       organism = synthetic construct
SEQUENCE: 1230
YISYDGSNNY NPSLKN                                                       16

SEQ ID NO: 1231        moltype = AA  length = 11
FEATURE                Location/Qualifiers
source                 1..11
                       mol_type = protein
                       organism = synthetic construct
SEQUENCE: 1231
PSPGTGYAVD Y                                                            11

SEQ ID NO: 1232        moltype = AA  length = 8
FEATURE                Location/Qualifiers
source                 1..8
                       mol_type = protein
                       organism = synthetic construct
SEQUENCE: 1232
GYSITSGY                                                                8

SEQ ID NO: 1233        moltype = AA  length = 6
FEATURE                Location/Qualifiers
source                 1..6
                       mol_type = protein
                       organism = synthetic construct
SEQUENCE: 1233
SYDGSN                                                                  6

SEQ ID NO: 1234        moltype = AA  length = 11
FEATURE                Location/Qualifiers
source                 1..11
                       mol_type = protein
                       organism = synthetic construct
SEQUENCE: 1234
GYSITSGYFW N                                                            11

SEQ ID NO: 1235        moltype = AA  length = 16
FEATURE                Location/Qualifiers
source                 1..16
                       mol_type = protein
                       organism = synthetic construct
SEQUENCE: 1235
RSSQSLVHSN GNTYLH                                                       16

SEQ ID NO: 1236        moltype = AA  length = 7
FEATURE                Location/Qualifiers
source                 1..7
                       mol_type = protein
                       organism = synthetic construct
SEQUENCE: 1236
KVSNRFS                                                                 7

SEQ ID NO: 1237        moltype = AA  length = 9
FEATURE                Location/Qualifiers
source                 1..9
                       mol_type = protein
                       organism = synthetic construct
SEQUENCE: 1237
SQSTHVPFT                                                               9

SEQ ID NO: 1238        moltype = AA  length = 12
FEATURE                Location/Qualifiers
source                 1..12
                       mol_type = protein
                       organism = synthetic construct
SEQUENCE: 1238
SQSLVHSNGN TY                                                           12

SEQ ID NO: 1239        moltype = AA  length = 112
FEATURE                Location/Qualifiers
source                 1..112
                       mol_type = protein
```

```
                       organism = synthetic construct
SEQUENCE: 1239
NVVMTQTPLS LPVSLGDQAS ISCRSSQSLV HSNGNTYLHW YLQKPGQSPK FLIYKVSNRF  60
SGVPDRFSGG GSGTEFTLKI SRVEAEDLGV YFCSQSTHVP FTFGSGTKLE IK          112

SEQ ID NO: 1240        moltype = AA  length = 120
FEATURE                Location/Qualifiers
source                 1..120
                       mol_type = protein
                       organism = synthetic construct
SEQUENCE: 1240
NVQLQESGPG LVKPSQSLSL TCSVAGYSIT SGYFWNWIRQ FPGNKLEWMG YISYDGSNNY  60
NPSLKNRISI TRDTSKNQFF LKLNSVTTED TATYYCASPS PGTGYAVDYW GQGTSVTVSS  120

SEQ ID NO: 1241        moltype = AA  length = 120
FEATURE                Location/Qualifiers
source                 1..120
                       mol_type = protein
                       organism = synthetic construct
SEQUENCE: 1241
QVQLQESGPG LVKPSETLSL TCTVSGYSIT SGYFWNWIRQ PPGKGLEWIG YISYDGSNNY  60
NPSLKNRVTI SRDTSKNQFS LKLSSVTAAD TAVYYCASPS PGTGYAVDYW GQGTLVTVSS  120

SEQ ID NO: 1242        moltype = AA  length = 120
FEATURE                Location/Qualifiers
source                 1..120
                       mol_type = protein
                       organism = synthetic construct
SEQUENCE: 1242
QVQLQESGPG LVKPSETLSL TCTVSGYSIT SGYFWNWIRQ PPGKGLEWIG YISYDGSNNY  60
NPSLKNRVTI SRDTSKNQFS LKLSSVTAAD TAVYYCASPS PGTGYAVDYW GQGTLVTVSS  120

SEQ ID NO: 1243        moltype = AA  length = 120
FEATURE                Location/Qualifiers
source                 1..120
                       mol_type = protein
                       organism = synthetic construct
SEQUENCE: 1243
QVQLVESGGG LVQPGGSLRL SCSVSGYSIT SGYFWNWVRQ APGKGLEWVG YISYDGSNNY  60
NPSLKNRFTI SRDTSKNTFY LQMNSLRAED TAVYYCASPS PGTGYAVDYW GQGTLVTVSS  120

SEQ ID NO: 1244        moltype = AA  length = 111
FEATURE                Location/Qualifiers
source                 1..111
                       mol_type = protein
                       organism = synthetic construct
SEQUENCE: 1244
VVMTQSPGTL SLSPGERATL SCRSSQSLVH SNGNTYLHWY QQKPGQAPRF LIYKVSNRFS  60
GIPDRFSGSG SGTDFTLTIS RLEPEDFAVY FCSQSTHVPF TFGQGTKLEI K           111

SEQ ID NO: 1245        moltype = AA  length = 112
FEATURE                Location/Qualifiers
source                 1..112
                       mol_type = protein
                       organism = synthetic construct
SEQUENCE: 1245
EVVMTQSPAT LSLSPGERAT LSCRSSQSLV HSNGNTYLHW YQQKPGQAPR FLIYKVSNRF  60
SGIPARFSGS GSGTDFTLTI SSLEPEDFAV YFCSQSTHVP FTFGQGTKLE IK          112

SEQ ID NO: 1246        moltype = AA  length = 112
FEATURE                Location/Qualifiers
source                 1..112
                       mol_type = protein
                       organism = synthetic construct
SEQUENCE: 1246
EVVMTQSPAT LSVSPGERAT LSCRSSQSLV HSNGNTYLHW YQQKPGQAPR FLIYKVSNRF  60
SGIPARFSGS GSGTEFTLTI SSLQSEDFAV YFCSQSTHVP FTFGQGTKLE IK          112

SEQ ID NO: 1247        moltype = AA  length = 112
FEATURE                Location/Qualifiers
source                 1..112
                       mol_type = protein
                       organism = synthetic construct
SEQUENCE: 1247
DVQMTQSPSS LSASVGDRVT ITCRSSQSLV HSNGNTYLHW YQQKPGKAPK FLIYKVSNRF  60
SGVPSRFSGS GSGTDFTFTI SSLQPEDIAT YFCSQSTHVP FTFGQGTKLE IK          112

SEQ ID NO: 1248        moltype = AA  length = 5
FEATURE                Location/Qualifiers
```

```
source                  1..5
                        mol_type = protein
                        organism = synthetic construct
SEQUENCE: 1248
DYIVH                                                              5

SEQ ID NO: 1249         moltype = AA  length = 17
FEATURE                 Location/Qualifiers
source                  1..17
                        mol_type = protein
                        organism = synthetic construct
SEQUENCE: 1249
WINTYTGTPT YADDFEG                                                 17

SEQ ID NO: 1250         moltype = AA  length = 13
FEATURE                 Location/Qualifiers
source                  1..13
                        mol_type = protein
                        organism = synthetic construct
SEQUENCE: 1250
SWRRGIRGIG FDY                                                     13

SEQ ID NO: 1251         moltype = AA  length = 7
FEATURE                 Location/Qualifiers
source                  1..7
                        mol_type = protein
                        organism = synthetic construct
SEQUENCE: 1251
GYTFTDY                                                            7

SEQ ID NO: 1252         moltype = AA  length = 6
FEATURE                 Location/Qualifiers
source                  1..6
                        mol_type = protein
                        organism = synthetic construct
SEQUENCE: 1252
NTYTGT                                                             6

SEQ ID NO: 1253         moltype = AA  length = 10
FEATURE                 Location/Qualifiers
source                  1..10
                        mol_type = protein
                        organism = synthetic construct
SEQUENCE: 1253
GYTFTDYIVH                                                         10

SEQ ID NO: 1254         moltype = AA  length = 11
FEATURE                 Location/Qualifiers
source                  1..11
                        mol_type = protein
                        organism = synthetic construct
SEQUENCE: 1254
KASKSINKYL A                                                       11

SEQ ID NO: 1255         moltype = AA  length = 7
FEATURE                 Location/Qualifiers
source                  1..7
                        mol_type = protein
                        organism = synthetic construct
SEQUENCE: 1255
DGSTLQS                                                            7

SEQ ID NO: 1256         moltype = AA  length = 9
FEATURE                 Location/Qualifiers
source                  1..9
                        mol_type = protein
                        organism = synthetic construct
SEQUENCE: 1256
QQHNEYPPT                                                          9

SEQ ID NO: 1257         moltype = AA  length = 7
FEATURE                 Location/Qualifiers
source                  1..7
                        mol_type = protein
                        organism = synthetic construct
SEQUENCE: 1257
SKSINKY                                                            7

SEQ ID NO: 1258         moltype = AA  length = 107
```

```
FEATURE               Location/Qualifiers
source                1..107
                      mol_type = protein
                      organism = synthetic construct
SEQUENCE: 1258
DVQMTQSPYN LAASPGESVS INCKASKSIN KYLAWYQQKP GKPNKLLIYD GSTLQSGIPS  60
RFSGSGSGTD FTLTIRGLEP EDFGLYYCQQ HNEYPPTFGA GTKLELK              107

SEQ ID NO: 1259       moltype = AA  length = 122
FEATURE               Location/Qualifiers
source                1..122
                      mol_type = protein
                      organism = synthetic construct
SEQUENCE: 1259
QLQLVQSGPE LREPGESVKI SCKASGYTFT DYIVHWVKQA PGKGLKWMGW INTYTGTPTY  60
ADDFEGRFVF SLEASASTAN LQISNLKNED TATYFCARSW RRGIRGIGFD YWGQGVMVTV  120
SS                                                                 122

SEQ ID NO: 1260       moltype = AA  length = 122
FEATURE               Location/Qualifiers
source                1..122
                      mol_type = protein
                      organism = synthetic construct
SEQUENCE: 1260
QLQLVQSGAE VKKPGASVKV SCKASGYTFT DYIVHWVRQA PGQGLEWMGW INTYTGTPTY  60
ADDFEGWVTM TLDASISTAY MELSRLRSDD TAVYYCARSW RRGIRGIGFD YWGQGTMVTV  120
SS                                                                 122

SEQ ID NO: 1261       moltype = AA  length = 122
FEATURE               Location/Qualifiers
source                1..122
                      mol_type = protein
                      organism = synthetic construct
SEQUENCE: 1261
QLQLVQSGAE VKKPGASVKV SCKASGYTFT DYIVHWVRQA PGQGLEWMGW INTYTGTPTY  60
ADDFEGRVTM TLDASTSTAY MELSSLRSED TAVYYCARSW RRGIRGIGFD YWGQGTMVTV  120
SS                                                                 122

SEQ ID NO: 1262       moltype = AA  length = 122
FEATURE               Location/Qualifiers
source                1..122
                      mol_type = protein
                      organism = synthetic construct
SEQUENCE: 1262
QLQLVQSGAE VKKPGASVKV SCKASGYTFT DYIVHWVRQA PGQRLEWMGW INTYTGTPTY  60
ADDFEGRVTI TLDASASTAY MELSSLRSED MAVYYCARSW RRGIRGIGFD YWGQGTMVTV  120
SS                                                                 122

SEQ ID NO: 1263       moltype = AA  length = 122
FEATURE               Location/Qualifiers
source                1..122
                      mol_type = protein
                      organism = synthetic construct
SEQUENCE: 1263
QLQLVQSGAE VKKPGASVKV SCKASGYTFT DYIVHWVRQA TGQGLEWMGW INTYTGTPTY  60
ADDFEGRVTM TLNASISTAY MELSSLRSED TAVYYCARSW RRGIRGIGFD YWGQGTMVTV  120
SS                                                                 122

SEQ ID NO: 1264       moltype = AA  length = 107
FEATURE               Location/Qualifiers
source                1..107
                      mol_type = protein
                      organism = synthetic construct
SEQUENCE: 1264
EVVMTQSPGT LSLSPGERAT LSCKASKSIN KYLAWYQQKP GQAPRLLIYD GSTLQSGIPD  60
RFSGSGSGTD FTLTISRLEP EDFAVYYCQQ HNEYPPTFGQ GTKLEIK              107

SEQ ID NO: 1265       moltype = AA  length = 107
FEATURE               Location/Qualifiers
source                1..107
                      mol_type = protein
                      organism = synthetic construct
SEQUENCE: 1265
EVVMTQSPAT LSLSPGERAT LSCKASKSIN KYLAWYQQKP GQAPRLLIYD GSTLQSGIPA  60
RFSGSGSGTD FTLTISSLEP EDFAVYYCQQ HNEYPPTFGQ GTKLEIK              107

SEQ ID NO: 1266       moltype = AA  length = 107
FEATURE               Location/Qualifiers
source                1..107
```

```
                        mol_type = protein
                        organism = synthetic construct
SEQUENCE: 1266
DVQMTQSPSS LSASVGDRVT ITCKASKSIN KYLAWYQQKP GKAPKLLIYD GSTLQSGVPS  60
RFSGSGSGTD FTLTISSLQP EDFATYYCQQ HNEYPPTFGQ GTKLEIK                107

SEQ ID NO: 1267         moltype = AA  length = 107
FEATURE                 Location/Qualifiers
source                  1..107
                        mol_type = protein
                        organism = synthetic construct
SEQUENCE: 1267
AVRMTQSPSS FSASTGDRVT ITCKASKSIN KYLAWYQQKP GKAPKLLIYD GSTLQSGVPS  60
RFSGSGSGTD FTLTISCLQS EDFATYYCQQ HNEYPPTFGQ GTKLEIK                107

SEQ ID NO: 1268         moltype = AA  length = 5
FEATURE                 Location/Qualifiers
source                  1..5
                        mol_type = protein
                        organism = synthetic construct
SEQUENCE: 1268
NYGVH                                                              5

SEQ ID NO: 1269         moltype = AA  length = 16
FEATURE                 Location/Qualifiers
source                  1..16
                        mol_type = protein
                        organism = synthetic construct
SEQUENCE: 1269
VIWSDGSTDY DTAFIS                                                  16

SEQ ID NO: 1270         moltype = AA  length = 9
FEATURE                 Location/Qualifiers
source                  1..9
                        mol_type = protein
                        organism = synthetic construct
SEQUENCE: 1270
RAVVADFDY                                                          9

SEQ ID NO: 1271         moltype = AA  length = 6
FEATURE                 Location/Qualifiers
source                  1..6
                        mol_type = protein
                        organism = synthetic construct
SEQUENCE: 1271
GFSLTN                                                             6

SEQ ID NO: 1272         moltype = AA  length = 9
FEATURE                 Location/Qualifiers
source                  1..9
                        mol_type = protein
                        organism = synthetic construct
SEQUENCE: 1272
VIWSDGSTD                                                          9

SEQ ID NO: 1273         moltype = AA  length = 10
FEATURE                 Location/Qualifiers
source                  1..10
                        mol_type = protein
                        organism = synthetic construct
SEQUENCE: 1273
GFSLTNYGVH                                                         10

SEQ ID NO: 1274         moltype = AA  length = 117
FEATURE                 Location/Qualifiers
source                  1..117
                        mol_type = protein
                        organism = synthetic construct
SEQUENCE: 1274
QVQLKQSGPG LLQPSQSLSI TCTVSGFSLT NYGVHWVRQS PGKGLEWLGV IWSDGSTDYD  60
TAFISRLSIS KDNSKSQVFF KLNSLQADDT AIYYCARRAV VADFDYWGQG TTLTVSS     117

SEQ ID NO: 1275         moltype = AA  length = 16
FEATURE                 Location/Qualifiers
source                  1..16
                        mol_type = protein
                        organism = synthetic construct
SEQUENCE: 1275
KASKEVTIFG SISALH                                                  16
```

```
SEQ ID NO: 1276        moltype = AA  length = 7
FEATURE                Location/Qualifiers
source                 1..7
                       mol_type = protein
                       organism = synthetic construct
SEQUENCE: 1276
NGAKLES                                                           7

SEQ ID NO: 1277        moltype = AA  length = 9
FEATURE                Location/Qualifiers
source                 1..9
                       mol_type = protein
                       organism = synthetic construct
SEQUENCE: 1277
LQNKEVPFT                                                         9

SEQ ID NO: 1278        moltype = AA  length = 119
FEATURE                Location/Qualifiers
source                 1..119
                       mol_type = protein
                       organism = synthetic construct
SEQUENCE: 1278
DIVLTQSPAS LAVSLGQKAT ISCKASKEVT IFGSISALHW YQQKPGQPPK LIYNGAKLES  60
GVSARFSDSG SQNRSPFGNQ LSFTLTIAPV EADDAATYYC LQNKEVPFTF GSGTKLEIK   119

SEQ ID NO: 1279        moltype = AA  length = 117
FEATURE                Location/Qualifiers
source                 1..117
                       mol_type = protein
                       organism = synthetic construct
SEQUENCE: 1279
DIVLTQSPDS LAVSLGERAT INCKASKEVT IFGSISALHW YQQKPGQPPK LLYNGAKLES  60
GVSARFGVPD RFSRSGSGLD FTLTISSLQA EDVAVYYCLQ NKEVPFTFGQ GTKLEIK     117

SEQ ID NO: 1280        moltype = AA  length = 117
FEATURE                Location/Qualifiers
source                 1..117
                       mol_type = protein
                       organism = synthetic construct
SEQUENCE: 1280
EIVLTQSPDF QSVTPKEKVT ITCKASKEVT IFGSISALHW YQQKPDQSPK LLYNGAKLES  60
GVSARFGVPS RFSRSGSGLD FTLTINSLEA EDAATYYCLQ NKEVPFTFGQ GTKLEIK     117

SEQ ID NO: 1281        moltype = AA  length = 117
FEATURE                Location/Qualifiers
source                 1..117
                       mol_type = protein
                       organism = synthetic construct
SEQUENCE: 1281
AIQLTQSPSS LSASVGDRVT ITCKASKEVT IFGSISALHW YQQKPGKAPK LLYNGAKLES  60
GVSARFGVPS RFSRSGSGLD FTLTISSLQP EDFATYYCLQ NKEVPFTFGQ GTKLEIK     117

SEQ ID NO: 1282        moltype = AA  length = 117
FEATURE                Location/Qualifiers
source                 1..117
                       mol_type = protein
                       organism = synthetic construct
SEQUENCE: 1282
DIVLTQTPLS LSVTPGQPAS ISCKASKEVT IFGSISALHW YLQKPGQPPK LLYNGAKLES  60
GVSARFGVPD RFSRSGSGLD FTLKISRVEA EDVGVYYCLQ NKEVPFTFGQ GTKLEIK     117

SEQ ID NO: 1283        moltype = AA  length = 117
FEATURE                Location/Qualifiers
source                 1..117
                       mol_type = protein
                       organism = synthetic construct
SEQUENCE: 1283
QVTLKESGPV LVKPTETLTL TCTVSGFSLT NYGVHWVRQP PGKALEWLGV IWSDGSTDYD  60
TAFISRLTIS KDNSKSQVVL TMTNMDPVDT ATYYCARRAV VADFDYWGQG TTVTVSS     117

SEQ ID NO: 1284        moltype = AA  length = 117
FEATURE                Location/Qualifiers
source                 1..117
                       mol_type = protein
                       organism = synthetic construct
SEQUENCE: 1284
QVQLQESGPG LVKPSGTLSL TCAVSGFSLT NYGVHWVRQP PGKGLEWLGV IWSDGSTDYD  60
TAFISRLTIS KDNSKSQVSL KLSSVTAADT AVYYCARRAV VADFDYWGQG TTVTVSS     117
```

```
SEQ ID NO: 1285        moltype = AA  length = 117
FEATURE                Location/Qualifiers
source                 1..117
                       mol_type = protein
                       organism = synthetic construct
SEQUENCE: 1285
QVQLQQSGPG LVKPSQTLSL TCAVSGFSLT NYGVHWVRQS PSRGLEWLGV IWSDGSTDYD  60
TAFISRLTIN KDNSKSQVSL QLNSVTPEDT AVYYCARRAV VADFDYWGQG TTVTVSS     117

SEQ ID NO: 1286        moltype = AA  length = 117
FEATURE                Location/Qualifiers
source                 1..117
                       mol_type = protein
                       organism = synthetic construct
SEQUENCE: 1286
EVQLVESGGG LVQPGPSLRL SCTVSGFSLT NYGVHWVRQA PGKGLEWLGV IWSDGSTDYD  60
TAFISRLTIS KDNSKSIVYL QMNSLKTEDT AVYYCARRAV VADFDYWGQG TTVTVSS     117

SEQ ID NO: 1287        moltype = AA  length = 117
FEATURE                Location/Qualifiers
source                 1..117
                       mol_type = protein
                       organism = synthetic construct
SEQUENCE: 1287
EVQLVQSGAE VKKPGESLRI SCKVSGFSLT NYGVHWVRQM PGKGLEWLGV IWSDGSTDYD  60
TAFISQLTIS KDNSISTVYL QWSSLKASDT AMYYCARRAV VADFDYWGQG TTVTVSS     117

SEQ ID NO: 1288        moltype = AA  length = 5
FEATURE                Location/Qualifiers
source                 1..5
                       mol_type = protein
                       organism = synthetic construct
SEQUENCE: 1288
SYGMS                                                              5

SEQ ID NO: 1289        moltype = AA  length = 17
FEATURE                Location/Qualifiers
source                 1..17
                       mol_type = protein
                       organism = synthetic construct
SEQUENCE: 1289
LISSGGSYTY YTDSVKG                                                 17

SEQ ID NO: 1290        moltype = AA  length = 8
FEATURE                Location/Qualifiers
source                 1..8
                       mol_type = protein
                       organism = synthetic construct
SEQUENCE: 1290
HGGNFFDY                                                           8

SEQ ID NO: 1291        moltype = AA  length = 7
FEATURE                Location/Qualifiers
source                 1..7
                       mol_type = protein
                       organism = synthetic construct
SEQUENCE: 1291
GFTFRSY                                                            7

SEQ ID NO: 1292        moltype = AA  length = 6
FEATURE                Location/Qualifiers
source                 1..6
                       mol_type = protein
                       organism = synthetic construct
SEQUENCE: 1292
SSGGSY                                                             6

SEQ ID NO: 1293        moltype = AA  length = 10
FEATURE                Location/Qualifiers
source                 1..10
                       mol_type = protein
                       organism = synthetic construct
SEQUENCE: 1293
GFTFRSYGMS                                                         10

SEQ ID NO: 1294        moltype = AA  length = 10
FEATURE                Location/Qualifiers
source                 1..10
```

```
                        mol_type = protein
                        organism = synthetic construct
SEQUENCE: 1294
SVSSSVSYMH                                                                10

SEQ ID NO: 1295         moltype = AA  length = 7
FEATURE                 Location/Qualifiers
source                  1..7
                        mol_type = protein
                        organism = synthetic construct
SEQUENCE: 1295
DTSKLAS                                                                   7

SEQ ID NO: 1296         moltype = AA  length = 10
FEATURE                 Location/Qualifiers
source                  1..10
                        mol_type = protein
                        organism = synthetic construct
SEQUENCE: 1296
QQWSSNPQYT                                                                10

SEQ ID NO: 1297         moltype = AA  length = 6
FEATURE                 Location/Qualifiers
source                  1..6
                        mol_type = protein
                        organism = synthetic construct
SEQUENCE: 1297
SSSVSY                                                                    6

SEQ ID NO: 1298         moltype = AA  length = 5
FEATURE                 Location/Qualifiers
source                  1..5
                        mol_type = protein
                        organism = synthetic construct
SEQUENCE: 1298
SSWMN                                                                     5

SEQ ID NO: 1299         moltype = AA  length = 17
FEATURE                 Location/Qualifiers
source                  1..17
                        mol_type = protein
                        organism = synthetic construct
SEQUENCE: 1299
RIYPGDGDTK YNGKFKG                                                        17

SEQ ID NO: 1300         moltype = AA  length = 10
FEATURE                 Location/Qualifiers
source                  1..10
                        mol_type = protein
                        organism = synthetic construct
SEQUENCE: 1300
RGTGGWYFDV                                                                10

SEQ ID NO: 1301         moltype = AA  length = 10
FEATURE                 Location/Qualifiers
source                  1..10
                        mol_type = protein
                        organism = synthetic construct
SEQUENCE: 1301
RGTGGWYFDV                                                                10

SEQ ID NO: 1302         moltype = AA  length = 7
FEATURE                 Location/Qualifiers
source                  1..7
                        mol_type = protein
                        organism = synthetic construct
SEQUENCE: 1302
GYAFSSS                                                                   7

SEQ ID NO: 1303         moltype = AA  length = 6
FEATURE                 Location/Qualifiers
source                  1..6
                        mol_type = protein
                        organism = synthetic construct
SEQUENCE: 1303
YPGDGD                                                                    6

SEQ ID NO: 1304         moltype = AA  length = 10
FEATURE                 Location/Qualifiers
```

```
source                  1..10
                        mol_type = protein
                        organism = synthetic construct
SEQUENCE: 1304
GYAFSSSWMN                                                     10

SEQ ID NO: 1305         moltype = AA  length = 15
FEATURE                 Location/Qualifiers
source                  1..15
                        mol_type = protein
                        organism = synthetic construct
SEQUENCE: 1305
RASESVDSSG NSFMH                                               15

SEQ ID NO: 1306         moltype = AA  length = 7
FEATURE                 Location/Qualifiers
source                  1..7
                        mol_type = protein
                        organism = synthetic construct
SEQUENCE: 1306
RASNLES                                                        7

SEQ ID NO: 1307         moltype = AA  length = 9
FEATURE                 Location/Qualifiers
source                  1..9
                        mol_type = protein
                        organism = synthetic construct
SEQUENCE: 1307
QQSFDDPFT                                                      9

SEQ ID NO: 1308         moltype = AA  length = 11
FEATURE                 Location/Qualifiers
source                  1..11
                        mol_type = protein
                        organism = synthetic construct
SEQUENCE: 1308
SESVDSSGNS F                                                   11

SEQ ID NO: 1309         moltype = AA  length = 246
FEATURE                 Location/Qualifiers
source                  1..246
                        mol_type = protein
                        organism = synthetic construct
SEQUENCE: 1309
QVQLVQSGAE VKKPGSSVKV SCKASGHDFD KFYIHWVRQA PGQGLEWMGR VSAGSGNVKY  60
NEKFKGRVTI TADTSTSTAY MELSSLRSED TAVYYCAGSY YSYDVLDYWG QGTTVTVSSG  120
GGGSGGGGSG GGGSGGGGSD IQMTQSPSFL SASVGDRVTI TCKASQNVGN RVAWYQQKPG  180
KAPKALIYSS SHRYKGVPSR FSGSGSGTEF TLTISSLQPE DFATYFCQQF KSYPLTFGQG  240
TKLEIK                                                         246

SEQ ID NO: 1310         moltype = AA  length = 119
FEATURE                 Location/Qualifiers
source                  1..119
                        mol_type = protein
                        organism = synthetic construct
SEQUENCE: 1310
QVQLVQSGAE VKKPGSSVKV SCKASGTDFK LTYIHWVRQA PGQGLEWMGR IFPGSGNVKY  60
NEKFKGRVTI TADTSTSTAY MELSSLRSED TAVYYCAGSY YSYDVLDYWG QGTTVTVSS   119

SEQ ID NO: 1311         moltype = AA  length = 119
FEATURE                 Location/Qualifiers
source                  1..119
                        mol_type = protein
                        organism = synthetic construct
SEQUENCE: 1311
QVQLVQSGAE VKKPGSSVKV SCKASGTDFK LTYIHWVRQA PGQGLEWMGR IFPGSGNVKY  60
NEKFKGRVTI TADTSTSTAY MELSSLRSED TAVYYCAVSY YSYDVLDYWG QGTTVTVSS   119

SEQ ID NO: 1312         moltype = AA  length = 119
FEATURE                 Location/Qualifiers
source                  1..119
                        mol_type = protein
                        organism = synthetic construct
SEQUENCE: 1312
QVQLVQSGAE VKKPGSSVKV SCKASGHDFR LTYIHWVRQA PGQGLEWMGR ISAGSGNVKY  60
NEKFKGRVTI TADTSTSTAY MELSSLRSED TAVYYCAVSY YSYDVLDYWG QGTTVTVSS   119

SEQ ID NO: 1313         moltype = AA  length = 107
FEATURE                 Location/Qualifiers
```

```
source                  1..107
                        mol_type = protein
                        organism = synthetic construct
SEQUENCE: 1313
DIQMTQSPSF LSASVGDRVT ITCKASQNVD NRVAWYQQKP GKAPKALIYS SSHRYKGVPS  60
RFSGSGSGTE FTLTISSLQP EDFATYFCQQ FKSYPLTFGQ GTKLEIK               107

SEQ ID NO: 1314         moltype = AA  length = 107
FEATURE                 Location/Qualifiers
source                  1..107
                        mol_type = protein
                        organism = synthetic construct
SEQUENCE: 1314
DIQMTQSPSF LSASVGDRVT ITCKASQNVA DRVAWYQQKP GKAPKALIYS SSHRYKGVPS  60
RFSGSGSGTE FTLTISSLQP EDFATYFCQQ FKSYPLTFGQ GTKLEIK               107

SEQ ID NO: 1315         moltype = AA  length = 5
FEATURE                 Location/Qualifiers
source                  1..5
                        mol_type = protein
                        organism = synthetic construct
SEQUENCE: 1315
AYGVN                                                             5

SEQ ID NO: 1316         moltype = AA  length = 16
FEATURE                 Location/Qualifiers
source                  1..16
                        mol_type = protein
                        organism = synthetic construct
SEQUENCE: 1316
MIWGDGNTDY NSALKS                                                 16

SEQ ID NO: 1317         moltype = AA  length = 12
FEATURE                 Location/Qualifiers
source                  1..12
                        mol_type = protein
                        organism = synthetic construct
SEQUENCE: 1317
DRVTATLYAM DY                                                     12

SEQ ID NO: 1318         moltype = AA  length = 7
FEATURE                 Location/Qualifiers
source                  1..7
                        mol_type = protein
                        organism = synthetic construct
SEQUENCE: 1318
GFSLTAY                                                           7

SEQ ID NO: 1319         moltype = AA  length = 5
FEATURE                 Location/Qualifiers
source                  1..5
                        mol_type = protein
                        organism = synthetic construct
SEQUENCE: 1319
WGDGN                                                             5

SEQ ID NO: 1320         moltype = AA  length = 10
FEATURE                 Location/Qualifiers
source                  1..10
                        mol_type = protein
                        organism = synthetic construct
SEQUENCE: 1320
GFSLTAYGVN                                                        10

SEQ ID NO: 1321         moltype = AA  length = 11
FEATURE                 Location/Qualifiers
source                  1..11
                        mol_type = protein
                        organism = synthetic construct
SEQUENCE: 1321
SASQGISNYL N                                                      11

SEQ ID NO: 1322         moltype = AA  length = 7
FEATURE                 Location/Qualifiers
source                  1..7
                        mol_type = protein
                        organism = synthetic construct
SEQUENCE: 1322
YTSSLHS                                                           7
```

```
SEQ ID NO: 1323        moltype = AA  length = 9
FEATURE                Location/Qualifiers
source                 1..9
                       mol_type = protein
                       organism = synthetic construct
SEQUENCE: 1323
QQYSKLPRT                                                          9

SEQ ID NO: 1324        moltype = AA  length = 107
FEATURE                Location/Qualifiers
source                 1..107
                       mol_type = protein
                       organism = synthetic construct
SEQUENCE: 1324
DIQMTQSPSS LSASVGDRVT ITCSASQGIS NYLNWYQQTP GKAPKLLIYY TSSLHSGVPS  60
RFSGSGSGTD YTFTISSLQP EDIATYYCQQ YSKLPRTFGQ GTKLQIT                107

SEQ ID NO: 1325        moltype = AA  length = 120
FEATURE                Location/Qualifiers
source                 1..120
                       mol_type = protein
                       organism = synthetic construct
SEQUENCE: 1325
QVQLQESGPG LVRPSQTLSL TCTVSGFSLT AYGVNWVRQP PGRGLEWLGM IWGDGNTDYN  60
SALKSRVTML KDTSKNQFSL RLSSVTAADT AVYYCARDRV TATLYAMDYW GQGSLVTVSS  120

SEQ ID NO: 1326        moltype = AA  length = 246
FEATURE                Location/Qualifiers
source                 1..246
                       mol_type = protein
                       organism = synthetic construct
SEQUENCE: 1326
QVQLVQSGAE VKKPGSSVKV SCKASGHDFR LTYIHWVRQA PGQGLEWMGR VSAGSGNTKY  60
NEKFKGRVTI TADTSTSTAY MELSSLRSED TAVYYCAVSY YSYDVLDYWG QGTTVTVSSG  120
GGGSGGGGSG GGGSGGGGSD IQMTQSPSFL SASVGDRVTI TCKASQNVGD RVVWHQQKPG  180
KAPKALIYSS SHRYKGVPSR FSGSGSGTEF TLTISSLQPE DFATYFCQQF KSYPLTFGQG  240
TKLEIK                                                             246

SEQ ID NO: 1327        moltype = AA  length = 246
FEATURE                Location/Qualifiers
source                 1..246
                       mol_type = protein
                       organism = synthetic construct
SEQUENCE: 1327
QVQLVQSGAE VKKPGSSVKV SCKASGHDFR LTYIHWVRQA PGQGLEWMGR VSAGSGNVKY  60
NEKFKGRVTI TADTSTSTAY MELSSLRSED TAVYYCAVSY YSYDVLDYWG QGTTVTVSSG  120
GGGSGGGGSG GGGSGGGGSD IQMTQSPSFL SASVGDRVTI TCKASQNVGN RVVWHQQKPG  180
KAPKALIYSS SHRYKGVPSR FSGSGSGTEF TLTISSLQPE DFATYFCQQF KSYPLTFGQG  240
TKLEIK                                                             246

SEQ ID NO: 1328        moltype = AA  length = 246
FEATURE                Location/Qualifiers
source                 1..246
                       mol_type = protein
                       organism = synthetic construct
SEQUENCE: 1328
QVQLVQSGAE VKKPGSSVKV SCKASGHDFR LTYIHWVRQA PGQGLEWMGR IYAGSGNVKY  60
NEKFKGRVTI TADTSTSTAY MELSSLRSED TAVYYCAVSY YSYDVLDYWG QGTTVTVSSG  120
GGGSGGGGSG GGGSGGGGSD IQMTQSPSFL SASVGDRVTI TCKASQNVAD RVVWHQQKPG  180
KAPKALIYSS SHRYKGVPSR FSGSGSGTEF TLTISSLQPE DFATYFCQQF KSYPLTFGQG  240
TKLEIK                                                             246

SEQ ID NO: 1329        moltype = AA  length = 246
FEATURE                Location/Qualifiers
source                 1..246
                       mol_type = protein
                       organism = synthetic construct
SEQUENCE: 1329
QVQLVQSGAE VKKPGSSVKV SCKASGHDFK LTYIHWVRQA PGQGLEWMGR VSAGSGNTKY  60
NEKFKGRVTI TADTSTSTAY MELSSLRSED TAVYYCAVSY YSYDVLDYWG QGTTVTVSSG  120
GGGSGGGGSG GGGSGGGGSD IQMTQSPSFL SASVGDRVTI TCKASQNVGD RVAWHQQKPG  180
KAPKALIYSS SHRYKGVPSR FSGSGSGTEF TLTISSLQPE DFATYFCQQF KSYPLTFGQG  240
TKLEIK                                                             246

SEQ ID NO: 1330        moltype = AA  length = 246
FEATURE                Location/Qualifiers
source                 1..246
                       mol_type = protein
```

```
                        organism = synthetic construct
SEQUENCE: 1330
QVQLVQSGAE VKKPGSSVKV SCKASGHDFK LTYIHWVRQA PGQGLEWMGR VSAGSGNTKY  60
NEKFKGRVTI TADTSTSTAY MELSSLRSED TAVYYCAVSY YSYDVLDYWG QGTTVTVSSG  120
GGGSGGGGSG GGGSGGGGSD IQMTQSPSFL SASVGDRVTI TCKASQNVDN RVAWHQQKPG  180
KAPKALIYSS SHRYKGVPSR FSGSGSGTEF TLTISSLQPE DFATYFCQQF KSYPLTFGQG  240
TKLEIK                                                             246

SEQ ID NO: 1331         moltype = AA  length = 246
FEATURE                 Location/Qualifiers
source                  1..246
                        mol_type = protein
                        organism = synthetic construct
SEQUENCE: 1331
QVQLVQSGAE VKKPGSSVKV SCKASGHDFR LTYIHWVRQA PGQGLEWMGR VSAGSGNVKY  60
NEKFKGRVTI TADTSTSTAY MELSSLRSED TAVYYCAVSY YSYDVLDYWG QGTTVTVSSG  120
GGGSGGGGSG GGGSGGGGSD IQMTQSPSFL SASVGDRVTI TCKASQNVAD RVVWHQQKPG  180
KAPKALIYSS SHRYKGVPSR FSGSGSGTEF TLTISSLQPE DFATYFCQQF KSYPLTFGQG  240
TKLEIK                                                             246

SEQ ID NO: 1332         moltype = AA  length = 246
FEATURE                 Location/Qualifiers
source                  1..246
                        mol_type = protein
                        organism = synthetic construct
SEQUENCE: 1332
QVQLVQSGAE VKKPGSSVKV SCKASGHDFR LTYIHWVRQA PGQGLEWMGR VYAGSGNTKY  60
NEKFKGRVTI TADTSTSTAY MELSSLRSED TAVYYCAVSY YSYDVLDYWG QGTTVTVSSG  120
GGGSGGGGSG GGGSGGGGSD IQMTQSPSFL SASVGDRVTI TCKASQNVED RVVWHQQKPG  180
KAPKALIYSS SHRYKGVPSR FSGSGSGTEF TLTISSLQPE DFATYFCQQF KSYPLTFGQG  240
TKLEIK                                                             246

SEQ ID NO: 1333         moltype = AA  length = 246
FEATURE                 Location/Qualifiers
source                  1..246
                        mol_type = protein
                        organism = synthetic construct
SEQUENCE: 1333
QVQLVQSGAE VKKPGSSVKV SCKASGHDFK LTYIHWVRQA PGQGLEWMGR VSAGSGNTKY  60
NEKFKGRVTI TADTSTSTAY MELSSLRSED TAVYYCAVSY YSYDVLDYWG QGTTVTVSSG  120
GGGSGGGGSG GGGSGGGGSD IQMTQSPSFL SASVGDRVTI TCKASQNVAD RVVWHQQKPG  180
KAPKALIYSS SHRYKGVPSR FSGSGSGTEF TLTISSLQPE DFATYFCQQF KSYPLTFGQG  240
TKLEIK                                                             246

SEQ ID NO: 1334         moltype = AA  length = 246
FEATURE                 Location/Qualifiers
source                  1..246
                        mol_type = protein
                        organism = synthetic construct
SEQUENCE: 1334
QVQLVQSGAE VKKPGSSVKV SCKASGHDFK LTYIHWVRQA PGQGLEWMGR ISAGSGNTKY  60
NEKFKGRVTI TADTSTSTAY MELSSLRSED TAVYYCAVSY YSYDVLDYWG QGTTVTVSSG  120
GGGSGGGGSG GGGSGGGGSD IQMTQSPSFL SASVGDRVTI TCKASQNVGD RVVWHQQKPG  180
KAPKALIYSS SHRYKGVPSR FSGSGSGTEF TLTISSLQPE DFATYFCQQF KSYPLTFGQG  240
TKLEIK                                                             246

SEQ ID NO: 1335         moltype = AA  length = 246
FEATURE                 Location/Qualifiers
source                  1..246
                        mol_type = protein
                        organism = synthetic construct
SEQUENCE: 1335
QVQLVQSGAE VKKPGSSVKV SCKASGHDFK LTYIHWVRQA PGQGLEWMGR IYAGSGNTKY  60
NEKFKGRVTI TADTSTSTAY MELSSLRSED TAVYYCAVSY YSYDVLDYWG QGTTVTVSSG  120
GGGSGGGGSG GGGSGGGGSD IQMTQSPSFL SASVGDRVTI TCKASQNVGD RVVWHQQKPG  180
KAPKALIYSS SHRYKGVPSR FSGSGSGTEF TLTISSLQPE DFATYFCQQF KSYPLTFGQG  240
TKLEIK                                                             246

SEQ ID NO: 1336         moltype = AA  length = 246
FEATURE                 Location/Qualifiers
source                  1..246
                        mol_type = protein
                        organism = synthetic construct
SEQUENCE: 1336
QVQLVQSGAE VKKPGSSVKV SCKASGTDFK LTYIHWVRQA PGQGLEWMGR IFPGSGNVKY  60
NEKFKGRVTI TADTSTSTAY MELSSLRSED TAVYYCAVSY YSYDVLDYWG QGTTVTVSSG  120
GGGSGGGGSG GGGSGGGGSD IQMTQSPSFL SASVGDRVTI TCKASQNVDN RVAWYQQKPG  180
KAPKALIYSS SHRYKGVPSR FSGSGSGTEF TLTISSLQPE DFATYFCQQF KSYPLTFGQG  240
TKLEIK                                                             246
```

```
SEQ ID NO: 1337         moltype = AA  length = 246
FEATURE                 Location/Qualifiers
source                  1..246
                        mol_type = protein
                        organism = synthetic construct
SEQUENCE: 1337
QVQLVQSGAE VKKPGSSVKV SCKASGHDFR LTYIHWVRQA PGQGLEWMGR ISAGSGNVKY  60
NEKFKGRVTI TADTSTSTAY MELSSLRSED TAVYYCAVSY YSYDVLDYWG QGTTVTVSSG  120
GGGSGGGGSG GGGSGGGGSD IQMTQSPSFL SASVGDRVTI TCKASQNVAD RVAWYQQKPG  180
KAPKALIYSS SHRYKGVPSR FSGSGSGTEF TLTISSLQPE DFATYFCQQF KSYPLTFGQG  240
TKLEIK                                                             246

SEQ ID NO: 1338         moltype = AA  length = 243
FEATURE                 Location/Qualifiers
source                  1..243
                        mol_type = protein
                        organism = synthetic construct
SEQUENCE: 1338
EVQLVESGGG LVQPGGSLRL SCAASGFTFS NFGMHWVRQA PGKGLEWVSY ISSGSSTIYY  60
ADTLKGRFTI SRDNSKNTLY LQMNSLRAED TAVYYCARRG EGAMDYWGQG TTVTVSSGGG  120
GSGGGGSGGG GSGGGGSDNQ LTQSPSSLSA SVGDRVTITC RASSSVNYIY WYQQKPGKAP  180
KLLIYYTSNL APGVPSRFSG SGSGNDYTLT ISSLQPEDFA TYYCQQFTSS PFTFGQGTKL  240
EIK                                                                243

SEQ ID NO: 1339         moltype = AA  length = 242
FEATURE                 Location/Qualifiers
source                  1..242
                        mol_type = protein
                        organism = synthetic construct
SEQUENCE: 1339
EVQLVESGGG LVQPGGSLRL SCAASGFTFS NFGMHWVRQA PGKGLEWVSY ISSGSSTIYY  60
ADTLKGRFTI SRDNSKNTLY LQMNSLRAED TAVYYCARRG EGAMDYWGQG TTVTVSSGGG  120
GSGGGGSGGG GSGGGGSSNE LTQPPSVSVS PGQTARITCR ASSSVNYIYW YQQKSGQAPV  180
LVIYYTSNLA PGIPERFSGS GSGNMYTLTI SGAQVEDEAD YYCQQFTSSP FTFGTGTKVT  240
VL                                                                 242

SEQ ID NO: 1340         moltype = AA  length = 243
FEATURE                 Location/Qualifiers
source                  1..243
                        mol_type = protein
                        organism = synthetic construct
SEQUENCE: 1340
QVQLVESGGG VVQPGRSLRL SCAASGFTFS NFGMHWVRQA PGKGLEWVAY ISSGSSTIYY  60
ADTLKGRFTI SRDNSKNTLY LQMNSLRAED TAVYYCARRG EGAMDYWGQG TTVTVSSGGG  120
GSGGGGSGGG GSGGGGSDNQ LTQSPSFLSA SVGDRVTITC RASSSVNYIY WYQQKPGKAP  180
KLLIYYTSNL APGVPSRFSG SGSGNEYTLT ISSLQPEDFA TYYCQQFTSS PFTFGQGTKL  240
EIK                                                                243

SEQ ID NO: 1341         moltype = AA  length = 243
FEATURE                 Location/Qualifiers
source                  1..243
                        mol_type = protein
                        organism = synthetic construct
SEQUENCE: 1341
QVQLVESGGG VVQPGRSLRL SCAASGFTFS NFGMHWVRQA PGKGLEWVAY ISSGSSTIYY  60
ADTLKGRFTI SRDNSKNTLY LQMNSLRAED TAVYYCARRG EGAMDYWGQG TTVTVSSGGG  120
GSGGGGSGGG GSGGGGSDNQ LTQSPSSLSA SVGDRVTITC RASSSVNYIY WYQQKPGKAP  180
KLLIYYTSNL APGVPSRFSG SGSGNDYTLT ISSLQPEDFA TYYCQQFTSS PFTFGQGTKL  240
EIK                                                                243

SEQ ID NO: 1342         moltype = AA  length = 242
FEATURE                 Location/Qualifiers
source                  1..242
                        mol_type = protein
                        organism = synthetic construct
SEQUENCE: 1342
QVQLVESGGG VVQPGRSLRL SCAASGFTFS NFGMHWVRQA PGKGLEWVAY ISSGSSTIYY  60
ADTLKGRFTI SRDNSKNTLY LQMNSLRAED TAVYYCARRG EGAMDYWGQG TTVTVSSGGG  120
GSGGGGSGGG GSGGGGSSNE LTQPPSVSVS PGQTARITCR ASSSVNYIYW YQQKSGQAPV  180
LVIYYTSNLA PGIPERFSGS GSGNMYTLTI SGAQVEDEAD YYCQQFTSSP FTFGTGTKVT  240
VL                                                                 242

SEQ ID NO: 1343         moltype =   length =
SEQUENCE: 1343
000

SEQ ID NO: 1344         moltype = AA  length = 119
FEATURE                 Location/Qualifiers
```

```
source                  1..119
                        mol_type = protein
                        organism = synthetic construct
SEQUENCE: 1344
QVQLVQSGAE VKKPGSSVKV SCKASGHDFR LTYIHWVRQA PGQGLEWMGR VSAGSGNTKY  60
NEKFKGRVTI TADTSTSTAY MELSSLRSED TAVYYCAVSY YSYDVLDYWG QGTTVTVSS   119

SEQ ID NO: 1345         moltype =   length =
SEQUENCE: 1345
000

SEQ ID NO: 1346         moltype = AA  length = 119
FEATURE                 Location/Qualifiers
source                  1..119
                        mol_type = protein
                        organism = synthetic construct
SEQUENCE: 1346
QVQLVQSGAE VKKPGSSVKV SCKASGHDFR LTYIHWVRQA PGQGLEWMGR VSAGSGNVKY  60
NEKFKGRVTI TADTSTSTAY MELSSLRSED TAVYYCAVSY YSYDVLDYWG QGTTVTVSS   119

SEQ ID NO: 1347         moltype = AA  length = 107
FEATURE                 Location/Qualifiers
source                  1..107
                        mol_type = protein
                        organism = synthetic construct
SEQUENCE: 1347
DIQMTQSPSF LSASVGDRVT ITCKASQNVG NRVVWHQQKP GKAPKALIYS SSHRYKGVPS  60
RFSGSGSGTE FTLTISSLQP EDFATYFCQQ FKSYPLTFGQ GTKLEIK                107

SEQ ID NO: 1348         moltype = AA  length = 119
FEATURE                 Location/Qualifiers
source                  1..119
                        mol_type = protein
                        organism = synthetic construct
SEQUENCE: 1348
QVQLVQSGAE VKKPGSSVKV SCKASGHDFR LTYIHWVRQA PGQGLEWMGR IYAGSGNVKY  60
NEKFKGRVTI TADTSTSTAY MELSSLRSED TAVYYCAVSY YSYDVLDYWG QGTTVTVSS   119

SEQ ID NO: 1349         moltype = AA  length = 107
FEATURE                 Location/Qualifiers
source                  1..107
                        mol_type = protein
                        organism = synthetic construct
SEQUENCE: 1349
DIQMTQSPSF LSASVGDRVT ITCKASQNVA DRVVWHQQKP GKAPKALIYS SSHRYKGVPS  60
RFSGSGSGTE FTLTISSLQP EDFATYFCQQ FKSYPLTFGQ GTKLEIK                107

SEQ ID NO: 1350         moltype = AA  length = 119
FEATURE                 Location/Qualifiers
source                  1..119
                        mol_type = protein
                        organism = synthetic construct
SEQUENCE: 1350
QVQLVQSGAE VKKPGSSVKV SCKASGHDFK LTYIHWVRQA PGQGLEWMGR VSAGSGNTKY  60
NEKFKGRVTI TADTSTSTAY MELSSLRSED TAVYYCAVSY YSYDVLDYWG QGTTVTVSS   119

SEQ ID NO: 1351         moltype = AA  length = 107
FEATURE                 Location/Qualifiers
source                  1..107
                        mol_type = protein
                        organism = synthetic construct
SEQUENCE: 1351
DIQMTQSPSF LSASVGDRVT ITCKASQNVG DRVAWHQQKP GKAPKALIYS SSHRYKGVPS  60
RFSGSGSGTE FTLTISSLQP EDFATYFCQQ FKSYPLTFGQ GTKLEIK                107

SEQ ID NO: 1352         moltype =   length =
SEQUENCE: 1352
000

SEQ ID NO: 1353         moltype = AA  length = 107
FEATURE                 Location/Qualifiers
source                  1..107
                        mol_type = protein
                        organism = synthetic construct
SEQUENCE: 1353
DIQMTQSPSF LSASVGDRVT ITCKASQNVD NRVAWHQQKP GKAPKALIYS SSHRYKGVPS  60
RFSGSGSGTE FTLTISSLQP EDFATYFCQQ FKSYPLTFGQ GTKLEIK                107

SEQ ID NO: 1354         moltype =   length =
```

```
SEQUENCE: 1354
000

SEQ ID NO: 1355        moltype =   length =
SEQUENCE: 1355
000

SEQ ID NO: 1356        moltype = AA  length = 119
FEATURE                Location/Qualifiers
source                 1..119
                       mol_type = protein
                       organism = synthetic construct
SEQUENCE: 1356
QVQLVQSGAE VKKPGSSVKV SCKASGHDFR LTYIHWVRQA PGQGLEWMGR VYAGSGNTKY  60
NEKFKGRVTI TADTSTSTAY MELSSLRSED TAVYYCAVSY YSYDVLDYWG QGTTVTVSS   119

SEQ ID NO: 1357        moltype = AA  length = 107
FEATURE                Location/Qualifiers
source                 1..107
                       mol_type = protein
                       organism = synthetic construct
SEQUENCE: 1357
DIQMTQSPSF LSASVGDRVT ITCKASQNVE DRVVWHQQKP GKAPKALIYS SSHRYKGVPS  60
RFSGSGSGTE FTLTISSLQP EDFATYFCQQ FKSYPLTFGQ GTKLEIK                107

SEQ ID NO: 1358        moltype =   length =
SEQUENCE: 1358
000

SEQ ID NO: 1359        moltype =   length =
SEQUENCE: 1359
000

SEQ ID NO: 1360        moltype = AA  length = 119
FEATURE                Location/Qualifiers
source                 1..119
                       mol_type = protein
                       organism = synthetic construct
SEQUENCE: 1360
QVQLVQSGAE VKKPGSSVKV SCKASGHDFK LTYIHWVRQA PGQGLEWMGR ISAGSGNTKY  60
NEKFKGRVTI TADTSTSTAY MELSSLRSED TAVYYCAVSY YSYDVLDYWG QGTTVTVSS   119

SEQ ID NO: 1361        moltype = AA  length = 107
FEATURE                Location/Qualifiers
source                 1..107
                       mol_type = protein
                       organism = synthetic construct
SEQUENCE: 1361
DIQMTQSPSF LSASVGDRVT ITCKASQNVG DRVVWHQQKP GKAPKALIYS SSHRYKGVPS  60
RFSGSGSGTE FTLTISSLQP EDFATYFCQQ FKSYPLTFGQ GTKLEIK                107

SEQ ID NO: 1362        moltype = AA  length = 119
FEATURE                Location/Qualifiers
source                 1..119
                       mol_type = protein
                       organism = synthetic construct
SEQUENCE: 1362
QVQLVQSGAE VKKPGSSVKV SCKASGHDFK LTYIHWVRQA PGQGLEWMGR IYAGSGNTKY  60
NEKFKGRVTI TADTSTSTAY MELSSLRSED TAVYYCAVSY YSYDVLDYWG QGTTVTVSS   119

SEQ ID NO: 1363        moltype =   length =
SEQUENCE: 1363
000

SEQ ID NO: 1364        moltype =   length =
SEQUENCE: 1364
000

SEQ ID NO: 1365        moltype = AA  length = 107
FEATURE                Location/Qualifiers
source                 1..107
                       mol_type = protein
                       organism = synthetic construct
SEQUENCE: 1365
DIQMTQSPSF LSASVGDRVT ITCRASQNVD NRLGWHQQKP GKAPKALIYS SSHRYKGVPS  60
RFSGSGSGTE FTLTISSLQP EDFATYFCQQ FKSYPLTFGQ GTKLEIK                107

SEQ ID NO: 1366        moltype =   length =
SEQUENCE: 1366
```

```
000

SEQ ID NO: 1367        moltype = AA  length = 107
FEATURE                Location/Qualifiers
source                 1..107
                       mol_type = protein
                       organism = synthetic construct
SEQUENCE: 1367
DIQMTQSPSF LSASVGDRVT ITCKASQNVD NRVAWHQQKP GKAPKALIYA ASSLQKGVPS  60
RFSGSGSGTE FTLTISSLQP EDFATYFCQQ FKSYPLTFGQ GTKLEIK                107

SEQ ID NO: 1368        moltype =   length =
SEQUENCE: 1368
000

SEQ ID NO: 1369        moltype = AA  length = 107
FEATURE                Location/Qualifiers
source                 1..107
                       mol_type = protein
                       organism = synthetic construct
SEQUENCE: 1369
DIQMTQSPSF LSASVGDRVT ITCKASQNVD NRVAWHQQKP GKAPKALIYS SSHRYKGVPS  60
RFSGSGSGTE FTLTISSLQP EDFATYFCLQ HNSYPLTFGQ GTKLEIK                107

SEQ ID NO: 1370        moltype = AA  length = 119
FEATURE                Location/Qualifiers
source                 1..119
                       mol_type = protein
                       organism = synthetic construct
SEQUENCE: 1370
QVQLVQSGAE VKKPGSSVKV SCKASGHDFK LTYIHWVRQA PGQGLEWMGR VSAGSGNVNY  60
AQKFQGRVTI TADTSTSTAY MELSSLRSED TAVYYCAVSY YSYDVLDYWG QGTTVTVSS   119

SEQ ID NO: 1371        moltype =   length =
SEQUENCE: 1371
000

SEQ ID NO: 1372        moltype =   length =
SEQUENCE: 1372
000

SEQ ID NO: 1373        moltype =   length =
SEQUENCE: 1373
000

SEQ ID NO: 1374        moltype =   length =
SEQUENCE: 1374
000

SEQ ID NO: 1375        moltype =   length =
SEQUENCE: 1375
000

SEQ ID NO: 1376        moltype = AA  length = 252
FEATURE                Location/Qualifiers
source                 1..252
                       mol_type = protein
                       organism = synthetic construct
SEQUENCE: 1376
QVQLQQSGTE LMKPGASVKI SCKASGYTFS NYWIEWIKQR PGHGLEWVGE ILPGAGPTNY  60
NEKFKGKATF TADSSSNTAY MQLSSLTSED SAVYYCARTD YDYDWFAYWG QGTLVTVSAG  120
GGGSGGGGSG GGGSGGGGSD IVMSQSPSSL AVSVGEKVTM SCKSSQSLLY SGNQKNYLAW  180
YQQKPGQSPK LLIYWASTRE SGVPDRFTGS GSGTDFTLTI NSVKAEDLTV YYCQQYYGYP  240
RTFGGGTKVE IK                                                      252

SEQ ID NO: 1377        moltype =   length =
SEQUENCE: 1377
000

SEQ ID NO: 1378        moltype =   length =
SEQUENCE: 1378
000

SEQ ID NO: 1379        moltype =   length =
SEQUENCE: 1379
000

SEQ ID NO: 1380        moltype =   length =
SEQUENCE: 1380
```

000

SEQ ID NO: 1381 moltype = length =
SEQUENCE: 1381
000

SEQ ID NO: 1382 moltype = length =
SEQUENCE: 1382
000

SEQ ID NO: 1383 moltype = length =
SEQUENCE: 1383
000

SEQ ID NO: 1384 moltype = length =
SEQUENCE: 1384
000

SEQ ID NO: 1385 moltype = length =
SEQUENCE: 1385
000

SEQ ID NO: 1386 moltype = length =
SEQUENCE: 1386
000

SEQ ID NO: 1387 moltype = length =
SEQUENCE: 1387
000

SEQ ID NO: 1388 moltype = length =
SEQUENCE: 1388
000

SEQ ID NO: 1389 moltype = length =
SEQUENCE: 1389
000

SEQ ID NO: 1390 moltype = length =
SEQUENCE: 1390
000

SEQ ID NO: 1391 moltype = length =
SEQUENCE: 1391
000

SEQ ID NO: 1392 moltype = length =
SEQUENCE: 1392
000

SEQ ID NO: 1393 moltype = length =
SEQUENCE: 1393
000

SEQ ID NO: 1394 moltype = length =
SEQUENCE: 1394
000

SEQ ID NO: 1395 moltype = length =
SEQUENCE: 1395
000

SEQ ID NO: 1396 moltype = length =
SEQUENCE: 1396
000

SEQ ID NO: 1397 moltype = length =
SEQUENCE: 1397
000

SEQ ID NO: 1398 moltype = length =
SEQUENCE: 1398
000

SEQ ID NO: 1399 moltype = length =
SEQUENCE: 1399
000

SEQ ID NO: 1400 moltype = length =

SEQUENCE: 1400
000

SEQ ID NO: 1401 moltype = length =
SEQUENCE: 1401
000

SEQ ID NO: 1402 moltype = length =
SEQUENCE: 1402
000

SEQ ID NO: 1403 moltype = length =
SEQUENCE: 1403
000

SEQ ID NO: 1404 moltype = length =
SEQUENCE: 1404
000

SEQ ID NO: 1405 moltype = length =
SEQUENCE: 1405
000

SEQ ID NO: 1406 moltype = length =
SEQUENCE: 1406
000

SEQ ID NO: 1407 moltype = length =
SEQUENCE: 1407
000

SEQ ID NO: 1408 moltype = length =
SEQUENCE: 1408
000

SEQ ID NO: 1409 moltype = length =
SEQUENCE: 1409
000

SEQ ID NO: 1410 moltype = length =
SEQUENCE: 1410
000

SEQ ID NO: 1411 moltype = length =
SEQUENCE: 1411
000

SEQ ID NO: 1412 moltype = length =
SEQUENCE: 1412
000

SEQ ID NO: 1413 moltype = length =
SEQUENCE: 1413
000

SEQ ID NO: 1414 moltype = length =
SEQUENCE: 1414
000

SEQ ID NO: 1415 moltype = length =
SEQUENCE: 1415
000

SEQ ID NO: 1416 moltype = length =
SEQUENCE: 1416
000

SEQ ID NO: 1417 moltype = length =
SEQUENCE: 1417
000

SEQ ID NO: 1418 moltype = length =
SEQUENCE: 1418
000

SEQ ID NO: 1419 moltype = length =
SEQUENCE: 1419
000

-continued

SEQ ID NO: 1420 moltype = length =
SEQUENCE: 1420
000

SEQ ID NO: 1421 moltype = length =
SEQUENCE: 1421
000

SEQ ID NO: 1422 moltype = length =
SEQUENCE: 1422
000

SEQ ID NO: 1423 moltype = length =
SEQUENCE: 1423
000

SEQ ID NO: 1424 moltype = length =
SEQUENCE: 1424
000

SEQ ID NO: 1425 moltype = length =
SEQUENCE: 1425
000

SEQ ID NO: 1426 moltype = length =
SEQUENCE: 1426
000

SEQ ID NO: 1427 moltype = length =
SEQUENCE: 1427
000

SEQ ID NO: 1428 moltype = length =
SEQUENCE: 1428
000

SEQ ID NO: 1429 moltype = length =
SEQUENCE: 1429
000

SEQ ID NO: 1430 moltype = length =
SEQUENCE: 1430
000

SEQ ID NO: 1431 moltype = length =
SEQUENCE: 1431
000

SEQ ID NO: 1432 moltype = length =
SEQUENCE: 1432
000

SEQ ID NO: 1433 moltype = length =
SEQUENCE: 1433
000

SEQ ID NO: 1434 moltype = length =
SEQUENCE: 1434
000

SEQ ID NO: 1435 moltype = length =
SEQUENCE: 1435
000

SEQ ID NO: 1436 moltype = length =
SEQUENCE: 1436
000

SEQ ID NO: 1437 moltype = length =
SEQUENCE: 1437
000

SEQ ID NO: 1438 moltype = length =
SEQUENCE: 1438
000

SEQ ID NO: 1439 moltype = length =
SEQUENCE: 1439
000

SEQ ID NO: 1440 moltype = length =
SEQUENCE: 1440
000

SEQ ID NO: 1441 moltype = length =
SEQUENCE: 1441
000

SEQ ID NO: 1442 moltype = length =
SEQUENCE: 1442
000

SEQ ID NO: 1443 moltype = length =
SEQUENCE: 1443
000

SEQ ID NO: 1444 moltype = length =
SEQUENCE: 1444
000

SEQ ID NO: 1445 moltype = length =
SEQUENCE: 1445
000

SEQ ID NO: 1446 moltype = length =
SEQUENCE: 1446
000

SEQ ID NO: 1447 moltype = length =
SEQUENCE: 1447
000

SEQ ID NO: 1448 moltype = length =
SEQUENCE: 1448
000

SEQ ID NO: 1449 moltype = length =
SEQUENCE: 1449
000

SEQ ID NO: 1450 moltype = length =
SEQUENCE: 1450
000

SEQ ID NO: 1451 moltype = length =
SEQUENCE: 1451
000

SEQ ID NO: 1452 moltype = length =
SEQUENCE: 1452
000

SEQ ID NO: 1453 moltype = length =
SEQUENCE: 1453
000

SEQ ID NO: 1454 moltype = length =
SEQUENCE: 1454
000

SEQ ID NO: 1455 moltype = length =
SEQUENCE: 1455
000

SEQ ID NO: 1456 moltype = length =
SEQUENCE: 1456
000

SEQ ID NO: 1457 moltype = length =
SEQUENCE: 1457
000

SEQ ID NO: 1458 moltype = length =
SEQUENCE: 1458
000

SEQ ID NO: 1459 moltype = length =
SEQUENCE: 1459

000

SEQ ID NO: 1460 moltype = length =
SEQUENCE: 1460
000

SEQ ID NO: 1461 moltype = length =
SEQUENCE: 1461
000

SEQ ID NO: 1462 moltype = length =
SEQUENCE: 1462
000

SEQ ID NO: 1463 moltype = length =
SEQUENCE: 1463
000

SEQ ID NO: 1464 moltype = length =
SEQUENCE: 1464
000

SEQ ID NO: 1465 moltype = length =
SEQUENCE: 1465
000

SEQ ID NO: 1466 moltype = length =
SEQUENCE: 1466
000

SEQ ID NO: 1467 moltype = length =
SEQUENCE: 1467
000

SEQ ID NO: 1468 moltype = length =
SEQUENCE: 1468
000

SEQ ID NO: 1469 moltype = length =
SEQUENCE: 1469
000

SEQ ID NO: 1470 moltype = length =
SEQUENCE: 1470
000

SEQ ID NO: 1471 moltype = length =
SEQUENCE: 1471
000

SEQ ID NO: 1472 moltype = length =
SEQUENCE: 1472
000

SEQ ID NO: 1473 moltype = length =
SEQUENCE: 1473
000

SEQ ID NO: 1474 moltype = length =
SEQUENCE: 1474
000

SEQ ID NO: 1475 moltype = length =
SEQUENCE: 1475
000

SEQ ID NO: 1476 moltype = length =
SEQUENCE: 1476
000

SEQ ID NO: 1477 moltype = length =
SEQUENCE: 1477
000

SEQ ID NO: 1478 moltype = length =
SEQUENCE: 1478
000

SEQ ID NO: 1479 moltype = length =

SEQUENCE: 1479
000

SEQ ID NO: 1480 moltype = length =
SEQUENCE: 1480
000

SEQ ID NO: 1481 moltype = length =
SEQUENCE: 1481
000

SEQ ID NO: 1482 moltype = length =
SEQUENCE: 1482
000

SEQ ID NO: 1483 moltype = length =
SEQUENCE: 1483
000

SEQ ID NO: 1484 moltype = length =
SEQUENCE: 1484
000

SEQ ID NO: 1485 moltype = length =
SEQUENCE: 1485
000

SEQ ID NO: 1486 moltype = length =
SEQUENCE: 1486
000

SEQ ID NO: 1487 moltype = length =
SEQUENCE: 1487
000

SEQ ID NO: 1488 moltype = length =
SEQUENCE: 1488
000

SEQ ID NO: 1489 moltype = length =
SEQUENCE: 1489
000

SEQ ID NO: 1490 moltype = length =
SEQUENCE: 1490
000

SEQ ID NO: 1491 moltype = length =
SEQUENCE: 1491
000

SEQ ID NO: 1492 moltype = length =
SEQUENCE: 1492
000

SEQ ID NO: 1493 moltype = length =
SEQUENCE: 1493
000

SEQ ID NO: 1494 moltype = length =
SEQUENCE: 1494
000

SEQ ID NO: 1495 moltype = length =
SEQUENCE: 1495
000

SEQ ID NO: 1496 moltype = length =
SEQUENCE: 1496
000

SEQ ID NO: 1497 moltype = length =
SEQUENCE: 1497
000

SEQ ID NO: 1498 moltype = length =
SEQUENCE: 1498
000

SEQ ID NO: 1499 moltype = length =
SEQUENCE: 1499
000

SEQ ID NO: 1500 moltype = length =
SEQUENCE: 1500
000

SEQ ID NO: 1501 moltype = length =
SEQUENCE: 1501
000

SEQ ID NO: 1502 moltype = length =
SEQUENCE: 1502
000

SEQ ID NO: 1503 moltype = length =
SEQUENCE: 1503
000

SEQ ID NO: 1504 moltype = length =
SEQUENCE: 1504
000

SEQ ID NO: 1505 moltype = length =
SEQUENCE: 1505
000

SEQ ID NO: 1506 moltype = length =
SEQUENCE: 1506
000

SEQ ID NO: 1507 moltype = length =
SEQUENCE: 1507
000

SEQ ID NO: 1508 moltype = length =
SEQUENCE: 1508
000

SEQ ID NO: 1509 moltype = length =
SEQUENCE: 1509
000

SEQ ID NO: 1510 moltype = length =
SEQUENCE: 1510
000

SEQ ID NO: 1511 moltype = length =
SEQUENCE: 1511
000

SEQ ID NO: 1512 moltype = length =
SEQUENCE: 1512
000

SEQ ID NO: 1513 moltype = length =
SEQUENCE: 1513
000

SEQ ID NO: 1514 moltype = length =
SEQUENCE: 1514
000

SEQ ID NO: 1515 moltype = length =
SEQUENCE: 1515
000

SEQ ID NO: 1516 moltype = length =
SEQUENCE: 1516
000

SEQ ID NO: 1517 moltype = length =
SEQUENCE: 1517
000

SEQ ID NO: 1518 moltype = length =
SEQUENCE: 1518
000

SEQ ID NO: 1519 moltype = length =
SEQUENCE: 1519
000

SEQ ID NO: 1520 moltype = length =
SEQUENCE: 1520
000

SEQ ID NO: 1521 moltype = length =
SEQUENCE: 1521
000

SEQ ID NO: 1522 moltype = length =
SEQUENCE: 1522
000

SEQ ID NO: 1523 moltype = length =
SEQUENCE: 1523
000

SEQ ID NO: 1524 moltype = length =
SEQUENCE: 1524
000

SEQ ID NO: 1525 moltype = length =
SEQUENCE: 1525
000

SEQ ID NO: 1526 moltype = length =
SEQUENCE: 1526
000

SEQ ID NO: 1527 moltype = length =
SEQUENCE: 1527
000

SEQ ID NO: 1528 moltype = length =
SEQUENCE: 1528
000

SEQ ID NO: 1529 moltype = length =
SEQUENCE: 1529
000

SEQ ID NO: 1530 moltype = length =
SEQUENCE: 1530
000

SEQ ID NO: 1531 moltype = length =
SEQUENCE: 1531
000

SEQ ID NO: 1532 moltype = length =
SEQUENCE: 1532
000

SEQ ID NO: 1533 moltype = length =
SEQUENCE: 1533
000

SEQ ID NO: 1534 moltype = length =
SEQUENCE: 1534
000

SEQ ID NO: 1535 moltype = length =
SEQUENCE: 1535
000

SEQ ID NO: 1536 moltype = length =
SEQUENCE: 1536
000

SEQ ID NO: 1537 moltype = length =
SEQUENCE: 1537
000

SEQ ID NO: 1538 moltype = length =
SEQUENCE: 1538

000

SEQ ID NO: 1539 moltype = length =
SEQUENCE: 1539
000

SEQ ID NO: 1540 moltype = length =
SEQUENCE: 1540
000

SEQ ID NO: 1541 moltype = length =
SEQUENCE: 1541
000

SEQ ID NO: 1542 moltype = length =
SEQUENCE: 1542
000

SEQ ID NO: 1543 moltype = length =
SEQUENCE: 1543
000

SEQ ID NO: 1544 moltype = length =
SEQUENCE: 1544
000

SEQ ID NO: 1545 moltype = length =
SEQUENCE: 1545
000

SEQ ID NO: 1546 moltype = length =
SEQUENCE: 1546
000

SEQ ID NO: 1547 moltype = length =
SEQUENCE: 1547
000

SEQ ID NO: 1548 moltype = length =
SEQUENCE: 1548
000

SEQ ID NO: 1549 moltype = length =
SEQUENCE: 1549
000

SEQ ID NO: 1550 moltype = length =
SEQUENCE: 1550
000

SEQ ID NO: 1551 moltype = length =
SEQUENCE: 1551
000

SEQ ID NO: 1552 moltype = length =
SEQUENCE: 1552
000

SEQ ID NO: 1553 moltype = length =
SEQUENCE: 1553
000

SEQ ID NO: 1554 moltype = length =
SEQUENCE: 1554
000

SEQ ID NO: 1555 moltype = length =
SEQUENCE: 1555
000

SEQ ID NO: 1556 moltype = length =
SEQUENCE: 1556
000

SEQ ID NO: 1557 moltype = length =
SEQUENCE: 1557
000

SEQ ID NO: 1558 moltype = length =

SEQUENCE: 1558
000

SEQ ID NO: 1559 moltype = length =
SEQUENCE: 1559
000

SEQ ID NO: 1560 moltype = length =
SEQUENCE: 1560
000

SEQ ID NO: 1561 moltype = length =
SEQUENCE: 1561
000

SEQ ID NO: 1562 moltype = length =
SEQUENCE: 1562
000

SEQ ID NO: 1563 moltype = length =
SEQUENCE: 1563
000

SEQ ID NO: 1564 moltype = length =
SEQUENCE: 1564
000

SEQ ID NO: 1565 moltype = length =
SEQUENCE: 1565
000

SEQ ID NO: 1566 moltype = length =
SEQUENCE: 1566
000

SEQ ID NO: 1567 moltype = length =
SEQUENCE: 1567
000

SEQ ID NO: 1568 moltype = length =
SEQUENCE: 1568
000

SEQ ID NO: 1569 moltype = length =
SEQUENCE: 1569
000

SEQ ID NO: 1570 moltype = length =
SEQUENCE: 1570
000

SEQ ID NO: 1571 moltype = length =
SEQUENCE: 1571
000

SEQ ID NO: 1572 moltype = length =
SEQUENCE: 1572
000

SEQ ID NO: 1573 moltype = length =
SEQUENCE: 1573
000

SEQ ID NO: 1574 moltype = length =
SEQUENCE: 1574
000

SEQ ID NO: 1575 moltype = length =
SEQUENCE: 1575
000

SEQ ID NO: 1576 moltype = length =
SEQUENCE: 1576
000

SEQ ID NO: 1577 moltype = length =
SEQUENCE: 1577
000

SEQ ID NO: 1578 moltype = length =
SEQUENCE: 1578
000

SEQ ID NO: 1579 moltype = length =
SEQUENCE: 1579
000

SEQ ID NO: 1580 moltype = length =
SEQUENCE: 1580
000

SEQ ID NO: 1581 moltype = length =
SEQUENCE: 1581
000

SEQ ID NO: 1582 moltype = length =
SEQUENCE: 1582
000

SEQ ID NO: 1583 moltype = length =
SEQUENCE: 1583
000

SEQ ID NO: 1584 moltype = length =
SEQUENCE: 1584
000

SEQ ID NO: 1585 moltype = length =
SEQUENCE: 1585
000

SEQ ID NO: 1586 moltype = length =
SEQUENCE: 1586
000

SEQ ID NO: 1587 moltype = length =
SEQUENCE: 1587
000

SEQ ID NO: 1588 moltype = length =
SEQUENCE: 1588
000

SEQ ID NO: 1589 moltype = length =
SEQUENCE: 1589
000

SEQ ID NO: 1590 moltype = length =
SEQUENCE: 1590
000

SEQ ID NO: 1591 moltype = length =
SEQUENCE: 1591
000

SEQ ID NO: 1592 moltype = length =
SEQUENCE: 1592
000

SEQ ID NO: 1593 moltype = length =
SEQUENCE: 1593
000

SEQ ID NO: 1594 moltype = length =
SEQUENCE: 1594
000

SEQ ID NO: 1595 moltype = length =
SEQUENCE: 1595
000

SEQ ID NO: 1596 moltype = length =
SEQUENCE: 1596
000

SEQ ID NO: 1597 moltype = length =
SEQUENCE: 1597
000

SEQ ID NO: 1598 moltype = length =
SEQUENCE: 1598
000

SEQ ID NO: 1599 moltype = length =
SEQUENCE: 1599
000

SEQ ID NO: 1600 moltype = length =
SEQUENCE: 1600
000

SEQ ID NO: 1601 moltype = length =
SEQUENCE: 1601
000

SEQ ID NO: 1602 moltype = length =
SEQUENCE: 1602
000

SEQ ID NO: 1603 moltype = length =
SEQUENCE: 1603
000

SEQ ID NO: 1604 moltype = length =
SEQUENCE: 1604
000

SEQ ID NO: 1605 moltype = length =
SEQUENCE: 1605
000

SEQ ID NO: 1606 moltype = length =
SEQUENCE: 1606
000

SEQ ID NO: 1607 moltype = length =
SEQUENCE: 1607
000

SEQ ID NO: 1608 moltype = length =
SEQUENCE: 1608
000

SEQ ID NO: 1609 moltype = length =
SEQUENCE: 1609
000

SEQ ID NO: 1610 moltype = length =
SEQUENCE: 1610
000

SEQ ID NO: 1611 moltype = length =
SEQUENCE: 1611
000

SEQ ID NO: 1612 moltype = length =
SEQUENCE: 1612
000

SEQ ID NO: 1613 moltype = length =
SEQUENCE: 1613
000

SEQ ID NO: 1614 moltype = length =
SEQUENCE: 1614
000

SEQ ID NO: 1615 moltype = length =
SEQUENCE: 1615
000

SEQ ID NO: 1616 moltype = length =
SEQUENCE: 1616
000

SEQ ID NO: 1617 moltype = length =
SEQUENCE: 1617

000

SEQ ID NO: 1618 moltype = length =
SEQUENCE: 1618
000

SEQ ID NO: 1619 moltype = length =
SEQUENCE: 1619
000

SEQ ID NO: 1620 moltype = length =
SEQUENCE: 1620
000

SEQ ID NO: 1621 moltype = length =
SEQUENCE: 1621
000

SEQ ID NO: 1622 moltype = length =
SEQUENCE: 1622
000

SEQ ID NO: 1623 moltype = length =
SEQUENCE: 1623
000

SEQ ID NO: 1624 moltype = length =
SEQUENCE: 1624
000

SEQ ID NO: 1625 moltype = length =
SEQUENCE: 1625
000

SEQ ID NO: 1626 moltype = length =
SEQUENCE: 1626
000

SEQ ID NO: 1627 moltype = length =
SEQUENCE: 1627
000

SEQ ID NO: 1628 moltype = length =
SEQUENCE: 1628
000

SEQ ID NO: 1629 moltype = length =
SEQUENCE: 1629
000

SEQ ID NO: 1630 moltype = length =
SEQUENCE: 1630
000

SEQ ID NO: 1631 moltype = length =
SEQUENCE: 1631
000

SEQ ID NO: 1632 moltype = length =
SEQUENCE: 1632
000

SEQ ID NO: 1633 moltype = length =
SEQUENCE: 1633
000

SEQ ID NO: 1634 moltype = length =
SEQUENCE: 1634
000

SEQ ID NO: 1635 moltype = length =
SEQUENCE: 1635
000

SEQ ID NO: 1636 moltype = length =
SEQUENCE: 1636
000

SEQ ID NO: 1637 moltype = length =

SEQUENCE: 1637
000

SEQ ID NO: 1638 moltype = length =
SEQUENCE: 1638
000

SEQ ID NO: 1639 moltype = length =
SEQUENCE: 1639
000

SEQ ID NO: 1640 moltype = length =
SEQUENCE: 1640
000

SEQ ID NO: 1641 moltype = length =
SEQUENCE: 1641
000

SEQ ID NO: 1642 moltype = length =
SEQUENCE: 1642
000

SEQ ID NO: 1643 moltype = length =
SEQUENCE: 1643
000

SEQ ID NO: 1644 moltype = length =
SEQUENCE: 1644
000

SEQ ID NO: 1645 moltype = length =
SEQUENCE: 1645
000

SEQ ID NO: 1646 moltype = length =
SEQUENCE: 1646
000

SEQ ID NO: 1647 moltype = length =
SEQUENCE: 1647
000

SEQ ID NO: 1648 moltype = length =
SEQUENCE: 1648
000

SEQ ID NO: 1649 moltype = length =
SEQUENCE: 1649
000

SEQ ID NO: 1650 moltype = length =
SEQUENCE: 1650
000

SEQ ID NO: 1651 moltype = length =
SEQUENCE: 1651
000

SEQ ID NO: 1652 moltype = length =
SEQUENCE: 1652
000

SEQ ID NO: 1653 moltype = length =
SEQUENCE: 1653
000

SEQ ID NO: 1654 moltype = length =
SEQUENCE: 1654
000

SEQ ID NO: 1655 moltype = length =
SEQUENCE: 1655
000

SEQ ID NO: 1656 moltype = length =
SEQUENCE: 1656
000

SEQ ID NO: 1657 moltype = length =
SEQUENCE: 1657
000

SEQ ID NO: 1658 moltype = length =
SEQUENCE: 1658
000

SEQ ID NO: 1659 moltype = length =
SEQUENCE: 1659
000

SEQ ID NO: 1660 moltype = length =
SEQUENCE: 1660
000

SEQ ID NO: 1661 moltype = length =
SEQUENCE: 1661
000

SEQ ID NO: 1662 moltype = length =
SEQUENCE: 1662
000

SEQ ID NO: 1663 moltype = length =
SEQUENCE: 1663
000

SEQ ID NO: 1664 moltype = length =
SEQUENCE: 1664
000

SEQ ID NO: 1665 moltype = length =
SEQUENCE: 1665
000

SEQ ID NO: 1666 moltype = length =
SEQUENCE: 1666
000

SEQ ID NO: 1667 moltype = length =
SEQUENCE: 1667
000

SEQ ID NO: 1668 moltype = length =
SEQUENCE: 1668
000

SEQ ID NO: 1669 moltype = length =
SEQUENCE: 1669
000

SEQ ID NO: 1670 moltype = length =
SEQUENCE: 1670
000

SEQ ID NO: 1671 moltype = length =
SEQUENCE: 1671
000

SEQ ID NO: 1672 moltype = length =
SEQUENCE: 1672
000

SEQ ID NO: 1673 moltype = length =
SEQUENCE: 1673
000

SEQ ID NO: 1674 moltype = length =
SEQUENCE: 1674
000

SEQ ID NO: 1675 moltype = length =
SEQUENCE: 1675
000

SEQ ID NO: 1676 moltype = length =
SEQUENCE: 1676
000

SEQ ID NO: 1677 moltype = length =
SEQUENCE: 1677
000

SEQ ID NO: 1678 moltype = length =
SEQUENCE: 1678
000

SEQ ID NO: 1679 moltype = length =
SEQUENCE: 1679
000

SEQ ID NO: 1680 moltype = length =
SEQUENCE: 1680
000

SEQ ID NO: 1681 moltype = length =
SEQUENCE: 1681
000

SEQ ID NO: 1682 moltype = length =
SEQUENCE: 1682
000

SEQ ID NO: 1683 moltype = length =
SEQUENCE: 1683
000

SEQ ID NO: 1684 moltype = length =
SEQUENCE: 1684
000

SEQ ID NO: 1685 moltype = length =
SEQUENCE: 1685
000

SEQ ID NO: 1686 moltype = length =
SEQUENCE: 1686
000

SEQ ID NO: 1687 moltype = length =
SEQUENCE: 1687
000

SEQ ID NO: 1688 moltype = length =
SEQUENCE: 1688
000

SEQ ID NO: 1689 moltype = length =
SEQUENCE: 1689
000

SEQ ID NO: 1690 moltype = length =
SEQUENCE: 1690
000

SEQ ID NO: 1691 moltype = length =
SEQUENCE: 1691
000

SEQ ID NO: 1692 moltype = length =
SEQUENCE: 1692
000

SEQ ID NO: 1693 moltype = length =
SEQUENCE: 1693
000

SEQ ID NO: 1694 moltype = length =
SEQUENCE: 1694
000

SEQ ID NO: 1695 moltype = length =
SEQUENCE: 1695
000

SEQ ID NO: 1696 moltype = length =
SEQUENCE: 1696

000

SEQ ID NO: 1697 moltype = length =
SEQUENCE: 1697
000

SEQ ID NO: 1698 moltype = length =
SEQUENCE: 1698
000

SEQ ID NO: 1699 moltype = length =
SEQUENCE: 1699
000

SEQ ID NO: 1700 moltype = length =
SEQUENCE: 1700
000

SEQ ID NO: 1701 moltype = length =
SEQUENCE: 1701
000

SEQ ID NO: 1702 moltype = length =
SEQUENCE: 1702
000

SEQ ID NO: 1703 moltype = length =
SEQUENCE: 1703
000

SEQ ID NO: 1704 moltype = length =
SEQUENCE: 1704
000

SEQ ID NO: 1705 moltype = length =
SEQUENCE: 1705
000

SEQ ID NO: 1706 moltype = length =
SEQUENCE: 1706
000

SEQ ID NO: 1707 moltype = length =
SEQUENCE: 1707
000

SEQ ID NO: 1708 moltype = length =
SEQUENCE: 1708
000

SEQ ID NO: 1709 moltype = length =
SEQUENCE: 1709
000

SEQ ID NO: 1710 moltype = length =
SEQUENCE: 1710
000

SEQ ID NO: 1711 moltype = length =
SEQUENCE: 1711
000

SEQ ID NO: 1712 moltype = length =
SEQUENCE: 1712
000

SEQ ID NO: 1713 moltype = length =
SEQUENCE: 1713
000

SEQ ID NO: 1714 moltype = length =
SEQUENCE: 1714
000

SEQ ID NO: 1715 moltype = length =
SEQUENCE: 1715
000

SEQ ID NO: 1716 moltype = length =

SEQUENCE: 1716
000

SEQ ID NO: 1717 moltype = length =
SEQUENCE: 1717
000

SEQ ID NO: 1718 moltype = length =
SEQUENCE: 1718
000

SEQ ID NO: 1719 moltype = length =
SEQUENCE: 1719
000

SEQ ID NO: 1720 moltype = length =
SEQUENCE: 1720
000

SEQ ID NO: 1721 moltype = length =
SEQUENCE: 1721
000

SEQ ID NO: 1722 moltype = length =
SEQUENCE: 1722
000

SEQ ID NO: 1723 moltype = length =
SEQUENCE: 1723
000

SEQ ID NO: 1724 moltype = length =
SEQUENCE: 1724
000

SEQ ID NO: 1725 moltype = length =
SEQUENCE: 1725
000

SEQ ID NO: 1726 moltype = length =
SEQUENCE: 1726
000

SEQ ID NO: 1727 moltype = length =
SEQUENCE: 1727
000

SEQ ID NO: 1728 moltype = length =
SEQUENCE: 1728
000

SEQ ID NO: 1729 moltype = length =
SEQUENCE: 1729
000

SEQ ID NO: 1730 moltype = length =
SEQUENCE: 1730
000

SEQ ID NO: 1731 moltype = length =
SEQUENCE: 1731
000

SEQ ID NO: 1732 moltype = length =
SEQUENCE: 1732
000

SEQ ID NO: 1733 moltype = length =
SEQUENCE: 1733
000

SEQ ID NO: 1734 moltype = length =
SEQUENCE: 1734
000

SEQ ID NO: 1735 moltype = length =
SEQUENCE: 1735
000

SEQ ID NO: 1736 moltype = length =
SEQUENCE: 1736
000

SEQ ID NO: 1737 moltype = length =
SEQUENCE: 1737
000

SEQ ID NO: 1738 moltype = length =
SEQUENCE: 1738
000

SEQ ID NO: 1739 moltype = length =
SEQUENCE: 1739
000

SEQ ID NO: 1740 moltype = length =
SEQUENCE: 1740
000

SEQ ID NO: 1741 moltype = length =
SEQUENCE: 1741
000

SEQ ID NO: 1742 moltype = length =
SEQUENCE: 1742
000

SEQ ID NO: 1743 moltype = length =
SEQUENCE: 1743
000

SEQ ID NO: 1744 moltype = length =
SEQUENCE: 1744
000

SEQ ID NO: 1745 moltype = length =
SEQUENCE: 1745
000

SEQ ID NO: 1746 moltype = length =
SEQUENCE: 1746
000

SEQ ID NO: 1747 moltype = length =
SEQUENCE: 1747
000

SEQ ID NO: 1748 moltype = length =
SEQUENCE: 1748
000

SEQ ID NO: 1749 moltype = length =
SEQUENCE: 1749
000

SEQ ID NO: 1750 moltype = length =
SEQUENCE: 1750
000

SEQ ID NO: 1751 moltype = length =
SEQUENCE: 1751
000

SEQ ID NO: 1752 moltype = length =
SEQUENCE: 1752
000

SEQ ID NO: 1753 moltype = length =
SEQUENCE: 1753
000

SEQ ID NO: 1754 moltype = length =
SEQUENCE: 1754
000

SEQ ID NO: 1755 moltype = length =
SEQUENCE: 1755
000

SEQ ID NO: 1756 moltype = length =
SEQUENCE: 1756
000

SEQ ID NO: 1757 moltype = length =
SEQUENCE: 1757
000

SEQ ID NO: 1758 moltype = length =
SEQUENCE: 1758
000

SEQ ID NO: 1759 moltype = length =
SEQUENCE: 1759
000

SEQ ID NO: 1760 moltype = length =
SEQUENCE: 1760
000

SEQ ID NO: 1761 moltype = length =
SEQUENCE: 1761
000

SEQ ID NO: 1762 moltype = length =
SEQUENCE: 1762
000

SEQ ID NO: 1763 moltype = length =
SEQUENCE: 1763
000

SEQ ID NO: 1764 moltype = length =
SEQUENCE: 1764
000

SEQ ID NO: 1765 moltype = length =
SEQUENCE: 1765
000

SEQ ID NO: 1766 moltype = length =
SEQUENCE: 1766
000

SEQ ID NO: 1767 moltype = length =
SEQUENCE: 1767
000

SEQ ID NO: 1768 moltype = length =
SEQUENCE: 1768
000

SEQ ID NO: 1769 moltype = length =
SEQUENCE: 1769
000

SEQ ID NO: 1770 moltype = length =
SEQUENCE: 1770
000

SEQ ID NO: 1771 moltype = length =
SEQUENCE: 1771
000

SEQ ID NO: 1772 moltype = length =
SEQUENCE: 1772
000

SEQ ID NO: 1773 moltype = length =
SEQUENCE: 1773
000

SEQ ID NO: 1774 moltype = length =
SEQUENCE: 1774
000

SEQ ID NO: 1775 moltype = length =
SEQUENCE: 1775

000

SEQ ID NO: 1776 moltype = length =
SEQUENCE: 1776
000

SEQ ID NO: 1777 moltype = length =
SEQUENCE: 1777
000

SEQ ID NO: 1778 moltype = length =
SEQUENCE: 1778
000

SEQ ID NO: 1779 moltype = length =
SEQUENCE: 1779
000

SEQ ID NO: 1780 moltype = length =
SEQUENCE: 1780
000

SEQ ID NO: 1781 moltype = length =
SEQUENCE: 1781
000

SEQ ID NO: 1782 moltype = length =
SEQUENCE: 1782
000

SEQ ID NO: 1783 moltype = length =
SEQUENCE: 1783
000

SEQ ID NO: 1784 moltype = length =
SEQUENCE: 1784
000

SEQ ID NO: 1785 moltype = length =
SEQUENCE: 1785
000

SEQ ID NO: 1786 moltype = length =
SEQUENCE: 1786
000

SEQ ID NO: 1787 moltype = length =
SEQUENCE: 1787
000

SEQ ID NO: 1788 moltype = length =
SEQUENCE: 1788
000

SEQ ID NO: 1789 moltype = length =
SEQUENCE: 1789
000

SEQ ID NO: 1790 moltype = length =
SEQUENCE: 1790
000

SEQ ID NO: 1791 moltype = length =
SEQUENCE: 1791
000

SEQ ID NO: 1792 moltype = length =
SEQUENCE: 1792
000

SEQ ID NO: 1793 moltype = length =
SEQUENCE: 1793
000

SEQ ID NO: 1794 moltype = length =
SEQUENCE: 1794
000

SEQ ID NO: 1795 moltype = length =

SEQUENCE: 1795
000

SEQ ID NO: 1796 moltype = length =
SEQUENCE: 1796
000

SEQ ID NO: 1797 moltype = length =
SEQUENCE: 1797
000

SEQ ID NO: 1798 moltype = length =
SEQUENCE: 1798
000

SEQ ID NO: 1799 moltype = length =
SEQUENCE: 1799
000

SEQ ID NO: 1800 moltype = length =
SEQUENCE: 1800
000

SEQ ID NO: 1801 moltype = length =
SEQUENCE: 1801
000

SEQ ID NO: 1802 moltype = length =
SEQUENCE: 1802
000

SEQ ID NO: 1803 moltype = length =
SEQUENCE: 1803
000

SEQ ID NO: 1804 moltype = length =
SEQUENCE: 1804
000

SEQ ID NO: 1805 moltype = length =
SEQUENCE: 1805
000

SEQ ID NO: 1806 moltype = length =
SEQUENCE: 1806
000

SEQ ID NO: 1807 moltype = length =
SEQUENCE: 1807
000

SEQ ID NO: 1808 moltype = length =
SEQUENCE: 1808
000

SEQ ID NO: 1809 moltype = length =
SEQUENCE: 1809
000

SEQ ID NO: 1810 moltype = length =
SEQUENCE: 1810
000

SEQ ID NO: 1811 moltype = length =
SEQUENCE: 1811
000

SEQ ID NO: 1812 moltype = length =
SEQUENCE: 1812
000

SEQ ID NO: 1813 moltype = length =
SEQUENCE: 1813
000

SEQ ID NO: 1814 moltype = length =
SEQUENCE: 1814
000

SEQ ID NO: 1815 moltype = length =
SEQUENCE: 1815
000

SEQ ID NO: 1816 moltype = length =
SEQUENCE: 1816
000

SEQ ID NO: 1817 moltype = length =
SEQUENCE: 1817
000

SEQ ID NO: 1818 moltype = length =
SEQUENCE: 1818
000

SEQ ID NO: 1819 moltype = length =
SEQUENCE: 1819
000

SEQ ID NO: 1820 moltype = length =
SEQUENCE: 1820
000

SEQ ID NO: 1821 moltype = length =
SEQUENCE: 1821
000

SEQ ID NO: 1822 moltype = length =
SEQUENCE: 1822
000

SEQ ID NO: 1823 moltype = length =
SEQUENCE: 1823
000

SEQ ID NO: 1824 moltype = length =
SEQUENCE: 1824
000

SEQ ID NO: 1825 moltype = length =
SEQUENCE: 1825
000

SEQ ID NO: 1826 moltype = length =
SEQUENCE: 1826
000

SEQ ID NO: 1827 moltype = length =
SEQUENCE: 1827
000

SEQ ID NO: 1828 moltype = length =
SEQUENCE: 1828
000

SEQ ID NO: 1829 moltype = length =
SEQUENCE: 1829
000

SEQ ID NO: 1830 moltype = length =
SEQUENCE: 1830
000

SEQ ID NO: 1831 moltype = length =
SEQUENCE: 1831
000

SEQ ID NO: 1832 moltype = length =
SEQUENCE: 1832
000

SEQ ID NO: 1833 moltype = length =
SEQUENCE: 1833
000

SEQ ID NO: 1834 moltype = length =
SEQUENCE: 1834
000

SEQ ID NO: 1835 moltype = length =
SEQUENCE: 1835
000

SEQ ID NO: 1836 moltype = length =
SEQUENCE: 1836
000

SEQ ID NO: 1837 moltype = length =
SEQUENCE: 1837
000

SEQ ID NO: 1838 moltype = length =
SEQUENCE: 1838
000

SEQ ID NO: 1839 moltype = length =
SEQUENCE: 1839
000

SEQ ID NO: 1840 moltype = length =
SEQUENCE: 1840
000

SEQ ID NO: 1841 moltype = length =
SEQUENCE: 1841
000

SEQ ID NO: 1842 moltype = length =
SEQUENCE: 1842
000

SEQ ID NO: 1843 moltype = length =
SEQUENCE: 1843
000

SEQ ID NO: 1844 moltype = length =
SEQUENCE: 1844
000

SEQ ID NO: 1845 moltype = length =
SEQUENCE: 1845
000

SEQ ID NO: 1846 moltype = length =
SEQUENCE: 1846
000

SEQ ID NO: 1847 moltype = length =
SEQUENCE: 1847
000

SEQ ID NO: 1848 moltype = length =
SEQUENCE: 1848
000

SEQ ID NO: 1849 moltype = length =
SEQUENCE: 1849
000

SEQ ID NO: 1850 moltype = length =
SEQUENCE: 1850
000

SEQ ID NO: 1851 moltype = length =
SEQUENCE: 1851
000

SEQ ID NO: 1852 moltype = length =
SEQUENCE: 1852
000

SEQ ID NO: 1853 moltype = length =
SEQUENCE: 1853
000

SEQ ID NO: 1854 moltype = length =
SEQUENCE: 1854

000

SEQ ID NO: 1855 moltype = length =
SEQUENCE: 1855
000

SEQ ID NO: 1856 moltype = length =
SEQUENCE: 1856
000

SEQ ID NO: 1857 moltype = length =
SEQUENCE: 1857
000

SEQ ID NO: 1858 moltype = length =
SEQUENCE: 1858
000

SEQ ID NO: 1859 moltype = length =
SEQUENCE: 1859
000

SEQ ID NO: 1860 moltype = length =
SEQUENCE: 1860
000

SEQ ID NO: 1861 moltype = length =
SEQUENCE: 1861
000

SEQ ID NO: 1862 moltype = length =
SEQUENCE: 1862
000

SEQ ID NO: 1863 moltype = length =
SEQUENCE: 1863
000

SEQ ID NO: 1864 moltype = length =
SEQUENCE: 1864
000

SEQ ID NO: 1865 moltype = length =
SEQUENCE: 1865
000

SEQ ID NO: 1866 moltype = length =
SEQUENCE: 1866
000

SEQ ID NO: 1867 moltype = length =
SEQUENCE: 1867
000

SEQ ID NO: 1868 moltype = length =
SEQUENCE: 1868
000

SEQ ID NO: 1869 moltype = length =
SEQUENCE: 1869
000

SEQ ID NO: 1870 moltype = length =
SEQUENCE: 1870
000

SEQ ID NO: 1871 moltype = length =
SEQUENCE: 1871
000

SEQ ID NO: 1872 moltype = length =
SEQUENCE: 1872
000

SEQ ID NO: 1873 moltype = length =
SEQUENCE: 1873
000

SEQ ID NO: 1874 moltype = length =

SEQUENCE: 1874
000

SEQ ID NO: 1875 moltype = length =
SEQUENCE: 1875
000

SEQ ID NO: 1876 moltype = length =
SEQUENCE: 1876
000

SEQ ID NO: 1877 moltype = length =
SEQUENCE: 1877
000

SEQ ID NO: 1878 moltype = length =
SEQUENCE: 1878
000

SEQ ID NO: 1879 moltype = length =
SEQUENCE: 1879
000

SEQ ID NO: 1880 moltype = length =
SEQUENCE: 1880
000

SEQ ID NO: 1881 moltype = length =
SEQUENCE: 1881
000

SEQ ID NO: 1882 moltype = length =
SEQUENCE: 1882
000

SEQ ID NO: 1883 moltype = length =
SEQUENCE: 1883
000

SEQ ID NO: 1884 moltype = length =
SEQUENCE: 1884
000

SEQ ID NO: 1885 moltype = length =
SEQUENCE: 1885
000

SEQ ID NO: 1886 moltype = length =
SEQUENCE: 1886
000

SEQ ID NO: 1887 moltype = length =
SEQUENCE: 1887
000

SEQ ID NO: 1888 moltype = length =
SEQUENCE: 1888
000

SEQ ID NO: 1889 moltype = length =
SEQUENCE: 1889
000

SEQ ID NO: 1890 moltype = length =
SEQUENCE: 1890
000

SEQ ID NO: 1891 moltype = length =
SEQUENCE: 1891
000

SEQ ID NO: 1892 moltype = length =
SEQUENCE: 1892
000

SEQ ID NO: 1893 moltype = length =
SEQUENCE: 1893
000

SEQ ID NO: 1894 moltype = length =
SEQUENCE: 1894
000

SEQ ID NO: 1895 moltype = length =
SEQUENCE: 1895
000

SEQ ID NO: 1896 moltype = length =
SEQUENCE: 1896
000

SEQ ID NO: 1897 moltype = length =
SEQUENCE: 1897
000

SEQ ID NO: 1898 moltype = length =
SEQUENCE: 1898
000

SEQ ID NO: 1899 moltype = length =
SEQUENCE: 1899
000

SEQ ID NO: 1900 moltype = length =
SEQUENCE: 1900
000

SEQ ID NO: 1901 moltype = length =
SEQUENCE: 1901
000

SEQ ID NO: 1902 moltype = length =
SEQUENCE: 1902
000

SEQ ID NO: 1903 moltype = length =
SEQUENCE: 1903
000

SEQ ID NO: 1904 moltype = length =
SEQUENCE: 1904
000

SEQ ID NO: 1905 moltype = length =
SEQUENCE: 1905
000

SEQ ID NO: 1906 moltype = length =
SEQUENCE: 1906
000

SEQ ID NO: 1907 moltype = length =
SEQUENCE: 1907
000

SEQ ID NO: 1908 moltype = length =
SEQUENCE: 1908
000

SEQ ID NO: 1909 moltype = length =
SEQUENCE: 1909
000

SEQ ID NO: 1910 moltype = length =
SEQUENCE: 1910
000

SEQ ID NO: 1911 moltype = length =
SEQUENCE: 1911
000

SEQ ID NO: 1912 moltype = length =
SEQUENCE: 1912
000

SEQ ID NO: 1913 moltype = length =
SEQUENCE: 1913
000

SEQ ID NO: 1914 moltype = length =
SEQUENCE: 1914
000

SEQ ID NO: 1915 moltype = length =
SEQUENCE: 1915
000

SEQ ID NO: 1916 moltype = length =
SEQUENCE: 1916
000

SEQ ID NO: 1917 moltype = length =
SEQUENCE: 1917
000

SEQ ID NO: 1918 moltype = length =
SEQUENCE: 1918
000

SEQ ID NO: 1919 moltype = length =
SEQUENCE: 1919
000

SEQ ID NO: 1920 moltype = length =
SEQUENCE: 1920
000

SEQ ID NO: 1921 moltype = length =
SEQUENCE: 1921
000

SEQ ID NO: 1922 moltype = length =
SEQUENCE: 1922
000

SEQ ID NO: 1923 moltype = length =
SEQUENCE: 1923
000

SEQ ID NO: 1924 moltype = length =
SEQUENCE: 1924
000

SEQ ID NO: 1925 moltype = length =
SEQUENCE: 1925
000

SEQ ID NO: 1926 moltype = length =
SEQUENCE: 1926
000

SEQ ID NO: 1927 moltype = length =
SEQUENCE: 1927
000

SEQ ID NO: 1928 moltype = length =
SEQUENCE: 1928
000

SEQ ID NO: 1929 moltype = length =
SEQUENCE: 1929
000

SEQ ID NO: 1930 moltype = length =
SEQUENCE: 1930
000

SEQ ID NO: 1931 moltype = length =
SEQUENCE: 1931
000

SEQ ID NO: 1932 moltype = length =
SEQUENCE: 1932
000

SEQ ID NO: 1933 moltype = length =
SEQUENCE: 1933

000

SEQ ID NO: 1934 moltype = length =
SEQUENCE: 1934
000

SEQ ID NO: 1935 moltype = length =
SEQUENCE: 1935
000

SEQ ID NO: 1936 moltype = length =
SEQUENCE: 1936
000

SEQ ID NO: 1937 moltype = length =
SEQUENCE: 1937
000

SEQ ID NO: 1938 moltype = length =
SEQUENCE: 1938
000

SEQ ID NO: 1939 moltype = length =
SEQUENCE: 1939
000

SEQ ID NO: 1940 moltype = length =
SEQUENCE: 1940
000

SEQ ID NO: 1941 moltype = length =
SEQUENCE: 1941
000

SEQ ID NO: 1942 moltype = length =
SEQUENCE: 1942
000

SEQ ID NO: 1943 moltype = length =
SEQUENCE: 1943
000

SEQ ID NO: 1944 moltype = length =
SEQUENCE: 1944
000

SEQ ID NO: 1945 moltype = length =
SEQUENCE: 1945
000

SEQ ID NO: 1946 moltype = length =
SEQUENCE: 1946
000

SEQ ID NO: 1947 moltype = length =
SEQUENCE: 1947
000

SEQ ID NO: 1948 moltype = length =
SEQUENCE: 1948
000

SEQ ID NO: 1949 moltype = length =
SEQUENCE: 1949
000

SEQ ID NO: 1950 moltype = length =
SEQUENCE: 1950
000

SEQ ID NO: 1951 moltype = length =
SEQUENCE: 1951
000

SEQ ID NO: 1952 moltype = length =
SEQUENCE: 1952
000

SEQ ID NO: 1953 moltype = length =

SEQUENCE: 1953
000

SEQ ID NO: 1954 moltype = length =
SEQUENCE: 1954
000

SEQ ID NO: 1955 moltype = length =
SEQUENCE: 1955
000

SEQ ID NO: 1956 moltype = length =
SEQUENCE: 1956
000

SEQ ID NO: 1957 moltype = length =
SEQUENCE: 1957
000

SEQ ID NO: 1958 moltype = length =
SEQUENCE: 1958
000

SEQ ID NO: 1959 moltype = length =
SEQUENCE: 1959
000

SEQ ID NO: 1960 moltype = length =
SEQUENCE: 1960
000

SEQ ID NO: 1961 moltype = length =
SEQUENCE: 1961
000

SEQ ID NO: 1962 moltype = length =
SEQUENCE: 1962
000

SEQ ID NO: 1963 moltype = length =
SEQUENCE: 1963
000

SEQ ID NO: 1964 moltype = length =
SEQUENCE: 1964
000

SEQ ID NO: 1965 moltype = length =
SEQUENCE: 1965
000

SEQ ID NO: 1966 moltype = length =
SEQUENCE: 1966
000

SEQ ID NO: 1967 moltype = length =
SEQUENCE: 1967
000

SEQ ID NO: 1968 moltype = length =
SEQUENCE: 1968
000

SEQ ID NO: 1969 moltype = length =
SEQUENCE: 1969
000

SEQ ID NO: 1970 moltype = length =
SEQUENCE: 1970
000

SEQ ID NO: 1971 moltype = length =
SEQUENCE: 1971
000

SEQ ID NO: 1972 moltype = length =
SEQUENCE: 1972
000

SEQ ID NO: 1973 moltype = length =
SEQUENCE: 1973
000

SEQ ID NO: 1974 moltype = length =
SEQUENCE: 1974
000

SEQ ID NO: 1975 moltype = length =
SEQUENCE: 1975
000

SEQ ID NO: 1976 moltype = length =
SEQUENCE: 1976
000

SEQ ID NO: 1977 moltype = length =
SEQUENCE: 1977
000

SEQ ID NO: 1978 moltype = length =
SEQUENCE: 1978
000

SEQ ID NO: 1979 moltype = length =
SEQUENCE: 1979
000

SEQ ID NO: 1980 moltype = length =
SEQUENCE: 1980
000

SEQ ID NO: 1981 moltype = length =
SEQUENCE: 1981
000

SEQ ID NO: 1982 moltype = length =
SEQUENCE: 1982
000

SEQ ID NO: 1983 moltype = length =
SEQUENCE: 1983
000

SEQ ID NO: 1984 moltype = length =
SEQUENCE: 1984
000

SEQ ID NO: 1985 moltype = length =
SEQUENCE: 1985
000

SEQ ID NO: 1986 moltype = length =
SEQUENCE: 1986
000

SEQ ID NO: 1987 moltype = length =
SEQUENCE: 1987
000

SEQ ID NO: 1988 moltype = length =
SEQUENCE: 1988
000

SEQ ID NO: 1989 moltype = length =
SEQUENCE: 1989
000

SEQ ID NO: 1990 moltype = length =
SEQUENCE: 1990
000

SEQ ID NO: 1991 moltype = length =
SEQUENCE: 1991
000

SEQ ID NO: 1992 moltype = length =
SEQUENCE: 1992
000

SEQ ID NO: 1993 moltype = length =
SEQUENCE: 1993
000

SEQ ID NO: 1994 moltype = length =
SEQUENCE: 1994
000

SEQ ID NO: 1995 moltype = length =
SEQUENCE: 1995
000

SEQ ID NO: 1996 moltype = length =
SEQUENCE: 1996
000

SEQ ID NO: 1997 moltype = length =
SEQUENCE: 1997
000

SEQ ID NO: 1998 moltype = length =
SEQUENCE: 1998
000

SEQ ID NO: 1999 moltype = length =
SEQUENCE: 1999
000

SEQ ID NO: 2000 moltype = length =
SEQUENCE: 2000
000

SEQ ID NO: 2001 moltype = length =
SEQUENCE: 2001
000

SEQ ID NO: 2002 moltype = length =
SEQUENCE: 2002
000

SEQ ID NO: 2003 moltype = length =
SEQUENCE: 2003
000

SEQ ID NO: 2004 moltype = length =
SEQUENCE: 2004
000

SEQ ID NO: 2005 moltype = length =
SEQUENCE: 2005
000

SEQ ID NO: 2006 moltype = length =
SEQUENCE: 2006
000

SEQ ID NO: 2007 moltype = length =
SEQUENCE: 2007
000

SEQ ID NO: 2008 moltype = length =
SEQUENCE: 2008
000

SEQ ID NO: 2009 moltype = length =
SEQUENCE: 2009
000

SEQ ID NO: 2010 moltype = length =
SEQUENCE: 2010
000

SEQ ID NO: 2011 moltype = length =
SEQUENCE: 2011
000

SEQ ID NO: 2012 moltype = length =
SEQUENCE: 2012

000

SEQ ID NO: 2013 moltype = length =
SEQUENCE: 2013
000

SEQ ID NO: 2014 moltype = length =
SEQUENCE: 2014
000

SEQ ID NO: 2015 moltype = length =
SEQUENCE: 2015
000

SEQ ID NO: 2016 moltype = length =
SEQUENCE: 2016
000

SEQ ID NO: 2017 moltype = length =
SEQUENCE: 2017
000

SEQ ID NO: 2018 moltype = length =
SEQUENCE: 2018
000

SEQ ID NO: 2019 moltype = length =
SEQUENCE: 2019
000

SEQ ID NO: 2020 moltype = length =
SEQUENCE: 2020
000

SEQ ID NO: 2021 moltype = length =
SEQUENCE: 2021
000

SEQ ID NO: 2022 moltype = length =
SEQUENCE: 2022
000

SEQ ID NO: 2023 moltype = length =
SEQUENCE: 2023
000

SEQ ID NO: 2024 moltype = length =
SEQUENCE: 2024
000

SEQ ID NO: 2025 moltype = length =
SEQUENCE: 2025
000

SEQ ID NO: 2026 moltype = length =
SEQUENCE: 2026
000

SEQ ID NO: 2027 moltype = length =
SEQUENCE: 2027
000

SEQ ID NO: 2028 moltype = length =
SEQUENCE: 2028
000

SEQ ID NO: 2029 moltype = length =
SEQUENCE: 2029
000

SEQ ID NO: 2030 moltype = length =
SEQUENCE: 2030
000

SEQ ID NO: 2031 moltype = length =
SEQUENCE: 2031
000

SEQ ID NO: 2032 moltype = length =

SEQUENCE: 2032
000

SEQ ID NO: 2033 moltype = length =
SEQUENCE: 2033
000

SEQ ID NO: 2034 moltype = length =
SEQUENCE: 2034
000

SEQ ID NO: 2035 moltype = length =
SEQUENCE: 2035
000

SEQ ID NO: 2036 moltype = length =
SEQUENCE: 2036
000

SEQ ID NO: 2037 moltype = length =
SEQUENCE: 2037
000

SEQ ID NO: 2038 moltype = length =
SEQUENCE: 2038
000

SEQ ID NO: 2039 moltype = length =
SEQUENCE: 2039
000

SEQ ID NO: 2040 moltype = length =
SEQUENCE: 2040
000

SEQ ID NO: 2041 moltype = length =
SEQUENCE: 2041
000

SEQ ID NO: 2042 moltype = length =
SEQUENCE: 2042
000

SEQ ID NO: 2043 moltype = length =
SEQUENCE: 2043
000

SEQ ID NO: 2044 moltype = length =
SEQUENCE: 2044
000

SEQ ID NO: 2045 moltype = length =
SEQUENCE: 2045
000

SEQ ID NO: 2046 moltype = length =
SEQUENCE: 2046
000

SEQ ID NO: 2047 moltype = length =
SEQUENCE: 2047
000

SEQ ID NO: 2048 moltype = length =
SEQUENCE: 2048
000

SEQ ID NO: 2049 moltype = length =
SEQUENCE: 2049
000

SEQ ID NO: 2050 moltype = length =
SEQUENCE: 2050
000

SEQ ID NO: 2051 moltype = length =
SEQUENCE: 2051
000

SEQ ID NO: 2052 moltype = length =
SEQUENCE: 2052
000

SEQ ID NO: 2053 moltype = length =
SEQUENCE: 2053
000

SEQ ID NO: 2054 moltype = length =
SEQUENCE: 2054
000

SEQ ID NO: 2055 moltype = length =
SEQUENCE: 2055
000

SEQ ID NO: 2056 moltype = length =
SEQUENCE: 2056
000

SEQ ID NO: 2057 moltype = length =
SEQUENCE: 2057
000

SEQ ID NO: 2058 moltype = length =
SEQUENCE: 2058
000

SEQ ID NO: 2059 moltype = length =
SEQUENCE: 2059
000

SEQ ID NO: 2060 moltype = length =
SEQUENCE: 2060
000

SEQ ID NO: 2061 moltype = length =
SEQUENCE: 2061
000

SEQ ID NO: 2062 moltype = length =
SEQUENCE: 2062
000

SEQ ID NO: 2063 moltype = length =
SEQUENCE: 2063
000

SEQ ID NO: 2064 moltype = length =
SEQUENCE: 2064
000

SEQ ID NO: 2065 moltype = length =
SEQUENCE: 2065
000

SEQ ID NO: 2066 moltype = length =
SEQUENCE: 2066
000

SEQ ID NO: 2067 moltype = length =
SEQUENCE: 2067
000

SEQ ID NO: 2068 moltype = length =
SEQUENCE: 2068
000

SEQ ID NO: 2069 moltype = length =
SEQUENCE: 2069
000

SEQ ID NO: 2070 moltype = length =
SEQUENCE: 2070
000

SEQ ID NO: 2071 moltype = length =
SEQUENCE: 2071
000

SEQ ID NO: 2072 moltype = length =
SEQUENCE: 2072
000

SEQ ID NO: 2073 moltype = length =
SEQUENCE: 2073
000

SEQ ID NO: 2074 moltype = length =
SEQUENCE: 2074
000

SEQ ID NO: 2075 moltype = length =
SEQUENCE: 2075
000

SEQ ID NO: 2076 moltype = length =
SEQUENCE: 2076
000

SEQ ID NO: 2077 moltype = length =
SEQUENCE: 2077
000

SEQ ID NO: 2078 moltype = length =
SEQUENCE: 2078
000

SEQ ID NO: 2079 moltype = length =
SEQUENCE: 2079
000

SEQ ID NO: 2080 moltype = length =
SEQUENCE: 2080
000

SEQ ID NO: 2081 moltype = length =
SEQUENCE: 2081
000

SEQ ID NO: 2082 moltype = length =
SEQUENCE: 2082
000

SEQ ID NO: 2083 moltype = length =
SEQUENCE: 2083
000

SEQ ID NO: 2084 moltype = length =
SEQUENCE: 2084
000

SEQ ID NO: 2085 moltype = length =
SEQUENCE: 2085
000

SEQ ID NO: 2086 moltype = length =
SEQUENCE: 2086
000

SEQ ID NO: 2087 moltype = length =
SEQUENCE: 2087
000

SEQ ID NO: 2088 moltype = length =
SEQUENCE: 2088
000

SEQ ID NO: 2089 moltype = length =
SEQUENCE: 2089
000

SEQ ID NO: 2090 moltype = length =
SEQUENCE: 2090
000

SEQ ID NO: 2091 moltype = length =
SEQUENCE: 2091

000

SEQ ID NO: 2092 moltype = length =
SEQUENCE: 2092
000

SEQ ID NO: 2093 moltype = length =
SEQUENCE: 2093
000

SEQ ID NO: 2094 moltype = length =
SEQUENCE: 2094
000

SEQ ID NO: 2095 moltype = length =
SEQUENCE: 2095
000

SEQ ID NO: 2096 moltype = length =
SEQUENCE: 2096
000

SEQ ID NO: 2097 moltype = length =
SEQUENCE: 2097
000

SEQ ID NO: 2098 moltype = length =
SEQUENCE: 2098
000

SEQ ID NO: 2099 moltype = length =
SEQUENCE: 2099
000

SEQ ID NO: 2100 moltype = length =
SEQUENCE: 2100
000

SEQ ID NO: 2101 moltype = length =
SEQUENCE: 2101
000

SEQ ID NO: 2102 moltype = length =
SEQUENCE: 2102
000

SEQ ID NO: 2103 moltype = length =
SEQUENCE: 2103
000

SEQ ID NO: 2104 moltype = length =
SEQUENCE: 2104
000

SEQ ID NO: 2105 moltype = length =
SEQUENCE: 2105
000

SEQ ID NO: 2106 moltype = length =
SEQUENCE: 2106
000

SEQ ID NO: 2107 moltype = length =
SEQUENCE: 2107
000

SEQ ID NO: 2108 moltype = length =
SEQUENCE: 2108
000

SEQ ID NO: 2109 moltype = length =
SEQUENCE: 2109
000

SEQ ID NO: 2110 moltype = length =
SEQUENCE: 2110
000

SEQ ID NO: 2111 moltype = length =

SEQUENCE: 2111
000

SEQ ID NO: 2112 moltype = length =
SEQUENCE: 2112
000

SEQ ID NO: 2113 moltype = length =
SEQUENCE: 2113
000

SEQ ID NO: 2114 moltype = length =
SEQUENCE: 2114
000

SEQ ID NO: 2115 moltype = length =
SEQUENCE: 2115
000

SEQ ID NO: 2116 moltype = length =
SEQUENCE: 2116
000

SEQ ID NO: 2117 moltype = length =
SEQUENCE: 2117
000

SEQ ID NO: 2118 moltype = length =
SEQUENCE: 2118
000

SEQ ID NO: 2119 moltype = length =
SEQUENCE: 2119
000

SEQ ID NO: 2120 moltype = length =
SEQUENCE: 2120
000

SEQ ID NO: 2121 moltype = length =
SEQUENCE: 2121
000

SEQ ID NO: 2122 moltype = length =
SEQUENCE: 2122
000

SEQ ID NO: 2123 moltype = length =
SEQUENCE: 2123
000

SEQ ID NO: 2124 moltype = length =
SEQUENCE: 2124
000

SEQ ID NO: 2125 moltype = length =
SEQUENCE: 2125
000

SEQ ID NO: 2126 moltype = length =
SEQUENCE: 2126
000

SEQ ID NO: 2127 moltype = length =
SEQUENCE: 2127
000

SEQ ID NO: 2128 moltype = length =
SEQUENCE: 2128
000

SEQ ID NO: 2129 moltype = length =
SEQUENCE: 2129
000

SEQ ID NO: 2130 moltype = length =
SEQUENCE: 2130
000

SEQ ID NO: 2131 moltype = length =
SEQUENCE: 2131
000

SEQ ID NO: 2132 moltype = length =
SEQUENCE: 2132
000

SEQ ID NO: 2133 moltype = length =
SEQUENCE: 2133
000

SEQ ID NO: 2134 moltype = length =
SEQUENCE: 2134
000

SEQ ID NO: 2135 moltype = length =
SEQUENCE: 2135
000

SEQ ID NO: 2136 moltype = length =
SEQUENCE: 2136
000

SEQ ID NO: 2137 moltype = length =
SEQUENCE: 2137
000

SEQ ID NO: 2138 moltype = length =
SEQUENCE: 2138
000

SEQ ID NO: 2139 moltype = length =
SEQUENCE: 2139
000

SEQ ID NO: 2140 moltype = length =
SEQUENCE: 2140
000

SEQ ID NO: 2141 moltype = length =
SEQUENCE: 2141
000

SEQ ID NO: 2142 moltype = length =
SEQUENCE: 2142
000

SEQ ID NO: 2143 moltype = length =
SEQUENCE: 2143
000

SEQ ID NO: 2144 moltype = length =
SEQUENCE: 2144
000

SEQ ID NO: 2145 moltype = length =
SEQUENCE: 2145
000

SEQ ID NO: 2146 moltype = length =
SEQUENCE: 2146
000

SEQ ID NO: 2147 moltype = length =
SEQUENCE: 2147
000

SEQ ID NO: 2148 moltype = length =
SEQUENCE: 2148
000

SEQ ID NO: 2149 moltype = length =
SEQUENCE: 2149
000

SEQ ID NO: 2150 moltype = length =
SEQUENCE: 2150
000

SEQ ID NO: 2151 moltype = length =
SEQUENCE: 2151
000

SEQ ID NO: 2152 moltype = length =
SEQUENCE: 2152
000

SEQ ID NO: 2153 moltype = length =
SEQUENCE: 2153
000

SEQ ID NO: 2154 moltype = length =
SEQUENCE: 2154
000

SEQ ID NO: 2155 moltype = length =
SEQUENCE: 2155
000

SEQ ID NO: 2156 moltype = length =
SEQUENCE: 2156
000

SEQ ID NO: 2157 moltype = length =
SEQUENCE: 2157
000

SEQ ID NO: 2158 moltype = length =
SEQUENCE: 2158
000

SEQ ID NO: 2159 moltype = length =
SEQUENCE: 2159
000

SEQ ID NO: 2160 moltype = length =
SEQUENCE: 2160
000

SEQ ID NO: 2161 moltype = length =
SEQUENCE: 2161
000

SEQ ID NO: 2162 moltype = length =
SEQUENCE: 2162
000

SEQ ID NO: 2163 moltype = length =
SEQUENCE: 2163
000

SEQ ID NO: 2164 moltype = length =
SEQUENCE: 2164
000

SEQ ID NO: 2165 moltype = length =
SEQUENCE: 2165
000

SEQ ID NO: 2166 moltype = length =
SEQUENCE: 2166
000

SEQ ID NO: 2167 moltype = length =
SEQUENCE: 2167
000

SEQ ID NO: 2168 moltype = length =
SEQUENCE: 2168
000

SEQ ID NO: 2169 moltype = length =
SEQUENCE: 2169
000

SEQ ID NO: 2170 moltype = AA length = 114
FEATURE Location/Qualifiers

```
source                  1..114
                        mol_type = protein
                        organism = Homo sapiens
SEQUENCE: 2170
NWVNVISDLK KIEDLIQSMH IDATLYTESD VHPSCKVTAM KCFLLELQVI SLESGDASIH  60
DTVENLIILA NNSLSSNGNV TESGCKECEE LEEKNIKEFL QSFVHIVQMF INTS        114

SEQ ID NO: 2171         moltype =   length =
SEQUENCE: 2171
000

SEQ ID NO: 2172         moltype =   length =
SEQUENCE: 2172
000

SEQ ID NO: 2173         moltype =   length =
SEQUENCE: 2173
000

SEQ ID NO: 2174         moltype =   length =
SEQUENCE: 2174
000

SEQ ID NO: 2175         moltype =   length =
SEQUENCE: 2175
000

SEQ ID NO: 2176         moltype =   length =
SEQUENCE: 2176
000

SEQ ID NO: 2177         moltype =   length =
SEQUENCE: 2177
000

SEQ ID NO: 2178         moltype =   length =
SEQUENCE: 2178
000

SEQ ID NO: 2179         moltype =   length =
SEQUENCE: 2179
000

SEQ ID NO: 2180         moltype = AA  length = 77
FEATURE                 Location/Qualifiers
source                  1..77
                        mol_type = protein
                        note = IL15Ralpha sequence
                        organism = unidentified
SEQUENCE: 2180
MAPRRARGCR TLGLPALLLL LLLRPPATRG ITCPPPMSVE HADIWVKSYS LYSRERYICN  60
SGFKRKAGTS SLTECVL                                                 77

SEQ ID NO: 2181         moltype =   length =
SEQUENCE: 2181
000

SEQ ID NO: 2182         moltype =   length =
SEQUENCE: 2182
000

SEQ ID NO: 2183         moltype =   length =
SEQUENCE: 2183
000

SEQ ID NO: 2184         moltype =   length =
SEQUENCE: 2184
000

SEQ ID NO: 2185         moltype =   length =
SEQUENCE: 2185
000

SEQ ID NO: 2186         moltype =   length =
SEQUENCE: 2186
000

SEQ ID NO: 2187         moltype =   length =
SEQUENCE: 2187
```

```
000

SEQ ID NO: 2188        moltype =   length =
SEQUENCE: 2188
000

SEQ ID NO: 2189        moltype =   length =
SEQUENCE: 2189
000

SEQ ID NO: 2190        moltype = AA  length = 20
FEATURE                Location/Qualifiers
source                 1..20
                       mol_type = protein
                       organism = synthetic construct
SEQUENCE: 2190
SGGSGGGGSG GGSGGGGSLQ                                              20

SEQ ID NO: 2191        moltype = AA  length = 133
FEATURE                Location/Qualifiers
source                 1..133
                       mol_type = protein
                       organism = Homo sapiens
SEQUENCE: 2191
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFCQSIIS TLT                                                     133

SEQ ID NO: 2192        moltype = AA  length = 157
FEATURE                Location/Qualifiers
source                 1..157
                       mol_type = protein
                       organism = Homo sapiens
SEQUENCE: 2192
YFGKLESKLS VIRNLNDQVL FIDQGNRPLF EDMTDSDCRD NAPRTIFIIS MYKDSQPRGM  60
AVTISVKCEK ISTLSCENKI ISFKEMNPPD NIKDTKSDII FFQRSVPGHD NKMQFESSSY  120
EGYFLACEKE RDLFKLILKK EDELGDRSIM FTVQNED                           157

SEQ ID NO: 2193        moltype = AA  length = 133
FEATURE                Location/Qualifiers
source                 1..133
                       mol_type = protein
                       organism = Homo sapiens
SEQUENCE: 2193
QGQDRHMIRM RQLIDIVDQL KNYVNDLVPE FLPAPEDVET NCEWSAFSCF QKAQLKSANT  60
GNNERIINVS IKKLKRKPPS TNAGRRQKHR LTCPSCDSYE KKPPKEFLER FKSLLQKMIH  120
QHLSSRTHGS EDS                                                     133

SEQ ID NO: 2194        moltype = AA  length = 138
FEATURE                Location/Qualifiers
source                 1..138
                       mol_type = protein
                       organism = Homo sapiens
SEQUENCE: 2194
QDPYVKEAEN LKKYFNAGHS DVADNGTLFL GILKNWKEES DRKIMQSQIV SFYFKLFKNF  60
KDDQSIQKSV ETIKEDMNVK FFNSNKKKRD DFEKLTNYSV TDLNVQRKAI HELIQVMAEL  120
SPAAKTGKRK RSQMLFRG                                                138

SEQ ID NO: 2195        moltype =   length =
SEQUENCE: 2195
000

SEQ ID NO: 2196        moltype =   length =
SEQUENCE: 2196
000

SEQ ID NO: 2197        moltype =   length =
SEQUENCE: 2197
000

SEQ ID NO: 2198        moltype =   length =
SEQUENCE: 2198
000

SEQ ID NO: 2199        moltype =   length =
SEQUENCE: 2199
000

SEQ ID NO: 2200        moltype =   length =
```

SEQUENCE: 2200
000

SEQ ID NO: 2201 moltype = length =
SEQUENCE: 2201
000

SEQ ID NO: 2202 moltype = length =
SEQUENCE: 2202
000

SEQ ID NO: 2203 moltype = length =
SEQUENCE: 2203
000

SEQ ID NO: 2204 moltype = length =
SEQUENCE: 2204
000

SEQ ID NO: 2205 moltype = length =
SEQUENCE: 2205
000

SEQ ID NO: 2206 moltype = length =
SEQUENCE: 2206
000

SEQ ID NO: 2207 moltype = length =
SEQUENCE: 2207
000

SEQ ID NO: 2208 moltype = length =
SEQUENCE: 2208
000

SEQ ID NO: 2209 moltype = length =
SEQUENCE: 2209
000

SEQ ID NO: 2210 moltype = length =
SEQUENCE: 2210
000

SEQ ID NO: 2211 moltype = length =
SEQUENCE: 2211
000

SEQ ID NO: 2212 moltype = length =
SEQUENCE: 2212
000

SEQ ID NO: 2213 moltype = length =
SEQUENCE: 2213
000

SEQ ID NO: 2214 moltype = length =
SEQUENCE: 2214
000

SEQ ID NO: 2215 moltype = length =
SEQUENCE: 2215
000

SEQ ID NO: 2216 moltype = length =
SEQUENCE: 2216
000

SEQ ID NO: 2217 moltype = length =
SEQUENCE: 2217
000

SEQ ID NO: 2218 moltype = length =
SEQUENCE: 2218
000

SEQ ID NO: 2219 moltype = length =
SEQUENCE: 2219
000

SEQ ID NO: 2220 moltype = length =
SEQUENCE: 2220
000

SEQ ID NO: 2221 moltype = length =
SEQUENCE: 2221
000

SEQ ID NO: 2222 moltype = length =
SEQUENCE: 2222
000

SEQ ID NO: 2223 moltype = length =
SEQUENCE: 2223
000

SEQ ID NO: 2224 moltype = length =
SEQUENCE: 2224
000

SEQ ID NO: 2225 moltype = length =
SEQUENCE: 2225
000

SEQ ID NO: 2226 moltype = length =
SEQUENCE: 2226
000

SEQ ID NO: 2227 moltype = length =
SEQUENCE: 2227
000

SEQ ID NO: 2228 moltype = length =
SEQUENCE: 2228
000

SEQ ID NO: 2229 moltype = length =
SEQUENCE: 2229
000

SEQ ID NO: 2230 moltype = length =
SEQUENCE: 2230
000

SEQ ID NO: 2231 moltype = length =
SEQUENCE: 2231
000

SEQ ID NO: 2232 moltype = length =
SEQUENCE: 2232
000

SEQ ID NO: 2233 moltype = length =
SEQUENCE: 2233
000

SEQ ID NO: 2234 moltype = length =
SEQUENCE: 2234
000

SEQ ID NO: 2235 moltype = length =
SEQUENCE: 2235
000

SEQ ID NO: 2236 moltype = length =
SEQUENCE: 2236
000

SEQ ID NO: 2237 moltype = length =
SEQUENCE: 2237
000

SEQ ID NO: 2238 moltype = length =
SEQUENCE: 2238
000

SEQ ID NO: 2239 moltype = length =
SEQUENCE: 2239
000

SEQ ID NO: 2240 moltype = length =
SEQUENCE: 2240
000

SEQ ID NO: 2241 moltype = length =
SEQUENCE: 2241
000

SEQ ID NO: 2242 moltype = length =
SEQUENCE: 2242
000

SEQ ID NO: 2243 moltype = length =
SEQUENCE: 2243
000

SEQ ID NO: 2244 moltype = length =
SEQUENCE: 2244
000

SEQ ID NO: 2245 moltype = length =
SEQUENCE: 2245
000

SEQ ID NO: 2246 moltype = length =
SEQUENCE: 2246
000

SEQ ID NO: 2247 moltype = length =
SEQUENCE: 2247
000

SEQ ID NO: 2248 moltype = length =
SEQUENCE: 2248
000

SEQ ID NO: 2249 moltype = length =
SEQUENCE: 2249
000

SEQ ID NO: 2250 moltype = length =
SEQUENCE: 2250
000

SEQ ID NO: 2251 moltype = length =
SEQUENCE: 2251
000

SEQ ID NO: 2252 moltype = length =
SEQUENCE: 2252
000

SEQ ID NO: 2253 moltype = length =
SEQUENCE: 2253
000

SEQ ID NO: 2254 moltype = length =
SEQUENCE: 2254
000

SEQ ID NO: 2255 moltype = length =
SEQUENCE: 2255
000

SEQ ID NO: 2256 moltype = length =
SEQUENCE: 2256
000

SEQ ID NO: 2257 moltype = length =
SEQUENCE: 2257
000

SEQ ID NO: 2258 moltype = length =
SEQUENCE: 2258
000

SEQ ID NO: 2259 moltype = length =
SEQUENCE: 2259

```
000

SEQ ID NO: 2260        moltype =   length =
SEQUENCE: 2260
000

SEQ ID NO: 2261        moltype =   length =
SEQUENCE: 2261
000

SEQ ID NO: 2262        moltype =   length =
SEQUENCE: 2262
000

SEQ ID NO: 2263        moltype =   length =
SEQUENCE: 2263
000

SEQ ID NO: 2264        moltype =   length =
SEQUENCE: 2264
000

SEQ ID NO: 2265        moltype =   length =
SEQUENCE: 2265
000

SEQ ID NO: 2266        moltype =   length =
SEQUENCE: 2266
000

SEQ ID NO: 2267        moltype =   length =
SEQUENCE: 2267
000

SEQ ID NO: 2268        moltype =   length =
SEQUENCE: 2268
000

SEQ ID NO: 2269        moltype =   length =
SEQUENCE: 2269
000

SEQ ID NO: 2270        moltype = AA  length = 133
FEATURE                Location/Qualifiers
source                 1..133
                       mol_type = protein
                       note = IL-2 cytokine sequence
                       organism = unidentified
SEQUENCE: 2270
APTSSSTKKT QLQLEHLLLD LQMILNGINN YKNPKLTRML TFKFYMPKKA TELKHLQCLE  60
EELKPLEEVL NLAQSKNFHL RPRDLISNIN VIVLELKGSE TTFMCEYADE TATIVEFLNR  120
WITFAQSIIS TLT                                                     133

SEQ ID NO: 2271        moltype =   length =
SEQUENCE: 2271
000

SEQ ID NO: 2272        moltype =   length =
SEQUENCE: 2272
000

SEQ ID NO: 2273        moltype =   length =
SEQUENCE: 2273
000

SEQ ID NO: 2274        moltype =   length =
SEQUENCE: 2274
000

SEQ ID NO: 2275        moltype =   length =
SEQUENCE: 2275
000

SEQ ID NO: 2276        moltype =   length =
SEQUENCE: 2276
000

SEQ ID NO: 2277        moltype =   length =
SEQUENCE: 2277
```

```
000

SEQ ID NO: 2278        moltype =   length =
SEQUENCE: 2278
000

SEQ ID NO: 2279        moltype =   length =
SEQUENCE: 2279
000

SEQ ID NO: 2280        moltype = AA  length = 133
FEATURE                Location/Qualifiers
source                 1..133
                       mol_type = protein
                       note = IL-2 cytokine sequence
                       organism = unidentified
SEQUENCE: 2280
APASSSTKKT QLQLEHLLLD LQMILNGINN YKNPKLTRML TAKFAMPKKA TELKHLQCLE  60
EELKPLEEVL NGAQSKNFHL RPRDLISNIN VIVLELKGSE TTFMCEYADE TATIVEFLNR  120
WITFAQSIIS TLT                                                     133

SEQ ID NO: 2281        moltype =   length =
SEQUENCE: 2281
000

SEQ ID NO: 2282        moltype =   length =
SEQUENCE: 2282
000

SEQ ID NO: 2283        moltype =   length =
SEQUENCE: 2283
000

SEQ ID NO: 2284        moltype =   length =
SEQUENCE: 2284
000

SEQ ID NO: 2285        moltype =   length =
SEQUENCE: 2285
000

SEQ ID NO: 2286        moltype =   length =
SEQUENCE: 2286
000

SEQ ID NO: 2287        moltype =   length =
SEQUENCE: 2287
000

SEQ ID NO: 2288        moltype =   length =
SEQUENCE: 2288
000

SEQ ID NO: 2289        moltype =   length =
SEQUENCE: 2289
000

SEQ ID NO: 2290        moltype = AA  length = 518
FEATURE                Location/Qualifiers
source                 1..518
                       mol_type = protein
                       organism = synthetic construct
SEQUENCE: 2290
IWELKKDVYV VELDWYPDAP GEMVVLTCDT PEEDGITWTL DQSSEVLGSG KTLTIQVKEF  60
GDAGQYTCHK GGEVLSHSLL LLHKKEDGIW STDILKDQKE PKNKTFLRCE AKNYSGRFTC  120
WWLTTISTDL TFSVKSSRGS SDPQGVTCGA ATLSAERVRG DNKEYEYSVE CQEDSACPAA  180
EESLPIEVMV DAVHKLKYEN YTSSFFIRDI IKPDPPKNLQ LKPLKNSRQV EVSWEYPDTW  240
STPHSYFSLT FCVQVQGKSK REKKDRVFTD KTSATVICRK NASISVRAQD RYYSSSWSEW  300
ASVPCSGGGG SGGGGSGGGG SRNLPVATPD PGMFPCLHHS QNLLRAVSNM LQKARQTLEF  360
YPCTSEEIDH EDITKDKTST VEACLPLELT KNESCLNSRE TSFITNGSCL ASRKTSFMMA  420
LCLSSIYEDL KMYQVEFKTM NAKLLMDPKR QIFLDQNMLA VIDELMQALN FNSETVPQKS  480
SLEEPDFYKT KIKLCILLHA FRIRAVTIDR VMSYLNAS                          518

SEQ ID NO: 2291        moltype =   length =
SEQUENCE: 2291
000

SEQ ID NO: 2292        moltype =   length =
SEQUENCE: 2292
```

```
000

SEQ ID NO: 2293        moltype =   length =
SEQUENCE: 2293
000

SEQ ID NO: 2294        moltype =   length =
SEQUENCE: 2294
000

SEQ ID NO: 2295        moltype =   length =
SEQUENCE: 2295
000

SEQ ID NO: 2296        moltype =   length =
SEQUENCE: 2296
000

SEQ ID NO: 2297        moltype =   length =
SEQUENCE: 2297
000

SEQ ID NO: 2298        moltype =   length =
SEQUENCE: 2298
000

SEQ ID NO: 2299        moltype =   length =
SEQUENCE: 2299
000

SEQ ID NO: 2300        moltype = AA  length = 340
FEATURE                Location/Qualifiers
source                 1..340
                       mol_type = protein
                       organism = synthetic construct
SEQUENCE: 2300
SPGQGTQSEN SCTHFPGNLP NMLRDLRDAF SRVKTFFQMK DQLDNLLLKE SLLEDFKGYL  60
GCQALSEMIQ FYLEEVMPQA ENQDPDIKAH VNSLGENLKT LRLRLRRCHR FLPCENKSKA  120
VEQVKNAFNK LQEKGIYKAM SEFDIFINYI EAYMTMKIRN GGGGSGGGGS GGGGSGGGGS  180
SPGQGTQSEN SCTHFPGNLP NMLRDLRDAF SRVKTFFQMK DQLDNLLLKE SLLEDFKGYL  240
GCQALSEMIQ FYLEEVMPQA ENQDPDIKAH VNSLGENLKT LRLRLRRCHR FLPCENKSKA  300
VEQVKNAFNK LQEKGIYKAM SEFDIFINYI EAYMTMKIRN                       340

SEQ ID NO: 2301        moltype =   length =
SEQUENCE: 2301
000

SEQ ID NO: 2302        moltype =   length =
SEQUENCE: 2302
000

SEQ ID NO: 2303        moltype =   length =
SEQUENCE: 2303
000

SEQ ID NO: 2304        moltype =   length =
SEQUENCE: 2304
000

SEQ ID NO: 2305        moltype =   length =
SEQUENCE: 2305
000

SEQ ID NO: 2306        moltype =   length =
SEQUENCE: 2306
000

SEQ ID NO: 2307        moltype =   length =
SEQUENCE: 2307
000

SEQ ID NO: 2308        moltype =   length =
SEQUENCE: 2308
000

SEQ ID NO: 2309        moltype =   length =
SEQUENCE: 2309
000
```

```
SEQ ID NO: 2310        moltype = AA  length = 166
FEATURE                Location/Qualifiers
source                 1..166
                       mol_type = protein
                       note = IL-10 cytokine sequence
                       organism = unidentified
SEQUENCE: 2310
SPGQGTQSEN SCTHFPGNLP NMLRDLRDAF SRVKTFFQMK DQLDNLLLKE SLLEDFKGYL  60
GCQALSEMIQ FYLEEVMPQA ENQDPDIKAH VNSLGENLKT LRLRLRRCHR FLPCENGGGS  120
GGKSKAVEQV KNAFNKLQEK GIYKAMSEFD IFINYIEAYM TMKIRN                 166

SEQ ID NO: 2311        moltype =   length =
SEQUENCE: 2311
000

SEQ ID NO: 2312        moltype =   length =
SEQUENCE: 2312
000

SEQ ID NO: 2313        moltype =   length =
SEQUENCE: 2313
000

SEQ ID NO: 2314        moltype =   length =
SEQUENCE: 2314
000

SEQ ID NO: 2315        moltype =   length =
SEQUENCE: 2315
000

SEQ ID NO: 2316        moltype =   length =
SEQUENCE: 2316
000

SEQ ID NO: 2317        moltype =   length =
SEQUENCE: 2317
000

SEQ ID NO: 2318        moltype =   length =
SEQUENCE: 2318
000

SEQ ID NO: 2319        moltype =   length =
SEQUENCE: 2319
000

SEQ ID NO: 2320        moltype = AA  length = 114
FEATURE                Location/Qualifiers
source                 1..114
                       mol_type = protein
                       note = IL-15 cytokine sequence
                       organism = unidentified
SEQUENCE: 2320
NWVNVISDLK KIEDLIQSMH IDATLYTESD VHPSCKVTAM KCFLLELQVI SLASGDASIH  60
DTVENLIILA NNSLSSNGAV TESGCKECEE LEEKNIKEFL QSFVHIVQMF INTS        114

SEQ ID NO: 2321        moltype =   length =
SEQUENCE: 2321
000

SEQ ID NO: 2322        moltype =   length =
SEQUENCE: 2322
000

SEQ ID NO: 2323        moltype =   length =
SEQUENCE: 2323
000

SEQ ID NO: 2324        moltype =   length =
SEQUENCE: 2324
000

SEQ ID NO: 2325        moltype =   length =
SEQUENCE: 2325
000

SEQ ID NO: 2326        moltype =   length =
SEQUENCE: 2326
```

000

SEQ ID NO: 2327 moltype = length =
SEQUENCE: 2327
000

SEQ ID NO: 2328 moltype = length =
SEQUENCE: 2328
000

SEQ ID NO: 2329 moltype = length =
SEQUENCE: 2329
000

SEQ ID NO: 2330 moltype = length =
SEQUENCE: 2330
000

SEQ ID NO: 2331 moltype = length =
SEQUENCE: 2331
000

SEQ ID NO: 2332 moltype = length =
SEQUENCE: 2332
000

SEQ ID NO: 2333 moltype = length =
SEQUENCE: 2333
000

SEQ ID NO: 2334 moltype = length =
SEQUENCE: 2334
000

SEQ ID NO: 2335 moltype = length =
SEQUENCE: 2335
000

SEQ ID NO: 2336 moltype = length =
SEQUENCE: 2336
000

SEQ ID NO: 2337 moltype = length =
SEQUENCE: 2337
000

SEQ ID NO: 2338 moltype = length =
SEQUENCE: 2338
000

SEQ ID NO: 2339 moltype = length =
SEQUENCE: 2339
000

SEQ ID NO: 2340 moltype = length =
SEQUENCE: 2340
000

SEQ ID NO: 2341 moltype = length =
SEQUENCE: 2341
000

SEQ ID NO: 2342 moltype = length =
SEQUENCE: 2342
000

SEQ ID NO: 2343 moltype = length =
SEQUENCE: 2343
000

SEQ ID NO: 2344 moltype = length =
SEQUENCE: 2344
000

SEQ ID NO: 2345 moltype = length =
SEQUENCE: 2345
000

SEQ ID NO: 2346 moltype = length =

SEQUENCE: 2346
000

SEQ ID NO: 2347 moltype = length =
SEQUENCE: 2347
000

SEQ ID NO: 2348 moltype = length =
SEQUENCE: 2348
000

SEQ ID NO: 2349 moltype = length =
SEQUENCE: 2349
000

SEQ ID NO: 2350 moltype = length =
SEQUENCE: 2350
000

SEQ ID NO: 2351 moltype = length =
SEQUENCE: 2351
000

SEQ ID NO: 2352 moltype = length =
SEQUENCE: 2352
000

SEQ ID NO: 2353 moltype = length =
SEQUENCE: 2353
000

SEQ ID NO: 2354 moltype = length =
SEQUENCE: 2354
000

SEQ ID NO: 2355 moltype = length =
SEQUENCE: 2355
000

SEQ ID NO: 2356 moltype = length =
SEQUENCE: 2356
000

SEQ ID NO: 2357 moltype = length =
SEQUENCE: 2357
000

SEQ ID NO: 2358 moltype = length =
SEQUENCE: 2358
000

SEQ ID NO: 2359 moltype = length =
SEQUENCE: 2359
000

SEQ ID NO: 2360 moltype = length =
SEQUENCE: 2360
000

SEQ ID NO: 2361 moltype = length =
SEQUENCE: 2361
000

SEQ ID NO: 2362 moltype = length =
SEQUENCE: 2362
000

SEQ ID NO: 2363 moltype = length =
SEQUENCE: 2363
000

SEQ ID NO: 2364 moltype = length =
SEQUENCE: 2364
000

SEQ ID NO: 2365 moltype = length =
SEQUENCE: 2365
000

SEQ ID NO: 2366 moltype = length =
SEQUENCE: 2366
000

SEQ ID NO: 2367 moltype = length =
SEQUENCE: 2367
000

SEQ ID NO: 2368 moltype = length =
SEQUENCE: 2368
000

SEQ ID NO: 2369 moltype = length =
SEQUENCE: 2369
000

SEQ ID NO: 2370 moltype = length =
SEQUENCE: 2370
000

SEQ ID NO: 2371 moltype = length =
SEQUENCE: 2371
000

SEQ ID NO: 2372 moltype = length =
SEQUENCE: 2372
000

SEQ ID NO: 2373 moltype = length =
SEQUENCE: 2373
000

SEQ ID NO: 2374 moltype = length =
SEQUENCE: 2374
000

SEQ ID NO: 2375 moltype = length =
SEQUENCE: 2375
000

SEQ ID NO: 2376 moltype = length =
SEQUENCE: 2376
000

SEQ ID NO: 2377 moltype = length =
SEQUENCE: 2377
000

SEQ ID NO: 2378 moltype = length =
SEQUENCE: 2378
000

SEQ ID NO: 2379 moltype = length =
SEQUENCE: 2379
000

SEQ ID NO: 2380 moltype = length =
SEQUENCE: 2380
000

SEQ ID NO: 2381 moltype = length =
SEQUENCE: 2381
000

SEQ ID NO: 2382 moltype = length =
SEQUENCE: 2382
000

SEQ ID NO: 2383 moltype = length =
SEQUENCE: 2383
000

SEQ ID NO: 2384 moltype = length =
SEQUENCE: 2384
000

SEQ ID NO: 2385 moltype = length =
SEQUENCE: 2385
000

SEQ ID NO: 2386 moltype = length =
SEQUENCE: 2386
000

SEQ ID NO: 2387 moltype = length =
SEQUENCE: 2387
000

SEQ ID NO: 2388 moltype = length =
SEQUENCE: 2388
000

SEQ ID NO: 2389 moltype = length =
SEQUENCE: 2389
000

SEQ ID NO: 2390 moltype = length =
SEQUENCE: 2390
000

SEQ ID NO: 2391 moltype = length =
SEQUENCE: 2391
000

SEQ ID NO: 2392 moltype = length =
SEQUENCE: 2392
000

SEQ ID NO: 2393 moltype = length =
SEQUENCE: 2393
000

SEQ ID NO: 2394 moltype = length =
SEQUENCE: 2394
000

SEQ ID NO: 2395 moltype = length =
SEQUENCE: 2395
000

SEQ ID NO: 2396 moltype = length =
SEQUENCE: 2396
000

SEQ ID NO: 2397 moltype = length =
SEQUENCE: 2397
000

SEQ ID NO: 2398 moltype = length =
SEQUENCE: 2398
000

SEQ ID NO: 2399 moltype = length =
SEQUENCE: 2399
000

SEQ ID NO: 2400 moltype = length =
SEQUENCE: 2400
000

SEQ ID NO: 2401 moltype = length =
SEQUENCE: 2401
000

SEQ ID NO: 2402 moltype = length =
SEQUENCE: 2402
000

SEQ ID NO: 2403 moltype = length =
SEQUENCE: 2403
000

SEQ ID NO: 2404 moltype = length =
SEQUENCE: 2404
000

SEQ ID NO: 2405 moltype = length =
SEQUENCE: 2405

000

SEQ ID NO: 2406 moltype = length =
SEQUENCE: 2406
000

SEQ ID NO: 2407 moltype = length =
SEQUENCE: 2407
000

SEQ ID NO: 2408 moltype = length =
SEQUENCE: 2408
000

SEQ ID NO: 2409 moltype = length =
SEQUENCE: 2409
000

SEQ ID NO: 2410 moltype = length =
SEQUENCE: 2410
000

SEQ ID NO: 2411 moltype = length =
SEQUENCE: 2411
000

SEQ ID NO: 2412 moltype = length =
SEQUENCE: 2412
000

SEQ ID NO: 2413 moltype = length =
SEQUENCE: 2413
000

SEQ ID NO: 2414 moltype = length =
SEQUENCE: 2414
000

SEQ ID NO: 2415 moltype = length =
SEQUENCE: 2415
000

SEQ ID NO: 2416 moltype = length =
SEQUENCE: 2416
000

SEQ ID NO: 2417 moltype = length =
SEQUENCE: 2417
000

SEQ ID NO: 2418 moltype = length =
SEQUENCE: 2418
000

SEQ ID NO: 2419 moltype = length =
SEQUENCE: 2419
000

SEQ ID NO: 2420 moltype = length =
SEQUENCE: 2420
000

SEQ ID NO: 2421 moltype = length =
SEQUENCE: 2421
000

SEQ ID NO: 2422 moltype = length =
SEQUENCE: 2422
000

SEQ ID NO: 2423 moltype = length =
SEQUENCE: 2423
000

SEQ ID NO: 2424 moltype = length =
SEQUENCE: 2424
000

SEQ ID NO: 2425 moltype = length =

SEQUENCE: 2425
000

SEQ ID NO: 2426 moltype = length =
SEQUENCE: 2426
000

SEQ ID NO: 2427 moltype = length =
SEQUENCE: 2427
000

SEQ ID NO: 2428 moltype = length =
SEQUENCE: 2428
000

SEQ ID NO: 2429 moltype = length =
SEQUENCE: 2429
000

SEQ ID NO: 2430 moltype = length =
SEQUENCE: 2430
000

SEQ ID NO: 2431 moltype = length =
SEQUENCE: 2431
000

SEQ ID NO: 2432 moltype = length =
SEQUENCE: 2432
000

SEQ ID NO: 2433 moltype = length =
SEQUENCE: 2433
000

SEQ ID NO: 2434 moltype = length =
SEQUENCE: 2434
000

SEQ ID NO: 2435 moltype = length =
SEQUENCE: 2435
000

SEQ ID NO: 2436 moltype = length =
SEQUENCE: 2436
000

SEQ ID NO: 2437 moltype = length =
SEQUENCE: 2437
000

SEQ ID NO: 2438 moltype = length =
SEQUENCE: 2438
000

SEQ ID NO: 2439 moltype = length =
SEQUENCE: 2439
000

SEQ ID NO: 2440 moltype = length =
SEQUENCE: 2440
000

SEQ ID NO: 2441 moltype = length =
SEQUENCE: 2441
000

SEQ ID NO: 2442 moltype = length =
SEQUENCE: 2442
000

SEQ ID NO: 2443 moltype = length =
SEQUENCE: 2443
000

SEQ ID NO: 2444 moltype = length =
SEQUENCE: 2444
000

SEQ ID NO: 2445 moltype = length =
SEQUENCE: 2445
000

SEQ ID NO: 2446 moltype = length =
SEQUENCE: 2446
000

SEQ ID NO: 2447 moltype = length =
SEQUENCE: 2447
000

SEQ ID NO: 2448 moltype = length =
SEQUENCE: 2448
000

SEQ ID NO: 2449 moltype = length =
SEQUENCE: 2449
000

SEQ ID NO: 2450 moltype = length =
SEQUENCE: 2450
000

SEQ ID NO: 2451 moltype = length =
SEQUENCE: 2451
000

SEQ ID NO: 2452 moltype = length =
SEQUENCE: 2452
000

SEQ ID NO: 2453 moltype = length =
SEQUENCE: 2453
000

SEQ ID NO: 2454 moltype = length =
SEQUENCE: 2454
000

SEQ ID NO: 2455 moltype = length =
SEQUENCE: 2455
000

SEQ ID NO: 2456 moltype = length =
SEQUENCE: 2456
000

SEQ ID NO: 2457 moltype = length =
SEQUENCE: 2457
000

SEQ ID NO: 2458 moltype = length =
SEQUENCE: 2458
000

SEQ ID NO: 2459 moltype = length =
SEQUENCE: 2459
000

SEQ ID NO: 2460 moltype = length =
SEQUENCE: 2460
000

SEQ ID NO: 2461 moltype = length =
SEQUENCE: 2461
000

SEQ ID NO: 2462 moltype = length =
SEQUENCE: 2462
000

SEQ ID NO: 2463 moltype = length =
SEQUENCE: 2463
000

SEQ ID NO: 2464 moltype = length =
SEQUENCE: 2464
000

SEQ ID NO: 2465 moltype = length =
SEQUENCE: 2465
000

SEQ ID NO: 2466 moltype = length =
SEQUENCE: 2466
000

SEQ ID NO: 2467 moltype = length =
SEQUENCE: 2467
000

SEQ ID NO: 2468 moltype = length =
SEQUENCE: 2468
000

SEQ ID NO: 2469 moltype = length =
SEQUENCE: 2469
000

SEQ ID NO: 2470 moltype = length =
SEQUENCE: 2470
000

SEQ ID NO: 2471 moltype = length =
SEQUENCE: 2471
000

SEQ ID NO: 2472 moltype = length =
SEQUENCE: 2472
000

SEQ ID NO: 2473 moltype = length =
SEQUENCE: 2473
000

SEQ ID NO: 2474 moltype = length =
SEQUENCE: 2474
000

SEQ ID NO: 2475 moltype = length =
SEQUENCE: 2475
000

SEQ ID NO: 2476 moltype = length =
SEQUENCE: 2476
000

SEQ ID NO: 2477 moltype = length =
SEQUENCE: 2477
000

SEQ ID NO: 2478 moltype = length =
SEQUENCE: 2478
000

SEQ ID NO: 2479 moltype = length =
SEQUENCE: 2479
000

SEQ ID NO: 2480 moltype = length =
SEQUENCE: 2480
000

SEQ ID NO: 2481 moltype = length =
SEQUENCE: 2481
000

SEQ ID NO: 2482 moltype = length =
SEQUENCE: 2482
000

SEQ ID NO: 2483 moltype = length =
SEQUENCE: 2483
000

SEQ ID NO: 2484 moltype = length =
SEQUENCE: 2484

000

SEQ ID NO: 2485 moltype = length =
SEQUENCE: 2485
000

SEQ ID NO: 2486 moltype = length =
SEQUENCE: 2486
000

SEQ ID NO: 2487 moltype = length =
SEQUENCE: 2487
000

SEQ ID NO: 2488 moltype = length =
SEQUENCE: 2488
000

SEQ ID NO: 2489 moltype = length =
SEQUENCE: 2489
000

SEQ ID NO: 2490 moltype = length =
SEQUENCE: 2490
000

SEQ ID NO: 2491 moltype = length =
SEQUENCE: 2491
000

SEQ ID NO: 2492 moltype = length =
SEQUENCE: 2492
000

SEQ ID NO: 2493 moltype = length =
SEQUENCE: 2493
000

SEQ ID NO: 2494 moltype = length =
SEQUENCE: 2494
000

SEQ ID NO: 2495 moltype = length =
SEQUENCE: 2495
000

SEQ ID NO: 2496 moltype = length =
SEQUENCE: 2496
000

SEQ ID NO: 2497 moltype = length =
SEQUENCE: 2497
000

SEQ ID NO: 2498 moltype = length =
SEQUENCE: 2498
000

SEQ ID NO: 2499 moltype = length =
SEQUENCE: 2499
000

SEQ ID NO: 2500 moltype = length =
SEQUENCE: 2500
000

SEQ ID NO: 2501 moltype = length =
SEQUENCE: 2501
000

SEQ ID NO: 2502 moltype = length =
SEQUENCE: 2502
000

SEQ ID NO: 2503 moltype = length =
SEQUENCE: 2503
000

SEQ ID NO: 2504 moltype = length =

SEQUENCE: 2504
000

SEQ ID NO: 2505 moltype = length =
SEQUENCE: 2505
000

SEQ ID NO: 2506 moltype = length =
SEQUENCE: 2506
000

SEQ ID NO: 2507 moltype = length =
SEQUENCE: 2507
000

SEQ ID NO: 2508 moltype = length =
SEQUENCE: 2508
000

SEQ ID NO: 2509 moltype = length =
SEQUENCE: 2509
000

SEQ ID NO: 2510 moltype = length =
SEQUENCE: 2510
000

SEQ ID NO: 2511 moltype = length =
SEQUENCE: 2511
000

SEQ ID NO: 2512 moltype = length =
SEQUENCE: 2512
000

SEQ ID NO: 2513 moltype = length =
SEQUENCE: 2513
000

SEQ ID NO: 2514 moltype = length =
SEQUENCE: 2514
000

SEQ ID NO: 2515 moltype = length =
SEQUENCE: 2515
000

SEQ ID NO: 2516 moltype = length =
SEQUENCE: 2516
000

SEQ ID NO: 2517 moltype = length =
SEQUENCE: 2517
000

SEQ ID NO: 2518 moltype = length =
SEQUENCE: 2518
000

SEQ ID NO: 2519 moltype = length =
SEQUENCE: 2519
000

SEQ ID NO: 2520 moltype = length =
SEQUENCE: 2520
000

SEQ ID NO: 2521 moltype = length =
SEQUENCE: 2521
000

SEQ ID NO: 2522 moltype = length =
SEQUENCE: 2522
000

SEQ ID NO: 2523 moltype = length =
SEQUENCE: 2523
000

SEQ ID NO: 2524 moltype = length =
SEQUENCE: 2524
000

SEQ ID NO: 2525 moltype = length =
SEQUENCE: 2525
000

SEQ ID NO: 2526 moltype = length =
SEQUENCE: 2526
000

SEQ ID NO: 2527 moltype = length =
SEQUENCE: 2527
000

SEQ ID NO: 2528 moltype = length =
SEQUENCE: 2528
000

SEQ ID NO: 2529 moltype = length =
SEQUENCE: 2529
000

SEQ ID NO: 2530 moltype = length =
SEQUENCE: 2530
000

SEQ ID NO: 2531 moltype = length =
SEQUENCE: 2531
000

SEQ ID NO: 2532 moltype = length =
SEQUENCE: 2532
000

SEQ ID NO: 2533 moltype = length =
SEQUENCE: 2533
000

SEQ ID NO: 2534 moltype = length =
SEQUENCE: 2534
000

SEQ ID NO: 2535 moltype = length =
SEQUENCE: 2535
000

SEQ ID NO: 2536 moltype = length =
SEQUENCE: 2536
000

SEQ ID NO: 2537 moltype = length =
SEQUENCE: 2537
000

SEQ ID NO: 2538 moltype = length =
SEQUENCE: 2538
000

SEQ ID NO: 2539 moltype = length =
SEQUENCE: 2539
000

SEQ ID NO: 2540 moltype = length =
SEQUENCE: 2540
000

SEQ ID NO: 2541 moltype = length =
SEQUENCE: 2541
000

SEQ ID NO: 2542 moltype = length =
SEQUENCE: 2542
000

SEQ ID NO: 2543 moltype = length =
SEQUENCE: 2543
000

SEQ ID NO: 2544 moltype = length =
SEQUENCE: 2544
000

SEQ ID NO: 2545 moltype = length =
SEQUENCE: 2545
000

SEQ ID NO: 2546 moltype = length =
SEQUENCE: 2546
000

SEQ ID NO: 2547 moltype = length =
SEQUENCE: 2547
000

SEQ ID NO: 2548 moltype = length =
SEQUENCE: 2548
000

SEQ ID NO: 2549 moltype = length =
SEQUENCE: 2549
000

SEQ ID NO: 2550 moltype = length =
SEQUENCE: 2550
000

SEQ ID NO: 2551 moltype = length =
SEQUENCE: 2551
000

SEQ ID NO: 2552 moltype = length =
SEQUENCE: 2552
000

SEQ ID NO: 2553 moltype = length =
SEQUENCE: 2553
000

SEQ ID NO: 2554 moltype = length =
SEQUENCE: 2554
000

SEQ ID NO: 2555 moltype = length =
SEQUENCE: 2555
000

SEQ ID NO: 2556 moltype = length =
SEQUENCE: 2556
000

SEQ ID NO: 2557 moltype = length =
SEQUENCE: 2557
000

SEQ ID NO: 2558 moltype = length =
SEQUENCE: 2558
000

SEQ ID NO: 2559 moltype = length =
SEQUENCE: 2559
000

SEQ ID NO: 2560 moltype = length =
SEQUENCE: 2560
000

SEQ ID NO: 2561 moltype = length =
SEQUENCE: 2561
000

SEQ ID NO: 2562 moltype = length =
SEQUENCE: 2562
000

SEQ ID NO: 2563 moltype = length =
SEQUENCE: 2563

000

SEQ ID NO: 2564 moltype = length =
SEQUENCE: 2564
000

SEQ ID NO: 2565 moltype = length =
SEQUENCE: 2565
000

SEQ ID NO: 2566 moltype = length =
SEQUENCE: 2566
000

SEQ ID NO: 2567 moltype = length =
SEQUENCE: 2567
000

SEQ ID NO: 2568 moltype = length =
SEQUENCE: 2568
000

SEQ ID NO: 2569 moltype = length =
SEQUENCE: 2569
000

SEQ ID NO: 2570 moltype = length =
SEQUENCE: 2570
000

SEQ ID NO: 2571 moltype = length =
SEQUENCE: 2571
000

SEQ ID NO: 2572 moltype = length =
SEQUENCE: 2572
000

SEQ ID NO: 2573 moltype = length =
SEQUENCE: 2573
000

SEQ ID NO: 2574 moltype = length =
SEQUENCE: 2574
000

SEQ ID NO: 2575 moltype = length =
SEQUENCE: 2575
000

SEQ ID NO: 2576 moltype = length =
SEQUENCE: 2576
000

SEQ ID NO: 2577 moltype = length =
SEQUENCE: 2577
000

SEQ ID NO: 2578 moltype = length =
SEQUENCE: 2578
000

SEQ ID NO: 2579 moltype = length =
SEQUENCE: 2579
000

SEQ ID NO: 2580 moltype = length =
SEQUENCE: 2580
000

SEQ ID NO: 2581 moltype = length =
SEQUENCE: 2581
000

SEQ ID NO: 2582 moltype = length =
SEQUENCE: 2582
000

SEQ ID NO: 2583 moltype = length =

SEQUENCE: 2583
000

SEQ ID NO: 2584 moltype = length =
SEQUENCE: 2584
000

SEQ ID NO: 2585 moltype = length =
SEQUENCE: 2585
000

SEQ ID NO: 2586 moltype = length =
SEQUENCE: 2586
000

SEQ ID NO: 2587 moltype = length =
SEQUENCE: 2587
000

SEQ ID NO: 2588 moltype = length =
SEQUENCE: 2588
000

SEQ ID NO: 2589 moltype = length =
SEQUENCE: 2589
000

SEQ ID NO: 2590 moltype = length =
SEQUENCE: 2590
000

SEQ ID NO: 2591 moltype = length =
SEQUENCE: 2591
000

SEQ ID NO: 2592 moltype = length =
SEQUENCE: 2592
000

SEQ ID NO: 2593 moltype = length =
SEQUENCE: 2593
000

SEQ ID NO: 2594 moltype = length =
SEQUENCE: 2594
000

SEQ ID NO: 2595 moltype = length =
SEQUENCE: 2595
000

SEQ ID NO: 2596 moltype = length =
SEQUENCE: 2596
000

SEQ ID NO: 2597 moltype = length =
SEQUENCE: 2597
000

SEQ ID NO: 2598 moltype = length =
SEQUENCE: 2598
000

SEQ ID NO: 2599 moltype = length =
SEQUENCE: 2599
000

SEQ ID NO: 2600 moltype = length =
SEQUENCE: 2600
000

SEQ ID NO: 2601 moltype = length =
SEQUENCE: 2601
000

SEQ ID NO: 2602 moltype = length =
SEQUENCE: 2602
000

SEQ ID NO: 2603 moltype = length =
SEQUENCE: 2603
000

SEQ ID NO: 2604 moltype = length =
SEQUENCE: 2604
000

SEQ ID NO: 2605 moltype = length =
SEQUENCE: 2605
000

SEQ ID NO: 2606 moltype = length =
SEQUENCE: 2606
000

SEQ ID NO: 2607 moltype = length =
SEQUENCE: 2607
000

SEQ ID NO: 2608 moltype = length =
SEQUENCE: 2608
000

SEQ ID NO: 2609 moltype = length =
SEQUENCE: 2609
000

SEQ ID NO: 2610 moltype = length =
SEQUENCE: 2610
000

SEQ ID NO: 2611 moltype = length =
SEQUENCE: 2611
000

SEQ ID NO: 2612 moltype = length =
SEQUENCE: 2612
000

SEQ ID NO: 2613 moltype = length =
SEQUENCE: 2613
000

SEQ ID NO: 2614 moltype = length =
SEQUENCE: 2614
000

SEQ ID NO: 2615 moltype = length =
SEQUENCE: 2615
000

SEQ ID NO: 2616 moltype = length =
SEQUENCE: 2616
000

SEQ ID NO: 2617 moltype = length =
SEQUENCE: 2617
000

SEQ ID NO: 2618 moltype = length =
SEQUENCE: 2618
000

SEQ ID NO: 2619 moltype = length =
SEQUENCE: 2619
000

SEQ ID NO: 2620 moltype = length =
SEQUENCE: 2620
000

SEQ ID NO: 2621 moltype = length =
SEQUENCE: 2621
000

SEQ ID NO: 2622 moltype = length =
SEQUENCE: 2622
000

SEQ ID NO: 2623 moltype = length =
SEQUENCE: 2623
000

SEQ ID NO: 2624 moltype = length =
SEQUENCE: 2624
000

SEQ ID NO: 2625 moltype = length =
SEQUENCE: 2625
000

SEQ ID NO: 2626 moltype = length =
SEQUENCE: 2626
000

SEQ ID NO: 2627 moltype = length =
SEQUENCE: 2627
000

SEQ ID NO: 2628 moltype = length =
SEQUENCE: 2628
000

SEQ ID NO: 2629 moltype = length =
SEQUENCE: 2629
000

SEQ ID NO: 2630 moltype = length =
SEQUENCE: 2630
000

SEQ ID NO: 2631 moltype = length =
SEQUENCE: 2631
000

SEQ ID NO: 2632 moltype = length =
SEQUENCE: 2632
000

SEQ ID NO: 2633 moltype = length =
SEQUENCE: 2633
000

SEQ ID NO: 2634 moltype = length =
SEQUENCE: 2634
000

SEQ ID NO: 2635 moltype = length =
SEQUENCE: 2635
000

SEQ ID NO: 2636 moltype = length =
SEQUENCE: 2636
000

SEQ ID NO: 2637 moltype = length =
SEQUENCE: 2637
000

SEQ ID NO: 2638 moltype = length =
SEQUENCE: 2638
000

SEQ ID NO: 2639 moltype = length =
SEQUENCE: 2639
000

SEQ ID NO: 2640 moltype = length =
SEQUENCE: 2640
000

SEQ ID NO: 2641 moltype = length =
SEQUENCE: 2641
000

SEQ ID NO: 2642 moltype = length =
SEQUENCE: 2642

000

SEQ ID NO: 2643 moltype = length =
SEQUENCE: 2643
000

SEQ ID NO: 2644 moltype = length =
SEQUENCE: 2644
000

SEQ ID NO: 2645 moltype = length =
SEQUENCE: 2645
000

SEQ ID NO: 2646 moltype = length =
SEQUENCE: 2646
000

SEQ ID NO: 2647 moltype = length =
SEQUENCE: 2647
000

SEQ ID NO: 2648 moltype = length =
SEQUENCE: 2648
000

SEQ ID NO: 2649 moltype = length =
SEQUENCE: 2649
000

SEQ ID NO: 2650 moltype = length =
SEQUENCE: 2650
000

SEQ ID NO: 2651 moltype = length =
SEQUENCE: 2651
000

SEQ ID NO: 2652 moltype = length =
SEQUENCE: 2652
000

SEQ ID NO: 2653 moltype = length =
SEQUENCE: 2653
000

SEQ ID NO: 2654 moltype = length =
SEQUENCE: 2654
000

SEQ ID NO: 2655 moltype = length =
SEQUENCE: 2655
000

SEQ ID NO: 2656 moltype = length =
SEQUENCE: 2656
000

SEQ ID NO: 2657 moltype = length =
SEQUENCE: 2657
000

SEQ ID NO: 2658 moltype = length =
SEQUENCE: 2658
000

SEQ ID NO: 2659 moltype = length =
SEQUENCE: 2659
000

SEQ ID NO: 2660 moltype = length =
SEQUENCE: 2660
000

SEQ ID NO: 2661 moltype = length =
SEQUENCE: 2661
000

SEQ ID NO: 2662 moltype = length =

SEQUENCE: 2662
000

SEQ ID NO: 2663 moltype = length =
SEQUENCE: 2663
000

SEQ ID NO: 2664 moltype = length =
SEQUENCE: 2664
000

SEQ ID NO: 2665 moltype = length =
SEQUENCE: 2665
000

SEQ ID NO: 2666 moltype = length =
SEQUENCE: 2666
000

SEQ ID NO: 2667 moltype = length =
SEQUENCE: 2667
000

SEQ ID NO: 2668 moltype = length =
SEQUENCE: 2668
000

SEQ ID NO: 2669 moltype = length =
SEQUENCE: 2669
000

SEQ ID NO: 2670 moltype = length =
SEQUENCE: 2670
000

SEQ ID NO: 2671 moltype = length =
SEQUENCE: 2671
000

SEQ ID NO: 2672 moltype = length =
SEQUENCE: 2672
000

SEQ ID NO: 2673 moltype = length =
SEQUENCE: 2673
000

SEQ ID NO: 2674 moltype = length =
SEQUENCE: 2674
000

SEQ ID NO: 2675 moltype = length =
SEQUENCE: 2675
000

SEQ ID NO: 2676 moltype = length =
SEQUENCE: 2676
000

SEQ ID NO: 2677 moltype = length =
SEQUENCE: 2677
000

SEQ ID NO: 2678 moltype = length =
SEQUENCE: 2678
000

SEQ ID NO: 2679 moltype = length =
SEQUENCE: 2679
000

SEQ ID NO: 2680 moltype = length =
SEQUENCE: 2680
000

SEQ ID NO: 2681 moltype = length =
SEQUENCE: 2681
000

SEQ ID NO: 2682 moltype = length =
SEQUENCE: 2682
000

SEQ ID NO: 2683 moltype = length =
SEQUENCE: 2683
000

SEQ ID NO: 2684 moltype = length =
SEQUENCE: 2684
000

SEQ ID NO: 2685 moltype = length =
SEQUENCE: 2685
000

SEQ ID NO: 2686 moltype = length =
SEQUENCE: 2686
000

SEQ ID NO: 2687 moltype = length =
SEQUENCE: 2687
000

SEQ ID NO: 2688 moltype = length =
SEQUENCE: 2688
000

SEQ ID NO: 2689 moltype = length =
SEQUENCE: 2689
000

SEQ ID NO: 2690 moltype = length =
SEQUENCE: 2690
000

SEQ ID NO: 2691 moltype = length =
SEQUENCE: 2691
000

SEQ ID NO: 2692 moltype = length =
SEQUENCE: 2692
000

SEQ ID NO: 2693 moltype = length =
SEQUENCE: 2693
000

SEQ ID NO: 2694 moltype = length =
SEQUENCE: 2694
000

SEQ ID NO: 2695 moltype = length =
SEQUENCE: 2695
000

SEQ ID NO: 2696 moltype = length =
SEQUENCE: 2696
000

SEQ ID NO: 2697 moltype = length =
SEQUENCE: 2697
000

SEQ ID NO: 2698 moltype = length =
SEQUENCE: 2698
000

SEQ ID NO: 2699 moltype = length =
SEQUENCE: 2699
000

SEQ ID NO: 2700 moltype = length =
SEQUENCE: 2700
000

SEQ ID NO: 2701 moltype = length =
SEQUENCE: 2701
000

SEQ ID NO: 2702 moltype = length =
SEQUENCE: 2702
000

SEQ ID NO: 2703 moltype = length =
SEQUENCE: 2703
000

SEQ ID NO: 2704 moltype = length =
SEQUENCE: 2704
000

SEQ ID NO: 2705 moltype = length =
SEQUENCE: 2705
000

SEQ ID NO: 2706 moltype = length =
SEQUENCE: 2706
000

SEQ ID NO: 2707 moltype = length =
SEQUENCE: 2707
000

SEQ ID NO: 2708 moltype = length =
SEQUENCE: 2708
000

SEQ ID NO: 2709 moltype = length =
SEQUENCE: 2709
000

SEQ ID NO: 2710 moltype = length =
SEQUENCE: 2710
000

SEQ ID NO: 2711 moltype = length =
SEQUENCE: 2711
000

SEQ ID NO: 2712 moltype = length =
SEQUENCE: 2712
000

SEQ ID NO: 2713 moltype = length =
SEQUENCE: 2713
000

SEQ ID NO: 2714 moltype = length =
SEQUENCE: 2714
000

SEQ ID NO: 2715 moltype = length =
SEQUENCE: 2715
000

SEQ ID NO: 2716 moltype = length =
SEQUENCE: 2716
000

SEQ ID NO: 2717 moltype = length =
SEQUENCE: 2717
000

SEQ ID NO: 2718 moltype = length =
SEQUENCE: 2718
000

SEQ ID NO: 2719 moltype = length =
SEQUENCE: 2719
000

SEQ ID NO: 2720 moltype = length =
SEQUENCE: 2720
000

SEQ ID NO: 2721 moltype = length =
SEQUENCE: 2721

000

SEQ ID NO: 2722 moltype = length =
SEQUENCE: 2722
000

SEQ ID NO: 2723 moltype = length =
SEQUENCE: 2723
000

SEQ ID NO: 2724 moltype = length =
SEQUENCE: 2724
000

SEQ ID NO: 2725 moltype = length =
SEQUENCE: 2725
000

SEQ ID NO: 2726 moltype = length =
SEQUENCE: 2726
000

SEQ ID NO: 2727 moltype = length =
SEQUENCE: 2727
000

SEQ ID NO: 2728 moltype = length =
SEQUENCE: 2728
000

SEQ ID NO: 2729 moltype = length =
SEQUENCE: 2729
000

SEQ ID NO: 2730 moltype = length =
SEQUENCE: 2730
000

SEQ ID NO: 2731 moltype = length =
SEQUENCE: 2731
000

SEQ ID NO: 2732 moltype = length =
SEQUENCE: 2732
000

SEQ ID NO: 2733 moltype = length =
SEQUENCE: 2733
000

SEQ ID NO: 2734 moltype = length =
SEQUENCE: 2734
000

SEQ ID NO: 2735 moltype = length =
SEQUENCE: 2735
000

SEQ ID NO: 2736 moltype = length =
SEQUENCE: 2736
000

SEQ ID NO: 2737 moltype = length =
SEQUENCE: 2737
000

SEQ ID NO: 2738 moltype = length =
SEQUENCE: 2738
000

SEQ ID NO: 2739 moltype = length =
SEQUENCE: 2739
000

SEQ ID NO: 2740 moltype = length =
SEQUENCE: 2740
000

SEQ ID NO: 2741 moltype = length =

SEQUENCE: 2741
000

SEQ ID NO: 2742 moltype = length =
SEQUENCE: 2742
000

SEQ ID NO: 2743 moltype = length =
SEQUENCE: 2743
000

SEQ ID NO: 2744 moltype = length =
SEQUENCE: 2744
000

SEQ ID NO: 2745 moltype = length =
SEQUENCE: 2745
000

SEQ ID NO: 2746 moltype = length =
SEQUENCE: 2746
000

SEQ ID NO: 2747 moltype = length =
SEQUENCE: 2747
000

SEQ ID NO: 2748 moltype = length =
SEQUENCE: 2748
000

SEQ ID NO: 2749 moltype = length =
SEQUENCE: 2749
000

SEQ ID NO: 2750 moltype = length =
SEQUENCE: 2750
000

SEQ ID NO: 2751 moltype = length =
SEQUENCE: 2751
000

SEQ ID NO: 2752 moltype = length =
SEQUENCE: 2752
000

SEQ ID NO: 2753 moltype = length =
SEQUENCE: 2753
000

SEQ ID NO: 2754 moltype = length =
SEQUENCE: 2754
000

SEQ ID NO: 2755 moltype = length =
SEQUENCE: 2755
000

SEQ ID NO: 2756 moltype = length =
SEQUENCE: 2756
000

SEQ ID NO: 2757 moltype = length =
SEQUENCE: 2757
000

SEQ ID NO: 2758 moltype = length =
SEQUENCE: 2758
000

SEQ ID NO: 2759 moltype = length =
SEQUENCE: 2759
000

SEQ ID NO: 2760 moltype = length =
SEQUENCE: 2760
000

SEQ ID NO: 2761 moltype = length =
SEQUENCE: 2761
000

SEQ ID NO: 2762 moltype = length =
SEQUENCE: 2762
000

SEQ ID NO: 2763 moltype = length =
SEQUENCE: 2763
000

SEQ ID NO: 2764 moltype = length =
SEQUENCE: 2764
000

SEQ ID NO: 2765 moltype = length =
SEQUENCE: 2765
000

SEQ ID NO: 2766 moltype = length =
SEQUENCE: 2766
000

SEQ ID NO: 2767 moltype = length =
SEQUENCE: 2767
000

SEQ ID NO: 2768 moltype = length =
SEQUENCE: 2768
000

SEQ ID NO: 2769 moltype = length =
SEQUENCE: 2769
000

SEQ ID NO: 2770 moltype = length =
SEQUENCE: 2770
000

SEQ ID NO: 2771 moltype = length =
SEQUENCE: 2771
000

SEQ ID NO: 2772 moltype = length =
SEQUENCE: 2772
000

SEQ ID NO: 2773 moltype = length =
SEQUENCE: 2773
000

SEQ ID NO: 2774 moltype = length =
SEQUENCE: 2774
000

SEQ ID NO: 2775 moltype = length =
SEQUENCE: 2775
000

SEQ ID NO: 2776 moltype = length =
SEQUENCE: 2776
000

SEQ ID NO: 2777 moltype = length =
SEQUENCE: 2777
000

SEQ ID NO: 2778 moltype = length =
SEQUENCE: 2778
000

SEQ ID NO: 2779 moltype = length =
SEQUENCE: 2779
000

SEQ ID NO: 2780 moltype = length =
SEQUENCE: 2780
000

SEQ ID NO: 2781 moltype = length =
SEQUENCE: 2781
000

SEQ ID NO: 2782 moltype = length =
SEQUENCE: 2782
000

SEQ ID NO: 2783 moltype = length =
SEQUENCE: 2783
000

SEQ ID NO: 2784 moltype = length =
SEQUENCE: 2784
000

SEQ ID NO: 2785 moltype = length =
SEQUENCE: 2785
000

SEQ ID NO: 2786 moltype = length =
SEQUENCE: 2786
000

SEQ ID NO: 2787 moltype = length =
SEQUENCE: 2787
000

SEQ ID NO: 2788 moltype = length =
SEQUENCE: 2788
000

SEQ ID NO: 2789 moltype = length =
SEQUENCE: 2789
000

SEQ ID NO: 2790 moltype = length =
SEQUENCE: 2790
000

SEQ ID NO: 2791 moltype = length =
SEQUENCE: 2791
000

SEQ ID NO: 2792 moltype = length =
SEQUENCE: 2792
000

SEQ ID NO: 2793 moltype = length =
SEQUENCE: 2793
000

SEQ ID NO: 2794 moltype = length =
SEQUENCE: 2794
000

SEQ ID NO: 2795 moltype = length =
SEQUENCE: 2795
000

SEQ ID NO: 2796 moltype = length =
SEQUENCE: 2796
000

SEQ ID NO: 2797 moltype = length =
SEQUENCE: 2797
000

SEQ ID NO: 2798 moltype = length =
SEQUENCE: 2798
000

SEQ ID NO: 2799 moltype = length =
SEQUENCE: 2799
000

SEQ ID NO: 2800 moltype = length =
SEQUENCE: 2800

000

SEQ ID NO: 2801 moltype = length =
SEQUENCE: 2801
000

SEQ ID NO: 2802 moltype = length =
SEQUENCE: 2802
000

SEQ ID NO: 2803 moltype = length =
SEQUENCE: 2803
000

SEQ ID NO: 2804 moltype = length =
SEQUENCE: 2804
000

SEQ ID NO: 2805 moltype = length =
SEQUENCE: 2805
000

SEQ ID NO: 2806 moltype = length =
SEQUENCE: 2806
000

SEQ ID NO: 2807 moltype = length =
SEQUENCE: 2807
000

SEQ ID NO: 2808 moltype = length =
SEQUENCE: 2808
000

SEQ ID NO: 2809 moltype = length =
SEQUENCE: 2809
000

SEQ ID NO: 2810 moltype = length =
SEQUENCE: 2810
000

SEQ ID NO: 2811 moltype = length =
SEQUENCE: 2811
000

SEQ ID NO: 2812 moltype = length =
SEQUENCE: 2812
000

SEQ ID NO: 2813 moltype = length =
SEQUENCE: 2813
000

SEQ ID NO: 2814 moltype = length =
SEQUENCE: 2814
000

SEQ ID NO: 2815 moltype = length =
SEQUENCE: 2815
000

SEQ ID NO: 2816 moltype = length =
SEQUENCE: 2816
000

SEQ ID NO: 2817 moltype = length =
SEQUENCE: 2817
000

SEQ ID NO: 2818 moltype = length =
SEQUENCE: 2818
000

SEQ ID NO: 2819 moltype = length =
SEQUENCE: 2819
000

SEQ ID NO: 2820 moltype = length =

SEQUENCE: 2820
000

SEQ ID NO: 2821 moltype = length =
SEQUENCE: 2821
000

SEQ ID NO: 2822 moltype = length =
SEQUENCE: 2822
000

SEQ ID NO: 2823 moltype = length =
SEQUENCE: 2823
000

SEQ ID NO: 2824 moltype = length =
SEQUENCE: 2824
000

SEQ ID NO: 2825 moltype = length =
SEQUENCE: 2825
000

SEQ ID NO: 2826 moltype = length =
SEQUENCE: 2826
000

SEQ ID NO: 2827 moltype = length =
SEQUENCE: 2827
000

SEQ ID NO: 2828 moltype = length =
SEQUENCE: 2828
000

SEQ ID NO: 2829 moltype = length =
SEQUENCE: 2829
000

SEQ ID NO: 2830 moltype = length =
SEQUENCE: 2830
000

SEQ ID NO: 2831 moltype = length =
SEQUENCE: 2831
000

SEQ ID NO: 2832 moltype = length =
SEQUENCE: 2832
000

SEQ ID NO: 2833 moltype = length =
SEQUENCE: 2833
000

SEQ ID NO: 2834 moltype = length =
SEQUENCE: 2834
000

SEQ ID NO: 2835 moltype = length =
SEQUENCE: 2835
000

SEQ ID NO: 2836 moltype = length =
SEQUENCE: 2836
000

SEQ ID NO: 2837 moltype = length =
SEQUENCE: 2837
000

SEQ ID NO: 2838 moltype = length =
SEQUENCE: 2838
000

SEQ ID NO: 2839 moltype = length =
SEQUENCE: 2839
000

SEQ ID NO: 2840 moltype = length =
SEQUENCE: 2840
000

SEQ ID NO: 2841 moltype = length =
SEQUENCE: 2841
000

SEQ ID NO: 2842 moltype = length =
SEQUENCE: 2842
000

SEQ ID NO: 2843 moltype = length =
SEQUENCE: 2843
000

SEQ ID NO: 2844 moltype = length =
SEQUENCE: 2844
000

SEQ ID NO: 2845 moltype = length =
SEQUENCE: 2845
000

SEQ ID NO: 2846 moltype = length =
SEQUENCE: 2846
000

SEQ ID NO: 2847 moltype = length =
SEQUENCE: 2847
000

SEQ ID NO: 2848 moltype = length =
SEQUENCE: 2848
000

SEQ ID NO: 2849 moltype = length =
SEQUENCE: 2849
000

SEQ ID NO: 2850 moltype = length =
SEQUENCE: 2850
000

SEQ ID NO: 2851 moltype = length =
SEQUENCE: 2851
000

SEQ ID NO: 2852 moltype = length =
SEQUENCE: 2852
000

SEQ ID NO: 2853 moltype = length =
SEQUENCE: 2853
000

SEQ ID NO: 2854 moltype = length =
SEQUENCE: 2854
000

SEQ ID NO: 2855 moltype = length =
SEQUENCE: 2855
000

SEQ ID NO: 2856 moltype = length =
SEQUENCE: 2856
000

SEQ ID NO: 2857 moltype = length =
SEQUENCE: 2857
000

SEQ ID NO: 2858 moltype = length =
SEQUENCE: 2858
000

SEQ ID NO: 2859 moltype = length =
SEQUENCE: 2859
000

SEQ ID NO: 2860 moltype = length =
SEQUENCE: 2860
000

SEQ ID NO: 2861 moltype = length =
SEQUENCE: 2861
000

SEQ ID NO: 2862 moltype = length =
SEQUENCE: 2862
000

SEQ ID NO: 2863 moltype = length =
SEQUENCE: 2863
000

SEQ ID NO: 2864 moltype = length =
SEQUENCE: 2864
000

SEQ ID NO: 2865 moltype = length =
SEQUENCE: 2865
000

SEQ ID NO: 2866 moltype = length =
SEQUENCE: 2866
000

SEQ ID NO: 2867 moltype = length =
SEQUENCE: 2867
000

SEQ ID NO: 2868 moltype = length =
SEQUENCE: 2868
000

SEQ ID NO: 2869 moltype = length =
SEQUENCE: 2869
000

SEQ ID NO: 2870 moltype = length =
SEQUENCE: 2870
000

SEQ ID NO: 2871 moltype = length =
SEQUENCE: 2871
000

SEQ ID NO: 2872 moltype = length =
SEQUENCE: 2872
000

SEQ ID NO: 2873 moltype = length =
SEQUENCE: 2873
000

SEQ ID NO: 2874 moltype = length =
SEQUENCE: 2874
000

SEQ ID NO: 2875 moltype = length =
SEQUENCE: 2875
000

SEQ ID NO: 2876 moltype = length =
SEQUENCE: 2876
000

SEQ ID NO: 2877 moltype = length =
SEQUENCE: 2877
000

SEQ ID NO: 2878 moltype = length =
SEQUENCE: 2878
000

SEQ ID NO: 2879 moltype = length =
SEQUENCE: 2879

000

SEQ ID NO: 2880 moltype = length =
SEQUENCE: 2880
000

SEQ ID NO: 2881 moltype = length =
SEQUENCE: 2881
000

SEQ ID NO: 2882 moltype = length =
SEQUENCE: 2882
000

SEQ ID NO: 2883 moltype = length =
SEQUENCE: 2883
000

SEQ ID NO: 2884 moltype = length =
SEQUENCE: 2884
000

SEQ ID NO: 2885 moltype = length =
SEQUENCE: 2885
000

SEQ ID NO: 2886 moltype = length =
SEQUENCE: 2886
000

SEQ ID NO: 2887 moltype = length =
SEQUENCE: 2887
000

SEQ ID NO: 2888 moltype = length =
SEQUENCE: 2888
000

SEQ ID NO: 2889 moltype = length =
SEQUENCE: 2889
000

SEQ ID NO: 2890 moltype = length =
SEQUENCE: 2890
000

SEQ ID NO: 2891 moltype = length =
SEQUENCE: 2891
000

SEQ ID NO: 2892 moltype = length =
SEQUENCE: 2892
000

SEQ ID NO: 2893 moltype = length =
SEQUENCE: 2893
000

SEQ ID NO: 2894 moltype = length =
SEQUENCE: 2894
000

SEQ ID NO: 2895 moltype = length =
SEQUENCE: 2895
000

SEQ ID NO: 2896 moltype = length =
SEQUENCE: 2896
000

SEQ ID NO: 2897 moltype = length =
SEQUENCE: 2897
000

SEQ ID NO: 2898 moltype = length =
SEQUENCE: 2898
000

SEQ ID NO: 2899 moltype = length =

SEQUENCE: 2899
000

SEQ ID NO: 2900 moltype = length =
SEQUENCE: 2900
000

SEQ ID NO: 2901 moltype = length =
SEQUENCE: 2901
000

SEQ ID NO: 2902 moltype = length =
SEQUENCE: 2902
000

SEQ ID NO: 2903 moltype = length =
SEQUENCE: 2903
000

SEQ ID NO: 2904 moltype = length =
SEQUENCE: 2904
000

SEQ ID NO: 2905 moltype = length =
SEQUENCE: 2905
000

SEQ ID NO: 2906 moltype = length =
SEQUENCE: 2906
000

SEQ ID NO: 2907 moltype = length =
SEQUENCE: 2907
000

SEQ ID NO: 2908 moltype = length =
SEQUENCE: 2908
000

SEQ ID NO: 2909 moltype = length =
SEQUENCE: 2909
000

SEQ ID NO: 2910 moltype = length =
SEQUENCE: 2910
000

SEQ ID NO: 2911 moltype = length =
SEQUENCE: 2911
000

SEQ ID NO: 2912 moltype = length =
SEQUENCE: 2912
000

SEQ ID NO: 2913 moltype = length =
SEQUENCE: 2913
000

SEQ ID NO: 2914 moltype = length =
SEQUENCE: 2914
000

SEQ ID NO: 2915 moltype = length =
SEQUENCE: 2915
000

SEQ ID NO: 2916 moltype = length =
SEQUENCE: 2916
000

SEQ ID NO: 2917 moltype = length =
SEQUENCE: 2917
000

SEQ ID NO: 2918 moltype = length =
SEQUENCE: 2918
000

SEQ ID NO: 2919 moltype = length =
SEQUENCE: 2919
000

SEQ ID NO: 2920 moltype = length =
SEQUENCE: 2920
000

SEQ ID NO: 2921 moltype = length =
SEQUENCE: 2921
000

SEQ ID NO: 2922 moltype = length =
SEQUENCE: 2922
000

SEQ ID NO: 2923 moltype = length =
SEQUENCE: 2923
000

SEQ ID NO: 2924 moltype = length =
SEQUENCE: 2924
000

SEQ ID NO: 2925 moltype = length =
SEQUENCE: 2925
000

SEQ ID NO: 2926 moltype = length =
SEQUENCE: 2926
000

SEQ ID NO: 2927 moltype = length =
SEQUENCE: 2927
000

SEQ ID NO: 2928 moltype = length =
SEQUENCE: 2928
000

SEQ ID NO: 2929 moltype = length =
SEQUENCE: 2929
000

SEQ ID NO: 2930 moltype = length =
SEQUENCE: 2930
000

SEQ ID NO: 2931 moltype = length =
SEQUENCE: 2931
000

SEQ ID NO: 2932 moltype = length =
SEQUENCE: 2932
000

SEQ ID NO: 2933 moltype = length =
SEQUENCE: 2933
000

SEQ ID NO: 2934 moltype = length =
SEQUENCE: 2934
000

SEQ ID NO: 2935 moltype = length =
SEQUENCE: 2935
000

SEQ ID NO: 2936 moltype = length =
SEQUENCE: 2936
000

SEQ ID NO: 2937 moltype = length =
SEQUENCE: 2937
000

SEQ ID NO: 2938 moltype = length =
SEQUENCE: 2938
000

SEQ ID NO: 2939 moltype = length =
SEQUENCE: 2939
000

SEQ ID NO: 2940 moltype = length =
SEQUENCE: 2940
000

SEQ ID NO: 2941 moltype = length =
SEQUENCE: 2941
000

SEQ ID NO: 2942 moltype = length =
SEQUENCE: 2942
000

SEQ ID NO: 2943 moltype = length =
SEQUENCE: 2943
000

SEQ ID NO: 2944 moltype = length =
SEQUENCE: 2944
000

SEQ ID NO: 2945 moltype = length =
SEQUENCE: 2945
000

SEQ ID NO: 2946 moltype = length =
SEQUENCE: 2946
000

SEQ ID NO: 2947 moltype = length =
SEQUENCE: 2947
000

SEQ ID NO: 2948 moltype = length =
SEQUENCE: 2948
000

SEQ ID NO: 2949 moltype = length =
SEQUENCE: 2949
000

SEQ ID NO: 2950 moltype = length =
SEQUENCE: 2950
000

SEQ ID NO: 2951 moltype = length =
SEQUENCE: 2951
000

SEQ ID NO: 2952 moltype = length =
SEQUENCE: 2952
000

SEQ ID NO: 2953 moltype = length =
SEQUENCE: 2953
000

SEQ ID NO: 2954 moltype = length =
SEQUENCE: 2954
000

SEQ ID NO: 2955 moltype = length =
SEQUENCE: 2955
000

SEQ ID NO: 2956 moltype = length =
SEQUENCE: 2956
000

SEQ ID NO: 2957 moltype = length =
SEQUENCE: 2957
000

SEQ ID NO: 2958 moltype = length =
SEQUENCE: 2958

000

SEQ ID NO: 2959 moltype = length =
SEQUENCE: 2959
000

SEQ ID NO: 2960 moltype = length =
SEQUENCE: 2960
000

SEQ ID NO: 2961 moltype = length =
SEQUENCE: 2961
000

SEQ ID NO: 2962 moltype = length =
SEQUENCE: 2962
000

SEQ ID NO: 2963 moltype = length =
SEQUENCE: 2963
000

SEQ ID NO: 2964 moltype = length =
SEQUENCE: 2964
000

SEQ ID NO: 2965 moltype = length =
SEQUENCE: 2965
000

SEQ ID NO: 2966 moltype = length =
SEQUENCE: 2966
000

SEQ ID NO: 2967 moltype = length =
SEQUENCE: 2967
000

SEQ ID NO: 2968 moltype = length =
SEQUENCE: 2968
000

SEQ ID NO: 2969 moltype = length =
SEQUENCE: 2969
000

SEQ ID NO: 2970 moltype = length =
SEQUENCE: 2970
000

SEQ ID NO: 2971 moltype = length =
SEQUENCE: 2971
000

SEQ ID NO: 2972 moltype = length =
SEQUENCE: 2972
000

SEQ ID NO: 2973 moltype = length =
SEQUENCE: 2973
000

SEQ ID NO: 2974 moltype = length =
SEQUENCE: 2974
000

SEQ ID NO: 2975 moltype = length =
SEQUENCE: 2975
000

SEQ ID NO: 2976 moltype = length =
SEQUENCE: 2976
000

SEQ ID NO: 2977 moltype = length =
SEQUENCE: 2977
000

SEQ ID NO: 2978 moltype = length =

SEQUENCE: 2978
000

SEQ ID NO: 2979 moltype = length =
SEQUENCE: 2979
000

SEQ ID NO: 2980 moltype = length =
SEQUENCE: 2980
000

SEQ ID NO: 2981 moltype = length =
SEQUENCE: 2981
000

SEQ ID NO: 2982 moltype = length =
SEQUENCE: 2982
000

SEQ ID NO: 2983 moltype = length =
SEQUENCE: 2983
000

SEQ ID NO: 2984 moltype = length =
SEQUENCE: 2984
000

SEQ ID NO: 2985 moltype = length =
SEQUENCE: 2985
000

SEQ ID NO: 2986 moltype = length =
SEQUENCE: 2986
000

SEQ ID NO: 2987 moltype = length =
SEQUENCE: 2987
000

SEQ ID NO: 2988 moltype = length =
SEQUENCE: 2988
000

SEQ ID NO: 2989 moltype = length =
SEQUENCE: 2989
000

SEQ ID NO: 2990 moltype = length =
SEQUENCE: 2990
000

SEQ ID NO: 2991 moltype = length =
SEQUENCE: 2991
000

SEQ ID NO: 2992 moltype = length =
SEQUENCE: 2992
000

SEQ ID NO: 2993 moltype = length =
SEQUENCE: 2993
000

SEQ ID NO: 2994 moltype = length =
SEQUENCE: 2994
000

SEQ ID NO: 2995 moltype = length =
SEQUENCE: 2995
000

SEQ ID NO: 2996 moltype = length =
SEQUENCE: 2996
000

SEQ ID NO: 2997 moltype = length =
SEQUENCE: 2997
000

```
SEQ ID NO: 2998        moltype =   length =
SEQUENCE: 2998
000

SEQ ID NO: 2999        moltype =   length =
SEQUENCE: 2999
000

SEQ ID NO: 3000        moltype = AA  length = 107
FEATURE                Location/Qualifiers
source                 1..107
                       mol_type = protein
                       organism = synthetic construct
SEQUENCE: 3000
DIQMTQSPSF LSASVGDRVT ITCSASQGIS NYLNWYQQKP GKAVKLLIYY TSSLHSGVPS  60
RFSGSGSGTE YTLTISSLQP EDFATYYCQQ YSKLPRTFGG GTKVEIK                107

SEQ ID NO: 3001        moltype = AA  length = 107
FEATURE                Location/Qualifiers
source                 1..107
                       mol_type = protein
                       organism = synthetic construct
SEQUENCE: 3001
DIQMTQSPSS LSASVGDRVT ITCSASQGIS NYLNWYQQKP GKAVKLLIYY TSSLHSGVPS  60
RFSGSGSGTD YTLTISSLQP EDFATYYCQQ YSKLPRTFGG GTKVEIK                107

SEQ ID NO: 3002        moltype = AA  length = 107
FEATURE                Location/Qualifiers
source                 1..107
                       mol_type = protein
                       organism = synthetic construct
SEQUENCE: 3002
DIQMTQSPSS LSASVGDRVT ITCSASQGIS NYLNWYQQKP GKVVKLLIYY TSSLHSGVPS  60
RFSGSGSGTD YTLTISSLQP EDVATYYCQQ YSKLPRTFGG GTKVEIK                107

SEQ ID NO: 3003        moltype = AA  length = 107
FEATURE                Location/Qualifiers
source                 1..107
                       mol_type = protein
                       organism = synthetic construct
SEQUENCE: 3003
DIQMTQSPSS LSASVGDRVT ITCSASQGIS NYLNWYQQKP GQAVKLLIYY TSSLHSGVPS  60
RFSGSGSGTD YTLTISSLQP EDVATYYCQQ YSKLPRTFGG GTKVEIK                107

SEQ ID NO: 3004        moltype = AA  length = 107
FEATURE                Location/Qualifiers
source                 1..107
                       mol_type = protein
                       organism = synthetic construct
SEQUENCE: 3004
DIQMTQSPSS LSASVGDRVT ITCSASQGIS NYLNWYQQKP GKAVKLLIYY TSSLHSGVPS  60
RFSGSGSGTD YTFTISSLQP EDIATYYCQQ YSKLPRTFGG GTKVEIK                107

SEQ ID NO: 3005        moltype = AA  length = 107
FEATURE                Location/Qualifiers
source                 1..107
                       mol_type = protein
                       organism = synthetic construct
SEQUENCE: 3005
DIQMTQSPSS LSASVGDRVT ITCSASQGIS NYLNWYQQKP GKTVKLLIYY TSSLHSGIPS  60
RFSGSGSGTD YTLTIRSLQP EDFATYYCQQ YSKLPRTFGG GTKVEIK                107

SEQ ID NO: 3006        moltype = AA  length = 107
FEATURE                Location/Qualifiers
source                 1..107
                       mol_type = protein
                       organism = synthetic construct
SEQUENCE: 3006
AIQMTQSPSS LSASVGDRVT ITCSASQGIS NYLNWYQQKP GKAVKLLIYY TSSLHSGVPS  60
RFSGSGSGTD YTLTISSLQP EDFATYYCQQ YSKLPRTFGG GTKVEIK                107

SEQ ID NO: 3007        moltype = AA  length = 107
FEATURE                Location/Qualifiers
source                 1..107
                       mol_type = protein
                       organism = synthetic construct
SEQUENCE: 3007
DIQMTQSPSS VSASVGDRVT ITCSASQGIS NYLNWYQQKP GKAVKLLIYY TSSLHSGVPS  60
RFSGSGSGTD YTLTISSLQP EDFATYYCQQ YSKLPRTFGG GTKVEIK                107
```

```
SEQ ID NO: 3008        moltype = AA  length = 107
FEATURE                Location/Qualifiers
source                 1..107
                       mol_type = protein
                       organism = synthetic construct
SEQUENCE: 3008
DIQMTQSPSS LSASVGDRVT ITCSASQGIS NYLNWYQQKP GKAVKRLIYY TSSLHSGVPS  60
RFSGSGSGTE YTLTISNLQP EDFATYYCQQ YSKLPRTFGG GTKVEIK                107

SEQ ID NO: 3009        moltype = AA  length = 107
FEATURE                Location/Qualifiers
source                 1..107
                       mol_type = protein
                       organism = synthetic construct
SEQUENCE: 3009
AIRMTQSPFS LSASVGDRVT ITCSASQGIS NYLNWYQQKP AKAVKLFIYY TSSLHSGVPS  60
RFSGSGSGTD YTLTISSLQP EDFATYYCQQ YSKLPRTFGG GTKVEIK                107

SEQ ID NO: 3010        moltype = AA  length = 107
FEATURE                Location/Qualifiers
source                 1..107
                       mol_type = protein
                       organism = synthetic construct
SEQUENCE: 3010
DIQMTQSPSS LSASVGDRVT ITCSASQGIS NYLNWYQQKP GKAVKRLIYY TSSLHSGVPS  60
RFSGSGSGTE YTLTISSLQP EDFATYYCQQ YSKLPRTFGG GTKVEIK                107

SEQ ID NO: 3011        moltype = AA  length = 107
FEATURE                Location/Qualifiers
source                 1..107
                       mol_type = protein
                       organism = synthetic construct
SEQUENCE: 3011
DIQMTQSPST LSASVGDRVT ITCSASQGIS NYLNWYQQKP GKAVKLLIYY TSSLHSGVPS  60
RFSGSGSGTE YTLTISSLQP DDFATYYCQQ YSKLPRTFGG GTKVEIK                107

SEQ ID NO: 3012        moltype = AA  length = 107
FEATURE                Location/Qualifiers
source                 1..107
                       mol_type = protein
                       organism = synthetic construct
SEQUENCE: 3012
DIQMTQSPSS LSASVGDRVT ITCSASQGIS NYLNWYQQKP GKAVKSLIYY TSSLHSGVPS  60
RFSGSGSGTD YTLTISSLQP EDFATYYCQQ YSKLPRTFGG GTKVEIK                107

SEQ ID NO: 3013        moltype = AA  length = 107
FEATURE                Location/Qualifiers
source                 1..107
                       mol_type = protein
                       organism = synthetic construct
SEQUENCE: 3013
DIQMTQSPSS LSASVGDRVT ITCSASQGIS NYLNWYQQKP GKAVKSLIYY TSSLHSGVPS  60
KFSGSGSGTD YTLTISSLQP EDFATYYCQQ YSKLPRTFGG GTKVEIK                107

SEQ ID NO: 3014        moltype = AA  length = 107
FEATURE                Location/Qualifiers
source                 1..107
                       mol_type = protein
                       organism = synthetic construct
SEQUENCE: 3014
DIQMTQSPSS LSASVGDRVT ITCSASQGIS NYLNWYQQKP EKAVKSLIYY TSSLHSGVPS  60
RFSGSGSGTD YTLTISSLQP EDFATYYCQQ YSKLPRTFGG GTKVEIK                107

SEQ ID NO: 3015        moltype = AA  length = 107
FEATURE                Location/Qualifiers
source                 1..107
                       mol_type = protein
                       organism = synthetic construct
SEQUENCE: 3015
DIQMTQSPSA MSASVGDRVT ITCSASQGIS NYLNWYQQKP GKVVKRLIYY TSSLHSGVPS  60
RFSGSGSGTE YTLTISSLQP EDFATYYCQQ YSKLPRTFGG GTKVEIK                107

SEQ ID NO: 3016        moltype = AA  length = 107
FEATURE                Location/Qualifiers
source                 1..107
                       mol_type = protein
                       organism = synthetic construct
SEQUENCE: 3016
```

```
DIVMTQSPDS LAVSLGERAT INCSASQGIS NYLNWYQQKP GQPVKLLIYY TSSLHSGVPD  60
RFSGSGSGTD YTLTISSLQA EDVAVYYCQQ YSKLPRTFGG GTKVEIK               107

SEQ ID NO: 3017        moltype = AA  length = 107
FEATURE                Location/Qualifiers
source                 1..107
                       mol_type = protein
                       organism = synthetic construct
SEQUENCE: 3017
EIVMTQSPGT LSLSPGERAT LSCSASQGIS NYLNWYQQKP GQAVKLLIYY TSSLHSGIPD  60
RFSGSGSGTD YTLTISRLEP EDFAVYYCQQ YSKLPRTFGG GTKVEIK               107

SEQ ID NO: 3018        moltype = AA  length = 107
FEATURE                Location/Qualifiers
source                 1..107
                       mol_type = protein
                       organism = synthetic construct
SEQUENCE: 3018
EIVMTQSPPT LSLSPGERVT LSCSASQGIS NYLNWYQQKP GQAVKLLIYY TSSLHSGIPA  60
RFSGSGSGTD YTLTISSLQP EDFAVYYCQQ YSKLPRTFGG GTKVEIK               107

SEQ ID NO: 3019        moltype = AA  length = 107
FEATURE                Location/Qualifiers
source                 1..107
                       mol_type = protein
                       organism = synthetic construct
SEQUENCE: 3019
EIVMTQSPPT LSLSPGERVT LSCSASQGIS NYLNWYQQKP GQAVKLLIYY TSSLHSSIPA  60
RFSGSGSGTD YTLTISSLQP EDFAVYYCQQ YSKLPRTFGG GTKVEIK               107

SEQ ID NO: 3020        moltype = AA  length = 107
FEATURE                Location/Qualifiers
source                 1..107
                       mol_type = protein
                       organism = synthetic construct
SEQUENCE: 3020
EIVMTQSPAT LSLSPGERAT LSCSASQGIS NYLNWYQQKP GQAVKLLIYY TSSLHSGIPA  60
RFSGSGSGTD YTLTISSLEP EDFAVYYCQQ YSKLPRTFGG GTKVEIK               107

SEQ ID NO: 3021        moltype = AA  length = 107
FEATURE                Location/Qualifiers
source                 1..107
                       mol_type = protein
                       organism = synthetic construct
SEQUENCE: 3021
EIVMTQSPAT LSLSPGERAT LSCSASQGIS NYLNWYQQKP GQAVKLLIYY TSSLHSGIPA  60
RFSGSGSGTD YTLTISRLEP EDFAVYYCQQ YSKLPRTFGG GTKVEIK               107

SEQ ID NO: 3022        moltype = AA  length = 107
FEATURE                Location/Qualifiers
source                 1..107
                       mol_type = protein
                       organism = synthetic construct
SEQUENCE: 3022
EIVMTQSPAT LSLSPGERAT LSCSASQGIS NYLNWYQQKP GQAVKLLIYY TSSLHSGIPD  60
RFSGSGSGTD YTLTISRLEP EDFAVYYCQQ YSKLPRTFGG GTKVEIK               107

SEQ ID NO: 3023        moltype = AA  length = 107
FEATURE                Location/Qualifiers
source                 1..107
                       mol_type = protein
                       organism = synthetic construct
SEQUENCE: 3023
EIVMTQSPAT LSLSPGERAT LSCSASQGIS NYLNWYQQKP GLAVKLLIYY TSSLHSGIPD  60
RFSGSGSGTD YTLTISRLEP EDFAVYYCQQ YSKLPRTFGG GTKVEIK               107

SEQ ID NO: 3024        moltype = AA  length = 107
FEATURE                Location/Qualifiers
source                 1..107
                       mol_type = protein
                       organism = synthetic construct
SEQUENCE: 3024
DIQMIQSPSF LSASVGDRVS IICSASQGIS NYLNWYLQKP GKSVKLFIYY TSSLHSGVSS  60
RFSGRGSGTD YTLTIISLKP EDFAAYYCQQ YSKLPRTFGG GTKVEIK               107

SEQ ID NO: 3025        moltype = AA  length = 107
FEATURE                Location/Qualifiers
source                 1..107
                       mol_type = protein
```

```
                        organism = synthetic construct
SEQUENCE: 3025
EIVMTQSPAT LSLSPGERAT LSCSASQGIS NYLNWYQQKP GQAVKLLIYY TSSLHSGIPA  60
RFSGSGSGTD YTLTISSLQP EDFAVYYCQQ YSKLPRTFGG GTKVEIK                107

SEQ ID NO: 3026         moltype = AA  length = 107
FEATURE                 Location/Qualifiers
source                  1..107
                        mol_type = protein
                        organism = synthetic construct
SEQUENCE: 3026
EIVMTQSPAT LSLSPGERAT LSCSASQGIS NYLNWYQQKP GQAVKLLIYY TSSLHSGIPA  60
RFSGSGPGTD YTLTISSLEP EDFAVYYCQQ YSKLPRTFGG GTKVEIK                107

SEQ ID NO: 3027         moltype = AA  length = 107
FEATURE                 Location/Qualifiers
source                  1..107
                        mol_type = protein
                        organism = synthetic construct
SEQUENCE: 3027
DIVMTQTPLS LSVTPGQPAS ISCSASQGIS NYLNWYLQKP GQSVKLLIYY TSSLHSGVPD  60
RFSGSGSGTD YTLKISRVEA EDVGVYYCQQ YSKLPRTFGG GTKVEIK                107

SEQ ID NO: 3028         moltype = AA  length = 107
FEATURE                 Location/Qualifiers
source                  1..107
                        mol_type = protein
                        organism = synthetic construct
SEQUENCE: 3028
DIVMTQTPLS LSVTPGQPAS ISCSASQGIS NYLNWYLQKP GQPVKLLIYY TSSLHSGVPD  60
RFSGSGSGTD YTLKISRVEA EDVGVYYCQQ YSKLPRTFGG GTKVEIK                107

SEQ ID NO: 3029         moltype = AA  length = 107
FEATURE                 Location/Qualifiers
source                  1..107
                        mol_type = protein
                        organism = synthetic construct
SEQUENCE: 3029
DIVMTQSPAF LSVTPGEKVT ITCSASQGIS NYLNWYQQKP DQAVKLLIYY TSSLHSGVPS  60
RFSGSGSGTD YTFTISSLEA EDAATYYCQQ YSKLPRTFGG GTKVEIK                107

SEQ ID NO: 3030         moltype = AA  length = 107
FEATURE                 Location/Qualifiers
source                  1..107
                        mol_type = protein
                        organism = synthetic construct
SEQUENCE: 3030
DIVMTQSPLS LPVTPGEPAS ISCSASQGIS NYLNWYLQKP GQSVKLLIYY TSSLHSGVPD  60
RFSGSGSGTD YTLKISRVEA EDVGVYYCQQ YSKLPRTFGG GTKVEIK                107

SEQ ID NO: 3031         moltype = AA  length = 107
FEATURE                 Location/Qualifiers
source                  1..107
                        mol_type = protein
                        organism = synthetic construct
SEQUENCE: 3031
DIVMTQTPLS LPVTPGEPAS ISCSASQGIS NYLNWYLQKP GQSVKLLIYY TSSLHSGVPD  60
RFSGSGSGTD YTLKISRVEA EDVGVYYCQQ YSKLPRTFGG GTKVEIK                107

SEQ ID NO: 3032         moltype = AA  length = 107
FEATURE                 Location/Qualifiers
source                  1..107
                        mol_type = protein
                        organism = synthetic construct
SEQUENCE: 3032
EIVMTQSPAT LSVSPGERAT LSCSASQGIS NYLNWYQQKP GQAVKLLIYY TSSLHSGIPA  60
RFSGSGSGTE YTLTISILQS EDFAVYYCQQ YSKLPRTFGG GTKVEIK                107

SEQ ID NO: 3033         moltype = AA  length = 107
FEATURE                 Location/Qualifiers
source                  1..107
                        mol_type = protein
                        organism = synthetic construct
SEQUENCE: 3033
EIVMTQSPAT LSVSPGERAT LSCSASQGIS NYLNWYQQKP GQAVKLLIYY TSSLHSGIPA  60
RFSGSGSGTE YTLTISSLQS EDFAVYYCQQ YSKLPRTFGG GTKVEIK                107

SEQ ID NO: 3034         moltype = AA  length = 107
FEATURE                 Location/Qualifiers
```

```
source                  1..107
                        mol_type = protein
                        organism = synthetic construct
SEQUENCE: 3034
DIVMTQSPLS LPVTLGQPAS ISCSASQGIS NYLNWYQQRP GQSVKRLIYY TSSLHSGVPD  60
RFSGSGSGTD YTLKISRVEA EDVGVYYCQQ YSKLPRTFGG GTKVEIK               107

SEQ ID NO: 3035         moltype = AA  length = 107
FEATURE                 Location/Qualifiers
source                  1..107
                        mol_type = protein
                        organism = synthetic construct
SEQUENCE: 3035
EITMTQSPAF MSATPGDKVN ISCSASQGIS NYLNWYQQKP GEAVKFIIYY TSSLHSGIPP  60
RFSGSGYGTD YTLTINNIES EDAAYYYCQQ YSKLPRTFGG GTKVEIK               107

SEQ ID NO: 3036         moltype = AA  length = 107
FEATURE                 Location/Qualifiers
source                  1..107
                        mol_type = protein
                        organism = synthetic construct
SEQUENCE: 3036
DIVMTQTPLS SPVTLGQPAS ISCSASQGIS NYLNWYQQRP GQPVKLLIYY TSSLHSGVPD  60
RFSGSGAGTD YTLKISRVEA EDVGVYYCQQ YSKLPRTFGG GTKVEIK               107

SEQ ID NO: 3037         moltype = AA  length = 107
FEATURE                 Location/Qualifiers
source                  1..107
                        mol_type = protein
                        organism = synthetic construct
SEQUENCE: 3037
EIVMTQSPDF QSVTPKEKVT ITCSASQGIS NYLNWYQQKP DQSVKLLIYY TSSLHSGVPS  60
RFSGSGSGTD YTLTINSLEA EDAATYYCQQ YSKLPRTFGG GTKVEIK               107

SEQ ID NO: 3038         moltype = AA  length = 107
FEATURE                 Location/Qualifiers
source                  1..107
                        mol_type = protein
                        organism = synthetic construct
SEQUENCE: 3038
EIVMTQTPLS LSITPGEQAS ISCSASQGIS NYLNWYLQKA RPVVKLLIYY TSSLHSGVPD  60
RFSGSGSGTD YTLKISRVEA EDFGVYYCQQ YSKLPRTFGG GTKVEIK               107

SEQ ID NO: 3039         moltype = AA  length = 107
FEATURE                 Location/Qualifiers
source                  1..107
                        mol_type = protein
                        organism = synthetic construct
SEQUENCE: 3039
EIVMTQTPLS LSITPGEQAS MSCSASQGIS NYLNWYLQKA RPVVKLLIYY TSSLHSGVPD  60
RFSGSGSGTD YTLKISRVEA EDFGVYYCQQ YSKLPRTFGG GTKVEIK               107

SEQ ID NO: 3040         moltype = AA  length = 120
FEATURE                 Location/Qualifiers
source                  1..120
                        mol_type = protein
                        organism = synthetic construct
SEQUENCE: 3040
QVTLKESGPV LVKPTETLTL TCTVSGFSLT AYGVNWVRQP PGKALEWLGM IWGDGNTDYN  60
SALKSRLTIS KDNSKSQVVL TMTNMDPVDT ATYYCARDRV TATLYAMDYW GQGTLVTVSS  120

SEQ ID NO: 3041         moltype = AA  length = 120
FEATURE                 Location/Qualifiers
source                  1..120
                        mol_type = protein
                        organism = synthetic construct
SEQUENCE: 3041
QVTLKESGPA LVKPTETLTL TCTVSGFSLT AYGVNWVRQP PGKALEWLGM IWGDGNTDYN  60
SALKSRLIIS KDNSKSQVVL TMTNMDPVDT ATYYCARDRV TATLYAMDYW GQGTLVTVSS  120

SEQ ID NO: 3042         moltype = AA  length = 120
FEATURE                 Location/Qualifiers
source                  1..120
                        mol_type = protein
                        organism = synthetic construct
SEQUENCE: 3042
QVTLKESGPA LVKPTQTLTL TCTVSGFSLT AYGVNWVRQP PGKALEWLGM IWGDGNTDYN  60
SALKSRLTIS KDNSKSQVVL TMTNMDPVDT ATYYCARDRV TATLYAMDYW GQGTLVTVSS  120
```

```
SEQ ID NO: 3043        moltype = AA  length = 120
FEATURE                Location/Qualifiers
source                 1..120
                       mol_type = protein
                       organism = synthetic construct
SEQUENCE: 3043
QVQLQESGPG LVKPSGTLSL TCAVSGFSLT AYGVNWVRQP PGKGLEWLGM IWGDGNTDYN  60
SALKSRLTIS KDNSKSQVSL KLSSVTAADT AVYYCARDRV TATLYAMDYW GQGTLVTVSS  120

SEQ ID NO: 3044        moltype = AA  length = 120
FEATURE                Location/Qualifiers
source                 1..120
                       mol_type = protein
                       organism = synthetic construct
SEQUENCE: 3044
QVTLKESGPT LVKPTQTLTL TCTVSGFSLT AYGVNWVRQP PGKALEWLGM IWGDGNTDYN  60
SALKSRLTIT KDNSKSQVVL TMTNMDPVDT ATYYCARDRV TATLYAMDYW GQGTLVTVSS  120

SEQ ID NO: 3045        moltype = AA  length = 120
FEATURE                Location/Qualifiers
source                 1..120
                       mol_type = protein
                       organism = synthetic construct
SEQUENCE: 3045
QVTLKESGPA LVKPTQTLTL TCTVSGFSLT AYGVNWVRQP PGKALEWLGM IWGDGNTDYN  60
SALKSRLTIT KDNSKSQVVL TMTNMDPVDT ATYYCARDRV TATLYAMDYW GQGTLVTVSS  120

SEQ ID NO: 3046        moltype = AA  length = 120
FEATURE                Location/Qualifiers
source                 1..120
                       mol_type = protein
                       organism = synthetic construct
SEQUENCE: 3046
QVQLQESGPG LVKPSQTLSL TCTVSGFSLT AYGVNWVRQP PGKGLEWLGM IWGDGNTDYN  60
SALKSRLTIS KDNSKSQVSL KLSSVTAADT AVYYCARDRV TATLYAMDYW GQGTLVTVSS  120

SEQ ID NO: 3047        moltype = AA  length = 120
FEATURE                Location/Qualifiers
source                 1..120
                       mol_type = protein
                       organism = synthetic construct
SEQUENCE: 3047
QVQLQESGPG LVKPSETLSL TCTVSGFSLT AYGVNWVRQP PGKGLEWLGM IWGDGNTDYN  60
SALKSRLTIS KDNSKSQVSL KLSSVTAADT AVYYCARDRV TATLYAMDYW GQGTLVTVSS  120

SEQ ID NO: 3048        moltype = AA  length = 120
FEATURE                Location/Qualifiers
source                 1..120
                       mol_type = protein
                       organism = synthetic construct
SEQUENCE: 3048
QVQLQESGPG LVKPSQTLSL TCAVSGFSLT AYGVNWVRQP PGKGLEWLGM IWGDGNTDYN  60
SALKSRLTIS KDNSKSQVSL KLSSVTAADT AVYYCARDRV TATLYAMDYW GQGTLVTVSS  120

SEQ ID NO: 3049        moltype = AA  length = 120
FEATURE                Location/Qualifiers
source                 1..120
                       mol_type = protein
                       organism = synthetic construct
SEQUENCE: 3049
QVQLQESGPG LVKPSDTLSL TCTVSGFSLT AYGVNWVRQP PGKGLEWLGM IWGDGNTDYN  60
SALKSRLTIS KDNSKSQVSL KLSSVTAADT AVYYCARDRV TATLYAMDYW GQGTLVTVSS  120

SEQ ID NO: 3050        moltype = AA  length = 120
FEATURE                Location/Qualifiers
source                 1..120
                       mol_type = protein
                       organism = synthetic construct
SEQUENCE: 3050
QVQLQESGPG LVKPSQTLSL TCTVSGFSLT AYGVNWVRQH PGKGLEWLGM IWGDGNTDYN  60
SALKSRLTIS KDNSKSQVSL KLSSVTAADT AVYYCARDRV TATLYAMDYW GQGTLVTVSS  120

SEQ ID NO: 3051        moltype = AA  length = 120
FEATURE                Location/Qualifiers
source                 1..120
                       mol_type = protein
                       organism = synthetic construct
SEQUENCE: 3051
QVQLQESGPG LVKPSQTLSL TCTVSGFSLT AYGVNWVRQP AGKGLEWLGM IWGDGNTDYN  60
```

```
SALKSRLTIS KDNSKSQVSL KLSSVTAADT AVYYCARDRV TATLYAMDYW GQGTLVTVSS  120

SEQ ID NO: 3052        moltype = AA  length = 120
FEATURE                Location/Qualifiers
source                 1..120
                       mol_type = protein
                       organism = synthetic construct
SEQUENCE: 3052
QVQLQESGPG LVKPSQTLSL TCAVSGFSLT AYGVNWVRQP PGKGLEWLGM IWGDGNTDYN  60
SALKSRLTIS KDNSKSQVSL KLSSVTAVDT AVYYCARDRV TATLYAMDYW GQGTLVTVSS  120

SEQ ID NO: 3053        moltype = AA  length = 120
FEATURE                Location/Qualifiers
source                 1..120
                       mol_type = protein
                       organism = synthetic construct
SEQUENCE: 3053
QVQLQESGPG LVKPSETLSL TCTVSGFSLT AYGVNWVRQP PGKGLEWLGM IWGDGNTDYN  60
SALKSRLTIS KDNSKSHVSL KLSSVTAADT AVYYCARDRV TATLYAMDYW GQGTLVTVSS  120

SEQ ID NO: 3054        moltype = AA  length = 120
FEATURE                Location/Qualifiers
source                 1..120
                       mol_type = protein
                       organism = synthetic construct
SEQUENCE: 3054
QVQLQESGPG LVKPSETLSL TCAVSGFSLT AYGVNWVRQP PGKGLEWLGM IWGDGNTDYN  60
SALKSRLTIS KDNSKSQVSL KLSSVTAADT AVYYCARDRV TATLYAMDYW GQGTLVTVSS  120

SEQ ID NO: 3055        moltype = AA  length = 120
FEATURE                Location/Qualifiers
source                 1..120
                       mol_type = protein
                       organism = synthetic construct
SEQUENCE: 3055
QVQLQESGPG LVKPSQTLSL TCAVYGFSLT AYGVNWVRQP PGKGLEWLGM IWGDGNTDYN  60
SALKSRLTIS KDNSKSQVSL KLSSVTAADT AVYYCARDRV TATLYAMDYW GQGTLVTVSS  120

SEQ ID NO: 3056        moltype = AA  length = 120
FEATURE                Location/Qualifiers
source                 1..120
                       mol_type = protein
                       organism = synthetic construct
SEQUENCE: 3056
RVQLQESGPG LVKPSETLSL TCTVSGFSLT AYGVNWVRQP PGKGLEWLGM IWGDGNTDYN  60
SALKSRLTIS KDNSKSQVPL KLSSVTAADT AVYYCARDRV TATLYAMDYW GQGTLVTVSS  120

SEQ ID NO: 3057        moltype = AA  length = 120
FEATURE                Location/Qualifiers
source                 1..120
                       mol_type = protein
                       organism = synthetic construct
SEQUENCE: 3057
QVQLQESGPG LVKPSQTLSL TCTVSGFSLT AYGVNWVRQH PGKGLEWLGM IWGDGNTDYN  60
SALKSLLTIS KDNSKSQVSL KLSSVTAADT AVYYCARDRV TATLYAMDYW GQGTLVTVSS  120

SEQ ID NO: 3058        moltype = AA  length = 120
FEATURE                Location/Qualifiers
source                 1..120
                       mol_type = protein
                       organism = synthetic construct
SEQUENCE: 3058
QVQLQESGPG LVKPSDTLSL TCAVSGFSLT AYGVNWVRQP PGKGLEWLGM IWGDGNTDYN  60
SALKSRLTIS KDNSKSQVSL KLSSVTALDT AVYYCARDRV TATLYAMDYW GQGTLVTVSS  120

SEQ ID NO: 3059        moltype = AA  length = 120
FEATURE                Location/Qualifiers
source                 1..120
                       mol_type = protein
                       organism = synthetic construct
SEQUENCE: 3059
QVQLQESGPG LVKPSDTLSL TCAVSGFSLT AYGVNWVRQP PGKGLEWLGM IWGDGNTDYN  60
SALKSRLTIS KDNSKSQVSL KLSSVTAVDT AVYYCARDRV TATLYAMDYW GQGTLVTVSS  120

SEQ ID NO: 3060        moltype = AA  length = 120
FEATURE                Location/Qualifiers
source                 1..120
                       mol_type = protein
                       organism = synthetic construct
```

SEQUENCE: 3060
QVQLQESGSG LVKPSQTLSL TCAVSGFSLT AYGVNWVRQP PGKGLEWLGM IWGDGNTDYN 60
SALKSRLTIS KDNSKSQVSL KLSSVTAADT AVYYCARDRV TATLYAMDYW GQGTLVTVSS 120

SEQ ID NO: 3061 moltype = AA length = 120
FEATURE Location/Qualifiers
source 1..120
mol_type = protein
organism = synthetic construct
SEQUENCE: 3061
EVQLVESGGG LVQPGRSLRL SCTVSGFSLT AYGVNWVRQA PGKGLEWLGM IWGDGNTDYN 60
SALKSRLTIS KDNSKSIVYL QMNSLKTEDT AVYYCARDRV TATLYAMDYW GQGTLVTVSS 120

SEQ ID NO: 3062 moltype = AA length = 120
FEATURE Location/Qualifiers
source 1..120
mol_type = protein
organism = synthetic construct
SEQUENCE: 3062
EVQLVESGGG LVQPGPSLRL SCTVSGFSLT AYGVNWVRQA PGKGLEWLGM IWGDGNTDYN 60
SALKSRLTIS KDNSKSIVYL QMNSLKTEDT AVYYCARDRV TATLYAMDYW GQGTLVTVSS 120

SEQ ID NO: 3063 moltype = AA length = 120
FEATURE Location/Qualifiers
source 1..120
mol_type = protein
organism = synthetic construct
SEQUENCE: 3063
QVQLQESGSG LVKPSQTLSL TCAVSGFSLT AYGVNWVRQS PGKGLEWLGM IWGDGNTDYN 60
SALKSRLTIS KDNSKSQVSL KLSSVTAADT AVYYCARDRV TATLYAMDYW GQGTLVTVSS 120

SEQ ID NO: 3064 moltype = AA length = 120
FEATURE Location/Qualifiers
source 1..120
mol_type = protein
organism = synthetic construct
SEQUENCE: 3064
QVQLQESGPG LVKPSETLSL TCTVSGFSLT AYGVNWVRQP AGKGLEWLGM IWGDGNTDYN 60
SALKSRLTIS KDNSKSQVSL KLSSVTAADT AVYYCARDRV TATLYAMDYW GQGTLVTVSS 120

SEQ ID NO: 3065 moltype = AA length = 120
FEATURE Location/Qualifiers
source 1..120
mol_type = protein
organism = synthetic construct
SEQUENCE: 3065
EVQLVESGGG LVKPGRSLRL SCTVSGFSLT AYGVNWVRQA PGKGLEWLGM IWGDGNTDYN 60
SALKSRLTIS KDNSKSIVYL QMNSLKTEDT AVYYCARDRV TATLYAMDYW GQGTLVTVSS 120

SEQ ID NO: 3066 moltype = AA length = 120
FEATURE Location/Qualifiers
source 1..120
mol_type = protein
organism = synthetic construct
SEQUENCE: 3066
QVQLQESGPG LVKPSETLSL TCAVYGFSLT AYGVNWVRQP PGKGLEWLGM IWGDGNTDYN 60
SALKSRLTIS KDNSKSQVYL KLSSVTAADT AVYYCARDRV TATLYAMDYW GQGTLVTVSS 120

SEQ ID NO: 3067 moltype = AA length = 120
FEATURE Location/Qualifiers
source 1..120
mol_type = protein
organism = synthetic construct
SEQUENCE: 3067
QVQLQESGPG LVKPSDTLSL TCAVSGFSLT AYGVNWVRQP PGKGLEWLGM IWGDGNTDYN 60
SALKSRLTIS KDNSKSQVSL KLSSVTAVDT GVYYCARDRV TATLYAMDYW GQGTLVTVSS 120

SEQ ID NO: 3068 moltype = AA length = 120
FEATURE Location/Qualifiers
source 1..120
mol_type = protein
organism = synthetic construct
SEQUENCE: 3068
EVQLVESGGG LVQPGGSLRL SCAVSGFSLT AYGVNWVRQA PGKGLEWLGM IWGDGNTDYN 60
SALKSRLTIS KDNSKSSVYL QMNSLKTEDT AVYYCARDRV TATLYAMDYW GQGTLVTVSS 120

SEQ ID NO: 3069 moltype = AA length = 120
FEATURE Location/Qualifiers
source 1..120

```
                        mol_type = protein
                        organism = synthetic construct
SEQUENCE: 3069
EVQLVESGGG LVKPGGSLRL SCAVSGFSLT AYGVNWVRQA PGKGLEWLGM IWGDGNTDYN  60
SALKSRLTIS KDNSKSTVYL QMNSLKTEDT AVYYCARDRV TATLYAMDYW GQGTLVTVSS  120

SEQ ID NO: 3070         moltype = AA  length = 120
FEATURE                 Location/Qualifiers
source                  1..120
                        mol_type = protein
                        organism = synthetic construct
SEQUENCE: 3070
QVQLQQSGPG LVKPSQTLSL TCAVSGFSLT AYGVNWVRQS PSRGLEWLGM IWGDGNTDYN  60
SALKSRLTIN KDNSKSQVSL QLNSVTPEDT AVYYCARDRV TATLYAMDYW GQGTLVTVSS  120

SEQ ID NO: 3071         moltype = AA  length = 120
FEATURE                 Location/Qualifiers
source                  1..120
                        mol_type = protein
                        organism = synthetic construct
SEQUENCE: 3071
QVQLVESGGG LVQPGGSLRL SCSVSGFSLT AYGVNWVRQA PGKGLEWLGM IWGDGNTDYN  60
SALKSRLTIS KDNSKSTVYL QMNSLRAEDT AVYYCARDRV TATLYAMDYW GQGTLVTVSS  120

SEQ ID NO: 3072         moltype = AA  length = 120
FEATURE                 Location/Qualifiers
source                  1..120
                        mol_type = protein
                        organism = synthetic construct
SEQUENCE: 3072
QVQLQQWGAG LLKPSETLSL TCAVYGFSLT AYGVNWVRQP PGKGLEWLGM IWGDGNTDYN  60
SALKSRLTIS KDNSKSQVSL KLSSVTAADT AVYYCARDRV TATLYAMDYW GQGTLVTVSS  120

SEQ ID NO: 3073         moltype = AA  length = 120
FEATURE                 Location/Qualifiers
source                  1..120
                        mol_type = protein
                        organism = synthetic construct
SEQUENCE: 3073
QVQLVESGGG VVQPGRSLRL SCAVSGFSLT AYGVNWVRQA PGKGLEWLGM IWGDGNTDYN  60
SALKSRLTIS KDNSTSTVFL QMNSLRAEDT AVYYCARDRV TATLYAMDYW GQGTLVTVSS  120

SEQ ID NO: 3074         moltype = AA  length = 120
FEATURE                 Location/Qualifiers
source                  1..120
                        mol_type = protein
                        organism = synthetic construct
SEQUENCE: 3074
EVQLVESGGG LVQPGGSLRL SCAVSGFSLT AYGVNWVRQA PGKGLEWLGM IWGDGNTDYN  60
SALKSRLTIS KDNSKSTVYL QMNSLRAEDT AVYYCARDRV TATLYAMDYW GQGTLVTVSS  120

SEQ ID NO: 3075         moltype = AA  length = 120
FEATURE                 Location/Qualifiers
source                  1..120
                        mol_type = protein
                        organism = synthetic construct
SEQUENCE: 3075
EVQLVESGGG LVQPGGSLRL SCAVSGFSLT AYGVNWVRQA PGKGLEWLGM IWGDGNTDYN  60
SALKSRLTIS KDNAKSSVYL QMNSLRDEDT AVYYCARDRV TATLYAMDYW GQGTLVTVSS  120

SEQ ID NO: 3076         moltype = AA  length = 120
FEATURE                 Location/Qualifiers
source                  1..120
                        mol_type = protein
                        organism = synthetic construct
SEQUENCE: 3076
EVQLLESGGG LVQPGGSLRL SCAVSGFSLT AYGVNWVRQA PGKGLEWLGM IWGDGNTDYN  60
SALKSRLTIS KDNSKSTVYL QMNSLRAEDT AVYYCARDRV TATLYAMDYW GQGTLVTVSS  120

SEQ ID NO: 3077         moltype = AA  length = 120
FEATURE                 Location/Qualifiers
source                  1..120
                        mol_type = protein
                        organism = synthetic construct
SEQUENCE: 3077
QVQLVESGGG LVKPGGSLRL SCAVSGFSLT AYGVNWVRQA PGKGLEWLGM IWGDGNTDYN  60
SALKSRLTIS KDNAKSSVYL QMNSLRAEDT AVYYCARDRV TATLYAMDYW GQGTLVTVSS  120

SEQ ID NO: 3078         moltype = AA  length = 120
```

```
FEATURE                Location/Qualifiers
source                 1..120
                       mol_type = protein
                       organism = synthetic construct
SEQUENCE: 3078
EVQLVESGGG LVQPGGSLKL SCAVSGFSLT AYGVNWVRQA SGKGLEWLGM IWGDGNTDYN  60
SALKSRLTIS KDNSKSTVYL QMNSLKTEDT AVYYCARDRV TATLYAMDYW GQGTLVTVSS  120

SEQ ID NO: 3079        moltype = AA  length = 120
FEATURE                Location/Qualifiers
source                 1..120
                       mol_type = protein
                       organism = synthetic construct
SEQUENCE: 3079
QVQLLESGGG LVKPGGSLRL SCAVSGFSLT AYGVNWVRQA PGKGLEWLGM IWGDGNTDYN  60
SALKSRLTIS KDNAKSSVYL QMNSLRAEDT AVYYCARDRV TATLYAMDYW GQGTLVTVSS  120

SEQ ID NO: 3080        moltype = AA  length = 120
FEATURE                Location/Qualifiers
source                 1..120
                       mol_type = protein
                       organism = synthetic construct
SEQUENCE: 3080
QVQLVESGGG VVQPGRSLRL SCAVSGFSLT AYGVNWVRQA PGKGLEWLGM IWGDGNTDYN  60
SALKSRLTIS KDNSKSTVYL QMNSLRAEDT AVYYCARDRV TATLYAMDYW GQGTLVTVSS  120

SEQ ID NO: 3081        moltype = AA  length = 120
FEATURE                Location/Qualifiers
source                 1..120
                       mol_type = protein
                       organism = synthetic construct
SEQUENCE: 3081
QVQLVESGGG VVQPGRSLRL SCAVSGFSLT AYGVNWVRQA PGKGLEWLGM IWGDGNTDYN  60
SALKSRLTIS KDNSKSRVYL QMNSLRAEDT AVYYCARDRV TATLYAMDYW GQGTLVTVSS  120

SEQ ID NO: 3082        moltype = AA  length = 120
FEATURE                Location/Qualifiers
source                 1..120
                       mol_type = protein
                       organism = synthetic construct
SEQUENCE: 3082
QVQLVESGGG VVQPGRSLRL SCAVSGFSLT AYGVNWVRQA PGKGLEWLGM IWGDGNTDYN  60
SALKSRLAIS KDNSKSTVYL QMNSLRAEDT AVYYCARDRV TATLYAMDYW GQGTLVTVSS  120

SEQ ID NO: 3083        moltype = AA  length = 120
FEATURE                Location/Qualifiers
source                 1..120
                       mol_type = protein
                       organism = synthetic construct
SEQUENCE: 3083
QVQLVESGGG VVQPGGSLRL SCAVSGFSLT AYGVNWVRQA PGKGLEWLGM IWGDGNTDYN  60
SALKSRLTIS KDNSKSTVYL QMNSLRAEDT AVYYCARDRV TATLYAMDYW GQGTLVTVSS  120

SEQ ID NO: 3084        moltype = AA  length = 120
FEATURE                Location/Qualifiers
source                 1..120
                       mol_type = protein
                       organism = synthetic construct
SEQUENCE: 3084
EVQLVESGGG LVQPGGSLRL SCAVSGFSLT AYGVNWVRQA PGKGLEWLGM IWGDGNTDYN  60
SALKSRLTIS KDNAKSTVYL QMNSLRAEDT AVYYCARDRV TATLYAMDYW GQGTLVTVSS  120

SEQ ID NO: 3085        moltype = AA  length = 120
FEATURE                Location/Qualifiers
source                 1..120
                       mol_type = protein
                       organism = synthetic construct
SEQUENCE: 3085
EVQLVESGGG LVQPGGSLRL SCAVSGFSLT AYGVNWVRQA PGKGLEWLGM IWGDGNTDYN  60
SALKSRLTIS KDNAKSSVYL QMNSLRAEDT AVYYCARDRV TATLYAMDYW GQGTLVTVSS  120

SEQ ID NO: 3086        moltype = AA  length = 120
FEATURE                Location/Qualifiers
source                 1..120
                       mol_type = protein
                       organism = synthetic construct
SEQUENCE: 3086
EVQLVESGGV VVQPGGSLRL SCAVSGFSLT AYGVNWVRQA PGKGLEWLGM IWGDGNTDYN  60
SALKSRLTIS KDNSKSSVYL QMNSLRTEDT ALYYCARDRV TATLYAMDYW GQGTLVTVSS  120
```

```
SEQ ID NO: 3087        moltype = AA  length = 120
FEATURE                Location/Qualifiers
source                 1..120
                       mol_type = protein
                       organism = synthetic construct
SEQUENCE: 3087
EVQLVESGGG LVQPGGSLRL SCAVSGFSLT AYGVNWVRQA PGKGLEWLGM IWGDGNTDYN  60
SALKSRLTIS KHNSKSTVYL QMNSLRAEDT AVYYCARDRV TATLYAMDYW GQGTLVTVSS  120

SEQ ID NO: 3088        moltype = AA  length = 120
FEATURE                Location/Qualifiers
source                 1..120
                       mol_type = protein
                       organism = synthetic construct
SEQUENCE: 3088
EVQLVESGGG LVKPGGSLRL SCAVSGFSLT AYGVNWVRQA PGKGLEWLGM IWGDGNTDYN  60
SALKSRLTIS KDNAKSSVYL QMNSLRAEDT AVYYCARDRV TATLYAMDYW GQGTLVTVSS  120

SEQ ID NO: 3089        moltype = AA  length = 120
FEATURE                Location/Qualifiers
source                 1..120
                       mol_type = protein
                       organism = synthetic construct
SEQUENCE: 3089
EVQLVESGGG LIQPGGSLRL SCAVSGFSLT AYGVNWVRQP PGKGLEWLGM IWGDGNTDYN  60
SALKSRLTIS KDNSKSTVYL QMNSLRAEDT AVYYCARDRV TATLYAMDYW GQGTLVTVSS  120

SEQ ID NO: 3090        moltype =   length =
SEQUENCE: 3090
000

SEQ ID NO: 3091        moltype = AA  length = 119
FEATURE                Location/Qualifiers
source                 1..119
                       mol_type = protein
                       organism = synthetic construct
SEQUENCE: 3091
QVQLQQSGPE LVKPGASVKI SCKASGYAFS SSWMNWVKQR PGQGLEWIGR IYPGDGDTKY  60
NGKFKGKATL TADKSSSTAY MHLSSLTSVD SAVYFCARRG TGGWYFDVWG AGTTVTVSS   119

SEQ ID NO: 3092        moltype = AA  length = 111
FEATURE                Location/Qualifiers
source                 1..111
                       mol_type = protein
                       organism = synthetic construct
SEQUENCE: 3092
DIVLTQSPAS LAVSLGQRAT ISCRASESVD SSGNSFMHWY QQKPGQPPQL LIYRASNLES  60
GIPARFSGSG SRTDFTLTIN PVEADDVATF YCQQSFDDPF TFGSGTKLEI K           111

SEQ ID NO: 3093        moltype = AA  length = 111
FEATURE                Location/Qualifiers
source                 1..111
                       mol_type = protein
                       organism = synthetic construct
SEQUENCE: 3093
DIVLTQSPDS LAVSLGERAT INCRASESVD SSGNSFMHWY QQKPGQPPQL LIYRASNLES  60
GVPDRFSGSG SRTDFTLTIS SLQAEDVAVY YCQQSFDDPF TFGQGTKLEI K           111

SEQ ID NO: 3094        moltype = AA  length = 111
FEATURE                Location/Qualifiers
source                 1..111
                       mol_type = protein
                       organism = synthetic construct
SEQUENCE: 3094
EIVLTQSPAT LSLSPGERAT LSCRASESVD SSGNSFMHWY QQKPGQAPQL LIYRASNLES  60
GIPARFSGSG SRTDFTLTIS SLEPEDFAVY YCQQSFDDPF TFGQGTKLEI K           111

SEQ ID NO: 3095        moltype = AA  length = 111
FEATURE                Location/Qualifiers
source                 1..111
                       mol_type = protein
                       organism = synthetic construct
SEQUENCE: 3095
EIVLTQSPAT LSLSPGERAT LSCRASESVD SSGNSFMHWY QQKPGQAPQL LIYRASNLES  60
GIPARFSGSG SRTDFTLTIS RLEPEDFAVY YCQQSFDDPF TFGQGTKLEI K           111

SEQ ID NO: 3096        moltype = AA  length = 111
FEATURE                Location/Qualifiers
```

```
source                  1..111
                        mol_type = protein
                        organism = synthetic construct
SEQUENCE: 3096
EIVLTQSPAT LSLSPGERAT LSCRASESVD SSGNSFMHWY QQKPGQAPQL LIYRASNLES  60
GIPARFSGSG SRTDFTLTIS SLQPEDFAVY YCQQSFDDPF TFGQGTKLEI K           111

SEQ ID NO: 3097         moltype = AA  length = 111
FEATURE                 Location/Qualifiers
source                  1..111
                        mol_type = protein
                        organism = synthetic construct
SEQUENCE: 3097
DIQLTQSPSS LSASVGDRVT ITCRASESVD SSGNSFMHWY QQKPGQAPQL LIYRASNLES  60
GVPSRFSGSG SRTDFTLTIS SLQPEDVATY YCQQSFDDPF TFGQGTKLEI K           111

SEQ ID NO: 3098         moltype = AA  length = 111
FEATURE                 Location/Qualifiers
source                  1..111
                        mol_type = protein
                        organism = synthetic construct
SEQUENCE: 3098
EIVLTQSPAT LSLSPGERAT LSCRASESVD SSGNSFMHWY QQKPGQAPQL LIYRASNLES  60
GIPARFSGSG PRTDFTLTIS SLEPEDFAVY YCQQSFDDPF TFGQGTKLEI K           111

SEQ ID NO: 3099         moltype = AA  length = 111
FEATURE                 Location/Qualifiers
source                  1..111
                        mol_type = protein
                        organism = synthetic construct
SEQUENCE: 3099
EIVLTQSPAT LSLSPGERAT LSCRASESVD SSGNSFMHWY QQKPGQAPQL LIYRASNLES  60
GIPDRFSGSG SRTDFTLTIS RLEPEDFAVY YCQQSFDDPF TFGQGTKLEI K           111

SEQ ID NO: 3100         moltype = AA  length = 111
FEATURE                 Location/Qualifiers
source                  1..111
                        mol_type = protein
                        organism = synthetic construct
SEQUENCE: 3100
DIQLTQSPSS LSASVGDRVT ITCRASESVD SSGNSFMHWY QQKPGKVPQL LIYRASNLES  60
GVPSRFSGSG SRTDFTLTIS SLQPEDVATY YCQQSFDDPF TFGQGTKLEI K           111

SEQ ID NO: 3101         moltype = AA  length = 111
FEATURE                 Location/Qualifiers
source                  1..111
                        mol_type = protein
                        organism = synthetic construct
SEQUENCE: 3101
DIQLTQSPSS LSASVGDRVT ITCRASESVD SSGNSFMHWY QQKPGKTPQL LIYRASNLES  60
GIPSRFSGSG SRTDFTLTIR SLQPEDFATY YCQQSFDDPF TFGQGTKLEI K           111

SEQ ID NO: 3102         moltype = AA  length = 111
FEATURE                 Location/Qualifiers
source                  1..111
                        mol_type = protein
                        organism = synthetic construct
SEQUENCE: 3102
EIVLTQSPGT LSLSPGERAT LSCRASESVD SSGNSFMHWY QQKPGQAPQL LIYRASNLES  60
GIPDRFSGSG SRTDFTLTIS RLEPEDFAVY YCQQSFDDPF TFGQGTKLEI K           111

SEQ ID NO: 3103         moltype = AA  length = 111
FEATURE                 Location/Qualifiers
source                  1..111
                        mol_type = protein
                        organism = synthetic construct
SEQUENCE: 3103
EIVLTQSPAT LSLSPGERAT LSCRASESVD SSGNSFMHWY QQKPGLAPQL LIYRASNLES  60
GIPDRFSGSG SRTDFTLTIS RLEPEDFAVY YCQQSFDDPF TFGQGTKLEI K           111

SEQ ID NO: 3104         moltype = AA  length = 111
FEATURE                 Location/Qualifiers
source                  1..111
                        mol_type = protein
                        organism = synthetic construct
SEQUENCE: 3104
DIQLTQSPSS LSASVGDRVT ITCRASESVD SSGNSFMHWY QQKPGKAPQL LIYRASNLES  60
GVPSRFSGSG SRTDFTLTIS SLQPEDFATY YCQQSFDDPF TFGQGTKLEI K           111
```

```
SEQ ID NO: 3105        moltype = AA  length = 111
FEATURE                Location/Qualifiers
source                 1..111
                       mol_type = protein
                       organism = synthetic construct
SEQUENCE: 3105
DIQLTQSPSS VSASVGDRVT ITCRASESVD SSGNSFMHWY QQKPGKAPQL LIYRASNLES  60
GVPSRFSGSG SRTDFTLTIS SLQPEDFATY YCQQSFDDPF TFGQGTKLEI K           111

SEQ ID NO: 3106        moltype = AA  length = 111
FEATURE                Location/Qualifiers
source                 1..111
                       mol_type = protein
                       organism = synthetic construct
SEQUENCE: 3106
AIQLTQSPSS LSASVGDRVT ITCRASESVD SSGNSFMHWY QQKPGKAPQL LIYRASNLES  60
GVPSRFSGSG SRTDFTLTIS SLQPEDFATY YCQQSFDDPF TFGQGTKLEI K           111

SEQ ID NO: 3107        moltype = AA  length = 111
FEATURE                Location/Qualifiers
source                 1..111
                       mol_type = protein
                       organism = synthetic construct
SEQUENCE: 3107
DIQLTQSPSF LSASVGDRVT ITCRASESVD SSGNSFMHWY QQKPGKAPQL LIYRASNLES  60
GVPSRFSGSG SRTEFTLTIS SLQPEDFATY YCQQSFDDPF TFGQGTKLEI K           111

SEQ ID NO: 3108        moltype = AA  length = 111
FEATURE                Location/Qualifiers
source                 1..111
                       mol_type = protein
                       organism = synthetic construct
SEQUENCE: 3108
DIQLTQSPSS LSASVGDRVT ITCRASESVD SSGNSFMHWY QQKPGKAPQL LIYRASNLES  60
GVPSRFSGSG SRTDFTFTIS SLQPEDIATY YCQQSFDDPF TFGQGTKLEI K           111

SEQ ID NO: 3109        moltype = AA  length = 111
FEATURE                Location/Qualifiers
source                 1..111
                       mol_type = protein
                       organism = synthetic construct
SEQUENCE: 3109
EIVLTQSPAT LSVSPGERAT LSCRASESVD SSGNSFMHWY QQKPGQAPQL LIYRASNLES  60
GIPARFSGSG SRTEFTLTIS ILQSEDFAVY YCQQSFDDPF TFGQGTKLEI K           111

SEQ ID NO: 3110        moltype = AA  length = 111
FEATURE                Location/Qualifiers
source                 1..111
                       mol_type = protein
                       organism = synthetic construct
SEQUENCE: 3110
EIVLTQSPAT LSVSPGERAT LSCRASESVD SSGNSFMHWY QQKPGQAPQL LIYRASNLES  60
GIPARFSGSG SRTEFTLTIS SLQSEDFAVY YCQQSFDDPF TFGQGTKLEI K           111

SEQ ID NO: 3111        moltype = AA  length = 111
FEATURE                Location/Qualifiers
source                 1..111
                       mol_type = protein
                       organism = synthetic construct
SEQUENCE: 3111
AIRLTQSPFS LSASVGDRVT ITCRASESVD SSGNSFMHWY QQKPAKAPQL FIYRASNLES  60
GVPSRFSGSG SRTDFTLTIS SLQPEDFATY YCQQSFDDPF TFGQGTKLEI K           111

SEQ ID NO: 3112        moltype = AA  length = 111
FEATURE                Location/Qualifiers
source                 1..111
                       mol_type = protein
                       organism = synthetic construct
SEQUENCE: 3112
DIQLTQSPSS LSASVGDRVT ITCRASESVD SSGNSFMHWY QQKPGKAPQS LIYRASNLES  60
GVPSRFSGSG SRTDFTLTIS SLQPEDFATY YCQQSFDDPF TFGQGTKLEI K           111

SEQ ID NO: 3113        moltype = AA  length = 111
FEATURE                Location/Qualifiers
source                 1..111
                       mol_type = protein
                       organism = synthetic construct
SEQUENCE: 3113
DIQLTQSPSS LSASVGDRVT ITCRASESVD SSGNSFMHWY QQKPGKAPQR LIYRASNLES  60
```

```
GVPSRFSGSG SRTEFTLTIS NLQPEDFATY YCQQSFDDPF TFGQGTKLEI K          111

SEQ ID NO: 3114        moltype = AA  length = 111
FEATURE                Location/Qualifiers
source                 1..111
                       mol_type = protein
                       organism = synthetic construct
SEQUENCE: 3114
DIQLTQSPST LSASVGDRVT ITCRASESVD SSGNSFMHWY QQKPGKAPQL LIYRASNLES  60
GVPSRFSGSG SRTEFTLTIS SLQPDDFATY YCQQSFDDPF TFGQGTKLEI K          111

SEQ ID NO: 3115        moltype = AA  length = 111
FEATURE                Location/Qualifiers
source                 1..111
                       mol_type = protein
                       organism = synthetic construct
SEQUENCE: 3115
EIVLTQSPDF QSVTPKEKVT ITCRASESVD SSGNSFMHWY QQKPDQSPQL LIYRASNLES  60
GVPSRFSGSG SRTDFTLTIN SLEAEDAATY YCQQSFDDPF TFGQGTKLEI K          111

SEQ ID NO: 3116        moltype = AA  length = 111
FEATURE                Location/Qualifiers
source                 1..111
                       mol_type = protein
                       organism = synthetic construct
SEQUENCE: 3116
DIQLTQSPSS LSASVGDRVT ITCRASESVD SSGNSFMHWY QQKPGKAPQS LIYRASNLES  60
GVPSKFSGSG SRTDFTLTIS SLQPEDFATY YCQQSFDDPF TFGQGTKLEI K          111

SEQ ID NO: 3117        moltype = AA  length = 111
FEATURE                Location/Qualifiers
source                 1..111
                       mol_type = protein
                       organism = synthetic construct
SEQUENCE: 3117
DIQLTQSPSS LSASVGDRVT ITCRASESVD SSGNSFMHWY QQKPGKAPQR LIYRASNLES  60
GVPSRFSGSG SRTEFTLTIS SLQPEDFATY YCQQSFDDPF TFGQGTKLEI K          111

SEQ ID NO: 3118        moltype = AA  length = 111
FEATURE                Location/Qualifiers
source                 1..111
                       mol_type = protein
                       organism = synthetic construct
SEQUENCE: 3118
DIVLTQTPLS LSVTPGQPAS ISCRASESVD SSGNSFMHWY LQKPGQPPQL LIYRASNLES  60
GVPDRFSGSG SRTDFTLKIS RVEAEDVGVY YCQQSFDDPF TFGQGTKLEI K          111

SEQ ID NO: 3119        moltype = AA  length = 111
FEATURE                Location/Qualifiers
source                 1..111
                       mol_type = protein
                       organism = synthetic construct
SEQUENCE: 3119
DIQLTQSPSS LSASVGDRVT ITCRASESVD SSGNSFMHWY QQKPEKAPQS LIYRASNLES  60
GVPSRFSGSG SRTDFTLTIS SLQPEDFATY YCQQSFDDPF TFGQGTKLEI K          111

SEQ ID NO: 3120        moltype = AA  length = 111
FEATURE                Location/Qualifiers
source                 1..111
                       mol_type = protein
                       organism = synthetic construct
SEQUENCE: 3120
EIVLTQSPPT LSLSPGERVT LSCRASESVD SSGNSFMHWY QQKPGQAPQL LIYRASNLES  60
GIPARFSGSG SRTDFTLTIS SLQPEDFAVY YCQQSFDDPF TFGQGTKLEI K          111

SEQ ID NO: 3121        moltype = AA  length = 111
FEATURE                Location/Qualifiers
source                 1..111
                       mol_type = protein
                       organism = synthetic construct
SEQUENCE: 3121
DIQLTQSPSA MSASVGDRVT ITCRASESVD SSGNSFMHWY QQKPGKVPQR LIYRASNLES  60
GVPSRFSGSG SRTEFTLTIS SLQPEDFATY YCQQSFDDPF TFGQGTKLEI K          111

SEQ ID NO: 3122        moltype = AA  length = 111
FEATURE                Location/Qualifiers
source                 1..111
                       mol_type = protein
                       organism = synthetic construct
```

```
SEQUENCE: 3122
DIVLTQSPLS LPVTPGEPAS ISCRASESVD SSGNSFMHWY LQKPGQSPQL LIYRASNLES  60
GVPDRFSGSG SRTDFTLKIS RVEAEDVGVY YCQQSFDDPF TFGQGTKLEI K           111

SEQ ID NO: 3123         moltype = AA  length = 111
FEATURE                 Location/Qualifiers
source                  1..111
                        mol_type = protein
                        organism = synthetic construct
SEQUENCE: 3123
DIVLTQTPLS LPVTPGEPAS ISCRASESVD SSGNSFMHWY LQKPGQSPQL LIYRASNLES  60
GVPDRFSGSG SRTDFTLKIS RVEAEDVGVY YCQQSFDDPF TFGQGTKLEI K           111

SEQ ID NO: 3124         moltype = AA  length = 111
FEATURE                 Location/Qualifiers
source                  1..111
                        mol_type = protein
                        organism = synthetic construct
SEQUENCE: 3124
DIVLTQTPLS LSVTPGQPAS ISCRASESVD SSGNSFMHWY LQKPGQSPQL LIYRASNLES  60
GVPDRFSGSG SRTDFTLKIS RVEAEDVGVY YCQQSFDDPF TFGQGTKLEI K           111

SEQ ID NO: 3125         moltype = AA  length = 111
FEATURE                 Location/Qualifiers
source                  1..111
                        mol_type = protein
                        organism = synthetic construct
SEQUENCE: 3125
EIVLTQSPPT LSLSPGERVT LSCRASESVD SSGNSFMHWY QQKPGQAPQL LIYRASNLES  60
SIPARFSGSG SRTDFTLTIS SLQPEDFAVY YCQQSFDDPF TFGQGTKLEI K           111

SEQ ID NO: 3126         moltype = AA  length = 111
FEATURE                 Location/Qualifiers
source                  1..111
                        mol_type = protein
                        organism = synthetic construct
SEQUENCE: 3126
DIVLTQSPLS LPVTLGQPAS ISCRASESVD SSGNSFMHWY QQRPGQSPQR LIYRASNLES  60
GVPDRFSGSG SRTDFTLKIS RVEAEDVGVY YCQQSFDDPF TFGQGTKLEI K           111

SEQ ID NO: 3127         moltype = AA  length = 111
FEATURE                 Location/Qualifiers
source                  1..111
                        mol_type = protein
                        organism = synthetic construct
SEQUENCE: 3127
DIVLTQTPLS SPVTLGQPAS ISCRASESVD SSGNSFMHWY QQRPGQPPQL LIYRASNLES  60
GVPDRFSGSG ARTDFTLKIS RVEAEDVGVY YCQQSFDDPF TFGQGTKLEI K           111

SEQ ID NO: 3128         moltype = AA  length = 111
FEATURE                 Location/Qualifiers
source                  1..111
                        mol_type = protein
                        organism = synthetic construct
SEQUENCE: 3128
DIVLTQSPAF LSVTPGEKVT ITCRASESVD SSGNSFMHWY QQKPDQAPQL LIYRASNLES  60
GVPSRFSGSG SRTDFTFTIS SLEAEDAATY YCQQSFDDPF TFGQGTKLEI K           111

SEQ ID NO: 3129         moltype = AA  length = 111
FEATURE                 Location/Qualifiers
source                  1..111
                        mol_type = protein
                        organism = synthetic construct
SEQUENCE: 3129
DIQLIQSPSF LSASVGDRVS IICRASESVD SSGNSFMHWY LQKPGKSPQL FIYRASNLES  60
GVSSRFSGRG SRTDFTLTII SLKPEDFAAY YCQQSFDDPF TFGQGTKLEI K           111

SEQ ID NO: 3130         moltype = AA  length = 111
FEATURE                 Location/Qualifiers
source                  1..111
                        mol_type = protein
                        organism = synthetic construct
SEQUENCE: 3130
EIVLTQTPLS LSITPGEQAS ISCRASESVD SSGNSFMHWY LQKARPVPQL LIYRASNLES  60
GVPDRFSGSG SRTDFTLKIS RVEAEDFGVY YCQQSFDDPF TFGQGTKLEI K           111

SEQ ID NO: 3131         moltype = AA  length = 111
FEATURE                 Location/Qualifiers
source                  1..111
```

```
                        mol_type = protein
                        organism = synthetic construct
SEQUENCE: 3131
EIVLTQTPLS LSITPGEQAS MSCRASESVD SSGNSFMHWY LQKARPVPQL LIYRASNLES  60
GVPDRFSGSG SRTDFTLKIS RVEAEDFGVY YCQQSFDDPF TFGQGTKLEI K          111

SEQ ID NO: 3132         moltype = AA  length = 111
FEATURE                 Location/Qualifiers
source                  1..111
                        mol_type = protein
                        organism = synthetic construct
SEQUENCE: 3132
EITLTQSPAF MSATPGDKVN ISCRASESVD SSGNSFMHWY QQKPGEAPQF IIYRASNLES  60
GIPPRFSGSG YRTDFTLTIN NIESEDAAYY YCQQSFDDPF TFGQGTKLEI K          111

SEQ ID NO: 3133         moltype = AA  length = 119
FEATURE                 Location/Qualifiers
source                  1..119
                        mol_type = protein
                        organism = synthetic construct
SEQUENCE: 3133
QVQLVQSGAE VKKPGASVKV SCKASGYAFS SSWMNWVRQA PGQGLEWIGR IYPGDGDTKY  60
NGKFKGRATL TADKSTSTAY MELSSLRSED TAVYYCARRG TGGWYFDVWG QGTTVTVSS   119

SEQ ID NO: 3134         moltype = AA  length = 119
FEATURE                 Location/Qualifiers
source                  1..119
                        mol_type = protein
                        organism = synthetic construct
SEQUENCE: 3134
QVQLVQSGAE VKKPGSSVKV SCKASGYAFS SSWMNWVRQA PGQGLEWIGR IYPGDGDTKY  60
NGKFKGRATL TADKSTSTAY MELSSLRSED TAVYYCARRG TGGWYFDVWG QGTTVTVSS   119

SEQ ID NO: 3135         moltype = AA  length = 119
FEATURE                 Location/Qualifiers
source                  1..119
                        mol_type = protein
                        organism = synthetic construct
SEQUENCE: 3135
QVQLVQSGAE VKKPGASVKV SCKASGYAFS SSWMNWVRQA PGKGLEWIGR IYPGDGDTKY  60
NGKFKGRATL TADKSTSTAY MELSSLRSED TAVYYCARRG TGGWYFDVWG QGTTVTVSS   119

SEQ ID NO: 3136         moltype = AA  length = 119
FEATURE                 Location/Qualifiers
source                  1..119
                        mol_type = protein
                        organism = synthetic construct
SEQUENCE: 3136
QVQLVQSGAE VKKPGASVKV SCKASGYAFS SSWMNWVRQA PGQELEWIGR IYPGDGDTKY  60
NGKFKGRATL TADKSISTAY MELSSLRSED TATYYCARRG TGGWYFDVWG QGTTVTVSS   119

SEQ ID NO: 3137         moltype = AA  length = 119
FEATURE                 Location/Qualifiers
source                  1..119
                        mol_type = protein
                        organism = synthetic construct
SEQUENCE: 3137
EVQLVQSGAE VKKPGATVKI SCKASGYAFS SSWMNWVQQA PGKGLEWIGR IYPGDGDTKY  60
NGKFKGRATL TADKSTSTAY MELSSLRSED TAVYYCARRG TGGWYFDVWG QGTTVTVSS   119

SEQ ID NO: 3138         moltype = AA  length = 119
FEATURE                 Location/Qualifiers
source                  1..119
                        mol_type = protein
                        organism = synthetic construct
SEQUENCE: 3138
QVQLVQSGAE VKKTGSSVKV SCKASGYAFS SSWMNWVRQA PGQALEWIGR IYPGDGDTKY  60
NGKFKGRATL TADKSMSTAY MELSSLRSED TAMYYCARRG TGGWYFDVWG QGTTVTVSS   119

SEQ ID NO: 3139         moltype = AA  length = 119
FEATURE                 Location/Qualifiers
source                  1..119
                        mol_type = protein
                        organism = synthetic construct
SEQUENCE: 3139
QVQLVQSGAE VKKPGASVKV SCKASGYAFS SSWMNWVRQA PGQRLEWIGR IYPGDGDTKY  60
NGKFKGRATL TADKSASTAY MELSSLRSED MAVYYCARRG TGGWYFDVWG QGTTVTVSS   119

SEQ ID NO: 3140         moltype = AA  length = 119
```

```
FEATURE                Location/Qualifiers
source                 1..119
                       mol_type = protein
                       organism = synthetic construct
SEQUENCE: 3140
QVQLVQSGAE VKKPGASVKV SCKASGYAFS SSWMNWVRQA PGQGLEWIGR IYPGDGDTKY  60
NGKFKGRATL TADKSTSTAY MELRSLRSDD MAVYYCARRG TGGWYFDVWG QGTTVTVSS   119

SEQ ID NO: 3141        moltype = AA  length = 119
FEATURE                Location/Qualifiers
source                 1..119
                       mol_type = protein
                       organism = synthetic construct
SEQUENCE: 3141
QVQLVQSGAE VKKPGASVKV SCKASGYAFS SSWMNWVRQA PGQRLEWIGR IYPGDGDTKY  60
NGKFKGRATL TADKSASTAY MELSSLRSED TAVYYCARRG TGGWYFDVWG QGTTVTVSS   119

SEQ ID NO: 3142        moltype = AA  length = 119
FEATURE                Location/Qualifiers
source                 1..119
                       mol_type = protein
                       organism = synthetic construct
SEQUENCE: 3142
QVQLVQSGAE VKKPGASVKV SCKASGYAFS SSWMNWVRQA PGQGLEWIGR IYPGDGDTKY  60
NGKFKGRATL TADKSTSTAY MELRSLRSDD TAVYYCARRG TGGWYFDVWG QGTTVTVSS   119

SEQ ID NO: 3143        moltype = AA  length = 119
FEATURE                Location/Qualifiers
source                 1..119
                       mol_type = protein
                       organism = synthetic construct
SEQUENCE: 3143
QVQLVQSGAE VKKPGASVKV SCKASGYAFS SSWMNWVRQA PGQGLEWIGR IYPGDGDTKY  60
NGKFKGRATL TADKSISTAY MELSRLRSDD TAVYYCARRG TGGWYFDVWG QGTTVTVSS   119

SEQ ID NO: 3144        moltype = AA  length = 119
FEATURE                Location/Qualifiers
source                 1..119
                       mol_type = protein
                       organism = synthetic construct
SEQUENCE: 3144
QVQLVQSGAE VKKPGASVKV SCKASGYAFS SSWMNWVRQA PGQGLEWIGR IYPGDGDTKY  60
NGKFKGRATL TADKSISTAY MELSRLRSDD TVVYYCARRG TGGWYFDVWG QGTTVTVSS   119

SEQ ID NO: 3145        moltype = AA  length = 119
FEATURE                Location/Qualifiers
source                 1..119
                       mol_type = protein
                       organism = synthetic construct
SEQUENCE: 3145
QVQLVQSGAE VKKPGASVKV SCKASGYAFS SSWMNWVRQA PGQGLEWIGR IYPGDGDTKY  60
NGKFKGWATL TADKSISTAY MELSRLRSDD TAVYYCARRG TGGWYFDVWG QGTTVTVSS   119

SEQ ID NO: 3146        moltype = AA  length = 119
FEATURE                Location/Qualifiers
source                 1..119
                       mol_type = protein
                       organism = synthetic construct
SEQUENCE: 3146
QVQLVQSGAE VKKPGASVKV SCKASGYAFS SSWMNWVRQA TGQGLEWIGR IYPGDGDTKY  60
NGKFKGRATL TANKSISTAY MELSSLRSED TAVYYCARRG TGGWYFDVWG QGTTVTVSS   119

SEQ ID NO: 3147        moltype = AA  length = 119
FEATURE                Location/Qualifiers
source                 1..119
                       mol_type = protein
                       organism = synthetic construct
SEQUENCE: 3147
QVQLVQSGSE LKKPGASVKV SCKASGYAFS SSWMNWVRQA PGQGLEWIGR IYPGDGDTKY  60
NGKFKGRAVL SADKSVSTAY LQISSLKAED TAVYYCARRG TGGWYFDVWG QGTTVTVSS   119

SEQ ID NO: 3148        moltype = AA  length = 119
FEATURE                Location/Qualifiers
source                 1..119
                       mol_type = protein
                       organism = synthetic construct
SEQUENCE: 3148
QVQLVQSGPE VKKPGTSVKV SCKASGYAFS SSWMNWVRQA RGQRLEWIGR IYPGDGDTKY  60
NGKFKGRATL TADKSTSTAY MELSSLRSED TAVYYCARRG TGGWYFDVWG QGTTVTVSS   119
```

```
SEQ ID NO: 3149        moltype = AA  length = 119
FEATURE                Location/Qualifiers
source                 1..119
                       mol_type = protein
                       organism = synthetic construct
SEQUENCE: 3149
EVQLVQSGAE VKKPGESLKI SCKASGYAFS SSWMNWVRQM PGKGLEWIGR IYPGDGDTKY  60
NGKFKGQATL SADKSISTAY LQWSSLKASD TAMYYCARRG TGGWYFDVWG QGTTVTVSS   119

SEQ ID NO: 3150        moltype = AA  length = 119
FEATURE                Location/Qualifiers
source                 1..119
                       mol_type = protein
                       organism = synthetic construct
SEQUENCE: 3150
QVQLVQSGSE LKKPGASVKV SCKASGYAFS SSWMNWVRQA PGQGLEWIGR IYPGDGDTKY  60
NGKFKGRAVL SADKSVSMAY LQISSLKAED TAVYYCARRG TGGWYFDVWG QGTTVTVSS   119

SEQ ID NO: 3151        moltype = AA  length = 119
FEATURE                Location/Qualifiers
source                 1..119
                       mol_type = protein
                       organism = synthetic construct
SEQUENCE: 3151
QVQLVQSGHE VKQPGASVKV SCKASGYAFS SSWMNWVPQA PGQGLEWIGR IYPGDGDTKY  60
NGKFKGRAVL SADKSASTAY LQISSLKAED MAMYYCARRG TGGWYFDVWG QGTTVTVSS   119

SEQ ID NO: 3152        moltype = AA  length = 119
FEATURE                Location/Qualifiers
source                 1..119
                       mol_type = protein
                       organism = synthetic construct
SEQUENCE: 3152
EVQLVQSGAE VKKPGESLKI SCKASGYAFS SSWMNWVRQM PGKGLEWIGR IYPGDGDTKY  60
NGKFKGQATL SADKPISTAY LQWSSLKASD TAMYYCARRG TGGWYFDVWG QGTTVTVSS   119

SEQ ID NO: 3153        moltype = AA  length = 119
FEATURE                Location/Qualifiers
source                 1..119
                       mol_type = protein
                       organism = synthetic construct
SEQUENCE: 3153
EVQLVQSGAE VKKPGESLRI SCKASGYAFS SSWMNWVRQM PGKGLEWIGR IYPGDGDTKY  60
NGKFKGQATL SADKSISTAY LQWSSLKASD TAMYYCARRG TGGWYFDVWG QGTTVTVSS   119

SEQ ID NO: 3154        moltype = AA  length = 119
FEATURE                Location/Qualifiers
source                 1..119
                       mol_type = protein
                       organism = synthetic construct
SEQUENCE: 3154
EVQLVQSGAE VKKPGESLRI SCKASGYAFS SSWMNWVRQM PGKGLEWIGR IYPGDGDTKY  60
NGKFKGHATL SADKSISTAY LQWSSLKASD TAMYYCARRG TGGWYFDVWG QGTTVTVSS   119

SEQ ID NO: 3155        moltype = AA  length = 119
FEATURE                Location/Qualifiers
source                 1..119
                       mol_type = protein
                       organism = synthetic construct
SEQUENCE: 3155
QVQLVQSGAE VKKTGSSVKV SCKASGYAFS SSWMNWVRQA PRQALEWIGR IYPGDGDTKY  60
NGKFKGRATL TADKSMSTAY MELSSLRSED TAMYYCARRG TGGWYFDVWG QGTTVTVSS   119

SEQ ID NO: 3156        moltype = AA  length = 119
FEATURE                Location/Qualifiers
source                 1..119
                       mol_type = protein
                       organism = synthetic construct
SEQUENCE: 3156
EVQLVESGGG LVQPGRSLRL SCTASGYAFS SSWMNWVRQA PGKGLEWIGR IYPGDGDTKY  60
NGKFKGRATL SADKSKSIAY LQMNSLKTED TAVYYCARRG TGGWYFDVWG QGTTVTVSS   119

SEQ ID NO: 3157        moltype = AA  length = 119
FEATURE                Location/Qualifiers
source                 1..119
                       mol_type = protein
                       organism = synthetic construct
SEQUENCE: 3157
```

```
EVQLVESGGG LVQPGPSLRL SCTASGYAFS SSWMNWVRQA PGKGLEWIGR IYPGDGDTKY  60
NGKFKGRATL SADKSKSIAY LQMNSLKTED TAVYYCARRG TGGWYFDVWG QGTTVTVSS   119

SEQ ID NO: 3158        moltype = AA  length = 119
FEATURE                Location/Qualifiers
source                 1..119
                       mol_type = protein
                       organism = synthetic construct
SEQUENCE: 3158
QVQLQESGPG LVKPSQTLSL TCTASGYAFS SSWMNWVRQP PGKGLEWIGR IYPGDGDTKY  60
NGKFKGRATL SADKSKSQAS LKLSSVTAAD TAVYYCARRG TGGWYFDVWG QGTTVTVSS   119

SEQ ID NO: 3159        moltype = AA  length = 119
FEATURE                Location/Qualifiers
source                 1..119
                       mol_type = protein
                       organism = synthetic construct
SEQUENCE: 3159
QVQLQESGPG LVKPSGTLSL TCAASGYAFS SSWMNWVRQP PGKGLEWIGR IYPGDGDTKY  60
NGKFKGRATL SADKSKSQAS LKLSSVTAAD TAVYYCARRG TGGWYFDVWG QGTTVTVSS   119

SEQ ID NO: 3160        moltype = AA  length = 119
FEATURE                Location/Qualifiers
source                 1..119
                       mol_type = protein
                       organism = synthetic construct
SEQUENCE: 3160
EVQLVESGGG LVKPGRSLRL SCTASGYAFS SSWMNWVRQA PGKGLEWIGR IYPGDGDTKY  60
NGKFKGRATL SADKSKSIAY LQMNSLKTED TAVYYCARRG TGGWYFDVWG QGTTVTVSS   119

SEQ ID NO: 3161        moltype = AA  length = 119
FEATURE                Location/Qualifiers
source                 1..119
                       mol_type = protein
                       organism = synthetic construct
SEQUENCE: 3161
EVQLVESGGG LVQPGGSLKL SCAASGYAFS SSWMNWVRQA SGKGLEWIGR IYPGDGDTKY  60
NGKFKGRATL SADKSKSTAY LQMNSLKTED TAVYYCARRG TGGWYFDVWG QGTTVTVSS   119

SEQ ID NO: 3162        moltype = AA  length = 119
FEATURE                Location/Qualifiers
source                 1..119
                       mol_type = protein
                       organism = synthetic construct
SEQUENCE: 3162
QVQLQESGPG LVKPSQTLSL TCAASGYAFS SSWMNWVRQP PGKGLEWIGR IYPGDGDTKY  60
NGKFKGRATL SADKSKSQAS LKLSSVTAAD TAVYYCARRG TGGWYFDVWG QGTTVTVSS   119

SEQ ID NO: 3163        moltype = AA  length = 119
FEATURE                Location/Qualifiers
source                 1..119
                       mol_type = protein
                       organism = synthetic construct
SEQUENCE: 3163
EVQLVESGGG LVKPGGSLRL SCAASGYAFS SSWMNWVRQA PGKGLEWIGR IYPGDGDTKY  60
NGKFKGRATL SADKSKSTAY LQMNSLKTED TAVYYCARRG TGGWYFDVWG QGTTVTVSS   119

SEQ ID NO: 3164        moltype = AA  length = 119
FEATURE                Location/Qualifiers
source                 1..119
                       mol_type = protein
                       organism = synthetic construct
SEQUENCE: 3164
EVQLVESGGA LVKPGGSLRL SCAASGYAFS SSWMNWVRQA PGKGLEWIGR IYPGDGDTKY  60
NGKFKGRATL SADKSKSTAY LQMNSLKTED TAVYYCARRG TGGWYFDVWG QGTTVTVSS   119

SEQ ID NO: 3165        moltype = AA  length = 119
FEATURE                Location/Qualifiers
source                 1..119
                       mol_type = protein
                       organism = synthetic construct
SEQUENCE: 3165
QVQLQESGPG LVKPSQTLSL TCAAYGYAFS SSWMNWVRQP PGKGLEWIGR IYPGDGDTKY  60
NGKFKGRATL SADKSKSQAS LKLSSVTAAD TAVYYCARRG TGGWYFDVWG QGTTVTVSS   119

SEQ ID NO: 3166        moltype = AA  length = 119
FEATURE                Location/Qualifiers
source                 1..119
                       mol_type = protein
```

```
                        organism = synthetic construct
SEQUENCE: 3166
QVQLQESGSG LVKPSQTLSL TCAASGYAFS SSWMNWVRQP PGKGLEWIGR IYPGDGDTKY  60
NGKFKGRATL SADKSKSQAS LKLSSVTAAD TAVYYCARRG TGGWYFDVWG QGTTVTVSS   119

SEQ ID NO: 3167         moltype = AA  length = 119
FEATURE                 Location/Qualifiers
source                  1..119
                        mol_type = protein
                        organism = synthetic construct
SEQUENCE: 3167
EVQLVESGGG LVQPGGSLRL SCAASGYAFS SSWMNWVRQA PGKGLEWIGR IYPGDGDTKY  60
NGKFKGRATL SADKSKSSAY LQMNSLKTED TAVYYCARRG TGGWYFDVWG QGTTVTVSS   119

SEQ ID NO: 3168         moltype = AA  length = 119
FEATURE                 Location/Qualifiers
source                  1..119
                        mol_type = protein
                        organism = synthetic construct
SEQUENCE: 3168
QVQLQESGPG LVKPSDTLSL TCTASGYAFS SSWMNWVRQP PGKGLEWIGR IYPGDGDTKY  60
NGKFKGRATL SADKSKSQAS LKLSSVTAAD TAVYYCARRG TGGWYFDVWG QGTTVTVSS   119

SEQ ID NO: 3169         moltype = AA  length = 119
FEATURE                 Location/Qualifiers
source                  1..119
                        mol_type = protein
                        organism = synthetic construct
SEQUENCE: 3169
QVQLQESGPG LVKPSQTLSL TCTASGYAFS SSWMNWVRQH PGKGLEWIGR IYPGDGDTKY  60
NGKFKGRATL SADKSKSQAS LKLSSVTAAD TAVYYCARRG TGGWYFDVWG QGTTVTVSS   119

SEQ ID NO: 3170         moltype = AA  length = 119
FEATURE                 Location/Qualifiers
source                  1..119
                        mol_type = protein
                        organism = synthetic construct
SEQUENCE: 3170
QVQLQESGPG LVKPSQTLSL TCTASGYAFS SSWMNWVRQH PGKGLEWIGR IYPGDGDTKY  60
NGKFKGLATL SADKSKSQAS LKLSSVTAAD TAVYYCARRG TGGWYFDVWG QGTTVTVSS   119

SEQ ID NO: 3171         moltype = AA  length = 119
FEATURE                 Location/Qualifiers
source                  1..119
                        mol_type = protein
                        organism = synthetic construct
SEQUENCE: 3171
QVQLVESGGG VVQPGRSLRL SCAASGYAFS SSWMNWVRQA PGKGLEWIGR IYPGDGDTKY  60
NGKFKGRATL SADKSKSTAY LQMSSLRAED TAVYYCARRG TGGWYFDVWG QGTTVTVSS   119

SEQ ID NO: 3172         moltype = AA  length = 119
FEATURE                 Location/Qualifiers
source                  1..119
                        mol_type = protein
                        organism = synthetic construct
SEQUENCE: 3172
QVQLVESGGG LVKPGGSLRL SCAASGYAFS SSWMNWVRQA PGKGLEWIGR IYPGDGDTKY  60
NGKFKGRATL SADKAKSSAY LQMNSLRAED TAVYYCARRG TGGWYFDVWG QGTTVTVSS   119

SEQ ID NO: 3173         moltype = AA  length = 119
FEATURE                 Location/Qualifiers
source                  1..119
                        mol_type = protein
                        organism = synthetic construct
SEQUENCE: 3173
QVQLVESGGG LVQPGGSLRL SCSASGYAFS SSWMNWVRQA PGKGLEWIGR IYPGDGDTKY  60
NGKFKGRATL SADKSKSTAY LQMNSLRAED TAVYYCARRG TGGWYFDVWG QGTTVTVSS   119

SEQ ID NO: 3174         moltype = AA  length = 119
FEATURE                 Location/Qualifiers
source                  1..119
                        mol_type = protein
                        organism = synthetic construct
SEQUENCE: 3174
QVQLLESGGG LVKPGGSLRL SCAASGYAFS SSWMNWVRQA PGKGLEWIGR IYPGDGDTKY  60
NGKFKGRATL SADKAKSSAY LQMNSLRAED TAVYYCARRG TGGWYFDVWG QGTTVTVSS   119

SEQ ID NO: 3175         moltype = AA  length = 119
FEATURE                 Location/Qualifiers
```

```
source                  1..119
                        mol_type = protein
                        organism = synthetic construct
SEQUENCE: 3175
EVQLVESGGG LVQPGGSLRL SCSASGYAFS SSWMNWVRQA PGKGLEWIGR IYPGDGDTKY  60
NGKFKGRATL SADKSKSTAY LQMSSLRAED TAVYYCARRG TGGWYFDVWG QGTTVTVSS   119

SEQ ID NO: 3176         moltype = AA  length = 119
FEATURE                 Location/Qualifiers
source                  1..119
                        mol_type = protein
                        organism = synthetic construct
SEQUENCE: 3176
QVQLQESGPG LVKPSDTLSL TCAASGYAFS SSWMNWVRQP PGKGLEWIGR IYPGDGDTKY  60
NGKFKGRATL SADKSKSQAS LKLSSVTAVD TAVYYCARRG TGGWYFDVWG QGTTVTVSS   119

SEQ ID NO: 3177         moltype = AA  length = 119
FEATURE                 Location/Qualifiers
source                  1..119
                        mol_type = protein
                        organism = synthetic construct
SEQUENCE: 3177
QVQLQESGPG LVKPSQTLSL TCAASGYAFS SSWMNWVRQP PGKGLEWIGR IYPGDGDTKY  60
NGKFKGRATL SADKSKSQAS LKLSSVTAVD TAVYYCARRG TGGWYFDVWG QGTTVTVSS   119

SEQ ID NO: 3178         moltype = AA  length = 119
FEATURE                 Location/Qualifiers
source                  1..119
                        mol_type = protein
                        organism = synthetic construct
SEQUENCE: 3178
EVQLVESGGG LVQPGGSLRL SCSASGYAFS SSWMNWVRQA PGKGLEWIGR IYPGDGDTKY  60
NGKFKGRATL SADKSKSTAY VQMSSLRAED TAVYYCARRG TGGWYFDVWG QGTTVTVSS   119

SEQ ID NO: 3179         moltype = AA  length = 119
FEATURE                 Location/Qualifiers
source                  1..119
                        mol_type = protein
                        organism = synthetic construct
SEQUENCE: 3179
QVQLVDSGGG VVQPGRSLRL SCAASGYAFS SSWMNWVRQA PGKGLEWIGR IYPGDGDTKY  60
NGKFKGRATL SADKSKSTAY LQMNSLRAED TAVYYCARRG TGGWYFDVWG QGTTVTVSS   119

SEQ ID NO: 3180         moltype = AA  length = 119
FEATURE                 Location/Qualifiers
source                  1..119
                        mol_type = protein
                        organism = synthetic construct
SEQUENCE: 3180
QVQLVESGGG VVQPGRSLRL SCAASGYAFS SSWMNWVRQA PGKGLEWIGR IYPGDGDTKY  60
NGKFKGRATL SADKSKSTAY LQMNSLRAEG TAVYYCARRG TGGWYFDVWG QGTTVTVSS   119

SEQ ID NO: 3181         moltype = AA  length = 119
FEATURE                 Location/Qualifiers
source                  1..119
                        mol_type = protein
                        organism = synthetic construct
SEQUENCE: 3181
QVQLVESGGG VVQPGRSLRL SCAASGYAFS SSWMNWVRQA PGKGLEWIGR IYPGDGDTKY  60
NGKFKGRATL SADKSKSTAY LQMNSLRAED TAVYYCARRG TGGWYFDVWG QGTTVTVSS   119

SEQ ID NO: 3182         moltype = AA  length = 119
FEATURE                 Location/Qualifiers
source                  1..119
                        mol_type = protein
                        organism = synthetic construct
SEQUENCE: 3182
EVQLVESGGG LVQPGGSLRL SCAASGYAFS SSWMNWVRQA PGKGLEWIGR IYPGDGDTKY  60
NGKFKGRATL SADKSKSTAY LQMNSLRAED TAVYYCARRG TGGWYFDVWG QGTTVTVSS   119

SEQ ID NO: 3183         moltype = AA  length = 117
FEATURE                 Location/Qualifiers
source                  1..117
                        mol_type = protein
                        organism = synthetic construct
SEQUENCE: 3183
EVQLVESGGD LVKPGGSLKL SCAVSGFTFR SYGMSWVRQT PDKRLEWVAL ISSGGSYTYY  60
TDSVKGRFTI SRDNAKNTLY LQMSSLKSED TAIYYCSRHG GNFFDYWGQG TTLTVSS     117
```

```
SEQ ID NO: 3184        moltype = AA  length = 107
FEATURE                Location/Qualifiers
source                 1..107
                       mol_type = protein
                       organism = synthetic construct
SEQUENCE: 3184
QIVLTQSPSI MSASPGEKVT MTCSVSSSVS YMHWYQQKSG TSPKRWIYDT SKLASGVPAR  60
FSGSGSGTSY SLTISSMEAE DAATYYCQQW SSNPQYTFGG GTKLEIK                107

SEQ ID NO: 3185        moltype = AA  length = 107
FEATURE                Location/Qualifiers
source                 1..107
                       mol_type = protein
                       organism = synthetic construct
SEQUENCE: 3185
DIVLTQSPAF LSVTPGEKVT ITCSVSSSVS YMHWYQQKPD QAPKLLIYDT SKLASGVPSR  60
FSGSGSGTDY TFTISSLEAE DAATYYCQQW SSNPQYTFGQ GTKLEIK                107

SEQ ID NO: 3186        moltype = AA  length = 107
FEATURE                Location/Qualifiers
source                 1..107
                       mol_type = protein
                       organism = synthetic construct
SEQUENCE: 3186
AIQLTQSPSS LSASVGDRVT ITCSVSSSVS YMHWYQQKPG KAPKLLIYDT SKLASGVPSR  60
FSGSGSGTDY TLTISSLQPE DFATYYCQQW SSNPQYTFGQ GTKLEIK                107

SEQ ID NO: 3187        moltype = AA  length = 107
FEATURE                Location/Qualifiers
source                 1..107
                       mol_type = protein
                       organism = synthetic construct
SEQUENCE: 3187
DIQLTQSPSF LSASVGDRVT ITCSVSSSVS YMHWYQQKPG KAPKLLIYDT SKLASGVPSR  60
FSGSGSGTEY TLTISSLQPE DFATYYCQQW SSNPQYTFGQ GTKLEIK                107

SEQ ID NO: 3188        moltype = AA  length = 107
FEATURE                Location/Qualifiers
source                 1..107
                       mol_type = protein
                       organism = synthetic construct
SEQUENCE: 3188
DIQLTQSPSS LSASVGDRVT ITCSVSSSVS YMHWYQQKPG KAPKLLIYDT SKLASGVPSR  60
FSGSGSGTDY TLTISSLQPE DFATYYCQQW SSNPQYTFGQ GTKLEIK                107

SEQ ID NO: 3189        moltype = AA  length = 107
FEATURE                Location/Qualifiers
source                 1..107
                       mol_type = protein
                       organism = synthetic construct
SEQUENCE: 3189
DIQLTQSPSS VSASVGDRVT ITCSVSSSVS YMHWYQQKPG KAPKLLIYDT SKLASGVPSR  60
FSGSGSGTDY TLTISSLQPE DFATYYCQQW SSNPQYTFGQ GTKLEIK                107

SEQ ID NO: 3190        moltype = AA  length = 107
FEATURE                Location/Qualifiers
source                 1..107
                       mol_type = protein
                       organism = synthetic construct
SEQUENCE: 3190
DIQLTQSPSS LSASVGDRVT ITCSVSSSVS YMHWYQQKPG KVPKLLIYDT SKLASGVPSR  60
FSGSGSGTDY TLTISSLQPE DVATYYCQQW SSNPQYTFGQ GTKLEIK                107

SEQ ID NO: 3191        moltype = AA  length = 107
FEATURE                Location/Qualifiers
source                 1..107
                       mol_type = protein
                       organism = synthetic construct
SEQUENCE: 3191
DIQLTQSPSS LSASVGDRVT ITCSVSSSVS YMHWYQQKPG QAPKLLIYDT SKLASGVPSR  60
FSGSGSGTDY TLTISSLQPE DVATYYCQQW SSNPQYTFGQ GTKLEIK                107

SEQ ID NO: 3192        moltype = AA  length = 107
FEATURE                Location/Qualifiers
source                 1..107
                       mol_type = protein
                       organism = synthetic construct
SEQUENCE: 3192
EIVLTQSPDF QSVTPKEKVT ITCSVSSSVS YMHWYQQKPD QSPKLLIYDT SKLASGVPSR  60
```

```
FSGSGSGTDY TLTINSLEAE DAATYYCQQW SSNPQYTFGQ GTKLEIK                107

SEQ ID NO: 3193        moltype = AA  length = 107
FEATURE                Location/Qualifiers
source                 1..107
                       mol_type = protein
                       organism = synthetic construct
SEQUENCE: 3193
AIRLTQSPFS LSASVGDRVT ITCSVSSSVS YMHWYQQKPA KAPKLFIYDT SKLASGVPSR  60
FSGSGSGTDY TLTISSLQPE DFATYYCQQW SSNPQYTFGQ GTKLEIK                107

SEQ ID NO: 3194        moltype = AA  length = 107
FEATURE                Location/Qualifiers
source                 1..107
                       mol_type = protein
                       organism = synthetic construct
SEQUENCE: 3194
DIQLTQSPSS LSASVGDRVT ITCSVSSSVS YMHWYQQKPG KAPKLLIYDT SKLASGVPSR  60
FSGSGSGTDY TFTISSLQPE DIATYYCQQW SSNPQYTFGQ GTKLEIK                107

SEQ ID NO: 3195        moltype = AA  length = 107
FEATURE                Location/Qualifiers
source                 1..107
                       mol_type = protein
                       organism = synthetic construct
SEQUENCE: 3195
EIVLTQSPAT LSLSPGERAT LSCSVSSSVS YMHWYQQKPG QAPKLLIYDT SKLASGIPAR  60
FSGSGSGTDY TLTISSLEPE DFAVYYCQQW SSNPQYTFGQ GTKLEIK                107

SEQ ID NO: 3196        moltype = AA  length = 107
FEATURE                Location/Qualifiers
source                 1..107
                       mol_type = protein
                       organism = synthetic construct
SEQUENCE: 3196
DIQLTQSPST LSASVGDRVT ITCSVSSSVS YMHWYQQKPG KAPKLLIYDT SKLASGVPSR  60
FSGSGSGTEY TLTISSLQPD DFATYYCQQW SSNPQYTFGQ GTKLEIK                107

SEQ ID NO: 3197        moltype = AA  length = 107
FEATURE                Location/Qualifiers
source                 1..107
                       mol_type = protein
                       organism = synthetic construct
SEQUENCE: 3197
DIQLTQSPSS LSASVGDRVT ITCSVSSSVS YMHWYQQKPG KTPKLLIYDT SKLASGIPSR  60
FSGSGSGTDY TLTIRSLQPE DFATYYCQQW SSNPQYTFGQ GTKLEIK                107

SEQ ID NO: 3198        moltype = AA  length = 107
FEATURE                Location/Qualifiers
source                 1..107
                       mol_type = protein
                       organism = synthetic construct
SEQUENCE: 3198
EIVLTQSPPT LSLSPGERVT LSCSVSSSVS YMHWYQQKPG QAPKLLIYDT SKLASGIPAR  60
FSGSGSGTDY TLTISSLQPE DFAVYYCQQW SSNPQYTFGQ GTKLEIK                107

SEQ ID NO: 3199        moltype = AA  length = 107
FEATURE                Location/Qualifiers
source                 1..107
                       mol_type = protein
                       organism = synthetic construct
SEQUENCE: 3199
DIQLTQSPSS LSASVGDRVT ITCSVSSSVS YMHWYQQKPG KAPKRLIYDT SKLASGVPSR  60
FSGSGSGTEY TLTISSLQPE DFATYYCQQW SSNPQYTFGQ GTKLEIK                107

SEQ ID NO: 3200        moltype = AA  length = 107
FEATURE                Location/Qualifiers
source                 1..107
                       mol_type = protein
                       organism = synthetic construct
SEQUENCE: 3200
EIVLTQSPAT LSLSPGERAT LSCSVSSSVS YMHWYQQKPG QAPKLLIYDT SKLASGIPAR  60
FSGSGPGTDY TLTISSLEPE DFAVYYCQQW SSNPQYTFGQ GTKLEIK                107

SEQ ID NO: 3201        moltype = AA  length = 107
FEATURE                Location/Qualifiers
source                 1..107
                       mol_type = protein
                       organism = synthetic construct
```

```
SEQUENCE: 3201
EIVLTQSPAT LSLSPGERAT LSCSVSSSVS YMHWYQQKPG QAPKLLIYDT SKLASGIPAR  60
FSGSGSGTDY TLTISRLEPE DFAVYYCQQW SSNPQYTFGQ GTKLEIK               107

SEQ ID NO: 3202        moltype = AA  length = 107
FEATURE                Location/Qualifiers
source                 1..107
                       mol_type = protein
                       organism = synthetic construct
SEQUENCE: 3202
EIVLTQSPAT LSLSPGERAT LSCSVSSSVS YMHWYQQKPG QAPKLLIYDT SKLASGIPAR  60
FSGSGSGTDY TLTISSLQPE DFAVYYCQQW SSNPQYTFGQ GTKLEIK               107

SEQ ID NO: 3203        moltype = AA  length = 107
FEATURE                Location/Qualifiers
source                 1..107
                       mol_type = protein
                       organism = synthetic construct
SEQUENCE: 3203
EIVLTQSPAT LSVSPGERAT LSCSVSSSVS YMHWYQQKPG QAPKLLIYDT SKLASGIPAR  60
FSGSGSGTEY TLTISSLQSE DFAVYYCQQW SSNPQYTFGQ GTKLEIK               107

SEQ ID NO: 3204        moltype = AA  length = 107
FEATURE                Location/Qualifiers
source                 1..107
                       mol_type = protein
                       organism = synthetic construct
SEQUENCE: 3204
EIVLTQSPAT LSVSPGERAT LSCSVSSSVS YMHWYQQKPG QAPKLLIYDT SKLASGIPAR  60
FSGSGSGTEY TLTISILQSE DFAVYYCQQW SSNPQYTFGQ GTKLEIK               107

SEQ ID NO: 3205        moltype = AA  length = 107
FEATURE                Location/Qualifiers
source                 1..107
                       mol_type = protein
                       organism = synthetic construct
SEQUENCE: 3205
EIVLTQSPPT LSLSPGERVT LSCSVSSSVS YMHWYQQKPG QAPKLLIYDT SKLASSIPAR  60
FSGSGSGTDY TLTISSLQPE DFAVYYCQQW SSNPQYTFGQ GTKLEIK               107

SEQ ID NO: 3206        moltype = AA  length = 107
FEATURE                Location/Qualifiers
source                 1..107
                       mol_type = protein
                       organism = synthetic construct
SEQUENCE: 3206
DIQLTQSPSS LSASVGDRVT ITCSVSSSVS YMHWYQQKPG KAPKSLIYDT SKLASGVPSR  60
FSGSGSGTDY TLTISSLQPE DFATYYCQQW SSNPQYTFGQ GTKLEIK               107

SEQ ID NO: 3207        moltype = AA  length = 107
FEATURE                Location/Qualifiers
source                 1..107
                       mol_type = protein
                       organism = synthetic construct
SEQUENCE: 3207
DIQLTQSPSS LSASVGDRVT ITCSVSSSVS YMHWYQQKPG KAPKRLIYDT SKLASGVPSR  60
FSGSGSGTEY TLTISNLQPE DFATYYCQQW SSNPQYTFGQ GTKLEIK               107

SEQ ID NO: 3208        moltype = AA  length = 107
FEATURE                Location/Qualifiers
source                 1..107
                       mol_type = protein
                       organism = synthetic construct
SEQUENCE: 3208
DIQLTQSPSA MSASVGDRVT ITCSVSSSVS YMHWYQQKPG KVPKRLIYDT SKLASGVPSR  60
FSGSGSGTEY TLTISSLQPE DFATYYCQQW SSNPQYTFGQ GTKLEIK               107

SEQ ID NO: 3209        moltype = AA  length = 107
FEATURE                Location/Qualifiers
source                 1..107
                       mol_type = protein
                       organism = synthetic construct
SEQUENCE: 3209
EIVLTQSPAT LSLSPGERAT LSCSVSSSVS YMHWYQQKPG QAPKLLIYDT SKLASGIPDR  60
FSGSGSGTDY TLTISRLEPE DFAVYYCQQW SSNPQYTFGQ GTKLEIK               107

SEQ ID NO: 3210        moltype = AA  length = 107
FEATURE                Location/Qualifiers
source                 1..107
```

```
                        mol_type = protein
                        organism = synthetic construct
SEQUENCE: 3210
EIVLTQSPAT LSLSPGERAT LSCSVSSSVS YMHWYQQKPG LAPKLLIYDT SKLASGIPDR  60
FSGSGSGTDY TLTISRLEPE DFAVYYCQQW SSNPQYTFGQ GTKLEIK                107

SEQ ID NO: 3211         moltype = AA  length = 107
FEATURE                 Location/Qualifiers
source                  1..107
                        mol_type = protein
                        organism = synthetic construct
SEQUENCE: 3211
EIVLTQSPGT LSLSPGERAT LSCSVSSSVS YMHWYQQKPG QAPKLLIYDT SKLASGIPDR  60
FSGSGSGTDY TLTISRLEPE DFAVYYCQQW SSNPQYTFGQ GTKLEIK                107

SEQ ID NO: 3212         moltype = AA  length = 107
FEATURE                 Location/Qualifiers
source                  1..107
                        mol_type = protein
                        organism = synthetic construct
SEQUENCE: 3212
DIQLTQSPSS LSASVGDRVT ITCSVSSSVS YMHWYQQKPG KAPKSLIYDT SKLASGVPSK  60
FSGSGSGTDY TLTISSLQPE DFATYYCQQW SSNPQYTFGQ GTKLEIK                107

SEQ ID NO: 3213         moltype = AA  length = 107
FEATURE                 Location/Qualifiers
source                  1..107
                        mol_type = protein
                        organism = synthetic construct
SEQUENCE: 3213
DIQLTQSPSS LSASVGDRVT ITCSVSSSVS YMHWYQQKPE KAPKSLIYDT SKLASGVPSR  60
FSGSGSGTDY TLTISSLQPE DFATYYCQQW SSNPQYTFGQ GTKLEIK                107

SEQ ID NO: 3214         moltype = AA  length = 107
FEATURE                 Location/Qualifiers
source                  1..107
                        mol_type = protein
                        organism = synthetic construct
SEQUENCE: 3214
DIVLTQSPDS LAVSLGERAT INCSVSSSVS YMHWYQQKPG QPPKLLIYDT SKLASGVPDR  60
FSGSGSGTDY TLTISSLQAE DVAVYYCQQW SSNPQYTFGQ GTKLEIK                107

SEQ ID NO: 3215         moltype = AA  length = 107
FEATURE                 Location/Qualifiers
source                  1..107
                        mol_type = protein
                        organism = synthetic construct
SEQUENCE: 3215
EIVLTQTPLS LSITPGEQAS MSCSVSSSVS YMHWYLQKAR PVPKLLIYDT SKLASGVPDR  60
FSGSGSGTDY TLKISRVEAE DFGVYYCQQW SSNPQYTFGQ GTKLEIK                107

SEQ ID NO: 3216         moltype = AA  length = 107
FEATURE                 Location/Qualifiers
source                  1..107
                        mol_type = protein
                        organism = synthetic construct
SEQUENCE: 3216
EIVLTQTPLS LSITPGEQAS ISCSVSSSVS YMHWYLQKAR PVPKLLIYDT SKLASGVPDR  60
FSGSGSGTDY TLKISRVEAE DFGVYYCQQW SSNPQYTFGQ GTKLEIK                107

SEQ ID NO: 3217         moltype = AA  length = 107
FEATURE                 Location/Qualifiers
source                  1..107
                        mol_type = protein
                        organism = synthetic construct
SEQUENCE: 3217
DIVLTQSPLS LPVTPGEPAS ISCSVSSSVS YMHWYLQKPG QSPKLLIYDT SKLASGVPDR  60
FSGSGSGTDY TLKISRVEAE DVGVYYCQQW SSNPQYTFGQ GTKLEIK                107

SEQ ID NO: 3218         moltype = AA  length = 107
FEATURE                 Location/Qualifiers
source                  1..107
                        mol_type = protein
                        organism = synthetic construct
SEQUENCE: 3218
DIVLTQSPLS LPVTLGQPAS ISCSVSSSVS YMHWYQQRPG QSPKRLIYDT SKLASGVPDR  60
FSGSGSGTDY TLKISRVEAE DVGVYYCQQW SSNPQYTFGQ GTKLEIK                107

SEQ ID NO: 3219         moltype = AA  length = 107
```

```
FEATURE                Location/Qualifiers
source                 1..107
                       mol_type = protein
                       organism = synthetic construct
SEQUENCE: 3219
DIVLTQTPLS LPVTPGEPAS ISCSVSSSVS YMHWYLQKPG QSPKLLIYDT SKLASGVPDR  60
FSGSGSGTDY TLKISRVEAE DVGVYYCQQW SSNPQYTFGQ GTKLEIK               107

SEQ ID NO: 3220        moltype = AA  length = 107
FEATURE                Location/Qualifiers
source                 1..107
                       mol_type = protein
                       organism = synthetic construct
SEQUENCE: 3220
DIVLTQTPLS LSVTPGQPAS ISCSVSSSVS YMHWYLQKPG QSPKLLIYDT SKLASGVPDR  60
FSGSGSGTDY TLKISRVEAE DVGVYYCQQW SSNPQYTFGQ GTKLEIK               107

SEQ ID NO: 3221        moltype = AA  length = 107
FEATURE                Location/Qualifiers
source                 1..107
                       mol_type = protein
                       organism = synthetic construct
SEQUENCE: 3221
DIVLTQTPLS LSVTPGQPAS ISCSVSSSVS YMHWYLQKPG QPPKLLIYDT SKLASGVPDR  60
FSGSGSGTDY TLKISRVEAE DVGVYYCQQW SSNPQYTFGQ GTKLEIK               107

SEQ ID NO: 3222        moltype = AA  length = 107
FEATURE                Location/Qualifiers
source                 1..107
                       mol_type = protein
                       organism = synthetic construct
SEQUENCE: 3222
DIQLIQSPSF LSASVGDRVS IICSVSSSVS YMHWYLQKPG KSPKLFIYDT SKLASGVSSR  60
FSGRGSGTDY TLTIISLKPE DFAAYYCQQW SSNPQYTFGQ GTKLEIK               107

SEQ ID NO: 3223        moltype = AA  length = 107
FEATURE                Location/Qualifiers
source                 1..107
                       mol_type = protein
                       organism = synthetic construct
SEQUENCE: 3223
DIVLTQTPLS SPVTLGQPAS ISCSVSSSVS YMHWYQQRPG QPPKLLIYDT SKLASGVPDR  60
FSGSGAGTDY TLKISRVEAE DVGVYYCQQW SSNPQYTFGQ GTKLEIK               107

SEQ ID NO: 3224        moltype = AA  length = 107
FEATURE                Location/Qualifiers
source                 1..107
                       mol_type = protein
                       organism = synthetic construct
SEQUENCE: 3224
EITLTQSPAF MSATPGDKVN ISCSVSSSVS YMHWYQQKPG EAPKFIIYDT SKLASGIPPR  60
FSGSGYGTDY TLTINNIESE DAAYYYCQQW SSNPQYTFGQ GTKLEIK               107

SEQ ID NO: 3225        moltype = AA  length = 117
FEATURE                Location/Qualifiers
source                 1..117
                       mol_type = protein
                       organism = synthetic construct
SEQUENCE: 3225
EVQLVESGGG LVKPGGSLRL SCAVSGFTFR SYGMSWVRQA PGKGLEWVAL ISSGGSYTYY  60
TDSVKGRFTI SRDNSKNTLY LQMNSLKTED TAVYYCSRHG GNFFDYWGQG TTVTVSS     117

SEQ ID NO: 3226        moltype = AA  length = 117
FEATURE                Location/Qualifiers
source                 1..117
                       mol_type = protein
                       organism = synthetic construct
SEQUENCE: 3226
EVQLVESGGA LVKPGGSLRL SCAVSGFTFR SYGMSWVRQA PGKGLEWVAL ISSGGSYTYY  60
TDSVKGRFTI SRDNSKNTLY LQMNSLKTED TAVYYCSRHG GNFFDYWGQG TTVTVSS     117

SEQ ID NO: 3227        moltype = AA  length = 117
FEATURE                Location/Qualifiers
source                 1..117
                       mol_type = protein
                       organism = synthetic construct
SEQUENCE: 3227
EVQLVESGGG LVQPGGSLRL SCAVSGFTFR SYGMSWVRQA PGKGLEWVAL ISSGGSYTYY  60
TDSVKGRFTI SRDNAKNTLY LQMNSLRAED TAVYYCSRHG GNFFDYWGQG TTVTVSS     117
```

```
SEQ ID NO: 3228        moltype = AA  length = 117
FEATURE                Location/Qualifiers
source                 1..117
                       mol_type = protein
                       organism = synthetic construct
SEQUENCE: 3228
EVQLVESGGG LVQPGGSLRL SCAVSGFTFR SYGMSWVRQA PGKGLEWVAL ISSGGSYTYY  60
TDSVKGRFTI SRDNAKNSLY LQMNSLRAED TAVYYCSRHG GNFFDYWGQG TTVTVSS     117

SEQ ID NO: 3229        moltype = AA  length = 117
FEATURE                Location/Qualifiers
source                 1..117
                       mol_type = protein
                       organism = synthetic construct
SEQUENCE: 3229
EVQLVESGGG LVQPGGSLRL SCAVSGFTFR SYGMSWVRQA PGKGLEWVAL ISSGGSYTYY  60
TDSVKGRFTI SRDNSKNSLY LQMNSLKTED TAVYYCSRHG GNFFDYWGQG TTVTVSS     117

SEQ ID NO: 3230        moltype = AA  length = 117
FEATURE                Location/Qualifiers
source                 1..117
                       mol_type = protein
                       organism = synthetic construct
SEQUENCE: 3230
EVQLVESGGG LVQPGGSLRL SCAVSGFTFR SYGMSWVRQA PGKGLEWVAL ISSGGSYTYY  60
TDSVKGRFTI SRDNAKNSLY LQMNSLRAED MAVYYCSRHG GNFFDYWGQG TTVTVSS     117

SEQ ID NO: 3231        moltype = AA  length = 117
FEATURE                Location/Qualifiers
source                 1..117
                       mol_type = protein
                       organism = synthetic construct
SEQUENCE: 3231
EVQLVESGGG LVQPGGSLRL SCAVSGFTFR SYGMSWVRQA PGKGLEWVAL ISSGGSYTYY  60
TDSVKGQFTI SRDNAKNTLY LQMNSLRAED MAVYYCSRHG GNFFDYWGQG TTVTVSS     117

SEQ ID NO: 3232        moltype = AA  length = 117
FEATURE                Location/Qualifiers
source                 1..117
                       mol_type = protein
                       organism = synthetic construct
SEQUENCE: 3232
EVQLVESGGG LVKPGRSLRL SCTVSGFTFR SYGMSWVRQA PGKGLEWVAL ISSGGSYTYY  60
TDSVKGRFTI SRDNSKNILY LQMNSLKTED TAVYYCSRHG GNFFDYWGQG TTVTVSS     117

SEQ ID NO: 3233        moltype = AA  length = 117
FEATURE                Location/Qualifiers
source                 1..117
                       mol_type = protein
                       organism = synthetic construct
SEQUENCE: 3233
EVQLVESGGG LVKPGGSLRL SCAVSGFTFR SYGMSWVRQA PGKGLEWVAL ISSGGSYTYY  60
TDSVKGRFTI SRDNAKNSLY LQMNSLRAED TAVYYCSRHG GNFFDYWGQG TTVTVSS     117

SEQ ID NO: 3234        moltype = AA  length = 117
FEATURE                Location/Qualifiers
source                 1..117
                       mol_type = protein
                       organism = synthetic construct
SEQUENCE: 3234
EVQLVESGGG LVQPGGSLKL SCAVSGFTFR SYGMSWVRQA SGKGLEWVAL ISSGGSYTYY  60
TDSVKGRFTI SRDNSKNTLY LQMNSLKTED TAVYYCSRHG GNFFDYWGQG TTVTVSS     117

SEQ ID NO: 3235        moltype = AA  length = 117
FEATURE                Location/Qualifiers
source                 1..117
                       mol_type = protein
                       organism = synthetic construct
SEQUENCE: 3235
QVQLVESGGG VVQPGGSLRL SCAVSGFTFR SYGMSWVRQA PGKGLEWVAL ISSGGSYTYY  60
TDSVKGRFTI SRDNSKNTLY LQMNSLRAED TAVYYCSRHG GNFFDYWGQG TTVTVSS     117

SEQ ID NO: 3236        moltype = AA  length = 117
FEATURE                Location/Qualifiers
source                 1..117
                       mol_type = protein
                       organism = synthetic construct
SEQUENCE: 3236
```

```
QVQLVESGGG VVQPGRSLRL SCAVSGFTFR SYGMSWVRQA PGKGLEWVAL ISSGGSYTYY  60
TDSVKGRFTI SRDNSKNTLY LQMSSLRAED TAVYYCSRHG GNFFDYWGQG TTVTVSS     117

SEQ ID NO: 3237        moltype = AA  length = 117
FEATURE                Location/Qualifiers
source                 1..117
                       mol_type = protein
                       organism = synthetic construct
SEQUENCE: 3237
EVQLVESGGG LVQPGGSLRL SCPVSGFTFR SYGMSWVRQA PGKGLEWVAL ISSGGSYTYY  60
TDSVKGRFTI SRDNANNSLY LQMNSLRAED TAVYYCSRHG GNFFDYWGQG TTVTVSS     117

SEQ ID NO: 3238        moltype = AA  length = 117
FEATURE                Location/Qualifiers
source                 1..117
                       mol_type = protein
                       organism = synthetic construct
SEQUENCE: 3238
EVQLVESGGG LVQPGRSLRL SCTVSGFTFR SYGMSWVRQA PGKGLEWVAL ISSGGSYTYY  60
TDSVKGRFTI SRDNSKNILY LQMNSLKTED TAVYYCSRHG GNFFDYWGQG TTVTVSS     117

SEQ ID NO: 3239        moltype = AA  length = 117
FEATURE                Location/Qualifiers
source                 1..117
                       mol_type = protein
                       organism = synthetic construct
SEQUENCE: 3239
EVQLVESGGG LVQPGPSLRL SCTVSGFTFR SYGMSWVRQA PGKGLEWVAL ISSGGSYTYY  60
TDSVKGRFTI SRDNSKNILY LQMNSLKTED TAVYYCSRHG GNFFDYWGQG TTVTVSS     117

SEQ ID NO: 3240        moltype = AA  length = 117
FEATURE                Location/Qualifiers
source                 1..117
                       mol_type = protein
                       organism = synthetic construct
SEQUENCE: 3240
EVQLVESGGG LVQPGGSLRL SCAVSGFTFR SYGMSWVRQA PGKGLEWVAL ISSGGSYTYY  60
TDSVKGRFTI SRDNSKNTLY LQMNSLRAED TAVYYCSRHG GNFFDYWGQG TTVTVSS     117

SEQ ID NO: 3241        moltype = AA  length = 117
FEATURE                Location/Qualifiers
source                 1..117
                       mol_type = protein
                       organism = synthetic construct
SEQUENCE: 3241
EVQLVESGGG LVQPGGSLRL SCAVSGFTFR SYGMSWVRQA PGKGLEWVAL ISSGGSYTYY  60
TDSVKGRFTI SRDNAKNSLY LQMNSLRDED TAVYYCSRHG GNFFDYWGQG TTVTVSS     117

SEQ ID NO: 3242        moltype = AA  length = 117
FEATURE                Location/Qualifiers
source                 1..117
                       mol_type = protein
                       organism = synthetic construct
SEQUENCE: 3242
QVQLVESGGG LVKPGGSLRL SCAVSGFTFR SYGMSWVRQA PGKGLEWVAL ISSGGSYTYY  60
TDSVKGRFTI SRDNAKNSLY LQMNSLRAED TAVYYCSRHG GNFFDYWGQG TTVTVSS     117

SEQ ID NO: 3243        moltype = AA  length = 117
FEATURE                Location/Qualifiers
source                 1..117
                       mol_type = protein
                       organism = synthetic construct
SEQUENCE: 3243
QVQLVESGGG VVQPGRSLRL SCAVSGFTFR SYGMSWVRQA PGKGLEWVAL ISSGGSYTYY  60
TDSVKGRFTI SRDNSKNTLY LQMNSLRAED TAVYYCSRHG GNFFDYWGQG TTVTVSS     117

SEQ ID NO: 3244        moltype = AA  length = 117
FEATURE                Location/Qualifiers
source                 1..117
                       mol_type = protein
                       organism = synthetic construct
SEQUENCE: 3244
EVQLLESGGG LVQPGGSLRL SCAVSGFTFR SYGMSWVRQA PGKGLEWVAL ISSGGSYTYY  60
TDSVKGRFTI SRDNSKNTLY LQMNSLRAED TAVYYCSRHG GNFFDYWGQG TTVTVSS     117

SEQ ID NO: 3245        moltype = AA  length = 117
FEATURE                Location/Qualifiers
source                 1..117
                       mol_type = protein
```

```
                       organism = synthetic construct
SEQUENCE: 3245
EVQLVESGGG LVQPGGSLRL SCAVSGFTFR SYGMSWVRQA PGKGLEWVAL ISSGGSYTYY  60
TDSVKGRFTI SRHNSKNTLY LQMNSLRAED TAVYYCSRHG GNFFDYWGQG TTVTVSS     117

SEQ ID NO: 3246        moltype = AA  length = 117
FEATURE                Location/Qualifiers
source                 1..117
                       mol_type = protein
                       organism = synthetic construct
SEQUENCE: 3246
EVQLVESGGG LIQPGGSLRL SCAVSGFTFR SYGMSWVRQP PGKGLEWVAL ISSGGSYTYY  60
TDSVKGRFTI SRDNSKNTLY LQMNSLRAED TAVYYCSRHG GNFFDYWGQG TTVTVSS     117

SEQ ID NO: 3247        moltype = AA  length = 117
FEATURE                Location/Qualifiers
source                 1..117
                       mol_type = protein
                       organism = synthetic construct
SEQUENCE: 3247
EVQLVESGGG LIQPGGSLRL SCAVSGFTFR SYGMSWVRQA PGKGLEWVAL ISSGGSYTYY  60
TDSVKGRFTI SRDNSKNTLY LQMNSLRAED TAVYYCSRHG GNFFDYWGQG TTVTVSS     117

SEQ ID NO: 3248        moltype = AA  length = 117
FEATURE                Location/Qualifiers
source                 1..117
                       mol_type = protein
                       organism = synthetic construct
SEQUENCE: 3248
EVQLVESGGG LVQPGRSLRL SCAVSGFTFR SYGMSWVRQA PGKGLEWVAL ISSGGSYTYY  60
TDSVKGRFTI SRDNAKNSLY LQMNSLRAED TALYYCSRHG GNFFDYWGQG TTVTVSS     117

SEQ ID NO: 3249        moltype = AA  length = 117
FEATURE                Location/Qualifiers
source                 1..117
                       mol_type = protein
                       organism = synthetic construct
SEQUENCE: 3249
QVQLVESGGG VVQPGRSLRL SCAVSGFTFR SYGMSWVRQA PGKGLEWVAL ISSGGSYTYY  60
TDSVKGRFTI SRDNSKNRLY LQMNSLRAED TAVYYCSRHG GNFFDYWGQG TTVTVSS     117

SEQ ID NO: 3250        moltype = AA  length = 117
FEATURE                Location/Qualifiers
source                 1..117
                       mol_type = protein
                       organism = synthetic construct
SEQUENCE: 3250
QVQLVESGGG VVQPGRSLRL SCAVSGFTFR SYGMSWVRQA PGKGLEWVAL ISSGGSYTYY  60
TDSVKGRFTI SRDNSKNTLY LQMNSLRAEG TAVYYCSRHG GNFFDYWGQG TTVTVSS     117

SEQ ID NO: 3251        moltype = AA  length = 117
FEATURE                Location/Qualifiers
source                 1..117
                       mol_type = protein
                       organism = synthetic construct
SEQUENCE: 3251
QVQLVESGGG VVQPGRSLRL SCAVSGFTFR SYGMSWVRQA PGKGLEWVAL ISSGGSYTYY  60
TDSVKGRFAI SRDNSKNTLY LQMNSLRAED TAVYYCSRHG GNFFDYWGQG TTVTVSS     117

SEQ ID NO: 3252        moltype = AA  length = 117
FEATURE                Location/Qualifiers
source                 1..117
                       mol_type = protein
                       organism = synthetic construct
SEQUENCE: 3252
QVQLVDSGGG VVQPGRSLRL SCAVSGFTFR SYGMSWVRQA PGKGLEWVAL ISSGGSYTYY  60
TDSVKGRFTI SRDNSKNTLY LQMNSLRAED TAVYYCSRHG GNFFDYWGQG TTVTVSS     117

SEQ ID NO: 3253        moltype = AA  length = 117
FEATURE                Location/Qualifiers
source                 1..117
                       mol_type = protein
                       organism = synthetic construct
SEQUENCE: 3253
EVQLVESGGG VVRPGGSLRL SCAVSGFTFR SYGMSWVRQA PGKGLEWVAL ISSGGSYTYY  60
TDSVKGRFTI SRDNAKNSLY LQMNSLRAED TALYHCSRHG GNFFDYWGQG TTVTVSS     117

SEQ ID NO: 3254        moltype = AA  length = 117
FEATURE                Location/Qualifiers
```

source 1..117
mol_type = protein
organism = synthetic construct
SEQUENCE: 3254
EVQLVESGGV VVQPGGSLRL SCAVSGFTFR SYGMSWVRQA PGKGLEWVAL ISSGGSYTYY 60
TDSVKGRFTI SRDNSKNSLY LQMNSLRAED TALYYCSRHG GNFFDYWGQG TTVTVSS 117

SEQ ID NO: 3255 moltype = AA length = 117
FEATURE Location/Qualifiers
source 1..117
mol_type = protein
organism = synthetic construct
SEQUENCE: 3255
EVQLVESGGG VVQPGGSLRL SCAVSGFTFR SYGMSWVRQA PGKGLEWVAL ISSGGSYTYY 60
TDSVKGRFTI SRDNSKNSLY LQMNSLRTED TALYYCSRHG GNFFDYWGQG TTVTVSS 117

SEQ ID NO: 3256 moltype = AA length = 117
FEATURE Location/Qualifiers
source 1..117
mol_type = protein
organism = synthetic construct
SEQUENCE: 3256
EVQLVESGGV VVQPGGSLRL SCAVSGFTFR SYGMSWVRQA PGKGLEWVAL ISSGGSYTYY 60
TDSVKGRFTI SRDNSKNSLY LQMNSLRTED TALYYCSRHG GNFFDYWGQG TTVTVSS 117

SEQ ID NO: 3257 moltype = AA length = 117
FEATURE Location/Qualifiers
source 1..117
mol_type = protein
organism = synthetic construct
SEQUENCE: 3257
EVQLVETGGG LIQPGGSLRL SCAVSGFTFR SYGMSWVRQA PGKGLEWVAL ISSGGSYTYY 60
TDSVKGRFTI SRDNSKNTLY LQMNSLRAED TAVYYCSRHG GNFFDYWGQG TTVTVSS 117

SEQ ID NO: 3258 moltype = AA length = 117
FEATURE Location/Qualifiers
source 1..117
mol_type = protein
organism = synthetic construct
SEQUENCE: 3258
EVQLVESGGG LVQPGGSLRL SCAVSGFTFR SYGMSWVRQA TGKGLEWVAL ISSGGSYTYY 60
TDSVKGRFTI SRENAKNSLY LQMNSLRAGD TAVYYCSRHG GNFFDYWGQG TTVTVSS 117

SEQ ID NO: 3259 moltype = AA length = 117
FEATURE Location/Qualifiers
source 1..117
mol_type = protein
organism = synthetic construct
SEQUENCE: 3259
EVQLVESRGV LVQPGGSLRL SCAVSGFTFR SYGMSWVRQA PGKGLEWVAL ISSGGSYTYY 60
TDSVKGRFTI SRDNSKNTLH LQMNSLRAED TAVYYCSRHG GNFFDYWGQG TTVTVSS 117

SEQ ID NO: 3260 moltype = AA length = 117
FEATURE Location/Qualifiers
source 1..117
mol_type = protein
organism = synthetic construct
SEQUENCE: 3260
EVQLVESGGG LVQPGRSLRL SCAVSGFTFR SYGMSWVRQA PGKGLEWVAL ISSGGSYTYY 60
TDSVKGRFTI SRDNAKNSLY LQMNSLRAED MALYYCSRHG GNFFDYWGQG TTVTVSS 117

SEQ ID NO: 3261 moltype = AA length = 117
FEATURE Location/Qualifiers
source 1..117
mol_type = protein
organism = synthetic construct
SEQUENCE: 3261
QVQLVESGGG LVQPGGSLRL SCSVSGFTFR SYGMSWVRQA PGKGLEWVAL ISSGGSYTYY 60
TDSVKGRFTI SRDNSKNTLY LQMNSLRAED TAVYYCSRHG GNFFDYWGQG TTVTVSS 117

SEQ ID NO: 3262 moltype = AA length = 117
FEATURE Location/Qualifiers
source 1..117
mol_type = protein
organism = synthetic construct
SEQUENCE: 3262
EVQLVESGGG LVQPGGSLRL SCSVSGFTFR SYGMSWVRQA PGKGLEWVAL ISSGGSYTYY 60
TDSVKGRFTI SRDNSKNTLY LQMSSLRAED TAVYYCSRHG GNFFDYWGQG TTVTVSS 117

```
SEQ ID NO: 3263        moltype = AA  length = 117
FEATURE                Location/Qualifiers
source                 1..117
                       mol_type = protein
                       organism = synthetic construct
SEQUENCE: 3263
QVQLVESGGG VVQPGRSLRL SCAVSGFTFR SYGMSWVRQA PGKGLEWVAL ISSGGSYTYY  60
TDSVKGRFTI SRDNSTNTLF LQMNSLRAED TAVYYCSRHG GNFFDYWGQG TTVTVSS     117

SEQ ID NO: 3264        moltype = AA  length = 117
FEATURE                Location/Qualifiers
source                 1..117
                       mol_type = protein
                       organism = synthetic construct
SEQUENCE: 3264
QVQLLESGGG LVKPGGSLRL SCAVSGFTFR SYGMSWVRQA PGKGLEWVAL ISSGGSYTYY  60
TDSVKGRFTI SRDNAKNSLY LQMNSLRAED TAVYYCSRHG GNFFDYWGQG TTVTVSS     117

SEQ ID NO: 3265        moltype = AA  length = 117
FEATURE                Location/Qualifiers
source                 1..117
                       mol_type = protein
                       organism = synthetic construct
SEQUENCE: 3265
EVQLVESGEG LVQPGGSLRL SCAVSGFTFR SYGMSWVRQA PGKGLEWVAL ISSGGSYTYY  60
TDSVKGRFTI SRDNSKNTLY LQMGSLRAED MAVYYCSRHG GNFFDYWGQG TTVTVSS     117

SEQ ID NO: 3266        moltype = AA  length = 117
FEATURE                Location/Qualifiers
source                 1..117
                       mol_type = protein
                       organism = synthetic construct
SEQUENCE: 3266
EVQLVESGGG LVQPGGSLRL SCAVSGFTFR SYGMSWVRQA PGKGLEWVAL ISSGGSYTYY  60
TDSVKGRFTI SRDNSKNTLY LQMGSLRAED MAVYYCSRHG GNFFDYWGQG TTVTVSS     117

SEQ ID NO: 3267        moltype = AA  length = 117
FEATURE                Location/Qualifiers
source                 1..117
                       mol_type = protein
                       organism = synthetic construct
SEQUENCE: 3267
EVQLVESGGG LVQPGGSLRL SCSVSGFTFR SYGMSWVRQA PGKGLEWVAL ISSGGSYTYY  60
TDSVKGRFTI SRDNSKNTLY VQMSSLRAED TAVYYCSRHG GNFFDYWGQG TTVTVSS     117

SEQ ID NO: 3268        moltype = AA  length = 117
FEATURE                Location/Qualifiers
source                 1..117
                       mol_type = protein
                       organism = synthetic construct
SEQUENCE: 3268
EVQLVESGGG LVQPGGSLRL SCAVSGFTFR SYGMSWVRQA PGKGLEWVAL ISSGGSYTYY  60
TDSVKGRFII SRDNSRNSLY LQKNRRRAED MAVYYCSRHG GNFFDYWGQG TTVTVSS     117

SEQ ID NO: 3269        moltype = AA  length = 117
FEATURE                Location/Qualifiers
source                 1..117
                       mol_type = protein
                       organism = synthetic construct
SEQUENCE: 3269
EVQLVESGGG LVQPGGSLRL SCAVSGFTFR SYGMSWVHQA PGKGLEWVAL ISSGGSYTYY  60
TDSVKGRFII SRDNSRNTLY LQTNSLRAED TAVYYCSRHG GNFFDYWGQG TTVTVSS     117

SEQ ID NO: 3270        moltype = AA  length = 117
FEATURE                Location/Qualifiers
source                 1..117
                       mol_type = protein
                       organism = synthetic construct
SEQUENCE: 3270
EVHLVESGGG LVQPGGALRL SCAVSGFTFR SYGMSWVRQA TGKGLEWVAL ISSGGSYTYY  60
TDSVKGRFTI SRENAKNSLY LQMNSLRAGD TAVYYCSRHG GNFFDYWGQG TTVTVSS     117

SEQ ID NO: 3271        moltype = AA  length = 117
FEATURE                Location/Qualifiers
source                 1..117
                       mol_type = protein
                       organism = synthetic construct
SEQUENCE: 3271
EVQLVESGGG LVQPRGSLRL SCAVSGFTFR SYGMSWVRQA PGKGLEWVAL ISSGGSYTYY  60
```

```
TDSVKGRFTI SRDNSKNTLY LQMNNLRAEG TAVYYCSRHG GNFFDYWGQG TTVTVSS     117

SEQ ID NO: 3272        moltype = AA  length = 117
FEATURE                Location/Qualifiers
source                 1..117
                       mol_type = protein
                       organism = synthetic construct
SEQUENCE: 3272
EVQLVESGGG LVQPRGSLRL SCAVSGFTFR SYGMSWVRQA PGKGLEWVAL ISSGGSYTYY  60
TDSVKGRFTI SRDNSKNTLY LQMNNLRAEG TAAYYCSRHG GNFFDYWGQG TTVTVSS     117

SEQ ID NO: 3273        moltype = AA  length = 117
FEATURE                Location/Qualifiers
source                 1..117
                       mol_type = protein
                       organism = synthetic construct
SEQUENCE: 3273
QVQLVQSGAE VKKPGASVKV SCKVSGFTFR SYGMSWVRQA PGKGLEWVAL ISSGGSYTYY  60
TDSVKGRFTI TRDNSTNTLY MELSSLRSED TAVYYCSRHG GNFFDYWGQG TTVTVSS     117

SEQ ID NO: 3274        moltype = AA  length = 117
FEATURE                Location/Qualifiers
source                 1..117
                       mol_type = protein
                       organism = synthetic construct
SEQUENCE: 3274
QVQLVQSGSE LKKPGASVKV SCKVSGFTFR SYGMSWVRQA PGQGLEWVAL ISSGGSYTYY  60
TDSVKGRFVI SRDNSVNTLY LQISSLKAED TAVYYCSRHG GNFFDYWGQG TTVTVSS     117

SEQ ID NO: 3275        moltype = AA  length = 470
FEATURE                Location/Qualifiers
source                 1..470
                       mol_type = protein
                       organism = synthetic construct
SEQUENCE: 3275
METDTLLLWV LLLWVPGSTG QVQLVESGGG VVQPGRSLRL SCAASGIDFS RYWMSWVRQA  60
PGKGLEWVGE INPDSSTINY APSLKDRFTI SRDNSKNTLY LQMSSLRAED TAVYYCASLY  120
YDYGDAMDYW GQGTTVTVSS ASTKGPSVFP LAPSSKSTSG GTAALGCLVK DYFPEPVTVS  180
WNSGALTSGV HTFPAVLQSS GLYSLSSVVT VPSSSLGTQT YICNVNHKPS NTKVDKRVEP  240
KSCDKTHTCP PCPAPELLGG PSVFLFPPKP KDTLMISRTP EVTCVVVDVS HEDPEVKFNW  300
YVDGVEVHNA KTKPREEQYN ATYRVVSVLT VLHQDWLNGK EYKCKVSNKA LPAPIEKTIS  360
KAKGQPREPQ VYTLPPCREE MTKNQVSLWC LVKGFYPSDI AVEWESNGQP ENNYKTTPPV  420
LDSDGSFFLY SKLTVDKSRW QQGNVFSCSV MHEALHNHYT QKSLSLSPGK             470

SEQ ID NO: 3276        moltype = AA  length = 503
FEATURE                Location/Qualifiers
source                 1..503
                       mol_type = protein
                       organism = synthetic construct
SEQUENCE: 3276
METDTLLLWV LLLWVPGSTG QVQLVQSGAE VKKPGSSVKV SCKASGYSFT TYYIHWVRQA  60
PGQGLEWMGW FFPGSGNIKY NEKFKGRVTI TADTSTSTAY MELSSLRSED TAVYYCAGSY  120
YSYDVLDYWG QGTTVTVSSG GGGSGGGGSG GGGSGGGGSD IQMTQSPSFL SASVGDRVTI  180
TCKASQNVGI NVVWHQQKPG KAPKALIYSS SHRYSGVPSR FSGSGSGTEF TLTISSLQPE  240
DFATYFCQQF KSYPLTFGQG TKLEIKGGGG SGGGGSDKTH TCPPCPAPEL LGGPSVFLFP  300
PKPKDTLMIS RTPEVTCVVV DVSHEDPEVK FNWYVDGVEV HNAKTKPREE QYASTYRVVS  360
VLTVLHQDWL NGKEYKCKVS NKALPAPIEK TISKAKGQPR EPQVCTLPPS REEMTKNQVS  420
LSCAVKGFYP SDIAVEWESN GQPENNYKTT PPVLDSDGSF FLVSKLTVDK SRWQQGNVFS  480
CSVMHEALHN HYTQKSLSLS PGK                                          503

SEQ ID NO: 3277        moltype = AA  length = 234
FEATURE                Location/Qualifiers
source                 1..234
                       mol_type = protein
                       organism = synthetic construct
SEQUENCE: 3277
METDTLLLWV LLLWVPGSTG DIQMTQSPSS LSASVGDRVT ITCKASQSVD SNVAWYQQKP  60
EKAPKALIFS ASLRFSGVPS RFSGSGSGTD FTLTISSLQP EDFATYFCQQ YNNYPLTFGQ  120
GTKLEIKRTV AAPSVFIFPP SDEQLKSGTA SVVCLLNNFY PREAKVQWKV DNALQSGNSQ  180
ESVTEQDSKD STYSLSSTLT LSKADYEKHK VYACEVTHQG LSSPVTKSFN RGEC         234

SEQ ID NO: 3278        moltype = AA  length = 469
FEATURE                Location/Qualifiers
source                 1..469
                       mol_type = protein
                       organism = synthetic construct
SEQUENCE: 3278
METDTLLLWV LLLWVPGSTG QVQLVQSGAE VKKPGSSVKV SCKASGYSFT TYYIHWVRQA  60
PGQGLEWMGW FFPGSGNIKY NEKFKGRVTI TADTSTSTAY MELSSLRSED TAVYYCAGSY  120
```

```
YSYDVLDYWG QGTTVTVSSA STKGPSVFPL APSSKSTSGG TAALGCLVKD YFPEPVTVSW  180
NSGALTSGVH TFPAVLQSSG LYSLSSVVTV PSSSLGTQTY ICNVNHKPSN TKVDKRVEPK  240
SCDKTHTCPP CPAPELLGGP SVFLFPPKPK DTLMISRTPE VTCVVVDVSH EDPEVKFNWY  300
VDGVEVHNAK TKPREEQYNS TYRVVSVLTV LHQDWLNGKE YKCKVSNKAL PAPIEKTISK  360
AKGQPREPQV YTLPPSREEM TKNQVSLTCL VKGFYPSDIA VEWESNGQPE NNYKTTPPVL  420
DSDGSFFLYS KLTVDKSRWQ QGNVFSCSVM HEALHNHYTQ KSLSLSPGK             469

SEQ ID NO: 3279        moltype = AA  length = 234
FEATURE                Location/Qualifiers
source                 1..234
                       mol_type = protein
                       organism = synthetic construct
SEQUENCE: 3279
METDTLLLWV LLLWVPGSTG DIQMTQSPSS LSASVGDRVT ITCKASQNVG INVVWHQQKP  60
GKVPKALIYS SSHRYSGVPS RFSGSGSGTD FTLTISSLQP EDVATYFCQQ FKSYPLTFGQ  120
GTKLEIKRTV AAPSVFIFPP SDEQLKSGTA SVVCLLNNFY PREAKVQWKV DNALQSGNSQ  180
ESVTEQDSKD STYSLSSTLT LSKADYEKHK VYACEVTHQG LSSPVTKSFN RGEC        234

SEQ ID NO: 3280        moltype = AA  length = 247
FEATURE                Location/Qualifiers
source                 1..247
                       mol_type = protein
                       organism = synthetic construct
SEQUENCE: 3280
METDTLLLWV LLLWVPGSTG DKTHTCPPCP APELLGGPSV FLFPPKPKDT LMISRTPEVT  60
CVVVDVSHED PEVKFNWYVD GVEVHNAKTK PREEQYNSTY RVVSVLTVLH QDWLNGKEYK  120
CKVSNKALPA PIEKTISKAK GQPREPQVYT LPPCREEMTK NQVSLWCLVK GFYPSDIAVE  180
WESNGQPENN YKTTPPVLDS DGSFFLYSKL TVDKSRWQQG NVFSCSVMHE ALHNRFTQKS  240
LSLSPGK                                                            247

SEQ ID NO: 3281        moltype = AA  length = 520
FEATURE                Location/Qualifiers
source                 1..520
                       mol_type = protein
                       organism = synthetic construct
SEQUENCE: 3281
METDTLLLWV LLLWVPGSTG EVQLVESGGG LVQPGGSLRL SCAASGFTFS NFGMHWVRQA  60
PGKGLEWVSY ISSGSSTIYY ADTLKGRFTI SRDNSKNTLY LQMNSLRAED TAVYYCARRG  120
EGAMDYWGQG TTVTVSSGGG GSGGGGSGGG GSGGGGSDNQ LTQSPSFLSA SVGDRVTITC  180
RASSSVNYIY WYQQKPGKAP KLLIYYTSNL APGVPSRFSG SGSGNEYTLT ISSLQPEDFA  240
TYYCQQFTSS PFTFGQGTKL EIKGGGGSDK THTCPPCPAP ELLGGPSVFL FPPKPKDTLM  300
ISRTPEVTCV VVDVSHEDPE VKFNWYVDGV EVHNAKTKPR EEQYNSTYRV VSVLTVLHQD  360
WLNGKEYKCK VSNKALPAPI EKTISKAKGQ PREPQVCTLP PSREEMTKNQ VSLSCAVKGF  420
YPSDIAVEWE SNGQPENNYK TTPPVLDSDG SFFLVSKLTV DKSRWQQGNV FSCSVMHEAL  480
HNHYTQKSLS LSPGKGGGGS GGGGSGLNDI FEAQKIEWHE                        520

SEQ ID NO: 3282        moltype = AA  length = 284
FEATURE                Location/Qualifiers
source                 1..284
                       mol_type = protein
                       organism = synthetic construct
SEQUENCE: 3282
METDTLLLWV LLLWVPGSTG GLNDIFEAQK IEWHEGGGGS EPRTDTDTCP NPPDPCPTCP  60
TPDLLGGPSV FIFPPKPKDV LMISLTPKIT CVVVDVSEEE PDVQFNWYVN NVEDKTAQTE  120
TRQRQYNSTY RVVSVLPIKH QDWMSGKVFK CKVNNNALPS PIEKTISKPR GQVRVPQIYT  180
FPPPIEQTVK KDVSVTCLVT GFLPQDIHVE WESNGQPQPE QNYKNTQPVL DSDGSYFLYS  240
KLNVPKSRWD QGDSFTCSVI HEALHNHHMT KTISRSLGNG GGGS                   284

SEQ ID NO: 3283        moltype = AA  length = 272
FEATURE                Location/Qualifiers
source                 1..272
                       mol_type = protein
                       organism = synthetic construct
SEQUENCE: 3283
METDTLLLWV LLLWVPGSTG DKTHTCPPCP APELLGGPSV FLFPPKPKDT LMISRTPEVT  60
CVVVDVSHED PEVKFNWYVD GVEVHNAKTK PREEQYNSTY RVVSVLTVLH QDWLNGKEYK  120
CKVSNKALPA PIEKTISKAK GQPREPQVYT LPPSREEMTK NQVSLTCLVK GFYPSDIAVE  180
WESNGQPENN YKTTPPVLDS DGSFFLYSKL TVDKSRWQQG NVFSCSVMHE ALHNHYTQKS  240
LSLSPGKGGG GSGGGGSGLN DIFEAQKIEW HE                                272

SEQ ID NO: 3284        moltype = AA  length = 469
FEATURE                Location/Qualifiers
source                 1..469
                       mol_type = protein
                       organism = synthetic construct
SEQUENCE: 3284
METDTLLLWV LLLWVPGSTG QVQLQQSGPE LVKPGASVKI SCKASGYAFS SSWMNWVKQR  60
PGQGLEWIGR IYPGDGDTKY NGKFKGKATL TADKSSSTAY MHLSSLTSVD SAVYFCARRG  120
TGGWYFDVWG AGTTVTVSSA KTTAPSVYPL APVCGDTTGS SVTLGCLVKG YFPEPVTLTW  180
```

```
NSGSLSSGVH TFPAVLQSDL YTLSSSVTVT SSTWPSQSIT CNVAHPASST KVDKKIEPRG  240
PTIKPCPPCK CPAPNLLGGP SVFIFPPKIK DVLMISLSPI VTCVVVDVSE DDPDVQISWF  300
VNNVEVHTAQ TQTHREDYNS TLRVVSALPI QHQDWMSGKE FKCKVNNKDL PAPIERTISK  360
PKGSVRAPQV YVLPPPEEEM TKKQVTLTCM VTDFMPEDIY VEWTNNGKTE LNYKNTEPVL  420
DSDGSYFMYS KLRVEKKNWV ERNSYSCSVV HEGLHNHHTT KSFSRTPGK            469

SEQ ID NO: 3285        moltype = AA  length = 238
FEATURE                Location/Qualifiers
source                 1..238
                       mol_type = protein
                       organism = synthetic construct
SEQUENCE: 3285
METDTLLLWV LLLWVPGSTG DIVLTQSPAS LAVSLGQRAT ISCRASESVD SSGNSFMHWY  60
QQKPGQPPQL LIYRASNLES GIPARFSGSG SRTDFTLTIN PVEADDVATF YCQQSFDDPF  120
TFGSGTKLEI KRADAAPTVS IFPPSSEQLT SGGASVVCFL NNFYPKDINV KWKIDGSERQ  180
NGVLNSWTDQ DSKDSTYSMS STLTLTKDEY ERHNSYTCEA THKTSTSPIV KSFNRNEC    238

SEQ ID NO: 3286        moltype = AA  length = 739
FEATURE                Location/Qualifiers
source                 1..739
                       mol_type = protein
                       organism = synthetic construct
SEQUENCE: 3286
METDTLLLWV LLLWVPGSTG QVQLVESGGG VVQPGRSLRL SCAASGIDFS RYWMSWVRQA  60
PGKGLEWVGE INPDSSTINY APSLKDRFTI SRDNSKNTLY LQMSSLRAED TAVYYCASLY  120
YDYGDAMDYW GQGTTVTVSS ASTKGPSVFP LAPSSKSTSG GTAALGCLVK DYFPEPVTVS  180
WNSGALTSGV HTFPAVLQSS GLYSLSSVVT VPSSSLGTQT YICNVNHKPS NTKVDKRVEP  240
KSCDKTHTCP PCPAPELLGG PSVFLFPPKP KDTLMISRTP EVTCVVVDVS HEDPEVKFNW  300
YVDGVEVHNA KTKPREEQYN STYRVVSVLT VLHQDWLNGK EYKCKVSNKA LPAPIEKTIS  360
KAKGQPREPQ VYTLPPCREE MTKNQVSLWC LVKGFYPSDI AVEWESNGQP ENNYKTTPPV  420
LDSDGSFFLY SKLTVDKSRW QQGNVFSCSV MHEALHNHYT QKSLSLSPGK GGGGSGGGGS  480
GGGGSEVQLV ESGGGLVQPG GSLRLSCAAS GFTFSTYAMN WVRQAPGKGL EWVSRIRSKY  540
NNYATYYADS VKDRFTISRD DSKNTLYLQM NSLKTEDTAV YYCVRHGNFG NSYVSWFAYW  600
GQGTLVTVSS GGGGSGGGGS GGGGSGGGGS QAVVTQEPSL TVSPGGTVTL TCRSSTGAVT  660
TSNYANWVQQ KPGQAPRGLI GGTNKRAPWT PARFSGSLLG GKAALTLSGA QPEDEAEYYC  720
ALWYSNLWVF GGGTKLTVL                                              739

SEQ ID NO: 3287        moltype = AA  length = 247
FEATURE                Location/Qualifiers
source                 1..247
                       mol_type = protein
                       organism = synthetic construct
SEQUENCE: 3287
METDTLLLWV LLLWVPGSTG DKTHTCPPCP APELLGGPSV FLFPPKPKDT LMISRTPEVT  60
CVVVDVSHED PEVKFNWYVD GVEVHNAKTK PREEQYNSTY RVVSVLTVLH QDWLNGKEYK  120
CKVSNKALPA PIEKTISKAK GQPREPQVCT LPPSREEMTK NQVSLSCAVK GFYPSDIAVE  180
WESNGQPENN YKTTPPVLDS DGSFFLVSKL TVDKSRWQQG NVFSCSVMHE ALHNHYTQKS  240
LSLSPGK                                                           247

SEQ ID NO: 3288        moltype = AA  length = 20
FEATURE                Location/Qualifiers
source                 1..20
                       mol_type = protein
                       organism = synthetic construct
SEQUENCE: 3288
METDTLLLWV LLLWVPGSTG                                             20

SEQ ID NO: 3289        moltype = AA  length = 107
FEATURE                Location/Qualifiers
VARIANT                30
                       note = G, E, A, or D
VARIANT                31
                       note = N or D
VARIANT                32
                       note = R or K
VARIANT                36
                       note = Y or H
VARIANT                56
                       note = K or S
source                 1..107
                       mol_type = protein
                       organism = synthetic construct
SEQUENCE: 3289
DIQMTQSPSF LSASVGDRVT ITCKASQNVX XXVAWXQQKP GKAPKALIYS SSHRYXGVPS  60
RFSGSGSGTE FTLTISSLQP EDFATYFCQQ FKSYPLTFGQ GTKLEIK              107

SEQ ID NO: 3290        moltype = AA  length = 119
FEATURE                Location/Qualifiers
VARIANT                27
```

```
                          note = H, T, G, or Y
VARIANT                   28
                          note = D, T, or S
VARIANT                   30
                          note = H, R, D, K, or T
VARIANT                   31
                          note = L, D, K, T, or N
VARIANT                   32
                          note = W, F, T, I, Y, or G
VARIANT                   50
                          note = R or W
VARIANT                   51
                          note = V, I, or F
VARIANT                   52
                          note = F, S, or Y
VARIANT                   53
                          note = A or P
VARIANT                   57
                          note = N or S
VARIANT                   58
                          note = T, V, Y, or I
VARIANT                   59
                          note = K or R
VARIANT                   98
                          note = G or V
VARIANT                   100
                          note = Y or I
VARIANT                   103
                          note = Y or A
VARIANT                   104
                          note = D or G
source                    1..119
                          mol_type = protein
                          organism = synthetic construct
SEQUENCE: 3290
QVQLVQSGAE VKKPGSSVKV SCKASGXXFX XXYIHWVRQA PGQGLEWMGX XXXGSGXXXY  60
NEKFKGRVTI TADTSTSTAY MELSSLRSED TAVYYCAXSX YSXXVLDYWG QGTTVTVSS   119

SEQ ID NO: 3291           moltype = AA  length = 238
FEATURE                   Location/Qualifiers
source                    1..238
                          mol_type = protein
                          note = B7-6 sequence
                          organism = unidentified
SEQUENCE: 3291
DLKVEMMAGG TQITPLNDNV TIFCNIFYSQ PLNITSMGIT WFWKSLTFDK EVKVFEFFGD  60
HQEAFRPGAI VSPWRLKSGD ASLRLPGIQL EEAGEYRCEV VVTPLKAQGT VQLEVVASPA  120
SRLLLDQVGM KENEDKYMCE SSGFYPEAIN ITWEKQTQKF PHPIEISEDV ITGPTIKNMD  180
GTFNVTSCLK LNSSQEDPGT VYQCVVRHAS LHTPLRSNFT LTAARHSLSE TEKTDNFS    238

SEQ ID NO: 3292           moltype = AA  length = 284
FEATURE                   Location/Qualifiers
source                    1..284
                          mol_type = protein
                          note = MICA sequence
                          organism = unidentified
SEQUENCE: 3292
EPHSLRYNLT VLSWDGSVQS GFLTEVHLDG QPFLRCDRQK CRAKPQGQWA EDVLGNKTWD  60
RETRDLTGNG KDLRMTLAHI KDQKEGLHSL QEIRVCEIHE DNSTRSSQHF YYDGELFLSQ  120
NLETKEWTMP QSSRAQTLAM NVRNFLKEDA MKTKTHYHAM HADCLQELRR YLKSGVVLRR  180
TVPPMVNVTR SEASEGNITV TCRASGFYPW NITLSWRQDG VSLSHDTQQW GDVLPDGNGT  240
YQTWVATRIC QGEEQRFTCY MEHSGNHSTH PVPSGKVLVL QSHW                   284

SEQ ID NO: 3293           moltype = AA  length = 287
FEATURE                   Location/Qualifiers
source                    1..287
                          mol_type = protein
                          note = MICB sequence
                          organism = unidentified
SEQUENCE: 3293
AEPHSLRYNL MVLSQDESVQ SGFLAEGHLD GQPFLRYDRQ KRRAKPQGQW AEDVLGAKTW  60
DTETEDLTEN GQDLRRTLTH IKDQKGGLHS LQEIRVCEIH EDSSTRGSRH FYYDGELFLS  120
QNLETQESTV PQSSRAQTLA MNVTNFWKED AMKTKTHYRA MQADCLQKLQ RYLKSGVAIR  180
RTVPPMVNVT CSEVSEGNIT VTCRASSFYP RNITLTWRQD GVSLSHNTQQ WGDVLPDGNG  240
TYQTWVATRI RQGEEQRFTC YMEHSGNHGT HPVPSGKVLV LQSQRTD                287

SEQ ID NO: 3294           moltype = AA  length = 191
FEATURE                   Location/Qualifiers
source                    1..191
```

```
                        mol_type = protein
                        note = ULBP1 sequence
                        organism = unidentified
SEQUENCE: 3294
GWVDTHCLCY DFIITPKSRP EPQWCEVQGL VDERPFLHYD CVNHKAKAFA SLGKKVNVTK  60
TWEEQTETLR DVVDFLKGQL LDIQVENLIP IEPLTLQARM SCEHEAHGHG RGSWQFLFNG  120
QKFLLFDSNN RKWTALHPGA KKMTEKWEKN RDVTMFFQKI SLGDCKMWLE EFLMYWEQML  180
DPTKPPSLAP G                                                      191

SEQ ID NO: 3295         moltype = AA  length = 329
FEATURE                 Location/Qualifiers
source                  1..329
                        mol_type = protein
                        note = NECTIN2 sequence
                        organism = unidentified
SEQUENCE: 3295
QDVRVQVLPE VRGQLGGTVE LPCHLLPPVP GLYISLVTWQ RPDAPANHQN VAAFHPKMGP  60
SFPSPKPGSE RLSFVSAKQS TGQDTEAELQ DATLALHGLT VEDEGNYTCE FATFPKGSVR  120
GMTWLRVIAK PKNQAEAQKV TFSQDPTTVA LCISKEGRPP ARISWLSSLD WEAKETQVSG  180
TLAGTVTVTS RFTLVPSGRA DGVTVTCKVE HESFEEPALI PVTLSVRYPP EVSISGYDDN  240
WYLGRTDATL SCDVRSNPEP TGYDWSTTSG TFPTSAVAQG SQLVIHAVDS LFNTTFVCTV  300
TNAVGMGRAE QVIFVRETPN TAGAGATGG                                   329

SEQ ID NO: 3296         moltype = AA  length = 323
FEATURE                 Location/Qualifiers
source                  1..323
                        mol_type = protein
                        note = NECL5 sequence
                        organism = unidentified
SEQUENCE: 3296
WPPPGTGDVV VQAPTQVPGF LGDSVTLPCY LQVPNMEVTH VSQLTWARHG ESGSMAVFHQ  60
TQGPSYSESK RLEFVAARLG AELRNASLRM FGLRVEDEGN YTCLFVTFPQ GSRSVDIWLR  120
VLAKPQNTAE VQKVQLTGEP VPMARCVSTG GRPPAQITWH SDLGGMPNTS QVPGFLSGTV  180
TVTSLWILVP SSQVDGKNVT CKVEHESFEK PQLLTVNLTV YYPPEVSISG YDNNWYLGQN  240
EATLTCDARS NPEPTGYNWS TTMGPLPPFA VAQGAQLLIR PVDKPINTTL ICNVTNALGA  300
RQAELTVQVK EGPPSEHSGI SRN                                         323

SEQ ID NO: 3297         moltype = AA  length = 330
FEATURE                 Location/Qualifiers
source                  1..330
                        mol_type = protein
                        note = NECL2 sequence
                        organism = unidentified
SEQUENCE: 3297
QNLFTKDVTV IEGEVATISC QVNKSDDSVI QLLNPNRQTI YFRDFRPLKD SRFQLLNFSS  60
SELKVSLTNV SISDEGRYFC QLYTDPPQES YTTITVLVPP RNLMIDIQKD TAVEGEEIEV  120
NCTAMASKPA TTIRWFKGNT ELKGKSEVEE WSDMYTVTSQ LMLKVHKEDD GVPVICQVEH  180
PAVTGNLQTQ RYLEVQYKPQ VHIQMTYPLQ GLTREGDALE LTCEAIGKPQ PVMVTWVRVD  240
DEMPQHAVLS GPNLFINNLN KTDNGTYRCE ASNIVGKAHS DYMLYVYDPP TTIPPPTTTT  300
TTTTTTTTTI LTIITDSRAG EEGSIRAVDH                                  330

SEQ ID NO: 3298         moltype = AA  length = 155
FEATURE                 Location/Qualifiers
source                  1..155
                        mol_type = protein
                        note = CD70 sequence
                        organism = unidentified
SEQUENCE: 3298
QRFAQAQQQL PLESLGWDVA ELQLNHTGPQ QDPRLYWQGG PALGRSFLHG PELDKGQLRI  60
HRDGIYMVHI QVTLAICSST TASRHHPTTL AVGICSPASR SISLLRLSFH QGCTIASQRL  120
TPLARGDTLC TNLTGTLLPS RNTDETFFGV QWVRP                             155

SEQ ID NO: 3299         moltype = AA  length = 294
FEATURE                 Location/Qualifiers
source                  1..294
                        mol_type = protein
                        note = L-selectin sequence
                        organism = unidentified
SEQUENCE: 3299
WTYHYSEKPM NWQRARRFCR DNYTDLVAIQ NKAEIEYLEK TLPFSRSYYW IGIRKIGGIW  60
TWVGTNKSLT EEAENWGDGE PNNKKNKEDC VEIYIKRNKD AGKWNDDACH KLKAALCYTA  120
SCQPWSCSGH GECVEIINNY TCNCDVGYYG PQCQFVIQCE PLEAPELGTM DCTHPLGNFS  180
FSSQCAFSCS EGTNLTGIEE TTCGPFGNWS SPEPTCQVIQ CEPLSAPDLG IMNCSHPLAS  240
FSFTSACTFI CSEGTELIGK KKTICESSGI WSNPSPICQK LDKSFSMIKE GDYN        294

SEQ ID NO: 3300         moltype = AA  length = 243
FEATURE                 Location/Qualifiers
source                  1..243
                        mol_type = protein
```

```
                         note = CD72 sequence
                         organism = unidentified
SEQUENCE: 3300
RYLQVSQQLQ QTNRVLEVTN SSLRQQLRLK ITQLGQSAED LQGSRRELAQ SQEALQVEQR  60
AHQAAEGQLQ ACQADRQKTK ETLQSEEQQR RALEQKLSNM ENRLKPFFTC GSADTCCPSG  120
WIMHQKSCFY ISLTSKNWQE SQKQCETLSS KLATFSEIYP QSHSYYFLNS LLPNGGSGNS  180
YWTGLSSNKD WKLTDDTQRT RTYAQSSKCN KVHKTWSWWT LESESCRSSL PYICEMTAFR  240
FPD                                                               243

SEQ ID NO: 3301          moltype = AA  length = 124
FEATURE                  Location/Qualifiers
source                   1..124
                         mol_type = protein
                         note = CLEC2B (AICL) sequence
                         organism = unidentified
SEQUENCE: 3301
KLTRDSQSLC PYDWIGFQNK CYYFSKEEGD WNSSKYNCST QHADLTIIDN IEEMNFLRRY  60
KCSSDHWIGL KMAKNRTGQW VDGATFTKSF GMRGSEGCAY LSDDGAATAR CYTERKWICR  120
KRIH                                                              124

SEQ ID NO: 3302          moltype = AA  length = 194
FEATURE                  Location/Qualifiers
source                   1..194
                         mol_type = protein
                         note = CD48 sequence
                         organism = unidentified
SEQUENCE: 3302
QGHLVHMTVV SGSNVTLNIS ESLPENYKQL TWFYTFDQKI VEWDSRKSKY FESKFKGRVR  60
LDPQSGALYI SKVQKEDNST YIMRVLKKTG NEQEWKIKLQ VLDPVPKPVI KIEKIEDMDD  120
NCYLKLSCVI PGESVNYTWY GDKRPFPKEL QNSVLETTLM PHNYSRCYTC QVSNSVSSKN  180
GTVCLSPPCT LARS                                                   194

SEQ ID NO: 3303          moltype = AA  length = 133
FEATURE                  Location/Qualifiers
source                   1..133
                         mol_type = protein
                         note = OX40L sequence
                         organism = unidentified
SEQUENCE: 3303
QVSHRYPRIQ SIKVQFTEYK KEKGFILTSQ KEDEIMKVQN NSVIINCDGF YLISLKGYFS  60
QEVNISLHYQ KDEEPLFQLK KVRSVNSLMV ASLTYKDKVY LNVTTDNTSL DDFHVNGGEL  120
ILIHQNPGEF CVL                                                    133

SEQ ID NO: 3304          moltype = AA  length = 149
FEATURE                  Location/Qualifiers
source                   1..149
                         mol_type = protein
                         note = CD40L sequence
                         organism = unidentified
SEQUENCE: 3304
MQKGDQNPQI AAHVISEASS KTTSVLQWAE KGYYTMSNNL VTLENGKQLT VKRQGLYYIY  60
AQVTFCSNRE ASSQAPFIAS LCLKSPGRFE RILLRAANTH SSAKPCGQQS IHLGGVFELQ  120
PGASVFVNVT DPSQVSHGTG FTSFGLLKL                                   149

SEQ ID NO: 3305          moltype = AA  length = 205
FEATURE                  Location/Qualifiers
source                   1..205
                         mol_type = protein
                         note = 41BB ligand sequence
                         organism = unidentified
SEQUENCE: 3305
ACPWAVSGAR ASPGSAASPR LREGPELSPD DPAGLLDLRQ GMFAQLVAQN VLLIDGPLSW  60
YSDPGLAGVS LTGGLSYKED TKELVVAKAG VYYVFFQLEL RRVVAGEGSG SVSLALHLQP  120
LRSAAGAAAL ALTVDLPPAS SEARNSAFGF QGRLLHLSAG QRLGVHLHTE ARARHAWQLT  180
QGATVLGLFR VTPEIPAGLP SPRSE                                       205

SEQ ID NO: 3306          moltype = AA  length = 455
FEATURE                  Location/Qualifiers
source                   1..455
                         mol_type = protein
                         organism = synthetic construct
SEQUENCE: 3306
LNFRAPPVIP NVPFLWAWNA PSEFCLGKFD EPLDMSLFSF IGSPRINATG QGVTIFYVDR  60
LGYYPYIDSI TGVTVNGGIP QKISLQDHLD KAKKDITFYM PVDNLGMAVI DWEEWRPTWA  120
RNWKPKDVYK NRSIELVQQQ NVQLSLTEAT EKAKQEFEKA GKDFLVETIK LGKLLRPNHL  180
WGYYLFPDCY NHHYKKPGYN GSCFNVEIKR NDDLSWLWNE STALYPSIYL NTQQSPVAAT  240
LYVRNRVREA IRVSKIPDAK SPLPVFAYTR IVFTDQVLKF LSQDELVYTF GETVALGASG  300
IVIWGTLSIM RSMKSCLLLD NYMETILNPY IINVTLAAKM CSQVLCQEQG VCIRKNWNSS  360
DYLHLNPDNF AIQLEKGGKF TVRGKPTLED LEQFSEKFYC SCYSTLSCKE KADVKDTDAV  420
```

```
DVCIADGVCI DAFLKPPMET EEPQIFYNAS PSTLS                         455

SEQ ID NO: 3307        moltype = AA  length = 5
FEATURE                Location/Qualifiers
source                 1..5
                       mol_type = protein
                       organism = synthetic construct
SEQUENCE: 3307
GGGGS                                                          5

SEQ ID NO: 3308        moltype = AA  length = 10
FEATURE                Location/Qualifiers
source                 1..10
                       mol_type = protein
                       organism = synthetic construct
SEQUENCE: 3308
GGGGSGGGGS                                                     10

SEQ ID NO: 3309        moltype = AA  length = 15
FEATURE                Location/Qualifiers
source                 1..15
                       mol_type = protein
                       organism = synthetic construct
SEQUENCE: 3309
GGGGSGGGGS GGGGS                                               15

SEQ ID NO: 3310        moltype = AA  length = 17
FEATURE                Location/Qualifiers
source                 1..17
                       mol_type = protein
                       organism = synthetic construct
SEQUENCE: 3310
DVPSGPGGGG GSGGGGS                                             17

SEQ ID NO: 3311        moltype = AA  length = 455
FEATURE                Location/Qualifiers
source                 1..455
                       mol_type = protein
                       note = Hyaluronidase sequence
                       organism = unidentified
SEQUENCE: 3311
LNFRAPPVIP NVPFLWAWNA PSEFCLGKFD EPLDMSLFSF IGSPRINATG QGVTIFYVDR  60
LGYYPYIDSI TGVTVNGGIP QKISLQDHLD KAKKDITFYM PVDNLGMAVI DWEEWRPTWA  120
RNWKPKDVYK NRSIELVQQQ NVQLSLTEAT EKAKQEFEKA GKDFLVETIK LGKLLRPNHL  180
WGYYLFPDCY NHHYKKPGYN GSCFNVEIKR NDDLSWLWNE STALYPSIYL NTQQSPVAAT  240
LYVRNRVREA IRVSKIPDAK SPLPVFAYTR IVFTDQVLKF LSQDELVYTF GETVALGASG  300
IVIWGTLSIM RSMKSCLLLD NYMETILNPY IINVTLAAKM CSQVLCQEQG VCIRKNWNSS  360
DYLHLNPDNF AIQLEKGGKF TVRGKPTLED LEQFSEKFYC SCYSTLSCKE KADVKDTDAV  420
DVCIADGVCI DAFLKPPMET EEPQIFYNAS PSTLS                         455

SEQ ID NO: 3312        moltype = AA  length = 413
FEATURE                Location/Qualifiers
source                 1..413
                       mol_type = protein
                       note = HYAL1 sequence
                       organism = unidentified
SEQUENCE: 3312
FRGPLLPNRP FTTVWNANTQ WCLERHGVDV DVSVFDVVAN PGQTFRGPDM TIFYSSQGTY  60
PYYTPTGEPV FGGLPQNASL IAHLARTFQD ILAAIPAPDF SGLAVIDWEA WRPRWAFNWD  120
TKDIYRQRSR ALVQAQHPDW PAPQVEAVAQ DQFQGAARAW MAGTLQLGRA LRPRGLWGFY  180
GFPDCYNYDF LSPNYTGQCP SGIRAQNDQL GWLWGQSRAL YPSIYMPAVL EGTGKSQMYV  240
QHRVAEAFRV AVAAGDPNLP VLPYVQIFYD TTNHFLPLDE LEHSLGESAA QGAAGVVLWV  300
SWENTRTKES CQAIKEYMDT TLGPFILNVT SGALLCSQAL CSGHGRCVRR TSHPKALLLL  360
NPASFSIQLT PGGGPLSLRG ALSLEDQAQM AVEFKCRCYP GWQAPWCERK SMW         413

SEQ ID NO: 3313        moltype = AA  length = 551
FEATURE                Location/Qualifiers
source                 1..551
                       mol_type = protein
                       note = Collagenase molecule IV sequence
                       organism = unidentified
SEQUENCE: 3313
YNFFPRKPKW DKNQITYRII GYTPDLDPET VDDAFARAFQ VWSDVTPLRF SRIHDGEADI  60
MINFGRWEHG DGYPFDGKDG LLAHAFAPGT GVGGDSHFDD DELWTLGEGQ VVRVKYGNAD  120
GEYCKFPFLF NGKEYNSCTD TGRSDGFLWC STTYNFEKDG KYGFCPHEAL FTMGGNAEGQ  180
PCKFPFRFQG TSYDSCTTEG RTDGYRWCGT TEDYDRDKKY GFCPETAMST VGGNSEGAPC  240
VFPFTFLGNK YESCTSAGRS DGKMWCATTA NYDDDRKWGF CPDQGYSLFL VAAHEFGHAM  300
GLEHSQDPGA LMAPIYTYTK NFRLSQDDIK GIQELYGASP DIDLGTGPTP TLGPVTPEIC  360
KQDIVFDGIA QIRGEIFFFK DRFIWRTVTP RDKPMGPLLV ATFWPELPEK IDAVYEAPQE  420
```

```
EKAVFFAGNE YWIYSASTLE RGYPKPLTSL GLPPDVQRVD AAFNWSKNKK TYIFAGDKFW  480
RYNEVKKKMD PGFPKLIADA WNAIPDNLDA VVDLQGGGHS YFFKGAYYLK LENQSLKSVK  540
FGSIKSDWLG C                                                       551

SEQ ID NO: 3314         moltype = AA  length = 14
FEATURE                 Location/Qualifiers
source                  1..14
                        mol_type = protein
                        organism = synthetic construct
SEQUENCE: 3314
AEAAAKEAAA KAAA                                                    14

SEQ ID NO: 3315         moltype = AA  length = 19
FEATURE                 Location/Qualifiers
source                  1..19
                        mol_type = protein
                        organism = synthetic construct
SEQUENCE: 3315
AEAAAKEAAA KEAAAKAAA                                               19

SEQ ID NO: 3316         moltype = AA  length = 24
FEATURE                 Location/Qualifiers
source                  1..24
                        mol_type = protein
                        organism = synthetic construct
SEQUENCE: 3316
AEAAAKEAAA KEAAAKEAAA KAAA                                         24

SEQ ID NO: 3317         moltype = AA  length = 29
FEATURE                 Location/Qualifiers
source                  1..29
                        mol_type = protein
                        organism = synthetic construct
SEQUENCE: 3317
AEAAAKEAAA KEAAAKEAAA KEAAAKAAA                                    29

SEQ ID NO: 3318         moltype =   length =
SEQUENCE: 3318
000

SEQ ID NO: 3319         moltype =   length =
SEQUENCE: 3319
000

SEQ ID NO: 3320         moltype =   length =
SEQUENCE: 3320
000

SEQ ID NO: 3321         moltype =   length =
SEQUENCE: 3321
000

SEQ ID NO: 3322         moltype =   length =
SEQUENCE: 3322
000

SEQ ID NO: 3323         moltype =   length =
SEQUENCE: 3323
000

SEQ ID NO: 3324         moltype =   length =
SEQUENCE: 3324
000

SEQ ID NO: 3325         moltype =   length =
SEQUENCE: 3325
000

SEQ ID NO: 3326         moltype =   length =
SEQUENCE: 3326
000

SEQ ID NO: 3327         moltype =   length =
SEQUENCE: 3327
000

SEQ ID NO: 3328         moltype =   length =
SEQUENCE: 3328
000
```

SEQ ID NO: 3329 moltype = length =
SEQUENCE: 3329
000

SEQ ID NO: 3330 moltype = length =
SEQUENCE: 3330
000

SEQ ID NO: 3331 moltype = length =
SEQUENCE: 3331
000

SEQ ID NO: 3332 moltype = length =
SEQUENCE: 3332
000

SEQ ID NO: 3333 moltype = length =
SEQUENCE: 3333
000

SEQ ID NO: 3334 moltype = length =
SEQUENCE: 3334
000

SEQ ID NO: 3335 moltype = length =
SEQUENCE: 3335
000

SEQ ID NO: 3336 moltype = length =
SEQUENCE: 3336
000

SEQ ID NO: 3337 moltype = length =
SEQUENCE: 3337
000

SEQ ID NO: 3338 moltype = length =
SEQUENCE: 3338
000

SEQ ID NO: 3339 moltype = length =
SEQUENCE: 3339
000

SEQ ID NO: 3340 moltype = length =
SEQUENCE: 3340
000

SEQ ID NO: 3341 moltype = length =
SEQUENCE: 3341
000

SEQ ID NO: 3342 moltype = length =
SEQUENCE: 3342
000

SEQ ID NO: 3343 moltype = length =
SEQUENCE: 3343
000

SEQ ID NO: 3344 moltype = length =
SEQUENCE: 3344
000

SEQ ID NO: 3345 moltype = length =
SEQUENCE: 3345
000

SEQ ID NO: 3346 moltype = length =
SEQUENCE: 3346
000

SEQ ID NO: 3347 moltype = length =
SEQUENCE: 3347
000

SEQ ID NO: 3348 moltype = length =
SEQUENCE: 3348

000

SEQ ID NO: 3349 moltype = length =
SEQUENCE: 3349
000

SEQ ID NO: 3350 moltype = length =
SEQUENCE: 3350
000

SEQ ID NO: 3351 moltype = length =
SEQUENCE: 3351
000

SEQ ID NO: 3352 moltype = length =
SEQUENCE: 3352
000

SEQ ID NO: 3353 moltype = length =
SEQUENCE: 3353
000

SEQ ID NO: 3354 moltype = length =
SEQUENCE: 3354
000

SEQ ID NO: 3355 moltype = length =
SEQUENCE: 3355
000

SEQ ID NO: 3356 moltype = length =
SEQUENCE: 3356
000

SEQ ID NO: 3357 moltype = length =
SEQUENCE: 3357
000

SEQ ID NO: 3358 moltype = length =
SEQUENCE: 3358
000

SEQ ID NO: 3359 moltype = length =
SEQUENCE: 3359
000

SEQ ID NO: 3360 moltype = length =
SEQUENCE: 3360
000

SEQ ID NO: 3361 moltype = length =
SEQUENCE: 3361
000

SEQ ID NO: 3362 moltype = length =
SEQUENCE: 3362
000

SEQ ID NO: 3363 moltype = length =
SEQUENCE: 3363
000

SEQ ID NO: 3364 moltype = length =
SEQUENCE: 3364
000

SEQ ID NO: 3365 moltype = length =
SEQUENCE: 3365
000

SEQ ID NO: 3366 moltype = length =
SEQUENCE: 3366
000

SEQ ID NO: 3367 moltype = length =
SEQUENCE: 3367
000

SEQ ID NO: 3368 moltype = length =

```
SEQUENCE: 3368
000

SEQ ID NO: 3369        moltype =   length =
SEQUENCE: 3369
000

SEQ ID NO: 3370        moltype =   length =
SEQUENCE: 3370
000

SEQ ID NO: 3371        moltype =   length =
SEQUENCE: 3371
000

SEQ ID NO: 3372        moltype =   length =
SEQUENCE: 3372
000

SEQ ID NO: 3373        moltype =   length =
SEQUENCE: 3373
000

SEQ ID NO: 3374        moltype =   length =
SEQUENCE: 3374
000

SEQ ID NO: 3375        moltype =   length =
SEQUENCE: 3375
000

SEQ ID NO: 3376        moltype =   length =
SEQUENCE: 3376
000

SEQ ID NO: 3377        moltype = AA  length = 107
FEATURE                Location/Qualifiers
source                 1..107
                       mol_type = protein
                       organism = synthetic construct
SEQUENCE: 3377
DIQMTQSPSF LSASVGDRVT ITCKASQNVE NKVAWHQQKP GKAPKALIYS SSHRYKGVPS  60
RFSGSGSGTE FTLTISSLQP EDFATYFCQQ FKSYPLTFGQ GTKLEIK                107

SEQ ID NO: 3378        moltype = AA  length = 107
FEATURE                Location/Qualifiers
source                 1..107
                       mol_type = protein
                       organism = synthetic construct
SEQUENCE: 3378
DIQMTQSPSF LSASVGDRVT ITCKASQNVD NKVAWHQQKP GKAPKALIYS SSHRYKGVPS  60
RFSGSGSGTE FTLTISSLQP EDFATYFCQQ FKSYPLTFGQ GTKLEIK                107

SEQ ID NO: 3379        moltype = AA  length = 107
FEATURE                Location/Qualifiers
source                 1..107
                       mol_type = protein
                       organism = synthetic construct
SEQUENCE: 3379
DIQMTQSPSF LSASVGDRVT ITCKASQNVD NRVAWHQQKP GKAPKALIYS SSHRYKGVPS  60
RFSGSGSGTE FTLTISSLQP EDFATYFCQQ FKSYPLTFGQ GTKLEIK                107

SEQ ID NO: 3380        moltype = AA  length = 107
FEATURE                Location/Qualifiers
source                 1..107
                       mol_type = protein
                       organism = synthetic construct
SEQUENCE: 3380
DIQMTQSPSF LSASVGDRVT ITCKASQNVE DRVAWHQQKP GKAPKALIYS SSHRYKGVPS  60
RFSGSGSGTE FTLTISSLQP EDFATYFCQQ FKSYPLTFGQ GTKLEIK                107

SEQ ID NO: 3381        moltype = AA  length = 107
FEATURE                Location/Qualifiers
source                 1..107
                       mol_type = protein
                       organism = synthetic construct
SEQUENCE: 3381
DIQMTQSPSF LSASVGDRVT ITCKASQNVD DRVAWYQQKP GKAPKALIYS SSHRYKGVPS  60
RFSGSGSGTE FTLTISSLQP EDFATYFCQQ FKSYPLTFGQ GTKLEIK                107
```

```
SEQ ID NO: 3382        moltype = AA  length = 107
FEATURE                Location/Qualifiers
source                 1..107
                       mol_type = protein
                       organism = synthetic construct
SEQUENCE: 3382
DIQMTQSPSF LSASVGDRVT ITCKASQNVG DRVAWHQQKP GKAPKALIYS SSHRYKGVPS  60
RFSGSGSGTE FTLTISSLQP EDFATYFCQQ FKSYPLTFGQ GTKLEIK                107

SEQ ID NO: 3383        moltype = AA  length = 107
FEATURE                Location/Qualifiers
source                 1..107
                       mol_type = protein
                       organism = synthetic construct
SEQUENCE: 3383
DIQMTQSPSF LSASVGDRVT ITCKASQNVE DKVAWYQQKP GKAPKALIYS SSHRYKGVPS  60
RFSGSGSGTE FTLTISSLQP EDFATYFCQQ FKSYPLTFGQ GTKLEIK                107

SEQ ID NO: 3384        moltype = AA  length = 107
FEATURE                Location/Qualifiers
source                 1..107
                       mol_type = protein
                       organism = synthetic construct
SEQUENCE: 3384
DIQMTQSPSF LSASVGDRVT ITCKASQNVA DRVAWYQQKP GKAPKALIYS SSHRYKGVPS  60
RFSGSGSGTE FTLTISSLQP EDFATYFCQQ FKSYPLTFGQ GTKLEIK                107

SEQ ID NO: 3385        moltype = AA  length = 107
FEATURE                Location/Qualifiers
source                 1..107
                       mol_type = protein
                       organism = synthetic construct
SEQUENCE: 3385
DIQMTQSPSF LSASVGDRVT ITCKASQNVE DRVAWYQQKP GKAPKALIYS SSHRYKGVPS  60
RFSGSGSGTE FTLTISSLQP EDFATYFCQQ FKSYPLTFGQ GTKLEIK                107

SEQ ID NO: 3386        moltype = AA  length = 107
FEATURE                Location/Qualifiers
source                 1..107
                       mol_type = protein
                       organism = synthetic construct
SEQUENCE: 3386
DIQMTQSPSF LSASVGDRVT ITCKASQNVD NRVAWYQQKP GKAPKALIYS SSHRYKGVPS  60
RFSGSGSGTE FTLTISSLQP EDFATYFCQQ FKSYPLTFGQ GTKLEIK                107

SEQ ID NO: 3387        moltype = AA  length = 107
FEATURE                Location/Qualifiers
source                 1..107
                       mol_type = protein
                       organism = synthetic construct
SEQUENCE: 3387
DIQMTQSPSF LSASVGDRVT ITCKASQNVG DRVAWYQQKP GKAPKALIYS SSHRYKGVPS  60
RFSGSGSGTE FTLTISSLQP EDFATYFCQQ FKSYPLTFGQ GTKLEIK                107

SEQ ID NO: 3388        moltype = AA  length = 107
FEATURE                Location/Qualifiers
source                 1..107
                       mol_type = protein
                       organism = synthetic construct
SEQUENCE: 3388
DIQMTQSPSF LSASVGDRVT ITCKASQNVG NRVAWYQQKP GKAPKALIYS SSHRYSGVPS  60
RFSGSGSGTE FTLTISSLQP EDFATYFCQQ FKSYPLTFGQ GTKLEIK                107

SEQ ID NO: 3389        moltype = AA  length = 107
FEATURE                Location/Qualifiers
source                 1..107
                       mol_type = protein
                       organism = synthetic construct
SEQUENCE: 3389
DIQMTQSPSF LSASVGDRVT ITCKASQNVG NRVAWYQQKP GKAPKALIYS SSHRYKGVPS  60
RFSGSGSGTE FTLTISSLQP EDFATYFCQQ FKSYPLTFGQ GTKLEIK                107

SEQ ID NO: 3390        moltype = AA  length = 119
FEATURE                Location/Qualifiers
source                 1..119
                       mol_type = protein
                       organism = synthetic construct
SEQUENCE: 3390
```

```
QVQLVQSGAE VKKPGSSVKV SCKASGYSFT LGYIHWVRQA PGQGLEWMGW FFPGSGNIKY  60
NEKFKGRVTI TADTSTSTAY MELSSLRSED TAVYYCAGSY YSYDVLDYWG QGTTVTVSS   119

SEQ ID NO: 3391        moltype = AA  length = 119
FEATURE                Location/Qualifiers
source                 1..119
                       mol_type = protein
                       organism = synthetic construct
SEQUENCE: 3391
QVQLVQSGAE VKKPGSSVKV SCKASGYSFR LTYIHWVRQA PGQGLEWMGW FFPGSGNIKY  60
NEKFKGRVTI TADTSTSTAY MELSSLRSED TAVYYCAGSY YSYDVLDYWG QGTTVTVSS   119

SEQ ID NO: 3392        moltype = AA  length = 119
FEATURE                Location/Qualifiers
source                 1..119
                       mol_type = protein
                       organism = synthetic construct
SEQUENCE: 3392
QVQLVQSGAE VKKPGSSVKV SCKASGYSFH NWYIHWVRQA PGQGLEWMGW FFPGSGNIKY  60
NEKFKGRVTI TADTSTSTAY MELSSLRSED TAVYYCAGSY YSYDVLDYWG QGTTVTVSS   119

SEQ ID NO: 3393        moltype = AA  length = 119
FEATURE                Location/Qualifiers
source                 1..119
                       mol_type = protein
                       organism = synthetic construct
SEQUENCE: 3393
QVQLVQSGAE VKKPGSSVKV SCKASGYSFT TYYIHWVRQA PGQGLEWMGW FFPGSGNIKY  60
NEKFKGRVTI TADTSTSTAY MELSSLRSED TAVYYCAGSI YSAGVLDYWG QGTTVTVSS   119

SEQ ID NO: 3394        moltype = AA  length = 119
FEATURE                Location/Qualifiers
source                 1..119
                       mol_type = protein
                       organism = synthetic construct
SEQUENCE: 3394
QVQLVQSGAE VKKPGSSVKV SCKASGYSFT TYYIHWVRQA PGQGLEWMGR IFPGSGNIKY  60
NEKFKGRVTI TADTSTSTAY MELSSLRSED TAVYYCAGSY YSYDVLDYWG QGTTVTVSS   119

SEQ ID NO: 3395        moltype = AA  length = 119
FEATURE                Location/Qualifiers
source                 1..119
                       mol_type = protein
                       organism = synthetic construct
SEQUENCE: 3395
QVQLVQSGAE VKKPGSSVKV SCKASGYSFT TYYIHWVRQA PGQGLEWMGW FFPGSGNTKY  60
NEKFKGRVTI TADTSTSTAY MELSSLRSED TAVYYCAGSY YSYDVLDYWG QGTTVTVSS   119

SEQ ID NO: 3396        moltype = AA  length = 119
FEATURE                Location/Qualifiers
source                 1..119
                       mol_type = protein
                       organism = synthetic construct
SEQUENCE: 3396
QVQLVQSGAE VKKPGSSVKV SCKASGYSFT TYYIHWVRQA PGQGLEWMGW FSPGSGNTKY  60
NEKFKGRVTI TADTSTSTAY MELSSLRSED TAVYYCAGSY YSYDVLDYWG QGTTVTVSS   119

SEQ ID NO: 3397        moltype = AA  length = 119
FEATURE                Location/Qualifiers
source                 1..119
                       mol_type = protein
                       organism = synthetic construct
SEQUENCE: 3397
QVQLVQSGAE VKKPGSSVKV SCKASGYSFT TYYIHWVRQA PGQGLEWMGW FSPGSGNTKY  60
NEKFKGRVTI TADTSTSTAY MELSSLRSED TAVYYCAVSY YSYDVLDYWG QGTTVTVSS   119

SEQ ID NO: 3398        moltype = AA  length = 119
FEATURE                Location/Qualifiers
source                 1..119
                       mol_type = protein
                       organism = synthetic construct
SEQUENCE: 3398
QVQLVQSGAE VKKPGSSVKV SCKASGYSFT TYYIHWVRQA PGQGLEWMGW FSAGSGNTKY  60
NEKFKGRVTI TADTSTSTAY MELSSLRSED TAVYYCAVSY YSYDVLDYWG QGTTVTVSS   119

SEQ ID NO: 3399        moltype = AA  length = 119
FEATURE                Location/Qualifiers
source                 1..119
                       mol_type = protein
```

```
                        organism = synthetic construct
SEQUENCE: 3399
QVQLVQSGAE VKKPGSSVKV SCKASGYSFT TYYIHWVRQA PGQGLEWMGW FSAGSGNTKY  60
NEKFKGRVTI TADTSTSTAY MELSSLRSED TAVYYCAGSY YSYDVLDYWG QGTTVTVSS   119

SEQ ID NO: 3400         moltype = AA  length = 119
FEATURE                 Location/Qualifiers
source                  1..119
                        mol_type = protein
                        organism = synthetic construct
SEQUENCE: 3400
QVQLVQSGAE VKKPGSSVKV SCKASGGTFR LTYIHWVRQA PGQGLEWMGR VYPGSGNTKY  60
NEKFKGRVTI TADTSTSTAY MELSSLRSED TAVYYCAGSY YSYDVLDYWG QGTTVTVSS   119

SEQ ID NO: 3401         moltype = AA  length = 119
FEATURE                 Location/Qualifiers
source                  1..119
                        mol_type = protein
                        organism = synthetic construct
SEQUENCE: 3401
QVQLVQSGAE VKKPGSSVKV SCKASGHDFK LTYIHWVRQA PGQGLEWMGR VSPGSGNTKY  60
NEKFKGRVTI TADTSTSTAY MELSSLRSED TAVYYCAGSY YSYDVLDYWG QGTTVTVSS   119

SEQ ID NO: 3402         moltype = AA  length = 119
FEATURE                 Location/Qualifiers
source                  1..119
                        mol_type = protein
                        organism = synthetic construct
SEQUENCE: 3402
QVQLVQSGAE VKKPGSSVKV SCKASGTDFR LTYIHWVRQA PGQGLEWMGR ISPGSGNTKY  60
NEKFKGRVTI TADTSTSTAY MELSSLRSED TAVYYCAGSY YSYDVLDYWG QGTTVTVSS   119

SEQ ID NO: 3403         moltype = AA  length = 119
FEATURE                 Location/Qualifiers
source                  1..119
                        mol_type = protein
                        organism = synthetic construct
SEQUENCE: 3403
QVQLVQSGAE VKKPGSSVKV SCKASGTDFK LTYIHWVRQA PGQGLEWMGR ISPGSGNTKY  60
NEKFKGRVTI TADTSTSTAY MELSSLRSED TAVYYCAGSY YSYDVLDYWG QGTTVTVSS   119

SEQ ID NO: 3404         moltype = AA  length = 119
FEATURE                 Location/Qualifiers
source                  1..119
                        mol_type = protein
                        organism = synthetic construct
SEQUENCE: 3404
QVQLVQSGAE VKKPGSSVKV SCKASGTDFK LTYIHWVRQA PGQGLEWMGR VSAGSGNVKY  60
NEKFKGRVTI TADTSTSTAY MELSSLRSED TAVYYCAGSY YSYDVLDYWG QGTTVTVSS   119

SEQ ID NO: 3405         moltype = AA  length = 119
FEATURE                 Location/Qualifiers
source                  1..119
                        mol_type = protein
                        organism = synthetic construct
SEQUENCE: 3405
QVQLVQSGAE VKKPGSSVKV SCKASGTDFR LTYIHWVRQA PGQGLEWMGR VSPGSGNTKY  60
NEKFKGRVTI TADTSTSTAY MELSSLRSED TAVYYCAGSY YSYDVLDYWG QGTTVTVSS   119

SEQ ID NO: 3406         moltype = AA  length = 119
FEATURE                 Location/Qualifiers
source                  1..119
                        mol_type = protein
                        organism = synthetic construct
SEQUENCE: 3406
QVQLVQSGAE VKKPGSSVKV SCKASGTDFK LTYIHWVRQA PGQGLEWMGR VSPGSGNTKY  60
NEKFKGRVTI TADTSTSTAY MELSSLRSED TAVYYCAGSY YSYDVLDYWG QGTTVTVSS   119

SEQ ID NO: 3407         moltype = AA  length = 119
FEATURE                 Location/Qualifiers
source                  1..119
                        mol_type = protein
                        organism = synthetic construct
SEQUENCE: 3407
QVQLVQSGAE VKKPGSSVKV SCKASGTDFK LTYIHWVRQA PGQGLEWMGR VSPGSGNVKY  60
NEKFKGRVTI TADTSTSTAY MELSSLRSED TAVYYCAGSY YSYDVLDYWG QGTTVTVSS   119

SEQ ID NO: 3408         moltype = AA  length = 119
FEATURE                 Location/Qualifiers
```

```
source                  1..119
                        mol_type = protein
                        organism = synthetic construct
SEQUENCE: 3408
QVQLVQSGAE VKKPGSSVKV SCKASGTDFK LTYIHWVRQA PGQGLEWMGR ISPGSGNVKY  60
NEKFKGRVTI TADTSTSTAY MELSSLRSED TAVYYCAGSY YSYDVLDYWG QGTTVTVSS   119

SEQ ID NO: 3409         moltype = AA  length = 119
FEATURE                 Location/Qualifiers
source                  1..119
                        mol_type = protein
                        organism = synthetic construct
SEQUENCE: 3409
QVQLVQSGAE VKKPGSSVKV SCKASGTDFR LTYIHWVRQA PGQGLEWMGR IFPGSGNTKY  60
NEKFKGRVTI TADTSTSTAY MELSSLRSED TAVYYCAGSY YSYDVLDYWG QGTTVTVSS   119

SEQ ID NO: 3410         moltype = AA  length = 119
FEATURE                 Location/Qualifiers
source                  1..119
                        mol_type = protein
                        organism = synthetic construct
SEQUENCE: 3410
QVQLVQSGAE VKKPGSSVKV SCKASGTDFK LTYIHWVRQA PGQGLEWMGR IFPGSGNVKY  60
NEKFKGRVTI TADTSTSTAY MELSSLRSED TAVYYCAGSY YSYDVLDYWG QGTTVTVSS   119

SEQ ID NO: 3411         moltype = AA  length = 119
FEATURE                 Location/Qualifiers
source                  1..119
                        mol_type = protein
                        organism = synthetic construct
SEQUENCE: 3411
QVQLVQSGAE VKKPGSSVKV SCKASGTDFK LTYIHWVRQA PGQGLEWMGR IFPGSGNTKY  60
NEKFKGRVTI TADTSTSTAY MELSSLRSED TAVYYCAGSY YSYDVLDYWG QGTTVTVSS   119

SEQ ID NO: 3412         moltype = AA  length = 119
FEATURE                 Location/Qualifiers
source                  1..119
                        mol_type = protein
                        organism = synthetic construct
SEQUENCE: 3412
QVQLVQSGAE VKKPGSSVKV SCKASGGTFK LTYIHWVRQA PGQGLEWMGR VSAGSGNVKY  60
NEKFKGRVTI TADTSTSTAY MELSSLRSED TAVYYCAGSY YSYDVLDYWG QGTTVTVSS   119

SEQ ID NO: 3413         moltype = AA  length = 119
FEATURE                 Location/Qualifiers
source                  1..119
                        mol_type = protein
                        organism = synthetic construct
SEQUENCE: 3413
QVQLVQSGAE VKKPGSSVKV SCKASGGTFR LTYIHWVRQA PGQGLEWMGR ISAGSGNVKY  60
NEKFKGRVTI TADTSTSTAY MELSSLRSED TAVYYCAGSY YSYDVLDYWG QGTTVTVSS   119

SEQ ID NO: 3414         moltype = AA  length = 119
FEATURE                 Location/Qualifiers
source                  1..119
                        mol_type = protein
                        organism = synthetic construct
SEQUENCE: 3414
QVQLVQSGAE VKKPGSSVKV SCKASGTDFK LTYIHWVRQA PGQGLEWMGR ISAGSGNTKY  60
NEKFKGRVTI TADTSTSTAY MELSSLRSED TAVYYCAGSY YSYDVLDYWG QGTTVTVSS   119

SEQ ID NO: 3415         moltype = AA  length = 119
FEATURE                 Location/Qualifiers
source                  1..119
                        mol_type = protein
                        organism = synthetic construct
SEQUENCE: 3415
QVQLVQSGAE VKKPGSSVKV SCKASGHDFR LTYIHWVRQA PGQGLEWMGR ISAGSGNVKY  60
NEKFKGRVTI TADTSTSTAY MELSSLRSED TAVYYCAGSY YSYDVLDYWG QGTTVTVSS   119

SEQ ID NO: 3416         moltype = AA  length = 119
FEATURE                 Location/Qualifiers
source                  1..119
                        mol_type = protein
                        organism = synthetic construct
SEQUENCE: 3416
QVQLVQSGAE VKKPGSSVKV SCKASGHDFK LTYIHWVRQA PGQGLEWMGR ISAGSGNVKY  60
NEKFKGRVTI TADTSTSTAY MELSSLRSED TAVYYCAGSY YSYDVLDYWG QGTTVTVSS   119
```

```
SEQ ID NO: 3417        moltype = AA  length = 119
FEATURE                Location/Qualifiers
source                 1..119
                       mol_type = protein
                       organism = synthetic construct
SEQUENCE: 3417
QVQLVQSGAE VKKPGSSVKV SCKASGTDFK LTYIHWVRQA PGQGLEWMGR ISAGSGNVKY  60
NEKFKGRVTI TADTSTSTAY MELSSLRSED TAVYYCAGSY YSYDVLDYWG QGTTVTVSS   119

SEQ ID NO: 3418        moltype = AA  length = 119
FEATURE                Location/Qualifiers
source                 1..119
                       mol_type = protein
                       organism = synthetic construct
SEQUENCE: 3418
QVQLVQSGAE VKKPGSSVKV SCKASGHDFD KTYIHWVRQA PGQGLEWMGR IYPGSGNVKY  60
NEKFKGRVTI TADTSTSTAY MELSSLRSED TAVYYCAGSY YSYDVLDYWG QGTTVTVSS   119

SEQ ID NO: 3419        moltype = AA  length = 119
FEATURE                Location/Qualifiers
source                 1..119
                       mol_type = protein
                       organism = synthetic construct
SEQUENCE: 3419
QVQLVQSGAE VKKPGSSVKV SCKASGGTFD KTYIHWVRQA PGQGLEWMGR ISAGSGNTKY  60
NEKFKGRVTI TADTSTSTAY MELSSLRSED TAVYYCAGSY YSYDVLDYWG QGTTVTVSS   119

SEQ ID NO: 3420        moltype = AA  length = 119
FEATURE                Location/Qualifiers
source                 1..119
                       mol_type = protein
                       organism = synthetic construct
SEQUENCE: 3420
QVQLVQSGAE VKKPGSSVKV SCKASGTDFD KTYIHWVRQA PGQGLEWMGR ISAGSGNVKY  60
NEKFKGRVTI TADTSTSTAY MELSSLRSED TAVYYCAGSY YSYDVLDYWG QGTTVTVSS   119

SEQ ID NO: 3421        moltype = AA  length = 119
FEATURE                Location/Qualifiers
source                 1..119
                       mol_type = protein
                       organism = synthetic construct
SEQUENCE: 3421
QVQLVQSGAE VKKPGSSVKV SCKASGTDFD KIYIHWVRQA PGQGLEWMGR VSAGSGNTKY  60
NEKFKGRVTI TADTSTSTAY MELSSLRSED TAVYYCAGSY YSYDVLDYWG QGTTVTVSS   119

SEQ ID NO: 3422        moltype = AA  length = 119
FEATURE                Location/Qualifiers
source                 1..119
                       mol_type = protein
                       organism = synthetic construct
SEQUENCE: 3422
QVQLVQSGAE VKKPGSSVKV SCKASGTDFD KIYIHWVRQA PGQGLEWMGR IFAGSGNTKY  60
NEKFKGRVTI TADTSTSTAY MELSSLRSED TAVYYCAGSY YSYDVLDYWG QGTTVTVSS   119

SEQ ID NO: 3423        moltype = AA  length = 119
FEATURE                Location/Qualifiers
source                 1..119
                       mol_type = protein
                       organism = synthetic construct
SEQUENCE: 3423
QVQLVQSGAE VKKPGSSVKV SCKASGTDFD KIYIHWVRQA PGQGLEWMGR ISAGSGNVKY  60
NEKFKGRVTI TADTSTSTAY MELSSLRSED TAVYYCAGSY YSYDVLDYWG QGTTVTVSS   119

SEQ ID NO: 3424        moltype = AA  length = 119
FEATURE                Location/Qualifiers
source                 1..119
                       mol_type = protein
                       organism = synthetic construct
SEQUENCE: 3424
QVQLVQSGAE VKKPGSSVKV SCKASGTDFD KIYIHWVRQA PGQGLEWMGR ISAGSGNTKY  60
NEKFKGRVTI TADTSTSTAY MELSSLRSED TAVYYCAGSY YSYDVLDYWG QGTTVTVSS   119

SEQ ID NO: 3425        moltype = AA  length = 119
FEATURE                Location/Qualifiers
source                 1..119
                       mol_type = protein
                       organism = synthetic construct
SEQUENCE: 3425
QVQLVQSGAE VKKPGSSVKV SCKASGTDFD KIYIHWVRQA PGQGLEWMGR ISAGSGNIKY  60
```

```
NEKFKGRVTI TADTSTSTAY MELSSLRSED TAVYYCAGSY YSYDVLDYWG QGTTVTVSS   119

SEQ ID NO: 3426        moltype = AA  length = 119
FEATURE                Location/Qualifiers
source                 1..119
                       mol_type = protein
                       organism = synthetic construct
SEQUENCE: 3426
QVQLVQSGAE VKKPGSSVKV SCKASGHDFD KFYIHWVRQA PGQGLEWMGR ISAGSGNTKY  60
NEKFKGRVTI TADTSTSTAY MELSSLRSED TAVYYCAGSY YSYDVLDYWG QGTTVTVSS   119

SEQ ID NO: 3427        moltype = AA  length = 119
FEATURE                Location/Qualifiers
source                 1..119
                       mol_type = protein
                       organism = synthetic construct
SEQUENCE: 3427
QVQLVQSGAE VKKPGSSVKV SCKASGHDFD KFYIHWVRQA PGQGLEWMGR VSAGSGNTKY  60
NEKFKGRVTI TADTSTSTAY MELSSLRSED TAVYYCAGSY YSYDVLDYWG QGTTVTVSS   119

SEQ ID NO: 3428        moltype = AA  length = 119
FEATURE                Location/Qualifiers
source                 1..119
                       mol_type = protein
                       organism = synthetic construct
SEQUENCE: 3428
QVQLVQSGAE VKKPGSSVKV SCKASGHDFD KFYIHWVRQA PGQGLEWMGR IFAGSGNVKY  60
NEKFKGRVTI TADTSTSTAY MELSSLRSED TAVYYCAGSY YSYDVLDYWG QGTTVTVSS   119

SEQ ID NO: 3429        moltype = AA  length = 119
FEATURE                Location/Qualifiers
source                 1..119
                       mol_type = protein
                       organism = synthetic construct
SEQUENCE: 3429
QVQLVQSGAE VKKPGSSVKV SCKASGTDFD KFYIHWVRQA PGQGLEWMGR VSAGSGNVKY  60
NEKFKGRVTI TADTSTSTAY MELSSLRSED TAVYYCAGSY YSYDVLDYWG QGTTVTVSS   119

SEQ ID NO: 3430        moltype = AA  length = 119
FEATURE                Location/Qualifiers
source                 1..119
                       mol_type = protein
                       organism = synthetic construct
SEQUENCE: 3430
QVQLVQSGAE VKKPGSSVKV SCKASGHDFD KFYIHWVRQA PGQGLEWMGR VSAGSGNVKY  60
NEKFKGRVTI TADTSTSTAY MELSSLRSED TAVYYCAGSY YSYDVLDYWG QGTTVTVSS   119

SEQ ID NO: 3431        moltype = AA  length = 119
FEATURE                Location/Qualifiers
source                 1..119
                       mol_type = protein
                       organism = synthetic construct
SEQUENCE: 3431
QVQLVQSGAE VKKPGSSVKV SCKASGHDFD KTYIHWVRQA PGQGLEWMGR VSAGSGNVKY  60
NEKFKGRVTI TADTSTSTAY MELSSLRSED TAVYYCAGSY YSYDVLDYWG QGTTVTVSS   119

SEQ ID NO: 3432        moltype = AA  length = 119
FEATURE                Location/Qualifiers
source                 1..119
                       mol_type = protein
                       organism = synthetic construct
SEQUENCE: 3432
QVQLVQSGAE VKKPGSSVKV SCKASGHDFR DFYIHWVRQA PGQGLEWMGR VYPGSGSYRY  60
NEKFKGRVTI TADTSTSTAY MELSSLRSED TAVYYCAGSY YSYDVLDYWG QGTTVTVSS   119

SEQ ID NO: 3433        moltype = AA  length = 119
FEATURE                Location/Qualifiers
source                 1..119
                       mol_type = protein
                       organism = synthetic construct
SEQUENCE: 3433
QVQLVQSGAE VKKPGSSVKV SCKASGTDFH LWYIHWVRQA PGQGLEWMGR VFAGSGSYRY  60
NEKFKGRVTI TADTSTSTAY MELSSLRSED TAVYYCAGSY YSYDVLDYWG QGTTVTVSS   119

SEQ ID NO: 3434        moltype = AA  length = 119
FEATURE                Location/Qualifiers
source                 1..119
                       mol_type = protein
                       organism = synthetic construct
```

```
SEQUENCE: 3434
QVQLVQSGAE VKKPGSSVKV SCKASGHDFH LWYIHWVRQA PGQGLEWMGR ISPGSGNVKY  60
NEKFKGRVTI TADTSTSTAY MELSSLRSED TAVYYCAGSY YSYDVLDYWG QGTTVTVSS   119

SEQ ID NO: 3435        moltype = AA  length = 119
FEATURE                Location/Qualifiers
source                 1..119
                       mol_type = protein
                       organism = synthetic construct
SEQUENCE: 3435
QVQLVQSGAE VKKPGSSVKV SCKASGHDFH LWYIHWVRQA PGQGLEWMGR VSAGSGNVKY  60
NEKFKGRVTI TADTSTSTAY MELSSLRSED TAVYYCAGSY YSYDVLDYWG QGTTVTVSS   119

SEQ ID NO: 3436        moltype = AA  length = 119
FEATURE                Location/Qualifiers
source                 1..119
                       mol_type = protein
                       organism = synthetic construct
SEQUENCE: 3436
QVQLVQSGAE VKKPGSSVKV SCKASGHDFH LWYIHWVRQA PGQGLEWMGR VFAGSGNTKY  60
NEKFKGRVTI TADTSTSTAY MELSSLRSED TAVYYCAGSY YSYDVLDYWG QGTTVTVSS   119

SEQ ID NO: 3437        moltype = AA  length = 27
FEATURE                Location/Qualifiers
VARIANT                7..26
                       note = EAAAK repeating units may be deleted
source                 1..27
                       mol_type = protein
                       organism = synthetic construct
SEQUENCE: 3437
AEAAAKEAAA KEAAAKEAAA KEAAAKA                                     27

SEQ ID NO: 3438        moltype = AA  length = 117
FEATURE                Location/Qualifiers
source                 1..117
                       mol_type = protein
                       organism = synthetic construct
SEQUENCE: 3438
EVQLVESGGG LVQPGGSLRL SCAASGFTFS NFGMHWVRQA PGKGLEWVSY ISSGSSTIYY  60
ADTLKGRFTI SRDNAKNSLY LQMNSLRAED TAVYYCARRG EGAMDYWGQG TTVTVSS     117

SEQ ID NO: 3439        moltype = AA  length = 116
FEATURE                Location/Qualifiers
source                 1..116
                       mol_type = protein
                       organism = synthetic construct
SEQUENCE: 3439
EVQLLESGGG LVQPGGSLRL SCAASGFTFS SYAMSWVRQA PGKGLEWVSA ISGSGGSTYY  60
ADSVKGRFTI SRDNSKNTLY LQMNSLRAED TAVYYCAKVL GWFDYWGQGT LVTVSS      116

SEQ ID NO: 3440        moltype = AA  length = 109
FEATURE                Location/Qualifiers
source                 1..109
                       mol_type = protein
                       organism = synthetic construct
SEQUENCE: 3440
EIVLTQSPGT LSLSPGERAT LSCRASQSVS SSYLAWYQQK PGQAPRLLIY GASSRATGIP  60
DRFSGSGSGT DFTLTISRLE PEDFAVYYCQ QYGYPPDFTF GQGTKVEIK             109

SEQ ID NO: 3441        moltype = AA  length = 119
FEATURE                Location/Qualifiers
source                 1..119
                       mol_type = protein
                       organism = synthetic construct
SEQUENCE: 3441
EVQLLESGGG LVQPGGSLRL SCAASGFTFS SYAMSWVRQA PGKGLEWVSA ISGSGGSTYY  60
ADSVKGRFTI SRDNSKNTLY LQMNSLRAED TAVYYCAKVA PYFAPFDYWG QGTLVTVSS   119

SEQ ID NO: 3442        moltype = AA  length = 109
FEATURE                Location/Qualifiers
source                 1..109
                       mol_type = protein
                       organism = synthetic construct
SEQUENCE: 3442
EIVLTQSPGT LSLSPGERAT LSCRASQSVS SSYLAWYQQK PGQAPRLLIY GASSRATGIP  60
DRFSGSGSGT DFTLTISRLE PEDFAVYYCQ QYGNPPLYTF GQGTKVEIK             109

SEQ ID NO: 3443        moltype = AA  length = 116
FEATURE                Location/Qualifiers
```

```
source                  1..116
                        mol_type = protein
                        organism = synthetic construct
SEQUENCE: 3443
EVQLVQSGAE VKKPGESLKI SCKGSGYSFT SYWIGWVRQM PGKGLEWMGI IYPGDSDTRY  60
SPSFQGQVTI SADKSISTAY LQWSSLKASD TAMYYCARNG YLGDYWGQGT LVTVSS      116

SEQ ID NO: 3444         moltype = AA  length = 111
FEATURE                 Location/Qualifiers
source                  1..111
                        mol_type = protein
                        organism = synthetic construct
SEQUENCE: 3444
DIVMTQSPLS LPVTPGEPAS ISCRSSQSLL HSNGYNYLDW YLQKPGQSPQ LLIYLGSNRA  60
SGVPDRFSGS GSGTDFTLKI SRVEAEDVGV YYCMQAMQIP TFGQGTKVEI K           111

SEQ ID NO: 3445         moltype = AA  length = 120
FEATURE                 Location/Qualifiers
source                  1..120
                        mol_type = protein
                        organism = synthetic construct
SEQUENCE: 3445
QVQLQQSGGG LVQPGGSLKL SCAASGIDFS RYWMSWVRRA PGKGLEWIGE INPDSSTINY  60
APSLKDKFII SRDNAKNTLY LQMSKVRSED TALYYCASLY YDYGDAMDYW GQGTSVTVSS  120

SEQ ID NO: 3446         moltype = AA  length = 108
FEATURE                 Location/Qualifiers
source                  1..108
                        mol_type = protein
                        organism = synthetic construct
SEQUENCE: 3446
DIVMTQSQRF MTTSVGDRVS VTCKASQSVD SNVAWYQQKP RQSPKALIFS ASLRFSGVPA  60
RFTGSGSGTD FTLTISNLQS EDLAEYFCQQ YNNYPLTFGA GTKLELKR              108

SEQ ID NO: 3447         moltype = AA  length = 123
FEATURE                 Location/Qualifiers
source                  1..123
                        mol_type = protein
                        organism = synthetic construct
SEQUENCE: 3447
EVQLVESGGG LVKPGGSLRL SCAASGFTFG DYALSWFRQA PGKGLEWVGV SRSKAYGGTT  60
DYAASVKGRF TISRDDSKST AYLQMNSLKT EDTAVYYCAS SGYSSGWTPF DYWGQGTLVT  120
VSS                                                                123

SEQ ID NO: 3448         moltype = AA  length = 111
FEATURE                 Location/Qualifiers
source                  1..111
                        mol_type = protein
                        organism = synthetic construct
SEQUENCE: 3448
QSVLTQPPSA SGTPGQRVTI SCSGSSSNIG SNTVNWYQQL PGTAPKLLIF NYHQRPSGVP  60
DRFSGSKSGS SASLAISGLQ SEDEADYYCA AWDDSLNGWV FGGGTKLTVL G           111

SEQ ID NO: 3449         moltype = AA  length = 101
FEATURE                 Location/Qualifiers
source                  1..101
                        mol_type = protein
                        organism = synthetic construct
SEQUENCE: 3449
IAGITQAPTS QILAAGRRMT LRCTQDMRHN AMYWYRQDLG LGLRLIHYSN TAGTTGKGEV  60
PDGYSVSRAN TDDFPLTLAS AVPSQTSVYF CASSWSFGTE A                      101

SEQ ID NO: 3450         moltype = AA  length = 100
FEATURE                 Location/Qualifiers
source                  1..100
                        mol_type = protein
                        organism = synthetic construct
SEQUENCE: 3450
GVTQTPKFQV LKTGQSMTLQ CAQDMNHEYM SWYRQDPGMG LRLIHYSVGA GITDQGEVPN  60
GYNVSRSTTE DFPLRLLSAA PSQTSVYFCA SSYVGNTGEL                        100

SEQ ID NO: 3451         moltype = AA  length = 100
FEATURE                 Location/Qualifiers
source                  1..100
                        mol_type = protein
                        organism = synthetic construct
SEQUENCE: 3451
KVTQSSRYLV KRTGEKVFLE CVQDMDHENM FWYRQDPGLG LRLIYFSYDV KMKEKGDIPE  60
GYSVSREKKE RFSLILASAS TDQTSMYLCA SSFLGTGVEQ                        100
```

```
SEQ ID NO: 3452        moltype = AA  length = 100
FEATURE                Location/Qualifiers
source                 1..100
                       mol_type = protein
                       organism = synthetic construct
SEQUENCE: 3452
GGITQSPKYL FRKEGQNVTL SCEQNLNHDA MYWYRQDPGQ GLRLIYYSQI VNDFQKGDIA  60
EGYSVSREKK ESFPLTVTSA QKNPTAFYLC ASSSRSSYEQ                        100

SEQ ID NO: 3453        moltype = AA  length = 101
FEATURE                Location/Qualifiers
source                 1..101
                       mol_type = protein
                       organism = synthetic construct
SEQUENCE: 3453
GVTQTPKHLI TATGQRVTLR CSPRSGDLSV YWYQQSLDQG LQFLIQYYNG EERAKGNILE  60
RFSAQQFPDL HSELNLSSLE LGDSALYFCA SSVAGTPSYE Q                      101

SEQ ID NO: 3454        moltype = AA  length = 100
FEATURE                Location/Qualifiers
source                 1..100
                       mol_type = protein
                       organism = synthetic construct
SEQUENCE: 3454
AGVTQTPRYL IKTRGQQVTL SCSPISGHRS VSWYQQTPGQ GLQFLFEYFS ETQRNKGNFP  60
GRFSGRQFSN SRSEMNVSTL ELGDSALYLC ASSFNMATGQ                        100

SEQ ID NO: 3455        moltype = AA  length = 99
FEATURE                Location/Qualifiers
source                 1..99
                       mol_type = protein
                       organism = synthetic construct
SEQUENCE: 3455
AVVSQHPSRV IVKSGTSVKI ECRSLDFQAT TMFWYRQFPS LMLMATSNEG SKATYEQGVE  60
KDKFLINHAS LTLSTLTVTS AHPEDSGFYI CSALAGDTQ                         99

SEQ ID NO: 3456        moltype = AA  length = 106
FEATURE                Location/Qualifiers
source                 1..106
                       mol_type = protein
                       organism = synthetic construct
SEQUENCE: 3456
MDAGVIQSPR HEVTEMGQQV TLRCKPISGH DYLFWYRQTM MRGLELLIYF NNNVPIDDSG  60
MPEDRFSAKM PNASFSTLKI QPSEPRDSAV YFCASSLWEK LAKNIQ                 106

SEQ ID NO: 3457        moltype = AA  length = 94
FEATURE                Location/Qualifiers
source                 1..94
                       mol_type = protein
                       organism = synthetic construct
SEQUENCE: 3457
DTGITQTPKY LVTAMGSKRT MKREHLGHDS MYWYRQKAKK SLEFMFYYNC KEFIENKTVP  60
NHFTPECPDS SRLYLHVVAL QQEDSAAYLC TSSQ                              94

SEQ ID NO: 3458        moltype = AA  length = 96
FEATURE                Location/Qualifiers
source                 1..96
                       mol_type = protein
                       organism = synthetic construct
SEQUENCE: 3458
EPEVTQTPSH QVTQMGQEVI LRCVPISNHL YFYWYRQILG QKVEFLVSFY NNEISEKSEI  60
FDDQFSVERP DGSNFTLKIR STKLEDSAMY FCASSE                            96

SEQ ID NO: 3459        moltype = AA  length = 95
FEATURE                Location/Qualifiers
source                 1..95
                       mol_type = protein
                       organism = synthetic construct
SEQUENCE: 3459
DTAVSQTPKY LVTQMGNDKS IKCEQNLGHD TMYWYKQDSK KFLKIMFSYN NKELIINETV  60
PNRFSPKSPD KAHLNLHINS LELGDSAVYF CASSQ                             95

SEQ ID NO: 3460        moltype = AA  length = 94
FEATURE                Location/Qualifiers
source                 1..94
                       mol_type = protein
                       organism = synthetic construct
SEQUENCE: 3460
```

```
DTAVSQTPKY LVTQMGKKES LKEQNLGHNA MYWYKQDSKK FLKTMFIYSN KEPILNETVP  60
NRFSPDSPDK AHLNLHINSL ELGDSAVYFC ASSQ                              94

SEQ ID NO: 3461         moltype = AA  length = 95
FEATURE                 Location/Qualifiers
source                  1..95
                        mol_type = protein
                        organism = synthetic construct
SEQUENCE: 3461
DTEVTQTPKH LVMGMTNKKS LKCEQHMGHR AMYWYKQKAK KPPELMFVYS YEKLSINESV  60
PSRFSPECPN SSLLNLHLHA LQPEDSALYL CASSQ                             95

SEQ ID NO: 3462         moltype = AA  length = 95
FEATURE                 Location/Qualifiers
source                  1..95
                        mol_type = protein
                        organism = synthetic construct
SEQUENCE: 3462
ETGVTQTPRH LVMGMTNKKS LKCEQHLGHN AMYWYKQSAK KPLELMFVYN FKEQTENNSV  60
PSRFSPECPN SSHLFLHLHT LQPEDSALYL CASSQ                             95

SEQ ID NO: 3463         moltype = AA  length = 95
FEATURE                 Location/Qualifiers
source                  1..95
                        mol_type = protein
                        organism = synthetic construct
SEQUENCE: 3463
ETGVTQTPRH LVMGMTNKKS LKCEQHLGHN AMYWYKQSAK KPLELMFVYS LEERVENNSV  60
PSRFSPECPN SSHLFLHLHT LQPEDSALYL CASSQ                             95

SEQ ID NO: 3464         moltype = AA  length = 95
FEATURE                 Location/Qualifiers
source                  1..95
                        mol_type = protein
                        organism = synthetic construct
SEQUENCE: 3464
KAGVTQTPRY LIKTRGQQVT LSCSPISGHR SVSWYQQTPG QGLQFLFEYF SETQRNKGNF  60
PGRFSGRQFS NSRSEMNVST LELGDSALYL CASSL                             95

SEQ ID NO: 3465         moltype = AA  length = 95
FEATURE                 Location/Qualifiers
source                  1..95
                        mol_type = protein
                        organism = synthetic construct
SEQUENCE: 3465
EAGVTQSPTH LIKTRGQQVT LRCSPISGHS SVSWYQQAPG QGPQFIFEYA NELRRSEGNF  60
PNRFSGRQFH DCCSEMNVSA LELGDSALYL CARSL                             95

SEQ ID NO: 3466         moltype = AA  length = 95
FEATURE                 Location/Qualifiers
source                  1..95
                        mol_type = protein
                        organism = synthetic construct
SEQUENCE: 3466
ETGVTQSPTH LIKTRGQQVT LRCSSQSGHN TVSWYQQALG QGPQFIFQYY REEENGRGNF  60
PPRFSGLQFP NYSSELNVNA LELDDSALYL CASSL                             95

SEQ ID NO: 3467         moltype = AA  length = 95
FEATURE                 Location/Qualifiers
source                  1..95
                        mol_type = protein
                        organism = synthetic construct
SEQUENCE: 3467
DAGVTQSPTH LIKTRGQQVT LRCSPISGHK SVSWYQQVLG QGPQFIFQYY EKEERGRGNF  60
PDRFSARQFP NYSSELNVNA LLLGDSALYL CASSL                             95

SEQ ID NO: 3468         moltype = AA  length = 95
FEATURE                 Location/Qualifiers
source                  1..95
                        mol_type = protein
                        organism = synthetic construct
SEQUENCE: 3468
DAGVTQSPTH LIKTRGQQVT LRCSPKSGHD TVSWYQQALG QGPQFIFQYY EEEERQRGNF  60
PDRFSGHQFP NYSSELNVNA LLLGDSALYL CASSL                             95

SEQ ID NO: 3469         moltype = AA  length = 95
FEATURE                 Location/Qualifiers
source                  1..95
                        mol_type = protein
```

```
                       organism = synthetic construct
SEQUENCE: 3469
DAGVTQSPTH LIKTRGQHVT LRCSPISGHT SVSSYQQALG QGPQFIFQYY EKEERGRGNF  60
PDQFSGHQFP NYSSELNVNA LLLGDSALYL CASSL                             95

SEQ ID NO: 3470        moltype = AA  length = 95
FEATURE                Location/Qualifiers
source                 1..95
                       mol_type = protein
                       organism = synthetic construct
SEQUENCE: 3470
EAGVTQSPTH LIKTRGQQAT LRCSPISGHT SVYWYQQALG LGLQFLLWYD EGEERNRGNF  60
PPRFSGRQFP NYSSELNVNA LELEDSALYL CASSL                             95

SEQ ID NO: 3471        moltype = AA  length = 95
FEATURE                Location/Qualifiers
source                 1..95
                       mol_type = protein
                       organism = synthetic construct
SEQUENCE: 3471
NAGVTQTPKF QVLKTGQSMT LQCAQDMNHN SMYWYRQDPG MGLRLIYYSA SEGTTDKGEV  60
PNGYNVSRLN KREFSLRLES AAPSQTSVYF CASSE                             95

SEQ ID NO: 3472        moltype = AA  length = 95
FEATURE                Location/Qualifiers
source                 1..95
                       mol_type = protein
                       organism = synthetic construct
SEQUENCE: 3472
NAGVTQTPKF RVLKTGQSMT LLCAQDMNHE YMYWYRQDPG MGLRLIHYSV GEGTTAKGEV  60
PDGYNVSRLK KQNFLLGLES AAPSQTSVYF CASSY                             95

SEQ ID NO: 3473        moltype = AA  length = 95
FEATURE                Location/Qualifiers
source                 1..95
                       mol_type = protein
                       organism = synthetic construct
SEQUENCE: 3473
NAGVTQTPKF RVLKTGQSMT LLCAQDMNHE YMYWYRQDPG MGLRLIHYSV GEGTTAKGEV  60
PDGYNVSRLK KQNFLLGLES AAPSQTSVYF CASSY                             95

SEQ ID NO: 3474        moltype = AA  length = 95
FEATURE                Location/Qualifiers
source                 1..95
                       mol_type = protein
                       organism = synthetic construct
SEQUENCE: 3474
IAGITQAPTS QILAAGRRMT LRCTQDMRHN AMYWYRQDLG LGLRLIHYSN TAGTTGKGEV  60
PDGYSVSRAN TDDFPLTLAS AVPSQTSVYF CASSD                             95

SEQ ID NO: 3475        moltype = AA  length = 95
FEATURE                Location/Qualifiers
source                 1..95
                       mol_type = protein
                       organism = synthetic construct
SEQUENCE: 3475
NAGVTQTPKF QVLKTGQSMT LQCAQDMNHE YMSWYRQDPG MGLRLIHYSV GAGITDQGEV  60
PNGYNVSRST TEDFPLRLLS AAPSQTSVYF CASSY                             95

SEQ ID NO: 3476        moltype = AA  length = 95
FEATURE                Location/Qualifiers
source                 1..95
                       mol_type = protein
                       organism = synthetic construct
SEQUENCE: 3476
NAGVTQTPKF RILKIGQSMT LQCTQDMNHN YMYWYRQDPG MGLKLIYYSV GAGITDKGEV  60
PNGYNVSRST TEDFPLRLEL AAPSQTSVYF CASSY                             95

SEQ ID NO: 3477        moltype = AA  length = 95
FEATURE                Location/Qualifiers
source                 1..95
                       mol_type = protein
                       organism = synthetic construct
SEQUENCE: 3477
NAGVTQTPKF HVLKTGQSMT LLCAQDMNHE YMYRYRQDPG KGLRLIYYSV AAALTDKGEV  60
PNGYNVSRSN TEDFPLKLES AAPSQTSVYF CASSY                             95

SEQ ID NO: 3478        moltype = AA  length = 94
FEATURE                Location/Qualifiers
```

```
source                  1..94
                        mol_type = protein
                        organism = synthetic construct
SEQUENCE: 3478
NAGVTQTPKF HILKTGQSMT LQCAQDMNHG YMSWYRQDPG MGLRLIYYSA AAGTTDKEVP  60
NGYNVSRLNT EDFPLRLVSA APSQTSVYLC ASSY                              94

SEQ ID NO: 3479         moltype = AA  length = 95
FEATURE                 Location/Qualifiers
source                  1..95
                        mol_type = protein
                        organism = synthetic construct
SEQUENCE: 3479
NAGVTQTPKF HILKTGQSMT LQCAQDMNHG YLSWYRQDPG MGLRRIHYSV AAGITDKGEV  60
PDGYNVSRSN TEDFPLRLES AAPSQTSVYF CASSY                             95

SEQ ID NO: 3480         moltype = AA  length = 96
FEATURE                 Location/Qualifiers
source                  1..96
                        mol_type = protein
                        organism = synthetic construct
SEQUENCE: 3480
GAGVSQSLRH KVAKKGKDVA LRYDPISGHN ALYWYRQSLG QGLEFPIYFQ GKDAADKSGL  60
PRDRFSAQRS EGSISTLKFQ RTQQGDLAVY LCASSS                            96

SEQ ID NO: 3481         moltype = AA  length = 96
FEATURE                 Location/Qualifiers
source                  1..96
                        mol_type = protein
                        organism = synthetic construct
SEQUENCE: 3481
GAGVSQSPSN KVTEKGKDVE LRCDPISGHT ALYWYRQSLG QGLEFLIYFQ GNSAPDKSGL  60
PSDRFSAERT GGSVSTLTIQ RTQQEDSAVY LCASSL                            96

SEQ ID NO: 3482         moltype = AA  length = 96
FEATURE                 Location/Qualifiers
source                  1..96
                        mol_type = protein
                        organism = synthetic construct
SEQUENCE: 3482
GAGVSQTPSN KVTEKGKYVE LRCDPISGHT ALYWYRQSLG QGPEFLIYFQ GTGAADDSGL  60
PNDRFFAVRP EGSVSTLKIQ RTERGDSAVY LCASSL                            96

SEQ ID NO: 3483         moltype = AA  length = 96
FEATURE                 Location/Qualifiers
source                  1..96
                        mol_type = protein
                        organism = synthetic construct
SEQUENCE: 3483
GAGVSQSPRY KVAKRGRDVA LRCDSISGHV TLYWYRQTLG QGSEVLTYSQ SDAQRDKSGR  60
PSGRFSAERP ERSVSTLKIQ RTEQGDSAVY LCASSL                            96

SEQ ID NO: 3484         moltype = AA  length = 96
FEATURE                 Location/Qualifiers
source                  1..96
                        mol_type = protein
                        organism = synthetic construct
SEQUENCE: 3484
GAGVSQSPRY KVTKRGQDVA LRCDPISGHV SLYWYRQALG QGPEFLTYFN YEAQQDKSGL  60
PNDRFSAERP EGSISTLTIQ RTEQRDSAMY RCASSL                            96

SEQ ID NO: 3485         moltype = AA  length = 96
FEATURE                 Location/Qualifiers
source                  1..96
                        mol_type = protein
                        organism = synthetic construct
SEQUENCE: 3485
GAGVSQSPRY KVTKRGQDVT LRCDPISSHA TLYWYQQALG QGPEFLTYFN YEAQPDKSGL  60
PSDRFSAERP EGSISTLTIQ RTEQRDSAMY RCASSL                            96

SEQ ID NO: 3486         moltype = AA  length = 96
FEATURE                 Location/Qualifiers
source                  1..96
                        mol_type = protein
                        organism = synthetic construct
SEQUENCE: 3486
GAGVSQSPRY KVAKRGQDVA LRCDPISGHV SLFWYQQALG QGPEFLTYFQ NEAQLDKSGL  60
PSDRFFAERP EGSVSTLKIQ RTQQEDSAVY LCASSL                            96
```

```
SEQ ID NO: 3487        moltype = AA  length = 96
FEATURE                Location/Qualifiers
source                 1..96
                       mol_type = protein
                       organism = synthetic construct
SEQUENCE: 3487
DTGVSQNPRH KITKRGQNVT FRCDPISEHN RLYWYRQTLG QGPEFLTYFQ NEAQLEKSRL  60
LSDRFSAERP KGSFSTLEIQ RTEQGDSAMY LCASSL                            96

SEQ ID NO: 3488        moltype = AA  length = 95
FEATURE                Location/Qualifiers
source                 1..95
                       mol_type = protein
                       organism = synthetic construct
SEQUENCE: 3488
DSGVTQTPKH LITATGQRVT LRCSPRSGDL SVYWYQQSLD QGLQFLIQYY NGEERAKGNI  60
LERFSAQQFP DLHSELNLSS LELGDSALYF CASSV                             95

SEQ ID NO: 3489        moltype = AA  length = 95
FEATURE                Location/Qualifiers
source                 1..95
                       mol_type = protein
                       organism = synthetic construct
SEQUENCE: 3489
DAEITQSPRH KITETGRQVT LACHQTWNHN NMFWYRQDLG HGLRLIHYSY GVQDTNKGEV  60
SDGYSVSRSN TEDLPLTLES AASSQTSVYF CASSE                             95

SEQ ID NO: 3490        moltype = AA  length = 95
FEATURE                Location/Qualifiers
source                 1..95
                       mol_type = protein
                       organism = synthetic construct
SEQUENCE: 3490
DAGITQSPRY KITETGRQVT LMCHQTWSHS YMFWYRQDLG HGLRLIYYSA AADITDKGEV  60
PDGYVVSRSK TENFPLTLES ATRSQTSVYF CASSE                             95

SEQ ID NO: 3491        moltype = AA  length = 95
FEATURE                Location/Qualifiers
source                 1..95
                       mol_type = protein
                       organism = synthetic construct
SEQUENCE: 3491
DAGITQSPRH KVTETGTPVT LRCHQTENHR YMYWYRQDPG HGLRLIHYSY GVKDTDKGEV  60
SDGYSVSRSK TEDFLLTLES ATSSQTSVYF CAISE                             95

SEQ ID NO: 3492        moltype = AA  length = 96
FEATURE                Location/Qualifiers
source                 1..96
                       mol_type = protein
                       organism = synthetic construct
SEQUENCE: 3492
EAEVAQSPRY KITEKSQAVA FWCDPISGHA TLYWYRQILG QGPELLVQFQ DESVVDDSQL  60
PKDRFSAERL KGVDSTLKIQ PAELGDSAMY LCASSL                            96

SEQ ID NO: 3493        moltype = AA  length = 96
FEATURE                Location/Qualifiers
source                 1..96
                       mol_type = protein
                       organism = synthetic construct
SEQUENCE: 3493
EAGVAQSPRY KIIEKRQSVA FWCNPISGHA TLYWYQQILG QGPKLLIQFQ NNGVVDDSQL  60
PKDRFSAERL KGVDSTLKIQ PAKLEDSAVY LCASSL                            96

SEQ ID NO: 3494        moltype = AA  length = 96
FEATURE                Location/Qualifiers
source                 1..96
                       mol_type = protein
                       organism = synthetic construct
SEQUENCE: 3494
EAGVVQSPRY KIIEKKQPVA FWCNPISGHN TLYWYLQNLG QGPELLIRYE NEEAVDDSQL  60
PKDRFSAERL KGVDSTLKIQ PAELGDSAVY LCASSL                            96

SEQ ID NO: 3495        moltype = AA  length = 95
FEATURE                Location/Qualifiers
source                 1..95
                       mol_type = protein
                       organism = synthetic construct
SEQUENCE: 3495
DAGVIQSPRH KVTEMGQSVT LRCEPISGHN DLLWYRQTFV QGLELLNYFC SWTLVDDSGV  60
```

```
SKDFSAQMPD VSFSTLRIQP MEPRDLGLYF CASSF                          95

SEQ ID NO: 3496         moltype = AA  length = 95
FEATURE                 Location/Qualifiers
source                  1..95
                        mol_type = protein
                        organism = synthetic construct
SEQUENCE: 3496
DAGIIQSPKH EVTEMGQTVT LRCEPIFGHN FLFWYRDTFV QGLELLSYFR SSIIDNAGMP  60
TERFSAERPD GSFSTLKIQP AEQGDSAVYV CASRL                          95

SEQ ID NO: 3497         moltype = AA  length = 96
FEATURE                 Location/Qualifiers
source                  1..96
                        mol_type = protein
                        organism = synthetic construct
SEQUENCE: 3497
DAGVIQSPRH EVTEMGQEVT LRCKPISGHN SLFWYRQTMM RGLELLIYFN NNVPIDDSGM  60
PEDRFSAKMP NASFSTLKIQ PSEPRDSAVY FCASSL                         96

SEQ ID NO: 3498         moltype = AA  length = 96
FEATURE                 Location/Qualifiers
source                  1..96
                        mol_type = protein
                        organism = synthetic construct
SEQUENCE: 3498
DAGVIQSPRH EVTEMGQEVT LRCKPISGHD YLFWYRQTMM RGLELLIYFN NNVPIDDSGM  60
PEDRFSAKMP NASFSTLKIQ PSEPRDSAVY FCASSL                         96

SEQ ID NO: 3499         moltype = AA  length = 96
FEATURE                 Location/Qualifiers
source                  1..96
                        mol_type = protein
                        organism = synthetic construct
SEQUENCE: 3499
DARVTQTPRH KVTEMGQEVT MRCQPILGHN TVFWYRQTMM QGLELLAYFR NRAPLDDSGM  60
PKDRFSAEMP DATLATLKIQ PSEPRDSAVY FCASGL                         96

SEQ ID NO: 3500         moltype = AA  length = 95
FEATURE                 Location/Qualifiers
source                  1..95
                        mol_type = protein
                        organism = synthetic construct
SEQUENCE: 3500
AAGVIQSPRH LIKEKRETAT LKCYPIPRHD TVYWYQQGPG QDPQFLISFY EKMQSDKGSI  60
PDRFSAQQFS DYHSELNMSS LELGDSALYF CASSL                          95

SEQ ID NO: 3501         moltype = AA  length = 96
FEATURE                 Location/Qualifiers
source                  1..96
                        mol_type = protein
                        organism = synthetic construct
SEQUENCE: 3501
EAGVTQFPSH SVIEKGQTVT LRCDPISGHD NLYWYRRVMG KEIKFLLHFV KESKQDESGM  60
PNNRFLAERT GGTYSTLKVQ PAELEDSGVY FCASSQ                         96

SEQ ID NO: 3502         moltype = AA  length = 95
FEATURE                 Location/Qualifiers
source                  1..95
                        mol_type = protein
                        organism = synthetic construct
SEQUENCE: 3502
DAMVIQNPRY QVTQFGKPVT LSCSQTLNHN VMYWYQQKSS QAPKLLFHYY DKDFNNEADT  60
PDNFQSRRPN TSFCFLDIRS PGLGDTAMYL CATSR                          95

SEQ ID NO: 3503         moltype = AA  length = 96
FEATURE                 Location/Qualifiers
source                  1..96
                        mol_type = protein
                        organism = synthetic construct
SEQUENCE: 3503
GEEVAQTPKH LVRGEGQKAK LYCAPIKGHS YVFWYQQVLK NEFKFLISFQ NENVFDETGM  60
PKERFSAKCL PNSPCSLEIQ ATKLEDSAVY FCASSQ                         96

SEQ ID NO: 3504         moltype = AA  length = 95
FEATURE                 Location/Qualifiers
source                  1..95
                        mol_type = protein
                        organism = synthetic construct
```

```
SEQUENCE: 3504
EPGVSQTPRH KVTNMGQEVI LRCDPSSGHM FVHWYRQNLR QEMKLLISFQ YQNIAVDSGM  60
PKERFTAERP NGTSSTLKIH PAEPRDSAVY LYSSG                             95

SEQ ID NO: 3505        moltype = AA  length = 96
FEATURE                Location/Qualifiers
source                 1..96
                       mol_type = protein
                       organism = synthetic construct
SEQUENCE: 3505
NAGVMQNPRH LVRRRGQEAR LRCSPMKGHS HVYWYRQLPE EGLKFMVYLQ KENIIDESGM  60
PKERFSAEFP KEGPSILRIQ QVVRGDSAAY FCASSP                            96

SEQ ID NO: 3506        moltype = AA  length = 95
FEATURE                Location/Qualifiers
source                 1..95
                       mol_type = protein
                       organism = synthetic construct
SEQUENCE: 3506
DGGITQSPKY LFRKEGQNVT LSCEQNLNHD AMYWYRQDPG QGLRLIYYSQ IVNDFQKGDI  60
AEGYSVSREK KESFPLTVTS AQKNPTAFYL CASSI                             95

SEQ ID NO: 3507        moltype = AA  length = 97
FEATURE                Location/Qualifiers
source                 1..97
                       mol_type = protein
                       organism = synthetic construct
SEQUENCE: 3507
GAVVSQHPSW VICKSGTSVK IECRSLDFQA TTMFWYRQFP KQSLMLMATS NEGSKATYEQ  60
GVEKDKFLIN HASLTLSTLT VTSAHPEDSS FYICSAR                           97

SEQ ID NO: 3508        moltype = AA  length = 96
FEATURE                Location/Qualifiers
source                 1..96
                       mol_type = protein
                       organism = synthetic construct
SEQUENCE: 3508
DTKVTQRPRL LVKASEQKAK MDCVPIKAHS YVYWYRKKLE EELKFLVYFQ NEELIQKAEI  60
INERFLAQCS KNSSCTLEIQ STESGDTALY FCASSK                            96

SEQ ID NO: 3509        moltype = AA  length = 96
FEATURE                Location/Qualifiers
source                 1..96
                       mol_type = protein
                       organism = synthetic construct
SEQUENCE: 3509
HAKVTQTPGH LVKGKGQKTK MDCTPEKGHT FVYWYQQNQN KEFMLLISFQ NEQVLQETEM  60
HKKRFSSQCP KNAPCSLAIL SSEPGDTALY LCASSQ                            96

SEQ ID NO: 3510        moltype = AA  length = 96
FEATURE                Location/Qualifiers
source                 1..96
                       mol_type = protein
                       organism = synthetic construct
SEQUENCE: 3510
DADVTQTPRN RITKTGKRIM LECSQTKGHD RMYWYRQDPG LGLRLIYYSF DVKDINKGEI  60
SDGYSVSRQA QAKFSLSLES AIPNQTALYF CATSDL                            96

SEQ ID NO: 3511        moltype = AA  length = 95
FEATURE                Location/Qualifiers
source                 1..95
                       mol_type = protein
                       organism = synthetic construct
SEQUENCE: 3511
EADIYQTPRY LVIGTGKKIT LECSQTMGHD KMYWYQQDPG MELHLIHYSY GVNSTEKGDL  60
SSESTVSRIR TEHFPLTLES ARPSHTSQYL CASSE                             95

SEQ ID NO: 3512        moltype = AA  length = 94
FEATURE                Location/Qualifiers
source                 1..94
                       mol_type = protein
                       organism = synthetic construct
SEQUENCE: 3512
DAVVTQFPRH RIIGTGKEFI LQCSQNMNHV TMYWYRQDPG LGLKLVYYSP GTGSTEKGDI  60
SEGYHVSNTI ASFPLTLKSA STNQTSVYLY ASSS                              94

SEQ ID NO: 3513        moltype = AA  length = 95
FEATURE                Location/Qualifiers
source                 1..95
```

```
                         mol_type = protein
                         organism = synthetic construct
SEQUENCE: 3513
EAQVTQNPRY LITVTGKKLT VTCSQNMNHE YMSWYRQDPG LGLRQIYYSM NVEVTDKGDV  60
PEGYKVSRKE KRNFPLILES PSPNQTSLYF CASSL                             95

SEQ ID NO: 3514          moltype = AA  length = 95
FEATURE                  Location/Qualifiers
source                   1..95
                         mol_type = protein
                         organism = synthetic construct
SEQUENCE: 3514
DVKVTQSSRY LVKRTGEKVF LECVQDMDHE NMFWYRQDPG LGLRLIYFSY DVKMKEKGDI  60
PEGYSVSREK KERFSLILES ASTNQTSMYL CASSL                             95

SEQ ID NO: 3515          moltype = AA  length = 96
FEATURE                  Location/Qualifiers
source                   1..96
                         mol_type = protein
                         organism = synthetic construct
SEQUENCE: 3515
SAVISQKPSR DICQRGTSLT IQCQVDSQVT MMFWYRQQPG QSLTLIATAN QGSEATYESG  60
FVIDKFPISR PNLTFSTLTV SNMSPEDSSI YLCSVE                            96

SEQ ID NO: 3516          moltype = AA  length = 94
FEATURE                  Location/Qualifiers
source                   1..94
                         mol_type = protein
                         organism = synthetic construct
SEQUENCE: 3516
SQTIHQWPAT LVQPVGSPLS LECTVEGTSN PNLYWYRQAA GRGLQLLFYS VGIGQISSEV  60
PQNLSASRPQ DRQFILSSKK LLLSDSGFYL CAWS                              94

SEQ ID NO: 3517          moltype =   length =
SEQUENCE: 3517
000

SEQ ID NO: 3518          moltype =   length =
SEQUENCE: 3518
000

SEQ ID NO: 3519          moltype =   length =
SEQUENCE: 3519
000

SEQ ID NO: 3520          moltype =   length =
SEQUENCE: 3520
000

SEQ ID NO: 3521          moltype =   length =
SEQUENCE: 3521
000

SEQ ID NO: 3522          moltype =   length =
SEQUENCE: 3522
000

SEQ ID NO: 3523          moltype =   length =
SEQUENCE: 3523
000

SEQ ID NO: 3524          moltype =   length =
SEQUENCE: 3524
000

SEQ ID NO: 3525          moltype =   length =
SEQUENCE: 3525
000

SEQ ID NO: 3526          moltype =   length =
SEQUENCE: 3526
000

SEQ ID NO: 3527          moltype =   length =
SEQUENCE: 3527
000

SEQ ID NO: 3528          moltype =   length =
SEQUENCE: 3528
```

000

SEQ ID NO: 3529 moltype = length =
SEQUENCE: 3529
000

SEQ ID NO: 3530 moltype = length =
SEQUENCE: 3530
000

SEQ ID NO: 3531 moltype = length =
SEQUENCE: 3531
000

SEQ ID NO: 3532 moltype = length =
SEQUENCE: 3532
000

SEQ ID NO: 3533 moltype = length =
SEQUENCE: 3533
000

SEQ ID NO: 3534 moltype = length =
SEQUENCE: 3534
000

SEQ ID NO: 3535 moltype = length =
SEQUENCE: 3535
000

SEQ ID NO: 3536 moltype = length =
SEQUENCE: 3536
000

SEQ ID NO: 3537 moltype = length =
SEQUENCE: 3537
000

SEQ ID NO: 3538 moltype = length =
SEQUENCE: 3538
000

SEQ ID NO: 3539 moltype = length =
SEQUENCE: 3539
000

SEQ ID NO: 3540 moltype = length =
SEQUENCE: 3540
000

SEQ ID NO: 3541 moltype = length =
SEQUENCE: 3541
000

SEQ ID NO: 3542 moltype = length =
SEQUENCE: 3542
000

SEQ ID NO: 3543 moltype = length =
SEQUENCE: 3543
000

SEQ ID NO: 3544 moltype = length =
SEQUENCE: 3544
000

SEQ ID NO: 3545 moltype = length =
SEQUENCE: 3545
000

SEQ ID NO: 3546 moltype = length =
SEQUENCE: 3546
000

SEQ ID NO: 3547 moltype = length =
SEQUENCE: 3547
000

SEQ ID NO: 3548 moltype = length =

SEQUENCE: 3548
000

SEQ ID NO: 3549 moltype = length =
SEQUENCE: 3549
000

SEQ ID NO: 3550 moltype = length =
SEQUENCE: 3550
000

SEQ ID NO: 3551 moltype = length =
SEQUENCE: 3551
000

SEQ ID NO: 3552 moltype = length =
SEQUENCE: 3552
000

SEQ ID NO: 3553 moltype = length =
SEQUENCE: 3553
000

SEQ ID NO: 3554 moltype = length =
SEQUENCE: 3554
000

SEQ ID NO: 3555 moltype = length =
SEQUENCE: 3555
000

SEQ ID NO: 3556 moltype = length =
SEQUENCE: 3556
000

SEQ ID NO: 3557 moltype = length =
SEQUENCE: 3557
000

SEQ ID NO: 3558 moltype = length =
SEQUENCE: 3558
000

SEQ ID NO: 3559 moltype = length =
SEQUENCE: 3559
000

SEQ ID NO: 3560 moltype = length =
SEQUENCE: 3560
000

SEQ ID NO: 3561 moltype = length =
SEQUENCE: 3561
000

SEQ ID NO: 3562 moltype = length =
SEQUENCE: 3562
000

SEQ ID NO: 3563 moltype = length =
SEQUENCE: 3563
000

SEQ ID NO: 3564 moltype = length =
SEQUENCE: 3564
000

SEQ ID NO: 3565 moltype = length =
SEQUENCE: 3565
000

SEQ ID NO: 3566 moltype = length =
SEQUENCE: 3566
000

SEQ ID NO: 3567 moltype = length =
SEQUENCE: 3567
000

SEQ ID NO: 3568 moltype = length =
SEQUENCE: 3568
000

SEQ ID NO: 3569 moltype = length =
SEQUENCE: 3569
000

SEQ ID NO: 3570 moltype = length =
SEQUENCE: 3570
000

SEQ ID NO: 3571 moltype = length =
SEQUENCE: 3571
000

SEQ ID NO: 3572 moltype = length =
SEQUENCE: 3572
000

SEQ ID NO: 3573 moltype = length =
SEQUENCE: 3573
000

SEQ ID NO: 3574 moltype = length =
SEQUENCE: 3574
000

SEQ ID NO: 3575 moltype = length =
SEQUENCE: 3575
000

SEQ ID NO: 3576 moltype = length =
SEQUENCE: 3576
000

SEQ ID NO: 3577 moltype = length =
SEQUENCE: 3577
000

SEQ ID NO: 3578 moltype = length =
SEQUENCE: 3578
000

SEQ ID NO: 3579 moltype = length =
SEQUENCE: 3579
000

SEQ ID NO: 3580 moltype = length =
SEQUENCE: 3580
000

SEQ ID NO: 3581 moltype = length =
SEQUENCE: 3581
000

SEQ ID NO: 3582 moltype = length =
SEQUENCE: 3582
000

SEQ ID NO: 3583 moltype = length =
SEQUENCE: 3583
000

SEQ ID NO: 3584 moltype = length =
SEQUENCE: 3584
000

SEQ ID NO: 3585 moltype = length =
SEQUENCE: 3585
000

SEQ ID NO: 3586 moltype = length =
SEQUENCE: 3586
000

SEQ ID NO: 3587 moltype = length =
SEQUENCE: 3587
000

SEQ ID NO: 3588 moltype = length =
SEQUENCE: 3588
000

SEQ ID NO: 3589 moltype = length =
SEQUENCE: 3589
000

SEQ ID NO: 3590 moltype = length =
SEQUENCE: 3590
000

SEQ ID NO: 3591 moltype = length =
SEQUENCE: 3591
000

SEQ ID NO: 3592 moltype = length =
SEQUENCE: 3592
000

SEQ ID NO: 3593 moltype = length =
SEQUENCE: 3593
000

SEQ ID NO: 3594 moltype = length =
SEQUENCE: 3594
000

SEQ ID NO: 3595 moltype = length =
SEQUENCE: 3595
000

SEQ ID NO: 3596 moltype = length =
SEQUENCE: 3596
000

SEQ ID NO: 3597 moltype = length =
SEQUENCE: 3597
000

SEQ ID NO: 3598 moltype = length =
SEQUENCE: 3598
000

SEQ ID NO: 3599 moltype = length =
SEQUENCE: 3599
000

SEQ ID NO: 3600 moltype = length =
SEQUENCE: 3600
000

SEQ ID NO: 3601 moltype = length =
SEQUENCE: 3601
000

SEQ ID NO: 3602 moltype = length =
SEQUENCE: 3602
000

SEQ ID NO: 3603 moltype = length =
SEQUENCE: 3603
000

SEQ ID NO: 3604 moltype = length =
SEQUENCE: 3604
000

SEQ ID NO: 3605 moltype = length =
SEQUENCE: 3605
000

SEQ ID NO: 3606 moltype = length =
SEQUENCE: 3606
000

SEQ ID NO: 3607 moltype = length =
SEQUENCE: 3607

000

SEQ ID NO: 3608 moltype = length =
SEQUENCE: 3608
000

SEQ ID NO: 3609 moltype = length =
SEQUENCE: 3609
000

SEQ ID NO: 3610 moltype = length =
SEQUENCE: 3610
000

SEQ ID NO: 3611 moltype = length =
SEQUENCE: 3611
000

SEQ ID NO: 3612 moltype = length =
SEQUENCE: 3612
000

SEQ ID NO: 3613 moltype = length =
SEQUENCE: 3613
000

SEQ ID NO: 3614 moltype = length =
SEQUENCE: 3614
000

SEQ ID NO: 3615 moltype = length =
SEQUENCE: 3615
000

SEQ ID NO: 3616 moltype = length =
SEQUENCE: 3616
000

SEQ ID NO: 3617 moltype = length =
SEQUENCE: 3617
000

SEQ ID NO: 3618 moltype = length =
SEQUENCE: 3618
000

SEQ ID NO: 3619 moltype = length =
SEQUENCE: 3619
000

SEQ ID NO: 3620 moltype = length =
SEQUENCE: 3620
000

SEQ ID NO: 3621 moltype = length =
SEQUENCE: 3621
000

SEQ ID NO: 3622 moltype = length =
SEQUENCE: 3622
000

SEQ ID NO: 3623 moltype = length =
SEQUENCE: 3623
000

SEQ ID NO: 3624 moltype = length =
SEQUENCE: 3624
000

SEQ ID NO: 3625 moltype = length =
SEQUENCE: 3625
000

SEQ ID NO: 3626 moltype = length =
SEQUENCE: 3626
000

SEQ ID NO: 3627 moltype = length =

```
SEQUENCE: 3627
000

SEQ ID NO: 3628        moltype =   length =
SEQUENCE: 3628
000

SEQ ID NO: 3629        moltype =   length =
SEQUENCE: 3629
000

SEQ ID NO: 3630        moltype =   length =
SEQUENCE: 3630
000

SEQ ID NO: 3631        moltype =   length =
SEQUENCE: 3631
000

SEQ ID NO: 3632        moltype =   length =
SEQUENCE: 3632
000

SEQ ID NO: 3633        moltype =   length =
SEQUENCE: 3633
000

SEQ ID NO: 3634        moltype =   length =
SEQUENCE: 3634
000

SEQ ID NO: 3635        moltype =   length =
SEQUENCE: 3635
000

SEQ ID NO: 3636        moltype =   length =
SEQUENCE: 3636
000

SEQ ID NO: 3637        moltype =   length =
SEQUENCE: 3637
000

SEQ ID NO: 3638        moltype =   length =
SEQUENCE: 3638
000

SEQ ID NO: 3639        moltype =   length =
SEQUENCE: 3639
000

SEQ ID NO: 3640        moltype = AA  length = 10
FEATURE                Location/Qualifiers
source                 1..10
                       mol_type = protein
                       organism = synthetic construct
SEQUENCE: 3640
GFNIKSAYMH                                                        10

SEQ ID NO: 3641        moltype = AA  length = 11
FEATURE                Location/Qualifiers
source                 1..11
                       mol_type = protein
                       organism = synthetic construct
SEQUENCE: 3641
SESVDSYGNS F                                                      11

SEQ ID NO: 3642        moltype = AA  length = 243
FEATURE                Location/Qualifiers
source                 1..243
                       mol_type = protein
                       organism = synthetic construct
SEQUENCE: 3642
EVQLVESGGG LVQPGGSLRL SCAASGFTFS NFGMHWVRQA PGKGLEWVSY ISSGSSTIYY  60
ADTLKGRFTI SRDNSKNTLY LQMNSLRAED TAVYYCARRG EGAMDYWGQG TTVTVSSGGG  120
GSGGGGSGGG GSGGGGSDNQ LTQSPSFLSA SVGDRVTITC RASSSVNYIY WYQQKPGKAP  180
KLLIYYTSNL APGVPSRFSG SGSGNEYTLT ISSLQPEDFA TYYCQQFTSS PFTFGQGTKL  240
EIK                                                               243
```

What is claimed is:

1. A pharmaceutical composition comprising a molecule that comprises an antigen binding domain that binds to a T cell receptor beta variable (TCRβV) region, wherein the antigen binding domain comprises (i) a heavy chain variable region (VH) comprising an HCDR3 comprising the sequence SYYSYDVLDY (SEQ ID NO: 47), an HCDR1 comprising the sequence GHDFRLTYIH (amino acids 26-35 of SEQ ID NO: 1346), and an HCDR2 comprising the sequence RVSAGSGNVKYNEKFKG (amino acids 50-66 of SEQ ID NO: 1346); and (ii) a light chain variable region (VL) comprising an LCDR3 comprising the sequence QQFKSYPLT (SEQ ID NO: 53), an LCDR1 comprising the sequence KASQNVADRVV (amino acids 24-34 of SEQ ID NO: 1349), and an LCDR2 comprising the sequence SSSHRYK (amino acids 50-56 of SEQ ID NO: 1349).

2. The pharmaceutical composition of claim 1, wherein the VH comprises a sequence having at least 80% sequence identity to the sequence of SEQ ID NO: 1346, and the VL comprises a sequence having at least 80% sequence identity to the sequence of SEQ ID NO: 1349.

3. The pharmaceutical composition of claim 1, wherein the VH comprises a sequence having at least 90% sequence identity to the sequence of SEQ ID NO: 1346, and the VL comprises a sequence having at least 90% sequence identity to the sequence of SEQ ID NO: 1349.

4. The pharmaceutical composition of claim 1, wherein the antigen binding domain is a Fab.

5. The pharmaceutical composition of claim 1, wherein the molecule comprises at least two non-contiguous polypeptide chains;

wherein the at least two non-contiguous polypeptide chains comprise a first polypeptide chain and a second polypeptide chain;

wherein the first polypeptide chain comprises a first Fc region, and the second polypeptide chain comprises a second Fc region; and wherein the first Fc region and the second Fc region comprise an Fc interface with a knob-in-a hole.

6. The pharmaceutical composition of claim 1, wherein:

(1) the first Fc region and the second Fc region each comprise an Asn297Ala mutation according to EU Numbering;

(2) the first Fc region and the second Fc region each comprise a sequence having at least 98% sequence identity to the sequence of SEQ ID NO: 41 or a sequence having at least 98% sequence identity to the sequence of SEQ ID NO: 42; or (3) any combination thereof.

7. The pharmaceutical composition of claim 5, wherein the second polypeptide chain comprises the antigen binding domain and a cytokine molecule, wherein the antigen binding domain comprises the sequence of SEQ ID NO: 1331, and the cytokine molecule comprises IL-2, wherein the IL-2 comprises the sequence of SEQ ID NO: 2270, and wherein the antigen binding domain, the cytokine molecule, and the second Fc region are linked.

8. The pharmaceutical composition of claim 1, wherein the VH comprises a sequence having at least 95% sequence identity to the sequence of SEQ ID NO: 1346, and the VL comprises a sequence having at least 95% sequence identity to the sequence of SEQ ID NO: 1349.

9. The pharmaceutical composition of claim 1, wherein the VH comprises the sequence of SEQ ID NO: 1346, and the VL comprises the sequence of SEQ ID NO: 1349.

10. The pharmaceutical composition of claim 1, wherein the antigen binding domain is a single chain Fv (scFv).

* * * * *